(12) United States Patent
Konteatis et al.

(10) Patent No.: US 10,329,298 B2
(45) Date of Patent: Jun. 25, 2019

(54) INHIBITORS OF CELLULAR METABOLIC PROCESSES

(71) Applicant: Agios Pharmaceuticals, Inc., Cambridge, MA (US)

(72) Inventors: Zenon D. Konteatis, Chatham, NJ (US); Zhihua Sui, Somerville, MA (US); Jeremy M. Travins, Southborough, MA (US); Zhixiong Ye, Beijing (CN)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/691,408

(22) Filed: Aug. 30, 2017

(65) Prior Publication Data

US 2018/0079753 A1 Mar. 22, 2018

Related U.S. Application Data

(63) Continuation-in-part of application No. PCT/CN2016/097524, filed on Aug. 31, 2016.

(60) Provisional application No. 62/548,738, filed on Aug. 22, 2017.

(51) Int. Cl.
*C07D 487/04* (2006.01)
*C07D 519/00* (2006.01)
*C07F 9/6561* (2006.01)

(52) U.S. Cl.
CPC ......... *C07D 487/04* (2013.01); *C07D 519/00* (2013.01); *C07F 9/6561* (2013.01)

(58) Field of Classification Search
CPC .................................................. C07D 487/04
See application file for complete search history.

(56) References Cited

U.S. PATENT DOCUMENTS

2012/0178915 A1 7/2012 Xu

FOREIGN PATENT DOCUMENTS

| JP | 7253630 A | 10/1995 |
| TW | 201811797 A | 4/2008 |
| WO | WO-2012103457 A2 | 8/2012 |
| WO | WO-2018039972 A1 | 3/2018 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
"International Application Serial No. PCT/US2017/049439, International Search Report dated Oct. 19, 2017", 4 pgs.
"International Application Serial No. PCT/US2017/049439, Written Opinion dated Oct. 19, 2017", 6 pgs.
Cai, Jiaxin, et al., "Differential Expression of Methionine Adenosyltransferase Genes Influences the Rate of Growth of Human Hepatocellular Carcinoma Cells1", Cancer Research 58, (Apr. 1, 1998), 1444-1450.
Chen, Hui, et al., "Role of Methionine Adenosyltransferase 2A and S-adenosylmethionine in Mitogen-Induced Growth of Human Colon Cancer Cells", Gastroenterology 133, (2007), 207-218.
Liu, Quanyan, et al., "Silencing MAT2A gene by RNA interference inhibited cell growth and induced apoptosis in human hepatoma cells", Hepatology Research 37, (2007), 376-388.
Tanvi, Jani S, et al., "Inhibition of methionine adenosyltransferase II induces FasL expression, Fas-DISC formation and caspase-8-dependent apoptotic death in T leukemic cells", Cell Research 19, (2009), 358-369.
"International Application Serial No. PCT/CN2016/097524, International Search Report dated Jun. 5, 2017", 6 pgs.
"International Application Serial No. PCT/CN2016/097524, Written Opinion dated Jun. 5, 2017", 6 pgs.

* cited by examiner

*Primary Examiner* — Shawquia Jackson
(74) *Attorney, Agent, or Firm* — Schwegman Lundberg & Woessner, P.A.

(57) ABSTRACT

The present disclosure provides MAT2A inhibitor compounds that are useful as therapeutic agents for treating malignancies, and wherein the compounds conform to general formula (IA):

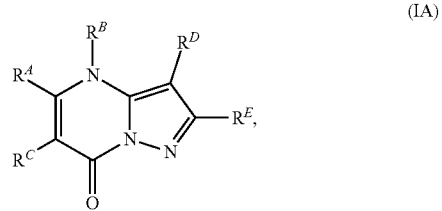

(IA)

wherein $R^A$, $R^B$, $R^C$, $R^D$, and $R^E$ are defined herein.

32 Claims, No Drawings

INHIBITORS OF CELLULAR METABOLIC PROCESSES

CLAIM FOR PRIORITY

This application claims the benefit of priority to U.S. Application Ser. No. 62/548,738, filed Aug. 22, 2017, and is also a continuation-in-part of International Patent Application Serial No. PCT/CN2016/097524, filed Aug. 31, 2016, the contents of which are each incorporated herein by reference in their entirety.

FIELD OF THE DISCLOSURE

The present disclosure relates to organic compounds useful for therapy and/or prophylaxis in a mammal, and in particular to inhibitors of MAT2A enzyme which are useful for treating certain cancers.

BACKGROUND

Methionine adenosyltransferase (MAT) also known as S-adenosylmethionine synthetase is a cellular enzyme that catalyzes the synthesis of S-adenosyl methionine (SAM or AdoMet) from methionine and ATP and is considered the rate-limiting step of the methionine cycle. SAM is the propylamino donor in polyamine biosynthesis and the principal methyl donor for DNA methylation and is involved in gene transcription and cellular proliferation as well as the production of secondary metabolites.

Two genes, MAT1A and MAT2A, encode two distinct catalytic MAT isoforms. A third gene, MAT2B, encodes a MAT2A regulatory subunit. MAT1A is specifically expressed in the adult liver, whereas MAT2A is widely distributed. Because MAT isoforms differ in catalytic kinetics and regulatory properties, MAT1A-expressing cells have considerably higher SAM levels than do MAT2A-expressing cells. It has been found that hypomethylation of the MAT2A promoter and histone acetylation causes upregulation of MAT2A expression.

In hepatocellular carcinoma (HCC), the downregulation of MAT1A and the up-regulation of MAT2A occur, which is known as the MAT1A:MAT2A switch. The switch, accompanied with up-regulation of MAT2B, results in lower SAM contents, which provide a growth advantage to hepatoma cells. Because MAT2A plays a crucial role in facilitating the growth of hepatoma cells, it is a target for antineoplastic therapy. Recent studies have shown that silencing by using small interfering RNA substantially suppresses growth and induces apoptosis in hepatoma cells. See, e.g., T. Li et al., *J. Cancer* 7(10) (2016) 1317-1327.

It has been reported by Marjon et al (Cell Reports 15(3) (2016) 574-587) that cancer cell lines that are MTAP deficient are particularly sensitive to inhibition of MAT2A. MTAP (methylthioadenosine phosphorylase) is an enzyme widely expressed in normal tissues that catalyzes the conversion of methylthioadenosine (MTA) into adenine and 5-methylthioribose-1-phosphate. The adenine is salvaged to generate adenosine monophosphate, and the 5-methylthioribose-1-phosphate is converted to methionine and formate. Because of this salvage pathway, MTA can serve as an alternative purine source when de novo purine synthesis is blocked, e.g., with antimetabolites, such as L-alanosine.

Many human and murine malignant cells lack MTAP activity. MTAP deficiency is not only found in tissue culture cells but the deficiency is also present in primary leukemias, gliomas, melanomas, pancreatic cancers, non-small cell lung cancers (NSLC), bladder cancers, astrocytomas, osteosarcomas, head and neck cancers, myxoid chondrosarcomas, ovarian cancers, endometrial cancers, breast cancers, soft tissue sarcomas, non-Hodgkin lymphomas, and mesotheliomas. The gene encoding for human MTAP maps to region 9p21 on human chromosome 9p. This region also contains the tumor suppressor genes p16INK4A (also known as CDKN2A), and p15INK4B. These genes code for p16 and p15, which are inhibitors of the cyclin D-dependent kinases cdk4 and cdk6, respectively.

The p16INK4A transcript can alternatively be ARF spliced into a transcript encoding p14ARF. p14ARF binds to MDM2 and prevents degradation of p53 (Pomerantz et al. (1998) Cell 92:713-723). The 9p21 chromosomal region is of interest because it is frequently homozygously deleted in a variety of cancers, including leukemias, NSLC, pancreatic cancers, gliomas, melanomas, and mesothelioma. The deletions often inactivate more than one gene. For example, Cairns et al. ((1995) Nat. Gen. 11:210-212) reported that after studying more than 500 primary tumors, almost all the deletions identified in such tumors involved a 170 kb region containing MTAP, p14ARF and P16INK4A. Carson et al (WO 99/67634) reported that a correlation exists between the stage of tumor development and loss of homozygosity of the gene encoding MTAP and the gene encoding p16. For example, deletion of the MTAP gene, but not p16INK4A was reported to be indicative of a cancer at an early stage of development, whereas deletion of the genes encoding for p16 and MTAP was reported to be indicative of a cancer at a more advanced stage of tumor development. Garcia-Castellano et al reported that in some osteosarcoma patients, the MTAP gene was present at diagnosis but was deleted at a later time point (Garcia-Castellano et al., supra).

SUMMARY

For the reasons above, the present disclosure satisfies a significant need for safe and effective compounds and methods for treating, preventing and managing cancers while reducing or avoiding the toxicities and/or side effects associated with the conventional therapies. The cancers include those that are refractory to standard treatments, such as surgery, radiation therapy, chemotherapy and hormonal therapy.

In accordance with some embodiments, the present disclosure provides a compound according to formula IA or a pharmaceutically acceptable salt thereof:

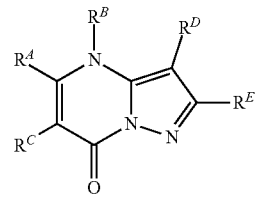

(IA)

In Formula IA, $R^A$ is selected from the group consisting of H, $C_1$-$C_6$-alkyl, $C_2$-$C_6$-alkenyl, $C_1$-$C_6$-alkoxy, $C_3$-$C_{14}$-carbocycle, ($C_3$-$C_{14}$-carbocyclo)-$C_1$-$C_6$-alkyl-, 3- to 14-membered heterocycle or heterocyclo-$C_1$-$C_6$-alkyl- (wherein 1 to 4 heterocycle ring members are heteroatoms selected from N, O, and S), (3- to 14-membered heterocyclo)oxy-, $C_6$-$C_{14}$-aryl, ($C_6$-$C_{14}$-aryl)-$C_1$-$C_6$-alkyl-, $C_6$-$C_{14}$-aryloxy-, —$(CH_2)_{0-6}NR^1(CH_2)_{0-6}(O)R^2$, —$NR^1R^2$, —C(O)

$NR^1R^2$, $NR^1C(NR^2)NR^1R^2$, $NR^1C(NR^2)(=NR^1)$, $SR^1$, —CN, and —OH. Each alkyl, alkenyl, alkoxy, aryl, and heterocycle is optionally substituted with one or more substituents selected from the group consisting of $R^1$, $OR^1$, halo, —N=N—$R^1$, $NR^1R^2$, —$(C_1$-$C_6$-alkyl)$NR^1R^2$, —$C(O)OR^1$, —$C(O)NR^1R^2$, —$OC(O)R^1$, —CN, —$OP(O)(OR^1)_{1-2}$, and oxo.

$R^B$ is selected from the group consisting of H, $C_2$-$C_6$-alkenyl, and $C_1$-$C_6$-alkyl, wherein $R^B$ is optionally substituted by one or more $R^1$.

$R^C$, $R^D$, and $R^E$ are independently selected from the group consisting of $C_3$-$C_{14}$-carbocycle, $C_6$-$C_{14}$-aryl, and 3- to 14-membered heterocycle (wherein 1 to 4 heterocycle ring members are heteroatoms selected from N, O, and S). $R^C$, $R^D$, and $R^E$ are optionally substituted with one or more substituents selected from the group consisting of $R^1$, —$OR^1$, halo, —$NR^1R^2$, $(C_1$-$C_6$-alkyl)-$NR^1R^2$, —$C(O)OR^1$, —$C(O)NR^1R^2$, —$NO_2$, —CN, and oxo.

$R^1$ and $R^2$ are independently selected from the group consisting of H, D ($^2$H), —CN, —OH, $C_1$-$C_6$-alkyl, $C_1$-$C_6$-alkoxy, $C_2$-$C_6$-alkenyl, $NH_2$, $C_2$-$C_6$-alkynyl, —$S(O)_{0-2}$—$(C_1$-$C_6$-alkyl), —$S(O)_{0-2}$—$(C_6$-$C_{14}$-aryl), —$C(O)(C_1$-$C_6$-alkyl), —$C(O)(C_3$-$C_{14}$-carbocyclo), —$C_3$-$C_{14}$-carbocycle, $C_6$-$C_{14}$-aryl, 3- to 14-membered heterocycle or heterocyclo$(C_1$-$C_6$-alkyl)- (wherein 1 to 4 heterocycle ring members are heteroatoms selected from N, O, and S).

Each alkyl, alkoxy, alkenyl, alkynyl, aryl, carbocycle, and heterocycle moiety of $R^1$ and $R^2$ is optionally substituted with one or more substituents selected from the group consisting of hydroxy, halo, —$NH_2$, —$NHC(O)(OC_1$-$C_6$-alkyl), —$NO_2$, —CN, oxo, —$C(O)OH$, —$C(O)O(C_1$-$C_6$-alkyl), —$C_1$-$C_6$-alkyl$(C_1$-$C_6$-alkoxy), —$C(O)NH_2$, $C_1$-$C_6$-alkyl, —$C(O)C_1$-$C_6$-alkyl, —$OC_1$-$C_6$-alkyl, —$Si(C_1$-$C_6$-alkyl)$_3$, $C_6$-$C_{14}$-aryl, —$(C_1$-$C_6$-alkyl)$(C_6$-$C_{14}$-aryl), 3- to 14-membered heterocycle or heterocyclo$(C_1$-$C_6$-alkyl)- (wherein 1 to 4 heterocycle ring members are heteroatoms selected from N, O, and S), and —$O(C_6$-$C_{14}$-aryl).

In another embodiment, there is provided a pharmaceutical composition comprising s compound of formula (IA) or a pharmaceutically acceptable salt thereof and a pharmaceutically acceptable carrier.

Another embodiment is a method for treating a disease or condition mediated by the overexpression of MAT2A in a mammal in need thereof, comprising administering to the mammal an effective amount of a compound of formula (IA) or a pharmaceutically acceptable salt thereof.

Yet another embodiment is a method of treating an MTAP null cancer in a subject comprising administering to the subject an effective amount of a compound of formula (IA) or a pharmaceutically acceptable salt thereof.

In yet another embodiment, the present disclosure provides a method for inhibiting the synthesis of S-adenosyl methionine (SAM) from methionine and ATP by MAT2A in a cell, comprising contacting the cell with an effective amount of a compound of formula (IA) or a pharmaceutically acceptable salt thereof.

Also provided in an embodiment is a method for treating a cancer in a subject suffering therefrom, wherein the cancer is characterized by a reduction or absence of methylthioadenosine phosphorylase (MTAP) gene expression, the absence of the MTAP gene, or reduced function of MTAP protein, comprising administering to the subject a therapeutically effective amount of a compound of formula (IA) or a pharmaceutically acceptable salt thereof.

In another embodiment, the present disclosure provides a compound of formula (IA) or a pharmaceutically acceptable salt thereof, for inhibiting the synthesis of S-adenosyl methionine (SAM) from methionine and ATP by MAT2A in a cell.

In still another embodiment, there is provided a compound of formula (IA) or a pharmaceutically acceptable salt thereof, for treating a disease or condition in a subject suffering therefrom, wherein the disease or condition is mediated by the overexpression of MAT2A.

Yet another embodiment provides a compound of formula (IA) or a pharmaceutically acceptable salt thereof, for treating a cancer in a subject suffering therefrom, wherein the cancer is characterized by a reduction or absence of methylthioadenosine phosphorylase (MTAP) gene expression, the absence of the MTAP gene, or reduced function of MTAP protein.

DETAILED DESCRIPTION

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, in an embodiment, having up to 12 carbon atoms unless otherwise specified, such as a $C_1$-$C_6$-alkyl. When used as part of another term, for example "alkylamino", the alkyl portion may be a saturated hydrocarbon chain, but also includes unsaturated hydrocarbon carbon chains such as "alkenylamino" and "alkynylamino. Examples of particular alkyl groups are methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted alkyl groups may contain one, for example two, three or four substituents which may be the same or different, and are chosen, unless otherwise specified, from halogen (F, Cl, Br, I), hydroxy, protected hydroxy, cyano, nitro, alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonylaminoalkyl, heterocyclyl, aryl, or other groups specified.

"Amino" means primary (i.e. —$NH_2$), secondary (i.e. —NRH) and tertiary (i.e. —NRR) amines in which R is H, alkyl, a carbocycle, a heterocycle, carbocycle-substituted alkyl or heterocycle-substituted alkyl. Particular secondary and tertiary amines are alkylamine, dialkylamine, arylamine, diarylamine, aralkylamine and diaralkylamine wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and disopropylamine.

"Aryl" when used alone or as part of another term means a carbocyclic aromatic group whether or not fused having the number of carbon atoms designated or if no number is designated, up to 14 carbon atoms, such as a $C_6$-$C_{14}$-aryl.

Particular aryl groups are phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). A particular aryl is phenyl. Substituted phenyl or substituted aryl means a phenyl group or aryl group substituted with one, two, three, four or five, for example 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonylaminoalkyl, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxy-phenyl, 3-methoxy-4-(1-chloromethyl)benzyloxy-phenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di (hydroxymethyl)phenyl; a mono- or di(aminomethyl)phenyl or (protected aminomethyl)phenyl such as 2-(aminomethyl) phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetra-substituted phenyl groups where the substituents are different such as 3-methoxy-4-benzyloxy-5-methyl-6-phenyl sulfonylamino. Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic carbon ring having 3 to 14 carbon atoms, for example 3 to 7 carbon atoms, which may be saturated, unsaturated, partially unsaturated, aromatic (aryl) or non-aromatic having the number of atoms designated, generally from 5 to about 14 ring atoms. Particular saturated carbocyclic groups are cyclopropyl, cyclobutyl, cyclopentyl and cyclohexyl groups. A particular saturated carbocycle is cyclopropyl. Another particular saturated carbocycle is cyclohexyl. Particular unsaturated carbocycles are aromatic e.g. aryl groups as previously defined, for example phenyl. Particular partially unsaturated carbocyclic groups are cyclobutene, cyclopentene, cyclohexene and cycloheptene. The terms "substituted carbocyclyl", "carbocycle" and "carbocyclo" mean these groups substituted by the same substituents as the "substituted alkyl" group unless specified otherwise.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated, unsaturated, partially unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen), for example 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles are morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2, 4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Substituents for "optionally substituted heterocycles", and further examples of the 5- and 6-membered ring systems discussed above can be found in W. Druckheimer et al., U.S. Pat. No. 4,278,793. In a particular embodiment, such optionally substituted heterocycle groups are substituted with one or more of hydroxyl, alkyl, alkoxy, acyl, halogen, mercapto, oxo, carboxyl, acyl, halo-substituted alkyl, amino, cyano, nitro, amidino, and guanidino.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and in a particular embodiment at least one heteroatom is nitrogen (*Lang's Handbook of Chemistry*, supra). Included in the definition are any bicyclic groups where any of the above heteroaryl rings are fused to a benzene ring. Particular heteroaryls incorporate a nitrogen or oxygen heteroatom. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particular "heteroaryl" is: 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(methylsulfonic acid)-1H-tetrazol-5-yl, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methyl-pyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]pyridazin-6-yl. An alternative group of "heteroaryl" includes; 4-(carboxymethyl)-5-methyl-1,3-thiazol-2-yl, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(methylsulfonic acid)-1H-tetrazol-5-yl, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl. Heteroaryl groups are optionally substituted as described for heterocycles.

"Inhibitor" means a compound which prevents or reduces the amount of synthesis of S-adenosylmethionine (SAM) from methionine and ATP by MAT2A. In an embodiment, an inhibitor binds to MAT2A.

"Optionally substituted" unless otherwise specified means that a group may be unsubstituted or substituted by one or more (e.g. 2, 3 or 4) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents.

"Pharmaceutically acceptable salts" include both acid and base addition salts. In an embodiment, compounds of the present disclosure are in the form of a pharmaceutically acceptable salt. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine. In an embodiment the compound of the present disclosure is a salt. In an embodiment, the compound of the present disclosure is a pharmaceutically acceptable salt. In an embodiment, the compound of the present disclosure is an acetate. In an embodiment, the compound of the present disclosure is a benzoate salt. In an embodiment, the compound of the present disclosure is a besylate salt. In an embodiment, the compound of the present disclosure is a bitartrate salt. In an embodiment, the compound of the present disclosure is a bromide salt. In an embodiment, the compound of the present disclosure is a carbonate salt. In an embodiment, the compound of the present disclosure is a chloride salt. In an embodiment, the compound of the present disclosure is a citrate salt. In an embodiment, the compound of the present disclosure is an edetate salt. In an embodiment, the compound of the present disclosure is an edisylate salt. In an embodiment, the compound of the present disclosure is a estolate salt. In an embodiment, the compound of the present disclosure is a fumerate salt. In an embodiment, the compound of the present disclosure is a glucepate salt. In an embodiment, the compound of the present disclosure is a gluconate salt. In an embodiment, the compound of the present disclosure is a hydrobromide salt. In an embodiment, the compound of the present disclosure is a hydrochloride salt. In an embodiment, the compound of the present disclosure is an iodide salt. In an embodiment, the compound of the present disclosure is a lactate salt. In an embodiment, the compound of the present disclosure is a lactobionate salt. In an embodiment, the compound of the present disclosure is a malate salt. In an embodiment, the compound of the present disclosure is a maleate salt. In an embodiment, the compound of the present disclosure is a madelate salt. In an embodiment, the compound of the present disclosure is a mesylate salt. In an embodiment, the compound of the present disclosure is a methyl bromide salt.

In an embodiment, the compound of the present disclosure is a methyl sulfate salt. In an embodiment, the compound of the present disclosure is a napsylate salt. In an embodiment, the compound of the present disclosure is a nitrate salt. In an embodiment, the compound of the present disclosure is a pamoate salt. In an embodiment, the compound of the present disclosure is a phosphate salt. In an embodiment, the compound of the present disclosure is a disphosphate salt. In an embodiment, the compound of the present disclosure is a salicylate salt. In an embodiment, the compound of the present disclosure is a disalicylate salt. In an embodiment, the compound of the present disclosure is a stearate salt. In an embodiment, the compound of the present disclosure is a succinate salt. In an embodiment, the compound of the present disclosure is a sulfate salt. In an embodiment, the compound of the present disclosure is a tartrate salt. In an embodiment, the compound of the present disclosure is a tosylate salt. In an embodiment, the compound of the present disclosure is a triethiodide salt. In an embodiment, the compound of the present disclosure is a valerate salt. In an embodiment, the compound of the present disclosure is an aluminum salt. In an embodiment, the compound of the present disclosure is a benzathine salt. In an embodiment, the compound of the present disclosure is a calcium salt. In an embodiment, the compound of the present disclosure is an ethylenediamine salt. In an embodiment, the compound of the present disclosure is a lysine salt. In an embodiment, the compound of the present disclosure is a magnesium salt. In an embodiment, the compound of the present disclosure is a meglumine salt. In an embodiment, the compound of the present disclosure is a potassium salt. In an embodiment, the compound of the present disclosure is a procaine salt. In an embodiment, the compound of the present disclosure is a sodium salt. In an embodiment, the compound of the present disclosure is a tromethamine salt. In an embodiment, the compound of the present disclosure is a zinc salt.

Compounds of the present disclosure may exist in different tautomeric forms. In an embodiment, the compounds are in the form as drawn or named. In another embodiment, the compounds are in a tautomeric form other than as drawn or named. Compounds of the present disclosure may exist as one or a mixture of salts and solvate forms. For example a compound of the present disclosure may be substantially pure in one particular salt or solvate form or else may be mixtures of two or more salt or solvate forms. In an embodiment, the compounds are in solvate form. In a particular embodiment, the compounds exist as hydrates.

Compounds

As described generally above, the present disclosure provides compounds and pharmaceutically acceptable salts thereof, wherein the compounds conform to formula (IA):

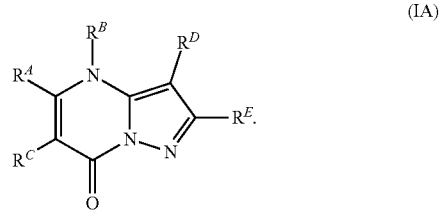

(IA)

In Formula IA, $R^A$ is selected from the group consisting of H, $C_1$-$C_6$-alkyl, $C_2$-$C_6$-alkenyl, $C_1$-$C_6$-alkoxy, $C_3$-$C_{14}$-carbocycle, ($C_3$-$C_{14}$-carbocyclo)-$C_1$-$C_6$-alkyl-, 3- to 14-membered heterocycle or heterocyclo($C_1$-$C_6$-alkyl)- (wherein 1 to 4 heterocycle ring members are heteroatoms selected from N, O, and S), (3- to 14-membered heterocyclo)oxy-, $C_6$-$C_{14}$-aryl, ($C_6$-$C_{14}$-aryl)-$C_1$-$C_6$-alkyl-, $C_6$-$C_{14}$-aryloxy-, —$(CH_2)_{0-6}NR^1(CH_2)_{0-6}C(O)R^2$, $NR^1R^2$, $C(O)NR^1R^2$, $NR^1C(NR^2)NR^1R^2$, $NR^1C(NR^2)(=NR^1)$, $SR^1$, —CN, and —OH. Each alkyl, alkenyl, alkoxy, aryl, and heterocycle is optionally substituted with one or more substituents independently selected from the group consisting of $R^1$, $OR^1$, halo, —N=N—$R^1$, $NR^1R^2$, —($C_1$-$C_6$-alkyl)$NR^1R^2$, —$C(O)OR^1$, —$C(O)NR^1R^2$, —$OC(O)R^1$, —CN, —$OP(O)(OR^1)_{1-2}$, and oxo.

$R^B$ is selected from the group consisting of H, $C_2$-$C_6$-alkenyl, and $C_1$-$C_6$-alkyl, wherein $R^B$ is optionally substituted by one or more $R^1$;

$R^C$, $R^D$, and $R^E$ are independently selected from the group consisting of $C_3$-$C_{14}$-carbocycle, $C_6$-$C_{14}$-aryl, and 3- to 14-membered heterocycle (wherein 1 to 4 heterocycle ring members are heteroatoms selected from N, O, and S). $R^C$, $R^D$, and $R^E$ are optionally substituted with one or more substituents independently selected from the group consisting of $R^1$, —$OR^1$, halo, —$NR^1R^2$, —($C_1$-$C_6$-alkyl)-$NR^1R^2$, —$C(O)OR^1$, —$C(O)NR^1R^2$, —$NO_2$, —CN, and oxo.

$R^1$ and $R^2$ are independently selected from the group consisting of H, D ($^2$H), —CN, —OH, $C_1$-$C_6$-alkyl, $C_1$-$C_6$-alkoxy, $C_2$-$C_6$-alkenyl, $NH_2$, $C_2$-$C_6$-alkynyl, —$S(O)_{0-2}$—($C_1$-$C_6$-alkyl), —$S(O)_{0-2}$—($C_6$-$C_{14}$-aryl), —$C(O)(C_1$-$C_6$-alkyl), —$C(O)(C_3$-$C_{14}$-carbocyclo), —$C_3$-$C_{14}$-carbocycle, $C_6$-$C_{14}$-aryl, 3- to 14-membered heterocycle or heterocyclo ($C_1$-$C_6$-alkyl)- (wherein 1 to 4 heterocycle ring members are heteroatoms selected from N, O, and S).

Each $R^1$ and $R^2$ is optionally substituted with one or more substituents independently selected from the group consisting of hydroxy, halo, —$NH_2$, —$NHC(O)(OC_1$-$C_6$-alkyl), —$NO_2$, —CN, oxo, —$C(O)OH$, —$C(O)O(C_1$-$C_6$-alkyl), —$C_1$-$C_6$-alkyl($C_1$-$C_6$-alkoxy), —$C(O)NH_2$, $C_1$-$C_6$-alkyl, —$C(O)C_1$-$C_6$-alkyl, —$OC_1$-$C_6$-alkyl, —$Si(C_1$-$C_6$-alkyl)$_3$, $C_6$-$C_{14}$-aryl, —($C_1$-$C_6$-alkyl)($C_6$-$C_{14}$-aryl), 3- to 14-membered heterocycle or heterocyclo($C_1$-$C_6$-alkyl)- (wherein 1 to 4 heterocycle ring members are heteroatoms selected from N, O, and S), and —$O(C_6$-$C_{14}$-aryl). Each alkyl, aryl, and heterocyclo in $R^1$ and $R^2$ is optionally substituted with one or more substituents independently selected from the group consisting of hydroxy, —$OC_1$-$C_6$-alkyl, halo, —$NH_2$, —($C_1$-$C_6$-alkyl)$NH_2$, —$C(O)OH$, CN, and oxo.

In some embodiments of Formula IA compounds, $R^D$ and $R^E$ are independently selected from $C_3$-$C_{14}$-carbocycle, $C_6$-$C_{14}$-aryl, and 3- to 14-membered heterocycle (wherein 1 to 4 heterocycle ring members are heteroatoms selected from N, O, and S). More specifically, $R^D$ and $R^E$ are independently selected from $C_3$-$C_{14}$-carbocycle and $C_6$-$C_{14}$-aryl, or $C_5$-$C_7$-carbocycle and $C_6$-$C_{10}$-aryl. In exemplary embodiments, $R^D$ and $R^E$ are independently selected from cyclopentyl, cyclopentenyl, cyclohexyl, cyclohexenyl, and phenyl. For instance, one of $R^D$ and $R^E$ is cyclohexyl or cyclohexenyl and the other is phenyl.

In other embodiments, optionally in combination with any other embodiment described herein, $R^4$ is selected from the group consisting of $C_1$-$C_6$-alkyl, $C_2$-$C_6$-alkenyl, $C_1$-$C_6$-alkoxy, $C_3$-$C_{14}$-carbocycle, ($C_3$-$C_{14}$-carbocyclo)-$C_1$-$C_6$-alkyl-, 3- to 14-membered heterocycle or heterocyclo($C_1$-$C_6$-alkyl)- (wherein 1 to 4 heterocycle ring members are heteroatoms selected from N, O, and S), $C_6$-$C_{14}$-aryl, ($C_6$-$C_{14}$-aryl)-$C_1$-$C_6$-alkyl-, $C_6$-$C_{14}$-aryloxy, —$(CH_2)_{0-6}NR^1$ $(CH_2)_{0-6}C(O)R^2$, $NR^1R^2$, $NR^1C(NR^2)NR^1R^2$, —CN, and —OH. Substituents $R^1$ and $R^2$ have the meanings described herein above for Formula IA.

Various other embodiments provide a Formula IA compound wherein $R^4$ is selected from the group consisting of H, OH, $NH_2$, CN, $C_1$-$C_6$-alkyl, hydroxy-$C_1$-$C_6$-alkyl-, NC—$C_1$-$C_6$-alkyl-, —$C_1$-$C_6$-alkyl-NH($C_1$-$C_6$-alkyl), $NH_2$—$C_1$-$C_6$-alkyl-, —$(CH_2)_{0-1}$—NH—C(O)$R^2$ (where $R^2$ is $NH_2$, $C_1$-$C_6$-alkyl optionally substituted with one or more substituents independently selected from halo, hydroxy-$C_1$-$C_6$-alkyl-, 3- to 14-membered heterocycle optionally substituted with one or more of $C_1$-$C_6$-alkyl and oxo, and $C_3$-$C_{14}$-carbocycle), —$NHR^2$ (wherein $R^2$ is 3- to 14-membered heterocycle optionally substituted with one or more substituents independently selected from the group consisting of $R^1$, $OR^1$, halo, —N=N—$R^1$, $NR^1R^2$, —($C_1$-$C_6$-alkyl) $NR^1R^2$, —C(O)$OR^1$, —OC(O)$R^1$, —CN, —OP(O)$(OR^1)_{1-2}$, and oxo), —C(O)$NR^1R^2$ (wherein $R^1$ and $R^2$ are independently H, $C_1$-$C_6$-alkyl, hydroxy-$C_1$-$C_6$-alkyl-, 3- to 14-membered heterocyclo-$C_1$-$C_6$-alkyl-, $C_6$-$C_{14}$-aryloxy-, or (3- to 14-membered heterocyclo)oxy-).

In some embodiments, $R^4$ is selected from the group consisting of $C_1$-$C_6$-alkyl, —$(CH_2)_{0-6}NR^1(CH_2)_{0-6}C(O)R^2$, $NR^1R^2$, and $NR^1C(NR^2)NR^1R^2$. For example, $R^4$ can be $C_1$-$C_6$-alkyl or $NR^1R^2$. In exemplary embodiments, $R^4$ is $NR^1R^2$. Some Formula IA compounds, in accordance with various embodiments, have $R^4$ as a secondary amino group, i.e., $R^4$ is $NR^1R^2$, where $R^1$ is H and $R^2$ is as defined hereinabove.

In various embodiments, some Formula IA compounds conform to Formula IB:

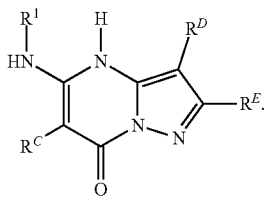

(IB)

In Formula IB compounds and pharmaceutically acceptable salts thereof, according to various embodiments, $R^C$ is a $C_3$-$C_4$-carbocycle or a 3- to 14-membered heterocycle (wherein 1 to 4 heterocycle ring members are heteroatoms selected from N, O, and S). $R^C$ is optionally substituted with one or more substituents selected from the group consisting of hydroxy, halogen, —$NH_2$, $C_6$-$C_{14}$-aryl, ($C_6$-$C_{14}$-aryl)-$C_1$-$C_6$-alkyl-, carboxy, —CN, oxo, $C_1$-$C_6$-alkyl, $C_1$-$C_6$-alkoxy, and —NH($C_1$-$C_6$-alkyl). The $C_1$-$C_6$-alkyl, $C_1$-$C_6$-alkoxy, and NH($C_1$-$C_6$-alkyl) are independently and optionally substituted with one or more of hydroxy, halogen, —$NH_2$, carboxy, —CN, and oxo.

Substituents $R^D$ and $R^E$ are independently a $C_3$-$C_{14}$-carbocycle or a 3- to 14-membered heterocycle (wherein 1 to 4 heterocycle ring members are heteroatoms selected from N, O, and S). $R^D$ and $R^E$ are optionally substituted with one or more substituents selected from the group consisting of hydroxy, halogen, —$NH_2$, $C_6$-$C_{14}$-aryl, ($C_6$-$C_{14}$-aryl)-$C_1$-$C_6$-alkyl-, carboxy, —CN, oxo, $C_1$-$C_6$-alkyl, $C_1$-$C_6$-alkoxy, and —NH($C_1$-$C_6$-alkyl). The $C_1$-$C_6$-alkyl, $C_1$-$C_6$-alkoxy, and NH($C_1$-$C_6$-alkyl) are independently and optionally substituted with one or more of hydroxy, halogen, —$NH_2$, carboxy, —CN, and oxo.

Substituent $R^1$ is selected from the group consisting of H, $C_1$-$C_6$-alkyl, $C_3$-$C_{14}$-carbocycle, and 3- to 14-membered heterocycle (wherein 1 to 4 heterocycle ring members are heteroatoms selected from N, O, and S). $R^1$ is optionally substituted with one or more substituents selected from the group consisting of hydroxy, halogen, —$NH_2$, —$NO_2$, —CN, oxo, carboxy, —C(O)O$C_1$-$C_6$-alkyl, ($C_1$-$C_6$-alkyl) O$C_1$-$C_6$-alkyl, —C(O)$NH_2$, $C_1$-$C_6$-alkyl, —C(O)H, $C_1$-$C_6$-alkoxy, ($C_1$-$C_6$-alkyl)N(H)-aryl-, ($C_6$-$C_{14}$-aryl)$C_1$-$C_6$-alkyl-, 5- to 7-membered heteroaryl, (5- to 7-membered heteroaryl)-$C_1$-$C_6$-alkyl-, $C_6$-$C_{14}$-aryloxy, ($C_6$-$C_{14}$-aryl)($C_1$-$C_6$-alkoxy)-, (5- to 7-membered heteroaryl)oxy-, and (5- to 7-membered heteroaryl)($C_1$-$C_6$-alkoxy)-. The $C_1$-$C_6$-alkyl, $C_1$-$C_6$-alkoxy, ($C_1$-$C_6$-alkyl)N(H)—, —C(O)O$C_1$-$C_6$-alkyl, ($C_1$-$C_6$-alkyl)O$C_1$-$C_6$-alkyl-, —C(O)$NH_2$, $C_6$-$C_{14}$-aryl, ($C_6$-$C_{14}$-aryl)$C_1$-$C_6$-alkyl-, 5- to 7-membered heteroaryl, (5- to 7-membered heteroaryl)-$C_1$-$C_6$-alkyl-, $C_6$-$C_{14}$-aryloxy, ($C_6$-$C_{14}$-aryl)($C_1$-$C_6$-alkoxy)-, (5- to 7-membered heteroaryl) oxy-, and (5- to 7-membered heteroaryl)($C_1$-$C_6$-alkoxy)-, are optionally substituted with one or more of hydroxy, halogen, —$NH_2$, ($C_1$-$C_6$-alkyl)N(H)—, —COOH, —CN, and oxo. Further, each heteroaryl in $R^1$ has 1 to 4 heteroaryl ring members that are heteroatoms selected from N, O, and S.

In some Formula IB compounds, according to various embodiments, $R^D$ is $C_3$-$C_{14}$-carbocycle optionally substituted with one or more members of the group consisting of hydroxy, halogen, —$NH_2$, —C(O)OH, —CN, oxo, alkyl, $C_1$-$C_6$-alkyl, $C_1$-$C_6$-alkoxy, and ($C_1$-$C_6$-alkyl)N(H)—. The $C_1$-$C_6$-alkyl, $C_1$-$C_6$-alkoxy, and ($C_1$-$C_6$-alkyl)N(H)— are optionally substituted with one or more of hydroxy, halogen, —$NH_2$, —C(O)OH, —CN, and oxo.

Some embodiments provide Formula IB compounds wherein $R^D$ is phenyl. In other embodiments, $R^D$ is cyclohex-1-en-1-yl.

In other Formula IB compounds, in accordance with additional embodiments, $R^E$ is $C_3$-$C_{14}$-carbocycle optionally substituted with one or more members of the group consisting of hydroxy, halogen, —$NH_2$, —C(O)OH, —CN, oxo, alkyl, $C_1$-$C_6$-alkyl, $C_1$-$C_6$-alkoxy, and ($C_1$-$C_6$-alkyl)N (H)—. The $C_1$-$C_6$-alkyl, $C_1$-$C_6$-alkoxy, and ($C_1$-$C_6$-alkyl)N (H)— are optionally substituted with one or more of hydroxy, halogen, —$NH_2$, —C(O)OH, —CN, and oxo.

Specific examples of $R^E$ include but are not limited to a member selected from the group consisting of cyclohex-1-en-1-yl, ($^2H_9$)cyclohex-1-en-1-yl, cyclohexan-1,3-dien-1-yl, 4,4-difluorocyclohex-1-en-1-yl, cyclopent-1-en-1yl, cyclopentyl, pyridin-3-yl, pyridin-2-yl, 4-methoxypyridin-3-yl, pyridin-2-yl, 1H-pyrazol-4-yl, 1H-pyrrol-3-yl, 4,4-difluoropiperidin-1-yl, 5,6-dihydro-2H-pyran-3-yl, 3,6-dihydro-2H-pyran-4-yl, 1H-pyrrol-3-yl, 1H-pyrrol-1-yl, tetrahydrofuran-3-yl, 3,3-difluoropyrrolidin-1-yl, and 3,6-dihydro-2H-pyran-4-yl.

For example, in some Formula IB compounds $R^E$ is phenyl. Optionally in combination with this embodiment, $R^D$ is cyclohex-1-en-1-yl.

In another embodiment, $R^D$ or $R^E$ is phenyl optionally substituted, such as with one or more groups consisting of halogen, amino, hydroxy and alkoxy. For instance, $R^D$ or $R^E$ is phenyl substituted with one or more groups consisting of F, Cl, $NH_2$ and OH. In a particular embodiment ring $R^D$ is phenyl, such as 2-fluorophenyl, 3-fluorophenyl, 3-chlorophenyl, 4-aminophenyl, or 4-hydroxyphenyl.

In other embodiments concerning Formula IB, $R^C$ is $C_3$-$C_{14}$-carbocycle or 3- to 14-membered heterocycle (wherein 1 to 4 heterocycle ring members are heteroatoms selected from N, O, and S) and that is optionally substituted with one or more substituents selected from the group consisting of hydroxy, halogen, —$NH_2$, —C(O)OH, —CN, oxo, $C_1$-$C_6$-alkyl, $C_1$-$C_6$-alkoxy, and ($C_1$-$C_6$-alkyl)N(H)—. The $C_1$-$C_6$-alkyl, $C_1$-$C_6$-alkoxy, and ($C_1$-$C_6$-alkyl)N(H)— are optionally substituted with hydroxy, halogen, —$NH_2$, —C(O)OH, —CN and oxo.

In various embodiments, $R^D$ is a carbocycle or a heterocycle each optionally substituted with one or more substituents selected from the group consisting of hydroxy, halogen, $NH_2$, carboxy, CN, oxo, alkyl, alkoxy and alkylamino wherein said alkyl, alkoxy and alkylamino are optionally substituted with hydroxy, halogen, $NH_2$, carboxy, CN and oxo. In one embodiment, $R^D$ is an optionally substituted carbocycle that is saturated or partially unsaturated. The carbocycle is optionally substituted with one or more members of the group consisting of hydroxy, halogen, $NH_2$, carboxy, CN, oxo, alkyl, alkoxy and alkylamino wherein said alkyl, alkoxy and alkylamino are optionally substituted with hydroxy, halogen, $NH_2$, carboxy, CN and oxo. In another embodiment, the saturated or partially unsaturated carbocycle is substituted with one or more halogen, such as one or two F. More specific examples of $R^D$ include optionally substituted cyclohex-1-en-yl and a saturated or partially unsaturated ring that is deuterated. In a particular embodiment, the ring is fully deuterated. Illustrative examples of $R^D$ include cyclohex-1-en-1-yl (E), ($^2H_9$)cyclohex-1-en-1-yl, cyclohexa-E,Z-1,3-dien-1-yl, 4,4-difluorocyclohex-1-en-1-yl, cyclopent-E1-en-1yl, and cyclopentyl.

In some embodiments $R^D$ is a heterocycle optionally substituted with one or more substituents selected from the group consisting of hydroxy, halogen, $NH_2$, carboxy, CN, oxo, alkyl, alkoxy and alkylamino wherein said alkyl, alkoxy and alkylamino are optionally substituted with hydroxy, halogen, $NH_2$, carboxy, CN and oxo. For example, the heterocycle is aromatic, i.e. heteroaryl. Examples include pyridyl, such as pyridin-3-yl or pyridin-2-yl. Other examples include pyrazolyl, 4-methoxypyridin-3-yl, 1H-pyrazol-4-yl, 1H-pyrrol-3-yl, 4,4-difluoropiperidin-1-yl, 5,6-dihydro-2H-pyran-3-yl (Z), 3,6-dihydro-2H-pyran-4-yl, 1H-pyrrol-3-yl, 1H-pyrrol-1-yl, tetrahydrofuran-3-yl, 3,3-difluoropyrrolidin-1-yl, and 3,6-dihydro-2H-pyran-4-yl.

In other embodiments, $R^D$ is a non-aromatic heterocycle that is optionally substituted with one or more halogen or alkoxy. For instance, the halogen is one or two F.

In other embodiments, $R^D$ is a deuterated heterocycle. In one embodiment, the heterocycle is fully deuterated. In a particular embodiment, $R^D$ is piperidin-1-yl, such as ($^2H_{10}$) piperidin-1-yl.

In various embodiments $R^E$ is a carbocycle or a heterocycle each optionally substituted with one or more substituents selected from the group consisting of hydroxy, halogen, $NH_2$, carboxy, CN, oxo, alkyl, alkoxy and alkylamino wherein said alkyl, alkoxy and alkylamino are optionally substituted with hydroxy, halogen, $NH_2$, carboxy, CN and oxo. In a particular embodiment $R^E$ is phenyl, such as 2-fluorophenyl, 3-fluorophenyl, 3-chlorophenyl, 4-aminophenyl, and 4-hydroxyphenyl. In an embodiment, $R^E$ is a saturated or partially unsaturated carbocycle that is optionally substituted with one or more members of the group consisting of hydroxy, halogen, $NH_2$, carboxy, CN, oxo, alkyl, alkoxy and alkylamino wherein said alkyl, alkoxy and alkylamino are optionally substituted with hydroxy, halogen, $NH_2$, carboxy, CN or oxo. In some embodiments, the saturated or partially unsaturated carbocycle is substituted with one or more halogen, such as one or two F. For instance, $R^E$ is optionally substituted cyclohex-1-en-yl, or is a saturated or partially unsaturated ring that is partially or fully deuterated. Illustrative examples of $R^E$ include cyclohex-1-en-1-yl (E), ($^2H_9$)cyclohex-1-en-1-yl, cyclohexa-E,Z-1,3-dien-1-yl, 4,4-difluorocyclohex-1-en-1-yl, cyclopent-E1-en-1yl, and cyclopentyl.

In other embodiments $R^E$ is a heterocycle optionally substituted with one or more substituents selected from the group consisting of hydroxy, halogen, $NH_2$, carboxy, CN, oxo, alkyl, alkoxy and alkylamino wherein said alkyl, alkoxy and alkylamino are optionally substituted with hydroxy, halogen, $NH_2$, carboxy, CN and oxo. In an embodiment, the heterocycle is aromatic, i.e. heteroaryl, including pyridyl such as pyridin-3-yl and pyridin-2-yl. In some embodiments the heteroaryl is pyrazole, 4-methoxypyridin-3-yl, 1H-pyrazol-4-yl, or 1H-pyrrol-3-yl.

In an embodiment, $R^E$ is a non-aromatic heterocycle that is optionally substituted with one or more halogen or alkoxy. For instance, in one embodiment where $R^E$ is substituted by halogen, the halogen is one or two F. In other embodiments, the heterocycle is deuterated, such as fully deuterated. Illustrative examples of $R^E$ include piperidin-1-yl, ($^2H_{10}$) piperidin-1-yl, 4,4-difluoropiperidin-1-yl, 5,6-dihydro-2H-pyran-3-yl (Z), 3,6-dihydro-2H-pyran-4-yl, 1H-pyrrol-3-yl, 1H-pyrrol-1-yl, tetrahydrofuran-3-yl, 3,3-difluoropyrrolidin-1-yl, and 3,6-dihydro-2H-pyran-4-yl.

In other embodiments, $R^D$ and $R^E$ are the same as defined herein. In an embodiment ring A and ring B are both phenyl. In an embodiment, ring A and ring B are different and are as defined herein. In an embodiment, ring A is phenyl and ring B is selected from the group consisting of 2-fluorophenyl, 3-fluorophenyl, 4-aminophenyl, 4-hydroxyphenyl, 4-methoxypyridin-3-yl, pyridin-2-yl, 1H-pyrazol-4-yl, 3,6-dihydro-2H-pyran-4-yl, and 1H-pyrrol-3-yl. In an embodiment, ring B is phenyl and ring A is selected from the group consisting of 2-fluorophenyl, 3-fluorophenyl, 3-chlorophenyl, piperidin-1-yl, ($^2H_{10}$)piperidin-1-yl, 4,4-difluoropiperidin-1-yl, cyclohex-1-en-1-yl (E), ($^2H_9$)cyclohex-1-en-1-yl, cyclohexa-E,Z-1,3-dien-1-yl, 4,4-difluorocyclohex-1-en-1-yl, 5,6-dihydro-2H-pyran-3-yl (Z), 3,6-dihydro-2H-pyran-4-yl, cyclopentyl, cyclopent-E1-en-1yl, 1H-pyrrol-3-yl, 1H-pyrrol-1-yl, tetrahydrofuran-3-yl, and 3,3-difluoropyrrolidin-1-yl.

In various embodiments, $R^E$ is phenyl and $R^D$ is cyclohex-1-en-1-yl (E). Other $R^E/R^D$ combinations are contemplated in additional embodiments, such as phenyl/2-fluorophenyl, phenyl/3-fluorophenyl, phenyl/3-chlorophenyl, phenyl/piperidin-1-yl, phenyl/($^2H_{10}$)piperidin-1-yl, phenyl/4,4-difluoropiperidin-1-yl, phenyl/cyclohex-1-en-1-yl (E), phenyl/($^2H_9$)cyclohex-1-en-1-yl, phenyl/cyclohexa-E,Z-1,3-dien-1-yl, phenyl/4,4-difluorocyclohex-1-en-1-yl, phenyl/5,6-dihydro-2H-pyran-3-yl (Z), phenyl/3,6-dihydro-2H-pyran-4-yl, phenyl/cyclopentyl, phenyl/cyclopent-E1-en-1yl, phenyl/1H-pyrrol-3-yl, phenyl/1H-pyrrol-1-yl, phenyl/tetrahydrofuran-3-yl, phenyl/3,3-difluoropyrrolidin-1-yl, and pyridin-2-yl/phenyl.

As described more generally above, in accordance with various embodiments, $R^C$ is a carbocycle or a heterocycle each optionally substituted with one or more substituents selected from the group consisting of hydroxy, halogen, amino, carboxy, CN, oxo, alkyl, alkoxy, alkylamino, acyl, acylamino, acyloxy, cycloalkoxy, a carbocycle or a heterocycle wherein the alkyl, alkoxy, alkylamino, acyl, acylamino, acyloxy, cycloalkoxy, carbocycle and heterocycle are optionally substituted with hydroxy, halogen, $NH_2$, carboxy, CN, oxo, a carbocycle or a heterocycle wherein the carbocycle and heterocycle are optionally substituted with one or more OH, oxo, amino, halo and haloalkyl. In additional embodiments, $R^C$ is a carbocycle or a heterocycle each optionally substituted with one or more substituents selected from the group consisting of hydroxy, halogen, amino, carboxy, CN, oxo, alkyl, alkoxy and alkylamino wherein the alkyl, alkoxy and alkylamino are optionally substituted with hydroxy, halogen, amino, carboxy, CN and oxo. Alternatively, $R^C$ is a carbocycle optionally substituted with one or more substituents selected from the group consisting of hydroxy, halogen, amino, carboxy, CN, oxo, phosphate, sulfate, alkyl, alkoxy, alkylamino, acyl, acylamino, acyloxy, cycloalkoxy, a carbocycle or a heterocycle wherein the alkyl, alkoxy, alkylamino, acyl, acylamino, acyloxy, cycloalkoxy, carbocycle and heterocycle are optionally substituted with hydroxy, halogen, $NH_2$, carboxy, CN, oxo, phosphate, sulfate, a carbocycle or a heterocycle wherein the carbocycle and heterocycle are optionally substituted with one or more OH, oxo, amino, halo and haloalkyl. For example, the optionally substituted carbocycle is aromatic, i.e. aryl, optionally substituted with one or more substituents selected from the group consisting of OH, amino, halogen, alkyl, alkoxy and cycloalkoxy wherein the alkyl, alkoxy, cycloalkoxy are optionally substituted with one or more OH, halogen, amino, oxo, a carbocycle or heterocycle wherein the carbocycle and heterocycle are optionally substituted with one or more hydroxy, halogen, oxo, alkyl and haloalkyl. In one embodiment, the aryl group, such as phenyl, is optionally substituted with OH, halogen, alkoxy, amino, haloalkoxy, aminoethoxy and hydroxyethoxy. Specific examples of $R^C$ include phenyl optionally substituted with a substituent selected from OH, F, Cl, methyl, methoxy, ethoxy, trifluoromethoxy, 2,2,2-trifluoroethoxy, dimethylaminoethoxy, 2-hydroxyethoxy and phosphate.

In various embodiments, $R^C$ is selected from the group consisting of 3-hydroxyphenyl, 4-hydroxyphenyl, 4-chlorophenyl, 4-fluorophenyl, 4-methoxyphenyl, 4-ethoxyphenyl, 4-trifluoromethoxyphenyl, 4-hydroxy-2-methylphenyl, 4-hydroxy-2-methoxyphenyl, 3,4-dihydroxyphenyl, 4-(2,2,2-trifluoroethoxy)phenyl, 4-(2-(dimethylamino)ethoxy)phenyl, 3-fluoro-4-hydroxyphenyl, 3-fluoro-4-methoxyphenyl, 2-chloro-4-hydroxyphenyl, 2-fluoro-4-methoxyphenyl, 3-amino-4-hydroxyphenyl, 3-amino-4-fluorophenyl, 3-(N,N-dimethylaminoethoxy)-4-hydroxyphenyl, 3-chloro-2-hydroxyphenyl, 3-hydroxyethoxy-4-hydroxyphenyl,

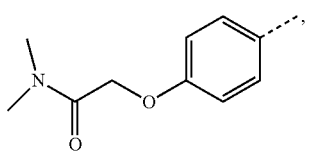

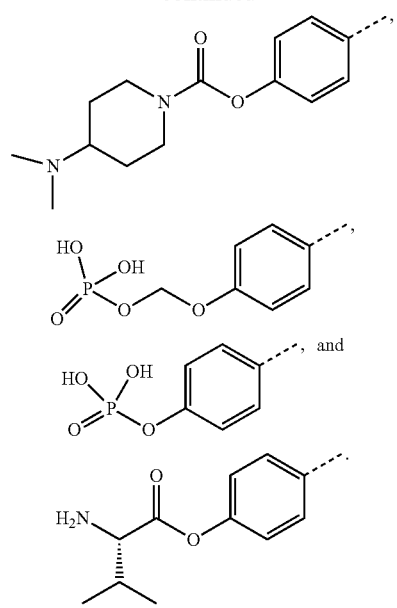

In still other embodiments, $R^C$ is a heterocycle optionally substituted with one or more substituents selected from the group consisting of hydroxy, halogen, amino, carboxyl, CN, oxo, phosphate, sulfate, alkyl, alkoxy, alkylamino, acyl, acylamino, acyloxy, cycloalkoxy, a carbocycle or a heterocycle wherein the alkyl, alkoxy, alkylamino, acyl, acylamino, acyloxy, cycloalkoxy, carbocycle and heterocycle are optionally substituted with one or more hydroxy, halogen, $NH_2$, carboxy, CN, oxo, phosphate, sulfate, a carbocycle or a heterocycle wherein said carbocycle and heterocycle are optionally substituted with OH, oxo, amino, halo and haloalkyl. For example, the heterocycle is aromatic, such as a heteroaryl optionally substituted with one or more substituents selected from the group consisting of OH, amino, halogen, alkyl, alkoxy and cycloalkoxy wherein said alkyl, alkoxy and cycloalkoxy are optionally substituted with one or more OH, halogen, amino, oxo, a carbocycle or heterocycle wherein said carbocycle and heterocycle are optionally substituted with hydroxy, halogen, oxo, alkyl and haloalkyl. In some embodiments, $R^C$ is a heteroaryl group optionally substituted with one or more OH, amino, alkyl, carboxyl, alkyl, alkoxy and cycloalkoxy wherein the alkyl is optionally substituted with OH, amino, oxo, alkoxy, a heterocycle optionally substituted with oxo and wherein the cycloalkoxy is optionally substituted with OH. Specific examples of $R^C$ include 6-methoxypyridin-3-yl, 2-methoxypyridin-4-yl, 1H-pyrazol-4-yl, quinolin-6-yl, 2-methylquinolin-6-yl, 2-methoxyquinolin-6-yl, 2-hydroxymethylquinolin-6-yl, 3-hydroxy-2-methylquinolin-6-yl, 2-aminoquniazolin-6-yl, 4-aminoquinazolin-6-yl, cinnolin-6-yl, quinoxalin-6-yl, 2-chloroquinoxalin-6-yl, 3-chloroquinoxalin-6-yl, 3-aminoquinoxalin-6-yl, 3-hydroxyquinoxalin-6-yl, 3-methoxyquinoxalin-6-yl, 1,8-naphthyridin-3-yl, or imidazo[1,2-a]pyridin-6-yl.

In other embodiments, $R^C$ is selected from the group consisting of 6-methoxypyridin-3-yl, 2-methoxypyridin-4-yl, 1H-pyrazol-4-yl, quinolin-6-yl, 2-methylquinolin-6-yl, 2-methoxyquinolin-6-yl, 2-hydroxymethylquinolin-6-yl, 3-hydroxy-2-methylquinolin-6-yl, 2-aminoquniazolin-6-yl, 4-aminoquinazolin-6-yl, cinnolin-6-yl, quinoxalin-6-yl, 2-chloroquinoxalin-6-yl, 3-chloroquinoxalin-6-yl, 3-aminoquinoxalin-6-yl, 3-hydroxyquinoxalin-6-yl, 3-methoxyquinoxalin-6-yl, 1,8-naphthyridin-3-yl, imidazo[1,2-a]pyridin-6-yl,

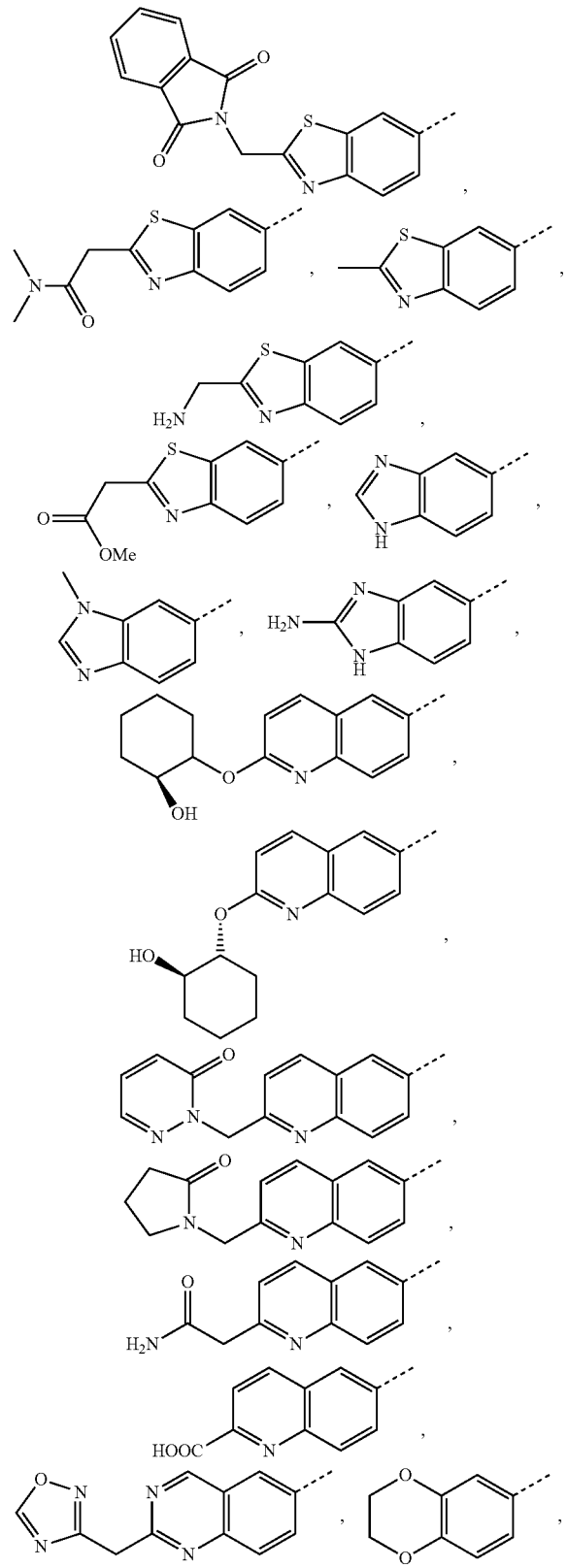

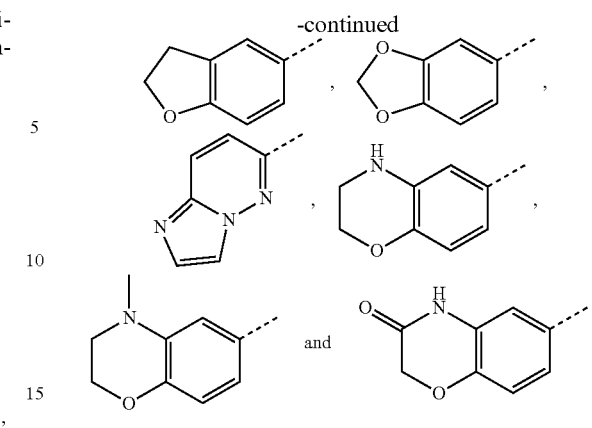

Alternatively, illustrative Formula IB compounds provide for $R^C$ as 4-methoxyphenyl.

In various embodiments, $R^1$ is H or alkyl, a carbocycle or a heterocycle each optionally substituted with one or more substituents selected from the group consisting of hydroxy, halogen, $NH_2$, $NO_2$, carboxy, alkoxycarbonyl, alkoxyalkyl, alkylaminocarbonyl, CN, oxo, alkyl, acyl, alkoxy and alkylamino, and wherein the alkyl, alkoxy, alkylamino, alkoxycarbonyl, alkoxyalkyl and alkylaminocarbonyl are optionally substituted with hydroxy, halogen, amino, alkylamino, carboxy, CN and oxo. In one embodiment, $R_1$ is alkyl optionally substituted with one or more substituents selected from the group consisting of hydroxy, halogen, $NH_2$, $NO_2$, carboxy, alkoxycarbonyl, alkylaminocarbonyl, CN, oxo, alkyl, acyl, alkoxy and alkylamino wherein the alkyl, alkoxy, alkylamino, alkoxycarbonyl, alkylaminocarbonyl are optionally substituted with hydroxy, halogen, $NH_2$, alkylamino, carboxy, CN and oxo. In another embodiment, $R_1$ is alkyl substituted with OH and oxo. In various other embodiments, $R_1$ is hydroxyethanoyl; a carbocycle optionally substituted with one or more substituents selected from the group consisting of hydroxy, halogen, $NH_2$, $NO_2$, carboxy, alkoxycarbonyl, alkylaminocarbonyl, CN, oxo, alkyl, acyl, alkoxy and alkylamino wherein said alkyl, alkoxy, alkylamino, alkoxycarbonyl, alkylaminocarbonyl are optionally substituted with hydroxy, halogen, $NH_2$, alkylamino, carboxy, CN and oxo; or a heterocycle optionally substituted with one or more substituents selected from the group consisting of hydroxy, halogen, $NH_2$, $NO_2$, carboxy, alkoxycarbonyl, alkylaminocarbonyl, CN, oxo, alkyl, acyl, alkoxy and alkylamino wherein said alkyl, alkoxy, alkylamino, alkoxycarbonyl, alkylaminocarbonyl are optionally substituted with hydroxy, halogen, $NH_2$, alkylamino, carboxy, CN and oxo. In accordance with some embodiments, the optionally substituted heterocycle is pyridyl, pyrazinyl, pyrimidinyl, pyridazinyl, 1,3,5-triazinyl, 1,2,4-triazinyl, pyridin-2-yl, pyrazin-2-yl, pyrimidin-2-yl, pyrimidin-4-yl, pyrimidin-5-yl, pyridazin-3-yl, 1,3,5-triazin-2-yl or 1,2,4-triazin-3-yl. In an embodiment, $R_1$ is pyridyl, pyrazinyl, pyrimidinyl, pyridazinyl, 1,3,5-triazinyl or 1,2,4-triazinyl each of which is optionally substituted with one or more F, Cl, CN, OH, $NO_2$, $NH_2$, NHMe—C(O)$NH_2$ and methoxy. In an embodiment the substituent is F, Cl, CN or OH. In another embodiment, the optionally substituted heterocycle is pyridin-2-yl, pyrazin-2-yl, pyrimidin-2-yl, pyrimidin-4-yl, pyrimidin-5-yl, pyridazin-3-yl, 1,3,5-triazin-2-yl or 1,2,4-triazin-3-yl each of which is optionally substituted with one or more F, Cl, CN, OH, $NO_2$, $NH_2$, NHMe-C(O)$NH_2$ and methoxy. In an embodiment the substituent is F, Cl, CN or OH.

According to various embodiments, optionally in combination with any other embodiments described herein, the present disclosure provides for Formula IB compounds wherein $R^1$ is selected from a 3- to 14-membered heterocycle optionally substituted with one or more substituents selected from the group consisting of hydroxy, halogen, —$NH_2$, —$NO_2$, —C(O)OH, —C(O)O$C_1$-$C_6$-alkyl, ($C_1$-$C_6$-alkyl)N(H)C(O)—, —CN, oxo, $C_1$-$C_6$-alkyl, —C(O)H, $C_1$-$C_6$-alkoxy, and ($C_1$-$C_6$-alkyl)N(H)—. The $C_1$-$C_6$-alkyl, $C_1$-$C_6$-alkoxy, and ($C_1$-$C_6$-alkyl)N(H)—, C(O)O$C_1$-$C_6$-alkyl, and ($C_1$-$C_6$-alkyl)N(H)C(O)— are optionally substituted with one or more of hydroxy, halogen, —$NH_2$, ($C_1$-$C_6$-alkyl)N(H)—, —C(O)H, —CN, and oxo.

In more specific embodiments. $R^1$ is selected from the group consisting of pyridin-2-yl, pyrazin-2-yl, pyrimidin-2-yl, pyrimidin-4-yl, pyrimidin-5-yl, pyridazin-3-yl, 1,3,5-triazin-2-yl, 1,2,4-triazin-3-yl, each of which is optionally substituted with one or more of F, Cl, CN, OH, —$NO_2$, —$NH_2$, —NHMe, —C(O)$NH_2$, and methoxy.

Illustrative moieties for $R^1$ are selected from the group consisting of:

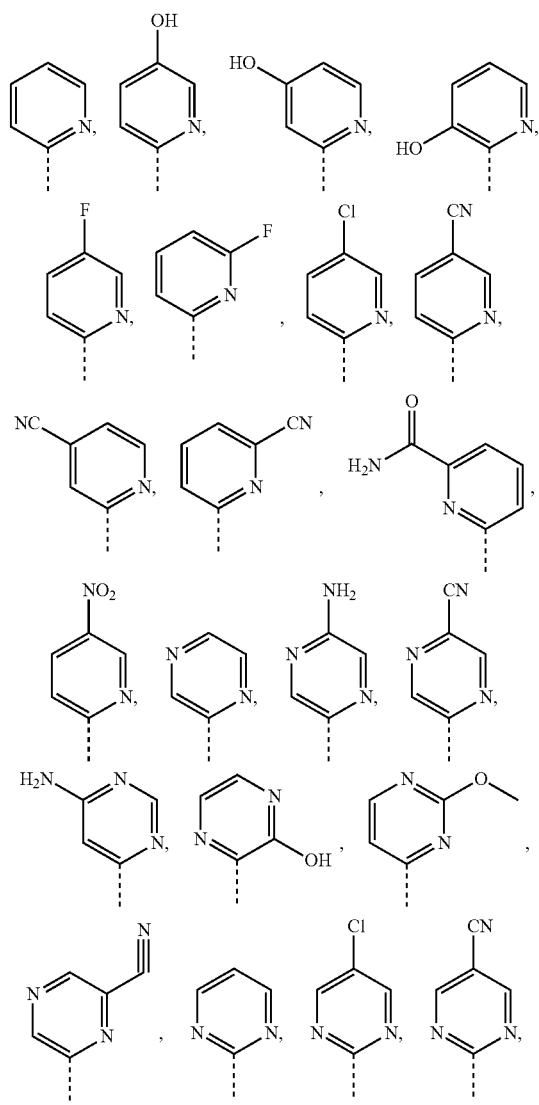

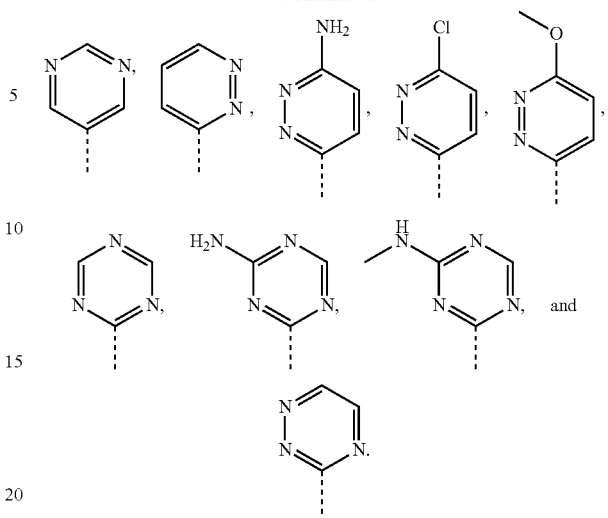

In an embodiment, $R_1$ is a 5-member heterocycle optionally substituted with OH, amino, alkyl, alkoxy and alkoxyalkyl wherein said alkyl, alkoxy and alkoxyalkyl are optionally substituted with one or more OH, oxo, amino, alkoxy and acyloxy. For example, $R^1$ is imidazole, pyrazolyl, isoxazole, thiazolyl, 4,5-dihydrothiazolyl, 1H-1,2,4-triazolyl, 2H-1,2,3-triazolyl, 1,3,4-oxadiazolyl, 1,2,5-oxadiazolyl, 1,2,4-thiadiazolyl or 1,3,4-thiadiazol-2-yl optionally substituted with OH, amino, alkyl, alkoxy, alkoxyalkyl, wherein the alkyl, alkoxy and alkoxyalkyl groups are optionally substituted with OH, oxo and amino.

Alternatively, in accordance with other embodiments, $R^1$ is imidazol-2-yl, imidazol-4-yl, pyrazol-3-yl, pyrazol-5-yl, isoxazol-3-yl, isoxazol-4-yl, isoxazol-5-yl, thiazol-2-yl, 4,5-dihydrothiazol-2-yl, 1H-1,2,4-triazol-3-yl, 2H-1,2,3-triazol-4-yl, 1,3,4-oxadiazol-2-yl, 1,2,5-oxadiazol-3-yl, 1,2,4-thiadiazol-5-yl or 1,3,4-thiadiazol-2-yl optionally substituted with OH, amino, alkyl, alkoxy, alkoxyalkyl, wherein the alkyl, alkoxy and alkoxyalkyl groups are optionally substituted with OH, oxo and amino.

Specific examples of $R^1$ are selected from the group consisting of:

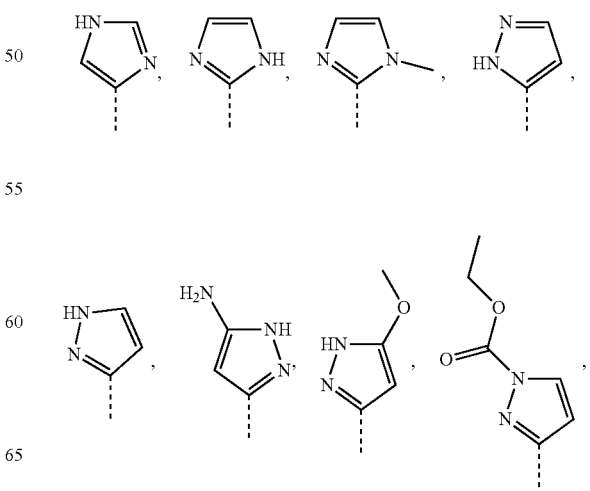

-continued

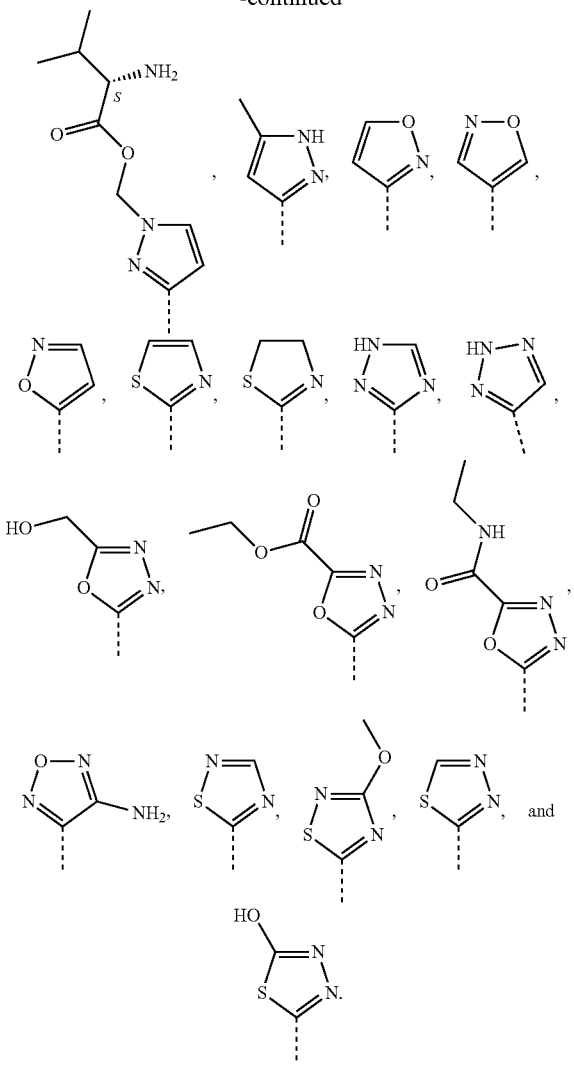

The present disclosure also provides compounds having the general formula I:

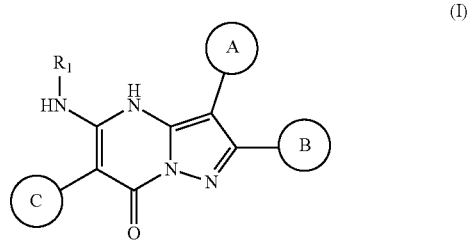

(I)

wherein ring A and ring B are independently a carbocycle or a heterocycle each optionally substituted with one or more substituents selected from the group consisting of hydroxy, halogen, amino, carboxy, CN, oxo, alkyl, alkoxy and alkylamino wherein said alkyl, alkoxy and alkylamino are optionally substituted with hydroxy, halogen, amino, carboxy, CN and oxo;

In this embodiment, ring C is a carbocycle or a heterocycle each optionally substituted with one or more substituents selected from the group consisting of hydroxy, halogen, amino, carboxy, CN, oxo, alkyl, alkoxy, alkylamino, acyl, acylamino, acyloxy, cycloalkoxy, a carbocycle or a heterocycle wherein said alkyl, alkoxy, alkylamino, acyl, acylamino, acyloxy, cycloalkoxy, carbocycle and heterocycle are optionally substituted with hydroxy, halogen, $NH_2$, carboxy, CN, oxo, a carbocycle or a heterocycle wherein said carbocycle and heterocycle are optionally substituted with OH, oxo, amino, halo and haloalkyl;

$R_1$ is H or alkyl, a carbocycle or a heterocycle each optionally substituted with one or more substituents selected from the group consisting of hydroxy, halogen, amino, $NO_2$, CN, OXO, carboxy, alkoxycarbonyl, alkoxyalkyl, aminocarbonyl, alkyl, acyl, alkoxy, alkylamino aryl, aralkyl, heteroaryl, heteroaralkyl, aryloxy, aralkoxy, heteroaryloxy and heteroaralkoxy wherein said alkyl, alkoxy, alkylamino, alkoxycarbonyl, alkoxyalkyl, aminocarbonyl, aryl, aralkyl, heteroaryl, heteroaralkyl, aryloxy, aralkoxy, heteroaryloxy and heteroaralkoxy are optionally substituted with hydroxy, halogen, amino, alkylamino, carboxy, CN or oxo.

Compounds of the present disclosure may also comprise one or more isotopic substitutions. For example, H may be in any isotopic form, including $^1H$, $^2H$ (D or deuterium), and $^3H$ (T or tritium); C may be in any isotopic form, including $^{11}C$, $^{12}C$, $^{13}C$, and $^{14}C$; N may be in any isotopic form, including $^{13}N$, $^{14}N$ and $^{15}N$; O may be in any isotopic form, including $^{15}O$, $^{16}O$ and $^{18}O$; F may be in any isotopic form, including $^{18}F$; and the like. For example, the compound is enriched in a specific isotopic form of H, C, N, O and/or F by at least about 60%, 65%, 70%, 75%, 80%, 85%, 90%, 95%, 96%, 97%, 98%, or 99%. Such compounds may be referred to as "isotopologues" and may be useful of the methods of treatment disclosed herein or may be useful in assays for detection of the compound, for example, in competition assays to test other non-isotope containing compounds. In an embodiment, compounds of the present disclosure comprise an isotope. In an embodiment the isotope is deuterium.

Specific compounds conforming to formula IA, or pharmaceutically acceptable salts thereof, include those in Table 1 below:

TABLE 1

204

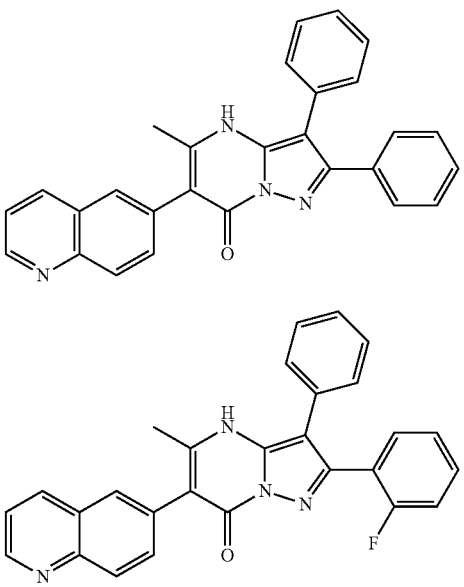

205

TABLE 1-continued
206
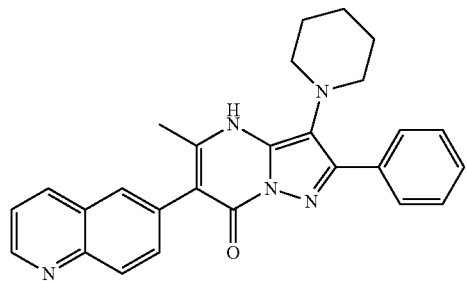 [SMILES: Cc1[nH]c2c(N3CCCCC3)c(-c3ccccc3)nn2c(=O)c1-c1ccc2ncccc2c1]
207
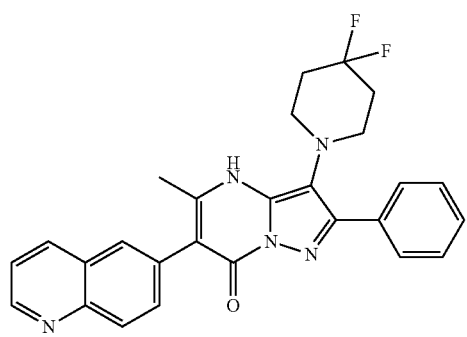 [SMILES: Cc1[nH]c2c(N3CCC(F)(F)CC3)c(-c3ccccc3)nn2c(=O)c1-c1ccc2ncccc2c1]
208
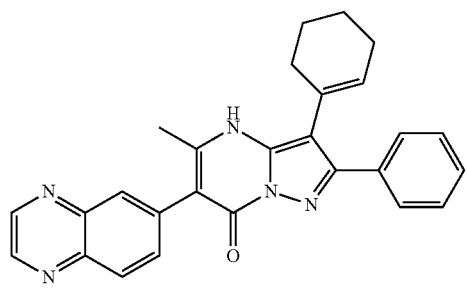 [SMILES: Cc1[nH]c2c(C3=CCCCC3)c(-c3ccccc3)nn2c(=O)c1-c1ccc2nccnc2c1]
209
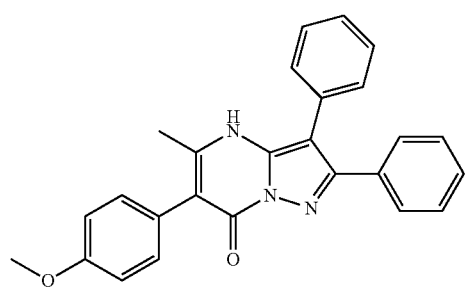 [SMILES: COc1ccc(-c2c(C)[nH]c3c(-c4ccccc4)c(-c4ccccc4)nn3c2=O)cc1]
210
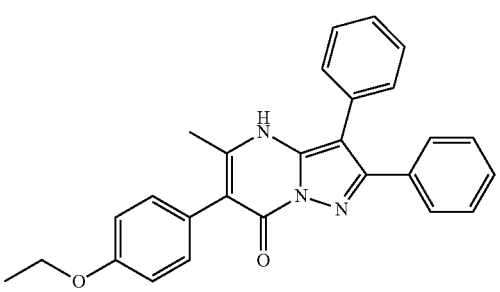 [SMILES: CCOc1ccc(-c2c(C)[nH]c3c(-c4ccccc4)c(-c4ccccc4)nn3c2=O)cc1]
TABLE 1-continued
211
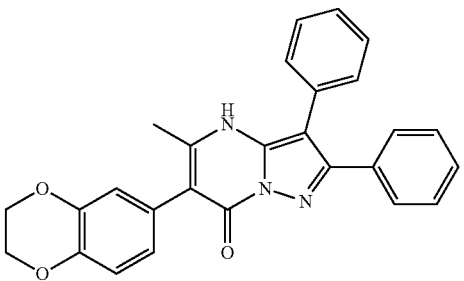 [SMILES: Cc1[nH]c2c(-c3ccccc3)c(-c3ccccc3)nn2c(=O)c1-c1ccc2c(c1)OCCO2]
212
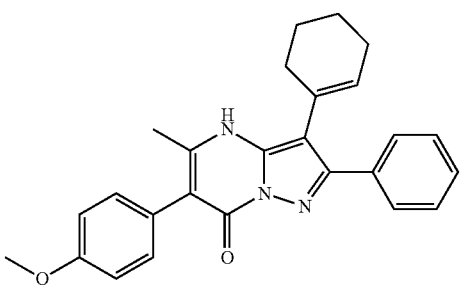 [SMILES: COc1ccc(-c2c(C)[nH]c3c(C4=CCCCC4)c(-c4ccccc4)nn3c2=O)cc1]
213
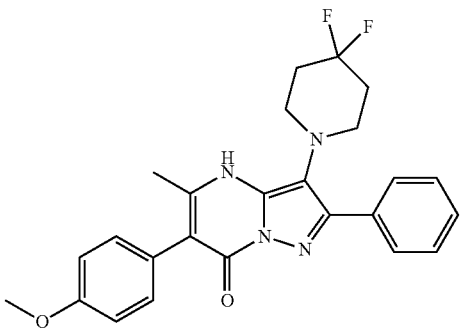 [SMILES: COc1ccc(-c2c(C)[nH]c3c(N4CCC(F)(F)CC4)c(-c4ccccc4)nn3c2=O)cc1]
215
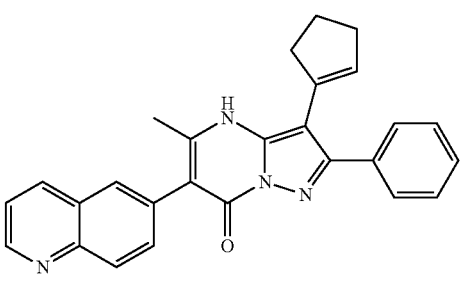 [SMILES: Cc1[nH]c2c(C3=CCCC3)c(-c3ccccc3)nn2c(=O)c1-c1ccc2ncccc2c1]
216
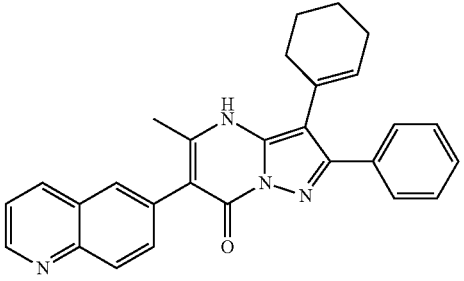 [SMILES: Cc1[nH]c2c(C3=CCCCC3)c(-c3ccccc3)nn2c(=O)c1-c1ccc2ncccc2c1]

TABLE 1-continued
217
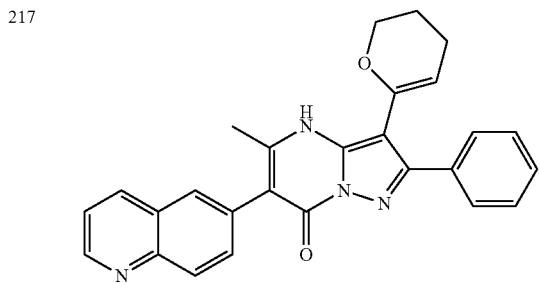
218
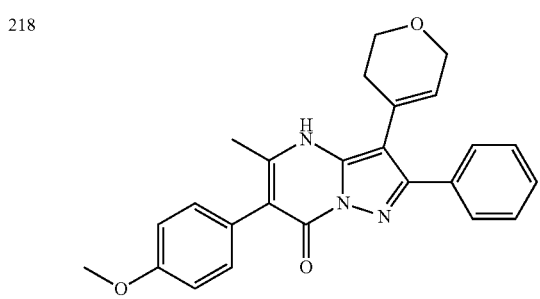
219
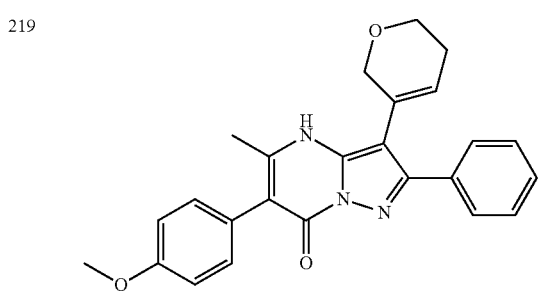
220
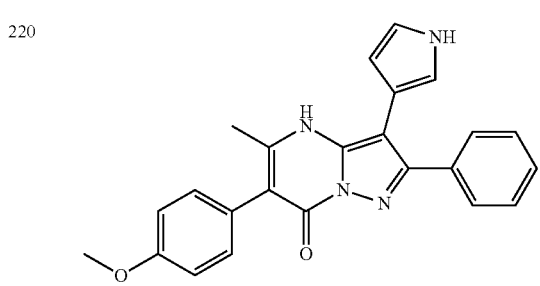
221
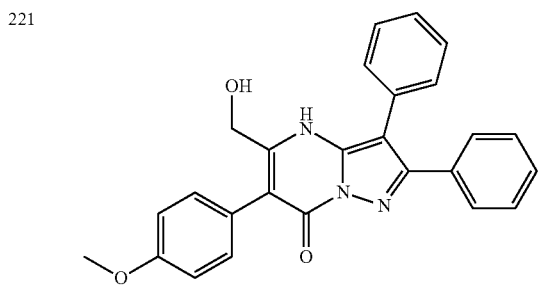
TABLE 1-continued
222
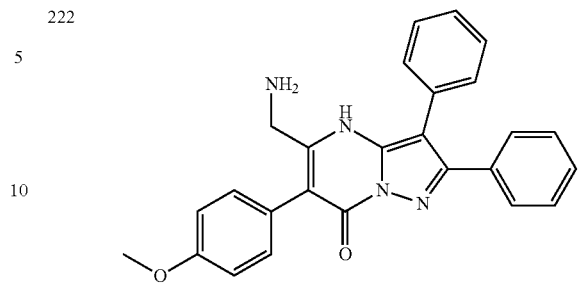
223
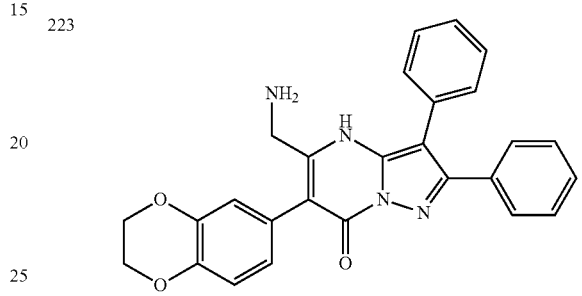
224
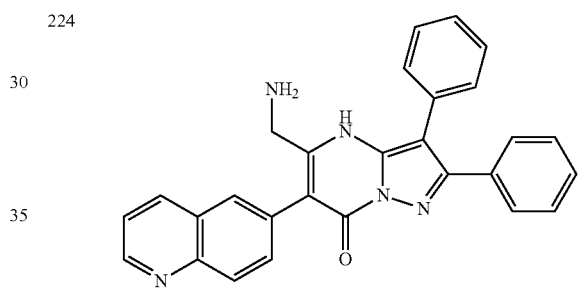
225
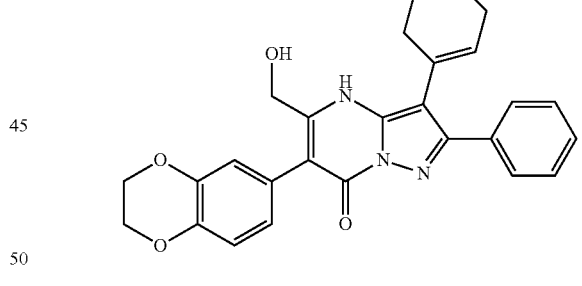
226
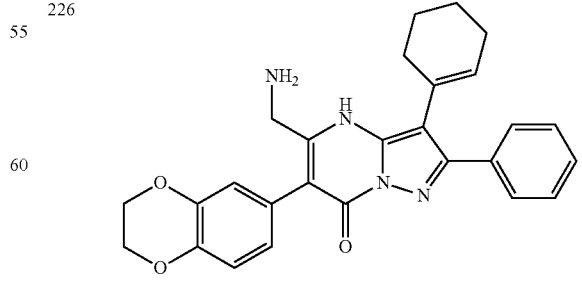

TABLE 1-continued
227 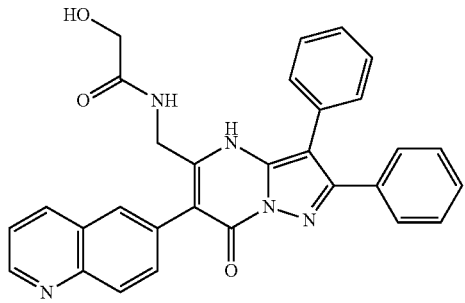 [SMILES: O=C(CO)NCc1[nH]c2c(-c3ccccc3)c(-c3ccccc3)nn2c(=O)c1-c1ccc2ncccc2c1]
228 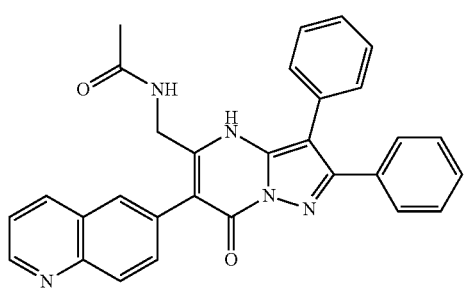 [SMILES: CC(=O)NCc1[nH]c2c(-c3ccccc3)c(-c3ccccc3)nn2c(=O)c1-c1ccc2ncccc2c1]
229 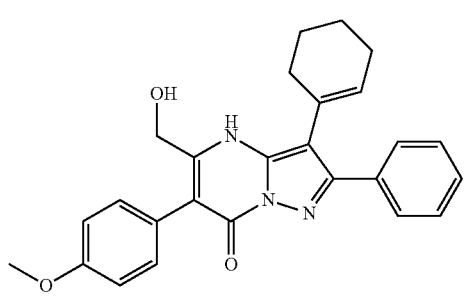
230 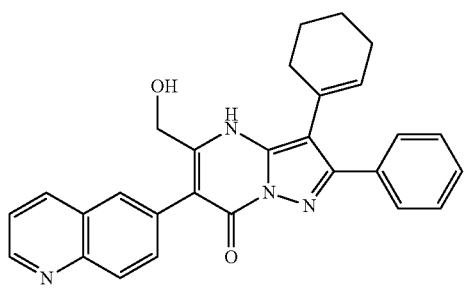
231 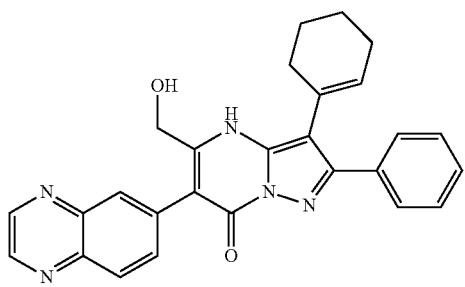 [SMILES: O=c1c(-c2ccc3nccnc3c2)c(CO)[nH]c2c(C3=CCCCC3)c(-c3ccccc3)nn12]
TABLE 1-continued
232 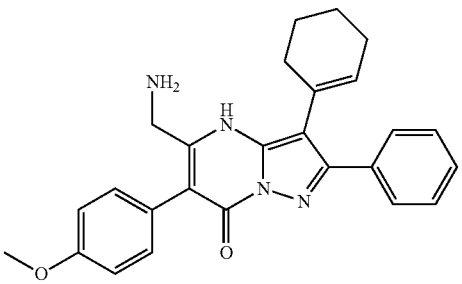
233 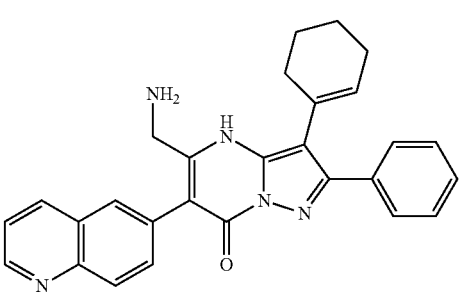 [SMILES: NCc1[nH]c2c(C3=CCCCC3)c(-c3ccccc3)nn2c(=O)c1-c1ccc2ncccc2c1]
234 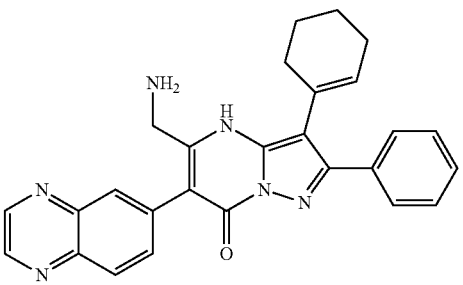 [SMILES: NCc1[nH]c2c(C3=CCCCC3)c(-c3ccccc3)nn2c(=O)c1-c1ccc2nccnc2c1]
235 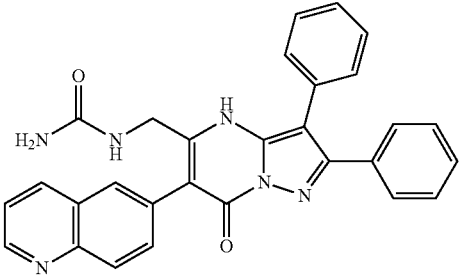 [SMILES: NC(=O)NCc1[nH]c2c(-c3ccccc3)c(-c3ccccc3)nn2c(=O)c1-c1ccc2ncccc2c1]
236 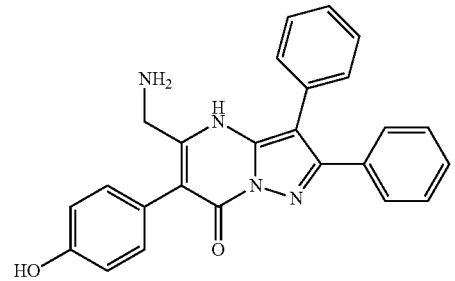 [SMILES: NCc1[nH]c2c(-c3ccccc3)c(-c3ccccc3)nn2c(=O)c1-c1ccc(O)cc1]

TABLE 1-continued
237
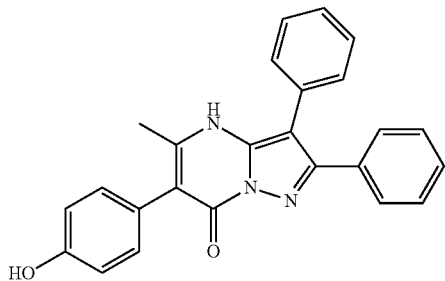 [SMILES: Cc1[nH]c2c(-c3ccccc3)c(-c3ccccc3)nn2c(=O)c1-c1ccc(O)cc1]
238
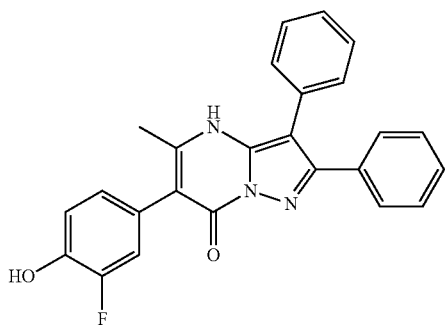 [SMILES: Cc1[nH]c2c(-c3ccccc3)c(-c3ccccc3)nn2c(=O)c1-c1ccc(O)c(F)c1]
239
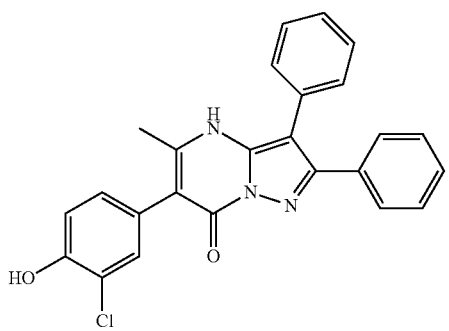 [SMILES: Cc1[nH]c2c(-c3ccccc3)c(-c3ccccc3)nn2c(=O)c1-c1ccc(O)c(Cl)c1]
240
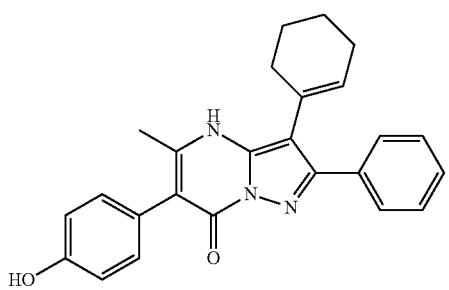 [SMILES: Cc1[nH]c2c(C3=CCCCC3)c(-c3ccccc3)nn2c(=O)c1-c1ccc(O)cc1]
241
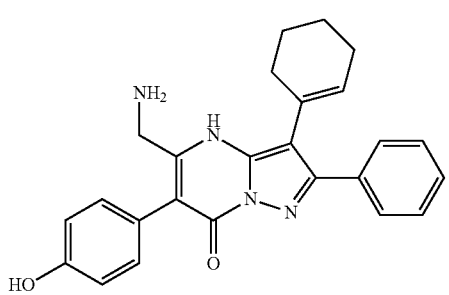 [SMILES: NCc1[nH]c2c(C3=CCCCC3)c(-c3ccccc3)nn2c(=O)c1-c1ccc(O)cc1]
TABLE 1-continued
242
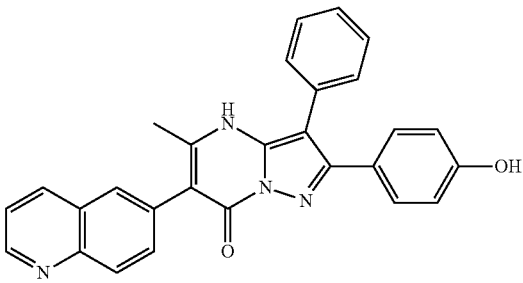 [SMILES: Cc1[nH]c2c(-c3ccccc3)c(-c3ccc(O)cc3)nn2c(=O)c1-c1ccc2ncccc2c1]
243
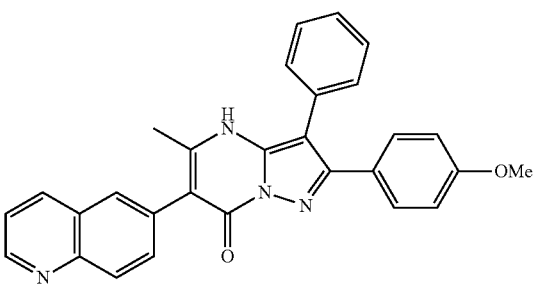 [SMILES: COc1ccc(-c2nn3c(=O)c(-c4ccc5ncccc5c4)c(C)[nH]c3c2-c2ccccc2)cc1]
244
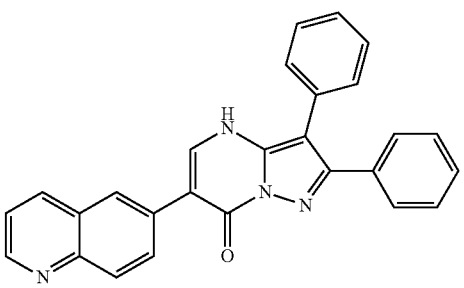 [SMILES: O=c1c(-c2ccc3ncccc3c2)c[nH]c2c(-c3ccccc3)c(-c3ccccc3)nn12]
245
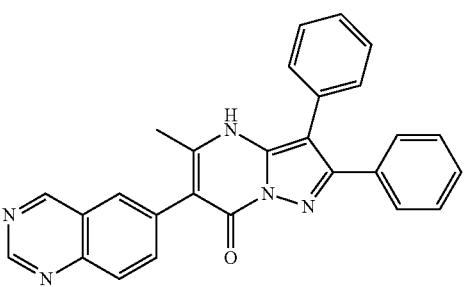 [SMILES: Cc1[nH]c2c(-c3ccccc3)c(-c3ccccc3)nn2c(=O)c1-c1ccc2ncncc2c1]
246
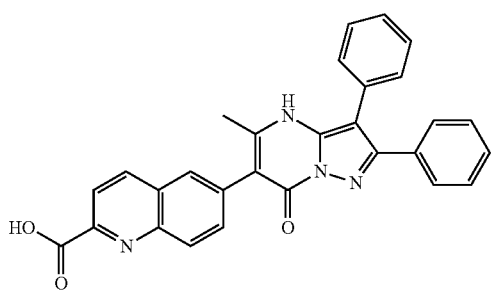 [SMILES: Cc1[nH]c2c(-c3ccccc3)c(-c3ccccc3)nn2c(=O)c1-c1ccc2nc(C(=O)O)ccc2c1]

TABLE 1-continued
247
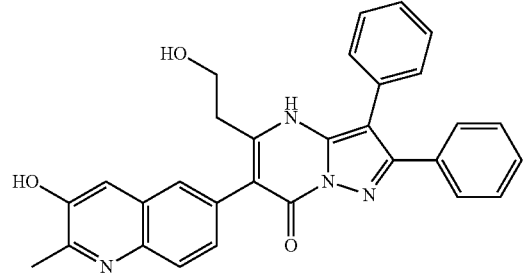 [SMILES: Cc1nc2ccc(-c3c(CCO)[nH]c4c(-c5ccccc5)c(-c5ccccc5)nn4c3=O)cc2cc1O]
248
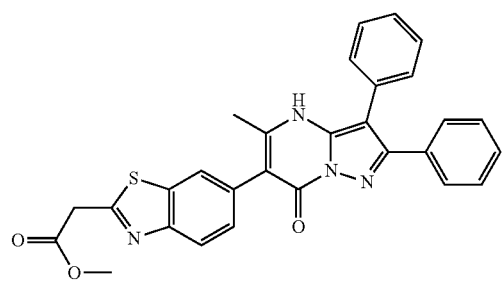 [SMILES: COC(=O)Cc1nc2ccc(-c3c(C)[nH]c4c(-c5ccccc5)c(-c5ccccc5)nn4c3=O)cc2s1]
249
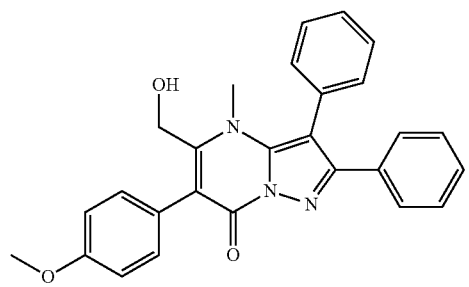 [SMILES: COc1ccc(-c2c(CO)n(C)c3c(-c4ccccc4)c(-c4ccccc4)nn3c2=O)cc1]
250
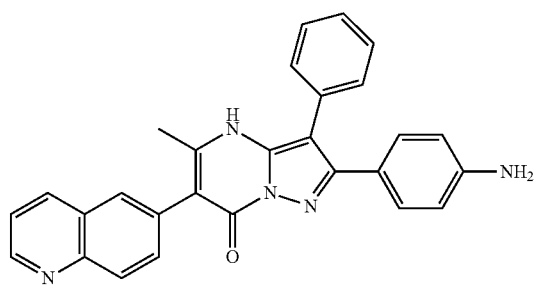
251
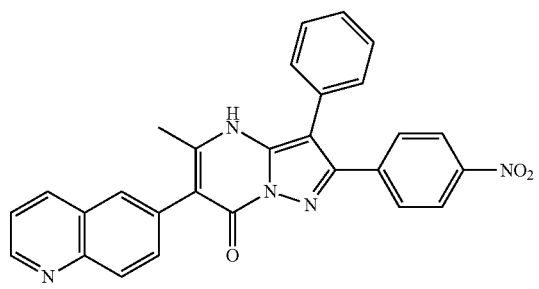
252
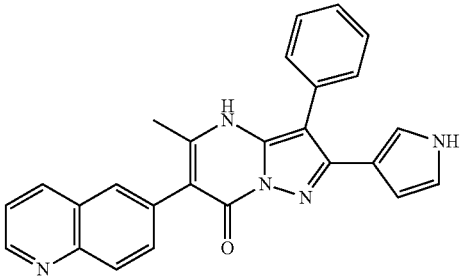 [SMILES: Cc1[nH]c2c(-c3ccccc3)c(-c3cc[nH]c3)nn2c(=O)c1-c1ccc2ncccc2c1]
253
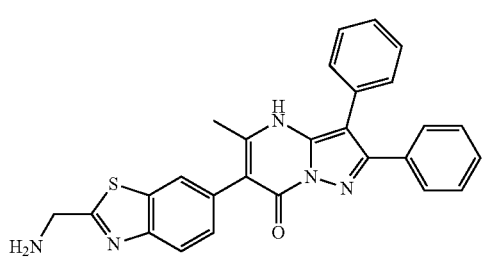 [SMILES: Cc1[nH]c2c(-c3ccccc3)c(-c3ccccc3)nn2c(=O)c1-c1ccc2nc(CN)sc2c1]
254
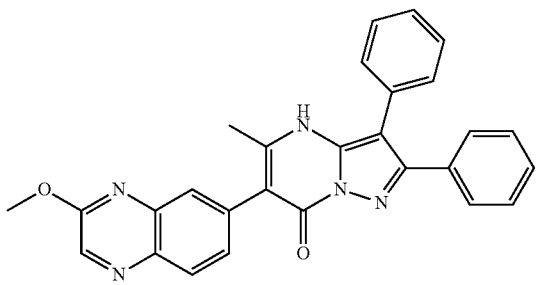 [SMILES: COc1cnc2ccc(-c3c(C)[nH]c4c(-c5ccccc5)c(-c5ccccc5)nn4c3=O)cc2n1]
255
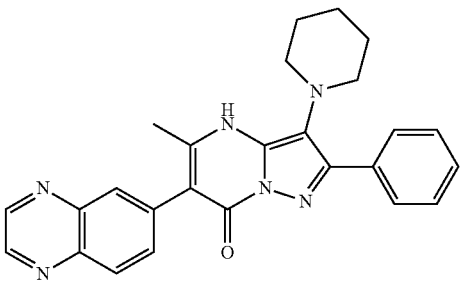 [SMILES: Cc1[nH]c2c(N3CCCCC3)c(-c3ccccc3)nn2c(=O)c1-c1ccc2nccnc2c1]
256
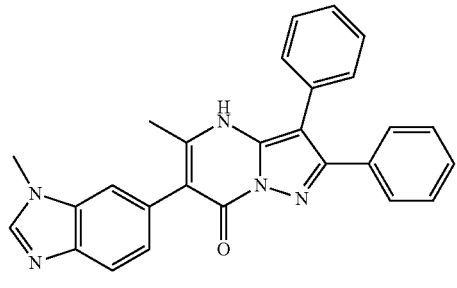 [SMILES: Cc1[nH]c2c(-c3ccccc3)c(-c3ccccc3)nn2c(=O)c1-c1ccc2ncn(C)c2c1]

TABLE 1-continued
257
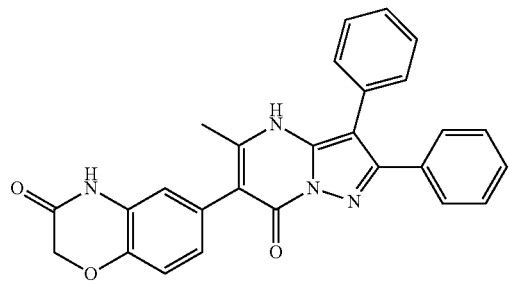 [SMILES: Cc1[nH]c2c(-c3ccccc3)c(-c3ccccc3)nn2c(=O)c1-c1ccc2c(c1)NC(=O)CO2]
258
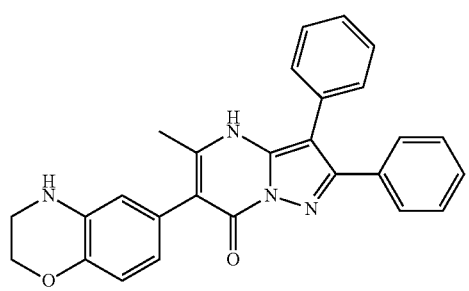 [SMILES: Cc1[nH]c2c(-c3ccccc3)c(-c3ccccc3)nn2c(=O)c1-c1ccc2c(c1)NCCO2]
259
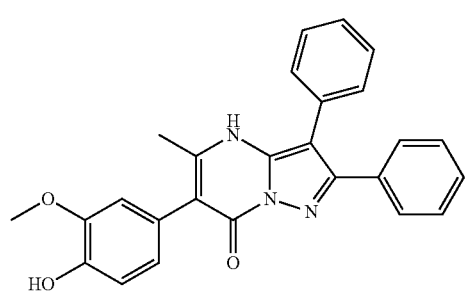 [SMILES: COc1cc(-c2c(C)[nH]c3c(-c4ccccc4)c(-c4ccccc4)nn3c2=O)ccc1O]
260
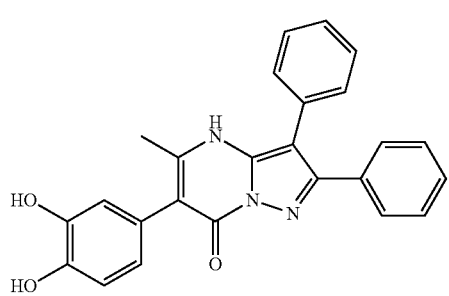 [SMILES: Cc1[nH]c2c(-c3ccccc3)c(-c3ccccc3)nn2c(=O)c1-c1ccc(O)c(O)c1]
261
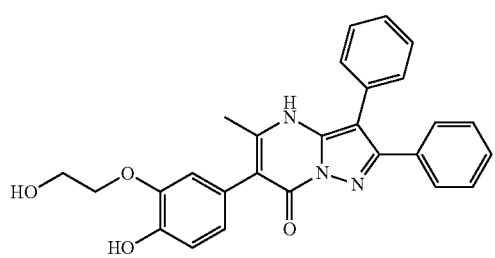 [SMILES: Cc1[nH]c2c(-c3ccccc3)c(-c3ccccc3)nn2c(=O)c1-c1ccc(O)c(OCCO)c1]
TABLE 1-continued
262
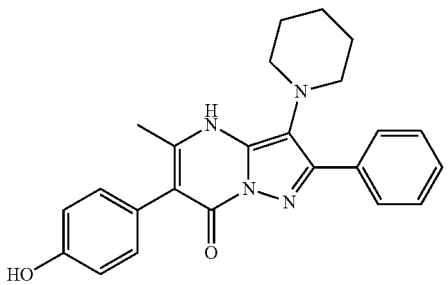 [SMILES: Cc1[nH]c2c(N3CCCCC3)c(-c3ccccc3)nn2c(=O)c1-c1ccc(O)cc1]
263
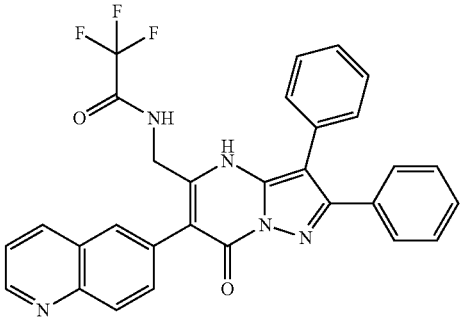 [SMILES: O=C(NCc1[nH]c2c(-c3ccccc3)c(-c3ccccc3)nn2c(=O)c1-c1ccc2ncccc2c1)C(F)(F)F]
264
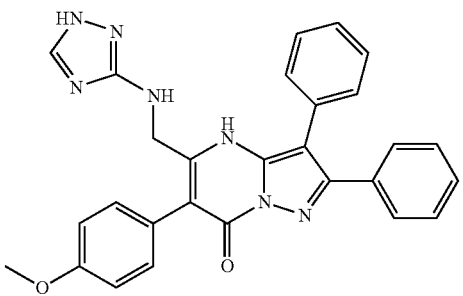 [SMILES: COc1ccc(-c2c(CNc3nc[nH]n3)[nH]c3c(-c4ccccc4)c(-c4ccccc4)nn3c2=O)cc1]
265
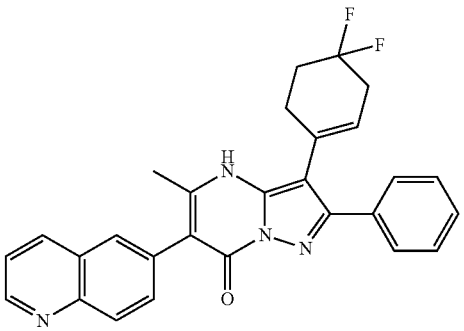 [SMILES: Cc1[nH]c2c(C3=CCC(F)(F)CC3)c(-c3ccccc3)nn2c(=O)c1-c1ccc2ncccc2c1]
266
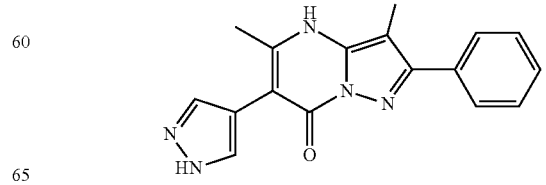

TABLE 1-continued
267 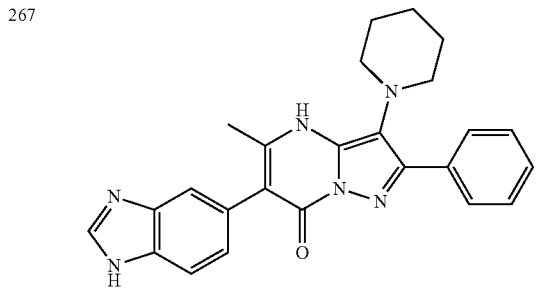
268 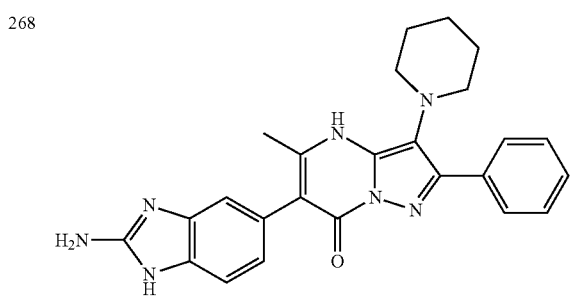
269 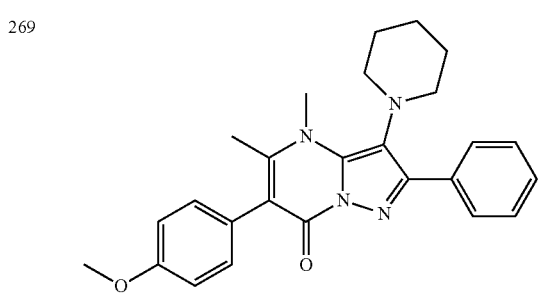
271 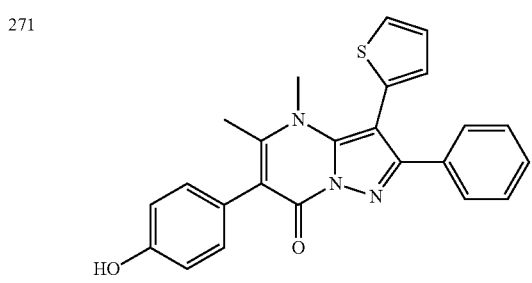
272 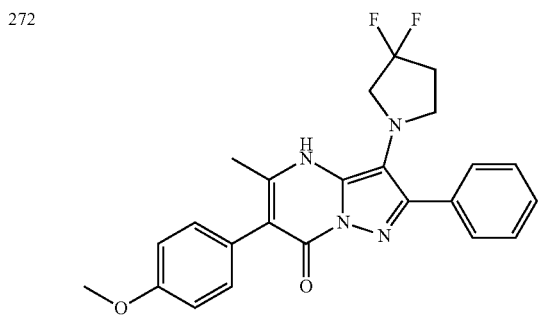
TABLE 1-continued
273 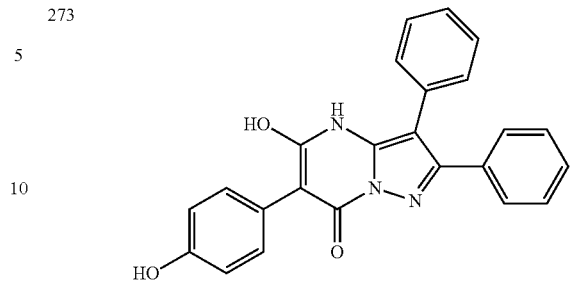
274 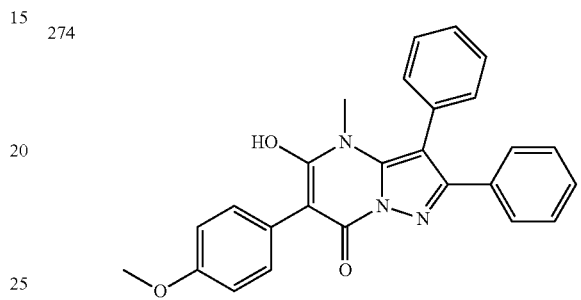
275 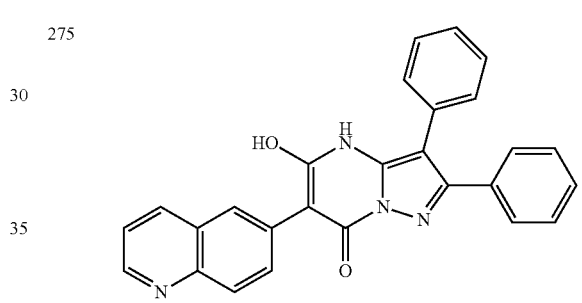
276 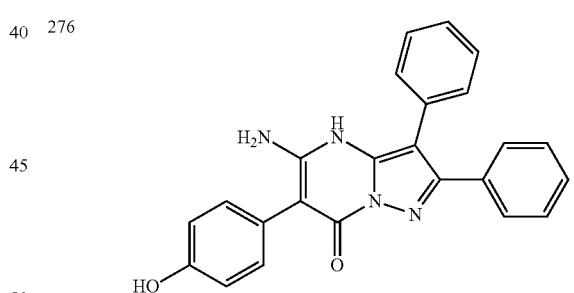
277 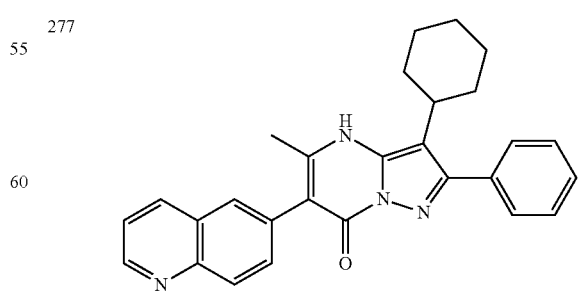

TABLE 1-continued
278 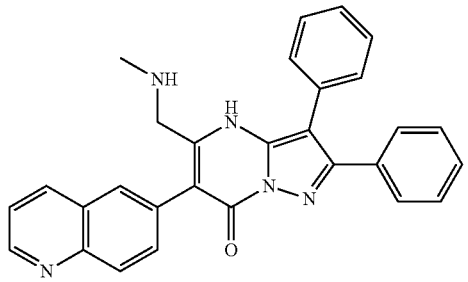 [SMILES: CNCc1[nH]c2c(-c3ccccc3)c(-c3ccccc3)nn2c(=O)c1-c1ccc2ncccc2c1]
279 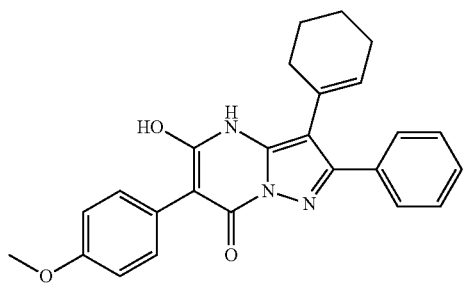 [SMILES: COc1ccc(-c2c(O)[nH]c3c(C4=CCCCC4)c(-c4ccccc4)nn3c2=O)cc1]
280 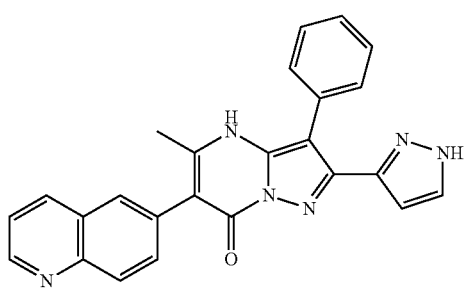 [SMILES: Cc1[nH]c2c(-c3ccccc3)c(-c3cc[nH]n3)nn2c(=O)c1-c1ccc2ncccc2c1]
281 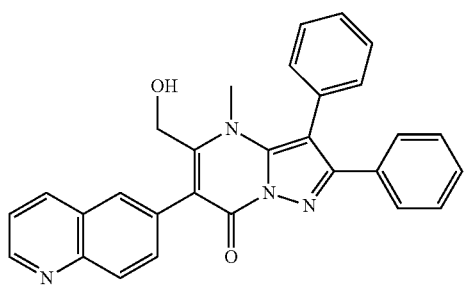 [SMILES: Cn1c(CO)c(-c2ccc3ncccc3c2)c(=O)n2nc(-c3ccccc3)c(-c3ccccc3)c12]
282 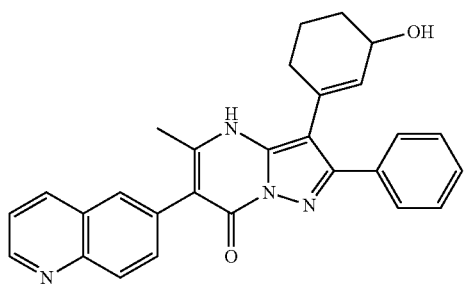 [SMILES: Cc1[nH]c2c(C3=CC(O)CCC3)c(-c3ccccc3)nn2c(=O)c1-c1ccc2ncccc2c1]
TABLE 1-continued
283 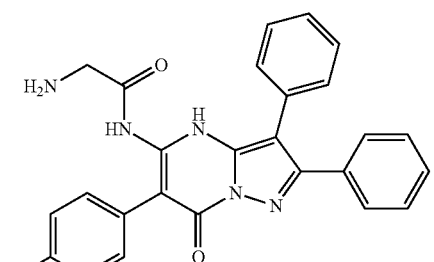
285 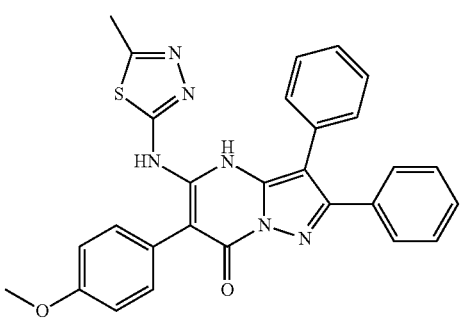 [SMILES: COc1ccc(-c2c(Nc3nnc(C)s3)[nH]c3c(-c4ccccc4)c(-c4ccccc4)nn3c2=O)cc1]
286 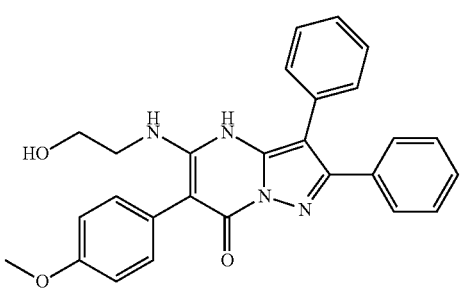 [SMILES: COc1ccc(-c2c(NCCO)[nH]c3c(-c4ccccc4)c(-c4ccccc4)nn3c2=O)cc1]
287 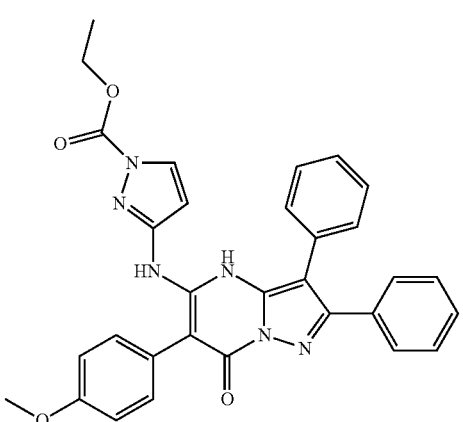
288 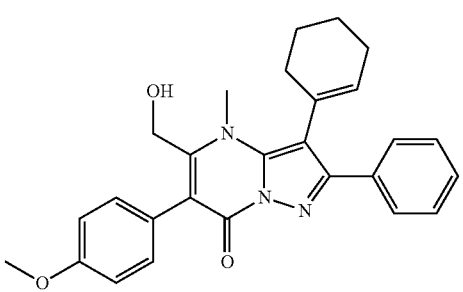 [SMILES: COc1ccc(-c2c(CO)n(C)c3c(C4=CCCCC4)c(-c4ccccc4)nn3c2=O)cc1]

TABLE 1-continued
290
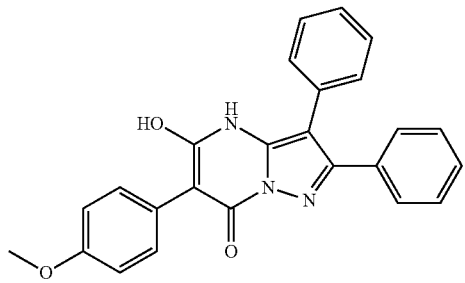 [SMILES: COc1ccc(-c2c(O)[nH]c3c(-c4ccccc4)c(-c4ccccc4)nn3c2=O)cc1]
292
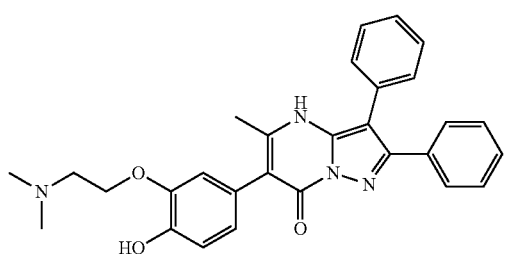 [SMILES: Cc1[nH]c2c(-c3ccccc3)c(-c3ccccc3)nn2c(=O)c1-c1ccc(O)c(OCCN(C)C)c1]
294
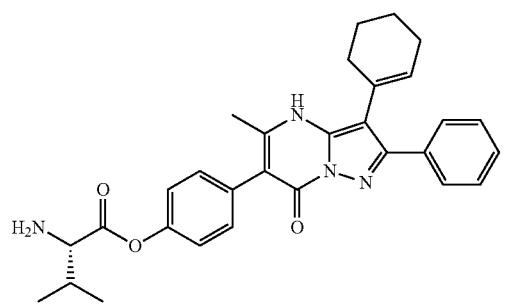 [SMILES: Cc1[nH]c2c(C3=CCCCC3)c(-c3ccccc3)nn2c(=O)c1-c1ccc(OC(=O)[C@@H](N)C(C)C)cc1]
295
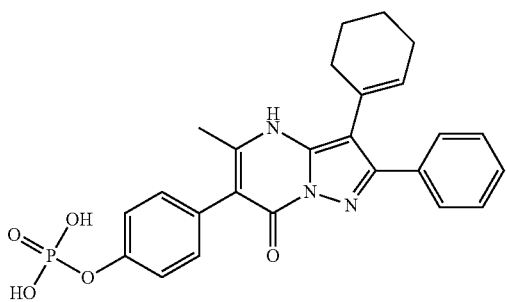 [SMILES: Cc1[nH]c2c(C3=CCCCC3)c(-c3ccccc3)nn2c(=O)c1-c1ccc(OP(=O)(O)O)cc1]
296
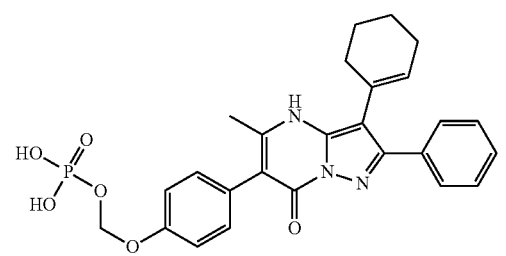 [SMILES: Cc1[nH]c2c(C3=CCCCC3)c(-c3ccccc3)nn2c(=O)c1-c1ccc(OCOP(=O)(O)O)cc1]
TABLE 1-continued
297
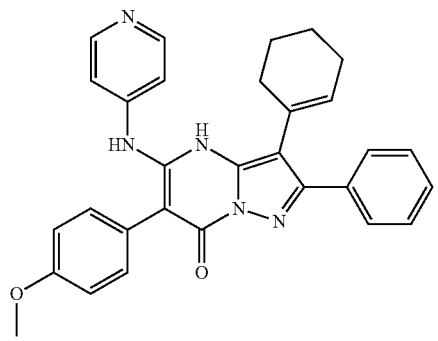 [SMILES: COc1ccc(-c2c(Nc3ccncc3)[nH]c3c(C4=CCCCC4)c(-c4ccccc4)nn3c2=O)cc1]
298
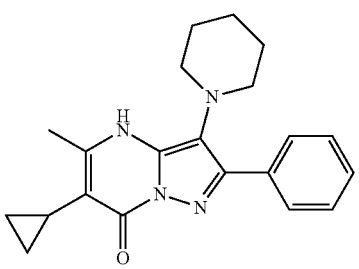 [SMILES: Cc1[nH]c2c(N3CCCCC3)c(-c3ccccc3)nn2c(=O)c1C1CC1]
299
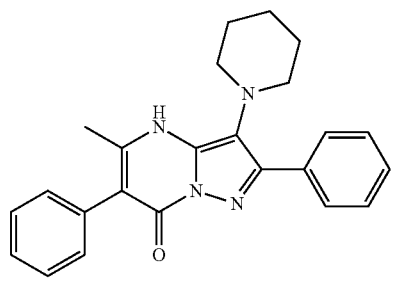 [SMILES: Cc1[nH]c2c(N3CCCCC3)c(-c3ccccc3)nn2c(=O)c1-c1ccccc1]
300
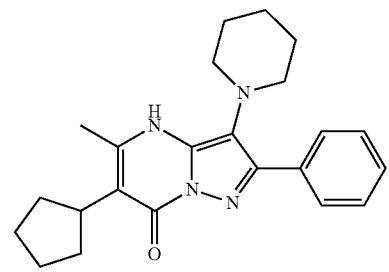 [SMILES: Cc1[nH]c2c(N3CCCCC3)c(-c3ccccc3)nn2c(=O)c1C1CCCC1]
301
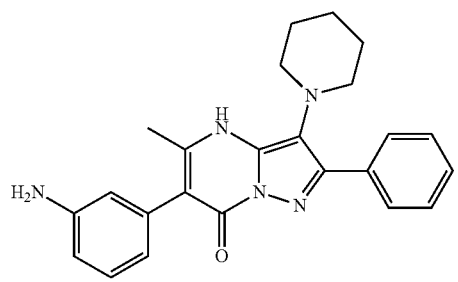 [SMILES: Cc1[nH]c2c(N3CCCCC3)c(-c3ccccc3)nn2c(=O)c1-c1cccc(N)c1]

TABLE 1-continued
302 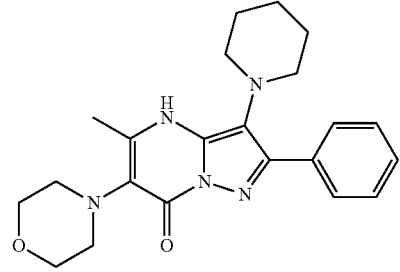 [SMILES: Cc1[nH]c2c(N3CCCCC3)c(-c3ccccc3)nn2c(=O)c1N1CCOCC1]
303 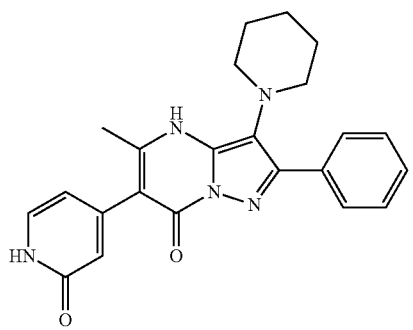 [SMILES: Cc1[nH]c2c(N3CCCCC3)c(-c3ccccc3)nn2c(=O)c1-c1cc[nH]c(=O)c1]
304 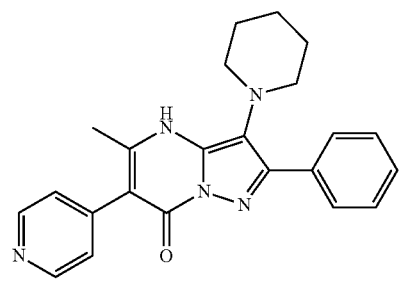 [SMILES: Cc1[nH]c2c(N3CCCCC3)c(-c3ccccc3)nn2c(=O)c1-c1ccncc1]
305 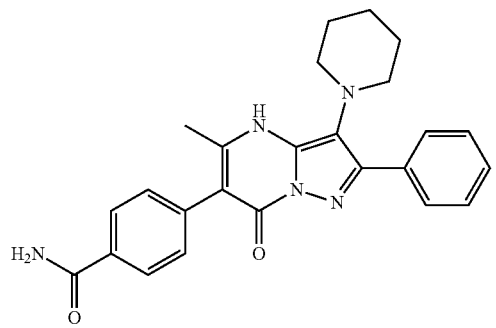 [SMILES: Cc1[nH]c2c(N3CCCCC3)c(-c3ccccc3)nn2c(=O)c1-c1ccc(C(N)=O)cc1]
306 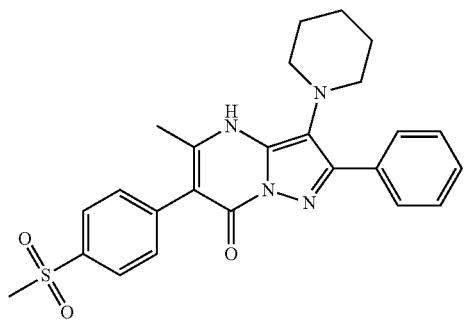 [SMILES: Cc1[nH]c2c(N3CCCCC3)c(-c3ccccc3)nn2c(=O)c1-c1ccc(S(C)(=O)=O)cc1]
TABLE 1-continued
307 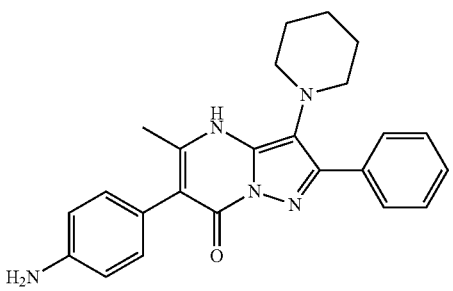 [SMILES: Cc1[nH]c2c(N3CCCCC3)c(-c3ccccc3)nn2c(=O)c1-c1ccc(N)cc1]
308 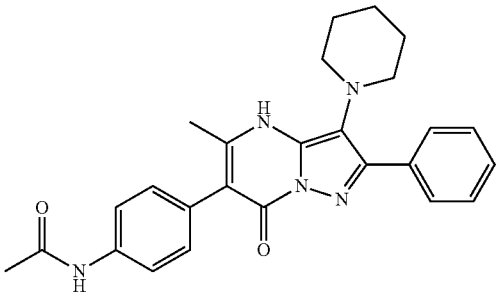 [SMILES: CC(=O)Nc1ccc(-c2c(C)[nH]c3c(N4CCCCC4)c(-c4ccccc4)nn3c2=O)cc1]
309 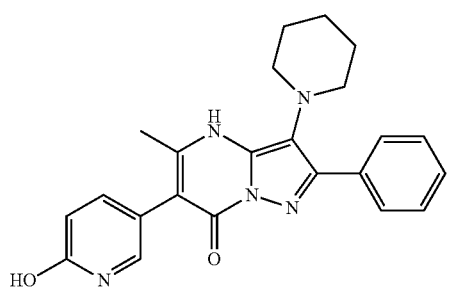
310 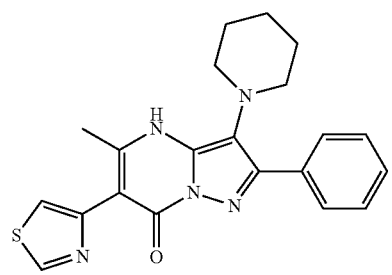 [SMILES: Cc1[nH]c2c(N3CCCCC3)c(-c3ccccc3)nn2c(=O)c1-c1cscn1]
311 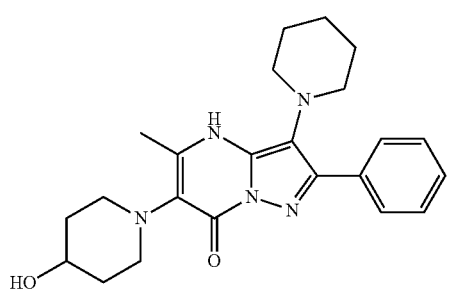 [SMILES: Cc1[nH]c2c(N3CCCCC3)c(-c3ccccc3)nn2c(=O)c1N1CCC(O)CC1]

TABLE 1-continued
312 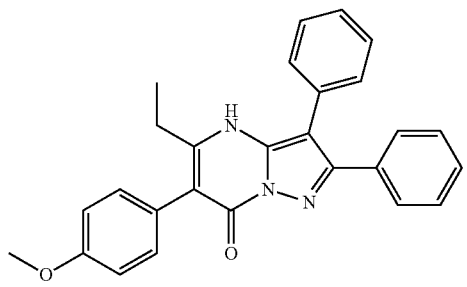 [SMILES: CCc1[nH]c2c(-c3ccccc3)c(-c3ccccc3)nn2c(=O)c1-c1ccc(OC)cc1]
313 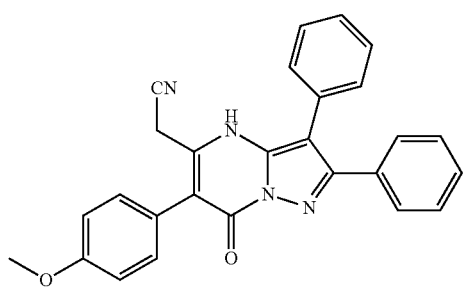
314 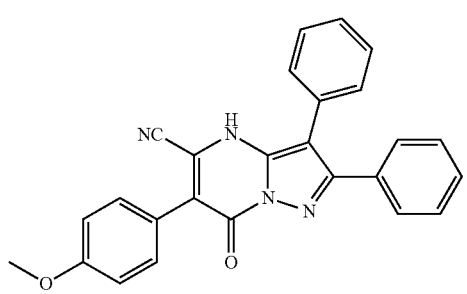
315 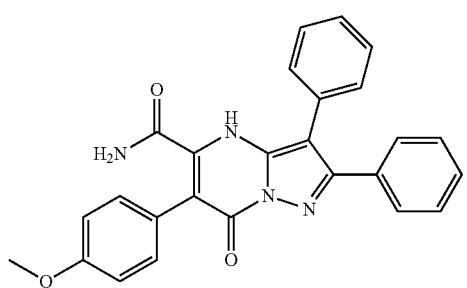 [SMILES: COc1ccc(-c2c(C(N)=O)[nH]c3c(-c4ccccc4)c(-c4ccccc4)nn3c2=O)cc1]
316 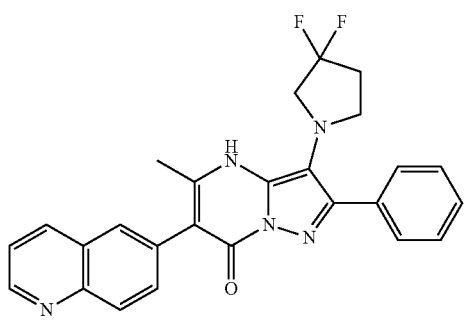 [SMILES: Cc1[nH]c2c(N3CCC(F)(F)C3)c(-c3ccccc3)nn2c(=O)c1-c1ccc2ncccc2c1]
TABLE 1-continued
317 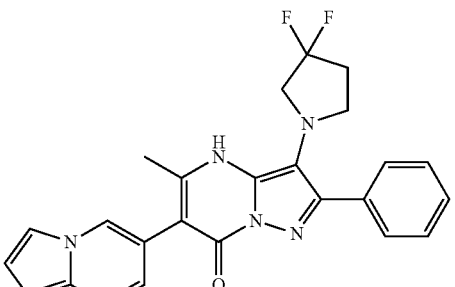
318 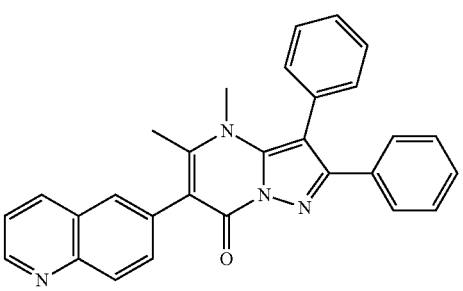 [SMILES: Cc1c(-c2ccc3ncccc3c2)c(=O)n2nc(-c3ccccc3)c(-c3ccccc3)c2n1C]
319 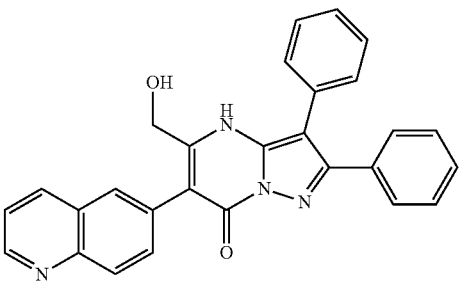
320 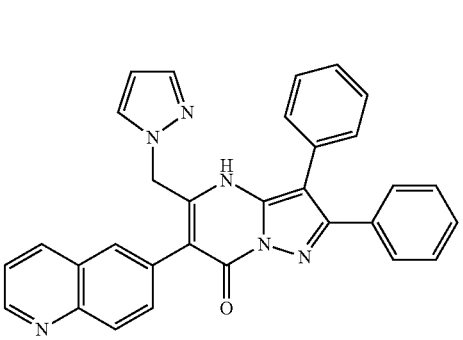 [SMILES: O=c1c(-c2ccc3ncccc3c2)c(Cn2cccn2)[nH]c2c(-c3ccccc3)c(-c3ccccc3)nn12]
321

TABLE 1-continued
322 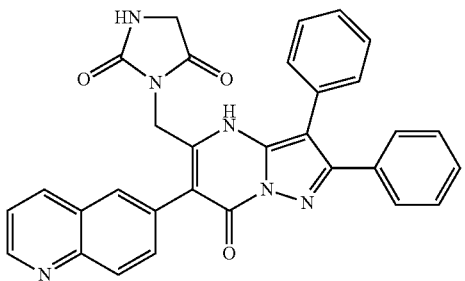 [SMILES: O=C1CNC(=O)N1Cc1[nH]c2c(-c3ccccc3)c(-c3ccccc3)nn2c(=O)c1-c1ccc2ncccc2c1]
323 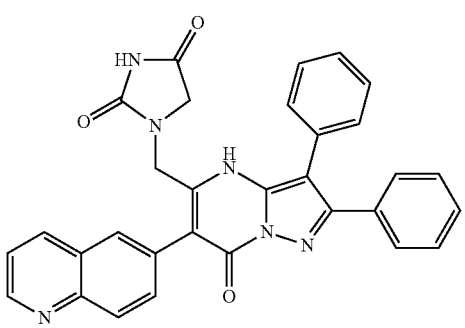 [SMILES: O=C1CN(Cc2[nH]c3c(-c4ccccc4)c(-c4ccccc4)nn3c(=O)c2-c2ccc3ncccc3c2)C(=O)N1]
324 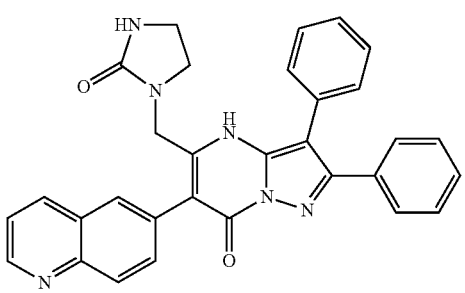 [SMILES: O=C1NCCN1Cc1[nH]c2c(-c3ccccc3)c(-c3ccccc3)nn2c(=O)c1-c1ccc2ncccc2c1]
325 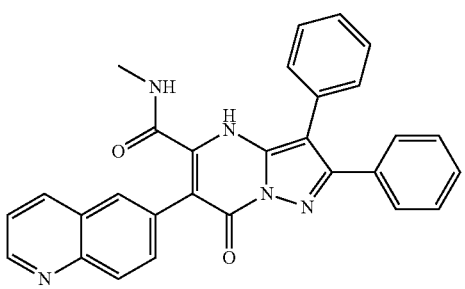 [SMILES: CNC(=O)c1[nH]c2c(-c3ccccc3)c(-c3ccccc3)nn2c(=O)c1-c1ccc2ncccc2c1]
326 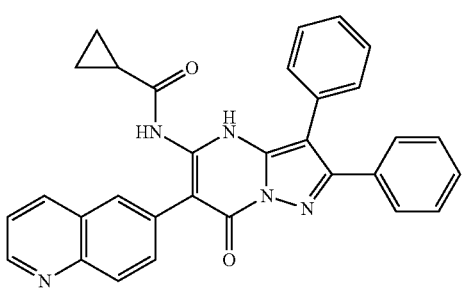 [SMILES: O=C(Nc1[nH]c2c(-c3ccccc3)c(-c3ccccc3)nn2c(=O)c1-c1ccc2ncccc2c1)C1CC1]
TABLE 1-continued
327 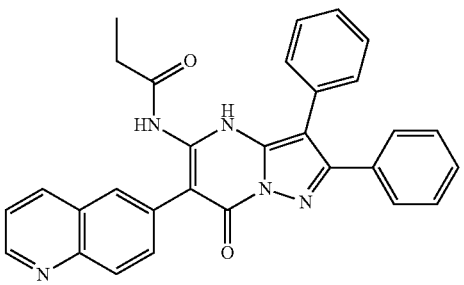 [SMILES: CCC(=O)Nc1[nH]c2c(-c3ccccc3)c(-c3ccccc3)nn2c(=O)c1-c1ccc2ncccc2c1]
328 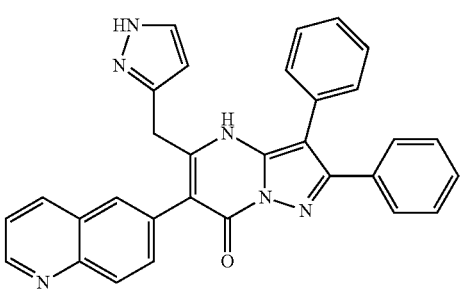 [SMILES: O=c1c(-c2ccc3ncccc3c2)c(Cc2cc[nH]n2)[nH]c2c(-c3ccccc3)c(-c3ccccc3)nn12]
329 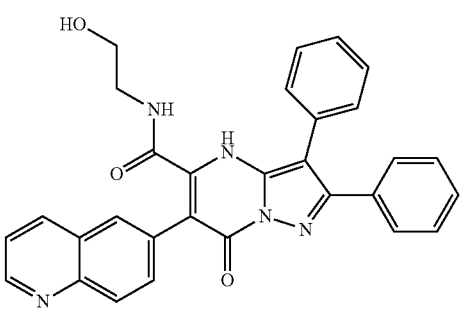 [SMILES: O=C(NCCO)c1[nH]c2c(-c3ccccc3)c(-c3ccccc3)nn2c(=O)c1-c1ccc2ncccc2c1]
330 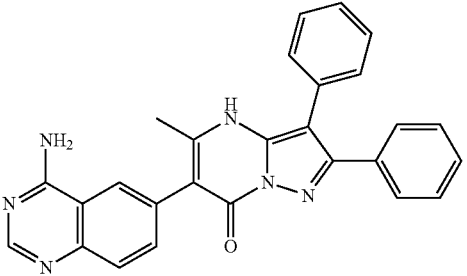 [SMILES: Cc1[nH]c2c(-c3ccccc3)c(-c3ccccc3)nn2c(=O)c1-c1ccc2ncnc(N)c2c1]
331 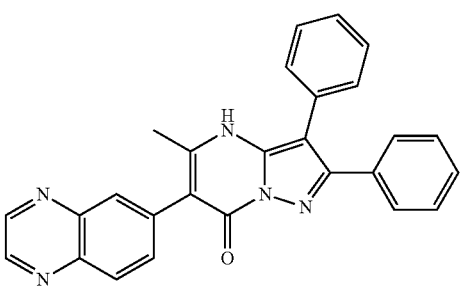

TABLE 1-continued
332 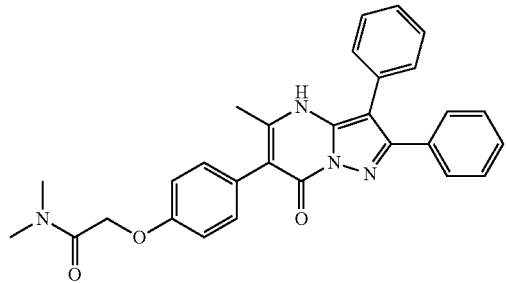 [SMILES: Cc1[nH]c2c(-c3ccccc3)c(-c3ccccc3)nn2c(=O)c1-c1ccc(OCC(=O)N(C)C)cc1]
333 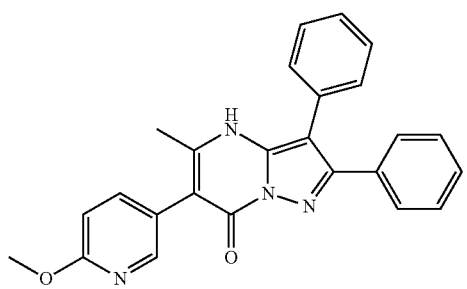 [SMILES: COc1ccc(-c2c(C)[nH]c3c(-c4ccccc4)c(-c4ccccc4)nn3c2=O)cn1]
334 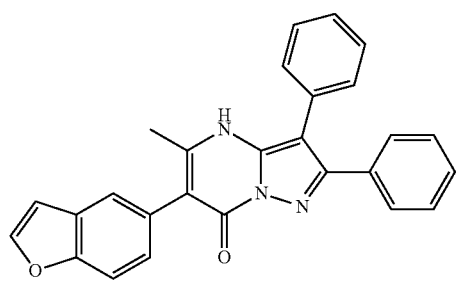 [SMILES: Cc1[nH]c2c(-c3ccccc3)c(-c3ccccc3)nn2c(=O)c1-c1ccc2occc2c1]
335 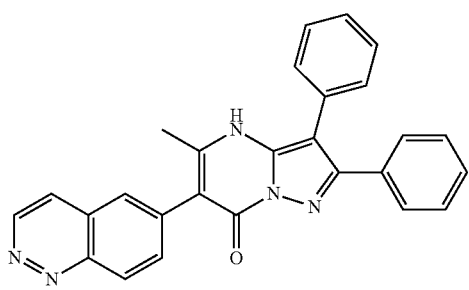 [SMILES: Cc1[nH]c2c(-c3ccccc3)c(-c3ccccc3)nn2c(=O)c1-c1ccc2nnccc2c1]
336 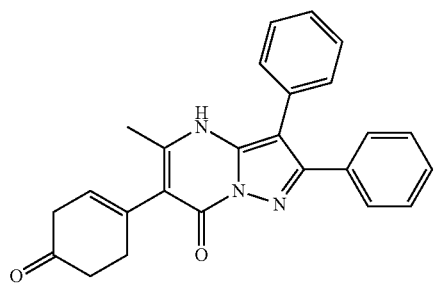 [SMILES: Cc1[nH]c2c(-c3ccccc3)c(-c3ccccc3)nn2c(=O)c1C1=CCC(=O)CC1]
TABLE 1-continued
337 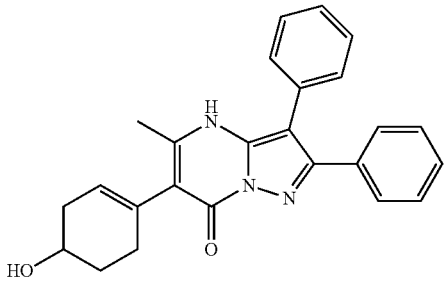 [SMILES: Cc1[nH]c2c(-c3ccccc3)c(-c3ccccc3)nn2c(=O)c1C1=CCC(O)CC1]
338 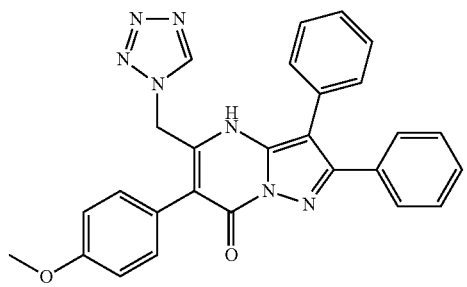 [SMILES: COc1ccc(-c2c(Cn3cnnn3)[nH]c3c(-c4ccccc4)c(-c4ccccc4)nn3c2=O)cc1]
339 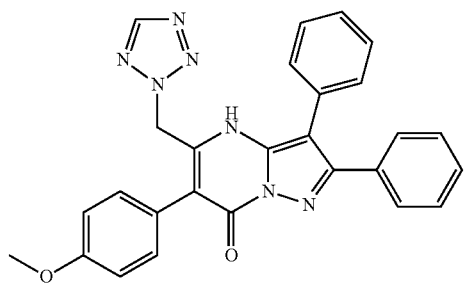 [SMILES: COc1ccc(-c2c(Cn3ncnn3)[nH]c3c(-c4ccccc4)c(-c4ccccc4)nn3c2=O)cc1]
340 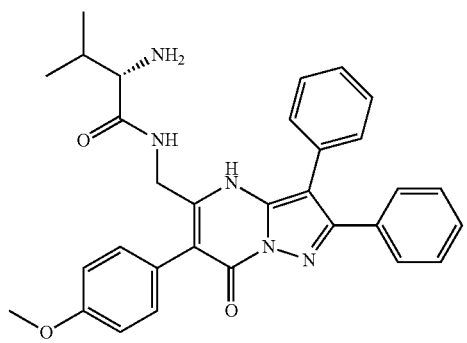 [SMILES: COc1ccc(-c2c(CNC(=O)[C@@H](N)C(C)C)[nH]c3c(-c4ccccc4)c(-c4ccccc4)nn3c2=O)cc1]
346 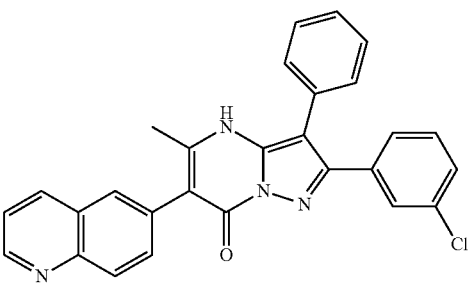 [SMILES: Cc1[nH]c2c(-c3ccccc3)c(-c3cccc(Cl)c3)nn2c(=O)c1-c1ccc2ncccc2c1]

TABLE 1-continued
| | |
|---|---|
| 347 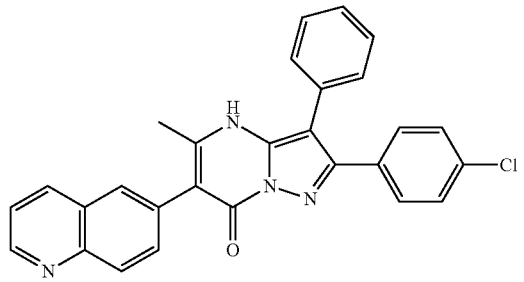 [SMILES: Cc1[nH]c2c(-c3ccccc3)c(-c3ccc(Cl)cc3)nn2c(=O)c1-c1ccc2ncccc2c1] | 352 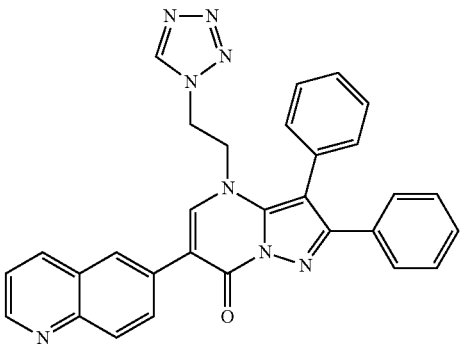 |
| 348 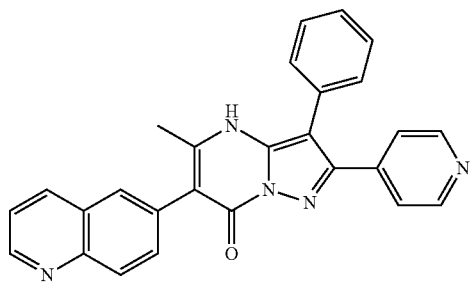 [SMILES: Cc1[nH]c2c(-c3ccccc3)c(-c3ccncc3)nn2c(=O)c1-c1ccc2ncccc2c1] | 353 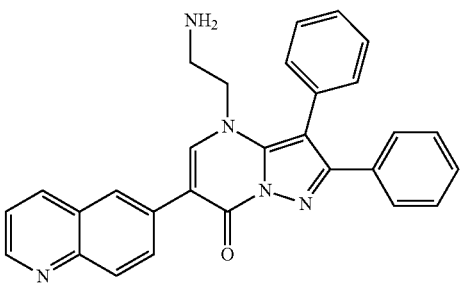 |
| 349 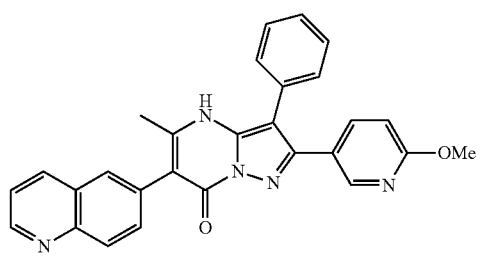 [SMILES: COc1ccc(-c2nn3c(=O)c(-c4ccc5ncccc5c4)c(C)[nH]c3c2-c2ccccc2)cn1] | 354 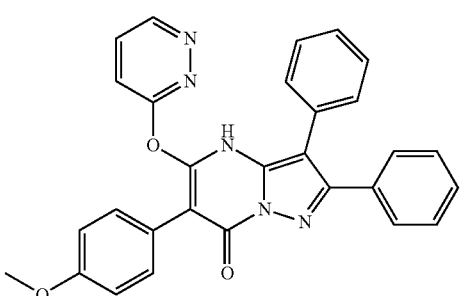 |
| 350 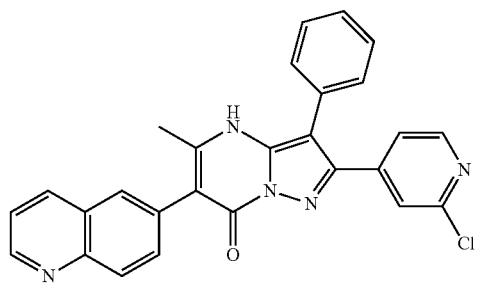 [SMILES: Cc1[nH]c2c(-c3ccccc3)c(-c3ccnc(Cl)c3)nn2c(=O)c1-c1ccc2ncccc2c1] | 355 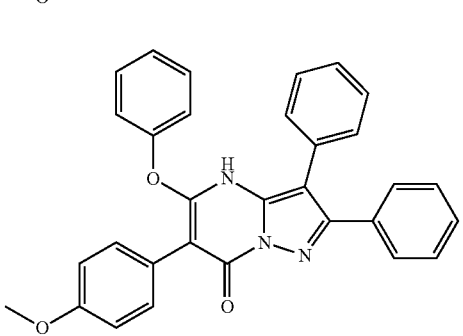 |
| 351 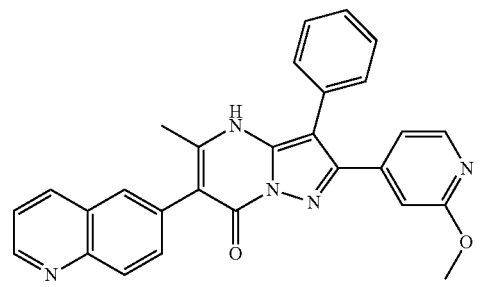 [SMILES: COc1cc(-c2nn3c(=O)c(-c4ccc5ncccc5c4)c(C)[nH]c3c2-c2ccccc2)ccn1] | 356 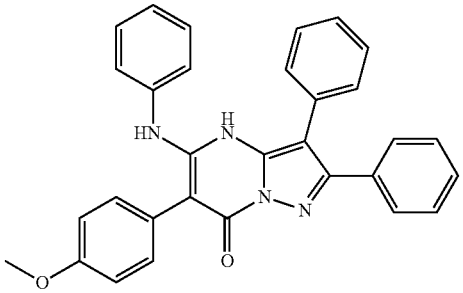 |

TABLE 1-continued
358 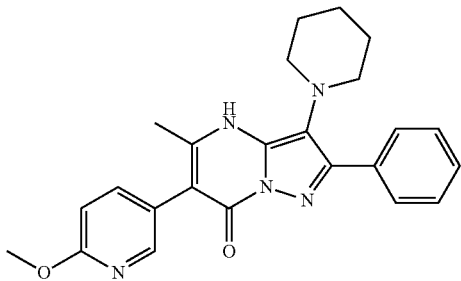 [SMILES: COc1ccc(-c2c(C)[nH]c3c(N4CCCCC4)c(-c4ccccc4)nn3c2=O)cn1]
Specific compounds conforming to formula IB, or pharmaceutically acceptable salts thereof, include those of Table 2:
TABLE 2
101 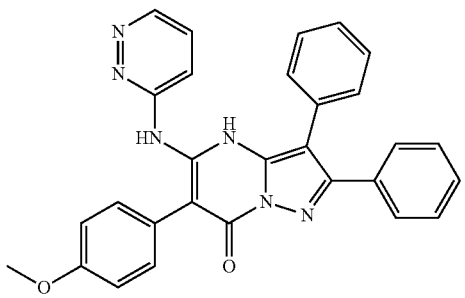 [SMILES: COc1ccc(-c2c(Nc3cccnn3)[nH]c3c(-c4ccccc4)c(-c4ccccc4)nn3c2=O)cc1]
102 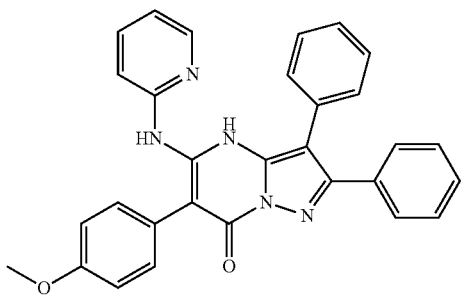 [SMILES: COc1ccc(-c2c(Nc3ccccn3)[nH]c3c(-c4ccccc4)c(-c4ccccc4)nn3c2=O)cc1]
103 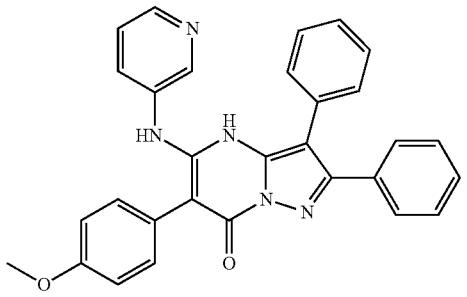 [SMILES: COc1ccc(-c2c(Nc3cccnc3)[nH]c3c(-c4ccccc4)c(-c4ccccc4)nn3c2=O)cc1]
TABLE 2-continued
104 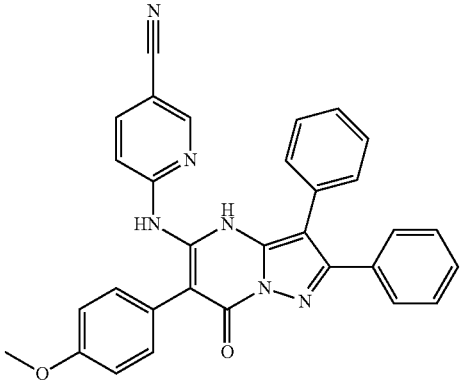 [SMILES: COc1ccc(-c2c(Nc3ccc(C#N)cn3)[nH]c3c(-c4ccccc4)c(-c4ccccc4)nn3c2=O)cc1]
105 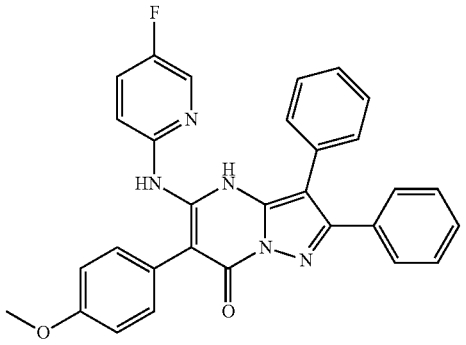
106 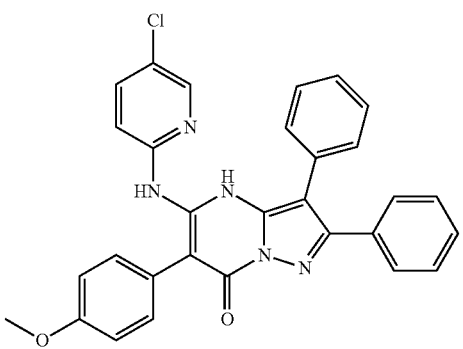
107 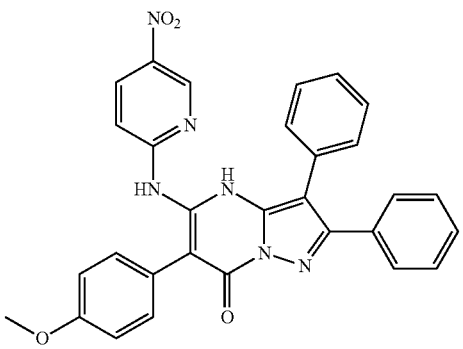

TABLE 2-continued
108 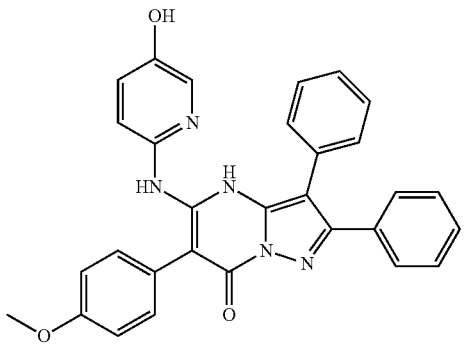 [SMILES: COc1ccc(-c2c(Nc3ccc(O)cn3)[nH]c3c(-c4ccccc4)c(-c4ccccc4)nn3c2=O)cc1]
109 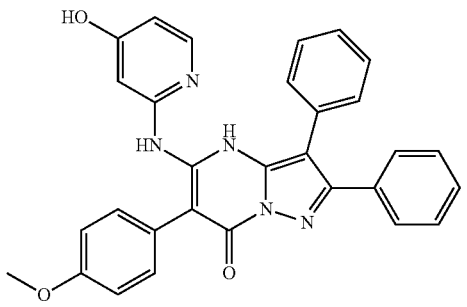 [SMILES: COc1ccc(-c2c(Nc3cc(O)ccn3)[nH]c3c(-c4ccccc4)c(-c4ccccc4)nn3c2=O)cc1]
110 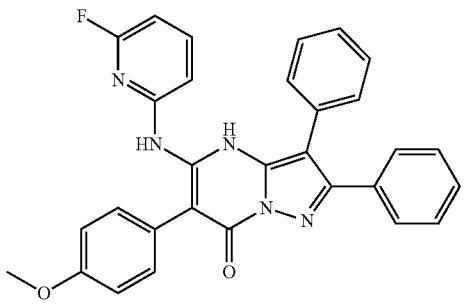 [SMILES: COc1ccc(-c2c(Nc3cccc(F)n3)[nH]c3c(-c4ccccc4)c(-c4ccccc4)nn3c2=O)cc1]
111 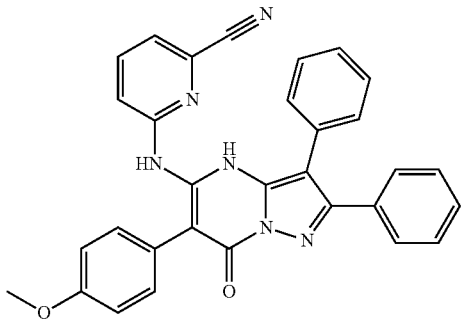 [SMILES: COc1ccc(-c2c(Nc3cccc(C#N)n3)[nH]c3c(-c4ccccc4)c(-c4ccccc4)nn3c2=O)cc1]
112 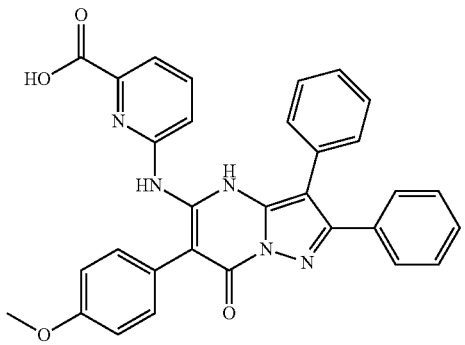 [SMILES: COc1ccc(-c2c(Nc3cccc(C(=O)O)n3)[nH]c3c(-c4ccccc4)c(-c4ccccc4)nn3c2=O)cc1]
113 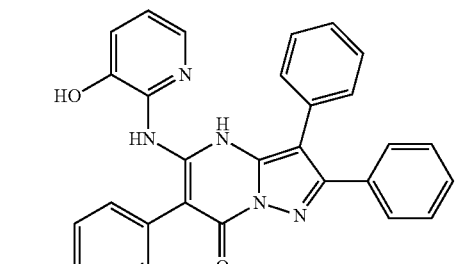
114 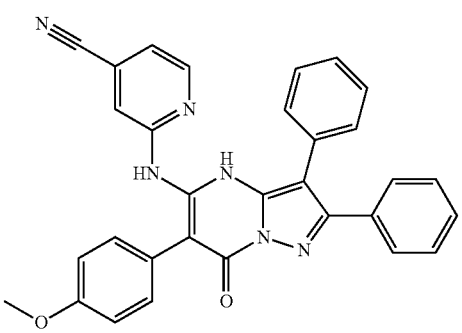 [SMILES: COc1ccc(-c2c(Nc3cc(C#N)ccn3)[nH]c3c(-c4ccccc4)c(-c4ccccc4)nn3c2=O)cc1]
115 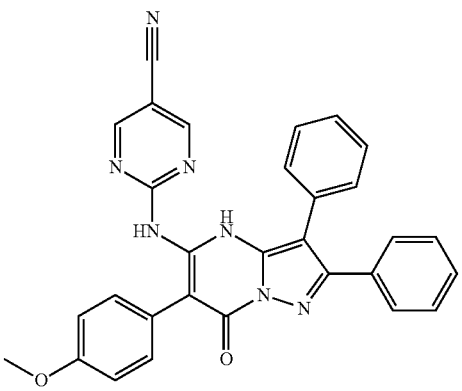
116 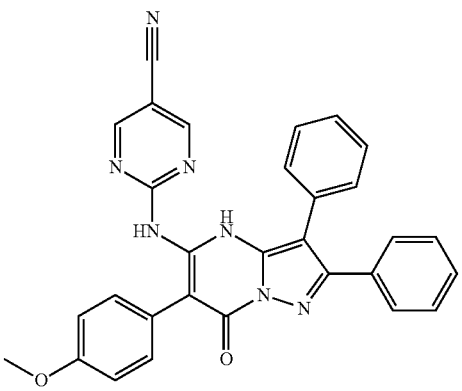
117 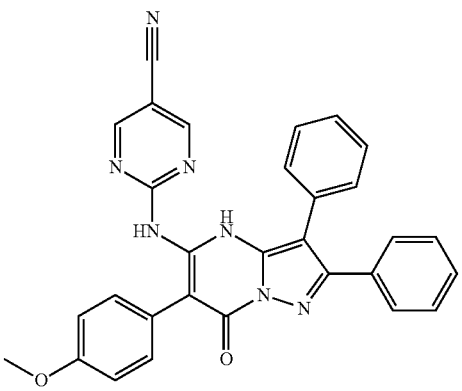

TABLE 2-continued
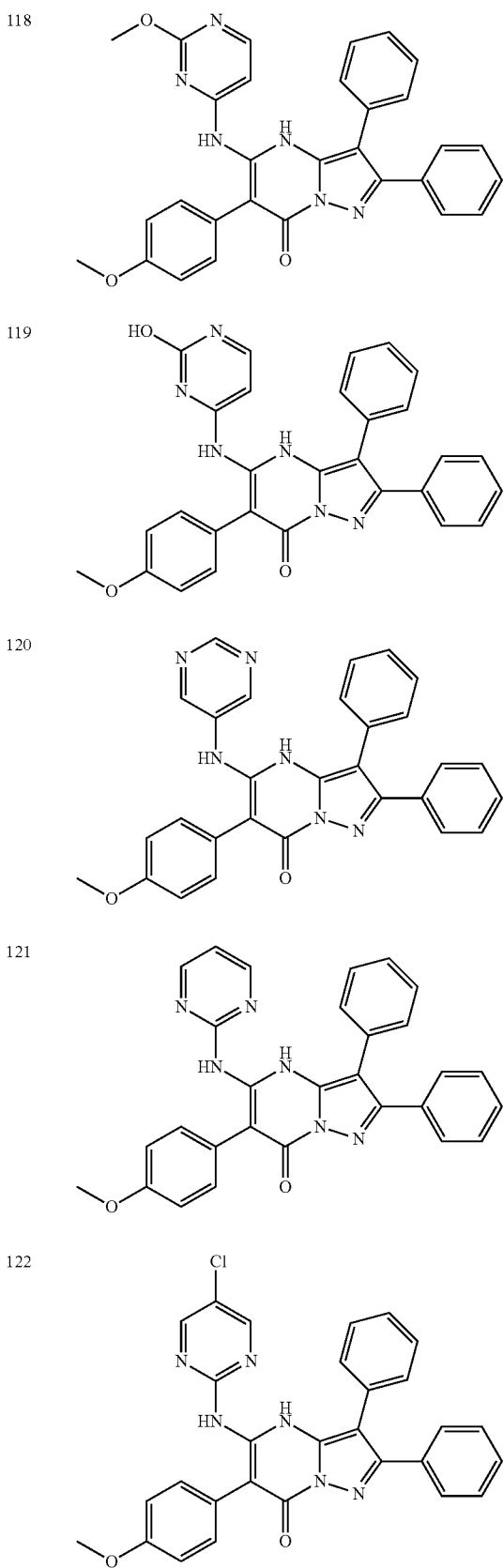
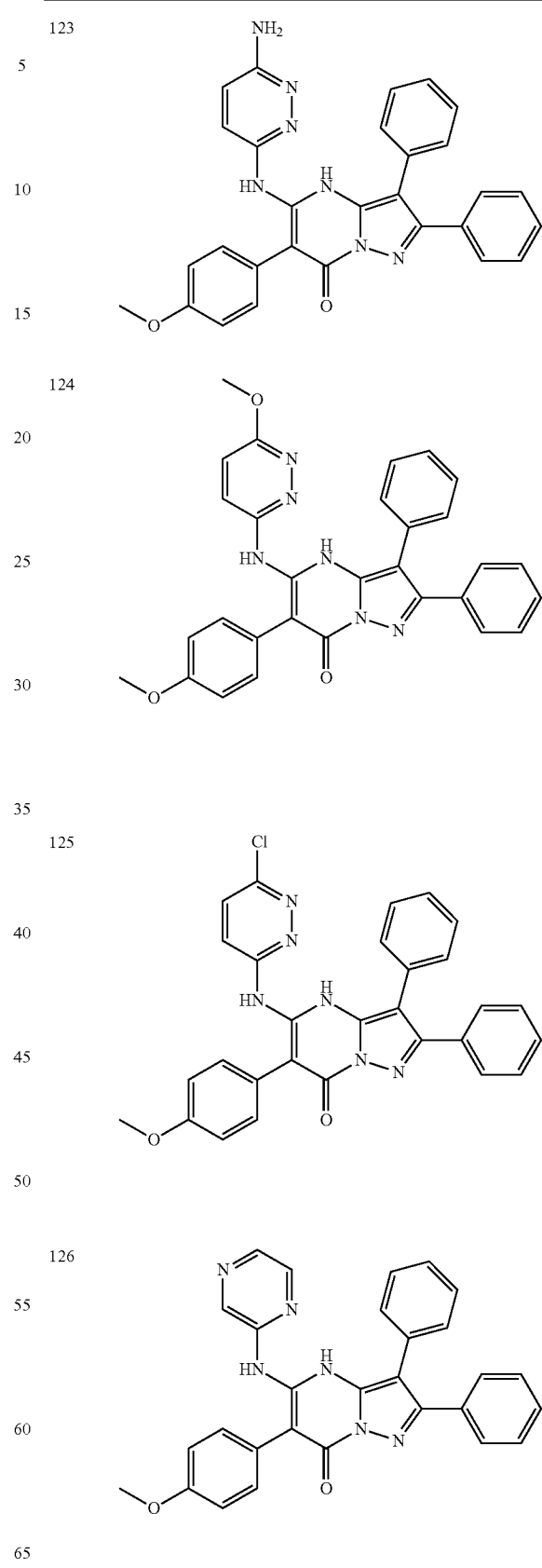

TABLE 2-continued
| | |
|---|---|
| 127 | 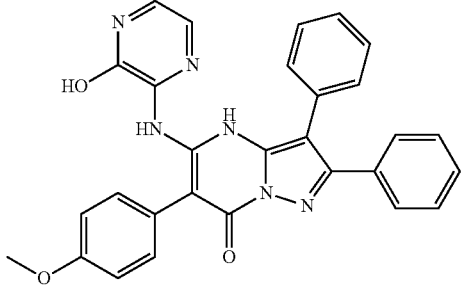 [SMILES: COc1ccc(-c2c(Nc3nccnc3O)[nH]c3c(-c4ccccc4)c(-c4ccccc4)nn3c2=O)cc1] |
| 128 | 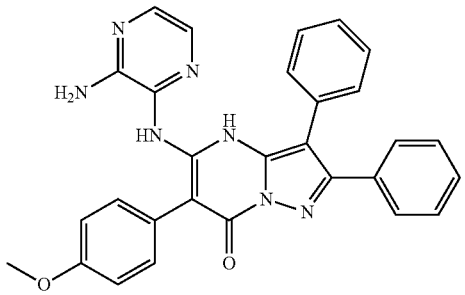 [SMILES: COc1ccc(-c2c(Nc3nccnc3N)[nH]c3c(-c4ccccc4)c(-c4ccccc4)nn3c2=O)cc1] |
| 129 | 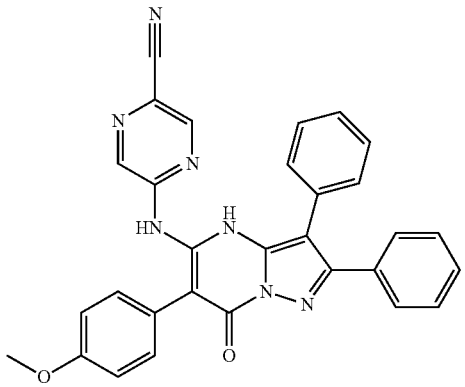 [SMILES: COc1ccc(-c2c(Nc3cnc(C#N)cn3)[nH]c3c(-c4ccccc4)c(-c4ccccc4)nn3c2=O)cc1] |
| 130 | 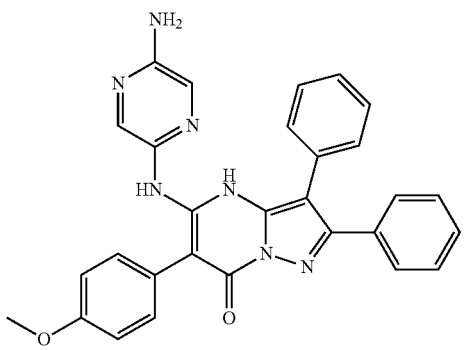 |
| 131 | 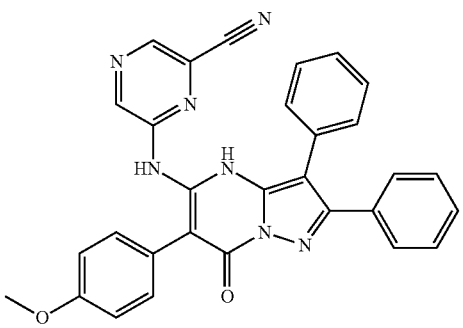 [SMILES: COc1ccc(-c2c(Nc3cncc(C#N)n3)[nH]c3c(-c4ccccc4)c(-c4ccccc4)nn3c2=O)cc1] |
| 132 | 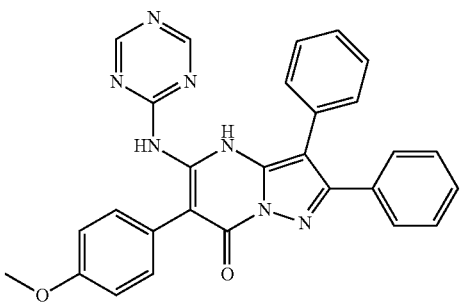 [SMILES: COc1ccc(-c2c(Nc3ncncn3)[nH]c3c(-c4ccccc4)c(-c4ccccc4)nn3c2=O)cc1] |
| 133 | 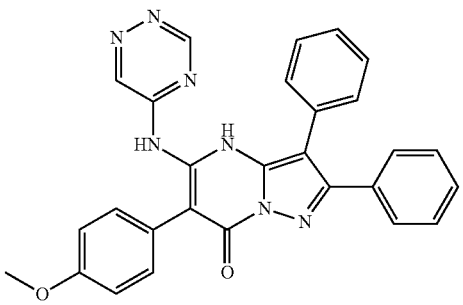 [SMILES: COc1ccc(-c2c(Nc3cnncn3)[nH]c3c(-c4ccccc4)c(-c4ccccc4)nn3c2=O)cc1] |
| 134 | 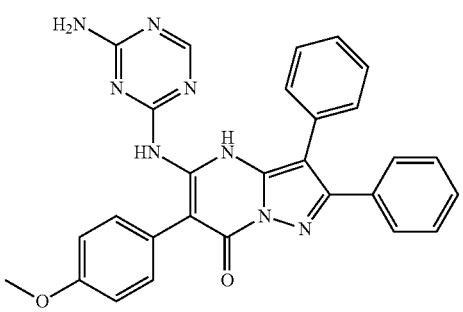 [SMILES: COc1ccc(-c2c(Nc3ncnc(N)n3)[nH]c3c(-c4ccccc4)c(-c4ccccc4)nn3c2=O)cc1] |
| 135 | 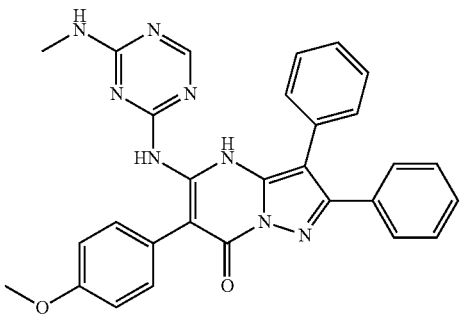 [SMILES: CNc1ncnc(Nc2[nH]c3c(-c4ccccc4)c(-c4ccccc4)nn3c(=O)c2-c2ccc(OC)cc2)n1] |

TABLE 2-continued
136 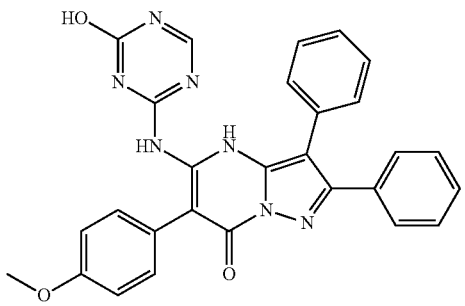 [SMILES: COc1ccc(-c2c(Nc3ncnc(O)n3)[nH]c3c(-c4ccccc4)c(-c4ccccc4)nn3c2=O)cc1]
137 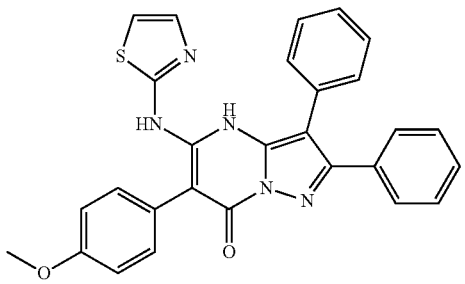 [SMILES: COc1ccc(-c2c(Nc3nccs3)[nH]c3c(-c4ccccc4)c(-c4ccccc4)nn3c2=O)cc1]
138 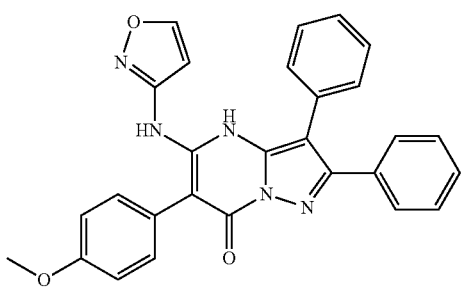
139 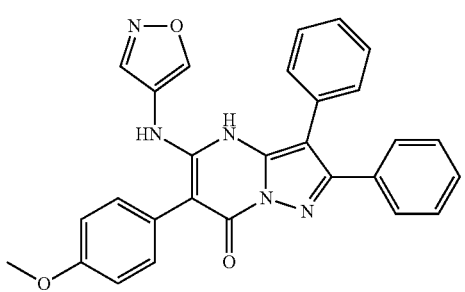 [SMILES: COc1ccc(-c2c(Nc3cnoc3)[nH]c3c(-c4ccccc4)c(-c4ccccc4)nn3c2=O)cc1]
140 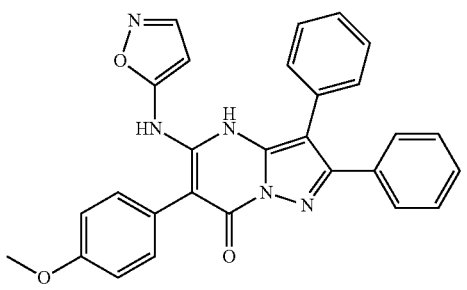 [SMILES: COc1ccc(-c2c(Nc3ccno3)[nH]c3c(-c4ccccc4)c(-c4ccccc4)nn3c2=O)cc1]
TABLE 2-continued
141 
142 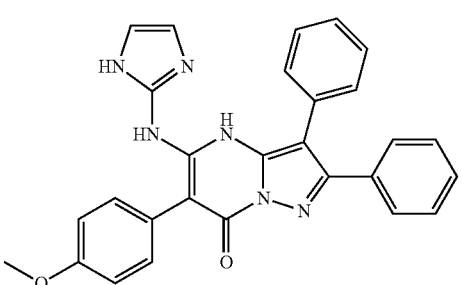
143 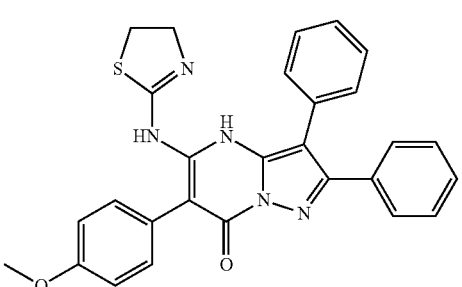
144 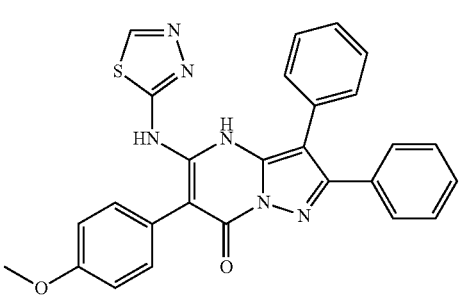
145 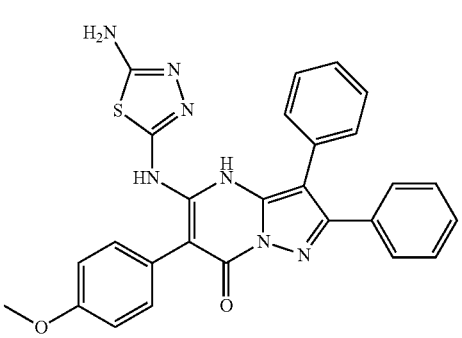 [SMILES: COc1ccc(-c2c(Nc3nnc(N)s3)[nH]c3c(-c4ccccc4)c(-c4ccccc4)nn3c2=O)cc1]

TABLE 2-continued
| 146 | 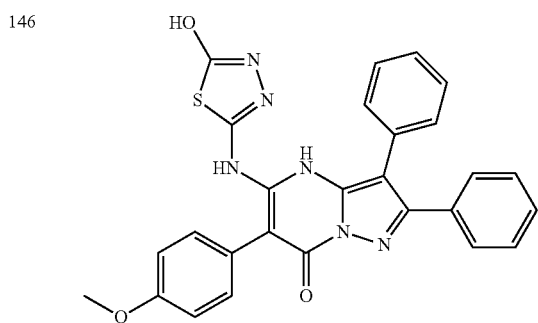 |
| --- | --- |
| 147 | 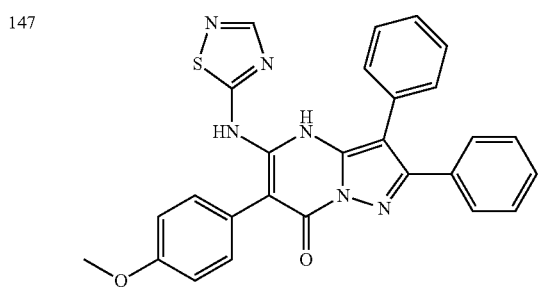 |
| 148 | 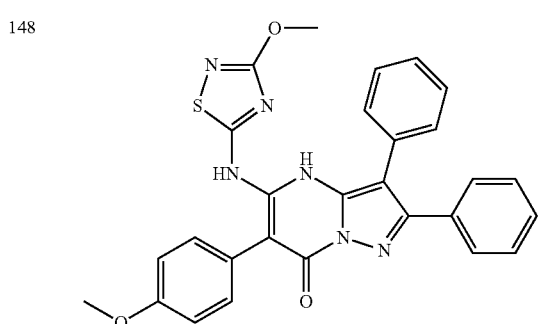 |
| 149 | 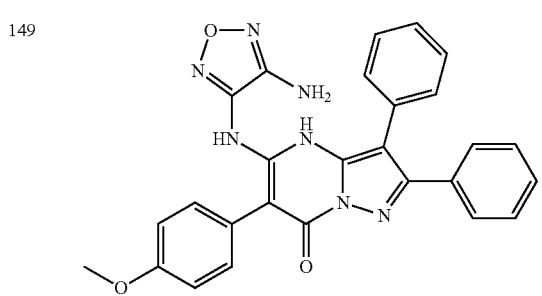 |
| 150 | 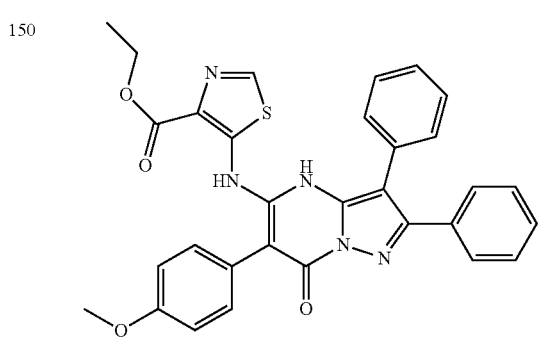 |
| 151 | 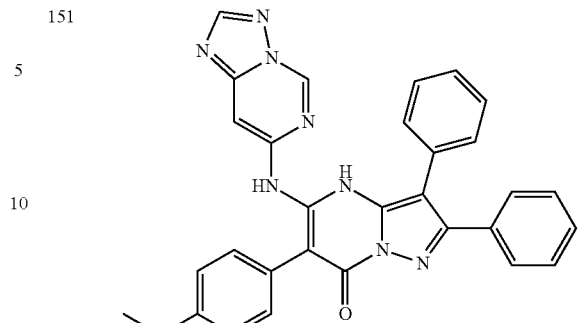 |
| 152 | 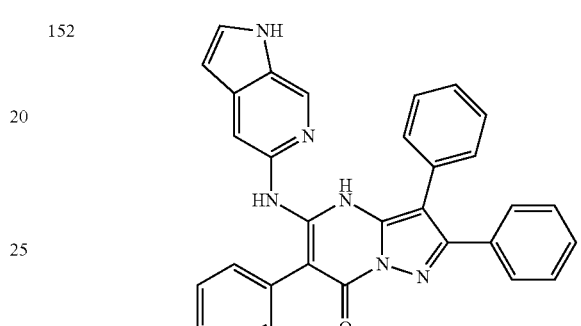 |
| 153 | 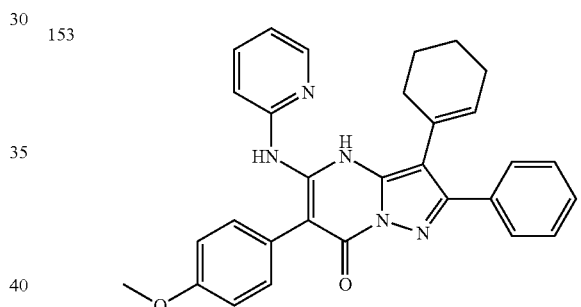 |
| 154 | 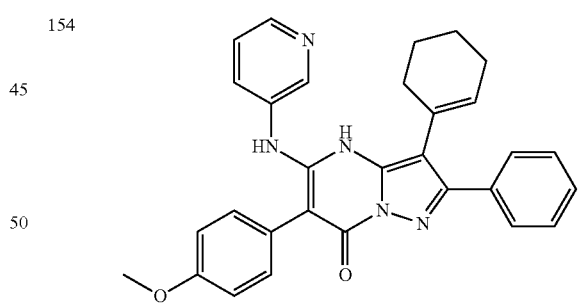 |
| 155 | 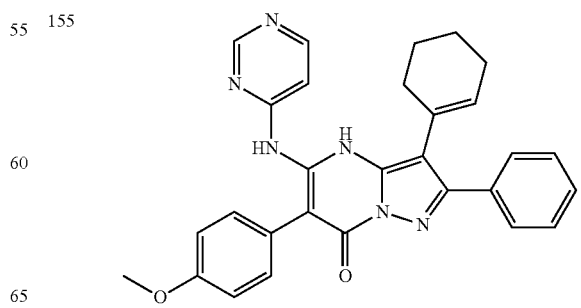 |

TABLE 2-continued
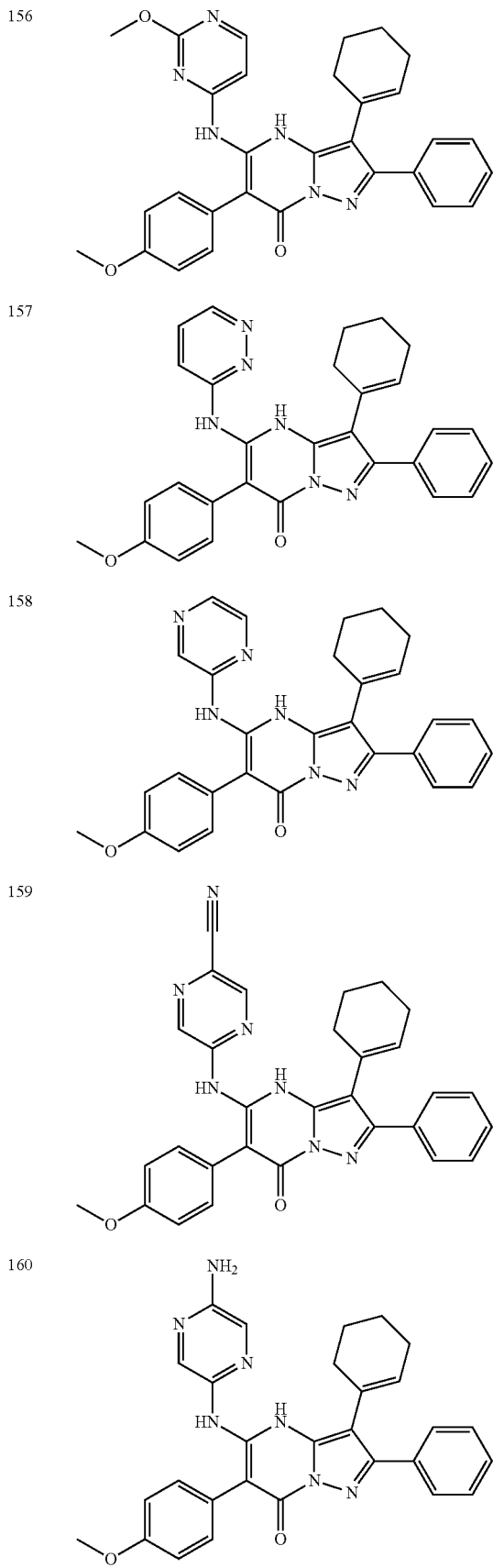
TABLE 2-continued
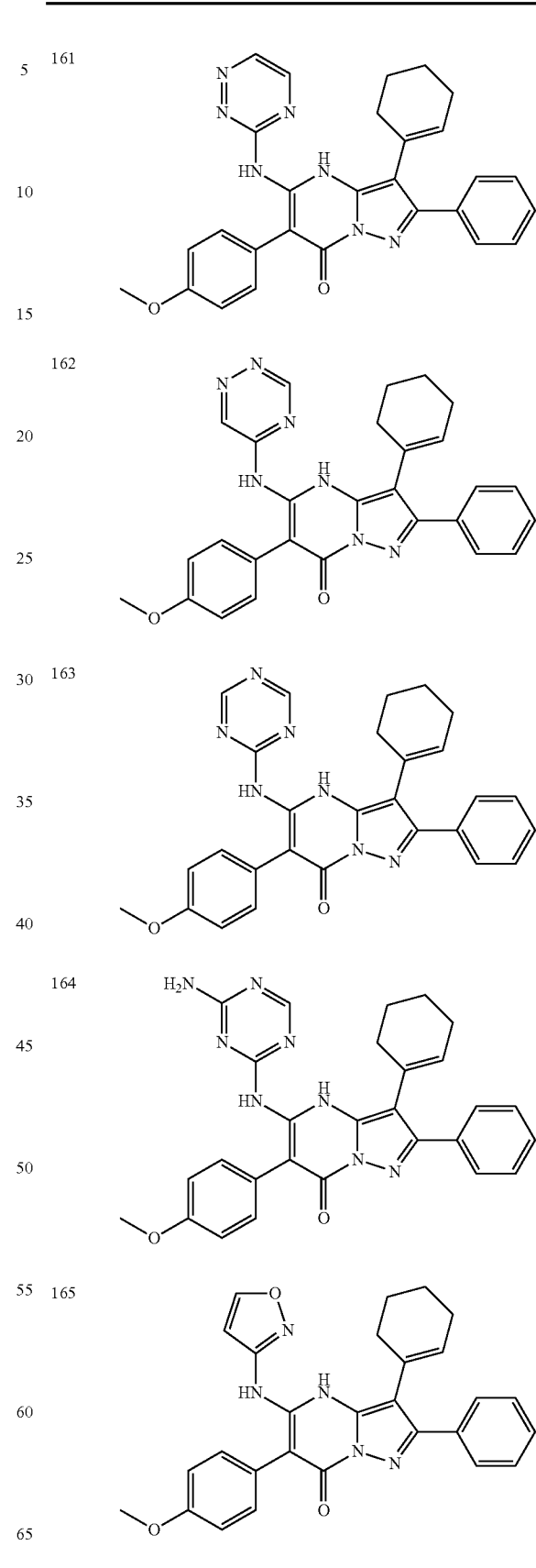

TABLE 2-continued
| 166 | 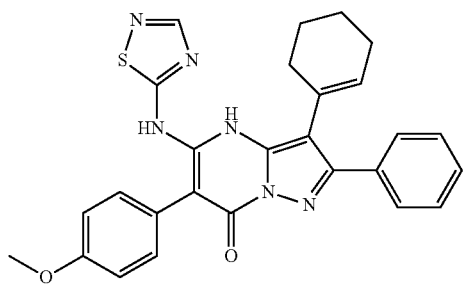 [SMILES: COc1ccc(-c2c(Nc3ncns3)[nH]c3c(C4=CCCCC4)c(-c4ccccc4)nn3c2=O)cc1] |
| --- | --- |
| 167 | 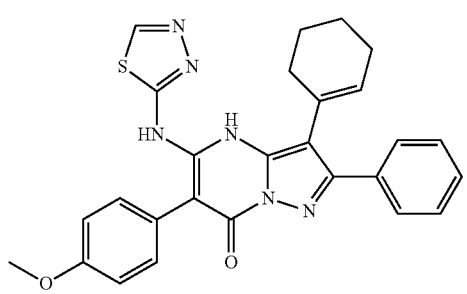 |
| 168 | 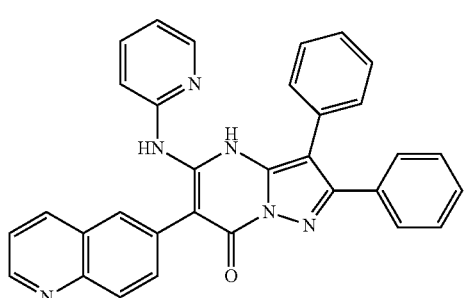 |
| 169 | 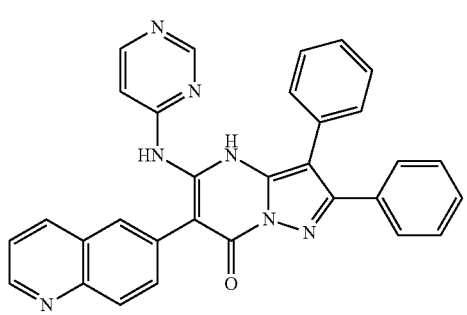 [SMILES: O=c1c(-c2ccc3ncccc3c2)c(Nc2ccncn2)[nH]c2c(-c3ccccc3)c(-c3ccccc3)nn12] |
| 170 | 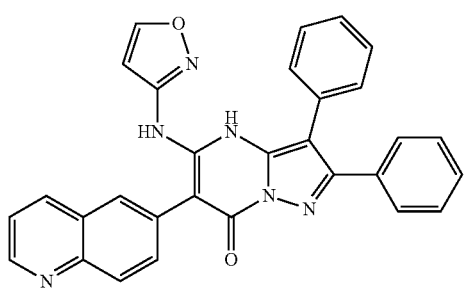 [SMILES: O=c1c(-c2ccc3ncccc3c2)c(Nc2ccon2)[nH]c2c(-c3ccccc3)c(-c3ccccc3)nn12] |
| 171 | 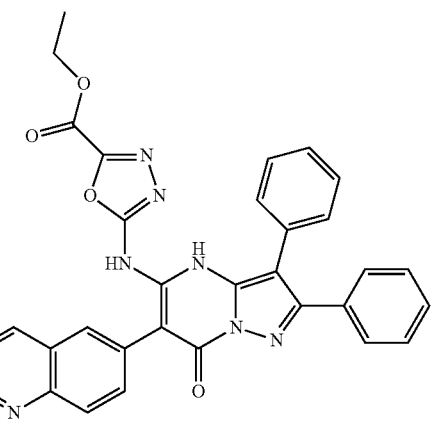 |
| 172 | 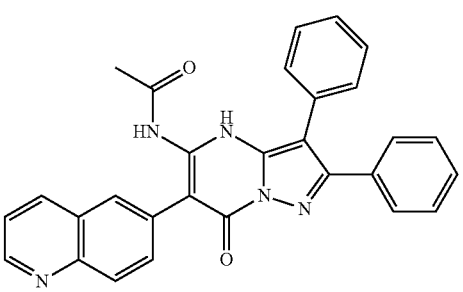 [SMILES: CC(=O)Nc1[nH]c2c(-c3ccccc3)c(-c3ccccc3)nn2c(=O)c1-c1ccc2ncccc2c1] |
| 173 | 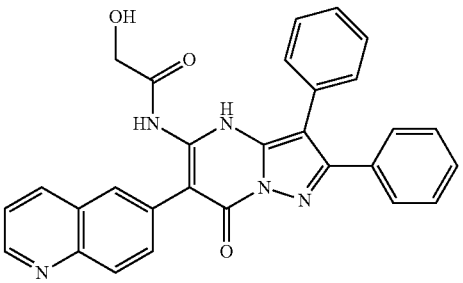 |
| 174 | 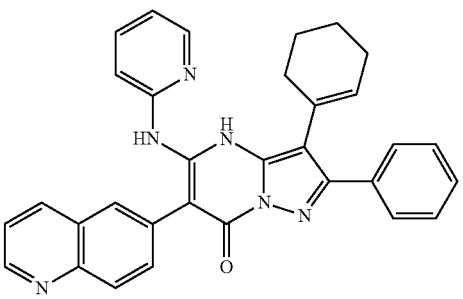 |
| 175 | 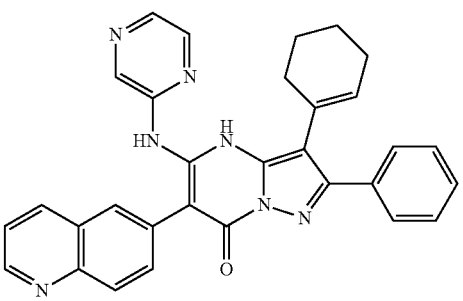 |

TABLE 2-continued
176 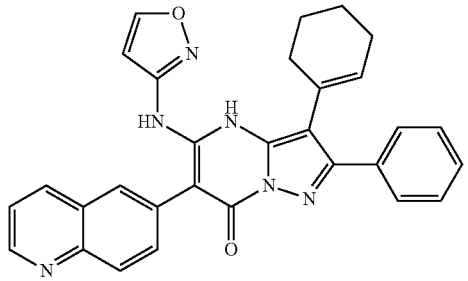
177 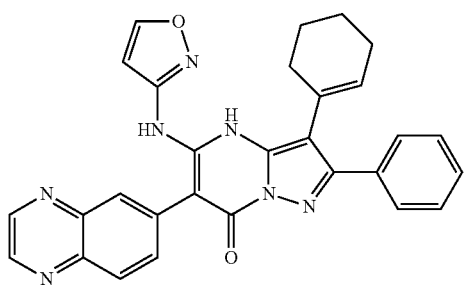 [SMILES: O=c1c(-c2ccc3nccnc3c2)c(Nc2ccon2)[nH]c2c(C3=CCCCC3)c(-c3ccccc3)nn12]
178 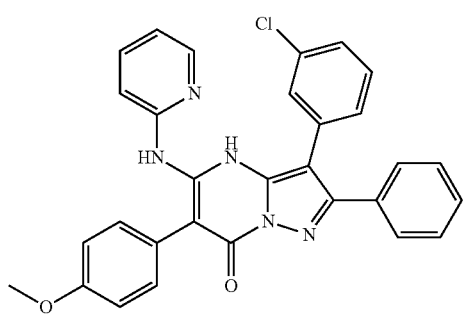 [SMILES: COc1ccc(-c2c(Nc3ccccn3)[nH]c3c(-c4cccc(Cl)c4)c(-c4ccccc4)nn3c2=O)cc1]
179 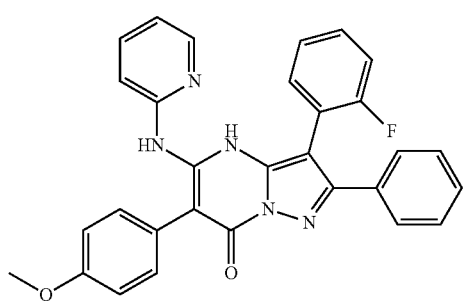 [SMILES: COc1ccc(-c2c(Nc3ccccn3)[nH]c3c(-c4ccccc4F)c(-c4ccccc4)nn3c2=O)cc1]
180 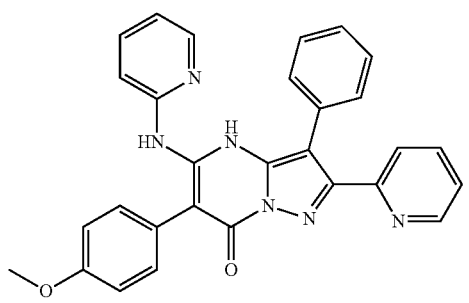 [SMILES: COc1ccc(-c2c(Nc3ccccn3)[nH]c3c(-c4ccccc4)c(-c4ccccn4)nn3c2=O)cc1]
TABLE 2-continued
181 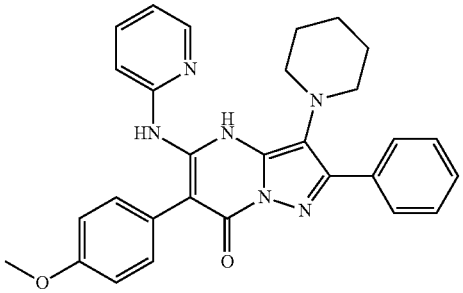 [SMILES: COc1ccc(-c2c(Nc3ccccn3)[nH]c3c(N4CCCCC4)c(-c4ccccc4)nn3c2=O)cc1]
182 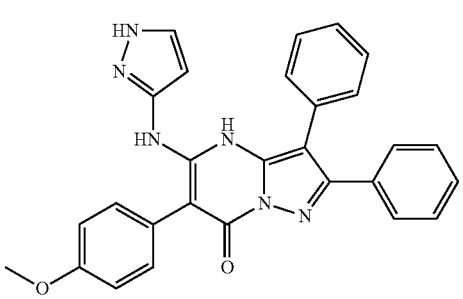
183 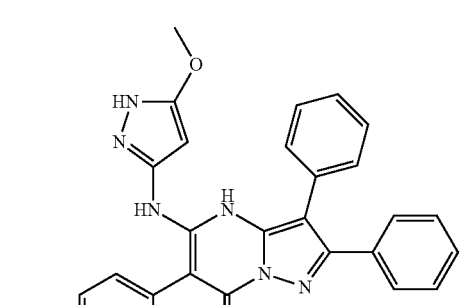
184 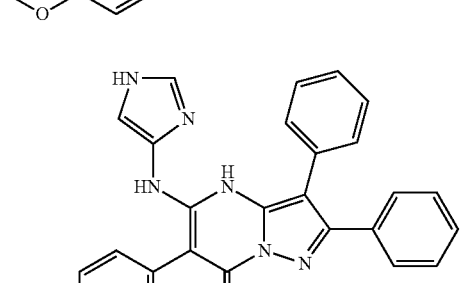
185 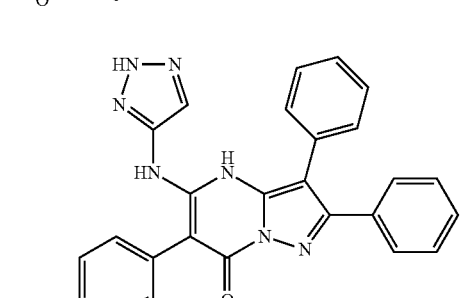

TABLE 2-continued
186 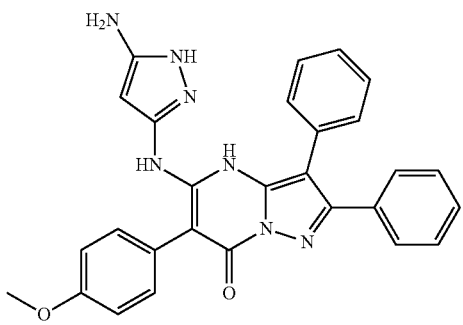
187 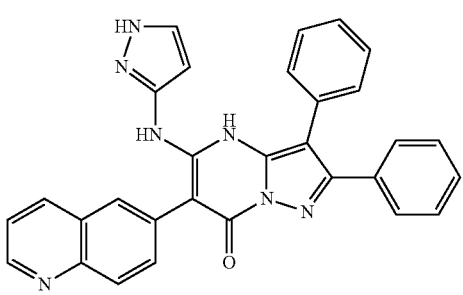 [SMILES: O=c1c(-c2ccc3ncccc3c2)c(Nc2cc[nH]n2)[nH]c2c(-c3ccccc3)c(-c3ccccc3)nn12]
188 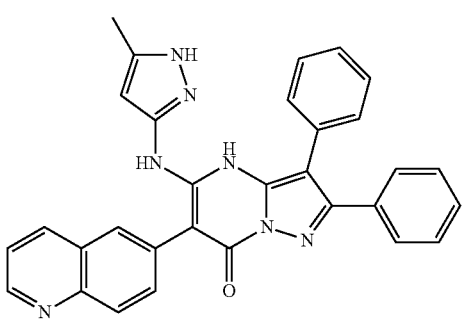 [SMILES: Cc1cc(Nc2[nH]c3c(-c4ccccc4)c(-c4ccccc4)nn3c(=O)c2-c2ccc3ncccc3c2)n[nH]1]
189 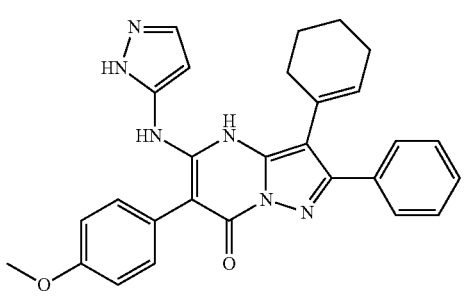 [SMILES: COc1ccc(-c2c(Nc3ccn[nH]3)[nH]c3c(C4=CCCCC4)c(-c4ccccc4)nn3c2=O)cc1]
190 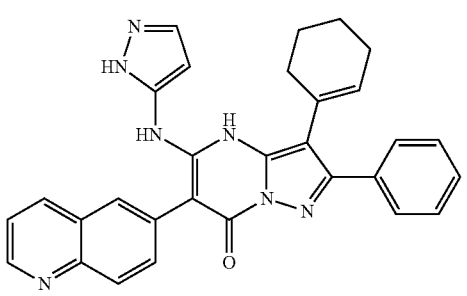 [SMILES: O=c1c(-c2ccc3ncccc3c2)c(Nc2ccn[nH]2)[nH]c2c(C3=CCCCC3)c(-c3ccccc3)nn12]
TABLE 2-continued
191 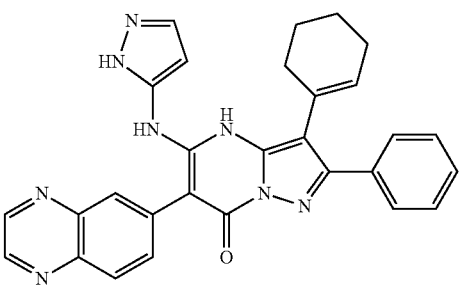 [SMILES: O=c1c(-c2ccc3nccnc3c2)c(Nc2ccn[nH]2)[nH]c2c(C3=CCCCC3)c(-c3ccccc3)nn12]
192 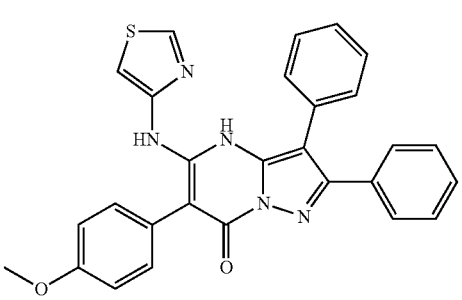 [SMILES: COc1ccc(-c2c(Nc3cscn3)[nH]c3c(-c4ccccc4)c(-c4ccccc4)nn3c2=O)cc1]
193 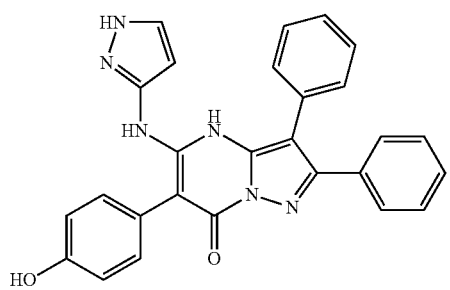 [SMILES: O=c1c(-c2ccc(O)cc2)c(Nc2cc[nH]n2)[nH]c2c(-c3ccccc3)c(-c3ccccc3)nn12]
194 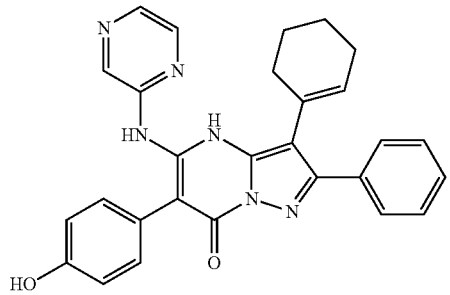 [SMILES: O=c1c(-c2ccc(O)cc2)c(Nc2cnccn2)[nH]c2c(C3=CCCCC3)c(-c3ccccc3)nn12]
195 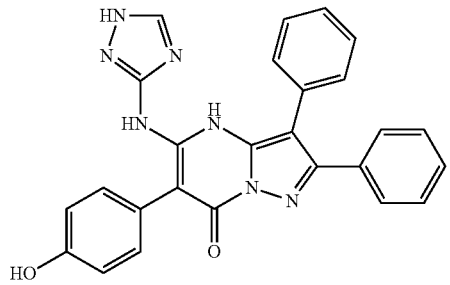

TABLE 2-continued

196 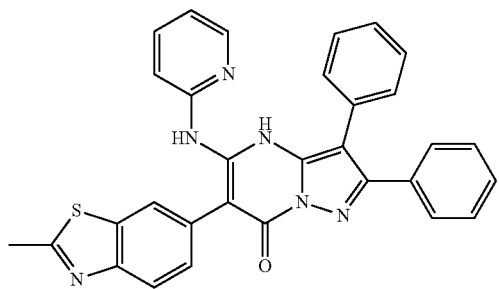 [SMILES: Cc1nc2ccc(-c3c(Nc4ccccn4)[nH]c4c(-c5ccccc5)c(-c5ccccc5)nn4c3=O)cc2s1]

197 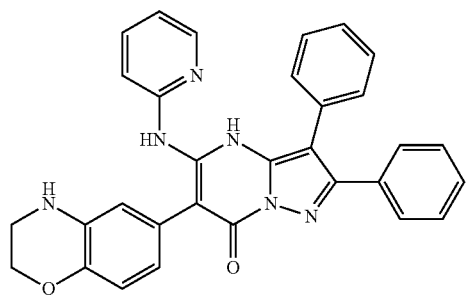 [SMILES: O=c1c(-c2ccc3c(c2)NCCO3)c(Nc2ccccn2)[nH]c2c(-c3ccccc3)c(-c3ccccc3)nn12]

198 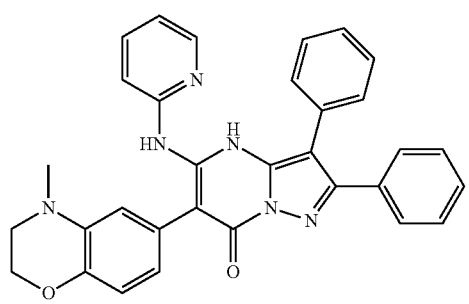 [SMILES: CN1CCOc2ccc(-c3c(Nc4ccccn4)[nH]c4c(-c5ccccc5)c(-c5ccccc5)nn4c3=O)cc21]

199 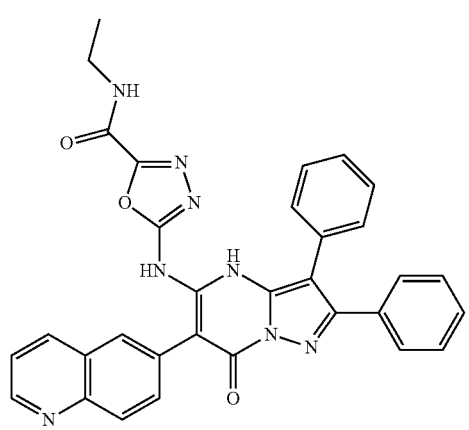 [SMILES: CCNC(=O)c1nnc(Nc2[nH]c3c(-c4ccccc4)c(-c4ccccc4)nn3c(=O)c2-c2ccc3ncccc3c2)o1]

200 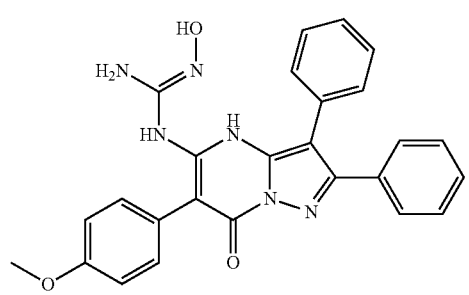 [SMILES: COc1ccc(-c2c(N/C(N)=N/O)[nH]c3c(-c4ccccc4)c(-c4ccccc4)nn3c2=O)cc1]

TABLE 2-continued

201 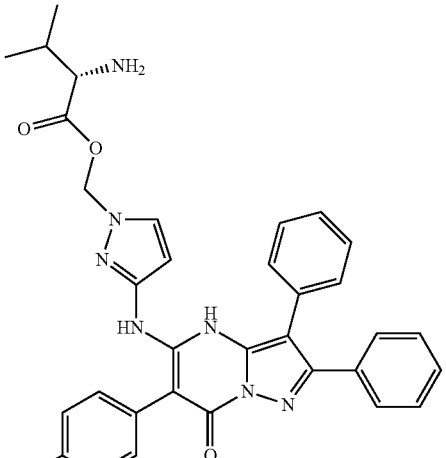

203 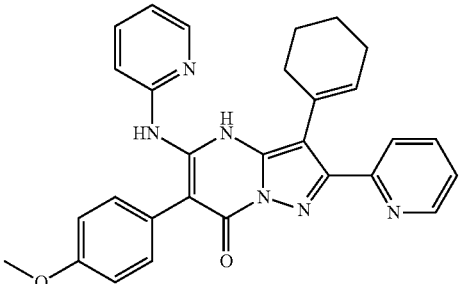

The present disclosure also encompasses prodrugs of the compounds described above. Suitable prodrugs where applicable include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R'") group, an alkoxycarbonyl (—CO—OR'"), an acyloxyalkyl-alkoxycarbonyl (—CO—O—R'"—O—CO—R'") group where R'" is a monovalent or divalent group and as defined above or a group having the formula —C(O)—O—CP1P2-haloalkyl, where P1 and P2 are the same or different and are H, lower alkyl, lower alkoxy, cyano, halo, lower alkyl or aryl. In a particular embodiment, the nitrogen atom is one of the nitrogen atoms of the amidino group of the compounds of the present disclosure. These prodrug compounds are prepared reacting the compounds of the present disclosure described above with an activated acyl compound to bond a nitrogen atom in the compound of the present disclosure to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50° C. The reactions are usually also carried out in the presence of an inorganic base such as potassium carbonate or sodium bicarbonate, or an organic base such as an amine, including pyridine, triethylamine, etc. One manner of preparing prodrugs is described in WO 9846576, the content of which is incorporated herein by reference in its entirety.

Compounds of the present disclosure may exist in different resonance forms and that all such resonance forms are within the scope of the present disclosure herein.

Compounds of the present disclosure are prepared using standard organic synthetic techniques from commercially available starting materials and reagents. It will be appreciated that synthetic procedures employed in the preparation of compounds of the present disclosure will depend on the particular substituents present in a compound and that various protection and deprotection steps that are standard in organic synthesis may be required but may not be illustrated in the following general schemes.

In a particular embodiment, compounds of the present disclosure conforming to formula IB may be prepared by the general Scheme 1.

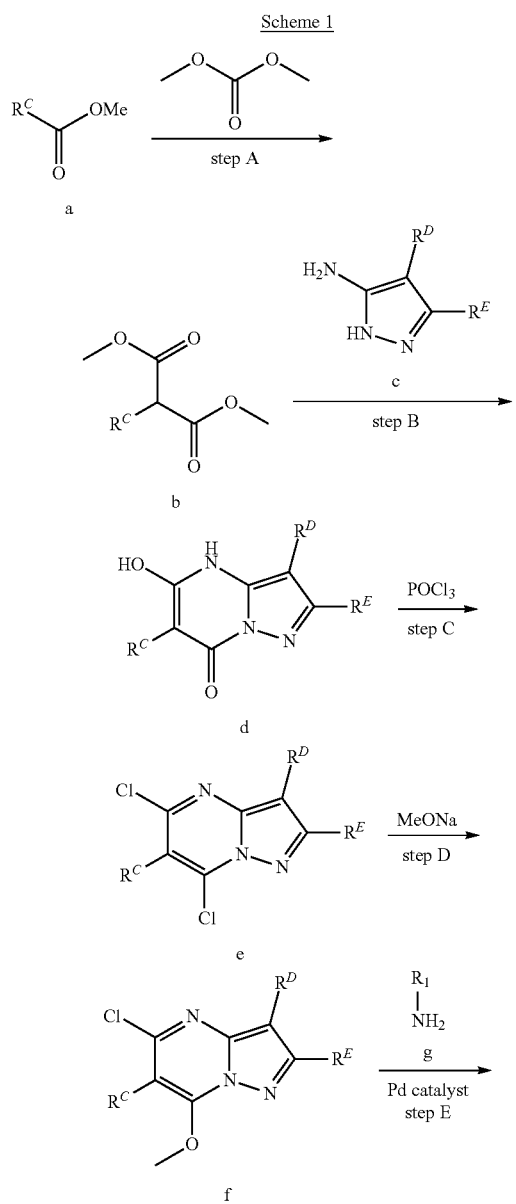

In step A of scheme 1, acetate starting material a incorporating $R^C$ is reacted with dimethyl carbonate in presence of a suitable strong base, such as potassium t-butoxide, to provide dimethyl malonate intermediate b, which is reacted in a suitable solvent such as xylene with intermediate c, 1H-pyrazol-5-amine substituted with $R^D$ and $R^E$, to provide the 5-hydroxy substituted pyrazolopyrimidone intermediate d incorporating rings $R^C$, $R^D$, and $R^E$. The 5-hydroxy group is then converted to the chloro intermediate e by reacting with phosphoryl chloride which also converts the 7-keto group to a chloro. The 7-chloro group is converted to a methoxy group in step D by reacting intermediate e with sodium methoxide to give intermediate f which is then aminated at the 5-position of the pyrazolopyrimidone ring in step E by reacting with the amine intermediate g in the presence of a palladium catalyst to give intermediate h. Finally, the 7-methoxy group is hydrolyzed to a ketone in step F to give the final product of formula (IB).

Aminopyrazole intermediate c from scheme 1 may be prepared using standard organic synthetic techniques from commercially available starting materials and reagents. Scheme 2 illustrates a general procedure for preparing the intermediate.

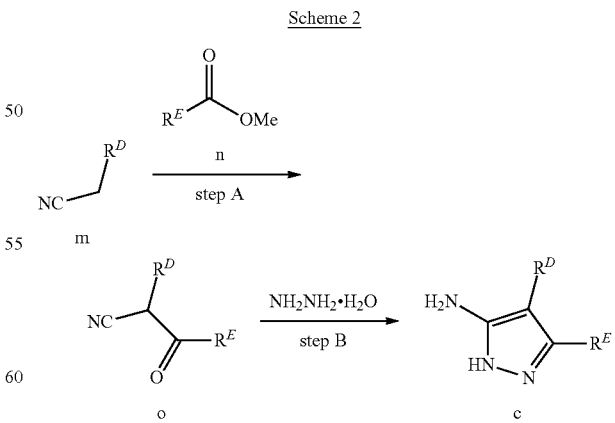

Acetonitrile intermediate m incorporating $R^D$ is reacted with ester n incorporating $R^E$ with an appropriate base catalyst such as sodium hexamethyldisilazide to form 3-oxo-propanenitrile intermediate o containing both $R^D$ and $R^E$.

This is then reacted with hydrazine hydrate to form 5-aminopyrazolo intermediate c which may be used in scheme 1 to prepare compounds of the present disclosure.

In an aspect of the present disclosure, there is provided a process for preparing a compound of formula IA or IB

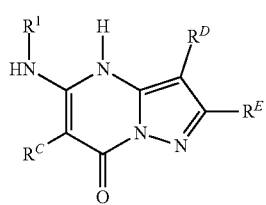
(IB)

wherein $R^C$, $R^D$, $R^E$, and $R_1$ are as defined herein, comprising hydrolyzing a compound of formula h

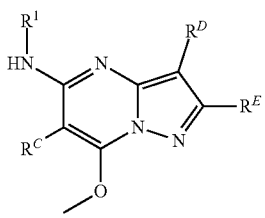
h

There is provided a process for preparing a compound of formula h

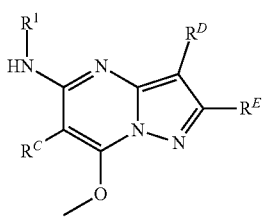
h comprising reacting a compound having the formula f

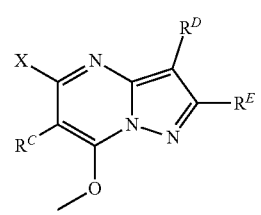
f wherein X is a halogen, with an amine of formula g

g wherein $R_1$ is as defined herein.

In an embodiment, X is Cl. In an embodiment, the reaction is catalyzed with a palladium complex, such as a palladium-Xantphos complex. For instance, the reaction is catalyzed with $Pd(OAc)_2$-Xantphos complex. In one embodiment, the reaction is performed in dioxane solvent.

In another embodiment, there is provided a process for preparing a compound of formula f

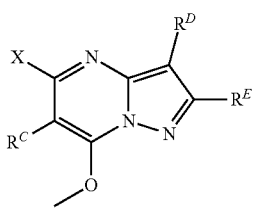
f comprising reacting a compound of formula e

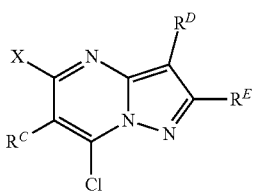
e with sodium methoxide. In an embodiment the reaction is performed in methanol.

In an embodiment, there is provided a process for preparing a compound of formula e

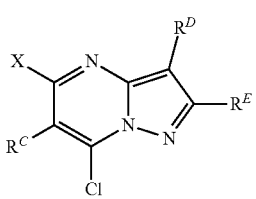
e comprising reacting a compound of formula d

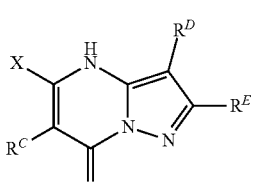
d with phosphoryl chloride. In an embodiment, the reaction is heated.

In an embodiment, there is provided a process for preparing a compound of formula d

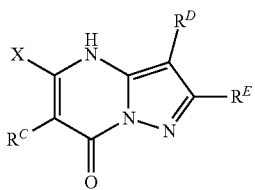

comprising reacting a compound of formula c

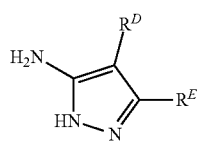

with a compound of formula b

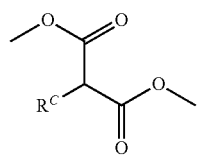

In an embodiment, there is provided a process for preparing a compound of formula b

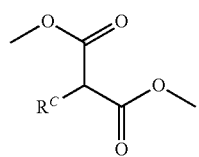

comprising reacting a compound of formula a

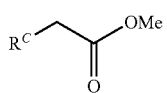

with dimethyl carbonate.

Methods of Use

The MAT2A enzyme catalyzes the synthesis of S-adenosyl methionine (SAM) from methionine and ATP in cells. Accordingly, in another aspect of the present disclosure there is provided a method of inhibiting in a cell the synthesis of SAM from methionine and ATP comprising introducing into said cell an effective amount of a compound of formula IA or IB or a salt thereof. In another aspect of the present disclosure, compounds of formula IA or IB may be used to identify other compounds that are inhibitors of MAT2A, for example, in a competition assay for binding to MAT2A or for the inhibition of SAM production. Binding to MAT2A or the inhibition of SAM production by a test compound having a detectable label can be measured with and without the presence of an unlabeled compound of the present disclosure.

Overexpression of the enzyme MAT2A has been demonstrated to mediate certain cancers. Accordingly, in an aspect of the present disclosure there is provided a method for treating a cancer mediated by the overexpression of MAT2A comprising contacting said cancer with an effective amount of a compound of formula IA or IB or a pharmaceutically acceptable salt thereof. In another aspect of the present disclosure there is provided a method for treating a disease or condition mediated by the overexpression of MAT2A in a mammal, comprising administering to said mammal an effective amount of a compound of formula IA or IB or a pharmaceutically acceptable salt thereof. In an embodiment, the cancer is neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma. In an embodiment, the cancer is lung cancer, non-small cell lung (NSLC) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers.

Methylthioadenosine phosphorylase (MTAP) is an enzyme found in all normal tissues that catalyzes the conversion of methylthioadenosine (MTA) into adenine and 5-methylthioribose-1-phosphate. The adenine is salvaged to generate adenosine monophosphate, and the 5-methylthioribose-1-phosphate is converted to methionine and formate. Because of this salvage pathway, MTA can serve as an alternative purine source when de novo purine synthesis is blocked, e.g., with antimetabolites, such as L-alanosine. Many human and murine malignant cells lack MTAP activity. MTAP deficiency is not only found in tissue culture cells but the deficiency is also present in primary leukemias, gliomas, melanomas, pancreatic cancers, non-small cell lung cancers (NSLC), bladder cancers, astrocytomas, osteosarcomas, head and neck cancers, myxoid chondrosarcomas, ovarian cancers, endometrial cancers, breast cancers, soft tissue sarcomas, non-Hodgkin lymphomas, and mesotheliomas. It has been reported by K. Marjon et al., Cell Reports 15 (2016) 574-587, incorporated herein by reference, that proliferation of cancer cells that are MTAP null is inhibited by knocking down MAT2A expression with shRNA which was confirmed using small molecule inhibitors of MAT2A such as those of the present disclosure. An MTAP null cancer is a cancer in which the MTAP gene has been deleted or lost or otherwise deactivated or a cancer in which the MTAP protein has a reduced or impaired function.

Accordingly, in an embodiment of the present disclosure there is provided a method for treating an MTAP null cancer in a subject wherein said cancer is characterized by a reduction or absence of MTAP expression or absence of the MTAP gene or reduced function of MTAP protein as compared to cancers where the MTAP gene is present and fully functioning, said method comprising administering to the subject a therapeutically effective amount of a compound of formula IA or IB or a pharmaceutically acceptable salt thereof. In another embodiment, there is provided a method of treating an MTAP null cancer in a subject comprising administering to the subject an effective amount of a compound of formula IA or IB or a pharmaceutically acceptable salt thereof. In an embodiment, the MTAP null cancer is leukemia, glioma, melanoma, pancreatic, non-small cell lung cancer (NSLC), bladder cancer, astrocytoma, osteosarcoma, head and neck cancer, myxoid chondrosarcoma, ovarian cancer, endometrial cancer, breast cancer, soft tissue sarcoma, non-Hodgkin lymphoma or mesothelioma. In an embodiment, the MTAP null cancer is pancreatic cancer. In an embodiment, the MTAP null cancer is bladder cancer, melanoma, brain cancer, lung cancer, pancreatic cancer, breast cancer, esophageal cancer, head and neck cancer, kidney cancer, colon cancer, diffuse large B cell lymphoma (DLBCL), acute lymphoblastic leukemia (ALL) or mantle cell lymphoma (MCL). In an embodiment, the MTAP null cancer is pancreatic cancer. In an embodiment, the MTAP null cancer is gastric cancer. In an embodiment, the cancer is colon cancer. In an embodiment, the MTAP null cancer is liver cancer. In an embodiment, the MTAP null cancer is glioblastoma multiforme (GBM). In an embodiment, the MTAP null cancer is bladder cancer. In an embodiment, the MTAP null cancer is esophageal cancer. In an embodiment, the MTAP null cancer is breast cancer. In an embodiment, the MTAP null cancer is NSLCC. In an embodiment, the MTAP null cancer is MCL. In an embodiment, the MTAP null cancer is DLBCL. In an embodiment, the MTAP null cancer is ALL.

Genomic analysis of MTAP null cell lines revealed that in cell lines that also incorporate a KRAS mutation or a p53 mutation were sensitive to MAT2A inhibition. Accordingly, one aspect of the present disclosure provides a method for treating a cancer in a subject wherein said cancer is characterized by reduction or absence of MTAP expression or absence of the MTAP gene or reduced function of MTAP protein, said method comprising administering to the subject a therapeutically effective amount of a compound of formula IA or IB, wherein said cancer is further characterized by the presence of mutant KRAS or mutant p53. In another aspect of the present disclosure there is provided a method of treating an MTAP null cancer having a mutant KRAS or mutant p53 in a subject, comprising administering to the subject an effective amount of a compound of formula IA or IB or a pharmaceutically acceptable salt thereof. In an embodiment, the cancer is MTAP null and KRAS mutant. In an embodiment, the cancer is MTAP null and p53 mutant. In an embodiment, the cancer is MTAP null, KRAS mutant and p53 mutant.

The term "mutant KRAS" or "KRAS mutation" refers to KRAS protein incorporating an activating mutation that alters its normal function and the gene encoding such a protein. For example, a mutant KRAS protein may incorporate a single amino acid substitution at position 12 or 13. In a particular embodiment, the KRAS mutant incorporates a G12X or G13X substitution, wherein X represents any amino acid change at the indicated position. In a particular embodiment, the substitution is G12V, G12R, G12C or G13D. In another embodiment, the substitution is G13D. By "mutant p53" or "p53 mutation" is meant p53 protein (or gene encoding said protein) incorporating a mutation that inhibits or eliminates its tumor suppressor function. In an embodiment, said p53 mutation is, Y126_splice, K132Q, M133K, R174fs, R175H, R196*, C238S, C242Y, G245S, R248W, R248Q, I255T, D259V, S261_splice, R267P, R273C, R282W, A159V or R280K. In an embodiment, the foregoing cancer is non-small cell lung cancer (NSLCC), pancreatic cancer, head and neck cancer, gastric cancer, breast cancer, colon cancer or ovarian cancer.

The compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a particular embodiment, compounds of the present disclosure are coadministered with a cytostatic compound selected from the group consisting of cisplatin, doxorubicin, taxol, taxotere and mitomycin C. In a particular embodiment, the cytostatic compound is doxorubicin.

In another embodiment, compounds of the present disclosure may be used alone as an immuno-oncology therapy or in combination with an immuno-oncology therapy. In an embodiment, the compound of the present disclosure is administered prior to, concomitantly with, or following administration of an immune checkpoint inhibitor. In an embodiment, the checkpoint inhibitor is a PD-1 inhibitor. In an embodiment, the checkpoint inhibitor is a PD-L1 inhibitor. In an embodiment, the checkpoint inhibitor is ipilimumab. In an embodiment, the checkpoint inhibitor is pembrolizumab, nivolumab, or atezolizumab.

The compounds of the present disclosure can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread.

Examples of radiotherapeutic agents are provided in, but not limited to, radiation therapies known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy. Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme: they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present disclosure. Furthermore, the present disclosure encompasses types of non-ionizing radiation like e.g. ultraviolet (UV) radiation, high energy visible light, microwave radiation (hyperthermia therapy), infrared (IR) radiation and lasers. In a particular embodiment of the present disclosure UV radiation is applied.

Pharmaceutical Compositions

The present disclosure also includes pharmaceutical compositions or medicaments containing the compounds of the present disclosure and a pharmaceutically acceptable carrier, as well as methods of using the compounds of the present disclosure to prepare such compositions and medicaments. Typically, the compounds of formula IA or IB used in the methods of the present disclosure are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, and it can range from about 3 to about 8. Formulation in an acetate buffer at pH 5 is a suitable embodiment. In an embodiment, the inhibitory compound for use herein is sterile. The compound ordinarily will be stored as a solid composition, although lyophilized formulations or aqueous solutions are acceptable.

In another embodiment, pharmaceutical compositions of the present disclosure may comprise a compound of formula IA or IB or a pharmaceutically acceptable salt thereof, and one or more polymer(s) as part of a solid dispersion (e.g., an amorphous solid dispersion). In an embodiment, the solid dispersion further comprises one or more surfactants. In an embodiment, the pharmaceutical composition comprising a compound of the present disclosure is a solid spray-dried dispersion. Pharmaceutical compositions comprising solid dispersions of a compound of the present disclosure in a matrix may provide improved chemical and physical properties and can be prepared by forming a homogeneous solution or melt of the compound of the present disclosure and matrix material followed by solidifying the mixture by cooling, or removal of the solvent. Such solid dispersions may show enhanced bioavailability when administered orally relative to oral compositions comprising the undispersed compound. A dispersion refers to a disperse system in which one substance, the dispersed phase, is distributed, in discrete units, throughout a second substance (the continuous phase or vehicle). The size of the dispersed phase can vary considerably (e.g., colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline therapeutically active compound (dispersed phase) in an amorphous polymer(s) (continuous phase), or alternatively, an amorphous therapeutically active compound (dispersed phase) in an amorphous polymer (continuous phase). An amorphous solid dispersion generally refers to a solid dispersion of two or more components, such as a compound of the present disclosure and polymer (or plurality of polymers), but possibly containing other components such as surfactants or other pharmaceutical excipients, where the compound of the present disclosure is in the amorphous phase. In some embodiments, an amorphous solid dispersion includes the polymer(s) (and optionally a surfactant) constituting the dispersed phase, and the compound of the present disclosure constitutes the continuous phase. In some embodiments, an amorphous solid dispersion includes the polymer(s) (and optionally a surfactant) constituting the continuous phase, and the compound of the present disclosure constitutes the dispersed phase.

An exemplary solid dispersion is a co-precipitate or a co-melt of a compound of the present disclosure with one or more polymer(s). A "co-precipitate" is produced after dissolving a compound of the present disclosure and one or more polymers in a solvent or solvent mixture followed by the removal of the solvent or solvent mixture. Sometimes the one or more polymers can be suspended in the solvent or solvent mixture. The solvent or solvent mixture includes organic solvents and supercritical fluids. The solvent or solvent mixture can also contain a non-volatile solvent. A "co-melt" is produced after heating a compound of the present disclosure and one or more polymers to melt, optionally in the presence of a solvent or solvent mixture, followed by mixing, removal of at least a portion of the solvent if applicable, and cooling to room temperature at a selected rate. In some cases, solid dispersions are prepared by adding a solution of a therapeutically active compound and solid polymers followed by mixing and removal of the solvent or solvent mixture. To remove the solvent or solvent mixture, vacuum drying, spray drying, tray drying, lyophilization, and other drying procedures may be applied. Applying any of these methods using appropriate processing parameters, according to this disclosure, would provide the particular therapeutically active compound in an amorphous state in the final solid dispersion product.

The composition of the present disclosure will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit MAT2A activity. Such amount may be below the amount that is toxic to normal cells, or the mammal as a whole. Generally, the initial pharmaceutically effective amount of the compound of the present disclosure administered parenterally per dose will be in the range of about 0.01-2000 mg/kg, for example about 0.01 to about 200 mg/kg, about 0.1 to 20 mg/kg of patient body weight per day, with the typical initial range of compound used being 0.3 to 15 mg/kg/day. Oral unit dosage forms, such as tablets and capsules, may contain from about 25 to about 200 mg of the compound of the present disclosure.

The compound of the present disclosure may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 1 mg, 2 mg, 5 mg, 10 gm, 15 mg 25 mg, 50 mg, 100 mg, 250 mg, 500 mg, 750 mg, 1000 mg, 1250 mg, 1500 mg, 1750 mg or 2000 mg of the compound of the present disclosure.

EXAMPLES

The present disclosure will be more fully understood by reference to the following examples. They should not, however, be construed as limiting the scope of the present disclosure. Reagents and solvents were obtained from commercial sources and used as received.

Abbreviations and Terms List anhy. anhydrous
aq. aqueous
min minute(s)
mL milliliter
mmol millimole(s)
mol mole(s)
MS mass spectrometry
NMR nuclear magnetic resonance
TLC thin layer chromatography
HPLC high-performance liquid chromatography
RT (r.t.) room temperature
Spectrum
  Spectrum:
  Hz hertz
  δ chemical shift
  J coupling constant
  s singlet
  d doublet
  t triplet
  q quartet
  m multiplet
  br broad
  qd quartet of doublets
  dquin doublet of quintets
  dd doublet of doublets
  dt doublet of triplets
Solvents and Reagents:
  $CHCl_3$ chloroform
  DCM dichloromethane
  DMF dimethylformamide
  $Et_2O$ diethyl ether
  EtOH ethyl alcohol
  EtOAc ethyl acetate
  EA ethyl acetate
  MeOH methyl alcohol
  MeCN acetonitrile
  PE petroleum ether
  THF tetrahydrofuran
  AcOH acetic acid
  HCl hydrochloric acid
  $H_2SO_4$ sulfuric acid
  $NH_4Cl$ ammonium chloride
  KOH potassium hydroxide
  NaOH sodium hydroxide
  $K_2CO_3$ potassium carbonate
  $Na_2CO_3$ sodium carbonate
  TFA trifluoroacetic acid
  $Na_2SO_4$ sodium sulfate
  $NaBH_4$ sodium borohydride
  $NaHCO_3$ sodium bicarbonate
  LiHMDS lithium hexamethyldisilylamide
  NaHMDS sodium hexamethyldisilylamide
  LAH lithium aluminum hydride
  $NaBH_4$ sodium borohydride
  LDA lithium diisopropylamide
  $Et_3N$ triethylamine
  DMAP 4-(dimethylamino)pyridine
  DIPEA N,N-diisopropylethylamine
  $NH_4OH$ ammonium hydroxide
  EDCI 1-ethyl-3-(3-dimethylaminopropyl)carbodiimide
  HOBt 1-hydroxybenzotriazole
  HATU O-(7-azabenzotriazol-1-yl)-N,N,N'N'-tetra-methyluronium
  Xphos 2-Dicyclohexylphosphino-2',4',6'-triisopropylbiphenyl
  BINAP 2,2'-bis(diphenylphosphanyl)-1,1'-binaphthyl Example 1 Synthesis of Compounds General Experimental Notes In the following examples, the reagents (chemicals) were purchased from commercial sources (such as Alfa, Acros, Sigma Aldrich, TCI and Shanghai Chemical Reagent Company), and used without further purification. Flash chromatography was performed on an Ez Purifier III using column with silica gel particles of 200-300 mesh. Analytical and preparative thin layer chromatography (TLC) plates were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA). HPLC chromatographs were record on an Agilent 1200 Liquid Chromatography (Agilent, USA, column: Ultimate 4.6 mm×50 mm, 5 μm, mobile phase A: 0.1% formic acid in water; mobile phase B: acetonitrile). Microwave reactions were run on an Initiator 2.5 Microwave Synthesizer (Biotage, Sweden).

Compound 101: 6-(4-methoxyphenyl)-2,3-diphenyl-5-(pyridazin-3-ylamino)pyrazolo[1,5-a]pyrimidin-7(4H)-one

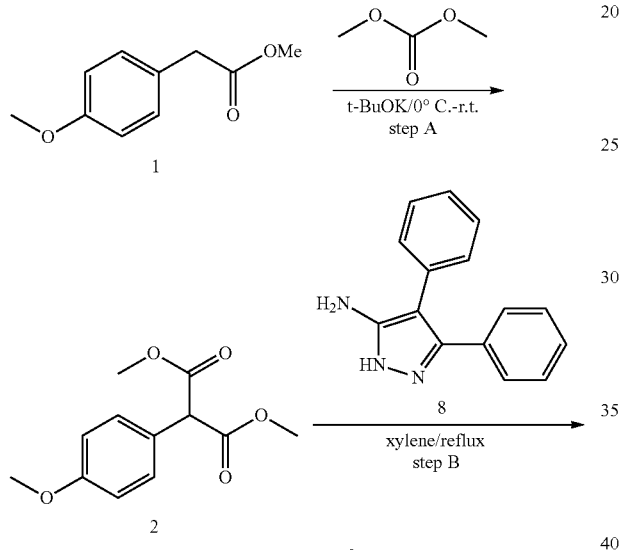

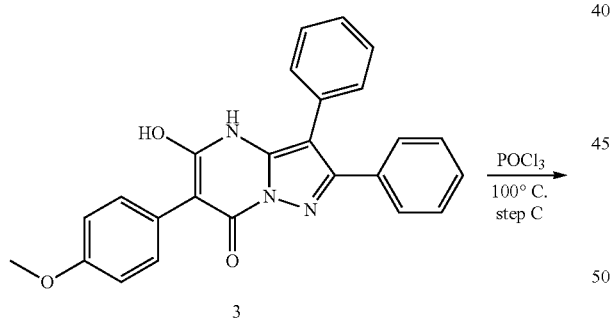

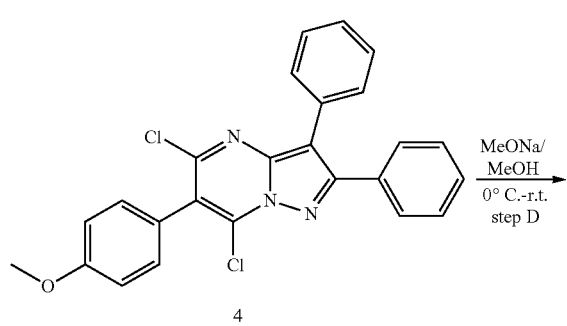

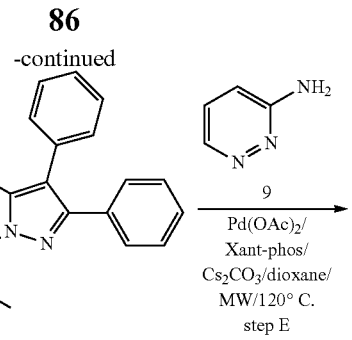

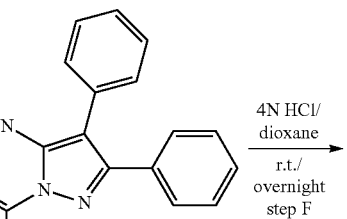

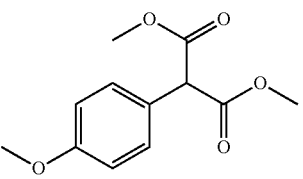

Step A: Dimethyl 2-(4-methoxyphenyl)malonate

To dimethyl carbonate (3.2 L) was added slowly t-BuOK (500 g) at 0° C. and the mixture was stirred for 1 h at room temperature. Then methyl 2-(4-methoxyphenyl)acetate (400 g) was added dropwise over 2 h and stirred at room temperature overnight. The reaction was quenched with water (1.5 L), followed by extraction with EA (1 L*3). The combined organic layers were washed with brine (1 L), dried over anhydrous $Na_2SO_4$, and concentrated in vacuo. The residue was purified by flash chromatography eluting with PE/EA (20/1~5/1) to obtain the desired product as white solid (400 g).

$^1$H NMR (CHLOROFORM-d): δ 7.33 (d, J=8.6 Hz, 2H), 6.90 (d, J=8.9 Hz, 2H), 4.61 (s, 1H), 3.80 (s, 3H), 3.75 (s, 6H).

Step B: 5-hydroxy-6-(4-methoxyphenyl)-2,3-diphenylpyrazolo[1,5-a]pyrimidin-7(4H)-one Step D: 5-chloro-7-methoxy-6-(4-methoxyphenyl)-2,3-diphenylpyrazolo[1,5-a]pyrimidine

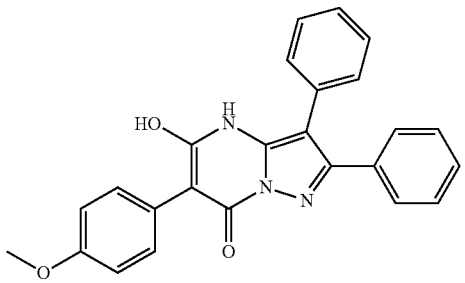

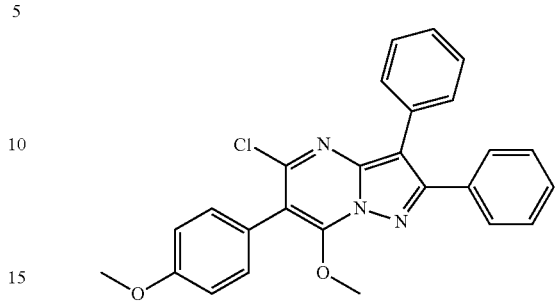

The mixture of 3, 4-diphenyl-1H-pyrazol-5-amine 8 (470 g, 2 mol) and dimethyl-2-(4-methoxyphenyl)-malonate 2 (571 g, 2.4 mol, 1.2 eq.) in xylene (5 L) was refluxed for 18 h. The white precipitate was filtered off and washed with DCM (5 L) to afford the title compound as white solid (610 g) which was used in the next step without further purification.

$^1$H NMR (DMSO-d$_6$): δ 11.57 (br. s, 1H), 7.26-7.49 (m, 12H), 6.90-6.99 (m, 2H), 3.78 (s, 3H). LC-MS: m/z 410.2 (M+H)$^+$.

Step C: 5,7-dichloro-6-(4-methoxyphenyl)-2,3-diphenylpyrazolo[1,5-a]pyrimidine

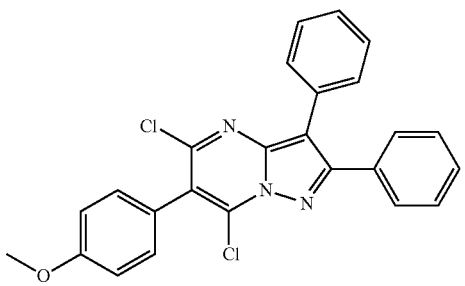 [SMILES: COc1ccc(-c2c(Cl)nc3c(-c4ccccc4)c(-c4ccccc4)nn3c2Cl)cc1]

The 6-(4-methoxyphenyl)-2, 3-diphenylpyrazolo [1,5-a] pyrimidine-5, 7(4H, 6H)-dioxane (300 g, 0.73 mol) and phosphorus oxychloride (1200 mL, 12.90 mol) were added into a 2 L bottle. The reaction mixture was stirred at 100° C. for 16 h. TLC indicated that the reaction was complete. The solvent and volatile were removed in vacuo and the residue was dissolved in DCM (500 mL). The mixture was added dropwise into the MeOH (2500 mL) at 0° C. A yellow suspension formed during the course of addition. The mixture was stirred at RT for 2 h and the precipitate was collected by filtration and dried in vacuo to give desired product as yellow solid (290g) which was used in the next step without further purification. LC-MS: m/z 446.1, 448.1 (M+H)$^+$.

The 5, 7-dichloro-6-(4-methoxyphenyl)-2, 3-diphenylpyrazolo [1, 5-a] pyrimidine 4 (1.78 kg, 4 mol) and DCM (20 L) were added into the 30 L reactor. The mixture was cooled to −10° C. The sodium methoxide (1.48 L, 8 mol, 30% in MeOH) was dropwise such that the internal temperature is maintained below 0° C. The reaction mixture was stirred at RT for 2 h. TLC indicated that the reaction was completed. The ice water (10 L) was added and the reaction mixture was stirred at RT for 1 h. The organic layer was collected and the aqueous layer was extracted with DCM (5 L*1). The combined organic layers were dried over anhydrous Na$_2$SO$_4$ and concentrated. The residue was dissolved in DCM (15 L) and the MeOH (60 L) was added. The turbid liquid was stirred at RT for 3 h and the precipitate was collected by filtration and dried in vacuo to give the title Intermediate 5 as a yellow solid (1.35 kg).

$^1$H NMR (CHLOROFORM-d): δ 7.66-7.73 (m, 2H), 7.53-7.61 (m, 2H), 7.30-7.46 (m, 8H), 7.00-7.09 (m, 2H), 4.16 (s, 3H), 3.92 (s, 3H). LC-MS: m/z 442.1 (M+H)$^+$.

Step E: 7-methoxy-6-(4-methoxyphenyl)-2,3-diphenyl-N-(pyridazin-3-yl)pyrazolo[1,5-a]pyrimidin-5-amine

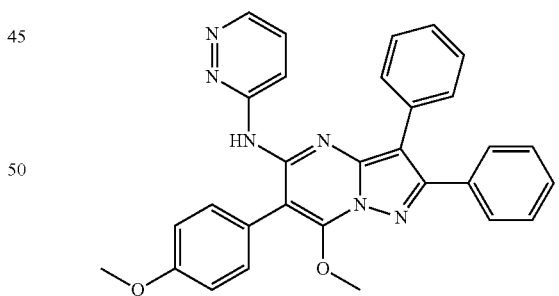

A suspension of Intermediate 5, 5-chloro-7-methoxy-6-(4-methoxyphenyl)-2,3-diphenylpyrazolo [1,5-a]pyrimidine, (600 mg, 1.36 mmol), 3-aminopyridazine (258 mg, 2.72 mmol, 2 eq.), Pd(OAc)$_2$ (61 mg, 0.27 mmol, 0.2 eq.), Xantphos (197 mg, 0.34 mmol, 0.25 eq.) and Cs$_2$CO$_3$ (890 mg, 2.72 mmol, 2.0 eq.) in 1.4-dioxane (5 mL) was stirred at 120° C. through microwave irradiation for 1 hour under N$_2$ atmosphere. The mixture was filtered through celite and the filtrate was concentrated in vacuo. The residue was purified by flash chromatography to afford the desired product 6 as a yellow solid. LC-MS: m/z 501.0 (M+H)$^+$.

Step F: 6-(4-methoxyphenyl)-2,3-diphenyl-5-(pyridazin-3-ylamino)pyrazolo[1,5-a]pyrimidin-7(4H)-one

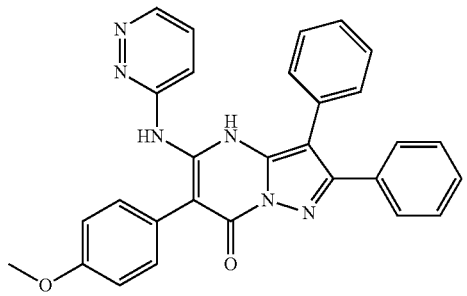 [SMILES: COc1ccc(-c2c(Nc3cccnn3)[nH]c3c(-c4ccccc4)c(-c4ccccc4)nn3c2=O)cc1]

A solution of Intermediate 6 (360 mg, 0.72 mmol) in 4M HCl in 1.4-dioxane (5 mL) was stirred at r.t. for 2 hours. Solvent and volatile were removed in vacuo. The residue was dissolved in DCM (5 mL) and treated with aq saturated NaHCO$_3$. The organic phase was separated and washed with brine, dried over anhydrous Na$_2$SO$_4$ and concentrated in vacuo to afford the desired product 7.

$^1$H NMR (DMSO-d$_6$): δ 15.25 (br. s., 1H), 9.21 (br. s., 1H), 8.86 (br. s., 1H), 7.63 (br. s., 2H), 7.44-7.58 (m, 4H), 7.28-7.44 (m, 8H), 7.05 (d, J=8.6 Hz, 2H), 3.82 (s, 3H). LC-MS: m/z 486.9 (M+H)$^+$.

The following compounds were prepared according to the procedure for compound 101, step E and F, starting from intermediate 5 therein. Step E was performed using appropriate amine 9, base (Cs$_2$CO$_3$, K$_2$CO$_3$, Na$_2$CO$_3$, and etc.) and catalyst/ligand under microwave or thermal heating, in 1,4-dioxane unless otherwise noted. Step F was performed using 5 mL of 4M HCl in dioxane unless otherwise noted. Purifications were performed using the methods used in Example 101, unless otherwise noted.

Compound 102: 6-(4-methoxyphenyl)-2,3-diphenyl-5-(pyridin-2-ylamino)pyrazolo[1,5-a]pyrimidin-7(4H)-one

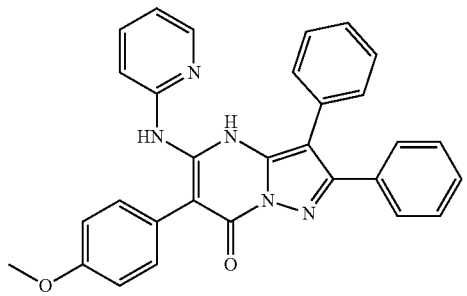 [SMILES: COc1ccc(-c2c(Nc3ccccn3)[nH]c3c(-c4ccccc4)c(-c4ccccc4)nn3c2=O)cc1]

Step E stoichiometry: Intermediate 5 (500 mg, 1.13 mmol), pyridin-2-amine (213 mg, 2.26 mmol), Pd(OAc)$_2$ (50 mg, 0.23 mmol), xantphos (165 mg, 0.28 mmol), and Na$_2$CO$_3$ (240 mg, 2.26 mmol) in 1,4-dioxane (10 mL) under heating at 100° C. for 4 h under N$_2$. LC-MS: m/z 500.0 (M+H)$^+$.

Step F: 7-methoxy-6-(4-methoxyphenyl)-2,3-diphenyl-N-(pyridin-2-yl)pyrazolo[1,5-a]pyrimidin-5-amine (300 mg, 0.6 mmol) was dissolved in HCl/1,4-dioxane (5 mL). The solution was stirred at r.t. overnight. The precipitate was filtered off and washed with CH$_2$Cl$_2$ (3*1 mL) to give a yellow solid. The solid was then dissolved in CH$_2$Cl$_2$/MeOH (10/1, 3 mL). After 3 mL of NH$_3$-MeOH was added, the solution was stirred at r.t. overnight to give the title compound.

$^1$H NMR (TRIFLUOROACETIC ACID-d): δ 8.05-8.15 (m, 1H), 7.79 (d, J=5.6 Hz, 1H), 7.59 (d, J=7.2 Hz, 2H), 7.46-7.56 (m, 6H), 7.36-7.46 (m, 4H), 7.25-7.34 (m, 2H), 7.16 (d, J=8.8 Hz, 2H), 3.97 (s, 3H). LC-MS: m/z 486.2 (M+H)$^+$.

Compound 103: 6-(4-methoxyphenyl)-2,3-diphenyl-5-(pyridin-3-ylamino)pyrazolo[1,5-a]pyrimidin-7(4H)-one

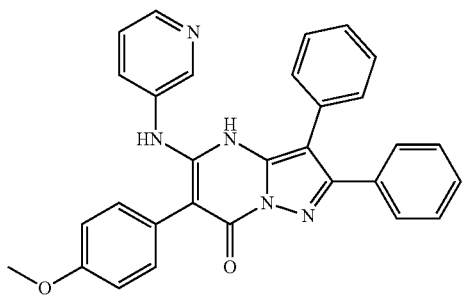 [SMILES: COc1ccc(-c2c(Nc3cccnc3)[nH]c3c(-c4ccccc4)c(-c4ccccc4)nn3c2=O)cc1]

Step E stoichiometry: Intermediate 5 (500 mg, 1.13 mmol), pyridin-3-amine (117 mg, 1.24 mmol), Pd(OAc)$_2$ (25 mg, 0.113 mmol), xantphos (131 mg, 0.226 mmol), Cs$_2$CO$_3$ (737 mg, 2.26 mmo) in dioxane (20 mL) under heating to 110° C. for 4 h under N$_2$. LC-MS: m/z 500.2 (M+H)$^+$.

Step F: To a solution of 7-methoxy-6-(4-methoxyphenyl)-2,3-diphenyl-N-(pyridin-3-yl)pyrazolo[1,5-a]pyrimidin-5-amine (150 mg, 0.309 mmol) in MeOH (10 mL) was added 4N HCl solution in dioxane (10 mL). The reaction mixture was heated to 50° C. for 2 h. The mixture was concentrated in vacuo. The residue was suspended in saturated NaHCO$_3$ solution to give the desired product 6-(4-methoxyphenyl)-2,3-diphenyl-5-(pyridin-3-ylamino)pyrazolo[1,5-a]pyrimidin-7(4H)-one.

$^1$H NMR (DMSO-d$_6$): δ 8.48 (br. s., 1H), 8.30 (br. s., 1H), 8.10 (d, J=4.6 Hz, 1H), 7.71 (br. s., 1H), 7.46 (br. s., 3H), 7.14-7.41 (m, 11H), 6.93 (d, J=8.1 Hz, 2H), 3.76 (s, 3H). LC-MS: m/z 486.2 (M+H)$^+$.

Compound 104: 6-((6-(4-methoxyphenyl)-7-oxo-2,3-diphenyl-4,7-dihydropyrazolo[1,5-a]pyrimidin-5-yl)amino)nicotinonitrile

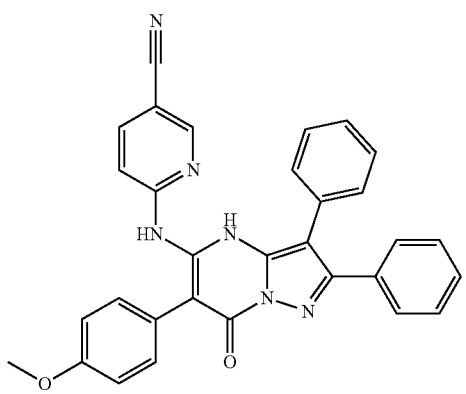

Step E stoichiometry: Intermediate 5 (300 mg, 0.68 mmol), 6-aminonicotinonitrile (161.7 mg, 1.36 mmol), palladium diacetate (30.5 mg, 0.14 mmol), Xantphos (117.8 mg, 0.20 mmol) and Cesium carbonate (553.0 mg, 1.70 mmol) in 1,4-dioxane (10 mL) under heating to 110° C. for 12 hours under nitrogen atmosphere. LC-MS: m/z 525.2 (M+H)+.

Step F: The solution of 6-((7-methoxy-6-(4-methoxyphenyl)-2,3-diphenylpyrazolo[1,5-a]pyrimidin-5-yl)amino) nicotinonitrile (40 mg, 0.07 mmol) in HCl solution (1.0 M in 1,4-dioxane, 6 mL) was stirred at room temperature for 12 hours. The mixture was concentrated, and NH$_4$OH (5 mL) was added thereto to obtain 6-((6-(4-methoxyphenyl)-7-oxo-2,3-diphenyl-4,7-dihydropyrazolo[1,5-a]pyrimidin-5-yl)amino)nicotinonitrile.

$^1$H NMR (DMSO-d$_6$): δ 14.21 (br. s., 1H), 9.53 (s, 1H), 8.53 (d, J=2.1 Hz, 1H), 8.11 (dd, J=8.9, 2.1 Hz, 1H), 7.50-7.62 (m, 4H), 7.36-7.45 (m, 6H), 7.29-7.36 (m, 3H), 7.03 (d, J=8.6 Hz, 2H), 3.82 (s, 3H). LC-MS: m/z 511.3 (M+H)+.

Compound 105: 5-((5-fluoropyridin-2-yl)amino)-6-(4-methoxyphenyl)-2,3-diphenylpyrazolo[1,5-a]pyrimidin-7(4H)-one

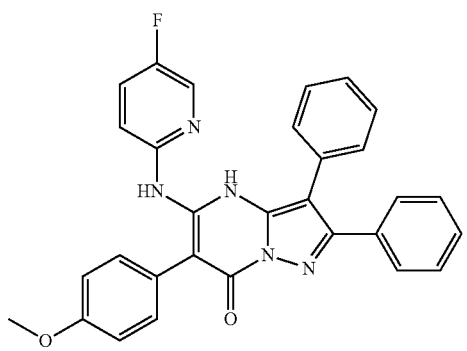

Step E stoichiometry: Intermediate 5 (220 mg, 0.5 mmol), 5-fluoropyridin-2-amine (112 mg, 1.0 mmol), Pd(OAc)$_2$ (56 mg, 0.25 mmol), xantphos (173 mg, 0.3 mmol), Cs$_2$CO$_3$ (117 mg, 1.1 mmo) in dioxane (20 mL) under heating to 100° C. for 4 h under N$_2$. LC-MS: m/z 518.2 (M+H)+.

Step F: To a solution of N-(5-fluoropyridin-2-yl)-7-methoxy-6-(4-methoxyphenyl)-2,3-diphenylpyrazolo[1,5-a]pyrimidin-5-amine (50 mg, 0.10 mmol) in MeOH (10 mL) was added 4N HCl solution in dioxane (10 mL). The reaction mixture was heated to 50° C. for 2 h. The mixture was concentrated in vacuo. The residue was suspended in saturated NaHCO$_3$ solution to give the desired product 5-((5-fluoropyridin-2-yl)amino)-6-(4-methoxyphenyl)-2,3-diphenylpyrazolo[1,5-a]pyrimidin-7(4H)-one.

$^1$H NMR (DMSO-d$_6$): δ 14.87 (br. s., 1H), 9.08 (s, 1H), 7.94-8.07 (m, 1H), 7.71-7.88 (m, 1H), 7.50-7.64 (m, 4H), 7.38-7.44 (m, 6H), 7.29-7.35 (m, J=8.5 Hz, 2H), 6.99-7.10 (m, J=8.5 Hz, 2H), 3.83 (s, 3H). LC-MS: m/z 503.9 (M+H)+.

Compound 106: 5-((5-chloropyridin-2-yl)amino)-6-(4-methoxyphenyl)-2,3-diphenylpyrazolo[1,5-a]pyrimidin-7(4H)-one

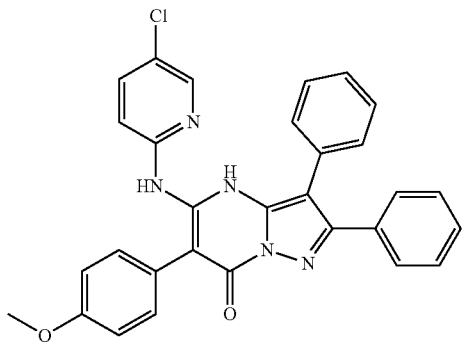 [SMILES: COc1ccc(-c2c(Nc3ccc(F)cn3)[nH]c3c(-c4ccccc4)c(-c4ccccc4)nn3c2=O)cc1]

Step E stoichiometry: Intermediate 5 (200 mg, 0.45 mmol), 5-chloropyridin-2-amine (135 mg, 0.9 mmol), Pd(OAc)$_2$ (51 mg, 0.23 mmol), xantphos (156 mg, 0.27 mmol), and Na$_2$CO$_3$ (105 mg, 0.9 mmol) in 1,4-dioxane (5 mL) under heating at 100° C. for 16 h under N$_2$. LC-MS: m/z 533.9, 535.9 (M+H)+.

Step F: N-(5-chloropyridin-2-yl)-7-methoxy-6-(4-methoxyphenyl)-2,3-diphenylpyrazolo[1,5-a]pyrimidin-5-amine (80 mg, 0.15 mmol) was dissolved in HCl-1,4-dioxane (5 mL). The solution was stirred at r.t. overnight. The precipitate was filtered off and washed with CH$_2$Cl$_2$(3 mL) to give a yellow solid. The solid was then dissolved in CH$_2$Cl$_2$/MeOH (10/1, 2 mL). After 1 mL of NH$_3$-MeOH was added, the solution was stirred at r.t. overnight to give the title compound 7.

$^1$H NMR (DMSO-d$_6$): δ 14.72 (s, 1H), 9.16 (s, 1H), 8.01 (s, 1H), 7.88 (d, J=9.2 Hz, 1H), 7.49-7.66 (m, 4H), 7.40 (d, J=7.2 Hz, 9H), 7.32 (d, J=8.2 Hz, 2H), 7.04 (d, J=8.2 Hz, 2H), 3.82 (s, 3H). LC-MS: m/z 519.9, 521.9 (M+H)+.

Compound 107: 6-(4-methoxyphenyl)-5-((5-nitropyridin-2-yl)amino)-2,3-diphenylpyrazolo[1,5-a]pyrimidin-7(4H)-one

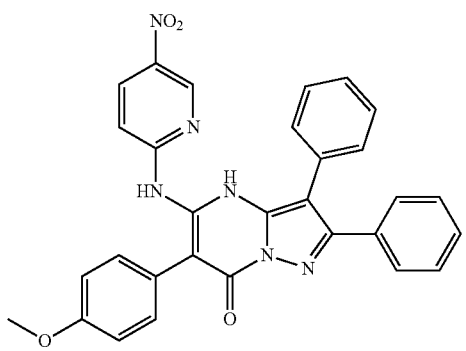 [SMILES: COc1ccc(-c2c(Nc3ccc([N+](=O)[O-])cn3)[nH]c3c(-c4ccccc4)c(-c4ccccc4)nn3c2=O)cc1]

Step E stoichiometry: Intermediate 5 (500 mg, 1.13 mmol) and 5-nitropyridin-2-amine (472 mg, 3.39 mmol, 3 eq) and Pd(OAc)$_2$ (51 mg, 0.23 mmol, 0.2 eq), Xantphos (262 mg, 0.45 mmol, 0.4 eq) and Na$_2$CO$_3$ (360 mg, 3.394 mmol, 3 eq) in 1,4-dioxane (10 mL) was stirred and warmed up to 100° C. under microwave irradiation for 1 hours under N$_2$ atmosphere.

¹H NMR (DMSO-d₆) δ 9.03 (d, J=2.7 Hz, 1H), 8.55-8.66 (m, 2H), 8.12 (s, 1H), 7.58-7.65 (m, 2H), 7.43-7.54 (m, 9H), 7.31-7.36 (m, 1H), 7.19 (d, J=8.5 Hz, 2H), 4.16 (s, 3H), 3.87 (s, 3H). LC-MS: m/z 545.2 (M+H)⁺.

Step F: A solution of 7-methoxy-6-(4-methoxyphenyl)-N-(5-nitropyridin-2-yl)-2,3-diphenylpyrazolo[1,5-a]pyrimidin-5-amine (50 mg, 0.092 mmol) in 4M HCl in 1.4-dioxane (10 mL) was stirred at room temperature for 3 hours. The reaction mixture was concentrate in vacuo, The residue was dissolved in 7N amine in methanol and stirred at room temperature for 2 h. The mixture was concentrated in vacuo to give 6-(4-methoxyphenyl)-5-((5-nitropyridin-2-yl)amino)-2,3-diphenylpyrazolo[1,5-a]pyrimidin-7(4H)-one.

¹H NMR (DMSO-d₆) δ: 13.95 (br. s., 1H), 9.82-9.91 (m, 1H), 8.85 (br. s., 1H), 8.45 (br. s., 1H), 7.54 (dd, J=6.18, 2.96 Hz, 4H), 7.37-7.45 (m, 5H), 7.33 (m, J=8.86 Hz, 2H), 7.02 (m, J=8.60 Hz, 2H), 3.81 (s, 3H). LC-MS: m/z 531.0 (M+H)⁺.

Compound 108: 5-(5-hydroxypyridin-2-ylamino)-6-(4-methoxyphenyl)-2,3-diphenylpyrazolo[1,5-a]pyrimidin-7(4H)-one

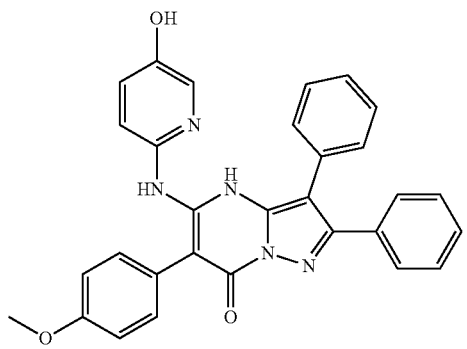 [SMILES: COc1ccc(-c2c(Nc3ccc(O)cn3)[nH]c3c(-c4ccccc4)c(-c4ccccc4)nn3c2=O)cc1]

Step E stoichiometry: Intermediate 5 (160 mg, 0.362 mmol), 5-(tert-butyldimethylsilyloxy) pyridin-2-amine (162 mg, 0.724 mmol), palladium(II) acetate (16 mg, 0.0724 mmol), xantphos (84 mg, 0.145 mmol) and sodium carbonate (77 mg, 0.724 mmol) in 1.4-dioxane (10 mL) under heating to reflux for 4 hours under nitrogen atmosphere. LC-MS: m/z 630.3 (M+H)⁺.

Step F: A mixture of N-(5-(tert-butyldimethyl-silyloxy)pyridin-2-yl)-7-methoxy-6-(4-methoxyphenyl)-2,3-diphenylpyrazolo[1,5-a]pyrimidin-5-amine (80 mg, 0.127 mmol) and HCl solution (4N in dioxane, 10 mL) was stirred at room temperature for 6 h. Then conc. HCl (0.5 mL) was added into the mixture. The resulting mixture was stirred at the same temperature for 4 h. The mixture was quenched with ammonia solution (7N in methanol) to pH 7 to afford 5-(5-hydroxypyridin-2-ylamino)-6-(4-methoxyphenyl)-2,3-diphenylpyrazolo[1,5-a] pyrimidin-7(4H)-one as a white solid.

¹H NMR (TFA-d): δ 7.71-7.80 (m, 1H), 7.57 (d, J=7.32 Hz, 2H), 7.44-7.54 (m, 7H) 7.30-7.43 (m, 4H), 7.18 (d, J=9.46 Hz, 1H), 7.13 (d, J=8.54 Hz, 2H), 3.94 (s, 3H). LC-MS: m/z 502.4 (M+H)⁺.

Compound 109: 5-((4-hydroxypyridin-2-yl)amino)-6-(4-methoxyphenyl)-2,3-diphenylpyrazolo[1,5-a]pyrimidin-7(4H)-one

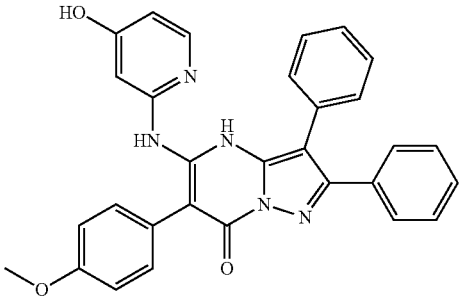 [SMILES: COc1ccc(-c2c(Nc3cc(O)ccn3)[nH]c3c(-c4ccccc4)c(-c4ccccc4)nn3c2=O)cc1]

Step E stoichiometry: Intermediate 5 (80 mg, 0.18 mmol) and 2-aminopyridin-4-ol (30 mg, 0.27 mmol, 1.5 eq) and Pd(OAc)₂ (6.1 mg, 0.03 mmol, 0.15 eq), Xantphos (15.7 mg, 0.03 mmol, 0.15 eq) and Cs₂CO₃ (120 mg, 0.36 mmol, 2.0 eq) in 1.4-dioxane (3 mL) at 110° C. for 1 h under microwave radiation under N₂ atmosphere. LC-MS: m/z 516.0 (M+H)⁺.

Step F: A solution of 2-((7-methoxy-6-(4-methoxyphenyl)-2,3-diphenylpyrazolo[1,5-a]pyrimidin-5-yl)amino)pyridin-4-ol (40 mg, 0.08 mmol) in 4M HCl in 1.4-dioxane (10 mL) was stirred at 30° C. for 2 hours to obtain the title compound.

¹H NMR (CHLOROFORM-d): δ 7.66 (s, 1H), 7.57 (d, J=7.2 Hz, 2H), 7.54-7.44 (m, 6H), 7.44-7.34 (m, 4H), 7.11 (s, 2H), 6.72 (m, 2H), 3.99 (s, 1H), 3.94 (s, 3H). LC-MS: m/z 502.0 (M+H)⁺.

Compound 110: 5-(((6-fluoropyridin-2-yl)amino)-6-(4-methoxyphenyl)-2,3-diphenylpyrazolo[1,5-a]pyrimidin-7(4H)-one

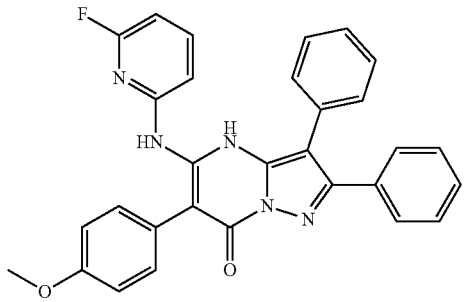 [SMILES: COc1ccc(-c2c(Nc3cccc(F)n3)[nH]c3c(-c4ccccc4)c(-c4ccccc4)nn3c2=O)cc1]

Step E stoichiometry: Intermediate 5 (200 mg, 0.45 mmol), 6-fluoropyridin-2-amine (101 mg, 0.9 mmol), Pd(OAc)₂ (20 mg, 0.09 mmol), xantphos (65 mg, 0.11 mmol), and Cs₂CO₃ (293 mg, 0.9 mmol) in 1,4-dioxane (5 mL) under heating at 100° C. for 16 h under N₂. LC-MS: m/z 518.1 (M+H)⁺.

Step F: N-(6-fluoropyridin-2-yl)-7-methoxy-6-(4-methoxyphenyl)-2,3-diphenylpyrazolo[1,5-a]pyrimidin-5-amine (120 mg, 0.23 mmol) was dissolved in HCl-1,4-dioxane (5 mL). The solution was stirred at r.t. overnight. The precipitate was filtered off and washed with CH₂Cl₂ (3 mL) to give a yellow solid. The solid was then dissolved in CH₂Cl₂/MeOH (10/1, 2 mL). After 1 mL of NH₃-MeOH was added, the solution was stirred at r.t. overnight to give the title compound 7.

¹H NMR (DMSO-d₆): δ 13.33 (s, 1H), 9.16 (s, 1H), 7.86 (q, J=8.4 Hz, 1H), 7.54-7.48 (m, 2H), 7.34-7.48 (m, 8H), 7.32 (d, J=8.6 Hz, 2H), 7.09 (d, J=8.4 Hz, 1H), 7.03 (d, J=8.6 Hz, 2H), 6.73 (d, J=8.4 Hz, 1H), 3.81 (s, 3H). LC-MS: m/z 503.9 (M+H)⁺.

Compound 111: 6-((6-(4-methoxyphenyl)-7-oxo-2,3-diphenyl-4,7-dihydropyrazolo[1,5-a]pyrimidin-5-yl)amino)picolinonitrile

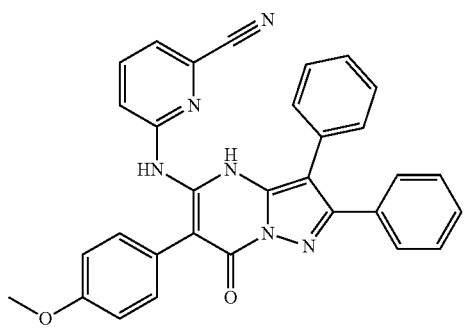 [SMILES: COc1ccc(-c2c(Nc3cccc(C#N)n3)[nH]c3c(-c4ccccc4)c(-c4ccccc4)nn3c2=O)cc1]

Compound 112 6-((6-(4-methoxyphenyl)-7-oxo-2,3-diphenyl-4,7-dihydropyrazolo[1,5-a]pyrimidin-5-yl)amino)picolinamide

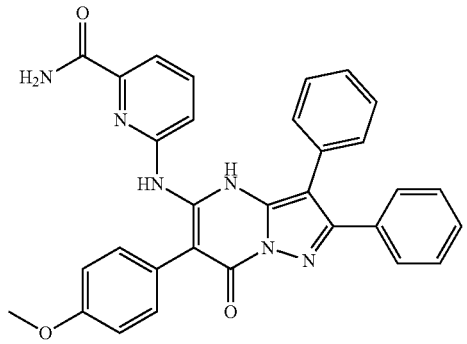 [SMILES: COc1ccc(-c2c(Nc3cccc(C(N)=O)n3)[nH]c3c(-c4ccccc4)c(-c4ccccc4)nn3c2=O)cc1]

Step E stoichiometry: Intermediate 5 (800 mg, 1.8 mmol) and 6-aminopicolinonitrile (281 mg, 2.36 mmol, 1.3 eq) and Pd(OAc)₂ (61.2 mg, 0.27 mmol, 0.15 eq), Xantphos (157.4 mg, 0.27 mmol, 0.15 eq) and Cs₂CO₃ (1.2 g, 3.63 mmol, 2.0 eq) in 1.4-dioxane (15 mL) at 110° C. for 1 h under microwave irradiation under N₂ atmosphere. LC-MS: m/z 524.9 (M+H)⁺.

Step F: A solution of 6-((7-methoxy-6-(4-methoxyphenyl)-2,3-diphenylpyrazolo[1,5-a]pyrimidin-5-yl)amino)picolinonitrile (220 mg, 0.42 mmol) in 4M HCl in 1.4-dioxane (10 mL) was stirred at 30° C. for 5 hours to obtain the title compounds 6-((6-(4-methoxyphenyl)-7-oxo-2,3-diphenyl-4,7-dihydropyrazolo[1,5-a]pyrimidin-5-yl)amino)picolinonitrile and 6-((6-(4-methoxyphenyl)-7-oxo-2,3-diphenyl-4,7-dihydropyrazolo[1,5-a]pyrimidin-5-yl)amino)picolinamide.

6-((6-(4-methoxyphenyl)-7-oxo-2,3-diphenyl-4,7-dihydropyrazolo[1,5-a]pyrimidin-5-yl)amino)picolinonitrile ¹H NMR (DMSO-d₆) δ: 12.69 (s, 1H), 9.31 (s, 1H), 7.87 (dd, J=8.8, 7.6 Hz, 1H), 7.60 (d, J=7.2 Hz, 1H), 7.54-7.45 (m, 4H), 7.44-7.34 (m, 7H), 7.32 (d, J=8.8 Hz, 2H), 7.01 (d, J=8.8 Hz, 2H), 3.80 (s, 3H). LC-MS: m/z 510.9 (M+H)⁺.

6-((6-(4-methoxyphenyl)-7-oxo-2,3-diphenyl-4,7-dihydropyrazolo[1,5-a]pyrimidin-5-yl)amino)picolinamide ¹H NMR (DMSO-d₆) δ: 12.42 (s, 1H), 9.00 (s, 1H), 7.97 (s, 1H), 7.79 (t, J=8.0 Hz, 1H), 7.55-7.43 (m, 4H), 7.37 (m, 10H), 7.19 (d, J=8.4 Hz, 1H), 7.00 (d, J=8.4 Hz, 2H), 3.79 (s, 3H). LC-MS: m/z 529.0 (M+H)⁺.

Compound 113: 5-(3-hydroxypyridin-2-ylamino)-6-(4-methoxy-phenyl)-2,3-diphenylpyrazolo[1,5-a]pyrimidin-7(4H)-one

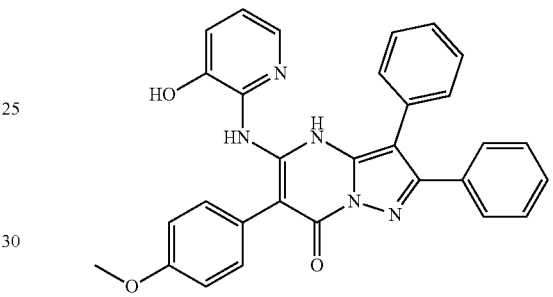

A suspension of Intermediate 5 (200 mg, 0.452 mmol), 3-(tert-butyl-dimethylsilyloxy)pyridin-2-amine (202 mg, 0.904 mmol), palladium(II) acetate (31 mg, 0.136 mmol), xantphos (157 mg, 0.272 mmol) and sodium carbonate (96 mg, 0.904 mmol) in 1.4-dioxane (10 mL) was stirred and heated to reflux for 4 hours under nitrogen atmosphere. The reaction was then cooled to room temperature and filtered. The filtrate was concentrated in vacuum to afford 5-(3-hydroxypyridin-2-ylamino)-6-(4-methoxy-phenyl)-2,3-diphenylpyrazolo[1,5-a]pyrimidin-7(4H)-one.

¹H NMR (TFA-d): δ 8.33 (d, J=8.33 Hz, 1H), 7.99 (d, J=5.10 Hz, 1H), 7.56-7.71 (m, 8H), 7.48-7.54 (m, 4H), 7.42 (dd, J=8.33, 5.91 Hz, 1H), 7.34 (d, J=8.60 Hz, 2H), 4.10 (s, 3H). LC-MS: m/z 502.4 (M+H)⁺.

Compound 114: 2-(6-(4-methoxyphenyl)-7-oxo-2,3-diphenyl-4,7-dihydropyrazolo[1,5-a]pyrimidin-5-ylamino)isonicotinonitrile

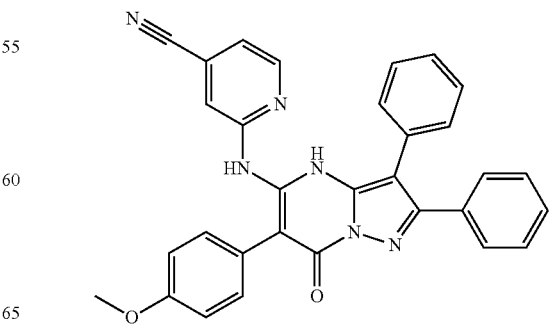

Step E stoichiometry: Intermediate 5 (200 mg, 0.452 mmol) and 2-aminoisonicotinonitrile (108 mg, 0.9 mmol) and Pd(OAc)$_2$ (102 mg, 0.434 mmol), Xantphos (315 mg, 0.54 mmol) and Cs$_2$CO$_3$ (327 mg, 1.0 mmol) in 1.4-dioxane (10 mL) under heating to 110° C. for 1 hour through microwave irradiation under N$_2$ atmosphere. LC-MS: m/z 525.2 (M+H)$^+$.

Step F: A mixture of 2-(7-methoxy-6-(4-methoxyphenyl)-2,3-diphenylpyrazolo[1,5-a]pyrimidin-5-ylamino) isonicotinonitrile (15 mg, 0.03 mmol) in HCl solution (4 M in dioxane, 1 mL) was stirred at room temperature overnight. The mixture was quenched with NH$_3$ solution (7M in methanol) to pH 7-8 to afford 6-(4-methoxyphenyl)-5-(2-methoxypyrimidin-4-ylamino)-2,3-diphenyl pyrazolo [1,5-a] pyrimidin-7(4H)-one.

$^1$H NMR (DMSO-d$_6$): δ 8.25 (d, J=5.37 Hz, 1H), 7.77 (s, 1H), 7.49-7.63 (m, 4H), 7.37-7.47 (m, 7H), 7.34 (m, J=8.60 Hz, 2H), 7.06 (m, J=8.60 Hz, 2H), 3.84 (s, 3H). LC-MS: m/z 511.2 (M+H)$^+$.

Compound 115: 2-(6-(4-methoxyphenyl)-7-oxo-2,3-diphenyl-4,7-dihydropyrazolo [1,5-a] pyrimidin-5-ylamino)pyrimidine-5-carbonitrile

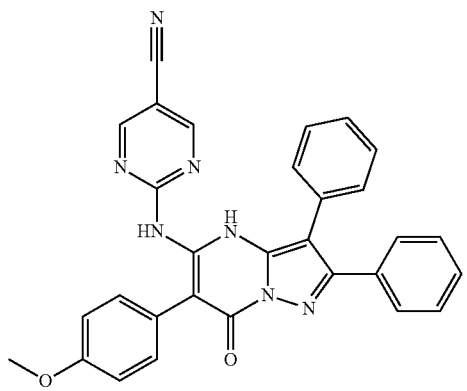 [SMILES: COc1ccc(-c2c(Nc3ncc(C#N)cn3)[nH]c3c(-c4ccccc4)c(-c4ccccc4)nn3c2=O)cc1]

A mixture of Intermediate 5 (200 mg, 0.452 mmol) and 2-aminopyrimidine-5-carbonitrile (108 mg, 0.904 mmol) and Pd(OAc)$_2$ (31 mg, 0.136 mmol), Xantphos (157 mg, 0.272 mmol) and Na$_2$CO$_3$ (96 g, 0.904 mmol) in 1.4-dioxane (10 mL) was stirred and heated to reflux for 4 hours under N$_2$ atmosphere. The reaction was then cooled to room temperature and filtered. The filtrate was concentrated in vacuum to afford 2-(6-(4-methoxyphenyl)-7-oxo-2,3-diphenyl-4,7-dihydropyrazolo[1,5-a]pyrimidin-5-ylamino)pyrimidine-5-carbonitrile.

$^1$H NMR (DMSO-d$_6$): δ 12.77 (bs, 1H), 10.27 (bs, 1H), 8.88 (s., 2H), 7.43-7.52 (m, 4H), 7.35-7.40 (m, 4H), 7.32 (d, J=7.63 Hz, 2H), 7.25 (d, J=8.54 Hz, 2H), 6.93 (d, J=8.24 Hz, 2H), 3.76 (s, 3H). LC-MS: m/z 512.2 (M+H)$^+$.

Compound 116: 6-(4-methoxyphenyl)-2,3-diphenyl-5-(pyrimidin-4-ylamino)pyrazolo[1,5-a]pyrimidin-7(4H)-one

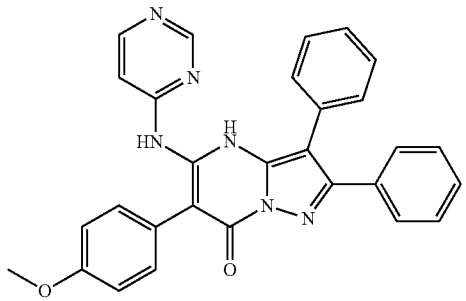 [SMILES: COc1ccc(-c2c(Nc3ccncn3)[nH]c3c(-c4ccccc4)c(-c4ccccc4)nn3c2=O)cc1]

Step E stoichiometry: Intermediate 5 (440 mg, 1 mmol), pyrimidin-4-amine (190 mg, 2 mmol, 2 eq.), Pd(OAc)$_2$ (22 mg, 0.1 mmol, 0.1 eq.), Xantphos (116 mg, 0.2 mmol, 0.2 eq.) and Cs$_2$CO$_3$ (390 mg, 1.2 mmol, 1.2 eq.) in 1.4-dioxane (10 mL) under heating at 100° C. through microwave irradiation for 1 hour under N$_2$ atmosphere. LC-MS: m/z 501.5 (M+H)$^+$.

Step F: A solution of 7-methoxy-6-(4-methoxyphenyl)-2,3-diphenyl-N-(pyrimidin-4-yl)pyrazolo[1,5-a]pyrimidin-5-amine (260 mg, 0.52 mmol) in 4M HCl in 1.4-dioxane (10 mL) was stirred at r.t. for 16 hours to give the title compound.

$^1$H NMR (DMSO-d$_6$): δ 13.13 (s, 1H), 11.25 (s, 1H), 8.90 (s, 1H), 8.45 (d, J=7.0 Hz, 1H), 7.44-7.53 (m, 4H), 7.25-7.42 (m, 7H), 7.18 (d, J=6.4 Hz, 1H), 6.95 (d, J=8.8 Hz, 2H), 3.77 (s, 3H). LC-MS: m/z 487.0 (M+H)$^+$.

Compound 117: 5-((6-aminopyrimidin-4-yl)amino)-6-(4-methoxyphenyl)-2,3-diphenylpyrazolo[1,5-a]pyrimidin-7(4H)-one

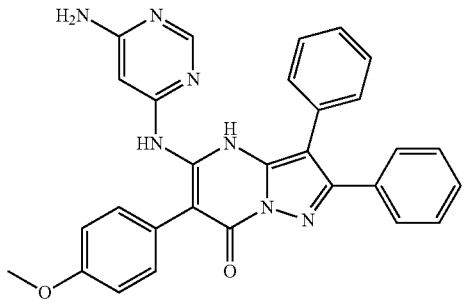

Step E stoichiometry: Intermediate 5 (237 mg, 0.538 mmol), pyrimidine-4,6-diamine (118.2 mg, 1.07 mmol, 2 eq.), Pd(OAc)$_2$ (60 mg, 0.269 mmol, 0.5 eq.), Xantphos (186.5 mg, 0.322 mmol, 0.6 eq.) and Na$_2$CO$_3$ (125 mg, 1.184 mmol, 2.2 eq.) in 1.4-dioxane (5 mL) under heating at 100° C. for 3 hour under N$_2$ atmosphere. LC-MS: m/z 516.5 (M+H)$^+$.

Step F: A solution of N4-(7-methoxy-6-(4-methoxyphenyl)-2,3-diphenylpyrazolo[1,5-a]pyrimidin-5-yl)pyrimidine-4,6-diamine (90 mg, 0.17 mmol) in 4M HCl in 1.4-dioxane (3 mL) was stirred at r.t. for 3 hours to give the title compound.

¹H NMR (DMSO-d₆): δ 13.54 (br. s., 1H), 9.94 (br. s., 1H), 8.27 (s, 1H), 7.82 (br. s., 2H), 7.43-7.52 (m, 4H), 7.31-7.42 (m, 6H), 7.28 (d, J=8.6 Hz, 2H), 6.98 (d, J=8.6 Hz, 2H), 6.02 (br. s., 1H), 3.78 (s, 3H). LC-MS: m/z 502.9 (M+H)⁺.

Compound 118: 6-(4-methoxyphenyl)-5-((2-methoxypyrimidin-4-yl)amino)-2,3-diphenylpyrazolo[1,5-a]pyrimidin-7(4H)-one

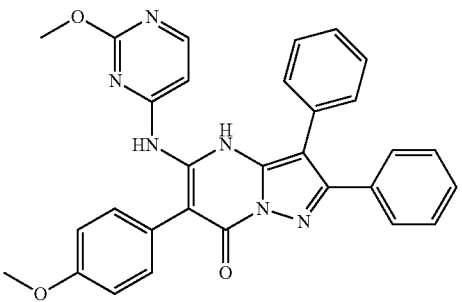 [SMILES: COc1ccc(-c2c(Nc3ccnc(OC)n3)[nH]c3c(-c4ccccc4)c(-c4ccccc4)nn3c2=O)cc1]

Step E stoichiometry: Intermediate 5 (300 mg, 0.67 mmol), 2-methoxypyrimidin-4-amine (169 mg, 1.25 mmol), Pd(OAc)₂ (48 mg, 0.067 mmol), xantphos (72 mg, 0.13 mmol), Cs₂CO₃ (409 mg, 1.25 mmo) in dioxane (20 mL) under heating to 110° C. for 4 h under N₂. LC-MS: m/z 531.2 (M+H)⁺.

Step F: To a solution of 7-methoxy-6-(4-methoxyphenyl)-N-(2-methoxypyrimidin-4-yl)-2,3-diphenylpyrazolo[1,5-a]pyrimidin-5-amine (100 mg, 0.19 mmol) in MeOH (10 mL) was added 4N HCl solution in dioxane (10 mL). The reaction mixture was heated to 50° C. for 2 h. The mixture was concentrated in vacuo. The residue was suspended in saturated NaHCO₃ solution to give the desired product 6-(4-methoxyphenyl)-5-((2-methoxypyrimidin-4-yl)amino)-2,3-diphenylpyrazolo[1,5-a]pyrimidin-7(4H)-one.

¹H NMR (TFA): δ 8.30 (d, J=7.0 Hz, 1H), 7.63-7.78 (m, 3H), 7.40-7.63 (m, 8H), 7.27 (d, J=7.5 Hz, 2H), 7.04 (d, J=7.0 Hz, 1H), 3.98 (s, 3H), 3.48 (s, 3H). LC-MS: m/z 517.0 (M+H)⁺.

Compound 119: 5-(2-hydroxypyrimidin-4-ylamino)-6-(4-methoxyphenyl)-2,3-diphenyl-pyrazolo[1,5-a]pyrimidin-7(4H)-one

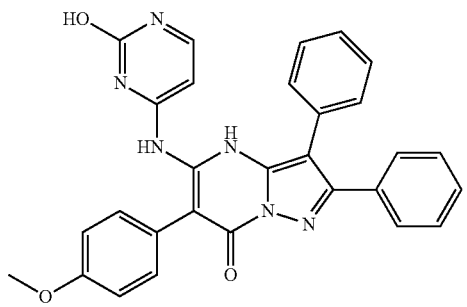

A mixture of 7-methoxy-6-(4-methoxyphenyl)-N-(2-methoxypyrimidin-4-yl)-2,3-diphenyl-pyrazolo[1,5-a]pyrimidin-5-amine (126 mg, 0.244 mmol) and conc.HCl (10 mL) was heated to reflux for 2 days. The mixture was quenched with ammonia solution (7N in methanol) to pH 7 and concentrated to afford 5-(2-hydroxypyrimidin-4-ylamino)-6-(4-methoxyphenyl)-2,3-diphenyl-pyrazolo[1,5-a] pyrimidin-7(4H)-one.

¹H NMR (DMSO-d₆): δ 7.52 (d, J=6.71 Hz, 3H), 7.45 (d, J=6.71 Hz, 2H), 7.20-7.40 (m, 9H), 7.05-7.19 (m, 2H), 6.99 (bs, 2H), 3.80 (s, 3H). LC-MS: m/z 503.2 (M+H)⁺.

Compound 120: 6-(4-methoxyphenyl)-2,3-diphenyl-5-(pyrimidin-5-ylamino)pyrazolo[1,5-a]pyrimidin-7(4H)-one

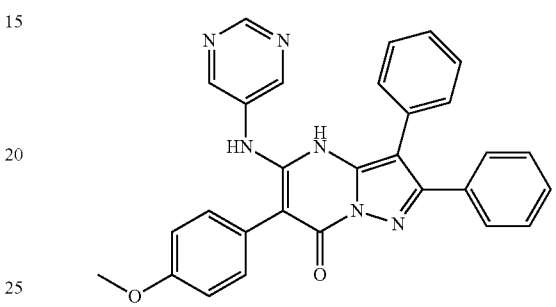

A suspension of Intermediate 5 (500 mg, 1.13 mmol) and pyrimidin-5-amine (323 mg, 3.39 mmol, 3 eq) and Pd(OAc)₂ (51 mg, 0.23 mmol, 0.2 eq), Xantphos (262 mg, 0.45 mmol, 0.4 eq) and Na₂CO₃ (356 mg, 3.39 mmol, 3 eq) in 1.4-dioxane (10 mL) was stirred and warmed up to 100° C. with microwave irradiation for 1 hours under N₂ atmosphere. The reaction was then cooled to r.t. to obtain 6-(4-methoxyphenyl)-2,3-diphenyl-5-(pyrimidin-5-ylamino)pyrazolo[1,5-a]pyrimidin-7(4H)-one.

¹H NMR (DMSO-d₆): δ 8.65 (s, 2H), 8.52 (br. s., 1H), 7.54 (d, J=8.87 Hz, 1H), 7.34-7.49 (m, 8H), 7.31 (br. s., 3H), 6.93 (br. s., 1H), 3.68-3.84 (m, 3H). LC-MS: m/z 487.0 (M+H)⁺.

Compound 121: 6-(4-methoxyphenyl)-2,3-diphenyl-5-(pyrimidin-2-ylamino)pyrazolo[1,5-a]pyrimidin-7(4H)-one

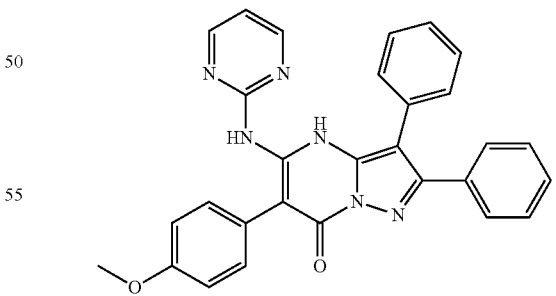

Step E stoichiometry: Intermediate 5 (200 mg, 0.4535 mmol), pyrimidin-2-amine (86 mg, 0.91 mmol, 2 eq.), Pd(OAc)₂ (102 mg, 0.4535 mmol, 1 eq.), Xantphos (314.5 mg, 0.54 mmol, 1.2 eq.) and Cs₂CO₃ (327 mg, 1 mmol, 2.2 eq.) in 1.4-dioxane (4 mL) under heating at 110° C. for 1 hour through microwave irradiation under N₂ atmosphere. LC-MS: m/z 501.6 (M+H)⁺.

Step F: A solution of 7-methoxy-6-(4-methoxyphenyl)-2,3-diphenyl-N-(pyrimidin-2-yl)pyrazolo[1,5-a]pyrimidin-5-amine (60 mg, 0.12 mmol) in 4M HCl in 1.4-dioxane (10 mL) was stirred at r.t. for 2 hours. Solvent and volatile were removed in vacuo. The residue was dissolved in DCM (5 mL) and treated with saturated NaHCO₃. The organic phase was separated and washed with brine, dried over anhydrous Na₂SO₄ and concentrated in vacuo to afford the title compound.

¹H NMR (DMSO-d₆): δ 14.08 (br. s., 1H), 8.60 (s, 1H), 8.57 (d, J=4.84 Hz, 2H), 7.52-7.62 (m, 4H), 7.40-7.49 (m, 6H), 7.37 (d, J=8.60 Hz, 2H), 7.18 (t, J=4.97 Hz, 1H), 7.08 (d, J=8.60 Hz, 2H), 3.84 (s, 3H). LC-MS: m/z 487.2 (M+H)⁺.

Compound 122: 5-((5-chloropyrimidin-2-yl)amino)-6-(4-methoxyphenyl)-2,3-diphenylpyrazolo[1,5-a]pyrimidin-7(4H)-one

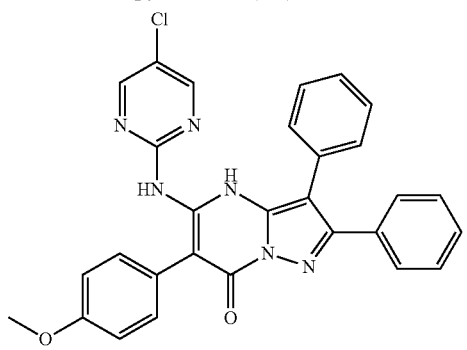

Step E stoichiometry: Intermediate 5 (220 mg, 0.5 mmol), 5-chloropyrimidin-2-amine (129 mg, 1.0 mmol), palladium diacetate (56 mg, 0.2 mmol), Xantphos (173 mg, 0.3 mmol) and sodium carbonate (117 mg, 1.1 mmol) in 1,4-dioxane (20 mL) under refluxing for 4 hours under nitrogen atmosphere. LC-MS: m/z 535.1 (M+H)⁺.

Step F: The solution of N-(5-chloropyrimidin-2-yl)-7-methoxy-6-(4-methoxyphenyl)-2,3-diphenylpyrazolo[1,5-a]pyrimidin-5-amine (50 mg, 0.1 mmol) in HCl solution (4.0 M in 1,4-dioxane, 5 mL) was stirred at room temperature for 2 hours. The mixture was concentrated, and NH₄OH (8 mL) was added thereto to obtain 6-((6-(4-methoxyphenyl)-7-oxo-2,3-diphenyl-4,7-dihydropyrazolo[1,5-a]pyrimidin-5-yl)amino)nicotinonitrile.

¹H NMR (DMSO-d₆): δ 13.13 (s, 1H), 9.27 (s., 1H), 8.60 (s, 2H), 7.29-7.55 (m, 12H), 7.00 (d, J=8.4 Hz, 2H), 3.80 (s, 3H). LC-MS: m/z 520.9 (M+H)⁺.

Compound 123: 5-((6-aminopyridazin-3-yl)amino)-6-(4-methoxyphenyl)-2,3-diphenylpyrazolo[1,5-a]pyrimidin-7(4H)-one

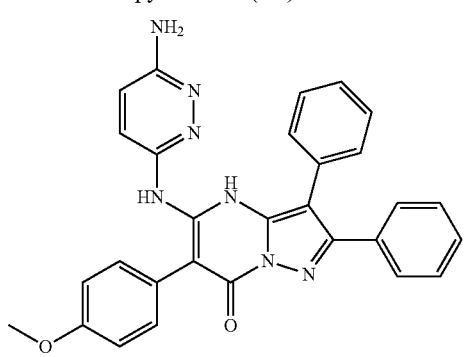

Step E stoichiometry: Intermediate 5 (132 mg, 0.3 mmol) and N-(6-aminopyridazin-3-yl)acetamide (93 mg, 0.2 mmol, 2 eq) and Pd(OAc)₂ (10 mg, 0.04 mmol, 0.4 eq), Xantphos (24 mg, 0.04 mmol, 0.4 eq) and Cs₂CO₃ (65 mg, 0.2 mmol, 2 eq) in 1.4-dioxane (5 mL) under heating at 120° C. through microwave irradiation for 1 hours under N₂ atmosphere. LC-MS: m/z 558.2 (M+H)⁺.

Step F: A mixture of N-(6-((7-methoxy-6-(4-methoxyphenyl)-2,3-diphenylpyrazolo[1,5-a]pyrimidin-5-yl)amino)pyridazin-3-yl)acetamide (55.7 mg, 0.1 mmol) and potassium tert-butoxide in 1.4-dioxane (5 mL) was stirred at 100° C. for 16 hours. The mixture was filtered and concentrated in vacuo to give 5-((6-aminopyridazin-3-yl)amino)-6-(4-methoxyphenyl)-2,3-diphenylpyrazolo[1,5-a]pyrimidin-7(4H)-one.

¹H NMR (DMSO-d₆): δ 7.50 (br. s., 2H), 7.40 (br. s., 3H), 7.33 (d. J=8.86 Hz, 8H), 7.04 (d, J=8.06 Hz, 3H), 6.89 (br. s., 1H), 3.82 (s, 4H). LC-MS: m/z 502.1 (M+H)⁺.

Compound 124: 6-(4-methoxyphenyl)-5-((6-methoxypyridazin-3-yl)amino)-2,3-diphenylpyrazolo[1,5-a]pyrimidin-7(4H)-one

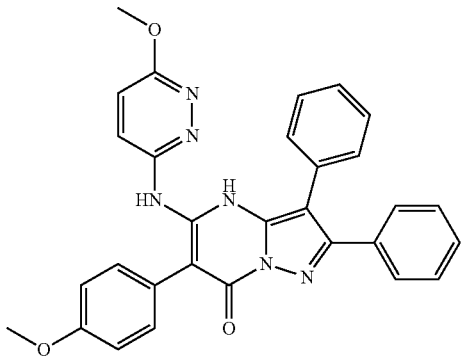 [SMILES: COc1ccc(-c2c(Nc3ccc(OC)nn3)[nH]c3c(-c4ccccc4)c(-c4ccccc4)nn3c2=O)cc1]

Step E stoichiometry: Intermediate 5 (200 mg, 0.453 mmol) and 6-methoxypyridazin-3-amine (169.8 mg, 1.358 mmol, 3 eq), Pd(OAc)₂ (20.3 mg, 0.091 mmol, 0.2 eq), Xant-phos (104.7 mg, 0.181 mmol, 0.4 eq) and Na₂CO₃ (143.9 mg, 1.358 mmol, 3 eq) in 1.4-dioxane (5 mL) under heating at 100° C. through microwave irradiation for 1 hour under N₂ atmosphere. LC-MS: m/z 531.2 (M+H)⁺.

Step F: A solution of 7-methoxy-6-(4-methoxyphenyl)-N-(6-methoxypyridazin-3-yl)-2,3-diphenylpyrazolo[1,5-a]pyrimidin-5-amine (50 mg, 0.094 mmol) in 4M HCl in 1.4-dioxane (10 mL) was stirred at room temperature for 3 hours. The reaction mixture was concentrated in vacuo to give the title compound.

¹H NMR (CHLOROFORM-d): δ 7.74 (d, J=9.46 Hz, 1H), 7.59 (d, J=9.46 Hz, 1H), 7.22-7.48 (m, 12H), 7.07 (d, J=6.41 Hz, 2H), 4.07 (s, 3H), 3.88 (s, 3H). LC-MS: m/z 517.0 (M+H)⁺.

Compound 125: 5-((6-chloropyridazin-3-yl)amino)-6-(4-methoxyphenyl)-2,3-diphenylpyrazolo[1,5-a]pyrimidin-7(4H)-one

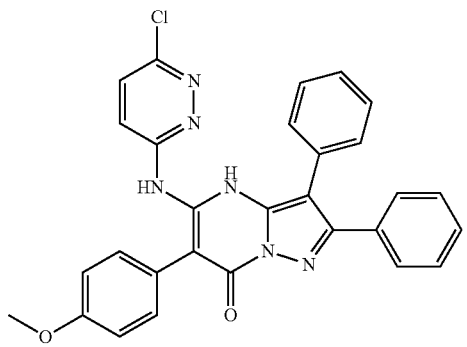

Step E stoichiometry: Intermediate 5 (200 mg, 0.45 mmol), 6-chloropyridazin-3-amine (101 mg, 0.9 mmol, 2 eq.), and Pd(OAc)$_2$ (20 mg, 0.09 mmol, 0.2 eq.), Xantphos (65 mg, 0.11 mmol, 0.3 eq.) and Cs$_2$CO$_3$ (293 mg, 0.9 mmol, 2.0 eq.) in 1.4-dioxane (5 mL) under heating at 120° C. through microwave irradiation for 1 hour under N$_2$ atmosphere. LC-MS: m/z 534.9, 536.9 (M+H)$^+$.

Step F: The solution of N-(6-chloropyridazin-3-yl)-7-methoxy-6-(4-methoxyphenyl)-2,3-diphenylpyrazolo[1,5-a]pyrimidin-5-amine (60 mg, 0.12 mmol) in 4M HCl in 1.4-dioxane (5 mL) was stirred at r.t. overnight. Solvent and volatile were removed in vacuo. The residue was dissolved in DCM (5 mL) and treated with saturated NaHCO$_3$. The organic phase was separated and washed with brine, dried over anhydrous Na$_2$SO$_4$ and concentrated in vacuo to afford the title compound.

$^1$H NMR (DMSO-d$_6$/TRIFLUOROACETIC ACID-d(v: 1/5)): δ 7.73 (d, J=9.4 Hz, 1H), 7.65 (d, J=9.4 Hz, 1H), 7.42-7.54 (m, 4H), 7.31-7.40 (m, 8H), 7.01 (d, J=8.6 Hz, 2H), 3.80 (s, 3H). LC-MS: m/z 520.9, 522.9 (M+H)$^+$.

Compound 126: 6-(4-methoxyphenyl)-2,3-diphenyl-5-(pyrazin-2-ylamino)pyrazolo[1,5-a]pyrimidin-7(4H)-one

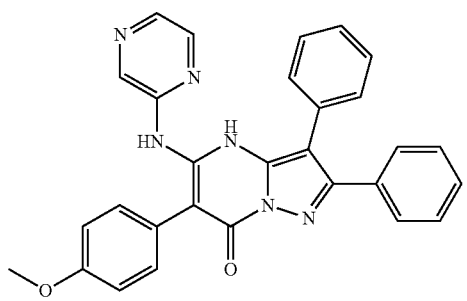 [SMILES: COc1ccc(-c2c(Nc3cnccn3)[nH]c3c(-c4ccccc4)c(-c4ccccc4)nn3c2=O)cc1]

Step E stoichiometry: Intermediate 5 (100 mg, 0.230 mmol), pyrazin-2-amine (44 mg, 0.460 mmol), palladium (II) acetate (57 mg, 0.250 mmol), xantphos (160 mg, 0.276 mmol) and cesium carbonate (165 mg, 0.506 mmol) in 1,4-dioxane (10 mL) under heating at 100° C. through microwave irradiation for 1 hour under nitrogen atmosphere. LC-MS: m/z 501.2 (M+H)$^+$.

Step F: A mixture of 7-methoxy-6-(4-methoxyphenyl)-2,3-diphenyl-N-(pyrazin-2-yl)pyrazolo [1,5-a] pyrimidin-5-amine (50 mg, 0.0996 mmol) in hydrogen chloride solution (4 M in dioxane, 3 mL) was stirred at room temperature for 10 hours. The mixture was evaporated to dryness. The residue was resolved in dichloromethane solution (with 10% methanol) and basified with aqueous ammonia to pH 8 to afford 6-(4-methoxyphenyl)-2,3-diphenyl-5-(pyrazin-2-ylamino)-pyrazolo[1,5-a] pyrimidin-7(4H)-one.

$^1$H NMR (DMSO-d$_6$): δ 14.27 (br. s., 1H), 9.93 (s., 1H), 9.38 (s, 1H), 8.61 (s, 1H), 8.23 (s, 1H), 8.08 (s., 1H), 7.56 (m, 5H), 7.36 (d, J=8.60 Hz, 5H), 7.06 (d, J=8.33 Hz, 3H), 3.83 (s, 3H). LC-MS: m/z 487.2 (M+H)$^+$.

Compound 127: 5-((3-hydroxypyrazin-2-yl)amino)-6-(4-methoxyphenyl)-2,3-diphenylpyrazolo[1,5-a]pyrimidin-7(4H)-one

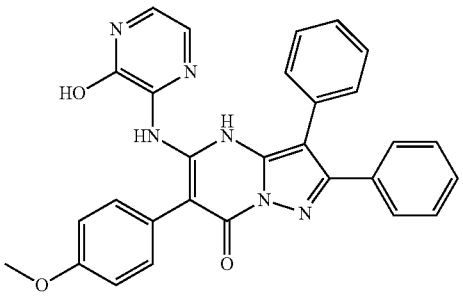 [SMILES: COc1ccc(-c2c(Nc3nccnc3O)[nH]c3c(-c4ccccc4)c(-c4ccccc4)nn3c2=O)cc1]

Step E stoichiometry: Intermediate 5 (150 mg, 0.34 mmol) and 3-aminopyrazin-2-ol (49 mg, 0.44 mmol, 1.3 eq), Pd(OAc)$_2$ (11 mg, 0.05 mmol, 0.15 eq), Xantphos (29 mg, 0.05 mmol, 0.15 eq) and Cs$_2$CO$_3$ (221 mg, 0.68 mmol, 2.0 eq) in 1.4-dioxane (10 mL). under heating at 110° C. through microwave irradiation for 1 hour under nitrogen atmosphere. LC-MS: m/z 516.9 (M+H)$^+$.

Step F: A solution of 3-((7-methoxy-6-(4-methoxyphenyl)-2,3-diphenylpyrazolo[1,5-a]pyrimidin-5-yl)amino) pyrazin-2-ol (15 mg, 0.03 mmol) in 4M HCl in 1.4-dioxane (5 mL) was stirred at 30° C. for 5 hours. The reaction mixture was concentrated in vacuum to obtain the title compound.

$^1$H NMR (DMSO-d$_6$): δ 14.12 (br. s., 1H), 12.64 (br. s., 1H), 8.50 (s, 1H), 7.51-7.65 (m, 4H), 7.33-7.47 (m, 8H), 7.02-7.17 (m, 3H), 6.78 (d, J=4.4 Hz, 1H), 3.85 (s, 3H). LC-MS: m/z 503.0 (M+H)$^+$.

Compound 128: 5-((3-aminopyrazin-2-yl)amino)-6-(4-methoxyphenyl)-2,3-diphenylpyrazolo[1,5-a]pyrimidin-7(4H)-one

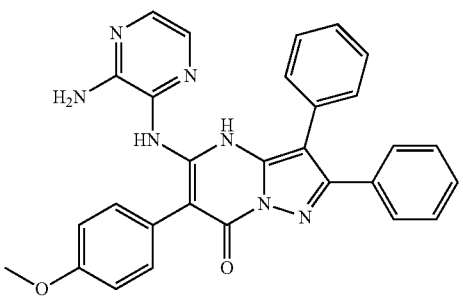

A suspension of Intermediate 5 (500 mg, 1.13 mmol), pyrazine-2,3-diamine (249 mg, 2.26 mmol, 2 eq.), Pd(OAc)$_2$ (254 mg, 1.13 mmol, 1 eq.), Xantphos (653 mg, 1.13 mmol, 1 eq.) and Cs$_2$CO$_3$ (737 mg, 2.26 mmol, 2.0 eq.) in 1,4-dioxane (15 mL) was stirred at 120° C. through microwave irradiation for 1 hour under N$_2$ atmosphere. The mixture was filtered through celite, and the filtrate was concentrated in vacuo to afford the title compound.

$^1$H NMR (TRIFLUOROACETIC ACID-d): δ 7.49-7.64 (m, 6H), 7.36-7.49 (m, 7H), 7.33 (d, J=4.0 Hz, 1H), 7.12 (d, J=8.6 Hz, 2H), 3.91 (s, 3H). LC-MS: m/z 502.1 (M+H)$^+$.

Compound 129: 5-(6-(4-methoxyphenyl)-7-oxo-2,3-diphenyl-4,7-dihydropyrazolo[1,5-a]pyrimidin-5-ylamino)pyrazine-2-carbonitrile

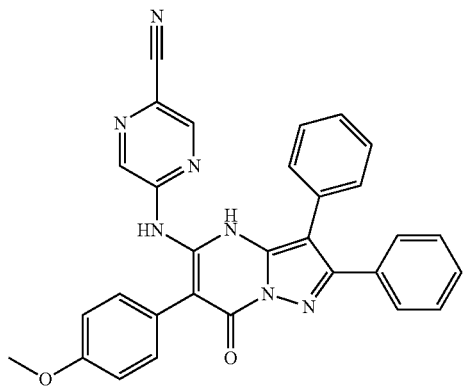 [SMILES: COc1ccc(-c2c(Nc3cnc(C#N)cn3)[nH]c3c(-c4ccccc4)c(-c4ccccc4)nn3c2=O)cc1]

Step E stoichiometry: Intermediate 5 (500 mg, 1.13 mmol), 5-aminopyrazine-2-carbonitrile (163 mg, 1.36 mmol), tris(dibenzylideneacetone)dipalladium(0) (311 mg, 0.34 mmol), xantphos (216 mg, 0.374 mmol) and sodium carbonate (264 mg, 2.5 mmol) in 1, 4-dioxane (20 mL) under heating to reflux for 1 hour under N$_2$ atmosphere. LC-MS: m/z 526.2 (M+H)$^+$.

Step F: To a solution of 5-(7-methoxy-6-(4-methoxyphenyl)-2,3-diphenylpyrazolo[1,5-a]pyrimidin-5-ylamino) pyrazine-2-carbonitrile (100 mg, 0.19 mmol) in dichloromethane (6 mL) was added HCl solution (4M in dioxane, 10 mL). The reaction mixture was stirred at room temperature for 16 h. The reaction mixture was quenched with ammonia solution (7M in methanol) to pH 7-8 to give 5-(6-(4-methoxyphenyl)-7-oxo-2,3-diphenyl-4,7-dihydropyrazolo[1,5-a]pyrimidin-5-ylamino)pyrazine-2-carbonitrile.

$^1$H NMR (DMSO-d$_6$): δ 9.79 (s, 1H), 8.60 (s, 1H), 7.95 (s, 1H), 7.57 (d, J=6.45 Hz, 2H), 7.47 (d, J=7.25 Hz, 2H), 7.27-7.42 (m, 7H), 7.17 (d, J=6.72 Hz, 1H), 7.01 (d, J=8.33 Hz, 2H), 3.81 (s, 3H). LC-MS: m/z 512.2 (M+H)$^+$.

Compound 130: 5-((5-aminopyrazin-2-yl)amino)-6-(4-methoxyphenyl)-2,3-diphenylpyrazolo[1,5-a]pyrimidin-7(4H)-one

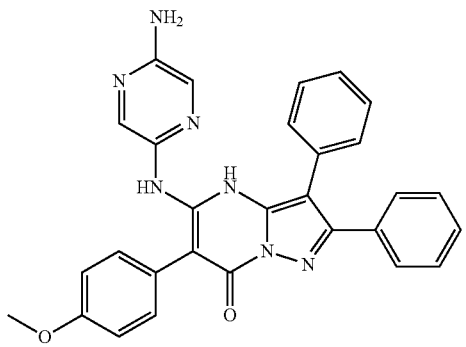

Step E stoichiometry: Intermediate 5 (440 mg, 1.0 mmol), pyrazine-2,5-diamine (293 mg, 2.0 mmol), palladium(II) acetate (112 mg, 0.50 mmol), xantphos (347 mg, 0.6 mmol) and cesium carbonate (1.2 g, 4.0 mmol) in 1, 4-dioxane (20 mL) under heating at 110° C. for 1 hour through microwave irradiation under N$_2$ atmosphere. LC-MS: m/z 516.2 (M+H)$^+$.

Step F: A mixture of N$^2$-(7-methoxy-6-(4-methoxyphenyl)-2,3-diphenylpyrazolo[1,5-a] pyrimidin-5-yl) pyrazine-2,5-diamine (50 mg, 0.10 mmol) in hydrogen chloride solution (4 M in dioxane, 5 mL) was stirred at room temperature for 16 hours. The mixture was evaporated to dryness. The residue was resolved in dichloromethane solution (with 10% methanol), basified with aqueous ammonia to pH 8 to afford 5-(5-aminopyrazin-2-ylamino)-6-(4-methoxyphenyl)-2,3-diphenylpyrazolo[1,5-a] pyrimidin-7 (4H)-one.

$^1$H NMR (DMSO-d$_6$): δ 14.30 (s, 1H), 8.77 (s., 1H), 8.07 (s, 1H), 7.54-7.51 (m, 4H), 731-7.43 (m, 7H), 7.05 (d, J=8.4 Hz, 2H), 6.23 (s., 2H), 3.83 (s, 1H). LC-MS: m/z 502.0 (M+H)$^+$.

Compound 131: 6-(6-(4-methoxyphenyl)-7-oxo-2,3-diphenyl-4,7-dihydropyrazolo[1,5-a]pyrimidin-5-ylamino)pyrazine-2-carbonitrile

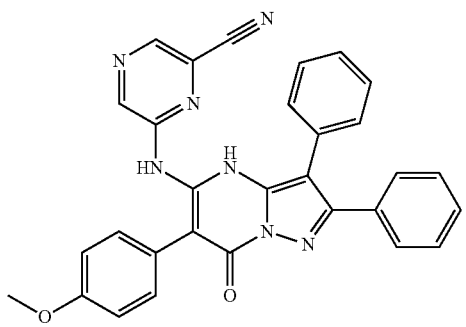 [SMILES: COc1ccc(-c2c(Nc3cncc(C#N)n3)[nH]c3c(-c4ccccc4)c(-c4ccccc4)nn3c2=O)cc1]

Step E stoichiometry: Intermediate 5 (500 mg, 1.13 mmol), 6-aminopyrazine-2-carbonitrile (163 mg, 1.36 mmol), palladium(II) acetate (84 mg, 0.374 mmol), xantphos (215 mg, 0.374 mmol) and cesium carbonate (741 mg, 2.27 mmol) in 1, 4-dioxane (10 mL) under heating at 110°

C. for 1 hour through microwave irradiation under N₂ atmosphere. LC-MS: m/z 526.2 (M+H)⁺.

Step F: To a solution of 6-(7-methoxy-6-(4-methoxyphenyl)-2,3-diphenylpyrazolo[1,5-a] pyrimidin-5-ylamino) pyrazine-2-carbonitrile (100 mg, 0.19 mmol) in dichloromethane (6 mL) was added HCl solution (4M in dioxane, 2 mL). The reaction mixture was stirred at room temperature for 18 h. The mixture was evaporated to dryness. The residue was resolved in dichloromethane solution (with 10% methanol) and washed with aqueous sodium bicarbonate to pH 8. The organic phase was dried over sodium afford 6-(6-(4-methoxyphenyl)-7-oxo-2,3-diphenyl-4,7-dihydropyrazolo[1,5-a]pyrimidin-5-ylamino)-pyrazine-2-carbonitrile.

¹H NMR (DMSO-d₆): δ 8.57-8.71 (m, 2H) 7.44-7.65 (m, 4H) 7.21-7.42 (m, 8H) 6.99 (d, J=8.55 Hz, 2H), 3.80 (s, 3H). LC-MS: m/z 512.2 (M+H)⁺.

Compound 132: 5-((1,3,5-triazin-2-yl)amino)-6-(4-methoxyphenyl)-2,3-diphenylpyrazolo[1,5-a]pyrimidin-7(4H)-one

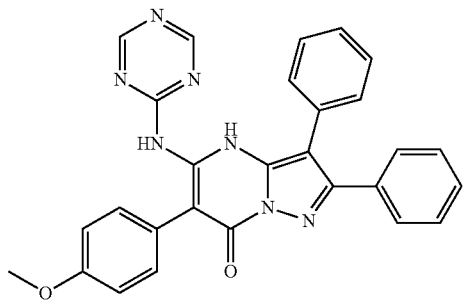

Step E stoichiometry: Intermediate 5 (800 mg, 1.81 mmol), 1,3,5-triazin-2-amine (348 mg, 3.62 mmol), and Pd(OAc)₂ (81 mg, 0.36 mmol), Xantphos (260 mg, 0.45 mmol) and Na₂CO₃ (384 mg, 3.62 mmol) in 1.4-dioxane (15 mL) under heating at 120° C. for 4 hours under N₂ atmosphere. LC-MS: m/z 502.0 (M+H)⁺.

Step F: 7-methoxy-6-(4-methoxyphenyl)-2,3-diphenyl-N-(1,3,5-triazin-2-yl)pyrazolo[1,5-a]pyrimidin-5-amine (500 mg, 1.0 mmol) was dissolved in HCl-1,4-dioxane (10 mL). The solution was stirred at r.t. for 2 h. The precipitate was filtered off and washed with CH₂Cl₂ (3*1 mL) to give a yellow solid. The solid was then dissolved in CH₂Cl₂/MeOH (10/1, 3 mL). After 3 mL of NH₃-MeOH was added, the solution was stirred at r.t. overnight to give the title compound.

¹H NMR (DMSO-d₆): δ 12.71 (br. s, 1H), 10.24 (br. s., 1H), 8.70 (s, 2H), 7.41-7.50 (m, 4H), 7.29-7.41 (m, 6H), 7.21-7.27 (m, 2H), 6.93 (d, J=8.6 Hz, 2H), 3.76 (s, 3H). LC-MS: m/z 488.0 (M+H)⁺.

Compound 133: 5-((1,2,4-triazin-5-yl)amino)-6-(4-methoxyphenyl)-2,3-diphenylpyrazolo[1,5-a]pyrimidin-7(4H)-one

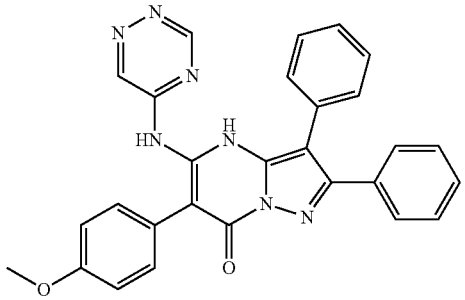

Step E stoichiometry: Intermediate 5 (220 mg, 0.5 mmol), 1,2,4-triazin-5-amine (100 mg, 1.0 mmol), palladium(II) acetate (56 mg, 0.25 mmol), xantphos (170 mg, 0.30 mmol) and cesium carbonate (375 mg, 1.1 mmol) in 1, 4-dioxane (15 mL) under heating at 105° C. through microwave irradiation for 45 min under N₂ atmosphere. LC-MS: m/z 502.2 (M+H)⁺.

Step F: A mixture of 7-methoxy-6-(4-methoxyphenyl)-2,3-diphenyl-N-(1,2,4-triazin-5-yl) pyrazolo[1,5-a] pyrimidin-5-amine (100 mg, 0.20 mmol) in hydrogen chloride solution (4 M in dioxane, 15 mL) was stirred at room temperature for 4 hours. The mixture was evaporated to dryness. The residue was resolved in dichloromethane solution (with 10% methanol), basified with aqueous ammonia to pH 8 to afford 5-(1,2,4-triazin-5-ylamino)-6-(4-methoxyphenyl)-2,3-diphenylpyrazolo[1,5-a] pyrimidin-7(4H)-one.

¹H NMR (DMSO-d₆): δ 9.14 (s, 1H), 8.74 (s., 1H), 7.31-7.51 (m, 12H), 6.76 (d, J=8.6 Hz, 2H), 3.79 (s, 3H). LC-MS: m/z 488.2 (M+H)⁺.

Compound 134: 5-((4-amino-1,3,5-triazin-2-yl)amino)-6-(4-methoxyphenyl)-2,3-diphenylpyrazolo[1,5-a]pyrimidin-7(4H)-one

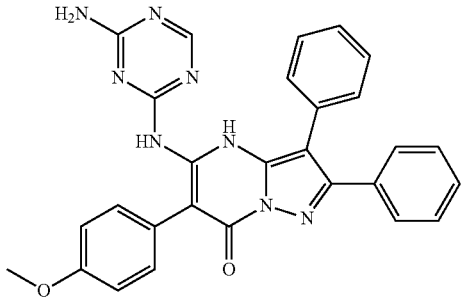 [SMILES: COc1ccc(-c2c(Nc3ncnc(N)n3)[nH]c3c(-c4ccccc4)c(-c4ccccc4)nn3c2=O)cc1]

Step E stoichiometry: Intermediate 5 (500 mg, 1.13 mmol), 1,3,5-triazine-2,4-diamine (189 mg, 1.7 mmol, 1.5 eq), Pd(OAc)₂ (38 mg, 0.17 mmol, 0.15 eq), Xantphos (98 mg, 0.17 mmol, 0.15 eq) and Cs₂CO₃ (360 mg, 3.34 mmol, 3.0 eq) in 1.4-dioxane (15 mL) under heating at 105° C. through microwave irradiation for 1 hour under N₂ atmosphere. LC-MS: m/z 516.9 (M+H)⁺.

Step F: A solution of 5-((4-amino-1,3,5-triazin-2-yl)amino)-6-(4-methoxyphenyl)-2,3-diphenylpyrazolo[1,5-a]

pyrimidin-7(4H)-one (156 mg, 0.3 mmol) in 4M HCl in 1.4-dioxane (5 mL) was stirred at 30° C. for 5 hours. The reaction mixture was concentrated in vacuum to obtain the title compound.

¹H NMR (DMSO-d₆): δ 13.80 (s, 1H), 8.17 (s, 2H), 7.66 (s, 1H), 7.51 (m, 4H), 7.38 (dd, J=9.8, 6.1 Hz, 7H), 7.33 (d, J=8.0 Hz, 2H), 7.03 (d, J=8.4 Hz, 2H), 3.80 (s, 3H). LC-MS: m/z 503.0 (M+H)⁺.

Compound 135: 6-(4-methoxyphenyl)-5-((4-(methylamino)-1,3,5-triazin-2-yl)amino)-2,3-diphenylpyrazolo[1,5-a]pyrimidin-7(4H)-one

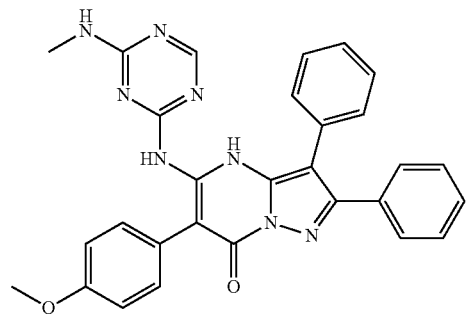 [SMILES: CNc1ncnc(Nc2[nH]c3c(-c4ccccc4)c(-c4ccccc4)nn3c(=O)c2-c2ccc(OC)cc2)n1]

Step E stoichiometry: Intermediate 5 (249 mg, 0.57 mmol), N2-methyl-1,3,5-triazine-2,4-diamine (106 mg, 0.85 mmol, 1.5 eq.), Pd(OAc)₂ (64 mg, 0.28 mmol, 0.5 eq.), Xantphos (197 mg, 0.34 mmol, 0.6 eq.) and Cs₂CO₃ (370 mg, 1.13 mmol, 2.0 eq.) in 1.4-dioxane (10 mL) under heating at 100° C. through microwave irradiation for 1 hour under N₂ atmosphere. LC-MS: m/z 531.0 (M+H)⁺.

Step F: A solution of N²-(7-methoxy-6-(4-methoxyphenyl)-2,3-diphenylpyrazolo[1,5-a]pyrimidin-5-yl)-N4-methyl-1,3,5-triazine-2,4-diamine (100 mg, 0.19 mmol) in 4M HCl in 1.4-dioxane (15 mL) was stirred at r.t. for 6 hours to afford the title compound.

¹H NMR (DMSO-d₆ & TRIFLUOROACETIC ACID-d (v:1/5)): δ 8.40 (s, 1H), 7.55 (d, J=6.2 Hz, 2H), 7.33-7.47 (m, 10H), 7.04 (d, J=8.6 Hz, 2H), 3.84 (s, 3H), 2.08 (s, 3H). LC-MS: m/z 517.0 (M+H)⁺.

Compound 136: 5-((4-hydroxy-1,3,5-triazin-2-yl)amino)-6-(4-methoxyphenyl)-2,3-diphenylpyrazolo[1,5-a]pyrimidin-7(4H)-one

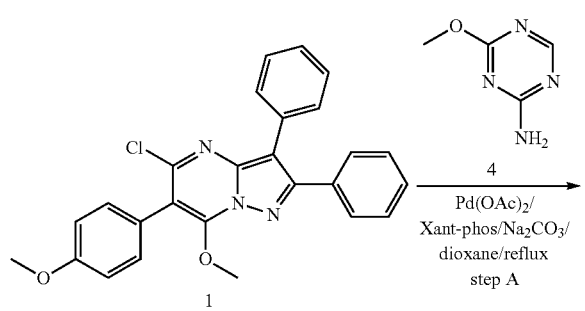

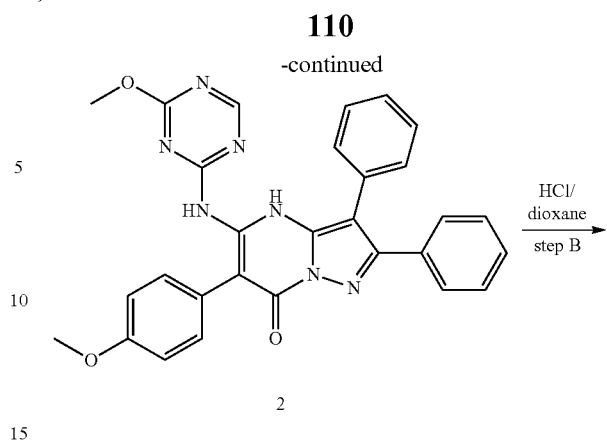

Step A: 5-((4-methoxy-1,3,5-triazin-2-yl)amino)-6-(4-methoxyphenyl)-2,3-diphenylpyrazolo[1,5-a]pyrimidin-7(4H)-one

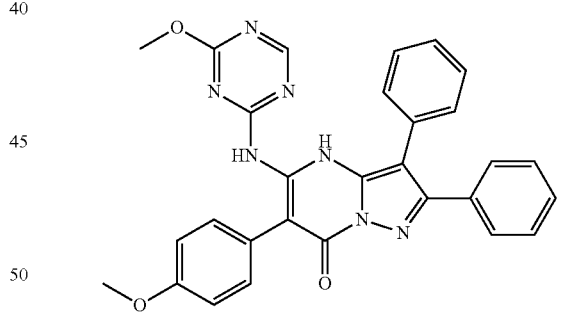

The mixture of 5-chloro-7-methoxy-6-(4-methoxyphenyl)-2,3-diphenylpyrazolo[1,5-a]pyrimidine (1.0 g, 2.26 mmol), 4-methoxy-1,3,5-triazin-2-amine (424.7 mg, 3.39 mmol), palladium diacetate (253.7 mg, 1.13 mmol), Xantphos (784.6 mg, 1.36 mmol) and sodium carbonate (383.3 mg, 3.62 mmol) in 1,4-dioxane (40 mL) was refluxed for 12 hours under nitrogen atmosphere. After cooling to room temperature, the mixture was filtered with celite, diluted with DCM (150 mL), washed with saturated brine (50 mL), dried over anhydrous sodium sulfate and concentrated to drynesss. The residue was purified to obtain 5-((4-methoxy-1,3,5-triazin-2-yl)amino)-6-(4-methoxyphenyl)-2,3-diphenylpyrazolo[1, 5-a]pyrimidin-7(4H)-one as yellow solid. LC-MS: m/z 518.2 (M+H)⁺.

Step B: 5-((4-hydroxy-1,3,5-triazin-2-yl)amino)-6-(4-methoxyphenyl)-2,3-diphenylpyrazolo [1,5-a]pyrimidin-7(4H)-one

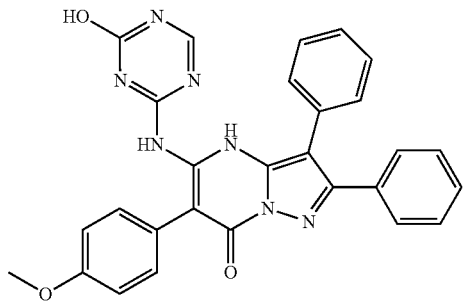 [SMILES: COc1ccc(-c2c(Nc3ncnc(O)n3)[nH]c3c(-c4ccccc4)c(-c4ccccc4)nn3c2=O)cc1]

A solution of 5-((4-methoxy-1,3,5-triazin-2-yl)amino)-6-(4-methoxyphenyl)-2,3-diphenylpyrazolo[1,5-a]pyrimidin-7(4H)-one (350 mg, 0.68 mmol) in 4M HCl in 1.4-dioxane (40 mL) was stirred at r.t. for 16 hours. The mixture was concentrated, and saturated NaHCO₃ (10 mL) was added to obtain 5-((4-hydroxy-1,3,5-triazin-2-yl)amino)-6-(4-methoxyphenyl)-2,3-diphenylpyrazolo[1,5-a]pyrimidin-7(4H)-one.

¹H NMR (DMSO-$d_6$): δ 8.07 (br. s., 1H), 7.47 (br. s., 3H), 7.16-7.43 (m, 15H), 6.94 (br. s., 2H), 3.78 (s, 3H). LC-MS: m/z 504.3 (M+H)⁺.

Compound 137: 6-(4-methoxyphenyl)-2,3-diphenyl-5-(thiazol-2-ylamino)pyrazolo[1,5-a]pyrimidin-7(4H)-one

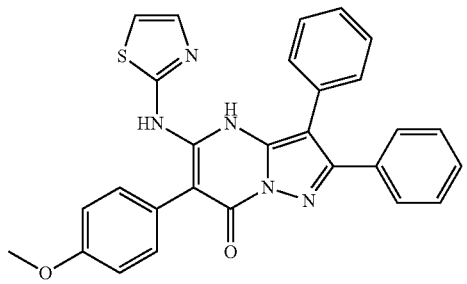

Step E stoichiometry: Intermediate 5 (220 mg, 0.5 mmol), thiazol-2-amine (100 mg, 1.0 mmol, 2 eq.), Pd(OAc)₂ (56 mg, 0.25 mmol, 0.5 eq.), Xantphos (174 mg, 0.3 mmol, 0.6 eq.) and Na₂CO₃ (117 mg, 1.1 mmol, 2.2 eq.) in 1.4-dioxane (5 mL) under heating at 100° C. for 3 h under N₂ atmosphere. LC-MS: m/z 506.1 (M+H)⁺.

Step F: The solution of N-(7-methoxy-6-(4-methoxyphenyl)-2,3-diphenylpyrazolo[1,5-a]pyrimidin-5-yl)thiazol-2-amine (110 mg, 0.23 mmol) in 4M HCl in 1.4-dioxane (10 mL) was stirred at r.t. for 10 h to afford the title compound.

¹H NMR (DMSO-$d_6$): δ 10.39 (br. s., 1H), 7.47-7.58 (m, 4H), 7.35-7.46 (m, 6H), 7.27-7.35 (m, 3H), 7.21 (d, J=3.6 Hz, 1K), 7.06 (d, J=8.8 Hz, 2H), 3.83 (s, 3H). LC-MS: m/z 491.9 (M+H)⁺.

Compound 138: 5-(isoxazol-3-ylamino)-6-(4-methoxyphenyl)-2,3-diphenylpyrazolo[1,5-a]pyrimidin-7(4H)-one

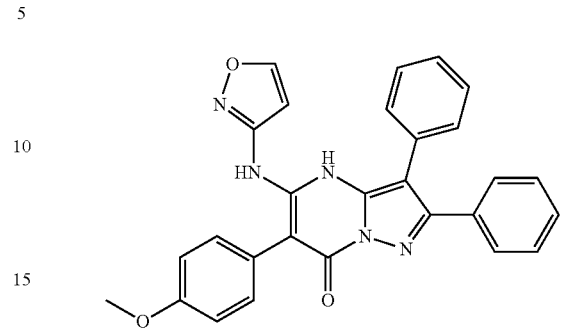

Step E stoichiometry: Intermediate 5 (400 mg, 0.9 mmol), isoxazol-3-amine (150 mg, 1.8 mmol, 2 eq.), Pd(OAc)₂ (20 mg, 0.09 mmol, 0.1 eq.), Xantphos (104 mg, 0.18 mmol, 0.2 eq.) and Na₂CO₃ (190 mg, 1.8 mmol, 2 eq.) in 1.4-dioxane (5 mL) under heating at 100° C. for 16 hours under N₂ atmosphere. LC-MS: m/z 490.5 (M+H)⁺.

Step F: A solution of 5-(isoxazol-3-ylamino)-6-(4-methoxyphenyl)-2,3-diphenylpyrazolo[1, 5-a]pyrimidin-7(4H)-one (90 mg, 0.17 mmol) in 4M HCl in 1.4-dioxane (3 mL) was stirred at r.t. for 2 hours. Solvent and volatile were removed in vacuo. The mixture was basified with NaHCO₃ solution to PH=8 and concentrated in vacuo to give the title compound ¹H NMR (DMSO-$d_6$): δ 12.01 (s, 1H), 9.39 (s, 1H), 8.75 (d, J=1.9 Hz, 1H), 7.45-7.52 (m, 3H), 7.36-7.45 (m, 6H), 7.30-7.36 (m, J=8.6 Hz, 2H), 6.99-7.10 (m, J=8.9 Hz, 2H), 6.49 (d, J=1.9 Hz, 1H), 3.83 (s, 3H). LC-MS: m/z 476.5 (M+H)⁺.

Compound 139: 5-(isoxazol-4-ylamino)-6-(4-methoxyphenyl)-2,3-diphenylpyrazolo[1,5-a]pyrimidin-7(4H)-one

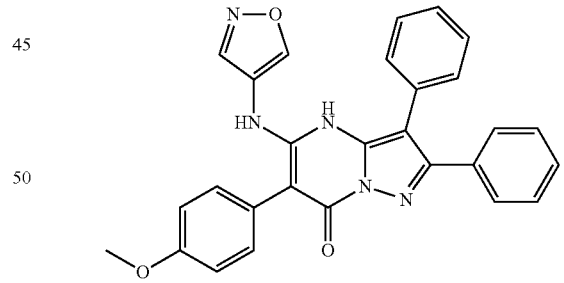

Step E stoichiometry: Intermediate 5 (150 mg, 0.34 mmol) and isoxazol-4-amine (57 mg, 0.68 mmol, 2.0 eq), Pd(OAc)₂ (16 mg, 0.07 mmol, 0.2 eq), Xantphos (41 mg, 0.07 mmol, 0.2 eq) and Cs₂CO₃ (442 mg, 1.36 mmol, 4.0 eq) in 1.4-dioxane (10 mL) under heating at 100° C. through microwave irradiation for 1 hour under N₂ atmosphere. LC-MS: m/z 490.2 (M+H)⁺.

Step F: A solution of N-(7-methoxy-6-(4-methoxyphenyl)-2,3-diphenylpyrazolo[1,5-a]pyrimidin-5-yl)isoxazol-4-amine (38 mg, 0.08 mmol) in 4M HCl in 1.4-dioxane (5 mL) was stirred at 30° C. for 5 hours. The reaction mixture was concentrated in vacuo to obtain the title compound.

¹H NMR (DMSO-d₆): δ 9.24 (br. s., 1H), 8.74 (br. s., 1H), 7.98 (br. s., 1H), 7.31-7.45 (m, 6H), 7.09-7.31 (m, 9H), 7.04 (br. s., 2H), 3.81 (br. s., 3H). LC-MS: m/z 476.1 (M+H)⁺.

Compound 140: 5-(isoxazol-5-ylamino)-6-(4-methoxyphenyl)-2,3-diphenylpyrazolo[1,5-a]pyrimidin-7(4H)-one

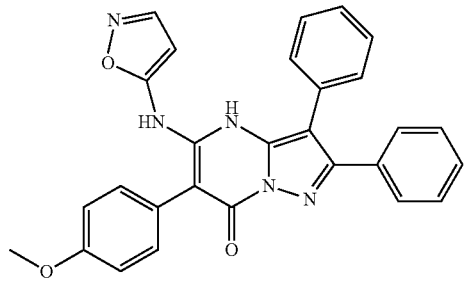 [SMILES: COc1ccc(-c2c(Nc3ccno3)[nH]c3c(-c4ccccc4)c(-c4ccccc4)nn3c2=O)cc1]

A suspension of intermediate 5 (100 mg, 0.22 mmol), isoxazol-5-amine (23 mg, 0.27 mmol, 1.2 eq.), Pd(OAc)₂ (20 mg, 0.09 mmol, 0.4 eq.), Xantphos (53 mg, 0.09 mmol, 0.4 eq.) and K₂CO₃ (63 mg, 0.45 mmol, 2.5 eq.) in dioxane (4 mL) was stirred at 100° C. through microwave irradiation for 1 hour under N₂ atmosphere. The mixture was filtered through celite and the filtrate was concentrated in vacuo to afford the title compound.

¹H NMR (DMSO-d₆): δ 12.38 (br. s., 1H), 10.40 (br. s., 1H), 7.24-7.54 (m, 15H), 7.00 (d, J=8.1 Hz, 2H), 3.81 (s, 3H). LC-MS: m/z 475.9 (M+H)⁺.

Compound 141: 6-(4-methoxyphenyl)-5-(1-methyl-1H-imidazol-2-ylamino)-2,3-diphenylpyrazolo[1,5-a]pyrimidin-7(4H)-one

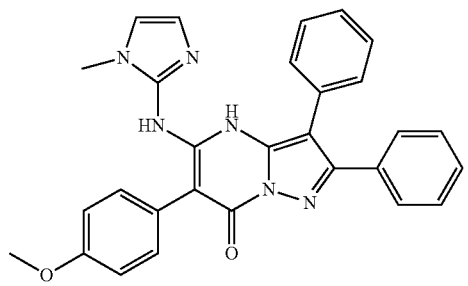 [SMILES: COc1ccc(-c2c(Nc3nccn3C)[nH]c3c(-c4ccccc4)c(-c4ccccc4)nn3c2=O)cc1]

Step E stoichiometry: Intermediate 5 (100 mg, 0.226 mmol), 1-methyl-1H-imidazol-2-amine (33 mg, 0.340 mmol), tris(dibenzylideneacetone)dipalladium (0) (206 mg, 0.226 mmol), xantphos (130 mg, 0.226 mmol) and sodium carbonate (48 mg, 0.515 mmol) in 1,4-dioxane (5 mL) under heating at 110° C. through microwave irradiation for 1 hour under N₂ atmosphere. LC-MS: m/z 503.2 (M+H)⁺.

Step F: A mixture of 7-methoxy-6-(4-methoxyphenyl)-N-(1-methyl-1H-imidazol-2-yl)-2,3-diphenylpyrazolo [1,5-a]pyrimidin-5-amine (50 mg, 1 mmol) in hydrogen chloride solution (4 M in dioxane, 10 mL) was stirred at 70° C. for 16 h. The mixture was evaporated to dryness. The residue was resolved in dichloromethane solution (with 10% methanol) and washed with aqueous sodium bicarbonate to pH 8. The organic phase was dried over sodium sulfate to afford 6-(4-methoxyphenyl)-5-(1-methyl-1H-imidazol-2-ylamino)-2,3-diphenylpyrazolo[1,5-a] pyrimidin-7(4H)-one.

¹H NMR (DMSO-d₆): δ 7.49-7.31 (m, 14H), 6.99 (d, J=7.63 Hz, 2H), 3.78 (s, 3H), 3.52 (s, 3H). LC-MS: m/z 489.2 (M+H)⁺.

Compound 142: 5-((1H-imidazol-2-yl)amino)-6-(4-methoxyphenyl)-2,3-diphenylpyrazolo[1,5-a]pyrimidin-7(4H)-one

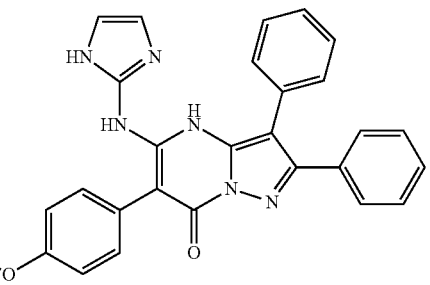

Step E stoichiometry: Intermediate 5 (441 mg, 1.0 mmol), 1H-imidazol-2-amine (83 mg, 1 mmol, 2 eq.), Pd₂(dba)₃ (91.5 mg, 0.1 mmol, 0.1 eq.), Xantphos (115.6 mg, 0.2 mmol, 0.2 eq.) and Na₂CO₃ (212 mg, 2 mmol, 2 eq.) in toluene (40 mL) under heating at 105° C. for 5 hour under N₂ atmosphere. LC-MS: m/z 489.5 (M+H)⁺.

Step F: A solution of N-(1H-imidazol-2-yl)-7-methoxy-6-(4-methoxyphenyl)-2,3-diphenylpyrazolo[1,5-a]pyrimidin-5-amine (40 mg, 0.08 mmol) in 4M HCl in 1.4-dioxane (15 mL) was stirred at r.t. for 16 hours. Solvent and volatile were removed in vacuo. The resultant residue was basified with NaHCO₃ solution to pH=8 and concentrated to afford the title compound.

¹H NMR (DMSO-d₆): δ 12.73 (br. s., 1H), 7.51 (br. s., 2H), 7.39-7.48 (m, 6H), 7.21-7.39 (m, 3H), 7.06 (s, 3H), 3.81 (s, 3H). LC-MS: m/z 475.5 (M+H)⁺.

Compound 143: 5-((4,5-dihydrothiazol-2-yl)amino)-6-(4-methoxyphenyl)-2,3-diphenylpyrazolo[1,5-a] pyrimidin-7(4H)-one

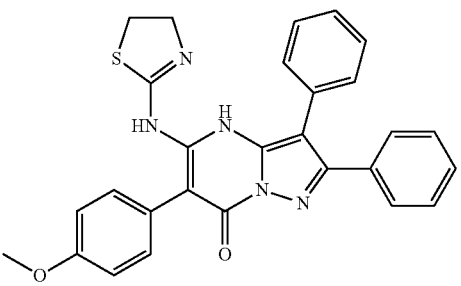 [SMILES: COc1ccc(-c2c(NC3=NCCS3)[nH]c3c(-c4ccccc4)c(-c4ccccc4)nn3c2=O)cc1]

Step E stoichiometry: Intermediate 5 (441 mg, 1.0 mmol), thiazol-2-amine (102 mg, 1 mmol, 2 eq.), Pd₂(dba)₃ (91.5 mg, 0.1 mmol, 0.1 eq.), Xantphos (115.6 mg, 0.2 mmol, 0.2 eq.) and Na₂CO₃ (212 mg, 2 mmol, 2 eq.) in toluene (40 mL) under heating at 105° C. for 5 hour under N₂ atmosphere. LC-MS: m/z 506.5 (M+H)⁺.

Step F: A solution of N-(7-methoxy-6-(4-methoxyphenyl)-2,3-diphenylpyrazolo[1,5-a]pyrimidin-5-yl)thiazol-2-amine (40 mg, 0.08 mmol) in 4M HCl in 1.4-dioxane (15 mL) was stirred at r.t. for 16 hours. Solvent and volatile were removed in vacuo. The resultant residue was basified with NaHCO₃ solution to pH=8 and concentrated to afford the title compound.

¹H NMR (DMSO-$d_6$): δ 7.31-7.49 (m, 9H), 7.26 (d, J=8.5 Hz, 3H), 6.94 (br. s., 2H), 3.78 (s, 3H), 3.60 (br. s., 1H), 3.50 (br. s., 1H), 3.31 (br. s., 2H). LC-MS: m/z 494.5 (M+H)⁺.

Compound 144: 5-((1,3,4-thiadiazol-2-yl)amino)-6-(4-methoxyphenyl)-2,3-diphenylpyrazolo[1,5-a]pyrimidin-7(4H)-one

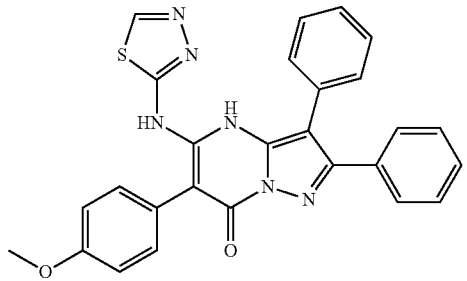

Step E stoichiometry: Intermediate 5 (442 mg, 1.0 mmol) and 1,3,4-thiadiazol-2-amine (101 mg, 1.0 mmol, 1 eq) and Pd(OAc)₂ (91.5 mg, 0.1 mmol, 0.1 eq), Xant-phos (115.6 mg, 0.2 mmol, 0.2 eq) and Na₂CO₃ (212 mg, 2.0 mmol, 2.0 eq) in toluene (40 mL) under heating at 110° C. for 5 hour under N₂ atmosphere. LC-MS: m/z 507.1 (M+H)⁺.

Step F: A mixture of N-(7-methoxy-6-(4-methoxyphenyl)-2,3-diphenylpyrazolo[1,5-a]pyrimidin-5-yl)-1,3,4-thiadiazol-2-amine (112 mg, 0.2 mmol) in 4N HCl in 1.4-dioxane (15 mL) was stirred at room temperature overnight. The reaction mixture was concentrate in vacuo. The residue was stirred with methanol and saturated sodium hydrogen carbonate solution to afford the title compound.

¹H NMR (DMSO-$d_6$): δ 13.83 (br. s., 1H), 10.57 (br. s., 1H), 9.05 (br. s., 1H), 7.54 (br. s., 4H), 7.42 (br. s., 5H), 7.34 (br. s., 3H), 7.08 (d, J=7.79 Hz, 2H), 3.85 (s, 3H). LC-MS: m/z 493.1 (M+H)⁺.

Compound 145: 5-((5-amino-1,3,4-thiadiazol-2-yl)amino)-6-(4-methoxyphenyl)-2,3-diphenylpyrazolo[1,5-a]pyrimidin-7(4H)-one

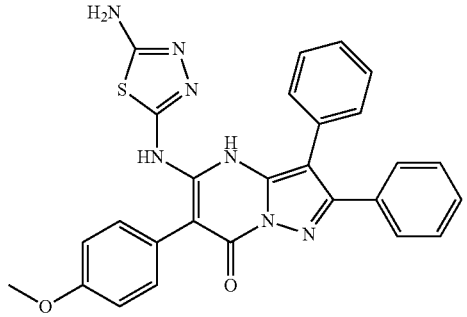 [SMILES: COc1ccc(-c2c(Nc3nnc(N)s3)[nH]c3c(-c4ccccc4)c(-c4ccccc4)nn3c2=O)cc1]

Step E stoichiometry: Intermediate 5 (600 mg, 1.36 mmol) and 1,3,4-thiadiazole-2,5-diamine (315 mg, 2.72 mmol, 2 eq.), Pd(OAc)₂ (306 mg, 0.1.36 mmol, 1 eq.), Xantphos (786 mg, 1.36 mmol, 1 eq.) and Cs₂CO₃ (887 mg, 2.72 mmol, 2.0 eq.) in 1.4-dioxane (18 mL) under heating at 120° C. through microwave irradiation for 1 hour under N₂ atmosphere. LC-MS: m/z 522.0 (M+H)⁺.

Step F: A solution of N2-(7-methoxy-6-(4-methoxyphenyl)-2,3-diphenylpyrazolo[1,5-a]pyrimidin-5-yl)-1,3,4-thiadiazole-2,5-diamine (100 mg, 0.19 mmol) in 4M HCl in 1.4-dioxane (5 mL) was stirred at r.t. overnight. Solvent and volatile were removed in vacuo. The residue was dissolved in DCM (5 mL) and basified with saturated NaHCO₃. The organic phase was separated and washed with brine, dried over anhydrous Na₂SO₄ and concentrated in vacuo to afford the title compound.

¹H NMR (DMSO-$d_6$): δ 9.96 (br. s., 1H), 7.37-7.57 (m, 9H), 7.32-7.37 (m, 1H), 7.29 (d, J=8.6 Hz, 2H), 7.04 (d, J=8.6 Hz, 2H), 3.82 (s, 3H). LC-MS: m/z 508.0 (M+H)⁺.

Compound 146: 5-((5-hydroxy-1,3,4-thiadiazol-2-yl)amino)-6-(4-methoxyphenyl)-2,3-diphenylpyrazolo[1,5-a]pyrimidin-7(4H)-one

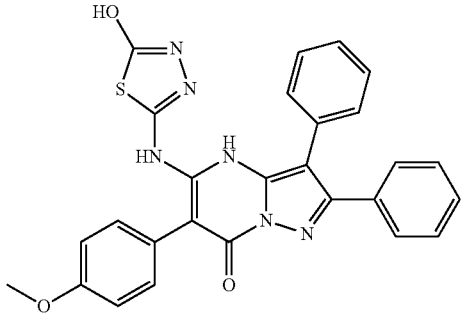 [SMILES: COc1ccc(-c2c(Nc3nnc(O)s3)[nH]c3c(-c4ccccc4)c(-c4ccccc4)nn3c2=O)cc1]

Step E stoichiometry: Intermediate 5 (442 mg, 1.0 mmol) and 5-methoxy-1,3,4-thiadiazol-2-amine (113 mg, 1.0 mmol, 1 eq), Pd(OAc)₂ (91.5 mg, 0.1 mmol, 0.1 eq), Xant-phos (115.6 mg, 0.2 mmol, 0.2 eq) and Na₂CO₃ (212 mg, 2.0 mmol, 2.0 eq) in toluene (40 mL) under heating at 110° C. for 5 hour under N₂ atmosphere. LC-MS: m/z 537.1 (M+H)⁺.

Step F: A mixture of 5-methoxy-N-(7-methoxy-6-(4-methoxyphenyl)-2,3-diphenylpyrazolo[1,5-a]pyrimidin-5-yl)-1,3,4-thiadiazol-2-amine (51.8 mg, 0.1 mmol) in 4N HCl in 1.4-dioxane (15 mL) was stirred at room temperature overnight. The reaction mixture was concentrated in vacuo. The residue was stirred with methanol and saturated sodium hydrogen carbonate solution to afford the title compound.

¹H NMR (DMSO-$d_6$): δ 12.43 (s, 0.5H), 12.12 (s, 0.5H), 11.87 (s, 0.5H), 9.80 (s, 0.5H), 7.50 (br. s., 3H), 7.41 (br. s., 4H), 7.30 (br. s., 4H), 7.04 (d, J=8.55 Hz, 2H), 3.82 (s, 3H). LC-MS: m/z 509.1 (M+H)⁺.

Compound 147: 5-((1,2,4-thiadiazol-5-yl)amino)-6-(4-methoxyphenyl)-2,3-diphenylpyrazolo[1,5-a]pyrimidin-7(4H)-one

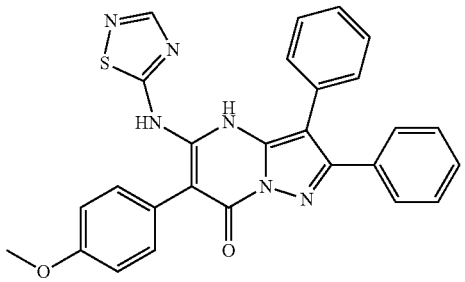 [SMILES: COc1ccc(-c2c(Nc3ncns3)[nH]c3c(-c4ccccc4)c(-c4ccccc4)nn3c2=O)cc1]

Step E stoichiometry: Intermediate 5 (600 mg, 1.3 mmol) and 1,2,4-thiadiazol-5-amine (179 mg, 1.77 mmol, 1.3 eq), Pd(OAc)$_2$ (46 mg, 0.2 mmol, 0.15 eq), Xantphos (118 mg, 0.2 mmol, 0.15 eq) and Cs$_2$CO$_3$ (844 mg, 2.72 mmol, 2.0 eq) in 1.4-dioxane (15 mL) under heating at 100 C through microwave irradiation for 1 hour under N$_2$ atmosphere. LC-MS: m/z 506.9H)$^+$.

Step F: A solution of N-(7-methoxy-6-(4-methoxyphenyl)-2,3-diphenylpyrazolo[1,5-a]pyrimidin-5-yl)-1,2,4-thiadiazol-5-amine (214 mg, 0.42 mmol) in 4M HCl in 1.4-dioxane (15 mL) was stirred at 30° C. for 5 hours. The reaction mixture was concentrated in vacuo to obtain the title compound.

$^1$H NMR (DMSO-d$_6$) δ: 10.13 (s, 1H), 8.21 (s, 1H), 7.55 (dd, J=7.6, 1.6 Hz, 2H), 7.53-7.38 (m, 8H), 7.35 (d, J=8.8 Hz, 2H), 7.06 (d, J=8.8 Hz, 2H), 6.28 (s, 2H), 3.84 (s, 3H). LC-MS: m/z 492.9 (M+H)$^+$.

Compound 148: 5-((3-methoxy-1,2,4-thiadiazol-5-yl)amino)-6-(4-methoxyphenyl)-2,3-diphenylpyrazolo[1,5-a]pyrimidin-7(4H)-one

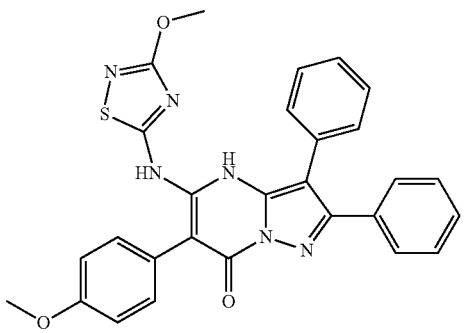 [SMILES: COc1ccc(-c2c(Nc3nc(OC)ns3)[nH]c3c(-c4ccccc4)c(-c4ccccc4)nn3c2=O)cc1]

Step E stoichiometry: Intermediate 5 (400 mg, 0.91 mmol) and 3-methoxy-1,2,4-thiadiazol-5-amine (155 mg, 1.18 mmol, 1.3 eq), Pd(OAc)$_2$ (11 mg, 0.14 mmol, 0.15 eq), Xantphos (78.7 mg, 0.14 mmol, 0.15 eq) and Cs$_2$CO$_3$ (590 mg, 1.8 mmol, 2.0 eq) in 1.4-dioxane (10 mL) under heating at 110° C. through microwave irradiation for 1 hour under N$_2$ atmosphere. LC-MS: m/z 537.0 (M+H)$^+$.

Step F: A solution of 3-methoxy-N-(7-methoxy-6-(4-methoxyphenyl)-2,3-diphenylpyrazolo[1,5-a]pyrimidin-5-yl)-1,2,4-thiadiazol-5-amine (100 mg, 0.19 mmol) in 4M HCl in 1.4-dioxane (5 mL) was stirred at 30° C. for 5 hours. The reaction mixture was concentrated in vacuo to obtain the title compound.

$^1$H NMR (DMSO-d$_6$): δ 10.27 (s, 1H), 7.57-7.52 (m, 2H), 7.51-7.36 (m, 8H), 7.31 (d, J=8.4 Hz, 2H), 7.04 (d, J=8.8 Hz, 2H), 3.82 (s, 6H). LC-MS: m/z 523.0 (M+H)$^+$.

Compound 149: 5-((4-amino-1,2,5-oxadiazol-3-yl)amino)-6-(4-methoxyphenyl)-2,3-diphenylpyrazolo[1,5-a]pyrimidin-7(4H)-one

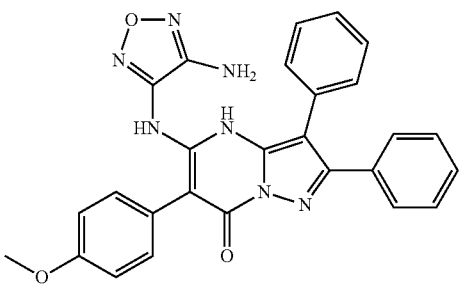 [SMILES: COc1ccc(-c2c(Nc3nonc3N)[nH]c3c(-c4ccccc4)c(-c4ccccc4)nn3c2=O)cc1]

Step E stoichiometry: Intermediate 5 (220 mg, 0.5 mmol), N3-(7-methoxy-6-(4-methoxyphenyl)-2,3-diphenylpyrazolo[1,5-a]pyrimidin-5-yl)-1,2,5-oxadiazole-3,4-diamine (101 mg, 1.0 mmol, 2.0 eq), Pd(OAc)$_2$ (11 mg, 0.05 mmol, 0.1 eq), Xantphos (116 mg, 0.2 mmol, 0.4 eq) and Cs$_2$CO$_3$ (325 mg, 1.0 mmol, 2.0 eq) in 1.4-dioxane (10 mL) under heating at 100° C. through microwave irradiation for 1 hour under N$_2$ atmosphere. LC-MS: m/z 506.1 (M+H)$^+$.

Step F: A solution of N3-(7-methoxy-6-(4-methoxyphenyl)-2,3-diphenylpyrazolo[1,5-a]pyrimidin-5-yl)-1,2,5-oxadiazole-3,4-diamine (237 mg, 0.47 mmol) in 4M HCl in 1.4-dioxane (20 mL) was stirred at 30° C. for 5 hours. The reaction mixture was concentrated in vacuo to obtain the title compound.

$^1$H NMR (DMSO-d$_6$): δ 8.51 (br. s., 1H), 7.25-7.55 (m, 12H), 7.00 (d, J=8.8 Hz, 2H), 3.79 (s, 3H). LC-MS: m/z 492.1 (M+H)$^+$.

Compound 150: ethyl 5-((6-(4-methoxyphenyl)-7-oxo-2,3-diphenyl-4,7-dihydropyrazolo[1,5-a]pyrimidin-5-yl)amino)thiazole-4-carboxylate

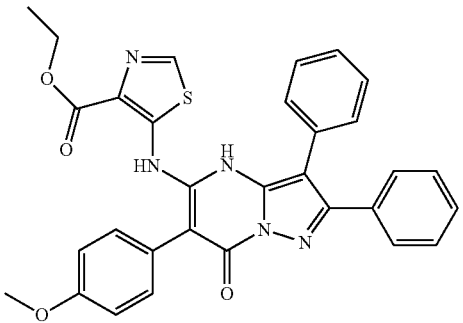 [SMILES: CCOC(=O)c1ncsc1Nc1[nH]c2c(-c3ccccc3)c(-c3ccccc3)nn2c(=O)c1-c1ccc(OC)cc1]

Step E stoichiometry: Intermediate 5 (500 mg, 1.13 mmol), ethyl 5-aminothiazole-4-carboxylate (292.3 mg, 1.70 mmol), and Pd(OAc)$_2$ (76.2 mg, 0.34 mmol), Xantphos (196.4 mg, 0.34 mmol) and Cs$_2$CO$_3$ (553.0 mg, 0.34 mmol)

in 1,4-dioxane (10 mL) under heating at 120° C. through microwave irradiation for 1.5 hours under N₂ atmosphere. LC-MS: m/z 578.3 (M+H)⁺.

Step F: A solution of ethyl 5-((7-methoxy-6-(4-methoxyphenyl)-2,3-diphenylpyrazolo[1,5-a]pyrimidin-5-yl)amino)thiazole-4-carboxylate (450 mg, 0.78 mmol) in 4M HCl in 1,4-dioxane (16 mL) was stirred at r.t. for 18 hours. The mixture was concentrated, and saturated NaHCO₃ (10 mL) was added to obtain ethyl 5-((6-(4-methoxyphenyl)-7-oxo-2,3-diphenyl-4,7-dihydropyrazolo[1,5-a]pyrimidin-5-yl)amino)thiazole-4-carboxylate.

¹H NMR (DMSO-d₆): δ 10.03 (s, 1H), 8.30 (s, 1H), 7.50-7.63 (m, 4H), 7.29-7.45 (m, 7H), 7.14-7.26 (m, 1H), 7.04 (d, J=8.9 Hz, 2H), 4.12 (q, J=7.0 Hz, 2H), 3.83 (s, 3H), 1.17 (t, J=7.1 Hz, 3H). LC-MS: m/z 564.3 (M+H)⁺.

Compound 151: 5-((1H-pyrrolo[2,3-c]pyridin-5-yl)amino)-6-(4-methoxyphenyl)-2,3-diphenylpyrazolo[1,5-a]pyrimidin-7(4H)-one

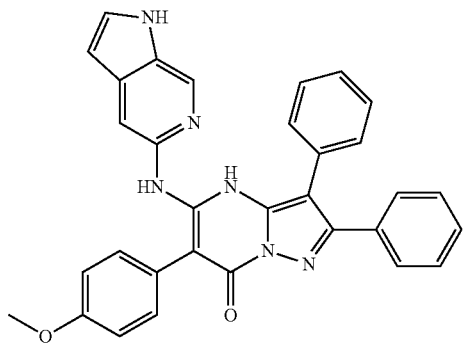 [SMILES: COc1ccc(-c2c(Nc3cc4cc[nH]c4cn3)[nH]c3c(-c4ccccc4)c(-c4ccccc4)nn3c2=O)cc1]

Step E stoichiometry: Intermediate 5 (200 mg, 0.450 mmol), 1H-pyrrolo[2,3-c]pyridin-5-amine (120 mg, 0.90 mmol), palladium(II) acetate (50 mg, 0.225 mmol), xantphos (196 mg, 0.340 mmol) and potassium carbonate (124 mg, 0.90 mmol) in 1,4-dioxane (10 mL) under heating at 100° C. through microwave irradiation for 1 hour under N₂ atmosphere. LC-MS: m/z 539.2 (M+H)⁺.

Step F: A mixture of 7-methoxy-6-(4-methoxyphenyl)-2,3-diphenyl-N-(1H-pyrrolo[2,3-c]pyridin-5-yl)-pyrazolo[1,5-a]pyrimidin-5-amine (80 mg, 0.148 mmol) in hydrogen chloride solution (4 M in dioxane, 5 mL) was stirred at room temperature for 16 hours. The mixture was evaporated to dryness. The residue was resolved in dichloromethane solution (with 10% methanol) and basified with aqueous ammonia to pH 8 to afford 5-(1H-pyrrolo [2,3-c]pyridin-5-ylamino)-6-(4-methoxyphenyl)-2,3-diphenylpyrazolo[1,5-a] pyrimidin-7(4H)-one.

¹H NMR (DMSO-d₆): δ 16.31 (s, 1H), 11.56 (s., 1H), 8.61 (s, 1H), 8.25 (s, 1H), 7.72-7.35 (m, 14H), 7.07 (d, J=8.8 Hz, 2H), 6.44 (s., 1H), 3.85 (s, 1H). LC-MS: m/z 525.2 (M+H)⁺.

5-chloro-3-(cyclohex-1-en-1-yl)-7-methoxy-6-(4-methoxyphenyl)-2-phenylpyrazolo[1,5-a]pyrimidine

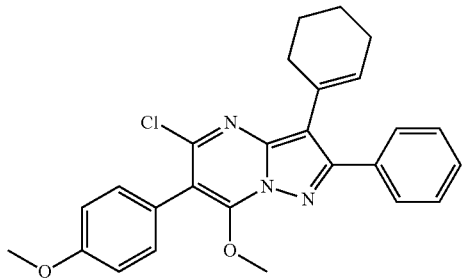 [SMILES: COc1ccc(-c2c(Cl)nc3c(C4=CCCCC4)c(-c4ccccc4)nn3c2OC)cc1]

This compound was prepared according to the procedure for preparing compound 101 by using Intermediate 8 as 4-(cyclohex-1-en-1-yl)-3-phenyl-1H-pyrazol-5-amine in step B.

Step B: To a solution of dimethyl 2-(4-methoxyphenyl)malonate (39.6 g, 166 mmol) in tri-n-butylamine (80 ml) at 198° C. was added 4-cyclohexenyl-3-phenyl-1H-pyrazol-5-amine (47.3 g, 199 mmol) in portions, and the resultant mixture was stirred for 1 h at 198° C. The mixture was cooled to the room temperature, and solvent was decanted. THF (150 mL) and HCl (6N, 600 mL) were added with stirring vigorously for 0.5 h. The precipitates were collected by filtration, washed with methanol, and dried under reduced pressure to give 3-(cyclohex-1-en-1-yl)-5-hydroxy-6-(4-methoxyphenyl)-2-phenylpyrazolo[1,5-a]pyrimidin-7(4H)-one (48 g) as a yellow solid.

¹H NMR (DMSO-d₆): δ 7.74 (d, J=6.98 Hz, 2H), 7.31-7.49 (m, 5H), 6.94 (d, J=8.60 Hz, 2H), 5.80 (br. s., 1H), 3.78 (s, 3H), 2.15 (br. s., 2H), 2.02 (br. s., 2H), 1.65 (br. s., 4H). LC-MS: m/z 414.2 (M+H)⁺.

Step C: A solution of 3-(cyclohex-1-en-1-yl)-5-hydroxy-6-(4-methoxyphenyl)-2-phenylpyrazolo[1,5-a]pyrimidin-7(4H)-one (47.0 g, 104 mmol) in phosphorus oxychloride (100 mL) was stirred at reflux for 16 hrs. The solvent was removed in vacuum. The residue was added slowly to methanol (100 mL) cooled at 0° C. The precipitates were collected by filtration, washed with methanol, and dried under reduced pressure to give 5,7-dichloro-3-(cyclohex-1-en-1-yl)-6-(4-methoxyphenyl)-2-phenylpyrazolo[1,5-a]pyrimidine (50 g) as a yellow solid.

¹H NMR (DMSO-d₆): δ 7.82 (d, J=7.25 Hz, 2H), 7.36-7.56 (m, 5H), 7.10 (d, J=8.60 Hz, 2H), 5.87 (br. s., 1H), 3.84 (s, 3H), 2.20 (br. s., 4H), 1.70 (d, J=4.57 Hz, 4H). LC-MS: m/z 450.2 (M+H)⁺.

Step D: To a solution of 5,7-dichloro-3-(cyclohex-1-en-1-yl)-6-(4-methoxyphenyl)-2-phenylpyrazolo[1,5-a]pyrimidine (40 g, 88 mmol) in dichloromethane (400 ml) at 0° C. was added sodium methoxide (30%0 in methanol, 80 g) dropwise. The resultant mixture was stirred for 10 min at 0° C. The reaction was quenched by adding ice water (100 mL) and extracted with dichloromethane (200 mL) three times. The combined organic layers were washed with brine (200 ml), dried over anhydrous sodium sulfate, and concentrated in vacuum. The residue was suspended in MeOH (50 mL). The precipitates were collected by filtration, washed with MeOH, and dried under reduced pressure to give 5-chloro-3-(cyclohex-1-en-1-yl)-7-methoxy-6-(4-methoxyphenyl)-2-phenylpyrazolo[1,5-a]pyrimidine as a yellow solid.

¹H NMR (DMSO-d₆): δ 7.78-7.91 (m, 2H), 7.42-7.58 (m, 3H), 7.33-7.42 (m, J=8.9 Hz, 2H), 7.00-7.14 (m, J=8.9 Hz,

2H), 5.83 (br. s., 1H), 4.14 (s, 3H), 3.84 (s, 3H), 2.20 (d, J=5.9 Hz, 4H), 1.61-1.77 (m, 4H). LC-MS: m/z 446.1 (M+H)⁺.

6-(5-chloro-7-methoxy-2,3-diphenylpyrazolo[1,5-a]pyrimidin-6-yl)quinoline

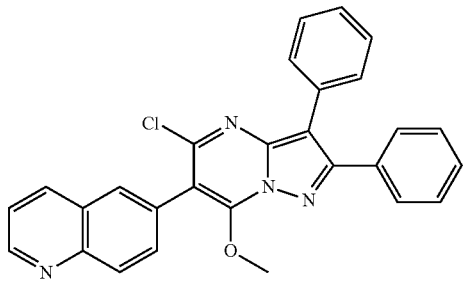 [SMILES: COc1c(-c2ccc3ncccc3c2)c(Cl)nc2c(-c3ccccc3)c(-c3ccccc3)nn12]

This compound was prepared according to the procedure for preparing compound 101 by using Intermediate 1 as methyl 2-(quinolin-6-yl)acetate in step A.

Step A: To dimethyl carbonate (150 mL) cooled at 0° C. was added potassium tert-butanolate (24 g, 216 mmol) in portions. The resultant mixture was stirred at 0° C. for 1 hour. Methyl 2-(quinolin-6-yl)acetate (20 g, 100 mmol) was added. The resultant mixture was slowly warmed up to room temperature and stirred for 1 hour. The reaction mixture was heated to 80° C. with stirring overnight. After cooling to room temperature, the mixture was diluted with EtOAc (1500 mL), washed with saturated NH₄Cl (300 mL) and brine (250 mL), dried over anhydrous sodium sulfate and concentrated in vacuo. The residue was purified by flash column (petroleum ether/ethyl acetate=3:1) to obtain dimethyl 2-(quinolin-6-yl)malonate (18.0 g) as a yellow solid. LC-MS: m/z 260.1 (M+H)⁺.

Step B: A suspension of dimethyl 2-(quinolin-6-yl)malonate (13 g, 50 mmol) and 3,4-diphenyl-1H-pyrazol-5-amine (11.8 g, 50 mmol) in tributylamine (100 mL) was stirred at 185° C. for 4 hours. After cooling to room temperature, the mixture was filtered. The residue was diluted with DCM (450 mL), washed with saturated NH₄Cl (150 ml) and brine (100 ml), dried over anhydrous sodium sulfate, and concentrated in vacuo. The residue was purified by flash column (DCM:MeOH=15:1) to obtain 2,3-diphenyl-6-(quinolin-6-yl)pyrazolo[1,5-a]pyrimidine-5,7(4H,6H)-dione (18 g) as a yellow solid. LC-MS: m/z 431.2 (M+H)⁺.

Step C: The solution of 2,3-diphenyl-6-(quinolin-6-yl)pyrazolo[1,5-a]pyrimidine-5,7(4H,6H)-dione (18 g, 42 mmol), DMAP (1 g) and PCl₅ (80 mg) in POCl₃ (180 ml) was stirred at 100° C. overnight. After cooling to room temperature, the solvent was removed by vacuum. The residue was cooled to 0° C. MeOH (60 mL) was added to quench the reaction. The resultant mixture was diluted with DCM (450 ml), washed with saturated NaHCO₃ (150 ml) and brine (100 ml), dried over anhydrous sodium sulfate, and concentrated to afford crude product of 6-(5,7-dichloro-2,3-diphenylpyrazolo[1,5-a]pyrimidin-6-yl)quinoline (13 g) which was used in the next step without further purification. LC-MS: m/z 467.1 (M+H)⁺.

Step D: To a solution of 6-(5,7-dichloro-2,3-diphenylpyrazolo[1,5-a]pyrimidin-6-yl)quinoline (13.0 g, crude, 27.8 mmol) in DCM/MeOH (200 mL, 1:1) cooled at 0° C. was added sodium methoxide (14.9 mL, 5.0 M in methanol) dropwise. Then the mixture was stirred at 0° C. for 1 hour. Saturated NH₄Cl (150 mL) was added to quench the reaction. The resultant mixture was extracted with DCM (500 mL), washed with brine (150 mL), dried over anhydrous sodium sulfate, and concentrated in vacuo. The residue was purified by flash column (DCM/MeOH=40:1) to obtain 6-(5-chloro-7-methoxy-2,3-diphenylpyrazolo[1,5-a]pyrimidin-6-yl)quinoline as a pale yellow solid.

¹H NMR (DMSO-d₆): δ 9.01 (dd, J=4.2, 1.7 Hz, 1H), 8.45-8.52 (m, 1H), 8.13-8.21 (m, 2H), 7.88 (dd, J=8.6, 1.9 Hz, 1H), 7.59-7.68 (m, 3H), 7.42-7.48 (m, 7H), 7.34-7.41 (m, 1H), 4.25 (s, 3H). LC-MS: m/z 463.1 (M+H)⁺.

6-(5-chloro-3-(cyclohex-1-en-1-yl)-7-methoxy-2-phenylpyrazolo[1,5-a]pyrimidin-6-yl)quinoline

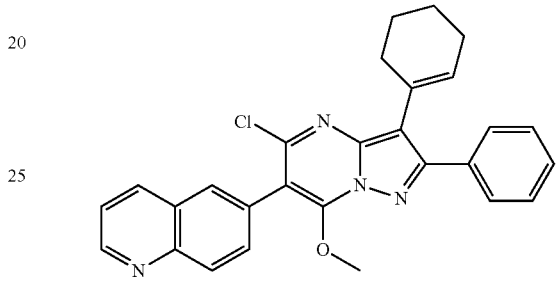

This compound was prepared according to the procedure for preparing compound 101 by using Intermediate 1 as methyl 2-(quinolin-6-yl)acetate e in step A and Intermediate 8 as 4-(cyclohex-1-en-1-yl)-3-phenyl-1H-pyrazol-5-amine in step B.

Step B: A suspension of dimethyl 2-(quinolin-6-yl)malonate (1.95 g, 7.52 mmol) and 4-(cyclohex-1-en-1-yl)-3-phenyl-1H-pyrazol-5-amine (1.8 g, 7.52 mmol) in tributylamine (20 mL) was stirred at 185° C. for 4 hours. After cooling to room temperature, the mixture was filtered. The residue was diluted with DCM (150 mL), washed with saturated NH₄Cl (50 ml) and brine (50 ml), dried over anhydrous sodium sulfate, and concentrated in vacuo. The residue was purified by flash column (DCM:MeOH=15:1) to obtain 3-(cyclohex-1-en-1-yl)-2-phenyl-6-(quinolin-6-yl)pyrazolo[1,5-a]pyrimidine-5,7(4H,6H)-dione (3.1 g) as a yellow solid. LC-MS: m/z 435.2 (M+H)⁺.

Step C: The solution of 3-(cyclohex-1-en-1-yl)-2-phenyl-6-(quinolin-6-yl)pyrazolo[1,5-a]pyrimidine-5,7(4H,6H)-dione (3.1 g, 7.13 mmol) in POCl₃ (12 ml) was stirred at 110° C. overnight. After cooling to room temperature, the solvent was removed by vacuum. MeOH (60 mL) was added slowly to the residue cooled at 0° C. to quench the reaction. The resultant mixture was diluted with DCM (150 ml), washed with saturated NaHCO₃ (50 ml) and brine (50 ml), dried over anhydrous sodium sulfate, and concentrated to afford crude product of 6-(5,7-dichloro-3-(cyclohex-1-en-1-yl)-2-phenylpyrazolo[1,5-a]pyrimidin-6-yl)quinoline (1.3 g) which was used in the next step without further purification. LC-MS: m/z 471.9 (M+H)⁺.

Step D: To a solution of 6-(5,7-dichloro-3-(cyclohex-1-en-1-yl)-2-phenylpyrazolo[1,5-a]pyrimidin-6-yl)quinoline (300 mg, crude, 0.64 mmol) in DCM/MeOH (6 mL, 1:1) cooled at 0° C. was added sodium methoxide (0.64 mL, 5.0 M in methanol) dropwise. Then the mixture was stirred at 0° C. for 1 hour. Saturated NH₄Cl (50 mL) was added to quench the reaction. The resultant mixture was extracted with DCM (150 mL), washed with brine (50 mL), dried over anhydrous sodium sulfate, and concentrated in vacuo. The residue was purified by flash column (DCM/MeOH=40:1) to obtain 6-(5-chloro-3-(cyclohex-1-en-1-yl)-7-methoxy-2-phenylpyrazolo[1,5-a]pyrimidin-6-yl)quinoline as a off-white solid.

$^1$H NMR (CHLOROFORM-d): δ 9.28 (d, J=3.8 Hz, 1H), 8.76 (d, J=8.6 Hz, 2H), 8.11 (s, 1H), 7.80-8.03 (m, 4H), 7.36-7.57 (m, 3H), 5.99 (br. s., 1H), 3.75 (s, 3H), 2.20-2.37 (m, 4H), 1.67-1.87 (m, 4H). LC-MS: m/z 467.2 (M+H)$^+$.

6-(5-chloro-3-(cyclohex-1-en-1-yl)-7-methoxy-2-phenylpyrazolo[1,5-a]pyrimidin-6-yl)quinoxaline

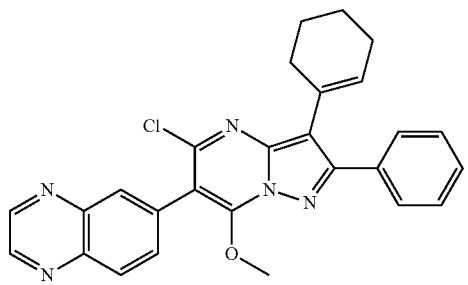 [SMILES: COc1c(-c2ccc3nccnc3c2)c(Cl)nc2c(C3=CCCCC3)c(-c3ccccc3)nn12]

This compound was prepared according to the procedure for preparing compound 101 by using Intermediate 1 as methyl 2-(quinoxalin-6-yl)acetate in step A and Intermediate 8 as 4-(cyclohex-1-en-1-yl)-3-phenyl-1H-pyrazol-5-amine in step B.

Step A: To dimethyl carbonate (30 mL) cooled at 0° C. was added potassium tert-butanolate (3.8 g, 34.12 mmol) in portions. The resultant mixture was stirred at 0° C. for 1 hour. Methyl 2-(quinoxalin-6-yl)acetate (2.3 g, 11.37 mmol) was added. The resultant mixture was slowly warmed up to room temperature and stirred for 1 hour. The reaction mixture was heated to 90° C. and stirred for 1.5 hours. After cooling to room temperature, the mixture was diluted with EtOAc (150 mL), washed with saturated NH$_4$Cl (80 mL) and brine (50 mL), dried over anhydrous sodium sulfate and concentrated in vacuo. The residue was purified by flash column (petroleum ether/ethyl acetate=3:1) to obtain dimethyl 2-(quinoxalin-6-yl)malonate (2.0 g) as a yellow solid.

$^1$H NMR (CHLOROFORM-d): δ 8.89 (s, 2H), 8.10-8.19 (m, 2H), 7.91 (dd, J=8.7, 2.0 Hz, 1H), 4.95 (s, 1H), 3.82 (s, 6H). LC-MS: m/z 261.1 (M+H)$^+$.

Step B: A suspension of 4-(cyclohex-1-en-1-yl)-3-phenyl-1H-pyrazol-5-amine (1.93 g, 8.07 mmol) and dimethyl 2-(quinoxalin-6-yl)malonate (2.1 g, 8.07 mmol) in tributylamine (20 mL) was stirred at 175° C. for 2 hours. After cooling to room temperature, the mixture was filtered. The residue was diluted with DCM (150 mL), washed with saturated NH$_4$Cl (50 ml) and brine (30 ml), dried over anhydrous sodium sulfate, and concentrated in vacuo. The residue was purified by flash column (DCM:MeOH=15:1) to obtain 3-(cyclohex-1-en-1-yl)-2-phenyl-6-(quinoxalin-6-yl)pyrazolo[1,5-a]pyrimidine-5,7(4H,6H)-dione (2.2 g) as a yellow solid.

$^1$H NMR (DMSO-d$_6$): δ 10.11 (br. s., 1H), 9.07 (br. s., 1H), 8.79 (s, 1H), 8.73 (s, 1H), 8.58 (s, 1H), 8.51 (d, J=8.9 Hz, 1H), 7.85 (d, J=8.9 Hz, 1H), 7.71 (d, J=7.3 Hz, 2H), 7.27-7.46 (m, 3H), 5.69 (br. s., 1H), 2.14 (br. s., 2H), 2.00 (br. s., 2H), 1.60-1.68 (m, 4H). LC-MS: m/z 436.2 (M+H)$^+$.

Step C: The solution of 3-(cyclohex-1-en-1-yl)-2-phenyl-6-(quinoxalin-6-yl)pyrazolo[1,5-a]pyrimidine-5,7(4H,6H)-dione (1.0 g, 2.30 mmol) in POCl$_3$ (6 ml) in a sealed tube was stirred at 110° C. for 8 hours. After cooling to room temperature, the solvent was removed by vacuum. The residue was cooled to 0° C. MeOH (6 mL) was added to quench the reaction. The resultant mixture was diluted with DCM (150 ml), washed with saturated NaHCO$_3$ (50 ml) and brine (30 ml), dried over anhydrous sodium sulfate, and concentrated to afford crude product of 6-(5,7-dichloro-3-(cyclohex-1-en-1-yl)-2-phenylpyrazolo[1,5-a]pyrimidin-6-yl)quinoxaline (800 mg) which was used in the next step without further purification. LC-MS: m/z 472.1 (M+H)$^+$.

Step D: To a solution of 6-(5,7-dichloro-3-(cyclohex-1-en-1-yl)-2-phenylpyrazolo[1,5-a]pyrimidin-6-yl)quinoxaline (800 mg, crude, 2.30 mmol) in DCM/MeOH (20 mL, 1:1) cooled at 0° C. was added sodium methoxide (2.3 mL, 5.0 M in methanol) dropwise. Then the mixture was stirred at 0° C. for 1 hour. Saturated NH$_4$Cl (50 mL) was added to quench the reaction. The resultant mixture was extracted with DCM (100 mL), washed with brine (30 mL), dried over anhydrous sodium sulfate, and concentrated in vacuo. The residue was purified by flash column (DCM/MeOH=40:1) to obtain 6-(5-chloro-3-(cyclohex-1-en-1-yl)-7-methoxy-2-phenylpyrazolo[1,5-a]pyrimidin-6-yl)quinoxaline as a brown solid.

$^1$H NMR (CHLOROFORM-d): δ 8.98 (s, 2H), 8.29 (d, J=8.9 Hz, 1H), 8.24 (d, J=1.6 Hz, 1H), 7.92 (dd, J=7.9, 1.5 Hz, 2H), 7.86 (dd, J=8.6, 1.9 Hz, 1H), 7.41-7.55 (m, 3H), 5.98 (dt, J=3.6, 1.9 Hz, 1H), 4.26-4.37 (m, 3H), 2.33 (br. s., 2H), 2.19-2.30 (m, 2H), 1.71-1.85 (m, 4H). LC-MS: m/z 468.2 (M+H)$^+$.

The following compounds were prepared according to Example 1, step E and F, starting from 5-chloro-3-(cyclohex-1-en-1-yl)-7-methoxy-6-(4-methoxyphenyl)-2-phenylpyrazolo[1,5-a]pyrimidine.

Compound 153: 3-(cyclohex-1-en-1-yl)-6-(4-methoxyphenyl)-2-phenyl-5-(pyridin-2-ylamino)pyrazolo[1,5-a]pyrimidin-7(4H)-one

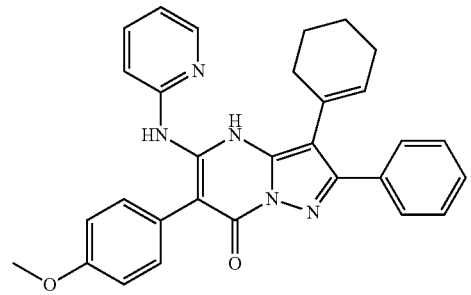

Step E stoichiometry: 5-chloro-3-(cyclohex-1-en-1-yl)-7-methoxy-6-(4-methoxyphenyl)-2-phenylpyrazolo[1,5-a]pyrimidine (200 mg, 0.0449 mol), pyridin-2-amine (63.4 m g, 0.674 mol, 1.5 eq.), Pd(OAc)$_2$ (20.2 mg, 0.0898 mol, 0.2 eq.), Xantphos (52 mg, 0.0898 mol, 0.2 eq.) and K$_2$CO$_3$ (265 mg, 1.12 mol, 2.5 eq.) in dioxane (5 mL) under heating at 120° C. for 1 hour under N$_2$ atmosphere. LC-MS: m/z 504.9 (M+H)$^+$.

Step F: A solution of 3-(cyclohex-1-en-1-yl)-7-methoxy-6-(4-methoxyphenyl)-2-phenyl-N-(pyridin-2-yl)pyrazolo[1,5-a] pyrimidin-5-amine (120 mg, 0.22 mol) in 4M HCl/1,4- dioxane (3 mL) was stirred at r.t. for 16 hours. The reaction mixture was basified with NaHCO₃ solution to pH=8 and filtered to afford the title compound.

¹H NMR (DMSO-d₆): δ 9.09 (br. s., 1H), 8.20 (d, J=4.3 Hz, 1H), 7.82 (t, J=7.3 Hz, 1H), 7.73 (d, J=7.3 Hz, 2H), 7.38-7.51 (m, 3H), 7.28-7.38 (m, 3H), 7.10-7.17 (m, 1H), 7.03 (d, J=8.5 Hz, 2H), 6.06 (br. s., 1H), 3.82 (s, 3H), 2.34 (br. s., 2H), 2.06 (br. s., 2H), 1.65-1.79 (m, 4H). LC-MS: m/z 490.2 (M+H)⁺.

Compound 154: 3-(cyclohex-1-en-1-yl)-6-(4-methoxyphenyl)-2-phenyl-5-(pyridin-3-ylamino)pyrazolo[1,5-a]pyrimidin-7(4H)-one

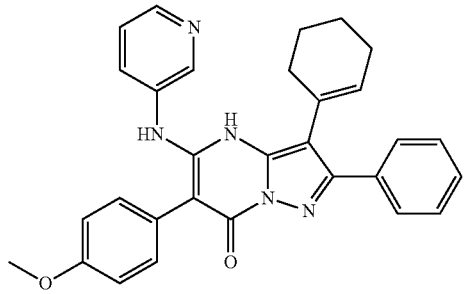

Step E stoichiometry: 5-chloro-3-(cyclohex-1-en-1-yl)-7-methoxy-6-(4-methoxyphenyl)-2-phenylpyrazolo[1,5-a]pyrimidine (200 mg, 0.45 mmol), pyridin-3-amine (85 mg, 0.90 mmol), Pd(OAc)₂ (36 mg, 0.045 mmol), xantphos (58 mg, 0.09 mmol), and Cs₂CO₃ (293 mg, 0.90 mmo) in dioxane (20 mL) under heating at 110° C. for 4 hours under N₂ atmosphere. LC-MS: m/z 504.2 (M+H)⁺.

Step F: To a solution of 3-(cyclohex-1-en-1-yl)-7-methoxy-6-(4-methoxyphenyl)-2-phenyl-N-(pyridin-3-yl)pyrazolo[1,5-a]pyrimidin-5-amine (60 mg, 0.12 mmol) in MeOH (10 mL) was added 4N HCl solution in dioxane (10 mL). The reaction mixture was heated to 50° C. for 2 h. The mixture was concentrated in vacuo. The crude product was basified with saturated NaHCO₃ solution to give the desired product 3-(cyclohex-1-en-1-yl)-6-(4-methoxyphenyl)-2-phenyl-5-(pyridin-3-ylamino)pyrazolo[1,5-a]pyrimidin-7(4H)-one.

¹H NMR (DMSO-d₆): δ 8.69 (br. s., 1H), 8.31 (d, J=5.4 Hz, 1H), 8.17 (d, J=8.3 Hz, 1H), 7.71-7.83 (m, 3H), 7.39-7.52 (m, 3H), 7.24-7.33 (m, J=8.6 Hz, 2H), 6.81-6.94 (m, J=8.9 Hz, 2H), 5.88 (br. s., 1H), 3.73 (s, 3H), 2.14 (br. s., 2H), 2.02-2.12 (m, 2H), 1.56-1.74 (m, 4H). LC-MS: m/z 490.2 (M+H)⁺.

Compound 155: 3-(cyclohex-1-en-1-yl)-6-(4-methoxyphenyl)-2-phenyl-5-(pyrimidin-4-ylamino)pyrazolo[1,5-a]pyrimidin-7(4H)-one

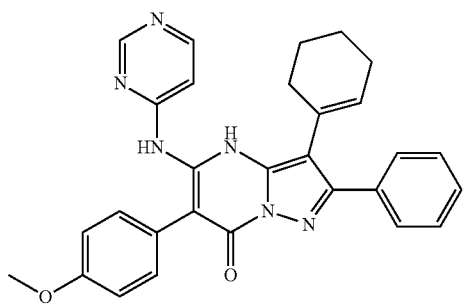

Step E stoichiometry: 5-chloro-3-(cyclohex-1-en-1-yl)-7-methoxy-6-(4-methoxyphenyl)-2-phenylpyrazolo[1,5-a]pyrimidine (400 mg, 0.897 mmol) and pyrimidin-4-amine (255.9 mg, 2.691 mmol, 3 eq), Pd(OAc)₂ (40.3 mg, 0.179 mmol, 0.2 eq), Xant-phos (578.6 mg, 0.359 mmol, 0.4 eq) and Cs₂CO₃ (285.2 mg, 2.691 mmol, 3 eq) in 1.4-dioxane (10 mL) under heating at 100° C. through microwave irradiation for 1 hour under N₂ atmosphere. LC-MS: m/z 505.0 (M+H)⁺.

Step F: A solution of 3-(cyclohex-1-en-1-yl)-7-methoxy-6-(4-methoxyphenyl)-2-phenyl-N-(pyrimidin-4-yl)pyrazolo[1,5-a]pyrimidin-5-amine (100 mg, 0.198 mmol) in 4M HCl in 1.4-dioxane (10 mL) was stirred at room temperature for 3 hours. The reaction mixture was concentrated in vacuo. The residue was dissolved in 7N NH₃ in methanol and stirred at room temperature for 2 hours to afford the title compound.

¹H NMR (DMSO-d₆): δ 8.98 (s, 1H), 8.49 (d, J=7.02 Hz, 1H), 7.79 (d, J=7.32 Hz, 2H), 7.41-7.52 (m, 3H), 7.27 (m, J=8.54 Hz, 2H), 7.18 (d, J=6.41 Hz, 1H), 6.93 (m, J=8.54 Hz, 2H), 5.87 (br. s., 1H), 2.18 (br. s., 2H), 2.06 (br. s., 2H), 1.67 (br. s., 4H). LC-MS: m/z 491.0 (M+H)⁺.

Compound 156: 3-cyclohexenyl-6-(4-methoxyphenyl)-5-(2-methoxypyrimidin-4-ylamino)-2-phenylpyrazolo [1,5-a]pyrimidin-7(4H)-one

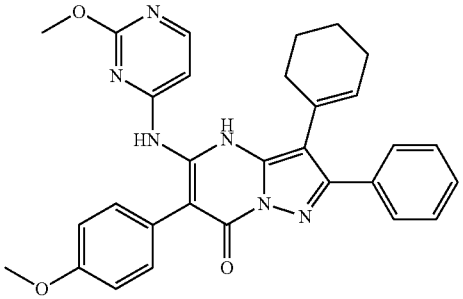 [SMILES: COc1ccc(-c2c(Nc3ccnc(OC)n3)[nH]c3c(C4=CCCCC4)c(-c4ccccc4)nn3c2=O)cc1]

Step E stoichiometry: 5-chloro-3-(cyclohex-1-en-1-yl)-7-methoxy-6-(4-methoxyphenyl)-2-phenylpyrazolo[1,5-a]pyrimidine (200 mg, 0.452 mmol) and 2-methoxypyrimidin-4-amine (113 mg, 0.904 mmol) and Pd(OAc)₂ (31 mg, 0.136 mmol), Xantphos (157 mg, 0.272 mmol) and Na₂CO₃ (96 g, 0.904 mmol) in 1.4-dioxane (10 mL) under heating at 110° C. for 4 hours under N₂ atmosphere.

¹HNMR (DMSO-d₆) δ 8.46 (d, J=5.6 Hz, 1H), 8.14 (d, J=5.6 Hz, 1H), 7.81 d, J=7.2 Hz, 2H), 7.56 (s, 1H), 7.42-7.51 (m, 4H), 7.16-7.18 (m, 2H), 5.88 (bs, 1H), 4.11 (s, 3H), 3.86 (s, 3H), 3.80 (s, 3H), 2.22-2.27 (m, 4H), 1.70-1.75 (m, 4H). LC-MS: m/z 535.2 (M+H)⁺.

Step F: A mixture of 3-cyclohexenyl-7-methoxy-6-(4-methoxyphenyl)-N-(2-methoxy-pyrimidin-4-yl)-2-phenyl-pyrazolo[1,5-a]pyrimidin-5-amine (55 mg, 0.103 mmol) and HCl solution (4N in dioxane, 6 mL) was stirred at room temperature overnight. The mixture was quenched with NH₃ solution (7N in methanol) to pH 7 to afford 3-cyclohexenyl-6-(4-methoxyphenyl)-5-(2-methoxypyrimidin-4-ylamino)-2-phenyl-pyrazolo [1,5-a]pyrimidin-7(4H)-one.

¹H NMR (DMSO-d₆): δ 13.82 (s, 1H), 9.38 (s, 1H), 8.28 (d, J=5.80 Hz, 1H), 7.75 (d, J=7.32 Hz, 2H), 7.45-7.51 (m, 2H), 7.42 (d, J=7.32 Hz, 1H), 7.29 (m, J=8.54 Hz, 2H), 7.02 (m, J=8.85 Hz, 2H), 6.86 (d, J=5.80 Hz, 1H), 5.99 (s, 1H), 3.92 (s, 3H), 3.81 (s, 3H), 2.28 (bs, 2H) 2.06 (bs, 2H), 1.70 (bs, 4H). LC-MS: m/z 521.5 (M+H)⁺.

Compound 157: 3-(cyclohex-1-en-1-yl)-6-(4-methoxyphenyl)-2-phenyl-5-(pyridazin-3-ylamino) pyrazolo[1,5-a]pyrimidin-7(4H)-one

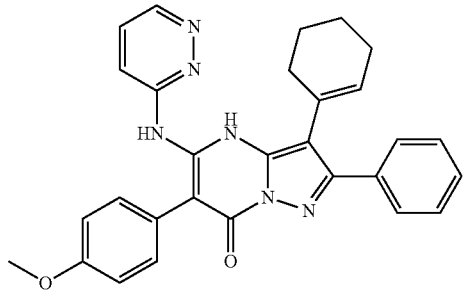

Step E stoichiometry: 5-chloro-3-(cyclohex-1-en-1-yl)-7-methoxy-6-(4-methoxyphenyl)-2-phenylpyrazolo[1,5-a]pyrimidine (150 mg, 0.34 mmol) and pyridazin-3-amine (65 mg, 0.68 mmol, 2.0 eq), Pd(OAc)$_2$ (16 mg, 0.07 mmol, 0.2 eq), Xantphos (41 mg, 0.07 mmol, 0.2 eq) and Cs$_2$CO$_3$ (442 mg, 1.36 mmol, 4.0 eq) in 1.4-dioxane (10 mL) under heating at 100° C. for 1 hour through microwave irradiation under nitrogen atmosphere. LC-MS: m/z 504.9 (M+H)⁺.

Step F: A solution of 3-(cyclohex-1-en-1-yl)-7-methoxy-6-(4-methoxyphenyl)-2-phenyl-N-(pyridazin-3-yl)pyrazolo[1,5-a]pyrimidin-5-amine (70 mg, 0.14 mmol) in 4M HCl in 1.4-dioxane (15 mL) was stirred at 30° C. for 5 hours. The reaction mixture was concentrated in vacuo to obtain the title compound.

$^1$H NMR (DMSO-d$_6$): δ 15.09 (s, 1H), 9.18 (s, 1H), 8.92 (d, J=2.8 Hz, 1H), 7.74 (d, J=7.2 Hz, 2H), 7.66 (d, J=6.0 Hz, 2H), 7.46-7.53 (m, 2H), 7.43 (d, J=7.6 Hz, 1H), 7.30-7.39 (m, J=8.6 Hz, 2H), 6.98-7.11 (m, J=8.6 Hz, 2H), 6.07 (br. s., 1H), 3.83 (s, 3H), 2.32-2.38 (m, 2H), 2.07 (br. s., 2H), 1.70 (br. s., 4H). LC-MS: m/z 491.1 (M+H)⁺.

Compound 158: 3-cyclohexenyl-6-(4-methoxyphenyl)-2-phenyl-5-(pyrazin-2-ylamino) pyrazolo [1,5-a]pyrimidin-7(4H)-one

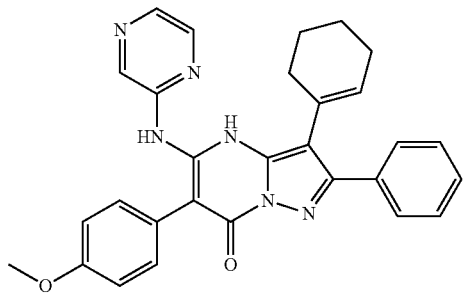

Step E stoichiometry: 5-chloro-3-(cyclohex-1-en-1-yl)-7-methoxy-6-(4-methoxyphenyl)-2-phenylpyrazolo[1,5-a]pyrimidine (200 mg, 0.450 mmol) and pyrazin-2-amine (86 mg, 0.900 mmol, 2 eq) and palladium(II) acetate (111 mg, 0.495 mmol, 1.1 eq), Xantphos (312 mg, 0.540 mmol, 1.2 eq) and sodium carbonate (323 mg, 0.990 mmol, 2.2 eq) in 1.4-dioxane (10 mL) under heating at 100° C. through microwave irradiation for 1 hour under nitrogen atmosphere. LC-MS: m/z 505.2 (M+H)⁺.

Step F: A solution of 3-cyclohexenyl-7-methoxy-6-(4-methoxyphenyl)-2-phenyl-N-(pyrazin-2-yl) pyrazolo [1,5-a]pyrimidin-5-amine (150 mg, 0.30 mmol) in 4M HCl/1.4-dioxane (5 mL) was stirred at room temperature for 24 hours. The reaction mixture was concentrated in vacuo. The residue was dissolved in dichloromethane:methanol=10:1 (10 mL) and washed with saturated sodium carbonate (5 mL) twice to pH 8. The organic layer was concentrated in vacuo to give 3-cyclohexenyl-6-(4-methoxyphenyl)-2-phenyl-5-(pyrazin-2-ylamino) pyrazolo [1,5-a] pyrimidin-7(4H)-one.

$^1$H NMR (DMSO-d$_6$): δ 3.90 (s, 1H), 9.35 (s, 1H), 8.64 (s, 1H), 8.25 (d, J=2.75 Hz, 1H), 8.20 (dd, J=2.75, 1.22 Hz, 1H), 7.67-7.77 (m, 2H) 7.44-7.53 (m, 2H), 7.37-7.44 (m, 1H), 7.27-7.36 (m, 2H), 6.98-7.06 (m, 2H), 6.04 (br. s., 1H) 3.81 (s, 3H), 2.34 (br. s., 2H), 2.05 (br. s., 2H), 1.70 (d, J=4.88 Hz, 4H). LC-MS: m/z 491.2 (M+H)⁺.

Compound 159: 5-(3-cyclohexenyl-6-(4-methoxyphenyl)-7-oxo-2-phenyl-4,7-dihydropyrazolo[1,5-a]pyrimidin-5-ylamino)pyrazine-2-carbonitrile

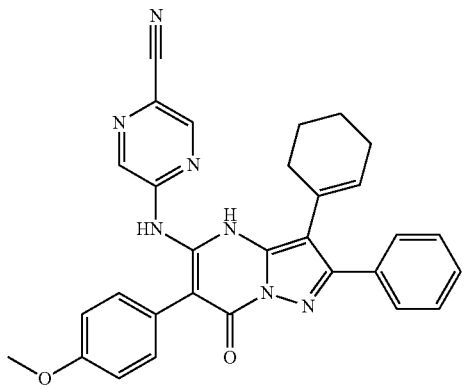 [SMILES: COc1ccc(-c2c(Nc3cnc(C#N)cn3)[nH]c3c(C4=CCCCC4)c(-c4ccccc4)nn3c2=O)cc1]

Step E stoichiometry: 5-chloro-3-(cyclohex-1-en-1-yl)-7-methoxy-6-(4-methoxyphenyl)-2-phenylpyrazolo[1,5-a]pyrimidine (500 mg, 1.07 mmol), 5-aminopyrazine-2-carbonitrile (257 mg, 2.15 mmol), palladium(II) acetate (48 mg, 0.214 mmol), xantphos (124 mg, 0.214 mmol) and sodium carbonate (230 mg, 0.215 mmol) in 1, 4-dioxane (10 mL) under heating at 110° C. for 4 hours under nitrogen atmosphere. LC-MS: m/z 530.2 (M+H)⁺.

Step F: A mixture of 5-(3-cyclohexenyl-7-methoxy-6-(4-methoxyphenyl)-2-phenylpyrazolo [1,5-a] pyrimidin-5-ylamino)pyrazine-2-carbonitrile (170 mg, 0.321 mmol) in hydrogen chloride solution (4 M in dioxane, 5 mL) was stirred at room temperature for 16 h. The mixture was evaporated to dryness. The residue was resolved in dichloromethane solution (with 10% methanol) and washed with aqueous sodium bicarbonate to pH 8. The organic phase was dried over sodium sulfate to afford 5-(3-cyclohexenyl-6-(4-methoxyphenyl)-7-oxo-2-phenyl-4,7-dihydropyrazolo[1,5-a] pyrimidin-5-ylamino) pyrazine-2-carbonitrile.

$^1$H NMR (DMSO-d$_6$): δ 12.76 (br. s., 1H), 10.15 (br. s., 1H), 8.73 (s, 1H) 8.44 (br. s., 1H), 7.75 (d, J=7.02 Hz, 2H), 7.36-7.54 (m, 3H), 7.28 (m, J=8.54 Hz, 2H), 6.97 (m, 0.1-8.55 Hz, 2H), 5.92 (br. s., 1H), 3.78 (s, 3H), 2.25 (br. s., 2H), 2.04 (br. s., 2H), 1.68 (br. s., 4H). LC-MS: m/z 516.2 (M+H)+.

Compound 160: 5-((5-aminopyrazin-2-yl)amino)-3-(cyclohex-1-en-1-yl)-6-(4-methoxyphenyl)-2-phenylpyrazolo[1,5-a]pyrimidin-7(4H)-one

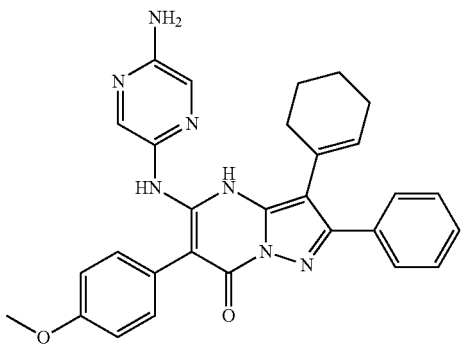

Step E stoichiometry: 5-chloro-3-(cyclohex-1-en-1-yl)-7-methoxy-6-(4-methoxyphenyl)-2-phenylpyrazolo[1,5-a]pyrimidine (44 mg, 0.0998 mmol), pyrazine-2,5-diamine (30 mg, 0.204 mmol), palladium(II) acetate (22 mg, 0.0998 mmol), xantphos (70 mg, 0.121 mmol) and cesium carbonate (130 g, 0.4 mmol) in 1, 4-dioxane (6 mL) under heating at 110° C. for 1 hour under nitrogen atmosphere. LC-MS: m/z 520.2 (M+H)+.

Step F: A mixture of N²-(3-cyclohexenyl-7-methoxy-6-(4-methoxyphenyl)-2-phenylpyrazolo [1,5-a] pyrimidin-5-yl)pyrazine-2,5-diamine (90 mg, 0.18 mmol) in hydrogen chloride solution (4 M in dioxane, 5 mL) was stirred at 50° C. for 3 hours. The mixture was evaporated to dryness. The residue was resolved in dichloromethane solution (with 10% methanol), basified with aqueous ammonia to pH 8 to afford 5-(5-aminopyrazin-2-ylamino)-3-cyclohexenyl-6-(4-methoxyphenyl)-2-phenylpyrazolo [1,5-a] pyrimidin-7 (4H)-one.

¹H NMR (DMSO-d₆): δ 13.92 (s, 1H), 8.70 (s, 1H), 8.08 (d, J=1.2 Hz, 1H), 7.71 (d, J=7.0 Hz, 2H), 7.56 (s, 1H), 7.44-7.51 (m, 2H), 7.41 (d, J=7.3 Hz, 1H), 7.27-7.33 (m, J=8.9 Hz, 2H), 7.01-7.07 (m, J=8.9 Hz, 2H), 6.23 (s, 2H), 6.04 (br. s., 1H), 3.83 (s, 3H), 2.33 (br. s., 2H), 2.04 (br. s., 2H), 1.71 (br. s., 4H). LC-MS: m/z 506.2 (M+H)+.

Compound 161: 5-((1,2,4-triazin-3-yl)amino)-3-(cyclohex-1-en-1-yl)-6-(4-methoxyphenyl)-2-phenylpyrazolo[1,5-a]pyrimidin-7(4H)-one

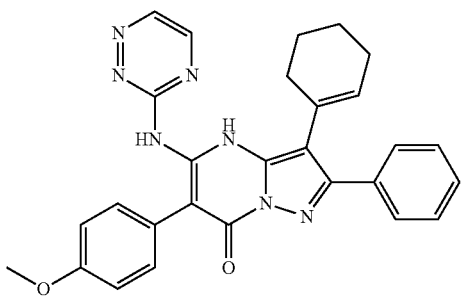

Step E stoichiometry: 5-chloro-3-(cyclohex-1-en-1-yl)-7-methoxy-6-(4-methoxyphenyl)-2-phenylpyrazolo[1,5-a]pyrimidine (150 mg, 0.34 mmol) and 1,2,4-triazin-3-amine (65 mg, 0.68 mmol, 2.0 eq), Pd(OAc)₂ (16 mg, 0.07 mmol, 0.2 eq), Xantphos (41 mg, 0.07 mmol, 0.2 eq) and Cs₂CO₃ (442 mg, 1.36 mmol, 4.0 eq) in 1.4-dioxane (10 mL) under heating at 100° C. for 1 hour through microwave irradiation under nitrogen atmosphere. LC-MS: m/z 505.9 (M+H)+.

Step F: A solution of 3-(cyclohex-1-en-1-yl)-7-methoxy-6-(4-methoxyphenyl)-2-phenyl-N-(1,2,4-triazin-3-yl)pyrazolo[1,5-a]pyrimidin-5-amine (30 mg, 0.06 mmol) in 4M HCl in 1.4-dioxane (15 mL) was stirred at 30° C. for 5 hours. The reaction mixture was concentrated in vacuum to obtain the title compound.

¹H NMR (DMSO-d₆): δ 12.81 (s, 1H), 9.78 (s, 1H), 8.92 (s, 1H), 8.51 (s, 1H), 7.77 (d, J=7.2 Hz, 2H), 7.39-7.52 (m, 3H), 7.26 (d, J=8.0 Hz, 2H), 6.93 (d, J=8.0 Hz, 2H), 3.76 (s, 3H), 2.21 (br. s., 2H), 2.06 (br. s., 2H), 1.66 (br. s., 4H). LC-MS: m/z 492.0 (M+H)+.

Compound 162: 5-((1,2,4-triazin-5-yl)amino)-3-(cyclohex-1-en-1-yl)-6-(4-methoxyphenyl)-2-phenylpyrazolo[1,5-a]pyrimidin-7(4H)-one

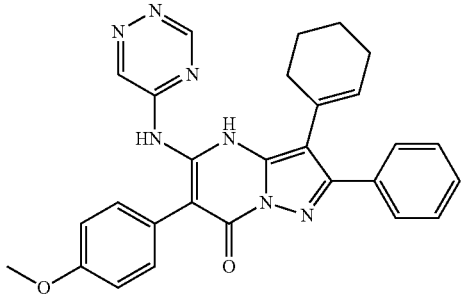 [SMILES: COc1ccc(-c2c(Nc3cnncn3)[nH]c3c(C4=CCCCC4)c(-c4ccccc4)nn3c2=O)cc1]

Step E stoichiometry: 5-chloro-3-cyclohexenyl-7-methoxy-6-(4-methoxyphenyl)-2-phenylpyrazolo [1,5-a]pyrimidine (110 mg, 0.25 mmol), 1,2,4-triazin-5-amine (50 mg, 0.50 mmol), palladium(II) acetate (28 mg, 0.125 mmol), xantphos (87 mg, 0.15 mmol) and cesium carbonate (180 mg, 0.55 mmol) in 1, 4-dioxane (15 mL) under heating at 105° C. through microwave irradiation for 45 min under nitrogen atmosphere. LC-MS: m/z 506.2 (M+H)+.

Step F: A mixture of 3-cyclohexenyl-7-methoxy-6-(4-methoxyphenyl)-2-phenyl-N-(1,2,4-triazin-5-yl) pyrazolo [1,5-a]pyrimidin-5-amine (50 mg, 0.10 mmol) in hydrogen chloride solution (4 M in dioxane, 5 mL) was stirred at room temperature for 4 hours. The mixture was evaporated to dryness. The residue was resolved in dichloromethane solution (with 10% methanol), basified with aqueous ammonia to pH 8 to afford 5-(1,2,4-triazin-5-ylamino)-3-cyclohexenyl-6-(4-methoxyphenyl)-2-phenylpyrazolo [1,5-a]pyrimidin-7(4H)-one.

¹H NMR (DMSO-d₆): δ 9.02 (s, 1H), 8.64 (br. s., 1H), 7.77 (d, J=7.0 Hz, 2H), 7.38-7.54 (m, 3H), 7.26 (d, J=8.6 Hz, 2H), 6.92 (d, J=8.9 Hz, 2H), 5.85 (br. s., 1H), 3.76 (s, 3H), 2.18 (br. s., 2H), 2.05 (br. s., 2H), 1.66 (br. s., 4H). LC-MS: m/z 492.2 (M+H)+.

Compound 163: 5-((1,3,5-triazin-2-yl)amino)-3-(cyclohex-1-en-1-yl)-6-(4-methoxyphenyl)-2-phenylpyrazolo[1,5-a]pyrimidin-7(4H)-one

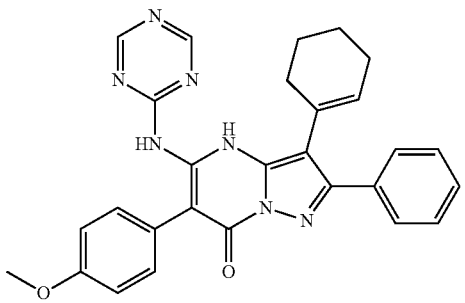 [SMILES: COc1ccc(-c2c(Nc3ncncn3)[nH]c3c(C4=CCCCC4)c(-c4ccccc4)nn3c2=O)cc1]

A suspension of 5-chloro-3-(cyclohex-1-en-1-yl)-7-methoxy-6-(4-methoxyphenyl)-2-phenylpyrazolo[1,5-a]pyrimidine (500 mg, 1.121 mmol) and 1,3,5-triazin-2-amine (323.2 mg, 3.364 mmol, 3 eq), Pd(OAc)$_2$ (50.3 mg, 0.224 mmol, 0.2 eq), Xant-phos (259.5 mg, 0.453 mmol, 0.4 eq) and Cs$_2$CO$_3$ (1.09 g, 3.364 mmol, 3 eq) in 1.4-dioxane (10 mL) was stirred and warmed up to 100° C. through microwave irradiation for 1 hour under N$_2$ atmosphere. The reaction was then cooled to room temperature, diluted with saturated sodium hydrogen carbonate solution, and extracted with EtOAc (20×3 mL). The combined organic layers were washed with brine (20 mL), dried over anhydrous sodium sulfate, and concentrated in vacuo to obtain the title compound.

$^1$H NMR (CHLOROFORM-d): δ 12.85 (br. s., 1H), 8.85 (s, 2H), 7.88 (d, J=6.18 Hz, 2H), 7.76 (br. s., 1H), 7.35-7.48 (m, 4H), 7.08 (d, J=8.06 Hz, 2H), 6.09 (br. s., 1H), 3.89 (s, 2H), 2.37 (br. s., 2H), 2.12 (br. s., 2H), 1.77 (br. s., 3H), 1.68 (br. s., 1H), 1.23-1.39 (m, 1H). LC-MS: m/z 492.0 (M+H)$^+$.

Compound 164: 5-((4-amino-1,3,5-triazin-2-yl)amino)-3-(cyclohex-1-en-1-yl)-6-(4-methoxyphenyl)-2-phenylpyrazolo[1,5-a]pyrimidin-7(4H)-one

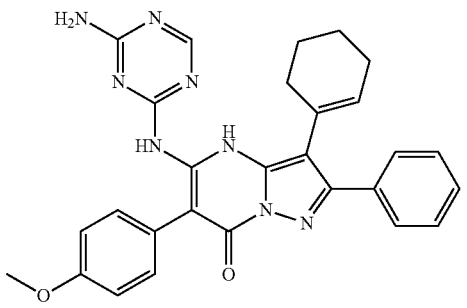 [SMILES: COc1ccc(-c2c(Nc3ncnc(N)n3)[nH]c3c(C4=CCCCC4)c(-c4ccccc4)nn3c2=O)cc1]

Step E stoichiometry: 5-chloro-3-(cyclohex-1-en-1-yl)-7-methoxy-6-(4-methoxyphenyl)-2-phenylpyrazolo[1,5-a]pyrimidine (222 g, 0.5 mmol), 1,3,5-triazine-2,4-diamine (83 mg, 0.75 mmol, 1.5 eq.), Pd(OAc)$_2$ (23 mg, 0.1 mmol, 0.2 eq.), Xantphos (115 mg, 0.2 mmol, 0.4 eq.) and Cs$_2$CO$_3$ (195 mg, 0.6 mmol, 12 eq.) in 1.4-dioxane (4 mL) under heating at 100° C. through microwave irradiation for 1 hour under N$_2$ atmosphere. LC-MS: m/z 521.0 (M+H)$^+$.

Step F: The solution of N-(3-(cyclohex-1-en-1-yl)-7-methoxy-6-(4-methoxyphenyl)-2-phenylpyrazolo[1,5-a]pyrimidin-5-yl)-1,3,5-triazine-2,4-diamine (80 mg, 0.15 mmol) in HCl-1,4-dioxane (5 mL). The solution was stirred at r.t. for 6 h. Solvent and volatile were removed in vacuo. The residue was dissolved in DCM (5 mL) and treated with saturated NaHCO$_3$. The organic phase was separated and washed with brine, dried over anhydrous Na$_2$SO$_4$ and concentrated in vacuo to afford the title compound.

$^1$H NMR (DMSO-d$_6$): δ 8.28 (br. s., 1H), 7.74 (d, J=7.2 Hz, 2H), 7.38-7.52 (m, 4H), 7.31 (d, J=8.2 Hz, 2H), 7.03 (d, J=8.2 Hz, 2H), 5.96 (br. s., 1H), 3.80 (s, 3H), 2.26 (br. s., 2H), 2.04 (br. s., 2H), 1.68 (br. s., 4H). LC-MS: m/z 507.0 (M+H)$^+$.

Compound 165: 3-(cyclohex-1-en-1-yl)-5-(isoxazol-3-ylamino)-6-(4-methoxyphenyl)-2-phenylpyrazolo[1,5-a]pyrimidin-7(4H)-one

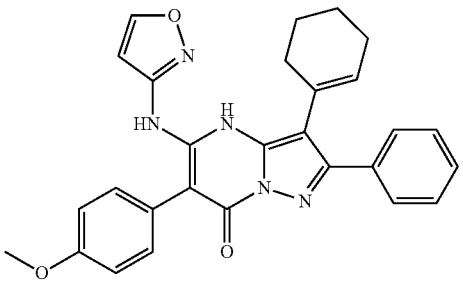 [SMILES: COc1ccc(-c2c(Nc3ccon3)[nH]c3c(C4=CCCCC4)c(-c4ccccc4)nn3c2=O)cc1]

Step E stoichiometry: 5-chloro-3-(cyclohex-1-en-1-yl)-7-methoxy-6-(4-methoxyphenyl)-2-phenylpyrazolo[1,5-a]pyrimidine (1.0 g, 2.24 mmol), isoxazol-3-amine (377.1 mg, 4.48 mmol), and palladium diacetate (101.0 mg, 0.45 mmol), Xantphos (388.8 mg, 0.67 mmol) and sodium carbonate (474.8 mg, 4.48 mmol) in 1,4-dioxane (50 mL) under heating at 110° C. for 12 hours under nitrogen atmosphere. LC-MS: m/z 494.2 (M+H)$^+$.

Step F: A solution of N-(3-(cyclohex-1-en-1-yl)-7-methoxy-6-(4-methoxyphenyl)-2-phenylpyrazolo[1,5-a]pyrimidin-5-yl)isoxazol-3-amine (450 mg, 0.91 mmol) in 4M HCl in 1.4-dioxane (40 mL) was stirred at r.t. for 2 hours. The mixture was concentrated at low temperature (<25° C.), and saturated NaHCO$_3$ (8 mL) was added to obtain 3-(cyclohex-1-en-1-yl)-5-(isoxazol-3-ylamino)-6-(4-methoxyphenyl)-2-phenylpyrazolo[1,5-a]pyrimidin-7(4H)-one as.

$^1$H NMR (DMSO-d$_6$): δ 11.97 (s, 1H), 9.40 (s, 1H), 8.79 (s, 1H), 7.72 (d, J=7.3 Hz, 2H), 7.37-7.56 (m, 3H), 7.23-7.37 (m, J=8.5 Hz, 2H), 6.98-7.13 (m, J=8.5 Hz, 2H), 6.51 (s, 1H), 6.03 (br. s., 1H), 3.82 (s, 3H), 2.28 (br. s., 2H), 2.03 (br. s., 2H), 1.68 (br. s., 4H). LC-MS: m/z 480.2 (M+H)$^+$.

Compound 166: 5-((1,2,4-thiadiazol-5-yl)amino)-3-(cyclohex-1-en-1-yl)-6-(4-methoxyphenyl)-2-phenylpyrazolo[1,5-a]pyrimidin-7(4H)-one

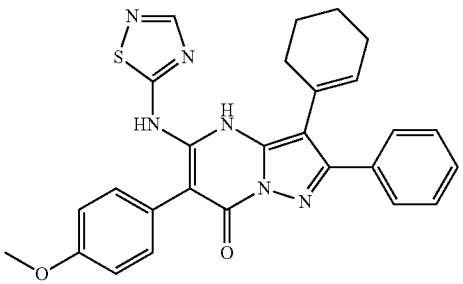 [SMILES: COc1ccc(-c2c(Nc3ncns3)[nH]c3c(C4=CCCCC4)c(-c4ccccc4)nn3c2=O)cc1]

Step E stoichiometry: 5-chloro-3-(cyclohex-1-en-1-yl)-7-methoxy-6-(4-methoxyphenyl)-2-phenylpyrazolo[1,5-a]pyrimidine (220 mg, 0.5 mmol), 1,2,4-thiadiazol-5-amine (101 mg, 1.0 mmol, 2.0 eq), Pd(OAc)$_2$ (22 mg, 0.1 mmol, 0.2 eq), Xantphos (57.8 mg, 0.1 mmol, 0.2 eq) and Cs$_2$CO$_3$ (325 mg, 1.0 mmol, 2.0 eq) in 1.4-dioxane (10 mL) under heating at 100° C. for 1 hour through microwave irradiation under nitrogen atmosphere. LC-MS: m/z 511.2 (M+H)$^+$.

Step F: A solution of N-(3-(cyclohex-1-en-1-yl)-7-methoxy-6-(4-methoxyphenyl)-2-phenylpyrazolo[1,5-a]pyrimidin-5-yl)-1,2,4-thiadiazol-5-amine (51 mg, 0.1 mmol) in 4M HCl in 1.4-dioxane (10 mL) was stirred at 30° C. for 5 hours. The reaction mixture was concentrated in vacuo to obtain the title compound.

$^1$H NMR (DMSO-d$_6$): δ 8.23 (s, 1H), 7.77 (d, J=7.0 Hz, 2H), 7.51 (d, J=7.2 Hz, 3H), 7.29-7.35 (d, J=8.4 Hz, 2H), 7.01-7.09 (d, J=8.0 Hz, 2H), 5.95 (br. s., 1H), 3.83 (s, 3H), 2.24 (br. s., 4H), 1.74 (br. s., 4H). LC-MS: m/z 497.1 (M+H)$^+$.

Compound 167: 5-((1,3,4-thiadiazol-2-yl)amino)-3-(cyclohex-1-en-1-yl)-6-(4-methoxyphenyl)-2-phenylpyrazolo[1,5-a]pyrimidin-7(4H)-one

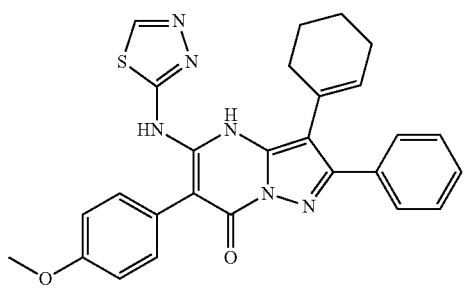

Step E stoichiometry: 5-chloro-3-(cyclohex-1-en-1-yl)-7-methoxy-6-(4-methoxyphenyl)-2-phenylpyrazolo[1,5-a]pyrimidine (446 mg, 1.0 mmol), 1,3,4-thiadiazol-2-amine (101 mg, 1.0 mmol, 1 eq) and Pd(OAc)$_2$ (91.5 mg, 0.1 mmol, 0.1 eq), xant-phos (115.6 mg, 0.2 mmol, 0.2 eq) and Na$_2$CO$_3$ (212 mg, 2.0 mmol, 2.0 eq) in toluene (40 mL) under heating at 110° C. for 5 hour under nitrogen atmosphere. LC-MS: m/z 511.2 (M+H)$^+$.

Step F: A mixture of N-(3-(cyclohex-1-en-1-yl)-7-methoxy-6-(4-methoxyphenyl)-2-phenylpyrazolo[1,5-a]pyrimidin-5-yl)-1,3,4-thiadiazol-2-aminein (102 mg, 0.2 mmol) in 4N HCl in 1.4-dioxane (15 mL) was stirred at room temperature overnight. The mixture was concentrated in vacuo. The residue was basified with saturated sodium hydrogen carbonate solution to afford the title compound.

$^1$H NMR (DMSO-d$_6$): δ 13.77 (br. s., 0.5H), 10.56 (br. s., 0.5H), 9.09 (br. s., 1H), 7.74 (d, J=7.02 Hz, 2H), 7.40-7.57 (m, 3H), 7.31 (m, J=8.24 Hz, 2H), 7.05 (m, J=8.55 Hz, 2H), 6.03 (br. s., 1H), 3.83 (s, 3H), 2.29 (br. s., 2H), 2.08 (br. s., 2H), 1.70 (br. s., 4H). LC-MS: m/z 497.1 (M+H)$^+$.

The following compounds were prepared according to the procedure for preparing compound 101, steps E-F, starting from 6-(5-chloro-7-methoxy-2,3-diphenylpyrazolo[1,5-a]pyrimidin-6-yl)quinoline.

Compound 168: 2,3-diphenyl-5-(pyridin-2-ylamino)-6-(quinolin-6-yl)pyrazolo[1,5-a]pyrimidin-7(4H)-one

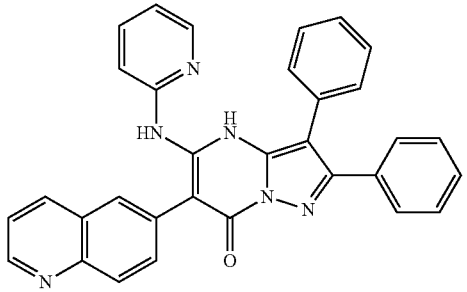 [SMILES: O=c1c(-c2ccc3ncccc3c2)c(Nc2ccccn2)[nH]c2c(-c3ccccc3)c(-c3ccccc3)nn12]

A mixture of 6-(5-chloro-7-methoxy-2,3-diphenylpyrazolo[1,5-a]pyrimidin-6-yl)quinoline (250 mg, 0.541 mmol), pyridin-2-amine (102 mg, 1.08 mmol), palladium(II) acetate (121 mg, 0.541 mmol), xantphos (296 mg, 0.541 mmol) and cesium carbonate (354 mg, 1.08 mmol) in 1, 4-dioxane (10 mL) was stirred under nitrogen atmosphere in a sealed tube and heated to 110° C. under microwave for 1 hour to afford 2, 3-diphenyl-5-(pyridin-2-ylamino)-6-(quinolin-6-yl)pyrazolo[1,5-a]pyrimidin-7(4H)-one.

$^1$H NMR (DMSO-d$_6$): δ 15.93 (br. s., 1H), 9.36 (s, 1H), 8.74 (d, J=8.06 Hz, 1H), 8.16-8.34 (m, 2H), 8.07 (d, J=3.76 Hz, 1H), 7.99 (d, J=8.33 Hz, 1H), 7.75-7.85 (m, 2H), 7.60 (t, J=7.52 Hz, 4H), 7.39-7.54 (m, 5H), 7.21-7.28 (m, 1H), 7.09-7.17 (m, 1H), 6.98 (s, 1H). LC-MS: m/z 507.2 (M+H)$^+$.

Compound 169: 2,3-diphenyl-5-(pyrimidin-4-ylamino)-6-(quinolin-6-yl)pyrazolo[1,5-a]pyrimidin-7(4H)-one

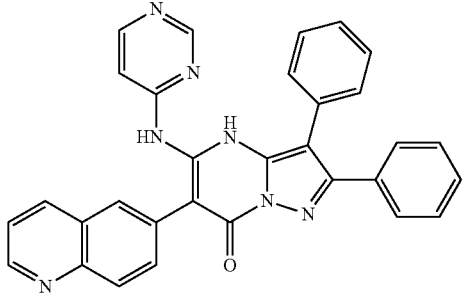 [SMILES: O=c1c(-c2ccc3ncccc3c2)c(Nc2ccncn2)[nH]c2c(-c3ccccc3)c(-c3ccccc3)nn12]

Step E stoichiometry: 6-(5-chloro-7-methoxy-2,3-diphenylpyrazolo[1,5-a]pyrimidin-6-yl)quinoline (600 mg, 1.3 mmol), pyrimidin-4-amine (148 mg, 1.56 mmol, 1.2 eq), Pd(OAc)$_2$ (43.7 mg, 0.19 mmol, 0.15 eq), Xantphos (112 mg, 0.19 mmol, 0.15 eq) and Cs$_2$CO$_3$ (844 mg, 2.6 mmol, 2.0 eq) in 1.4-dioxane (15 mL) under heating at 110° C. through microwave irradiation for 1 hour under nitrogen atmosphere. LC-MS: m/z 521.9 (M+H)$^+$.

Step F: A solution of 7-methoxy-2,3-diphenyl-N-(pyrimidin-4-yl)-6-(quinolin-6-yl)pyrazolo[1,5-a]pyrimidin-5-amine (271 mg, 0.52 mmol) in 4M HCl in 1.4-dioxane (15 mL) was stirred at 30° C. for 5 hours. The reaction mixture was concentrated in vacuo to obtain the title compound.

$^1$H NMR (DMSO-d$_6$): δ 14.65 (s, 1H), 9.64 (s, 1H), 8.92 (s, 1H), 8.43 (m, 4H), 8.12-7.96 (m, 2H), 7.83 (d, J=8.0 Hz,

2H), 7.55 (m, 3H), 7.50 (d, J=6.8 Hz, 2H), 7.37 (s, 4H), 7.19 (s, 1H). LC-MS: m/z 507.9 (M+H)⁺.

Compound 170: 5-(isoxazol-3-ylamino)-2,3-diphenyl-6-(quinolin-6-yl)pyrazolo[1,5-a]pyrimidin-7(4H)-one

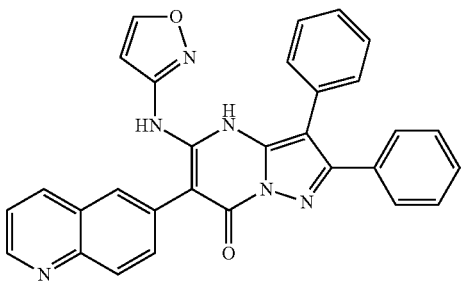

Step E stoichiometry: 6-(5-chloro-7-methoxy-2,3-diphenylpyrazolo[1,5-a]pyrimidin-6-yl)quinoline (100 mg, 0.216 mmol), isoxazol-3-amine (92 mg, 0.432 mmol), palladium (II) acetate (53 mg, 0.238 mmol), xantphos (150 mg, 0.259 mmol) and sodium carbonate (51 mg, 0.475 mmol) in 1,4-dioxane (10 mL) under heating at 100° C. through microwave irradiation for 1 hour under nitrogen atmosphere. LC-MS: m/z 511.2 (M+H)⁺.

Step F: A mixture of N-(7-methoxy-2,3-diphenyl-6-(quinolin-6-yl)pyrazolo[1,5-a]pyrimidin-5-yl) isoxazol-3-amine (90 mg, 0.097 mmol) in hydrogen chloride solution (4 M in dioxane, 4 mL) was stirred at room temperature for 10 h. The mixture was evaporated to dryness. The residue was resolved in dichloromethane solution (with 10% methanol) and basified with aqueous ammonia to pH 8 to afford 5-(isoxazol-3-ylamino)-2,3-diphenyl-6-(quinolin-6-yl)pyrazolo [1,5-a]pyrimidin-7(4H)-one.

¹H NMR (DMSO-d₆): δ 9.39 (d, J=4.03 Hz, 1H), 9.31 (d, J=8.33 Hz, 1H), 8.75 (d, J=1.61 Hz, 1H), 8.51 (s, 1H), 8.39 (d, J=8.87 Hz, 1H), 8.25 (d, J=8.87 Hz, 1H), 8.17 (dd, J=8.33, 5.37 Hz, 1H), 7.47-7.58 (m, 4H), 7.31-7.46 (m, 6H), 6.44 (bs, 1H). LC-MS: m/z 497.2 (M+H)⁺.

Compound 171: ethyl 5-((7-oxo-2,3-diphenyl-6-(quinolin-6-yl)-4,7-dihydropyrazolo[1,5-a]pyrimidin-5-yl)amino)-1,3,4-oxadiazole-2-carboxylate

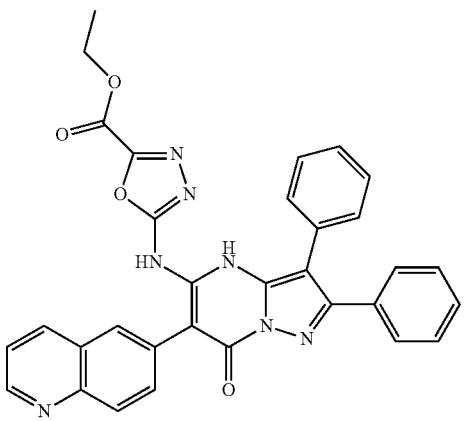 [SMILES: CCOC(=O)c1nnc(Nc2[nH]c3c(-c4ccccc4)c(-c4ccccc4)nn3c(=O)c2-c2ccc3ncccc3c2)o1]

A suspension of 6-(5-chloro-7-methoxy-2,3-diphenylpyrazolo[1,5-a]pyrimidin-6-yl)quinoline (200 mg, 0.43 mmol), ethyl 5-amino-1,3,4-oxadiazole-2-carboxylate (135 mg, 0.86 mmol, 2 eq.), Pd(OAc)₂ (20 mg, 0.09 mmol, 0.2 eq.), Xantphos (75 mg, 0.13 mmol, 0.3 eq.) and Cs₂CO₃ (282 mg, 0.87 mmol, 2.0 eq.) in 1,4-dioxane (5 mL) was stirred at 100° C. for 16 h under N₂ atmosphere. The mixture was filtered through celite, and the filtrate was concentrated in vacuo to afford the title compound.

¹H NMR (DMSO-d₆): δ 12.55 (br. s., 1H), 9.10 (br. s., 1H), 8.85 (br. s., 1H), 8.31 (br. s., 1H), 8.15-8.23 (m, 1H), 8.04-8.15 (m, 1H), 7.84 (br. s., 1H), 7.42-7.60 (m, 4H), 7.38 (d, J=6.2 Hz, 7H), 4.32 (q, J=7.2 Hz, 2H), 1.28 (t, J=7.2 Hz, 3H). LC-MS: m/z 570.0 (M+H)⁺.

Compound 172: N-(7-oxo-2,3-diphenyl-6-(quinolin-6-yl)-4,7-dihydropyrazolo[1,5-a]pyrimidin-5-yl)acetamide

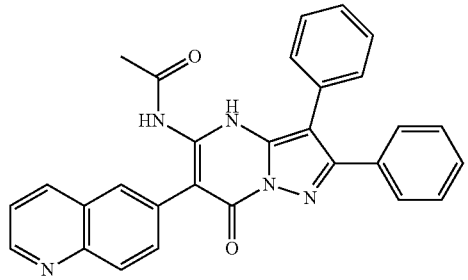 [SMILES: CC(=O)Nc1[nH]c2c(-c3ccccc3)c(-c3ccccc3)nn2c(=O)c1-c1ccc2ncccc2c1]

Step E stoichiometry: 6-(5-chloro-7-methoxy-2,3-diphenylpyrazolo[1,5-a]pyrimidin-6-yl)quinoline (230 mg, 0.5 mmol) and acetamide (59 mg, 1.0 mmol, 2.0 eq), Pd(OAc)₂ (11 mg, 0.05 mmol, 0.1 eq), Xantphos (116 mg, 0.2 mmol, 0.4 eq) and Cs₂CO₃ (325 mg, 1.0 mmol, 2.0 eq) in 1,4-dioxane (10 mL) under heating at 100° C. through microwave irradiation for 1 hour under nitrogen atmosphere. LC-MS: m/z 586.2 (M+H)⁺.

Step F: A solution of N-(7-methoxy-2,3-diphenyl-6-(quinolin-6-yl)pyrazolo[1,5-a]pyrimidin-5-yl)acetamide (100 mg, 0.21 mmol) in 4M HCl in 1,4-dioxane (20 mL) was stirred at 30° C. for 5 hours. The reaction mixture was concentrated in vacuo to obtain the title compound.

¹H NMR (DMSO-d₆): δ 12.96 (br. s., 1H), 10.12 (br. s., 1H), 8.92 (br. s., 1H), 8.40 (br. s., 1H), 8.05 (br. s., 1H), 7.99 (br. s., 1H), 7.76 (d, J=8.6 Hz, 1H), 7.42-7.64 (m, 5H), 7.30-7.42 (m, 5H), 1.86-2.03 (m, 3H). LC-MS: m/z 472.0 (M+H)⁺.

Compound 173: 2-hydroxy-N-(7-oxo-2,3-diphenyl-6-(quinolin-6-yl)-4,7-dihydropyrazolo[1,5-a] pyrimidin-5-yl)acetamide

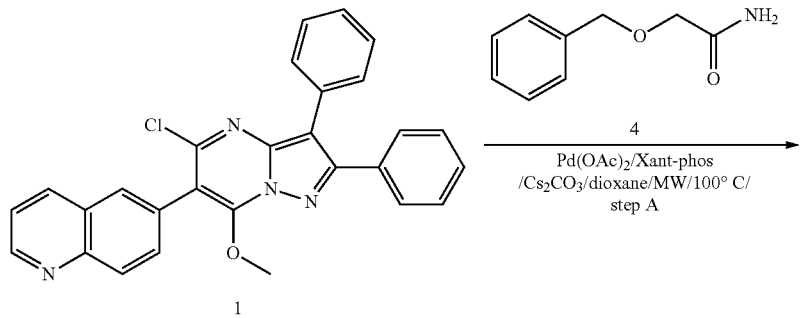

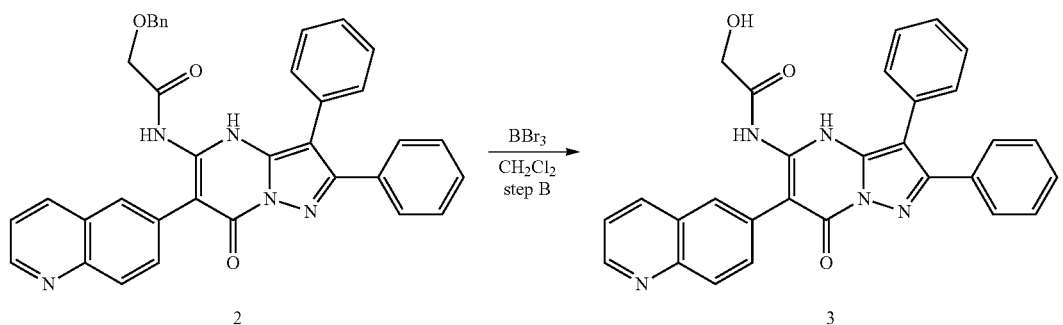

Step A: 2-(benzyloxy)-N-(7-oxo-2,3-diphenyl-6-(quinolin-6-yl)-4,7-dihydropyrazolo[1,5-a]pyrimidin-5-yl)acetamide

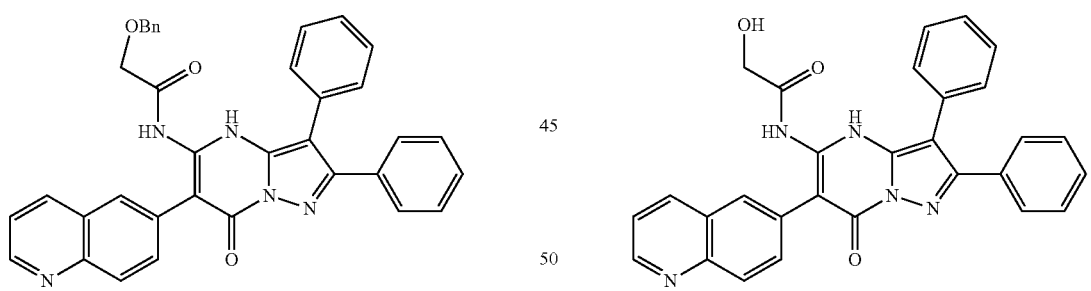

A suspension of 6-(5-chloro-7-methoxy-2,3-diphenylpyrazolo[1,5-a]pyrimidin-6-yl)quinoline (200 g, 0.43 mmol), 2-(benzyloxy)acetamide (143 mg, 0.86 mmol, 2 eq.), Pd(OAc)₂ (20 mg, 0.09 mmol, 0.2 eq.), Xantphos (75 mg, 0.13 mmol, 0.3 eq.) and Cs₂CO₃ (282 mg, 0.86 mmol, 2 eq.) in 1.4-dioxane (5 mL) was stirred at 100° C. through microwave irradiation for 1 hour under N₂ atmosphere. The mixture was filtered through celite and the filtrate was concentrated in vacuo. The residue was purified by prep-TLC (DCM/MeOH=10/1) to afford the desired product as a yellow solid (120 mg).

¹H NMR (DMSO-d₆): δ 12.66 (br. s., 1H), 9.65 (br. s., 1H), 8.91 (br. s., 1H), 8.33 (d, J=8.4 Hz, 1H), 7.96-8.06 (m, 2H), 7.74-7.82 (m, 1H), 7.44-7.56 (m, 4H), 7.33-7.44 (m, 7H), 7.13-7.23 (m, 3H), 7.01 (d, J=7.3 Hz, 2H), 4.32 (s, 2H), 3.97 (s, 2H). LC-MS: m/z 578.0 (M+H)⁺.

Step B: 2-hydroxy-N-(7-oxo-2,3-diphenyl-6-(quinolin-6-yl)-4,7-dihydropyrazolo[1,5-a] pyrimidin-5-yl)acetamide To a solution of 2-(benzyloxy)-N-(7-oxo-2,3-diphenyl-6-(quinolin-6-yl)-4,7-dihydropyrazolo[1,5-a]pyrimidin-5-yl) acetamide (90 mg, 0.156 mmol) in DCM (5 mL) was added BBr₃ (156 mg, 0.623 mmol, 4 eq.) at 0° C. The mixture was stirred at r.t. for 2 h. The reaction was quenched with MeOH at 0° C. to afford the title compound.

¹H NMR (DMSO-d₆): δ 12.67 (br. s., 1H), 10.91 (br. s., 1H), 8.79-8.93 (m, 1H), 8.28-8.40 (m, 1H), 7.90-8.09 (m, 2H), 7.73-7.85 (m, 1H), 7.26-7.56 (m, 11H), 6.20 (br. s., 1H), 3.85 (br. s., 2H). LC-MS: m/z 487.9 (M+H)⁺.

The following compounds were prepared according to the procedure for preparing compound 101, steps E-F, starting from 6-(5-chloro-3-(cyclohex-1-en-1-yl)-7-methoxy-2-phenylpyrazolo [1,5-a]pyrimidin-6-yl)quinoline.

Compound 174: 3-cyclohexenyl-2-phenyl-5-(pyridin-2-ylamino)-6-(quinolin-6-yl)pyrazolo[1,5-a]pyrimidin-7(4H)-one

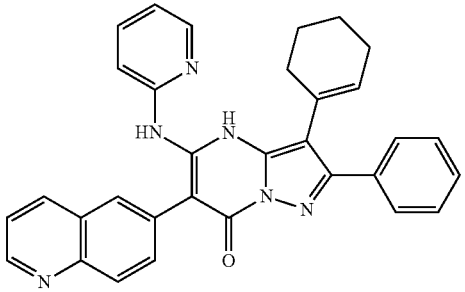 [SMILES: O=c1c(-c2ccc3ncccc3c2)c(Nc2ccccn2)[nH]c2c(C3=CCCCC3)c(-c3ccccc3)nn12]

Step E stoichiometry: 6-(5-chloro-3-cyclohexenyl-7-methoxy-2-phenylpyrazolo[1,5-a] pyrimidin-6-yl) quinoline (380 mg, 0.814 mmol), pyridin-2-amine (153 mg, 1.63 mmol), palladium(II) acetate (18 mg, 0.0814 mmol), xantphos (45 mg, 0.0814 mmol) and sodium carbonate (173 mg, 1.63 mmol) in 1, 4-dioxane (10 mL) under heating at 110° C. for 1 hour through microwave irradiation under nitrogen atmosphere. LC-MS: m/z 525.2 (M+H)$^+$.

Step F: A mixture of 7-methoxy-2,3-diphenyl-N-(pyrazin-2-yl)-6-(quinolin-6-yl)pyrazolo[1,5-a] pyrimidin-5-amine (125 mg, 0.238 mmol) in hydrogen chloride solution (4 M in dioxane, 5 mL) was stirred at room temperature for 16 h. The mixture was evaporated to dryness. The residue was resolved in dichloromethane solution (with 10% methanol) and washed with aqueous sodium bicarbonate to pH 8. The organic phase was dried over sodium sulfate to afford 3-cyclohexenyl-2-phenyl-5-(pyridin-2-ylamino)-6-(quinolin-6-yl)pyrazolo[1,5-a]-pyrimidin-7(4H)-one.

$^1$H NMR (DMSO-d$_6$): δ 15.37 (br. s., 1H), 9.35 (s, 1H), 9.18 (br. s., 1H), 8.87 (d, J=8.24 Hz, 1H), 8.18-8.36 (m, 3H), 8.04 (d, J=8.55 Hz, 1H), 7.88 (dd, J=7.93, 4.88 Hz, 1H), 7.81 (t, J=7.02 Hz, 1H), 7.75 (d, J=7.63 Hz, 2H), 7.47-7.56 (m, 2H), 7.38-7.46 (m, 1H), 7.22 (d, J=8.54 Hz, 1H), 7.10-7.18 (m, 1H), 6.11 (br. s., 1H), 2.38 (br. s., 2H), 2.09 (s, 2H), 1.73 (br. s., 4H). LC-MS: m/z 511.2 (M+H)$^+$.

Compound 175: 3-cyclohexenyl-2-phenyl-5-(pyrazin-2-ylamino)-6-(quinolin-6-yl)pyrazolo[1,5-a]pyrimidin-7(4H)-one

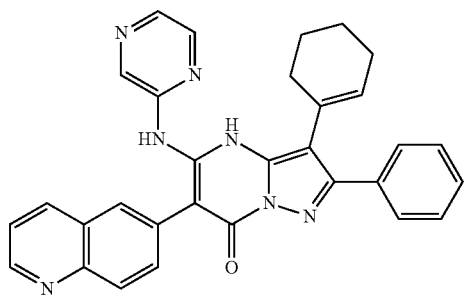 [SMILES: O=c1c(-c2ccc3ncccc3c2)c(Nc2cnccn2)[nH]c2c(C3=CCCCC3)c(-c3ccccc3)nn12]

Step E stoichiometry: 6-(5-chloro-3-cyclohexenyl-7-methoxy-2-phenylpyrazolo[1,5-a] pyrimidin-6-yl) quinoline (120 mg, 0.257 mmol), pyrazin-2-amine (50 mg, 0.515 mmol), palladium(II) acetate (11 mg, 0.050 mmol), xantphos (32 mg, 0.055 mmol) and cesium carbonate (171 mg, 0.515 mmol) in 1, 4-dioxane (5 mL) under heating at 110° C. for 1 hour through microwave irradiation under nitrogen atmosphere. LC-MS: m/z 526.2 (M+H)$^+$.

Step F: A mixture of 7-methoxy-2,3-diphenyl-N-(pyrazin-2-yl)-6-(quinolin-6-yl)pyrazolo[1,5-a] pyrimidin-5-amine (70 mg, 0.133 mmol) in hydrogen chloride solution (4 M in dioxane, 5 mL) was stirred at room temperature for 4 h. The mixture was evaporated to dryness. The residue was resolved in dichloromethane solution (with 10% methanol) and washed with aqueous sodium bicarbonate to pH 8. The organic phase was dried over sodium sulfate to afford 2,3-diphenyl-5-(pyrazin-2-ylamino)-6-(quinolin-6-yl)pyrazolo[1,5-a]pyrimidin-7(4H)-one.

$^1$H NMR (DMSO-d$_6$): δ 14.04 (s, 1H), 9.57 (s, 1H), 8.94 (br. s., 1H), 8.55 (s, 1H), 8.41 (d, J=7.93 Hz, 1H), 8.24 (s, 1H), 8.26 (s, 1H), 8.04-8.13 (m, 2H), 7.81 (d, J=8.54 Hz, 1H), 7.75 (d, J=7.32 Hz, 2H), 7.57 (br. s., 1H), 7.47-7.53 (m, 2H), 7.44 (d, J=7.02 Hz, 2H), 2.36 (br. s., 2H), 2.09 (br. s., 2H), 1.72 (br. s., 4H). LC-MS: m/z 512.2 (M+H)$^+$.

Compound 176: 3-cyclohexenyl-5-(isoxazol-3-ylamino)-2-phenyl-6-(quinolin-6-yl)pyrazolo[1,5-a]pyrimidin-7(4H)-one

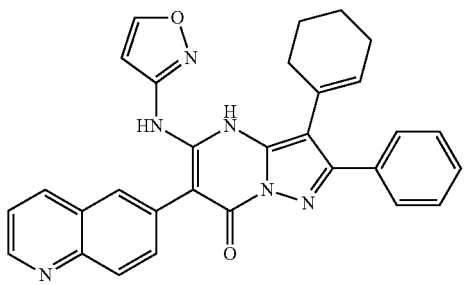

Step E stoichiometry: 6-(5-chloro-3-cyclohexenyl-7-methoxy-2-phenylpyrazolo[1,5-a] pyrimidin-6-yl) quinoline (240 mg, 0.510 mmol), isoxazol-3-amine (218 mg, 1.02 mmol), palladium(II) acetate (126 mg, 0.560 mmol), xantphos (354 mg, 0.612 mmol) and sodium carbonate (119 mg, 1.12 mmol) in 1, 4-dioxane (10 mL) under heating at 100° C. for 16 hours under nitrogen atmosphere. LC-MS: m/z 515.2 (M+H)$^+$.

Step F: A mixture of N-(3-cyclohexenyl-7-methoxy-2-phenyl-6-(quinolin-6-yl)pyrazolo[1,5-a] pyrimidin-5-yl) isoxazol-3-amine (50 mg, 0.097 mmol) in hydrogen chloride solution (4 M in dioxane, 4 mL) was stirred at room temperature for 2 h. The mixture was evaporated to dryness. The residue was resolved in dichloromethane solution (with 10% methanol) and basified with aqueous ammonia to pH 8 to afford 3-cyclohexenyl-5-(isoxazol-3-ylamino)-2-phenyl-6-(quinolin-6-yl)pyrazolo[1,5-a] pyrimidin-7(4H)-one.

$^1$H NMR (DMSO-d$_6$): δ 9.39 (d, J=4.30 Hz, 1H), 9.29 (d, J=8.33 Hz, 1H), 8.78 (s, 1H), 8.48 (s, 1H), 8.40 (d, J=8.86 Hz, 1H), 8.23 (d, J=8.86 Hz, 1H), 8.16 (dd, J=8.19, 5.51 Hz, 1H), 7.75 (d, J=7.25 Hz, 2H) 7.38-7.59 (m, 4H), 7.36 (bs, 1H), 6.43 (s, 1H), 6.06 (bs, 1H), 2.30 (bs, 2H), 2.06 (bs, 2H), 1.70 (bs, 2H) 1.23 (bs, 2H). LC-MS: m/z 501.2 (M+H)$^+$.

Compound 177: 3-(cyclohex-1-en-1-yl)-5-(isoxazol-3-ylamino)-2-phenyl-6-(quinoxalin-6-yl)pyrazolo[1,5-a]pyrimidin-7(4H)-one

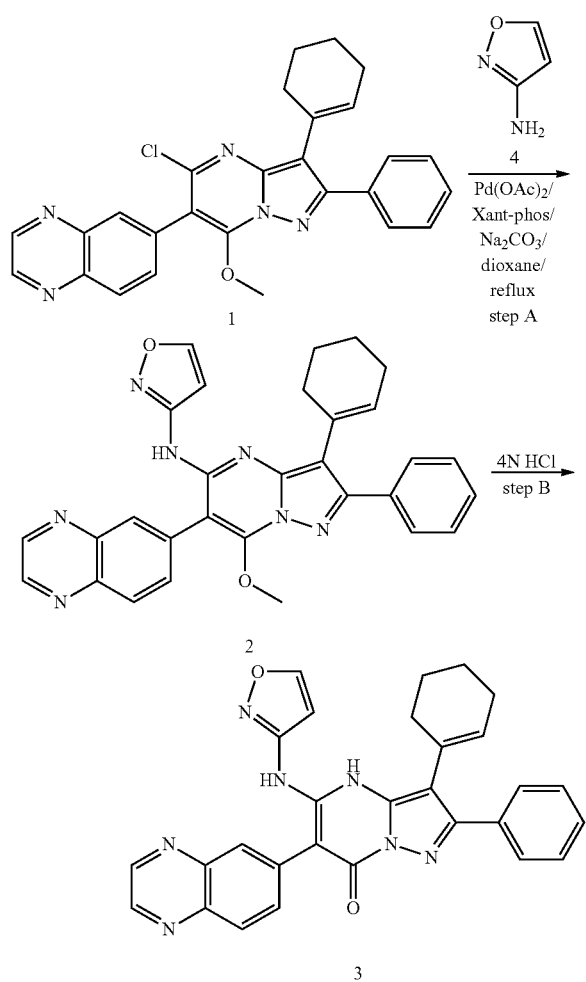

Step A: N-(3-(cyclohex-1-en-1-yl)-7-methoxy-2-phenyl-6-(quinoxalin-6-yl)pyrazolo[1,5-a]pyrimidin-5-yl)isoxazol-3-amine

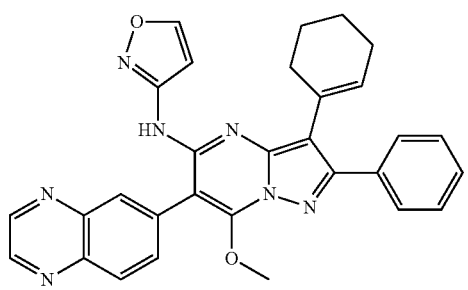 [SMILES: COc1c(-c2ccc3nccnc3c2)c(Nc2ccon2)nc2c(C3=CCCCC3)c(-c3ccccc3)nn12]

The solution of 6-(5-chloro-3-(cyclohex-1-en-1-yl)-7-methoxy-2-phenylpyrazolo[1,5-a]pyrimidin-6-yl)quinoxaline (80 mg, 0.17 mmol), isoxazol-3-amine (43.1 mg, 0.51 mmol), palladium diacetate (19.2 mg, 0.09 mmol), Xantphos (59.4 mg, 0.10 mmol) and sodium carbonate (54.1 mg, 0.51 mmol) in 1,4-dioxane (8 mL) was refluxed for 12 hours under nitrogen atmosphere. After cooling to room temperature, the mixture was concentrated to dryness. The residue was purified by flash column (DCM:MeOH=30:1) to obtain N-(3-(cyclohex-1-en-1-yl)-7-methoxy-2-phenyl-6-(quinoxalin-6-yl)pyrazolo[1,5-a]pyrimidin-5-yl)isoxazol-3-amine (12 mg) as yellow solid. LC-MS: m/z 516.2 (M+H)+.

Step B: 3-(cyclohex-1-en-1-yl)-5-(isoxazol-3-ylamino)-2-phenyl-6-(quinoxalin-6-yl)pyrazolo [1,5-a]pyrimidin-7(4H)-one

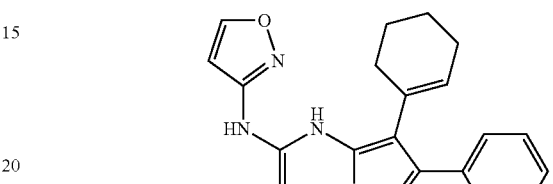

A solution of N-(3-(cyclohex-1-en-1-yl)-7-methoxy-2-phenyl-6-(quinoxalin-6-yl)pyrazolo[1,5-a]pyrimidin-5-yl)isoxazol-3-amine (12 mg, 0.02 mmol) in 4M HCl in 1,4-dioxane (2 mL) was stirred at r.t. for 2 hours. The mixture was concentrated, and saturated NaHCO$_3$ (3 mL) was added to obtain 3-(cyclohex-1-en-1-yl)-5-(isoxazol-3-ylamino)-2-phenyl-6-(quinoxalin-6-yl)pyrazolo[1,5-a]pyrimidin-7(4H)-one.

$^1$H NMR (TFA-d): δ 8.97 (s, 2H), 8.74 (d, J=1.6 Hz, 1H), 8.14-8.22 (nm, 2H), 7.91 (dd, J=8.6, 1.9 Hz, 1H), 7.75 (d, J=7.0 Hz, 2H), 7.36-7.54 (m, 3H), 6.42 (d, J=1.9 Hz, 1H), 6.07 (br. s., 1H), 2.30 (br. s., 2H), 2.06 (d, J=7.0 Hz, 2H), 1.70 (br. s., 4H). LC-MS: in/z 502.2 (M+H)+.

Compound 178: 3-(3-chlorophenyl)-6-(4-methoxyphenyl)-2-phenyl-5-(pyridin-2-ylamino)pyrazolo[1,5-a]pyrimidin-7(4H)-one

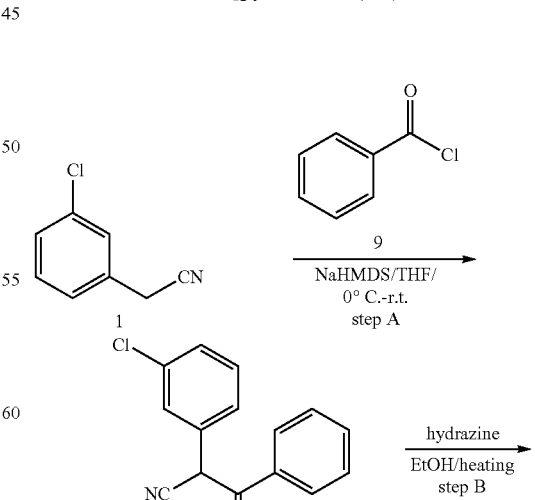

-continued

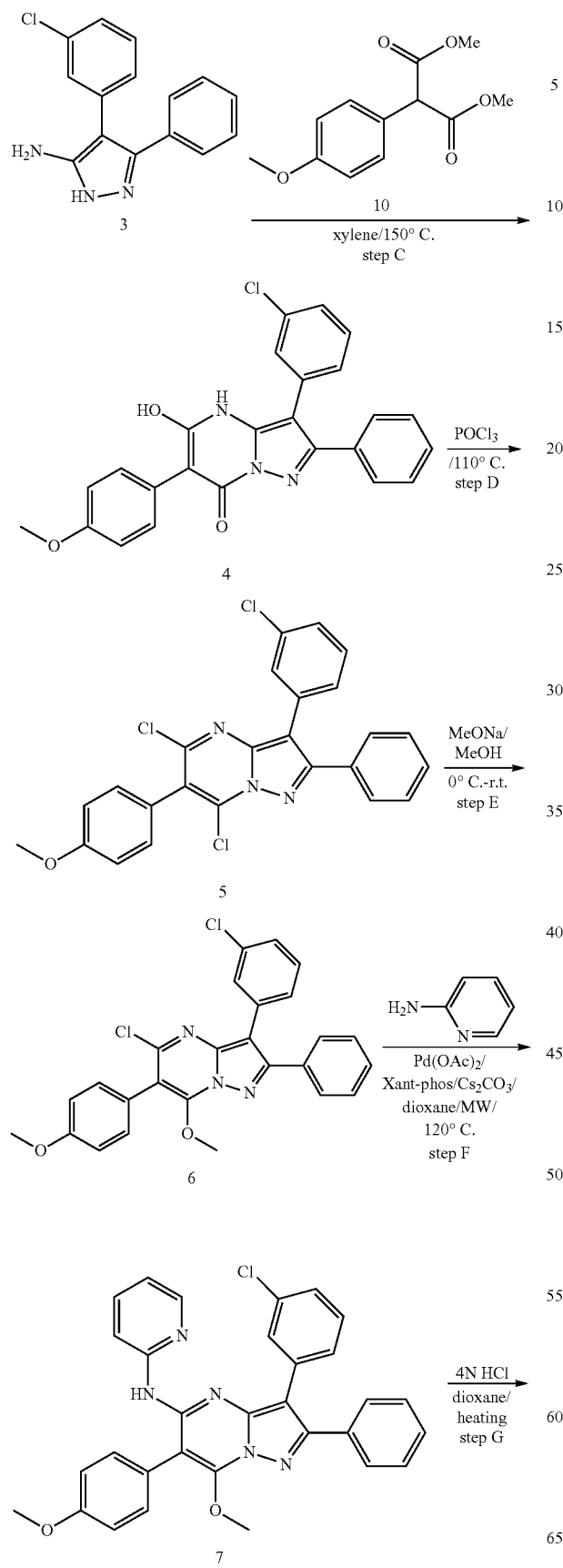

Step A:
2-(3-chlorophenyl)-3-oxo-3-phenylpropanenitrile

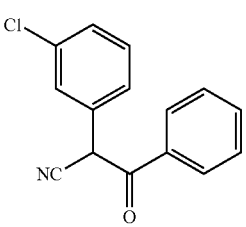 [SMILES: N#CC(C(=O)c1ccccc1)c1cccc(Cl)c1]

To a solution of 2-(3-chlorophenyl)acetonitrile (6.0 g, 39.58 mmol) in THF (40 mL) cooled at −78° C. was added NaHMDS (29.7 mL, 59.37 mmol, 2.0 M in THF) dropwise. After addition, the mixture was stirred at −78° C. for 1 hour. Then benzoyl chloride (5.5 mL, 47.50 mmol) was added dropwise. The reaction was slowly warmed to room temperature and stirred for 12 hours. The reaction was quenched by saturated $NH_4Cl$ (150 mL), extracted with ethyl acetate (200 mL), washed with water (60 mL) and brine (60 mL), dried over anhydrous sodium sulfate, and concentrated to obtain crude product (16 g) which was directly used in the next step without further purification.

Step B:
4-(3-chlorophenyl)-3-phenyl-1H-pyrazol-5-amine

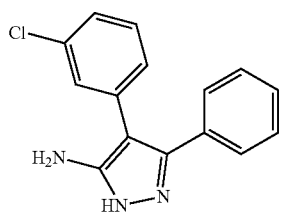 [SMILES: Nc1[nH]nc(-c2ccccc2)c1-c1cccc(Cl)c1]

The solution of 2-(3-chlorophenyl)-3-oxo-3-phenylpropanenitrile (16 g, crude) and $NH_2NH_2$ (11.5 mL, 237.48 mmol) in EtOH/AcOH (80 mL/20 mL) was stirred at 80° C. for 6 hours. After cooling to room temperature, the mixture was concentrated by vacuum. The residue was diluted with EtOAc (200 mL), washed with saturated $NaHCO_3$ (100 mL) and brine (50 mL), dried over anhydrous sodium sulfate and concentrated. The residue was purified by flash column (petroleum ether/ethyl acetate=3:1) to obtain 4-(3-chlorophenyl)-3-phenyl-1H-pyrazol-5-amine (1.6 g) as a yellow solid.

$^1$H NMR (CHLOROFORM-d): δ 7.79-7.85 (m, 3H), 7.51-7.56 (m, 1H), 7.42-7.48 (m, 3H), 7.29-7.36 (m, 2H). LC-MS: m/z 270.1 (M+H)$^+$.

Step C: 3-(3-chlorophenyl)-5-hydroxy-6-(4-methoxyphenyl)-2-phenylpyrazolo[1,5-a]pyrimidin-7(4H)-one

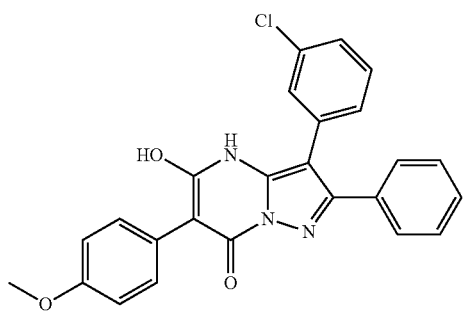 [SMILES: COc1ccc(-c2c(O)[nH]c3c(-c4cccc(Cl)c4)c(-c4ccccc4)nn3c2=O)cc1]

The suspension of 4-(3-chlorophenyl)-3-phenyl-1H-pyrazol-5-amine (1.6 g, 5.93 mmol) and dimethyl 2-(4-methoxyphenyl)malonate (1.7 g, 7.12 mmol) in xylene (30 mL) was stirred at 150° C. for 12 hours. After cooling to room temperature, the mixture was filtered and washed with MeOH (2 mL) to obtain 3-(3-chlorophenyl)-6-(4-methoxyphenyl)-2-phenylpyrazolo[1,5-a]pyrimidine-5,7(4H,6H)-dione (830 mg) as a white solid. LC-MS: m/z 444.1 (M+H)$^+$.

Step D: 5,7-dichloro-3-(3-chlorophenyl)-6-(4-methoxyphenyl)-2-phenylpyrazolo[1,5-a] pyrimidine

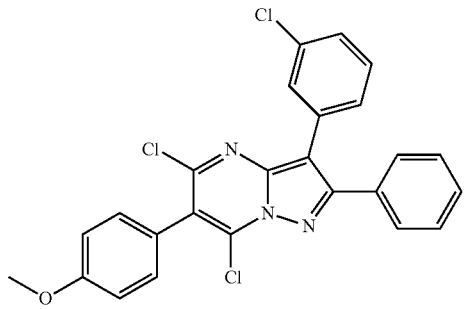 [SMILES: COc1ccc(-c2c(Cl)nc3c(-c4cccc(Cl)c4)c(-c4ccccc4)nn3c2Cl)cc1]

The solution of 3-(3-chlorophenyl)-6-(4-methoxyphenyl)-2-phenylpyrazolo[1,5-a]pyrimidine-5,7(4H,6H)-dione (800 mg, 1.80 mmol), N,N-dimethylaniline (436.8 mg, 3.60 mmol) and pentachlorophosphorane (375.3 mg, 1.80 mmol) in POCl$_3$(8 mL) in a sealed tube was stirred at 100° C. for 8 hours. After cooling to room temperature, the solvent was removed by vacuum. The residue was cooled to 0° C. and basified by adding MeOH (6 mL). The precipitate was filtered to obtain 5,7-dichloro-3-(3-chlorophenyl)-6-(4-methoxyphenyl)-2-phenylpyrazolo[1,5-a]pyrimidine (700 mg) as a yellow solid. LC-MS: m/z 480.1 (M+H)$^+$.

Step E: 5-chloro-3-(3-chlorophenyl)-7-methoxy-6-(4-methoxyphenyl)-2-phenylpyrazolo[1,5-a]pyrimidine

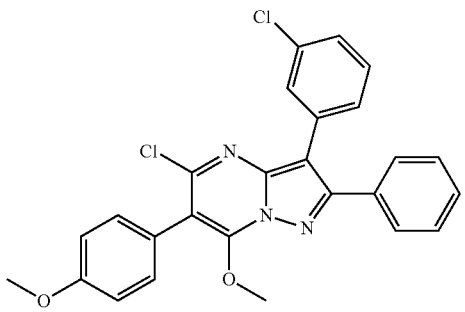 [SMILES: COc1ccc(-c2c(Cl)nc3c(-c4cccc(Cl)c4)c(-c4ccccc4)nn3c2OC)cc1]

To the solution of 5,7-dichloro-3-(3-chlorophenyl)-6-(4-methoxyphenyl)-2-phenylpyrazolo[1,5-a]pyrimidine (700 mg, 1.46 mmol) in DCM/MeOH (20 mL, 1:1) cooled at 0° C. was added sodium methanolate (0.9 mL, 5.0 M in methanol) dropwise. Then the mixture was stirred at 0° C. for 15 minutes. Saturated NH$_4$Cl (50 mL) was added to quench the reaction. The mixture was extracted with DCM (100 mL), washed with brine (30 mL), dried over anhydrous sodium sulfate, and concentrated. The residue was purified by flash column (petroleum ether/ethyl acetate/DCM=20:1:1) to obtain 5-chloro-3-(3-chlorophenyl)-7-methoxy-6-(4-methoxyphenyl)-2-phenylpyrazolo[1,5-a]pyrimidine (520 mg) as a yellow solid.

$^1$H NMR (CHLOROFORM-d): δ 7.64-7.68 (m, 2H), 7.56-7.59 (m, 1H), 7.39-7.45 (m, 4H), 7.34-7.37 (m, 2H), 7.30-7.33 (m, 2H), 7.03-7.08 (m, 2H), 4.16 (s, 3H), 3.92 (s, 3H). LC-MS: m/z 476.1 (M+H)$^+$.

Step F: 3-(3-chlorophenyl)-7-methoxy-6-(4-methoxyphenyl)-2-phenyl-N-(pyridin-2-yl)pyrazolo[1,5-a]pyrimidin-5-amine

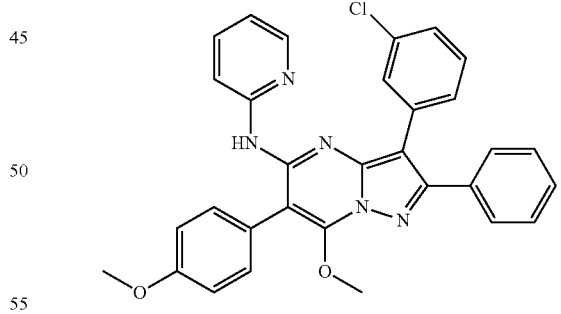

The mixture of 5-chloro-3-(3-chlorophenyl)-7-methoxy-6-(4-methoxyphenyl)-2-phenylpyrazolo-[1,5-a]pyrimidine (120 mg, 0.25 mmol), pyridin-2-amine (47.4 mg, 0.50 mmol), palladium diacetate (28.3 mg, 0.13 mmol), Xantphos (72.9 mg, 0.13 mmol) and cesium carbonate (123.1 mg, 0.38 mmol) in 1,4-dioxane (6 mL) was reacted in microwave reactor at 120° C. for 1.5 hours under nitrogen atmosphere. After cooling to room temperature, the mixture was filtered with celite, diluted with DCM (100 mL), washed with saturated brine (30 mL), dried over anhydrous sodium sulfate and concentrated to dryness. The residue was purified by flash column (petroleum ether/ethyl acetate/DCM/=6:1:1) to obtain 3-(3-chlorophenyl)-7-methoxy-6-(4-methoxyphenyl)-2-phenyl-N-(pyridin-2-yl)pyrazolo[1,5-a]pyrimidin-5-amine (78 mg) as a yellow solid. LC-MS: m/z 534.2 (M+H)⁺.

Step G: 3-(3-chlorophenyl)-6-(4-methoxyphenyl)-2-phenyl-5-(pyridin-2-ylamino)pyrazolo[1,5-a]pyrimidin-7(4H)-one A solution of 3-(3-chlorophenyl)-7-methoxy-6-(4-methoxyphenyl)-2-phenyl-N-(pyridin-2-yl)pyrazolo[1,5-a]pyrimidin-5-amine (70 mg, 0.13 mmol) in 4M HCl in 1,4-dioxane (6 mL) was stirred at r.t. for 3 hours. The mixture was concentrated, and saturated NaHCO₃ (6 mL) was added to obtain 3-(3-chlorophenyl)-6-(4-methoxyphenyl)-2-phenyl-5-(pyridin-2-ylamino)pyrazolo[1,5-a]pyrimidin-7(4H)-one.

¹H NMR (DMSO-d₆): δ 15.73 (s, 1H), 9.05 (s, 1H), 8.11 (d, J=3.8 Hz, 1H), 7.81 (t, J=8.1 Hz, 1H), 7.53-7.60 (m, 4H), 7.40-7.50 (m, 4H), 7.30-7.38 (m, 4H), 7.09-7.15 (m, 1H), 7.07 (d, J=8.6 Hz, 2H), 3.85 (s, 3H). LC-MS: m/z 520.3 (M+H)⁺.

Compound 179: 3-(2-fluorophenyl)-6-(4-methoxyphenyl)-2-phenyl-5-(pyridin-2-ylamino)pyrazolo[1,5-a]pyrimidin-7(4H)-one

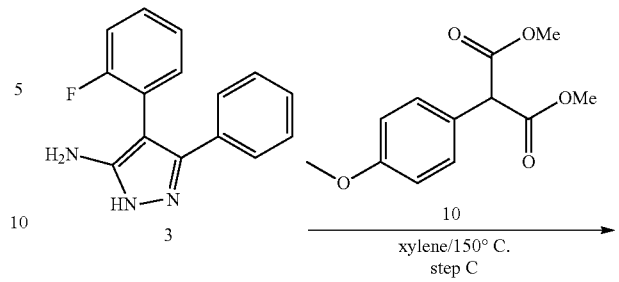
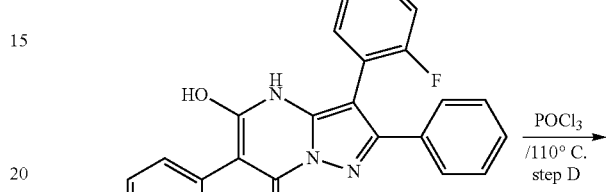
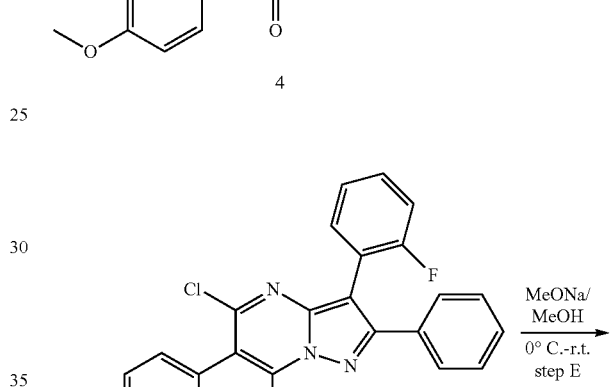
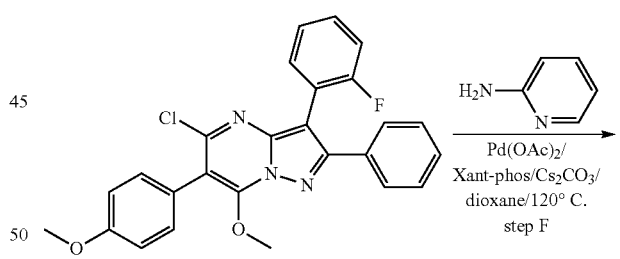
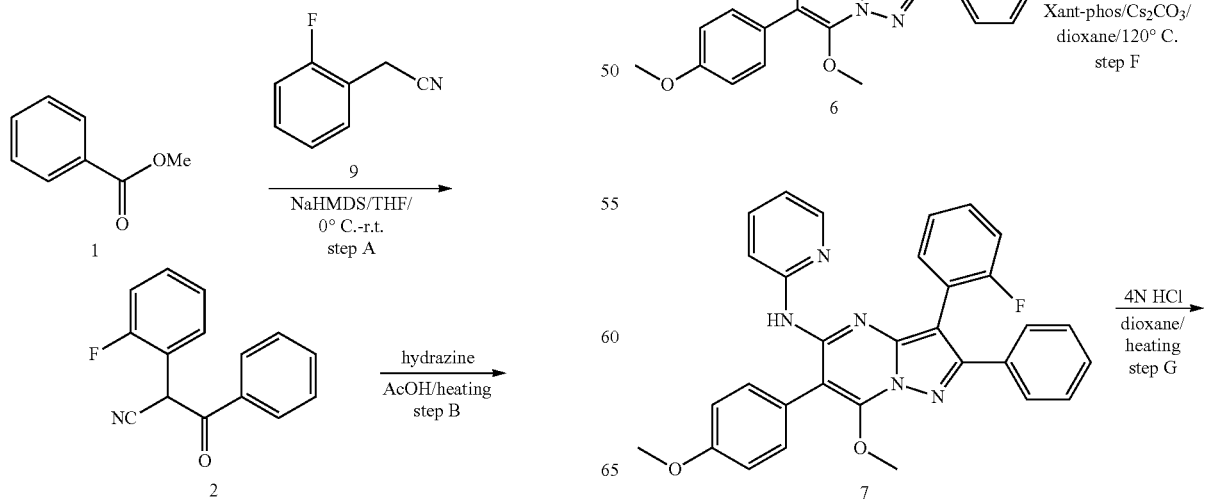

-continued

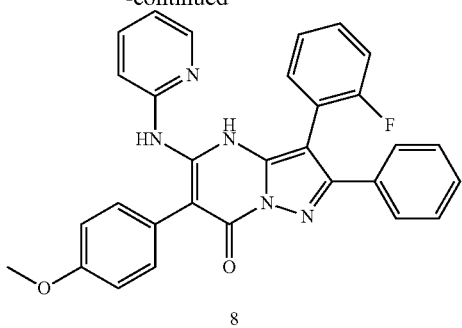

8

Step A:
2-(2-fluorophenyl)-3-oxo-3-phenylpropanenitrile

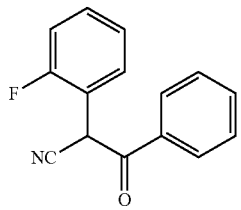 [SMILES: N#CC(C(=O)c1ccccc1)c1ccccc1F]

To a solution of 2-(2-fluorophenyl)acetonitrile (5.4 g, 40 mmol) in anhydrous THF (50 mL) was added dropwise of LDA (26 mL, 52 mmol, 1.3 eq) at −78° C. After addition, the mixture was stirred at −78° C. for 0.5 h. Then methyl benzoate (6.0 g, 44 mmol, 1.1 eq) in THF (10 mL) was added slowly and stirred at RT overnight. The suspension was quenched with NH$_4$Cl solution (30 mL) and extracted with EA. The organic phase was washed with water and brine, dried over anhydrous Na$_2$SO$_4$, filtered, and concentrated under reduced pressure to give 2-(2-fluorophenyl)-3-oxo-3-phenylpropanenitrile (12 g, crude) which was used directly to the next step without further purification. LC-MS: m/z 240.1 (M+H)$^+$.

Step B:
4-(2-fluorophenyl)-3-phenyl-1H-pyrazol-5-amine

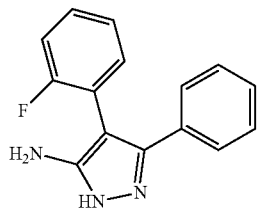 [SMILES: Nc1[nH]nc(-c2ccccc2)c1-c1ccccc1F]

To a solution of 2-(2-fluorophenyl)-3-oxo-3-phenylpropanenitrile (12 g, 40 mmol) in EtOH (80 mL) and AcOH (20 mL) was added hydrazine hydrate (4.48 g, 80 mmol, 2.0 eq). Then the reaction mixture was stirred at reflux for 4 h. The solvents were removed in vacuo, and the residue was adjusted to 8-9 with saturated sodium bicarbonate solution. The mixture was extracted with EtOAc, dried over anhydrous Na$_2$SO$_4$ and concentrated under reduced pressure. The residue was purified by column chromatography on silica gel (EtOAc/PE=1/1) to afford the desired product (1.3 g). LC-MS: m/z 254.1 (M+H)$^+$.

Step C: 3-(2-fluorophenyl)-5-hydroxy-6-(4-methoxyphenyl)-2-phenylpyrazolo[1,5-a]pyrimidin-7(4H)-one

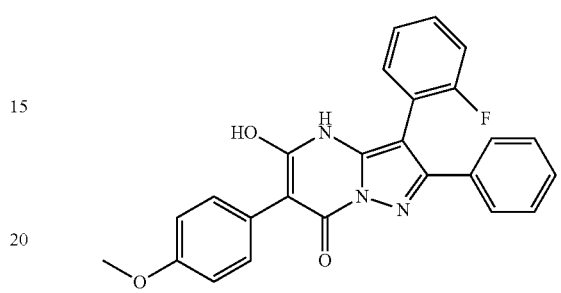

The dimethyl 2-(4-methoxyphenyl)malonate (886 mg, 3.7 mol, 1.2 eq), 4-(2-fluorophenyl)-3-phenyl-1H-pyrazol-5-amine (780 mg, 3.1 mol, 1.0 eq) and xylene (15 mL) were added into the 100 mL bottle and heated to 150° C. for 8 h. The reaction mixture was then cooled to room temperature. The mixture was filtered off, and the filter cake was washed with PE to afford the desired product 3-(2-fluorophenyl)-5-hydroxy-6-(4-methoxyphenyl)-2-phenylpyrazolo[1,5-a]pyrimidin-7(4H)-one (1 g) as a white solid. LC-MS: m/z 427.9 (M+H)$^+$.

Step D: 5,7-dichloro-3-(2-fluorophenyl)-6-(4-methoxyphenyl)-2-phenylpyrazolo[1,5-a] pyrimidine

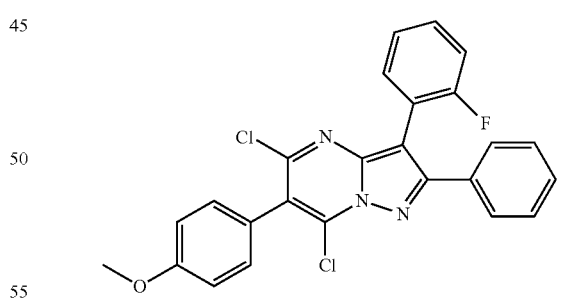

A solution of 3-(2-fluorophenyl)-5-hydroxy-6-(4-methoxyphenyl)-2-phenylpyrazolo[1,5-a]pyrimidin-7(4H)-one (1.0 g, 2.3 mmol) in phosphorus oxychloride (10 mL) was heated to reflux overnight. The mixture was concentrated under reduced pressure. The residue was added slowly into MeOH (10 mL) and filtered. The filter cake was washed with MeOH to afford the desired product 5,7-dichloro-3-(2-fluorophenyl)-6-(4-methoxyphenyl)-2-phenylpyrazolo[1,5-a]pyrimidine (890 mg) as a white solid. LC-MS: m/z 464.1 (M+H)$^+$.

Step E: 5-chloro-3-(2-fluorophenyl)-7-methoxy-6-(4-methoxyphenyl)-2-phenylpyrazolo[1,5-a]pyrimidine

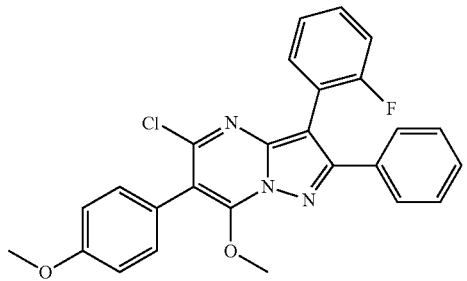 [SMILES: COc1ccc(-c2c(Cl)nc3c(-c4ccccc4F)c(-c4ccccc4)nn3c2OC)cc1]

To a solution of 5,7-dichloro-3-(2-fluorophenyl)-6-(4-methoxyphenyl)-2-phenylpyrazolo[1,5-a]pyrimidine (463 mg, 1 mmol) in DCM (10 mL) and MeOH (10 mL) cooled at 0° C. was added dropwise the sodium methoxide (1 mL, 5 mol, 30% in MeOH). Then the reaction mixture was stirred at 0° C. for 0.5 h. The suspension was quenched with NH$_4$Cl solution (30 mL) and extracted with EA. The combined organic phase was washed with water and brine, dried over anhydrous Na$_2$SO$_4$, filtered, and concentrated under reduced pressure. The residue was purified by column chromatography on silica gel (EtOAc/PE=1/5) to afford the desired product. 5-chloro-3-(2-fluorophenyl)-7-methoxy-6-(4-methoxyphenyl)-2-phenylpyrazolo[1,5-a]pyrimidine (390 mg). LC-MS: m/z 460.1 (M+H)$^+$.

Step F: 3-(2-fluorophenyl)-7-methoxy-6-(4-methoxyphenyl)-2-phenyl-N-(pyridin-2-yl)pyrazolo[1,5-a]pyrimidin-5-amine

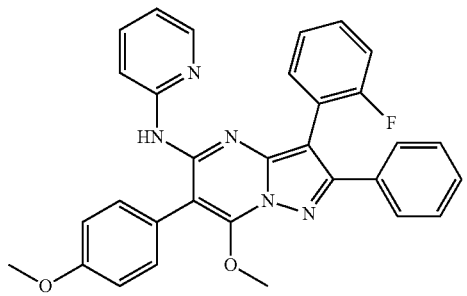 [SMILES: COc1ccc(-c2c(Nc3ccccn3)nc3c(-c4ccccc4F)c(-c4ccccc4)nn3c2OC)cc1]

A suspension of 5-chloro-3-(2-fluorophenyl)-7-methoxy-6-(4-methoxyphenyl)-2-phenylpyrazolo[1,5-a]pyrimidine (230 mg, 0.5 mmol), pyridin-2-amine (94 mg, 1 mmol, 2.0 eq), Pd(OAc)$_2$ (22 mg, 0.1 mmol, 20 mol %), Xantphos (115 mg, 0.2 mmol, 40 mol %) and Cs$_2$CO$_3$ (325 mg, 1 mmol, 2.0 eq) in 1.4-dioxane (10 mL) in a 10 mL microwave vial was heated at 100° C. under microwave irradiation for h under N$_2$ atmosphere. The reaction was then cooled and filtered. The dark filtrate was concentrated in vacuo. The residue was purified by column chromatography on silica gel (EtOAc/PE=1/4) to afford the desired product 3-(2-fluorophenyl)-7-methoxy-6-(4-methoxyphenyl)-2-phenyl-N-(pyridin-2-yl)pyrazolo[1,5-a]pyrimidin-5-amine (100 mg). LC-MS: m/z 518.2 (M+H)$^+$.

Step G: 3-(2-fluorophenyl)-6-(4-methoxyphenyl)-2-phenyl-5-(pyridin-2-ylamino)pyrazolo[1,5-a]pyrimidin-7(4H)-one

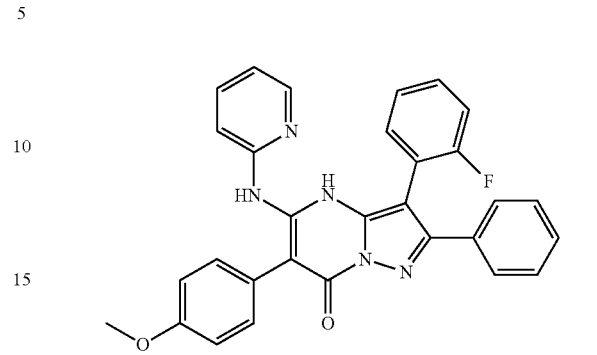

A solution of 3-(2-fluorophenyl)-7-methoxy-6-(4-methoxyphenyl)-2-phenyl-N-(pyridin-2-yl)pyrazolo[1,5-a]pyrimidin-5-amine (85 mg, 0.16 mmol) in 4M HCl in 1.4-dioxane (10 mL) was stirred at 30° C. for 18 hours. The reaction mixture was concentrated in vacuo to afford the title compound.

$^1$H NMR (DMSO-d$_6$): δ 8.04 (d, J=4.8 Hz, 1H), 7.89 (s, 1H), 7.49-7.59 (m, 3H), 7.31-7.45 (m, 9H), 7.11 (t, J=6.4 Hz, 1H), 7.03 (d, J=8.4 Hz, 2H), 3.82 (s, 3H). LC-MS: m/z 504.0 (M+H)$^+$.

Compound 180: 6-(4-methoxyphenyl)-3-phenyl-2-(pyridin-2-yl)-5-(pyridin-2-ylamino)pyrazolo[1,5-a]pyrimidin-7(4H)-one

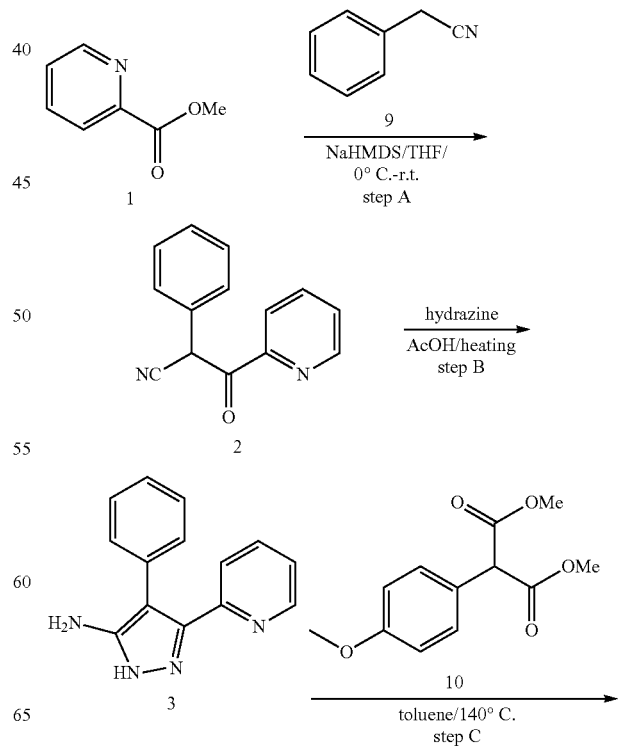

153
-continued

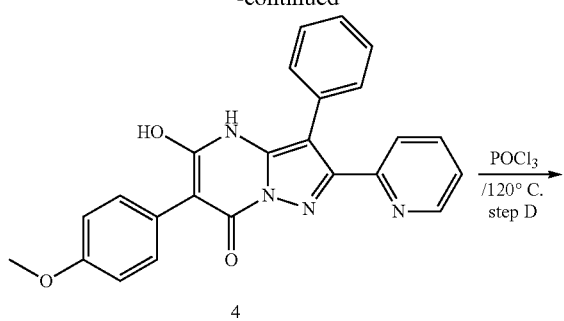

4

POCl₃
/120° C.
step D

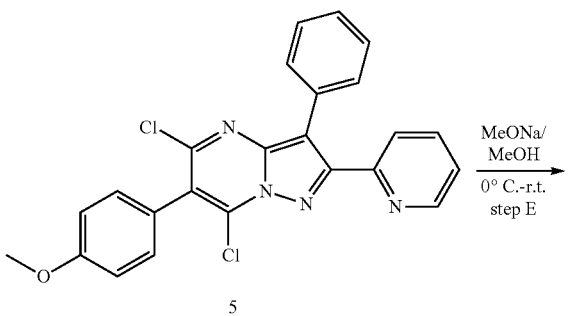

5

MeONa/
MeOH
0° C.-r.t.
step E

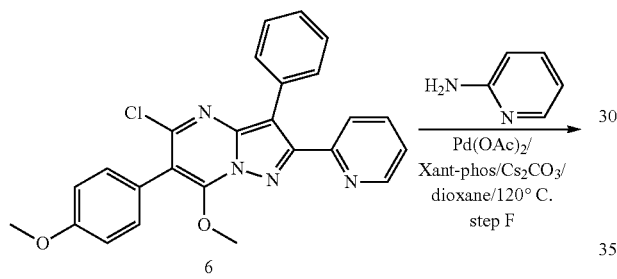

6

H₂N—⟨pyridine⟩
Pd(OAc)₂/
Xant-phos/Cs₂CO₃/
dioxane/120° C.
step F

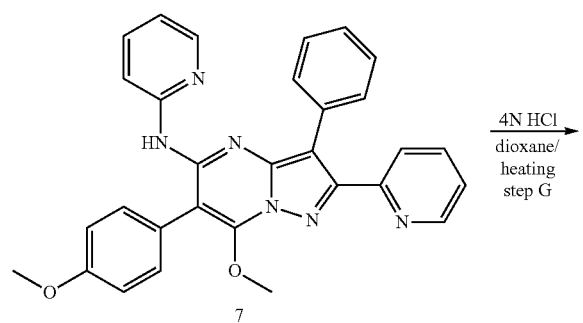

7

4N HCl
dioxane/
heating
step G

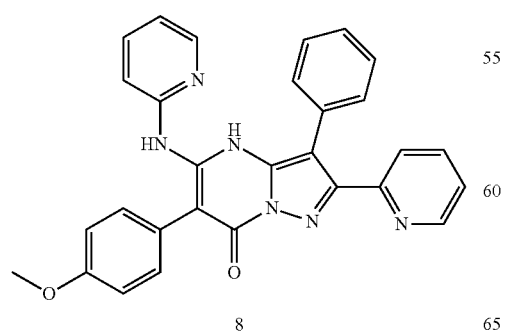

8

154

Step A:
3-oxo-2-phenyl-3-(pyridin-2-yl)propanenitrile

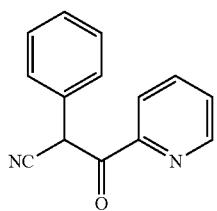 [SMILES: N#CC(C(=O)c1ccccn1)c1ccccc1]

To a solution of methyl picolinate (20 g, 0.15 mol) and 2-phenylacetonitrile (20 g, 0.18 mol) in THF (200 mL) was added slowly NaHDMS (80 mL, 2 mmol/mL) at 0° C. Then the reaction mixture was stirred for h at 0° C. and allowed to room temperature overnight. The mixture was poured into water and extracted with ethyl acetate (100 mL*3). The organic layer was dried over anhydrous sodium sulfate, filtered, and concentrated in vacuo to give 3-oxo-2-phenyl-3-(pyridin-2-yl)propanenitrile (crude, 25 g). LC-MS: m/z 223.3 (M+H)⁺.

Step B: 4-phenyl-3-(pyridin-2-yl)-1H-pyrazol-5-amine

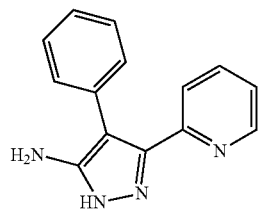 [SMILES: Nc1[nH]nc(-c2ccccn2)c1-c1ccccc1]

To a solution of 3-oxo-2-phenyl-3-(pyridin-2-yl)propanenitrile (25 g, 0.126 mol) in EtOH (200 mL) was added AcOH (20 mL). The reaction mixture was heated to 60° C. for 10 minutes, and then hydrazine monohydrate (7 g, 0.138 mol) was added dropwise via a syringe. Then the reaction mixture was stirred for 4 h at 60° C. The mixture was concentrated to dryness. The residue was poured into water and extracted with ethyl acetate (100 mL*3). The organic layer was dried over anhydrous sodium sulfate, filtered and concentrated to give the crude product. The crude product was purified by column chromatography on silica gel (eluting PE/EA=2:1) to give 4-phenyl-3-(pyridin-2-yl)-1H-pyrazol-5-amine (3 g). LC-MS: m/z 237.2 (M+H)⁺.

Step C: 6-(4-methoxyphenyl)-3-phenyl-2-(pyridin-2-yl)pyrazolo[1,5-a]pyrimidine-5,7(4H,6H)-dione

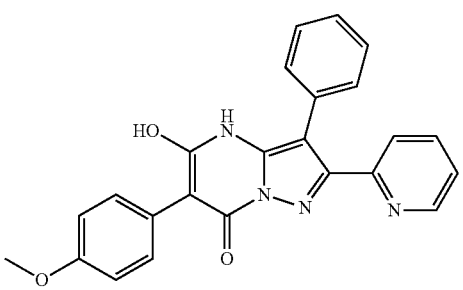 [SMILES: COc1ccc(-c2c(O)[nH]c3c(-c4ccccc4)c(-c4ccccn4)nn3c2=O)cc1]

A solution of 4-phenyl-3-(pyridin-2-yl)-1H-pyrazol-5-amine (1.5 g, 6.35 mmol) and dimethyl 2-(4-methoxyphenyl)malonate (1.67 g, 7.0 mmol) in toluene (50 mL) was heated to 140° C. overnight. The reaction mixture was cooled to room temperature. The precipitate was filtered off to give 6-(4-methoxyphenyl)-3-phenyl-2-(pyridin-2-yl)pyrazolo[1,5-a]pyrimidine-5,7(4H,6H)-dione (1.2 g). LC-MS: m/z 411.2 (M+H)+.

Step D: 5,7-dichloro-6-(4-methoxyphenyl)-3-phenyl-2-(pyridin-2-yl)pyrazolo[1,5-a]pyrimidine

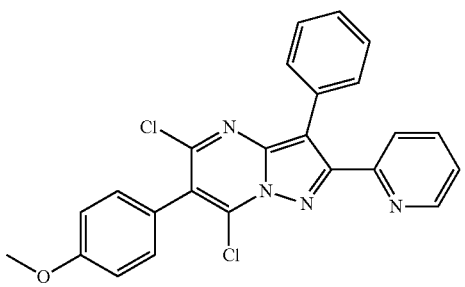 [SMILES: COc1ccc(-c2c(Cl)nc3c(-c4ccccc4)c(-c4ccccn4)nn3c2Cl)cc1]

A solution of 6-(4-methoxyphenyl)-3-phenyl-2-(pyridin-2-yl)pyrazolo[1,5-a]pyrimidine-5,7(4H,6H)-dione (1 g, 2.44 mmol) in POCl₃ (15 mL) in a sealed tube was heated to 120° C. overnight. The reaction mixture was cooled to room temperature and concentrated in vacuo. The residue was adjusted to PH=7 by adding saturated NaHCO₃ solution, extracted with ethyl acetate (50 mL*3), filtered, and concentrated to dryness. The residue was purified by column chromatography on silica gel (eluting PE/EA=10:1) to give 5,7-dichloro-6-(4-methoxyphenyl)-3-phenyl-2-(pyridin-2-yl)pyrazolo[1,5-a]pyrimidine (900 mg). LC-MS: m/z 447.3 (M+H)+.

Step E: 5-chloro-7-methoxy-6-(4-methoxyphenyl)-3-phenyl-2-(pyridin-2-yl)pyrazolo[1,5-a]pyrimidine

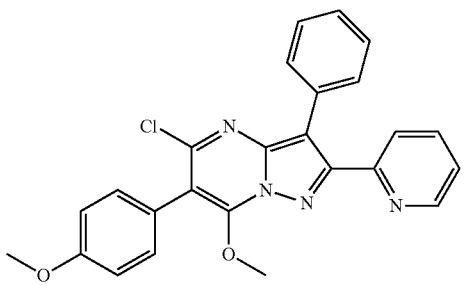 [SMILES: COc1ccc(-c2c(Cl)nc3c(-c4ccccc4)c(-c4ccccn4)nn3c2OC)cc1]

To a solution of 5,7-dichloro-6-(4-methoxyphenyl)-3-phenyl-2-(pyridin-2-yl)pyrazolo[1,5-a]pyrimidine (900 mg, 2.0 mmol) in MeOH (50 mL) was added NaOMe (0.5 mL, 5.0 mmol/mL) at 0° C. The reaction mixture was stirred for 30 mins. The mixture was adjusted to PH=7 by adding 1N HCl solution. Then the mixture was poured into water and extracted with ethyl acetate, dried over anhydrous Na₂SO₄, filtered, and concentrated. The resultant solid was washed with ethyl acetate to give the desired product 5-chloro-7-methoxy-6-(4-methoxyphenyl)-3-phenyl-2-(pyridin-2-yl)pyrazolo[1,5-a]pyrimidine (500 mg). LC-MS: m/z 443.4 (M+H)+.

Step F: 7-methoxy-6-(4-methoxyphenyl)-3-phenyl-N,2-di(pyridin-2-yl)pyrazolo[1,5-a] pyrimidin-5-amine

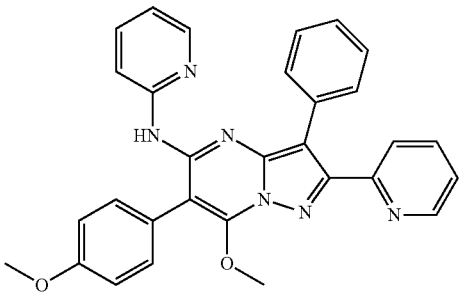 [SMILES: COc1ccc(-c2c(Nc3ccccn3)nc3c(-c4ccccc4)c(-c4ccccn4)nn3c2OC)cc1]

A mixture of 5-chloro-7-methoxy-6-(4-methoxyphenyl)-3-phenyl-2-(pyridin-2-yl)pyrazolo[1,5-a]pyrimidine (150 mg, 0.34 mmol), pyridin-2-amine (35 mg, 0.37 mmol), Pd(OAc)₂ (7.6 mg, 0.034 mmol), xantphos (40 mg, 0.068 mmol), and Cs₂CO₃ (222 mg) in dioxane (5 mL) was heated to 120° C. for 2 h under N₂. The mixture was cooled to room temperature and concentrated in vacuo. The residue was purified by column chromatography on silica gel (eluting DCM/MeOH=20:1) to give the desired product (crude, 80 mg), which was used directly to the next step without further purification.

Step G: 6-(4-methoxyphenyl)-3-phenyl-2-(pyridin-2-yl)-5-(pyridin-2-ylamino)pyrazolo[1,5-a]pyrimidin-7(4H)-one

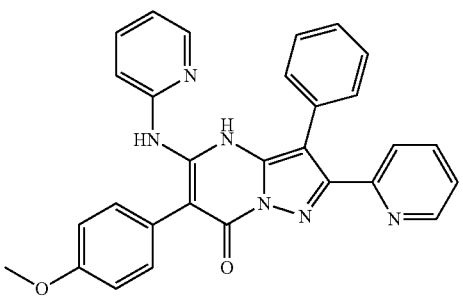 [SMILES: COc1ccc(-c2c(Nc3ccccn3)[nH]c3c(-c4ccccc4)c(-c4ccccn4)nn3c2=O)cc1]

To a solution of 7-methoxy-6-(4-methoxyphenyl)-3-phenyl-N,2-di(pyridin-2-yl)pyrazolo[1,5-a]pyrimidin-5-amine (crude 80 mg) in MeOH (5 mL) was added HCl in dioxane (5 mL, 4 mmol/mL). The reaction mixture was stirred for 30 mins. The reaction mixture was concentrated in vacuo. The residue was basified with saturated NaHCO₃ to give the desired product 6-(4-methoxyphenyl)-3-phenyl-2-(pyridin-2-yl)-5-(pyridin-2-ylamino)pyrazolo[1,5-a]pyrimidin-7 (4H)-one.

¹H NMR (DMSO-d₆): δ 15.86 (s, 1H), 9.05 (s, 1H), 8.52 (d, J=4.8 Hz, 1H), 7.98-8.10 (m, 1H), 7.92 (d, J=3.8 Hz, 2H), 7.80 (s, 1H), 7.45-7.60 (m, 4H), 7.27-7.45 (m, 5H), 7.00-7.14 (m, 3H), 3.84 (s, 3H). LC-MS: m/z 487.2 (M+H)+.

157

Compound 181: 6-(4-methoxyphenyl)-2-phenyl-3-(piperidin-1-yl)-5-(pyridin-2-ylamino)pyrazolo[1,5-a]pyrimidin-7(4H)-one

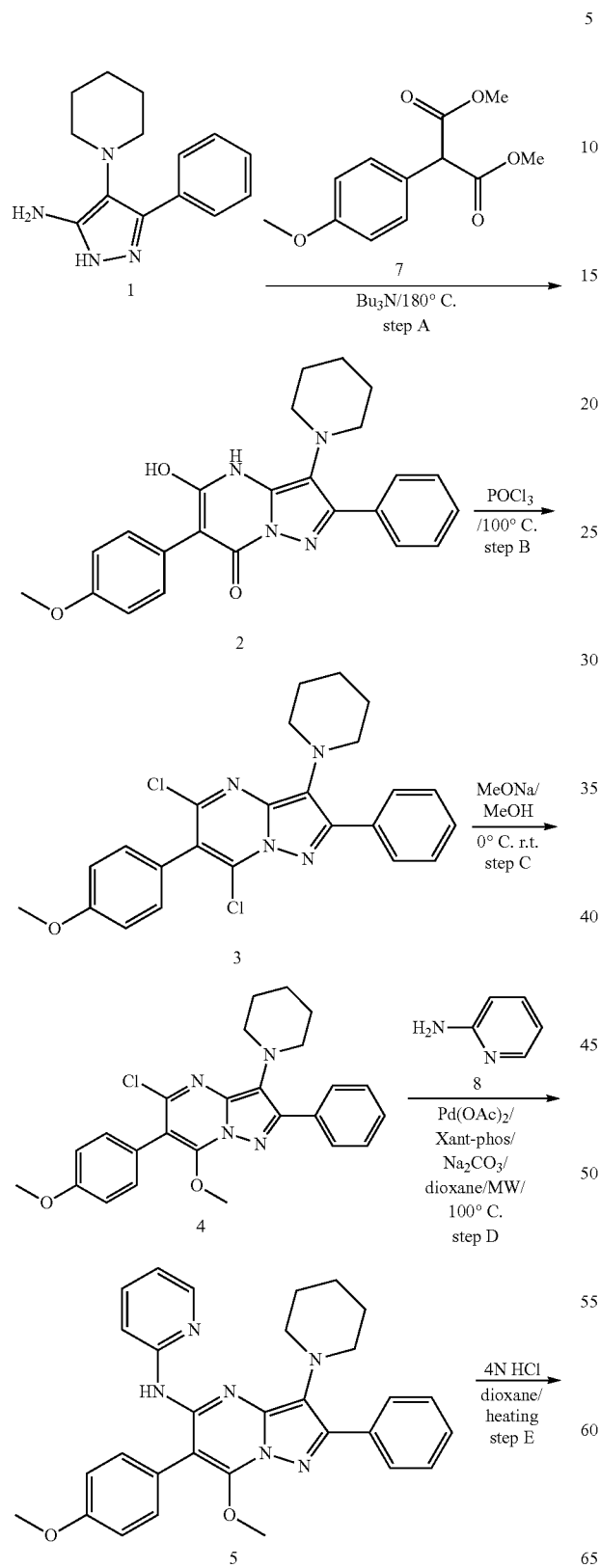

158

-continued

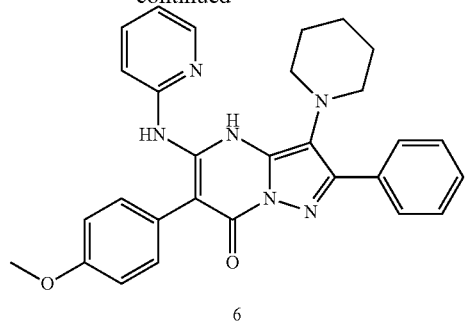

Step A: 5-hydroxy-6-(4-methoxyphenyl)-2-phenyl-3-(piperidin-1-yl)pyrazolo[1,5-a]pyrimidin-7(4H)-one

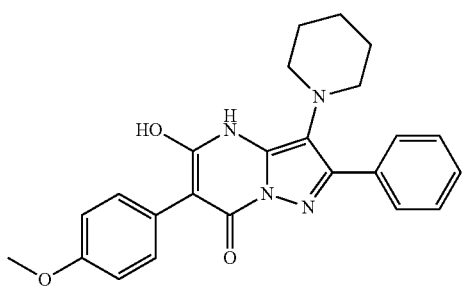

A suspension of 3-phenyl-4-(piperidin-1-yl)-1H-pyrazol-5-amine (2 g, 8.254 mmol) and dimethyl 2-(4-methoxyphenyl)malonate (2.95 g, 12.38 mmol) in tributylamine (25 mL) was warmed up to 180° C. for 2.5 hours under $N_2$ protection. The mixture was cooled to the room temperature and stirred with petroleum ether. The precipitates was filtered and washed with EtOAc to afford 5-hydroxy-6-(4-methoxyphenyl)-2-phenyl-3-(piperidin-1-yl)pyrazolo[1,5-a]pyrimidin-7(4H)-one (3 g) as a yellow solid. LC-MS: m/z 417.2 $(M+H)^+$.

Step B: 5,7-dichloro-6-(4-methoxyphenyl)-2-phenyl-3-(piperidin-1-yl)pyrazolo[1,5-a]pyrimidine

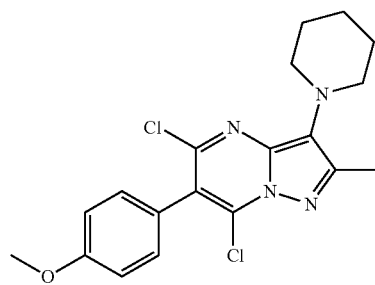

The solution of 5-hydroxy-6-(4-methoxyphenyl)-2-phenyl-3-(piperidin-1-yl)pyrazolo[1,5-a]pyrimidin-7(4H)-one (3 g, 7.203 mmol) in $POCl_3$ (30 mL) was warmed up to 100° C. overnight. The reaction mixture was concentrated to remove $POCl_3$. The residue was basified with saturated sodium hydrogen carbonate solution at 0° C., and extracted with EtOAc (3×30 mL). The combined organic layers were washed with brine (30 mL), dried over anhydrous sodium sulfate, and concentrated in vacuo to afford crude product (2.5 g) as a yellow solid. LC-MS: m/z 453.1 (M+H)+.

Step C: 5-chloro-7-methoxy-6-(4-methoxyphenyl)-2-phenyl-3-(piperidin-1-yl)pyrazolo[1,5-a]pyrimidine

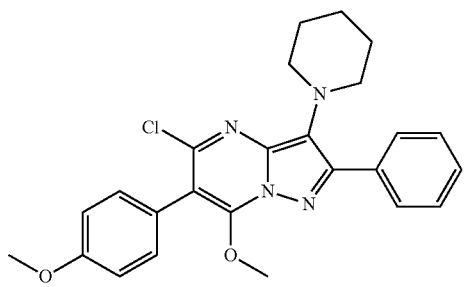 [SMILES: COc1ccc(-c2c(Cl)nc3c(N4CCCCC4)c(-c4ccccc4)nn3c2OC)cc1]

To a solution of 5,7-dichloro-6-(4-methoxyphenyl)-2-phenyl-3-(piperidin-1-yl)pyrazolo[1,5-a]pyrimidine (1 g, 2.4 mmol) in methanol (20 mL) was added MeONa (30% wt in methanol, 1.3 mL, 7.2 mmol) at 0° C. and stirred at 0° C. for 3 hours. The reaction was quenched with ice water at 0° C., diluted with saturated sodium hydrogen carbonate solution at 0° C., and extracted with EtOAc (2×20 mL). The combined organic layers were washed with brine (30 mL), dried over anhydrous sodium sulfate, and concentrated in vacuo. The residue was purified by silica gel column (DCM:MeOH=30:1) to afford 5-chloro-7-methoxy-6-(4-methoxyphenyl)-2-phenyl-3-(piperidin-1-yl)pyrazolo[1,5-a]pyrimidine (550 mg) as a yellow solid. LC-MS: m/z 449.2 (M+H)+.

Step D: 7-methoxy-6-(4-methoxyphenyl)-2-phenyl-3-(piperidin-1-yl)-N-(pyridin-2-yl)pyrazolo[1,5-a]pyrimidin-5-amine

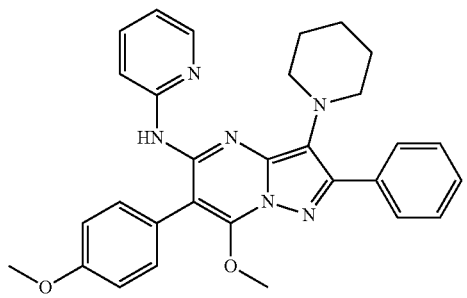 [SMILES: COc1ccc(-c2c(Nc3ccccn3)nc3c(N4CCCCC4)c(-c4ccccc4)nn3c2OC)cc1]

A suspension of 5-chloro-7-methoxy-6-(4-methoxyphenyl)-2-phenyl-3-(piperidin-1-yl)pyrazolo[1,5-a]pyrimidine (200 mg, 0.446 mmol), pyridin-2-amine (125 mg, 12.38 mmol, 3 eq), Pd(OAc)$_2$ (20 mg, 0.089 mmol, 0.2 eq), Xant-phos (103 mg, 0.178 mmol, 0.4 eq) and Na$_2$CO$_3$ (188 mg, 1.782 mmol, 4 eq) in 1,4-dioxane (5 mL) was stirred and warmed up to 100° C. through microwave irradiation for 1 hour under N$_2$ atmosphere. The reaction was cooled to room temperature, diluted with saturated sodium hydrogen carbonate solution, and extracted with EtOAc (2×30 mL). The combined organic layers were washed with brine (20 mL), dried over anhydrous sodium sulfate, and concentrated invacuo. The residue was purified by pre-TLC (eluting DCM/MeOH=20:1) to obtain 7-methoxy-6-(4-methoxyphenyl)-2-phenyl-3-(piperidin-1-yl)-N-(pyridin-2-yl)pyrazolo[1,5-a]pyrimidin-5-amine (80 mg) as a white solid.

$^1$H NMR (DMSO-d$_6$) δ 8.49 (d, J=5.64 Hz, 1H), 8.21-8.38 (m, 2H), 8.07 (d, J=7.25 Hz, 2H), 7.36-7.60 (m, 6H), 7.16 (d, J=8.60 Hz, 2H), 4.13 (s, 3H), 3.86 (s, 3H), 3.51 (br. s., 4H), 1.80 (br. s., 4H), 1.60 (br. s., 2H). LC-MS: m/z 507.2 (M+H)+.

Step E: 6-(4-methoxyphenyl)-2-phenyl-3-(piperidin-1-yl)-5-(pyridin-2-ylamino)pyrazolo[1,5-a]pyrimidin-7(4H)-one

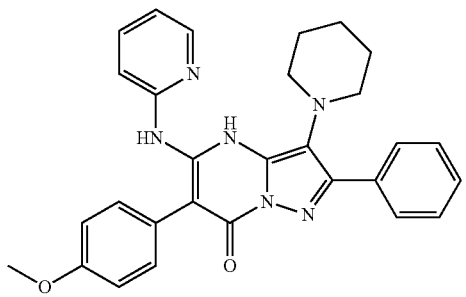 [SMILES: COc1ccc(-c2c(Nc3ccccn3)[nH]c3c(N4CCCCC4)c(-c4ccccc4)nn3c2=O)cc1]

A solution of 7-methoxy-6-(4-methoxyphenyl)-2-phenyl-3-(piperidin-1-yl)-N-(pyridin-2-yl)pyrazolo[1,5-a]pyrimidin-5-amine (100 mg, 0.198 mmol) in 4.0M HCl in 1.4-dioxane (10 mL) was stirred at room temperature for 2 hours. The reaction mixture was concentrate in vacuo. The residue was dissolved in 7N NH$_3$ in methanol and concentrated in vacuo to afford the title compound.

$^1$H NMR (DMSO-d$_6$): δ 8.31 (d, J=4.88 Hz, 1H), 8.12 (d, J=7.63 Hz, 2H), 7.94 (t, J=7.32 Hz, 1H), 7.41-7.53 (m, 4H), 7.34 (m, J=8.55 Hz, 2H), 7.19 (t, J=6.26 Hz, 1H), 7.03 (m, J=8.55 Hz, 2H), 3.82 (s, 3H), 3.20 (br. s., 4H), 1.73 (br. s., 4H), 1.53-1.68 (m, 2H). LC-MS: m/z 493.4 (M+H)+.

Compound 182: 5-((1H-pyrazol-3-yl)amino)-6-(4-methoxyphenyl)-2,3-diphenylpyrazolo[1,5-a]pyrimidin-7(4H)-one

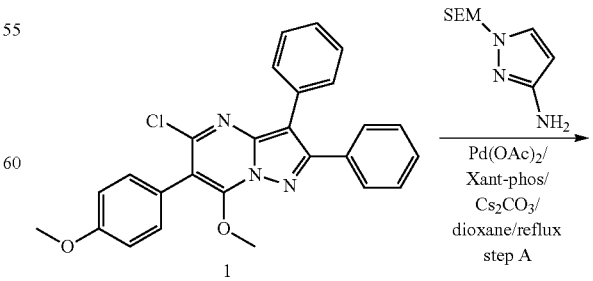

-continued

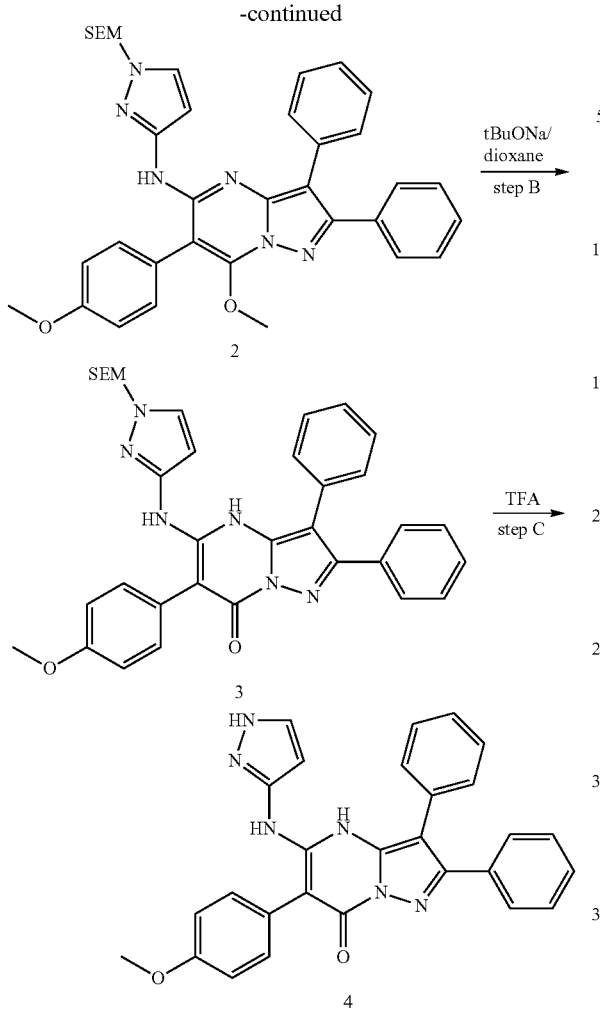

Step A: 7-methoxy-6-(4-methoxyphenyl)-2,3-diphenyl-N-(1-((2-(trimethylsilyl)ethoxy) methyl)-1H-pyrazol-3-yl)pyrazolo[1,5-a]pyrimidin-5-amine A suspension of 5-chloro-7-methoxy-6-(4-methoxyphenyl)-2,3-diphenylpyrazolo[1,5-a]pyrimidine (500 mg, 1.1 mmol) and 1-((2-(trimethylsilyl)ethoxy)methyl)-1H-pyrazol-3-amine (314 mg, 1.47 mmol) and Pd(OAc)₂ (38 mg, 0.16 mmol), Xantphos (98 mg, 0.16 mmol) and Cs₂CO₃ (740 mg, 2.2 mmol) in 1.4-dioxane (10 mL) was stirred and heated to reflux for 16 hours under N₂ atmosphere. The reaction was monitored by LC-MS until the complete conversion of the starting material. The reaction was then cooled to r.t. and filtered. The dark filtrate was concentrated in vacuo and purified by flash column chromatography eluting with DCM:MeOH=40:1 to obtain the Intermediate 2 (500 mg) as a white solid. LC-MS: m/z 619.5 (M+H)⁺.

Step B: 7-methoxy-6-(4-methoxyphenyl)-2,3-diphenyl-N-(1-((2-(trimethylsilyl)ethoxy) methyl)-1H-pyrazol-3-yl)pyrazolo[1,5-a]pyrimidin-5-amine The Intermediate 2 (500 mg, 0.81 mmol) and sodium 2-methylpropan-2-olate (155 mg, 1.62 mmol) in dioxane was stirred at 110° C. for 1 h under MW. The mixture was acidified to PH=7 and concentrated to give the crude product which was directly used to the next step without further purification. LC-MS: m/z 605.3 (M+H)⁺.

Step C: 5-((1H-pyrazol-3-yl)amino)-6-(4-methoxyphenyl)-2,3-diphenylpyrazolo[1,5-a] pyrimidin-7(4H)-one The Intermediate 3 (300 mg, 0.49 mmol) in DCM (5 mL) and TFA (5 mL) was stirred at 60° C. for 1 h. Then the mixture was concentrated to give the crude product which was added into ammonia water (5 mL) and stirred on for 1 h. The mixture was concentrated to give the desired product.

1H NMR (DMSO-d₆): δ 13.46 (s, 1H), 12.67 (br. s., 1H), 8.96 (br. s., 1H), 7.70 (br. s., 1H), 7.47-7.58 (m, 4H), 7.35-7.43 (m, 6H), 7.29 (s, 1H), 7.06 (d, J=8.6 Hz, 2H), 6.00-6.09 (m, 1H), 3.84 (s, 3H). LC-MS: m/z 475.5 (M+H)⁺.

Compound 183: 5-((5-methoxy-1H-pyrazol-3-yl)amino)-6-(4-methoxyphenyl)-2,3-diphenylpyrazolo[1,5-a]pyrimidin-7(4H)-one

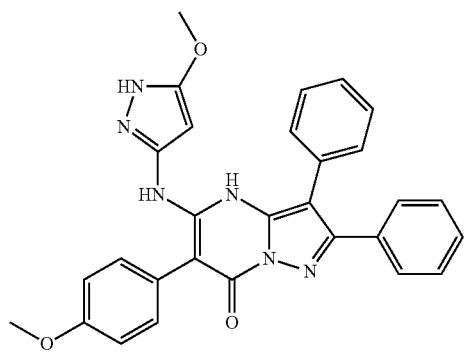 [SMILES: COc1ccc(-c2c(Nc3cc(OC)[nH]n3)[nH]c3c(-c4ccccc4)c(-c4ccccc4)nn3c2=O)cc1]

This compound was prepared according to the procedure for preparing compound 182 by using Intermediate 5 as 5-methoxy-1-(4-methoxybenzyl)-1H-pyrazol-3-amine in step A.

Step A: A suspension of 5-chloro-7-methoxy-6-(4-methoxyphenyl)-2,3-diphenylpyrazolo[1,5-a]pyrimidine (441 mg, 1 mmol), 5-methoxy-1-((2-(trimethylsilyl)ethoxy)methyl)-1H-pyrazol-3-amine (243 mg, 1 mmol, 1 eq.), Pd(OAc)₂ (44.8 mg, 0.2 mmol, 0.2 eq.), Xantphos (57.8 mg, 0.1 mmol, 0.1 eq.) and Cs₂CO₃ (650 mg, 2 mmol, 2 eq.) in 1.4-dioxane (5 mL) was stirred at 110° C. for 16 hour under N₂ atmosphere. The mixture was filtered through celite, and the filtrate was concentrated in vacuo. The crude product was directly used in the next step without further purification. LC-MS: m/z 649.4 (M+H)⁺

Step B: A mixture of 7-methoxy-N-(5-methoxy-1-((2-(trimethylsilyl)ethoxy)methyl)-1H-pyrazol-3-yl)-6-(4-methoxyphenyl)-3-phenyl-2-(pyridin-2-yl)pyrazolo[1,5-a]pyrimidin-5-amine (800 mg, 1.23 mmol) and sodium 2-methylpropan-2-olate (197 mg, 4.9 mmol) in dioxane (10 mL) was stirred at 100° C. for 2 h. The mixture was acidified to PH=7 and concentrated to give the crude product which was purified by silica gel chromatography (DCM:MeOH=40:1) to afford 5-((5-methoxy-1-((2-(trimethylsilyl)ethoxy)methyl)-1H-pyrazol-3-yl)amino)-6-(4-methoxyphenyl)-2,3-diphenylpyrazolo[1,5-a]pyrimidin-7(4H)-one (300 mg) as gray solid. LC-MS: m/z 635.3 (M+H)⁺.

Step C: A solution of 5-((5-methoxy-1-((2-(trimethylsilyl)ethoxy)methyl)-1H-pyrazol-3-yl)amino)-6-(4-methoxyphenyl)-2,3-diphenylpyrazolo[1,5-a]pyrimidin-7(4H)-one (100 mg, 0.19 mmol) in 4M HCl in dioxane (5 mL) was stirred at r.t. for 1 hour. Solvent and volatile were removed in vacuo. The residue was dissolved in DCM (5 mL) and treated with saturated NaHCO$_3$. The organic phase was separated and washed with brine, dried over anhydrous Na$_2$SO$_4$, and concentrated in vacuo to afford the title compound.

$^1$H NMR (CHLOROFORM-d): δ 7.49-7.66 (m, 3H), 7.45 (br. s., 3H), 7.37 (br. s., 4H), 7.31 (br. s., 4H), 7.06 (br. s., 2H), 5.27 (br. s., 1H), 3.84 (s, 3H), 3.87 (s, 3H). LC-MS: m/z 505.5 (M+H)$^+$.

Compound 184: 5-((1H-imidazol-4-yl)amino)-6-(4-methoxyphenyl)-2,3-diphenylpyrazolo[1,5-a]pyrimidin-7(4H)-one

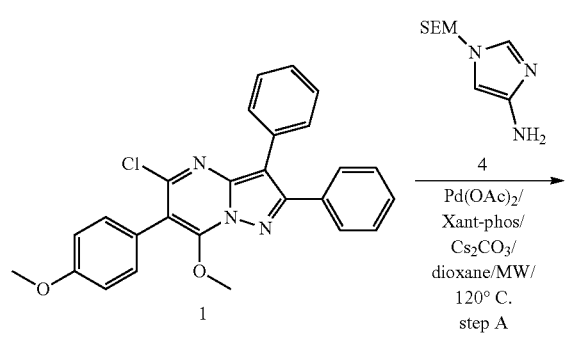

Step A: 6-(4-methoxyphenyl)-2,3-diphenyl-5-((1-((2-(trimethylsilyl)ethoxy)methyl)-1H-imidazol-4-yl)amino)pyrazolo[1,5-a]pyrimidin-7(4H)-one A mixture of 5-chloro-7-methoxy-6-(4-methoxyphenyl)-2,3-diphenylpyrazolo[1,5-a]pyrimidine (300 mg, 0.68 mmol), 1-((2-(trimethylsilyl)ethoxy)methyl)-1H-imidazol-4-amine (289.7 mg, 1.36 mmol), palladium diacetate (30.5 mg, 0.14 mmol), Xantphos (117.8 mg, 0.20 mmol) and cesium carbonate (486.6 mg, 1.49 mmol) in 1,4-dioxane (8 mL) was reacted in microwave reactor at 120° C. for 45 minutes under nitrogen atmosphere. After cooling to room temperature, the mixture was filtered with celite, diluted with DCM (100 mL), washed with saturated NH$_4$Cl (30 mL) and brine (30 mL), dried over anhydrous sodium sulfate and concentrated to dryness. The residue was purified by pre-TLC (DCM:MeOH=40:1) to obtain 7-methoxy-6-(4-methoxyphenyl)-2,3-diphenyl-N-(1-((2-(trimethylsilyl)ethoxy)methyl)-1H-imidazol-4-yl)pyrazolo[1,5-a]pyrimidin-5-amine (110 mg, yellow solid) and 6-(4-methoxyphenyl)-2,3-diphenyl-5-((1-((2-(trimethylsilyl)ethoxy)methyl)-1H-imidazol-4-yl)amino)pyrazolo[1,5-a]pyrimidin-7(4H)-one (40 mg, yellow solid). LC-MS: m/z 605.3 (M+H)$^+$.

Step B: 5-((1H-imidazol-4-yl)amino)-6-(4-methoxyphenyl)-2,3-diphenylpyrazolo[1,5-a] pyrimidin-7 (4H)-one To the solution of 6-(4-methoxyphenyl)-2,3-diphenyl-5-((1-((2-(trimethylsilyl)ethoxy)methyl)-1H-imidazol-4-yl)amino)pyrazolo[1,5-a]pyrimidin-7(4H)-one (40 mg, 0.1 mmol) in DCM (1.5 mL) cooled to 0° C. was added TFA (1.5 mL) dropwise. Then the mixture was stirred at room temperature for 8 h. The mixture was concentrated, and NaOH (1 M) was added to pH>7 to afford pure product.

$^1$H NMR (TFA-d): δ 8.54 (s, 1H), 7.41-7.67 (m, 11H), 7.37 (d, J=7.3 Hz, 2H), 7.22 (d, J=8.6 Hz, 2H), 4.05 (s, 3H). LC-MS: m/z 475.4 (M+H)$^+$.

Compound 185: 5-((2H-1,2,3-triazol-4-yl)amino)-6-(4-methoxyphenyl)-2,3-diphenylpyrazolo[1,5-a]pyrimidin-7(4H)-one

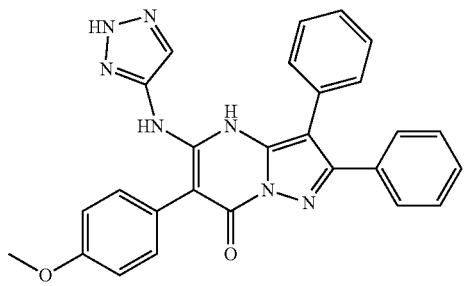 [SMILES: COc1ccc(-c2c(Nc3cn[nH]n3)[nH]c3c(-c4ccccc4)c(-c4ccccc4)nn3c2=O)cc1]

This compound was prepared according to The procedure for preparing compound 182 by using Intermediate 5 as 2-((2-(trimethylsilyl)ethoxy)methyl)-2H-1,2,3-triazol-4-amine in step A.

Step A: A suspension of 5-chloro-7-methoxy-6-(4-methoxyphenyl)-2,3-diphenylpyrazolo[1,5-a]pyrimidine (50 mg, 0.11 mmol), 2-((2-(trimethylsilyl)ethoxy)methyl)-2H-1,2,3-triazol-4-amine (31 mg, 0.147 mmol, 1.3 eq.), Pd(OAc)$_2$ (5.1 mg, 0.027 mmol, 0.2 eq.), Xantphos (13.1 mg, 0.027 mmol, 0.2 eq.) and Cs$_2$CO$_3$ (66.7 mg, 0.283 mmol, 2.5 eq.) in dioxane (6 mL) was stirred at 100° C. for 1 hour under N$_2$ atmosphere in microwave. The mixture was filtered through celite, and the filtrate was concentrated in vacuo. The residue was purified by flash chromatography (PE:EA=2/1) to afford 7-methoxy-6-(4-methoxyphenyl)-2,3-diphenyl-N-(2-((2-(trimethylsilyl)ethoxy)methyl)-2H-1,2,3-triazol-4-yl)pyrazolo[1, 5-a]pyrimidin-5-amine (30 mg) as a white solid. LC-MS: m/z 619.9 (M+H)$^+$.

Step B: A solution of 7-methoxy-6-(4-methoxyphenyl)-2,3-diphenyl-N-(2-((2-(trimethylsilyl)ethoxy)methyl)-2H-1,2,3-triazol-4-yl)pyrazolo[1,5-a]pyrimidin-5-amine (110 mg, 0.18 mmol) and KO$^t$Bu (50 mg, 0.44 mmol) in 1.4-dioxane (5 mL) was stirred at reflux for 2 hours. Solvent and volatile were removed in vacuo to afford 6-(4-methoxyphenyl)-2,3-diphenyl-5-((2-((2-(trimethylsilyl)ethoxy)methyl)-2H-1,2,3-triazol-4-yl)amino)pyrazolo[1,5-a]pyrimidin-7(4H)-one (130 mg) which was directly used in the next step without further purification. LC-MS: m/z 605.9 (M+H)$^+$.

Step C: A solution of 6-(4-methoxyphenyl)-2,3-diphenyl-5-((2-((2-(trimethylsilyl)ethoxy)-methyl)-2H-1,2,3-triazol-4-yl)amino)pyrazolo[1,5-a]pyrimidin-7(4H)-one (130 mg, 0.21 mmol) in TFA (10 mL) was stirred at r.t. for 1 hours. Solvent and volatile were removed in vacuo. The residue was basified with NH$_3$.H$_2$O to pH=8 and concentrated to afford the title compound.

$^1$H NMR (DMSO-d$_6$): δ 7.44-7.62 (m, 5H), 7.24-7.43 (m, 9H), 7.04 (d, J=8.1 Hz, 2H), 3.81 (s, 3H). LC-MS: m/z 476.3 (M+H)$^+$.

Compound 186: 5-((5-amino-1H-pyrazol-3-yl)amino)-6-(4-methoxyphenyl)-2,3-diphenylpyrazolo[1,5-a]pyrimidin-7(4H)-one

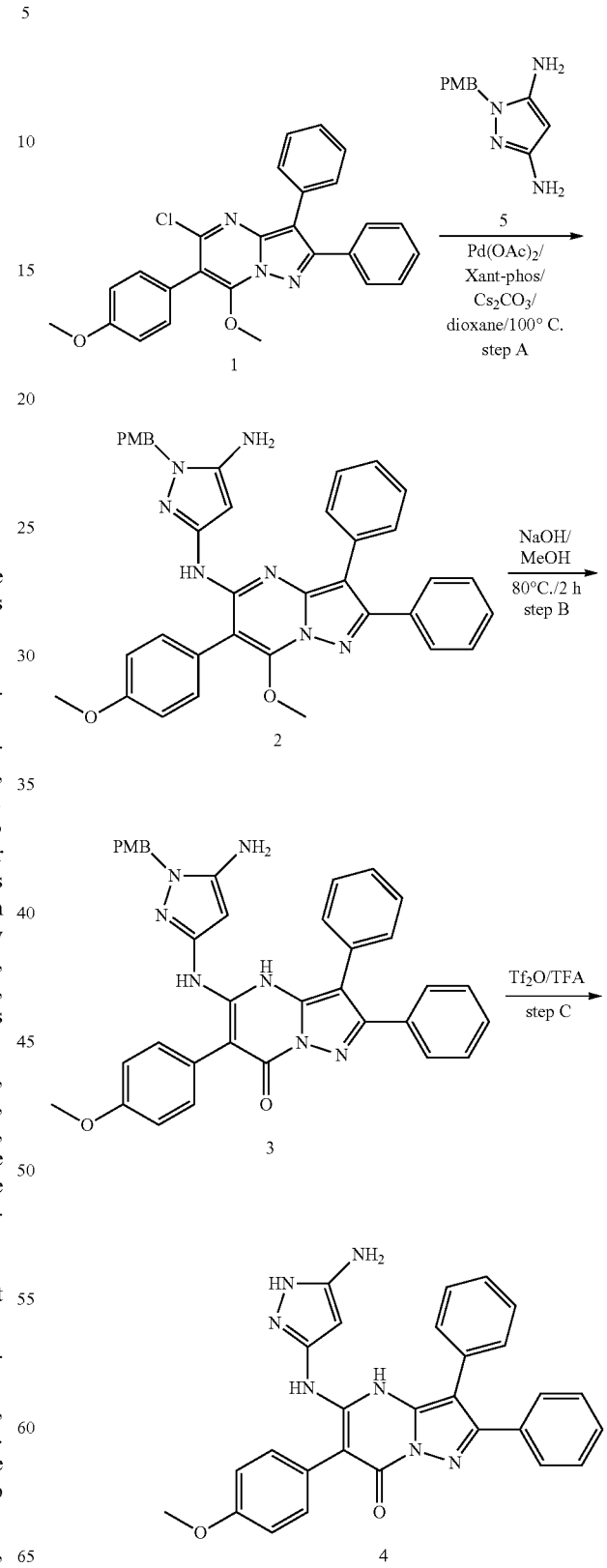

Step A: N3-(7-methoxy-6-(4-methoxyphenyl)-2,3-diphenylpyrazolo[1,5-a]pyrimidin-5-yl)-1-(4-methoxybenzyl)-1H-pyrazole-3,5-diamine Step C: 5-((5-amino-1H-pyrazol-3-yl)amino)-6-(4-methoxyphenyl)-2,3-diphenylpyrazolo[1,5-a]pyrimidin-7(4H)-one

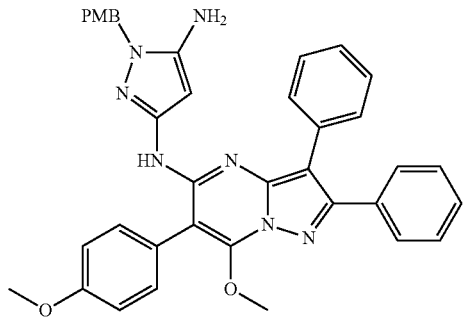

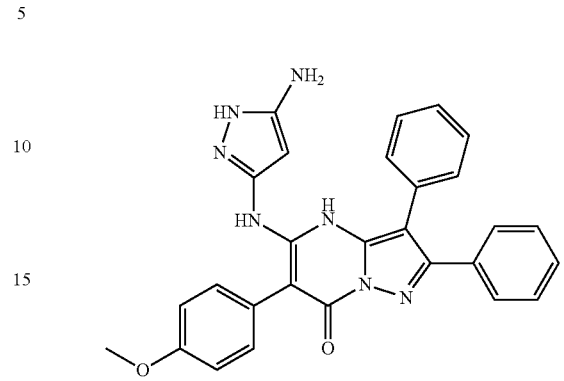

A suspension of 5-chloro-7-methoxy-6-(4-methoxyphenyl)-2,3-diphenylpyrazolo[1,5-a]-pyrimidine (300 mg, 0.68 mmol), 1-(4-methoxybenzyl)-1H-pyrazole-3,5-diamine (296 mg, 1.36 mmol, 2 eq.), Pd(OAc)$_2$ (30 mg, 0.14 mmol, 0.2 eq.), Xantphos (156 mg, 0.27 mmol, 0.4 eq.) and Cs$_2$CO$_3$ (441 mg, 1.36 mmol, 2 eq.) in 1.4-dioxane (20 mL) was stirred at 100° C. for 16 hour under N$_2$ atmosphere. The mixture was filtered through celite, and the filtrate was concentrated in vacuo. The residue was purified by flash chromatography (DCM:MeOH=50/1) to afford N3-(7-methoxy-6-(4-methoxyphenyl)-2,3-diphenylpyrazolo[15-a]pyrimidin-5-yl)-1-(4-methoxybenzyl)-1H-pyrazole-3,5-diamine (220 mg) as a white solid. LC-MS: m/z 625.5 (M+H)$^+$.

Step B: 5-((5-amino-1-(4-methoxybenzyl)-1H-pyrazol-3-yl)amino)-6-(4-methoxyphenyl)-2,3-diphenylpyrazolo[1,5-a]pyrimidin-7(4H)-one To a 5-((5-amino-1-(4-methoxybenzyl)-1H-pyrazol-3-yl)amino)-6-(4-methoxyphenyl)-2,3-diphenylpyrazolo[1,5-a]pyrimidin-7(4H)-one (20 mg, 0.03 mmol) in TFA (2 mL) was added Tf$_2$O (0.5 mL). The resultant mixture was stirred at rt for 4 h. Then the mixture was concentrated below 40° C. to give the title compound.

$^1$H NMR (DMSO-d$_6$): δ 13.94 (br. s., 1H), 11.27 (br. s., 1H), 8.67 (s, 1H), 7.44-7.56 (m, 4H), 7.31-7.40 (m, 6H), 7.21-7.30 (m, J=8.3 Hz, 2H), 6.95-7.06 (m, J=8.6 Hz, 2H), 5.25 (br. s., 2H), 5.13 (s, 1H), 3.82 (s, 3H). LC-MS: m/z 490.1 (M+H)$^+$.

Compound 187: 5-((1H-pyrazol-3-yl)amino)-2,3-diphenyl-6-(quinolin-6-yl)pyrazolo[1,5-a]pyrimidin-7(4H)-one

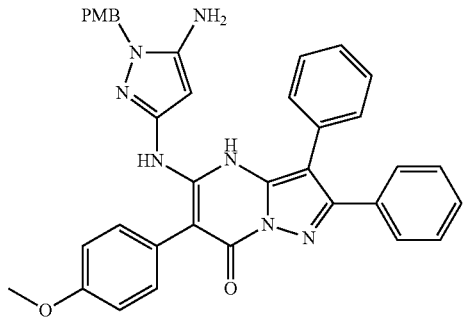

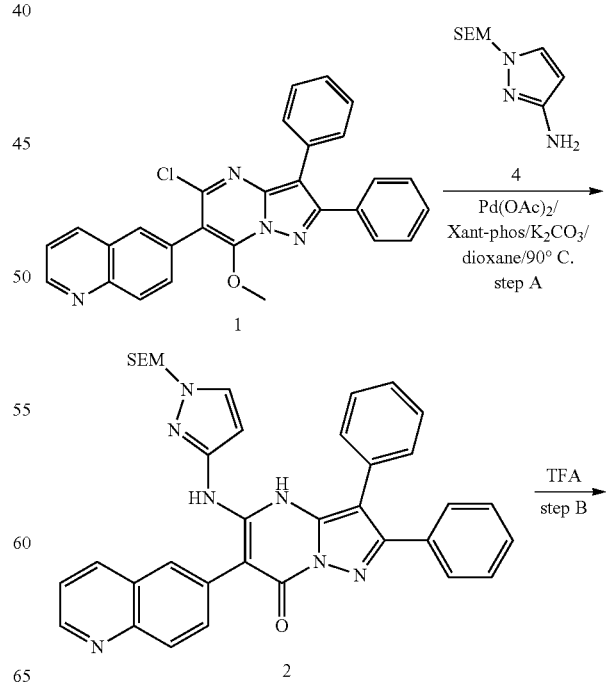

A solution of N3-(7-methoxy-6-(4-methoxyphenyl)-2,3-diphenylpyrazolo[1,5-a]pyrimidin-5-yl)-1-(4-methoxybenzyl)-1H-pyrazole-3,5-diamine (160 mg, 0.26 mmol) in MeOH (3 mL) was added 4N NaOH in MeOH (4 mL) and stirred at 80° C. for 2 hours. Solvent and volatile were removed in vacuo. The residue was partitioned between water (30 mL) and EA (50 mL). The EA layer was dried and concentrated to give 5-((5-amino-1-(4-methoxybenzyl)-1H-pyrazol-3-yl)amino)-6-(4-methoxyphenyl)-2,3-diphenylpyrazolo [1,5-a]pyrimidin-7(4H)-one (20 mg) as a white solid. LC-MS: m/z 610.5 (M+H)$^+$.

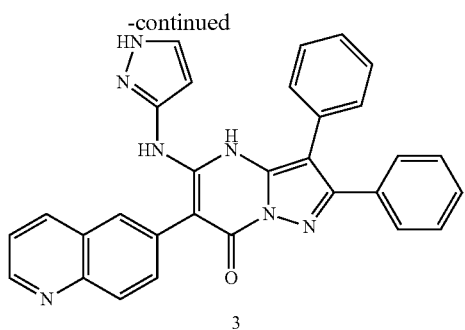

Step A: 2,3-diphenyl-6-(quinolin-6-yl)-5-((1-((2-(trimethylsilyl)ethoxy)methyl)-1H-pyrazol-3-yl)amino)pyrazolo[1,5-a]pyrimidin-7(4H)-one

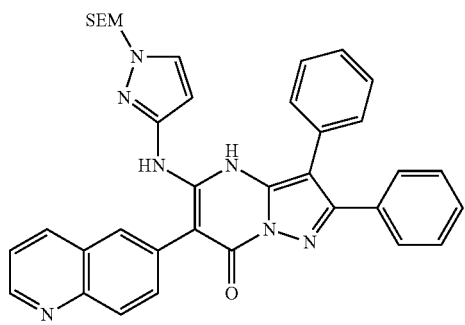 [SMILES: C[Si](C)(C)CCOCn1ccc(Nc2[nH]c3c(-c4ccccc4)c(-c4ccccc4)nn3c(=O)c2-c2ccc3ncccc3c2)n1]

A suspension of 6-(5-chloro-7-methoxy-2,3-diphenylpyrazolo[1,5-a]pyrimidin-6-yl)quinoline (300 mg, 0.65 mmol), 1-((2-(trimethylsilyl)ethoxy)methyl)-1H-pyrazol-3-amine (166 mg, 0.78 mmol, 1.2 eq.), Pd(OAc)$_2$ (30 mg, 0.13 mmol, 0.2 eq.), Xantphos (28 mg, 0.13 mmol, 0.2 eq.) and K$_2$CO$_3$ (147 g, 1.30 mmol, 2.0 eq.) in dioxane (10 mL) was stirred at 90° C. for 4 hour. The mixture was filtered through celite, and the filtrate was concentrated in vacuo. The residue was purified by flash chromatography (PE/EA/DCM=10/1/1) to afford 2,3-diphenyl-6-(quinolin-6-yl)-5-((1-((2-(trimethylsilyl)ethoxy)methyl)-1H-pyrazol-3-yl)amino) pyrazolo[1,5-a]pyrimidin-7(4H)-one (90 mg) as a white solid. LC-MS: m/z 625.9 (M+H)$^+$.

Step B: 5-((1H-pyrazol-3-yl)amino)-2,3-diphenyl-6-(quinolin-6-yl)pyrazolo[1,5-a]pyrimidin-7(4H)-one

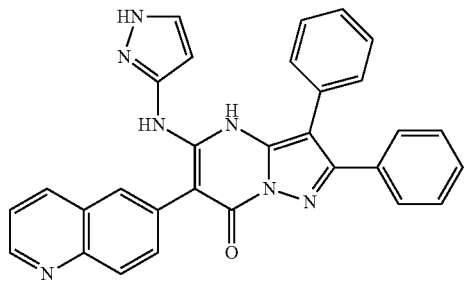 [SMILES: O=c1c(-c2ccc3ncccc3c2)c(Nc2cc[nH]n2)[nH]c2c(-c3ccccc3)c(-c3ccccc3)nn12]

A solution of 2,3-diphenyl-6-(quinolin-6-yl)-5-((1-((2-(trimethylsilyl)ethoxy)methyl)-1H-pyrazol-3-yl)amino) pyrazolo [1,5-a]pyrimidin-7(4H)-one (90 mg, 0.14 mmol) in TFA (8 mL) was stirred at rt for 1 hour. Solvent and volatile were removed in vacuo. The mixture was basified with ammonia to pH=8 and concentrated to give the crude product to afford the title compound.

$^1$H NMR (TFA-d): δ 9.32 (br. s., 1H), 9.25 (br. s., 1H), 8.66 (br. s., 1H), 8.57 (d, J=8.3 Hz, 1H), 8.43 (br. s., 1H), 8.25 (br. s., 1H), 7.80 (br. s., 2H), 7.64 (s, 3H), 7.68 (s, 2H), 7.57 (br. s., 4H), 6.27 (br. s., 1H). LC-MS: m/z 496.2 (M+H)$^+$.

Compound 188: 5-((5-methyl-1H-pyrazol-3-yl)amino)-2,3-diphenyl-6-(quinolin-6-yl)pyrazolo[1,5-a]pyrimidin-7(4H)-one

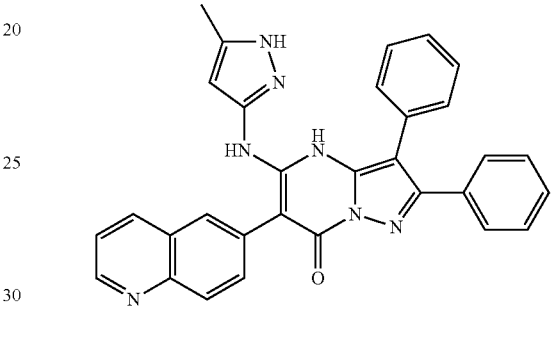

This compound was prepared according to the procedure for preparing compound 182 by using Intermediate 1 as 6-(5-chloro-7-methoxy-2,3-diphenylpyrazolo[1,5-a]pyrimidin-6-yl)quinoline and Intermediate 5 as 5-methyl-1-((2-(trimethylsilyl)ethoxy)methyl)-1H-pyrazol-3-amine in step A.

Step E stoichiometry: 6-(5-chloro-7-methoxy-2,3-diphenylpyrazolo[1,5-a]pyrimidin-6-yl)quinoline (200 mg, 0.432 mmol), 5-methyl-1-((2-(trimethylsilyl)ethoxy)methyl)-1H-pyrazol-3-amine (147 mg, 0.65 mmol), Pd(OAc)$_2$ (10 mg, 0.043 mmol), xantphos (50 mg, 0.086 mmol), Cs$_2$CO$_3$ (281 mg, 0.86 mmo) in dioxane (15 mL) under heating to 110° C. overnight under N$_2$. LC-MS: m/z 640.3 (M+H)$^+$.

Step F: To a solution of 5-((5-methyl-1-((2-(trimethylsilyl)ethoxy)methyl)-1H-pyrazol-3-yl)amino)-2,3-diphenyl-6-(quinolin-6-yl)pyrazolo[1,5-a]pyrimidin-7(4H)-one (40 mg, 0.63 mmol) in DCM (90 mL) was added TFA (3 mL). The reaction mixture was stirred for 30 mins at room temperature. The mixture was concentrated in vacuo. The residue was basified with ammonia (4 mL) and concentrated to give the desired product.

$^1$H NMR (DMSO-d$_6$): δ 13.65 (br. s., 1H), 12.35 (br. s., 1H), 9.15 (br. s., 1H), 8.94 (d, J=3.0 Hz, 1H), 8.42 (d, J=8.3 Hz, 1H), 8.10 (d, J=8.6 Hz, 1H), 8.02 (s, 1H), 7.77 (d, J=7.0 Hz, 1H), 7.48-7.59 (m, 4H), 7.26-7.47 (m, 5H), 5.74 (s, 1H), 2.18 (s, 3H). LC-MS: m/z 509.9 (M+H)$^+$.

Compound 189: 5-((1H-pyrazol-5-yl)amino)-3-(cyclohex-1-en-1-yl)-6-(4-methoxyphenyl)-2-phenyl pyrazolo[1,5-a]pyrimidin-7(4H)-one Step A: 3-(cyclohex-1-en-1-yl)-7-methoxy-6-(4-methoxyphenyl)-2-phenyl-N-(1-((2-(trimethylsilyl)ethoxy)methyl)-1H-pyrazol-3-yl)pyrazolo[1,5-a]pyrimidin-5-amine

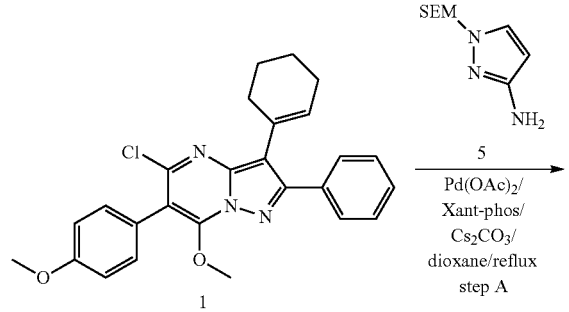

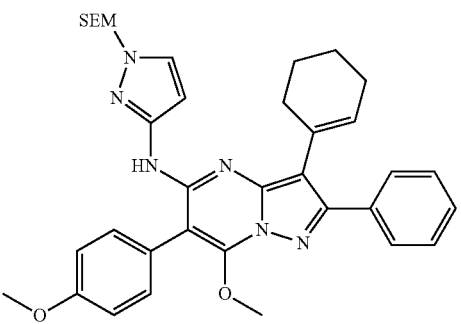 [SMILES: COc1ccc(-c2c(Nc3ccn(COCC[Si](C)(C)C)n3)nc3c(C4=CCCCC4)c(-c4ccccc4)nn3c2OC)cc1]

A mixture of 5-chloro-3-(cyclohex-1-en-1-yl)-7-methoxy-6-(4-methoxyphenyl)-2-phenylpyrazolo[1,5-a]pyrimidine (300 mg, 0.67 mmol), 1-((2-(trimethylsilyl)ethoxy)methyl)-1H-pyrazol-3-amine (430.8 mg, 2.02 mmol), palladium diacetate (30.2 mg, 0.13 mmol), Xantphos (116.8 mg, 0.20 mmol) and cesium carbonate (438.4 mg, 1.35 mmol) in 1,4-dioxane (6 mL) was reacted in microwave reactor at 100° C. under $N_2$ atmosphere for 45 minutes. After cooling to room temperature, the reaction mixture was diluted with DCM (100 mL), filtered with celite, washed with aqueous $NH_4Cl$ (30 mL) and saturated brine (30 mL), dried over anhydrous sodium sulfate, and concentrated. The residue was purified by flash column (petroleum ether/ethyl acetate=4:1) to obtain 3-(cyclohex-1-en-1-yl)-7-methoxy-6-(4-methoxyphenyl)-2-phenyl-N-(1-((2-(trimethylsilyl)ethoxy)methyl)-1H-pyrazol-3-yl)pyrazolo[1,5-a]pyrimidin-5-amine (220 mg) as a yellow solid. LC-MS: m/z 623.3 $(M+H)^+$.

Step B: 3-(cyclohex-1-en-1-yl)-6-(4-methoxyphenyl)-2-phenyl-5-((1-((2-(trimethylsilyl)ethoxy)methyl)-1H-pyrazol-3-yl)amino)pyrazolo[1,5-a]pyrimidin-7(4H)-one

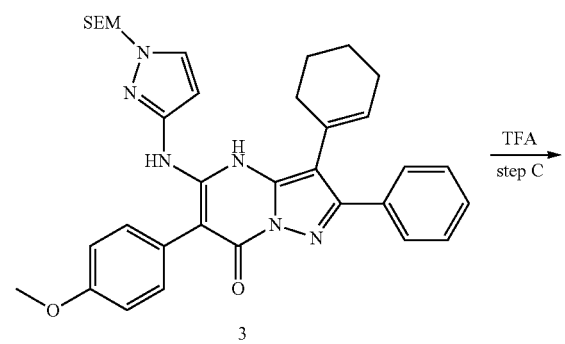

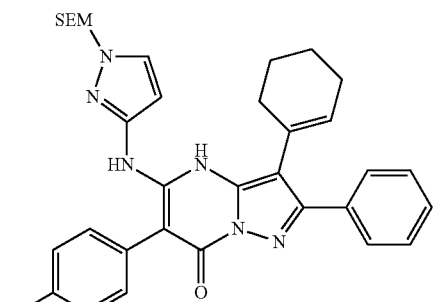

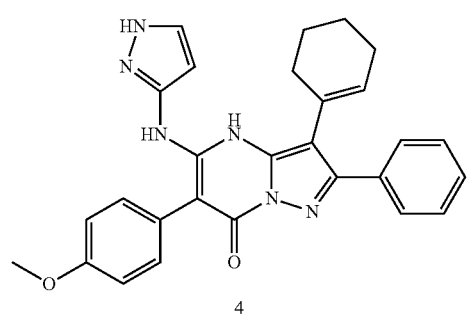

The solution of 3-(cyclohex-1-en-1-yl)-7-methoxy-6-(4-methoxyphenyl)-2-phenyl-N-(1-((2-(trimethylsilyl)ethoxy)methyl)-1H-pyrazol-3-yl)pyrazolo[1,5-a]pyrimidin-5-amine (220 mg, 0.35 mmol), sodium tert-butoxide (67.9 mg, 0.71 mmol) and water (3 drops) in 1,4-dioxane (8 mL) was reacted in microwave reactor at 100° C. for 1.5 hours. After cooling to room temperature, the mixture was diluted with DCM (100 mL), washed with water (25 mL) and brine (25 mL), dried over anhydrous sodium sulfate and concentrated. MeOH (4 mL) was added to the residue, and the precipitate was filtered, washed with MeOH (4 mL) to obtain 3-(cyclohex-1-en-1-yl)-6-(4-methoxyphenyl)-2-phenyl-5-((1-((2-(trimethylsilyl)ethoxy)methyl)-1H-pyrazol-3-yl)amino)pyrazolo[1,5-a]pyrimidin-7(4H)-one (130 mg) as a yellow solid. LC-MS: m/z 609.3 (M+H)+.

Step C: 5-((1H-pyrazol-5-yl)amino)-3-(cyclohex-1-en-1-yl)-6-(4-methoxyphenyl)-2-phenyl pyrazolo[1,5-a]pyrimidin-7(4H)-one

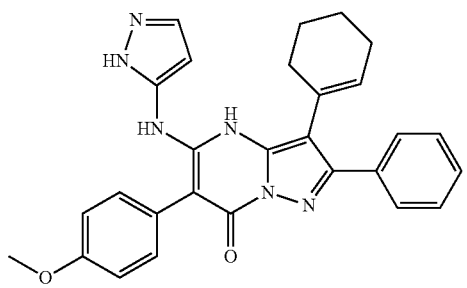 [SMILES: COc1ccc(-c2c(Nc3ccn[nH]3)[nH]c3c(C4=CCCCC4)c(-c4ccccc4)nn3c2=O)cc1]

The solution of 3-(cyclohex-1-en-1-yl)-6-(4-methoxyphenyl)-2-phenyl-5-((1-((2-(trimethylsilyl)ethoxy)methyl)-1H-pyrazol-3-yl)amino)pyrazolo[1,5-a]pyrimidin-7(4H)-one (130 mg, 0.21 mmol) in TFA/DCM (2 mL/1 mL) was stirred at room temperature for 4 hours to obtain 5-((1H-pyrazol-5-yl)amino)-3-(cyclohex-1-en-1-yl)-6-(4-methoxyphenyl)-2-phenylpyrazolo[1,5-a]pyrimidin-7(4H)-one.

$^1$H NMR (DMSO-$d_6$): δ 13.30 (s, 1H), 12.77 (br. s., 1H), 8.90 (s, 1H), 7.72 (d, J=7.3 Hz, 2H), 7.44-7.53 (m, 2H), 7.37-7.44 (m, 1H), 7.28 (d, J=8.6 Hz, 2H), 7.14 (s, 0.5H), 6.97-7.08 (m, 2.5H), 6.09 (s, 1H), 6.01 (br. s., 1H), 3.80-3.88 (m, 3H), 2.38 (br. s., 2H), 2.04 (br. s., 2H), 1.61-1.83 (m, 4H). LC-MS: m/z 479.1 (M+H)+.

Compound 190: 5-((1H-pyrazol-5-yl)amino)-3-(cyclohex-1-en-1-yl)-2-phenyl-6-(quinolin-6-yl)pyrazolo[1,5-a]pyrimidin-7(4H)-one

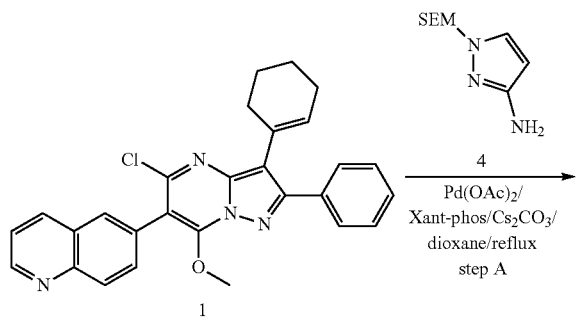

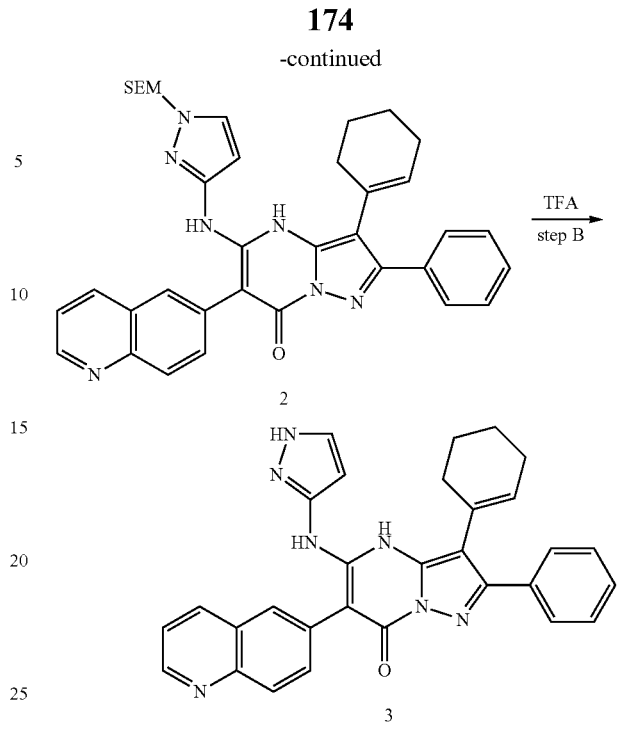

Step A: 3-(cyclohex-1-en-1-yl)-2-phenyl-6-(quinolin-6-yl)-5-((1-((2-(trimethylsilyl)ethoxy) methyl)-1H-pyrazol-3-yl)amino)pyrazolo[1,5-a]pyrimidin-7(4H)-one

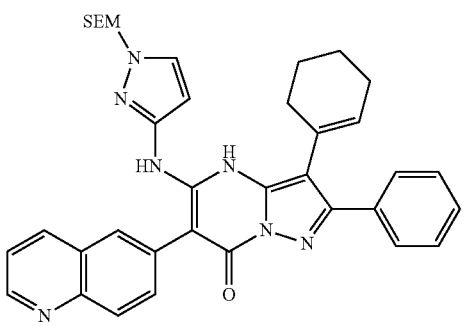 [SMILES: C[Si](C)(C)CCOCn1ccc(Nc2[nH]c3c(C4=CCCCC4)c(-c4ccccc4)nn3c(=O)c2-c2ccc3ncccc3c2)n1]

A suspension of 6-(5-chloro-3-(cyclohex-1-en-1-yl)-7-methoxy-2-phenylpyrazolo[1,5-a]pyrimidin-6-yl)quinoline (350 mg, 0.8 mmol) and 1-((2-(trimethylsilyl)ethoxy)methyl)-1H-pyrazol-3-amine (356.4 mg, 1.7 mmol) and Pd(OAc)$_2$ (206.3 mg, 0.9 mmol), Xantphos (579.9 mg, 1.0 mmol) and Cs$_2$CO$_3$ (597.7 mg, 1.8 mmol) in 1.4-dioxane (8 mL) was stirred and heated to reflux for 12 hours under N$_2$ atmosphere. The reaction was then cooled to r.t. and filtered with celite, diluted with DCM (60 mL), washed with saturated ammonium chloride (30 mL) and brine (30 mL), dried over anhydrous sodium sulfate and concentrated to dryness. The residue was purified by flash column (DCM:MeOH=25:1) to obtain 3-(cyclohex-1-en-1-yl)-2-phenyl-6-(quinolin-6-yl)-5-((1-((2-(trimethylsilyl)ethoxy)methyl)-1H-pyrazol-3-yl)amino)pyrazolo[1,5-a]pyrimidin-7(4H)-one (160 mg) as a brown solid. LC-MS: m/z 630.3 (M+H)+.

Step B: 5-((1H-pyrazol-5-yl)amino)-3-(cyclohex-1-en-1-yl)-2-phenyl-6-(quinolin-6-yl)pyrazolo[1,5-a]pyrimidin-7(4H)-one

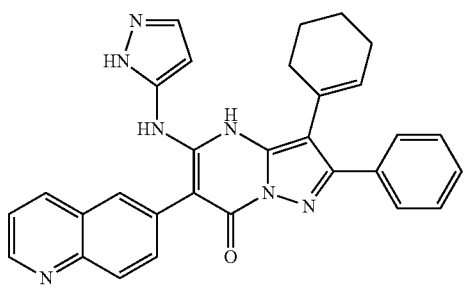 [SMILES: O=c1c(-c2ccc3ncccc3c2)c(Nc2ccn[nH]2)[nH]c2c(C3=CCCCC3)c(-c3ccccc3)nn12]

To the solution of 3-(cyclohex-1-en-1-yl)-2-phenyl-6-(quinolin-6-yl)-5-((1-((2-(trimethylsilyl)ethoxy)methyl)-1H-pyrazol-3-yl)amino)pyrazolo[1,5-a]pyrimidin-7(4H)-one (60 mg, 0.1 mmol) in DCM (1 mL) cooled to 0° C. was added TFA (2 mL) dropwise. The mixture was then stirred at room temperature for 2 h. The mixture was concentrated, and NH$_4$OH (5 mL) was added to obtain 5-((1H-pyrazol-5-yl)amino)-3-(cyclohex-1-en-1-yl)-2-phenyl-6-(quinolin-6-yl)pyrazolo[1,5-a]pyrimidin-7(4H)-one.

$^1$H NMR (DMSO-d$_6$): δ 13.37 (br. s., 1H), 9.13 (br. s., 1H), 8.88-8.98 (m, 1H), 8.41 (d, J=8.1 Hz, 1H), 8.09 (d, J=8.9 Hz, 1H), 8.00 (s, 1H), 7.67-7.82 (m, 4H), 7.33-7.63 (m, 5H), 6.02 (br. s., 2H), 2.38 (br. s., 2H), 2.09 (br. s., 2H), 1.72 (br. s., 4H). LC-MS: m/z 500.2 (M+H)$^+$.

Compound 191: 3-(cyclohex-1-en-1-yl)-2-phenyl-6-(quinoxalin-6-yl)-5-((1-((2-(trimethylsilyl)ethoxy)methyl)-1H-pyrazol-3-yl)amino)pyrazolo[1,5-a]pyrimidin-7(4H)-one

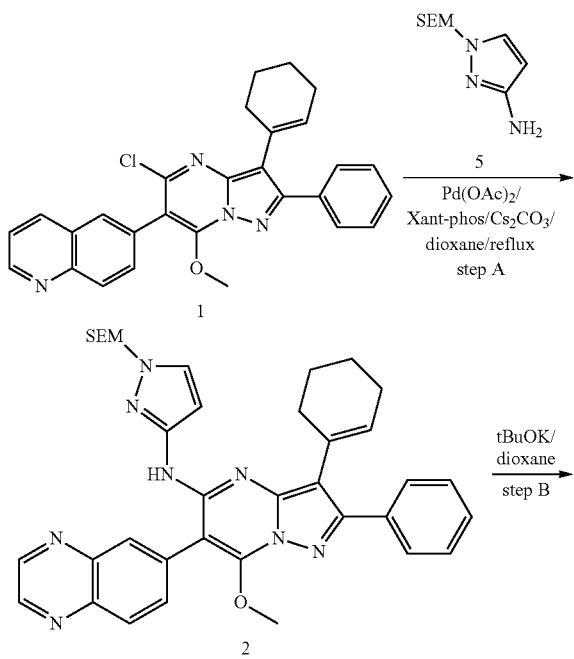

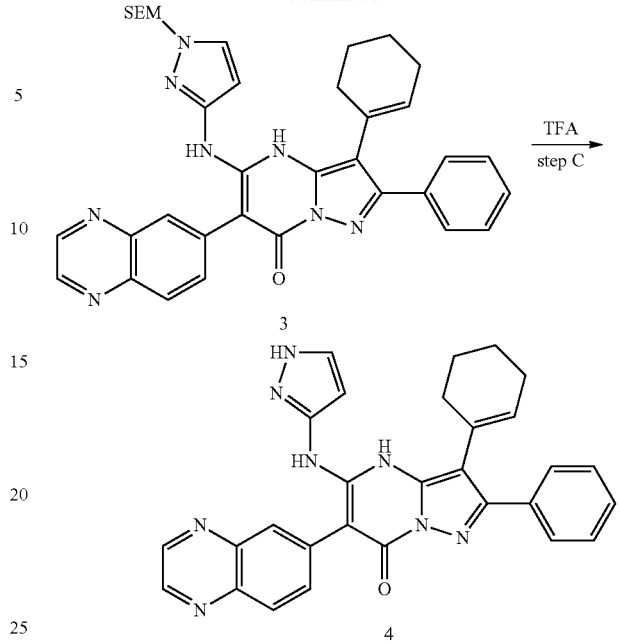

Step A: 3-(cyclohex-1-en-1-yl)-7-methoxy-2-phenyl-6-(quinoxalin-6-yl)-N-(1-((2-(trimethylsilyl)ethoxy)methyl)-1H-pyrazol-3-yl)pyrazolo[1,5-a]pyrimidin-5-amine

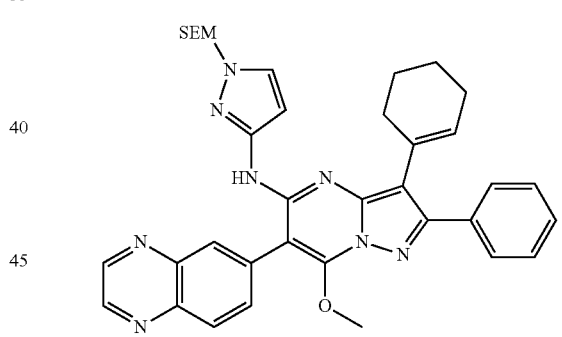

A mixture of 6-(5-chloro-3-(cyclohex-1-en-1-yl)-7-methoxy-2-phenylpyrazolo[1,5-a]pyrimidin-6-yl)quinoxaline (150 mg, 0.32 mmol), 1-((2-(trimethylsilyl)ethoxy)methyl)-1H-pyrazol-3-amine (137.0 mg, 0.65 mmol), palladium diacetate (14.5 mg, 0.05 mmol), Xantphos (55.5 mg, 0.10 mmol) and cesium carbonate (209.5 mg, 0.65 mmol) in 1,4-dioxane (6 mL) was reacted in microwave reactor at 100° C. under N$_2$ atmosphere for 45 minutes. After cooling to room temperature, the reaction mixture was diluted with DCM (100 mL), filtered with celite, washed with aqueous NH$_4$Cl (30 mL) and saturated brine (30 mL), dried over anhydrous sodium sulfate and concentrated. The residue was purified by prep-TLC (DCM/MeOH=30:1) to obtain 3-(cyclohex-1-en-1-yl)-7-methoxy-2-phenyl-6-(quinoxalin-6-yl)-N-(1-((2-(trimethylsilyl)ethoxy)methyl)-1H-pyrazol-3-yl)pyrazolo[1,5-a]pyrimidin-5-amine (80 mg) as a brown solid. LC-MS: m/z 645.3 (M+H)$^+$.

Step B: 3-(cyclohex-1-en-1-yl)-2-phenyl-6-(quinoxalin-6-yl)-5-((1-((2-(trimethylsilyl)ethoxy)methyl)-1H-pyrazol-3-yl)amino)pyrazolo[1,5-a]pyrimidin-7(4H)-one

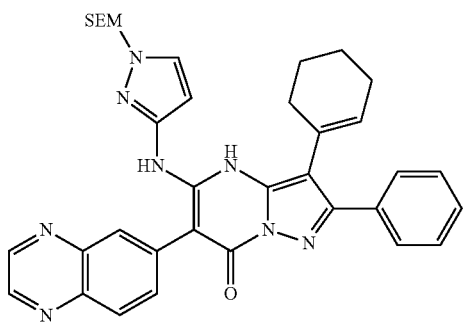 [SMILES: C[Si](C)(C)CCOCn1ccc(Nc2[nH]c3c(C4=CCCCC4)c(-c4ccccc4)nn3c(=O)c2-c2ccc3nccnc3c2)n1]

The solution of 3-(cyclohex-1-en-1-yl)-7-methoxy-2-phenyl-6-(quinoxalin-6-yl)-N-(1-((2-(trimethylsilyl)ethoxy)methyl)-1H-pyrazol-3-yl)pyrazolo[1,5-a]pyrimidin-5-amine (80 mg, 0.1 mmol) and $^{t}$BuOK (83.5 mg, 0.7 mmol) in dioxane/H$_2$O (6 mL/1 mL) was stirred at 100° C. for 8 h. After cooling to room temperature, the mixture was diluted with DCM (60 mL), washed with water (30 mL) and brine (20 mL), dried over Na$_2$SO$_4$ and concentrated to dryness. The residue was purified by prep-TLC (DCM:MeOH=15:1) to afford yellow solid (50 mg). LC-MS: m/z 631.3 (M+H)$^+$.

Step C: 5-((1H-pyrazol-5-yl)amino)-3-(cyclohex-1-en-1-yl)-2-phenyl-6-(quinoxalin-6-yl)pyrazolo[1,5-a]pyrimidin-7(4H)-one To the solution of 3-(cyclohex-1-en-1-yl)-2-phenyl-6-(quinoxalin-6-yl)-5-((1-((2-(trimethylsilyl)ethoxy)methyl)-1H-pyrazol-3-yl)amino)pyrazolo[1,5-a]pyrimidin-7(4H)-one (50 mg, 0.05 mmol) in DCM (1.5 mL) cooled to 0° C. was added TFA (1.5 mL) dropwise. The mixture was then stirred at room temperature for 2 h. The mixture was concentrated, and NH$_4$OH (5 mL) was added to obtain 5-((1H-pyrazol-5-yl)amino)-3-(cyclohex-1-en-1-yl)-2-phenyl-6-(quinoxalin-6-yl)pyrazolo[1,5-a]pyrimidin-7(4H)-one.

$^1$H NMR (DMSO-d$_6$): δ 13.38 (br. s., 1H), 12.83 (br. s., 1H), 9.29 (br. s., 1H), 8.97 (s, 2H), 8.17 (d, J=8.5 Hz, 1H), 8.11 (d, J=1.5 Hz, 1H), 7.89 (d, J=8.5 Hz, 1H), 7.74 (d, J=7.0 Hz, 3H), 7.45-7.52 (m, 2H), 7.37-7.44 (m, 1H), 6.04 (br. s., 1H), 5.97 (br. s., 1H), 2.39 (br. s., 2H), 2.03-2.11 (m, 2H), 1.72 (d, J=4.0 Hz, 5H). LC-MS: m/z 501.2 (M+H)$^+$.

Compound 192: 6-(4-methoxyphenyl)-2,3-diphenyl-5-(thiazol-4-ylamino)pyrazolo[1,5-a]pyrimidin-7(4H)-one

Step A: 7-methoxy-6-(4-methoxyphenyl)-2,3-diphenylpyrazolo[1,5-a]pyrimidin-5-amine

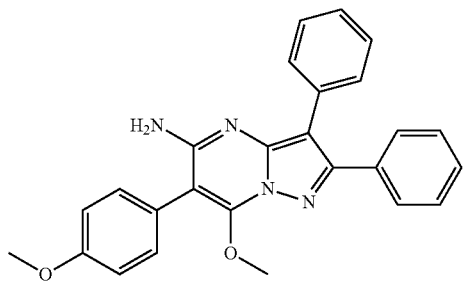 [SMILES: COc1ccc(-c2c(N)nc3c(-c4ccccc4)c(-c4ccccc4)nn3c2OC)cc1]

A suspension of Intermediate 1 (880 mg, 2 mmol), NH₃/dioxane (0.4N, 15 mL, 6.0 mmol, 3 eq) and tBu-Brettphos Pd G3 (540 mg, 0.4 mmol, 0.2 eq), tBuBrettphos (98 mg, 0.2 mmol, 0.1 eq), t-BuONa (580 mg, 6 mmol, 3.0 eq) and 1.4-dioxane (4 mL) in a 25 mL microwave vial under N₂ atmosphere. The vial was sealed and heated for 1 h at a constant temperature of 50° C. The reaction was then cooled to r.t. and filtered. The dark filtrate was concentrated in vacuum and purified by flash column chromatography silica gel (DCM/MeOH=20:1) to obtain the Intermediate 2 (400 mg).

$^1$H NMR (DMSO-d₆): δ 7.47-7.56 (m, 2H), 7.29-7.43 (m, 10H), 7.19-7.25 (m, 1H), 7.08 (d, J=8.8 Hz, 2H), 6.48-5.96 (s, 2H), 4.03 (s, 3H), 3.82 (s, 3H). LC-MS: m/z 423.2 (M+H)⁺.

Step B: N-(7-methoxy-6-(4-methoxyphenyl)-2,3-diphenylpyrazolo[1,5-a]pyrimidin-5-yl)thiazol-4-amine

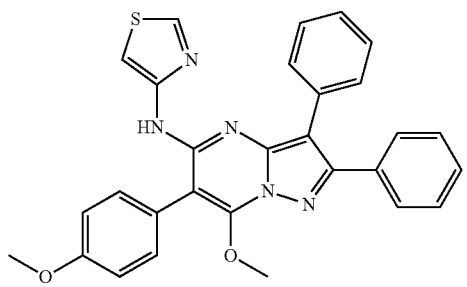 [SMILES: COc1ccc(-c2c(Nc3cscn3)nc3c(-c4ccccc4)c(-c4ccccc4)nn3c2OC)cc1]

A suspension of Intermediate 2 (84 mg, 0.2 mmol), 4-bromothiazole (164 mg, 1.0 mmol, 5 eq), tBuBrettphos Pd G3 (54 mg, 0.04 mmol, 0.2 eq), tBuBrettphos (9.8 mg, 0.02 mmol, 0.1 eq), t-BuONa (58 mg, 0.6 mmol, 3.0 eq) and 1.4-dioxane (2 mL) in a 10 mL microwave vial under N₂ atmosphere. The vial was sealed and heated for 1 h at a constant temperature of 80° C. The reaction was then cooled to r.t. and filtered. The dark filtrate was concentrated in vacuum and purified by flash column chromatography silica gel (DCM/MeOH=20:1) to give the Intermediate 3 (40 mg) as a white solid. LC-MS: m/z 406.1 (M+H)⁺.

Step C: 6-(4-methoxyphenyl)-2,3-diphenyl-5-(thiazol-4-ylamino)pyrazolo[1,5-a]pyrimidin-7(4H)-one A mixture of Intermediate 3 (40 mg, 0.08 mmol) in HCl/dioxane (5 mL, 1N) was stirred at RT for 1 h. The mixture was then concentrated under reduced pressure to afford the desired product 4.

$^1$H NMR (DMSO-d₆): δ 9.04 (d, J=2.4 Hz, 1H), 7.48-7.59 (m, 4H), 7.35-7.44 (m, 6H), 7.28-7.34 (m, J=8.8 Hz, 2H), 7.12 (d, J=2.4 Hz, 1H), 7.01-7.09 (m, J=9.2 Hz, 2H), 3.83 (s, 3H). LC-MS: m/z 492.1 (M+H)⁺.

Compound 152: 5-([1,2,4]triazolo[1,5-c]pyrimidin-7-ylamino)-6-(4-methoxyphenyl)-2,3-diphenylpyrazolo[1,5-a]pyrimidin-7(4H)-one

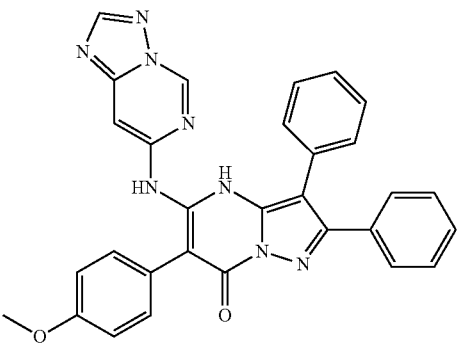 [SMILES: COc1ccc(-c2c(Nc3cc4ncnn4cn3)[nH]c3c(-c4ccccc4)c(-c4ccccc4)nn3c2=O)cc1]

This compound was prepared according to the procedures for preparing compound 192, step B-C, starting from 7-methoxy-6-(4-methoxyphenyl)-2,3-diphenylpyrazolo[1,5-a]pyrimidin-5-amine.

Step B stoichiometry: 7-methoxy-6-(4-methoxyphenyl)-2,3-diphenylpyrazolo[1,5-a]pyrimidin-5-amine (210 mg, 0.5 mmol), 7-chloro-[1,2,4]triazolo[1,5-c]pyrimidine (135 mg, 0.9 mmol), Pd(OAc)₂ (62 mg, 0.25 mmol, 0.5 eq.), xantphos (310 mg, 0.5 mmol, 1 eq.), and Cs₂CO₃ (500 mg, 1.5 mmol, 3 eq.) in 1,4-dioxane (15 mL) under heating at 100° C. through microwave irradiation for 1 hour under N₂ atmosphere. LC-MS: m/z 541.2 (M+H)⁺.

Step C: The solution of N-(7-methoxy-6-(4-methoxyphenyl)-2,3-diphenylpyrazolo[1, 5-a]pyrimidin-5-yl)-[1,2,4]triazolo[1,5-c]pyrimidin-7-amine (100 mg, 0.19 mmol) in HCl-1,4-dioxane (15 mL) was stirred at r.t. for 3 h. Solvent and volatile were removed in vacuo. The residue was dissolved in DCM (5 mL) and treated with saturated NaHCO₃. The organic phase was separated and washed with brine, dried over anhydrous Na₂SO₄ and concentrated in vacuo to afford the title compound.

$^1$H NMR (DMSO-d₆): δ 12.73 (br. s., 1H), 9.59 (br. s., 1H), 9.33 (br. s., 1H), 8.47 (s, 1H), 7.43-7.65 (m, 5H), 7.24-7.43 (m, 7H), 7.12 (s., 1H), 6.96 (d, J=8.2 Hz, 2H), 3.76 (s, 3H). LC-MS: m/z 527.2 (M+H)⁺.

Compound 193: 5-((1H-pyrazol-3-yl)amino)-6-(4-hydroxyphenyl)-2,3-diphenylpyrazolo[1,5-a]pyrimidin-7(4H)-one

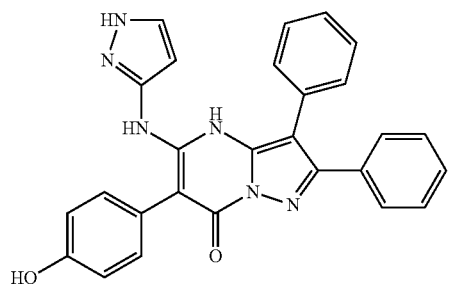 [SMILES: O=c1c(-c2ccc(O)cc2)c(Nc2cc[nH]n2)[nH]c2c(-c3ccccc3)c(-c3ccccc3)nn12]

To a solution of 5-((1H-pyrazol-3-yl)amino)-6-(4-methoxyphenyl)-2,3-diphenylpyrazolo[1,5-a]pyrimidin-7(4H)-one (Compound 182, 50 mg, 0.11 mmol) in anhydrous DCM (5 mL) was added a solution of BBr$_3$ (40 mg, 0.16 mmol, 1.5 eq) in DCM (0.5 mL) at −78° C. The reaction mixture was stirred at 0° C. for 2 h. The suspension was quenched with MeOH at −78° C. and extracted with EA. The combined organic phase was washed with water and brine, dried over anhydrous Na$_2$SO$_4$, filtered, and concentrated under reduced pressure to afford the desired product 5-((1H-pyrazol-3-yl)amino)-6-(4-hydroxyphenyl)-2,3-diphenylpyrazolo[1,5-a]pyrimidin-7(4H)-one.

$^1$H NMR (DMSO-d$_6$): δ 13.45 (s, 1H), 12.66 (s, 1H), 9.48 (s, 1H), 8.89 (s, 1H), 7.70 (s, 1H), 7.51 (d, J=7.2 Hz, 4H), 7.38 (t, J=7.6 Hz, 6H), 7.16 (d, J=8.4 Hz, 2H), 6.68 (d, J=8.4 Hz, 2H), 6.08 (s, 1H). LC-MS: m/z 461.7 (M+H)$^+$.

Compound 194: 3-cyclohexenyl-6-(4-hydroxyphenyl)-2-phenyl-5-(pyrazin-2-ylamino)pyrazolo[1,5-a]pyrimidin-7(4H)-one

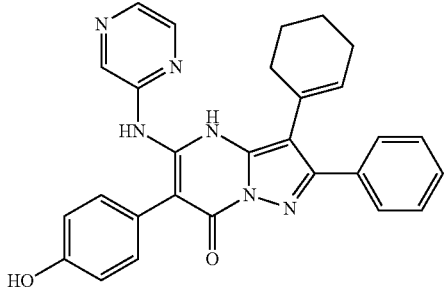 [SMILES: O=c1c(-c2ccc(O)cc2)c(Nc2cnccn2)[nH]c2c(C3=CCCCC3)c(-c3ccccc3)nn12]

A mixture of 3-cyclohexenyl-6-(4-methoxyphenyl)-2-phenyl-5-(pyrazin-2-ylamino) pyrazolo[1,5-a]pyrimidin-7(4H)-one (Compound 158, 100 mg, 0.204 mmol) and BBr$_3$ (1M in dichloromethane, 5 mL) was stirred at room temperature for 1 h. The mixture was quenched with methanol at 0° C. to afford 3-cyclohexenyl-6-(4-hydroxyphenyl)-2-phenyl-5-(pyrazin-2-ylamino)pyrazolo[1,5-a]pyrimidin-7(4H)-one.

$^1$H NMR (DMSO-d$_6$): δ 13.87 (s, 1H), 9.52 (s, 1H), 9.28 (s, 1H), 8.62 (s, 1H), 8.24 (d, J=2.75 Hz, 1H), 8.20 (s, 1H), 7.73 (d, J=7.02 Hz, 2H), 7.39-7.52 (m, 3H), 7.20 (d, J=8.54 Hz, 2H), 6.85 (d, J=8.24 Hz, 2H), 6.04 (br. s., 1H), 2.33 (br. s., 2H), 2.04 (br. s., 2H), 1.59-1.77 (m, 4H). LC-MS: m/z 477.2 (M+H)$^+$.

Compound 195: 5-((1H-1,2,4-triazol-3-yl)amino)-6-(4-hydroxyphenyl)-2,3-diphenylpyrazolo[1,5-a]pyrimidin-7(4H)-one

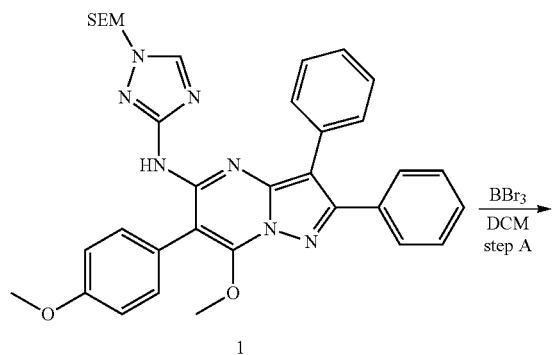

Intermediate 1 was prepared according to the procedure for preparing compound 101 (step A-E) by using Intermediate 9 as 1-((2-(trimethylsilyl)ethoxy)methyl)-1H-1,2,4-triazol-3-amine in step E. LC-MS: m/z 620.3 (M+H)$^+$.

Step A: To the solution of 7-methoxy-6-(4-methoxyphenyl)-2,3-diphenyl-N-(1-((2-(trimethylsilyl)ethoxy)methyl)-1H-1,2,4-triazol-3-yl)pyrazolo[1,5-a]pyrimidin-5-amine 1 (80 mg, 0.1 mmol) in DCM (2 mL) cooled to 0° C. was added BBr$_3$ (1.0 M in DCM, 1.5 mL) dropwise. The mixture was then stirred at 0° C. for 2 h. The reaction was quenched by carefully adding MeOH and concentrated in vacuo to give the product.

$^1$H NMR (DMSO-d$_6$): δ 14.10 (br. s., 1H), 13.12 (br. s., 1H), 9.51 (br. s., 1H), 9.00 (br. s., 1H), 8.54 (br. s., 1H), 7.46-7.59 (m, 4H), 7.29-7.45 (m, 6H), 7.18 (d, J=8.1 Hz, 2H), 6.88 (d, J=8.3 Hz, 2H). LC-MS: m/z 462.3 (M+H)$^+$.

Compound 196: 6-(2-methylbenzo[d]thiazol-6-yl)-2,3-diphenyl-5-(pyridin-2-ylamino)pyrazolo[1,5-a]pyrimidin-7(4H)-one

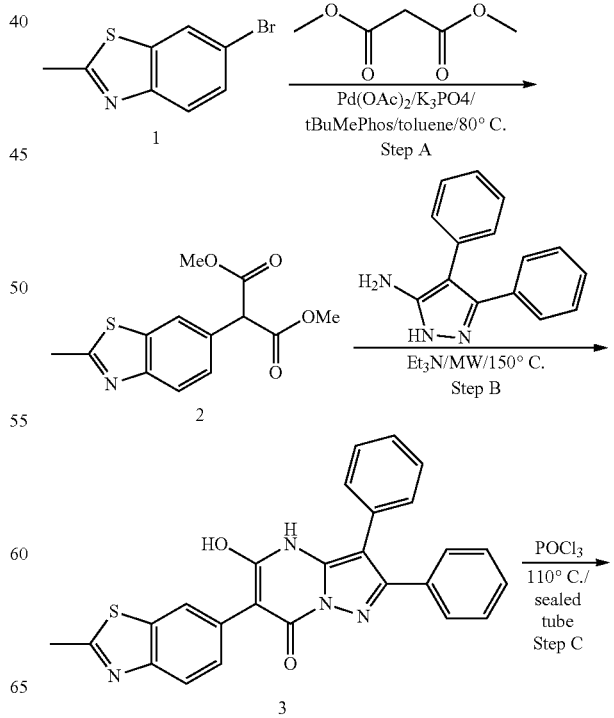

-continued

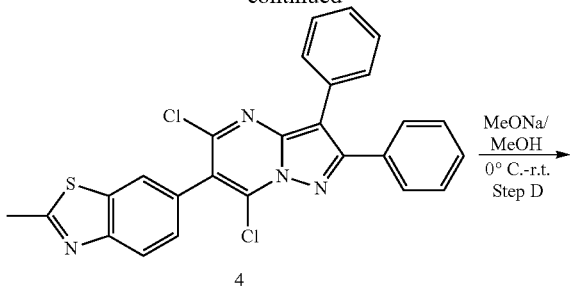

4

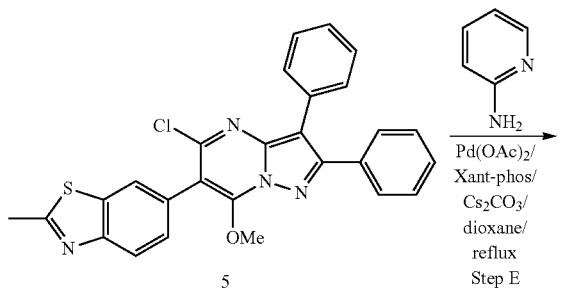

5

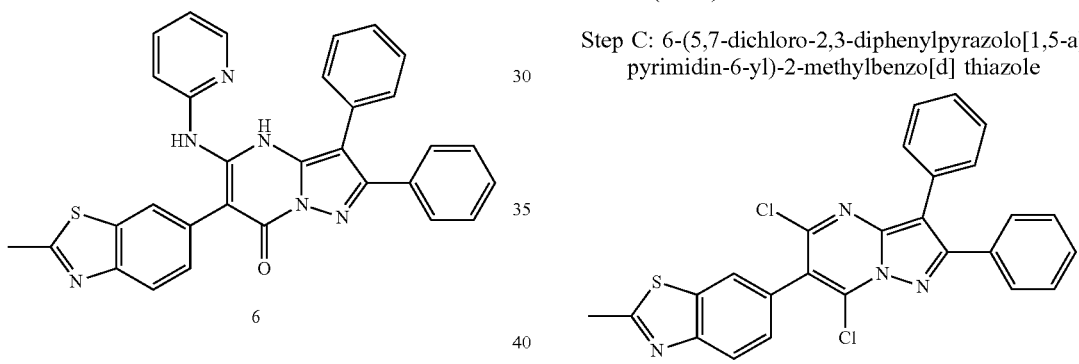

6

Step A: dimethyl 2-(2-methylbenzo[d]thiazol-6-yl)malonate

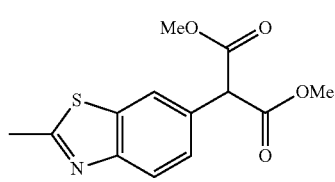 [SMILES: COC(=O)C(C(=O)OC)c1ccc2nc(C)sc2c1]

A mixture of 6-bromo-2-methylbenzo[d]thiazole (4.5 g, 19.7 mmol), dimethyl malonate (5.2 g, 39.4 mmol), Pd(OAc)₂ (882 mg, 3.94 mmol), t-BuMePhos (2.45 g, 7.88 mmol), and K₃PO₄ (9.5 g, 45.3 mmol) in 100 mL of anhydrous toluene was stirred at 80° C. under N₂ atmosphere for 16 h. The mixture was filtered and concentrated. The residue was purified by silica gel column (PE:EA=5:1) to afford Intermediate 2 as white solid (3.6 g).

¹H NMR (CHLOROFORM-d): δ 7.82-8.04 (m, 2H), 7.48 (dd, J=8.3, 1.9 Hz, 1H), 4.79 (s, 1H), 3.79 (s, 7H), 2.86 (s, 3H). LC-MS: m/z 280.5 (M+H)⁺.

Step B: 5-hydroxy-6-(2-methylbenzo[d]thiazol-6-yl)-2,3-diphenylpyrazolo[1,5-a]pyrimidin-7(4H)-one

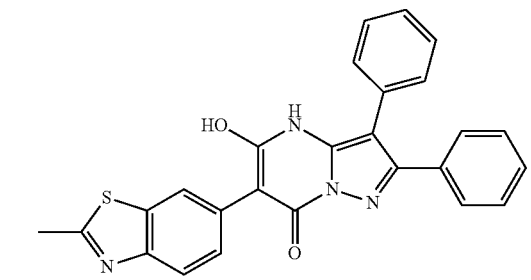 [SMILES: Cc1nc2ccc(-c3c(O)[nH]c4c(-c5ccccc5)c(-c5ccccc5)nn4c3=O)cc2s1]

A mixture of dimethyl 2-(2-methylbenzo[d]thiazol-6-yl)malonate (3 g, 10.7 mmol) and 3,4-diphenyl-1H-pyrazol-5-amine (2.1 g, 8.9 mmol) in TEA (20 mL) was stirred at 150° C. for 4 h. The mixture was then cooled to r.t. and filtered. The precipitates were suspended in a mixed solution of 2 mL THF and 20 mL HCl (1M) and stirred at r.t. for 0.5 h. The solid was filtered and washed with EA (10 mL) to give the desired product as a white solid (2.7 g) which was directly used to the next step without further purification. LC-MS: m/z 451.2 (M+H)⁺.

Step C: 6-(5,7-dichloro-2,3-diphenylpyrazolo[1,5-a]pyrimidin-6-yl)-2-methylbenzo[d] thiazole A mixture of Intermediate 3 (2.7 g, 6 mmol) in POCl₃ (20 mL) was stirred at 120° C. overnight in a sealed tube. The mixture was concentrated. The residue was basified with NaHCO₃ solution to PH=7, extracted with DCM (10 mL×3), dried, concentrated and purified by silica gel column (PE:EA=3:1) to give Intermediate 4 (2.1 g) as yellow solid. LC-MS: m/z 487.3 (M+H)⁺.

Step D: 6-(5-chloro-7-methoxy-2,3-diphenylpyrazolo[1,5-a]pyrimidin-6-yl)-2-methylbenzo[d] thiazole

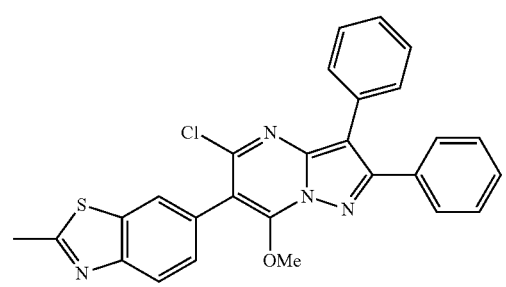 [SMILES: COc1c(-c2ccc3nc(C)sc3c2)c(Cl)nc2c(-c3ccccc3)c(-c3ccccc3)nn12]

The Intermediate 4 (2.1 g, 4.3 mmol) was dissolved in DCM (10 mL) and MeOH (20 mL) at 0° C. NaOMe (464 mg, 8.6 mmol) in MeOH (5 mL) was added dropwise and stirred on for 16 h at r.t. The mixture was concentrated. The residue was purified by silica gel column (PE:EA=5:1) to give the desired product 5 (1.6 g) as white solid.

¹H NMR (CHLOROFORM-d): δ 8.07 (d, J=8.2 Hz, 1H), 7.86 (d, J=1.2 Hz, 1H), 7.66 (dd, J=7.0, 2.4 Hz, 2H), 7.54 (d, J=7.0 Hz, 2H), 7.48 (dd, J=8.5, 1.5 Hz, 1H), 7.35-7.43 (m, 5H), 7.32 (d, J=7.3 Hz, 1H), 4.19 (s, 3H), 2.90 (s, 3H). LC-MS: m/z 483.6 (M+H)⁺.

Step E: 6-(2-methylbenzo[d]thiazol-6-yl)-2,3-diphenyl-5-(pyridin-2-ylamino)pyrazolo[1,5-a] pyrimidin-7(4H)-one

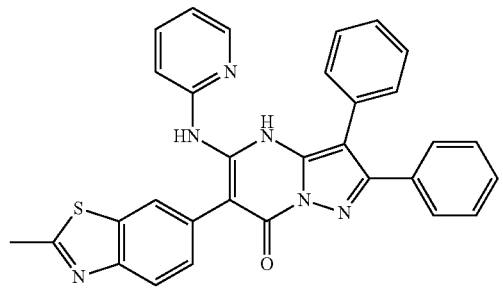 [SMILES: Cc1nc2ccc(-c3c(Nc4ccccn4)[nH]c4c(-c5ccccc5)c(-c5ccccc5)nn4c3=O)cc2s1]

A suspension of Intermediate 5 (482 g, 1 mmol), pyrazin-2-amine (94 mg, 1 mmol), Pd(OAc)₂ (42.2 mg, 0.2 mmol), Xantphos (23.1 mg, 0.4 mmol) and Cs₂CO₃ (652 mg, 2 mmol) in 1.4-dioxane (10 mL) was stirred and heated to reflux for 16 hours under N₂ atmosphere. The reaction was monitored by LC-MS until the complete conversion of the starting material. The reaction mixture was then cooled to r.t. and filtered. The dark filtrate was concentrated in vacuo to obtain the title compound 6.

¹H NMR (CHLOROFORM-d): δ 15.25 (s, 1H), 8.05 (d, J=4.0 Hz, 1H), 7.92-8.01 (m, 2H), 7.60-7.70 (m, 4H), 7.45-7.53 (m, 5H), 7.39 (dd, J=6.1, 2.4 Hz, 1H), 7.28 (d, J=4.0 Hz, 3H), 6.97 (dd, J=7.2, 5.0 Hz, 2H), 2.71 (s, 3H). LC-MS: m/z 527.5 (M+H)⁺.

Compound 197: 6-(3,4-dihydro-2H-benzo[b][1,4]oxazin-6-yl)-2,3-diphenyl-5-(pyridin-2-ylamino)pyrazolo[1,5-a]pyrimidin-7(4H)-one

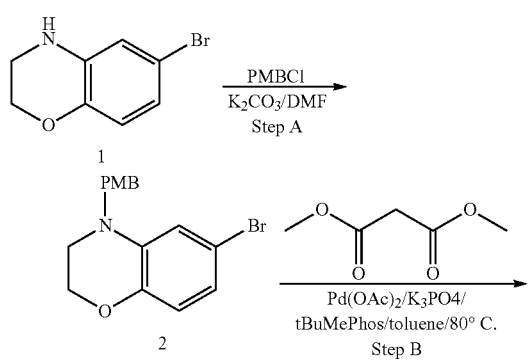

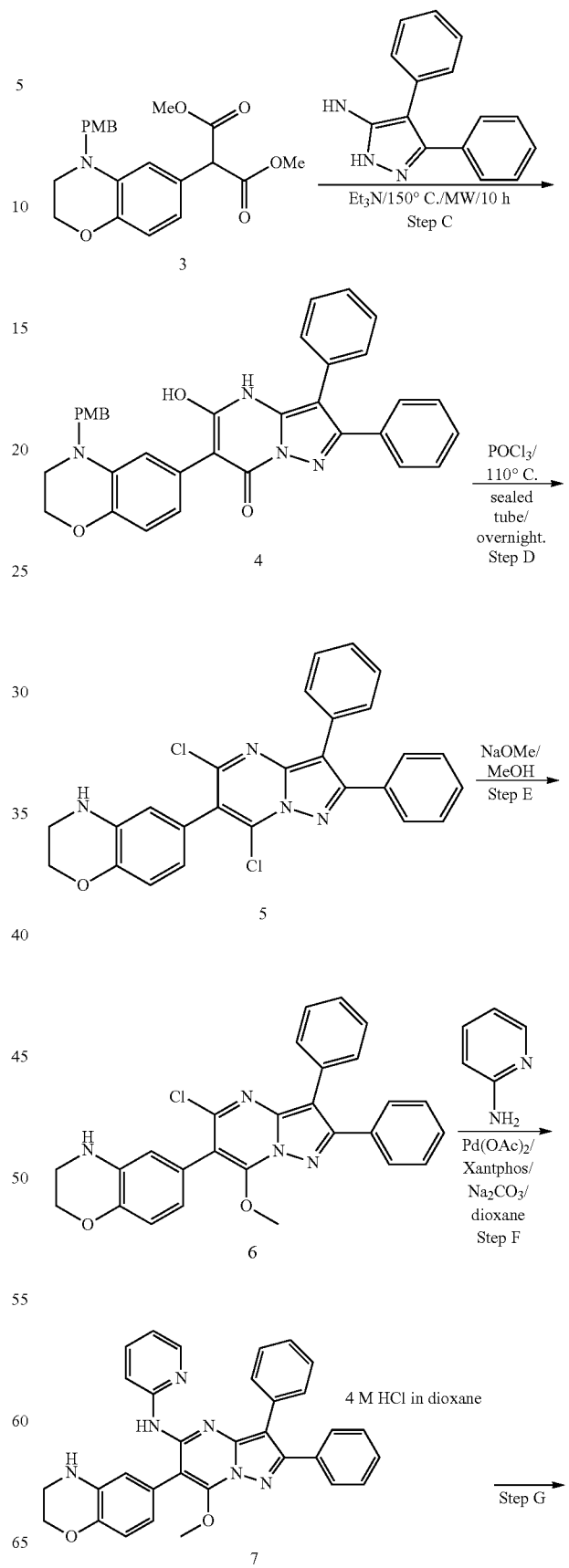

-continued

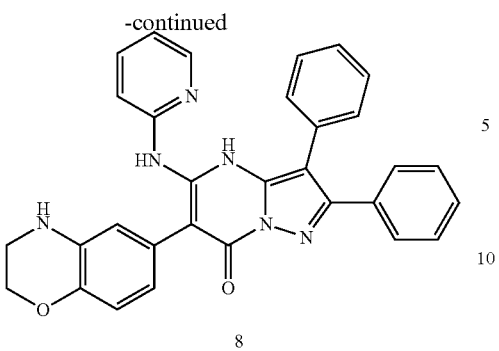

8

Step A: 6-bromo-4-(4-methoxybenzyl)-3,4-dihydro-2H-benzo[b][1,4]oxazine

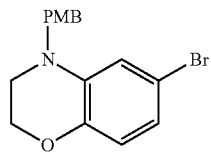

To the mixture of 6-bromo-3,4-dihydro-2H-benzo[b][1,4]oxazine (10 g, 47 mmol) and K₂CO₃ (13 g, 94 mmol) in DMF (100 mL). was added 1-(chloromethyl)-4-methoxybenzene (8.8 g, 56 mmol). The mixture was stirred at r.t. for 16 h. The mixture was poured into water (30 mL) and extracted with EA (30 Ml×3). The combined organic layers were dried, concentrated and purified by silica gel column (PE:EA=5:1) to give the desired product (1 g) as a white solid.

$^1$H NMR (CHLOROFORM-d): δ 7.12-7.20 (m, J=8.5 Hz, 2H), 6.84-6.90 (m, 2H), 6.80 (d, J=2.1 Hz, 1H), 6.61-6.73 (m, 2H), 4.32 (s, 2H), 4.15-4.20 (m, 2H), 3.76-3.80 (m, 3H), 3.22-3.30 (m, 2H). LC-MS: m/z 334.5 (M+H)⁺.

Step B: dimethyl 2-(4-(4-methoxybenzyl)-3,4-dihydro-2H-benzo[b][1,4]oxazin-6-yl) malonate

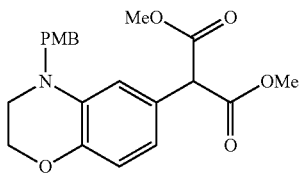

A mixture of Intermediate 2 (5.5 g, 16.5 mmol), dimethyl malonate (2.6 g, 19.8 mmol) Pd(OAc)₂ (370 mg, 1.65 mmol), t-BuMePhos (1.96 g, 3.63 mmol), and K₃PO₄(8 g, 37.95 mmol) in 30 mL of anhydrous toluene was stirred at 80° C. under N₂ atmosphere for 16 h. The mixture was filtered and concentrated. The residue was purified by silica gel column (PE:EA=4:1) to afford Intermediate 3 (5.7 g) as a white solid.

$^1$H NMR (CHLOROFORM-d): δ 7.18-7.24 (m, J=8.9 Hz, 2H), 6.83-6.89 (m, J=8.5 Hz, 2H), 6.73-6.79 (m, 2H), 6.62 (d, J=10.1 Hz, 1H), 4.48 (s, 1H), 4.38 (s, 2H), 4.20-4.26 (m, 2H), 3.79 (s, 3H), 3.69 (s, 6H), 3.24-3.31 (m, 2H). LC-MS: m/z 386.5 (M+H)⁺.

Step C: 5-hydroxy-6-(4-(4-methoxybenzyl)-3,4-dihydro-2H-benzo[b][1,4]oxazin-6-yl)-2,3-diphenylpyrazolo[1,5-a]pyrimidin-7(4H)-one

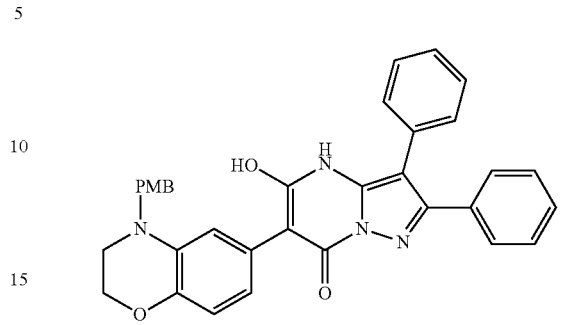

A mixture of Intermediate 3 (1.5 g, 3.8 mmol) and 3,4-diphenyl-1H-pyrazol-5-amine (760 mg, 3.2 mmol) in TEA (20 mL) was stirred at 150° C. for 4 h. The mixture was then cooled to r.t. and filtered. The filter cake was suspended in a mixed solution of 2 mL THF and 20 mL HCl (1M) and stirred at r.t. for 0.5 h. The precipitate was filtered and washed with EA (10 mL) to give the product (1.3 g) as a white solid which was directly used to the next step without further purification. LC-MS: m/z 557.2 (M+H)⁺.

Step D: 6-(5,7-dichloro-2,3-diphenylpyrazolo[1,5-a]pyrimidin-6-yl)-3,4-dihydro-2H-benzo[b][1,4]oxazine

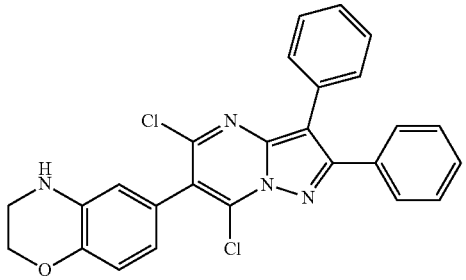 [SMILES: Clc1nc2c(-c3ccccc3)c(-c3ccccc3)nn2c(Cl)c1-c1ccc2c(c1)NCCO2]

The Intermediate 4 (1.3 g, 2.3 mmol) was dissolved in POCl₃ (15 mL) and stirred at 120° C. overnight in a sealed tube. The mixture was concentrated and basified with NaHCO₃ solution to PH=7. The resultant mixture was extracted with DCM (10 mL×3), dried, and concentrated to give crude Intermediate 5 (2.1 g) as a yellow solid. LC-MS: m/z 473.3 (M+H)⁺.

Step E: 6-(5-chloro-7-methoxy-2,3-diphenylpyrazolo[1,5-a]pyrimidin-6-yl)-3,4-dihydro-2H-benzo[b][1,4]oxazine

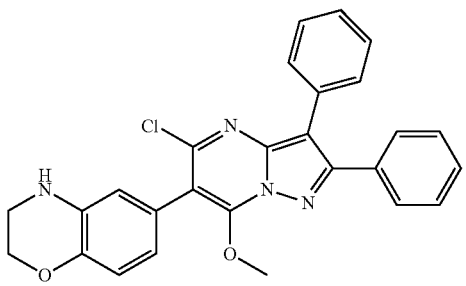 [SMILES: COc1c(-c2ccc3c(c2)NCCO3)c(Cl)nc2c(-c3ccccc3)c(-c3ccccc3)nn12]

The Intermediate 5 (500 mg, 1.06 mmol) was dissolved in DCM (5 mL) and MeOH (10 mL) at 0° C. NaOMe (114 mg, 2.1 mmol) in MeOH (5 mL) was added dropwise and stirred on for 16 h at r.t. The mixture was concentrated and purified by silica gel column (PE:EA=6:1) to give the desired product (230 mg) as a white solid.

$^1$H NMR (CHLOROFORM-d): δ 7.64-7.71 (m, 2H), 7.51-7.59 (m, 2H), 7.36-7.44 (m, 5H), 7.32 (d, J=7.3 Hz, 1H), 6.91 (d, J=8.1 Hz, 1H), 6.64-6.75 (m, 2H), 4.32-4.40 (m, 2H), 4.15-4.19 (m, 3H), 3.48-3.55 (m, 2H). LC-MS: m/z 469.4 (M+H)$^+$.

Step F: 6-(3,4-dihydro-2H-benzo[b][1,4]oxazin-6-yl)-7-methoxy-2,3-diphenyl-N-(pyridin-2-yl)pyrazolo[1,5-a]pyrimidin-5-amine

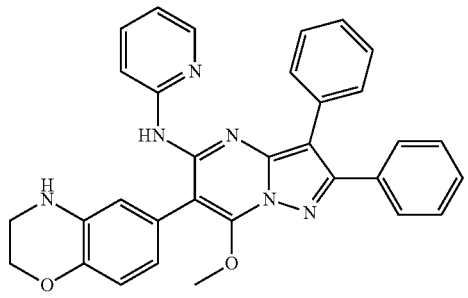 [SMILES: COc1c(-c2ccc3c(c2)NCCO3)c(Nc2ccccn2)nc2c(-c3ccccc3)c(-c3ccccc3)nn12]

A suspension of Intermediate 6 (200 mg, 0.43 mmol), pyrazin-2-amine (48 mg, 0.51 mmol), Pd(OAc)$_2$ (9.6 mg, 0.043 mmol), Xantphos (49.6 mg, 0.086 mmol) and Cs$_2$CO$_3$ (280 mg, 0.86 mmol) in 1.4-dioxane (10 mL) was heated to reflux for 16 hours under N$_2$ atmosphere. The reaction was monitored by LC-MS until the complete conversion of the starting material. The reaction mixture was then cooled to r.t. and filtered. The dark filtrate was concentrated in vacuo and purified by flash column chromatography eluting with DCM:MeOH=40:1 to obtain the Intermediate 7 (120 mg) as a white solid.

$^1$H NMR (CHLOROFORM-d): δ 8.79 (d, J=8.5 Hz, 1H), 8.18 (dd, J=4.9, 0.9 Hz, 1H), 7.61-7.71 (m, 5H), 7.48 (s, 1H), 7.30-7.44 (m, 6H), 6.89-6.97 (m, 2H), 6.63-6.75 (m, 2H), 4.34 (t, J=4.3 Hz, 2H), 4.08-4.11 (m, 3H), 3.50 (d, J=4.3 Hz, 2H). LC-MS: m/z 527.2 (M+H)$^+$.

Step G: 6-(3,4-dihydro-2H-benzo[b][1,4]oxazin-6-yl)-2,3-diphenyl-5-(pyridin-2-ylamino) pyrazolo[1,5-a]pyrimidin-7(4H)-one

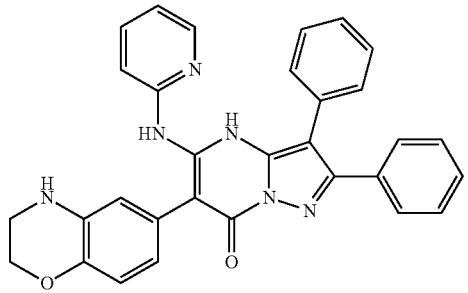

A solution of Intermediate 7 (50 mg, 0.095 mmol) in HCl (5 mL, 4M in 1.4-dioxane) was stirred at room temperature for 16 h. The mixture was concentrated, basified with ammonia (5 mL, 7M in MeOH) and concentrated in vacuo to give the title compound 8.

$^1$H NMR (DMSO-d$_6$): δ 15.73 (s, 1H), 8.92 (s, 1H), 8.03 (d, J=4.0 Hz, 1H), 7.78 (br. s., 1H), 7.51-7.60 (m, 4H), 7.32-7.47 (m, 7H), 7.09 (d, J=5.8 Hz, 1H), 6.74 (d, J=7.9 Hz, 1H), 6.62 (d, J=1.8 Hz, 1H), 6.46-6.54 (m, 1H), 5.85 (br. s., 1H), 4.19 (br. s., 2H), 3.34-3.35 (m, 2H). LC-MS: m/z 513.5 (M+H)$^+$.

Compound 198: 6-(4-methyl-3,4-dihydro-2H-benzo[b][1,4]oxazin-6-yl)-2,3-diphenyl-5-(pyridin-2-ylamino)pyrazolo[1, 5-a]pyrimidin-7(4H)-one

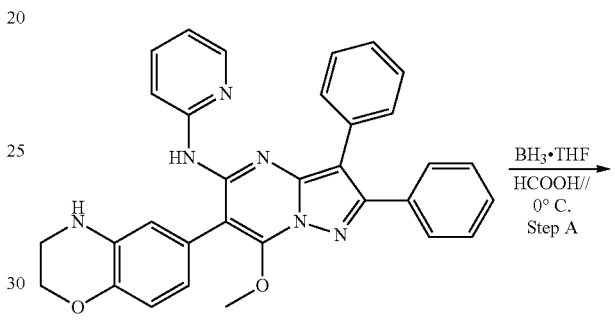

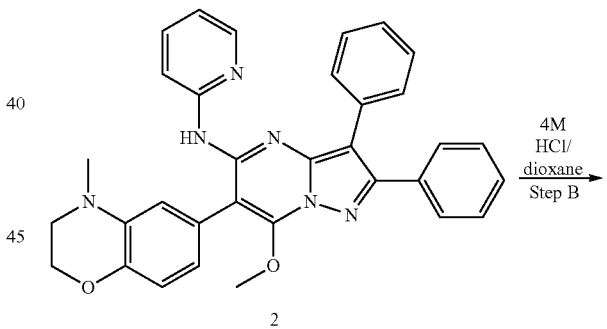

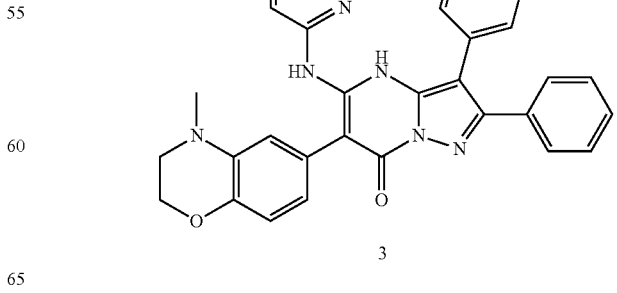

Step A: 7-methoxy-6-(4-methyl-3,4-dihydro-2H-benzo[b][1,4]oxazin-6-yl)-2,3-diphenyl-N-(pyridin-2-yl)pyrazolo[1,5-a]pyrimidin-5-amine

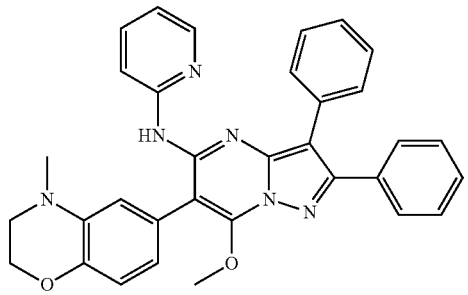 [SMILES: COc1c(-c2ccc3c(c2)N(C)CCO3)c(Nc2ccccn2)nc2c(-c3ccccc3)c(-c3ccccc3)nn12]

6-(3,4-dihydro-2H-benzo[b][1,4]oxazin-6-yl)-7-methoxy-2,3-diphenyl-N-(pyridin-2-yl)pyrazolo[1,5-a]pyrimidin-5-amine (50 mg, 0.095 mmol) in THF (10 mL) was cooled to 0° C., HCOOH (5.2 mg, 0.114 mmol) was added and stirred for 5 mins. BH$_3$ THF (0.19 mL, 1M) was added dropwise at 0° C., and the mixture was slowly warmed to r.t. and stirred on for 4 h. The reaction was quenched by careful adding NaHCO$_3$ solution. The resultant mixture was extracted with DCM (10 mL×3), dried, and concentrated. The residue was purified by silica gel column (PE:EA=3:1) to afford Intermediate 2 (30 mg) as a light yellow solid.

$^1$H NMR (CHLOROFORM-d): δ 8.83 (d, J=8.2 Hz, 1H), 8.17 (d, J=4.3 Hz, 1H), 7.59-7.73 (m, 5H), 7.35-7.43 (m, 5H), 7.26-7.30 (m, 1H), 6.93 (d, J=7.9 Hz, 2H), 6.64-6.75 (m, 2H), 4.39 (t, J=4.1 Hz, 2H), 4.07-4.12 (m, 3H), 3.37 (d, J=4.3 Hz, 2H), 2.90 (s, 3H). LC-MS: m/z 541.3 (M+H)$^+$.

Step B: 6-(4-methyl-3,4-dihydro-2H-benzo[b][1,4]oxazin-6-yl)-2,3-diphenyl-5-(pyridin-2-ylamino)pyrazolo[1, 5-a]pyrimidin-7(4H)-one

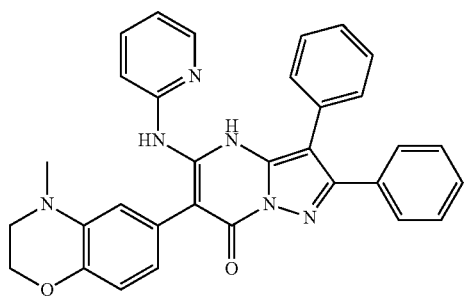 [SMILES: CN1CCOc2ccc(-c3c(Nc4ccccn4)[nH]c4c(-c5ccccc5)c(-c5ccccc5)nn4c3=O)cc21]

The Intermediate 2 (30 mg, 0.056 mmol) in HCl (10 mL, 4M in dioxane) was stirred at r.t. for 2 h. The mixture was concentrated, basified with ammonia (5 mL, 7M in MeOH) and concentrated in vacuo to afford the title compound 3.

$^1$H NMR (CHLOROFORM-d): δ 8.07 (d, J=4.6 Hz, 1H), 7.76 (br. s., 2H), 7.65 (br. s., 1H), 7.45-7.52 (m, 4H), 7.31-7.41 (m, 5H), 6.98 (br. s., 1H), 6.81-6.92 (m, 2H), 6.62-6.76 (m, 2H), 4.37 (br. s., 2H), 3.35 (br. s., 2H), 2.92 (s, 3H). LC-MS: m/z 527.5 (M+H)$^+$.

Compound 199: N-ethyl-5-((7-oxo-2,3-diphenyl-6-(quinolin-6-yl)-4,7-dihydropyrazolo[1,5-a]pyrimidin-5-yl)amino)-1,3,4-oxadiazole-2-carboxamide

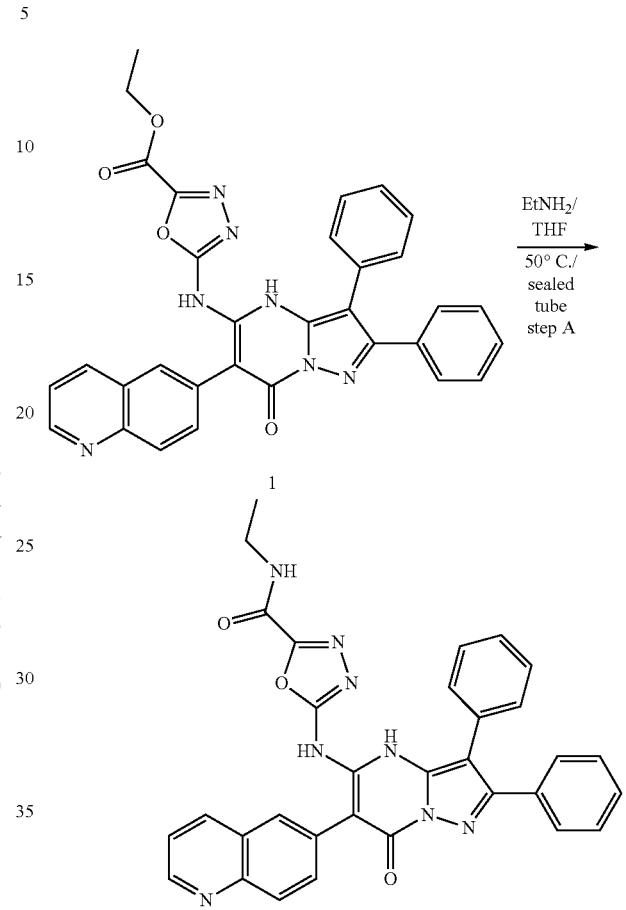

Step A: To a solution of 1 (20 mg, mmol) in THF (2 mL) was added ethylamine (aq. 0.1 mL) in a sealed tube, and the mixture was stirred at 50° C. overnight to afford the desired product 2.

$^1$H NMR (DMSO-d$_6$): δ 12.67 (br. s., 1H), 8.63-8.92 (m, 2H), 8.28-8.34 (m, 2H), 8.03 (s, 1H), 7.92 (s, 2H), 7.49-7.55 (m, 2H), 7.41-7.49 (m, 3H), 7.31-7.40 (m, 6H), 3.18 (dt, J=13.2, 7.2 Hz, 2H), 1.04 (t, J=7.2 Hz, 3H). LC-MS: m/z 569.0 (M+H)$^+$.

Compound 200: (E)-2-hydroxy-1-(6-(4-methoxyphenyl)-7-oxo-2,3-diphenyl-4,7-dihydropyrazolo[1,5-a]pyrimidin-5-yl)guanidine

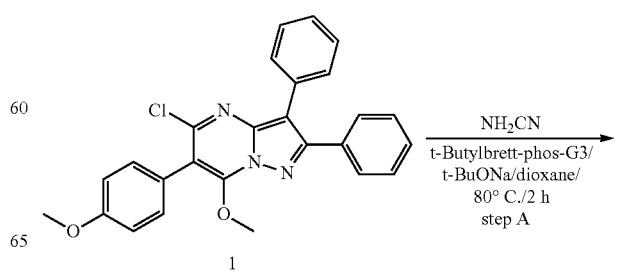

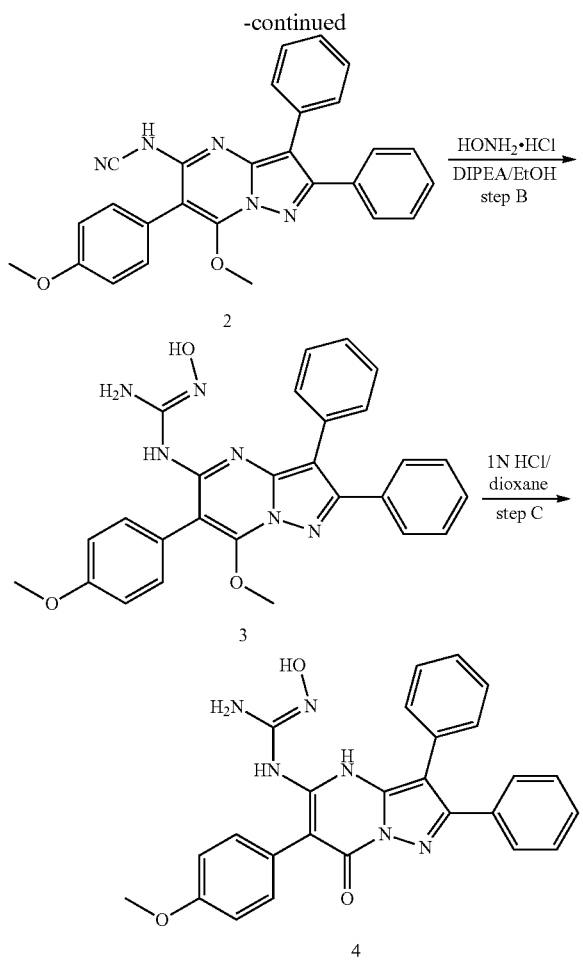

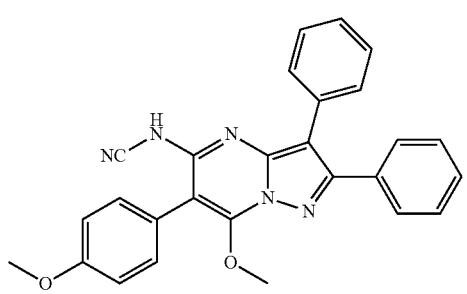 [SMILES: COc1ccc(-c2c(NC#N)nc3c(-c4ccccc4)c(-c4ccccc4)nn3c2OC)cc1]

Step A: N-(7-methoxy-6-(4-methoxyphenyl)-2,3-diphenyl-4,7-dihydropyrazolo[1,5-a]pyrimidin-5-yl)cyanamide A mixture of Intermediate 1 (441 mg, 1 mmol), NH₂CN (210 mg, 5.0 mmol, 5 eq), t-BuBrettphos Pd G3 (170 mg, 0.2 mmol, 0.2 eq), t-BuBrettphos (49 mg, 0.1 mmol, 0.1 eq) and t-BuONa (288 mg, 3.0 mmol, 3.0 eq) in 1,4-dioxane (12 mL) in a sealed microwave vial (25 mL) under N₂ atmosphere was heated to 80° C. for 1 h. The reaction mixture was then cooled to r.t. and filtered. The dark filtrate was concentrated in vacuo and purified by flash column chromatography silica gel (DCM/MeOH=100:1) to obtain Intermediate 2 (180 mg). LC-MS: m/z 448.1 (M+H)⁺

Step B: (E)-2-hydroxy-1-(7-methoxy-6-(4-methoxyphenyl)-2,3-diphenylpyrazolo[1,5-a]pyrimidin-5-yl)guanidine

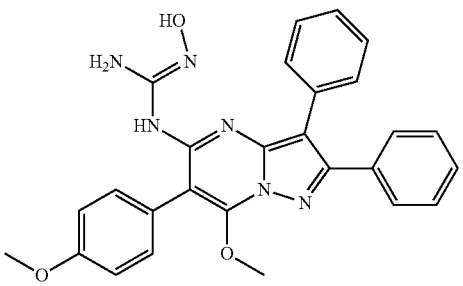 [SMILES: COc1ccc(-c2c(N/C(N)=N/O)nc3c(-c4ccccc4)c(-c4ccccc4)nn3c2OC)cc1]

To a mixture of Intermediate 2 (100 mg, 0.22 mmol) and DIPEA (145 mg, 1.12 mmol, 5.0 eq) in EtOH (5 mL) was added Hydroxylamine hydrochloride (47 mg, 0.67 mmol, 3.0 eq). Then the reaction mixture was stirred at r.t. overnight. The mixture was partitioned between EA and H₂O. The combined organic phase was washed with water and brine, dried over anhydrous Na₂SO₄, filtered, and concentrated under reduced pressure. The residue was purified by column chromatography on silica gel to afford the desired Intermediate 3 (30 mg). LC-MS: m/z 481.1 (M+H)⁺.

Step C: (E)-2-hydroxy-1-(6-(4-methoxyphenyl)-7-oxo-2,3-diphenyl-4,7-dihydropyrazolo[1,5-a]pyrimidin-5-yl)guanidine

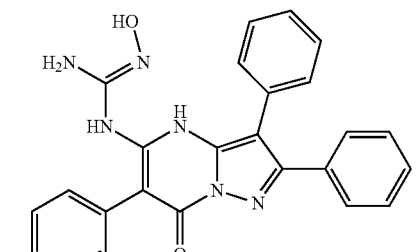

A mixture of Intermediate 3 (30 mg, 0.06 mmol) in HCl/dioxane (5 mL, 1N) was stirred at r.t. for 1 h. The mixture was then concentrated under reduced pressure to afford the desired compound 4.

¹H NMR (DMSO-d₆): δ 7.23-7.52 (m, 12H), 7.01 (d, J=9.2 Hz, 2H), 3.81 (s, 3H). LC-MS: m/z 467.2 (M+H)⁺.

Compound 201: (S)-(3-((6-(4-methoxyphenyl)-7-oxo-2,3-diphenyl-4,7-dihydropyrazolo[1,5-a]pyrimidin-5-yl)amino)-1H-pyrazol-1-yl)methyl 2-amino-3-methylbutanoate

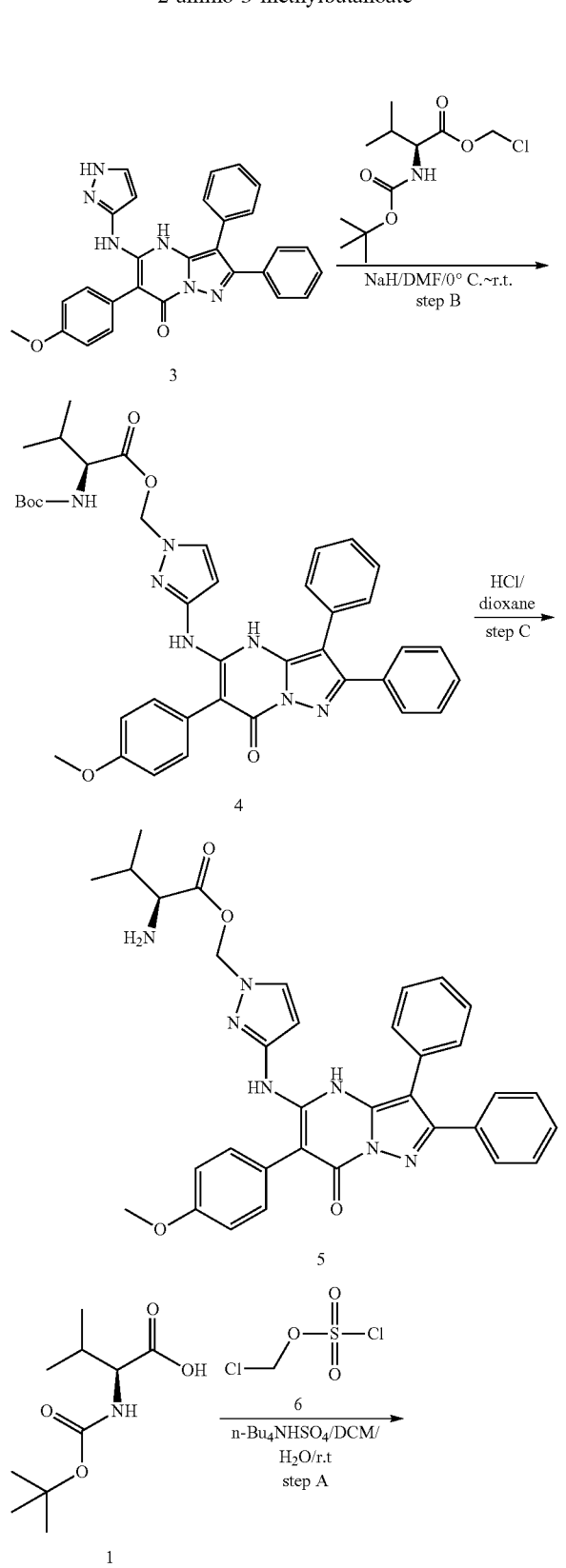

Step A: (S)-chloromethyl 2-((tert-butoxycarbonyl)amino)-3-methylbutanoate

To a solution of Intermediate 1 (1.4 g, 6.6 mmol) in DCM/H$_2$O (10 mL/10 mL) were added chloromethyl sulfochloridate 6 (1.3 g, 7.9 mmol, 1.2 eq.), NaHCO$_3$ (4 eq) and tetrabutylammonium hydrogensulfate (0.1 eq.). The mixture was stirred at r.t. overnight. The organic phase was separated, and the water phase was extracted with DCM (3*10 mL). The combined organic phase was washed with brine, dried over anhydrous Na$_2$SO$_4$ and concentrated in vacuo. The residue was purified by flash chromatography to afford the desired product 2 as a colorless oil (1.5 g). LC-MS: m/z 266.2 (M+H)$^+$.

Step B: (S)-(3-((6-(4-methoxyphenyl)-7-oxo-2,3-diphenyl-4,7-dihydropyrazolo[1,5-a]pyrimidin-5-yl)amino)-1H-pyrazol-1-yl)methyl 2-((tert-butoxycarbonyl)amino)-3-methylbutanoate To a solution of Intermediate 3 (300 mg, mmol) in DMF (20 mL) was added sodium hydride (3 eq.) at 0° C. (S)-chloromethyl 2-((tert-butoxycarbonyl)amino)-3-methylbutanoate 2 (3 eq.) was added dropwise after the mixture was stirred at 0° C. for 30 min. Then the mixture was stirred at r.t. overnight. The mixture was poured into water (100 mL) and extracted with DCM (3*20 mL), the combined organic phase was washed with brine, dried over anhydrous Na$_2$SO$_4$ and concentrated in vacuo. The residue was purified by flash chromatography to afford the desired product 4 as a white solid. (240 mg)
$^1$H NMR (DMSO-d$_6$): δ 13.07 (s, 1H), 9.11 (s, 1H), 7.95 (s, 1H), 7.83 (d, J=2.8 Hz, 1H), 7.49-7.57 (m, 4H), 7.36-7.42 (m, 6H), 7.28 (d, J=8.6 Hz, 2H), 7.05 (d, J=8.6 Hz, 2H), 6.14 (d, J=2.8 Hz, 1H), 5.97 (d, J=10.8 Hz, 1H), 5.77 (d, J=10.8 Hz, 1H), 3.83 (s, 3H), 3.76-3.81 (m, 1H), 1.84 (dt, J=13.2, 6.8 Hz, 1H), 1.35 (s, 9H), 0.74 (d, J=6.8 Hz, 3H), 0.71 (d, J=6.8 Hz, 3H). LC-MS: m/z 704.1 (M+H)$^+$ Step C: (S)-(3-((6-(4-methoxyphenyl)-7-oxo-2,3-diphenyl-4,7-dihydropyrazolo[1,5-a]pyrimidin-5-yl)amino)-1H-pyrazol-1-yl)methyl 2-amino-3-methylbutanoate To a solution of Intermediate 4 (220 mg, 0.31 mmol) in DCM (1 mL) was added HCl-dioxane (4 mol/L, 5 mL) at 0° C. The mixture was stirred at r.t. for 1 h. The white precipitate was filtered off and mixed with DCM (5 mL) and aq. NaHCO$_3$ solution. The organic phase was washed with brine, dried over anhydrous Na$_2$SO$_4$ and concentrated in vacuo to afford the desired product 5.
$^1$H NMR (DMSO-d$_6$): δ 8.14 (s, 1H), 7.75 (br. s., 1H), 7.51 (d, J=6.2 Hz, 2H), 7.45 (br. s., 2H), 7.34 (br. s., 6H), 7.27 (d, J=8.4 Hz, 2H), 7.10-7.23 (m, 1H), 7.03 (d, J=8.4 Hz, 2H), 5.87-6.02 (m, 2H), 3.81 (s, 3H), 3.52-3.69 (m, 1H), 1.79-2.05 (m, 1H), 0.78 (br. s., 6H). LC-MS: m/z 604.0 (M+H)+.

Compound 203: 3-(cyclohex-1-en-1-yl)-6-(4-methoxyphenyl)-2-(pyridin-2-yl)-5-(pyridin-2-ylamino)pyrazolo[1,5-a]pyrimidin-7(4H)-one

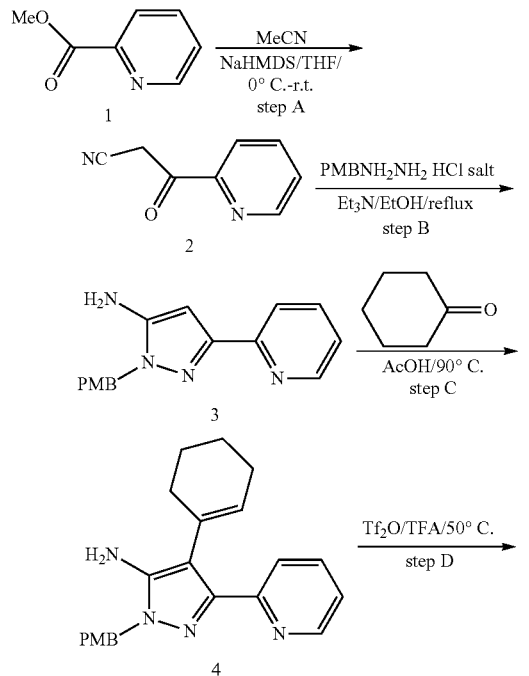

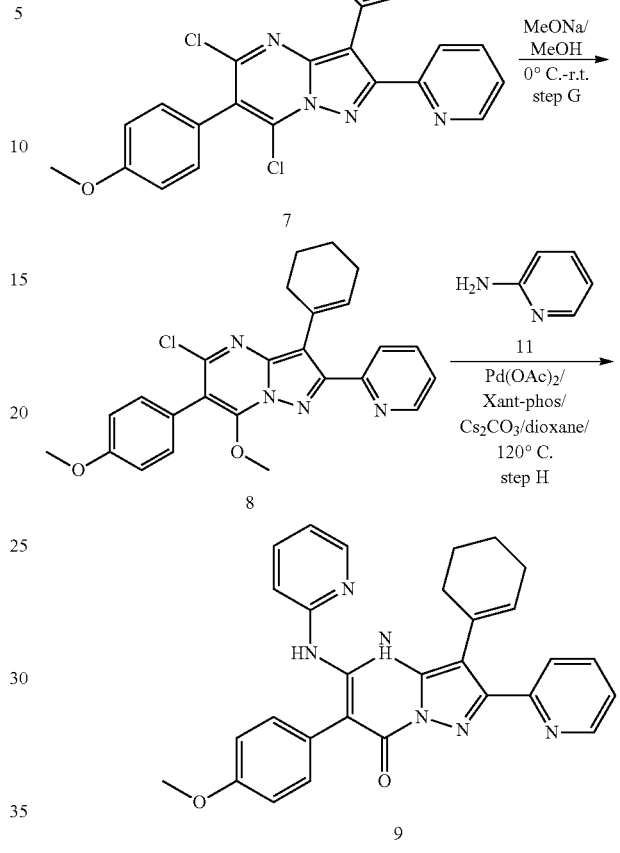

Step A: 3-oxo-3-(pyridin-2-yl)propanenitrile

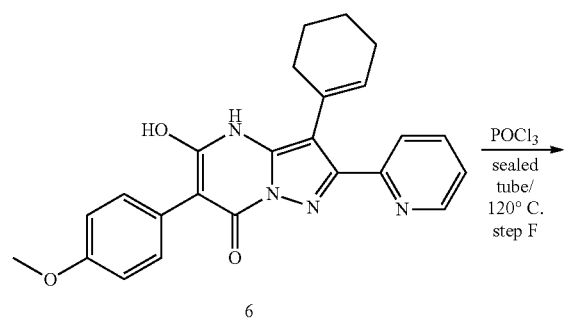

To a solution of methyl picolinate (13 g, 95 mmol) and acetonitrile (5.8 g, 142 mmol) in THF (150 ml) was added slowly NaHDMS (2 mol/L, 71 ml, 142 mmol) at 0° C. Then the reaction mixture was stirred at 0° C. for 0.5 h and allowed to warm up to room temperature for 2 h. The reaction was quenched with water, adjusted with HCl (2 mol/L) to pH=7, and extracted with DCM (100 ml*3). The combined organic layers were washed with brine, dried over anhydrous sodium sulfate, and concentrated in vacuo to give 3-oxo-3-(pyridin-2-yl)propanenitrile (12 g, 87% yield) as a dark brown solid.

$^1$H NMR (CHLOROFORM-d) δ: 8.70 (dd, J=4.8, 0.6 Hz, 1H), 8.03-8.17 (m, 1H), 7.92 (td, J=7.8, 1.6 Hz, 1H), 7.58 (ddd, J=7.6, 4.8, 1.4 Hz, 1H), 4.40 (s, 2H). LC-MS: m/z 147.1 (M+H)+.

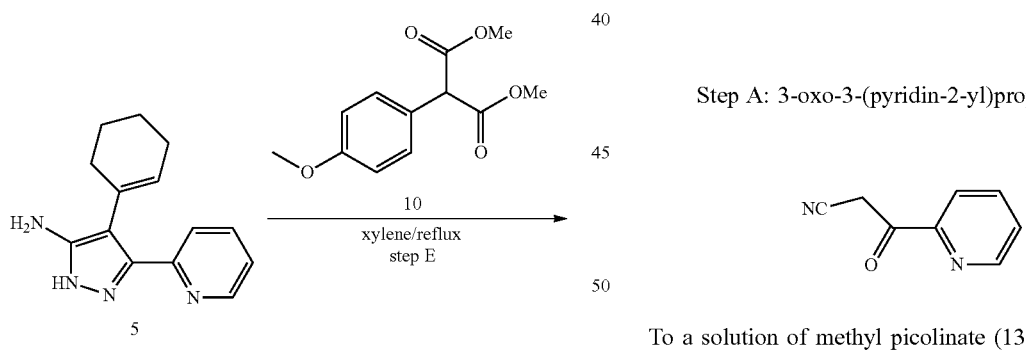

Step B: 1-(4-methoxybenzyl)-3-(pyridin-2-yl)-1H-pyrazol-5-amine

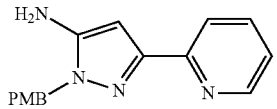

To a solution of 3-oxo-3-(pyridin-2-yl)propanenitrile (10 g, 68 mmol) in EtOH (80 ml) was added (4-methoxybenzyl) hydrazine hydrochloride (15.5 g, 82 mmol, 1.2 eq) and triethylamine (13.8 g, 137 mmol, 2 eq.). The reaction mixture was refluxed for 2 h under $N_2$ protection. Then the mixture was evaporated in vacuo. The residue was dissolved in EA (100 mL), washed with water, and extracted with EA (100 ml*2). The combined organic phase was washed with brine, dried over anhydrous sodium sulfate, and concentrated in vacuo to give the crude product as a yellow solid. The crude product was suspended in t-BuOMe (100 mL), stirred for 0.5 h and filtered off to give 1-(4-methoxybenzyl)-3-(pyridin-2-yl)-1H-pyrazol-5-amine as a pale yellow solid (15.1 g, 79% yield).

$^1$H NMR (DMSO-$d_6$) δ: 8.50 (d, J=4.8 Hz, 1H), 7.77-7.83 (m, 1H), 7.73 (dd, J=7.6, 1.6 Hz, 1H), 7.11-7.26 (m, 3H), 6.84-6.90 (m, 2H), 5.89 (s, 1H), 5.41 (s, 2H), 5.12 (s, 2H), 3.71 (s, 3H). LC-MS: m/z 281.2 (M+H)$^+$.

Step C: 4-(cyclohex-1-en-1-yl)-1-(4-methoxybenzyl)-3-(pyridin-2-yl)-1H-pyrazol-5-amine

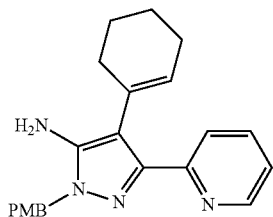

To a solution of 1-(4-methoxybenzyl)-3-(pyridin-2-yl)-1H-pyrazol-5-amine (15.0 g, 54 mmol) in acetic acid (100 mL) was added cyclohexanone (5.3 g, 54 mmol, 1 eq.). The mixture was stirred at 90° C. for 1 h. Then another 1 eq. of cyclohexanone was added, and the mixture was stirred at 90° C. for 1 h. Solvent was removed in vacuo. The resultant residue was dissolved in EA (100 mL) and treated with saturated NaHCO$_3$. The organic phase was separated, and the water phase was extracted with EA (100 mL*2). The combined organic phase was washed with brine, dried over anhydrous Na$_2$SO$_4$, and concentrated in vacuo. The residue was purified by flash chromatography (MeOH/DCM=1/20) to give 4-(cyclohex-1-en-1-yl)-1-(4-methoxybenzyl)-3-(pyridin-2-yl)-1H-pyrazol-5-amine as a brown solid (6.8 g, 35% yield).

$^1$H NMR (DMSO-$d_6$) δ: 8.49 (d, J=4.4 Hz, 1H), 7.72 (t, J=7.2 Hz, 1H), 7.65 (d, J=7.8 Hz, 1H), 7.07-7.29 (m, 3H), 6.88 (d, J=8.8 Hz, 2H), 5.47 (br. s., 1H), 5.14 (s, 2H), 4.94 (br. s., 2H), 3.71 (s, 3H), 2.12 (br. s., 2H), 1.98 (br. s., 2H), 1.59 (br. s., 4H). LC-MS: m/z 361.2 (M+H)$^+$.

Step D: 4-(cyclohex-1-en-1-yl)-3-(pyridin-2-yl)-1H-pyrazol-5-amine

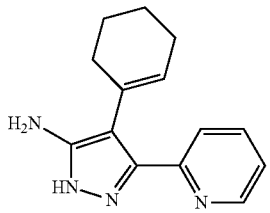 [SMILES: Nc1[nH]nc(-c2ccccn2)c1C1=CCCCC1]

The solution of 4-(cyclohex-1-en-1-yl)-1-(4-methoxybenzyl)-3-(pyridin-2-yl)-1H-pyrazol-5-amine (6.8 g, 19 mmol) in TFA/(CF$_3$SO$_2$)$_2$O (30 mL/10 mL) was stirred at 50° C. for 1 h. The solvent was removed in vacuo. The residue was dissolved in EA (50 mL) and treated with saturated NaHCO$_3$. The organic phase was separated, and the water phase was extracted with EA (50 mL*2). The combined organic phase was washed with brine, dried over anhydrous Na$_2$SO$_4$, and concentrated in vacuo. The residue was dissolved in NH$_3$/MeOH (7 mol/L, 50 mL), and hydrazine hydrate (g, mmol, 2 eq.) was added. The mixture was stirred at r.t. overnight. Solvent was removed in vacuo and the residue was purified by flash chromatography (MeOH/DCM 1/20) to give 4-(cyclohex-1-en-1-yl)-3-(pyridin-2-yl)-1H-pyrazol-5-amine (3.6 g, 790/% yield) as a brown solid. LC-MS: m/z 241.2 (M+H)$^+$.

Step E: 3-(cyclohex-1-en-1-yl)-5-hydroxy-6-(4-methoxyphenyl)-2-(pyridin-2-yl)pyrazolo[1,5-a]pyrimidin-7(4H)-one

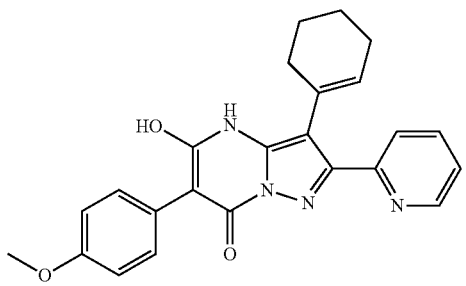 [SMILES: COc1ccc(-c2c(O)[nH]c3c(C4=CCCCC4)c(-c4ccccn4)nn3c2=O)cc1]

A solution of 4-phenyl-3-(pyridin-2-yl)-J H-pyrazol-5-amine (3.6 g, 15 mmol) and dimethyl 2-(4-methoxyphenyl) malonate (7.2 g, 30 mmol, 2 eq.) in xylene (50 ml) was refluxed for 8 h. The reaction mixture was cooled to room temperature. The precipitate was filtered off and washed with MeOH to give 3-(cyclohex-1-en-1-yl)-5-hydroxy-6-(4-methoxyphenyl)-2-(pyridin-2-yl)pyrazolo[1,5-a]pyrimidin-7(4H)-one (4.0 g, 64% yield) as a yellow solid. LC-MS: m/z 415.2 (M+H)$^+$.

Step F: 5,7-dichloro-3-(cyclohex-1-en-1-yl)-6-(4-methoxyphenyl)-2-(pyridin-2-yl)pyrazolo[1,5-a]pyrimidine

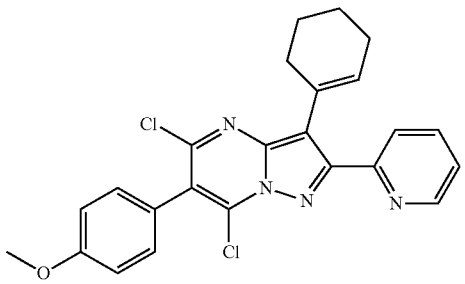 [SMILES: COc1ccc(-c2c(Cl)nc3c(C4=CCCCC4)c(-c4ccccn4)nn3c2Cl)cc1]

The solution of 3-(cyclohex-1-en-1-yl)-5-hydroxy-6-(4-methoxyphenyl)-2-(pyridin-2-yl)pyrazolo[1,5-a]pyrimidin-7(4H)-one (4.0 g, 10 mmol) in POCl₃ (30 ml) in a sealed tube was stirred at 120° C. overnight. The reaction mixture was cooled to room temperature and concentrated in vacuo. The residue was dissolved in DCM (50 mL) and poured into ice-water (100 mL). The mixture was adjusted to PH=7 by adding saturated NaHCO₃ solution. The organic phase was separated, and the water phase was extracted with DCM (50 ml*2). The combined organic phase was washed with brine, dried over anhydrous Na₂SO₄, and concentrated in vacuo. The residue was purified by column chromatography on silica gel (eluting PE/EA=1:1) to give 5, 7-dichloro-3-(cyclohex-1-en-1-yl)-6-(4-methoxyphenyl)-2-(pyridin-2-yl)pyrazolo[1,5-a]pyrimidine (2.8 g, 64% yield) as a yellow solid. LC-MS: m/z 451.1, 453.1 (M+H)⁺.

Step G: 5-chloro-3-(cyclohex-1-en-1-yl)-7-methoxy-6-(4-methoxyphenyl)-2-(pyridin-2-yl)pyrazolo[1,5-a]pyrimidine

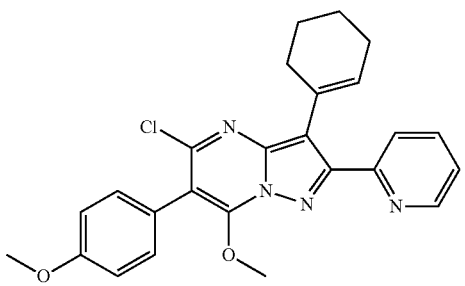

To a solution of 5,7-dichloro-3-(cyclohex-1-en-1-yl)-6-(4-methoxyphenyl)-2-(pyridin-2-yl)pyrazolo[1,5-a]pyrimidine (2.8 g, 6 mmol) in DCM (50 ml) was added NaOMe (6.2 mL, 5.0 mol/L in MeOH) at 0° C. The reaction mixture was stirred at 0° C. for 10 min and poured into ice-water (100 mL). The organic phase was separated, and the water phase was extracted with DCM (50 ml*2). The combined organic phase was washed with brine, dried over anhydrous Na₂SO₄, and concentrated in vacuo to give 5-chloro-3-(cyclohex-1-en-1-yl)-7-methoxy-6-(4-methoxyphenyl)-2-(pyridin-2-yl)pyrazolo[1,5-a]pyrimidine (2.7 g, 97% yield) as a yellow solid.

¹H NMR (DMSO-d₆) δ: 8.70 (dt, J=4.8, 1.2 Hz, 1H), 7.91-7.96 (m, 2H), 7.42-7.47 (m, 1H), 7.39 (d, J=8.6 Hz, 2H), 7.07 (d, J=8.6 Hz, 2H), 5.82 (br. s., 1H), 4.12 (s, 3H), 3.83 (s, 3H), 2.09-2.24 (m, 4H), 1.56-1.75 (m, 4H). LC-MS: m/z 447.2, 449.2 (M+H)⁺.

Step H: 3-(cyclohex-1-en-1-yl)-6-(4-methoxyphenyl)-2-(pyridin-2-yl)-5-(pyridin-2-ylamino) pyrazolo[1,5-a]pyrimidin-7(4H)-one

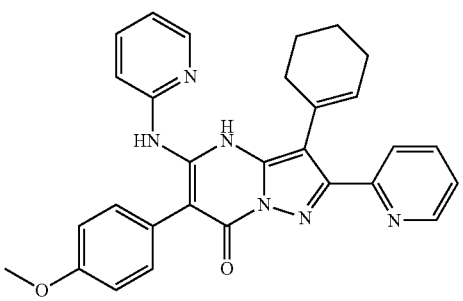 [SMILES: COc1ccc(-c2c(Nc3ccccn3)[nH]c3c(C4=CCCCC4)c(-c4ccccn4)nn3c2=O)cc1]

A suspension of 5-chloro-3-(cyclohex-1-en-1-yl)-7-methoxy-6-(4-methoxyphenyl)-2-(pyridin-2-yl)pyrazolo[1,5-a]pyrimidine (300 mg, 0.67 mmol), pyridin-2-amine (126 mg, 1.34 mmol, 2 eq.), Pd(OAc)₂ (90 mg, 0.40 mmol, 0.6 eq.), Xantphos (232 mg, 0.40 mmol, 0.6 eq.) and Cs₂CO₃ (437 mg, 1.34 mmol, 2.0 eq.) in 1.4-dioxane (10 mL) was stirred at 130° C. through microwave irradiation for 1.5 hour under N₂ atmosphere. The mixture was filtered through celite, and the filtrate was concentrated in vacuo to afford the title compound.

¹H NMR (DMSO-d₆) δ: 8.67 (d, J=8.2 Hz, 1H), 8.42 (br. s., 1H), 8.12 (d, J=4.4 Hz, 1H), 7.73 (t, J=7.2 Hz, 1H), 7.60-7.69 (m, 1H), 7.41-7.52 (m, 1H), 7.24-7.39 (m, 3H), 7.20 (s, 1H), 7.08 (d, J=7.6 Hz, 2H), 6.89-6.98 (m, 1H), 5.97 (br. s., 1H), 3.82 (s, 3H), 2.20 (br. s., 4H), 1.66 (br. s., 4H). LC-MS: m/z 491.2 (M+H)⁺.

3,4-diphenyl-1H-pyrazol-5-amine

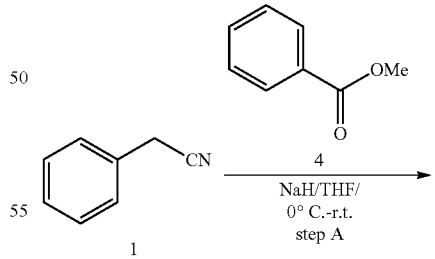

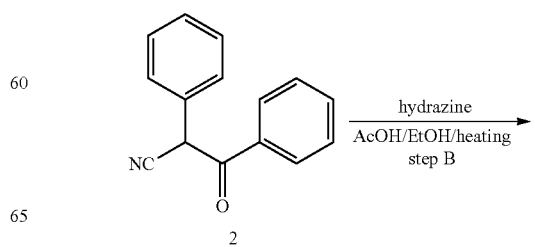

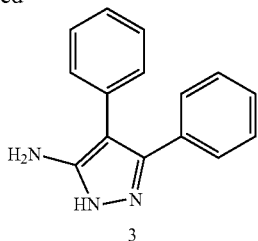

Step A: 3-oxo-2,3-diphenylpropanenitrile

To a solution of 2-phenylacetonitrile 1 (10 g, 85.3 mmol) and methyl benzoate 4 (12.2 g, 90 mmol) in THF (100 mL) was added sodium hydride (6.8 g, 170 mmol) at 0° C. After addition, the mixture was stirred at room temperature overnight. The mixture was quenched with 1 M hydrochloric acid to pH 6. The organic phase was dried over anhydrous sodium sulfate and concentrated under reduced pressure to dryness. The residue was added petroleum ether (60 mL) and the turbid liquid was stirred at room temperature for 3 h. The precipitate was collected by filtration and dried in vacuo to afford 3-oxo-2,3-diphenylpropanenitrile 2 (15.3 g) as a white solid. LC-MS: m/z 222.1 (M+H)$^+$.

Step B: 3,4-diphenyl-1H-pyrazol-5-amine

A mixture of 3-oxo-2, 3-diphenylpropanenitrile (15 g, 67.8 mmol), hydrazine hydrate (7.6 g, 150 mmol), acetic acid (15 mL) and the ethanol (60 mL) was heated to reflux overnight. The mixture was evaporated to remove ethanol and the residue was adjusted to pH 8 with saturated solution of sodium bicarbonate at 0° C. The mixture was extracted with ethyl acetate (80 mL) twice, and the combined organic phase was washed with brine, dried over anhydrous sodium sulfate and concentrated in vacuo to dryness. The resulting solid was recrystallized from 2-methoxy-2-methylpropane to give 3, 4-diphenyl-1H-pyrazol-5-amine (16 g) as a white solid. LC-MS: m/z 236.1 (M+H)$^+$.

3-(2-fluorophenyl)-4-phenyl-1H-pyrazol-5-amine

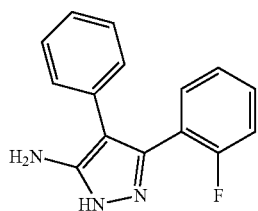 [SMILES: Nc1[nH]nc(-c2ccccc2F)c1-c1ccccc1]

This compound was prepared according to the procedures for preparing intermediate 3,4-diphenyl-1H-pyrazol-5-amine by using compound 4 as methyl 2-fluorobenzoate.

Step A stoichiometry: 2-phenylacetonitrile (5 g, 42.6 mmol), methyl 2-fluorobenzoate (6.9 g, 45 mmol) and sodium hydride (3.4 g, 85 mmol) in THF (60 mL) under cooling at 0° C. LC-MS: m/z 240.1 (M+H)$^+$.

Step B stoichiometry: 3-(2-fluorophenyl)-3-oxo-2-phenylpropanenitrile (3.25 g, 13.6 mmol), hydrazine hydrate (1.5 g, 30 mmol), acetic acid (3 mL) and the ethanol (15 mL) under heating to reflux overnight. LC-MS: m/z 254.2 (M+H)$^+$.

3-phenyl-4-(($^2$H$_{10}$)piperidin-1-yl)-1H-pyrazol-5-amine

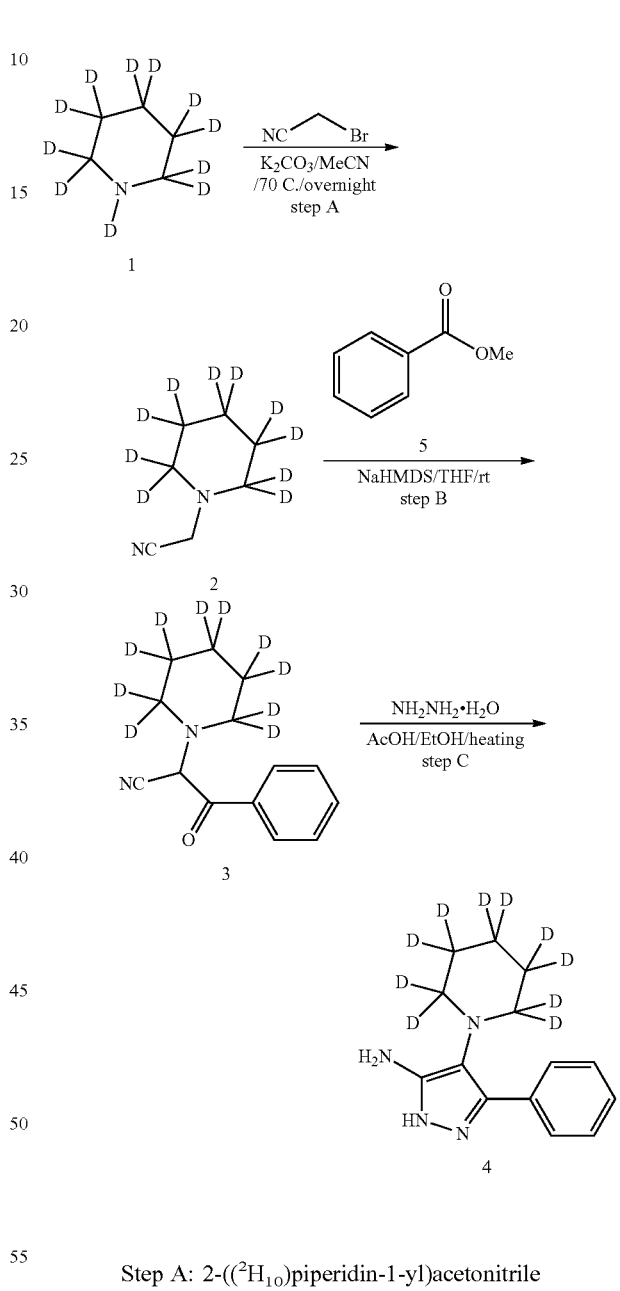

Step A: 2-(($^2$H$_{10}$)piperidin-1-yl)acetonitrile

The mixture of piperidine-d$_{10}$ (100 mg, 1.04 mmol, 1 eq.), 2-bromoacetonitrile (150 mg, 1.2 eq.), and K$_2$CO$_3$ (276 mg, 2 eq.) in CH$_3$CN (5 mL) was stirred at 70° C. overnight. Then the mixture was cooled to r.t. and filtered, the filtrate was poured into water (30 mL) and extracted with EA (10 mL*3). The combined organic phase was washed with brine, dried over anhydrous Na$_2$SO$_4$ and concentrated in vacuo to afford Intermediate 2 which was directly used to the next step without further purification. LC-MS: m/z 135.0 (M+H)$^+$.

Step B: 3-oxo-3-phenyl-2-(($^2$H$_{10}$)piperidin-1-yl)propanenitrile

To a mixture of Intermediate 2 (115 mg, 0.86 mmol, 1 eq.) and methyl benzoate (140 mg, 1.03 mmol, 1.2 eq.) in THF (8 mL) was added NaHMDS (2M in THF, 0.52 mL, 1.2 eq.) at 0° C. The mixture was stirred at r.t. overnight. The reaction mixture was diluted with EA (10 mL) and quenched with saturated NH$_4$Cl. The organic phase was separated, washed with brine, dried over anhydrous Na$_2$SO$_4$ and concentrated in vacuo. The residue was purified by flash chromatography to afford the desired Intermediate 3 as a white solid. LC-MS: m/z 239.1 (M+H)$^+$.

Step C: 3-phenyl-4-(($^2$H$_{10}$)piperidin-1-yl)-1H-pyrazol-5-amine

The mixture of Intermediate 3 (169 mg, 0.71 mmol, 1 eq.) and hydrazine (71 mg, 1.42 mmol, 2 eq.) in EtOH/AcOH (5/1.5 mL/1 mL) was refluxed for 5 h. Then the mixture was cooled to r.t. and evaporated. The residue was dissolved in EA (5 mL) and neutralized with 10%0 NaHCO$_3$. The organic phase was separated, and the water phase was extracted with EA (5 mL*3). The combined organic phase was washed with brine, dried over anhydrous Na$_2$SO$_4$ and concentrated in vacuo. The residue was purified by flash chromatography to afford the desired product 4 as a white solid.

$^1$H NMR (DMSO-d$_6$): δ 11.52 (br. s., 1H), 7.85 (d, J=7.6 Hz, 2H), 7.38 (t, J=7.6 Hz, 2H), 7.22-7.29 (m, 1H), 4.35 (br. s., 2H). LC-MS: m/z 253.1 (M+H)$^+$.

3-phenyl-4-(piperidin-1-yl)-1H-pyrazol-5-amine

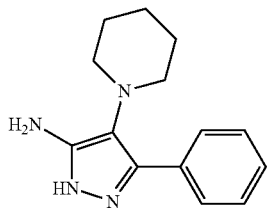 [SMILES: Nc1[nH]nc(-c2ccccc2)c1N1CCCCC1]

This compound was prepared according to the procedure for preparing intermediate 3-phenyl-4-(($^2$H$_{10}$)piperidin-1-yl)-1H-pyrazol-5-amine, step B-C, starting from 2-(piperidin-1-yl)acetonitrile.

Step B stoichiometry: 2-(piperidin-1-yl)acetonitrile (7.8 g, 62 mmol, 1 eq.), methyl benzoate (9.4 g, 68 mmol, 1.1 eq.) and NaHMDS (2 M in THF, 46 mL, 1.5 eq.) in THF (300 mL) at 0° C.-r.t.

Step C stoichiometry: 3-oxo-3-phenyl-2-(piperidin-1-yl)propanenitrile (5 g, 21.902 mmol) and hydrazine hydrate (3.3 g, 65.706 mmol) in EtOH/AcOH (5/1, 30 mL/6 mL) under heating to reflux for 16 h under N$_2$ protection.

$^1$H NMR (DMSO-d$_6$): 1.52 (br. s., 1H), 7.82 (br. s., 2H), 7.36 (t, J=7.2 Hz, 2H), 7.25 (d, J=7.3 Hz, 1H), 4.28 (br. s., 2H), 2.88 (t, J=5.0 Hz, 3H), 1.55 (br. s., 3H), 1.46 (d, J=4.0 Hz, 2H). LC-MS: m/z 243.2 (M+H)$^+$.

4-(4,4-difluoropiperidin-1-yl)-3-phenyl-1H-pyrazol-5-amine

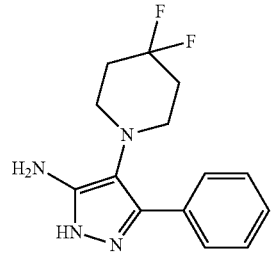 [SMILES: Nc1[nH]nc(-c2ccccc2)c1N1CCC(F)(F)CC1]

This compound was prepared according to the procedure for preparing intermediate 3-phenyl-4-(($^2$H$_{10}$)piperidin-1-yl)-1H-pyrazol-5-amine, step A-C, starting from 4,4-difluoropiperidine hydrochloride salt. Step A stoichiometry: 4,4-difluoropiperidine hydrochloride salt (1.0 g, 6.3 mmol, 1 eq.), 2-bromoacetonitrile (761 mg, 6.3 mmol, 1 eq.), triethylamine (2.2 g, 22.2 mmol, 3.5 eq.) in THF (30 mL) under heating at 60° C. overnight. LC-MS: m/z 161.0 (M+H)$^+$. Step B stoichiometry: 2-(4,4-difluoropiperidin-1-yl)acetonitrile (500 mg, 3.1 mmol, 1 eq.), methyl benzoate (467 mg, 3.4 mmol, 1.1 eq.) and NaHMDS (2 M in THF, 2.3 mL, 1.5 eq.) in THF (30 mL) at 0° C.-r.t. Step C stoichiometry: 2-(4,4-difluoropiperidin-1-yl)-3-oxo-3-phenylpropanenitrile (380 mg, 1.44 mmol, 1 eq.) and hydrazine hydrate (144 mg, 2.88 mmol, 2 eq.) in EtOH/AcOH (5/1, 15 mL/3 mL) under heating to reflux for 6 h. LC-MS: m/z 279.1 (M+H)$^+$.

4-(cyclohex-1-en-1-yl)-3-phenyl-1H-pyrazol-5-amine

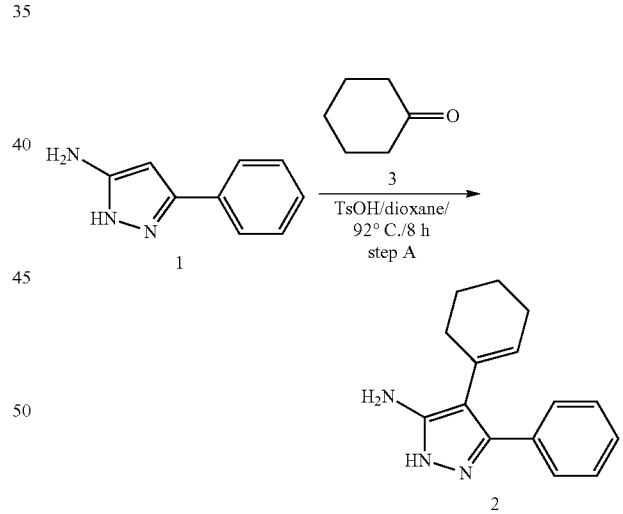

Step A: 4-(cyclohex-1-en-1-yl)-3-phenyl-1H-pyrazol-5-amine

A suspension of amino-pyrazole (10 g, 62.9 mmol) and cyclohexanone (13 mL, 126 mmol) and 4-methylbenzenesulfonic acid hydrate (11.4 g, 62.9 mmol) in 1.4-dioxane (50 mL) was stirred for 8 hours at 90° C. The precipitate was collected by filtration and washed with acetonitrile to afford crude product which was recrystallized from methanol to afford 4-cyclohexenyl-3-phenyl-1H-pyrazol-5-amine (4.18 g) as white solid.

¹H NMR (Chloroform-d): δ 7.51 (d, J=6.98 Hz, 2H), 7.31-7.43 (m, 3H), 5.81 (br. s., 1H), 2.19 (br. s., 2H), 1.98 (d, J=1.88 Hz, 2H), 1.59-1.70 (m, 4H). LC-MS: m/z 240.1 (M+H)⁺.

4-(cyclohex-1-en-1-yl)-3-phenyl-1H-pyrazol-5-amine

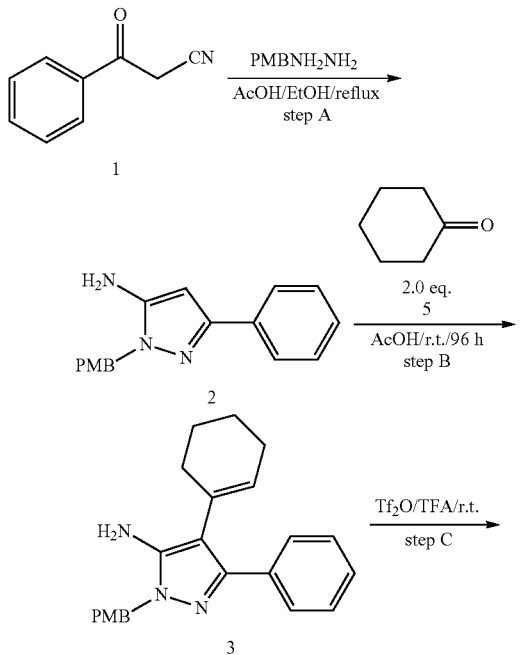

Step A: 1-(4-methoxybenzyl)-3-phenyl-1H-pyrazol-5-amine

A mixture of 3-oxo-3-phenylpropanenitrile (14.5 g, 0.1 mmol), (4-methoxybenzyl)hydrazine (15.2 g, 0.1 mmol), acetic acid (40 mL) and ethanol (150 mL) was heated to 85° C. overnight. The mixture was cooled to room temperature and poured to water (300 mL). The mixture was basified by adding aqueous sodium hydroxide at 0° C. to pH 7-8. The resulting suspension was filtrated. The filter cake was washed with water, dried in vacuo to afford 1-(4-methoxybenzyl)-3-phenyl-H-pyrazol-5-amine (14.4 g) as a white solid.

¹H NMR (Chloroform-d): δ 7.79 (d, J=8.8 Hz, 2H), 7.38-7.42 (m, 2H), 7.28-7.38 (m, 1H), 7.19 (d, J=8.8 Hz, 2H), 6.89 (d, J=8.8 Hz, 2H), 5.91 (s, 1H), 5.24 (s, 2H), 3.81 (s, 3H). LC-MS: m/z 280.1 (M+H)⁺.

Step B: 4-(cyclohex-1-en-1-yl)-1-(4-methoxybenzyl)-3-phenyl-1H-pyrazol-5-amine

A mixture of 1-(4-methoxybenzyl)-3-phenyl-1H-pyrazol-5-amine (9 g, 32.5 mmol) and cyclohexanone (6.4 g, 65.0 mmol) in acetic acid (50 mL) was stirred at room temperature for 16 h. The mixture was poured to water (150 mL). Aqueous sodium hydroxide was added into the mixture at 0° C. to pH 7-8. The resulting mixture was extracted with ethyl acetate (60 mL) three times. The combined organic phase was washed with brine, dried over anhydrous sodium sulfate and evaporated to dryness. The residue was purified with column chromatography (ethyl acetate:petroleum ether=1:3) on silica gel to afford 4-cyclohexenyl-1-(4-methoxybenzyl)-3-phenyl-1H-pyrazol-5-amine (6.5 g) as a white solid. LC-MS: m/z 360.2 (M+H)⁺.

Step C: 4-(cyclohex-1-en-1-yl)-3-phenyl-1H-pyrazol-5-amine

A mixture of 4-cyclohexenyl-1-(4-methoxybenzyl)-3-phenyl-1H-pyrazol-5-amine (6.0 g, 16.7 mmol) and trifluoromethanesulfonic anhydride (12 mL) in trifluoroacetic acid (36 mL) was stirred at 30° C. for 2 h. The mixture was poured to water (50 mL). Aqueous sodium hydroxide was added into the mixture at 0° C. to pH 7-8. The mixture was extracted with ethyl acetate (60 mL) three times. The combined organic phase was washed with brine, dried over anhydrous sodium sulfate and evaporated to dryness. The residue was purified with column chromatography (methanol:dichloromethane=1:20) on silica gel to afford 4-cyclohexenyl-3-phenyl-1H-pyrazol-5-amine (2.6 g) as a white solid.

¹H NMR (Chloroform-d) δ 7.51 (d, J=6.98 Hz, 2H), 7.31-7.43 (m, 3H), 5.81 (br. s., 1H), 2.19 (br. s., 2H), 1.98 (d, J=1.88 Hz, 2H), 1.59-1.70 (m, 4H). LC-MS: m/z 240.1 (M+H)⁺.

4-methoxy-1,3,5-triazin-2-amine

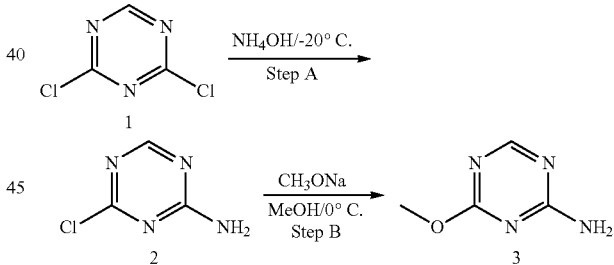

Step A: 4-chloro-1,3,5-triazin-2-amine 2,4-dichloro-1,3,5-triazine (8.0 g, 53.3 mmol) was added in portions to 200 mL of NH₄OH at −20° C. After addition, the mixture was stirred at −20° C. for 10 mins, and then filtered, washed with water and dried to give 4-chloro-1,3,5-triazin-2-amine (5.7 g) as a yellow solid which was used to the next step without further purification. LC-MS: m/z 131.1 (M+H)⁺.

Step B: 4-methoxy-1,3,5-triazin-2-amine

To the solution of 4-chloro-1,3,5-triazin-2-amine (5.7 g, 44.0 mmol) in MeOH (100 mL) cooled to 0° C. was added CH₃ONa (35.2 mL, 176.1 mmol, 5.0 M) dropwise. Then the mixture was stirred at room temperature for 1 h. Half of the solvent was removed by vacuum, and the precipitate was filtered, washed with water to afford 4-methoxy-1,3,5-triazin-2-amine as a white solid (1.0 g). LC-MS: m/z 127.1 (M+H)+.

N2-methyl-1,3,5-triazine-2,4-diamine

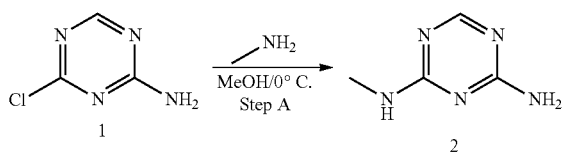

Step A: The mixture of 4-chloro-1,3,5-triazin-2-amine (200 mg, 1.5 mmol) in MeNH$_2$/THF (2 mol/L, 10 mL) was stirred at r.t. for 10 min. The mixture was concentrated in vacuo, and the residue was purified by flash chromatography (DCM/MeOH 10/1) to afford the desired product as a white solid. (106 mg). LC-MS: m/z 125.9 (M+H)+.

1-((2-(trimethylsilyl)ethoxy)methyl)-1H-pyrazol-3-amine

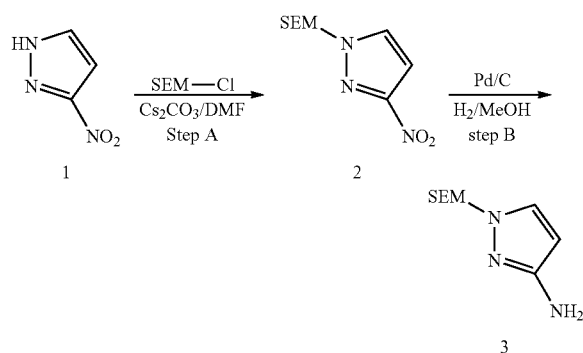

Step A: 3-nitro-1-((2-(trimethylsilyl)ethoxy)methyl)-1H-pyrazole

A mixture of compound 1 (10 g, 0.089 mmol) and Cs$_2$CO$_3$ (1.9 g, 0.116 mmol) in DMF (10 mL) was stirred at r.t. for 16 h. The mixture was diluted with water (20 mL) and extracted with EA (20 mL×3). The organic layer was dried, concentrated and purified by silica gel chromatography (PE:EA=3:1) to afford compound 2 (9 g) as a white solid.

$^1$H NMR (400 MHz, CHLOROFORM-d): δ 0.01-0.03 (m, 9H) 0.91-0.99 (m, 2H) 3.59-3.66 (m, 2H) 5.53 (s, 2H) 7.01 (d, J=2.69 Hz, 1H) 7.69 (d, J=2.69 Hz, 1H). LC-MS: m/z 244.5 (M+H)+.

Step B: 1-((2-(trimethylsilyl)ethoxy)methyl)-1H-pyrazol-3-amine

The compound 2 (9 g, 0.037 mmol) and Pd/C (0.9 g) in MeOH (30 mL) was stirred at r.t. for 16 h under H$_2$ atmosphere. The mixture was filtered and concentrated to give the crude product which was directly used to the next step without further purification. LC-MS: m/z 214.5 (M+H)+.

2-((2-(trimethylsilyl)ethoxy)methyl)-2H-1,2,3-triazol-4-amine

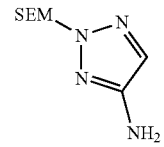

This compound was prepared according to the procedures for preparing 1-((2-(trimethylsilyl)ethoxy)methyl)-1H-pyrazol-3-amine by using intermediate 1 as 4-nitro-2H-1,2,3-triazole.

$^1$H NMR (DMSO-d$_6$): δ 7.00 (s, 1H), 5.35 (s, 2H), 5.13 (s, 2H), 3.49-3.58 (m, 2H), 0.69-0.89 (m, 2H), −0.04 (s, 9H). LC-MS: m/z 215.2 (M+H)+.

1-(4-methoxybenzyl)-1H-pyrazole-3,5-diamine

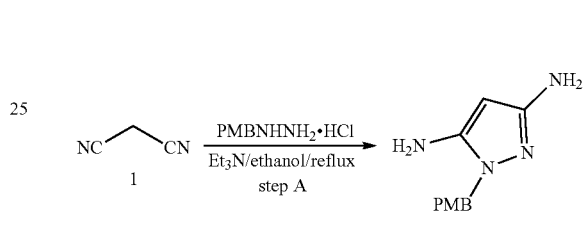

Step A: The mixture of malononitrile (1.9 g, 0.028 mmol) and (4-methoxybenzyl)hydrazine hydrochloride (5.4 g, 0.028 mmol) in EtOH (20 mL) and TEA (3 mL) was heated to reflux for 16 h. The mixture was concentrated to dryness. The residue was suspended in water and extracted with EA (10 mL×3). The combined organic layers were dried and concentrated to give the crude product which was directly used to the next step without further purification. LC-MS: m/z 219.5 (M+H)+.

Methyl 2-(2,3-dihydrobenzo[b][1,4]dioxin-6-yl)acetate

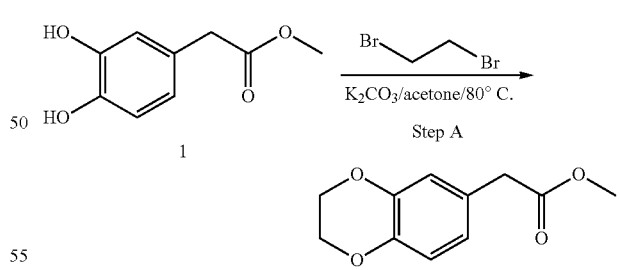

To a solution of methyl 2-(3,4-dihydroxyphenyl)acetate (4 g, 0.022 mol) in DMF (20 mL) were added 1,2-dibromoethane (4.09 g, 0.022 mol) and K$_2$CO$_3$ (6 g, 0.044 mol). The reaction mixture was heated to 80° C. for 4 h. The reaction mixture was then poured into water, extracted with ethyl acetate, dried over anhydrous Na$_2$SO$_4$, filtered, and concentrated to dryness. The residue was purified by column chromatography on silica gel (eluting PE/EA=10:1) to give the desired product (1.3 g).

$^1$H NMR (DMSO-d$_6$): δ 6.73-6.81 (m, 3H), 6.65-6.73 (m, 1H), 4.16-4.27 (m, 5H), 3.55 (s, 3H). LC-MS: m/z 223.1 (M+H)$^+$.

3-(tert-butyldimethylsilyloxy)pyridin-2-amine

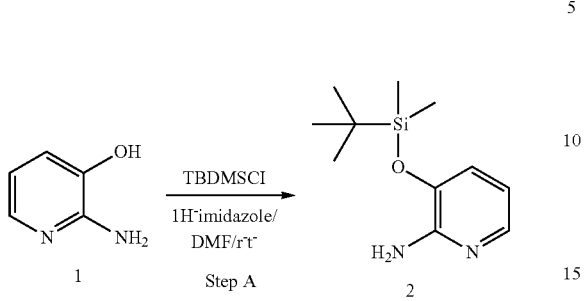

Step A: To a mixture of 2-aminopyridin-3-ol (220 mg, 2 mmol), 1H-imidazole (204 mg, 3 mmol) in chloroform (20 mL) was added tert-butylchlorodimethylsilane (302 mg, 2 mmol) slowly at room temperature. Then the reaction mixture was stirred at room temperature overnight. The mixture was evaporated to dryness. The residue was purified by column chromatography on silica gel (methanol:dichloromethane=1:50) to afford 3-(tert-butyl-dimethylsilyloxy) pyridin-2-amine (360 mg) as a white solid. LC-MS m/z: 225.1 (M+H)$^+$.

5-((tert-butyldimethylsilyl)oxy)pyridin-2-amine

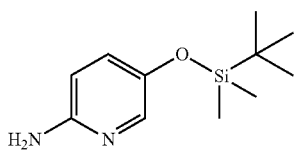

This compound was prepared according to 3-(tert-butyldimethylsilyloxy)pyridin-2-amine by using Intermediate 1 as 6-aminopyridin-3-ol in step A. LC-MS m/z: 225.1 (M+H)$^+$.

General procedure 2a

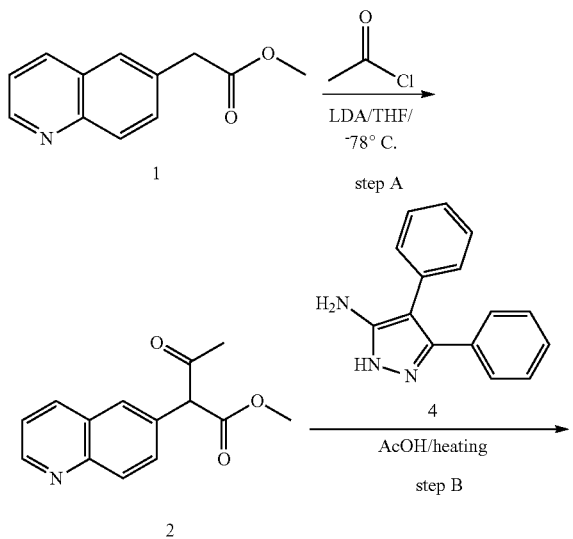

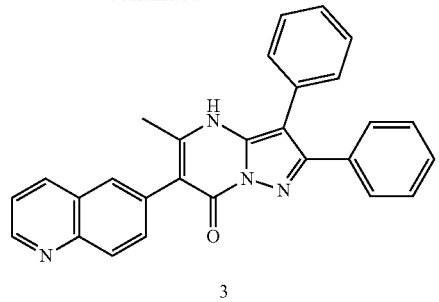

Step A: methyl 3-oxo-2-(quinolin-6-yl)butanoate

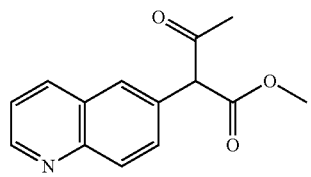 [SMILES: COC(=O)C(C(C)=O)c1ccc2ncccc2c1]

To a solution of methyl 2-(quinolin-6-yl)acetate 1 (148 g, 0.736 mol, 1.0 eq.) in THF (1 L) was added LDA (1.5 M in THF, 589 mL, 0.883 mol, 1.2 eq.) dropwise at −30~−35° C. The mixture was stirred at −30~−35° C. for 30 min and acetyl chloride (56 mL, 0.788 mol, 1.05 eq.) was added dropwise. Then the mixture was stirred at rt for 6 h. The mixture was poured slowly to saturated NH$_4$Cl and extracted with EA (3*350 mL). The combined organic phase was washed with brine, dried over anhydrous MgSO$_4$ and concentrated in vacuo. The residue was purified by flash chromatography to afford the desired Intermediate 2 as a brown oil (150 g, 84% yield).

Step B: Compound 204: 5-methyl-2,3-diphenyl-6-(quinolin-6-yl)pyrazolo[1,5-a]pyrimidin-7(4H)-one

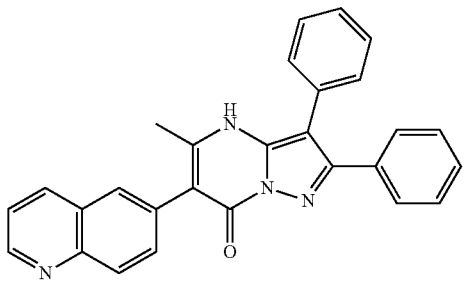

The mixture of Intermediate 2 (150 g) and 4 (1.0 eq) in AcOH (700 mL) was stirred at 90° C. for 4 h. A solid was filtered off and washed with EA (3*100 mL) to afford the desired product 3.

$^1$H NMR (DMSO-d$_6$) δ: 12.06 (s, 1H), 8.95 (dd, J=4.2, 1.7 Hz, 1H), 8.40 (d, J=7.5 Hz, 1H), 8.08 (d, J=8.9 Hz, 1H), 7.97 (d, J=1.6 Hz, 1H), 7.76 (dd, J=8.6, 1.9 Hz, 1H), 7.54-7.59 (m, 1H), 7.24-7.51 (m, 10H), 2.25 (s, 3H). LC-MS: m/z 429.3 (M+H)$^+$.

Compound 205: 2-(2-fluorophenyl)-5-methyl-3-phenyl-6-(quinolin-6-yl)pyrazolo[1,5-a]pyrimidin-7(4H)-one

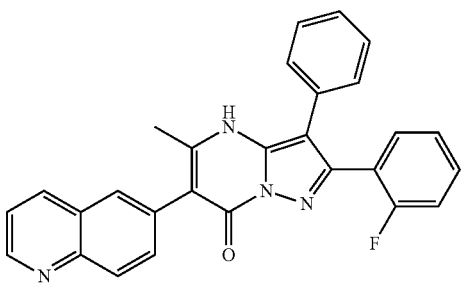 [SMILES: Cc1[nH]c2c(-c3ccccc3)c(-c3ccccc3F)nn2c(=O)c1-c1ccc2ncccc2c1]

This compound was prepared according to General procedure 2a by using Intermediate 4 as 3-(2-fluorophenyl)-4-phenyl-1H-pyrazol-5-amine e in step B.

Step B: The solution of 3-(2-fluorophenyl)-4-phenyl-1H-pyrazol-5-amine (50 mg, 0.20 mmol) and methyl 3-oxo-2-(quinolin-6-yl)butanoate (62.4 mg, 0.26 mmol) in AcOH (2 ml) was stirred at 100° C. for 1 hour. After cooling to room temperature, saturated $NaHCO_3$ was added till pH>7. The mixture was extracted with DCM (50 mL), washed with brine (20 mL), dried over anhydrous sodium sulfate and concentrated to dryness. The residue was purified by prep-TLC (DCM:MeOH=25:1) to obtain 2-(2-fluorophenyl)-5-methyl-3-phenyl-6-(quinolin-6-yl)pyrazolo[1,5-a]pyrimidin-7(4H)-one.

$^1$H NMR (DMSO-$d_6$) δ: 12.19 (br. s., 1H), 8.95 (dd, J=4.2, 1.7 Hz, 1H), 8.41 (d, J=7.5 Hz, 1H), 8.09 (d, J=8.6 Hz, 1H), 7.98 (d, J=1.9 Hz, 1H), 7.76 (dd, J=8.9, 1.9 Hz, 1H), 7.58 (dd, J=8.2, 4.2 Hz, 1H), 7.45-7.54 (m, 2H), 7.36-7.43 (m, 2H), 7.24-7.35 (m, 4H), 7.16-7.24 (m, 1H), 2.28 (s, 3H). LC-MS: m/z 447.1 (M+H)$^+$.

Compound 206: 5-methyl-2-phenyl-3-(piperidin-1-yl)-6-(quinolin-6-yl)pyrazolo[1,5-a]pyrimidin-7(4H)-one

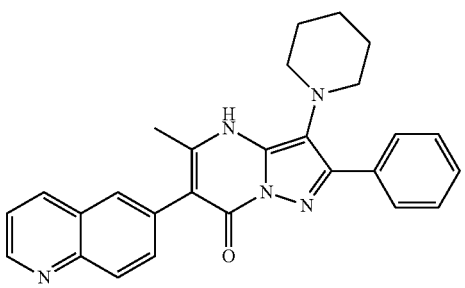 [SMILES: Cc1[nH]c2c(N3CCCCC3)c(-c3ccccc3)nn2c(=O)c1-c1ccc2ncccc2c1]

This compound was prepared according to General procedure 2a by using Intermediate 4 as 3-phenyl-4-(piperidin-1-yl)-1H-pyrazol-5-amine in step B.

Step B: methyl 3-oxo-2-(quinolin-6-yl)butanoate (200 mg, 0.82 mmol) and 5-phenyl-4-(piperidin-1-yl)-1H-pyrazol-3-amine (200 mg, 0.82 mmol) were dissolved in AcOH (8 ml). The mixture was stirred at 95° C. for 10 min. After cooling to room temperature, the mixture was poured into water and extracted with EA (50 ml*3). The EA layer was concentrated to dryness. The residue was basified with $NaHCO_3$ aq. solution and filtered. The filter cake was purified by prep-HPLC to give the title compound.

$^1$H NMR (DMSO-$d_6$) δ: 11.52 (br. s., 1H), 8.94 (dd, J=4.2, 1.7 Hz, 1H), 8.34-8.44 (m, 1H), 8.02-8.19 (m, 3H), 7.95 (d, J=1.9 Hz, 1H), 7.74 (dd, J=8.9, 1.9 Hz, 1H), 7.58 (dd, J=8.2, 4.2 Hz, 1H), 7.31-7.51 (m, 3H), 3.11 (t, J=4.8 Hz, 4H), 2.34 (s, 3H), 1.68 (br. s., 4H), 1.50-1.64 (m, 2H). LC-MS: m/z 436.4 (M+H)$^+$.

Compound 207: 3-(4,4-difluoropiperidin-1-yl)-5-methyl-2-phenyl-6-(quinolin-6-yl)pyrazolo[1,5-a]pyrimidin-7(4H)-one

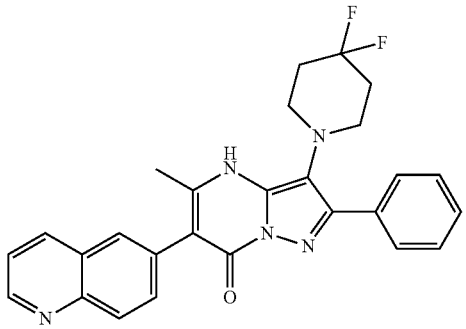 [SMILES: Cc1[nH]c2c(N3CCC(F)(F)CC3)c(-c3ccccc3)nn2c(=O)c1-c1ccc2ncccc2c1]

This compound was prepared according to General procedure 2a by using Intermediate 4 as 4-(4,4-difluoropiperidin-1-yl)-3-phenyl-1H-pyrazol-5-amine in step B.

Step B: The solution of 4-(4,4-difluoropiperidin-1-yl)-3-phenyl-1H-pyrazol-5-amine (200 mg, 0.72 mmol) and methyl 3-oxo-2-(quinolin-6-yl)butanoate (262.2 mg, 1.08 mmol) in AcOH (3 ml) was stirred at 100° C. for 1 hour. After cooling to room temperature, saturated $NaHCO_3$ was added till pH>7. The mixture was extracted with DCM (60 mL), washed with brine (20 mL), dried over anhydrous sodium sulfate and concentrated to dryness. The residue was purified by prep-TLC (DCM:MeOH=25:1) to obtain 3-(4,4-difluoropiperidin-1-yl)-5-methyl-2-phenyl-6-(quinolin-6-yl)pyrazolo[1,5-a]pyrimidin-7(4H)-one.

$^1$H NMR (DMSO-$d_6$) δ: 11.71 (s, 1H), 8.94 (d, J=2.7 Hz, 1H), 8.39 (d, J=7.8 Hz, 1H), 8.07 (d, J=8.9 Hz, 1H), 8.00 (d, J=7.0 Hz, 2H), 7.94 (s, 1H), 7.74 (dd, J=8.7, 2.0 Hz, 1H), 7.58 (dd, J=8.2, 4.2 Hz, 1H), 7.52 (t, J=7.4 Hz, 2H), 7.44 (t, J=7.3 Hz, 1H), 3.24 (m, 4H), 2.33 (s, 3H), 2.04-2.22 (m, 4H). LC-MS: m/z 472.2 (M+H)$^+$.

Compound 208: 3-(cyclohex-1-en-1-yl)-5-methyl-2-phenyl-6-(quinoxalin-6-yl)pyrazolo[1,5-a]pyrimidin-7(4H)-one

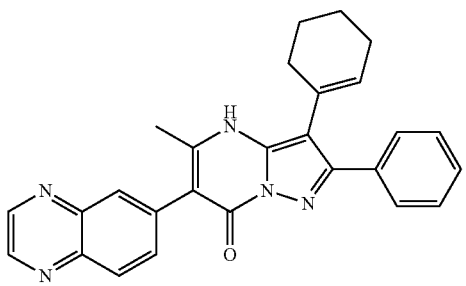

This compound was prepared according to General procedure 2a by using Intermediate 1 as methyl 2-(quinoxalin-6-yl)acetate in step A and Intermediate 4 as 4-(cyclohex-1-en-1-yl)-3-phenyl-1H-pyrazol-5-amine in step B.

Step B: The solution of 4-(cyclohex-1-en-1-yl)-3-phenyl-1H-pyrazol-5-amine (60 mg, 0.25 mmol) and methyl 3-oxo-2-(quinoxalin-6-yl)butanoate (79.6 mg, 0.33 mmol) in AcOH (5 ml) was stirred at 100° C. for 1 hour. After cooling to room temperature, solvent was removed by vacuum, and saturated NaHCO₃ was added till pH>7. The mixture was diluted with DCM (60 mL), washed with brine (20 mL), dried over anhydrous sodium sulfate and concentrated to dryness. The residue was purified by prep-TLC (DCM: MeOH=25:1) to obtain 3-(cyclohex-1-en-1-yl)-5-methyl-2-phenyl-6-(quinoxalin-6-yl)pyrazolo[1,5-a]pyrimidin-7(4H)-one.

$^1$H NMR (DMSO-d$_6$) δ: 11.90 (br. s., 1H), 9.00 (br. s., 2H), 7.48-8.26 (m, 8H), 5.89 (br. s., 1H), 2.10-2.52 (m, 7H), 1.72 (br. s., 4H). LC-MS: m/z 434.1 (M+H)⁺.

Compound 209: 6-(4-methoxyphenyl)-5-methyl-2,3-diphenylpyrazolo[15-a]pyrimidin-7(4H)-one

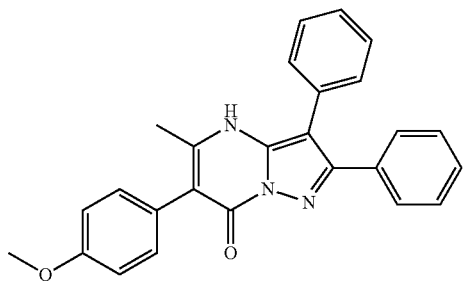

This compound was prepared according to General procedure 2a by using Intermediate 1 as methyl 2-(4-methoxyphenyl)acetate in step A and Intermediate 4 as 3, 4-diphenyl-1H-pyrazol-5-amine in step B.

Step B: The mixture of methyl 2-(4-methoxyphenyl)-3-oxobutanoate (300 mg, 1.3 mmol) and 3, 4-diphenyl-1H-pyrazol-5-amine (206 mg, 0.85 mmol) in AcOH (15 mL) was stirred at 100° C. for 2 h to afford the title compound.

$^1$H NMR (DMSO-d$_6$) δ: 11.88 (s, 1H), 7.37-7.49 (m, 5H), 7.28-7.36 (m, 5H), 7.21-7.28 (m, 2H), 6.95-7.05 (m, 2H), 3.80 (s, 3H), 2.17 (s, 3H). LC-MS: m/z 408.0 (M+H)⁺.

Compound 210: 6-(4-ethoxyphenyl)-5-methyl-2,3-diphenylpyrazolo[1,5-a]pyrimidin-7(4H)-one

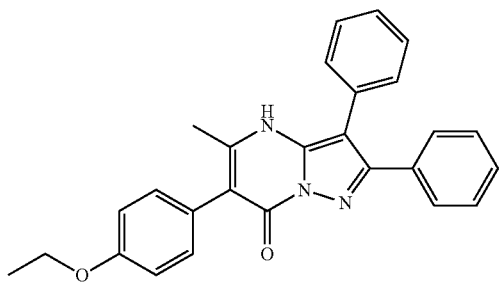 [SMILES: CCOc1ccc(-c2c(C)[nH]c3c(-c4ccccc4)c(-c4ccccc4)nn3c2=O)cc1]

This compound was prepared according to General procedure 2a by using Intermediate 1 as methyl 2-(4-ethoxyphenyl)acetate in step A and Intermediate 4 as 3, 4-diphenyl-1H-pyrazol-5-amine in step B.

Step B: The solution of 3,4-diphenyl-1H-pyrazol-5-amine (148 mg, 0.63 mmol) and methyl 2-(4-ethoxyphenyl)-3-oxobutanoate (150 mg, 0.63 mmol) in AcOH (5 ml) was stirred at 100° C. for 4 hour. After cooling to room temperature, the reaction mixture was filtered and washed with EA (6 mL) and MeOH (0.5 mL) to obtain title compound.

$^1$H NMR (DMSO-d$_6$) δ: 11.88 (s, 1H), 7.36-7.49 (m, 5H), 7.27-7.36 (m, 5H), 7.19-7.26 (m, 2H), 6.93-7.02 (m, 2H), 4.07 (q, J=7.0 Hz, 2H), 2.17 (s, 3H), 1.36 (t, J=7.2 Hz, 3H). LC-MS: m/z 422.0 (M+H)⁺.

Compound 211: 6-(2,3-dihydrobenzo[b][1,4]dioxin-6-yl)-5-methyl-2,3-diphenylpyrazolo[1,5-a]pyrimidin-7(4H)-one

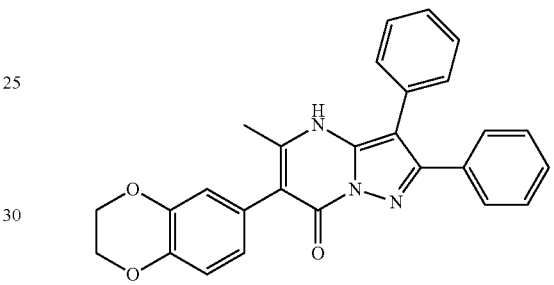

This compound was prepared according to General procedure 2a, step A-B, starting from methyl 2-(2,3-dihydrobenzo[b][1,4]dioxin-6-yl)acetate in step A.

Step A: methyl 2-(2,3-dihydrobenzo[b][1,4]dioxin-6-yl)-3-oxobutanoate

To a solution of methyl 2-(2,3-dihydrobenzo[b][1,4]dioxin-6-yl)acetate (1.3 g, 6.3 mmol) in THF (15 ml) was added slowly LDA (3.2 ml, 2 mmol/ml in THF) at −30° C. Then acetyl chloride (730 mg, 9.5 mmol) was added slowly. The reaction mixture was stirred for 30 mins at −30° C. and allowed to room temperature for 1 h. The mixture was poured into water, extracted over ethyl acetate, dried over anhydrous Na₂SO₄, filtered, and concentrated to give the crude product (1.3 g, crude) as a yellow liquid, which was used directly to the next step without further purification.

Step B: 6-(2,3-dihydrobenzo[b][1,4]dioxin-6-yl)-5-methyl-2,3-diphenylpyrazolo[1,5-a]pyrimidin-7(4H)-one A solution of methyl 2-(2,3-dihydrobenzo[b][1,4]dioxin-6-yl)-3-oxobutanoate (crude 400 mg) and 3,4-diphenyl-1H-pyrazol-5-amine (200 mg, 0.86 mmol) in AcOH (10 ml) was heated to 120° C. overnight. The reaction mixture was cooled to room temperature to give the desired product 6-(2,3-dihydrobenzo[b][1,4]dioxin-6-yl)-5-methyl-2,3-diphenylpyrazolo[1,5-a]pyrimidin-7(4H)-one.

$^1$H NMR (DMSO-d$_6$) δ: 11.88 (s, 1H), 7.38-7.52 (m, 5H), 7.24-7.38 (m, 5H), 6.91 (d, J=8.1 Hz, 1H), 6.83 (d, J=2.1 Hz, 1H), 6.77 (d, J=8.2, 2.0 Hz, 1H), 4.29 (s, 4H), 2.19 (s, 3H). LC-MS: m/z 435.9 (M+H)⁺.

Compound 212: 3-(cyclohex-1-en-1-yl)-6-(4-methoxyphenyl)-5-methyl-2-phenylpyrazolo[1,5-a]pyrimidin-7(4H)-one

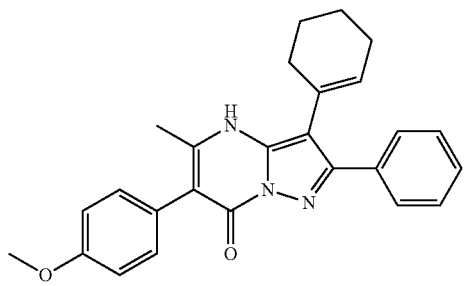 [SMILES: COc1ccc(-c2c(C)[nH]c3c(C4=CCCCC4)c(-c4ccccc4)nn3c2=O)cc1]

This compound was prepared according to General procedure 2a by using Intermediate 1 as methyl 2-(4-methoxyphenyl)acetate in step A and Intermediate 4 as 4-(cyclohex-1-en-1-yl)-3-phenyl-1H-pyrazol-5-amine in step B.

Step B: The solution of 4-(cyclohex-1-en-1-yl)-3-phenyl-1H-pyrazol-5-amine (200 mg, 0.84 mmol) and methyl 2-(4-methoxyphenyl)-3-oxobutanoate (371.5 mg, 1.67 mmol) in AcOH (5 ml) was stirred at 100° C. for 1 hour. After cooling to room temperature, solvent was removed by vacuum, and saturated NaHCO$_3$ was added to pH>7 to obtain 3-(cyclohex-1-en-1-yl)-6-(4-methoxyphenyl)-5-methyl-2-phenylpyrazolo[1,5-a]pyrimidin-7(4H)-one.

$^1$H NMR (DMSO-d$_6$) δ: 11.62 (s, 1H), 7.72-7.85 (m, 2H), 7.34-7.55 (m, 3H), 7.19-7.31 (m, 2H), 6.93-7.07 (m, 2H), 5.84 (br. s., 1H), 3.81 (s, 3H), 2.17-2.32 (m, 5H), 1.98-2.12 (m, 2H), 1.70 (br. s., 4H). LC-MS: m/z 412.3 (M+H)$^+$.

Compound 213: 3-(4,4-difluoropiperidin-1-yl)-6-(4-methoxyphenyl)-5-methyl-2-phenylpyrazolo[1,5-a]pyrimidin-7(4H)-one

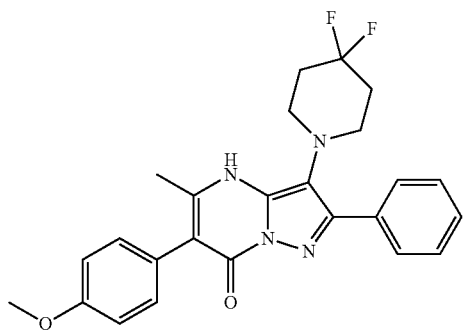 [SMILES: COc1ccc(-c2c(C)[nH]c3c(N4CCC(F)(F)CC4)c(-c4ccccc4)nn3c2=O)cc1]

This compound was prepared according to General procedure 2a by using Intermediate 1 as methyl 2-(4-methoxyphenyl)acetate in step A and Intermediate 4 as 4-(4,4-difluoropiperidin-1-yl)-3-phenyl-1H-pyrazol-5-amine in step B.

Step B: The mixture of 4-(4,4-difluoropiperidin-1-yl)-3-phenyl-1H-pyrazol-5-amine (321 mg, 1.4 mmol) and methyl 2-(4-methoxyphenyl)-3-oxobutanoate (200 mg, 0.72 mmol) in AcOH (20 mL) was stirred at 120° C. for 2 h to afford the title compound.

$^1$H NMR (CHLOROFORM-d) δ: 7.51 (br. s., 5H), 7.24 (d, J=8.6 Hz, 2H), 6.98 (d, J=8.6 Hz, 2H), 3.85 (s, 3H), 3.69 (br. s., 4H), 3.18 (br. s., 2H), 2.37 (s, 3H), 2.18 (s, 2H). LC-MS: m/z 451.3 (M+H)$^+$.

General procedure 2b:

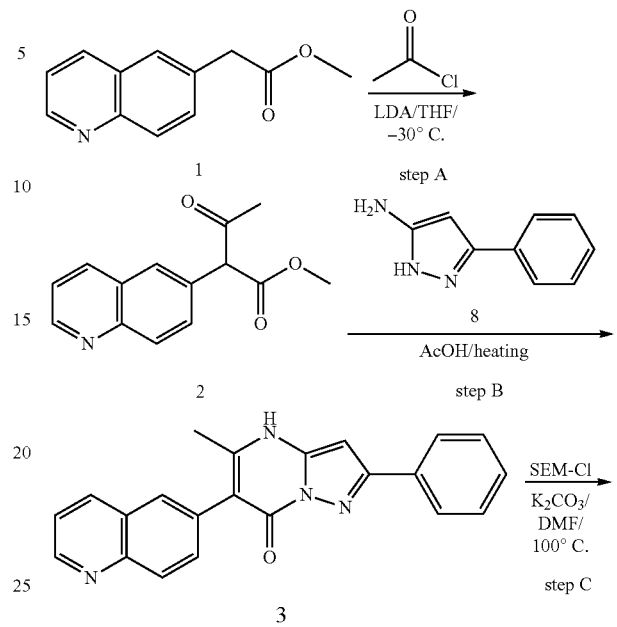

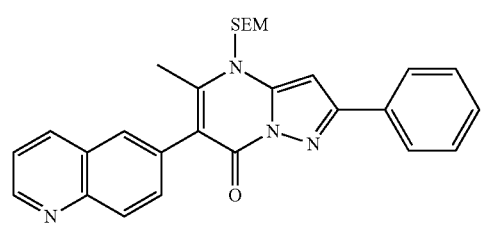

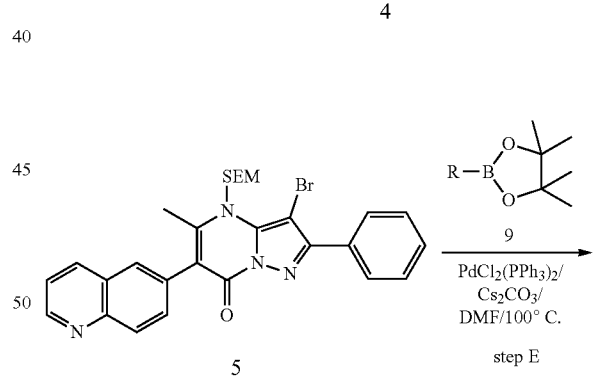

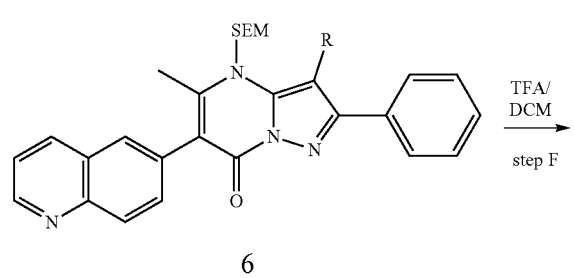

-continued

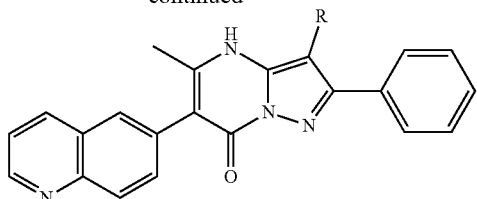

7

Step A: methyl 3-oxo-2-(quinolin-6-yl)butanoate

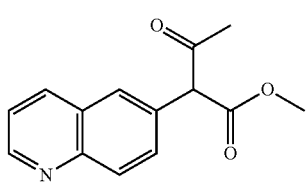 [SMILES: COC(=O)C(C(C)=O)c1ccc2ncccc2c1]

To a solution of methyl 2-(quinolin-6-yl)acetate (14.8 g, 73.6 mmol, 1.0 eq.) in THF (100 mL) was added LDA (1.5 M in THF, 60 mL, 88.3 mmol, 1.2 eq.) dropwise at −30~−35° C. The mixture was stirred at −30~−35° C. for 30 min and acetyl chloride (5.6 mL, 78.8 mmol, 1.05 eq.) was added dropwise. Then the mixture was stirred at r.t. for 6 h. The mixture was poured slowly to saturated NH$_4$Cl and extracted with EA (3×30 mL). The combined organic phase was washed with brine, dried over anhydrous MgSO$_4$ and concentrated in vacuo to get the title Intermediate 2 which was directly used to the next step without further purification.

Step B: 5-methyl-2-phenyl-6-(quinolin-6-yl)pyrazolo[1,5-a]pyrimidin-7(4H)-one

A suspension of methyl 3-oxo-2-(quinolin-6-yl)butanoate (1.98 g, 8.17 mmol) and 3-phenyl-1H-pyrazol-5-amine (1 g, 6.28 mmol) in 1,4-dioxane (10 ml) and AcOH (2 ml) was refluxed for 16 hours under N$_2$ protection. The mixture was cooled to the room temperature, concentrated, and neutralized with saturated sodium hydrogen carbonate solution to adjust to pH 7. The precipitates were collected by filtration, washed with petroleum ether and dried to give the Intermediate 3 (600 mg, 27% yield).

$^1$H NMR (DMSO-d$_6$) δ: 12.56 (br. s., 1H), 8.94 (dd, J=4.25, 1.61 Hz, 1H), 8.39 (d, J=7.63 Hz, 1H), 7.99-8.10 (m, 3H), 7.96 (d, J=1.76 Hz, 1H), 7.75 (dd, J=8.66, 1.91 Hz, 1H), 7.57 (dd, J=8.36, 4.25 Hz, 1H), 7.46-7.53 (m, 2H), 7.40-7.46 (m, 1H), 6.67 (s, 1H), 2.26 (s, 3H).

Step C: 5-methyl-2-phenyl-6-(quinolin-6-yl)-4-((2-(trimethylsilyl)ethoxy)methyl)pyrazolo[1,5-a]pyrimidin-7(4H)-one

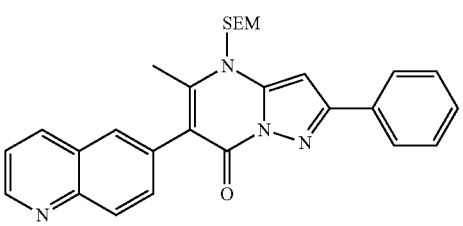 [SMILES: Cc1c(-c2ccc3ncccc3c2)c(=O)n2nc(-c3ccccc3)cc2n1COCC[Si](C)(C)C]

To a solution of Intermediate 3 (500 mg, 1.42 mmol) and K2CO3 (393 mg, 2.84 mmol) in DMF (15 ml) at ambient temperature was added (2-(chloromethoxy)ethyl)trimethylsilane (473 mg, 2.84 mmol) dropwise. The mixture was stirred for 10 min at ambient temperature and heated to 100° C. overnight. The mixture was cooled to the room temperature, washed with saturated sodium hydrogen carbonate solution, and extracted with DCM (2×30 mL). The combined organic layers were washed with brine (3×20 ml), dried over anhydrous sodium sulfate, and concentrated invacuo. The residue was purified by silica gel column eluting with DCM/MeOH (30/1 to 10/1) to obtain the Intermediate 4 as a white solid (350 g, 51% yield).

Step D: 3-bromo-5-methyl-2-phenyl-6-(quinolin-6-yl)-4-((2-(trimethylsilyl)ethoxy)methyl)pyrazolo[1,5-a]pyrimidin-7(4H)-one

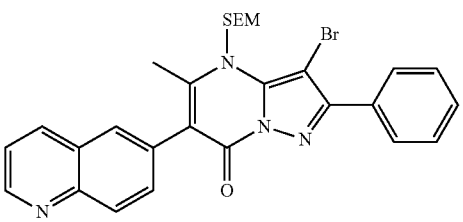 [SMILES: Cc1c(-c2ccc3ncccc3c2)c(=O)n2nc(-c3ccccc3)c(Br)c2n1COCC[Si](C)(C)C]

To a solution of Intermediate 4 (350 mg, 0.725 mmol) in DCM (5 ml) at ambient temperature was added NBS (163 mg, 0.92 mmol). The resultant mixture was stirred for 3 hours at ambient temperature, washed with water, and extracted with DCM (20 mL). The combined organic layers were washed with brine (20 ml), dried over anhydrous sodium sulfate, and concentrated in vacuo. The residue was purified by prep-TLC (DCM/MeOH=20/1) to obtain the Intermediate 5 (250 mg, 61% yield). LC-MS: m/z 561.1 (M+H)$^+$.

The following compounds were prepared according to General procedure 2b, step E and step F, starting from intermediate 5.

Compound 215: 3-(cyclopent-1-en-1-yl)-5-methyl-2-phenyl-6-(quinolin-6-yl)pyrazolo[1,5-a]pyrimidin-7(4H)-one

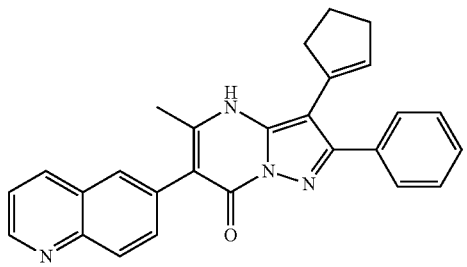 [SMILES: Cc1[nH]c2c(C3=CCCC3)c(-c3ccccc3)nn2c(=O)c1-c1ccc2ncccc2c1]

Step E stoichiometry: 3-bromo-5-methyl-2-phenyl-6-(quinolin-6-yl)-4-((2-(trimethylsilyl)ethoxy)methyl)pyrazolo[1,5-a]pyrimidin-7(4H)-one (150 mg, 0.27 mmol), 2-(cyclopent-1-en-1-yl)-4,4,5,5-tetramethyl-1,3,2-dioxaborolane (155.0 mg, 0.80 mmol), Bis(triphenylphosphine)palladium(II) chloride (19.2 mg, 0.03 mmol) and cesium carbonate (174.8 mg, 0.53 mmol) in 1,4-dioxane/H$_2$O (11 mL, 10:1) under heating at 100° C. for 1 hour through microwave irradiation under nitrogen atmosphere. LC-MS: m/z 549.3 (M+H)$^+$.

Step F: To the solution of 3-(cyclopent-1-en-1-yl)-5-methyl-2-phenyl-6-(quinolin-6-yl)-4-((2-(trimethylsilyl)ethoxy)methyl)pyrazolo[1,5-a]pyrimidin-7(4H)-one (50 mg, 0.09 mmol) in DCM (0.5 mL) cooled at 0° C. was added TFA (1 mL) dropwise. Then the mixture was stirred at room temperature for 2 hours. The mixture was concentrated, and NH$_4$OH added till pH>7. The mixture was diluted with DCM (60 mL), washed with water (15 mL) and brine (15 mL), dried over anhydrous sodium sulfate, and concentrated to obtain 3-(cyclopent-1-en-1-yl)-5-methyl-2-phenyl-6-(quinolin-6-yl)pyrazolo[1,5-a]pyrimidin-7(4H)-one.
$^1$H NMR (DMSO-d$_6$) δ: 11.76 (br. s., 1H), 8.85-9.08 (m, 1H), 8.39 (d, J=7.8 Hz, 1H), 8.07 (d, J=8.6 Hz, 1H), 7.96 (s, 1H), 7.68-7.79 (m, 3H), 7.57 (dd, J=7.9, 4.2 Hz, 1H), 7.39-7.52 (m, 3H), 5.94 (br. s., 1H), 2.54 (br. s., 2H), 2.43 (br. s., 2H), 2.30 (s, 3H), 1.88-2.11 (m, 2H). LC-MS: m/z 419.2 (M+H)$^+$.

Compound 216: 3-(cyclohex-1-en-1-yl)-5-methyl-2-phenyl-6-(quinolin-6-yl)pyrazolo[1,5-a]pyrimidin-7(4H)-one

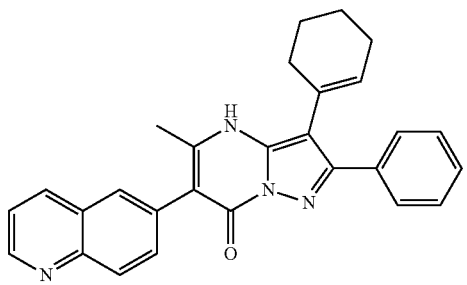

Step E stoichiometry: 3-bromo-5-methyl-2-phenyl-6-(quinolin-6-yl)-4-((2-(trimethylsilyl)ethoxy)methyl)pyrazolo[1,5-a]pyrimidin-7(4H)-one (200 mg, 0.36 mmol), 2-(cyclohex-1-en-1-yl)-4,4,5,5-tetramethyl-1,3,2-dioxaborolane (149.8 mg, 0.72 mmol), bis(triphenylphosphine)palladium(II) chloride (56.2 mg, 0.08 mmol) and cesium carbonate (234.6 mg, 0.72 mmol) in 1,4-dioxane/H$_2$O (16 mL, 10:1) under heating at 100° C. for 1 hour through microwave irradiation under nitrogen atmosphere. LC-MS: m/z 563.3 (M+H)$^+$.

Step F: To the solution of 3-(cyclohex-1-en-1-yl)-5-methyl-2-phenyl-6-(quinolin-6-yl)-4-((2-(trimethylsilyl)ethoxy)methyl)pyrazolo[1,5-a]pyrimidin-7(4H)-one (180 mg, 0.32 mmol) in DCM (0.5 mL) cooled to 0° C. was added TFA (2 mL) dropwise. The mixture was then stirred at room temperature for 2 hours. The mixture was concentrated, and NH$_4$OH added till pH>7. The mixture was diluted with DCM (120 mL), washed with water (30 mL) and brine (30 mL), dried over anhydrous sodium sulfate and concentrated to dryness to obtain 3-(cyclohex-1-en-1-yl)-5-methyl-2-phenyl-6-(quinolin-6-yl)pyrazolo[1,5-a]pyrimidin-7(4H)-one.
$^1$H NMR (DMSO-d$_6$) δ: 11.80 (s, 1H), 8.94 (dd, J=4.0, 1.6 Hz, 1H), 8.39 (d, J=7.3 Hz, 1H), 8.07 (d, J=8.6 Hz, 1H), 7.95 (d, J=1.6 Hz, 1H), 7.78-7.84 (m, 2H), 7.74 (dd, J=8.9, 1.9 Hz, 1H), 7.58 (dd, J=8.3, 4.3 Hz, 1H), 7.45-7.52 (m, 2H), 7.39-7.45 (m, 1H), 5.88 (br. s., 1H), 2.31 (s, 3H), 2.23 (br. s., 2H), 2.09 (br. s., 2H), 1.72 (br. s., 4H). LC-MS: m/z 433.4 (M+H)$^+$.

Compound 217: 3-(3,4-dihydro-2H-pyran-6-yl)-5-methyl-2-phenyl-6-(quinolin-6-yl)pyrazolo[1,5-a]pyrimidin-7(4H)-one

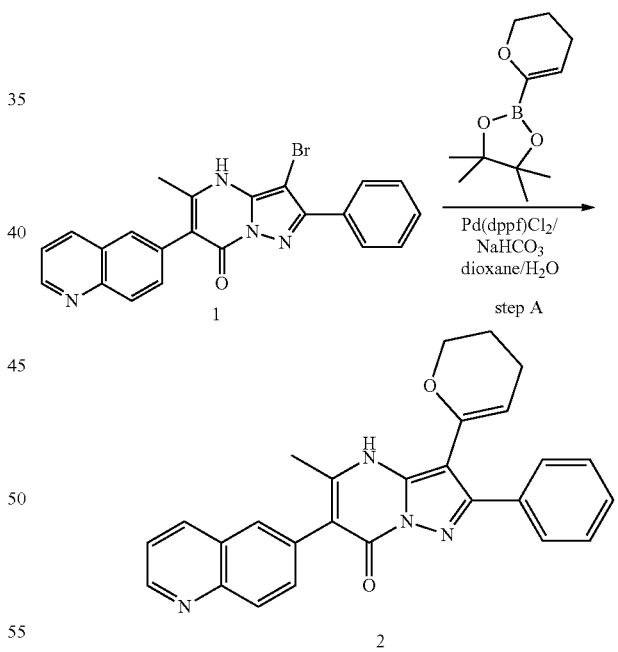

Step A: A mixture of 3-bromo-5-methyl-2-phenyl-6-(quinolin-6-yl)pyrazolo[1,5-a]pyrimidin-7(4H)-one (50 mg, 0.116 mmol), 2-(3,4-dihydro-2H-pyran-6-yl)-4,4,5,5-tetramethyl-1,3,2-dioxaborolane (49 mg, 0.232 mmol), Pd(dppf)Cl$_2$ (8.4 mg, 0.012 mmol), and NaHCO$_3$ (19 mg, 0.232 mmol) in dioxane (9 ml) and H$_2$O (3 ml) was heated to 100° C. for 4 h under N$_2$. The mixture was concentrated to dryness to give the desired product.
$^1$H NMR (METHANOL-d$_4$) δ: 8.90 (dd, J=4.3, 1.6 Hz, 1H), 8.42 (d, J=8.1 Hz, 1H), 8.13 (d, J=8.9 Hz, 1H), 7.95-8.02 (m, 1H), 7.79-7.91 (m, 3H), 7.59 (dd, J=8.2, 4.4 Hz, 1H), 7.38-7.50 (m, 3H), 4.97 (t, J=3.6 Hz, 1H), 4.12-4.22 (m, 2H), 2.36 (s, 3H), 2.15-2.27 (m, 2H), 1.90-2.04 (m, 2H). LC-MS: m/z 435.0 (M+H)⁺.

3-bromo-6-(4-methoxyphenyl)-5-methyl-2-phenyl-4-((2-(trimethylsilyl)ethoxy)methyl)pyrazolo[1,5-a]pyrimidin-7(4H)-one

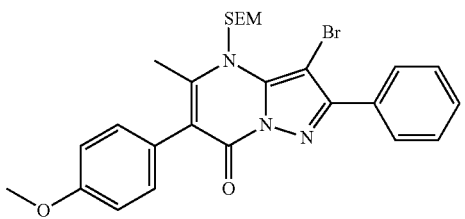 [SMILES: COc1ccc(-c2c(C)n(COCC[Si](C)(C)C)c3c(Br)c(-c4ccccc4)nn3c2=O)cc1]

This compound was prepared according to General procedure 2b by using Intermediate 1 as methyl 2-(4-methoxyphenyl)acetate in step A.

¹H NMR (CHLOROFORM-d) δ: 7.89-7.93 (m, 2H), 7.45-7.51 (m, 3H), 7.18-7.27 (m, J=8.3 Hz, 2H), 6.95-7.06 (m, J=8.3 Hz, 2H), 5.90 (br. s., 2H), 3.88 (s, 3H), 3.74-3.82 (m, 2H), 2.42 (s, 3H), 0.99-1.08 (m, 2H), 0.03-0.06 (m, 9H). LC-MS: m/z 468.2 (M+H)⁺.

Compound 218: 3-(3,6-dihydro-2H-pyran-4-yl)-6-(4-methoxyphenyl)-5-methyl-2-phenylpyrazolo[1,5-a]pyrimidin-7(4H)-one

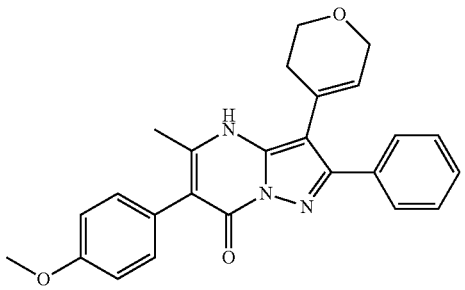 [SMILES: COc1ccc(-c2c(C)[nH]c3c(C4=CCOCC4)c(-c4ccccc4)nn3c2=O)cc1]

This compound was prepared according to General procedure 2b (step E-F) by using Intermediate 5 as 3-bromo-6-(4-methoxyphenyl)-5-methyl-2-phenyl-4-((2-(trimethylsilyl)ethoxy)methyl)pyrazolo[1,5-a]pyrimidin-7(4H)-one and Intermediate 9 as 2-(3,6-dihydro-2H-pyran-4-yl)-4,4,5,5-tetramethyl-1,3,2-dioxaborolane in step E.

Step E: A mixture of 3-bromo-6-(4-methoxyphenyl)-5-methyl-2-phenyl-4-((2-(trimethylsilyl)ethoxy)methyl)pyrazolo[1,5-a]pyrimidin-7(4H)-one (100 mg, 0.185 mmol), 2-(3,6-dihydro-2H-pyran-4-yl)-4,4,5,5-tetramethyl-1,3,2-dioxaborolane (194.39 mg, 0.925 mmol), PdCl₂(PPh₃)₂ (27.07 mg, 0.037 mmol), and Cs₂CO₃ (180.54 mg, 0.555 mmol) in 1,4 dioxane (3 ml) and water (0.3 ml) was heated at 100° C. for 1 hour through microwave irradiation. The mixture was cooled to the room temperature and poured into saturated sodium hydrogen carbonate solution. The resulting mixture was extracted with EtOAc (30 mL), washed with brine (20 ml), dried over anhydrous sodium sulfate, and concentrated in vacuo. The residue was purified by prep-TLC (DCM/MeOH=20/1) to obtain 3-(3,6-dihydro-2H-pyran-4-yl)-6-(4-methoxyphenyl)-5-methyl-2-phenyl-4-((2-(trimethylsilyl)ethoxy)methyl)pyrazolo[1,5-a]pyrazolo[1,5-a]pyrimidin-7(4H)-one (40 mg) as a white solid. LC-MS: m/z 544.2 (M+H)⁺.

Step F: To a solution of 3-(3,6-dihydro-2H-pyran-4-yl)-6-(4-methoxyphenyl)-5-methyl-2-phenyl-4-((2-(trimethylsilyl)ethoxy)methyl)pyrazolo[1,5-a]pyrimidin-7(4H)-one (40 mg, 0.074 mmol) in DCM (1 ml) was added TFA (3 ml) dropwise at 0° C. The mixture was stirred for overnight at ambient temperature and concentrated to dryness. The residue was washed with saturated sodium hydrogen carbonate solution and extracted with DCM (20 ml). The organic layer was washed with brine (20 ml), dried over anhydrous sodium sulfate, and concentrated in vacuo to obtain the title compound.

¹H NMR (DMSO-d₆) δ: 11.78 (s, 1H), 7.72-7.81 (m, 2H), 7.40-7.51 (m, 3H), 7.19-7.29 (m, 2H), 6.95-7.06 (m, 2H), 5.93 (s, 1H), 4.26 (d, J=2.42 Hz, 2H), 3.79-3.86 (m, 5H), 2.23 (s, 3H), 2.12-2.18 (m, 2H). LC-MS: m/z 414.0 (M+H)⁺.

Compound 219: 3-(5,6-dihydro-2H-pyran-3-yl)-6-(4-methoxyphenyl)-5-methyl-2-phenylpyrazolo[1,5-a]pyrimidin-7(4H)-one

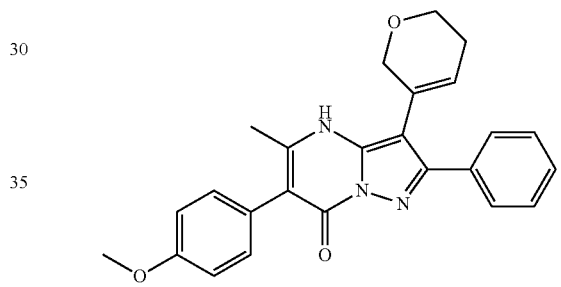

This compound was prepared according to General procedure 2b (step E-F) by using Intermediate 5 as 3-bromo-6-(4-methoxyphenyl)-5-methyl-2-phenyl-4-((2-(trimethylsilyl)ethoxy)methyl)pyrazolo[1,5-a]pyrimidin-7(4H)-one and Intermediate 9 as 2-(5,6-dihydro-2H-pyran-3-yl)-4,4,5,5-tetramethyl-1,3,2-dioxaborolane in step E.

Step E: A mixture of 3-bromo-6-(4-methoxyphenyl)-5-methyl-2-phenyl-4-((2-(trimethylsilyl)ethoxy)methyl)pyrazolo[1,5-a]pyrimidin-7(4H)-one (200 mg, 0.37 mmol), 2-(5,6-dihydro-2H-pyran-3-yl)-4,4,5,5-tetramethyl-1,3,2-dioxaborolane (156 mg, 0.74 mmol), Pd(dppf)Cl₂ (27 mg, 0.037 mmol), and Cs₂CO₃ (241 mg, 0.74 mmol) in dioxane (9 ml) and H₂O (3 ml) was heated to 100° C. for 4 h under N₂. The mixture was concentrated to dryness. The residue was purified by prep-TLC (eluting PE/EA=1:1) to give the desired product (40 mg, 20% yield). LC-MS: m/z 544.3 (M+H)⁺.

Step F: A solution of 3-(5,6-dihydro-2H-pyran-3-yl)-6-(4-methoxyphenyl)-5-methyl-2-phenyl-4-((2-(trimethylsilyl)ethoxy)methyl)pyrazolo[1,5-a]pyrimidin-7(4H)-one (40 mg, 0.074 mmol) in CH₂Cl₂/TFA (V:V=3:1, 8 ml) was stirred for 30 mins. Then the reaction mixture was concentrated to dryness. The residue was dissolved in MeOH (10 ml), basified with ammonia (3 ml), and concentrated in vacuo to give the desired product.

¹H NMR (METHANOL-d₄) δ: 7.86 (br. s., 2H), 7.45 (br. s., 3H), 7.20-7.33 (m, J=8.1 Hz, 2H), 6.90-7.11 (m, J=7.8

Hz, 2H), 6.13 (br. s., 1H), 4.06 (br. s., 2H), 3.91 (t, J=5.4 Hz, 2H), 3.86 (s, 3H), 2.41 (br. s., 2H), 2.30 (s, 3H). LC-MS: m/z 414.0 (M+H)⁺.

Compound 220: 6-(4-methoxyphenyl)-5-methyl-2-phenyl-3-(1H-pyrrol-3-yl)pyrazolo[1,5-a]pyrimidin-7(4H)-one

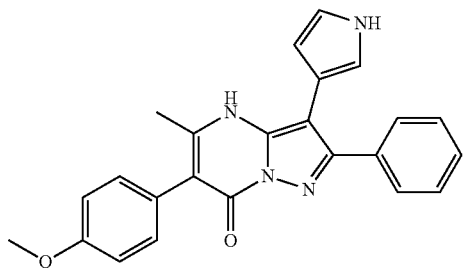 [SMILES: COc1ccc(-c2c(C)[nH]c3c(-c4cc[nH]c4)c(-c4ccccc4)nn3c2=O)cc1]

This compound was prepared according to General procedure 2b (step E-F) by using Intermediate 5 as 3-bromo-6-(4-methoxyphenyl)-5-methyl-2-phenyl-4-((2-(trimethylsilyl)ethoxy)methyl)pyrazolo[1,5-a]pyrimidin-7(4H)-one and compound 9 as (1-(triisopropylsilyl)-1H-pyrrol-3-yl) boronic acid in step E.

Step E: To a sealed tube charged with 3-bromo-6-(4-methoxyphenyl)-5-methyl-2-phenyl-4-((2-(trimethylsilyl)ethoxy)methyl)pyrazolo[1,5-a]pyrimidin-7(4H)-one (200 mg, 0.37 mmol), (1-(triisopropylsilyl)-1H-pyrrol-3-yl)boronic acid (395 mg, 1.48 mmol), PdCl₂(PPh₃)₂ (259 mg, 0.37 mmol), and Cs₂CO₃ (482 mg, 1.480 mmol) was added DMF (5 ml) and water (0.5 ml). The mixture was stirred for 1 hour at 120° C. through microwave irradiation. The reaction mixture was cooled to the room temperature, diluted with saturated sodium hydrogen carbonate solution (30 mL), and extracted with EtOAc (30 mL). The organic phase was washed with brine (20 ml), dried over anhydrous sodium sulfate, and concentrated in vacuo. The residue was purified by prep-TLC (DCM/MeOH=50/1) to obtain 6-(4-methoxyphenyl)-5-methyl-2-phenyl-3-(1H-pyrrol-3-yl)-4-((2-(trimethylsilyl)ethoxy)methyl)pyrazolo[1,5-a]pyrimidin-7(4H)-one (70 mg) as a white solid. LC-MS: m/z 527.2 (M+H)⁺.

Step F: A solution of 6-(4-methoxyphenyl)-5-methyl-2-phenyl-3-(1H-pyrrol-3-yl)-4-((2-(trimethylsilyl)ethoxy)methyl)pyrazolo[1,5-a]pyrimidin-7(4H)-one (30 mg, 0.057 mmol) in DMSO was warmed up to 150° C. in a sealed tube through microwave irradiation for 2 hours. The reaction mixture was diluted with saturated sodium hydrogen carbonate solution (20 mL) and extracted with EtOAc (20 mL). The organic phase was washed with brine (20 ml), dried over anhydrous sodium sulfate, and concentrated in vacuo to obtain the title compound.

¹H NMR (DMSO-d₆) δ: 11.63 (br. s., 1H), 11.02 (br. s., 1H), 7.61-7.71 (m, 2H), 7.31-7.39 (m, 3H), 7.24 (d, J=8.60 Hz, 2H), 6.99 (d, J=8.87 Hz, 2H), 6.84-6.92 (m, 2H), 5.97-6.06 (m, 1H), 3.80 (s, 3H), 2.18 (s, 3H). LC-MS: m/z 397.0 (M+H)⁺.

General procedure 3:

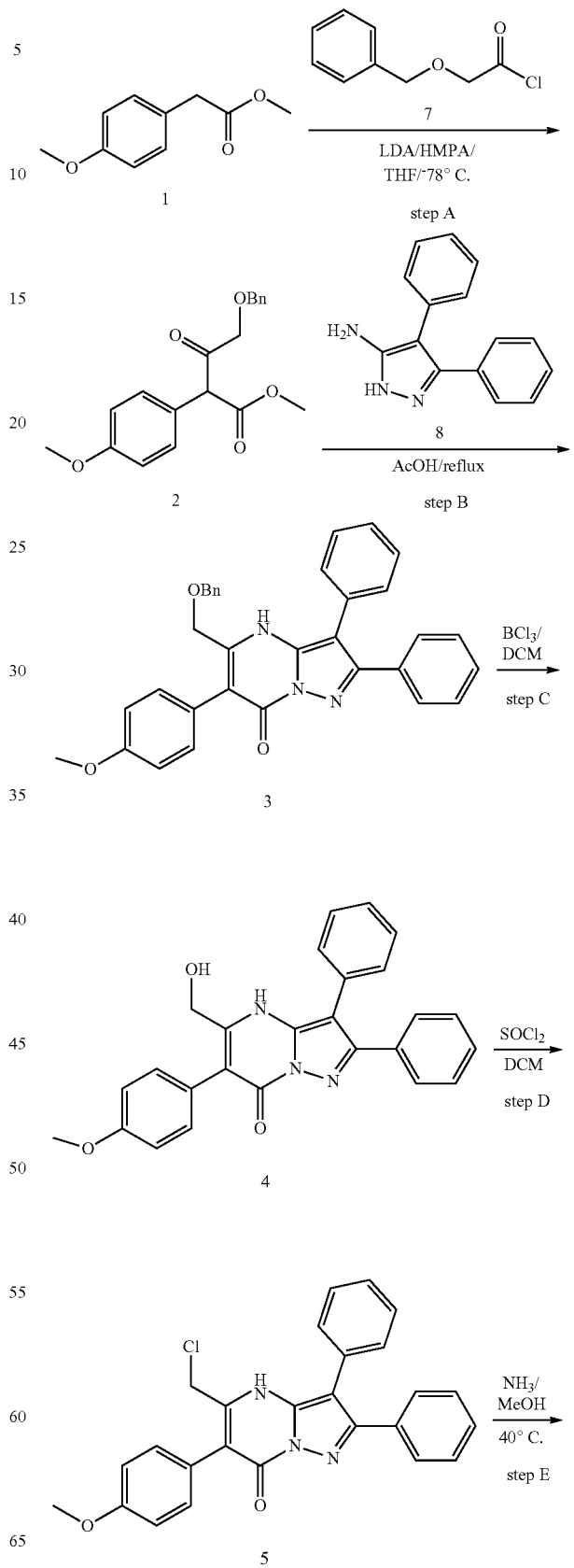

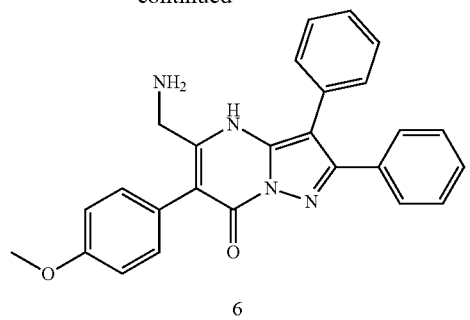

6

Step A: methyl 4-(benzyloxy)-2-(4-methoxyphenyl)-3-oxobutanoate

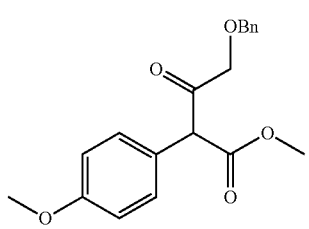

To the solution of Intermediate 1 (36 g, 0.2 mol) and HMPA (7.2 g, 0.02 mol) in THF at −78° C. was added LDA (2M in THF; 100 ml, 0.2 mol) over 20 min. After stirring for 1 hour at −78° C., 2-(benzyloxy)acetyl chloride (36.8 g, 0.2 mol) was added dropwise with a funnel. The mixture was warmed up to room temperature overnight. Saturated NH₄Cl aqueous solution was added. The resultant mixture was extracted with DCM (3×50 ml). The combined organic layers were washed with saturated NaCl (50 ml), dried over Na₂SO₄, filtered, and concentrated in vacuo. The residue was purified by silica gel column (PE/EtOAc=20/1) to give Intermediate 2 (38 g, 58%) as a brown oil.

Step B: 5-((benzyloxy)methyl)-6-(4-methoxyphenyl)-2,3-diphenylpyrazolo[1,5-a]pyrimidin-7(4H)-one

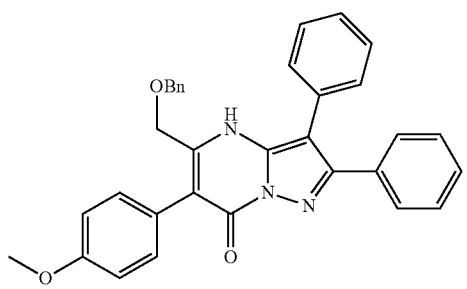

Intermediate 2 (38 g, 0.166 mol) and 3,4-diphenyl-1H-pyrazol-5-amine (40 g, 0.174 mol) were dissolved in AcOH (300 ml). The mixture was warmed up to 95° C. for 4 h. After cooling to room temperature, the solids were collected by filtration, wash with EtOAc, and dried under vacuum to give Intermediate 3 (28 g, 47% yield) as a white solid.

$^1$H NMR (DMSO-d$_6$) δ: 11.99 (br. s., 1H), 7.20-7.50 (m, 17H), 6.97 (d, J=8.8 Hz, 2H), 4.41 (s, 2H), 4.30 (s, 2H), 3.81 (s, 3H). LC-MS: m/z 514.3 (M+H)⁺.

Step C: Compound 221: 5-(hydroxymethyl)-6-(4-methoxyphenyl)-2,3-diphenylpyrazolo[1,5-a]pyrimidin-7(4H)-one

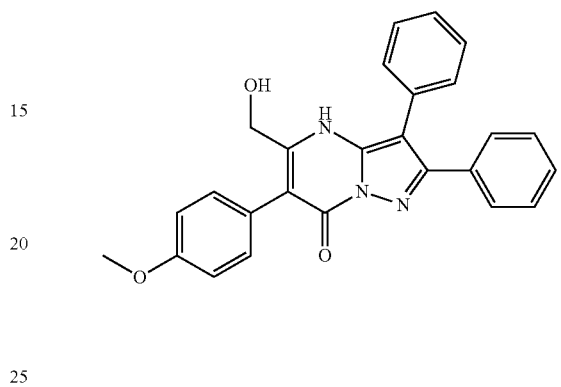

To a solution of Intermediate 3 (534 mg, 1 mmol) in DCM was added BCl₃ (1.0M in DCM, 3 ml, 3 mmol) at 0° C. The mixture was stirred at 0° C. for 4 hours. The reaction was quenched by careful adding MeOH and concentrated. The residue was mixed with sodium hydrogen carbonate solution and ethyl acetate with stirring for 30 min. The precipitates were filtered, wash with ethyl acetate, and dried under vacuum to give Intermediate 4 (400 mg, 94% yield).

$^1$H NMR (DMSO-d$_6$) δ: 11.40 (s, 1H), 7.39-7.54 (m, 5H), 7.21-7.39 (m, 7H), 6.93-7.06 (m, 2H), 5.59 (t, J=5.5 Hz, 1H), 4.30 (d, J=5.4 Hz, 2H), 3.82 (s, 3H). LC-MS: m/z 424.3 (M+H)⁺.

Step D: 5-(chloromethyl)-6-(4-methoxyphenyl)-2,3-diphenylpyrazolo[1,5-a]pyrimidin-7(4H)-one

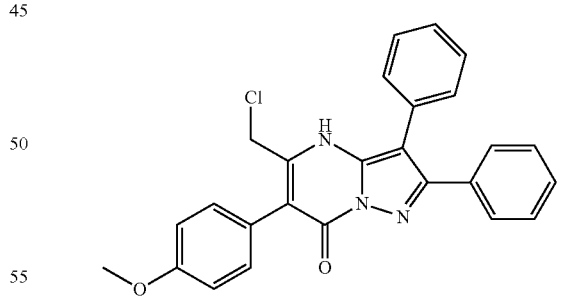

To a suspension of Intermediate 4 (88 g, 0.208 mol) in DCM (500 ml) was added SOCl₂ (120 ml) with a funnel. The mixture was stirred at room temperature for 1 hour. The precipitates were filtered, washed with ethyl acetate, and dried under vacuum to give Intermediate 5 (110 g) as a off-white solid which was directly used to the next step without further purification.

Step E: Compound 222: 5-(aminomethyl)-6-(4-methoxyphenyl)-2,3-diphenylpyrazolo[1,5-a]pyrimidin-7(4H)-one

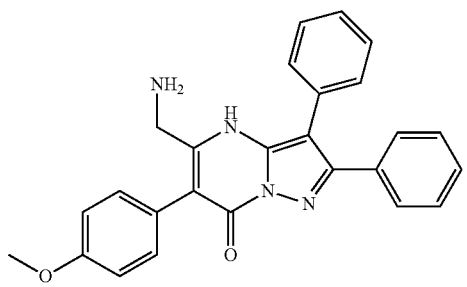 [SMILES: COc1ccc(-c2c(CN)[nH]c3c(-c4ccccc4)c(-c4ccccc4)nn3c2=O)cc1]

A mixture of Intermediate 5 (200 g, 0.453 mol) and NH₃ (7.0M in MeOH, 2500 ml, 17 mol) in a autoclave was stirred at 60° C. overnight. The precipitates were stirred in a mixed solution (50 ml, DMF:MeOH=1:1) at 45° C. for 4 h give the title compound 6.

$^1$H NMR (DMSO-d$_6$) δ: 11.97 (br. s., 1H), 8.38 (br. s., 3H), 7.29-7.59 (m, 12H), 7.06 (d, J=8.9 Hz, 2H), 3.90 (br. s., 2H), 3.83 (s, 3H). LC-MS: m/z 423.1 (M+H)$^+$.

Compound 223: 5-(aminomethyl)-6-(2,3-dihydrobenzo[b][1,4]dioxin-6-yl)-2,3-diphenylpyrazolo[1,5-a]pyrimidin-7(4H)-one

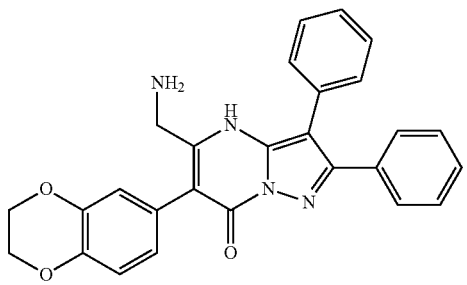

This compound was prepared according to General Procedure 3 by using Intermediate 1 as methyl 2-(2,3-dihydrobenzo[b][1,4]dioxin-6-yl)acetate in step A.

Step A: A solution of LDA (2M in THF; 14.1 ml, 28.1 mmol) was added over 20 min to the solution of methyl 2-(2,3-dihydrobenzo[b][1,4]dioxin-6-yl)acetate (3.9 g, 18.8 mmol) and HMPA (671 mg, 3.75 mmol) in THF at −78° C. After stirring for 1 hour at −78° C., 2-(benzyloxy)acetyl chloride (4.14 g, 22.5 mmol) was added dropwise with a funnel. The mixture was warmed up to room temperature overnight. Saturated aqueous NH₄Cl solution was added, and extracted with DCM (3×50 ml), The combined organic layers were washed with saturated NaCl (50 ml) and dried over Na₂SO₄. The residue was purified by column silica gel chromatography (PE/EtOAc=20/1) to get methyl 4-(benzyloxy)-2-(2,3-dihydrobenzo[b][1,4]dioxin-6-yl)-3-oxobutanoate (2.6 g) as a yellow oil. LC-MS: m/z 357.1 (M+H)$^+$.

Step B: methyl 4-(benzyloxy)-2-(2,3-dihydrobenzo[b][1,4]dioxin-6-yl)-3-oxobutanoate (600 mg, 1.68 mmol) and 3,4-diphenyl-1H-pyrazol-5-amine (356 mg, 1.52 mmol) was dissolved in AcOH (10 ml). The resultant mixture was warmed up to 100° C. for 16 h. The reaction was then cooled to room temperature, basified with saturated sodium hydrogen carbonate solution, and extracted with EtOAc (20 mL). The organic phase was washed with brine (20 ml), dried over anhydrous sodium sulfate, and concentrated in vacuo. The residue was purified by silica gel column (DCM:MeOH=30:1) to get 5-((benzyloxy)methyl)-6-(2,3-dihydrobenzo[b][1,4]dioxin-6-yl)-2,3-diphenylpyrazolo[1,5-a]pyrimidin-7(4H)-one (400 mg) as a white solid. LC-MS: m/z 542.2 (M+H)$^+$.

Step C: To a tube charged with 5-((benzyloxy)methyl)-6-(2,3-dihydrobenzo[b][1,4]dioxin-6-yl)-2,3-diphenylpyrazolo[1,5-a]pyrimidin-7(4H)-one (200 g, 0.37 mmol) was added BCl₃ (5 ml, 5 mmol, 1.0M in DCM) at 0° C. The mixture was stirred at room temperature for 4 hours. The reaction was quenched with MeOH and concentrated. The residue was basified with sodium hydrogen carbonate solution, extracted with DCM, and concentrated under vacuum to get 6-(2,3-dihydrobenzo[b][1,4]dioxin-6-yl)-5-(hydroxymethyl)-2,3-diphenylpyrazolo[1,5-a]pyrimidin-7(4H)-one (120 g) as a white solid. LC-MS: m/z 451.2 (M+H)$^+$.

Step D: To a suspension of 6-(2,3-dihydrobenzo[b][1,4]dioxin-6-yl)-5-(hydroxymethyl)-2,3-diphenylpyrazolo[1,5-a]pyrimidin-7(4H)-one (120 mg, 0.264 mmol) in DCM (5 ml) was added SOCl₂ (63 mg, 0.453 mmol) dropwise at 0° C. The resultant mixture was stirred at room temperature for 3 hours. The reaction was quenched by adding saturated sodium hydrogen carbonate solution and extracted with DCM (20 mL). The organic phase was washed with brine (20 ml), dried over anhydrous sodium sulfate, and concentrated invacuo. The residue was purified by silica gel column (PE:EA=1:1) to get 5-(chloromethyl)-6-(2,3-dihydrobenzo[b][1,4]dioxin-6-yl)-2,3-diphenylpyrazolo[1,5-a]pyrimidin-7(4H)-one (90 mg) as a yellow solid. LC-MS: m/z 470.1 (M+H)$^+$.

Step E: A mixture of 5-(chloromethyl)-6-(2,3-dihydrobenzo[b][1,4]dioxin-6-yl)-2,3-diphenylpyrazolo[1,5-a]pyrimidin-7(4H)-one (20 mg, 0.042 mmol) in 7N NH₃/MeOH (3 ml) in a sealed tube was stirred at 100° C. overnight to afford the title compound.

$^1$H NMR (DMSO-d$_6$) δ: 8.11 (br. s., 2H), 7.44 (br. s., 4H), 7.37 (br. s., 4H), 6.86-7.00 (m, 2H), 6.83 (br. s., 1H), 4.30 (s, 3H), 3.89 (br. s., 1H). LC-MS: m/z 452.1 (M+H)$^+$.

Compound 224: 5-(aminomethyl)-2,3-diphenyl-6-(quinolin-6-yl)pyrazolo[1,5-a]pyrimidin-7(4H)-one

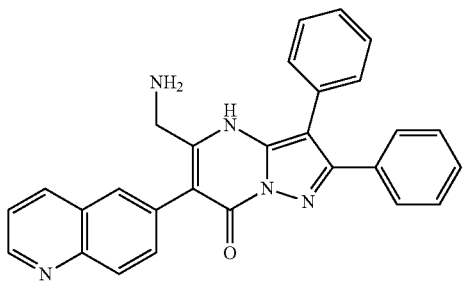

This compound was prepared according to General Procedure 3 by using Intermediate 1 as methyl 2-(quinolin-6-yl) acetate in step A.

Step B: methyl 4-(benzyloxy)-3-oxo-2-(quinolin-6-yl)butanoate (8.6 g, 0.024 mol) and 3,4-diphenyl-1H-pyrazol-5-amine (5.64 g, 0.024 mol) was dissolved in AcOH (300 ml).

The mixture was warmed up to 95° C. for 4 h. After cooling to room temperature, the precipitate was filtered, wash with EtOAc, and dried under vacuum to get 5-((benzyloxy)methyl)-2,3-diphenyl-6-(quinolin-6-yl)pyrazolo[1,5-a]pyrimidin-7(4H)-one (10 g, 78% yield) as a yellow solid. LC-MS: m/z 535.2 (M+H)+.

Step C: To a solution of 5-((benzyloxy)methyl)-2,3-diphenyl-6-(quinolin-6-yl)pyrazolo[1,5-a]pyrimidin-7(4H)-one (10 g, 18.7 mmol) in DCM (100 ml) was added BCl3 (25 ml, 25 mmol, 1.0M in DCM) at 0° C. The resultant mixture was stirred at 0° C. for 4 hours. The reaction was quenched with MeOH and concentrated. The residue was stirred with sodium hydrogen carbonate solution and ethyl acetate for 30 min. The solid was collected by filtration, wash with ethyl acetate, and dried under vacuum to get 5-(hydroxymethyl)-2,3-diphenyl-6-(quinolin-6-yl)pyrazolo[1,5-a]pyrimidin-7(4H)-one (8 g, 96% yield). LC-MS: m/z 445.1 (M+H)+.

Step D: To a suspension of 5-(hydroxymethyl)-2,3-diphenyl-6-(quinolin-6-yl)pyrazolo[1,5-a]pyrimidin-7(4H)-one (500 mg, 1.126 mmol,) in DCM (3 ml) cooled in ice-bath was added SOCl2 (670 mg, 5.631 mmol) dropwise. The resultant mixture was then stirred at room temperature overnight. The suspension was filtered, washed with ethyl acetate, and dried under vacuum. The residue was purified by prep-TLC (DCM:MeOH=20:1) to get 5-(chloromethyl)-2,3-diphenyl-6-(quinolin-6-yl)pyrazolo[1,5-a]pyrimidin-7(4H)-one (300 mg). LC-MS: m/z 463.1 (M+H)+.

Step E: To a solution of 5-(chloromethyl)-2,3-diphenyl-6-(quinolin-6-yl)pyrazolo[1,5-a]pyrimidin-7(4H)-one (150 mg, 0.324 mmol) in DMF was added 7N NH3 in methanol (15 ml) at 0° C. The reaction mixture was then warmed up to 40° C. for 65 hours in a sealed tube to get the title compound.

1H NMR (400 MHz, DMSO-d6) δ: 8.89 (dd, J=4.16, 1.75 Hz, 1H), 8.36 (d, J=7.52 Hz, 1H), 8.02 (d, J=8.87 Hz, 1H), 7.91 (s, 1H), 7.76-7.81 (m, 1H), 7.52-7.62 (m, 5H), 7.34-7.40 (m, 3H), 7.29 (t, J=7.52 Hz, 2H), 7.15 (d, J=7.25 Hz, 1H), 3.85 (br. s., 2H). LC-MS: m/z 444.8 (M+H)+.

Compound 225: 3-(cyclohex-1-en-1-yl)-6-(2,3-dihydrobenzo[b][1,4]dioxin-6-yl)-5-(hydroxymethyl)-2-phenylpyrazolo[1,5-a]pyrimidin-7(4H)-one

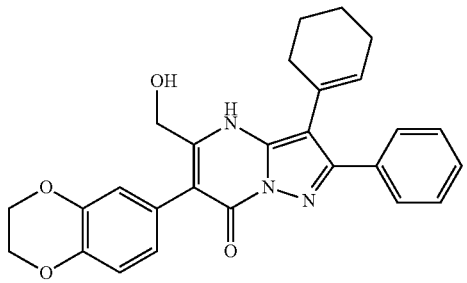

This compound was prepared according to General Procedure 3 (step B-C) by using Intermediate 2 as methyl 4-(benzyloxy)-2-(2,3-dihydrobenzo[b][1,4]dioxin-6-yl)-3-oxobutanoate and Intermediate 8 as 4-(cyclohex-1-en-1-yl)-3-phenyl-H-pyrazol-5-amine in step B.

Step B: methyl 4-(benzyloxy)-2-(2,3-dihydrobenzo[b][1,4]dioxin-6-yl)-3-oxobutanoate (662 mg, 1.85 mmol) and 4-(cyclohex-1-en-1-yl)-3-phenyl-1H-pyrazol-5-amine (400 mg, 1.67 mmol) were dissolved in AcOH (10 ml). The resultant mixture was warmed up to 100° C. for 16 h. The reaction was then cooled to room temperature, basified with saturated sodium hydrogen carbonate solution, and extracted with DCM (20 mL). The organic phase was washed with brine (20 ml), dried over anhydrous sodium sulfate, and concentrated in vacuo. The residue was purified by silica gel column (DCM:MeOH=30:1) to get 5-((benzyloxy)methyl)-3-(cyclohex-1-en-1-yl)-6-(2,3-dihydrobenzo[b][,4]dioxin-6-yl)-2-phenylpyrazolo[1,5-a]pyrimidin-7(4H)-one (400 mg) as a white solid. LC-MS: m/z 546.2 (M+H)+.

Step C: To a suspension of 5-((benzyloxy)methyl)-3-(cyclohex-1-en-1-yl)-6-(2,3-dihydrobenzo[b][1,4]dioxin-6-yl)-2-phenylpyrazolo[1,5-a]pyrimidin-7(4H)-one (260 mg, 0.48 mmol) in DCM (5 ml) was added 1.0M BCl3 in DCM (1.43 ml, 1.43 mmol), the mixture was stirred at room temperature for 3 hours. The reaction was quenched with saturated sodium hydrogen carbonate solution and extracted with EtOAc (20 mL) to obtain the title compound.

1H NMR (DMSO-d6) δ: 11.21 (s, 1H), 7.78 (d, J=6.98 Hz, 1H), 7.38-7.49 (m, 4H), 6.85-6.92 (m, 2H), 6.78-6.82 (m, 1H), 5.86 (br. s., 1H), 5.68 (s, 1H), 4.77 (s, 1H), 4.33 (d, J=5.10 Hz, 2H), 4.29 (s, 3H), 2.22 (br. s., 2H), 2.06 (br. s., 2H), 1.70 (br. s., 4H). LC-MS: m/z 456.2 (M+H)+.

Compound 226: 5-(aminomethyl)-3-(cyclohex-1-en-1-yl)-6-(2,3-dihydrobenzo[b][1,4]dioxin-6-yl)-2-phenylpyrazolo[1,5-a]pyrimidin-7(4H)-one

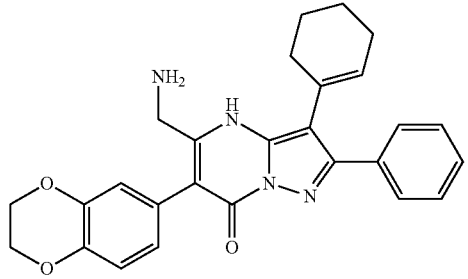

This compound was prepared according to General Procedure 3, step E-F, starting from 3-(cyclohex-1-en-1-yl)-6-(2, 3-dihydrobenzo[b][1,4]dioxin-6-yl)-5-(hydroxymethyl)-2-phenylpyrazolo[1,5-a]pyrimidin-7(4H)-one (Compound 225).

Step E: To a suspension of 3-(cyclohex-1-en-1-yl)-6-(2, 3-dihydrobenzo[b][1,4]dioxin-6-yl)-5-(hydroxymethyl)-2-phenylpyrazolo[1,5-a]pyrimidin-7(4H)-one (Compound 225, 100 mg, 0.264 mmol) in DCM (3 ml) cooled in a ice-bath was added SOCl2 (52 mg, 0.0.44 mmol) dropwise. The resultant mixture was stirred at room temperature for 3 hours. The reaction was quenched with saturated sodium hydrogen carbonate solution and extracted with DCM (20 mL). The organic phase was washed with brine (20 ml), dried over anhydrous sodium sulfate, and concentrated invacuo. The residue was purified by silica gel column (DCM:MeOH=40:1) to get 5-(chloromethyl)-3-(cyclohex-1-en-1-yl)-6-(2,3-dihydrobenzo[b][1,4]dioxin-6-yl)-2-phenylpyrazolo[1,5-a]pyrimidin-7(4H)-one (70 mg) as a yellow solid. LC-MS: m/z 474.2 (M+H)+.

Step F: A mixture of 5-(chloromethyl)-3-(cyclohex-1-en-1-yl)-6-(2,3-dihydrobenzo[b][1,4]dioxin-6-yl)-2-phenylpyrazolo[1,5-a]pyrimidin-7(4H)-one (70 mg, 0.148 mg) in 7N NH3/MeOH (5 ml) in a sealed tube was stirred at 100° C. overnight to get the title compound.

¹H NMR (DMSO-d₆) δ: 11.74 (br. s., 1H), 8.24 (br. s., 2H), 7.77 (d, J=7.32 Hz, 2H), 7.40-7.53 (m, 3H), 6.86-7.03 (m, 2H), 6.82 (d, J=8.24 Hz, 1H), 5.92 (br. s., 1H), 4.30 (s, 4H), 3.94 (br. s., 2H), 2.23 (br. s., 2H), 2.05 (br. s., 2H), 1.70 (br. s., 4H). LC-MS: m/z 455.2 (M+H)⁺.

Compound 227

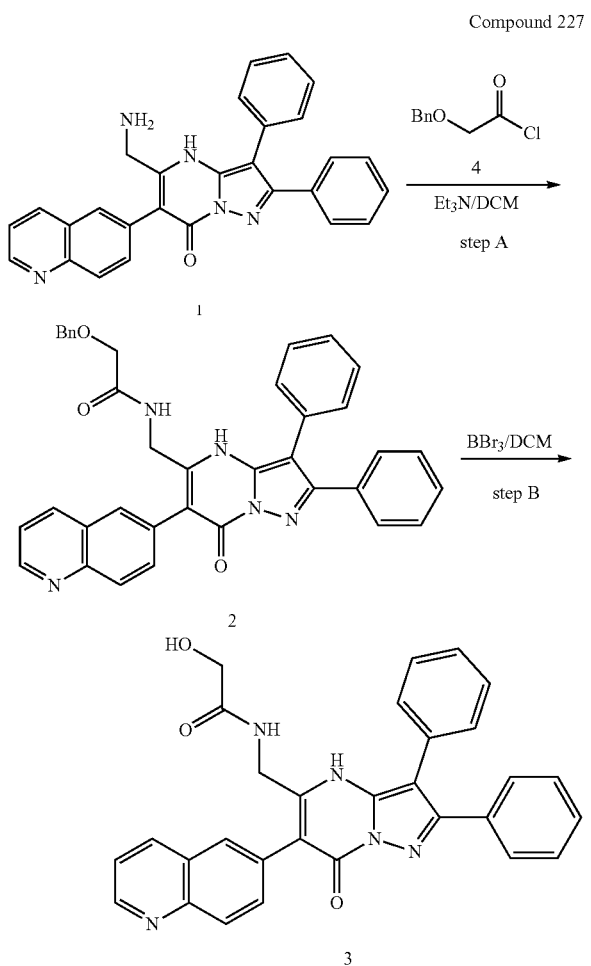

Step A: 2-(benzyloxy)-N-((7-oxo-2,3-diphenyl-6-(quinolin-6-yl)-4,7-dihydropyrazolo[1,5-a]pyrimidin-5-yl)methyl)acetamide

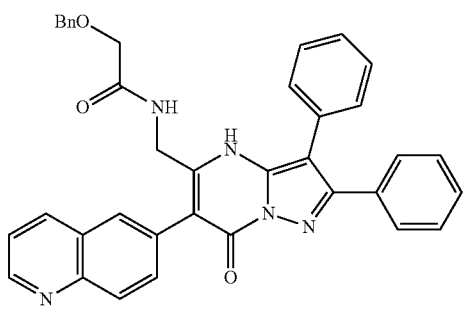 [SMILES: O=C(COCc1ccccc1)NCc1[nH]c2c(-c3ccccc3)c(-c3ccccc3)nn2c(=O)c1-c1ccc2ncccc2c1]

To a solution of Intermediate 1 (Compound 224, 100 mg, 0.226 mmol) and Et₃N (68.6 mg, 0.68 mmol) in DCM (3 ml) was added 2-(benzyloxy)acetyl chloride (42 mg, 0.45 mmol) dropwise. The mixture was stirred for 2 hours at ambient temperature. The reaction was quenched by adding saturated sodium hydrogen carbonate solution and extracted with DCM (20 mL). The combined organic layers were washed with brine (20 ml), dried over anhydrous sodium sulfate, and concentrated in vacuo. The residue was purified by prep-TLC (DCM/MeOH=20/1) to obtain the Intermediate 2 (40 mg, 30% yield).

Step B: Compound 227: 2-hydroxy-N-((7-oxo-2,3-diphenyl-6-(quinolin-6-yl)-4,7-dihydropyrazolo[1,5-a]pyrimidin-5-yl)methyl)acetamide

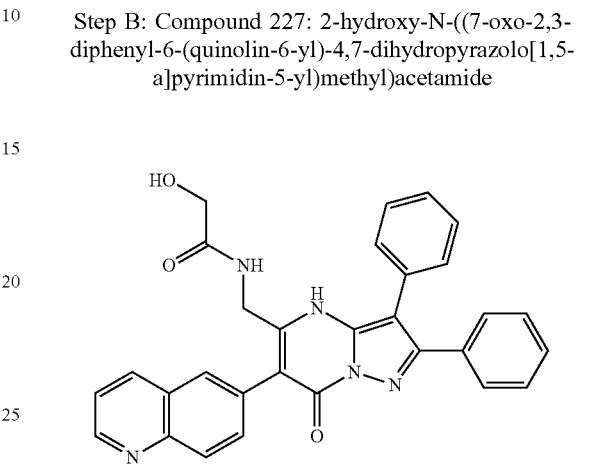

To a solution of Intermediate 2 (40 mg, 0.068 mmol) in DCM (1 ml) at 0° C. was carefully added 1M BBr₃ in DCM (3 ml, 3 mmol), the reaction mixture was stirred for 5 min at 0° C., and then warmed up to ambient temperature for 1 hour. The reaction was quenched by careful adding MeOH. The resultant mixture was poured into saturated sodium hydrogen carbonate solution and extracted with EtOAc (3*20 ml). The combined organic layers were washed with saturated NaCl (20 ml), dried over Na₂SO₄, and concentrated in vacuo to give the title compound 3.

¹H NMR (DMSO-d₆) δ: 11.94 (s, 1H), 8.95 (d, J=2.69 Hz, 1H), 8.38 (d, J=7.25 Hz, 1H), 8.07 (d, J=8.60 Hz, 1H), 7.98 (s, 1H), 7.76 (dd, J=8.60, 1.88 Hz, 1H), 7.59 (dd, J=8.33, 4.30 Hz, 1H), 7.42-7.53 (m, 5H), 7.32-7.41 (m, 5H), 5.59 (br. s., 1H), 4.25 (br. s., 2H), 3.77 (d, J=5.37 Hz, 2H), LC-MS: m/z 502.8 (M+H)⁺.

Compound 228: N-((7-oxo-2,3-diphenyl-6-(quinolin-6-yl)-4,7-dihydropyrazolo[1,5-a]pyrimidin-5-yl)methyl)acetamide

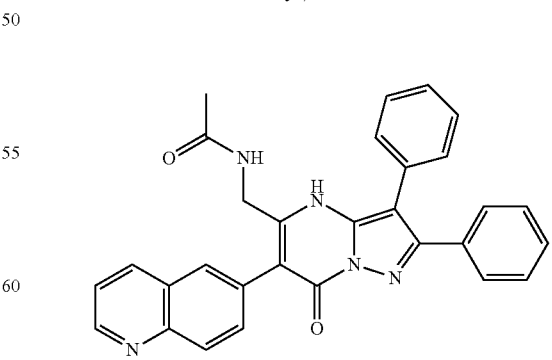

This compound was prepared according to Compound 227 (step A) by using Intermediate 4 as acetyl chloride in step A.

To a solution of 5-(aminomethyl)-2,3-diphenyl-6-(quinolin-6-yl)pyrazolo[1,5-a]pyrimidin-7(4H)-one (Compound 224, 100 mg, 0.226 mmol) and DIPEA (87.3 mg, 0.68 mmol) in DCM (3 ml) was added acetyl chloride (21.24 mg, 0.271 mmol) dropwise. After addition, the mixture was stirred for 2 hours at ambient temperature. The mixture was concentrated. The residue was basified with saturated sodium hydrogen carbonate solution and extracted with DCM (20 mL). The combined organic layers were washed with brine (20 ml), dried over anhydrous sodium sulfate, and concentrated in vacuo to obtain the title compound.

$^1$H NMR (DMSO-$d_6$) δ: 8.90 (br. s., 1H), 8.35 (d, J=8.87 Hz, 1H), 8.16 (s, 1H), 8.02 (d, J=8.60 Hz, 1H), 7.96 (br. s., 1H), 7.89 (br. s., 1H), 7.76 (d, J=7.79 Hz, 1H), 7.50-7.56 (m, 5H), 7.29-7.39 (m, 5H), 7.20 (d, J=6.98 Hz, 1H), 4.07 (br. s., 2H), 1.82 (s, 3H). LC-MS: m/z 485.9 (M+H)$^+$.

Compound 229: 3-(cyclohex-1-en-1-yl)-5-(hydroxymethyl)-6-(4-methoxyphenyl)-2-phenylpyrazolo[1,5-a]pyrimidin-7(4H)-one

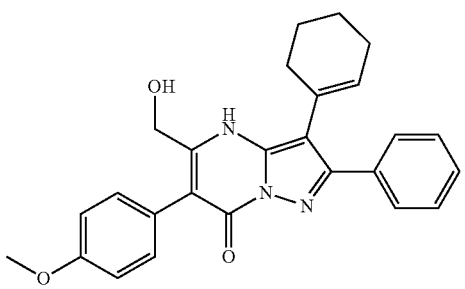

This compound was prepared according to General procedure 3, step B-C, by using Intermediate 8 as 4-(cyclohex-1-en-1-yl)-3-phenyl-1H-pyrazol-5-amine in step B.

Step B: methyl 4-(benzyloxy)-2-(4-methoxyphenyl)-3-oxobutanoate (597 mg, 1.67 mmol) and 4-(cyclohex-1-en-1-yl)-3-phenyl-1H-pyrazol-5-amine (400 mg, 1.67 mmol) were dissolved in AcOH (10 ml). The mixture was stirred at 100° C. for 4 h. After cooling to room temperature, the solids were collected by filtration, wash with EtOAc, and dried under vacuum to give 5-((benzyloxy)methyl)-3-(cyclohex-1-en-1-yl)-6-(4-methoxyphenyl)-2-phenylpyrazolo[1,5-a]pyrimidin-7(4H)-one (200 mg, 23% yield) as a white solid. LC-MS: m/z 513.9 (M+H)$^+$.

Step C: To a solution of 5-((benzyloxy)methyl)-3-(cyclohex-1-en-1-yl)-6-(4-methoxyphenyl)-2-phenylpyrazolo[1,5-a] pyrimidin-7(4H)-one (50 mg, 0.1 mmol) in MeOH (5 ml) was added Pd/C (50 mg) and HCl (3 drops). The mixture was stirred at rt under H$_2$ overnight. The reaction was filtered and concentrated. The residue was mixed with sodium hydrogen carbonate solution and ethyl acetate with stirring for 30 min to give the title compound.

$^1$H NMR (DMSO-$d_6$) δ: 11.27 (br. s., 1H), 7.64-7.91 (m, 2H), 7.35-7.62 (m, 4H), 7.22-7.35 (m, J=8.6 Hz, 2H), 6.90-7.02 (m, J=8.9 Hz, 2H), 5.87 (br. s., 1H), 5.75 (br. s., 1H), 4.26-4.45 (m, 2H), 3.81 (s, 3H), 2.22 (br. s., 2H), 1.98-2.11 (m, 2H), 1.70 (br. s., 4H). LC-MS: m/z 428.3 (M+H)$^+$.

Compound 230: 3-(cyclohex-1-en-1-yl)-5-(hydroxymethyl)-2-phenyl-6-(quinolin-6-yl)pyrazolo[1,5-a]pyrimidin-7(4H)-one

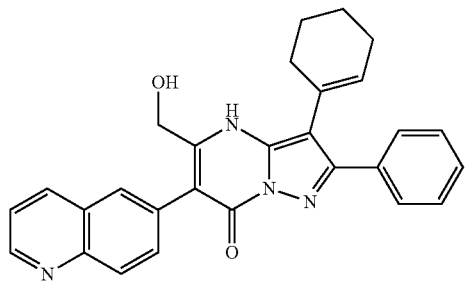

This compound was prepared according to General procedure 3 (step A-C) by using Intermediate 1 as methyl 2-(quinolin-6-yl)acetate in step A and Intermediate 8 as 4-(cyclohex-1-en-1-yl)-3-phenyl-1H-pyrazol-5-amine in step B.

Step B: methyl 4-(benzyloxy)-3-oxo-2-(quinolin-6-yl)butanoate (730 mg, 2.01 mmol) and 4-(cyclohex-1-en-1-yl)-3-phenyl-1H-pyrazol-5-amine (500 mg, 2.1 mmol) were dissolved in AcOH (15 ml). The mixture was warmed up to 100° C. for 16 h. After cooling to room temperature, the solids were collected by filtration, wash with EtOAc, and dried under vacuum to give 5-((benzyloxy)methyl)-3-(cyclohex-1-en-1-yl)-2-phenyl-6-(quinolin-6-yl) pyrazolo[1,5-a]pyrimidin-7(4H)-one (700 mg, 65% yield) as a white solid. LC-MS: m/z 538.9 (M+H)$^+$.

Step C: To a solution of 5-((benzyloxy)methyl)-3-(cyclohex-1-en-1-yl)-2-phenyl-6-(quinolin-6-yl) pyrazolo[1,5-a] pyrimidin-7(4H)-one (700 mg, 1.3 mmol) in DCM was added BCl$_3$ (1.0M in DCM, 2.2 ml, 2.2 mmol) at 0° C. The mixture was stirred at 0° C. for 2 hours. The reaction was quenched by careful adding MeOH and concentrated. The residue was mixed with sodium hydrogen carbonate solution and ethyl acetate with stirring for 30 min give the title compound.

$^1$H NMR (DMSO-$d_6$) δ: 8.87-8.96 (m, 1H), 8.37 (d, J=7.5 Hz, 1H), 8.03 (d, J=8.6 Hz, 1H), 7.94 (s, 1H), 7.73-7.82 (m, 3H), 7.55 (dd, J=8.3, 4.3 Hz, 1H), 7.43-7.51 (m, 2H), 7.40 (d, J=7.3 Hz, 1H), 5.82 (br. s., 1H), 4.35 (s, 2H), 2.19 (br. s., 4H), 1.70 (br. s., 4H).
LC-MS: m/z 449.3 (M+H)$^+$.

Compound 231: 3-(cyclohex-1-en-1-yl)-5-(hydroxymethyl)-2-phenyl-6-(quinoxalin-6-yl)pyrazolo[1,5-a]pyrimidin-7(4H)-one

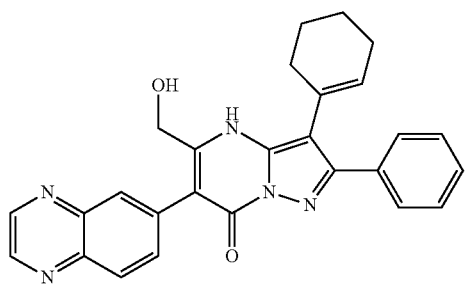

This compound was prepared according to General procedure 3 (step A-C) by using Intermediate 1 as methyl 2-(quinoxalin-6-yl)acetate in step A and Intermediate 8 as 4-(cyclohex-1-en-1-yl)-3-phenyl-1H-pyrazol-5-amine in step B.

Step C: To the solution of 5-((benzyloxy)methyl)-3-(cyclohex-1-en-1-yl)-2-phenyl-6-(quinoxalin-6-yl)pyrazolo[1,5-a]pyrimidin-7(4H)-one (170 mg, 0.32 mmol) in DCM (8 mL) cooled to 0° C. was added BCl₃ (1.5 mL, 1.0 M in DCM) dropwise. Then the mixture was stirred at 0° C. for 2 hours. The reaction was quenched by carefully adding saturated NaHCO₃ (8 mL), diluted with DCM (80 mL), washed with brine, dried over anhydrous sodium sulfate and concentrated to obtain 3-(cyclohex-1-en-1-yl)-5-(hydroxymethyl)-2-phenyl-6-(quinoxalin-6-yl)pyrazolo[1,5-a]pyrimidin-7(4H)-one.

$^1$H NMR (DMSO-d$_6$) δ: 11.57 (br. s., 1H), 8.99 (s, 2H), 8.07-8.22 (m, 2H), 7.89 (dd, J=8.5, 1.8 Hz, 1H), 7.73-7.84 (m, 2H), 7.38-7.58 (m, 3H), 5.90 (br. s., 1H), 5.77 (br. s., 1H), 4.42 (d, J=3.4 Hz, 2H), 2.23 (br. s., 2H), 2.09 (s, 2H), 1.72 (br. s., 4H). LC-MS: m/z 450.3 (M+H)$^+$.

Compound 232: 5-(aminomethyl)-3-(cyclohex-1-en-1-yl)-6-(4-methoxyphenyl)-2-phenylpyrazolo[1,5-a]pyrimidin-7(4H)-one

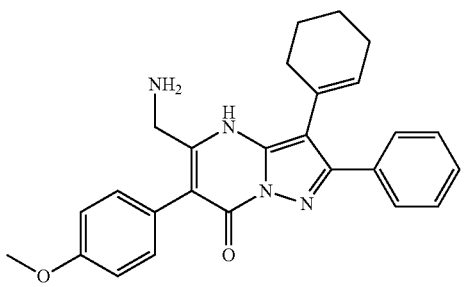

This compound was prepared according to General procedure 3, step D-E, starting from 3-(cyclohex-1-en-1-yl)-5-(hydroxymethyl)-6-(4-methoxyphenyl)-2-phenylpyrazolo[1,5-a]pyrimidin-7(4H)-one (Compound 229).

Step D: To a suspension of 3-(cyclohex-1-en-1-yl)-5-(hydroxymethyl)-6-(4-methoxyphenyl)-2-phenylpyrazolo[1,5-a]pyrimidin-7(4H)-one (Compound 229, 140 mg, 0.32 mol) in DCM (10 ml) was added SOCl₂ dropwise (386 mg, 3.2 mmol) at −20° C. The mixture was stirred at −20° C. for 1 hour until SM was consumed. Then the reaction was quenched by adding MeOH at −20° C. The mixture was concentrated and purified by silica gel chromatography (DMC:MeOH=50:1) to a 5-(chloromethyl)-3-(cyclohex-1-en-1-yl)-6-(4-methoxyphenyl)-2-phenylpyrazolo[1,5-a]pyrimidin-7(4H)-one (100 mg) as a white solid.

$^1$H NMR (DMSO-d$_6$) δ: 7.74-7.83 (m, 2H), 7.37-7.53 (m, 3H), 7.25-7.32 (m, 2H), 6.95-7.03 (m, 2H), 5.87 (br. s., 1H), 5.76 (s, 1H), 4.33 (br. s., 2H), 3.81 (s, 3H), 2.22 (br. s., 2H), 2.07 (br. s., 2H), 1.70 (br. s., 4H). LC-MS: m/z 446.3 (M+H)$^+$.

Step E: A suspension of 5-(chloromethyl)-3-(cyclohex-1-en-1-yl)-6-(4-methoxyphenyl)-2-phenylpyrazolo[1,5-a]pyrimidin-7(4H)-one (50 mg, 0.11 mmol) and KI (18 mg, 0.11 mmol) in NH₃ in MeOH (7M, 10 mL) was stirred at 80° C. for 1 h under microwave irradiation to get the title compound.

$^1$H NMR (DMSO-d$_6$) δ: 7.71 (d, J=7.3 Hz, 2H), 7.40 (t, J=7.5 Hz, 2H), 7.32 (br. s., 1H), 7.15-7.24 (m, J=8.6 Hz, 2H), 6.93-7.00 (m, J=8.6 Hz, 2H), 5.68 (br. s., 1H), 3.80 (s, 3H), 2.36 (br. s., 2H), 2.11 (d, J=3.0 Hz, 2H), 1.58-1.79 (m, 4H). LC-MS: m/z 427.4 (M+H)$^+$.

Compound 233: 5-(aminomethyl)-3-(cyclohex-1-en-1-yl)-2-phenyl-6-(quinolin-6-yl)pyrazolo[1,5-a]pyrimidin-7(4H)-one

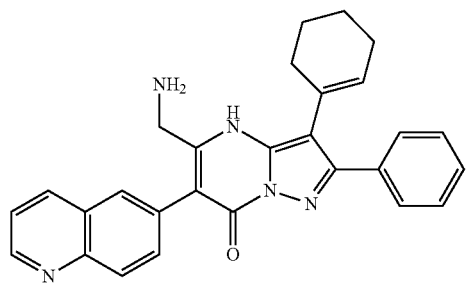

This compound was prepared according to General procedure 3, step D-E, starting from 3-(cyclohex-1-en-1-yl)-5-(hydroxymethyl)-2-phenyl-6-(quinolin-6-yl)pyrazolo[1,5-a]pyrimidin-7(4H)-one (Compound 230)

Step D: To a suspension of 3-(cyclohex-1-en-1-yl)-5-(hydroxymethyl)-2-phenyl-6-(quinolin-6-yl)pyrazolo[1,5-a]pyrimidin-7(4H)-one (Compound 230, 160 mg, 0.357 mol) in DCM (5 ml) was added SOCl₂ (1 ml) with a funnel. The mixture was stirred at room temperature for 1 hour. The precipitates were filtered, washed with ethyl acetate, and dried under vacuum to give 5-(chloromethyl)-3-(cyclohex-1-en-1-yl)-2-phenyl-6-(quinolin-6-yl)pyrazolo[1,5-a]pyrimidin-7(4H)-one (170 mg) as a off-white solid which was directly used to the next step without further purification. LC-MS: m/z 466.9 (M+H)$^+$ Step E: A mixture of 5-(chloromethyl)-3-(cyclohex-1-en-1-yl)-2-phenyl-6-(quinolin-6-yl)pyrazolo[1,5-a]pyrimidin-7(4H)-one (80 mg, 0.171 mol) and NH₃ (7.0M in MeOH, 10 ml, 70 mol) in autoclave was stirred at 40° C. for 2 days. The mixture was concentrated in vacuo. The residue was washed with water to afford the title compound.

$^1$H NMR (DMSO-d$_6$) δ: 8.84-8.93 (m, 1H), 8.34 (d, J=8.1 Hz, 1H), 8.01 (d, J=8.6 Hz, 1H), 7.87 (s, 1H), 7.68-7.78 (m, 3H), 7.52-7.58 (m, 1H), 7.28-7.47 (m, 3H), 5.71 (br. s., 1H), 3.85 (s, 2H), 2.39 (br. s., 2H), 2.11 (br. s., 2H), 1.57-1.79 (m, 4H). LC-MS: m/z 448.5 (M+H)$^+$.

Compound 234: 5-(aminomethyl)-3-(cyclohex-1-en-1-yl)-2-phenyl-6-(quinoxalin-6-yl)pyrazolo[1,5-a]pyrimidin-7(4H)-one

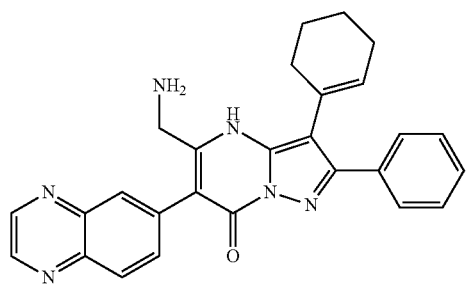 [SMILES: NCc1[nH]c2c(C3=CCCCC3)c(-c3ccccc3)nn2c(=O)c1-c1ccc2nccnc2c1]

This compound was prepared according to General procedure 3, step D-E, starting from 3-(cyclohex-1-en-1-yl)-5-(hydroxymethyl)-2-phenyl-6-(quinoxalin-6-yl)pyrazolo[1,5-a]pyrimidin-7(4H)-one (Compound 231).

Step D: To the solution of 3-(cyclohex-1-en-1-yl)-5-(hydroxymethyl)-2-phenyl-6-(quinoxalin-6-yl)pyrazolo[1,5-a]pyrimidin-7(4H)-one (Compound 231, 100 mg, 0.22 mmol) and DMF (1 drop, cat.) in DCM was added Thionyl chloride (0.2 mL) dropwise at 0° C. After addition, the mixture was continued to stir at 0° C. for 1 hour. The reaction was diluted with DCM (60 mL), washed with saturated $NaHCO_3$ (15 mL) and brine (20 mL), dried over anhydrous sodium sulfate and concentrated to dryness. The residue was purified by prep-TLC (DCM:MeOH: 25:1) to obtain 5-(chloromethyl)-3-(cyclohex-1-en-1-yl)-2-phenyl-6-(quinoxalin-6-yl)pyrazolo[1,5-a]pyrimidin-7(4H)-one (90 mg) as yellow solid. LC-MS: m/z 468.3 $(M+H)^+$.

Step E: The solution of 5-(chloromethyl)-3-(cyclohex-1-en-1-yl)-2-phenyl-6-(quinoxalin-6-yl)pyrazolo[1,5-a]pyrimidin-7(4H)-one (85 mg, 0.18 mmol) in $NH_3$ (4 mL, 7.0M in MeOH) was stirred at 40° C. in a sealed tube for 12 hours. After cooling to room temperature, the mixture was filtered off to obtain 5-(aminomethyl)-3-(cyclohex-1-en-1-yl)-2-phenyl-6-(quinoxalin-6-yl)pyrazolo[1,5-a]pyrimidin-7(4H)-one.

$^1$H NMR (DMSO-$d_6$) δ: 8.92 (dd, J=7.0, 1.9 Hz, 2H), 8.07 (d, J=8.6 Hz, 1H), 8.01 (d, J=1.9 Hz, 1H), 7.91 (dd, J=8.9, 1.9 Hz, 1H), 7.73 (d, J=7.0 Hz, 2H), 7.42 (t, J=7.5 Hz, 2H), 7.33 (t, J=7.4 Hz, 2H), 5.69 (br. s., 1H), 3.88 (s, 2H), 2.40 (br. s., 2H), 2.12 (br. s., 2H), 1.60-1.78 (m, 4H). LC-MS: m/z 449.3 $(M+H)^+$.

Compound 235: 1-((7-oxo-2,3-diphenyl-6-(quinolin-6-yl)-4,7-dihydropyrazolo[1,5-a]pyrimidin-5-yl)methyl)urea

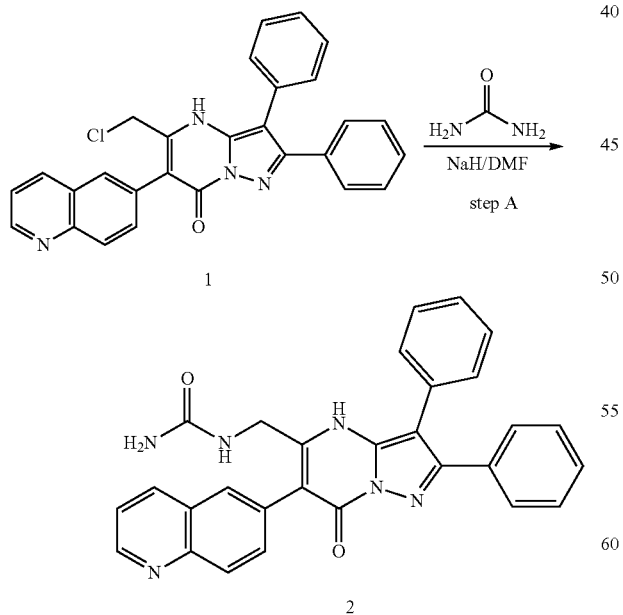

Intermediate 1 was prepared according to General procedure 3 (step A-D) by using Intermediate 1 as methyl 2-(quinolin-6-yl)acetate.

Step A: NaH (60% dispersion in mineral oil, 28.6 mg, 0.7 mmol) was added in portions to the solution of urea (41.0 mg, 0.6 mmol) in DMF (10 mL) cooled to 0° C. and stirred at this temperature for 20 min. 5-(chloromethyl)-2,3-diphenyl-6-(quinolin-6-yl)pyrazolo[1,5-a]pyrimidin-7(4H)-one (100 mg, 0.2 mmol) was then added and stirred at 80° C. for 10 h. After cooling to room temperature, water was added, and the precipitate was filtered to get 1-((7-oxo-2,3-diphenyl-6-(quinolin-6-yl)-4,7-dihydropyrazolo[1,5-a]pyrimidin-5-yl)methyl)urea.

$^1$H NMR (DMSO-$d_6$) δ: 8.89 (br. s., 1H), 8.36 (d, J=7.8 Hz, 1H), 8.02 (d, J=8.9 Hz, 1H), 7.89 (br. s., 1H), 7.77 (d, J=7.5 Hz, 1H), 7.44-7.59 (m, 6H), 7.24-7.36 (m, 5H), 7.14 (d, J=6.7 Hz, 1H), 6.10 (br. s., 1H), 5.76 (br. s., 2H), 4.02 (br. s., 2H). LC-MS: m/z 487.2 $(M+H)^+$.

General procedure 4:

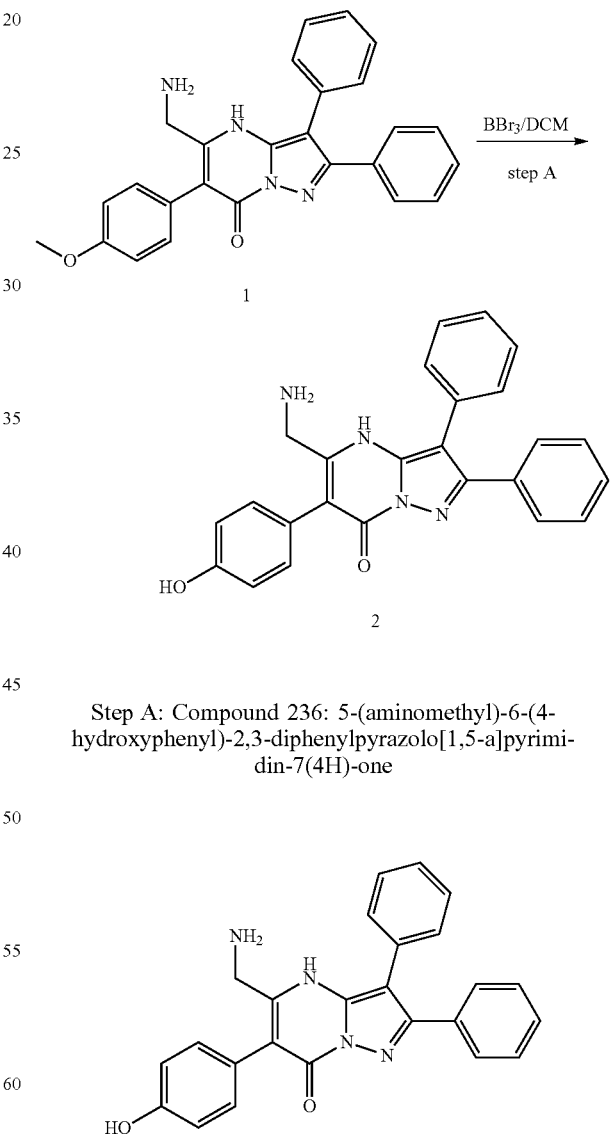

Step A: Compound 236: 5-(aminomethyl)-6-(4-hydroxyphenyl)-2,3-diphenylpyrazolo[1,5-a]pyrimidin-7(4H)-one To a solution of Intermediate 1 (Compound 222, 100 mg, 0.237 mmol) in 1 ml DCM was carefully added 5 ml $BBr_3$ (1.0M in DCM, 5 mmol) at 0° C. The mixture was stirred at 0° C. for 2 hours. The reaction was quenched by careful adding ice water at 0° C. The precipitated solids were filtered to give the title compound 2.

¹H NMR (DMSO-d₆) δ: 7.49-7.59 (m, 4H), 7.32-7.38 (m, 3H), 7.26 (t, J=7.52 Hz, 2H), 7.06-7.14 (m, 3H), 6.79 (d, J=8.33 Hz, 2H), 3.73 (s, 2H). LC-MS: m/z 409.0 (M+H)⁺.

Compound 237: 6-(4-hydroxyphenyl)-5-methyl-2,3-diphenylpyrazolo[1,5-a]pyrimidin-7(4H)-one

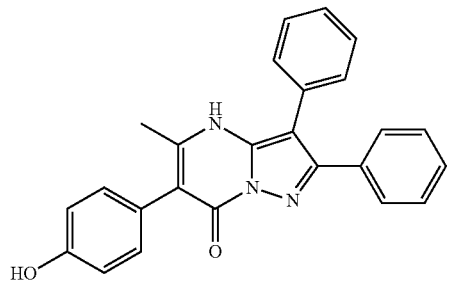 [SMILES: Cc1[nH]c2c(-c3ccccc3)c(-c3ccccc3)nn2c(=O)c1-c1ccc(O)cc1]

This compound was prepared according to General procedure 4 by using Intermediate 1 as 6-(4-methoxyphenyl)-5-methyl-2,3-diphenylpyrazolo[1,5-a]pyrimidin-7(4H)-one (Compound 209) in step A.

A mixture of 6-(4-methoxyphenyl)-5-methyl-2,3-diphenylpyrazolo[1,5-a]pyrimidin-7(4H)-one (Compound 209, 60 mg, 0.147 mmol) and BBr₃ (1M in dichloromethane, 5 mL) was stirred at room temperature for 3 h. The mixture was quenched with methanol at 0° C., and then evaporated to dryness to afford 6-(4-hydroxyphenyl)-5-methyl-2,3-diphenylpyrazolo[1,5-a]pyrimidin-7(4H)-one.

¹H NMR (DMSO-d₆) δ: 11.84 (s, 1H), 9.46 (s, 1H), 7.37-7.58 (m, 5H), 7.25-7.37 (m, 5H), 7.12 (d, J=8.60 Hz, 2H), 6.82 (d, J=8.60 Hz, 2H), 2.17 (s, 3H). LC-MS: m/z 394.1 (M+H)⁺.

Compound 238: 6-(3-fluoro-4-hydroxyphenyl)-5-methyl-2,3-diphenylpyrazolo[1,5-a]pyrimidin-7(4H)-one

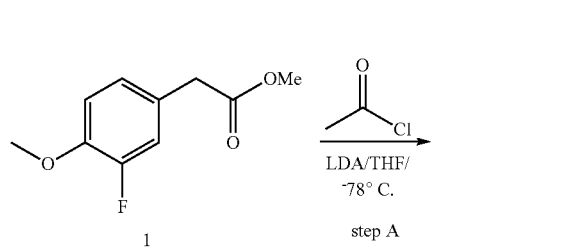

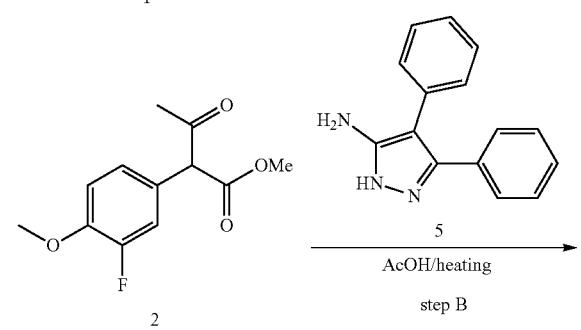

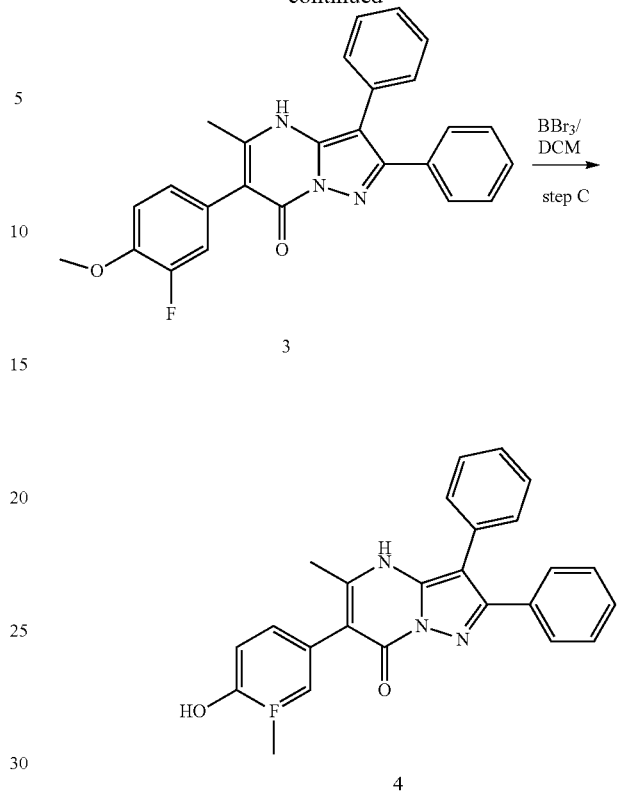

Step A: methyl 2-(3-fluoro-4-methoxyphenyl)-3-oxobutanoate

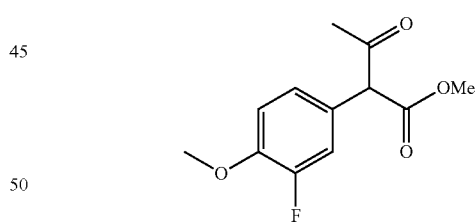

To a solution of methyl 2-(3-fluoro-4-methoxyphenyl) acetate (1 g, 5.0 mmol) in THF (15 ml) was added slowly LDA (2.5 ml, 2 mmol/ml in THF) at −30° C. Then acetyl chloride (500 mg, 6.5 mmol) was added slowly. The reaction mixture was stirred for 30 mins at −30° C. and allowed to room temperature for 1 h. The mixture was poured into water, extracted over ethyl acetate, dried over anhydrous Na₂SO₄, filtered, and concentrated to give the crude product (400 mg) as a yellow liquid, which was used directly to the next step without further purification.

Step B: 6-(3-fluoro-4-methoxyphenyl)-5-methyl-2,3-diphenylpyrazolo[1,5-a]pyrimidin-7(4H)-one

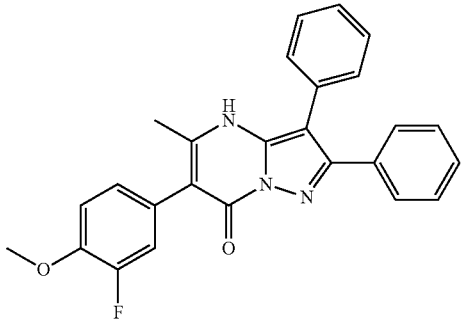 [SMILES: COc1ccc(-c2c(C)[nH]c3c(-c4ccccc4)c(-c4ccccc4)nn3c2=O)cc1F]

A solution of methyl 2-(3-fluoro-4-methoxyphenyl)-3-oxobutanoate (crude, 400 mg) and 3,4-diphenyl-1H-pyrazol-5-amine (200 mg, 0.86 mmol) in AcOH (10 ml) was heated to 120° C. overnight. The reaction mixture was cooled to room temperature. The precipitate was filtered off to give the desired product 6-(3-fluoro-4-methoxyphenyl)-5-methyl-2,3-diphenylpyrazolo[1, 5-a]pyrimidin-7(4H)-one (200 mg, 57% yield).

$^1$H NMR (DMSO-d$_6$) δ: 12.04 (s, 1H), 7.39-7.51 (m, 5H), 7.24-7.38 (m, 6H), 6.94 (dd, J=11.7, 2.6 Hz, 1H), 6.88 (dd, J=8.5, 2.6 Hz, 1H), 3.83 (s, 3H), 2.16 (s, 3H). LC-MS: m/z 426.2 (M+H)$^+$.

Step C: Compound 238: 6-(3-fluoro-4-hydroxyphenyl)-5-methyl-2,3-diphenylpyrazolo[1,5-a]pyrimidin-7(4H)-one

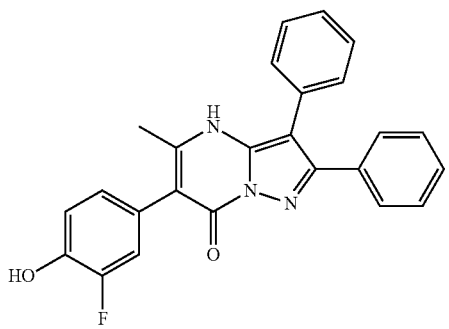 [SMILES: Cc1[nH]c2c(-c3ccccc3)c(-c3ccccc3)nn2c(=O)c1-c1ccc(O)c(F)c1]

To a solution of 6-(3-fluoro-4-methoxyphenyl)-5-methyl-2,3-diphenylpyrazolo[1,5-a]pyrimidin-7(4H)-one (200 mg, 0.47 mmol) in CH$_2$Cl$_2$ (20 ml) was added slowly BBr$_3$ (1 ml, 1 mmol/ml in CH$_2$Cl$_2$). And then the reaction mixture was stirred overnight. The mixture was adjusted to pH=7 with saturated NaHCO$_3$ solution. The precipitate was filtered off to give the desired product 6-(3-fluoro-4-hydroxyphenyl)-5-methyl-2,3-diphenylpyrazolo[1,5-a]pyrimidin-7(4H)-one.

$^1$H NMR (DMSO-d$_6$) δ: 9.57 (s, 1H), 7.54 (dd, J=7.7, 1.7 Hz, 2H), 7.44-7.50 (m, 2H), 7.29-7.38 (m, 3H), 7.26 (t, J=7.7 Hz, 2H), 7.06-7.14 (m, 1H), 7.02 (dd, J=12.8, 1.7 Hz, 1H), 6.85-6.96 (m, 2H), 2.11 (s, 3H). LC-MS: m/z 411.9 (M+H)$^+$.

Compound 239: 6-(3-chloro-4-hydroxyphenyl)-5-methyl-2,3-diphenylpyrazolo[1,5-a]pyrimidin-7(4H)-one

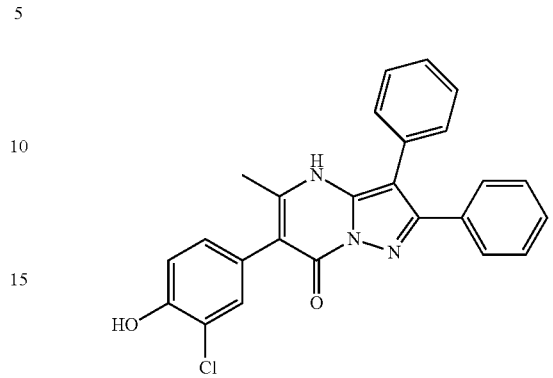

This compound was prepared according to Compound 238, step A-C, starting from methyl 2-(3-chloro-4-methoxyphenyl)acetate.

Step A: To a solution of methyl 2-(3-chloro-4-methoxyphenyl)acetate (2 g, 9.346 mmol) in THF (20 ml) was added LDA (1.5 M in THF, 8.1 mL, 12.15 mmol) dropwise at −78° C. The mixture was stirred at −78° C. for 30 min., and acetyl chloride (822 mg, 10.28 mmol) was added dropwise. Then the mixture was stirred at rt for 2 hours. The mixture was poured slowly into saturated NH$_4$Cl and extracted with EA (3×30 mL). The combined organic phase was washed with brine, dried over anhydrous MgSO$_4$ and concentrated in vacuo. The residue was purified by silica gel column (PE:EA=0-30%) to get methyl 2-(3-chloro-4-methoxyphenyl)-3-oxobutanoate (500 mg) as a yellow oil. LC-MS: m/z 257.1 (M+H)$^+$.

Step B: A suspension of methyl 2-(3-chloro-4-methoxyphenyl)-3-oxobutanoate (200 mg, 0.850 mmol) and 3,4-diphenyl-1H-pyrazol-5-amine (261 mg, 1.020 mmol) in 1,4-dioxane (5 ml) and AcOH (1 ml) was refluxed for 16 hours under N$_2$ protection. The solution was cooled to room temperature, concentrated, basified with saturated sodium hydrogen carbonate solution to adjust pH equal to 7, and filtered. The filter cake was purified by prep-TLC (DCM:MeOH=20:1) to get 6-(3-chloro-4-methoxyphenyl)-5-methyl-2,3-diphenylpyrazolo[15-a]pyrimidin-7(4H)-one (50 mg) as a white solid. LC-MS: m/z 442.1 (M+H)$^+$.

Step C: To a solution of 6-(3-chloro-4-methoxyphenyl)-5-methyl-2,3-diphenylpyrazolo[1,5-a]pyrimidin-7(4H)-one (50 mg, 0.113 mmol) in DCM (1 ml) was added 1.0M BBr$_3$ in DCM (3 ml, 3 mmol) dropwise. The mixture was stirred for 2 hours at ambient temperature. The reaction mixture was quenched by adding saturated sodium hydrogen carbonate solution and extracted with DCM (20 ml). The combined organic layers were washed with brine (20 ml), dried over anhydrous sodium sulfate, and concentrated in vacuo to obtain the title compound.

$^1$H NMR (DMSO-d$_6$) δ: 11.94 (br. s., 1H), 10.24 (s, 1H), 7.40-7.47 (m, 4H), 7.38 (d, J=7.25 Hz, 1H), 7.34 (d, J=5.10 Hz, 4H), 7.29 (d, J=1.88 Hz, 1H), 7.07-7.12 (m, 1H), 7.00-7.05 (m, 1H), 2.18 (s, 3H). LC-MS: m/z 428.1 (M+H)$^+$.

Compound 240: 3-(cyclohex-1-en-1-yl)-6-(4-hydroxyphenyl)-5-methyl-2-phenylpyrazolo[1,5-a]pyrimidin-7(4H)-one

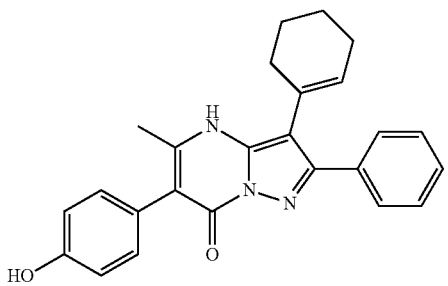 [SMILES: Cc1[nH]c2c(C3=CCCCC3)c(-c3ccccc3)nn2c(=O)c1-c1ccc(O)cc1]

This compound was prepared according to General procedure 4 by using Intermediate 1 as 3-(cyclohex-1-en-1-yl)-6-(4-methoxyphenyl)-5-methyl-2-phenylpyrazolo[1,5-a]pyrimidin-7(4H)-one (Compound 212) in step A.

To a solution of 3-(cyclohex-1-en-1-yl)-6-(4-methoxyphenyl)-5-methyl-2-phenylpyrazolo[1,5-a]pyrimidin-7(4H)-one (Compound 212, 50 mg, 0.118 mmol) in DCM (1 ml) was added 1.0M BBr$_3$ in DCM (3 ml, 3 mmol) dropwise at 0° C. The mixture was stirred for 3 hours at ambient temperature. The reaction was quenched with ice water at −10° C. and concentrated to obtain the title compound.

$^1$H NMR (DMSO-d$_6$) δ: 7.76 (d, J=7.02 Hz, 2H), 7.30-7.52 (m, 3H), 7.09 (m, J=7.93 Hz, 2H), 6.82 (m, J=7.93 Hz, 2H), 5.83 (br. s., 1H), 2.21 (br. s., 3H), 2.18 (br. s., 2H), 2.03 (br. s., 2H), 1.67 (br. s., 4H). LC-MS: m/z 398.0 (M+H)$^+$.

Compound 241: 5-(aminomethyl)-3-(cyclohex-1-en-1-yl)-6-(4-hydroxyphenyl)-2-phenylpyrazolo[1, 5-a]pyrimidin-7(4H)-one

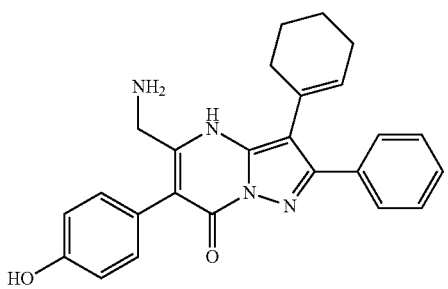 [SMILES: NCc1[nH]c2c(C3=CCCCC3)c(-c3ccccc3)nn2c(=O)c1-c1ccc(O)cc1]

This compound was prepared according to General procedure 4 by using Intermediate 1 as 5-(aminomethyl)-3-(cyclohex-1-en-1-yl)-6-(4-methoxyphenyl)-2-phenylpyrazolo[1,5-a]pyrimidin-7(4H)-one (Compound 232) in step A.

To a solution of 5-(aminomethyl)-3-(cyclohex-1-en-1-yl)-6-(4-methoxyphenyl)-2-phenylpyrazolo[1,5-a]pyrimidin-7(4H)-one (Compound 232, 85 mg, 0.2 mmol) in DCM (1 ml) was added 1.0M BBr$_3$ in DCM (3 ml, 3 mmol) dropwise. The mixture were stirred for 3 hours at ambient temperature, The reaction was quenched with ice water and concentrated to obtain the title compound.

$^1$H NMR (DMSO-d$_6$) δ: 8.21 (s, 1H), 7.69 (d, J=6.72 Hz, 2H), 7.37 (d, J=6.98 Hz, 2H), 7.31 (d, J=6.72 Hz, 1H), 7.06 (m, J=8.06 Hz, 2H), 6.77 (m, J=8.33 Hz, 2H), 5.66 (br. s., 1H), 3.68 (br. s., 3H), 2.34 (br. s., 2H), 2.09 (br. s., 2H), 1.53-1.74 (m, 4H). LC-MS: m/z 413.2 (M+H)$^+$.

Compound 242

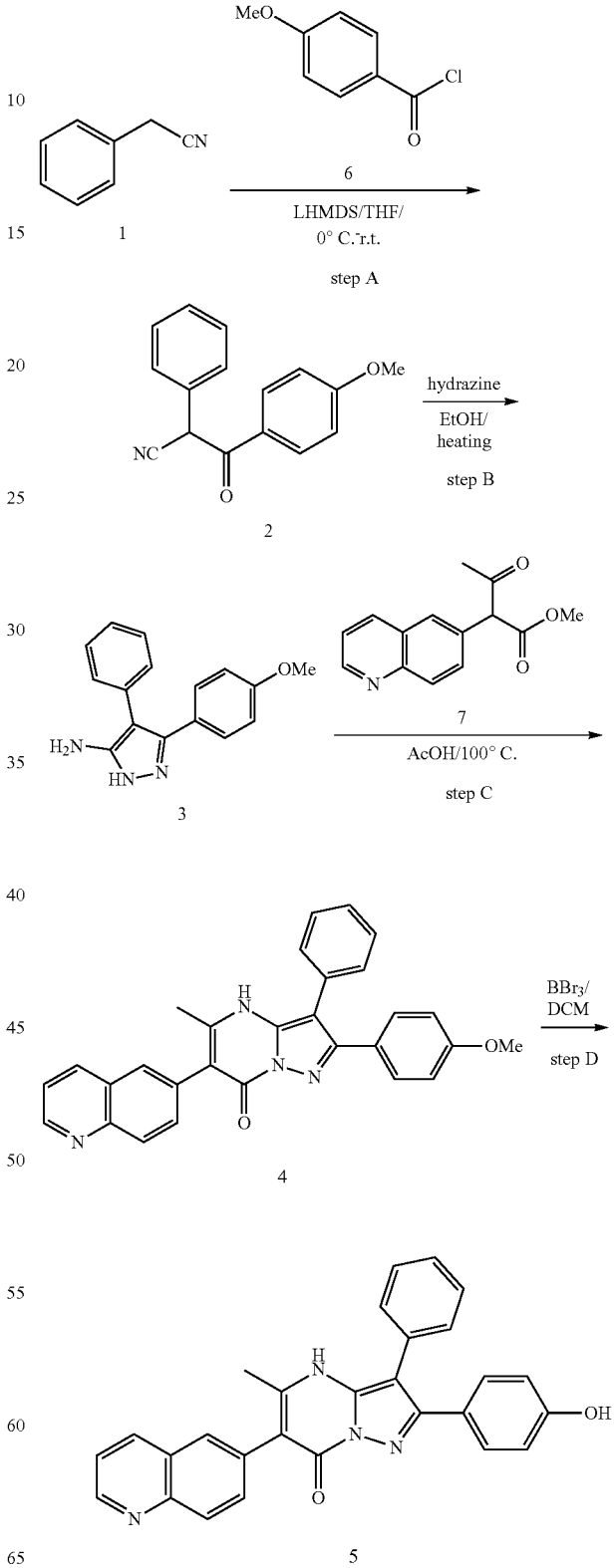

247

Step A:
3-(4-methoxyphenyl)-3-oxo-2-phenylpropanenitrile

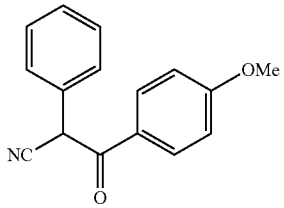 [SMILES: COc1ccc(C(=O)C(C#N)c2ccccc2)cc1]

To a solution of 2-phenylacetonitrile (1 g, 8.536 mmol) in THF (20 ml) was added LiHMDS (2.0 M in THF, 5.1 mL, 10.2 mmol) dropwise at 0° C. The mixture was stirred at 0° C. for 30 min and warmed up to room temperature for 15 min. 4-methoxybenzoyl chloride (1.75 g, 10.24 mmol) was added dropwise at 0° C. Then the mixture was stirred at room temperature for 16 hours. The mixture was poured slowly into saturated NH$_4$Cl and extracted with EA (3×10 mL). The combined organic phase was washed with brine, dried over anhydrous MgSO$_4$ and concentrated in vacuo to get crude product (2.5 g) as a yellow oil. LC-MS: m/z 252.1 (M+H)$^+$.

Step B:
3-(4-methoxyphenyl)-4-phenyl-1H-pyrazol-5-amine

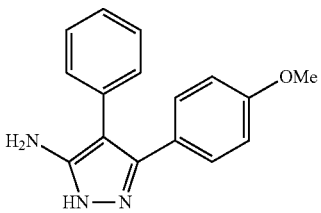 [SMILES: COc1ccc(-c2n[nH]c(N)c2-c2ccccc2)cc1]

A suspension of 3-(4-methoxyphenyl)-3-oxo-2-phenyl-propanenitrile (2 g, 8.761 mmol) and hydrazine hydrate (2.4 g, 43.804 mmol) in EtOH (10 ml) and AcOH (2 ml) was refluxed for 16 hours under N$_2$ protection. The solution was cooled to the room temperature and concentrated, basified with sodium hydrogen carbonate solution to adjust pH equal to 7, and extracted with EtOAc. The combined organic layers were washed with brine (30 ml), dried over anhydrous sodium sulfate, and concentrated in vacuo. The residue was purified by silica gel column (PE:EA=3:1) to get 3-(4-methoxyphenyl)-4-phenyl-1H-pyrazol-5-amine (700 mg) as a white solid.

$^1$H NMR (DMSO-d$_6$) δ 11.76-11.92 (m, 1H), 7.27-7.35 (m, 2H), 7.15-7.24 (m, 5H), 6.88 (d, J=8.3 Hz, 2H), 4.33-4.63 (m, 2H), 3.74 (s, 3H). LC-MS: m/z 266.1 (M+H)$^+$.

248

Step C: Compound 243: 2-(4-methoxyphenyl)-5-methyl-3-phenyl-6-(quinolin-6-yl)pyrazolo[1,5-a]pyrimidin-7(4H)-one

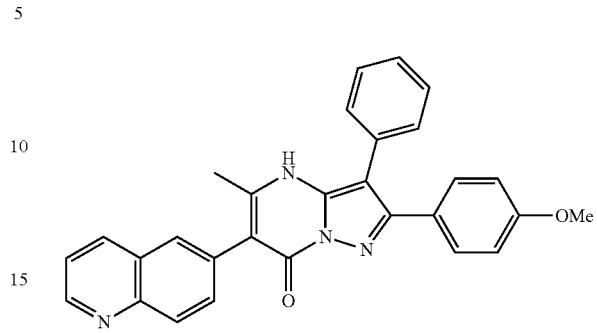

A suspension of 3-(4-methoxyphenyl)-4-phenyl-1H-pyrazol-5-amine (250 mg, 0.942 mmol) and methyl 3-oxo-2-(quinolin-6-yl)butanoate (458 mg, 1.885 mmol) in 1,4-dioxane (10 ml) and AcOH (2 ml) was refluxed for 16 hours under N$_2$ protection. The solution was cooled to the room temperature and concentrated, basified with saturated sodium hydrogen carbonate solution to adjust pH equal to 7, and filtered to afford 2-(4-methoxyphenyl)-5-methyl-3-phenyl-6-(quinolin-6-yl)pyrazolo[1,5-a]pyrimidin-7(4H)-one.

$^1$H NMR (DMSO-d$_6$) δ12.01 (s, 1H), 8.94 (d, J=2.75 Hz, 1H), 8.40 (d, J=7.93 Hz, 1H), 8.08 (d, J=8.54 Hz, 1H), 7.93-7.99 (m, 1H), 7.75 (dd, J=8.70, 1.68 Hz, 1H), 7.58 (dd, J=8.24, 4.27 Hz, 1H), 7.41-7.51 (m, 3H), 7.34-7.40 (m, 4H), 6.90 (d, J=8.55 Hz, 2H), 3.76 (s, 3H), 2.25 (s, 3H). LC-MS: m/z 459.2 (M+H)$^+$.

Step D: Compound 242: 2-(4-hydroxyphenyl)-5-methyl-3-phenyl-6-(quinolin-6-yl)pyrazolo[1,5-a]pyrimidin-7(4H)-one

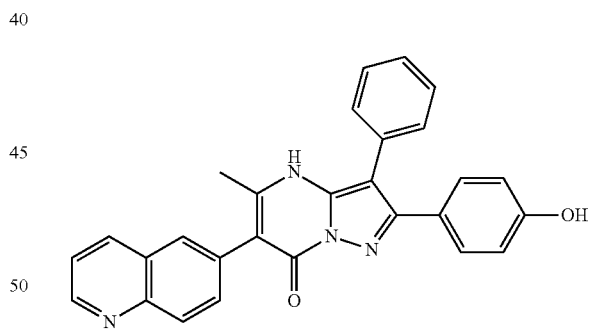

To a solution of 2-(4-methoxyphenyl)-5-methyl-3-phenyl-6-(quinolin-6-yl)pyrazolo[1,5-a]pyrimidin-7(4H)-one (100 mg, 0.225 mmol) in DCM (1 ml) was added 1.0 M BBr$_3$ in DCM (3 ml, 3 mmol) dropwise. The mixture was stirred for 2 hours at ambient temperature. The reaction mixture was quenched by adding saturated sodium hydrogen carbonate solution and extracted with DCM (20 mL). The combined organic layers were washed with brine (20 ml), dried over anhydrous sodium sulfate, and concentrated in vacuo to obtain the title compound.

$^1$H NMR (DMSO-d$_6$) δ: 11.97 (br. s., 1H), 9.63 (s, 1H), 8.93 (d, J=2.69 Hz, 1H), 8.39 (d, J=7.52 Hz, 1H), 8.07 (d, J=8.87 Hz, 1H), 7.95 (d, J=1.88 Hz, 1H), 7.75 (dd, J=8.60, 1.88 Hz, 1H), 7.57 (dd, J=8.33, 4.30 Hz, 1H), 7.42-7.49 (m,

2H), 7.35-7.41 (m, 3H), 7.27 (m, J=8.60 Hz, 2H), 6.71 (m, J=8.60 Hz, 2H), 2.24 (s, 3H). LC-MS: m/z 445.2 (M+H)+.

Step B: Compound 244: 2,3-diphenyl-6-(quinolin-6-yl)pyrazolo[1,5-a]pyrimidin-7(4H)-one

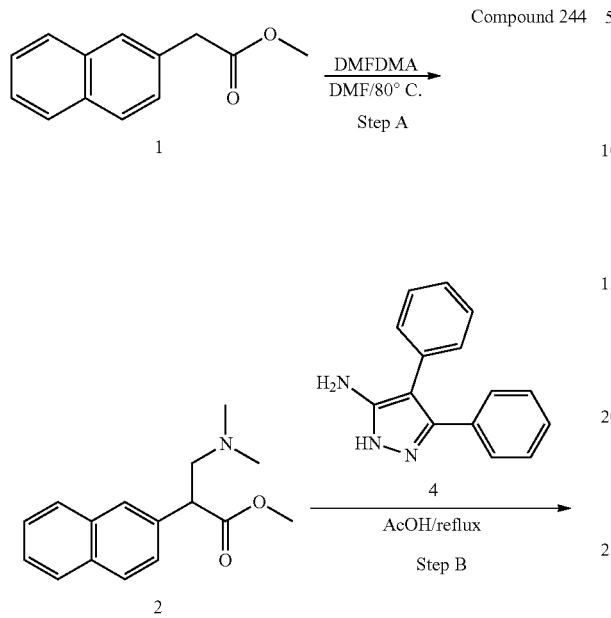

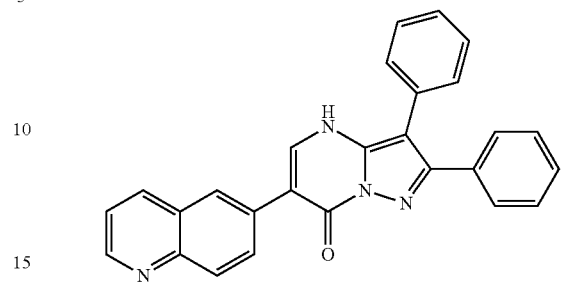

The solution of 3,4-diphenyl-1H-pyrazol-5-amine (200 mg, 0.9 mmol) and (E)-methyl 3-(dimethylamino)-2-(quinolin-6-yl)acrylate (283.2 mg, 1.1 mmol) in AcOH (3 mL) was stirred at 100° C. for 2 h. After cooling to room temperature, the solvent was removed by vacuum, saturated NaHCO$_3$ (6 mL) was added, and the precipitate was filtered. The filter cake was washed with water (2 mL) and MeOH (2 mL) to afford 2,3-diphenyl-6-(quinolin-6-yl)pyrazolo[1,5-a]pyrimidin-7(4H)-one.

$^1$H NMR (DMSO-d$_6$) δ: 12.69 (br. s., 1H), 8.91 (dd, J=4.0, 1.6 Hz, 1H), 8.37-8.47 (m, 1H), 8.32 (d, J=1.9 Hz, 1H), 8.10-8.16 (m, 2H), 8.03-8.10 (m, 1H), 7.56 (dd, J=8.3, 4.0 Hz, 1H), 7.45-7.54 (m, 4H), 7.32-7.45 (m, 6H). LC-MS: m/z 415.3 (M+H)+.

Compound 245

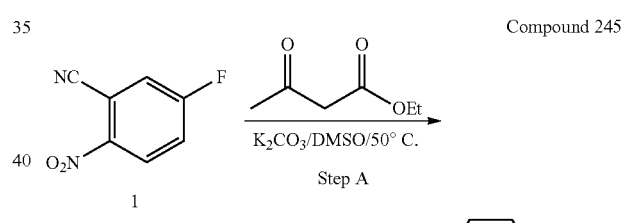

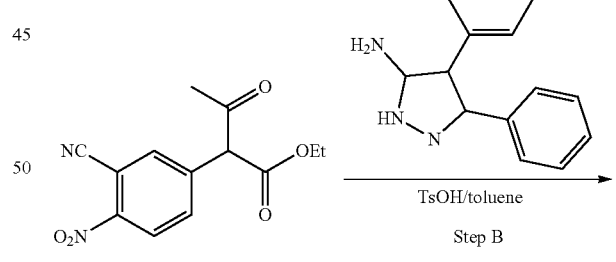

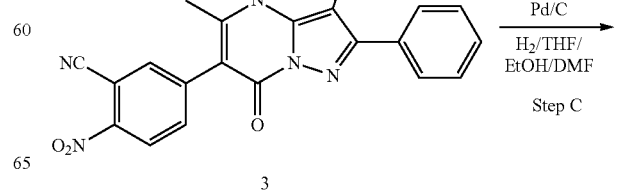

Step A: (E)-methyl 3-(dimethylamino)-2-(quinolin-6-yl)acrylate

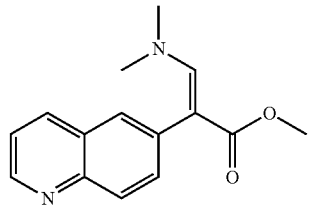 [SMILES: COC(=O)/C(=C/N(C)C)c1ccc2ncccc2c1]

The solution of methyl 2-(quinolin-6-yl)acetate (3.0 g, 14.9 mmol) and DMF-DMA (4.0 mL) in DMF was stirred at 85° C. for 12 h. After cooling to room temperature, the mixture was diluted with water, extracted with EtOAc, dried over Na$_2$SO$_4$, and concentrated to get the crude product (3.8 g) which was directly used to the next step without further purification. LC-MS: m/z 257.3 (M+H)+.

251

-continued

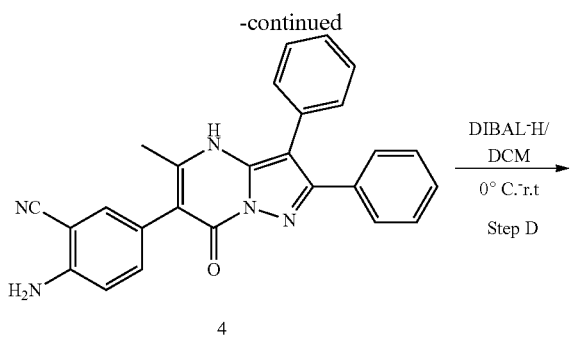

4

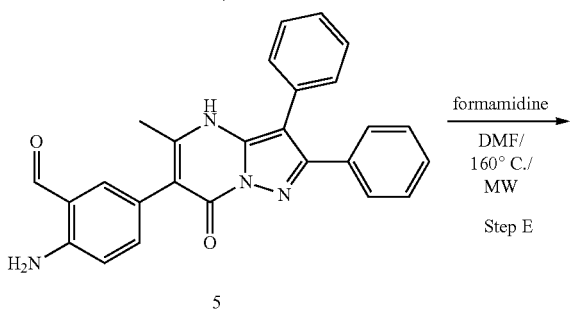

5

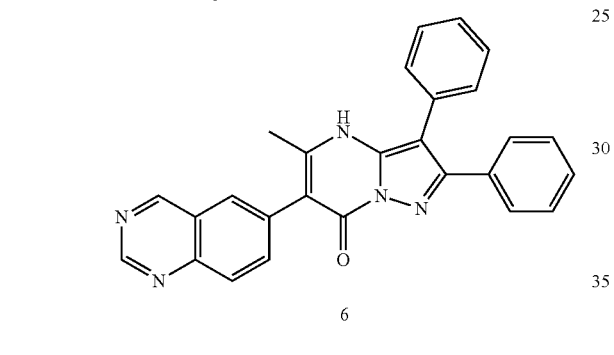

6

Step A: ethyl 2-(3-cyano-4-nitrophenyl)-3-oxobutanoate

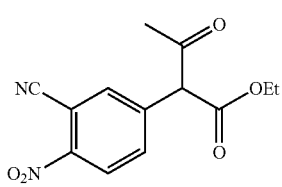 [SMILES: CCOC(=O)C(C(C)=O)c1ccc([N+](=O)[O-])c(C#N)c1]

5-fluoro-2-nitrobenzonitrile (5 g, 30 mmol), ethyl 3-oxobutanoate (7.8 g, 60 mmol) and $K_2CO_3$ (12.46 g, 90 mmol) in DMSO (50 mL) was stirred at 50° C. for 16 h. The mixture was acidified with HCl (1M) to pH=7 and extracted with EA (50 mL×3). The organic layer was dried and concentrated to give the crude which was purified by silica gel chromatography (PE:EA=3:1) to get Intermediate 2 (6.15 g, 77% yield).

$^1$H NMR (CHLOROFORM-d) δ: 8.33 (d, J=8.6 Hz, 1H), 7.75 (d, J=1.9 Hz, 1H), 7.63 (dd, J=8.6, 1.9 Hz, 1H), 3.84 (s, 1H), 3.76 (s, 3H), 1.95 (s, 3H). LC-MS: m/z 277.2 (M+H)$^+$.

252

Step B: 5-(5-methyl-7-oxo-2,3-diphenyl-4,7-dihydropyrazolo[1,5-a]pyrimidin-6-yl)-2-nitrobenzonitrile

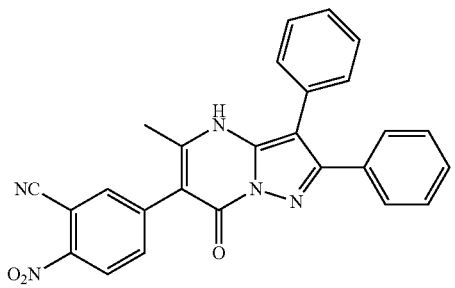

A mixture of Intermediate 2 (3 g, 11 mmol), 3,4-diphenyl-1H-pyrazol-5-amine (2.7 g, 11 mmol), and TsOH (200 mg, 1.1 mmol) in toluene (20 mL) was stirred at 120° C. for 4 h. The mixture was cooled to r.t. and filtered to give the crude yellow solid which was recrystallized from MeOH to give the pure Intermediate 3 (2.5 g, 51% yield).

$^1$H NMR (DMSO-d$_6$) δ: 8.45 (d, J=8.6 Hz, 1H), 8.14-8.30 (m, 1H), 8.01 (d, J=8.6 Hz, 1H), 7.20-7.50 (m, 10H), 2.28 (s, 3H). LC-MS: m/z 448.1 (M+H)$^+$.

Step C: 2-amino-5-(5-methyl-7-oxo-2,3-diphenyl-4,7-dihydropyrazolo[1,5-a]pyrimidin-6-yl) benzonitrile

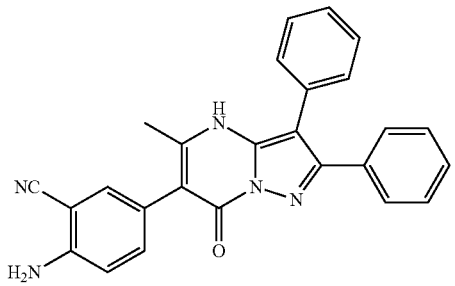 [SMILES: Cc1[nH]c2c(-c3ccccc3)c(-c3ccccc3)nn2c(=O)c1-c1ccc([N+](=O)[O-])c(C#N)c1]

The Intermediate 3 (3 g, 0.7 mmol) and 10% Pd/C (300 mg) in DMF (10 mL) and MeOH (50 mL) was stirred at r.t. for 16 h under $H_2$ atmosphere. The mixture was filtered and concentrated in vacuo. The residue was purified by silica gel column (PE:EA=10:1-1:1) to give Intermediate 4 (1.8 g, 64% yield).

$^1$H NMR (DMSO-d$_6$) δ: 11.91 (s, 1H), 7.38-7.52 (m, 5H), 7.21-7.38 (m, 7H), 6.85 (d, J=8.9 Hz, 1H), 6.16 (s, 2H), 2.20 (s, 3H). LC-MS: m/z 418.3 (M+H)$^+$.

Step D: 2-amino-5-(5-methyl-7-oxo-2,3-diphenyl-4,7-dihydropyrazolo[1,5-a]pyrimidin-6-yl) benzaldehyde

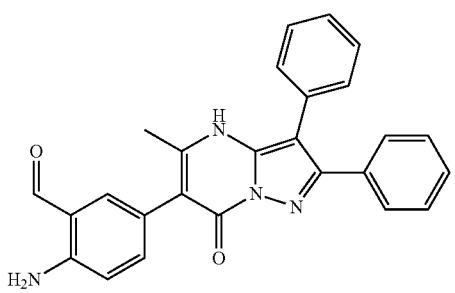 [SMILES: Cc1[nH]c2c(-c3ccccc3)c(-c3ccccc3)nn2c(=O)c1-c1ccc(N)c(C=O)c1]

The Intermediate 4 (800 mg, 1.9 mmol) in dry DCM (10 mL) was cooled to 0° C. and DIBAL-H (19 mmol, 2M) was added dropwise. The mixture was warmed up to r.t. for 16 h. The reaction was quenched with MeOH and concentrated. The residue was purified by silica gel column (PE;EA=1:1) to get Intermediate 5 (150 mg, 19% yield).

$^1$H NMR (DMSO-$d_6$) δ: 11.90 (br. s., 1H), 9.85 (s, 1H), 7.38-7.51 (m, 6H), 7.22-7.38 (m, 8H), 6.84 (d, J=8.6 Hz, 1H), 2.23 (s, 3H). LC-MS: m/z 421.5 (M+H)$^+$.

Step E: Compound 245: 5-methyl-2,3-diphenyl-6-(quinazolin-6-yl)pyrazolo[1,5-a]pyrimidin-7(4H)-one

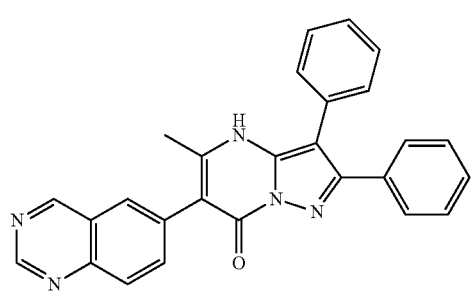

The Intermediate 5 (60 mg, 0.14 mmol) and formamidine (126 mg, 2.86 mmol) in DMF was stirred at 160° C. for 2 h. The mixture was concentrated to get the title compound 6.

$^1$H NMR (DMSO-$d_6$) δ: 12.13 (br. s., 1H), 9.66 (s, 1H), 9.35 (s, 1H), 8.17 (s, 1H), 8.08 (d, J=12.1 Hz, 1H), 7.95-8.05 (m, 1H), 7.41-7.52 (m, 6H), 7.34-7.41 (m, 5H), 2.27 (s, 3H). LC-MS: m/z 430.2 (M+H)$^+$.

Compound 246: 6-(5-methyl-7-oxo-2,3-diphenyl-4,7-dihydropyrazolo[1,5-a]pyrimidin-6-yl) quinoline-2-carboxylic acid

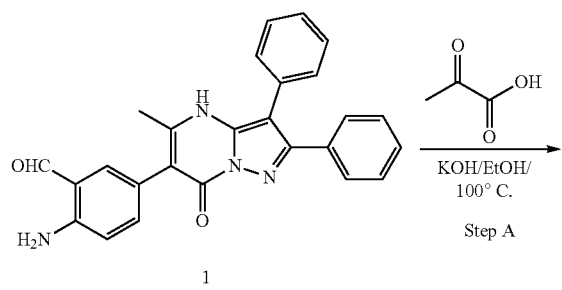

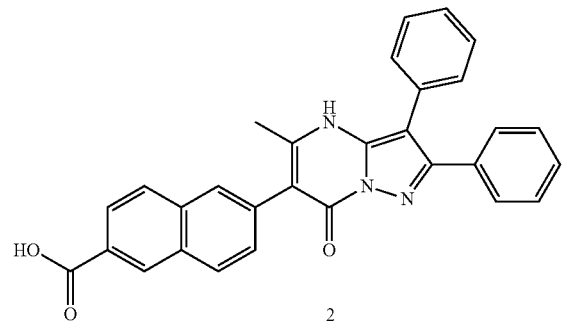

Step A: 2-amino-5-(5-methyl-7-oxo-2,3-diphenyl-4,7-dihydropyrazolo[1,5-a]pyrimidin-6-yl)benzalde-hyde (50 mg, 0.12 mmol), 2-oxopropanoic acid (52 mg, 0.6 mmol), and KOH (23 mg, 0.6 mmol) in EtOH (5 mL) was stirred at r.t. for 16 h. The mixture was acidified with 1 M HCl to pH=6 and extracted with DCM (10 ml×3). The organic layer was dried and concentrated to afford the desired product.

$^1$H NMR (DMSO-$d_6$) δ: 12.12 (br. s., 1H), 8.58 (d, J=8.3 Hz, 1H), 8.15-8.24 (m, 2H), 8.09 (br. s., 1H), 7.87 (d, J=8.3 Hz, 1H), 7.42-7.50 (m, 5H), 7.33-7.42 (m, 6H), 2.28 (s, 3H). LC-MS: m/z 473.5 (M+H)$^+$.

Compound 247

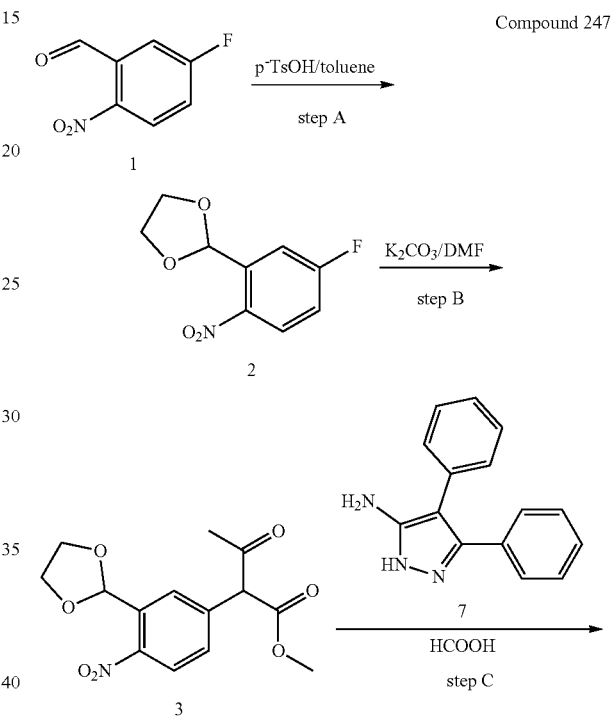

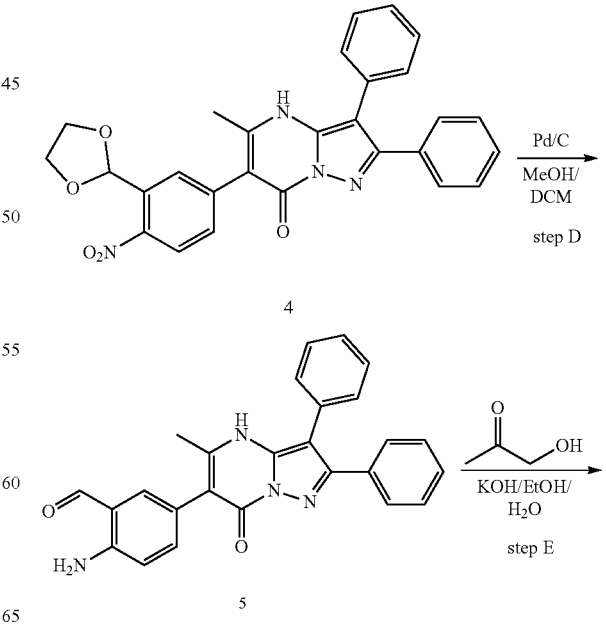

-continued

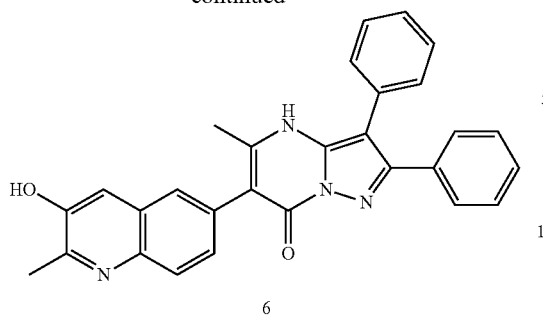

Step A: 2-(5-fluoro-2-nitrophenyl)-1,3-dioxolane

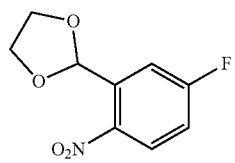 [SMILES: O=[N+]([O-])c1ccc(F)cc1C1OCCO1]

To a solution of 5-fluoro-2-nitrobenzaldehyde (5.0 g, 29.6 mmol) in toluene (150 mL) was added ethylene glycol (2.75 g, 44.4 mmol) and p-TSOH (500 mg). After addition, the mixture was heated to reflux overnight. The reaction mixture was cooled to RT and diluted with EtOAc. The combined organic phase was washed with water and brine, dried over anhydrous $Na_2SO_4$, filtered, and concentrated under reduced pressure to give Intermediate 2 (6.4 g) as a yellow oil which was directly used in the next step without further purification. LC-MS: m/z 214.6 $(M+H)^+$.

Step B: methyl 2-(3-(1,3-dioxolan-2-yl)-4-nitrophenyl)-3-oxobutanoate

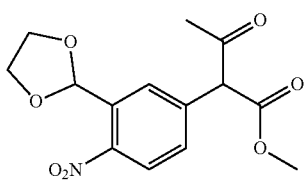

To a mixture of Intermediate 2 (5.4 g, 25.4 mmol) in DMF (150 mL) was added methyl 3-oxobutanoate (4.42 g, 38.0 mmol, 1.5 eq) and $K_2CO_3$ (5.24 g, 38.0 mmol, 1.5 eq) at RT. After addition, the mixture was heated to 55° C. overnight. The reaction mixture was cooled to RT and diluted with EtOAc. The combined organic phase was washed with water and brine, dried over anhydrous $Na_2SO_4$, filtered, and concentrated under reduced pressure. The residue was purified by column chromatography on silica gel (EtOAc/PE=1/10) to afford the desired product Intermediate 3 (4.23 g, 54% yield). LC-MS: m/z 309.9 $(M+H)^+$.

Step C: 6-(3-(1,3-dioxolan-2-yl)-4-nitrophenyl)-5-methyl-2,3-diphenylpyrazolo[1,5-a]pyrimidin-7(4H)-one

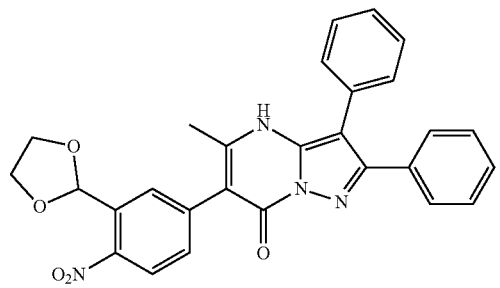 [SMILES: Cc1[nH]c2c(-c3ccccc3)c(-c3ccccc3)nn2c(=O)c1-c1ccc([N+](=O)[O-])c(C2OCCO2)c1]

A mixture of Intermediate 3 (4.23 g, 13.7 mmol) and 3,4-diphenyl-1H-pyrazol-5-amine (3.22 g, 13.7 mmol, 1.0 eq) in $CH_3COOH$ (200 mL) was stirred at 110° C. overnight, and then cooled to room temperature. The precipitate was collected by filtration and washed with EA to afford the desired product Intermediate 4 (4.01 g, yield 59%) as a yellow solid. LC-MS: m/z 494.9 $(M+H)^+$.

Step D: 2-amino-5-(5-methyl-7-oxo-2,3-diphenyl-4,7-dihydropyrazolo[1,5-a]pyrimidin-6-yl)benzaldehyde

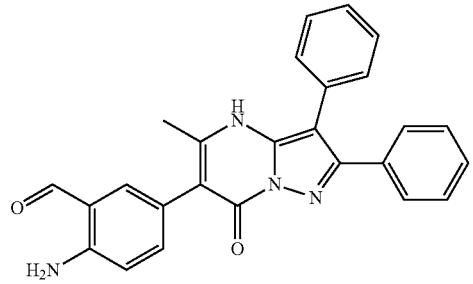 [SMILES: Cc1[nH]c2c(-c3ccccc3)c(-c3ccccc3)nn2c(=O)c1-c1ccc(N)c(C=O)c1]

To a solution of Intermediate 4 (1.0 g, 2.02 mmol) in a mixed solution of MeOH (50 mL)/DCM (5 mL)/$H_2O$ (5 mL) was added Pd/C (0.2 g) and $HCOONH_4$ (673 mg, 10.1 mmol, 5.0 eq) at RT under $N_2$. After addition, the mixture was heated to reflux overnight. The reaction mixture was cooled to room temperature, filtered, and concentrated under reduced pressure. The residue was purified by column chromatography on silica gel to afford Intermediate 5 (610 mg, 72% yield). LC-MS: m/z 420.9 $(M+H)^+$.

Step E: Compound 247

6-(3-hydroxy-2-methylquinolin-6-yl)-5-methyl-2,3-diphenylpyrazolo[1,5-a]pyrimidin-7(4H)-one

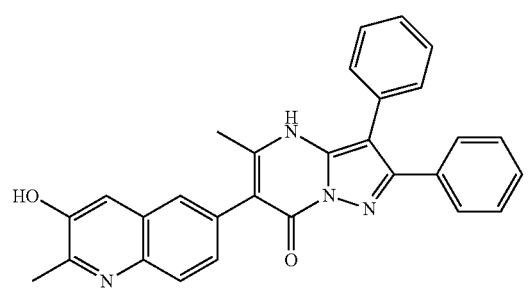 [SMILES: Cc1nc2ccc(-c3c(C)[nH]c4c(-c5ccccc5)c(-c5ccccc5)nn4c3=O)cc2cc1O]

To a mixture of Intermediate 5 (150 mg, 0.36 mmol) and 1-hydroxypropan-2-one (52.9 mg, 0.71 mmol, 2.0 eq) in EtOH (5 mL) was added KOH (40.1 mg, 0.71 mmol, 2.0 eq) at RT. After addition, the mixture was heated to reflux overnight. The reaction mixture was concentrated under reduced pressure to afford the title product.

$^1$H NMR (DMSO-$d_6$) δ12.00 (s, 1H), 10.32 (s, 1H), 7.85 (d, J=8.4 Hz, 1H), 7.70 (d, J=2.0 Hz, 1H), 7.50-7.39 (m, 7H), 7.38-7.30 (m, 5H), 2.56 (s, 3H), 2.22 (s, 3H). LC-MS: m/z 459.0 (M+H)$^+$.

To a mixture of Intermediate 1 (50 mg, 0.09 mmol) and DIPEA (23.2 mg, 0.18 mmol, 2.0 eq) in THF (5 mL) was added methyl 3-chloro-3-oxopropanoate (24.5 mg, 0.18 mmol, 2.0 eq). The reaction mixture was then stirred at rt for 8 h. The mixture was partitioned between EA and H$_2$O. The organic phase was washed with water and brine, dried over anhydrous Na$_2$SO$_4$, filtered, and concentrated under reduced pressure to give crude Intermediate 2 (50 mg) which was directly used to the next step without further purification. LC-MS: m/z 645.1 (M+H)$^+$.

Step B: Compound 248: 2-(6-(5-methyl-7-oxo-2,3-diphenyl-4,7-dihydropyrazolo[1,5-a]pyrimidin-6-yl)benzo[d]thiazol-2-yl)acetate A mixture of Intermediate 2 (50 mg, 0.08 mmol) in TFA (3 mL) was stirred at 75° C. for 3 h. The mixture was concentrated under reduced pressure to afford the desired product 3.

$^1$H NMR (DMSO-$d_6$) δ: 12.01 (s, 1H), 7.44 (m, 6H), 7.34 (m, 5H), 4.37 (s, 2H), 3.71 (s, 3H), 2.20 (s, 3H). LC-MS: m/z 507.0 (M+H)$^+$.

Step A: methyl 3-((2-((4-methoxybenzyl)thio)-4-(5-methyl-7-oxo-2,3-diphenyl-4,7-dihydropyrazolo[1,5-a]pyrimidin-6-yl)phenyl)amino)-3-oxopropanoate

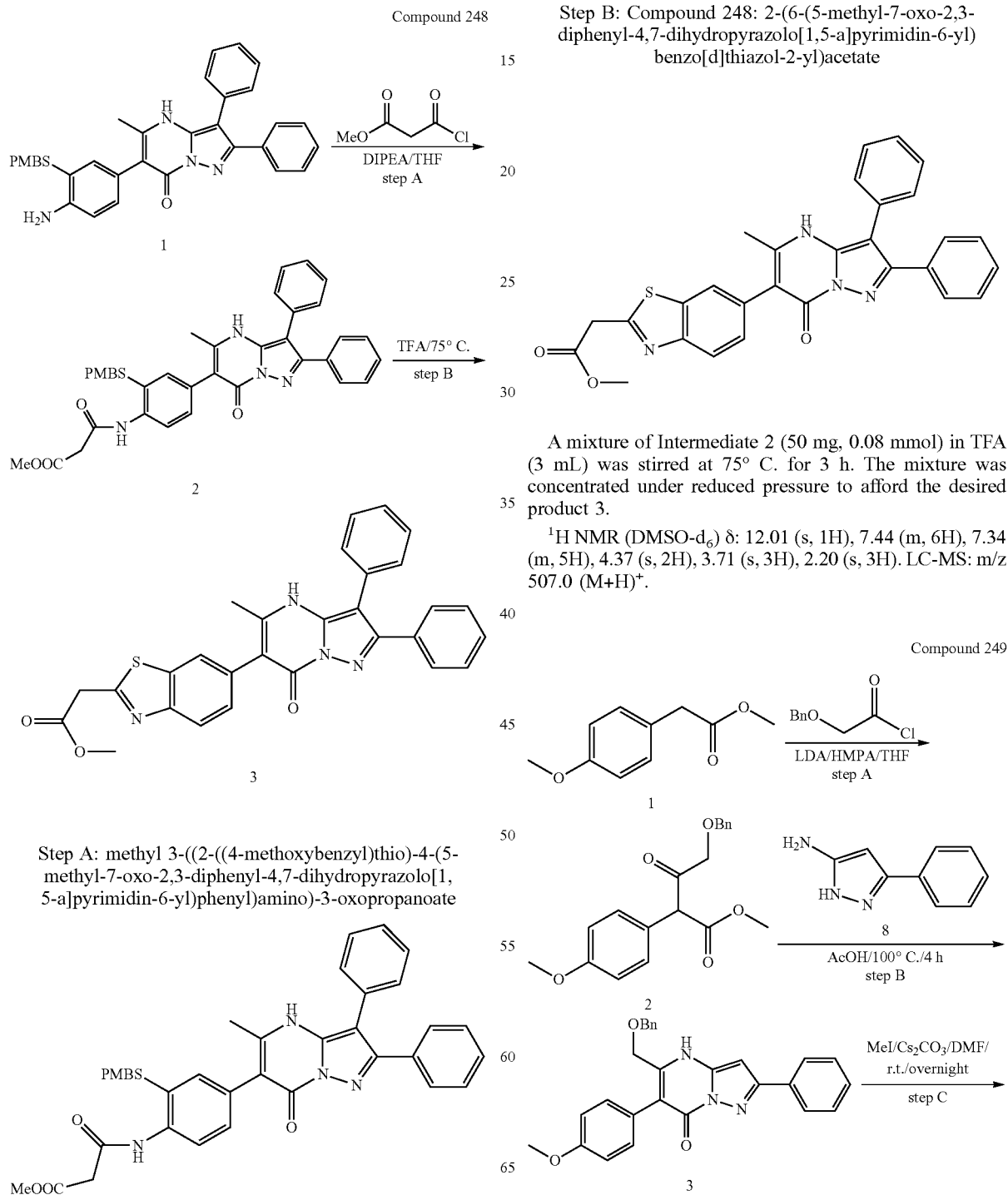

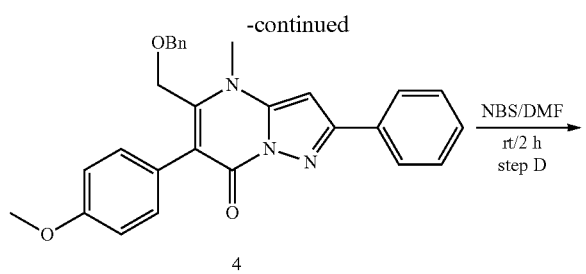

4

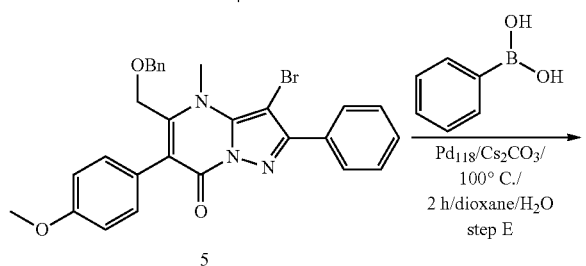

5

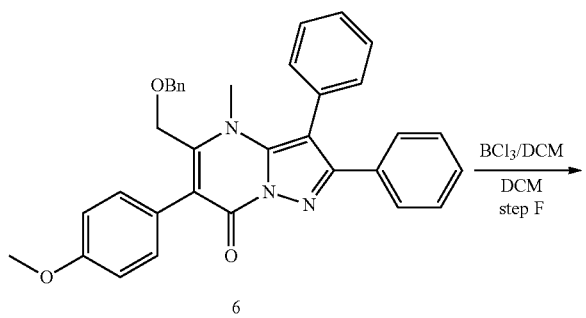

6

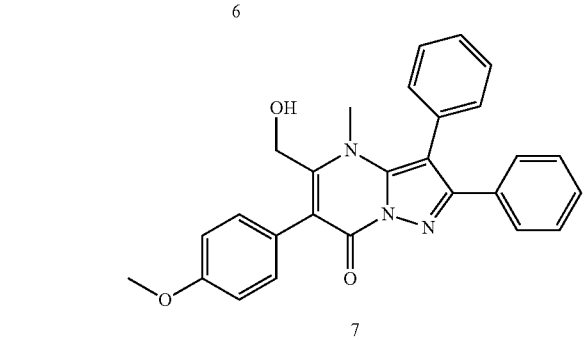

7

Step A: methyl 4-(benzyloxy)-2-(4-methoxyphenyl)-3-oxobutanoate

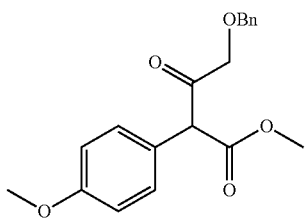

To a solution of methyl 2-(4-methoxyphenyl)acetate (3.0 g, 16.7 mmol) in THF (10 mL) was added dropwise LDA (10 mL, 19.98 mmol, 1.2 eq) and HMPA (598 mg, 3.33 mmol, 0.2 eq) at −78° C. After addition, the mixture was stirred at −48° C. for 0.5 h. The mixture was then cooled to −78° C., 2-(benzyloxy)acetyl chloride (3.69 g, 17 mmol) in dry THF (3 mL) was added slowly and stirred at RT overnight. The reaction was quenched with NH$_4$Cl solution, extracted with EA. The combined organic phase was washed with water and brine, dried over anhydrous Na$_2$SO$_4$, filtered, and concentrated under reduced pressure. The residue was purified by column chromatography on silica gel (EtOAc/PE=1/4) to afford Intermediate 2 (2.7 g, 49% yield). LC-MS: m/z 329.1 (M+H)$^+$.

Step B: 5-((benzyloxy)methyl)-6-(4-methoxyphenyl)-2-phenylpyrazolo 1,5-a] pyrimidin-7(4H)-one

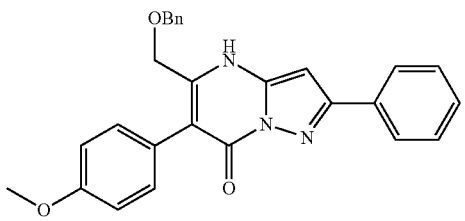 [SMILES: COc1ccc(-c2c(COCc3ccccc3)[nH]c3cc(-c4ccccc4)nn3c2=O)cc1]

A mixture of Intermediate 2 (2.7 g, 8.23 mmol) and compound 8 (1.3 g, 8.23 mmol, 1.0 eq) in CH$_3$COOH (10 mL) was stirred at 100° C. for 3 h and then cooled to room temperature. The mixture was concentrated under reduced pressure and washed with MeOH to afford the desired Intermediate 3 (2.4 g, yield 67%) as a white solid. LC-MS: m/z 437.9 (M+H)$^+$.

Step C: 5-((benzyloxy)methyl)-6-(4-methoxyphenyl)-4-methyl-2-phenylpyrazolo[1,5-a]pyrimidin-7(4H)-one

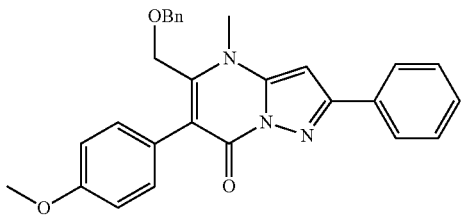 [SMILES: COc1ccc(-c2c(COCc3ccccc3)n(C)c3cc(-c4ccccc4)nn3c2=O)cc1]

To a mixture of Intermediate 3 (2.4 g, 5.49 mmol, 1 eq.) and Cs$_2$CO$_3$ (2.14 g, 6.59 mmol, 1.2 eq.), in DMF (8 ml) was added MeI (774 mg, 5.49 mmol, 1.0 eq). The mixture was then stirred at rt overnight. The mixture was poured into water (100 ml) and filtered. The filter cake was washed with MeOH to give Intermediate 4 (2.9 g) as a white solid. LC-MS: m/z 451.9 (M+H)$^+$.

Step D: 5-((benzyloxy)methyl)-3-bromo-6-(4-methoxyphenyl)-4-methyl-2-phenylpyrazolo[1,5-a]pyrimidin-7(4H)-one

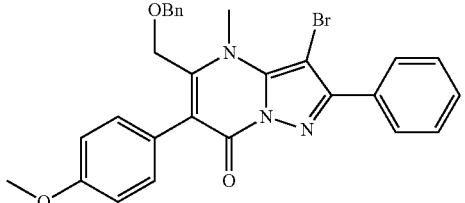

To a mixture of Intermediate 4 (2.9 g, 6.6 mmol, 1 eq) in DMF (20 ml) was added NBS (1.37 g, 7.94 mmol, 1.2 eq). The reaction mixture was then stirred at rt for 2 h. The mixture was poured into water (200 ml) and filtered to give Intermediate 5 (3.1 g, yield 91%) as a white solid. LC-MS: m/z 430.1 (M+H)+.

Step E: 5-((benzyloxy)methyl)-6-(4-methoxyphenyl)-4-methyl-2,3-diphenylpyrazolo[1,5-a]pyrimidin-7(4H)-one

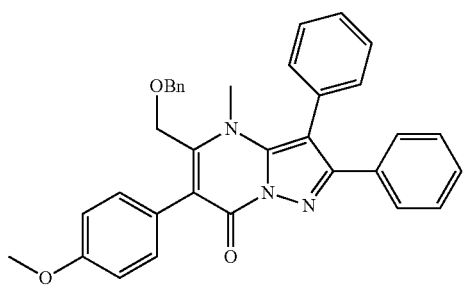

A suspension of Intermediate 5 (1.5 g, 2.83 mmol), phenylboronic acid (414 mg, 3.40 mmol, 1.2 eq), Pd$_{118}$ (368 mg, 0.57 mmol, 0.2 eq) and K$_2$CO$_3$ (982 mg, 7.1 mmol, 2.5 eq) in 1.4-dioxane (30 ml) and H$_2$O (1.5 ml) was stirred at 90° C. for 5 h under N$_2$ atmosphere. The reaction mixture was then cooled to r.t. and filtered. The filtrate was concentrated in vacuo and purified by flash column chromatography silica gel to obtain Intermediate 6 (300 mg, 20% yield). LC-MS: m/z 527.9 (M+H)+

Step F: Compound 249: 5-(hydroxymethyl)-6-(4-methoxyphenyl)-4-methyl-2,3-diphenylpyrazolo[1,5-a]pyrimidin-7(4H)-one

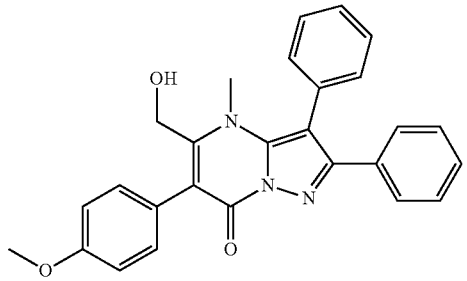

To a solution of Intermediate 6 (150 mg, 0.28 mmol) in dry DCM (5 mL) was added dropwise BCl$_3$/DCM (5 mL, 1N, 2.0 eq) at 0° C. After addition, the mixture was stirred at rt for 2 h. The mixture was quenched by careful adding ice-water and extracted with EA. The combined organic phase was washed with water and brine, dried over anhydrous Na$_2$SO$_4$, filtered, and concentrated under reduced pressure to give the title compound 7.

$^1$H NMR (DMSO-d$_6$) δ: 7.42-7.50 (m, 5H), 7.34-7.40 (m, 2H), 7.22-7.32 (m, 5H), 6.98-7.07 (m, 2H), 5.63 (t, J=4.8 Hz, 1H), 4.34 (d, J=4.8 Hz, 2H), 3.82 (s, 3H), 3.44 (s, 3H). LC-MS: m/z 438.0 (M+H)+.

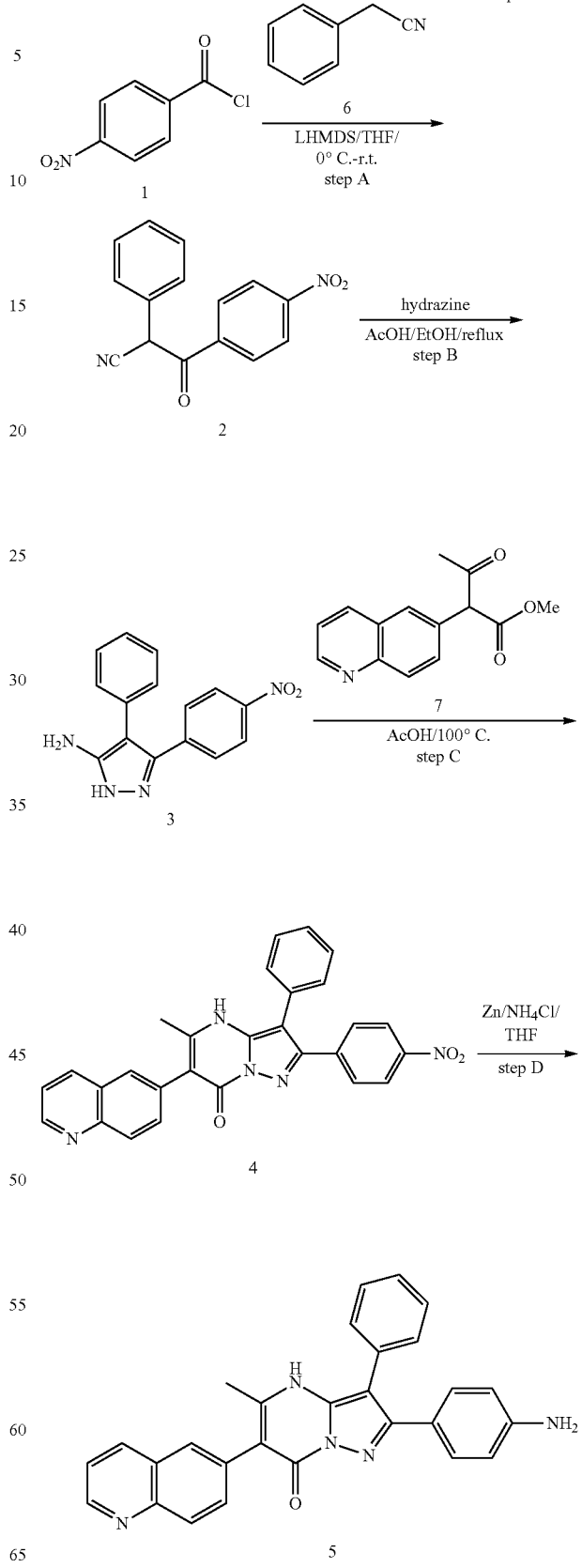

Compound 250

Step A:
3-(4-nitrophenyl)-3-oxo-2-phenylpropanenitrile

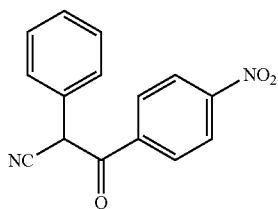 [SMILES: N#CC(C(=O)c1ccc([N+](=O)[O-])cc1)c1ccccc1]

To a solution of 2-phenylacetonitrile (585 mg, 5 mmol) in THF (30 mL) was added n-BuLi (2.5 mol/L, 2 mL, 1.0 eq.) at −78° C. 4-nitrobenzoyl chloride (1.1 eq) was added dropwise after the mixture was stirred at −78° C. for 30 min. The mixture was stirred at −78° C. for 15 min, and then warmed to r.t. and stirred for 3 h. The mixture was diluted with EA (30 mL) and quenched with saturated NH$_4$Cl. The organic phase was separated and washed with brine, dried over anhydrous Na$_2$SO$_4$ and concentrated in vacuo to get Intermediate 2 which was used to the next step without further purification. LC-MS: m/z 267.0 (M+H)$^+$.

Step B:
3-(4-nitrophenyl)-4-phenyl-1H-pyrazol-5-amine

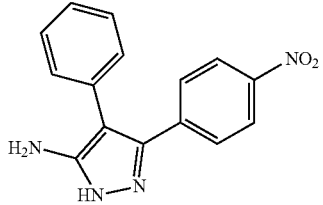 [SMILES: Nc1[nH]nc(-c2ccc([N+](=O)[O-])cc2)c1-c1ccccc1]

The mixture of Intermediate 2 (750 mg, 2.8 mmol, 1 eq.) and hydrazine hydrate (2 eq.) in EtOH/AcOH (5/1.10 mL/2 mL) was refluxed for 2 h. The mixture was then cooled to r.t. and evaporated. The residue was dissolved in EA (10 mL) and neutralized with 10% NaHCO$_3$. The organic phase was separated and the water phase was extracted with EA (10 mL*3). The combined organic phase was washed with brine, dried over anhydrous Na$_2$SO$_4$, and concentrated in vacuo. The residue was purified by prep-TLC to afford the desired Intermediate 3 as a bright yellow solid. LC-MS: m/z 281.1 (M+H)$^+$.

Step C: Compound 251: 5-methyl-2-(4-nitrophenyl)-3-phenyl-6-(quinolin-6-yl)pyrazolo[1,5-a]pyrimidin-7(4H)-one

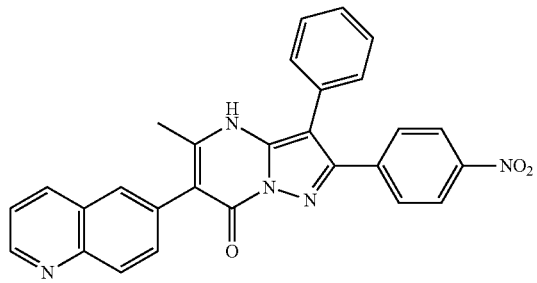

The mixture of Intermediate 3 (95 mg, 0.34 mmol, 1 eq.) and methyl 3-oxo-2-(quinolin-6-yl)butanoate 7 (1.5 eq.) in AcOH (5 mL) was stirred at 100° C. for 1 h. Then the mixture was cooled to r.t. and evaporated. The residue was dissolved in EA (5 mL) and neutralized with 10% NaHCO$_3$. The organic phase was separated and the water phase was extracted with EA (5 mL*3). The combined organic phase was washed with brine, dried over anhydrous Na$_2$SO$_4$ and concentrated in vacuo. The residue was purified by prep-TLC to afford Intermediate 4.

$^1$H NMR (DMSO-d$_6$) δ: 12.19 (br. s., 1H), 8.94 (dd, J=4.2, 1.6 Hz, 1H), 8.40 (d, J=7.8 Hz, 1H), 8.21 (d. J=8.8 Hz, 2H), 8.08 (d, J=8.6 Hz, 1H), 7.97 (d. J=1.6 Hz, 1H), 7.75 (dd, J=8.6, 1.8 Hz, 1H), 7.70 (d, J=8.8 Hz, 2H), 7.58 (dd, J=8.4, 4.4 Hz, 1H), 7.46-7.54 (m, 3H), 7.36-7.42 (m, 2H), 2.26 (s, 3H). LC-MS: m/z 474.0 (M+H)$^+$

Step D: Compound 250: 2-(4-aminophenyl)-5-methyl-3-phenyl-6-(quinolin-6-yl)pyrazolo[1,5-a]pyrimidin-7(4H)-one

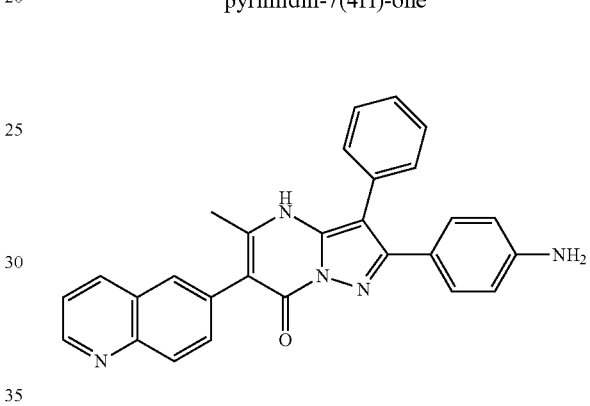

To a solution of Intermediate 4 (35 mg, 0.07 mmol) in THF (10 mL) was added saturated NH$_4$Cl (1 mL) and zinc powder (96 mg, 1.5 mmol, 20 eq.). The reaction was stirred at r.t. for 5 h. LCMS indicated that the reaction was completed. The mixture was filtered through celite. The filtrate was extracted with DCM (5 mL*3). The combined organic phase was washed with brine, dried over anhydrous Na$_2$SO$_4$ and concentrated in vacuo to afford the desired product compound 5.

$^1$H NMR (DMSO-d$_6$) δ: 8.82-8.94 (m, 1H), 8.22-8.43 (m, 3H), 8.00 (d, J=8.6 Hz, 1H), 7.89 (s, 1H), 7.75 (d, J=8.6 Hz, 1H), 7.52 (dd, J=8.2, 4.2 Hz, 1H), 7.47 (d, J=7.2 Hz, 2H), 7.33 (t, J=7.2 Hz, 2H), 7.20 (d, J=7.2 Hz, 1H), 7.15 (d, J=8.2 Hz, 2H), 6.49 (d, J=8.2 Hz, 2H), 2.19 (s, 3H). LC-MS: m/z 444.9 (M+H)$^+$.

Compound 252

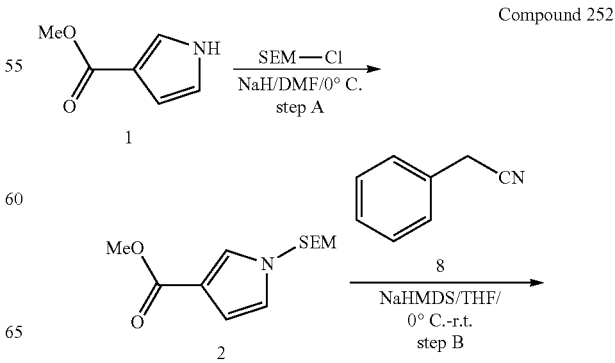

-continued

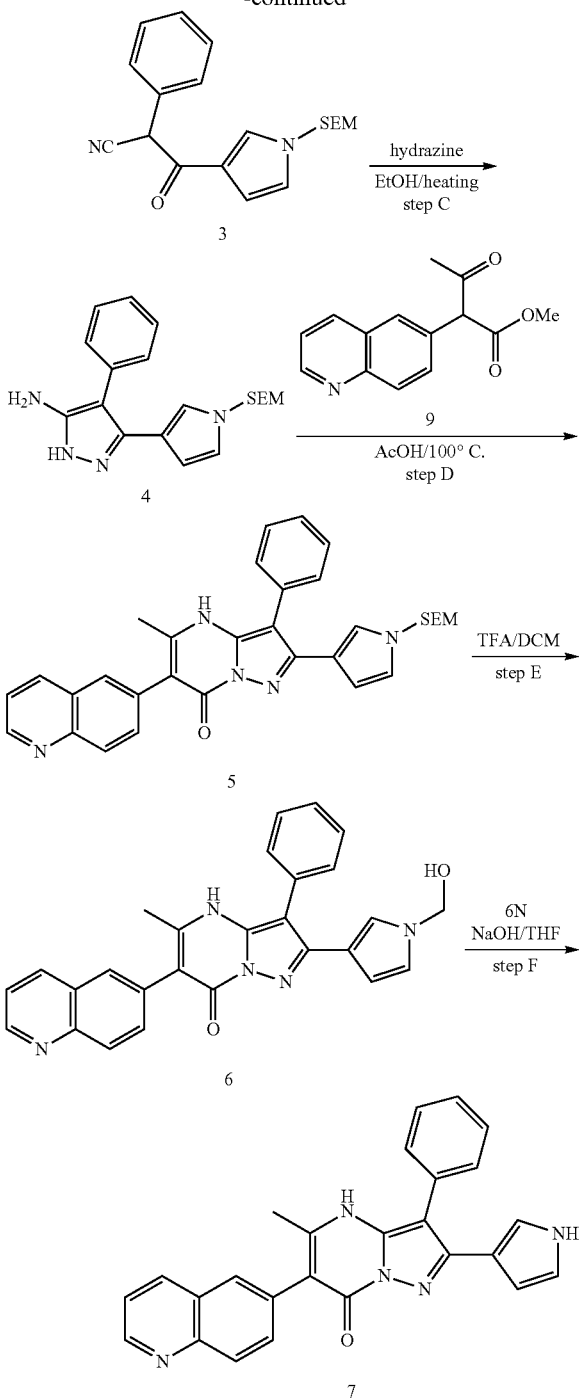

Step A: methyl 1-((2-(trimethylsilyl)ethoxy)methyl)-1H-pyrrole-3-carboxylate

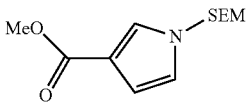 [SMILES: COC(=O)c1ccn(COCC[Si](C)(C)C)c1]

To a solution of methyl 1H-pyrrole-3-carboxylate (2 g, 16.0 mmol) in THF (80 mL) was added sodium hydride (768 mg, 60% content, 19.2 mmol, 1.2 eq.) at 0° C. (2-(chloromethoxy)ethyl)trimethylsilane (4.0 g, 24 mmol, 1.5 eq.) was added dropwise after the mixture was stirred at 0° C. for 30 min. Then the mixture was stirred at r.t. overnight. The mixture was diluted with EA (80 mL) and quenched with saturated NH$_4$Cl. The organic phase was separated and washed with brine, dried over anhydrous Na$_2$SO$_4$ and concentrated in vacuo. The residue was purified by flash chromatography to afford the desired product 2 as a colorless oil. (2.1 g, 51% yield)

$^1$H NMR (CHLOROFORM-d) δ: 7.40 (t, J=2.0 Hz, 1H), 6.72-6.75 (m, 1H), 6.62 (dd, J=3.0, 1.6 Hz, 1H), 5.19 (s, 2H), 3.82 (s, 3H), 3.45 (dd, J=8.8, 7.8 Hz, 2H), 0.86-0.93 (m, 2H), −0.02 (s, 9H). LC-MS: m/z 256.0 (M+H)$^+$

Step B: 3-oxo-2-phenyl-3-(1-((2-(trimethylsilyl)ethoxy)methyl)-1H-pyrrol-3-yl)propanenitrile

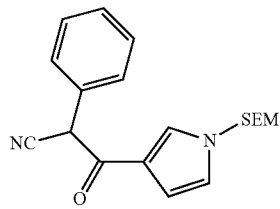 [SMILES: C[Si](C)(C)CCOCn1ccc(C(=O)C(C#N)c2ccccc2)c1]

To the mixture of Intermediate 2 (2.1 g, 8.2 mmol) and 2-phenylacetonitrile (1.16 g, 9.9 mmol, 1.2 eq.) in THF (80 mL) was added NaHMDS (2 mol/L in THF, 4.9 mL, 1.2 eq.) dropwise at 0° C. The mixture was then stirred at r.t. overnight. The mixture was diluted with EA (80 mL) and quenched with saturated NH$_4$Cl. The organic phase was separated and washed with brine, dried over anhydrous Na$_2$SO$_4$ and concentrated in vacuo. The residue was purified by flash chromatography to afford the desired product 3 as a light yellow solid (2 g, 71% yield).

$^1$H NMR (CHLOROFORM-d) δ: 7.45-7.50 (m, 3H), 7.35-7.42 (m, 3H), 6.76 (dd, J=3.0, 2.2 Hz, 1H), 6.66 (dd, J=3.0, 1.8 Hz, 1H), 5.21 (s, 1H), 5.18 (s, 2H), 3.40-3.47 (m, 2H), 0.85-0.92 (m, 2H), −0.03 (s, 9H). LC-MS: m/z 341.2 (M+H)$^+$

Step C: 4-phenyl-3-(1-((2-(trimethylsilyl)ethoxy)methyl)-1H-pyrrol-3-yl)-1H-pyrazol-5-amine

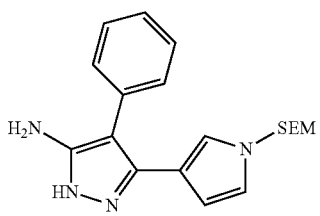 [SMILES: C[Si](C)(C)CCOCn1ccc(-c2n[nH]c(N)c2-c2ccccc2)c1]

The mixture of Intermediate 3 (2 g, 5.9 mmol, 1 eq.) and hydrazine hydrate (590 mg, 11.8 mmol, 2 eq.) in EtOH/AcOH (5/1, 40 mL/8 mL) was refluxed for 2 h. Then the mixture was cooled to r.t. and evaporated. The residue was dissolved in EA (40 mL) and neutralized with 10%, NaHCO₃. The organic phase was separated and the water phase was extracted with EA (10 mL*3). The combined organic phase was washed with brine, dried over anhydrous Na₂SO₄ and concentrated in vacuo. The residue was purified by flash chromatography to afford the desired Intermediate 4 as a yellow solid. (2 g, 99% yield)

¹H NMR (CHLOROFORM-d) δ: 7.37-7.42 (m, 4H), 7.28-7.31 (m, 1H), 6.77 (t, J=1.8 Hz, 1H), 6.72 (t, J=2.4 Hz, 1H), 6.20 (dd, J=2.8, 1.8 Hz, 1H), 5.10 (s, 2H), 3.37-3.44 (m, 2H), 0.83-0.90 (m, 2H), −0.05−−0.01 (m, 9H). LC-MS: m/z 355.3 (M+H)⁺

Step D: 5-methyl-3-phenyl-6-(quinolin-6-yl)-2-(1-((2-(trimethylsilyl)ethoxy)methyl)-1H-pyrrol-3-yl)pyrazolo[1,5-a]pyrimidin-7(4H)-one

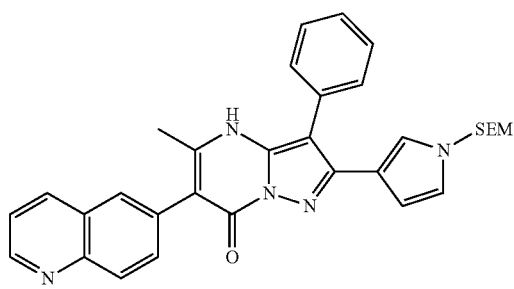 [SMILES: Cc1[nH]c2c(-c3ccccc3)c(-c3ccn(COCC[Si](C)(C)C)c3)nn2c(=O)c1-c1ccc2ncccc2c1]

The mixture of Intermediate 4 (500 mg, 1.4 mmol, 1 eq.) and methyl 3-oxo-2-(quinolin-6-yl)butanoate 9 (1.5 eq.) in AcOH (10 mL) was stirred at 100° C. for 1 h. Then the mixture was cooled to r.t. and evaporated. The residue was dissolved in EA (5 mL) and neutralized with 10% NaHCO₃. The organic phase was separated and the water phase was extracted with EA (5 mL*3). The combined organic phase was washed with brine, dried over anhydrous Na₂SO₄ and concentrated in vacuo. The residue was purified by flash chromatography (DCM/Methanol=10/1, silica gel, uv) to get Intermediate 5 (550 mg, 71% yield). LC-MS: m/z 548.4 (M+H)⁺

Step E: 2-(1-(hydroxymethyl)-1H-pyrrol-3-yl)-5-methyl-3-phenyl-6-(quinolin-6-yl)pyrazolo[1,5-a]-pyrimidin-7(4H)-one

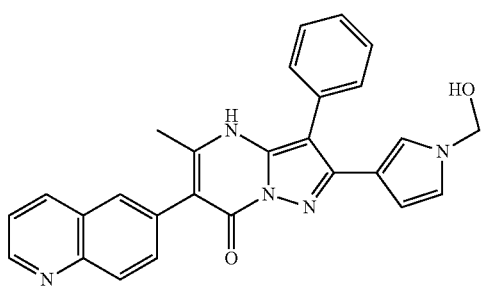 [SMILES: Cc1[nH]c2c(-c3ccccc3)c(-c3ccn(CO)c3)nn2c(=O)c1-c1ccc2ncccc2c1]

To a solution of Intermediate 5 (550 mg, 1.0 mmol) in DCM (15 mL) was added trifluoroacetic acid (1.5 mL). The mixture was stirred at r.t. overnight. The mixture was concentrated in vacuo to get Intermediate 6 which was used to the next step without further purification. (450 mg). LC-MS: m/z 448.2 (M+H)⁺

Step F: Compound 252: 5-methyl-3-phenyl-2-(1H-pyrrol-3-yl)-6-(quinolin-6-yl)pyrazolo[1,5-a]pyrimidin-7(4H)-one

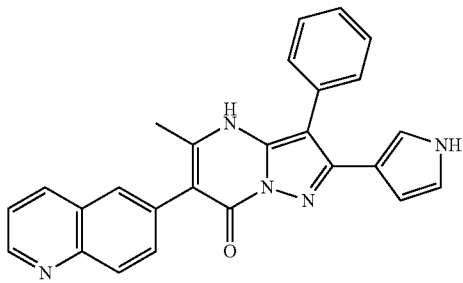

To a solution of Intermediate 6 (450 mg, 1.0 mmol) in THF (15 mL) was added aq. NaOH solution (6 mol/L, 3 mL). The mixture was stirred at r.t. for 2 h to give the desired product 7.

¹H NMR (DMSO-d₆) δ: 10.78 (br. s., 1H), 8.74-8.91 (m, 1H), 8.32 (d, J=8.4 Hz, 1H), 7.97 (d, J=8.6 Hz, 1H), 7.86 (s, 1H), 7.77 (d, J=8.6 Hz, 1H), 7.58 (d, J=7.4 Hz, 2H), 7.49 (dd, J=8.2, 4.4 Hz, 1H), 7.34 (t, J=7.4 Hz, 2H), 7.14-7.24 (m, 1H), 6.97 (br. s., 1H), 6.68 (br. s., 1H), 6.24 (br. s., 1H), 2.16 (s, 3H). LC-MS: m/z 418.0 (M+H)⁺.

Compound 253

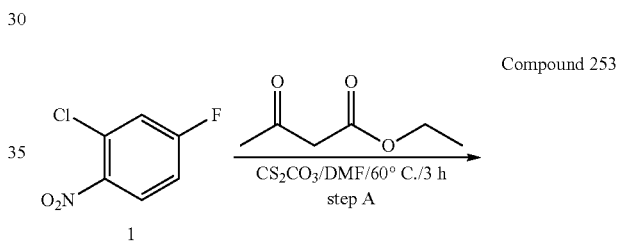

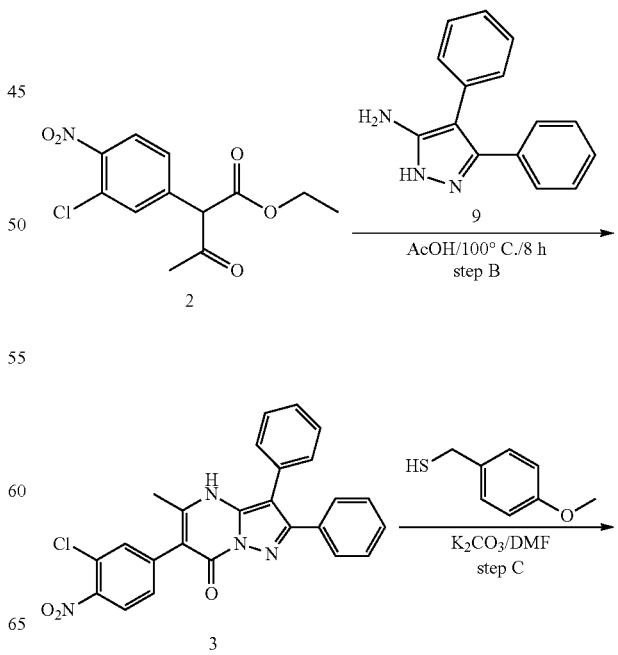

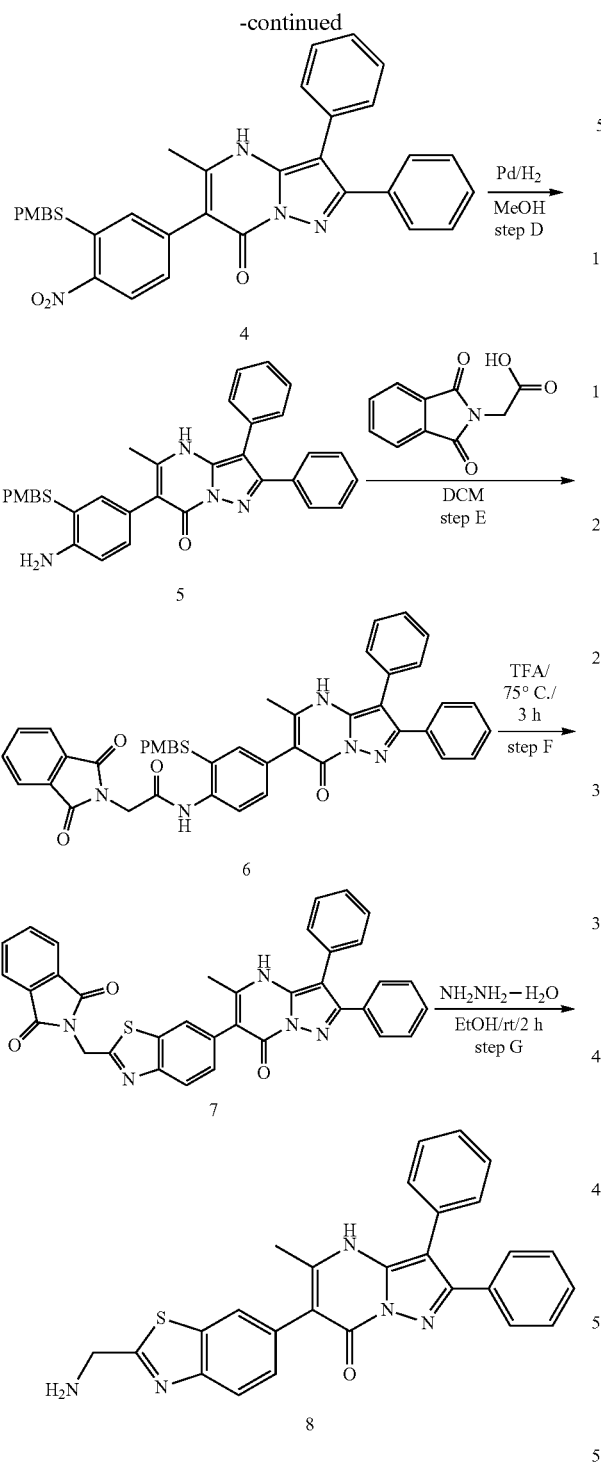

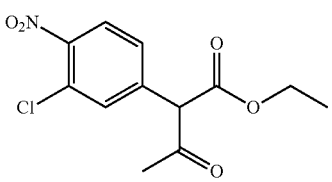 [SMILES: CCOC(=O)C(C(C)=O)c1ccc([N+](=O)[O-])c(Cl)c1]

Step A: ethyl 2-(3-chloro-4-nitrophenyl)-3-oxobutanoate

To a mixture of 2-chloro-4-fluoro-1-nitrobenzene (10.0 g, 57.1 mmol) and $Cs_2CO_3$ (22.3 g, 68.5 mmol, 1.2 eq) in DMF (100 mL) was added ethyl 3-oxobutanoate (7.42 g, 57.1 mmol, 1.0 eq). Then the reaction mixture was stirred at 60° C. for 5 h. The mixture was partitioned between EA and $H_2O$. The combined organic phase was washed with water and brine, dried over anhydrous $Na_2SO_4$, filtered, and concentrated under reduced pressure. The residue was purified by column chromatography on silica gel (EtOAc/PE=1/10) to afford the desired Intermediate 2 (9.0 g, 55% yield). LC-MS: m/z 285.9 $(M+H)^+$.

Step B: 6-(3-chloro-4-nitrophenyl)-5-methyl-2,3-diphenylpyrazolo[1,5-a]pyrimidin-7(4H)-one

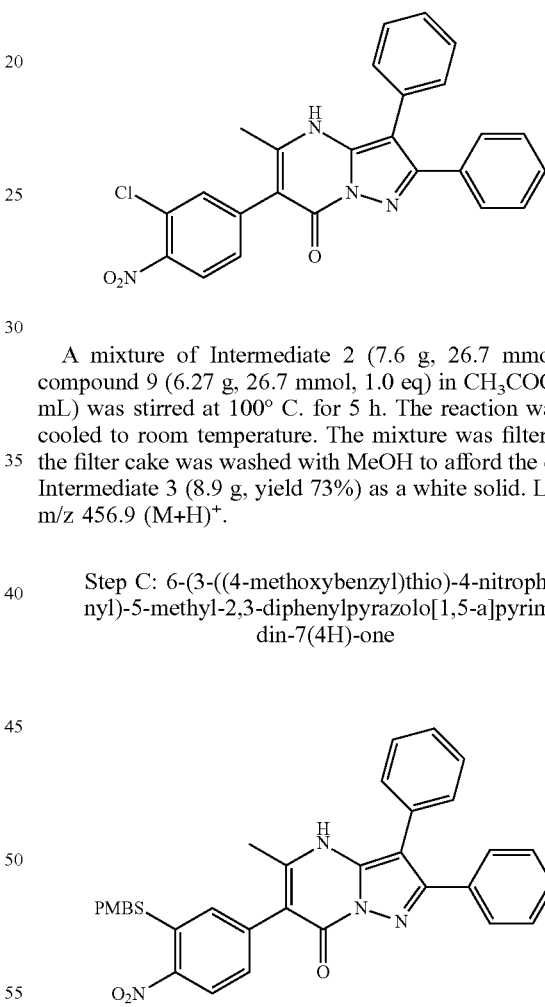

A mixture of Intermediate 2 (7.6 g, 26.7 mmol) and compound 9 (6.27 g, 26.7 mmol, 1.0 eq) in $CH_3COOH$ (30 mL) was stirred at 100° C. for 5 h. The reaction was then cooled to room temperature. The mixture was filtered and the filter cake was washed with MeOH to afford the desired Intermediate 3 (8.9 g, yield 73%) as a white solid. LC-MS: m/z 456.9 $(M+H)^+$.

Step C: 6-(3-((4-methoxybenzyl)thio)-4-nitrophenyl)-5-methyl-2,3-diphenylpyrazolo[1,5-a]pyrimidin-7(4H)-one A mixture of Intermediate 3 (8.0 g, 17.5 mmol), $K_2CO_3$ (6.1 g, 43.75 mmol, 2.5 eq) and (4-methoxyphenyl)methanethiol (5.4 g, 35.08 mmol, 1.0 eq) in DMF (35 mL) was stirred at 110° C. overnight. The mixture was partitioned between EA and $H_2O$. The combined organic phase was washed with water and brine, dried over anhydrous $Na_2SO_4$, filtered, and concentrated under reduced pressure. The residue was purified by column chromatography on silica gel to afford the desired Intermediate 4 (8.2 g, 81% yield). LC-MS: m/z 574.9 $(M+H)^+$.

Step D: 6-(4-amino-3-((4-methoxybenzyl)thio)phenyl)-5-methyl-2,3-diphenylpyrazolo[1,5-a]pyrimidin-7(4H)-one

Step F: 2-((6-(5-methyl-7-oxo-2,3-diphenyl-4,7-dihydropyrazolo[1,5-a]pyrimidin-6-yl)benzo[d]thiazol-2-yl)methyl)isoindoline-1,3-dione

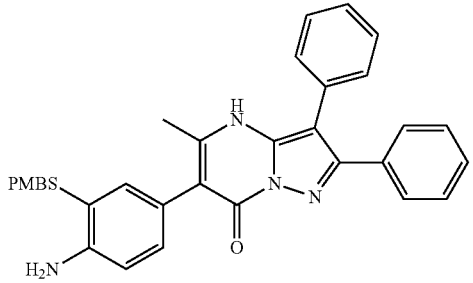

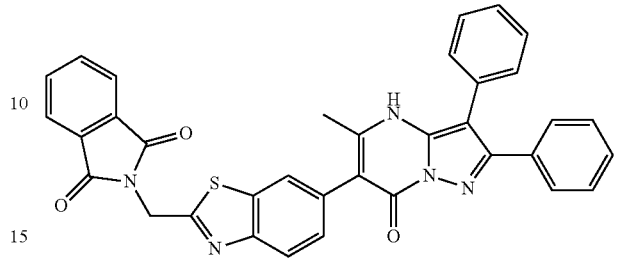

A mixture of Intermediate 6 (250 mg, 0.34 mmol) in TFA (5 mL) was stirred at 75° C. for 3 h. The mixture was concentrated under reduced pressure. The residue was washed with MeOH to afford the desired Intermediate 7 (220 mg, 94% yield). LC-MS: m/z 593.9 (M+H)$^+$.

Step G: Compound 253: 6-(2-(aminomethyl)benzo[d]thiazol-6-yl)-5-methyl-2,3-diphenylpyrazolo[1,5-a]pyrimidin-7(4H)-one To Intermediate 4 (1.0 g, 1.74 mmol, 1 eq.) in methanol (50 ml) and THF (60 ml) was added Pd/C (30 mg). The mixture was stirred rt under H$_2$ atmosphere overnight. The mixture was filtered through a celite pad, and the filtrate was concentrated in vacuo. The residue was purified by column chromatography on silica gel to afford the desired Intermediate 5 (700 mg, 74% yield). LC-MS: m/z 544.9 (M+H)$^+$.

Step E: 2-(1,3-dioxoisoindolin-2-yl)-N-(2-((4-methoxybenzyl)thio)-4-(5-methyl-7-oxo-2,3-diphenyl-4,7-dihydropyrazolo[1,5-a]pyrimidin-6-yl)phenyl)acetamide

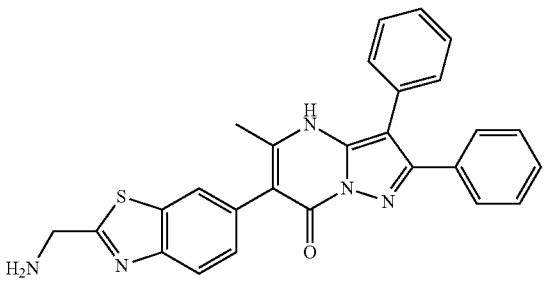

To a mixture of Intermediate 7 (200 mg, 0.33 mmol) in EtOH (8 mL) was added N$_2$H$_4$—H$_2$O (2 ml). Then the reaction mixture was stirred at rt for 3 h. The mixture was partitioned between EA and H$_2$O. The combined organic phase was washed with water and brine, dried over anhydrous Na$_2$SO$_4$, filtered, and concentrated under reduced pressure to afford the title Compound 8.

$^1$H NMR (DMSO-d$_6$) δ: 8.18 (s., 1H), 8.01 (s., 1H), 7.94 (d, J=8.4 Hz, 1H), 7.36-7.52 (m, 7H), 7.33 (m, 4H), 4.26 (s, 2H), 2.18 (s, 3H). LC-MS: m/z 464.1 (M+H)$^+$.

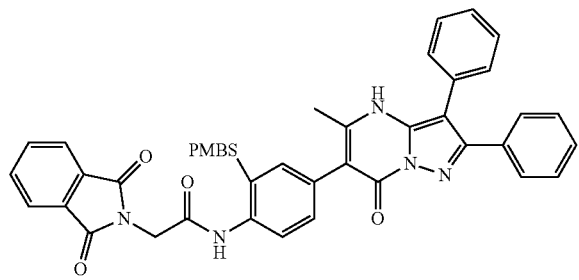

To a mixture of 2-(1,3-dioxoisoindolin-2-yl)acetic acid (452 mg, 2.20 mmol) in DCM (5 mL) was added oxalyl chloride (3 ml) and cat. DMF (1.0 drop) at 0° C. Then the reaction mixture was stirred at rt for 4 h. The reaction mixture was concentrated under reduced pressure. The residue was dissolved in DCM (2 ml) and added to a solution of Intermediate 5 (300 mg, 0.55 mmol) in DCM (5 ml) dropwise at 0° C. under N$_2$ atmosphere. The mixture was stirred rt overnight. The mixture was concentrated in vacuo. The residue was purified by column chromatography on silica gel (EtOAc/PE=1/5) to afford Intermediate 6 (250 mg, 62% yield). LC-MS: m/z 731.9 (M+H)$^+$.

Compound 254

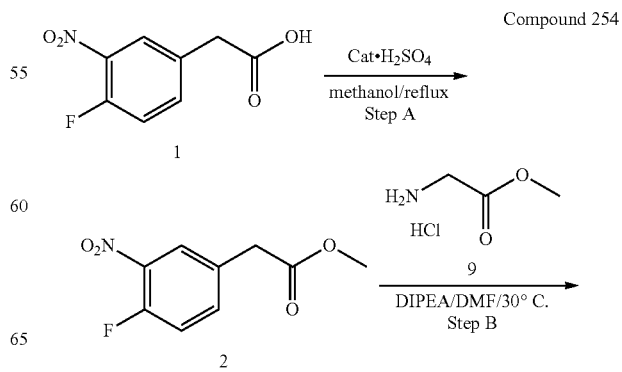

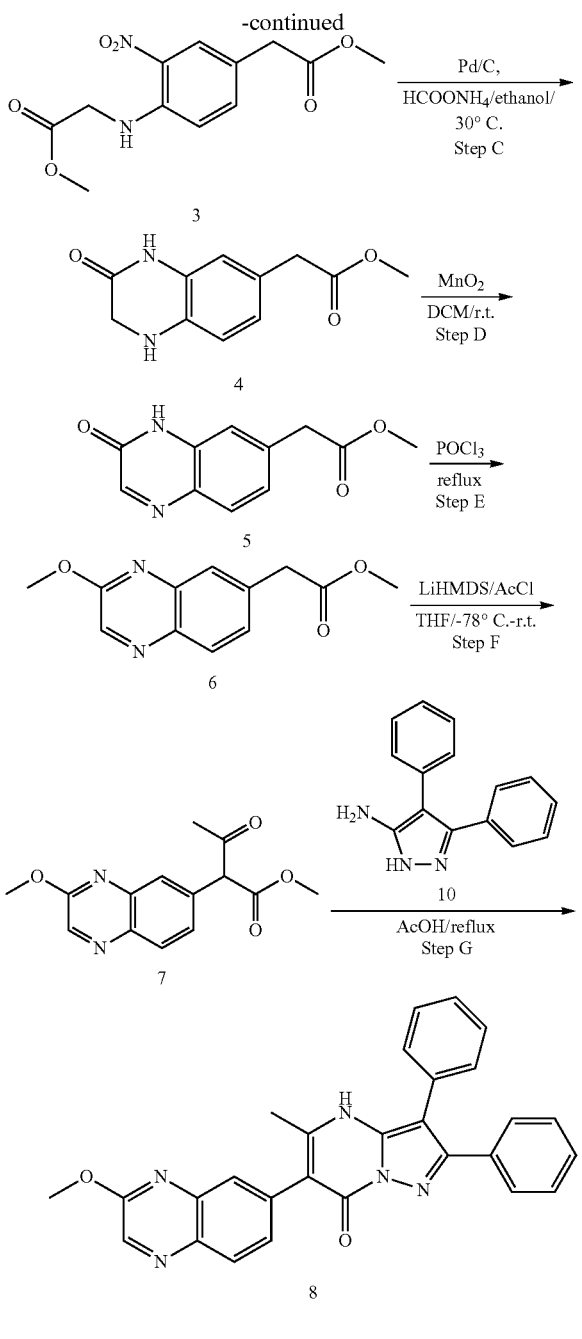

Step A: methyl 2-(4-fluoro-3-nitrophenyl) acetate

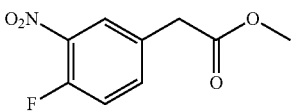

To a solution of 2-(4-fluoro-3-nitrophenyl) acetic acid (4.5 g, 22.6 mmol) in 50 mL of methanol was added 1 mL of conc. sulfuric acid at 0° C. The resulting mixture was then heated to reflux overnight. The mixture was concentrated in vacuo to 10 mL and quenched with aqueous sodium bicarbonate to pH 7. The resultant mixture was extracted with ethyl acetate (30 mL*3). The organic phase was washed with brine, dried over sodium sulfate and evaporated in vacuo to afford methyl 2-(4-fluoro-3-nitrophenyl) acetate (4.1 g, 85% yield) as a yellow solid which was used for next step without further purification.

1H NMR (Chloroform-d) δ: 8.02 (dd, J=6.98 Hz, 2.15 Hz, 1H), 7.59 (ddd, J=8.60 Hz, 4.03 Hz, 2.42 Hz, 1H), 7.21-7.38 (m, 1H), 3.75 (s, 3H), 3.71 (s, 2H). 19F NMR (Chloroform-d) δ-: 119.68 (s, 1 F).

Step B: methyl 2-(4-(2-methoxy-2-oxoethyl)-2-nitrophenyl-amino) acetate

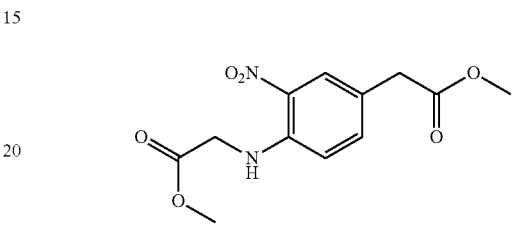

A mixture of methyl 2-(4-fluoro-3-nitrophenyl) acetate (4.1 g, 19.2 mmol), methyl 2-aminoacetate hydrochloride (2.67 g, 21.2 mmol), and N, N-diisopropylethylamine (5.4 g, 42.2 mmol) in N, N-dimethylformamide (50 mL) was heated to 30° C. overnight. The mixture was diluted with brine (100 mL) and extracted with ethyl acetate (30 mL*3). The combined organic phase was washed with brine, dried over sodium sulfate and evaporated in vacuo to afford methyl 2-(4-(2-methoxy-2-oxoethyl)-2-nitrophenyl-amino) acetate (4.6 g, 85% yield) as yellow solid which was used for next steps without further purification. LC-MS: m/z 283.1 (M+H)⁺.

Step C: methyl 2-(3-oxo-1, 2, 3, 4-tetrahydro-quinoxalin-6-yl) acetate

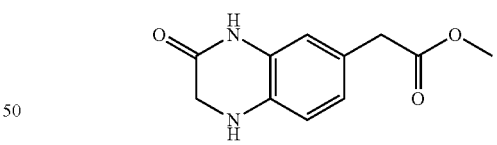

Under inert nitrogen atmosphere, a mixture of methyl 2-(4-(2-methoxy-2-oxoethyl)-2-nitrophenyl-amino) acetate (4.6 g, 16.3 mmol), Pd (w/w 100% on carbon, 1.73 g, 1.63 mmol), ammonium formate (15.4 g, 245 mmol) in ethanol (100 mL) was stirred at room temperature overnight. The reaction mixture was filtrated to remove Pd and ammonium formate. The filtrate obtained was evaporated to dryness. The solid was dissolved in ethyl acetate (100 mL) and washed with brine. The organic phase was then evaporated to dryness to afford methyl 2-(3-oxo-1, 2, 3, 4-tetrahydro-quinoxalin-6-yl) acetate (1.6 g, 45% yield) as yellow solid.

¹H NMR (DMSO-d6) δ 10.22 (bs, 1H), 6.65-6.58 (m, 3H), 5.92 (bs, 1H), 3.69 (s, 2H), 3.64 (s, 3H), 3.46 (s, 2H). LC-MS: m/z 221.1 (M+H)⁺.

Step D: methyl 2-(3-oxo-3, 4-dihydroquinoxalin-6-yl) acetate

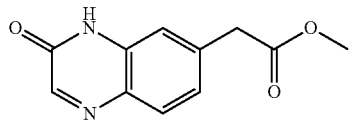 [SMILES: COC(=O)Cc1ccc2ncc(=O)[nH]c2c1]

A mixture of methyl 2-(3-oxo-1, 2, 3, 4-tetrahydro-quinoxalin-6-yl) acetate (3.4 g, 15.5 mmol) and manganese (IV) oxide (13.4 g, 155 mmol) in chloroform (200 mL) was heated to 50° C. overnight. The mixture was filtrated to remove manganese (IV) oxide. The filtrate obtained was evaporated to dryness to afford methyl 2-(3-oxo-3, 4-dihydroquinoxalin-6-yl) acetate (2.9 g, 86% yield) as grey solid. LC-MS: m/z 219.1 (M+H)+.

Step E: methyl 2-(3-methoxyquinoxalin-6-yl) acetate

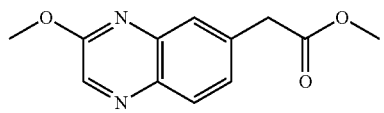

A mixture of 2-(3-oxo-3, 4-dihydroquinoxalin-6-yl) acetate (0.8 g, 3.67 mmol) in phosphoryl trichloride (6 mL) was heated to reflux for 2 h. The mixture was evaporated to remove phosphoryl trichloride. The crude oil was quenched with methanol at room temperature. The mixture was then evaporated to dryness. The crude was purified with column chromatography (methanol:dichloromethane=1:20) on silica gel to afford methyl 2-(3-methoxyquinoxalin-6-yl) acetate (320 mg, 38% yield) as white solid. LC-MS: m/z 233.1 (M+H)+.

Step F: methyl 2-(3-methoxyquinoxalin-6-yl)-3-oxobutanoate

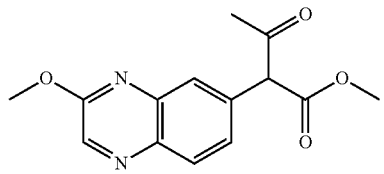

Under inert nitrogen atmosphere, to a mixture of methyl 2-(3-methoxyquinoxalin-6-yl) acetate (220 mg, 0.948 mmol) in tetrahydrofuran (10 mL) at −78° C. was added lithium hexamethyldisilylamide (2N, 0.95 mL, 1.89 mmol) dropwise. The mixture was then stirred at the same temperature for 1 h. Acetyl chloride (89 mg, 1.14 mmol) was added into the mixture at −78° C. The reaction mixture was warmed slowly to room temperature. The reaction was quenched with aqueous ammonium chloride and evaporated to dryness. The residue was purified with prep-TLC (methanol:dichloromethane=1:20) on silica gel to afford methyl 2-(3-methoxyquinoxalin-6-yl)-3-oxobutanoate (160 mg, 62% yield) as white solid. LC-MS: m/z 275.1 (M+H)+.

Step G: Compound 254: 6-(3-methoxy-quinoxalin-6-yl)-5-methyl-2, 3-diphenylpyrazolo [1, 5-a]-pyrimidin-7(4H)-one

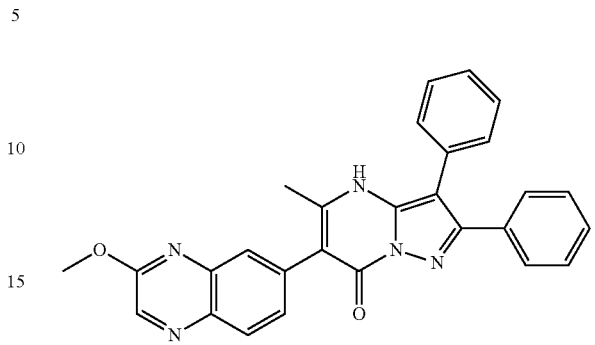

A mixture of methyl 2-(3-methoxyquinoxalin-6-yl)-3-oxobutanoate (223 mg, 0.814 mmol), 3,4-diphenyl-1H-pyrazol-5-amine (191 mg, 0.814 mmol) and acetate acid (2 mL) in dioxane (8 mL) was heated to 100° C. overnight. The mixture was concentrated to afford 6-(3-methoxy-quinoxalin-6-yl)-5-methyl-2, 3-diphenylpyrazolo [1, 5-a]-pyrimidin-7(4H)-one.

$^1$H NMR (DMSO-d6) δ: 12.07 (s, 1H), 8.64 (s, 1H), 8.07 (d, J=8 Hz, 1H), 7.84 (d, J=2 Hz, 1H), 7.64 (dd, J=8 Hz, 2 Hz, 1H), 7.43-7.50 (m, 5H), 7.34-7.38 (m, 5H), 4.08 (s, 3H), 2.27 (s, 3H). LC-MS: m/z 460.2 (M+H)+.

Compound 255

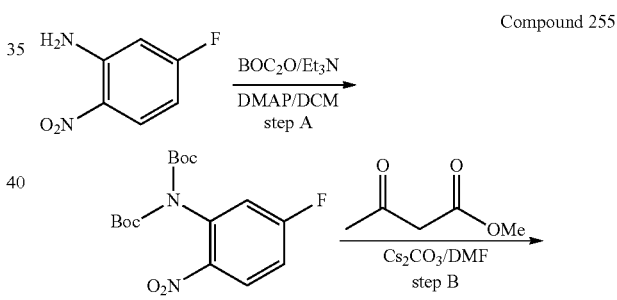

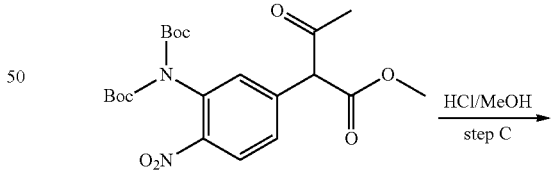

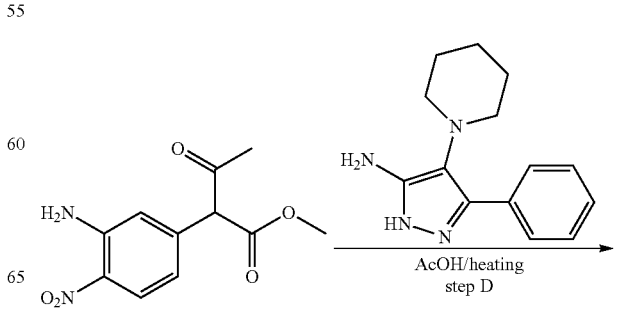

-continued

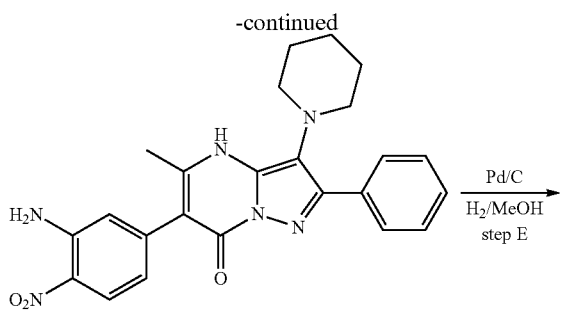

Pd/C
H₂/MeOH
step E

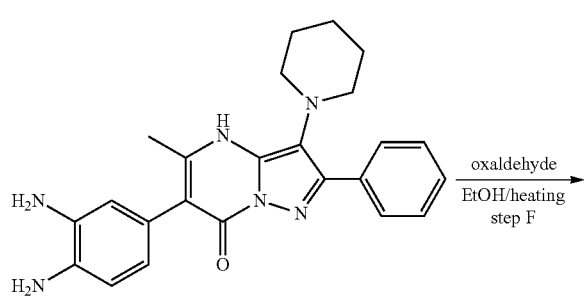

oxaldehyde
EtOH/heating
step F

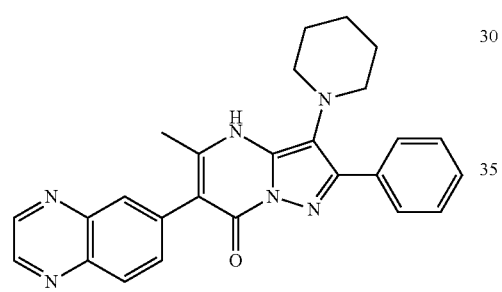

Step A: 5-fluoro-2-nitro-(N,N)-di-tert-butyl-carbonoaniline

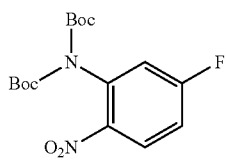 [SMILES: CC(C)(C)OC(=O)N(C(=O)OC(C)(C)C)c1cc(F)ccc1[N+](=O)[O-]]

To a solution of 5-fluoro-2-nitroaniline (5 g, 32 mmol) in CH₂Cl₂ was added N,N-dimethylpyridin-4-amine (390 mg, 3.2 mmol) and triethylamine (6.43 g, 64 mmol). The reaction mixture was stirred for 10 mins and then di-tert-butyl dicarbonate (20 g, 96 mmol) was added slowly and stirred overnight. The reaction mixture was concentrated in vacuo. The residue was purified by column chromatography on silica gel (eluting PE/EA=10:1) to give the desired product (8 g, 71% yield).

¹H NMR (CHLOROFORM-d) δ: 8.16 (dd, J=9.1, 5.4 Hz, 1H), 7.16-7.24 (m, 1H), 7.07 (dd, J=8.3, 2.7 Hz, 1H), 1.41-1.44 (m, 18H).

Step B: methyl 2-[(3-di-tert-butyldicarbo-amino-4-nitrophenyl]-3-oxobutanoate

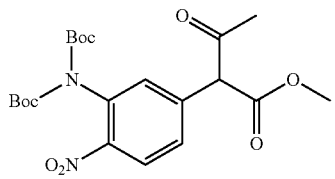 [SMILES: COC(=O)C(C(C)=O)c1ccc([N+](=O)[O-])c(N(C(=O)OC(C)(C)C)C(=O)OC(C)(C)C)c1]

To a solution of 2-[(3-di-tert-butyldicarbo-amino-4-nitrophenyl]-3-oxobutanoate (8 g, 22.4 mmol) in DMF (20 ml) was added cesium carbonate (7.3 g, 44.8 mmol) and methyl 3-oxobutanoate (2.6 g, 22.4 mmol). The mixture was heated to 100° C. for 4 h. The mixture was poured into water and extracted with ethyl acetate. The organic phase was washed with brine, dried over anhydrous Na₂SO₄, filtered, and concentrated. The residue was purified by column chromatography on silica gel (eluting PE/EA=10:1) to give the desired product (7 g, 69% yield).

Step C: methyl 2-(3-amino-4-nitrophenyl)-3-oxobutanoate

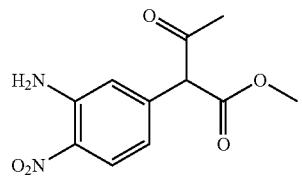 [SMILES: COC(=O)C(C(C)=O)c1ccc([N+](=O)[O-])c(N)c1]

A solution of methyl 2-[(3-di-tert-butyldicarbo-amino-4-nitrophenyl]-3-oxobutanoate (2 g, 4.4 mmol) in HCl/MeOH (10 ml) was stirred for 4 h. The reaction mixture was concentrated to give the desired product methyl 2-(3-amino-4-nitrophenyl)-3-oxobutanoate (1.1 g, 100% yield).

Step D: 6-(3-amino-4-nitrophenyl)-5-methyl-2-phenyl-3-(piperidin-1-yl)pyrazolo[1,5-a]pyrimidin-7(4H)-one

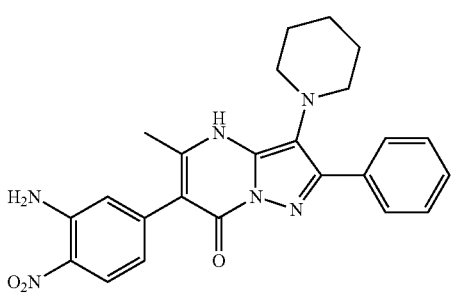

A solution of methyl 2-(3-amino-4-nitrophenyl)-3-oxobutanoate (1.1 g, 4.3 mmol), 3-phenyl-4-(piperidin-1-yl)-1H-pyrazol-5-amine (10 g, 4.3 mmol) in AcOH (10 ml) were heated to 120° C. overnight. The reaction mixture was concentrated. The residue was washed with ethyl acetate to give the desired product 6-(3-amino-4-nitrophenyl)-5- methyl-2-phenyl-3-(piperidin-1-yl)pyrazolo[1,5-a]pyrimidin-7(4H)-one (710 mg, 38% yield).

$^1$H NMR (DMSO-d$_6$) δ: 7.98-8.10 (m, 3H), 7.66 (br. s., 2H), 7.43-7.52 (m, 3H), 6.99 (d, J=1.6 Hz, 1H), 6.60 (dd, J=8.9, 1.9 Hz, 1H), 3.07-3.21 (m, 4H), 2.33 (s, 3H), 1.71 (br. s., 4H), 1.51-1.63 (m, 2H). LC-MS: m/z 445.2 (M+H)$^+$.

Step E: 6-(3,4-diaminophenyl)-5-methyl-2-phenyl-3-(piperidin-1-yl)pyrazolo[1,5-a]pyrimidin-7(4H)-one

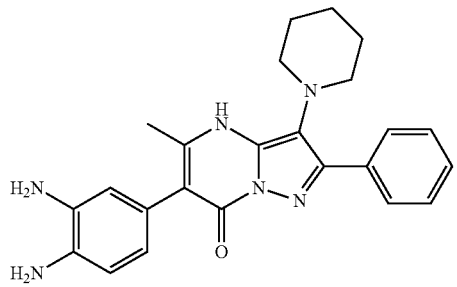 [SMILES: Cc1[nH]c2c(N3CCCCC3)c(-c3ccccc3)nn2c(=O)c1-c1ccc(N)c(N)c1]

To a solution of 6-(3-amino-4-nitrophenyl)-5-methyl-2-phenyl-3-(piperidin-1-yl)pyrazolo[1,5-a]pyrimidin-7(4H)-one (710 mg, 1.6 mmol) in MeOH (20 ml) was added Pd/C (71 mg) under H$_2$. The reaction mixture was stirred for 4 h. The mixture was filtered and the filtrate was concentrated to give the desired product 6-(3,4-diaminophenyl)-5-methyl-2-phenyl-3-(piperidin-1-yl)pyrazolo[1,5-a]pyrimidin-7(4H)-one (500 mg, 75% yield).

$^1$H NMR (DMSO-d$_6$) δ: 11.21 (br. s., 1H), 8.05-8.17 (m, 2H), 7.46 (t, J=7.4 Hz, 2H), 7.35-7.42 (m, 1H), 6.54 (d, J=7.8 Hz, 1H), 6.43 (d, J=1.9 Hz, 1H), 6.29 (dd, J=7.8, 1.9 Hz, 1H), 4.49 (br. s., 4H), 3.07 (d, J=5.1 Hz, 4H), 2.22-2.29 (m, 3H), 1.66 (br. s., 4H), 1.51-1.61 (m, 2H). LC-MS: m/z 415.2 (M+H)$^+$.

Step F: Compound 255: 5-methyl-2-phenyl-3-(piperidin-1-yl)-6-(quinoxalin-6-yl)pyrazolo[1,5-a]pyrimidin-7(4H)-one

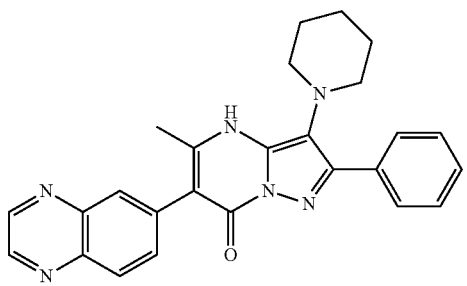

To a solution of 6-(3,4-diaminophenyl)-5-methyl-2-phenyl-3-(piperidin-1-yl)pyrazolo[1,5-a]pyrimidin-7(4H)-one (100 mg, 0.24 mmol) in EtOH (10 ml) was added oxalaldehyde (21 mg, 0.36 mmol). Then the reaction mixture was heated to 80° C. for 2 h. The reaction mixture was concentrated to give the desired product 5-methyl-2-phenyl-3-(piperidin-1-yl)-6-(quinoxalin-6-yl)pyrazolo[1,5-a]pyrimidin-7(4H)-one.

$^1$H NMR (CHLOROFORM-d) δ: 8.86-8.93 (m, 2H), 8.21 (d, J=8.6 Hz, 1H), 8.07 (s, 1H), 8.02 (br. s., 1H), 7.81-7.88 (m, 1H), 7.54 (br. s., 1H), 7.47 (br. s., 3H), 3.06 (br. s., 4H), 2.44 (br. s., 3H), 1.77 (br. s., 2H), 1.71 (br. s., 3H), 1.65 (br. s., 2H). LC-MS: m/z 437.4 (M+H)$^+$.

Compound 256

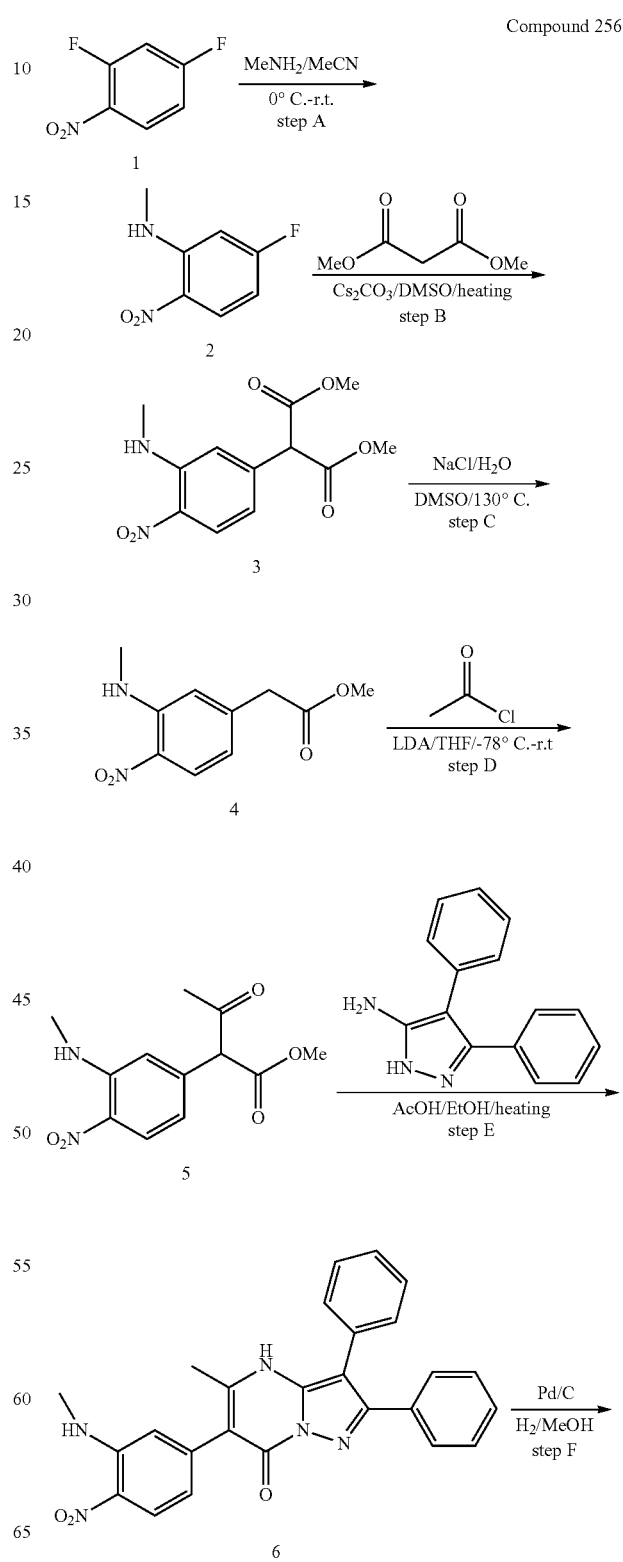

-continued

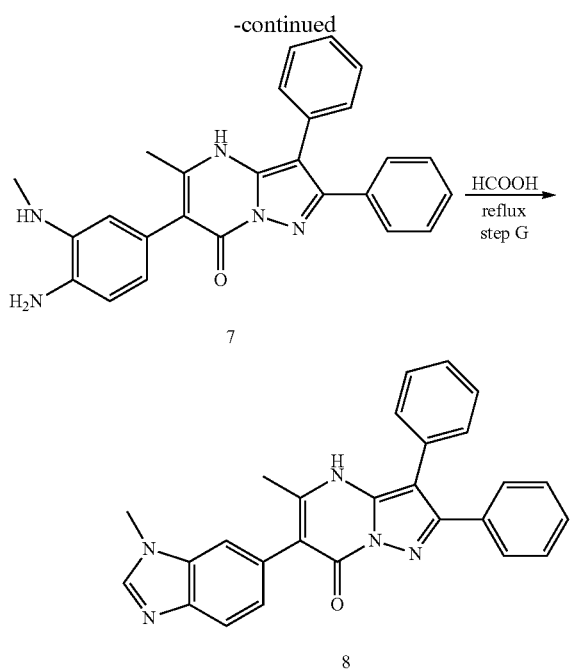

7

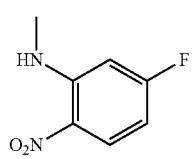

8

Step A: 5-fluoro-N-methyl-2-nitroaniline

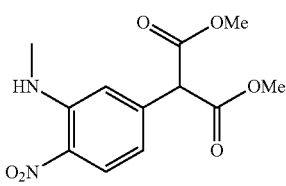 [SMILES: CNc1cc(C(C(=O)OC)C(=O)OC)ccc1[N+](=O)[O-]]

To a solution of 2,4-difluoro-1-nitrobenzene (10 g, 63 mmol) in MeCN was added CH₃NH₂ (63 ml, 1 mmol/ml in MeOH) at 0° C. The reaction mixture was stirred for 4 h. The mixture was filtered to give Intermediate 2 (10 g) as a yellow solid. LC-MS: m/z 170.2 (M+H)⁺.

Step B: dimethyl 2-(3-(methylamino)-4-nitrophenyl)malonate

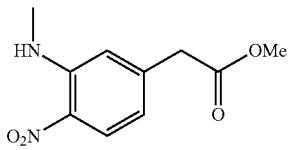 [SMILES: CNc1cc(CC(=O)OC)ccc1[N+](=O)[O-]]

To a solution of Intermediate 2 (5 g, 29.4 mmol) in DMSO (20 ml) was added dimethyl malonate (3.88 g, 29.4 mmol) and cesium carbonate (19.2 g, 58.8 mmol). The reaction mixture was heated to 120° C. for 4 h. The reaction mixture was then poured into water, extracted with ethyl acetate, dried over anhydrous Na₂SO₄, filtered, and concentrated. The residue was purified by column chromatography on silica gel (eluting PE/EA=2:1) to give the desired product (3.4 g).

$^1$H NMR (DMSO-d₆) δ: 8.13-8.25 (m, 1H), 8.07 (d, J=8.9 Hz, 1H), 7.04 (d, J=1.6 Hz, 1H), 6.67 (dd, J=8.9, 1.6 Hz, 1H), 5.16 (s, 1H), 3.71 (s, 6H) 2.92-2.98 (m, 3H). LC-MS: m/z 283.3 (M+H)⁺.

Step C: methyl 2-(3-(methylamino)-4-nitrophenyl)acetate

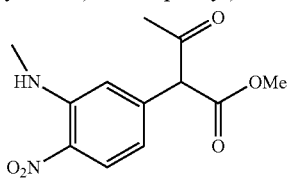

To a solution of dimethyl 2-(3-(methylamino)-4-nitrophenyl)malonate (3.4 g, 12 mmol) in DMSO (20 ml) was added saturated NaCl (5 ml). The reaction mixture was heated to 120° C. for 3 h. The reaction mixture was then poured into water, extracted with ethyl acetate, dried over anhydrous Na₂SO₄, filtered, and concentrated. The residue was purified by column chromatography on silica gel (eluting PE/EA=2:1) to give the desired product (200 mg).

$^1$H NMR (DMSO-d₆) δ: 8.19 (d, J=4.3 Hz, 1H), 8.02 (d, J=8.6 Hz, 1H), 6.87-6.96 (m, 1H), 6.59 (dd, J=8.9, 1.6 Hz, 1H), 3.76 (s, 3H), 2.95 (d, J=4.8 Hz, 4H). LC-MS: m/z 225.1 (M+H)⁺.

Step D: methyl 2-(3-(methylamino)-4-nitrophenyl)-3-oxobutanoate

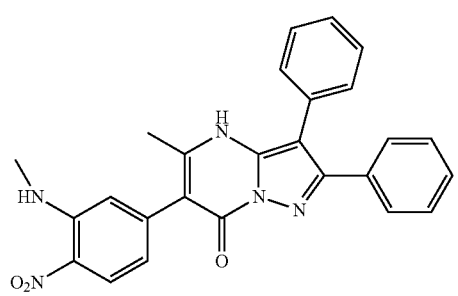

To a solution of methyl 2-(3-(methylamino)-4-nitrophenyl)acetate (200 mg, 0.89 mmol)) in THF (15 ml) was added slowly LDA (4.5 ml, 2 mmol/ml in THF) at −30° C. Then acetyl chloride (104 mg, 1.34 mmol) was added slowly. The reaction mixture was stirred for 30 mins at −30° C. and allowed to room temperature for 1 h. The mixture was poured into water, extracted by ethyl acetate, dried over anhydrous Na₂SO₄, filtered, and concentrated to give the crude product (200 mg) as a yellow liquid, which was used directly to the next step without further purification.

Step E: 5-methyl-6-(3-(methylamino)-4-nitrophenyl)-2,3-diphenylpyrazolo[1,5-a]pyrimidin-7(4H)-one A mixture of methyl 2-(3-(methylamino)-4-nitrophenyl)-3-oxobutanoate (crude, 200 mg) and 3,4-diphenyl-1H-pyrazol-5-amine (100 mg, 0.43 mmol) in AcOH (10 ml) was heated to 120° C. overnight. The reaction mixture was cooled to room temperature. The precipitate was filtered to give the desired product 5-methyl-6-(3-(methylamino)-4-nitrophenyl)-2,3-diphenylpyrazolo[1,5-a]pyrimidin-7(4H)-one (35 mg). LC-MS: m/z 452.3 (M+H)+.

Step F: 6-(4-amino-3-(methylamino)phenyl)-5-methyl-2,3-diphenylpyrazolo[1,5-a]pyrimidin-7(4H)-one

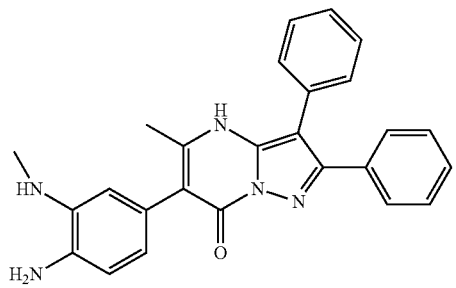 [SMILES: CNc1cc(-c2c(C)[nH]c3c(-c4ccccc4)c(-c4ccccc4)nn3c2=O)ccc1[N+](=O)[O-]]

To a solution of 5-methyl-6-(3-(methylamino)-4-nitrophenyl)-2,3-diphenylpyrazolo[1,5-a]pyrimidin-7(4H)-one (35 mg, 0.078 mmol) in MeOH (10 ml) was added Pd/C (5 mg) under H₂. The reaction mixture was stirred for 4 h. The mixture was filtered and the filtrate was concentrated to give the desired product 6-(4-amino-3-(methylamino)phenyl)-5-methyl-2,3-diphenylpyrazolo[1,5-a]pyrimidin-7(4H)-one (10 mg) as a solid. LC-MS: m/z 422.2 (M+H)+.

Step G: Compound 256: 5-methyl-6-(1-methyl-1H-benzo[d]imidazol-6-yl)-2,3-diphenylpyrazolo[1,5-a]pyrimidin-7(4H)-one

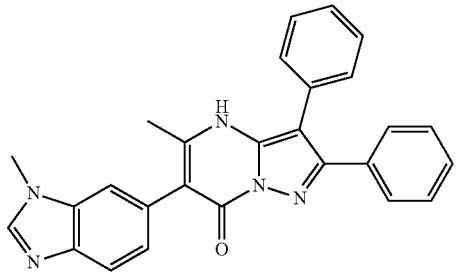 [SMILES: Cc1[nH]c2c(-c3ccccc3)c(-c3ccccc3)nn2c(=O)c1-c1ccc2ncn(C)c2c1]

A solution of 6-(4-amino-3-(methylamino)phenyl)-5-methyl-2,3-diphenylpyrazolo[1,5-a]pyrimidin-7(4H)-one (10 mg, 0.024 mmol) in HCOOH (5 ml) was heated to 120° C. for 1 h. The reaction mixture was concentrated in vacuo to give the desired product 5-methyl-6-(1-methyl-1H-benzo[d]imidazol-6-yl)-2,3-diphenylpyrazolo[1,5-a]pyrimidin-7(4H)-one.

$^1$H NMR (METHANOL-d₄) δ: 8.21 (s, 1H), 7.77 (d, J=7.8 Hz, 1H), 7.60 (s, 1H), 7.27-7.57 (m, 11H), 3.95 (s, 3H), 2.28 (s, 3H). LC-MS: m/z 432.0 (M+H)+.

Compound 257 and Compound 258

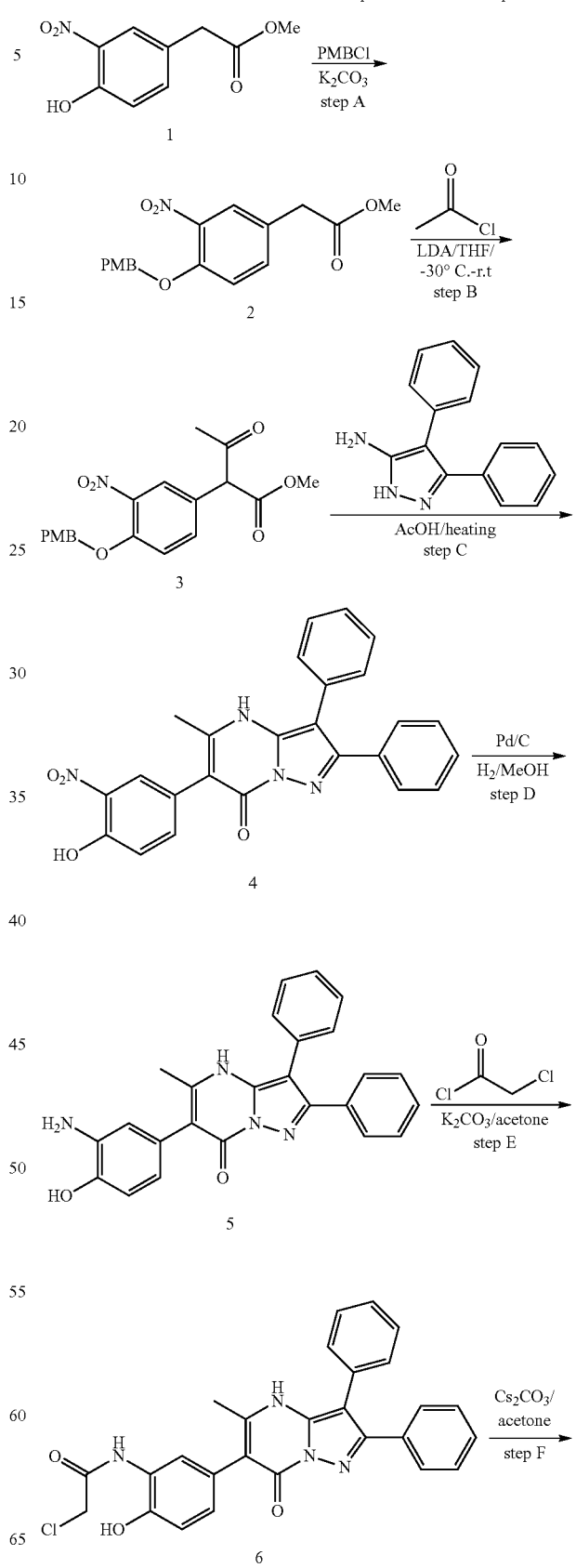

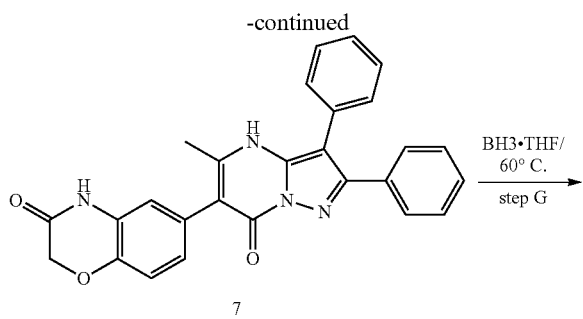

7

BH3·THF/
60° C.
──────→
step G

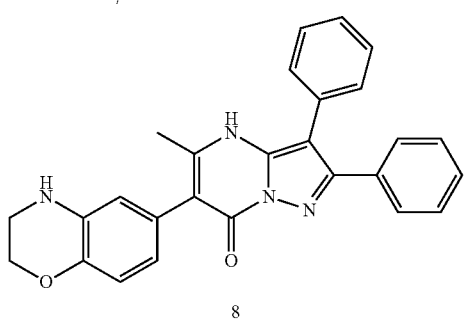

8

Step A: methyl 2-(4-((4-methoxybenzyl)oxy)-3-nitrophenyl)acetate

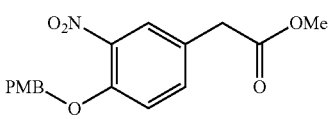

A mixture of methyl 2-(4-hydroxy-3-nitrophenyl)acetate (5 g, 0.024 mol), $K_2CO_3$ (6.5 g, 0.048 mol), and 1-(chloromethyl)-4-methoxybenzene (5.6 g 0.036 mol) was heated to 60° C. for 4 h. The reaction mixture was poured into water, extracted with ethyl acetate, dried over anhydrous $Na_2SO_4$, filtered, concentrated. The residue was purified by column chromatography on silica gel (eluting PE/EA=3:1) to give the desired product (2 g, 53% yield). LC-MS: m/z 332.2 (M+H)⁺.

Step B: methyl 2-(4-((4-methoxybenzyl)oxy)-3-nitrophenyl)-3-oxobutanoate

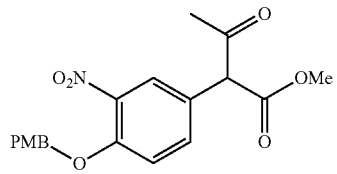

To a solution of methyl 2-(4-((4-methoxybenzyl)oxy)-3-nitrophenyl)acetate (2 g, 6.0 mmol) in THF (50 ml) was added slowly LDA (3 ml, 2 mmol/ml in THF) at −30° C. Then acetyl chloride (702 mg, 9.0 mmol) was added slowly. The reaction mixture was stirred for 30 mins at −30° C. and allowed to room temperature for 1 h. The mixture was poured into water, extracted with ethyl acetate, dried over anhydrous $Na_2SO_4$, filtered, and concentrated to give the crude product (1.5 g) as a yellow liquid, which was used directly to next step without further purification.

Step C: 6-(4-hydroxy-3-nitrophenyl)-5-methyl-2,3-diphenylpyrazolo[1,5-a]pyrimidin-7(4H)-one

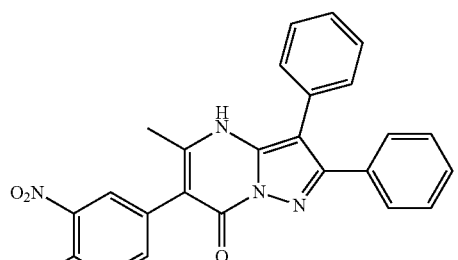

A solution of methyl 2-(4-((4-methoxybenzyl)oxy)-3-nitrophenyl)-3-oxobutanoate (crude, 1.5 g) and 3,4-diphenyl-1H-pyrazol-5-amine (1 g, 4.25 mmol) in AcOH (10 ml) was heated to 120° C. overnight. The reaction mixture was cooled to room temperature. The precipitate was filtered to give the desired product 6-(4-hydroxy-3-nitrophenyl)-5-methyl-2,3-diphenylpyrazolo[1,5-a]pyrimidin-7(4H)-one (600 mg, 32% yield). LC-MS: m/z 439.3 (M+H)⁺.

Step D: 6-(3-amino-4-hydroxyphenyl)-5-methyl-2,3-diphenylpyrazolo[1,5-a]pyrimidin-7(4H)-one

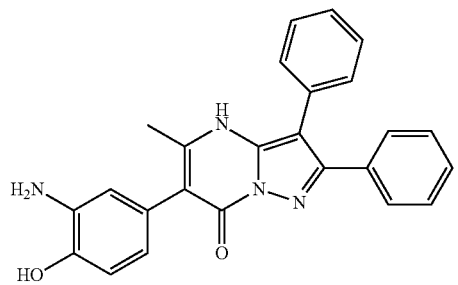 [SMILES: Cc1[nH]c2c(-c3ccccc3)c(-c3ccccc3)nn2c(=O)c1-c1ccc(O)c([N+](=O)[O-])c1]

To a solution of 6-(4-hydroxy-3-nitrophenyl)-5-methyl-2,3-diphenylpyrazolo[1,5-a]pyrimidin-7(4H)-one (600 mg, 1.37 mmol) in MeOH (50 ml) was added Pd/C (60 mg) under $H_2$. The reaction mixture was stirred for 4 h. The mixture was filtered and the filtrate was concentrated to give the desired product 6-(3-amino-4-hydroxyphenyl)-5-methyl-2,3-diphenylpyrazolo[1,5-a]pyrimidin-7(4H)-one (450 mg, 80% yield).

¹H NMR (DMSO-$d_6$) δ: 11.96 (s, 1H), 10.84 (br. s., 1H), 9.88 (br. s., 2H), 7.37-7.51 (m, 5H), 7.24-7.37 (m, 6H), 7.19 (dd, J=8.3, 1.9 Hz, 1H), 7.11 (d, J=8.3 Hz, 1H), 2.20 (s, 3H). LC-MS: m/z 409.2 (M+H)⁺.

Step E: 2-chloro-N-(2-hydroxy-5-(5-methyl-7-oxo-2,3-diphenyl-4,7-dihydropyrazolo[1,5-a]pyrimidin-6-yl)phenyl)acetamide

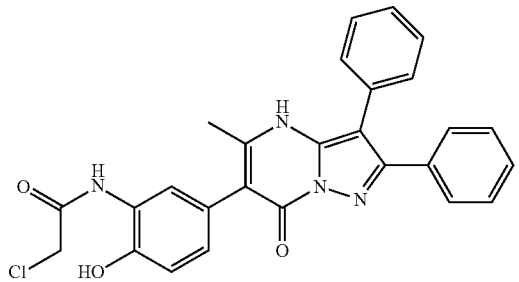 [SMILES: Cc1[nH]c2c(-c3ccccc3)c(-c3ccccc3)nn2c(=O)c1-c1ccc(O)c(NC(=O)CCl)c1]

A mixture of 6-(3-amino-4-hydroxyphenyl)-5-methyl-2,3-diphenylpyrazolo[1,5-a]pyrimidin-7(4H)-one (450 mg, 1.1 mmol), 2-chloroacetyl chloride (136 mg, 1.2 mmol), and $K_2CO_3$ (455 mg, 3.3 mmol) in acetone (50 ml) was heated to 80° C. overnight. The reaction mixture was poured into water, extracted with ethyl acetate, dried over anhydrous $Na_2SO_4$, filtered, and concentrated. The resultant solid was washed with ethyl acetate to give the desired product 2-chloro-N-(2-hydroxy-5-(5-methyl-7-oxo-2,3-diphenyl-4,7-dihydropyrazolo[1,5-a]pyrimidin-6-yl)phenyl)acetamide (250 mg, 47% yield). LC-MS: m/z 485.2 (M+H)$^+$.

Step F: Compound 257: 6-(5-methyl-7-oxo-2,3-diphenyl-4,7-dihydropyrazolo[1,5-a]pyrimidin-6-yl)-2H-benzo[b][1,4]oxazin-3(4H)-one

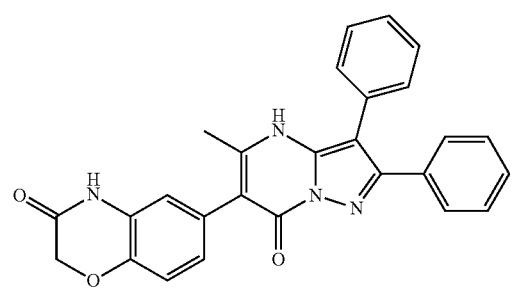 [SMILES: Cc1[nH]c2c(-c3ccccc3)c(-c3ccccc3)nn2c(=O)c1-c1ccc2c(c1)NC(=O)CO2]

A mixture of 2-chloro-N-(2-hydroxy-5-(5-methyl-7-oxo-2,3-diphenyl-4,7-dihydropyrazolo[1,5-a]pyrimidin-6-yl)phenyl)acetamide (250 mg, 0.52 mmol), and $Cs_2CO_3$ (258 mg, 1.04 mmol) in acetone (40 ml) was heated to 100° C. overnight. The reaction mixture was poured into water, extracted with ethyl acetate, dried over anhydrous $Na_2SO_4$, filtered, and concentrated to give the desired product 6-(5-methyl-7-oxo-2,3-diphenyl-4,7-dihydropyrazolo[1,5-a]pyrimidin-6-yl)-2H-benzo[b][1,4]oxazin-3(4H)-one.

$^1$H NMR (DMSO-$d_6$) δ: 11.93 (s, 1H), 10.79 (s, 1H), 7.38-7.56 (m, 5H), 7.24-7.38 (m, 4H), 7.01 (d, J=8.9 Hz, 1H), 6.81-6.92 (m, 2H), 4.63 (s, 2H), 2.18 (s, 3H). LC-MS: m/z 449.0 (M+H)$^+$.

Step G: Compound 258: 6-(3,4-dihydro-2H-benzo[b][1,4]oxazin-6-yl)-5-methyl-2,3-diphenylpyrazolo[1,5-a]pyrimidin-7(4H)-one

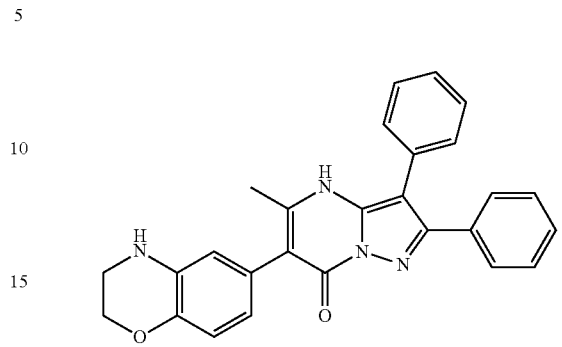

To a solution of 6-(5-methyl-7-oxo-2,3-diphenyl-4,7-dihydropyrazolo[1,5-a]pyrimidin-6-yl)-2H-benzo[b][1,4]oxazin-3(4H)-one (110 mg, 0.25 mmol) in THF (20 ml) was added $BH_3$.THF (1 ml, 1 mmol/ml). The reaction mixture was heated to 80° C. for 4 h. The reaction mixture was then cooled to room temperature. MeOH (10 ml) was added carefully, and then the reaction mixture was stirred for 10 mins. The mixture was concentrated to give the desired product.

$^1$H NMR (DMSO-$d_6$) δ: 11.82 (br. s., 1H), 7.39-7.51 (m, 5H), 7.33 (br. s., 5H), 6.68 (d, J=7.9 Hz, 1H), 6.50 (s, 1H), 6.38 (d, J=8.2 Hz, 1H), 5.80 (br. s., 1H), 4.16 (br. s., 2H), 3.31 (br. s., 2H), 2.17 (s, 3H). LC-MS: m/z 435.0 (M+H)$^+$.

Compound 259

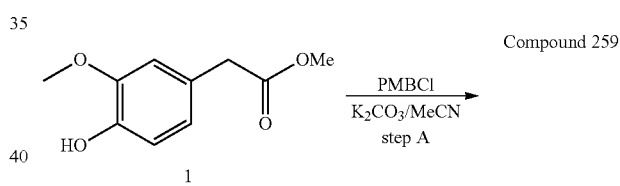

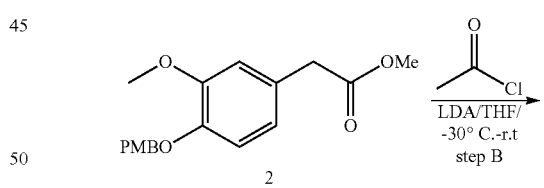

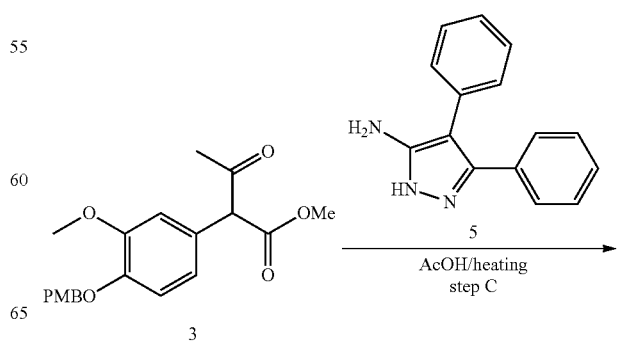

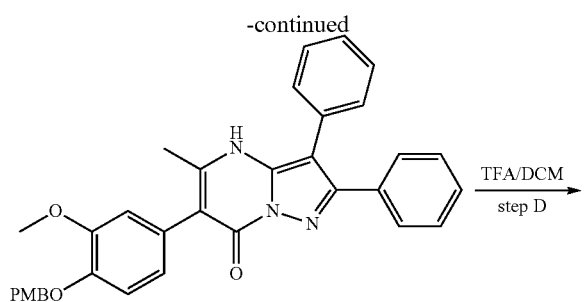

Step A: methyl 2-(3-methoxy-4-((4-methoxybenzyl)oxy)phenyl)acetate

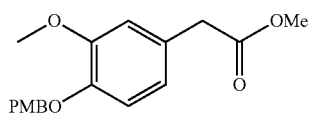

To a solution of methyl 2-(4-hydroxy-3-methoxyphenyl)acetate (1 g, 5.1 mmol) in CH₃CN (50 ml) was added K₂CO₃ (1.4 g, 10.2 mmol) and PMBCl (795 mg, 5.1 mmol). Then the mixture was heated to 80° C. for 2 h. The reaction mixture was poured into water, extracted with ethyl acetate, dried over anhydrous Na₂SO₄, filtered, and concentrated. The residue was purified by column chromatography on silica gel (eluting PE/EA=2:1) to give the desired product (900 mg, 56% yield). LC-MS: m/z 317.3 (M+H)⁺.

Step B: methyl 2-(3-methoxy-4-((4-methoxybenzyl)oxy)phenyl)-3-oxobutanoate

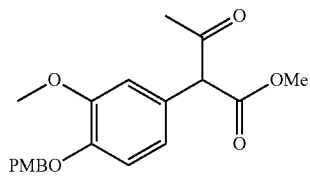

To a solution of methyl 2-(3-methoxy-4-((4-methoxybenzyl)oxy)phenyl)acetate (900 mg, 2.85 mmol) in THF (15 ml) was added slowly LDA (4.5 ml, 2 mmol/ml in THF) at −30° C. Then acetyl chloride (266 mg, 1.34 mmol) was added slowly. The reaction mixture was stirred for 30 mins at −30° C. and allowed to room temperature for 1 h. The mixture was poured into water, extracted with ethyl acetate, dried over anhydrous Na₂SO₄, filtered, and concentrated to give the crude product (700 mg) as a yellow liquid, which was used directly to the next step without further purification.

Step C: 6-(3-methoxy-4-((4-methoxybenzyl)oxy)phenyl)-5-methyl-2,3-diphenylpyrazolo[1,5-a]pyrimidin-7(4H)-one

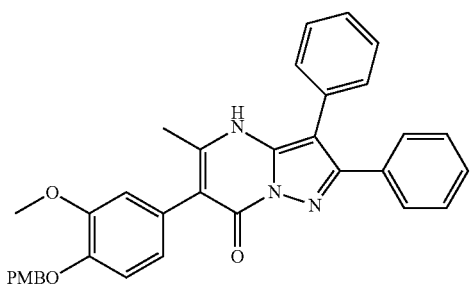

A solution of methyl 2-(3-methoxy-4-((4-methoxybenzyl)oxy)phenyl)-3-oxobutanoate (crude, 400 mg) and 3,4-diphenyl-1H-pyrazol-5-amine (200 mg, 0.86 mmol) in AcOH (10 ml) was heated to 120° C. overnight. The reaction mixture was cooled to room temperature. The precipitate was filtered to give the desired product 6-(3-methoxy-4-((4-methoxybenzyl)oxy)phenyl)-5-methyl-2,3-diphenylpyrazolo[1,5-a]pyrimidin-7(4H)-one (120 mg, 26% yield). LC-MS: m/z 544.2 (M+H)⁺.

Step D: Compound 259: 6-(4-hydroxy-3-methoxyphenyl)-5-methyl-2,3-diphenylpyrazolo[1,5-a]pyrimidin-7(4H)-one

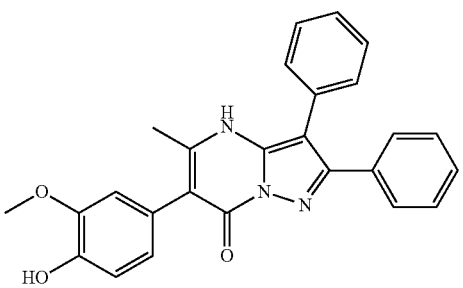 [SMILES: COc1cc(-c2c(C)[nH]c3c(-c4ccccc4)c(-c4ccccc4)nn3c2=O)ccc1O]

To a solution 6-(3-methoxy-4-((4-methoxybenzyl)oxy)phenyl)-5-methyl-2,3-diphenylpyrazolo[1,5-a]pyrimidin-7(4H)-one (120 mg, 0.22 mmol) in MeOH (10 ml) was added 4N HCl/dioxane solution (10 ml). The reaction mixture was stirred for 1 h. When the starting material was consumed, the mixture was concentrated in vacuo to give the desired product 6-(4-hydroxy-3-methoxyphenyl)-5-methyl-2,3-diphenylpyrazolo[1,5-a]pyrimidin-7(4H)-one.

$^1$H NMR (DMSO-$d_6$) δ: 11.85 (s, 1H), 9.04 (s, 1H), 7.37-7.52 (m, 6H), 7.27-7.37 (m, 6H), 6.79-6.90 (m, 2H), 6.72 (dd, J=8.1, 1.9 Hz, 1H), 2.19 (s, 3H). LC-MS: m/z 424.1 (M+H)⁺.

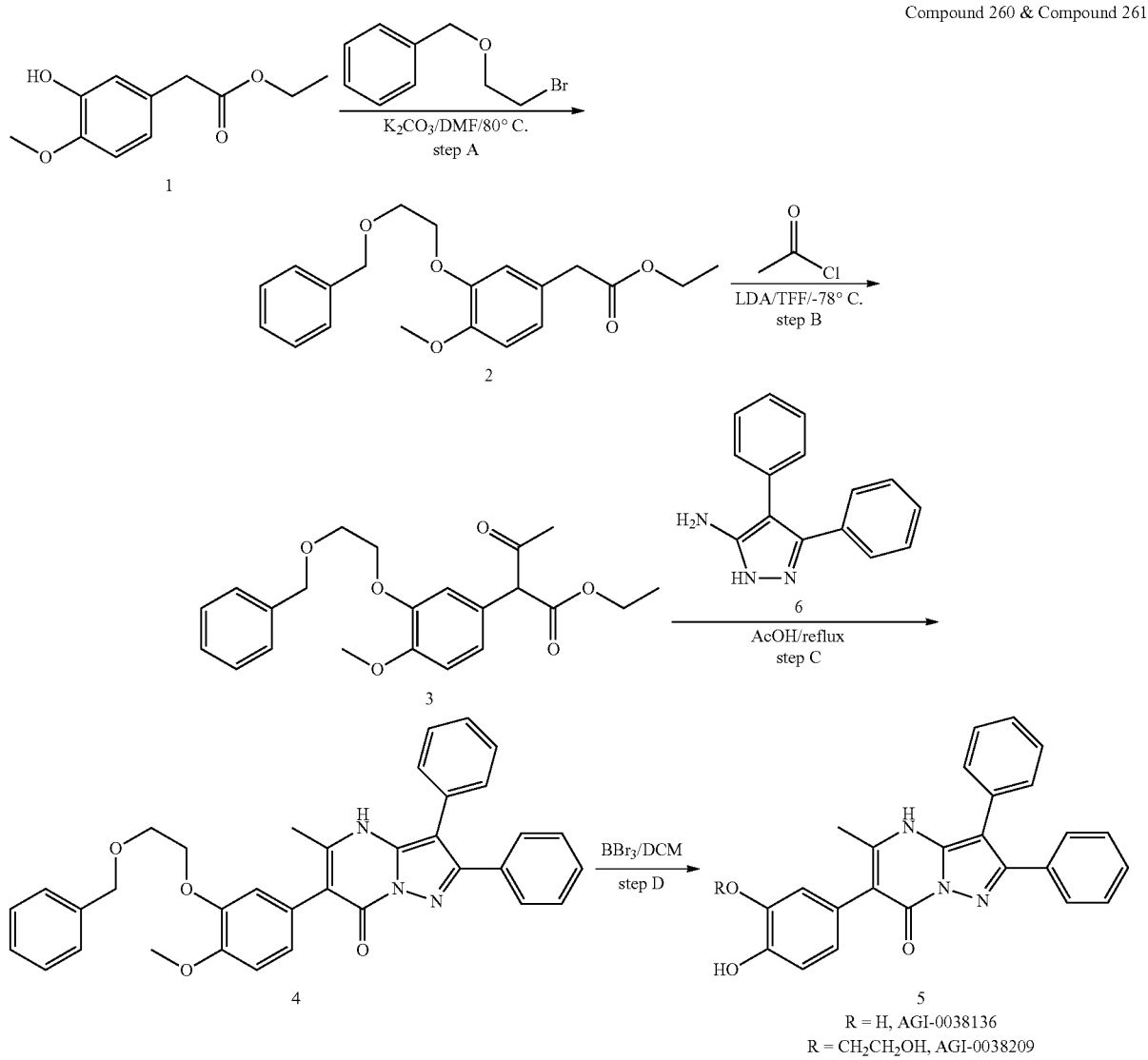

Compound 260 & Compound 261

Step A: ethyl 2-(3-(2-(benzyloxy)ethoxy)-4-methoxyphenyl)acetate

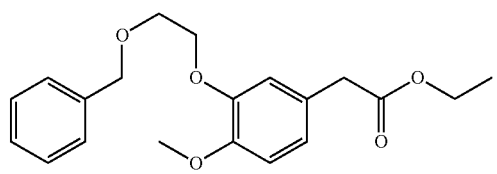 [SMILES: CCOC(=O)Cc1ccc(OC)c(OCCOCc2ccccc2)c1]

A mixture of ethyl 2-(3-hydroxy-4-methoxyphenyl) acetate (4.3 g, 20.5 mmol), ((2-bromoethoxy)methyl)benzene (7.88 g, 36.8 mmol), potassium carbonate (5.66 g, 41 mmol) in N,N-dimethylformamide (50 mL) was heated to 80° C. for 18 h. The mixture was cooled to room temperature, poured into water (100 mL), and extracted with ethyl acetate (100 mL) three times. The combined organic phase was washed with brine, dried over sodium sulfate and evaporated to dryness. The crude was purified by column chromatography (ethyl acetate:petroleum ether=1:5) to afford ethyl 2-(3-(2-(benzyloxy)ethoxy)-4-methoxyphenyl) acetate (3.8 g, 54% yield) as a colorless oil.

Step B: ethyl 2-(3-(2-(benzyloxy)ethoxy)-4-methoxyphenyl)-3-oxobutanoate

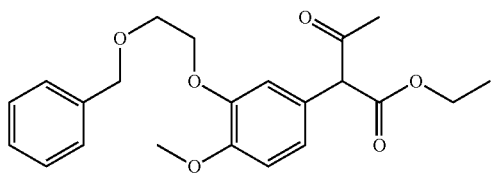 [SMILES: CCOC(=O)C(C(C)=O)c1ccc(OC)c(OCCOCc2ccccc2)c1]

To a mixture of ethyl 2-(3-(2-(benzyloxy)ethoxy)-4-methoxyphenyl)acetate (690 mg, 2 mmol) in tetrahydrofuran (10 mL) was added lithium diisopropylamide (2N, 1 mL, 2 mmol) at −78° C. under nitrogen atmosphere. The mixture was stirred at the same temperature for 1 h. Acetyl chloride (156 mg, 2 mmol) was added into the mixture at −78° C. slowly. After addition, the mixture was stirred at −78° C. for 1 h and warmed slowly to room temperature overnight. The mixture was quenched by adding aqueous ammonium chloride to pH 6-7 and extracted with ethyl acetate (20 mL) three times. The combined organic phase was washed with brine, dried over sodium sulfate and evaporated to dryness. The crude was purified by column chromatography on silica gel (ethyl acetate:petroleum ether=1:5) to afford ethyl 2-(3-(2-(benzyloxy)ethoxy)-4-methoxyphenyl)-3-oxobutanoate (280 mg, 38°% yield) as a colorless oil. LC-MS: m/z 387.2 (M+H)+.

Step C: 6-(3-(2-(benzyloxy)ethoxy)-4-methoxyphenyl)-5-methyl-2,3-diphenylpyrazolo[1,5-a]pyrimidin-7(4H)-one

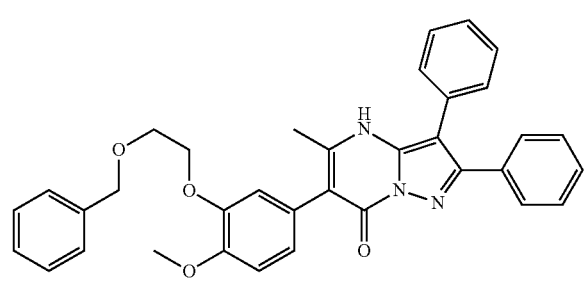 [SMILES: COc1ccc(-c2c(C)[nH]c3c(-c4ccccc4)c(-c4ccccc4)nn3c2=O)cc1OCCOCc1ccccc1]

A mixture of ethyl 2-(3-(2-(benzyloxy)ethoxy)-4-methoxyphenyl)-3-oxobutanoate (280 mg, 0.725 mmol) and 3,4-diphenyl-1H-pyrazol-5-amine (170 mg, 0.725 mmol) in acetic acid (5 mL) was heated to reflux for 2 h. The mixture was evaporated to remove acetic acid. The residue was purified with column chromatography (methanol:dichloromethane=1:20) to afford 6-(3-(2-(benzyloxy)ethoxy)-4-methoxyphenyl)-5-methyl-2,3-diphenylpyrazolo[1,5-a]pyrimidin-7(4H)-one (120 mg, 30% yield) as a yellow solid. LC-MS: m/z 558.2 (M+H)+.

Step D: Compound 260 & Compound 261: 6-(3,4-dihydroxyphenyl)-5-methyl-2,3-diphenylpyrazolo[1,5-a]pyrimidin-7(4H)-one

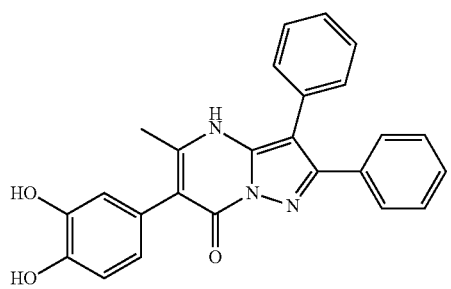 [SMILES: Cc1[nH]c2c(-c3ccccc3)c(-c3ccccc3)nn2c(=O)c1-c1ccc(O)c(O)c1]

6-(4-hydroxy-3-(2-hydroxyethoxy)phenyl)-5-methyl-2,3-diphenylpyrazolo[1,5-a]pyrimidin-7(4H)-one

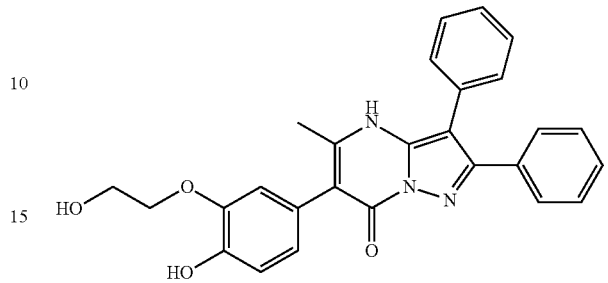

A mixture of 6-(3-(2-(benzyloxy)ethoxy)-4-methoxyphenyl)-5-methyl-2,3-diphenyl-pyrazolo[1,5-a]pyrimidin-7(4H)-one (200 mg, 0.359 mmol) and tribromoborane (1M in DCM, 2 mL) was stirred at room temperature for 1 h. The reaction was quenched with methanol at 0° C. The mixture was evaporated to dryness to afford 6-(3,4-dihydroxyphenyl)-5-methyl-2,3-diphenylpyrazolo[1,5-a]pyrimidin-7(4H)-one and 6-(4-hydroxy-3-(2-hydroxyethoxy)phenyl)-5-methyl-2,3-diphenylpyrazolo[1,5-a] pyrimidin-7(4H)-one.

6-(3,4-dihydroxyphenyl)-5-methyl-2,3-diphenylpyrazolo[1,5-a]pyrimidin-7(4H)-one (Compound 260)

$^1$H NMR (DMSO-$d_6$) δ: 11.82 (s, 1H), 7.37-7.52 (m, 5H), 7.20-7.37 (m, 5H), 6.78 (d, J=8.06 Hz, 1H), 6.66-6.73 (m, 1H), 6.55 (d, J=7.79 Hz, 1H), 2.17 (s, 3H). LC-MS: m/z 410.1 (M+H)+.

6-(4-hydroxy-3-(2-hydroxyethoxy)phenyl)-5-methyl-2,3-diphenylpyrazolo[1,5-a]pyrimidin-7(4H)-one (Compound 261)

$^1$H NMR (DMSO-$d_6$) δ: 11.85 (s, 1H), 8.82 (s, 1H), 7.38-7.58 (m, 5H), 7.24-7.38 (m, 5H), 6.81-6.92 (m, 2H), 6.73 (dd, J=8.06, 1.88 Hz, 1H), 4.91 (t, J=6.04 Hz, 1H), 3.97 (t, J=4.97 Hz, 2H), 3.74 (q, J=5.46 Hz, 2H), 2.06-2.22 (m, 3H). LC-MS: m/z 454.2 (M+H)+.

Compound 262

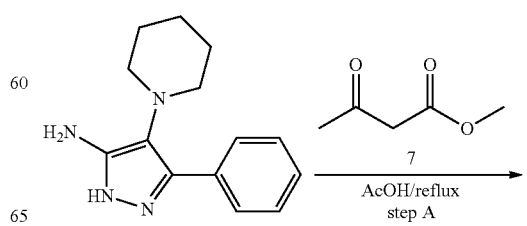

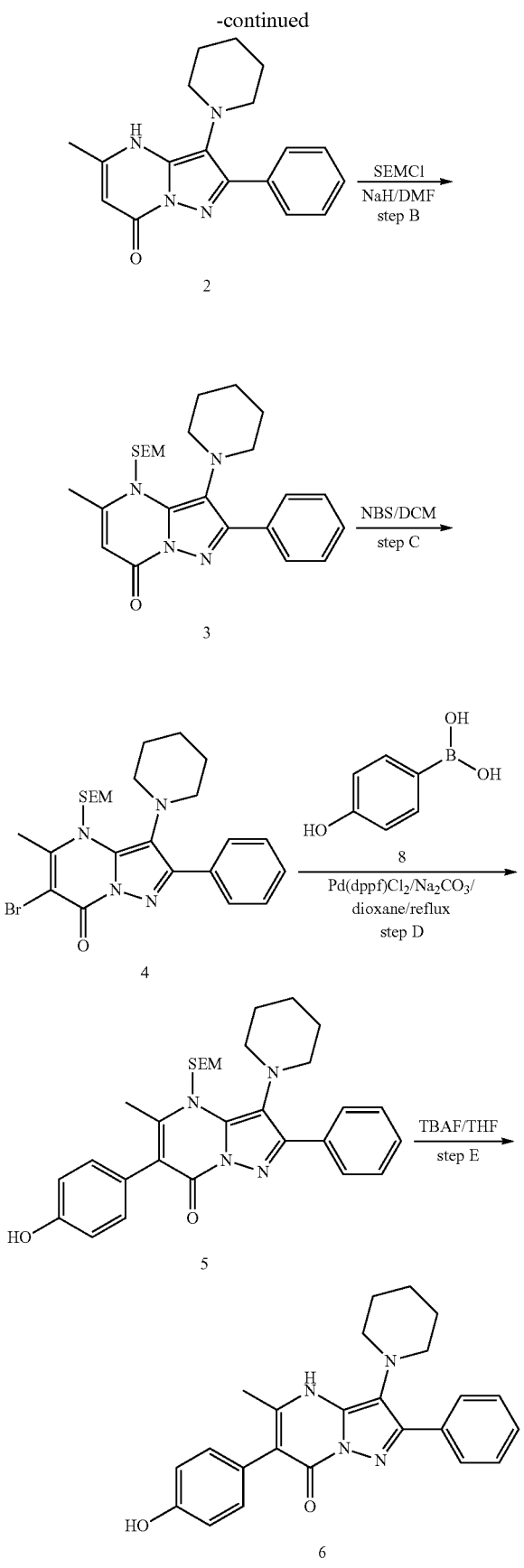

Step A: 5-methyl-2-phenyl-3-(piperidin-1-yl)pyrazolo[1,5-a]pyrimidin-7(4H)-one

A mixture of 3-phenyl-4-(piperidin-1-yl)-1H-pyrazol-5-amine (8.43 g, 34.8 mmol) and methyl 3-oxobutanoate (9 g, 69.2 mmol) in acetic acid (5 mL) was heated to reflux for 2 h. The mixture was cooled to room temperature. The suspension obtained was filtered. The resulting solid was washed with water and cold methanol to afford 5-methyl-2-phenyl-3-(piperidin-1-yl)pyrazolo[1,5-a]pyrimidin-7(4H)-one (7.9 g, 74% yield) as a white solid. LC-MS: m/z 309.2 (M+H)$^+$.

Step B: 5-methyl-2-phenyl-3-(piperidin-1-yl)-4-((2-(trimethylsilyl)ethoxy)methyl) pyrazolo [1,5-a]pyrimidin-7(4H)-one To a mixture of 5-methyl-2-phenyl-3-(piperidin-1-yl) pyrazolo[1,5-a] pyrimidin-7(4H)-one (5.5 g, 17.9 mmol) in N,N-dimethylformamide (50 mL) was added sodium hydride (1.4 g, 35.8 mmol) slowly at 0° C. After addition, the mixture was stirred at 0° C. for 1 h. (2-(Chloromethoxy)ethyl)trimethylsilane (3.6 g, 21.7 mmol) was added. The resulting mixture was stirred at room temperature overnight. The mixture was quenched with brine and extracted with ethyl acetate (50 mL) three times. The combined organic phase was washed with brine, dried over anhydrous sodium sulfate and concentrated in vacuo to dryness. The residue was purified by column chromatography (methanol:dichloromethane=1:20) to afford 5-methyl-2-phenyl-3-(piperidin-1-yl)-4-((2-(trimethylsilyl)ethoxy)methyl)pyrazolo[1,5-a] pyrimidin-7(4H)-one (2.5 g, 35% yield) as a white solid. LC-MS: m/z 439.2 (M+H)$^+$.

Step C: 6-bromo-5-methyl-2-phenyl-3-(piperidin-1-yl)-4-((2-(trimethylsilyl)ethoxy)methyl) pyrazolo[1,5-a]pyrimidin-7(4H)-one

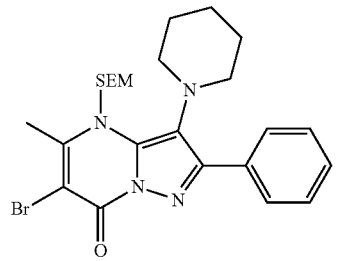 [SMILES: Cc1c(Br)c(=O)n2nc(-c3ccccc3)c(N3CCCCC3)c2n1COCC[Si](C)(C)C]

To a mixture of 5-methyl-2-phenyl-3-(piperidin-1-yl)-4-((2-(trimethylsilyl)ethoxy)-methyl)pyrazolo[1,5-a]pyrimidin-7(4H)-one (1.2 g, 2.74 mmol) and triethylamine (0.32 g, 3.16 mmol) in dichloromethane (20 mL) at room temperature was added N-bromosuccinimide (0.58 g, 3.47 mmol) at room temperature. Then the mixture was stirred at room temperature for 2 h. The mixture was concentrated. The residue was purified by column chromatography (methanol:dichloromethane=1:20) to afford 6-bromo-5-methyl-2-phenyl-3-(piperidin-1-yl)-4-((2-(trimethylsilyl)ethoxy)methyl) pyrazolo[1,5-a]pyrimidin-7(4H)-one (1.3 g, 80% yield) as a white solid. LC-MS: m/z 519.2, 517.2 (M+H)$^+$.

Step D: 6-(4-hydroxyphenyl)-5-methyl-2-phenyl-3-(piperidin-1-yl)-4-((2-(trimethylsilyl)ethoxy)methyl)pyrazolo[1,5-a]pyrimidin-7(4H)-one

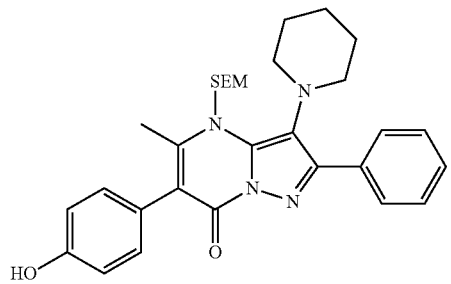 [SMILES: Cc1c(-c2ccc(O)cc2)c(=O)n2nc(-c3ccccc3)c(N3CCCCC3)c2n1COCC[Si](C)(C)C]

To a solution of 6-bromo-5-methyl-2-phenyl-3-(piperidin-1-yl)-4-((2-(trimethylsilyl)-ethoxy)methyl)pyrazolo[1,5-a]pyrimidin-7(4H)-one (100 mg, 0.194 mmol) and 4-hydroxyphenylboronic acid (41 mg, 0.293 mmol) in dioxane/H$_2$O (5 mL/1 mL) was added 1,1'-Bis(diphenylphosphino)ferrocene-palladium(II)dichloride dichloromethane complex (28 mg, 0.0344 mmol) and sodium carbonate (42 mg, 0.396 mmol). The reaction mixture was then refluxed under nitrogen atmosphere overnight. The reaction mixture was filtered and concentrated in vacuo. The residue was purified by column chromatography (methanol:dichloromethane=1/20) to afford 6-(4-hydroxyphenyl)-5-methyl-2-phenyl-3-(piperidin-1-yl)-4-((2-(trimethylsilyl)ethoxy)methyl)pyrazolo[1,5-a]pyrimidin-7(4H)-one (60 mg, 59% yield) as a white solid. LC-MS: m/z 531.3 (M+H)$^+$.

Step E: Compound 262: 6-(4-hydroxyphenyl)-5-methyl-2-phenyl-3-(piperidin-1-yl)pyrazolo[1,5-a]pyrimidin-7(4H)-one

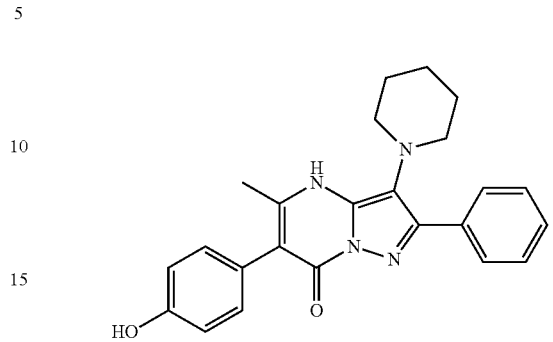

A mixture of 6-(4-hydroxyphenyl)-5-methyl-2-phenyl-3-(piperidin-1-yl)-4-((2-(trimethylsilyl) ethoxy)methyl)pyrazolo[1,5-a]pyrimidin-7(4H)-one (60 mg, 0.113 mmol) in CF$_3$COOH (2 mL) was heated to 60° C. for 3 h. The mixture was cooled to room temperature and concentrated in vacuo to remove solvent. The resulting residue was washed with saturated aqueous sodium bicarbonate. The suspension obtained was filtered to afford 6-(4-hydroxyphenyl)-5-methyl-2-phenyl-3-(piperidin-1-yl)pyrazolo[1,5-a] pyrimidin-7(4H)-one.

$^1$H NMR (Methanol-d$_4$) δ: 8.07 (d, J=6.72 Hz, 2H), 7.45 (d, J=7.52 Hz, 3H), 7.16 (d, J=8.33 Hz, 2H), 6.88 (d, J=8.33 Hz, 2H), 3.06-3.16 (m, 4H), 2.34 (s, 3H), 1.75-1.73 (m, 4H), 1.63-1.62 (m, 2H). LC-MS: m/z 401.2 (M+H)$^+$.

Compound 263

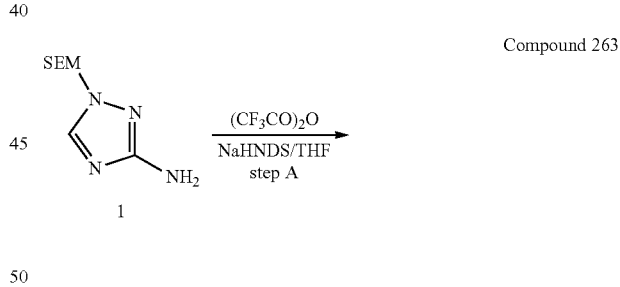

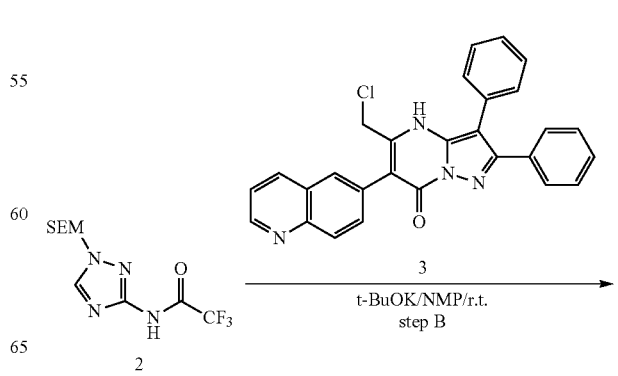

-continued

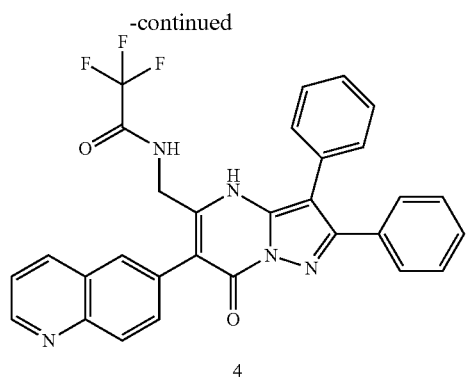

4

Step A: 2,2,2-trifluoro-N-(1-((2-(trimethylsilyl) ethoxy)methyl)-1H-1,2,4-triazol-3-yl)acetamide

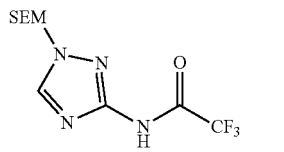 [SMILES: C[Si](C)(C)CCOCn1cnc(NC(=O)C(F)(F)F)n1]

To a solution of 1-((2-(trimethylsilyl)ethoxy)methyl)-1H-1,2,4-triazol-3-amine (3 g, 14 mmol) in THF (50 ml) was added slowly NaHMDS (14 ml, 1 mmol/ml) at −78° C. After addition, the mixture was stirred at −78° C. for 30 mins, and then allowed to −30° C. for 30 mins. TFAA (2 g, 21 mmol) was added slowly, and the mixture was stirred at −30° C. for 20 mins. The reaction mixture was allowed to warm to room temperature overnight. The mixture was poured into water, extracted with ethyl acetate, dried over anhydrous Na$_2$SO$_4$, and concentrated to dryness. The residue was purified by column chromatography on silica gel (eluting PE/EA=1:1) to give the desired product 2,2,2-trifluoro-N-(1-((2-(trimethylsilyl)ethoxy)methyl)-1H-1,2,4-triazol-3-yl)acetamide (2 g, 46% yield).

$^1$H NMR (DMSO-d$_6$) δ: 12.14 (s, 1H), 8.76 (s, 1H), 5.52 (s, 2H), 3.63-3.71 (m, 2H), 3.51-3.61 (m, 2H), 0.80-0.98 (m, 9H). LC-MS: m/z 311.2 (M+H)$^+$.

Step B: Compound 263: 2,2,2-trifluoro-N-((7-oxo-2,3-diphenyl-6-(quinolin-6-yl)-4,7-dihydropyrazolo[1,5-a]pyrimidin-5-yl)methyl)acetamide

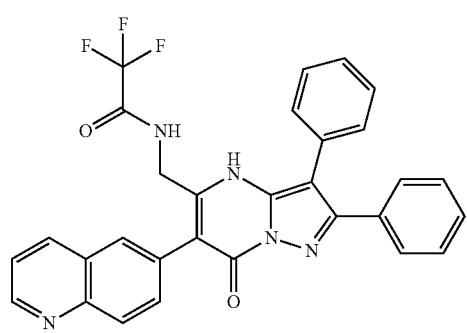 [SMILES: O=C(NCc1[nH]c2c(-c3ccccc3)c(-c3ccccc3)nn2c(=O)c1-c1ccc2ncccc2c1)C(F)(F)F]

To a solution of 2,2,2-trifluoro-N-(1-((2-(trimethylsilyl)ethoxy)methyl)-1H-1,2,4-triazol-3-yl)acetamide (200 mg, 0.65 mmol) in NMP (10 ml) was added t-BuOk (1 ml, 1 mmol/ml in THF). The reaction mixture was stirred for 30 mins, and then 5-(chloromethyl)-2,3-diphenyl-6-(quinolin-6-yl)pyrazolo[1,5-a]pyrimidin-7(4H)-one (100 mg, 0.22 mmol) was added. The reaction mixture was stirred at room temperature for 1 h. The mixture was poured into water, extracted with ethyl acetate, dried over anhydrous Na$_2$SO$_4$, filtered, and concentrated to give the desired product 2,2,2-trifluoro-N-((7-oxo-2,3-diphenyl-6-(quinolin-6-yl)-4,7-dihydropyrazolo[1,5-a]pyrimidin-5-yl)methyl)acetamide.

$^1$H NMR (DMSO-d$_6$) δ: 12.23 (s, 1H), 9.65 (br. s., 1H), 8.95 (br. s., 1H), 8.35 (d, J=8.1 Hz, 1H), 8.06 (d, J=8.3 Hz, 1H), 7.92 (s, 1H), 7.71 (d, J=8.6 Hz, 1H), 7.58 (dd, J=7.9, 4.2 Hz, 2H), 7.46 (br. s., 4H), 7.19-7.42 (m, 6H), 4.32 (br. s., 2H). LC-MS: m/z 540.0 (M+H)$^+$.

Compound 264

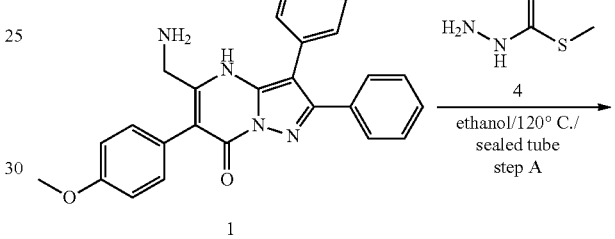

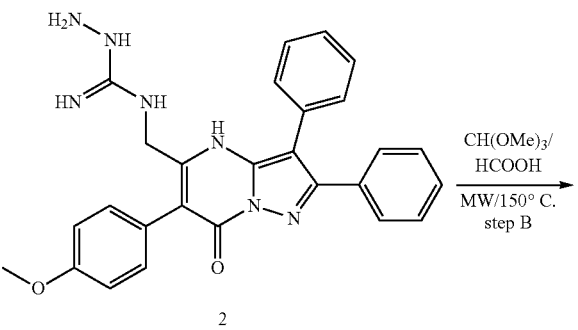

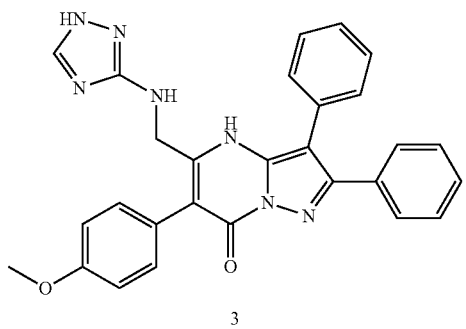

Step A: N-((6-(4-methoxyphenyl)-7-oxo-2,3-diphenyl-4,7-dihydropyrazolo[1,5-a]pyrimidin-5-yl)methyl)hydrazinecarboximidamide

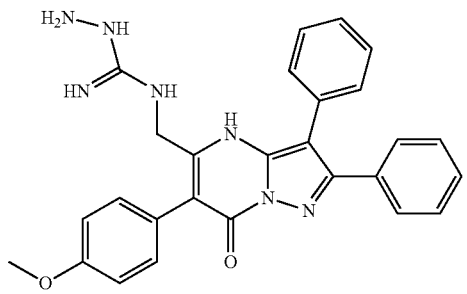 [SMILES: COc1ccc(-c2c(CNC(=N)NN)[nH]c3c(-c4ccccc4)c(-c4ccccc4)nn3c2=O)cc1]

A mixture of 5-(aminomethyl)-6-(4-methoxyphenyl)-2,3-diphenylpyrazolo[1,5-a]pyrimidin-7(4H)-one (Compound 222, 200 mg, 0.47 mmol) and methyl hydrazinecarbimidothioate (100 mg, 0.94 mmol) in EtOH (20 ml) in a seal tube were heated to 120° C. overnight. The reaction mixture was concentrated to dryness. The resultant solid was washed with ethyl acetate to give the desired product (170 mg, 75% yield);

$^1$H NMR (DMSO-$d_6$) δ: 8.62 (br. s., 1H), 7.49-7.58 (m, 4H), 7.31-7.42 (m, 4H), 7.17-7.30 (m, 4H), 7.04-7.14 (m, 1H), 6.96 (d, J=8.6 Hz, 2H), 4.72 (br. s., 2H), 4.07 (br. s., 2H), 3.80 (s, 3H). LC-MS: m/z 480.2 (M+H)$^+$.

Step B: Compound 264: 5-(((1H-1,2,4-triazol-3-yl)amino)methyl)-6-(4-methoxyphenyl)-2,3-diphenylpyrazolo[1,5-a]pyrimidin-7(4H)-one

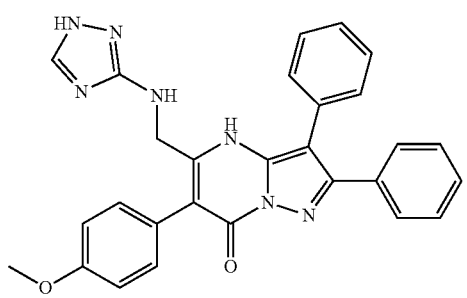 [SMILES: COc1ccc(-c2c(CNc3nc[nH]n3)[nH]c3c(-c4ccccc4)c(-c4ccccc4)nn3c2=O)cc1]

A solution of N-((6-(4-methoxyphenyl)-7-oxo-2,3-diphenyl-4,7-dihydropyrazolo[1,5-a]pyrimidin-5-yl)methyl)hydrazinecarboximidamide (170 mg, 0.355 mmol) in HCOOH (5 ml) and trimethoxymethane (5 ml) was heated to 150° C. for 4 h. When the reaction mixture was consumed, the mixture was concentrated to dryness. The residue was suspended in DMSO (10 ml) and stirred for 30 mins at 5° C. to give the desired product 5-(((1H-1,2,4-triazol-3-yl)amino)methyl)-6-(4-methoxyphenyl)-2,3-diphenylpyrazolo[1,5-a]pyrimidin-7(4H)-one.

$^1$H NMR (DMSO-$d_6$) δ: 8.44 (s, 1H), 7.28-7.49 (m, 11H), 7.11-7.24 (m, J=8.6 Hz, 2H), 6.87-7.04 (m, J=8.6 Hz, 2H), 4.90 (s, 2H), 3.74-3.86 (m, 3H). LC-MS: m/z 490.0 (M+H)$^+$.

Compound 265

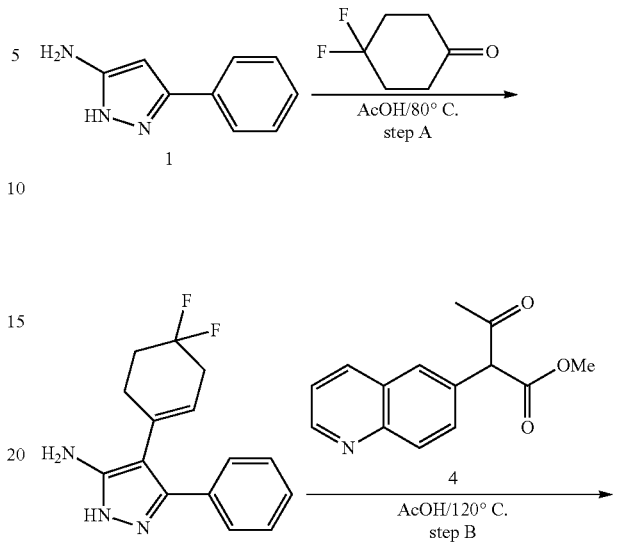

Step A: 4-(4,4-difluorocyclohex-1-en-1-yl)-3-phenyl-1H-pyrazol-5-amine

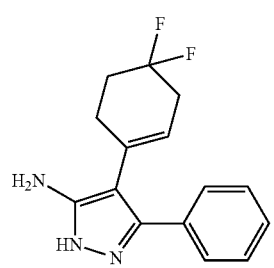 [SMILES: Nc1[nH]nc(-c2ccccc2)c1C1=CCC(F)(F)CC1]

To a solution of 3-phenyl-1H-pyrazol-5-amine (1 g, 6.3 mmol) and 4,4-difluorocyclohexanone (844 mg, 6.3 mmol) in AcOH (10 ml) were heated to 80° C. for 3 h. The reaction mixture was concentrated to give the crude product, which was used directly to the next step without further purification.

Step B: Compound 265: 3-(4,4-difluorocyclohex-1-en-1-yl)-5-methyl-2-phenyl-6-(quinolin-6-yl)pyrazolo[1,5-a]pyrimidin-7(4H)-one

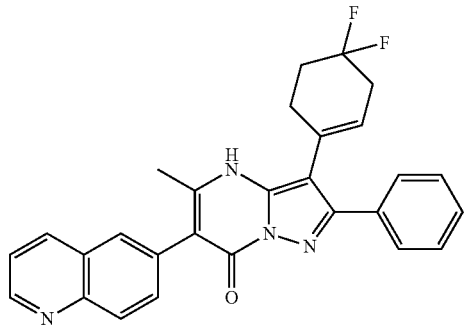 [SMILES: Cc1[nH]c2c(C3=CCC(F)(F)CC3)c(-c3ccccc3)nn2c(=O)c1-c1ccc2ncccc2c1]

A mixture of methyl 3-oxo-2-(quinolin-6-yl)butanoate (200 mg, 0.82 mmol) and 4-(4,4-difluorocyclohex-1-en-1-yl)-3-phenyl-1H-pyrazol-5-amine (100 mg, crude) in AcOH (10 ml) was heated to 120° C. for 2 h. The reaction mixture was cooled to room temperature to give the desired product.

$^1$H NMR (DMSO-d$_6$) δ: 11.86 (s, 1H), 8.95 (dd, J=4.2, 1.7 Hz, 1H), 8.40 (d, J=7.3 Hz, 1H), 8.08 (d, J=8.6 Hz, 1H), 7.96 (d, J=1.9 Hz, 1H), 7.67-7.81 (m, 3H), 7.58 (dd, J=8.3, 4.3 Hz, 1H), 7.38-7.52 (m, 3H), 5.78 (br. s., 1H), 2.78 (t, J=15.0 Hz, 2H), 2.37 (br. s., 2H), 2.31 (s, 3H), 2.11-2.23 (m, 2H). LC-MS: m/z 469.8 (M+H)$^+$.

Compound 266

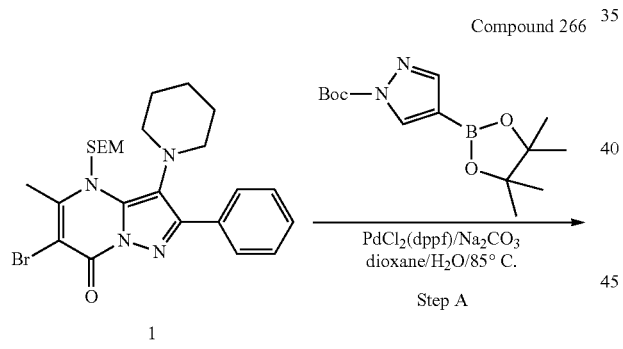

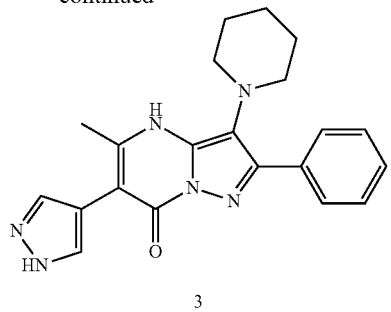

3

Step A: tert-butyl 4-(5-methyl-7-oxo-2-phenyl-3-(piperidin-1-yl)-4-((2-(trimethylsilyl)ethoxy)methyl)-4,7-dihydropyrazolo[1,5-a]pyrimidin-6-yl)-1H-pyrazole-1-carboxylate

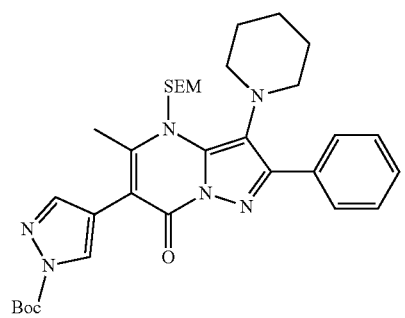 [SMILES: Cc1c(-c2cnn(C(=O)OC(C)(C)C)c2)c(=O)n2nc(-c3ccccc3)c(N3CCCCC3)c2n1COCC[Si](C)(C)C]

A suspension of 6-bromo-5-methyl-2-phenyl-3-(piperidin-1-yl)-4-((2-(trimethylsilyl)ethoxy)methyl)pyrazolo[1,5-a]pyrimidin-7(4H)-one (Synthesized in scheme of Compound 305, 200 mg, 0.39 mmol) and tert-butyl 4-(4,4,5,5-tetramethyl-1,3,2-dioxaborolan-2-yl)-1H-pyrazole-1-carboxylate (341 mg, 1.16 mmol), PdCl$_2$(dppf) (28 mg, 0.04 mmol) and Na$_2$CO$_3$ (82 mg, 0.78 mmol) in 1.4-dioxane/water (10 mL/1 mL) was stirred and heated to 85° C. for 16 h under N$_2$ atmosphere. The reaction was then cooled to RT and filtered. The dark filtrate was concentrated in vacuo. The residue was purified by flash column chromatography, eluting with PE/EA (4/1), to desired product (40 mg, 18% yield) as a white solid. LC-MS: m/z 605.3 (M+H)$^+$.

Step B: 5-methyl-2-phenyl-3-(piperidin-1-yl)-6-(1H-pyrazol-4-yl)pyrazolo[1,5-a]pyrimidin-7(4H)-one

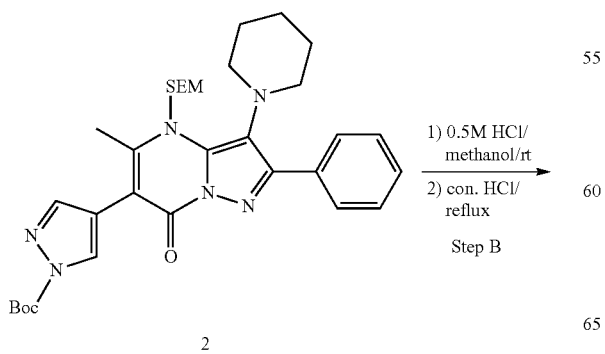

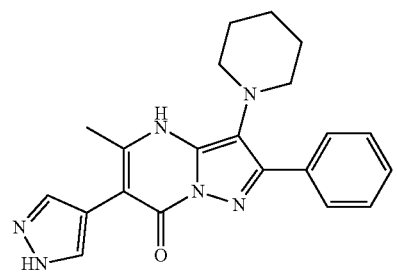 [SMILES: Cc1[nH]c2c(N3CCCCC3)c(-c3ccccc3)nn2c(=O)c1-c1cn[nH]c1]

The mixture of tert-butyl 4-(5-methyl-7-oxo-2-phenyl-3-(piperidin-1-yl)-4-((2-(trimethylsilyl)ethoxy)methyl)-4,7- dihydropyrazolo[1,5-a]pyrimidin-6-yl)-1H-pyrazole-1-carboxylate (40 mg, 0.07 mmol) and HCl in MeOH (0.5 mol, 10 mL, 5 mmol) was stirred at RT for 1 h. The mixture was then concentrated to dryness. The residue was dissolved into conc. hydrochloric acid (10 mL), and stirred at 100° C. for 24 h to get the desired product.

¹H NMR (DMSO-d₆) δ: 12.90 (br. s., 1H), 11.34 (br. s., 1H), 8.13 (d, J=7.2 Hz, 2H), 7.99-7.51 (m, 2H), 7.49-7.37 (m, 3H), 3.08 (br. s., 4H), 2.45 (s, 3H), 1.66 (br. s., 4H), 1.59 (br. s., 2H). LC-MS: m/z 375.2 (M+H)⁺.

Compound 267

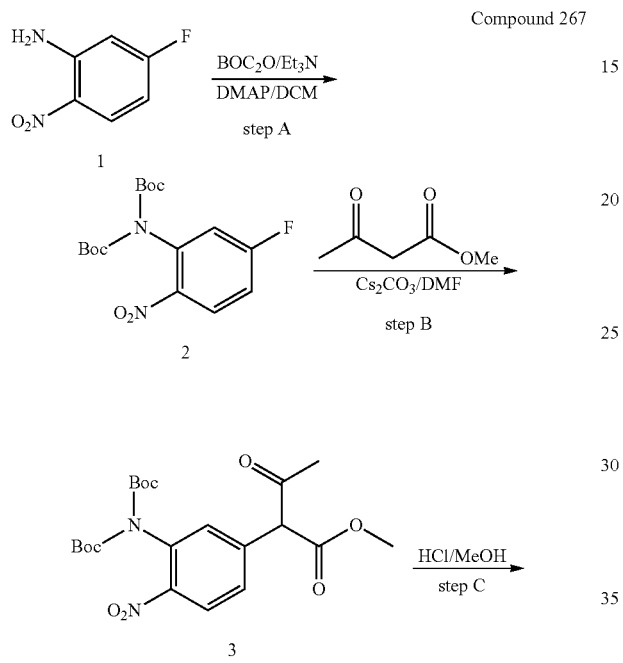

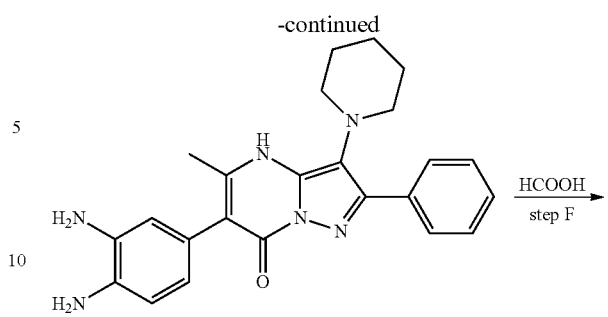

Step F: Compound 267: 6-(1H-benzo[d]imidazol-5-yl)-5-methyl-2-phenyl-3-(piperidin-1-yl)pyrazolo[1,5-a]pyrimidin-7(4H)-one A mixture of 6-(3,4-diaminophenyl)-5-methyl-2-phenyl-3-(piperidin-1-yl)pyrazolo[1,5-a]pyrimidin-7(4H)-one (Synthesized in scheme of Compound 255, 100 mg, 0.24 mmol) in HCOOH (10 ml) was stirred at 100° C. for 2 h. The reaction mixture was concentrated and washed with aq. NaHCO₃ solution to give the desired product 6-(1H-benzo[d]imidazol-5-yl)-5-methyl-2-phenyl-3-(piperidin-1-yl)pyrazolo[1,5-a]pyrimidin-7(4H)-one.

¹H NMR (DMSO-d₆) δ: 12.47 (br. s., 1H), 11.47 (br. s., 1H), 8.25 (s, 1H), 8.08-8.17 (m, 2H), 7.57 (br. s., 2H), 7.44-7.50 (m, 2H), 7.34-7.42 (m, 1H), 7.12 (br. s., 1H), 3.11 (br. s., 4H), 2.26 (s, 3H), 1.67 (br. s., 4H), 1.59 (br. s., 2H). LC-MS: m/z 425.3 (M+H)⁺.

Compound 268

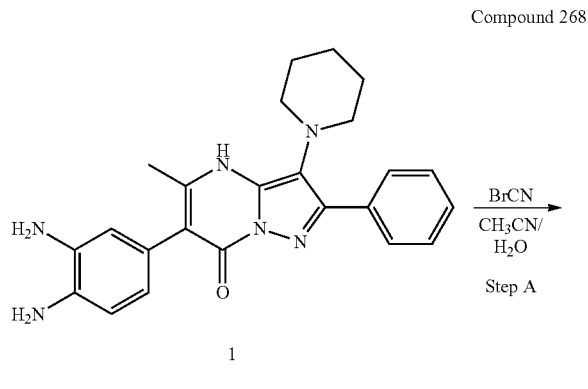

Step A: 6-(2-amino-1H-benzo[d]imidazol-5-yl)-5-methyl-2-phenyl-3-(piperidin-1-yl)pyrazolo[1,5-a]pyrimidin-7(4H)-one

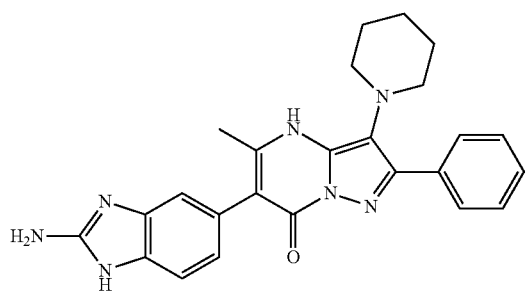 [SMILES: Cc1[nH]c2c(N3CCCCC3)c(-c3ccccc3)nn2c(=O)c1-c1ccc2[nH]c(N)nc2c1]

To the solution of 6-(3,4-diaminophenyl)-5-methyl-2-phenyl-3-(piperidin-1-yl)pyrazolo[1,5-a]pyrimidin-7(4H)-one (100 mg, 0.24 mmol) in CH$_3$CN (10 mL) and H$_2$O (5 mL) was added cyanic bromide (28 mg, 0.256 mmol). The mixture was stirred at r.t. for 1 h. The mixture was concentrated to give the crude product, which was washed with aq. NaHCO$_3$ solution and filtered to give the desired product 6-(2-amino-1H-benzo[d]imidazol-5-yl)-5-methyl-2-phenyl-3-(piperidin-1-yl)pyrazolo[1,5-a]pyrimidin-7(4H)-one.

$^1$H NMR (DMSO-d$_6$) δ: 10.64 (br. s., 1H), 8.31-8.33 (d, 2H), 7.35-8.39 (m, 2H), 7.24-7.28 (m, 1H), 6.98-7.04 (m, 2H), 6.74 (m, 1H), 5.99 (br. s., 1H), 3.23 (br. s., 4H), 2.08 (s, 3H), 1.66 (br. s., 4H), 1.54 (br. s., 2H). LC-MS: m/z 440.3 (M+H)$^+$.

Compound 269

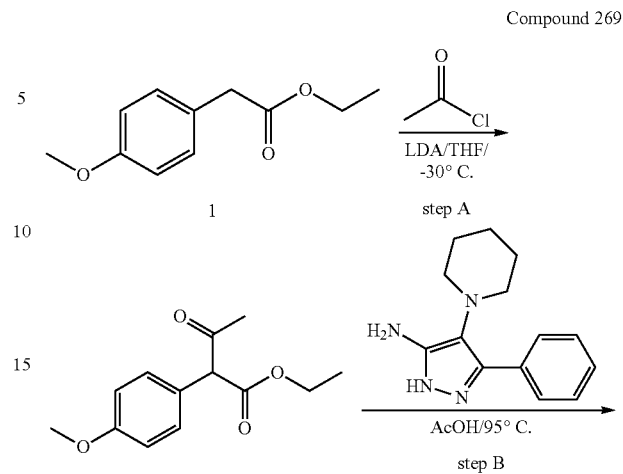

Step A: ethyl 2-(4-methoxyphenyl)-3-oxobutanoate

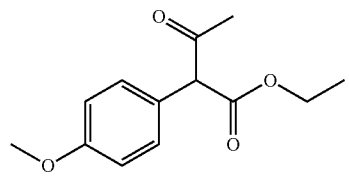 [SMILES: CCOC(=O)C(C(C)=O)c1ccc(OC)cc1]

To a solution of ethyl 2-(4-methoxyphenyl)acetate (5 g, 25.7 mmol) in THF (100 mL) was added LDA (1.5 M in THF, 20 mL, 30.84 mmol) dropwise at −30~−35° C. The mixture was stirred at −30~−35° C. for 30 min, and acetyl chloride (2.1 g, 27 mmol) was added dropwise. Then the mixture was stirred at rt for 6 h. The mixture was poured into saturated NH$_4$Cl and extracted with EA (3*100 mL). The combined organic phase was washed with brine, dried over anhydrous MgSO$_4$, filtered and concentrated in vacuo. The residue was purified by flash chromatography to afford the desired ethyl 2-(4-methoxyphenyl)-3-oxobutanoate as a brown oil (5.2 g, 86% yield).

Step B: 6-(4-methoxyphenyl)-5-methyl-2-phenyl-3-(piperidin-1-yl)pyrazolo[1,5-a]pyrimidin-7(4H)-one

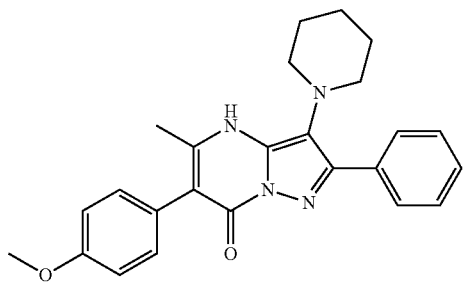

A mixture of ethyl 2-(4-methoxyphenyl)-3-oxobutanoate (292 mg, 1.24 mmol) and 3-phenyl-4-(piperidin-1-yl)-1H-pyrazol-5-amine (300 mg, 1.24 mmol) in AcOH (10 mL) was stirred at 95° C. for 4 h. After cooling to room temperature, the solids were collected by filtration, wash with ethyl acetate, and dried under vacuum to give 6-(4-methoxyphenyl)-5-methyl-2-phenyl-3-(piperidin-1-yl)pyrazolo[1,5-a]pyrimidin-7(4H)-one (210 mg, 41% yield) as a white solid. LC-MS: m/z 415.1 (M+H)⁺.

Step C: Compound 269: 6-(4-methoxyphenyl)-4,5-dimethyl-2-phenyl-3-(piperidin-1-yl)pyrazolo[1,5-a]pyrimidin-7(4H)-one

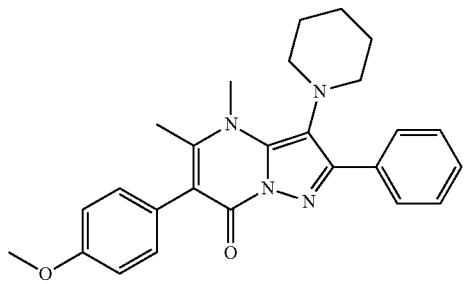

To a mixture of 6-(4-methoxyphenyl)-5-methyl-2-phenyl-3-(piperidin-1-yl)pyrazolo[1,5-a]pyrimidin-7(4H)-one (210 mg, 0.49 mmol) and Cs₂CO₃ (320 mg, 0.98 mmol) in DMF (10 mL) was added MeI (103 mg, 0.735 mmol). The mixture was then stirred at rt overnight to give the title compound.
¹H NMR (400 MHz, CHLOROFORM-d) δ: 7.62 (br. s., 2H), 7.45 (d, J=2.15 Hz, 3H), 7.23 (m, J=8.33 Hz, 2H), 6.98 (m, J=8.33 Hz, 2H), 4.26 (s, 3H), 3.86 (s, 3H), 3.00 (d, J=11.55 Hz, 4H), 2.31 (s, 3H), 1.78 (br. s., 4H), 1.66 (br. s., 2H). LC-MS: m/z 429.0 (M+H)⁺.

Compound 271

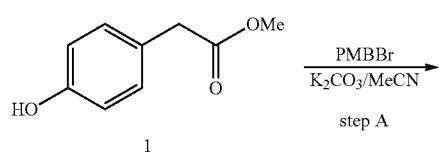

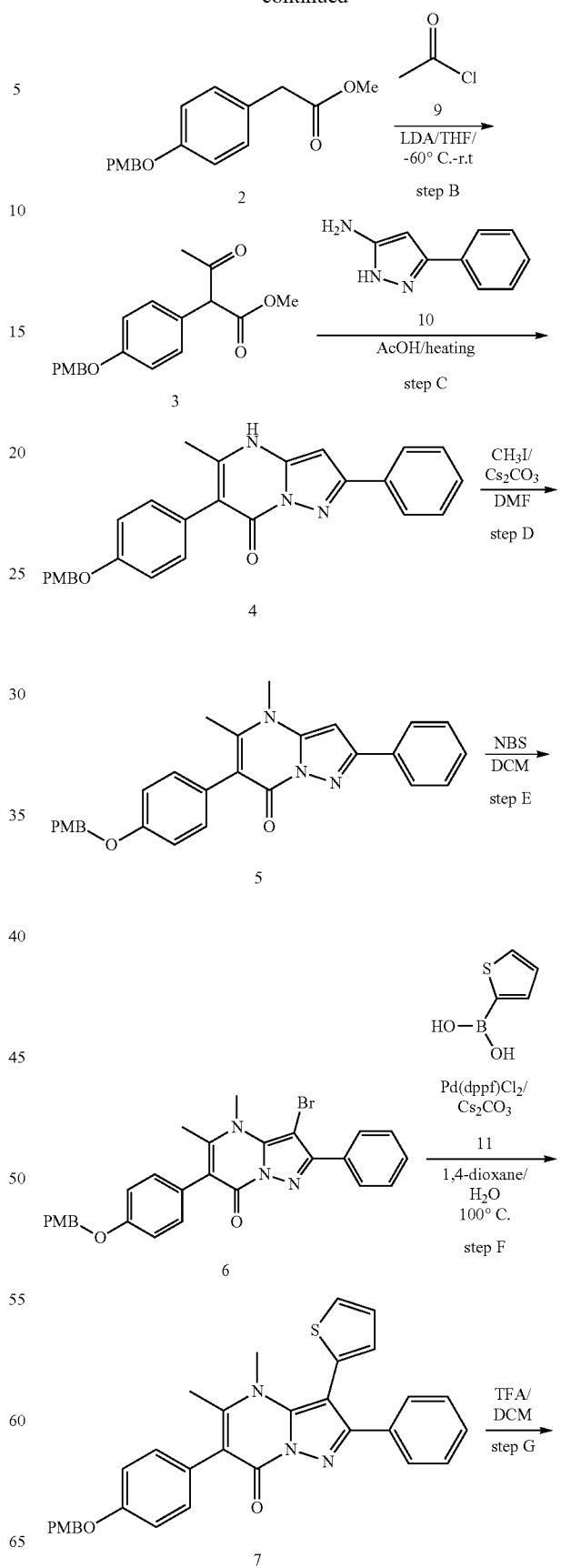

-continued

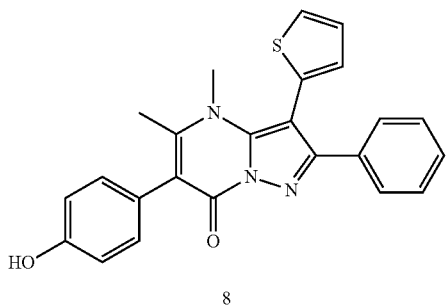

8

Step A: methyl
2-(4-((4-methoxybenzyl)oxy)phenyl)acetate

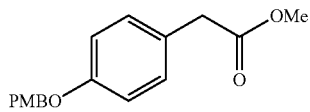

To a solution of methyl 2-(4-hydroxyphenyl)acetate (5.0 g, 30 mmol) in DMF (25 ml) was added K$_2$CO$_3$ (8.3 g, 60 mmol) at r.t. under N$_2$ atmosphere. After the mixture was stirred at r.t. for 30 min, 1-(bromomethyl)-4-methoxybenzene (7.2 g, 36 mmol) was added dropwise, and the mixture was stirred at r.t. for 2 h. The mixture was poured into H$_2$O (100 mL) and extracted with EA (3*50 mL). The combined organic phase was washed with brine, dried over anhydrous Na$_2$SO$_4$ and concentrated in vacuo. The residue was recrystallized from EtOH to afford the title compound 2 as a white solid (5.6 g, 65% yield). LC-MS: m/z 287.1 (M+H)$^+$.

Step B: methyl 2-(4-((4-methoxybenzyl)oxy)phenyl)-3-oxobutanoate

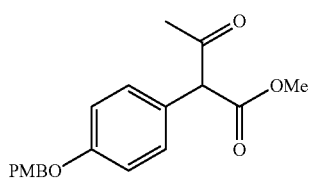

To a solution of Intermediate 2 (4.6 g, 16 mmol) in THF (50 mL) was added LDA (2 mol/l in THF, 16 ml) dropwise at −60° C. The mixture was stirred at −60° C. for 30 min. Then acetyl chloride (1.5 g, 19.2 mmol) was added dropwise. The mixture was stirred at −60° C. for 30 min and stirred at r.t. for 1 h. The mixture was diluted with EA (50 mL) and quenched with saturated NH$_4$Cl. The organic phase was separated and washed with water and brine, dried over anhydrous Na$_2$SO$_4$ and concentrated in vacuo to afford the title compound 3 as a yellow oil which was used to the next step without purification (5.2 g, 99% yield).

Step C: 6-(4-((4-methoxybenzyl)oxy)phenyl)-5-methyl-2-phenylpyrazolo[1,5-a]pyrimidin-7(4H)-one

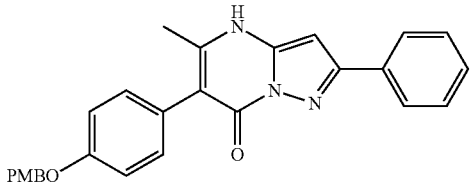

A solution of Intermediate 3 (5.3 g, 16 mmol) and 3-phenyl-1H-pyrazol-5-amine (1.9 g, 12 mmol) in AcOH (10 ml) was refluxed for 1 h. The reaction mixture was cooled to room temperature. The precipitate was filtered off and washed with EA (3*5 mL) to afford the title compound 4 (3.0 g, 43% yield). LC-MS: m/z 438.1 (M+H)$^+$.

Step D: 6-(4-((4-methoxybenzyl)oxy)phenyl)-4,5-dimethyl-2-phenylpyrazolo[1,5-a]pyrimidin-7(4H)-one

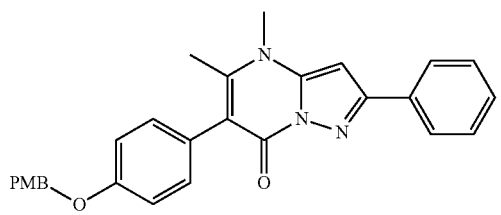

To a solution of Intermediate 4 (3.0 g, 6.9 mmol) in DMF (50 mL) were added Cs$_2$CO$_3$ (6.8 g, 20.7 mmol) and iodomethane (2.9 g, 20.7 mmol). The mixture was then stirred at r.t. overnight. The mixture was poured into water (200 mL). The white precipitate was filtered off, washed with H$_2$O (3*5 mL) and EA (3*5 mL) to afford the title compound 5 as a white solid (2.8 g, 88% yield). LC-MS: m/z 452.1 (M+H)$^+$.

Step E: 3-bromo-6-(4-((4-methoxybenzyl)oxy)phenyl)-4,5-dimethyl-2-phenylpyrazolo[1,5-a]pyrimidin-7(4H)-one

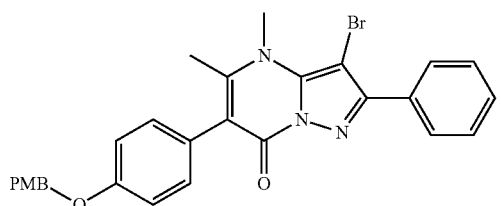

To a mixture of Intermediate 5 (2.8 g, 6.1 mmol) in DCM (50 ml) was added N-Bromosuccinimide (1.2 g, 6.7 mmol). The reaction mixture was then stirred at r.t. overnight. The mixture was poured into water (200 mL). The organic phase was separated, washed with brine, dried over anhydrous Na$_2$SO$_4$ and concentrated in vacuo to afford the title compound 6 (3.1 g, 94% yield) as a white solid. LC-MS: m/z 530.1/532.1 (M+H)$^+$.

Step F: 6-(4-((4-methoxybenzyl)oxy)phenyl)-4,5-dimethyl-2-phenyl-3-(thiophen-2-yl)pyrazolo[1,5-a]pyrimidin-7(4H)-one

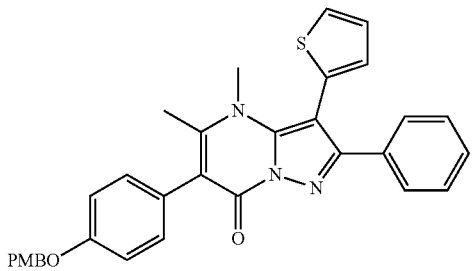

A suspension of Intermediate 6 (200 mg, 0.38 mmol), thiophen-2-ylboronic acid (242 mg, 1.89 mmol), Pd(dppf)Cl$_2$ (100 mg, 0.12 mmol) and Cs$_2$CO$_3$ (246 mg, 0.76 mmol) in 1.4-dioxane (16 mL) and H$_2$O (2 ml) was stirred at 90° C. overnight under N$_2$ atmosphere. The reaction mixture was then cooled to r.t., diluted with DCM (50 mL) and filtered through celite. The filtrate was washed with water and brine, dried over anhydrous Na$_2$SO$_4$ and concentrated in vacuo. The residue was purified by prep-TLC to afford compound 7 (70 mg, 35% yield). LC-MS: m/z 534.1 (M+H)$^+$.

Step G: 6-(4-hydroxyphenyl)-4,5-dimethyl-2-phenyl-3-(thiophen-2-yl)pyrazolo[1,5-a]pyrimidin-7(4H)-one

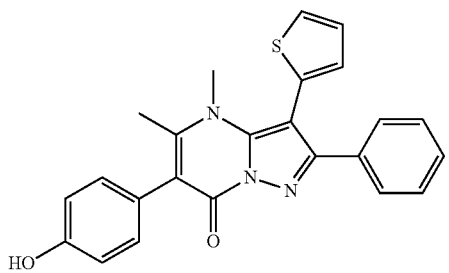 [SMILES: Cc1c(-c2ccc(O)cc2)c(=O)n2nc(-c3ccccc3)c(-c3cccs3)c2n1C]

To a solution of Intermediate 7 (25 mg, 0.05 mmol) in DCM (5 mL) was added TFA (0.5 mL). The reaction mixture was stirred at r.t. for 2 h. The mixture was concentrated in vacuo. The residue was dissolved in DCM (5 mL), washed with saturated NaHCO$_3$ solution and brine, dried over anhydrous Na$_2$SO$_4$ and concentrated in vacuo to give the title compound 8.

$^1$H NMR (CHLOROFORM-d) δ: 7.54-7.63 (m, 2H), 7.43-7.48 (m, 1H), 7.21-7.33 (m, 3H), 7.08-7.15 (m, 2H), 6.90-7.05 (m, 2H), 6.72-6.81 (m, 2H), 3.54 (br. s., 3H), 2.24 (br. s., 3H). LC-MS: m/z 414.1 (M+H)$^+$.

Compound 272

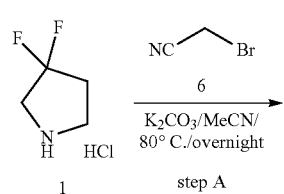

step A

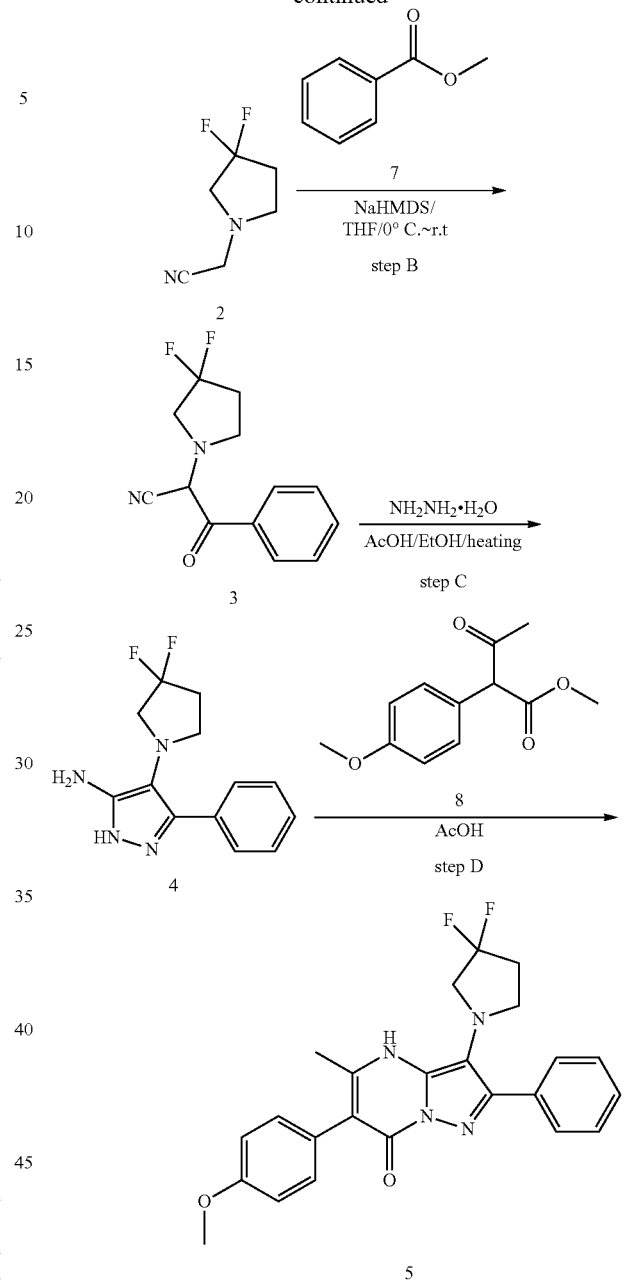

Step A: 2-(3,3-difluoropyrrolidin-1-yl)acetonitrile

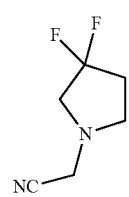

The mixture of 3,3-difluoropyrrolidine hydrochloride (3.6 g, 24.8 mmol), 2-bromoacetonitrile (3.0 g, 24.8 mmol), and K$_2$CO$_3$ (10.3 g, 74.4 mmol) in CH$_3$CN (50 mL) was stirred at 80° C. overnight. Then the mixture was cooled to r.t. and filtered. The filtrate was poured into water (100 mL) and extracted with EA (30 mL*3). The combined organic phase was washed with brine, dried over anhydrous $Na_2SO_4$ and concentrated in vacuo to afford the title compound 2 (2.9 g, 80% yield) which was directly used to the next step without further purification. LC-MS: m/z 147.0 $(M+H)^+$.

Step B: 2-(3,3-difluoropyrrolidin-1-yl)-3-oxo-3-phenylpropanenitrile

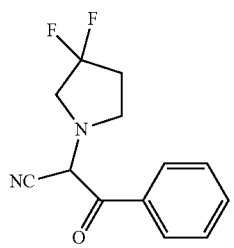 [SMILES: N#CC(C(=O)c1ccccc1)N1CCC(F)(F)C1]

To a mixture of Intermediate 2 (2.9 g, 20 mmol) and methyl benzoate (2.7 g, 20 mmol) in THF (40 mL) was added NaHMDS (2 mol/L in THF, 20 mL) at 0° C. The mixture was stirred at r.t. overnight. The reaction mixture was diluted with EA (50 mL) and quenched with saturated $NH_4Cl$. The organic phase was separated, washed with brine, dried over anhydrous $Na_2SO_4$ and concentrated in vacuo to afford the title compound 3 as a white solid (4.9 g, 97% yield) which was used to the next step without purification. LC-MS: m/z 251.0 $(M+H)^+$.

Step C: 4-(3,3-difluoropyrrolidin-1-yl)-3-phenyl-1H-pyrazol-5-amine

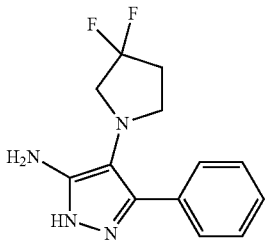 [SMILES: Nc1[nH]nc(-c2ccccc2)c1N1CCC(F)(F)C1]

The mixture of Intermediate 3 (4.9 g, 19.6 mmol) and hydrazine hydrate (1.5 g, 29.4 mmol,) in EtOH/AcOH (4/1.40 mL/10 mL) was refluxed overnight. Then the mixture was cooled to r.t. and evaporated. The residue was dissolved in EA (50 mL) and neutralized with 10% $NaHCO_3$. The organic phase was separated, and the water phase was extracted with EA (25 mL*3). The combined organic phase was washed with brine, dried over anhydrous $Na_2SO_4$ and concentrated in vacuo to afford the title compound 4 as a yellow solid (5.1 g, 98%) which was used to the next step without purification. LC-MS: m/z 265.1 $(M+H)^+$.

Step D: 3-(3,3-difluoropyrrolidin-1-yl)-6-(4-methoxyphenyl)-5-methyl-2-phenylpyrazolo[1,5-a]pyrimidin-7(4H)-one

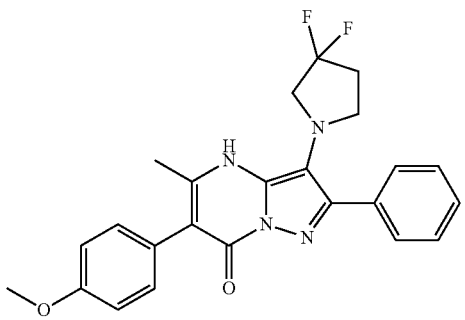 [SMILES: COc1ccc(-c2c(C)[nH]c3c(N4CCC(F)(F)C4)c(-c4ccccc4)nn3c2=O)cc1]

The mixture of Intermediate 4 (500 mg, 1.1 mmol) and methyl 2-(4-methoxyphenyl)-3-oxobutanoate (359 mg, 1.6 mmol) in AcOH (10 mL) was stirred at 100° C. for 1 h. Then the mixture was cooled to r.t. to afford the title compound 5.

$^1$H NMR (DMSO-$d_6$) δ 11.80 (br. s., 1H), 7.96-8.00 (m, 2H), 7.38-7.50 (m, 3H), 7.23 (d, J=8.6 Hz, 9H), 6.99 (d, J=8.6 Hz, 2H), 3.80 (s, 3H), 3.59 (t, J=12.8 Hz, 2H), 3.42 (t, J=7.0 Hz, 2H), 2.43-2.56 (m, 2H), 2.25 (s, 3H). LC-MS: m/z 437.7 $(M+H)^+$.

Compound 273

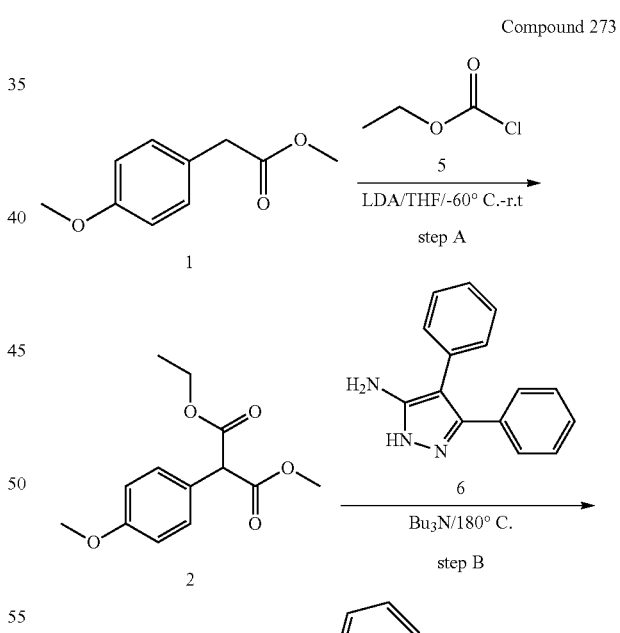

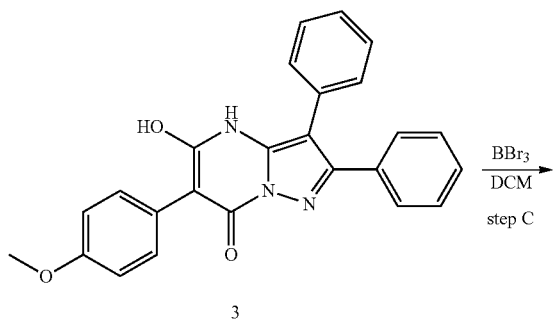

-continued

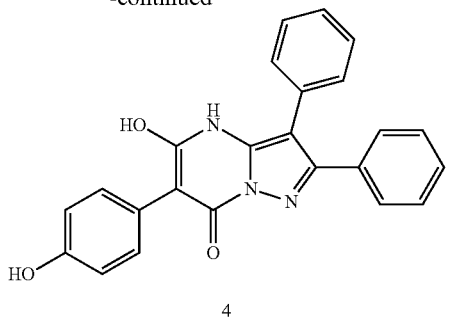

4

Step A: 1-ethyl 3-methyl 2-(4-methoxyphenyl)malonate

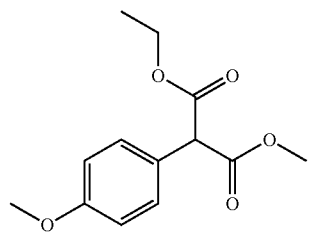

To a solution of methyl 2-(4-methoxyphenyl)acetate (5.0 g, 27.7 mmol) in THF (50 ml) was added LDA (2 mol/L in THF, 16.6 ml) dropwise at −60° C. The mixture was stirred at −60° C. for 30 min. Then ethyl carbonochloridate (3.6 g, 33.2 mmol) was added dropwise. The mixture was stirred at −60° C. for 30 min and then stirred at r.t. for 2 h. The mixture was diluted with EA (50 mL) and quenched with saturated NH$_4$Cl. The organic phase was separated and washed with water and brine, dried over anhydrous Na$_2$SO$_4$ and concentrated in vacuo. The residue was purified by flash chromatography (PE/EA=20:1) to afford the title compound 2 as a colorless oil (3.0 g, 43% yield). LC-MS: m/z 253.1 (M+H)$^+$.

Step B: 5-hydroxy-6-(4-methoxyphenyl)-2,3-diphenylpyrazolo[1,5-a]pyrimidin-7(4H)-one

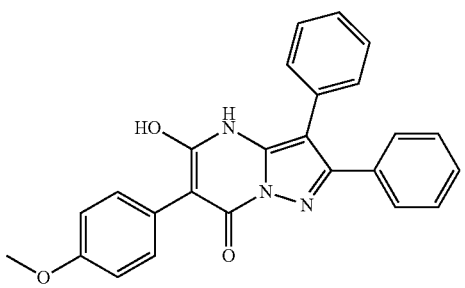

A mixture of Intermediate 2 (1.0 g, 4.0 mmol) and 3,4-diphenyl-1H-pyrazol-5-amine (933 mg, 4.0 mmol) in tributylamine (10 mL) was stirred at 185° C. for 1 h and then cooled to room temperature. The precipitate was collected by filtration, washed with MeOH (3*10 mL) to afford the title compound 3 as a white solid (1.1 g, 67% yield).

$^1$H NMR (DMSO-d$_6$) δ: 11.57 (br. s, 1H), 7.26-7.49 (m, 12H), 6.90-6.99 (m, 2H), 3.78 (s, 3H). LC-MS: m/z 410.1 (M+H)$^+$.

Step C: 5-hydroxy-6-(4-hydroxyphenyl)-2,3-diphenylpyrazolo[1,5-a]pyrimidin-7(4H)-one

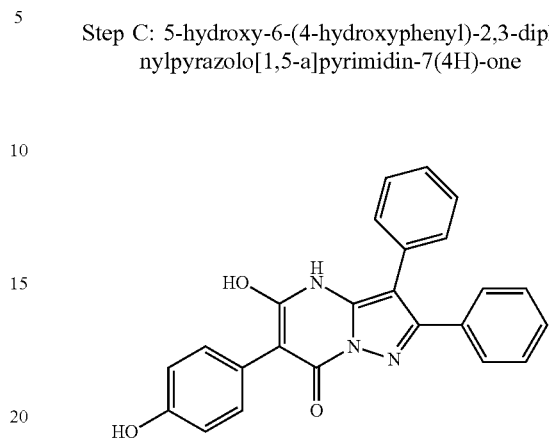

To a solution of Intermediate 3 (80 mg, 0.2 mmol) in DCM (3 mL) was added borontribromide (0.2 mL) at 0° C. dropwise. The mixture was stirred at 0° C. for 2 h. The reaction was quenched with MeOH at 0° C. and concentrated in vacuo to afford the desired compound 4.

$^1$H NMR (DMSO-d$_6$) δ: 9.66 (br. s., 1H), 8.93 (br. s., 1H), 7.39-7.50 (m, 4H), 7.17-7.36 (m, 8H), 6.62 (d, J=8.6 Hz, 2H). LC-MS: m/z 396.1 (M+H)$^+$.

Compound 274

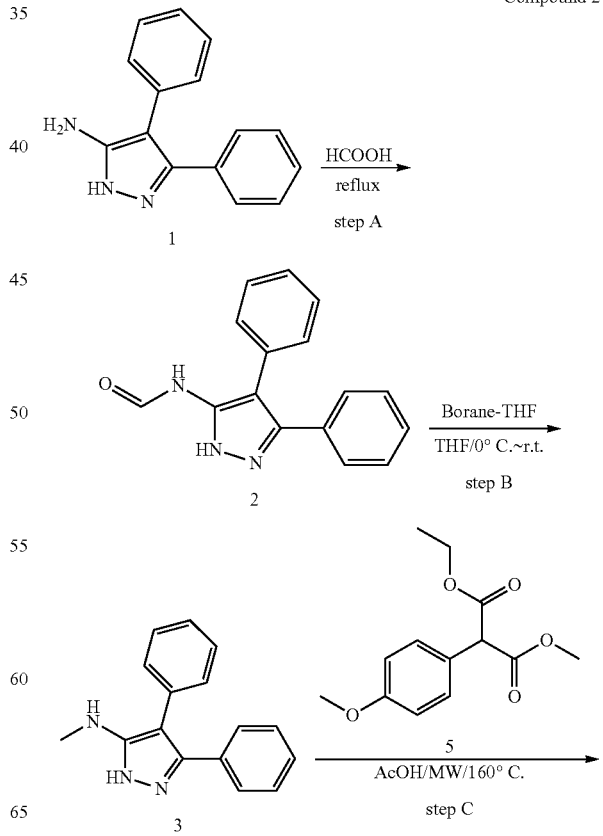

320

Step C: 5-hydroxy-6-(4-methoxyphenyl)-4-methyl-2,3-diphenylpyrazolo[1,5-a]pyrimidin-7(4H)-one

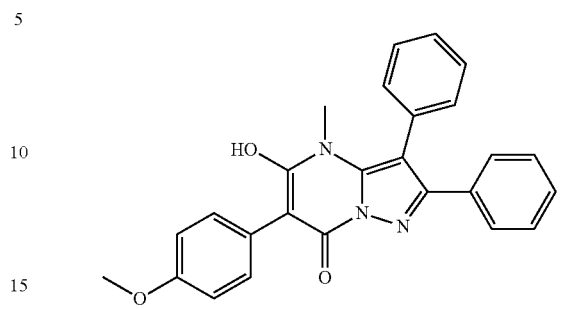

A mixture of Intermediate 3 (200 mg, 0.8 mmol) and 1-ethyl 3-methyl 2-(4-methoxyphenyl)malonate (200 mg, 0.8 mmol) in AcOH (5 mL) was stirred at 160° C. through microwave irradiation for 1 h and cooled to room temperature to afford the title compound 4.

$^1$H NMR (DMSO-d$_6$) δ: 7.33-7.49 (m, 9H), 7.22-7.33 (m, 3H), 6.94 (d, J=8.6 Hz, 2H), 3.78 (s, 3H), 3.05 (s, 3H). LC-MS: m/z 424.7 (M+H)$^+$.

Compound 275

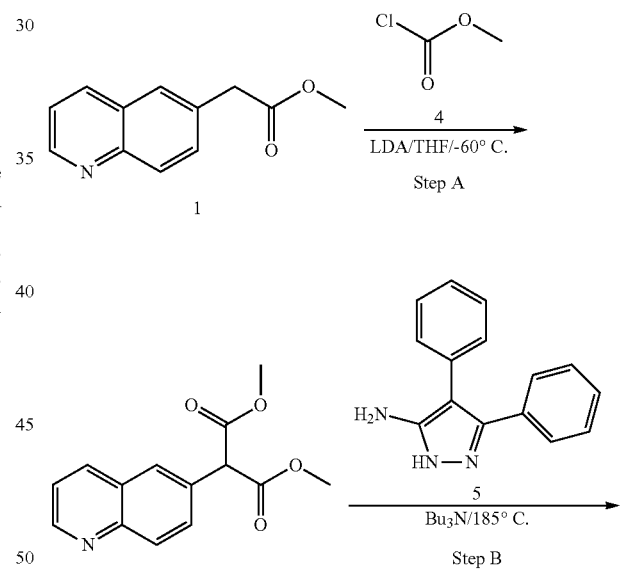

319

-continued

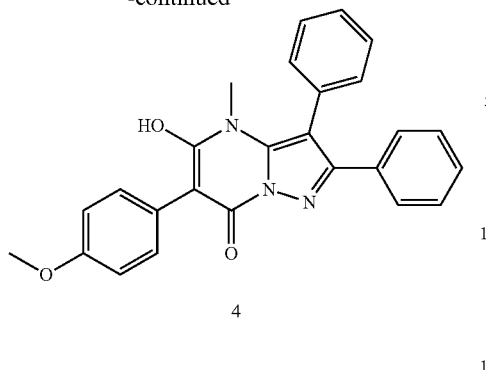

4

Step A:
N-(3,4-diphenyl-1H-pyrazol-5-yl)formamide

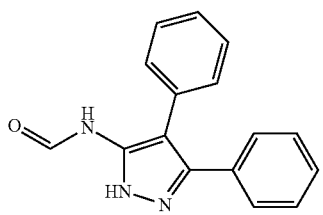 [SMILES: O=CNc1[nH]nc(-c2ccccc2)c1-c1ccccc1]

The mixture of 3,4-diphenyl-1H-pyrazol-5-amine (5.0 g, 21.3 mmol) in formic acid (30 mL) was refluxed for 1 h. The mixture was evaporated, and the residue was dissolved in EA (50 mL), washed with 10% NaHCO$_3$ aqueous solution, water and brine, dried over anhydrous Na$_2$SO$_4$ and concentrated in vacuo. The residue was purified by flash chromatography (PE/EA 1:1) to afford the title compound 2 as a light yellow solid (4.0 g, 72% yield). LC-MS: m/z 264.1 (M+H)$^+$.

Step B: N-methyl-3,4-diphenyl-1H-pyrazol-5-amine

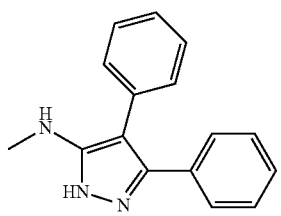 [SMILES: CNc1[nH]nc(-c2ccccc2)c1-c1ccccc1]

To a solution of Intermediate 2 (4.0 g, 15.2 mmol) in THF (30 mL) was added borane-THF (1 mol/L in THF, 15.2 mL) dropwise at 0° C. The mixture was stirred at r.t. overnight. The reaction was quenched by careful adding MeOH and concentrated in vacuo. The residue was purified by flash chromatography to afford the title compound 3 as a white solid (2.1 g, 56%). LC-MS: m/z 250.1 (M+H)$^+$

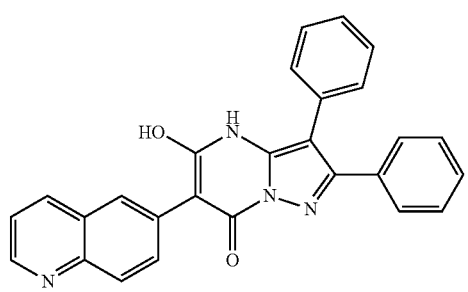

Step A: dimethyl 2-(quinolin-6-yl)malonate

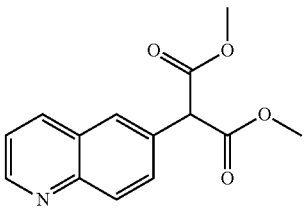 [SMILES: COC(=O)C(C(=O)OC)c1ccc2ncccc2c1]

To a solution of methyl 2-(quinolin-6-yl)acetate (2.0 g, 9.9 mmol) in THF (30 ml) was added LDA (2 mol/L in THF, 7.4 ml) dropwise at −60° C. The mixture was stirred at −60° C. for 30 min. Then methyl carbonochloridate (1.0 g, 10.9 mmol) was added dropwise. The mixture was stirred at −60° C. for 30 min and stirred at r.t. for 2 h. The mixture was diluted with EA (30 mL) and quenched with saturated NH$_4$Cl. The organic phase was separated and washed with water and brine, dried over anhydrous Na$_2$SO$_4$ and concentrated in vacuo. The residue was purified by flash chromatography (PE/EA=20:1) to afford the title compound 2 as a colorless oil (1.0 g, 39% yield). LC-MS: m/z 260.0 (M+H)$^+$.

Step B: 5-hydroxy-2,3-diphenyl-6-(quinolin-6-yl)pyrazolo[1,5-a]pyrimidin-7(4H)-one

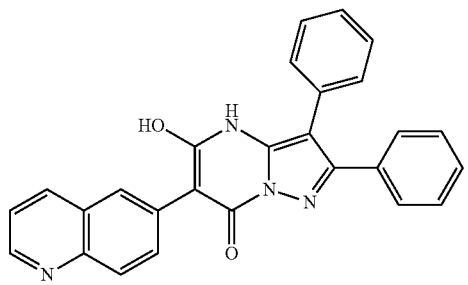 [SMILES: O=c1c(-c2ccc3ncccc3c2)c(O)[nH]c2c(-c3ccccc3)c(-c3ccccc3)nn12]

A mixture of Intermediate 2 (260 mg, 1.0 mmol) and 3,4-diphenyl-1H-pyrazol-5-amine (212 mg, 0.9 mmol) in tributylamine (10 mL) was stirred at 185° C. for 1 h and cooled to room temperature. The precipitate was collected by filtration to afford the title compound 3.

$^1$H NMR (DMSO-d$_6$) δ: 9.95 (br. s., 1H), 8.75 (d, J=3.8 Hz, 1H), 8.30-8.39 (m, 2H), 8.26 (d, J=7.8 Hz, 1H), 7.84 (d, J=8.0 Hz, 1H), 7.39-7.48 (m, 3H), 7.19-7.37 (m, 8H). LC-MS: m/z 431.1 (M+H)$^+$.

Compound 276

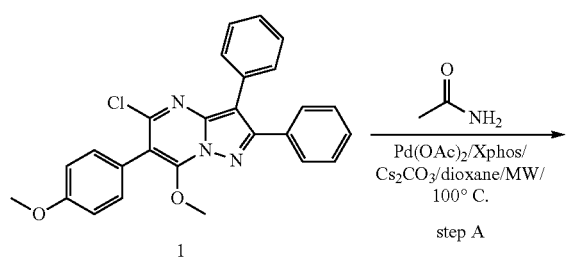

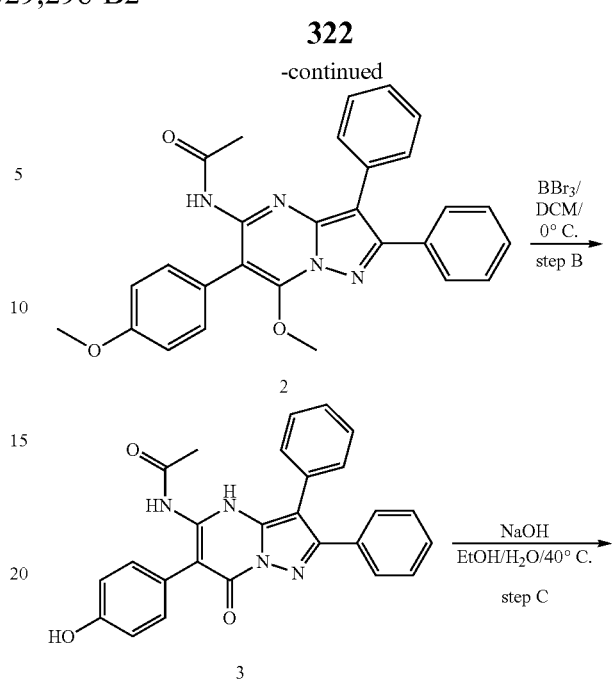

Step A: N-(7-methoxy-6-(4-methoxyphenyl)-2,3-diphenylpyrazolo[1,5-a]pyrimidin-5-yl)acetamide

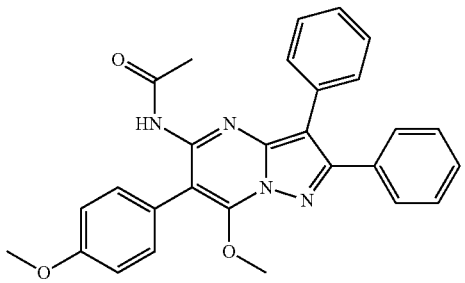 [SMILES: COc1ccc(-c2c(NC(C)=O)nc3c(-c4ccccc4)c(-c4ccccc4)nn3c2OC)cc1]

A suspension of 5-chloro-7-methoxy-6-(4-methoxyphenyl)-2,3-diphenylpyrazolo[1,5-a]pyrimidine (Synthesized in Scheme of Compound 101, 400 mg, 0.91 mmol), acetamide (230 mg, 1.81 mmol), Pd(OAc)$_2$ (40.5 mg, 0.18 mmol), Xantphos (158 mg, 0.27 mmol) and Cs$_2$CO$_3$ (650 mg, 1.99 mmol) in 1.4-dioxane (30 ml) was reacted in microwave reactor at 100° C. for 45 min under N$_2$ atmosphere. The reaction was then cooled to RT and filtered. The dark filtrate was concentrated in vacuo and purified by flash column chromatography, eluting with DCM/MeOH (40/1), to get the desired product as a yellow solid (100 mg, 23% yield). LC-MS: m/z 464.2 (M+H)$^+$.

Step B: N-(7-hydroxy-6-(4-hydroxyphenyl)-2,3-diphenylpyrazolo[1,5-a]pyrimidin-5-yl)acetamide

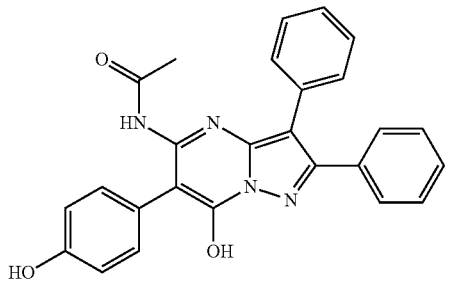 [SMILES: CC(=O)Nc1nc2c(-c3ccccc3)c(-c3ccccc3)nn2c(O)c1-c1ccc(O)cc1]

To a solution of N-(7-methoxy-6-(4-methoxyphenyl)-2,3-diphenylpyrazolo[1,5-a]pyrimidin-5-yl)acetamide (70 mg, 0.15 mmol) in DCM (2 mL) was carefully added BBr$_3$ (1.0 M in DCM, 0.5 ml, 5 mmol) at 0° C. The mixture was stirred at 0° C. for 2 h. The reaction was quenched by careful adding ice water at 0° C. The precipitated solids were filtered and purified by prep-HPLC to get the desired product as a yellow solid (50 mg, 75% yield). LC-MS: m/z 437.2 (M+H)$^+$.

Step C: 5-amino-6-(4-hydroxyphenyl)-2,3-diphenylpyrazolo[1,5-a]pyrimidin-7(4H)-one

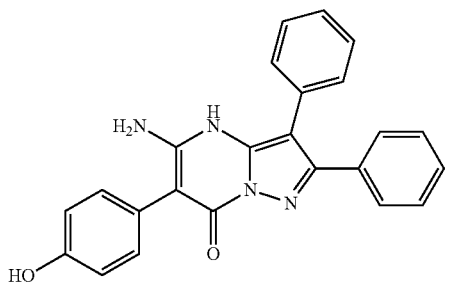

The N-(7-hydroxy-6-(4-hydroxyphenyl)-2,3-diphenylpyrazolo[1,5-a]pyrimidin-5-yl)acetamide (50 mg, 0.11 mmol) and NaOH (17.8 mg, 0.44 mmoL) in EtOH (10 mL) and water (0.5 mL) was stirred at 40° C. for 14 h. Then the mixture was concentrated to get the desired product.

$^1$H NMR (DMSO-d$_6$) δ: 9.20 (br. s., 1H), 7.53 (d, J=6.0 Hz, 2H), 7.42 (d, J=6.8 Hz, 2H), 7.35-7.30 (m, 3H), 7.20 (t, J=7.6 Hz, 2H), 7.15 (d, J=8.4 Hz, 2H), 6.77 (d, J=8.8 Hz, 2H), 4.71 (br. s., 2H). LC-MS: m/z 395.6 (M+H)$^+$.

Compound 277

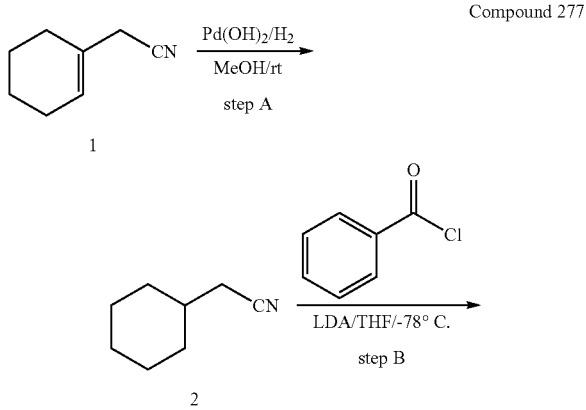

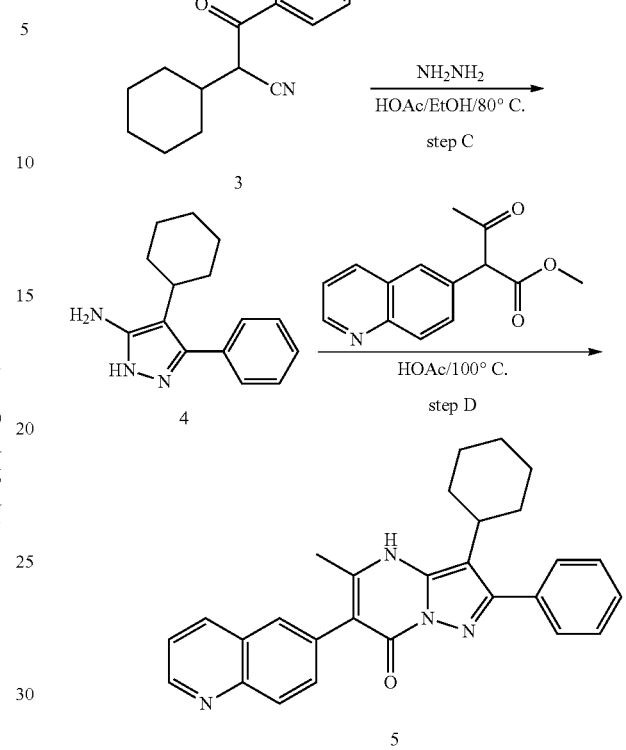

Step A: 2-cyclohexylacetonitrile

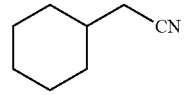

A mixture of 2-cyclohexenylacetonitrile (2.0 g, 16.5 mmol) and Pd(OH)$_2$/C (200 mg, 10%) in MeOH (100 mL) was stirred at RT under H$_2$ atmosphere for 10 h. The mixture was filtered and concentrated to get the desired product as a yellow solid (1.8 g, 90% yield). LC-MS: m/z 124.2 (M+H)$^+$.

Step B: 2-cyclohexyl-3-oxo-3-phenylpropanenitrile

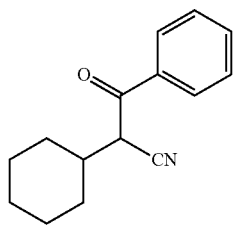 [SMILES: N#CC(C(=O)c1ccccc1)C1CCCCC1]

To a solution of 2-cyclohexylacetonitrile (1.8 g, 14.6 mmol) in THF (100 mL) was added LDA (2.0 M in THF, 8.8 mL, 17.5 mmol) dropwise at −78° C. The mixture was stirred at −78° C. for 30 min, and benzoyl chloride (0.17 mL, 2.33 mmol) was added dropwise. Then the mixture was slowly warmed to RT and stirred for 10 h. The mixture was poured slowly to saturated aq.NH₄Cl and extracted with EA (30 mL*3). The combined organic phase was washed with brine, dried over anhydrous MgSO₄ and concentrated in vacuo to get the desired product as a yellow oil (2.9 g, 88% yield). LC-MS: m/z 228.2 (M+H)⁺.

Step C: 4-cyclohexyl-3-phenyl-1H-pyrazol-5-amine

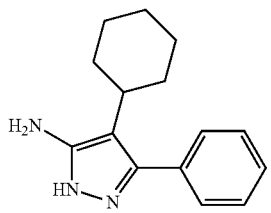 [SMILES: Nc1[nH]nc(-c2ccccc2)c1C1CCCCC1]

The solution of 2-cyclohexyl-3-oxo-3-phenylpropanenitrile (2.9 g, 12.8 mmol) and hydrazine hydrate (1.9 g, 38.6 mmol) in EtOH/AcOH (30 mL/6 mL) was heated to reflux for 16 h under N₂ protection. The reaction mixture was concentrated, filtered, washed with Et₂O, and dried to get the desired product as a yellow oil (2.9 g, 96° % yield). LC-MS: m/z 242.1 (M+H)⁺.

Step D: 3-cyclohexyl-5-methyl-2-phenyl-6-(quinolin-6-yl)pyrazolo[1,5-a]pyrimidin-7(4H)-one

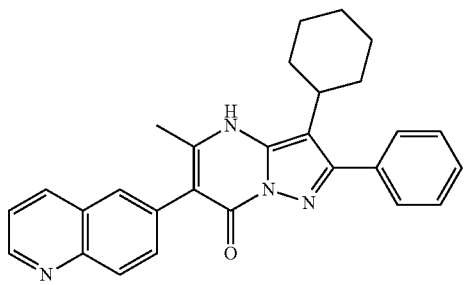 [SMILES: Cc1[nH]c2c(C3CCCCC3)c(-c3ccccc3)nn2c(=O)c1-c1ccc2ncccc2c1]

The mixture of 4-cyclohexyl-3-phenyl-1H-pyrazol-5-amine (230 mg, 0.96 mmol) and methyl 3-oxo-2-(quinolin-6-yl)butanoate (300 mg, 1.24 mmol) in AcOH (5 mL) was stirred at 100° C. for 1 h. After removal of AcOH, 10% of NaHCO₃ was added. The precipitate was filtered, washed with MeOH, and dried to get the desired product.

1H NMR (DMSO-d₆) δ: 11.56 (br. s., 1H), 8.94 (d, J=2.4 Hz, 1H), 8.39 (d, J=8.0 Hz, 1H), 8.07 (d, J=8.8 Hz, 1H), 7.95 (d, J=0.8 Hz, 1H), 7.74 (dd, J=1.6 Hz, 1.6 Hz, 1H), 7.58-7.40 (m, 6H), 2.80 (m, 1H), 2.34 (s, 3H), 1.81-1.60 (m, 8H), 1.30-1.23 (m, 2H). LC-MS: m/z 435.2 (M+H)⁺.

Compound 278

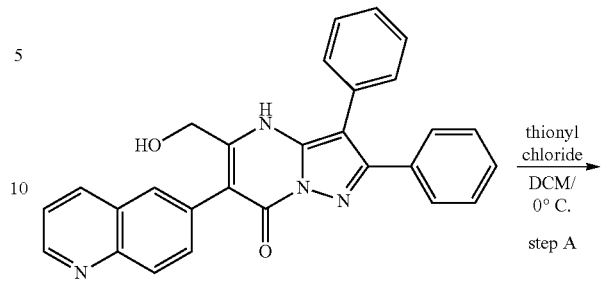

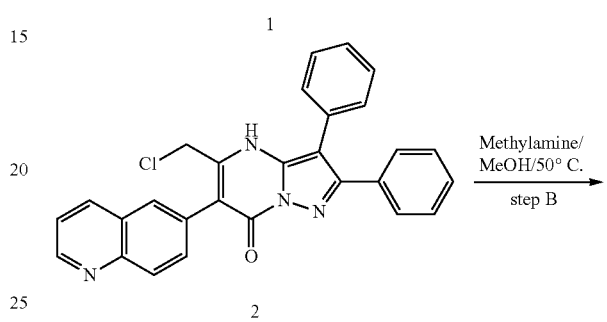

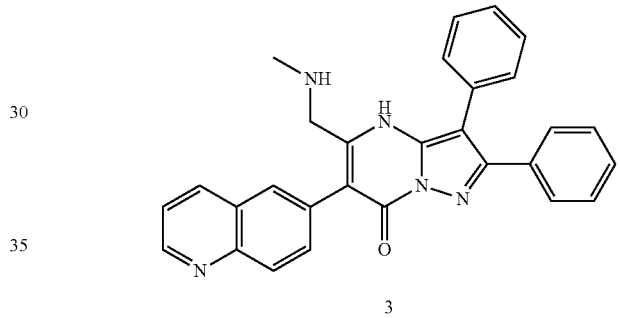

Step A: 5-(chloromethyl)-2,3-diphenyl-6-(quinolin-6-yl)pyrazolo[1,5-a]pyrimidin-7(4H)-one

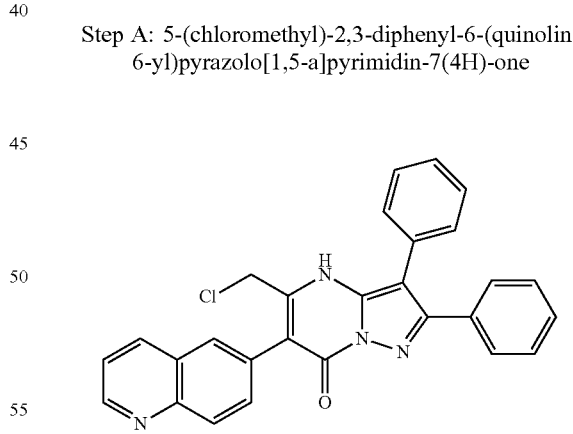

To a suspension of 5-(hydroxymethyl)-2,3-diphenyl-6-(quinolin-6-yl)pyrazolo[1,5-a]pyrimidin-7(4H)-one (Compound 319, 500 mg, 1.126 mmol,) in DCM (3 mL) cooled in ice-bath was added SOCl₂ (670 mg, 5.631 mmol) dropwise. The resultant mixture was then stirred at room temperature overnight. The suspension was filtered, washed with ethyl acetate, and dried under vacuum. The residue was purified by prep-TLC (DCM:MeOH=20:1) to get 5-(chloromethyl)-2,3-diphenyl-6-(quinolin-6-yl)pyrazolo[1,5-a]pyrimidin-7(4H)-one (300 mg). LC-MS: m/z 463.1 (M+H)⁺.

327

Step B: Compound 278: 5-((methylamino)methyl)-2,3-diphenyl-6-(quinolin-6-yl)pyrazolo[1,5-a]pyrimidin-7(4H)-one

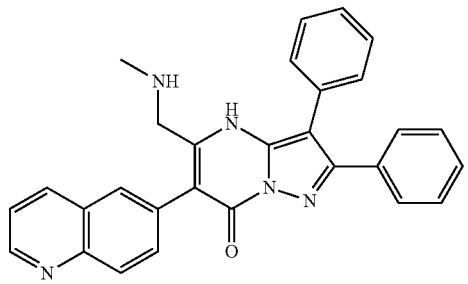

A solution of 5-(chloromethyl)-2,3-diphenyl-6-(quinolin-6-yl)pyrazolo[1,5-a]pyrimidin-7(4H)-one (150 mg, 0.324 mmol) in methylamine (2.0 M in MeOH, 5 mL) was stirred at 50° C. overnight. Water (10 mL) was added to quench the reaction. The resultant mixture was concentrated to get the title compound.

$^1$H NMR (400 MHz, TFA) δ: 9.26-9.48 (m, 2H), 8.57-8.76 (m, 2H), 8.42 (d, J=8.60 Hz, 1H), 8.35 (dd, J=8.33, 5.64 Hz, 1H), 7.64-7.81 (m, 6H), 7.55-7.62 (m, 2H), 7.51 (d, J=7.25 Hz, 2H), 4.80 (br. s., 2H), 2.95 (s, 3H). LC-MS: m/z 458.1 (M+H)$^+$.

328

Step A: 3-(cyclohex-1-en-1-yl)-5-hydroxy-6-(4-methoxyphenyl)-2-phenylpyrazolo[1,5-a]pyrimidin-7(4H)-one

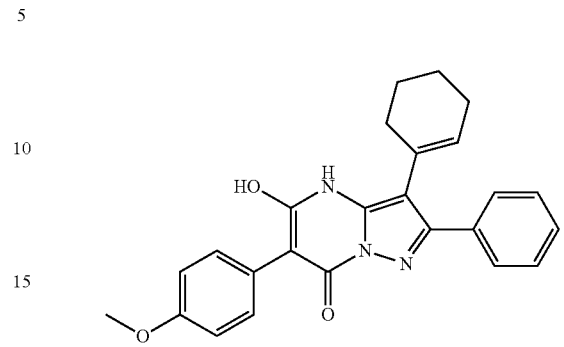

A suspension of 4-cyclohexenyl-3-phenyl-1H-pyrazol-5-amine (200 mg, 0.84 mmol) and dimethyl 2-(4-methoxyphenyl)malonate (240 mg, 1.00 mmol) in tributylamine (5 ml) was heated to 180° C. for 1 h under N$_2$ protection. The mixture was cooled to the RT and stirred with petroleum ether to get the desired product.

$^1$H NMR (DMSO-d$_6$) δ: 12.05 (br. s., 1H), 7.56-6.50 (m, 9H), 5.67 (s, 1H), 3.73 (s, 3H), 2.09 (br. s., 2H), 1.91 (br. s., 2H), 1.58 (br. s., 4H). LC-MS: m/z 414.0 (M+H)$^+$.

Compound 279

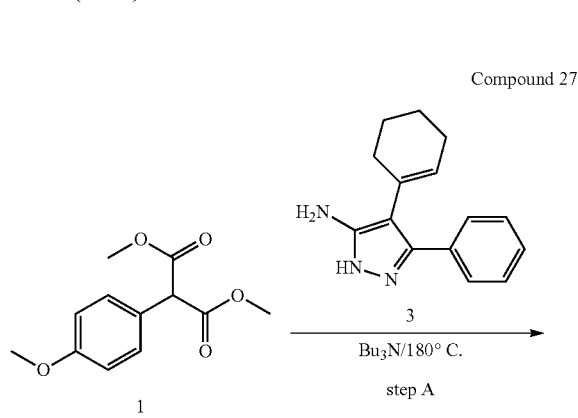

Compound 280

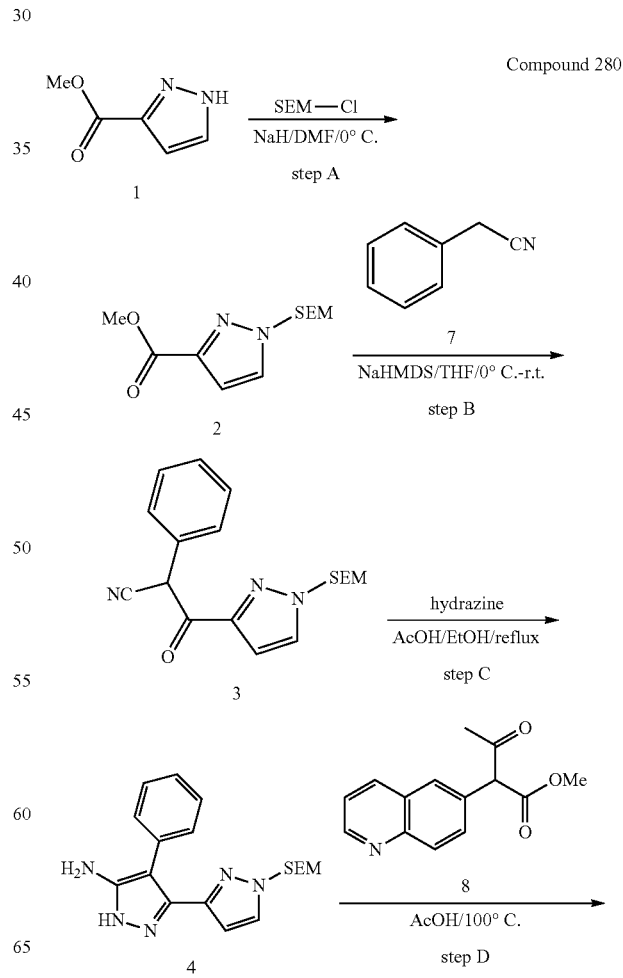

-continued

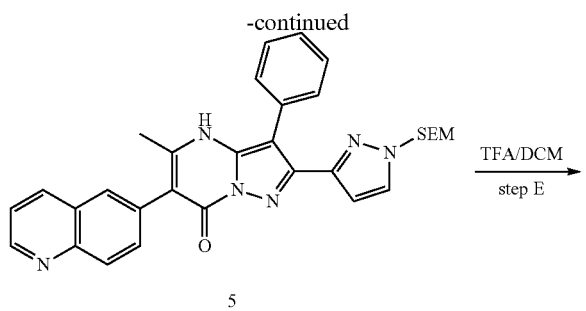

5

TFA/DCM
step E

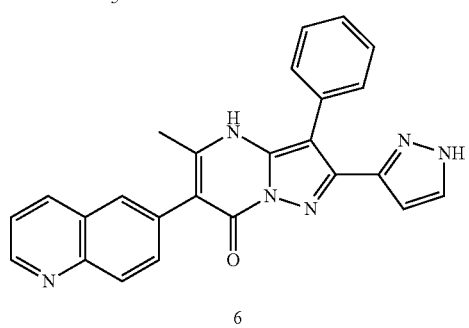

6

Step A: methyl 1-((2-(trimethylsilyl)ethoxy)methyl)-1H-pyrazole-3-carboxylate

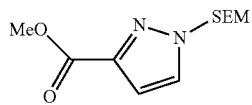

To a solution of methyl 1H-pyrazole-3-carboxylate (1 g, 7.9 mmol) in THF (30 mL) was added sodium hydride (380 mg, 60% dispersion in mineral oil, 9.5 mmol) at 0° C. After the mixture was stirred at 0° C. for 30 min, (2-(chloromethoxy)ethyl)trimethylsilane (1.6 g, 9.5 mmol) was added dropwise. Then the mixture was stirred at r.t. overnight. The mixture was diluted with EA (30 mL) and quenched with saturated NH₄Cl. The organic phase was separated and washed with brine, dried over anhydrous Na₂SO₄, and concentrated in vacuo. The residue was purified by flash chromatography to afford the intermediate 2 as a white solid (1.1 g, 54% yield).
¹H NMR (CHLOROFORM-d) δ: 7.55 (d, J=1.8 Hz, 1H), 6.91 (d, J=1.8 Hz, 1H), 5.86 (s, 2H), 3.90 (s, 3H), 3.59 (t, J=8.0 Hz, 2H), 0.90 (t, J=8.0 Hz, 2H), −0.04 (s, 9H). LC-MS: m/z 257.1 (M+H)⁺.

Step B: 3-oxo-2-phenyl-3-(1-((2-(trimethylsilyl)ethoxy)methyl)-1H-pyrazol-3-yl)propanenitrile

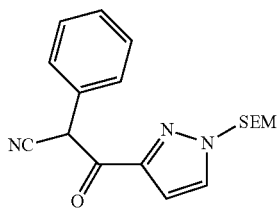 [SMILES: C[Si](C)(C)CCOCn1ccc(C(=O)C(C#N)c2ccccc2)n1]

To the mixture of Intermediate 2 (600 mg, 2.3 mmol) and 2-phenylacetonitrile (330 mg, 2.8 mmol) in THF (20 mL) was added NaHMDS (2.0 mol/L in THF, 1.4 mL) dropwise at 0° C. The mixture was kept at 0° C. for 30 min, and then stirred at r.t. overnight. The mixture was diluted with EA (20 mL) and quenched with saturated NH₄Cl. The organic phase was separated and washed with brine, dried over anhydrous Na₂SO₄, and concentrated in vacuo. The residue was purified by flash chromatography to afford the intermediate 3 as a light yellow solid (200 mg, 25% yield).
¹H NMR (DMSO-d₆) δ: 12.41 (br. s., 1H), 7.73-7.78 (m, 2H), 7.66 (d, J=1.8 Hz, 1H), 7.43 (t, J=7.8 Hz, 2H), 7.30 (t, J=7.4 Hz, 1H), 6.77 (d, J=1.8 Hz, 1H), 5.49 (s, 2H), 3.45 (t, J=8.0 Hz, 2H), 0.81 (t, J=8.0 Hz, 2H), −0.10 (s, 9H). LC-MS: m/z 342.1 (M+H)⁺.

Step C: 4-phenyl-1'-((2-(trimethylsilyl)ethoxy)methyl)-1H,1'H-[3,3'-bipyrazol]-5-amine

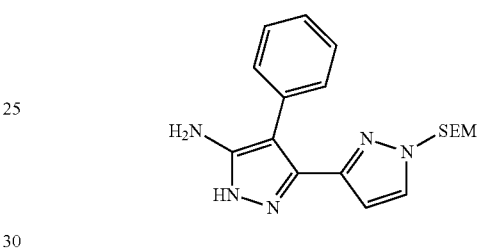

The mixture of Intermediate 3 (200 mg, 0.6 mmol) and hydrazine hydrate (59 mg, 1.2 mmol) in EtOH/AcOH (5/1, 10 mL/2 mL) was refluxed for 2 h. Then the mixture was cooled to r.t. and evaporated. The residue was dissolved in EA (20 mL) and neutralized with 10% NaHCO₃. The organic phase was separated and the water phase was extracted with EA (10 mL*3). The combined organic phase was washed with brine, dried over anhydrous Na₂SO₄, and concentrated in vacuo to afford the intermediate 4 as a yellow solid (200 mg, 96% yield) which was used to the next step without purification. LC-MS: m/z 356.1 (M+H)⁺.

Step D: 5-methyl-3-phenyl-6-(quinolin-6-yl)-2-(1-((2-(trimethylsilyl)ethoxy)methyl)-1H-pyrazol-3-yl)pyrazolo[1,5-a]pyrimidin-7(4H)-one

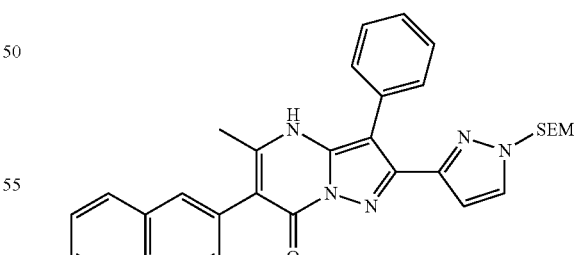

The mixture of Intermediate 4 (200 mg, 0.56 mmol) and methyl 3-oxo-2-(quinolin-6-yl)butanoate 8 (205 mg, 0.85 mmol) in AcOH (8 mL) was stirred at 100° C. for 1 h. Then the mixture was cooled to r.t. and evaporated. The residue was dissolved in EA (15 mL) and neutralized with 10%/o NaHCO₃. The organic phase was separated and the water phase was extracted with EA (15 mL*3). The combined organic phase was washed with brine, dried over anhydrous Na₂SO₄, and concentrated in vacuo to afford the intermediate 5 as a yellow solid (200 mg, 65% yield) which was used to the next step without purification. LC-MS: m/z 549.2 (M+H)⁺.

Step E: 5-methyl-3-phenyl-2-(1H-pyrazol-3-yl)-6-(quinolin-6-yl)pyrazolo[1,5-a]pyrimidin-7(4H)-one

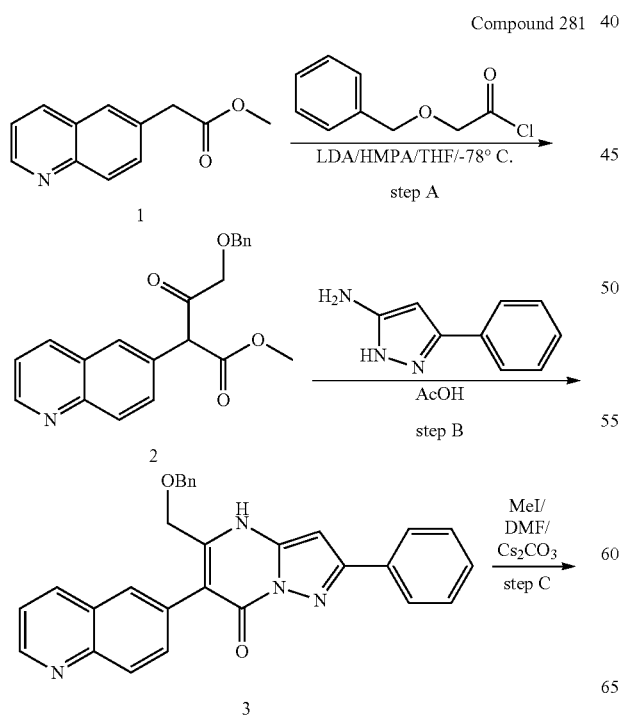

To a solution of Intermediate 5 (200 mg, 0.4 mmol) in DCM (10 mL) was added trifluoroacetic acid (0.5 mL). The mixture was stirred at r.t. overnight. The mixture was concentrated in vacuo and then dissolved in DCM (10 mL), washed with 10% NaHCO₃ and brined, dried over anhydrous Na₂SO₄, and concentrated in vacuo to afford the desired product 6.

¹H NMR (DMSO-d₆) δ: 12.84 (br. s., 1H), 8.91 (d, J=2.6 Hz, 1H), 8.37 (d, J=8.0 Hz, 1H), 8.17 (br. s., 1H), 8.05 (d, J=8.6 Hz, 1H), 7.94 (s, 1H), 7.75 (d, J=8.6 Hz, 1H), 7.40-7.63 (m, 6H), 7.36 (d, J=7.2 Hz, 1H), 6.18 (br. s., 1H), 2.22 (s, 3H). LC-MS: m/z 419.0 (M+H)⁺.

Compound 281

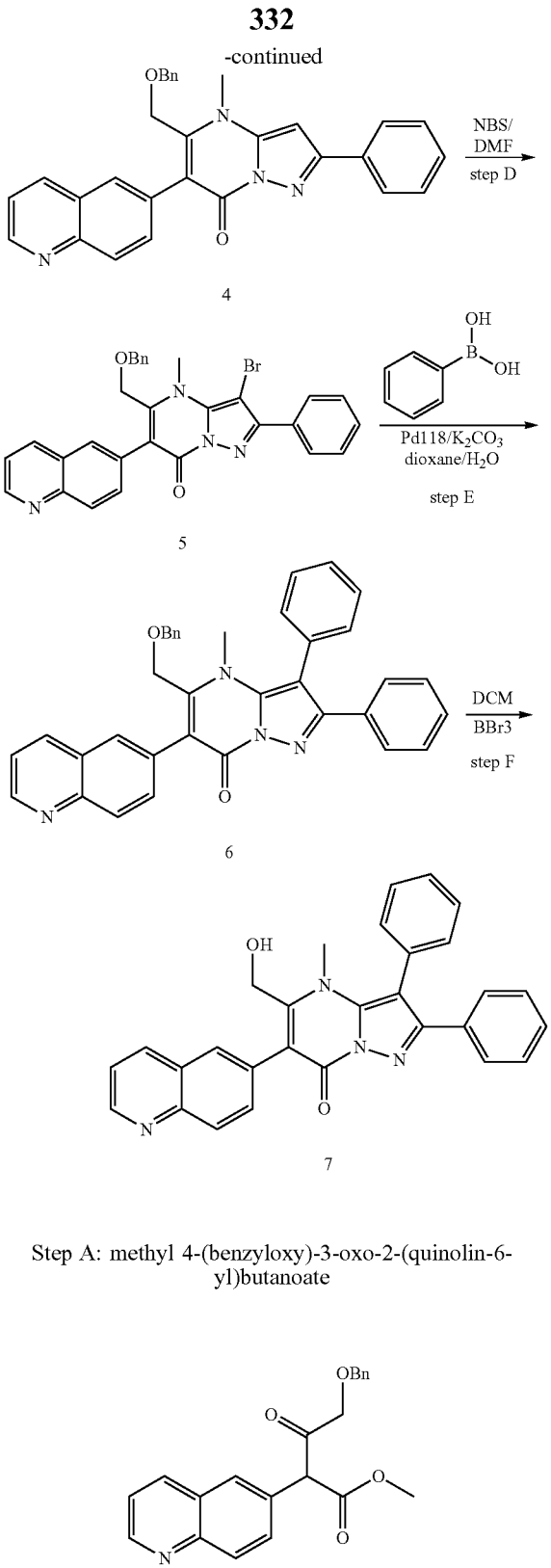

Step A: methyl 4-(benzyloxy)-3-oxo-2-(quinolin-6-yl)butanoate

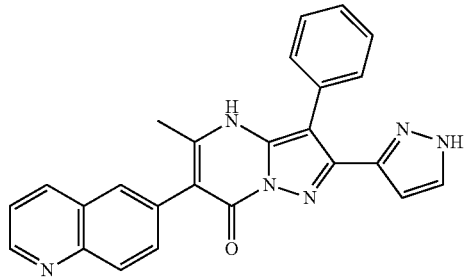 [SMILES: Cc1[nH]c2c(-c3ccccc3)c(-c3cc[nH]n3)nn2c(=O)c1-c1ccc2ncccc2c1]

To a mixture of methyl 2-(quinolin-6-yl)acetate (40.2 g, 0.2 mol) and HMPA (7.2 g, 0.02 mol) in THF was added LDA (2M in THF; 100 mL, 0.2 mol) over 20 min at −78° C. The mixture was stirring for 1 hour at −78° C., 2-(benzyloxy)acetyl chloride (36.8 g, 0.2 mol) was added dropwise with a funnel. The mixture was warmed up to room temperature overnight. Saturated NH₄Cl aqueous solution was added. The resultant mixture was extracted with DCM (3*50 mL). The combined organic layers were washed with saturated NaCl (50 mL), dried over Na₂SO₄, filtered, and concentrated in vacuo. The residue was purified by silica gel column (PE/EtOAc=20/1) to give the title compound (38 g, 58%) as a brown oil.

Step B: methyl 4-(benzyloxy)-3-oxo-2-(quinolin-6-yl)butanoate


Methyl 4-(benzyloxy)-3-oxo-2-(quinolin-6-yl)butanoate (1.2 g, 3.4 mmol) and 3,4-diphenyl-1H-pyrazol-5-amine (545 mg, 3.4 mmol) were dissolved in AcOH (10 mL). The mixture was warmed up to 95° C. for 4 h. After cooling to room temperature, the solids were collected by filtration, wash with EtOAc, and dried under vacuum to give methyl 4-(benzyloxy)-3-oxo-2-(quinolin-6-yl)butanoate (1.05 g, 67% yield) as a white solid. LC-MS: m/z 459.1 (M+H)⁺.

Step C: 5-(benzyloxymethyl)-4-methyl-2-phenyl-6-(quinolin-6-yl)pyrazolo[1,5-a]pyrimidin-7(4H)-one

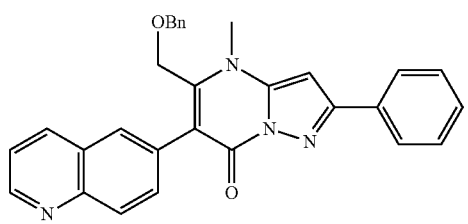 [SMILES: Cn1c(COCc2ccccc2)c(-c2ccc3ncccc3c2)c(=O)n2nc(-c3ccccc3)cc12]

To a mixture of methyl 4-(benzyloxy)-3-oxo-2-(quinolin-6-yl)butanoate (900 mg, 1.97 mmol) and Cs₂CO₃ (1.38 g, 4.25 mmol) in DMF (10 mL) was added MeI (416 mg, 2.95 mmol). The mixture was then stirred at rt overnight. The mixture was poured into water (100 mL) and filtered. The filter cake was washed with MeOH to give 5-(benzyloxymethyl)-4-methyl-2-phenyl-6-(quinolin-6-yl)pyrazolo[1,5-a]pyrimidin-7(4H)-one (900 mg) as a white solid. LC-MS: m/z 473.0 (M+H)⁺.

Step D: 5-(benzyloxymethyl)-3-bromo-4-methyl-2-phenyl-6-(quinolin-6-yl)pyrazolo[1,5-a]pyrimidin-7(4H)-one

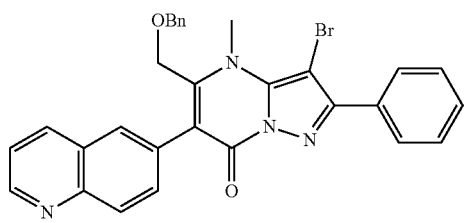 [SMILES: Cn1c(COCc2ccccc2)c(-c2ccc3ncccc3c2)c(=O)n2nc(-c3ccccc3)c(Br)c12]

To a solution of 5-(benzyloxymethyl)-4-methyl-2-phenyl-6-(quinolin-6-yl)pyrazolo[1,5-a]pyrimidin-7(4H)-one (900 mg, 1.9 mmol) in DMF (10 mL) was added NBS (374 mg, 2.1 mmol). The reaction mixture was then stirred at room temperature for 2 h. The mixture was poured into water (50 mL) and filtered to give 5-(benzyloxymethyl)-3-bromo-4-methyl-2-phenyl-6-(quinolin-6-yl)pyrazolo[1,5-a]pyrimidin-7(4H)-one (900 mg, yield 86%) as a white solid. LC-MS: m/z 551.0 (M+H)⁺.

Step E: 5-(benzyloxymethyl)-4-methyl-2,3-diphenyl-6-(quinolin-6-yl)pyrazolo[1,5-a]pyrimidin-7(4H)-one

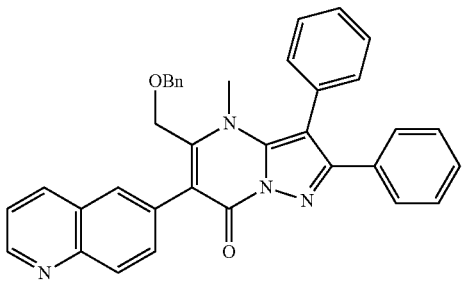

A mixture of 5-(benzyloxymethyl)-3-bromo-4-methyl-2-phenyl-6-(quinolin-6-yl)pyrazolo[1,5-a]pyrimidin-7(4H)-one (800 mg, 1.45 mmol), phenylboronic acid (230 mg, 1.89 mmol), Pd₁₁₈ (188 mg, 0.29 mmol) and K₂CO₃ (496 mg, 3.64 mmol) in 1.4-dioxane (6 mL) and H₂O (0.5 mL) was stirred at 100° C. for 12 h under N₂ atmosphere. The reaction mixture was then cooled to r.t. and filtered. The filtrate was concentrated in vacuo and purified by flash column chromatography silica gel to obtain 5-(benzyloxymethyl)-4-methyl-2,3-diphenyl-6-(quinolin-6-yl)pyrazolo[1,5-a]pyrimidin-7(4H)-one (700 mg, 88% yield). LC-MS: m/z 549.0 (M+H)⁺.

Step F: Compound 281: 5-(hydroxymethyl)-4-methyl-2,3-diphenyl-6-(quinolin-6-yl)pyrazolo[1,5-a]pyrimidin-7(4H)-one

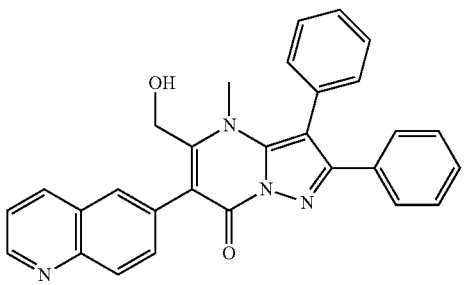 [SMILES: Cn1c(CO)c(-c2ccc3ncccc3c2)c(=O)n2nc(-c3ccccc3)c(-c3ccccc3)c12]

To a solution of 5-(benzyloxymethyl)-4-methyl-2,3-diphenyl-6-(quinolin-6-yl)pyrazolo[1,5-a]pyrimidin-7(4H)-one (700 mg, 1.28 mmol) in dry DCM (5 mL) was added dropwise BBr₃ (1M in DCM, 2.56 mL, 2.56 mmol) at 0° C. After addition, the mixture was stirred at rt for 2 h. The mixture was quenched by careful adding of ice-water and extracted with EA. The combined organic phase was washed with water and brine, dried over anhydrous Na₂SO₄, filtered, and concentrated under reduced pressure to give the title compound.

¹H NMR (400 MHz, DMSO-d₆) δ: 8.97 (br. s., 1H), 8.42 (d, J=7.79 Hz, 1H), 8.10 (d, J=8.87 Hz, 1H), 7.99 (d, J=1.88 Hz, 1H), 7.76 (dd, J=8.60, 1.88 Hz, 1H), 7.60 (dd, J=8.33, 4.03 Hz, 1H), 7.48 (s, 5H), 7.36-7.42 (m, 2H), 7.25-7.33 (m, 3H), 4.37 (br. s., 2H), 3.49 (s, 3H). LC-MS: m/z 459.0 (M+H)⁺

Compound 282

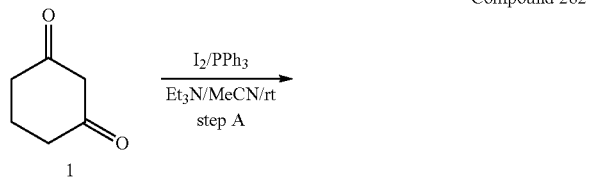

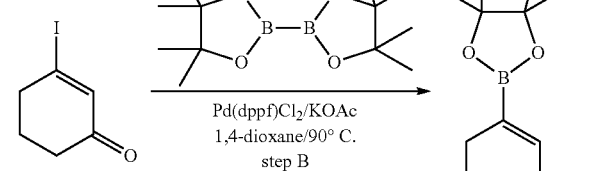

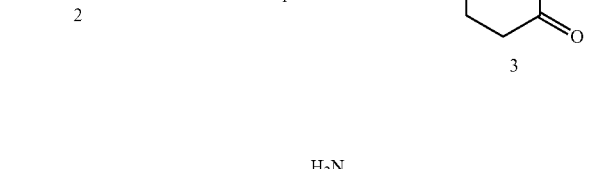

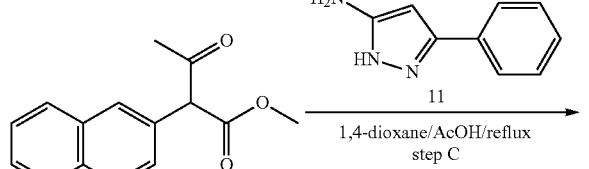

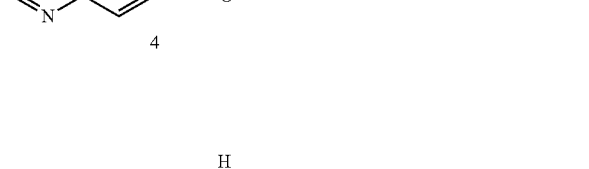

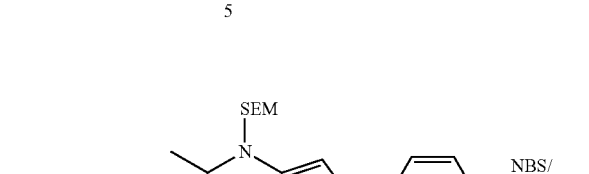

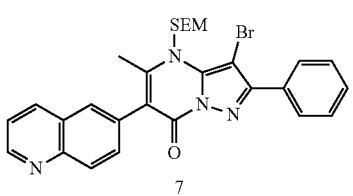

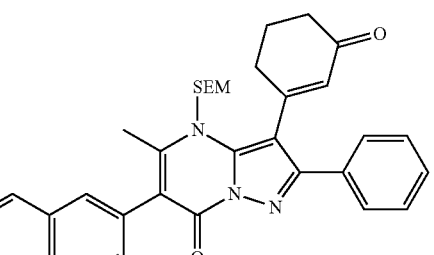

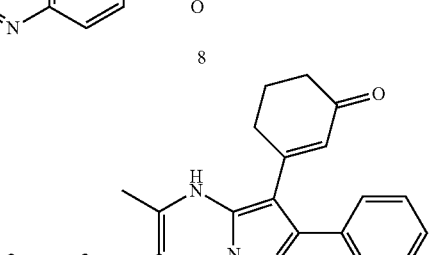

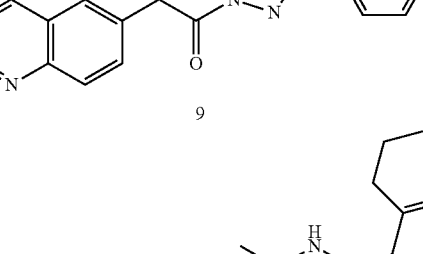

Step A: 3-iodocyclohex-2-enone

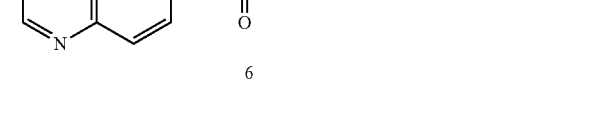

A mixture of PPh₃ (25 g, 96.5 mmol) and 12 (24 g, 94.8 mmol) in acetonitrile (400 mL) was stirred at r.t. for 2 h, then Et₃N (14.4 mL, 98.3 mmol) and cyclohexane-1,3-dione (10.0 g, 86.2 mmol) were added. The mixture was stirred at r.t. overnight. The mixture was concentrated in vacuo, and the residue was purified by chromatography to afford the title compound 2 as a yellow solid (4.0 g, 21% yield). LC-MS: m/z 222.9 (M+H)⁺.

Step B: 3-(4,4,5,5-tetramethyl-1,3,2-dioxaborolan-2-yl)cyclohex-2-enone

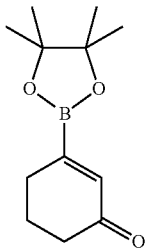 [SMILES: CC1(C)OB(C2=CC(=O)CCC2)OC1(C)C]

A suspension of Intermediate 2 (2.0 g, 9 mmol), 4,4,4',4',5,5,5',5'-octamethyl-2,2'-bi(1,3,2-dioxaborolane) (4.6 g, 18 mmol), KOAc (2.7 g, 27 mmol) and Pd(dppf)Cl₂ (0.6 g, 0.9 mmol) in 1,4-dioxane (50 mL) was stirred at 90° C. overnight. The mixture was filtered through celite and the filtrate was concentrated in vacuo. The residue was purified by flash chromatography to afford the title compound 3 as a yellow solid (1.0 g, 50% yield). LC-MS: m/z 223.1 (M+H)⁺.

Step C: 5-methyl-2-phenyl-6-(quinolin-6-yl)pyrazolo[1,5-a]pyrimidin-7(4H)-one

A suspension of methyl 3-oxo-2-(quinolin-6-yl)butanoate (2.0 g, 8.2 mmol) and 3-phenyl-1H-pyrazol-5-amine (1.0 g, 6.3 mmol) in 1,4-dioxane (10 mL) and AcOH (2 mL) was refluxed for 16 hours under N₂ protection. The mixture was cooled to the room temperature, concentrated, and neutralized with saturated NaHCO₃ solution until pH=7. The precipitate was collected by filtration, washed with petroleum ether and dried to afford the title compound 5 as a white solid (600 mg, 27% yield).

¹H NMR (DMSO-d₆) δ: 12.56 (br. s., 1H), 8.94 (dd, J=4.25, 1.61 Hz, 1H), 8.39 (d, J=7.63 Hz, 1H), 7.99-8.10 (m, 3H), 7.96 (d, J=1.76 Hz, 1H), 7.75 (dd, J=8.66, 1.91 Hz, 1H), 7.57 (dd, J=8.36, 4.25 Hz, 1H), 7.46-7.53 (m, 2H), 7.40-7.46 (m, 1H), 6.67 (s, 1H), 2.26 (s, 3H). LC-MS: m/z 353.1 (M+H)⁺.

Step D: 5-methyl-2-phenyl-6-(quinolin-6-yl)-4-((2-(trimethylsilyl)ethoxy)methyl)pyrazolo[1,5-a]pyrimidin-7(4H)-one

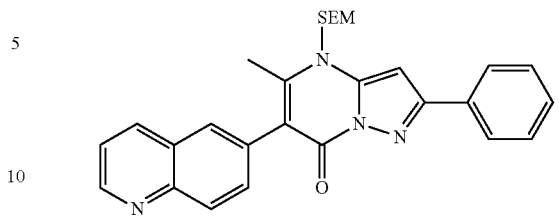

To a solution of Intermediate 5 (500 mg, 1.42 mmol) and K₂CO₃ (393 mg, 2.84 mmol) in DMF (15 ml) at ambient temperature was added (2-(chloromethoxy)ethyl)trimethylsilane (473 mg, 2.84 mmol) dropwise. The mixture was stirred for 10 min at ambient temperature and heated to 100° C. overnight. The mixture was cooled to the room temperature, washed with saturated sodium hydrogen carbonate solution, and extracted with DCM (2*30 mL). The combined organic layers were washed with brine (3*20 ml), dried over anhydrous sodium sulfate, and concentrated invacuo. The residue was purified by silica gel column, eluting with DCM/MeOH (30/1 to 10/1), to obtain the title compound 6 as a white solid (350 mg, 51% yield). LC-MS: m/z 483.1 (M+H)⁺.

Step E: 3-bromo-5-methyl-2-phenyl-6-(quinolin-6-yl)-4-((2-(trimethylsilyl)ethoxy)methyl)pyrazolo[1,5-a]pyrimidin-7(4H)-one

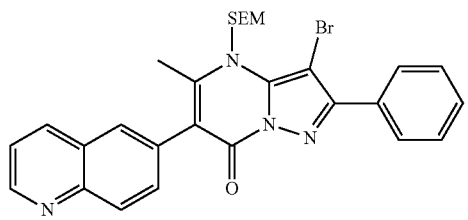 [SMILES: Cc1c(-c2ccc3ncccc3c2)c(=O)n2nc(-c3ccccc3)c(Br)c2n1COCC[Si](C)(C)C]

To a solution of Intermediate 6 (350 mg, 0.725 mmol) in DCM (5 ml) at ambient temperature was added N-Bromosuccinimide (163 mg, 0.92 mmol). The resultant mixture was stirred for 3 hours at ambient temperature, washed with water, and extracted with DCM (20 mL). The combined organic layers were washed with brine (20 ml), dried over anhydrous sodium sulfate, and concentrated in vacuo. The residue was purified by prep-TLC (DCM/MeOH=20/1) to obtain the title compound 7 as a yellow solid (250 mg, 61% yield). LC-MS: m/z 561.1 (M+H)⁺.

Step F: 5-methyl-3-(3-oxocyclohex-1-en-1-yl)-2-phenyl-6-(quinolin-6-yl)-4-((2-(trimethylsilyl)ethoxy)methyl)pyrazolo[1,5-a]pyrimidin-7(4H)-one

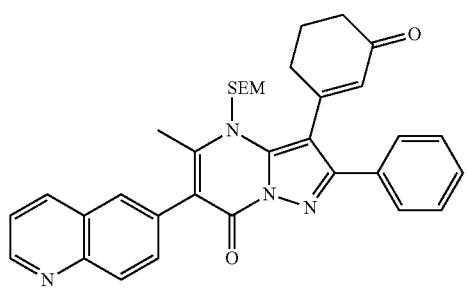 [SMILES: Cc1c(-c2ccc3ncccc3c2)c(=O)n2nc(-c3ccccc3)c(C3=CC(=O)CCC3)c2n1COCC[Si](C)(C)C]

A suspension of Intermediate 7 (600 mg, 1.1 mmol), 3-(4,4,5,5-tetramethyl-1,3,2-dioxaborolan-2-yl)cyclohex-2-enone (800 mg, 3.6 mmol), Pd(dppf)Cl$_2$ (80 mg, 0.1 mmol) and Cs$_2$CO$_3$ (1.4 g, 4.3 mmol) in 1,4-dioxane/H$_2$O (30 mL/5 mL) was refluxed for 4 h. The mixture was cooled to r.t. and filtered through celite, the filtrate was diluted with H$_2$O (10 mL) and extracted with EA (3*30 mL). The extracts was washed with brine, dried over anhydrous Na$_2$SO$_4$ and concentrated in vacuo. The residue was purified by flash chromatography (DCM/MeOH=20/1) to afford the title compound 8 as a yellow solid (300 mg, 49% yield). LC-MS: m/z 577.2 (M+H)$^+$.

Step G: 5-methyl-3-(3-oxocyclohex-1-en-1-yl)-2-phenyl-6-(quinolin-6-yl)pyrazolo[1,5-a]pyrimidin-7(4H)-one

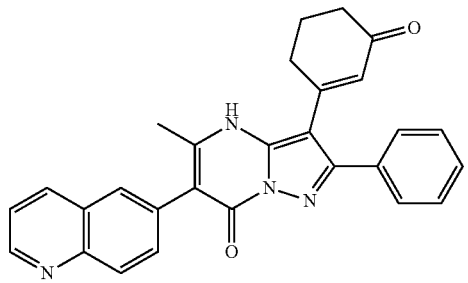 [SMILES: Cc1[nH]c2c(C3=CC(=O)CCC3)c(-c3ccccc3)nn2c(=O)c1-c1ccc2ncccc2c1]

To a solution of intermediate 8 (100 mg, 0.2 mmol) in DCM (10 mL) was added TFA (1 mL). The mixture was stirred at r.t. overnight. The mixture was concentrated in vacuo. The residue was dissolved in EA (10 mL) and neutralized with 10% NaHCO$_3$. The organic phase was separated and the water phase was extracted with EA (3*5 mL). The combined organic phase was washed with brine, dried over anhydrous Na$_2$SO$_4$ and concentrated in vacuo. The residue was purified by prep-TLC to get the title compound 9 as an orange solid (30 mg, 39% yield). LC-MS: m/z 447.1 (M+H)$^+$.

Step H: 3-(3-hydroxycyclohex-1-en-1-yl)-5-methyl-2-phenyl-6-(quinolin-6-yl)pyrazolo[1,5-a]pyrimidin-7(4H)-one

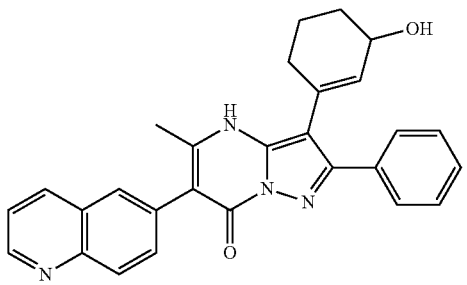 [SMILES: Cc1[nH]c2c(C3=CC(O)CCC3)c(-c3ccccc3)nn2c(=O)c1-c1ccc2ncccc2c1]

To a solution of intermediate 9 (30 mg, 0.07 mmol) and Cerium(III) chloride heptahydrate (43 mg, 0.1 mmol) in MeOH (3 mL) was added Sodium borohydride (5 mg, 0.1 mmol). The mixture was stirred at r.t. for 2 h and quenched with H$_2$O (0.5 mL). The mixture was evaporated. The residue was dissolved in EA (10 mL), washed with water and brine, dried over anhydrous Na$_2$SO$_4$ and concentrated in vacuo to get the title compound 10.

$^1$H NMR (METHANOL-d$_4$) δ: 8.83 (d, J=3.2 Hz, 1H), 8.39 (d, J=7.4 Hz, 1H), 8.07 (d, J=8.6 Hz, 1H), 7.95 (br. s., 1H), 7.81 (br. s., 3H), 7.55 (dd, J=8.2, 4.4 Hz, 1H), 7.35 (d, J=7.2 Hz, 1H), 7.38 (d, J=7.4 Hz, 2H), 5.97 (d, J=2.4 Hz, 1H), 4.32-4.38 (m, 1H), 2.29 (s, 3H), 2.05-2.15 (m, 2H), 1.92-1.98 (m, 1H), 1.80-1.89 (m, 1H), 1.62-1.75 (m, 2H). LC-MS: m/z 449.1 (M+H)$^+$.

Compound 283

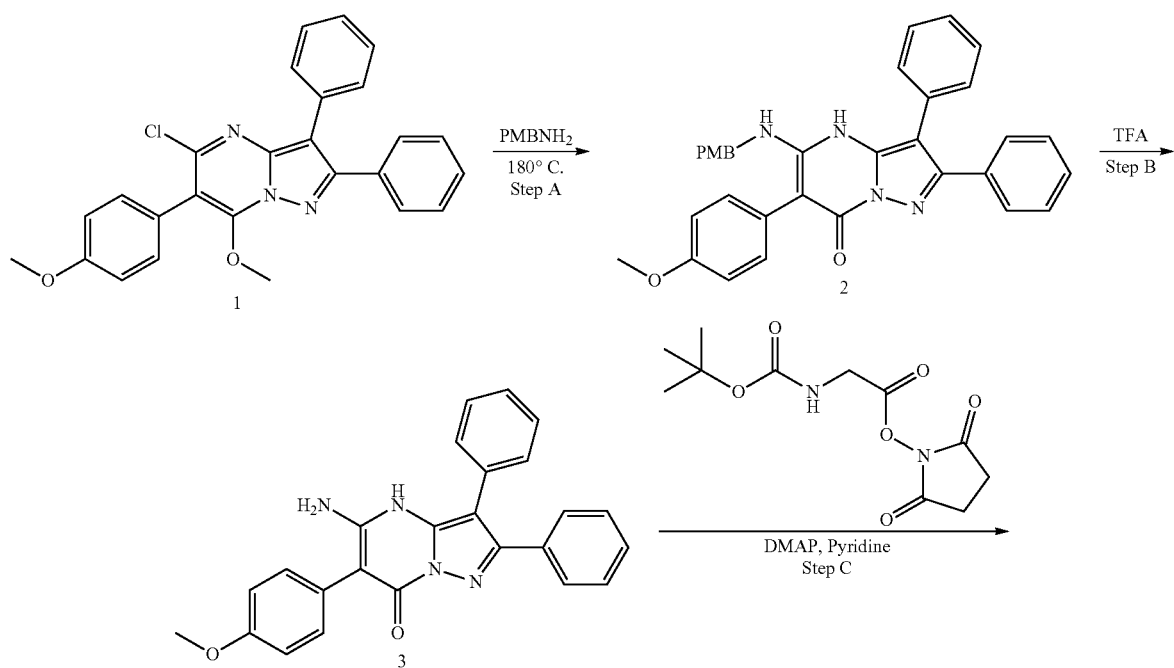

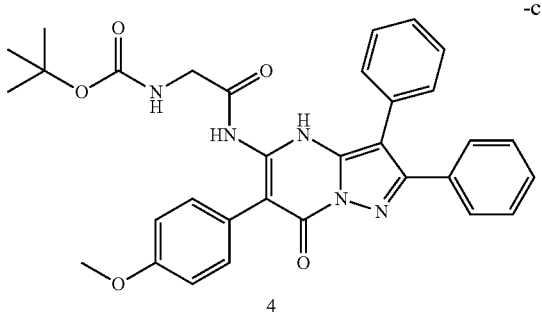

4

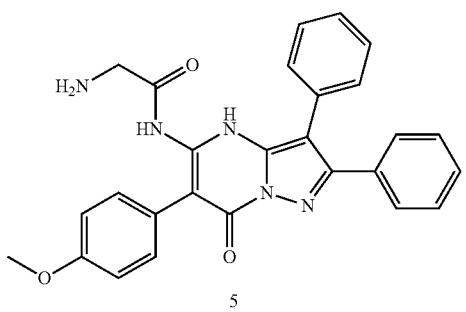

5

Step A: 5-((4-methoxybenzyl)amino)-6-(4-methoxyphenyl)-2,3-diphenylpyrazolo[1,5-a] pyrimidin-7(4H)-one

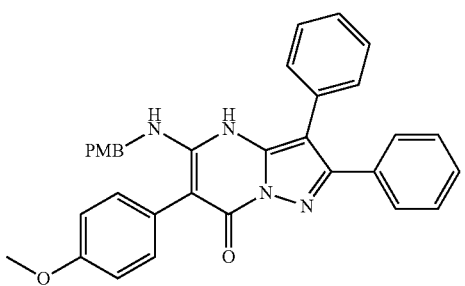

A mixture of 5-chloro-7-methoxy-6-(4-methoxyphenyl)-2,3-diphenylpyrazolo[1,5-a] pyrimidine (Synthesized in Scheme of Compound 101, 300 mg, 0.7 mmol) and (4-methoxyphenyl)methanamine (3 mL) was stirred at 180° C. for 40 mins in a microwave reactor. The mixture was cooled and directly purified by reverse phase column (MeOH/H$_2$O=0~50% 30 mins, 50%~50% 30 mins, 50%~100% 30 mins) to get crude product (600 mg) which was directly used to the next step without further purification. LC-MS: m/z 529.2 (M+H)$^+$.

Step B: 5-amino-6-(4-methoxyphenyl)-2,3-diphenylpyrazolo[1,5-a]pyrimidin-7(4H)-one

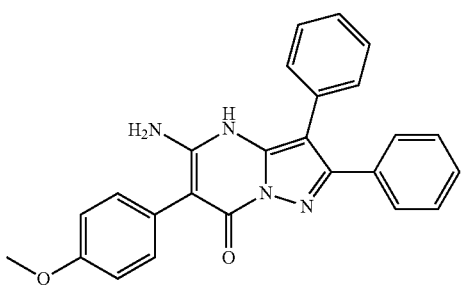

The solution of 5-((4-methoxybenzyl)amino)-6-(4-methoxyphenyl)-2,3-diphenylpyrazolo 1,5-a]pyrimidin-7(4H)-one (600 mg, 1.07 mmol) in DCM (5 mL) and TFA (5 mL) was stirred at 60° C. for 2 h. The mixture was concentrated, basified with aq.Na$_2$CO$_3$ solution to pH=8, and extracted with DCM (10 mL*3). The organic layer was dried over anhydrous sodium sulfate and concentrated in vacuo to dryness. The residue was purified by reverse phase column (MeOH/H$_2$O=0~100% 50 mins) to afford the desired product 5-amino-6-(4-methoxyphenyl)-2,3-diphenylpyrazolo[1,5-a]pyrimidin-7(4H)-one (480 mg, 80% purity) as a brown solid. LC-MS: m/z 409.2 (M+H)$^+$.

Step C: tert-butyl (2-((6-(4-methoxyphenyl)-7-oxo-2,3-diphenyl-4,7-dihydropyrazolo[1,5-a]pyrimidin-5-yl)amino)-2-oxoethyl)carbamate

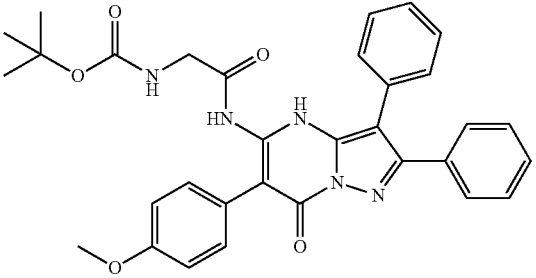 [SMILES: COc1ccc(-c2c(NC(=O)CNC(=O)OC(C)(C)C)[nH]c3c(-c4ccccc4)c(-c4ccccc4)nn3c2=O)cc1]

To a solution of 5-amino-6-(4-methoxyphenyl)-2,3-diphenylpyrazolo[1,5-a]pyrimidin-7(4H)-one (100 mg, 0.245 mmol) in pyridine (3 mL) was added 2,5-dioxopyrrolidin-1-yl 2-((tert-butoxycarbonyl)amino)acetate (333 mg, 1.22 mmol) and DMAP (cat.). The mixture was stirred at 120° C. for 45 mins through microwave irradiation. The mixture was concentrated in vacuo to dryness. The residue was separated between HCl (1M, 10 mL) and DCM (30 mL). The organic layer was dried over anhydrous sodium sulfate and concentrated in vacuo to dryness. The residue was purified by Prep-TLC (DCM/MeOH=50/1) to afford the desired product tert-butyl (2-((6-(4-methoxyphenyl)-7-oxo-2,3-diphenyl-4,7-dihydropyrazolo[1,5-a]pyrimidin-5-yl)amino)-2-oxoethyl)carbamate (20 mg, 14.5% yield) as a white solid. LC-MS: m/z 565.2 (M+H)$^+$.

Step D: Compound 283: 2-amino-N-(6-(4-methoxyphenyl)-7-oxo-2,3-diphenyl-4,7-dihydropyrazolo[1,5-a]pyrimidin-5-yl)acetamide

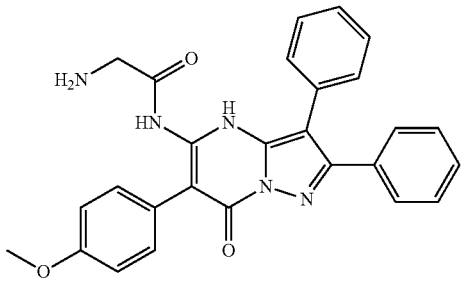 [SMILES: COc1ccc(-c2c(NC(=O)CN)[nH]c3c(-c4ccccc4)c(-c4ccccc4)nn3c2=O)cc1]

The solution of tert-butyl (2-((6-(4-methoxyphenyl)-7-oxo-2,3-diphenyl-4,7-dihydropyrazolo [1,5-a]pyrimidin-5-yl)amino)-2-oxoethyl)carbamate (20 mg, 0.035 mmol) in 4M HCl in 1.4-dioxane was stirred r.t. for 2 h. The mixture was concentrated to obtain 2-amino-N-(6-(4-methoxyphenyl)-7-oxo-2,3-diphenyl-4,7-dihydropyrazolo[1,5-a]pyrimidin-5-yl)acetamide.

$^1$H NMR (DMSO-$d_6$) δ: 7.61-7.42 (m, 5H), 7.42-7.25 (m, 9H), 7.00 (d, J=8.3 Hz, 2H), 3.82 (s, 3H), 3.62-3.59 (m, 2H). LC-MS: m/z 466.0 (M+H)$^+$.

Compound 285

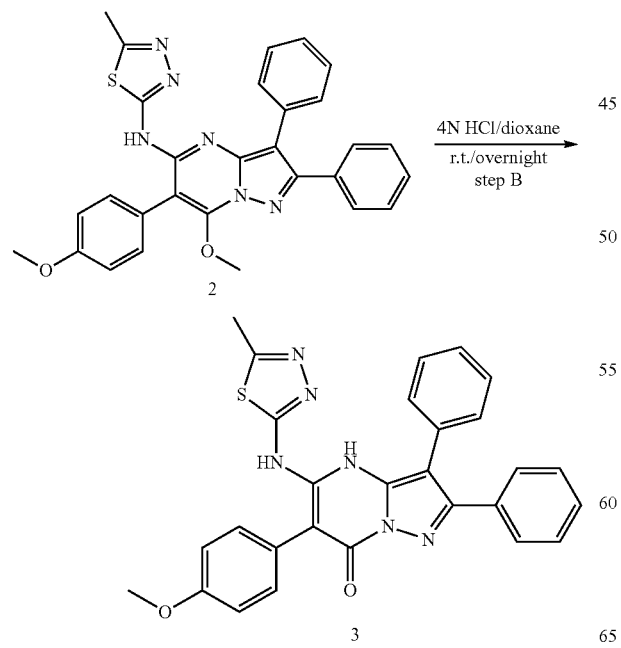

Step A: N-(7-methoxy-6-(4-methoxyphenyl)-2,3-diphenylpyrazolo[1,5-a]pyrimidin-5-yl)-5-methyl-1,3,4-thiadiazol-2-amine

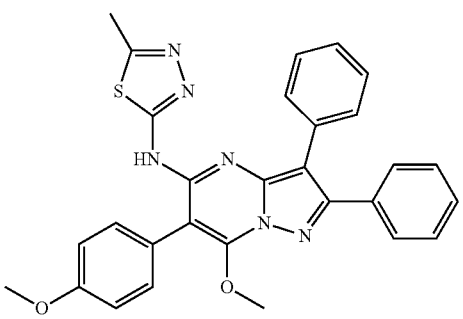 [SMILES: COc1ccc(-c2c(Nc3nnc(C)s3)nc3c(-c4ccccc4)c(-c4ccccc4)nn3c2OC)cc1]

A mixture of Intermediate 1 (Synthesized in Scheme of Compound 101, 200 mg, 0.45 mmol), 5-methyl-1,3,4-thiadiazol-2-amine (102 mg, 0.9 mmol, 2 eq.), Pd(OAc)$_2$ (10 mg, 0.045 mmol, 0.1 eq.), Xantphos (52 mg, 0.09 mmol, 0.2 eq.) and Cs$_2$CO$_3$ (293 mg, 0.9 mmol, 2 eq.) in 1.4-dioxane (3 mL) was heated at 100° C. for 3 h under N$_2$ atmosphere. The mixture was filtered through celite and the filtrate was concentrated in vacuo. The residue was purified by flash chromatography to afford the Intermediate 2 as a yellow solid (200 mg, 85° % yield). LC-MS: m/z 520.7 (M+H)$^+$.

Step B: Compound 285: 6-(4-methoxyphenyl)-5-((5-methyl-1,3,4-thiadiazol-2-yl)amino)-2,3-diphenylpyrazolo[1,5-a]pyrimidin-7(4H)-one

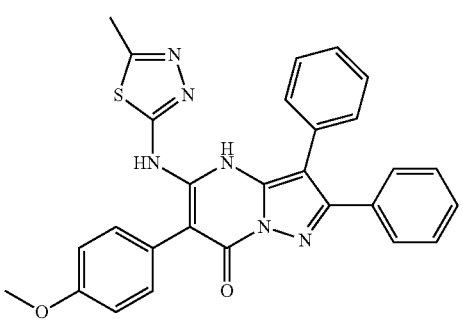 [SMILES: COc1ccc(-c2c(Nc3nnc(C)s3)[nH]c3c(-c4ccccc4)c(-c4ccccc4)nn3c2=O)cc1]

The solution of N-(7-methoxy-6-(4-methoxyphenyl)-2,3-diphenylpyrazolo[1,5-a]pyrimidin-5-yl)-5-methyl-1,3,4-thiadiazol-2-amine (180 mg, 0.346 mmol) in 4M HCl in 1.4-dioxane (10 mL) was stirred at r.t. for 10 h to afford the title compound 3.

$^1$H NMR (DMSO-$d_6$) δ: 7.53 (br. s., 3H), 7.49-7.37 (m, 7H), 7.32 (d, J=8.3 Hz, 3H), 7.06 (d, J=8.3 Hz, 2H), 3.83 (s, 3H), 2.55 (br. s., 3H). LC-MS: m/z 507.2 (M+H)$^+$.

Compound 286

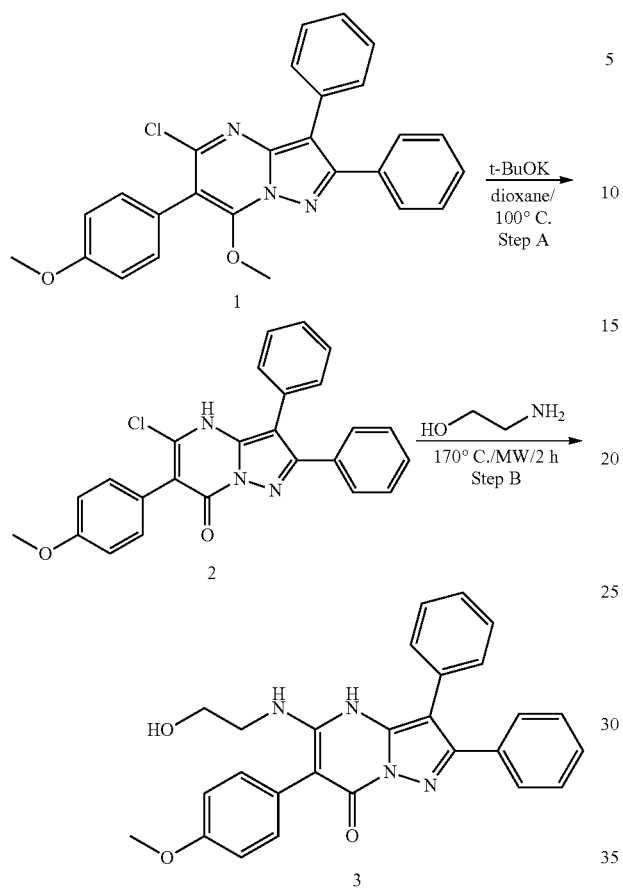

Step A: 5-chloro-6-(4-methoxyphenyl)-2,3-diphenylpyrazolo[1,5-a]pyrimidin-7(4H)-one A mixture of 5-chloro-7-methoxy-6-(4-methoxyphenyl)-2,3-diphenylpyrazolo[1,5-a]pyrimidine (Synthesized in Scheme of Compound 101, 200 mg, 0.45 mmol), potassium t-butoxide (50 mg, 0.45 mmol) in dioxane was stirred at 100° C. for 2 h. The mixture was concentrated to give the crude product (200 mg) which was used to the next step without further purification. LC-MS: m/z 428.1 (M+H)⁺.

Step B: Compound 286: 5-((2-hydroxyethyl)amino)-6-(4-methoxyphenyl)-2,3-diphenylpyrazolo[1,5-a]pyrimidin-7(4H)-one

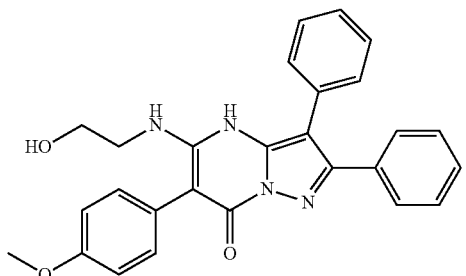

The mixture of 5-chloro-6-(4-methoxyphenyl)-2,3-diphenylpyrazolo [1,5-a]pyrimidin-7(4H)-one (100 mg, 0.23 mmol) and 2-aminoethanol (3 mL) was stirred at 170° C. for 4 h under microwave irradiation in a sealed tube to get 5-((2-hydroxyethyl)amino)-6-(4-methoxyphenyl)-2,3-diphenylpyrazolo[1,5-a]pyrimidin-7(4H)-one.

¹H NMR (DMSO-d₆) δ: 7.28 (br. s., 5H), 7.22 (d, J=7.25 Hz, 5H), 7.06-7.17 (m, 3H), 6.96 (d, J=7.79 Hz, 2H), 3.81 (s, 3H), 3.66 (br. s., 2H), 3.43 (br. s., 2H). LC-MS: m/z 453.2 (M+H)⁺.

Compound 287

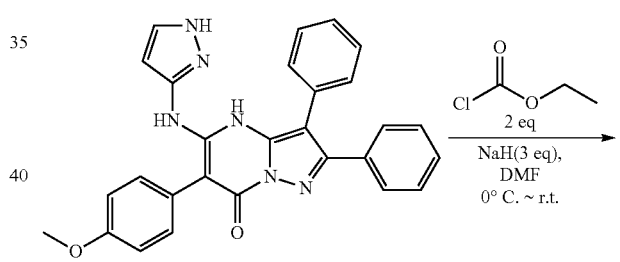

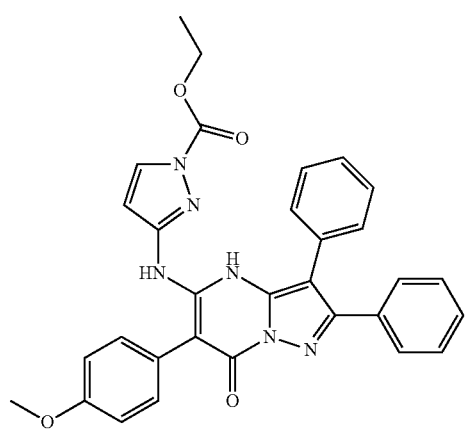

Step A: ethyl 3-((6-(4-methoxyphenyl)-7-oxo-2,3-diphenyl-4,7-dihydropyrazolo[1,5-a]pyrimidin-5-yl)amino)-1H-pyrazole-1-carboxylate

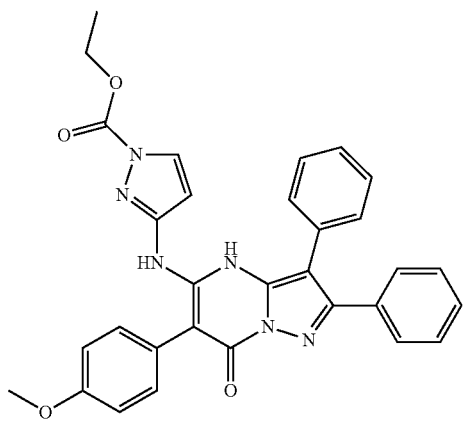 [SMILES: CCOC(=O)n1ccc(Nc2[nH]c3c(-c4ccccc4)c(-c4ccccc4)nn3c(=O)c2-c2ccc(OC)cc2)n1]

To a solution of 5-((1H-pyrazol-3-yl)amino)-6-(4-methoxyphenyl)-2,3-diphenylpyrazolo[1,5-a]pyrimidin-7(4H)-one (Compound 182, 50 mg, 0.1 mmol) in DMF (5 mL) was added sodium hydride (13 mg, 60% dispersion in mineral oil, 0.3 mmol) at 0° C. Ethyl chloroformate (24 mg, 0.2 mmol) was added dropwise after the mixture was stirred at 0° C. for 30 min. Then the mixture was stirred at r.t. overnight. The mixture was poured into water (10 mL) and extracted with DCM (3*5 mL), the combined organic phase was washed with brine, dried over anhydrous $Na_2SO_4$, and concentrated in vacuo to afford the desired product.

$^1$H NMR (DMSO-$d_6$ & TFA-d) δ: 8.22 (d, J=3.0 Hz, 1H), 7.43-7.50 (m, 4H), 7.34-7.41 (m, 6H), 7.31 (d, J=8.6 Hz, 2H), 7.05 (d, J=8.8 Hz, 2H), 6.36-6.45 (m, 1H), 4.35 (q, J=7.0 Hz, 2H), 1.26 (t, J=7.0 Hz, 3H). LC-MS: m/z 547.1 (M+H)$^+$.

Compound 288

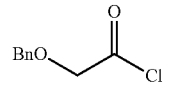
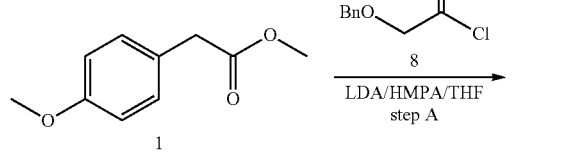

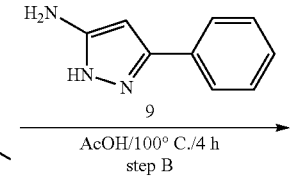
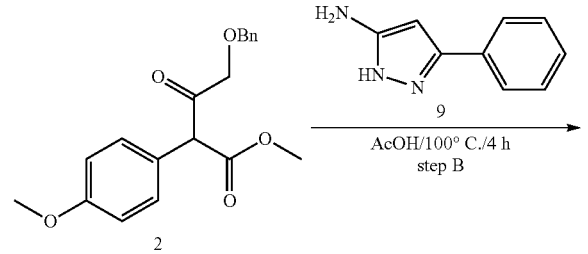

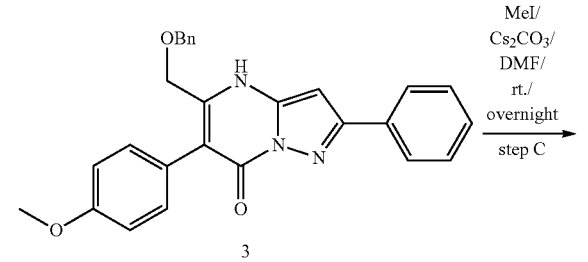

-continued

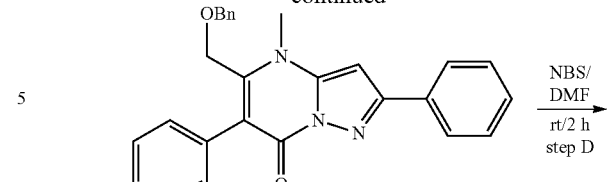

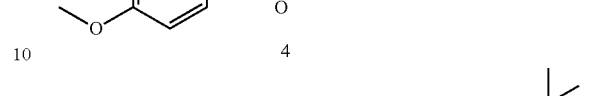

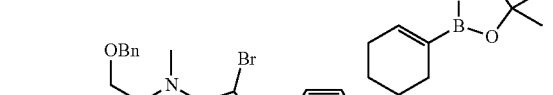

Step E: 5-((benzyloxy)methyl)-3-(cyclohex-1-en-1-yl)-6-(4-methoxyphenyl)-4-methyl-2-phenylpyrazolo[1,5-a]pyrimidin-7(4H)-one

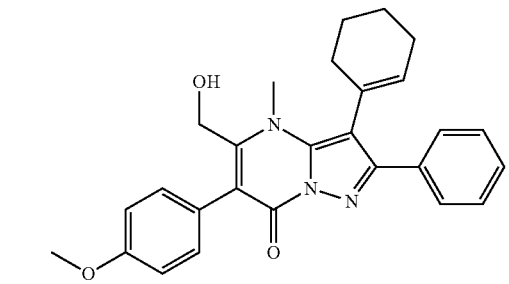

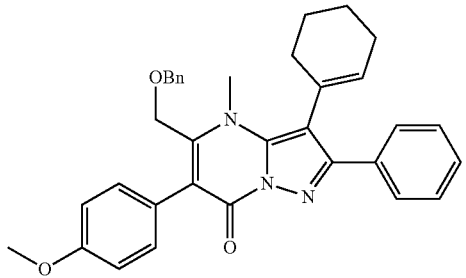 [SMILES: COc1ccc(-c2c(COCc3ccccc3)n(C)c3c(C4=CCCCC4)c(-c4ccccc4)nn3c2=O)cc1]

A suspension of Intermediate 5 (200 mg, 0.4 mmol, synthesized in scheme of Compound 249), 2-(cyclohex-1- en-1-yl)-4,4,5,5-tetramethyl-1,3,2-dioxaborolane (94 mg, 0.5 mmol, 1.2 eq), Pd$_{118}$ (48 mg, 0.07 mmol, 0.2 eq) and K$_2$CO$_3$ (103 mg, 0.7 mmol, 2.0 eq) in 1.4-dioxane (5 ml) and H$_2$O (0.3 ml) was stirred at 90° C. for 4 h under N$_2$ atmosphere. The reaction mixture was then cooled to r.t. and filtered. The filtrate was concentrated in vacuo and purified by flash column chromatography silica gel (PE/EA 2:1-1:2) to obtain Intermediate 6 (39 mg, 20% yield). LC-MS: m/z 532.0 (M+H)$^+$ Step F: 3-(cyclohex-1-en-1-yl)-5-(hydroxymethyl)-6-(4-methoxyphenyl)-4-methyl-2-phenylpyrazolo[1,5-a]pyrimidin-7(4H)-one

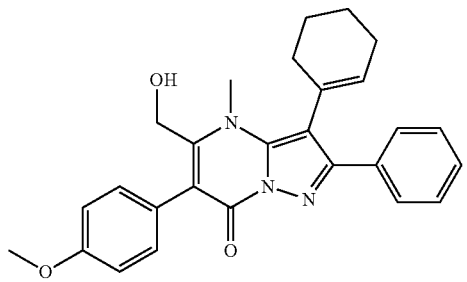 [SMILES: COc1ccc(-c2c(CO)n(C)c3c(C4=CCCCC4)c(-c4ccccc4)nn3c2=O)cc1]

To a solution of Intermediate 6 (29 mg, 0.05 mmol) in dry DCM (3 mL) was added dropwise BCl$_3$ (1 mol/L in DCM, 0.5 mL) at 0° C. After addition, the mixture was stirred at r.t. for 3 h. The mixture was quenched by ice-water (3 mL) and extracted with DCM (3*5 mL). The combined organic phase was washed with water and brine, dried over anhydrous Na$_2$SO$_4$, filtered and concentrated in vacuo to give the title compound 7.

$^1$H NMR (DMSO-d$_6$) δ: 7.82 (d, J=7.0 Hz, 2H), 7.39-7.50 (m, 3H), 7.25 (d, J=8.4 Hz, 2H), 7.00 (d, J=8.8 Hz, 2H), 5.92 (br. s., 1H), 5.69 (t, J=4.8 Hz, 1H), 4.36 (d, J=4.6 Hz, 2H), 3.90 (s, 3H), 3.81 (s, 3H), 2.20 (br. s., 2H), 2.12 (br. s., 2H), 1.66 (br. s., 4H). LC-MS: m/z 442.2 (M+H)$^+$.

Compound 290

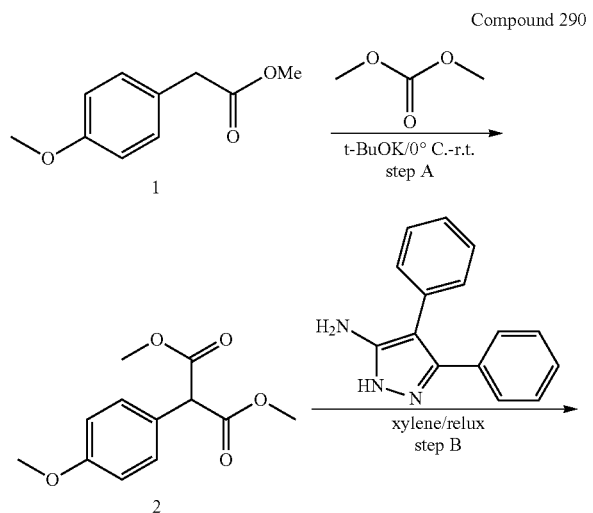

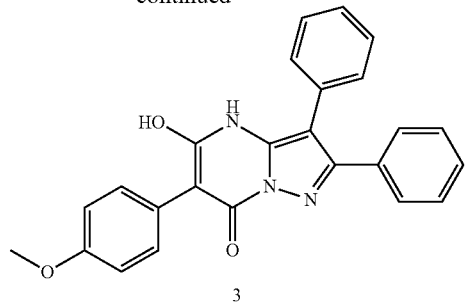

3

Step A: Dimethyl 2-(4-methoxyphenyl)malonate

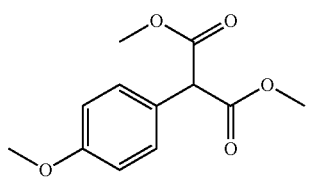

To a solution of t-BuOK (7.4 g, 0.066 mol) in dimethyl carbonate (60 mL) was added dropwise methyl 2-(4-methoxyphenyl)acetate (6 g, 0.033 mol) at 0° C. After addition, the mixture was allowed to warm to room temperature and stirred for 0.5 h. The mixture was then heated to 80° C. overnight. The suspension was diluted with EtOAc (200 mL), washed with water and brine, dried over anhydrous Na$_2$SO$_4$, filtered, and concentrated under reduced pressure. The residue was purified by column chromatography on silica gel (eluent: EtOAc/PE=1/10) to afford the desired product (5.7 g, 0.024 mol, yield 72.7%).

$^1$H NMR (CDCl$_3$) δ: 7.33 (d, J=8.6 Hz, 2H), 6.92 (d, J=8.9 Hz, 2H), 4.62 (s, 1H), 3.82 (s, 3H), 3.77 (s, 6H).

Step B: 5-hydroxy-6-(4-methoxyphenyl)-2,3-diphenylpyrazolo[1,5-a]pyrimidin-7(4H)-one

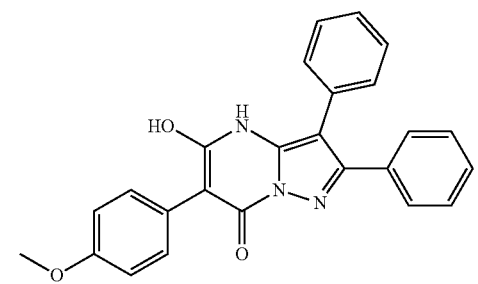

The mixture of 3, 4-diphenyl-1H-pyrazol-5-amine (5.64 g, 0.024 mol) and dimethyl-2-(4-methoxyphenyl)-malonate 2 (5.7 g, 0.024 mol) in xylene (350 mL) was refluxed for 18 h to afford the title compound.

$^1$H NMR (DMSO-d$_6$) δ: 11.57 (br. s, 1H), 7.26-7.49 (m, 12H), 6.90-6.99 (m, 2H), 3.78 (s, 3H). LC-MS: m/z 410.2 (M+H)$^+$.

Compound 291

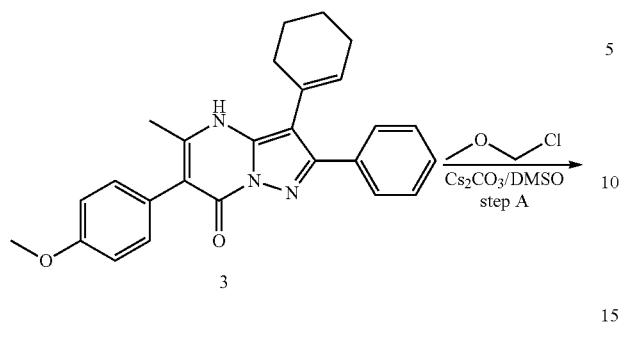

Step A: Compound 291: 3-cyclohexenyl-1-(methoxymethyl)-6-(4-methoxyphenyl)-5-methyl-2-phenylpyrazolo[1,5-a]pyrimidin-7(1H)-one

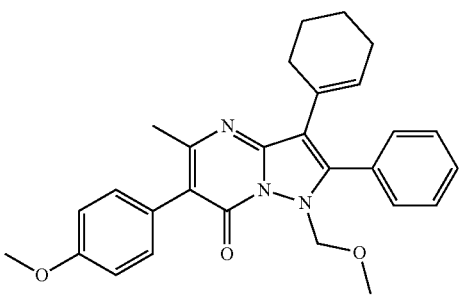 [SMILES: COCn1c(-c2ccccc2)c(C2=CCCCC2)c2nc(C)c(-c3ccc(OC)cc3)c(=O)n21]

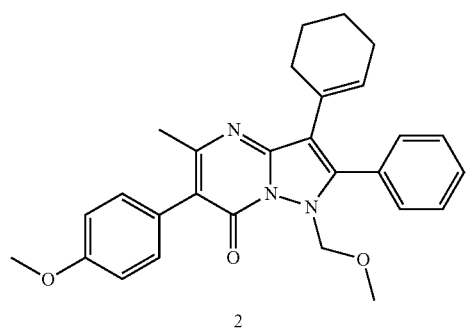

A mixture of 3-cyclohexenyl-6-(4-methoxyphenyl)-5-methyl-2-phenylpyrazolo[1,5-a]pyrimidin-7(4H)-one (Compound 212, 100 mg, 0.243 mmol), chloro(methoxy)methane (21.4 mg, 0.268 mmol) and $Cs_2CO_3$ (159 mg, 0.486 mmol) in DMSO (5 mL) was stirred at room temperature for 5 days. The mixture was poured into water (20 mL) and extracted with EtOAc (3*20 mL). The combined organic layers were washed with brine, dried over $Na_2SO_4$, filtered, and concentrated under reduced pressure to obtain the title compound.

$^1$H NMR (400 MHz, DMSO-$d_6$) δ: 7.54-7.64 (m, 5H), 7.21-7.27 (m, 2H), 6.99 (m, J=8.85 Hz, 2H), 5.88 (br. s., 1H), 5.65 (s, 2H), 3.80 (s, 3H), 2.96 (s, 3H), 2.21 (s, 3H), 2.14 (br. s., 2H), 2.01-2.08 (m, 2H), 1.51-1.64 (m, 4H). LC-MS: m/z 456.1 (M+H)$^+$.

Compound 292

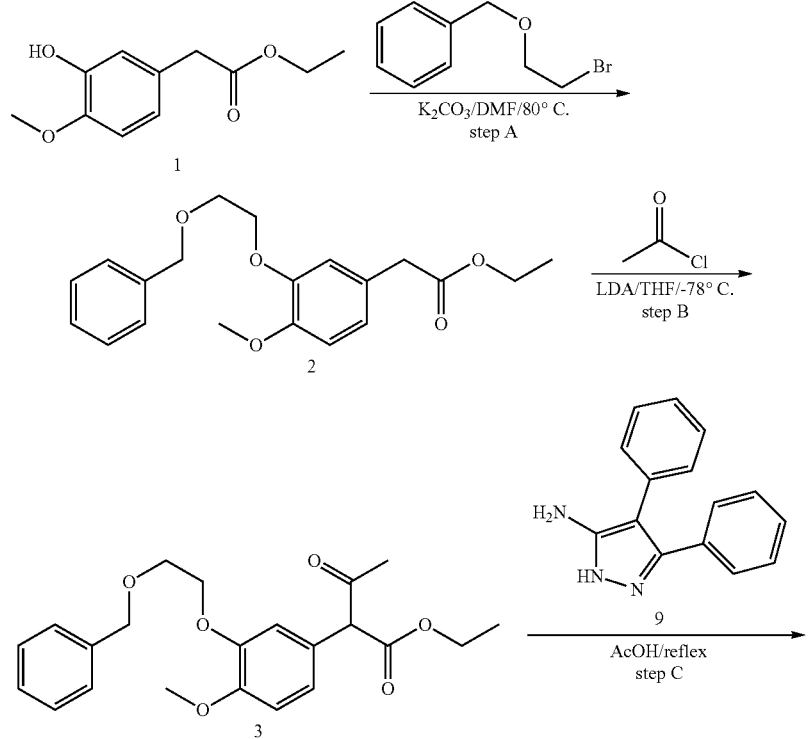

-continued
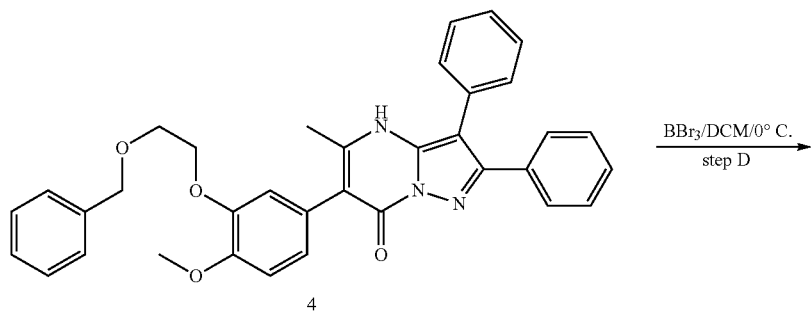
4
BBr₃/DCM/0° C.
step D
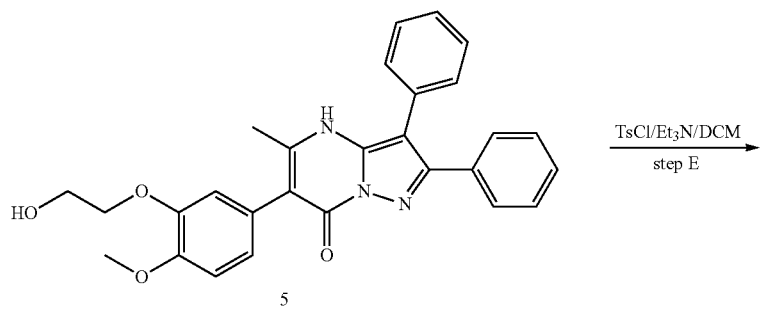
5
TsCl/Et₃N/DCM
step E
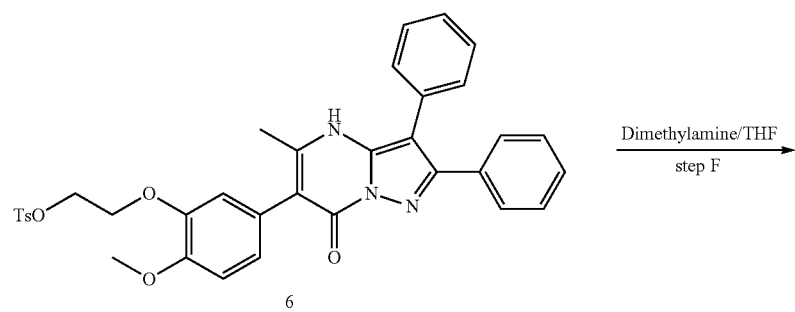
6
Dimethylamine/THF
step F
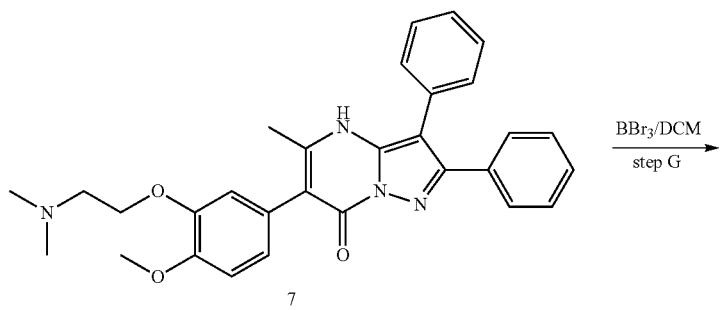
7
BBr₃/DCM
step G
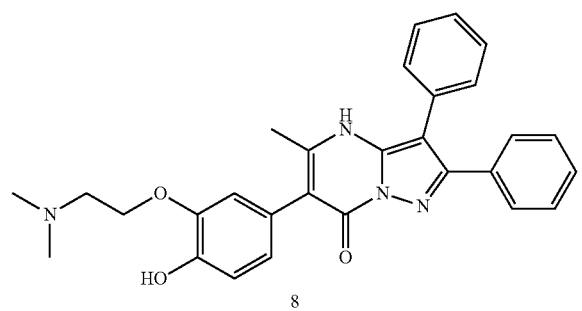
8

Step A: ethyl 2-(3-(2-(benzyloxy)ethoxy)-4-methoxyphenyl)acetate

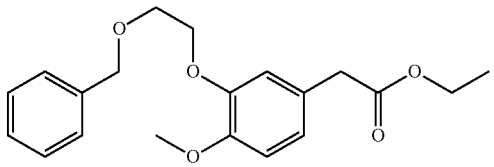 [SMILES: CCOC(=O)Cc1ccc(OC)c(OCCOCc2ccccc2)c1]

A mixture of ethyl 2-(3-hydroxy-4-methoxyphenyl)acetate (4.3 g, 20.5 mmol), ((2-bromoethoxy)methyl)benzene (7.88 g, 36.8 mmol), potassium carbonate (5.66 g, 41 mmol) in N,N-dimethylformamide (50 mL) was heated to 80° C. for 18 h. The mixture was cooled to room temperature, poured into water (100 mL), and extracted with ethyl acetate (100 mL) three times. The combined organic phase was washed with brine, dried over sodium sulfate and evaporated to dryness. The crude mixture was purified by column chromatography (ethyl acetate:petroleumether=1:5) to afford ethyl 2-(3-(2-(benzyloxy)ethoxy)-4-methoxyphenyl)acetate (3.8 g, 54% yield) as a colorless oil.

Step B: ethyl 2-(3-(2-(benzyloxy)ethoxy)-4-methoxyphenyl)-3-oxobutanoate

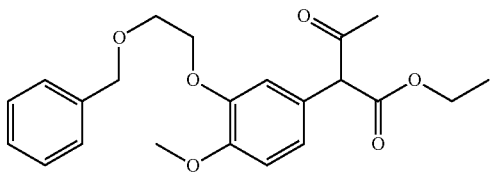 [SMILES: CCOC(=O)C(C(C)=O)c1ccc(OC)c(OCCOCc2ccccc2)c1]

To a solution of ethyl 2-(3-(2-(benzyloxy)ethoxy)-4-methoxyphenyl)acetate (690 mg, 2 mmol) in tetrahydrofuran (10 mL) was added lithium diisopropylamide (2N, 1 mL, 2 mmol) at −78° C. under nitrogen atmosphere dropwise. The mixture was stirred at the same temperature for 1 h. Acetyl chloride (156 mg, 2 mmol) was added into the mixture at −78° C. slowly. After addition, the mixture was stirred at −78° C. for 1 h and then warmed slowly to room temperature overnight. The mixture was quenched by adding aqueous ammonium chloride to pH 6-7 and extracted with ethyl acetate (20 mL) three times. The combined organic phase was washed with brine, dried over sodium sulfate and evaporated to dryness. The crude was purified by column chromatography on silica gel (ethyl acetate:petroleum ether=1:5) to afford ethyl 2-(3-(2-(benzyloxy)ethoxy)-4-methoxyphenyl)-3-oxobutanoate (280 mg, 38% yield) as a colorless oil. LC-MS: m/z 387.2 (M+H)$^+$.

Step C: 6-(3-(2-(benzyloxy)ethoxy)-4-methoxyphenyl)-5-methyl-2,3-diphenylpyrazolo[1,5-a] pyrimidin-7(4H)-one

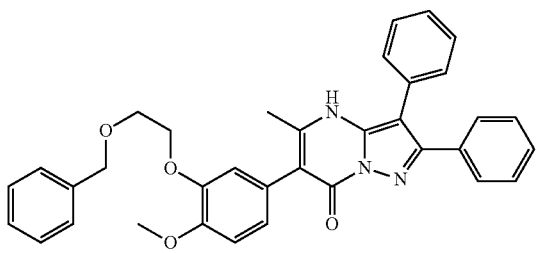 [SMILES: COc1ccc(-c2c(C)[nH]c3c(-c4ccccc4)c(-c4ccccc4)nn3c2=O)cc1OCCOCc1ccccc1]

A mixture of ethyl 2-(3-(2-(benzyloxy)ethoxy)-4-methoxyphenyl)-3-oxobutanoate (280 mg, 0.725 mmol) and 3,4-diphenyl-1H-pyrazol-5-amine (170 mg, 0.725 mmol) in acetic acid (5 mL) was heated to reflux for 2 h. The mixture was evaporated to remove acetic acid. The residue was purified by column chromatography (methanol:dichloromethane=1:20) to afford 6-(3-(2-(benzyloxy)ethoxy)-4-methoxyphenyl)-5-methyl-2,3-diphenylpyrazolo[1,5-a]pyrimidin-7(4H)-one (120 mg, 30% yield) as a yellow solid. LC-MS: m/z 558.2 (M+H)$^+$.

Step D: 6-(3-(2-hydroxyethoxy)-4-methoxyphenyl)-5-methyl-2,3-diphenylpyrazolo[1,5-a]pyrimidin-7(4H)-one

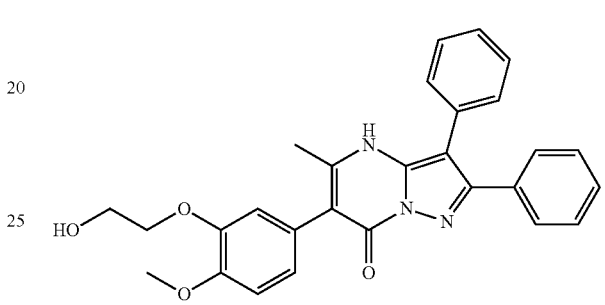

To a solution of 6-(3-(2-(benzyloxy)ethoxy)-4-methoxyphenyl)-5-methyl-2,3-diphenylpyrazolo[1,5-a]pyrimidin-7(4H)-one (100 mg, 0.18 mmol) in DCM (10 mL) was added 1M BBr$_3$ (0.5 mL) in DCM dropwise at 0° C., after addition, the mixture was stirred at room temperature for 1 h. MeOH (5 mL) was added carefully to quench the reaction. Then the mixture was evaporated, the residue was purified by prep-TLC (DCM/MeOH=100:10) to obtain the 6-(3-(2-hydroxyethoxy)-4-methoxyphenyl)-5-methyl-2,3-diphenylpyrazolo[1,5-a]pyrimidin-7(4H)-one (60 mg) as a white solid. LC-MS: m/z 468.2 (M+H)$^+$.

Step E: 2-(2-methoxy-5-(5-methyl-7-oxo-2,3-diphenyl-4,7-dihydropyrazolo[1,5-a]pyrimidin-6-yl)phenoxy)ethyl 4-methylbenzenesulfonate

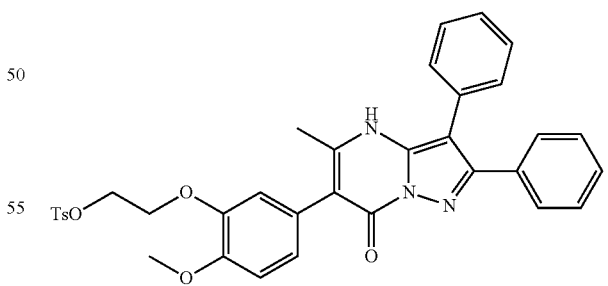

A mixture of 6-(3-(2-hydroxyethoxy)-4-methoxyphenyl)-5-methyl-2,3-diphenylpyrazolo[1,5-a]pyrimidin-7(4H)-one (200 mg, 0.427 mmol), TsCl (97 mg, 0.512 mmol), DMAP (52 mg, 0.427 mmol), Et$_3$N (130 mg, 1.281 mmol) in DCM (5 mL) was stirred at 50° C. for 18 h. The mixture was quenched by addition of water and extracted with DCM (2*20 mL). The combined organic layers were washed with brine and concentrated under reduced pressure. The residue was purified by prep-TLC (DCM/MeOH=100:5) to obtain the 2-(2-methoxy-5-(5-methyl-7-oxo-2,3-diphenyl-4,7-dihydropyrazolo[1,5-a]pyrimidin-6-yl)phenoxy)ethyl 4-methylbenzenesulfonate (150 mg) as a white solid. LC-MS: m/z 622.1 (M+H)+.

Step F: 6-(3-(2-(dimethylamino)ethoxy)-4-methoxyphenyl)-5-methyl-2,3-diphenylpyrazolo[1,5-a]pyrimidin-7(4H)-one

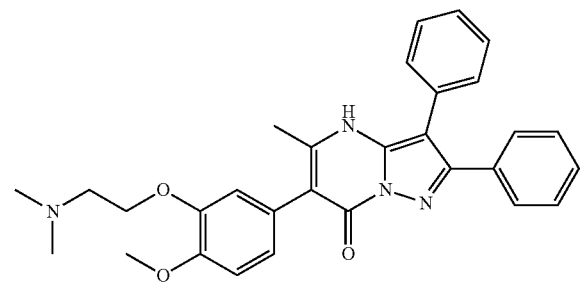 [SMILES: COc1ccc(-c2c(C)[nH]c3c(-c4ccccc4)c(-c4ccccc4)nn3c2=O)cc1OCCN(C)C]

A mixture of 2-(2-methoxy-5-(5-methyl-7-oxo-2,3-diphenyl-4,7-dihydropyrazolo[1,5-a]pyrimidin-6-yl)phenoxy)ethyl 4-methylbenzenesulfonate (150 mg, 0.241 mmol) and dimethylamine (30% in H₂O, 1 mL) in THF (5 mL) in a seal tube was stirred at 70° C. overnight. The reaction mixture was cooled to room temperature and evaporated under reduced pressure to get the crude 6-(3-(2-(dimethylamino)ethoxy)-4-methoxyphenyl)-5-methyl-2,3-diphenylpyrazolo[1,5-a]pyrimidin-7(4H)-one (140 mg) as an oil, which was used in the next step without further purification. LC-MS: m/z 495.0 (M+H)+.

Step G: Compound 292: 6-(3-(2-(dimethylamino)ethoxy)-4-hydroxyphenyl)-5-methyl-2,3-diphenylpyrazolo[1,5-a]pyrimidin-7(4H)-one

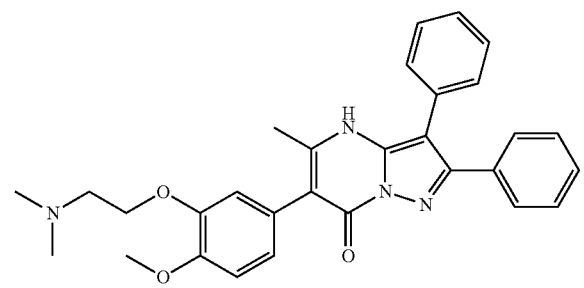 [SMILES: COc1ccc(-c2c(C)[nH]c3c(-c4ccccc4)c(-c4ccccc4)nn3c2=O)cc1OCCN(C)C]

To a solution of 6-(3-(2-(dimethylamino)ethoxy)-4-methoxyphenyl)-5-methyl-2,3-diphenylpyrazolo[1,5-a]pyrimidin-7(4H)-one (140 mg, 0.225 mmol) in DCM (4 mL) was added BBr₃ (1M in DCM, 1 mL) dropwise. The mixture was then stirred at room temperature for 2 h. The mixture was quenched by addition of MeOH and concentrated under reduced pressure to obtain 6-(3-(2-(dimethylamino)ethoxy)-4-hydroxyphenyl)-5-methyl-2,3-diphenylpyrazolo[1,5-a]pyrimidin-7(4H)-one.
¹H NMR (400 MHz, CHLOROFORM-d) δ: 7.38-7.62 (m, 10H), 7.17 (br. s., 1H), 7.02 (br. s., 2H), 4.44 (br. s., 2H), 3.66 (br. s., 2H), 3.07 (s, 6H), 2.33 (s, 3H). LC-MS: m/z 481.1 (M+H)+.

Compound 294

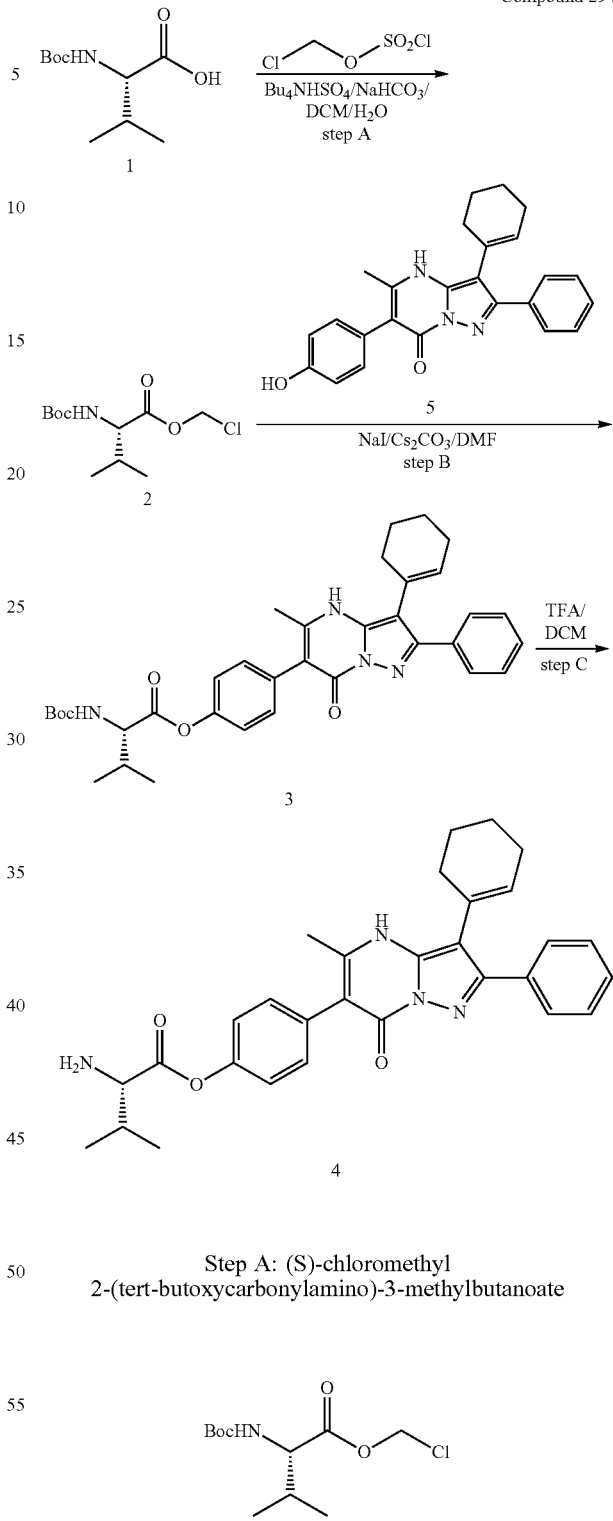

Step A: (S)-chloromethyl 2-(tert-butoxycarbonylamino)-3-methylbutanoate

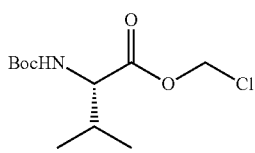 [SMILES: CC(C)[C@H](NC(=O)OC(C)(C)C)C(=O)OCCl]

A mixture of (S)-2-(tert-butoxycarbonylamino)-3-methylbutanoic acid (1 g, 4.6 mmol), chloromethyl sulfochloridate (912 mg, 5.53 mmol), NaHCO₃ (1.54 g, 18.4 mmol) in DCM (5 mL) and H₂O (5 mL) was stirred at room temperature overnight. Water (20 mL) was added. The mixture was extracted with DCM (3*20 mL). The combined organic layers were washed with brine, dried over Na₂SO₄, filtered, and concentrated under reduced pressure to get the title compound (800 mg) as a colorless oil.

$^1$H NMR (400 MHz, CHLOROFORM-d) δ: 5.90 (d, J=5.91 Hz, 1H), 5.64 (d, J=6.18 Hz, 1H), 5.00 (d, J=8.06 Hz, 1H), 4.29 (dd, J=8.87, 4.57 Hz, 1H), 2.21 (dd, J=12.09, 6.45 Hz, 1H), 1.02 (d, J=6.98 Hz, 3H), 0.94 (d, J=6.98 Hz, 3H).

Step B: (S)-4-(3-cyclohexenyl-5-methyl-7-oxo-2-phenyl-4,7-dihydropyrazolo[1,5-a]pyrimidin-6-yl)phenyl 2-(tert-butoxycarbonylamino)-3-methylbutanoate

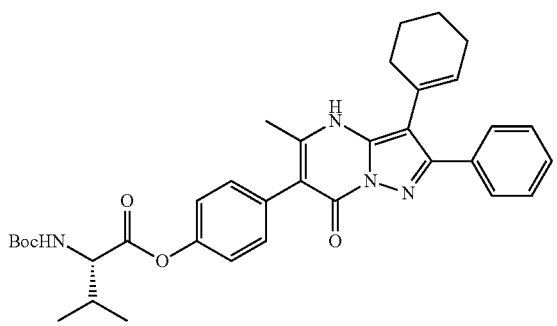 [SMILES: Cc1[nH]c2c(C3=CCCCC3)c(-c3ccccc3)nn2c(=O)c1-c1ccc(OC(=O)[C@@H](NC(=O)OC(C)(C)C)C(C)C)cc1]

To a mixture of 3-cyclohexenyl-6-(4-hydroxyphenyl)-5-methyl-2-phenylpyrazolo[1,5-a]pyrimidin-7(4H)-one (Compound 240, 200 mg, 0.504 mmol), NaI (76 mg, 0.504 mmol), Cs$_2$CO$_3$ (330 mg, 1.0 mmol) in DMF (5 mL) was added (S)-chloromethyl 2-(tert-butoxycarbonylamino)-3-methylbutanoate (200 mg, 0.755 mmol). The mixture was stirred at room temperature for 1 h. Then the mixture was quenched by addition of water (20 mL) and extracted with EtOAc (2*20 mL). The combined organic layers were concentrated. The residue was purified by column chromatography on silica gel (eluting PE/EA=2:1) to give the desired product (150 mg) as a white solid.

$^1$H NMR (400 MHz, DMSO-d$_6$) δ: 11.71 (s, 1H), 7.78 (d, J=7.25 Hz, 2H), 7.44-7.53 (m, 3H), 7.35-7.44 (m, 3H), 7.14 (d, J=8.33 Hz, 2H), 5.85 (br. s., 1H), 4.05-4.11 (m, 1H), 2.25 (s, 3H), 2.19-2.23 (m, 3H), 2.06 (br. s., 2H), 1.71 (br. s., 4H), 1.44 (s, 9H), 1.03 (d, J=6.72 Hz, 6H). LC-MS: m/z 597.2 (M+H)$^+$.

Step C: Compound 294: (S)-4-(3-cyclohexenyl-5-methyl-7-oxo-2-phenyl-4,7-dihydropyrazolo[1,5-a]pyrimidin-6-yl)phenyl 2-amino-3-methylbutanoate

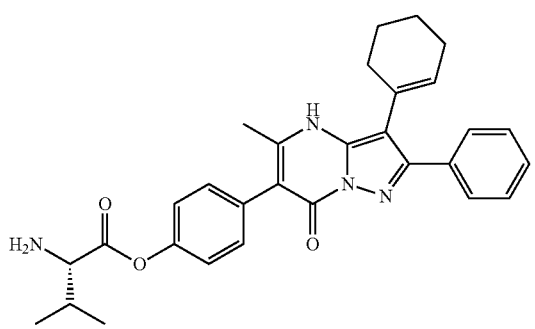 [SMILES: Cc1[nH]c2c(C3=CCCCC3)c(-c3ccccc3)nn2c(=O)c1-c1ccc(OC(=O)[C@@H](N)C(C)C)cc1]

To a solution of(S)-4-(3-cyclohexenyl-5-methyl-7-oxo-2-phenyl-4,7-dihydropyrazolo[1,5-a]pyrimidin-6-yl)phenyl 2-(tert-butoxycarbonylamino)-3-methylbutanoate (150 mg, 0.251 mmol) in DCM (5 mL) was added TFA (2 mL). Then the mixture was stirred at room temperature for 2 h, and evaporated under reduced pressure to get the title compound.

$^1$H NMR (DMSO-d$_6$+TFA) δ: 11.79 (s, 1H), 8.59 (br. s., 3H), 7.75-7.82 (m, 2H), 7.39-7.51 (m, 5H), 7.23-7.29 (m, 2H), 5.86 (br. s., 1H), 4.29 (br. s., 1H), 2.32-2.42 (m, 1H), 2.26 (s, 3H), 2.22 (br. s., 2H), 2.07 (br. s., 2H), 1.71 (br. s., 4H), 1.15 (d, J=6.98 Hz, 3H), 1.12 (d, J=6.98 Hz, 3H). LC-MS: m/z 497.1 (M+H)$^+$.

Compound 295

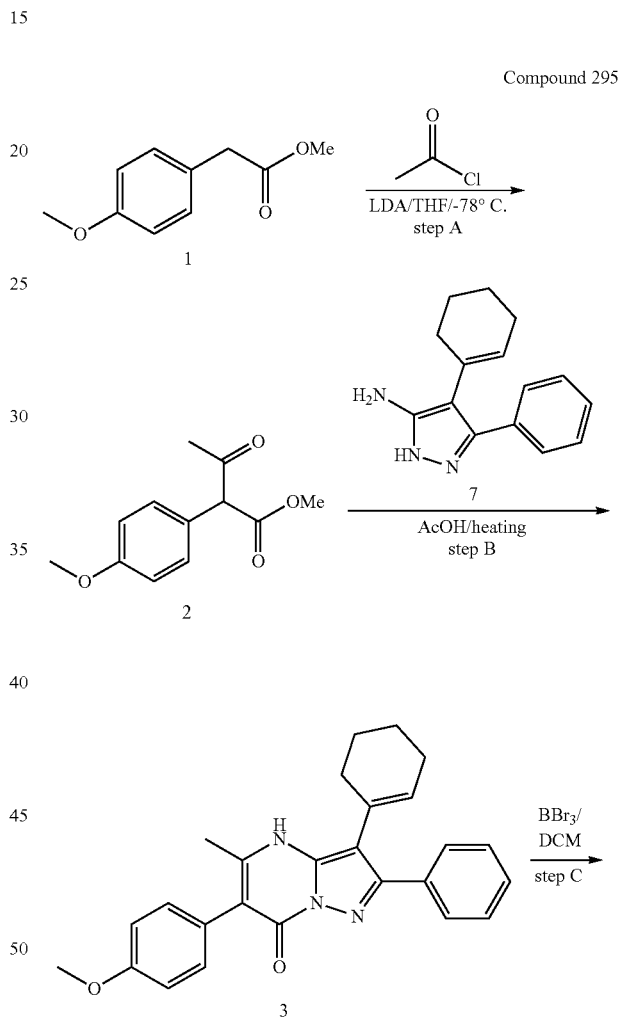

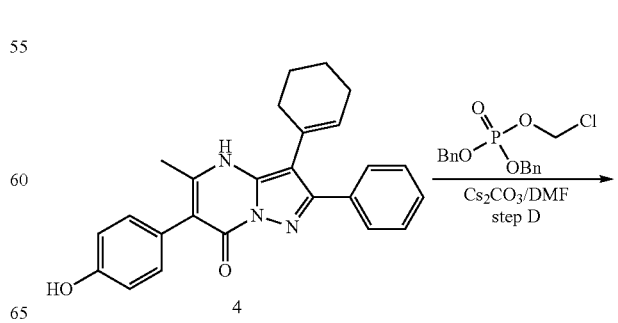

-continued

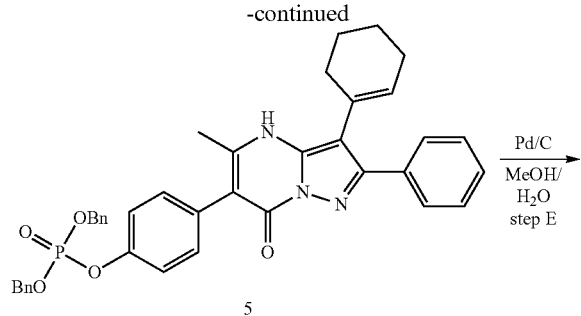

5

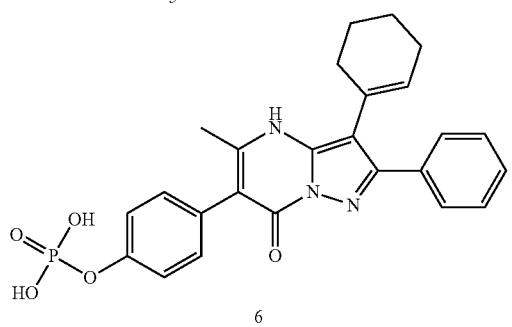

6

Step A: methyl 2-(4-methoxyphenyl)-3-oxobutanoate

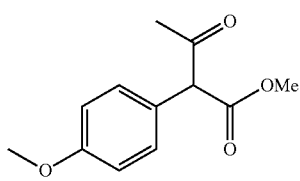 [SMILES: COC(=O)C(C(C)=O)c1ccc(OC)cc1]

To a solution of methyl 2-(4-methoxyphenyl)acetate (900 mg, 5.0 mmol)) in THF (15 mL) was added slowly LDA (2.5 mL, 2 mmol/mL in THF) at −30° C. Then acetyl chloride (500 mg, 6.5 mmol) was added slowly. The reaction mixture was stirred for 30 mins at −30° C. and allowed to room temperature for 1 h. The mixture was poured into water, extracted over ethyl acetate, dried over anhydrous $Na_2SO_4$, filtered, and concentrated to give the crude product (800 mg) as a yellow liquid, which was used directly to the next step without further purification.

Step B: 3-cyclohexenyl-6-(4-methoxyphenyl)-5-methyl-2-phenylpyrazolo[1,5-a]pyrimidin-7(4H)-one

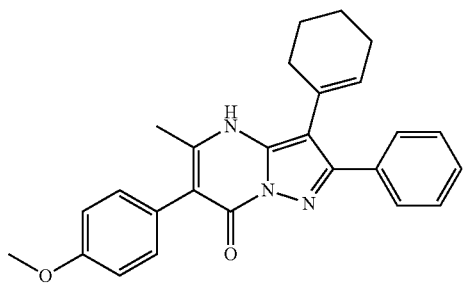

The solution of 4-(cyclohex-1-en-1-yl)-3-phenyl-1H-pyrazol-5-amine (200 mg, 0.84 mmol) and methyl 2-(4-methoxyphenyl)-3-oxobutanoate (371.5 mg, 1.67 mmol) in AcOH (5 mL) was stirred at 100° C. for 1 hour. After cooling to room temperature, solvent was removed by vacuum, and saturated $NaHCO_3$ was added till pH>7. The precipitate was filtered, washed with water (6 mL) and MeOH (0.5 mL) to obtain 3-(cyclohex-1-en-1-yl)-6-(4-methoxyphenyl)-5-methyl-2-phenylpyrazolo[1,5-a]pyrimidin-7(4H)-one (260 mg) as a white solid.

$^1$H NMR (DMSO-$d_6$) δ: 11.62 (s, 1H), 7.72-7.85 (m, 2H), 7.34-7.55 (m, 3H), 7.19-7.31 (m, 2H), 6.93-7.07 (m, 2H), 5.84 (br. s., 1H), 3.81 (s, 3H), 2.17-2.32 (m, 5H), 1.98-2.12 (m, 2H), 1.70 (br. s., 4H). LC-MS: m/z 412.3 $(M+H)^+$.

Step C: 3-cyclohexenyl-6-(4-hydroxyphenyl)-5-methyl-2-phenylpyrazolo[1,5-a]pyrimidin-7(4H)-one

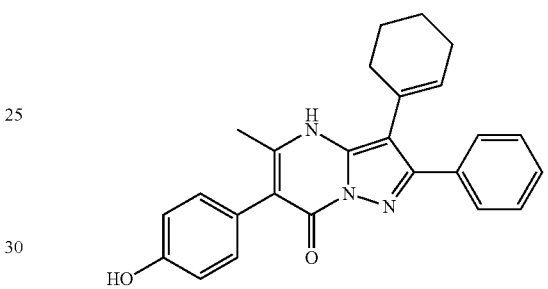

To a solution of 3-cyclohexenyl-6-(4-methoxyphenyl)-5-methyl-2-phenylpyrazolo[1,5-a]pyrimidin-7(4H)-one (50 mg, 0.118 mmol) in $CH_2Cl_2$ (1 mL) was added slowly $BBr_3$ (3 mL, 1 mmol/mL in $CH_2Cl_2$) at 0° C. And then the reaction mixture was stirred overnight. The reaction was quenched with ice water at −10° C. and concentrated. The residue was purified by prep-HPLC to obtain the title compound (15 mg) as a white solid.

$^1$H NMR (DMSO-$d_6$) δ: 7.76 (d, J=7.02 Hz, 2H), 7.30-7.52 (m, 3H), 7.09 (m, J=7.93 Hz, 2H), 6.82 (m, J=7.93 Hz, 2H), 5.83 (br. s., 1H), 2.21 (br. s., 3H), 2.18 (br. s., 2H), 2.03 (br. s., 2H), 1.67 (br. s., 4H). LC-MS: m/z 398.0 $(M+H)^+$.

Step D: dibenzyl 4-(3-cyclohexenyl-5-methyl-7-oxo-2-phenyl-4,7-dihydropyrazolo[1,5-a]pyrimidin-6-yl)phenyl phosphate

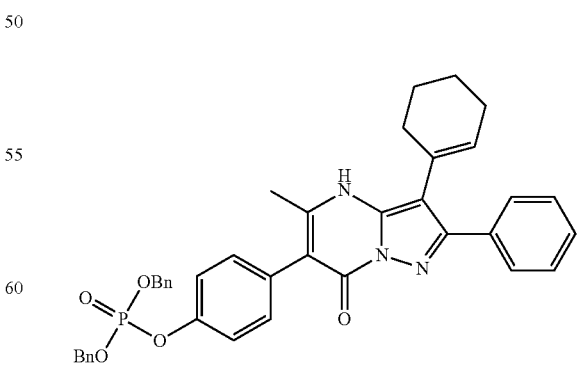

To a solution of 3-cyclohexenyl-6-(4-hydroxyphenyl)-5-methyl-2-phenylpyrazolo[1,5-a]pyrimidin-7(4H)-one (40 mg, 0.1 mmol) in DMF (5 mL) was added dibenzyl chloromethyl phosphate (50 mg, 0.15 mmol) in DMF (1 mL) and Cs₂CO₃ (100 mg, 0.31 mmol) at room temperature. The mixture was warmed to 80° C. and stirred overnight. The reaction mixture was cooled to room temperature, then poured into water (20 mL), and extracted with EtOAc (3*20 mL). The combined organic layers were washed with water (2*20 mL) and brine (20 mL), and then concentrated under reduced pressure. The residue was purified by prep TLC, eluting with EA/DCM=2:3, to get the title compound (20 mg) as a white solid. LC-MS: m/z 658.1 (M+H)⁺.

Step E: Compound 295: 4-(3-(cyclohex-1-en-1-yl)-5-methyl-7-oxo-2-phenyl-4,7-dihydropyrazolo[1,5-a]pyrimidin-6-yl)phenyl dihydrogen phosphate

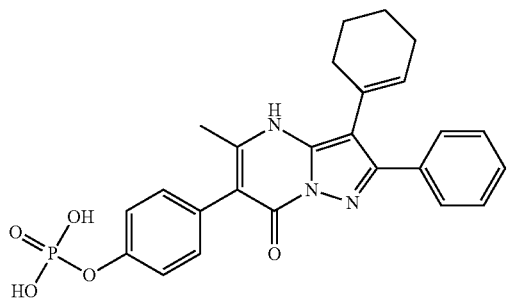 [SMILES: Cc1[nH]c2c(C3=CCCCC3)c(-c3ccccc3)nn2c(=O)c1-c1ccc(OP(=O)(O)O)cc1]

To a solution of dibenzyl 4-(3-cyclohexenyl-5-methyl-7-oxo-2-phenyl-4,7-dihydropyrazolo[1,5-a]pyrimidin-6-yl) phenyl phosphate (20 mg, 0.03 mmol) in MeOH (2 mL) was added Pd/C (3 mg). The mixture was stirred at room temperature under H₂ for 10 min and filtered. The filtrate was concentrated to afford the title compound (12 mg).

¹H NMR (400 MHz, DMSO-d₆) δ: 11.70 (br. s., 1H), 7.78 (d, J=7.25 Hz, 2H), 7.42-7.49 (m, 2H), 7.36-7.42 (m, 1H), 7.19 (br. s., 2H), 7.11 (d, J=8.06 Hz, 2H), 5.82 (br. s., 1H), 2.21 (br. s., 5H), 2.08 (br. s., 2H), 1.69 (br. s., 4H). LC-MS: m/z 477.9 (M+H)⁺.

Compound 296

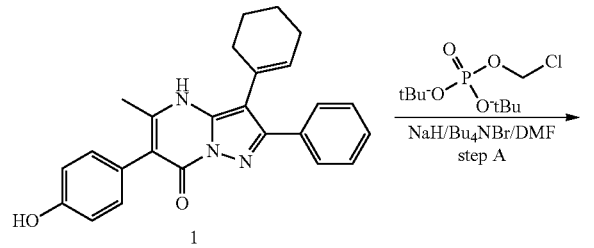

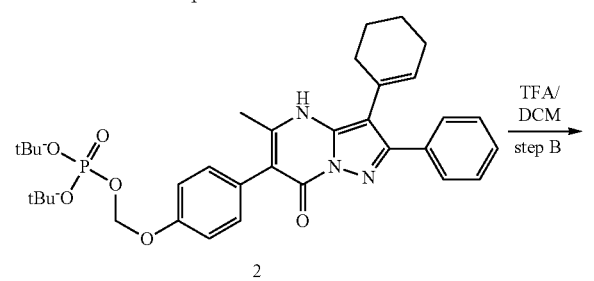

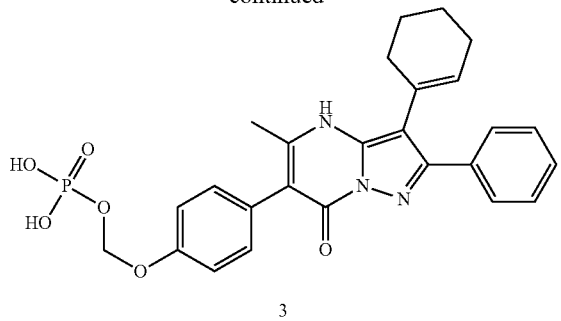

Step A: di-tert-butyl (4-(3-cyclohexenyl-5-methyl-7-oxo-2-phenyl-4,7-dihydropyrazolo[1,5-a]pyrimidin-6-yl)phenoxy)methyl phosphate

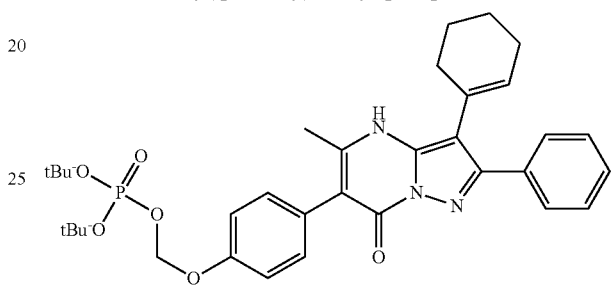

To a solution of 3-cyclohexenyl-6-(4-hydroxyphenyl)-5-methyl-2-phenylpyrazolo[1,5-a]pyrimidin-7(4H)-one (Compound 240, 300 mg, 0.75 mmol) in DMF (10 mL) was added NaH (60% dispersion in mineral oil, 75.6 mg, 1.89 mmol) and TBAB (36 mg, 0.15 mmol) at 0° C. for 5 min. Then di-tert-butyl chloromethyl phosphate (250 mg, 1.13 mmol) in DMF (5 mL) was added. The mixture was warmed to room temperature and stirred for 2 h. The reaction mixture was poured into water (20 mL), extracted with DCM (3*20 mL). The combined organic layers were washed with water (2*20 mL) and brine (20 mL), and concentrated under reduced pressure. The residue was purified by column chromatography on silica gel (ethyl acetate:DCM=1:3) to get the title compound (120 mg) as a white solid.

¹H NMR (400 MHz, DMSO-d₆) δ: 11.66 (s, 1H), 7.77 (d, J=7.02 Hz, 2H), 7.44-7.50 (m, 2H), 7.41 (d, J=7.32 Hz, 1H), 7.29 (m, J=8.54 Hz, 2H), 7.13 (m, J=8.54 Hz, 2H), 5.84 (br. s., 1H), 5.67 (d, J=12.21 Hz, 2H), 2.22 (s, 5H), 2.06 (br. s., 2H), 1.70 (br. s., 4H), 1.41 (s, 18H). LC-MS: m/z 620.1 (M+H)⁺.

Step B: Compound 296: (4-(3-cyclohexenyl-5-methyl-7-oxo-2-phenyl-4,7-dihydropyrazolo[1,5-a]pyrimidin-6-yl)phenoxy)methyl dihydrogen phosphate

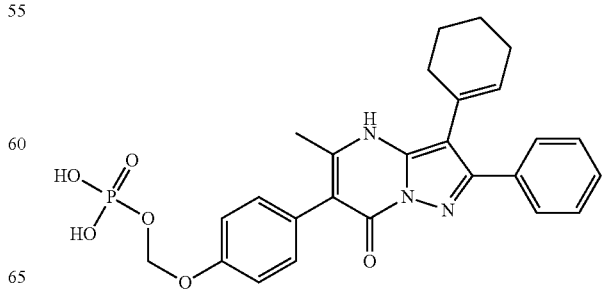

To a solution of di-tert-butyl (4-(3-cyclohexenyl-5-methyl-7-oxo-2-phenyl-4,7-dihydropyrazolo[1,5-a]pyrimidin-6-yl)phenoxy)methyl phosphate (110 mg, 0.177 mmol) in DCM (2 mL) was added TFA (1 mL). The mixture was stirred at room temperature under $N_2$ for 30 min. The reaction mixture was filtered off. The filter cake was washed with ether and dried to get the title compound.

1H NMR (400 MHz, DMSO-d6) δ: 11.65 (s, 1H), 7.73-7.83 (m, 2H), 7.44-7.50 (m, 2H), 7.38-7.44 (m, 1H), 7.25-7.31 (m, 2H), 7.14 (m, J=8.86 Hz, 2H), 5.85 (br. s., 1H), 5.62 (d, J=11.28 Hz, 2H), 2.24 (s, 3H), 2.22 (br. s., 2H), 2.06 (br. s., 2H), 1.71 (br. s., 4H). LC-MS: m/z 508.2 (M+H)⁺.

A solution of 3-(cyclohex-1-en-1-yl)-5-hydroxy-6-(4-methoxyphenyl)-2-phenylpyrazolo[1,5-a]pyrimidin-7(4H)-one (Synthesized in scheme of Compound 279, 47.0 g, 104 mmol) in phosphorus oxychloride (100 mL) was stirred at reflux for 16 hrs. The solvent was removed invacuo. The residue was added slowly to methanol (100 mL) cooled at 0° C. The precipitates were collected by filtration, washed with methanol, and dried under reduced pressure to give 5,7-dichloro-3-(cyclohex-1-en-1-yl)-6-(4-methoxyphenyl)-2-phenylpyrazolo[1,5-a]pyrimidine (50 g) as a yellow solid.

$^1$H NMR (DMSO-d$_6$): δ 1.70 (d, J=4.57 Hz, 4H) 2.20 (br. s., 4H) 3.84 (s, 4H) 5.87 (br. s., 1H) 7.10 (d, J=8.60 Hz, 2H) 7.36-7.56 (m, 5H) 7.82 (d, J=7.25 Hz, 2H). LC-MS: m/z 450.2 (M+H)⁺.

Step B$_1$: 5-chloro-3-(cyclohex-1-en-1-yl)-7-methoxy-6-(4-methoxyphenyl)-2-phenylpyrazolo[1,5-a]pyrimidine

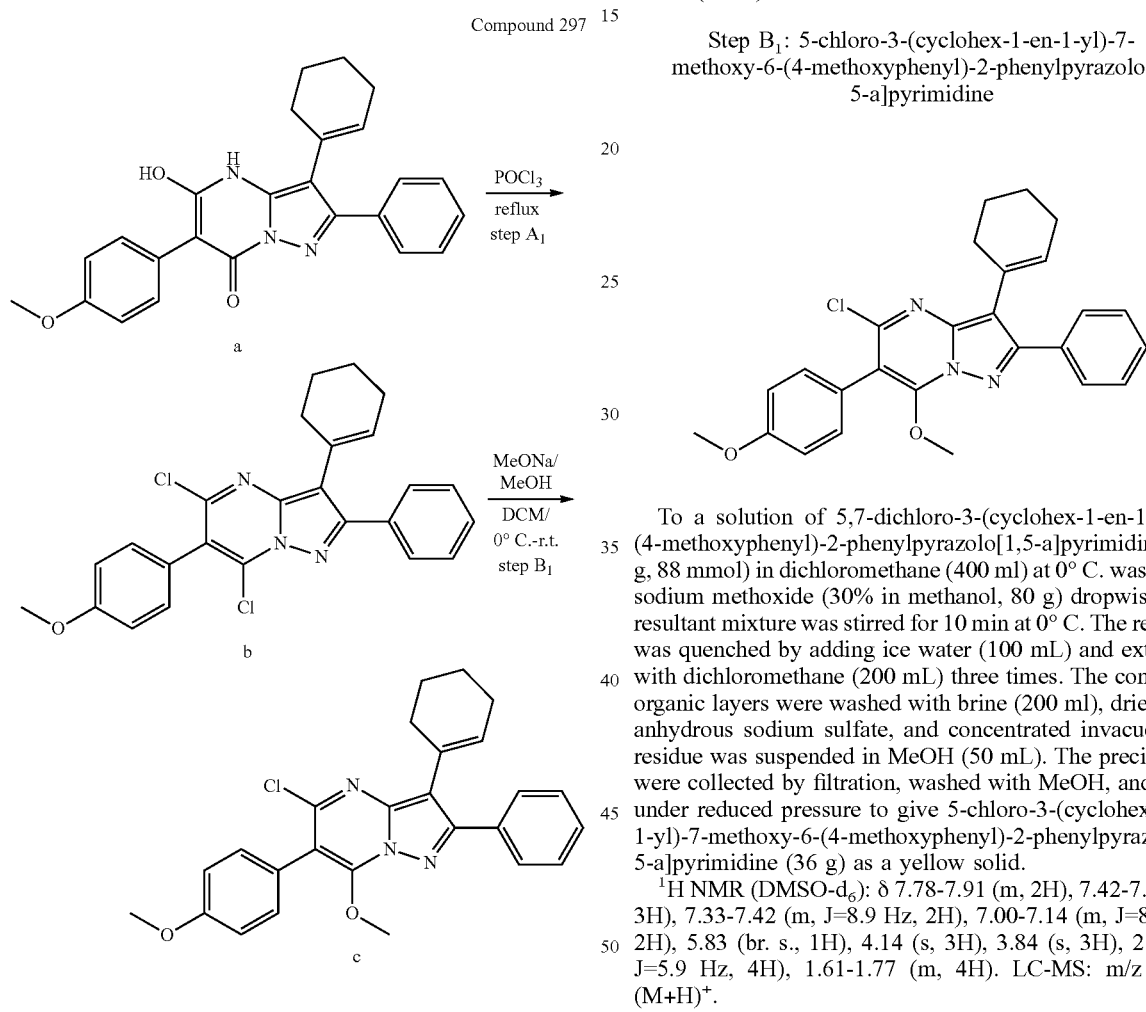

To a solution of 5,7-dichloro-3-(cyclohex-1-en-1-yl)-6-(4-methoxyphenyl)-2-phenylpyrazolo[1,5-a]pyrimidine (40 g, 88 mmol) in dichloromethane (400 ml) at 0° C. was added sodium methoxide (30% in methanol, 80 g) dropwise. The resultant mixture was stirred for 10 min at 0° C. The reaction was quenched by adding ice water (100 mL) and extracted with dichloromethane (200 mL) three times. The combined organic layers were washed with brine (200 ml), dried over anhydrous sodium sulfate, and concentrated invacuo. The residue was suspended in MeOH (50 mL). The precipitates were collected by filtration, washed with MeOH, and dried under reduced pressure to give 5-chloro-3-(cyclohex-1-en-1-yl)-7-methoxy-6-(4-methoxyphenyl)-2-phenylpyrazolo[1,5-a]pyrimidine (36 g) as a yellow solid.

$^1$H NMR (DMSO-d$_6$): δ 7.78-7.91 (m, 2H), 7.42-7.58 (m, 3H), 7.33-7.42 (m, J=8.9 Hz, 2H), 7.00-7.14 (m, J=8.9 Hz, 2H), 5.83 (br. s., 1H), 4.14 (s, 3H), 3.84 (s, 3H), 2.20 (d, J=5.9 Hz, 4H), 1.61-1.77 (m, 4H). LC-MS: m/z 446.1 (M+H)⁺.

Step A$_1$: 5,7-dichloro-3-(cyclohex-1-en-1-yl)-6-(4-methoxyphenyl)-2-phenylpyrazolo[1,5-a]pyrimidine

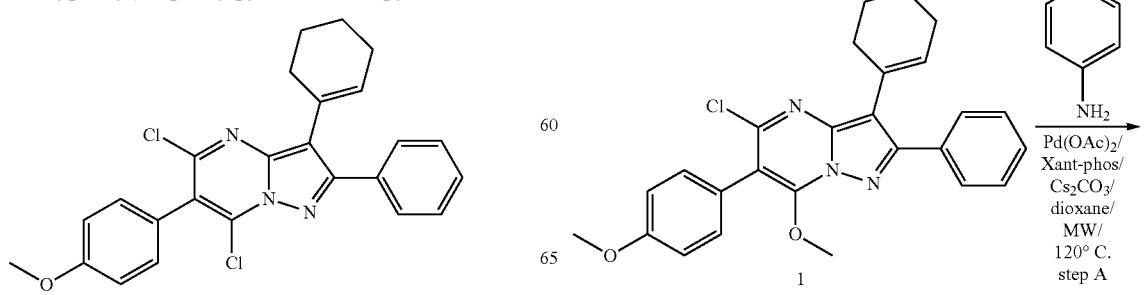

-continued

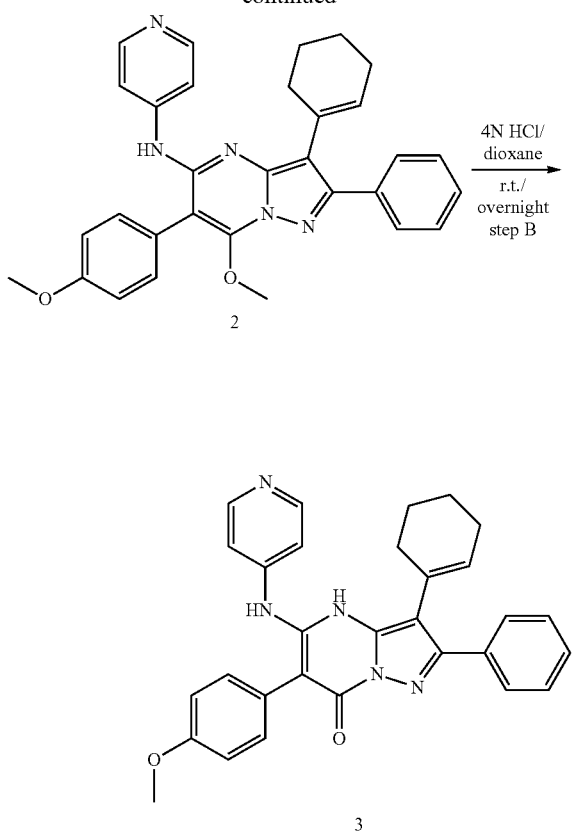

2

Step A: 3-(cyclohex-1-en-1-yl)-7-methoxy-6-(4-methoxyphenyl)-2-phenyl-N-(pyridin-4-yl)pyrazolo[1,5-a]pyrimidin-5-amine

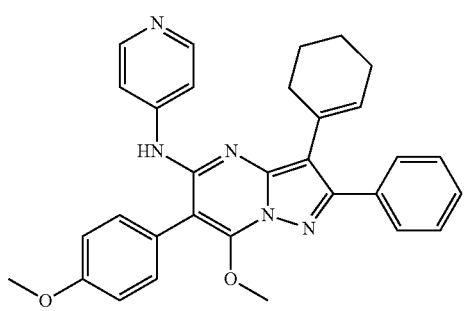 [SMILES: COc1ccc(-c2c(Nc3ccncc3)nc3c(C4=CCCCC4)c(-c4ccccc4)nn3c2OC)cc1]

A mixture of 5-chloro-3-(cyclohex-1-en-1-yl)-7-methoxy-6-(4-methoxyphenyl)-2-phenylpyrazolo[1,5-a]pyrimidine (300 mg, 0.68 mmol), pyridin-4-amine (70 mg, 0.75 mmol), and palladium diacetate (15 mg, 0.068 mmol), Xantphos (79 mg, 0.136 mmol) and $Cs_2CO_3$ (443 mg, 1.36 mmol) in 1,4-dioxane (20 mL) was heated at 110° C. for 2 hours under nitrogen atmosphere through microwave irradiation. The mixture was filtered through celite, and the filtrate was concentrated in vacuo. The residue was purified by flash chromatography to afford the desired product 2 (40 mg, 11.7% yield) as a light yellow solid. LC-MS: m/z 504.2 (M+H)$^+$.

Step B: Compound 297: 3-(cyclohex-1-en-1-yl)-6-(4-methoxyphenyl)-2-phenyl-5-(pyridin-4-ylamino)pyrazolo[1,5-a]pyrimidin-7(4H)-one

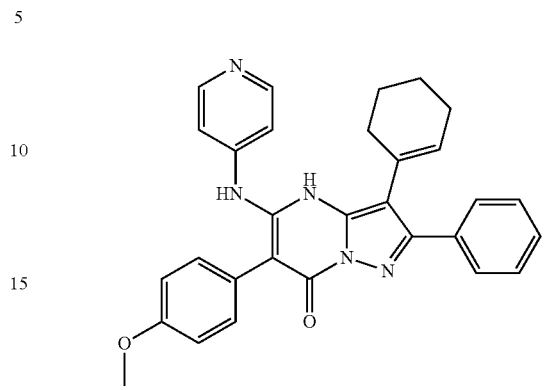

A solution of 3-(cyclohex-1-en-1-yl)-7-methoxy-6-(4-methoxyphenyl)-2-phenyl-N-(pyridin-4-yl)pyrazolo[1,5-a]pyrimidin-5-amine (40 mg, 0.0.8 mmol) in 4M HCl in 1,4-dioxane (5 mL) was stirred at r.t. for 2 hours. The mixture was concentrated at low temperature (<25° C.), and saturated $NaHCO_3$ (8 mL) was added. The precipitate was filtered. The filter cake was suspended in DCM/MeOH (14 mL, 1:6), filtered and washed with MeOH (2 mL) to obtain 3-(cyclohex-1-en-1-yl)-6-(4-methoxyphenyl)-2-phenyl-5-(pyridin-4-ylamino)pyrazolo[1,5-a]pyrimidin-7(4H)-one.

$^1$H NMR (DMSO-$d_6$) δ: 8.32 (d, J=7.02 Hz, 2H), 7.81 (d, J=7.02 Hz, 2H), 7.38-7.56 (m, 4H), 7.20-7.36 (m, 5H), 6.91 (d, J=8.85 Hz, 2H), 5.89 (br. s., 1H), 3.75 (s, 3H), 2.18 (br. s., 2H), 2.10 (br. s., 2H), 1.69 (br. s., 4H). LC-MS: m/z 490.1 (M+H)$^+$.

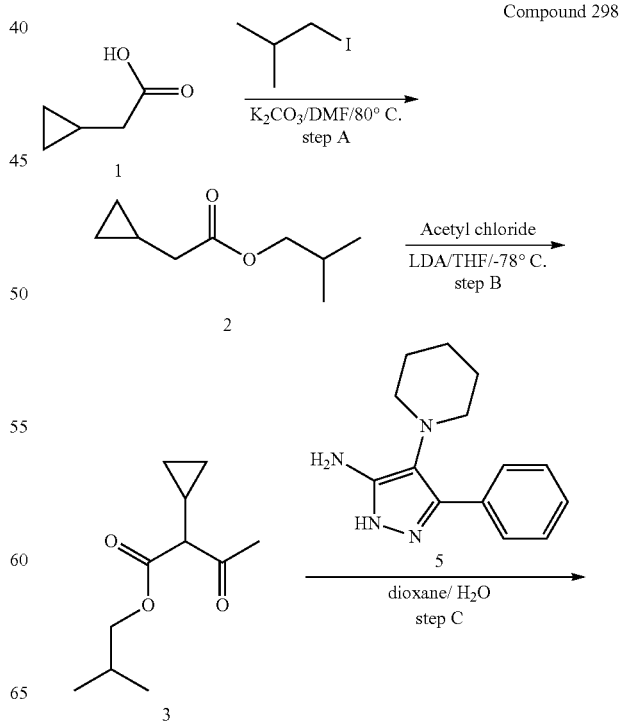

Compound 298

-continued

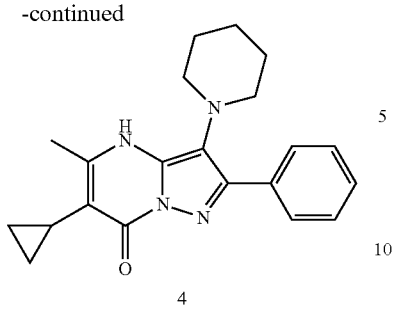

4

Step A: isobutyl 2-cyclopropylacetate

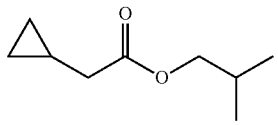

A mixture of 2-cyclopropylacetic acid (1 g, 10 mmol), 1-iodo-2-methylpropane (1.65 g, 12 mmol) and $Cs_2CO_3$ (6.5 g, 20 mmol) in DMF (50 mL) was stirred at 80° C. for 16 h. The mixture was poured slowly into saturated $NH_4Cl$ and extracted with EA (3*100 mL). The combined organic phase was washed with brine, dried over anhydrous $MgSO_4$, filtered and concentrated in vacuo. The residue was purified by flash chromatography to afford the desired ethyl isobutyl 2-cyclopropylacetate (500 mg) as a colorless oil.

$^1$H NMR (400 MHz, DMSO-$d_6$) δ: 3.82 (d, J=6.72 Hz, 2H), 2.23 (d, J=6.98 Hz, 2H), 1.81-1.93 (m, 1H), 0.92-1.02 (m, 1H), 0.89 (d, J=6.72 Hz, 6H), 0.43-0.51 (m, 2H), 0.11-0.17 (m, 2H).

Step B: isobutyl 2-cyclopropyl-3-oxobutanoate

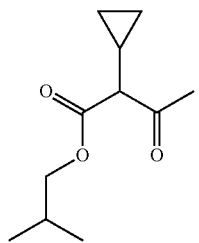

To a solution of 2-cyclopropylacetate (500 mg, 3.2 mmol) in THF (10 mL) was added LDA (1.5 M in THF, 2.5 mL, 3.84 mmol) dropwise at −78° C. The mixture was stirred at −78° C. for 30 min, and acetyl chloride (326 mg, 4.2 mmol) was added dropwise. Then the mixture was stirred at rt for 4 h. The mixture was poured slowly into saturated $NH_4Cl$ and extracted with EA (3*20 mL). The combined organic phase was washed with brine, dried over anhydrous $MgSO_4$, filtered and concentrated in vacuo. The residue was purified by flash chromatography to afford the desired isobutyl 2-cyclopropyl-3-oxobutanoate (380 mg) as a brown oil.

Step C: Compound 298: 6-cyclopropyl-5-methyl-2-phenyl-3-(piperidin-1-yl)pyrazolo[1,5-a]pyrimidin-7(4H)-one

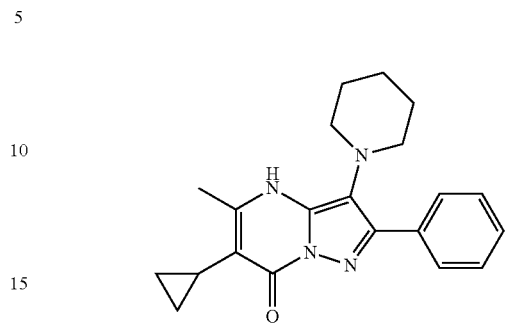

A mixture of 2-cyclopropyl-3-oxobutanoate (327 mg, 1.65 mmol) and 3-phenyl-4-(piperidin-1-yl)-1H-pyrazol-5-amine (200 mg, 0.825 mmol) in dioxane (5 mL) and water (1 mL) was stirred at 115° C. under microwave irradiation for 2 h. The solvent was removed under reduced pressure to give 6-cyclopropyl-5-methyl-2-phenyl-3-(piperidin-1-yl)pyrazolo[1,5-a]pyrimidin-7(4H)-one.

$^1$H NMR (400 MHz, DMSO-$d_6$) δ: 11.13 (br. s., 1H), 8.10 (d, J=7.25 Hz, 2H), 7.41-7.48 (m, 2H), 7.37 (d, J=7.25 Hz, 1H), 3.00-3.11 (m, 4H), 2.50 (s, 3H), 1.63 (br. s., 4H), 1.56 (br. s., 2H), 1.42-1.50 (m, 1H), 0.80-0.89 (m, 2H), 0.57-0.67 (m, 2H). LC-MS: m/z 349.6 (M+H)$^+$.

Compound 299

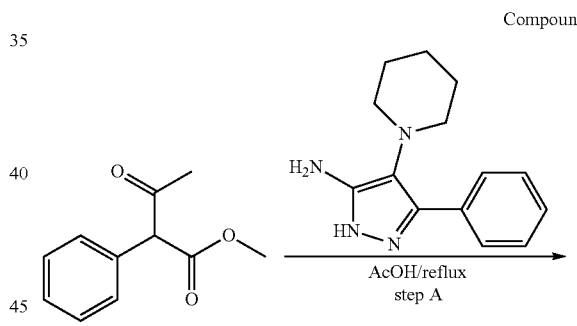

1

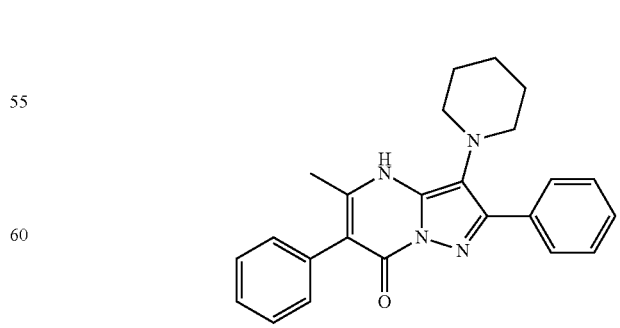

2

371

Step A: 5-methyl-2,6-diphenyl-3-(piperidin-1-yl)pyrazolo[1,5-a]pyrimidin-7(4H)-one

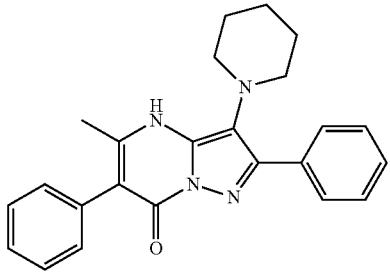 [SMILES: Cc1[nH]c2c(N3CCCCC3)c(-c3ccccc3)nn2c(=O)c1-c1ccccc1]

A suspension of 3-phenyl-4-(piperidin-1-yl)-1H-pyrazol-5-amine (70 mg, 0.29 mmol) and methyl 3-oxo-2-phenylbutanoate (120 mg, 0.58 mmol) in AcOH (2 ml) was refluxed for 30 min under N₂ protection. The mixture was cooled to the RT, concentrated, and neutralized with saturated sodium hydrogen carbonate solution to adjust to pH=7 to obtain the desired product.

$^1$H NMR (DMSO-$d_6$) δ: 11.40 (s, 1H), 8.12 (t, J=4.0 Hz, 2H), 7.49-7.31 (m, 8H), 3.08 (br. s., 4H), 2.26 (s, 3H), 1.67-1.50 (m, 6H). LC-MS: m/z 485.2 (M+H)$^+$.

Compound 300

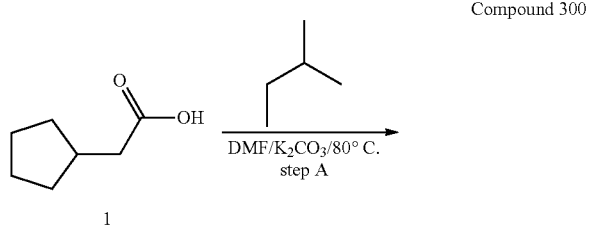

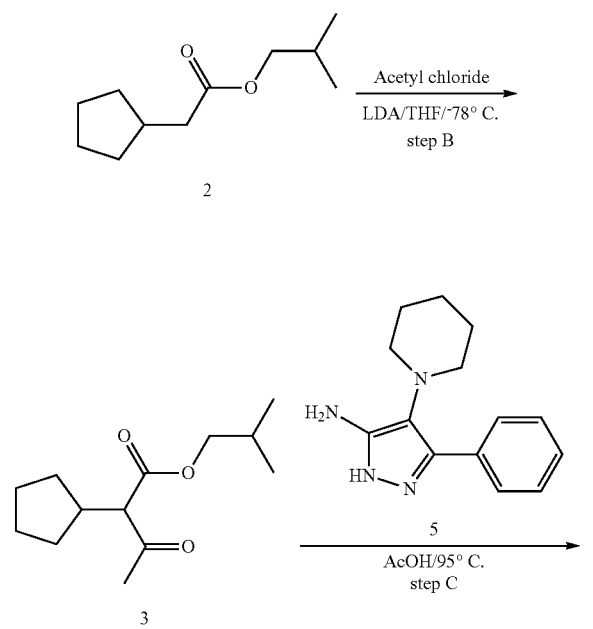

372

-continued

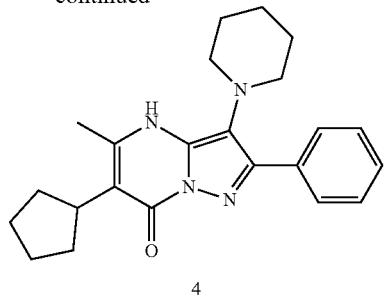

Step A: isobutyl 2-cyclopentylacetate

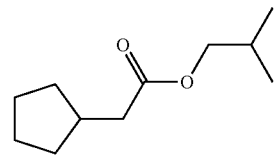

A mixture of 2-cyclopentylacetic acid (1 g, 7.8 mmol), 1-iodo-2-methylpropane (1.7 g, 9.36 mmol) and Cs$_2$CO$_3$ (5.1 g, 15.6 mmol) in DMF (40 mL) was stirred at 80° C. for 16 h. The mixture was poured slowly into saturated NH$_4$Cl and extracted with EA (3*100 mL). The combined organic phase was washed with brine, dried over anhydrous MgSO$_4$, filtered and concentrated in vacuo. The residue was purified by flash chromatography to afford the desired isobutyl 2-cyclopentylacetate (988 mg) as a colorless oil.

Step B: isobutyl 2-cyclopentyl-3-oxobutanoate

To a solution of 2-cyclopropylacetate (988 mg, 6.33 mmol) in THF (10 mL) was added LDA (1.5 M in THF, 4.6 mL, 6.96 mmol) dropwise at −78° C. The mixture was stirred at −78° C. for 30 min, and acetyl chloride (1.86 g, 23.72 mmol) was added dropwise. Then the mixture was stirred at rt for 4 h. The mixture was poured slowly into saturated NH$_4$Cl and extracted with EA (3*20 mL). The combined organic phase was washed with brine, dried over anhydrous MgSO$_4$, filtered and concentrated in vacuo. The residue was purified by flash chromatography to afford the desired isobutyl 2-cyclopentyl-3-oxobutanoate (700 mg) as a colorless oil.

Step C: Compound 300: 6-cyclopentyl-5-methyl-2-phenyl-3-(piperidin-1-yl)pyrazolo[1,5-a]pyrimidin-7(4H)-one

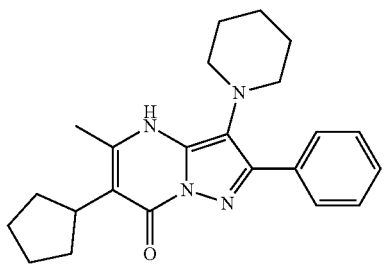 [SMILES: Cc1[nH]c2c(N3CCCCC3)c(-c3ccccc3)nn2c(=O)c1C1CCCC1]

2-cyclopentyl-3-oxobutanoate (467 mg, 2.06 mmol) and 3-phenyl-4-(piperidin-1-yl)-1H-pyrazol-5-amine (250 mg, 1.03 mmol) were dissolved in AcOH (10 mL). The mixture was warmed to 95° C. for 4 h. After cooling to room temperature, the solids were collected by filtration and washed with EtOAc to afford 6-cyclopentyl-5-methyl-2-phenyl-3-(piperidin-1-yl)pyrazolo[1,5-a]pyrimidin-7(4H)-one (120 mg).

$^1$H NMR (400 MHz, DMSO-$d_6$) δ: 10.98 (br. s., 1H), 8.06-8.17 (m, 2H), 7.43-7.49 (m, 2H), 7.36-7.41 (m, 1H), 3.03-3.07 (m, 4H), 2.46 (s, 3H), 1.92-2.05 (m, 3H), 1.84 (br. s., 2H), 1.54-1.74 (m, 10H). LC-MS: m/z 377.6 (M+H)$^+$.

Compound 301

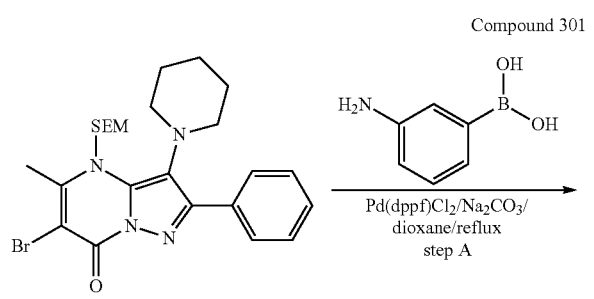

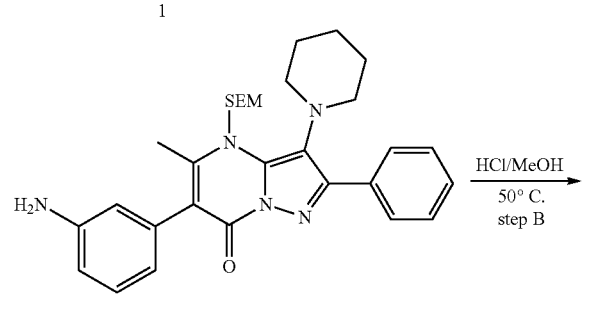

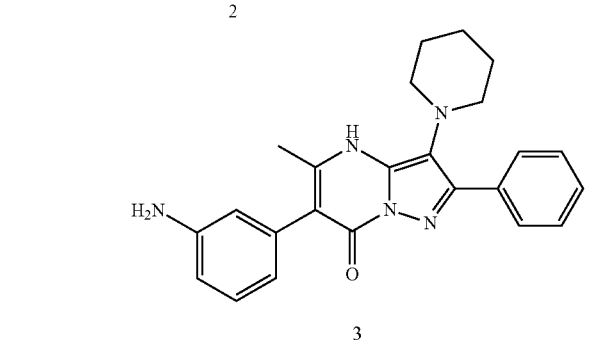

Step A: 6-(3-aminophenyl)-5-methyl-2-phenyl-3-(piperidin-1-yl)-4-((2-(trimethylsilyl)ethoxy)methyl)pyrazolo[1,5-a]pyrimidin-7(4H)-one

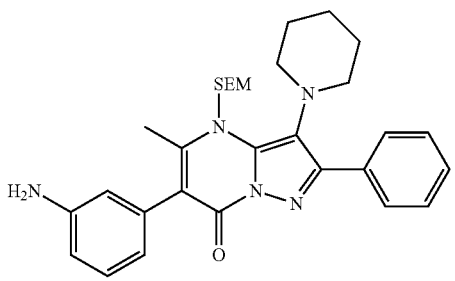 [SMILES: Cc1c(-c2cccc(N)c2)c(=O)n2nc(-c3ccccc3)c(N3CCCCC3)c2n1COCC[Si](C)(C)C]

To a solution of 6-bromo-5-methyl-2-phenyl-3-(piperidin-1-yl)-4-((2-(trimethylsilyl)ethoxy)methyl)pyrazolo[1,5-a]pyrimidin-7(4H)-one (Synthesized in scheme of Compound 305, 100 mg, 0.194 mmol) and (3-aminophenyl)boronic acid (53 mg, 0.386 mmol) in dioxane/H$_2$O (5 mL/1 mL) was added 1,1'-Bis(diphenylphosphino)ferrocene-palladium(II)dichloride dichloromethane complex (28 mg, 0.0344 mmol) and sodium carbonate (42 mg, 0.396 mmol). The reaction mixture was then refluxed under nitrogen atmosphere overnight. The reaction mixture was filtered and concentrated in vacuo. The residue was purified by column chromatography (methanol:dichloromethane=1/20) to afford 5-methyl-6-(4-(methylsulfonyl)phenyl)-2-phenyl-3-(piperidin-1-yl)-4-((2-(trimethylsilyl)ethoxy)methyl)pyrazolo[1,5-a]pyrimidin-7(4H)-one (35 mg, 34.3% yield) as a white solid. LC-MS: m/z 530.1 (M+H)$^+$.

Step B: Compound 301: 6-(3-aminophenyl)-5-methyl-2-phenyl-3-(piperidin-1-yl)pyrazolo[1,5-a]pyrimidin-7(4H)-one A mixture of 6-(3-aminophenyl)-5-methyl-2-phenyl-3-(piperidin-1-yl)-4-((2-(trimethylsilyl)ethoxy)methyl)pyrazolo[1,5-a]pyrimidin-7(4H)-on (35 mg, 0.1 mmol) in CF$_3$COOH (2 mL) was heated to 60° C. for 3 h. The mixture was cooled to room temperature and concentrated in vacuo to afford 6-(3-aminophenyl)-5-methyl-2-phenyl-3-(piperidin-1-yl)pyrazolo[1,5-a]pyrimidin-7(4H)-one.

$^1$H NMR (DMSO-$d_6$) δ: 11.33 (br. s., 1H), 8.12 (d, J=7.25 Hz, 2H), 7.44-7.50 (m, 2H), 7.41 (d, J=7.25 Hz, 1H), 7.06 (t, J=7.66 Hz, 1H), 6.55 (d, J=8.60 Hz, 1H), 6.48 (s, 1H), 6.41 (d, J=7.52 Hz, 1H), 5.08 (br. s., 2H), 3.09 (br. s., 4H), 2.25 (s, 3H), 1.66 (br. s., 4H), 1.59 (br. s., 2H). LC-MS: m/z 400.5 (M+H)$^+$.

Compound 302

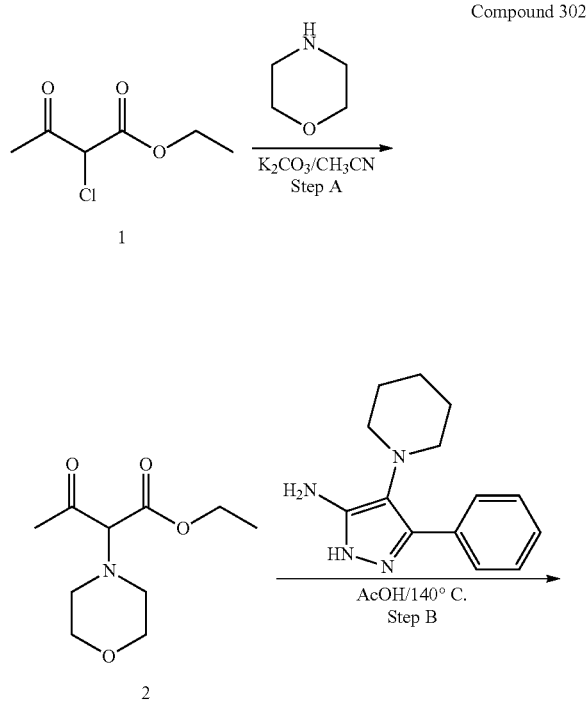

Step A: ethyl 2-morpholino-3-oxobutanoate

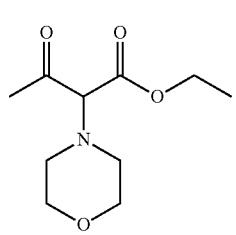

To the solution of morpholine (0.95 g, 27 mmol) in CH$_3$CN (20 mL) and K$_2$CO$_3$ (3.01 g, 54 mmol) and added dropwise ethyl 2-chloro-3-oxobutanoate (2 g, 27 mmol) over 2 h. After addition, The mixture was concentrated and purified by silica gel chromatography (PE/EA=5/1) to get ethyl 2-morpholino-3-oxobutanoate (1.5 g). LC-MS: m/z 216.3 (M+H)$^+$.

Step B: Compound 302: 5-methyl-6-morpholino-2-phenyl-3-(piperidin-1-yl)pyrazolo[1,5-a]pyrimidin-7(4H)-one

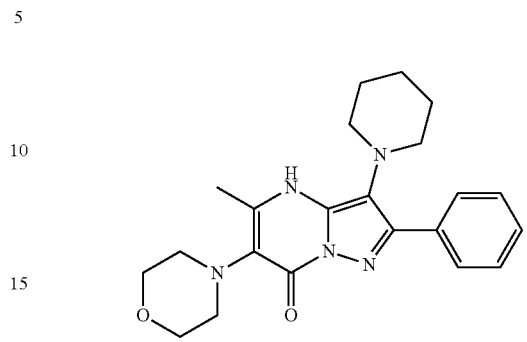

A solution of methyl ethyl 2-morpholino-3-oxobutanoate (500 mg, 2.3 mmol), 3-phenyl-4-(piperidin-1-yl)-1H-pyrazol-5-amine (565 mg, 2.3 mmol) in AcOH (20 ml) and xylene (20 mL) was heated to 140° C. for 16 h. The reaction mixture was concentrated to afford 5-methyl-6-morpholino-2-phenyl-3-(piperidin-1-yl)pyrazolo[1,5-a]pyrimidin-7(4H)-one.

$^1$H NMR (DMSO-d$_6$) δ: 7.97 (br. s., 2H), 7.43 (d, J=6.7 Hz, 2H), 3.87 (br. s., 2H), 3.81 (br. s., 2H), 3.74 (br. s., 2H), 3.00 (br. s., 4H), 2.54 (s, 5H), 1.68 (br. s., 4H), 1.54 (br. s., 2H). LC-MS: m/z 394.3 (M+H)$^+$.

Compound 303

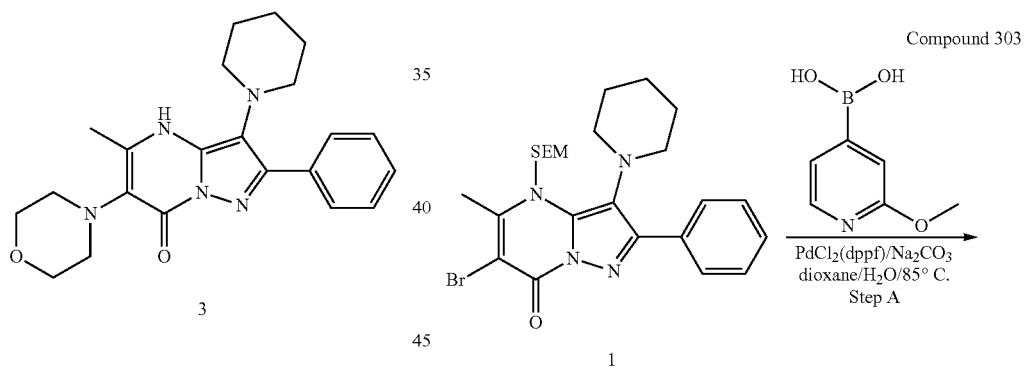

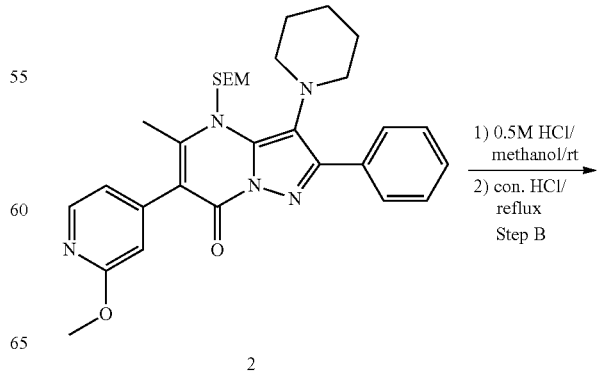

-continued

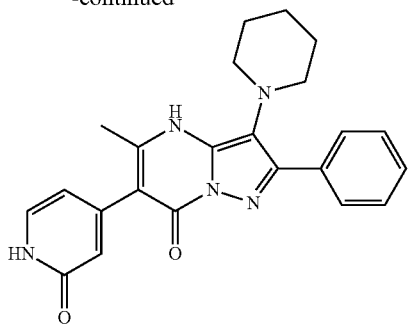

3

Step A: 6-(2-methoxypyridin-4-yl)-5-methyl-2-phenyl-3-(piperidin-1-yl)-4-((2-(trimethylsilyl)ethoxy)methyl)pyrazolo[1,5-a]pyrimidin-7(4H)-one

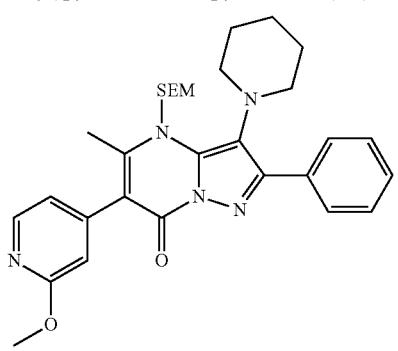 [SMILES: COc1cc(-c2c(C)n(COCC[Si](C)(C)C)c3c(N4CCCCC4)c(-c4ccccc4)nn3c2=O)ccn1]

A suspension of 6-bromo-5-methyl-2-phenyl-3-(piperidin-1-yl)-4-((2-(trimethylsilyl)ethoxy)methyl)pyrazolo[1,5-a]pyrimidin-7(4H)-one (Synthesized in scheme of Compound 305, 200 mg, 0.39 mmol) and 2-methoxypyridin-4-ylboronic acid (178 mg, 1.16 mmol), PdCl$_2$(dppf) (28 mg, 0.04 mmol) and Na$_2$CO$_3$ (82 mg, 0.78 mmol) in 1,4-dioxane/water (10 mL/1 mL) was stirred and heated to 85° C. for 16 h under N$_2$ atmosphere. The reaction was then cooled to RT and filtered. The dark filtrate was concentrated in vacuo. The residue was purified by flash column chromatography, eluting with PE/EA (4/1), to get desired product (40 mg, 18% yield) as a white solid. LC-MS: m/z 546.3 (M+H)$^+$.

Step B: 5-methyl-6-(2-oxo-1,2-dihydropyridin-4-yl)-2-phenyl-3-(piperidin-1-yl)pyrazolo[1,5-a]pyrimidin-7(4H)-one

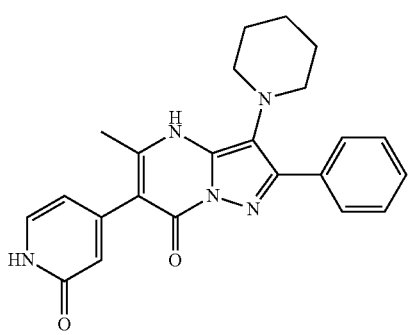 [SMILES: Cc1[nH]c2c(N3CCCCC3)c(-c3ccccc3)nn2c(=O)c1-c1cc[nH]c(=O)c1]

The mixture of 6-(2-methoxypyridin-4-yl)-5-methyl-2-phenyl-3-(piperidin-1-yl)-4-((2-(trimethylsilyl)ethoxy)methyl)pyrazolo[1,5-a]pyrimidin-7(4H)-one (40 mg, 0.07 mmol) and HCl in MeOH (0.5 mol, 1 mL, 0.5 mmol) was stirred at RT for 1 h. The mixture was then concentrated to dryness. The residue was dissolved into con. hydrochloric acid (10 mL) and stirred at 100° C. for 72 h. The reaction mixture was concentrated to afford the desired product.

$^1$H NMR (DMSO-d$_6$) δ: 11.20 (br. s., 1H), 8.30 (d, J=7.2 Hz, 2H), 7.41-7.37 (m, 2H), 7.30-7.22 (m, 2H), 6.21 (t, J=2.0 Hz, 2H), 3.19 (br. s., 4H), 2.33 (s, 3H), 1.62-1.50 (m, 6H). LC-MS: m/z 402.2 (M+H)$^+$.

Compound 304

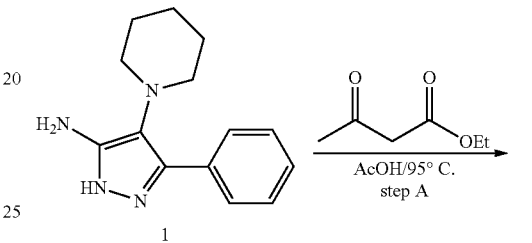

1

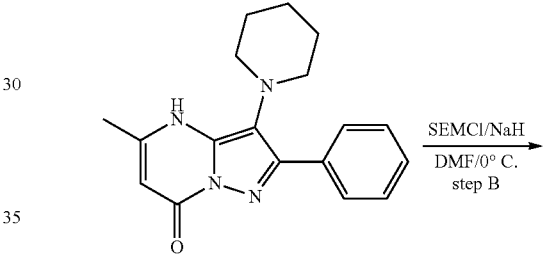

2

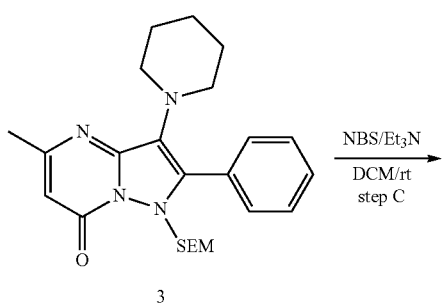

3

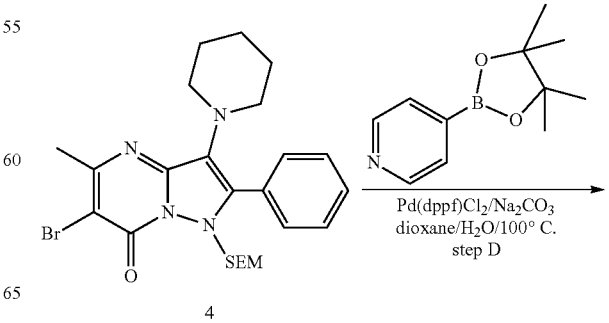

4

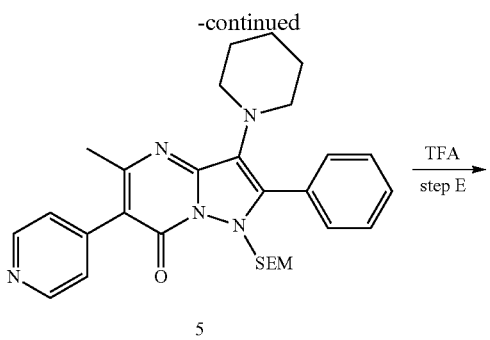

5

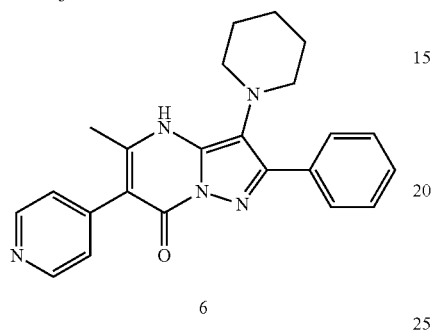

6

Step A: 5-methyl-2-phenyl-3-(piperidin-1-yl)pyrazolo[1,5-a]pyrimidin-7(4H)-one

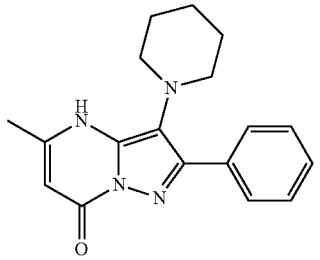 [SMILES: Cc1cc(=O)n2nc(-c3ccccc3)c(N3CCCCC3)c2[nH]1]

A mixture of ethyl 3-oxobutanoate (18.7 g, 0.143 mol) and 3-phenyl-4-(piperidin-1-yl)-1H-pyrazol-5-amine (synthesized in scheme of Compound 305, 17.5 g, 0.072 mol) in AcOH (100 mL) was stirred at 95° C. for 4 h. After cooling to room temperature, the solids were collected by filtration, washed with ethyl acetate, and dried under vacuum to give 5-methyl-2-phenyl-3-(piperidin-1-yl)pyrazolo[1,5-a]pyrimidin-7(4H)-one (15 g, 68% yield) as a white solid. LC-MS: m/z 309.1 (M+H)⁺.

Step B: 5-methyl-2-phenyl-3-(piperidin-1-yl)-1-((2-(trimethylsilyl)ethoxy)methyl)pyrazolo[1,5-a]pyrimidin-7(1H)-one

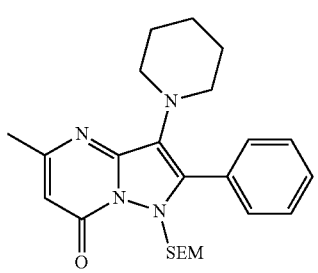 [SMILES: Cc1cc(=O)n2c(n1)c(N1CCCCC1)c(-c1ccccc1)n2COCC[Si](C)(C)C]

To a solution of 5-methyl-2-phenyl-3-(piperidin-1-yl)pyrazolo[1,5-a]pyrimidin-7(4H)-one (synthesized in scheme of Compound 305, 6.5 g, 21.1 mmol) in dry DMF (50 mL) was added NaH (60% dispersion in mineral oil, 1.7 g, 42.5 mmol) in portion at 0° C. After addition, the mixture was stirred at 0° C. for 1 h. Then the SEM-Cl (5.3 g, 31.7 mmol) was added, and the mixture was warmed to room temperature and stirred overnight. The reaction mixture was poured into water (200 mL) and extract with EtOAc (3*200 mL). The combined organic layers were washed with water (2*300 mL) and brine (300 mL), and concentrated under reduced pressure. The residue was purified by column chromatography on silica gel (ethyl acetate:PE=2:1) to get the title compound (3.8 g, 410% yield) as a white solid. LC-MS: m/z 439.1 (M+H)⁺.

Step C: 6-bromo-5-methyl-2-phenyl-3-(piperidin-1-yl)-1-((2-(trimethylsilyl)ethoxy)methyl)pyrazolo[1,5-a]pyrimidin-7(1H)-one

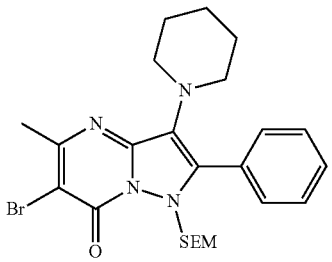 [SMILES: Cc1nc2c(N3CCCCC3)c(-c3ccccc3)n(COCC[Si](C)(C)C)n2c(=O)c1Br]

To a solution of 5-methyl-2-phenyl-3-(piperidin-1-yl)-1-((2-(trimethylsilyl)ethoxy)methyl)pyrazolo[1,5-a]pyrimidin-7(1H)-one (3.4 g, 7.76 mmol) in DCM (30 mL) were added NBS (1.3 g, 7.76 mmol) and Et₃N (0.82 g, 7.76 mmol). The resulting mixture was stirred at ambient temperature for 3 hours. Then the mixture was washed with water (30 mL), and the aqueous layer was extracted with DCM (30 mL). The combined organic layers were washed with brine (30 mL), dried over anhydrous sodium sulfate, and concentrated invacuo. The residue was purified by column chromatography on silica gel (ethyl acetate:PE=2:1) to get the title compound (3.1 g, 78% yield) as a white solid. LC-MS: m/z 517.2 (M+H)⁺.

Step D: 5-methyl-2-phenyl-3-(piperidin-1-yl)-6-(pyridin-4-yl)-1-((2-(trimethylsilyl)ethoxy)methyl)pyrazolo[1,5-a]pyrimidin-7(1H)-one

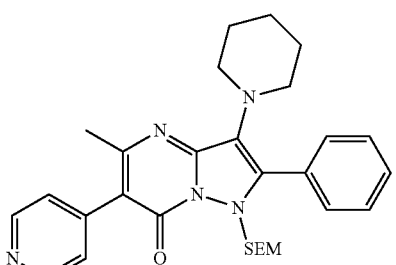

A mixture of 6-bromo-5-methyl-2-phenyl-3-(piperidin-1-yl)-1-((2-(trimethylsilyl)ethoxy)methyl)pyrazolo[1,5-a]pyrimidin-7(1H)-one (100 mg, 0.19 mmol), 4-(4,4,5,5-tetramethyl-1,3,2-dioxaborolan-2-yl)pyridine (59 mg, 0.288 mmol), Pd(dppf)Cl₂ (21 mg, 0.029 mmol) and Na₂CO₃ (41 mg, 0.386 mmol) in 1.4-dioxane (5 mL) and H₂O (0.5 mL) was stirred at 100° C. for 2 h under N₂. The reaction mixture was then cooled to r.t. and filtered. The filtrate was concentrated in vacuo and purified by prep TLC to obtain 5-methyl-2-phenyl-3-(piperidin-1-yl)-6-(pyridin-4-yl)-1-((2-(trimethylsilyl)ethoxy)methyl)pyrazolo[1,5-a]pyrimidin-7(1H)-one (50 mg) as a white solid. LC-MS: m/z 516.0 (M+H)⁺.

Step E: Compound 304: 5-methyl-2-phenyl-3-(piperidin-1-yl)-6-(pyridin-4-yl)pyrazolo[1,5-a]pyrimidin-7(4H)-one

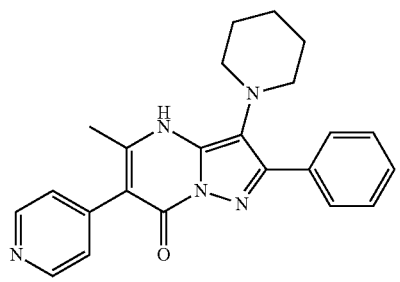 [SMILES: Cc1[nH]c2c(N3CCCCC3)c(-c3ccccc3)nn2c(=O)c1-c1ccncc1]

To a solution of 5-methyl-2-phenyl-3-(piperidin-1-yl)-6-(pyridin-4-yl)-1-((2-(trimethylsilyl)ethoxy)methyl)pyrazolo[1,5-a]pyrimidin-7(1H)-one (50 mg, 0.097 mmol) in DCM (3 mL) was added TFA (1 mL). The mixture was stirred at ambient temperature for 2 h. Then the mixture was concentrated to dryness. The residue was stirred with saturated sodium hydrogen carbonate solution to get the title compound.

¹H NMR (400 MHz, DMSO-d₆) δ: 8.50 (br. s., 2H), 8.26 (d, J=7.25 Hz, 2H), 7.39-7.45 (m, 2H), 7.35-7.38 (m, 2H), 7.28-7.34 (m, 1H), 3.18 (br. s., 4H), 2.22 (s, 3H), 1.61-1.66 (m, 4H), 1.52-1.57 (m, 2H). LC-MS: m/z 386.1 (M+H)⁺.

Compound 305

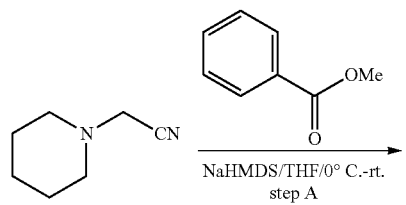

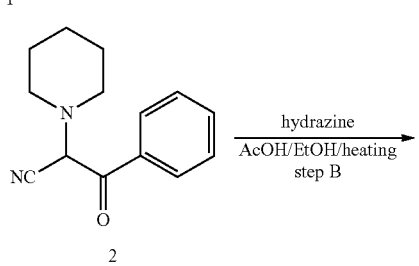

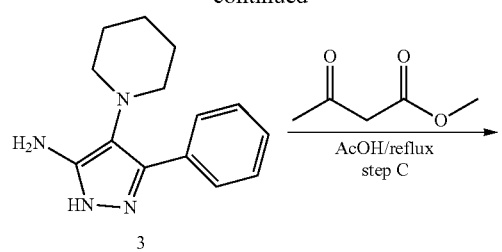

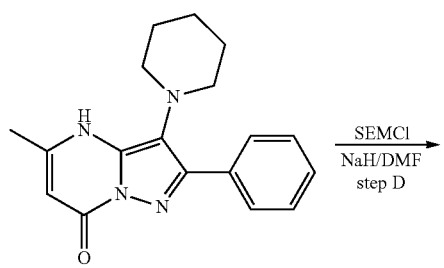

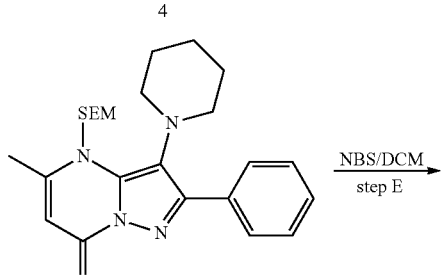

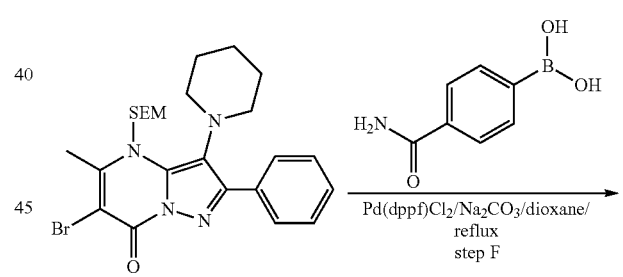

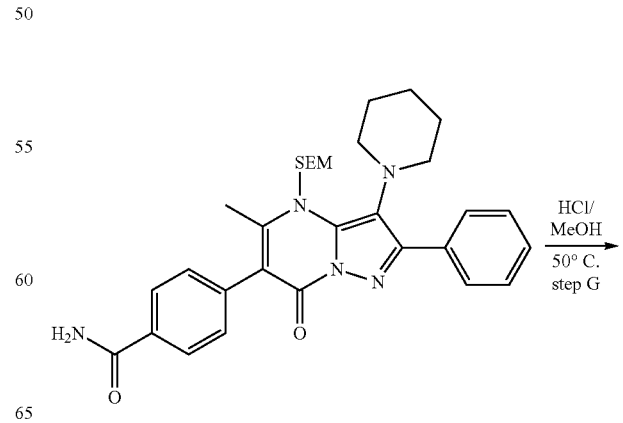

-continued

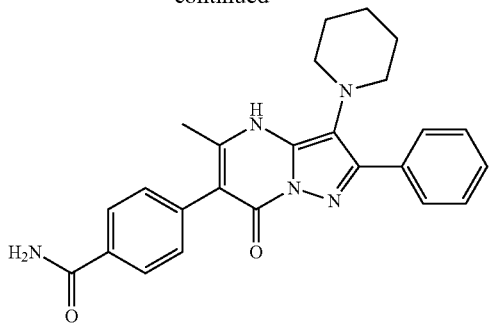

8

Step A:
3-oxo-3-phenyl-2-(piperidin-1-yl)propanenitrile

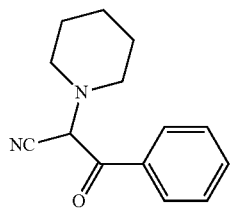 [SMILES: N#CC(C(=O)c1ccccc1)N1CCCCC1]

To a mixture of 2-(piperidin-1-yl)acetonitrile (7.8 g, 62 mmol) and methyl benzoate (9.4 g, 68 mmol) in THF (200 mL) was added NaHMDS (2M in THF, 46 mL, 1.2 eq.) at 0° C. The mixture was stirred at r.t. overnight. The reaction mixture was diluted with EA (300 mL) and quenched with saturated NH$_4$Cl. The organic phase was separated, washed with brine, dried over anhydrous Na$_2$SO$_4$ and concentrated in vacuo. The residue was purified by flash chromatography to afford the desired 3-oxo-3-phenyl-2-(piperidin-1-yl)propanenitrile as a white solid. LC-MS: m/z 229.1 (M+H)$^+$.

Step B: 3-phenyl-4-(piperidin-1-yl)-1H-pyrazol-5-amine

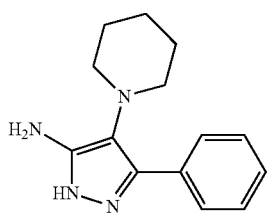 [SMILES: Nc1[nH]nc(-c2ccccc2)c1N1CCCCC1]

The mixture of 3-oxo-3-phenyl-2-(piperidin-1-yl)propanenitrile (5 g, 21.902 mmol) and hydrazine (3.3 g, 65.706 mmol) in EtOH/AcOH (5/1, 30 mL/6 mL) was refluxed for 16 h. Then the mixture was cooled to r.t. and evaporated. The residue was dissolved in EA (50 mL) and neutralized with 10% NaHCO$_3$. The organic phase was separated, and the water phase was extracted with EA (50 mL*2). The combined organic phase was washed with brine, dried over anhydrous Na$_2$SO$_4$ and concentrated in vacuo. The residue was purified by flash chromatography on silica gel (PE/EA=1/3) to afford 3-phenyl-4-(piperidin-1-yl)-1H-pyrazol-5-amine (2.2 g) as a white solid.

$^1$H NMR (DMSO-d$_6$) δ: 11.52 (br. s., 1H), 7.82 (br. s., 2H), 7.36 (t, J=7.2 Hz, 2H), 7.25 (d, J=7.3 Hz, 1H), 4.28 (br. s., 2H), 2.88 (t, J=5.0 Hz, 3H), 1.55 (br. s., 3H), 1.46 (d, J=4.0 Hz, 2H). LC-MS: m/z 243.2 (M+H)$^+$.

Step C: 5-methyl-2-phenyl-3-(piperidin-1-yl)pyrazolo[1,5-a]pyrimidin-7(4H)-one

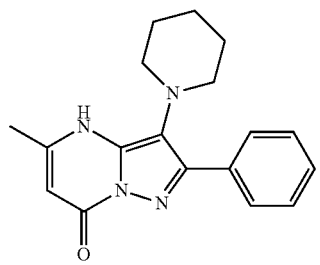 [SMILES: Cc1cc(=O)n2nc(-c3ccccc3)c(N3CCCCC3)c2[nH]1]

A mixture of 3-phenyl-4-(piperidin-1-yl)-1H-pyrazol-5-amine (8.43 g, 34.8 mmol) and methyl 3-oxobutanoate (9 g, 69.2 mmol) in acetic acid (5 mL) was heated to reflux for 2 h. The mixture was cooled to room temperature. The suspension was filtered off. The resulting solid was washed with water and cold methanol to afford 5-methyl-2-phenyl-3-(piperidin-1-yl)pyrazolo[1,5-a]pyrimidin-7(4H)-one (7.9 g, 74% yield) as a white solid. LC-MS: m/z 309.2 (M+H)$^+$.

Step D: 5-methyl-2-phenyl-3-(piperidin-1-yl)-4-((2-(trimethylsilyl)ethoxy)methyl) pyrazolo [1,5-a]pyrimidin-7(4H)-one

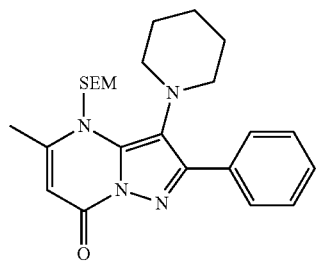 [SMILES: Cc1cc(=O)n2nc(-c3ccccc3)c(N3CCCCC3)c2n1COCC[Si](C)(C)C]

To a mixture of 5-methyl-2-phenyl-3-(piperidin-1-yl)pyrazolo[1,5-a] pyrimidin-7(4H)-one (5.5 g, 17.9 mmol) in N,N-dimethylformamide (50 mL) was added sodium hydride (1.4 g, 35.8 mmol) slowly at 0° C. After addition, the mixture was stirred at 0° C. for 1 h. (2-(Chloromethoxy)ethyl)trimethylsilane (3.6 g, 21.7 mmol) was added. The resulting mixture was stirred at room temperature overnight. The mixture was quenched with brine and extracted with ethyl acetate (50 mL) three times. The combined organic phase was washed with brine, dried over anhydrous sodium sulfate and concentrated in vacuo to dryness. The residue was purified by column chromatography (methanol:dichloromethane=1:20) to afford 5-methyl-2-phenyl-3-(piperidin-1-yl)-4-((2-(trimethylsilyl)ethoxy)methyl)pyrazolo[1,5-a]pyrimidin-7(4H)-one (2.5 g, 35% yield) as a white solid. LC-MS: m/z 439.2 (M+H)$^+$.

Step E: 6-bromo-5-methyl-2-phenyl-3-(piperidin-1-yl)-4-((2-(trimethylsilyl)ethoxy)methyl) pyrazolo[1,5-a]pyrimidin-7(4H)-one

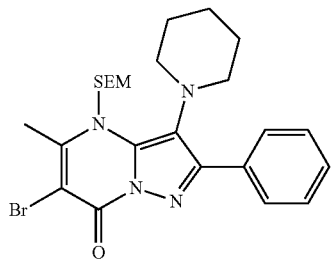 [SMILES: Cc1c(Br)c(=O)n2nc(-c3ccccc3)c(N3CCCCC3)c2n1COCC[Si](C)(C)C]

To a mixture of 5-methyl-2-phenyl-3-(piperidin-1-yl)-4-((2-(trimethylsilyl)ethoxy)-methyl)pyrazolo[1,5-a]pyrimidin-7(4H)-one (1.2 g, 2.74 mmol) and triethylamine (0.32 g, 3.16 mmol) in dichloromethane (20 mL) at room temperature was added N-bromosuccinimide (0.58 g, 3.47 mmol) at room temperature. Then the mixture was stirred at room temperature for 2 h. The mixture was concentrated. The residue was purified by column chromatography (methanol:dichloromethane=1:20) to afford 6-bromo-5-methyl-2-phenyl-3-(piperidin-1-yl)-4-((2-(trimethylsilyl)ethoxy)methyl)pyrazolo[1,5-a]pyrimidin-7(4H)-one (1.3 g, 80% yield) as a white solid. LC-MS: m/z 519.2, 517.2 (M+H)$^+$.

Step F: 4-(5-methyl-7-oxo-2-phenyl-3-(piperidin-1-yl)-4-((2-(trimethylsilyl)ethoxy) methyl)-4,7-dihydropyrazolo[1,5-a]pyrimidin-6-yl)benzamide

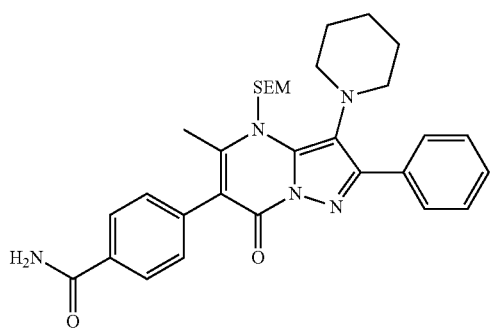 [SMILES: Cc1c(-c2ccc(C(N)=O)cc2)c(=O)n2nc(-c3ccccc3)c(N3CCCCC3)c2n1COCC[Si](C)(C)C]

To a solution of 6-bromo-5-methyl-2-phenyl-3-(piperidin-1-yl)-4-((2-(trimethylsilyl)ethoxy)methyl)pyrazolo[1,5-a]pyrimidin-7(4H)-one (100 mg, 0.194 mmol) and (4-carbamoylphenyl)boronic acid (48.3 mg, 0.293 mmol) in dioxane/H$_2$O (5 mL/1 mL) was added 1,1'-Bis(diphenylphosphino)ferrocene-palladium(II)dichloride dichloromethane complex (28 mg, 0.0344 mmol) and sodium carbonate (42 mg, 0.396 mmol). The reaction mixture was then refluxed under nitrogen atmosphere overnight. The reaction mixture was filtered and concentrated in vacuo. The residue was purified by column chromatography (methanol:dichloromethane=1/20) to afford 4-(5-methyl-7-oxo-2-phenyl-3-(piperidin-1-yl)-4-((2-(trimethylsilyl)ethoxy)methyl)-4,7-dihydropyrazolo[1,5-a]pyrimidin-6-yl)benzamide (60 mg, 55% yield) as a white solid. LC-MS: m/z 558.3 (M+H)$^+$.

Step G: Compound 305: 4-(5-methyl-7-oxo-2-phenyl-3-(piperidin-1-yl)-4,7-dihydropyrazolo[1,5-a]pyrimidin-6-yl)benzamide

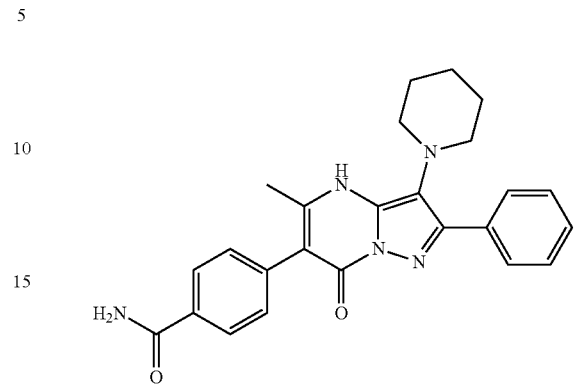

A mixture of 4-(5-methyl-7-oxo-2-phenyl-3-(piperidin-1-yl)-4-((2-(trimethylsilyl)ethoxy)methyl)-4,7-dihydropyrazolo[1,5-a]pyrimidin-6-yl)benzamide (60 mg, 0.11 mmol) in CF$_3$COOH (2 mL) was heated to 60° C. for 3 h. The mixture was cooled to room temperature and concentrated in vacuo to remove solvent. The resulting residue was washed with saturated aqueous sodium bicarbonate to afford 6-(4-hydroxyphenyl)-5-methyl-2-phenyl-3-(piperidin-1-yl)pyrazolo[1,5-a] pyrimidin-7(4H)-one.

$^1$H NMR (DMSO-d$_6$) δ: 7.96-8.06 (m, J=8.06 Hz, 2H), 7.68 (br. s., 2H), 7.59 (br. s., 3H), 7.46-7.54 (m, J=7.79 Hz, 2H), 3.55 (br. s., 4H), 2.42 (s, 3H), 1.94-2.10 (m, 4H), 1.59 (br. s., 2H). LC-MS: m/z 428.3 (M+H)$^+$.

Compound 306

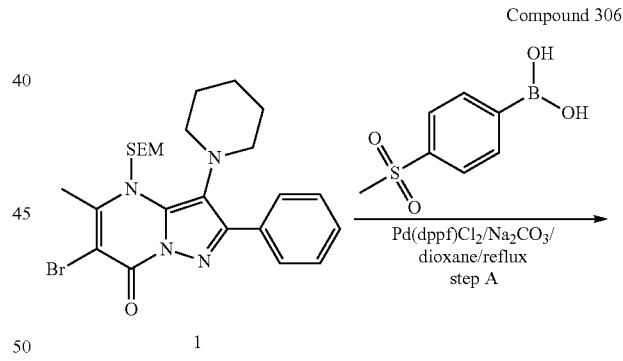

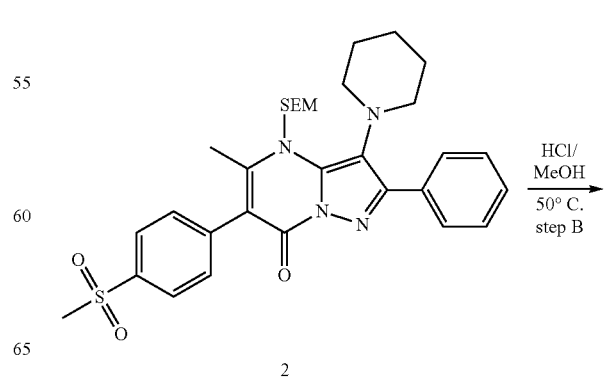

-continued

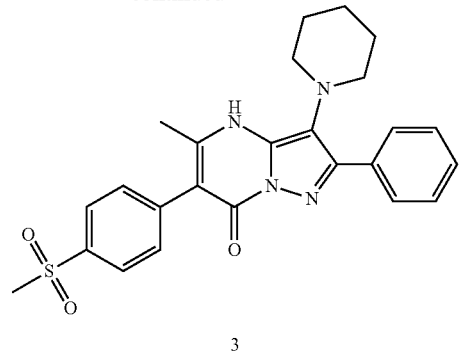

3

Step A: 5-methyl-6-(4-(methylsulfonyl)phenyl)-2-phenyl-3-(piperidin-1-yl)-4-((2-(trimethylsilyl)ethoxy)methyl)pyrazolo[1,5-a]pyrimidin-7(4H)-one

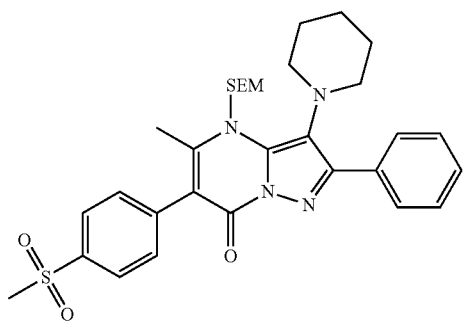 [SMILES: Cc1c(-c2ccc(S(C)(=O)=O)cc2)c(=O)n2nc(-c3ccccc3)c(N3CCCCC3)c2n1COCC[Si](C)(C)C]

To a solution of 6-bromo-5-methyl-2-phenyl-3-(piperidin-yl)-4-((2-(trimethylsilyl)ethoxy)methyl)pyrazolo[1,5-a]pyrimidin-7(4H)-one (Synthesized in scheme of Compound 305, 100 mg, 0.194 mmol) and (4-(methylsulfonyl)phenyl) boronic acid (78 mg, 0.386 mmol) in dioxane/H₂O (5 mL/1 mL) was added 1,1'-Bis(diphenylphosphino)ferrocene-palladium(II)dichloride dichloromethane complex (28 mg, 0.0344 mmol) and sodium carbonate (42 mg, 0.396 mmol). The reaction mixture was then refluxed under nitrogen atmosphere overnight. The reaction mixture was filtered and concentrated in vacuo. The residue was purified by column chromatography (methanol:dichloromethane=1/20) to afford 5-methyl-6-(4-(methylsulfonyl)phenyl)-2-phenyl-3-(piperidin-1-yl)-4-((2-(trimethylsilyl)ethoxy)methyl)pyrazolo[1,5-a]pyrimidin-7(4H)-one (60 mg, 52.6% yield) as a white solid. LC-MS: m/z 593.3 (M+H)⁺.

Step B: Compound 306: 5-methyl-6-(4-(methylsulfonyl)phenyl)-2-phenyl-3-(piperidin-1-yl)pyrazolo[1,5-a]pyrimidin-7(4H)-one

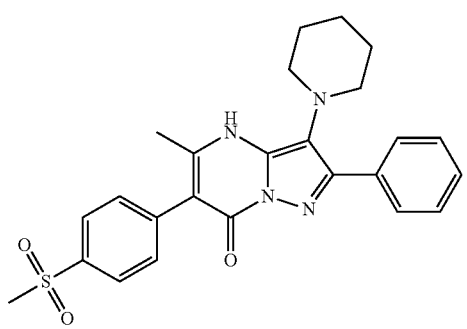 [SMILES: Cc1[nH]c2c(N3CCCCC3)c(-c3ccccc3)nn2c(=O)c1-c1ccc(S(C)(=O)=O)cc1]

A mixture of 5-methyl-6-(4-(methylsulfonyl)phenyl)-2-phenyl-3-(piperidin-1-yl)-4-((2-(trimethylsilyl)ethoxy)methyl)pyrazolo[1,5-a]pyrimidin-7(4H)-one (60 mg, 0.1 mmol) in CF₃COOH (2 mL) was heated to 60° C. for 3 h. The mixture was cooled to room temperature and concentrated in vacuo to remove solvent. The resulting residue was washed with saturated aqueous sodium bicarbonate to afford 5-methyl-6-(4-(methylsulfonyl)phenyl)-2-phenyl-3-(piperidin-1-yl)pyrazolo[1,5-a] pyrimidin-7(4H)-one.

¹H NMR (DMSO-d₆) δ: 8.05 (d, J=7.52 Hz, 2H), 7.44-7.69 (m, 7H), 3.70 (br. s., 2H), 3.33 (d, J=8.33 Hz, 2H), 3.13 (s, 3H), 2.58 (d, J=12.09 Hz, 2H), 2.44 (s, 3H), 1.73-1.97 (m, 3H). LC-MS: m/z 463.2 (M+H)⁺.

Compound 307

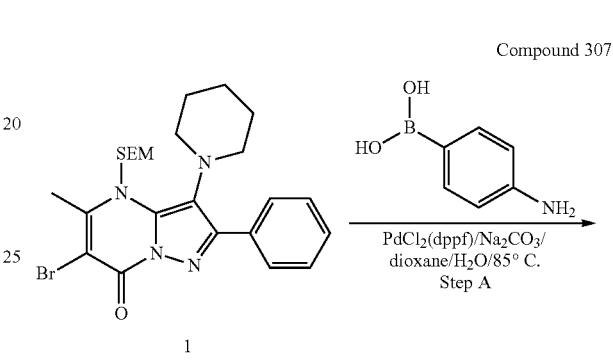

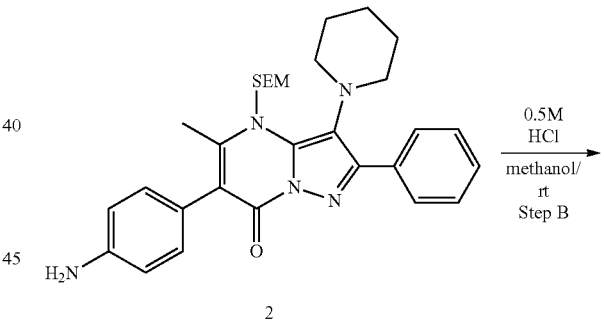

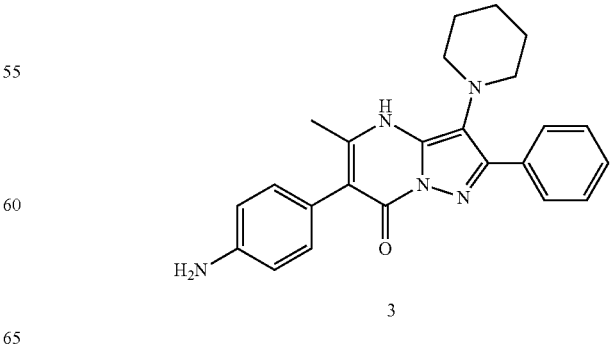

Step A: 6-(4-aminophenyl)-5-methyl-2-phenyl-3-(piperidin-1-yl)-4-((2-(trimethylsilyl)ethoxy)methyl)pyrazolo[1,5-a]pyrimidin-7(4H)-one

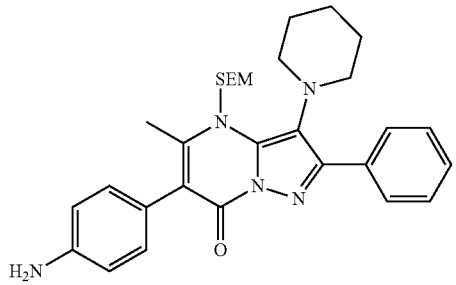 [SMILES: Cc1c(-c2ccc(N)cc2)c(=O)n2nc(-c3ccccc3)c(N3CCCCC3)c2n1COCC[Si](C)(C)C]

A suspension of 6-bromo-5-methyl-2-phenyl-3-(piperidin-1-yl)-4-((2-(trimethylsilyl)ethoxy)methyl)pyrazolo[1,5-a]pyrimidin-7(4H)-one (Synthesized in scheme of Compound 305, 100 mg, 0.19 mmol), 4-aminophenylboronic acid hydrochloric salt (60 mg, 0.58 mmol), PdCl$_2$(dppf) (8.4 mg, 0.02 mmol) and Na$_2$CO$_3$ (55 mg, 0.78 mmol) in 1.4-dioxane/water (10 mL/1 mL) was stirred and heated to 85° C. for 16 h under N$_2$ atmosphere. The reaction was then cooled to RT and filtered. The dark filtrate was concentrated in vacuo. The residue was purified by flash column chromatography, eluting with PE/EA (4/1), to give desired product (30 mg, 29% yield) as a white solid. LC-MS: m/z 530.3 (M+H)$^+$.

Step B: 6-(4-aminophenyl)-5-methyl-2-phenyl-3-(piperidin-1-yl)pyrazolo[1,5-a]pyrimidin-7(4H)-one

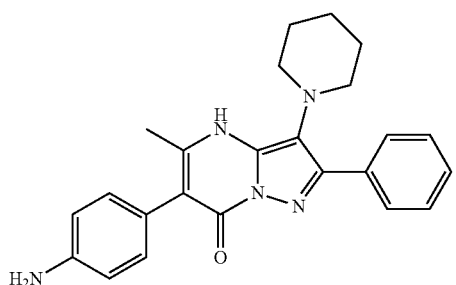

The mixture of tert-butyl 4-(5-methyl-7-oxo-2-phenyl-3-(piperidin-1-yl)-4-((2-(trimethylsilyl)ethoxy)methyl)-4,7-dihydropyrazolo[1,5-a]pyrimidin-6-yl)-1H-pyrazole-1-carboxylate (40 mg, 0.07 mmol) and HCl in MeOH (0.5 mol, 10 mL, 5 mmol) was stirred at RT for 1 h. The mixture was concentrated to afford the desired product.

$^1$H NMR (DMSO-d$_6$) δ: 11.27 (br. s., 1H), 8.12 (d, J=7.2 Hz, 2H), 7.47 (t, J=7.2 Hz, 2H), 7.40 (d, J=7.2 Hz, 1H), 6.93 (t, J=8.4 Hz, 2H), 6.60 (d, J=8.4 Hz, 2H), 5.12 (s, 2H), 3.08 (d, J=4.2 Hz, 4H), 2.26 (s, 3H), 1.62-1.50 (m, 6H). LC-MS: m/z 400.2 (M+H)$^+$.

Compound 308

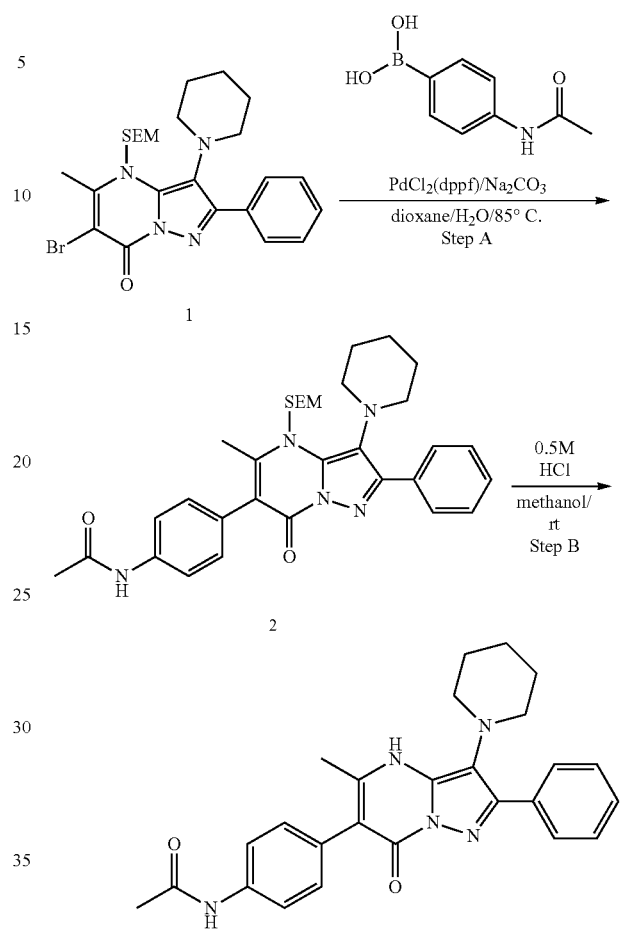

Step A: N-(4-(5-methyl-7-oxo-2-phenyl-3-(piperidin-1-yl)-4-((2-(trimethylsilyl)ethoxy)methyl)-4,7-dihydropyrazolo[1,5-a]pyrimidin-6-yl)phenyl)acetamide

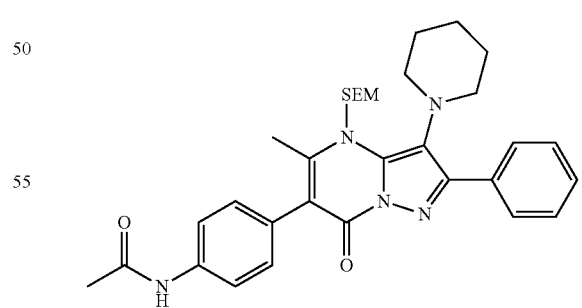

A suspension of 6-bromo-5-methyl-2-phenyl-3-(piperidin-1-yl)-4-((2-(trimethylsilyl)ethoxy)methyl)pyrazolo[1,5-a]pyrimidin-7(4H)-one (Synthesized in scheme of Compound 305, 100 mg, 0.19 mmol) and 4-acetamidophenylboronic acid (100 mg, 0.58 mmol), PdCl$_2$(dppf) (8.4 mg, 0.02 mmol) and Na$_2$CO$_3$ (55 mg, 0.78 mmol) in 1.4-dioxane/water (10 mL/1 mL) was stirred and heated to 85° C. for 16 h under N₂ atmosphere. The reaction was then cooled to RT and filtered. The dark filtrate was concentrated in vacuo The residue was purified by flash column chromatography, eluting with PE/EA (4/1), to give desired product (20 mg, 18% yield) as a white solid. LC-MS: m/z 572.3 (M+H)⁺.

Step B: N-(4-(5-methyl-7-oxo-2-phenyl-3-(piperidin-1-yl)-4,7-dihydropyrazolo[1,5-a]pyrimidin-6-yl)phenyl)acetamide

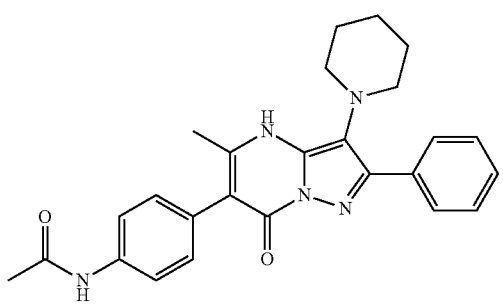 [SMILES: CC(=O)Nc1ccc(-c2c(C)[nH]c3c(N4CCCCC4)c(-c4ccccc4)nn3c2=O)cc1]

The mixture of N-(4-(5-methyl-7-oxo-2-phenyl-3-(piperidin-1-yl)-4-((2-(trimethylsilyl)ethoxy)methyl)-4,7-dihydropyrazolo[1,5-a]pyrimidin-6-yl)phenyl)acetamide (20 mg, 0.03 mmol) and HCl in MeOH (0.5 mol, 10 mL, 5 mmol) was stirred at RT for 1 h to afford the desired product.

¹H NMR (DMSO-d₆) δ: 11.35 (br. s., 1H), 10.02 (br. s., 1H), 8.12 (d, J=7.2 Hz, 2H), 7.62 (d, J=7.2 Hz, 2H), 7.47 (d, J=7.2 Hz, 1H), 7.40 (t, J=7.2 Hz, 1H), 7.22 (d, J=8.4 Hz, 2H), 3.08 (d, J=4.8 Hz, 4H), 2.26 (s, 3H), 2.07 (s, 3H), 1.67-1.50 (m, 6H). LC-MS: m/z 442.3 (M+H)⁺.

Step A: 6-(6-hydroxypyridin-3-yl)-5-methyl-2-phenyl-3-(piperidin-1-yl)pyrazolo[1,5-a]pyrimidin-7(4H)-one

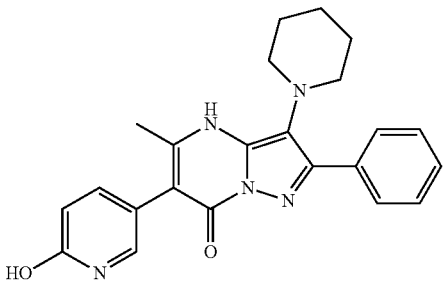 [SMILES: Cc1[nH]c2c(N3CCCCC3)c(-c3ccccc3)nn2c(=O)c1-c1ccc(O)nc1]

The mixture of 6-(6-methoxypyridin-3-yl)-5-methyl-2-phenyl-3-(piperidin-1-yl)pyrazolo[1,5-a]pyrimidin-7(4H)-one (Compound 358, 40 mg, 0.10 mmol) in con. hydrochloric acid (10 mL) was stirred at 100° C. for 48 h to afford the desired product.

¹H NMR (DMSO-d₆) δ: 8.29 (d, J=7.2 Hz, 2H), 7.39 (t, J=8.0 Hz, 3H), 7.26 (d, J=7.2 Hz, 1H), 7.14 (s, 1H), 6.30 (d, J=9.6 Hz, 1H), 3.19 (br. s., 4H), 2.12 (s, 3H), 1.62-1.50 (m, 6H). LC-MS: m/z 402.3 (M+H)⁺.

Compound 310

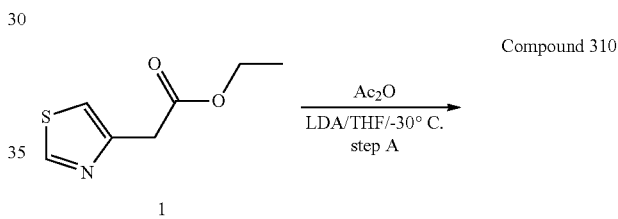

Compound 309

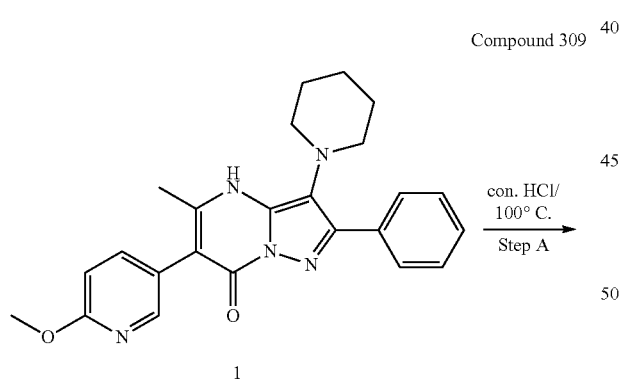

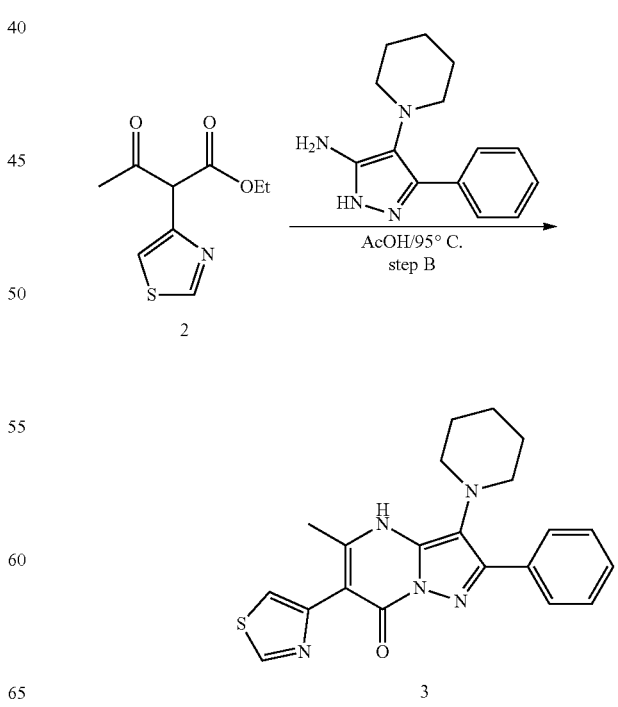

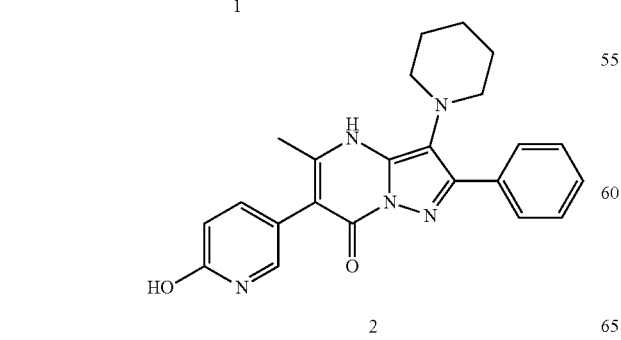

Step A: ethyl 3-oxo-2-(thiazol-4-yl)butanoate

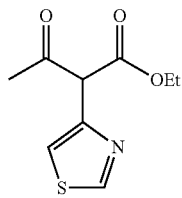

To a solution of ethyl 2-(thiazol-4-yl)acetate (500 mg, 2.92 mmol) in THF (10 mL) was added LDA (1.5 M in THF, 2.3 mL, 3.5 mmol) dropwise at −30~−35° C. The mixture was stirred at −30~−35° C. for 30 min, and acetic anhydride (360 mg, 3.5 mmol) was added dropwise. Then the mixture was warmed to room temperature and stirred for 6 h. The mixture was poured into saturated NH$_4$Cl and extracted with EA (3*10 mL). The combined organic phase was washed with brine, dried over anhydrous MgSO$_4$, filtered and concentrated in vacuo. The residue was purified by flash chromatography to afford the desired ethyl 3-oxo-2-(thiazol-4-yl)butanoate as a brown oil (500 mg, 80% yield).

Step B: Compound 310: 5-methyl-2-phenyl-3-(piperidin-1-yl)-6-(thiazol-4-yl)pyrazolo[1,5-a]pyrimidin-7(4H)-one

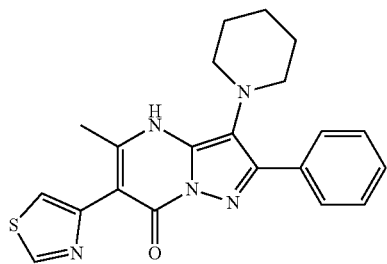 [SMILES: Cc1[nH]c2c(N3CCCCC3)c(-c3ccccc3)nn2c(=O)c1-c1cscn1]

A mixture of 3-oxo-2-(thiazol-4-yl)butanoate (200 mg, 0.94 mmol) and 3-phenyl-4-(piperidin-1-yl)-1H-pyrazol-5-amine (227 mg, 0.94 mmol) in AcOH (5 mL) was stirred at 95° C. for 2 h to give title compound.

$^1$H NMR (400 MHz, DMSO-d$_6$) δ: 11.52 (br. s., 1H), 9.17 (d, J=1.88 Hz, 1H), 8.13 (d, J=6.98 Hz, 2H), 7.82 (d, J=1.88 Hz, 1H), 7.45-7.51 (m, 2H), 7.37-7.44 (m, 1H), 3.08-3.11 (m, 4H), 2.42 (s, 3H), 1.67 (br. s., 4H), 1.56-1.61 (m, 2H). LC-MS: m/z 392.3 (M+H)$^+$.

Compound 311

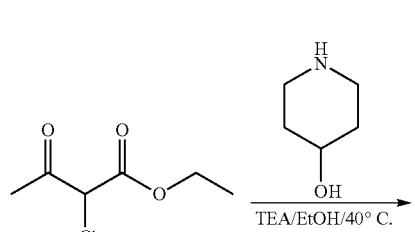

Step A: ethyl 2-(4-hydroxypiperidin-1-yl)-3-oxobutanoate

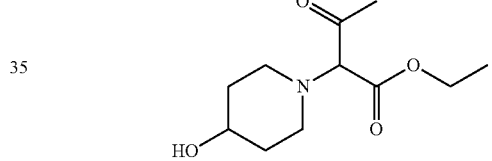

To a solution of piperidin-4-ol (200 mg, 2.0 mmol) and TEA (0.3 mL, 2.4 mmol) in EtOH (10 mL) was added ethyl 2-chloro-3-oxobutanoate (442 mg, 2.4 mmol) dropwise at 0° C. The mixture was stirred at 40° C. for 18 h. The mixture was concentrated and purified by flash column chromatography, eluting with PE/EA (4/1), to get the desired product as a yellow solid (120 mg, 26% yield). LC-MS: m/z 230.2 (M+H)$^+$.

Step B: 6-(4-hydroxypiperidin-1-yl)-5-methyl-2-phenyl-3-(piperidin-1-yl)pyrazolo[1,5-a]pyrimidin-7(4H)-one

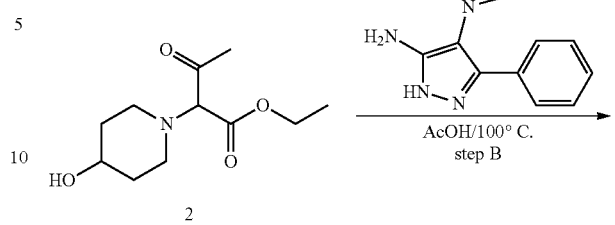

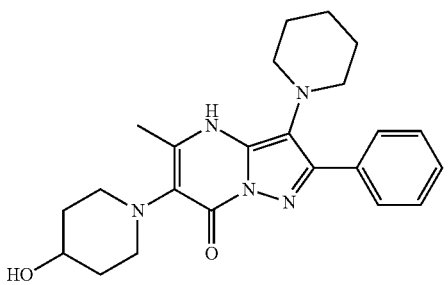 [SMILES: Cc1[nH]c2c(N3CCCCC3)c(-c3ccccc3)nn2c(=O)c1N1CCC(O)CC1]

The mixture of 3,4-diphenyl-1H-pyrazol-5-amine (116 mg, 0.66 mmol) and ethyl 2-(4-hydroxypiperidin-1-yl)-3-oxobutanoate (120 mg, 0.66 mmol) in AcOH (5 mL) was stirred at 100° C. for 1 h. After removal of AcOH, 10% of NaHCO$_3$ was added to afford the desired product.

$^1$H NMR (DMSO-d$_6$) δ: 11.16 (br. s., 1H), 8.08 (d, J=7.2 Hz, 2H), 7.46 (t, J=7.2 Hz, 2H), 7.39 (t, J=7.2 Hz, 1H), 3.42-3.17 (m, 3H), 3.03 (br. s., 4H), 2.68 (br. s., 2H), 2.51 (s, 3H), 1.82-1.79 (m, 2H), 1.64-1.56 (m, 6H), 1.21 (br. s., 2H). LC-MS: m/z 408.6 (M+H)$^+$.

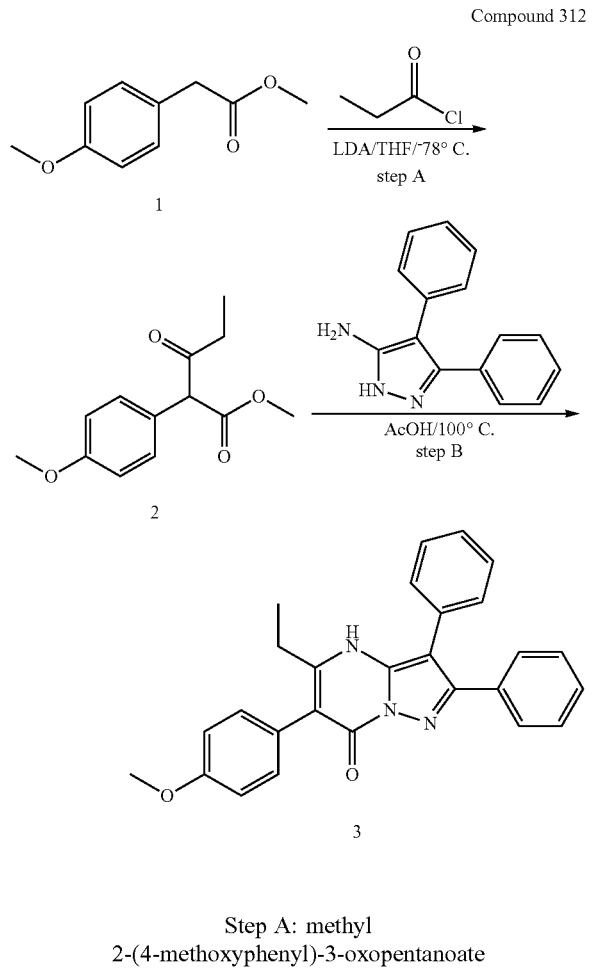

Step A: methyl 2-(4-methoxyphenyl)-3-oxopentanoate

To a solution of methyl 2-(4-methoxyphenyl)-3-oxopentanoate (2.0 g, 11.10 mmol.) in THF (20 mL) was added LDA (2.0 M in THF, 6.6 mL, 13.32 mmol) dropwise at −78° C. The mixture was stirred at −78° C. for 30 min, and propionyl chloride (1.1 mL, 13.32 mmol) was added dropwise. Then the mixture was slowly warmed to RT and stirred for 10 min. The mixture was poured slowly to saturated aq. NH$_4$Cl and extracted with EA (30 mL*3). The combined organic phase was washed with brine, dried over anhydrous MgSO$_4$, and concentrated in vacuo to get the desired product as a yellow oil (4.0 g, crude) which was directly used to the next step without further purification. LC-MS: m/z 237.2 (M+H)$^+$.

Step B: 5-ethyl-6-(4-methoxyphenyl)-2,3-diphenylpyrazolo[1,5-a]pyrimidin-7(4H)-one

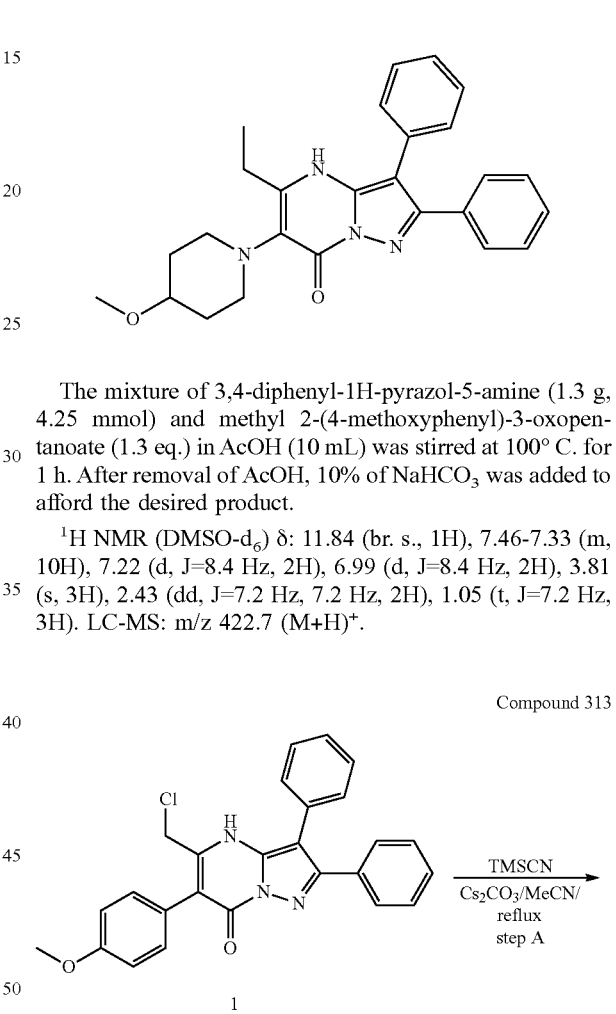

The mixture of 3,4-diphenyl-1H-pyrazol-5-amine (1.3 g, 4.25 mmol) and methyl 2-(4-methoxyphenyl)-3-oxopentanoate (1.3 eq.) in AcOH (10 mL) was stirred at 100° C. for 1 h. After removal of AcOH, 10% of NaHCO$_3$ was added to afford the desired product.

$^1$H NMR (DMSO-d$_6$) δ: 11.84 (br. s., 1H), 7.46-7.33 (m, 10H), 7.22 (d, J=8.4 Hz, 2H), 6.99 (d, J=8.4 Hz, 2H), 3.81 (s, 3H), 2.43 (dd, J=7.2 Hz, 7.2 Hz, 2H), 1.05 (t, J=7.2 Hz, 3H). LC-MS: m/z 422.7 (M+H)$^+$.

397

Step A: 2-(6-(4-methoxyphenyl)-7-oxo-2,3-diphenyl-4,7-dihydropyrazolo[1,5-a]pyrimidin-5-yl)acetonitrile

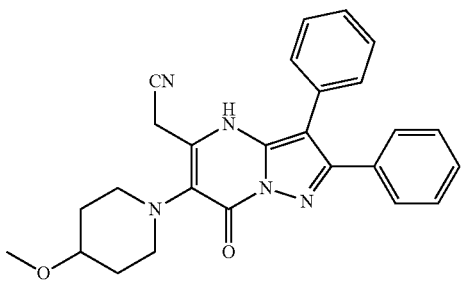 [SMILES: CCc1[nH]c2c(-c3ccccc3)c(-c3ccccc3)nn2c(=O)c1N1CCC(OC)CC1]

The solution of 5-(chloromethyl)-6-(4-methoxyphenyl)-2,3-diphenylpyrazolo[1,5-a]pyrimidin-7(4H)-one (Synthesized in scheme of Compound 340, 230 mg, 0.52 mmol), TMSCN (77.4 mg, 0.78 mmol) and $Cs_2CO_3$ (338.8 mg, 1.04 mmol) in acetonitrile (30 mL) was stirred at reflux for 8 h. The reaction was then cooled to RT and filtered. The dark filtrate was concentrated in vacuo to afford the desired product as a brown solid.

$^1$H NMR (DMSO-$d_6$) δ: 7.55 (m, 4H), 7.37 (dd, J=6.0 Hz, 7.2 Hz, 3H), 7.27-7.20 (m, 4H), 7.11 (d, J=7.2 Hz, 1H), 6.97 (dd, J=2.0 Hz, 2.0 Hz, 2H), 3.80 (s, 3H), 3.62 (s, 2H). LC-MS: m/z 433.8 (M+H)$^+$.

Compound 314

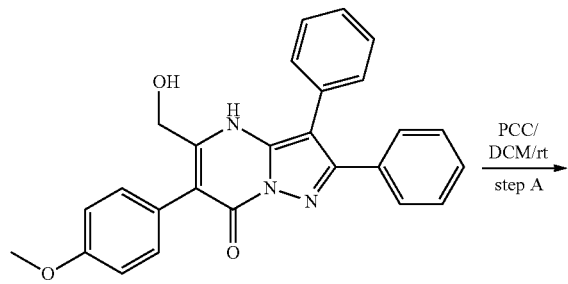

1

PCC/DCM/rt
step A

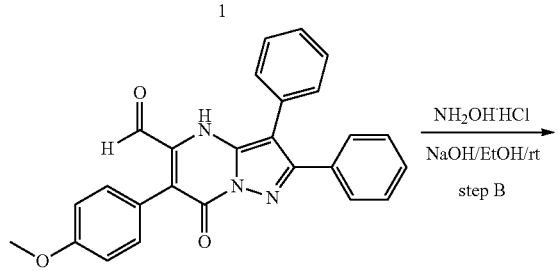

2

$NH_2OH·HCl$
NaOH/EtOH/rt
step B

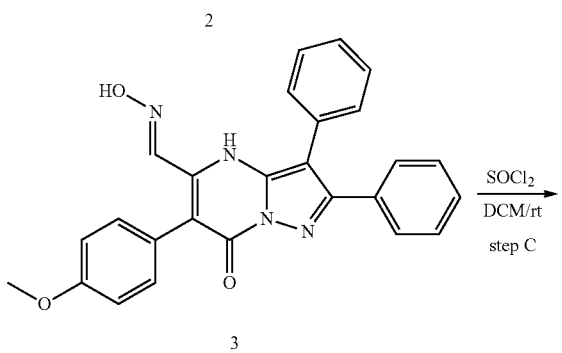

3

$SOCl_2$
DCM/rt
step C

398

-continued

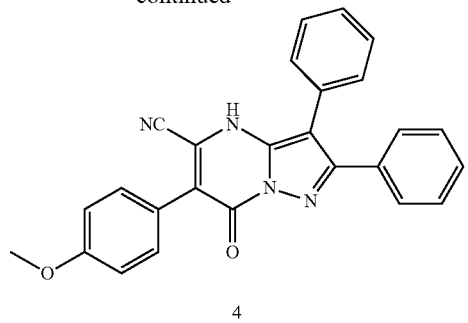

4

Step A: 6-(4-methoxyphenyl)-7-oxo-2,3-diphenyl-4,7-dihydropyrazolo[1,5-a]pyrimidine-5-carbaldehyde

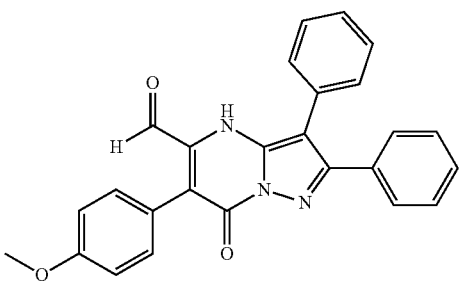 [SMILES: COc1ccc(-c2c(C=O)[nH]c3c(-c4ccccc4)c(-c4ccccc4)nn3c2=O)cc1]

A mixture of 5-(hydroxymethyl)-6-(4-methoxyphenyl)-2,3-diphenylpyrazolo[1,5-a]pyrimidin-7(4H)-one (900 mg, 2.12 mmol) and PCC (synthesized in scheme of Compound 338, 688 mg, 3.18 mmol) in DCM (100 mL) was stirred at RT overnight. The mixture was filtered, washed with DCM, and concentrated in vacuo to get the desired product as a yellow solid (900 mg, 100/o). LC-MS: m/z 422.2 (M+H)$^+$.

Step B: (E)-6-(4-methoxyphenyl)-7-oxo-2,3-diphenyl-4,7-dihydropyrazolo[1,5a]pyrimidine-5-carbaldehyde oxime

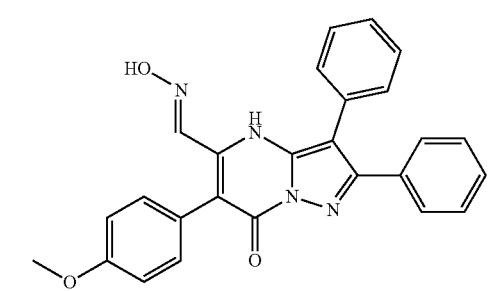 [SMILES: COc1ccc(-c2c(/C=N/O)[nH]c3c(-c4ccccc4)c(-c4ccccc4)nn3c2=O)cc1]

The solution of 6-(4-methoxyphenyl)-7-oxo-2,3-diphenyl-4,7-dihydropyrazolo[1,5-a]pyrimidine-5-carbaldehyde (1.0 g, 2.37 mmol), hydroxylamine hydrochloride (1.8 g, 26.1 mmol) and sodium hydroxide (104 mg, 2.61 mmol) in EtOH/$H_2O$ (90 ml/10 mL) was stirred at RT overnight. The reaction mixture was concentrated in vacuo and purified by flash column chromatography, eluting with DCM/MeOH Step C: 6-(4-methoxyphenyl)-7-oxo-2,3-diphenyl-4,7-dihydropyrazolo[1,5-a]pyrimidine-5-carbonitrile

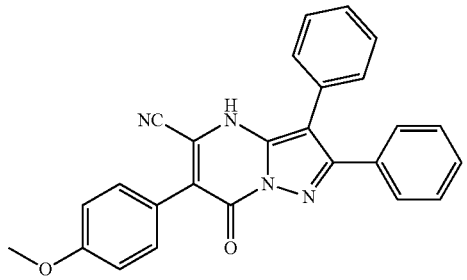 [SMILES: COc1ccc(-c2c(C#N)[nH]c3c(-c4ccccc4)c(-c4ccccc4)nn3c2=O)cc1]

The solution of (E)-6-(4-methoxyphenyl)-7-oxo-2,3-diphenyl-4,7-dihydropyrazolo[1,5-a]pyrimidine-5-carbaldehyde oxime (150 mg, 0.34 mmol) in DCM (10 mL) was added thionyl chloride (0.2 mL, 3.44 mmol) dropwise at RT for 3 h. The reaction mixture was diluted with DCM, washed with saturated NaHCO$_3$ and extracted with DCM (30 mL*3). The combined organic phase was washed with brine, dried over anhydrous MgSO$_4$ and concentrated to afford the desired product.

$^1$H NMR (DMSO-d$_6$) δ: 7.51-7.01 (m, 12H), 7.7.01-6.99 (m, 2H), 3.81 (s, 3H), 3.18 (s, 1H). LC-MS: m/z 418.9 (M+H)$^+$.

(30/1), to get the desired product as a yellow solid (330 mg, 32% yield). LC-MS: m/z 437.2 (M+H)$^+$.

Step A: 6-(4-methoxyphenyl)-7-oxo-2,3-diphenyl-4,7-dihydropyrazolo[1,5-a]pyrimidine-5-carboxamide

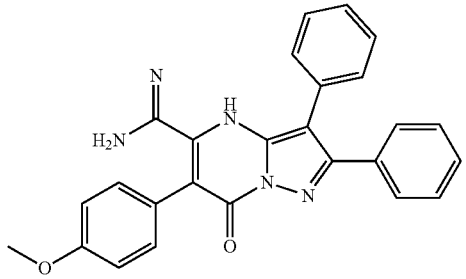 [SMILES: COc1ccc(-c2c(C(=N)N)[nH]c3c(-c4ccccc4)c(-c4ccccc4)nn3c2=O)cc1]

A solution of 6-(4-methoxyphenyl)-7-oxo-2,3-diphenyl-4,7-dihydropyrazolo[1,5-a]pyrimidine-5-carbonitrile (Compound 314, 40 mg, 0.10 mmol) in MeOH (10 ml) were added hydrogen peroxide (30%, 32.5 mg, 0.96 mmol) and sodium hydroxide (1N, 38.4 mg, 0.96 mmol). The resultant mixture was stirred at 40° C. for 1 h. The saturated sodium sulfite was added to afford the desired product.

$^1$H NMR (DMSO-d$_6$) δ: 7.55-7.46 (m, 4H), 7.34-7.02 (m, 8H), 6.86-0.83 (m, 2H), 3.77 (s, 3H). LC-MS: m/z 436.9 (M+H)$^+$.

Compound 315

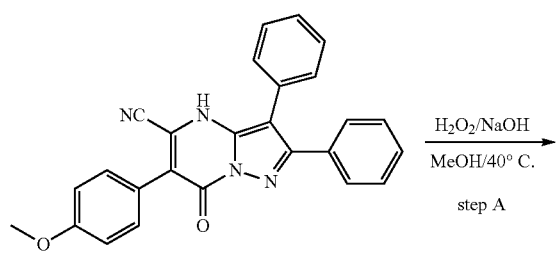

Compound 316

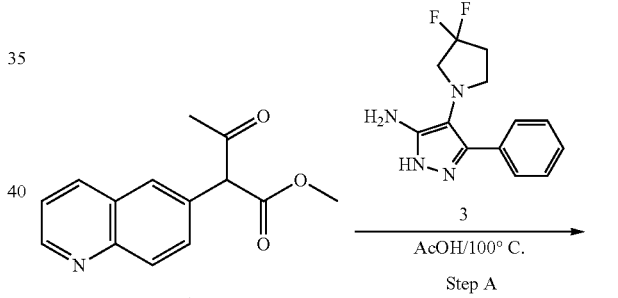

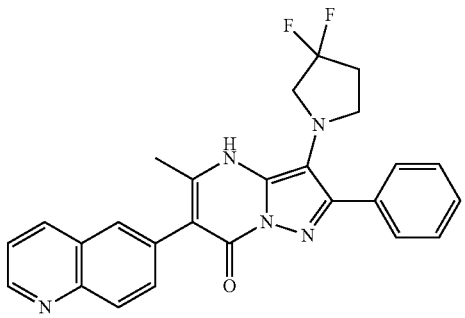

Step A: 3-(3,3-difluoropyrrolidin-1-yl)-5-methyl-2-phenyl-6-(quinolin-6-yl)pyrazolo[1,5-a]pyrimidin-7(4H)-one

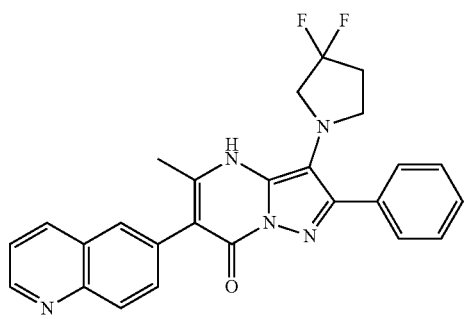 [SMILES: Cc1[nH]c2c(N3CCC(F)(F)C3)c(-c3ccccc3)nn2c(=O)c1-c1ccc2ncccc2c1]

The mixture of methyl 3-oxo-2-(quinolin-6-yl)butanoate (184 mg, 0.76 mmol) and 4-(3,3-difluoropyrrolidin-1-yl)-3-phenyl-1H-pyrazol-5-amine (200 mg, 0.76 mmol, synthesized in the scheme of Compound 272) in AcOH (50 mL) was stirred at 100° C. for 1 h to afford the title compound 2.

$^1$H NMR (DMSO-$d_6$) δ: 11.99 (s, 1H), 8.94 (dd, J=4.2, 1.6 Hz, 1H), 8.29-8.44 (m, 1H), 8.07 (d, J=8.8 Hz, 1H), 7.99 (dd, J=8.2, 1.2 Hz, 2H), 7.94 (d, J=1.8 Hz, 1H), 7.73 (dd, J=8.6, 2.0 Hz, 1H), 7.57 (dd, J=8.2, 4.2 Hz, 1H), 7.40-7.52 (m, 3H), 3.62 (t, J=12.8 Hz, 2H), 3.45 (t, J=7.0 Hz, 2H), 2.42-2.59 (m, 2H), 2.32 (s, 3H). LC-MS: m/z 458.0 (M+H)$^+$.

Compound 317

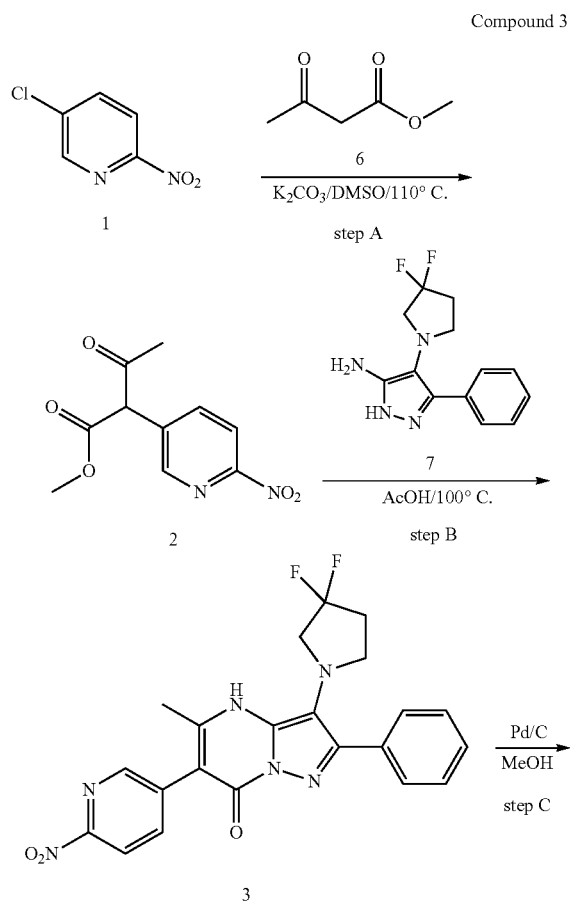

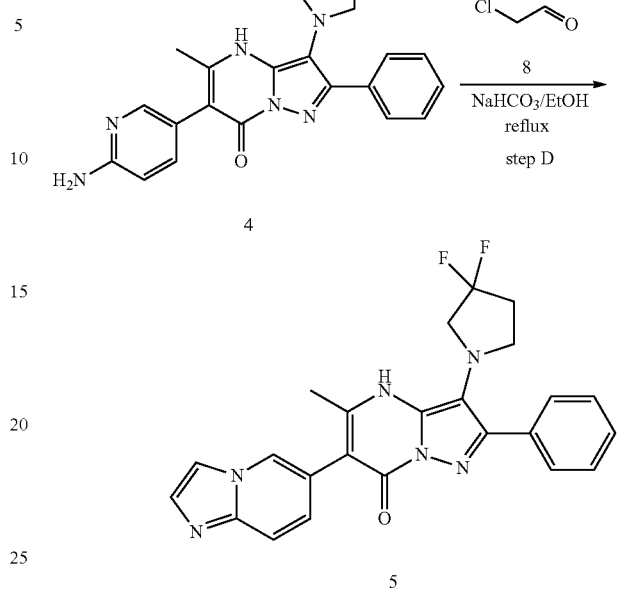

Step A: methyl 2-(6-nitropyridin-3-yl)-3-oxobutanoate

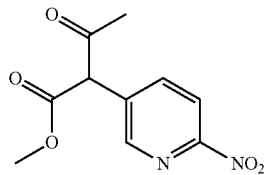 [SMILES: COC(=O)C(C(C)=O)c1ccc([N+](=O)[O-])nc1]

To a solution of 5-chloro-2-nitropyridine (3.2 g, 20 mmol) in DMSO (20 mL) were added methyl 3-oxobutanoate (3.5 g, 30 mmol) and K$_2$CO$_3$ (5.5 g, 40 mmol). The mixture was stirred at 110° C. for 8 h. The mixture was cooled to r.t. and poured into H$_2$O (60 mL) and extracted with EA (3*50 mL). The extract was washed with brine, dried over anhydrous Na$_2$SO$_4$ and concentrated in vacuo. The residue was purified by flash chromatography to afford the title compound 2 as a yellow solid (470 mg, 10% yield). LC-MS: m/z 239.0 (M+H)$^+$.

Step B: 3-(3,3-difluoropyrrolidin-1-yl)-5-methyl-6-(6-nitropyridin-3-yl)-2-phenylpyrazolo[1,5-a]pyrimidin-7(4H)-one

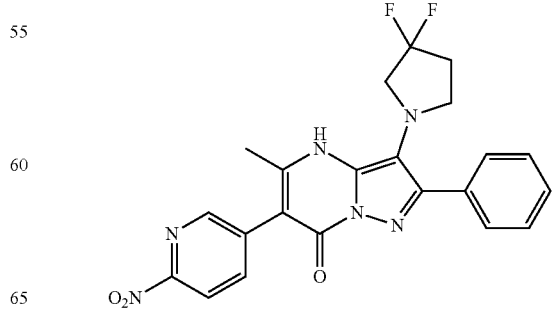

The mixture of intermediate 2 (470 mg, 2.0 mmol) and 4-(3,3-difluoropyrrolidin-1-yl)-3-phenyl-1H-pyrazol-5-amine (521 mg, 2.0 mmol, synthesized in the scheme of Compound 272) in AcOH (8 mL) was stirred at 100° C. for 1 h. Then the mixture was cooled to r.t., concentrated, and neutralized with saturated NaHCO₃ solution until pH=7. The precipitate was filtered off and washed with EA (3*2 mL) to afford the title compound 3 as a yellow solid (400 mg, 45% yield).

$^1$H NMR (DMSO-d$_6$) δ: 12.17 (s, 1H), 8.63-8.73 (m, 1H), 8.41 (d, J=8.2 Hz, 1H), 8.25 (dd, J=8.2, 2.0 Hz, 1H), 7.98 (d, J=6.6 Hz, 2H), 7.38-7.55 (m, 3H), 3.61 (t, J=12.8 Hz, 2H), 3.44 (t, J=6.8 Hz, 2H), 2.44-2.58 (m, 2H), 2.37 (s, 3H). LC-MS: m/z 452.9 (M+H)$^+$.

Step C: 6-(6-aminopyridin-3-yl)-3-(3,3-difluoropyrrolidin-1-yl)-5-methyl-2-phenylpyrazolo[1,5-a]pyrimidin-7(4H)-one

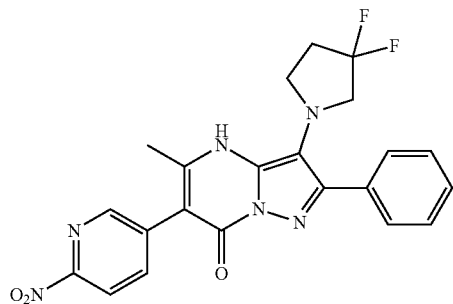 [SMILES: Cc1[nH]c2c(N3CCC(F)(F)C3)c(-c3ccccc3)nn2c(=O)c1-c1ccc([N+](=O)[O-])nc1]

To a solution of intermediate 3 (390 mg, 0.09 mmol) in MeOH (8 mL) was added Pd/C (10 mg). The mixture was stirred at r.t. under H₂ atmosphere overnight. The mixture was filtered through celite, and the filtrate was concentrated in vacuo. The residue was purified by flash chromatography (DCM/MeOH 20:1) to afford the title compound 4 as a yellow solid (270 mg, 74% yield). LC-MS: m/z 422.9 (M+H)$^+$.

Step D: 3-(3,3-difluoropyrrolidin-1-yl)-6-(imidazo[1,2-a]pyridin-6-yl)-5-methyl-2-phenylpyrazolo[1,5-a]pyrimidin-7(4H)-one

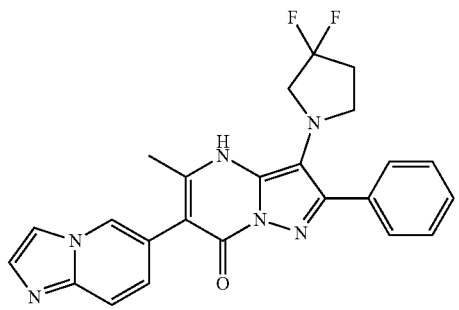 [SMILES: Cc1[nH]c2c(N3CCC(F)(F)C3)c(-c3ccccc3)nn2c(=O)c1-c1ccc2nccn2c1]

To a solution of intermediate 4 (270 mg, 0.6 mmol) in EtOH (5 mL) was added 2-chloroacetaldehyde (40% in water, 0.3 mL) and NaHCO₃ (161 mg, 1.9 mmol). The mixture was refluxed for 2 h. The mixture was cooled to r.t. and evaporated. The residue was dissolved in DCM (10 mL), washed with brine, dried over anhydrous Na₂SO₄ and concentrated in vacuo to afford the title compound 5.

$^1$H NMR (DMSO-d$_6$) δ: 12.38 (br. s., 1H), 8.94 (s, 1H), 8.38 (d, J=1.8 Hz, 1H), 8.23 (d, J=1.8 Hz, 1H), 8.04 (d, J=9.4 Hz, 1H), 7.96-8.01 (m, 2H), 7.90-7.95 (m, 1H), 7.44-7.52 (m, 3H), 3.64 (t, J=12.8 Hz, 2H), 3.47 (t, J=7.0 Hz, 2H), 2.47-2.60 (m, 2H), 2.40 (s, 3H). LC-MS: m/z 446.9 (M+H)$^+$.

Compound 318

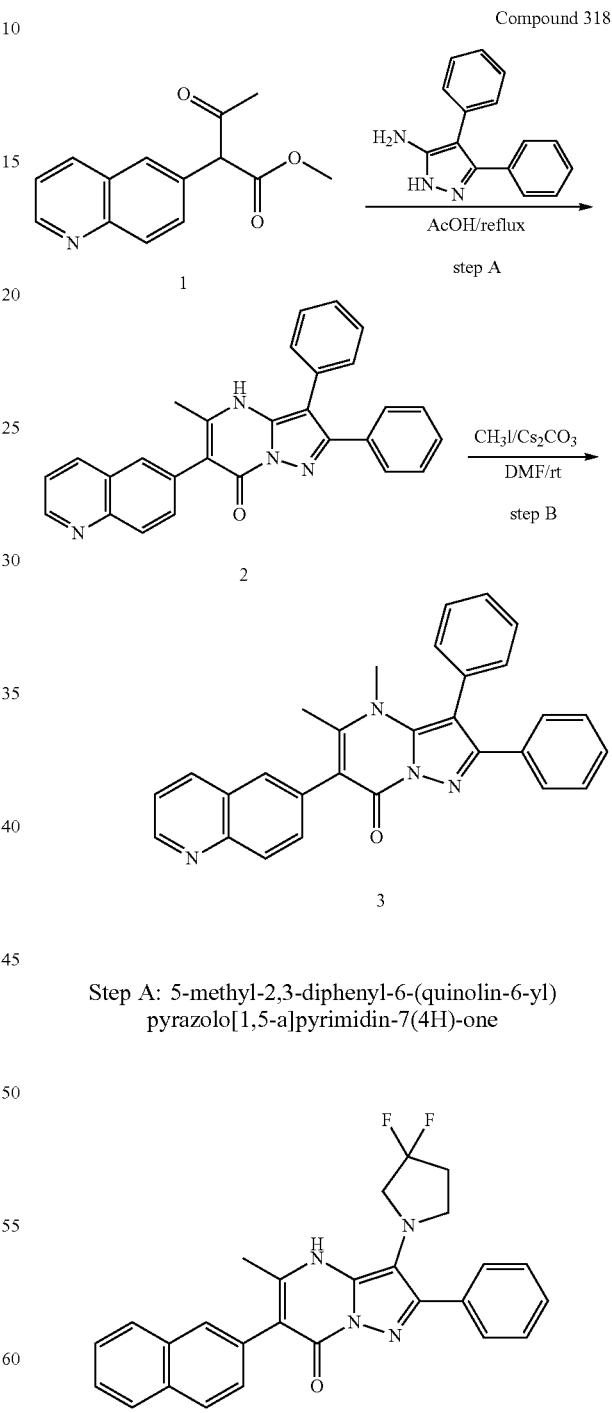

Step A: 5-methyl-2,3-diphenyl-6-(quinolin-6-yl)pyrazolo[1,5-a]pyrimidin-7(4H)-one

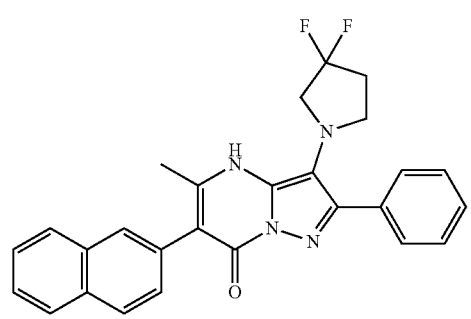 [SMILES: Cc1[nH]c2c(N3CCC(F)(F)C3)c(-c3ccccc3)nn2c(=O)c1-c1ccc2ccccc2c1]

A suspension of methyl 3,4-diphenyl-1H-pyrazol-5-amine (200 mg, 0.8 mmol) and methyl 3-oxo-2-(quinolin-6-yl)butanoate (200 mg, 0.85 mmol) in AcOH (2 ml) was refluxed for 30 min under N₂ protection. The mixture was cooled to the RT, concentrated, and neutralized with saturated sodium hydrogen carbonate solution to adjust to pH=7. The precipitates were collected by filtration, washed with petroleum ether, and dried to obtain the desired product as a yellow solid (50 mg, 62% yield). LC-MS: m/z 429.2 (M+H)$^+$ Step B: 4,5-dimethyl-2,3-diphenyl-6-(quinolin-6-yl)pyrazolo[1,5-a]pyrimidin-7(4H)-one To a solution of 5-methyl-2,3-diphenyl-6-(quinolin-6-yl)pyrazolo[1,5-a]pyrimidin-7(4H)-one (34 mg, 0.08 mmol) and Cs$_2$CO$_3$ (26 mg, 0.08 mmol) in DMF (2 ml) at ambient temperature was added MeI (22 mg, 0.16 mmol) dropwise. The mixture was stirred for 4 h at ambient temperature. The mixture was cooled to the RT, washed with saturated sodium hydrogen carbonate solution, and extracted with DCM (3*30 mL). The combined organic layers were washed with brine, dried over anhydrous sodium sulfate, and concentrated in vacuo to obtain the desired product.

$^1$H NMR (DMSO-d$_6$) δ: 8.95 (dd, J=1.6 Hz, 1.6 Hz, 1H), 8.42 (d, J=7.6 Hz, 1H), 8.11 (d, J=8.8 Hz, 1H), 7.93 (d, J=2.0 Hz, 1H), 7.70 (dd, J=2.0 Hz, 2.0 Hz, 1H), 7.59 (dd, J=4.4 Hz, 4.0 Hz, 1H), 7.47 (s, 5H), 7.39-7.37 (m, 2H), 7.32-7.28 (m, 3H), 3.37 (s, 3H), 2.27 (s, 3H). LC-MS: m/z 443.3 (M+H)$^+$.

Compound 319

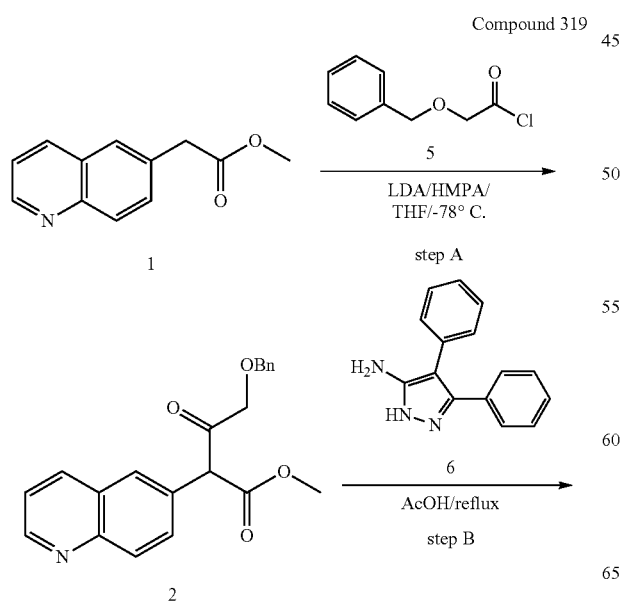

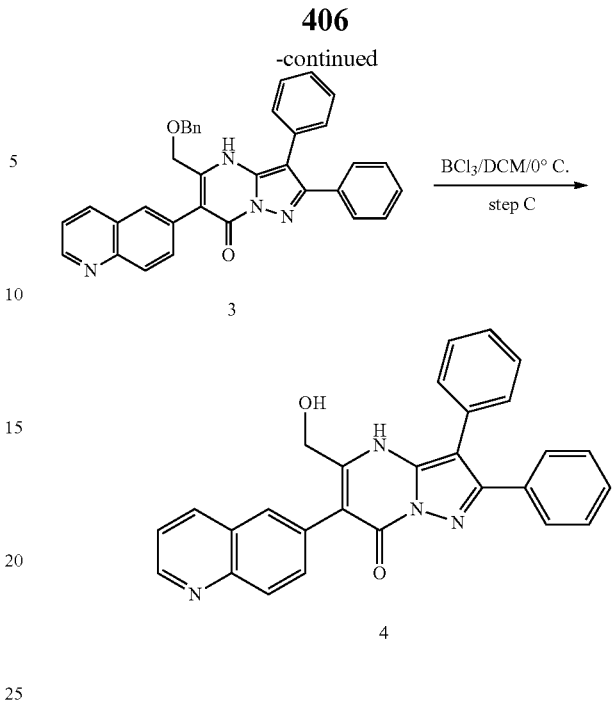

Step A: methyl 4-(benzyloxy)-3-oxo-2-(quinolin-6-yl)butanoate

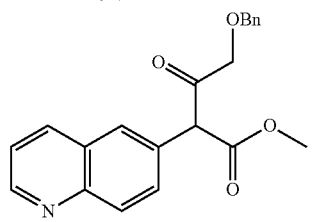

To a solution of methyl 2-(quinolin-6-yl)acetate (10 g, 49.7 mmol) in THF (300 mL) was added dropwise LDA (1.5 M in THF, 39.8 mL, 59.7 mmol) at −30~−35° C. The mixture was stirred at −30~−35° C. for 30 min and 2-(benzyloxy)acetyl chloride (9.15 g, 49.7 mol) was added dropwise. Then the mixture was stirred at r.t. for 6 h. The mixture was poured slowly to saturated NH$_4$Cl and extracted with EA (50 mL×3). The combined organic phase was washed with brine, dried over anhydrous MgSO$_4$ and concentrated in vacuo. The residue was purified by flash chromatography to afford the desired methyl 4-(benzyloxy)-3-oxo-2-(quinolin-6-yl)butanoate as a brown oil (13.6 g, 80% yield). LC-MS: m/z 350.2 (M+H)$^+$.

Step B: 5-((benzyloxy)methyl)-2,3-diphenyl-6-(quinolin-6-yl)pyrazolo[1,5-a]pyrimidin-7(4H)-one

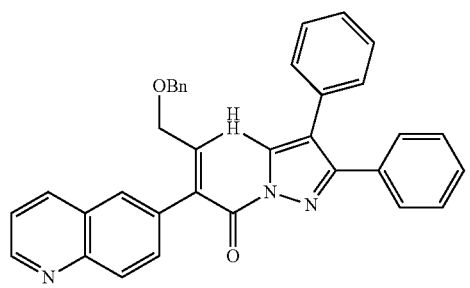

A mixture of methyl 4-(benzyloxy)-3-oxo-2-(quinolin-6-yl)butanoate (8.6 g, 0.024 mol) and 3,4-diphenyl-1H-pyrazol-5-amine (5.64 g, 0.024 mol) was dissolved in AcOH (300 ml). The mixture was warmed up to 95° C. for 4 h. After cooling to room temperature, the precipitate was filtered, wash with EtOAc, and dried under vacuum to get 5-((benzyloxy)methyl)-2,3-diphenyl-6-(quinolin-6-yl)pyrazolo[1,5-a]pyrimidin-7(4H)-one (10 g, 78% yield) as a yellow solid. LC-MS: m/z 535.2 (M+H)+.

Step C: Compound 319: 5-((benzyloxy)methyl)-2,3-diphenyl-6-(quinolin-6-yl)pyrazolo[1,5-a]pyrimidin-7(4H)-one

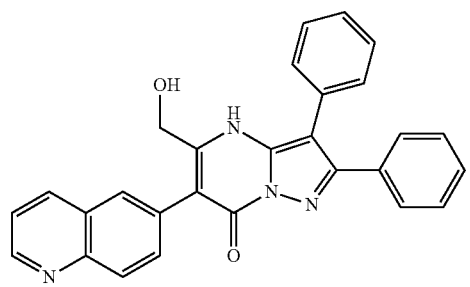 [SMILES: O=c1c(-c2ccc3ncccc3c2)c(CO)[nH]c2c(-c3ccccc3)c(-c3ccccc3)nn12]

To a solution of 5-((benzyloxy)methyl)-2,3-diphenyl-6-(quinolin-6-yl)pyrazolo[1,5-a] pyrimidin-7(4H)-one (10 g, 18.7 mmol) in DCM (100 ml) was added BCl$_3$ (25 ml, 25 mmol, 1.0M in DCM) at 0° C. The resultant mixture was stirred at 0° C. for 4 hours. The reaction was quenched with MeOH and concentrated. The residue was stirred with sodium hydrogen carbonate solution and ethyl acetate for 30 min to afford 5-(hydroxymethyl)-2,3-diphenyl-6-(quinolin-6-yl)pyrazolo[1,5-a]pyrimidin-7(4H)-one.

$^1$H NMR (DMSO-d$_6$) δ: 11.65 (br. s., 1H), 8.96 (d, J=2.69 Hz, 1H), 8.40 (d, J=7.79 Hz, 1H), 8.08 (d, J=8.60 Hz, 1H), 8.01 (s, 1H), 7.79 (d, J=8.87 Hz, 1H), 7.59 (dd, J=4.03, 8.06 Hz, 1H), 7.36-7.51 (m, 9H), 5.64 (br. s., 1H), 4.36 (br. s., 2H). LC-MS: m/z 445.8 (M+H)+.

Compound 320

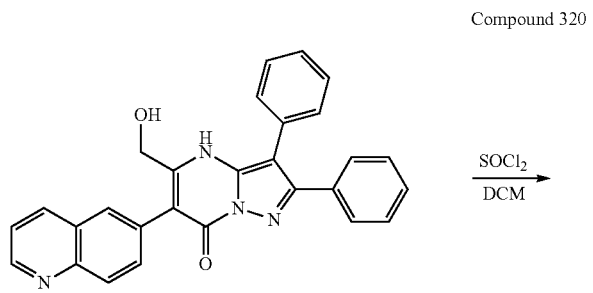

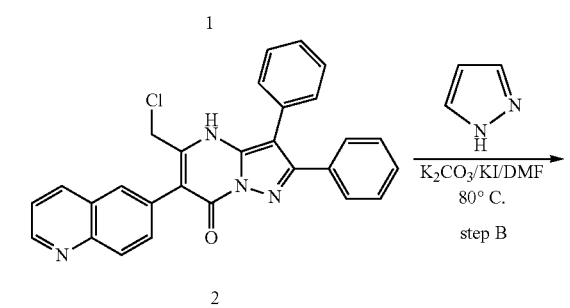

Step A: 5-(chloromethyl)-2,3-diphenyl-6-(quinolin-6-yl)pyrazolo[1,5-a]pyrimidin-7(4H)-one

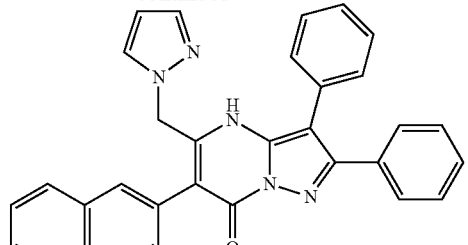

To a suspension of 5-(hydroxymethyl)-2,3-diphenyl-6-(quinolin-6-yl)pyrazolo[1,5-a] pyrimidin-7(4H)-one (Compound 319, 500 mg, 1.126 mmol,) in DCM (3 ml) was added dropwise SOCl$_2$ (670 mg, 5.631 mmol) at 0° C. The resultant mixture was then stirred at room temperature overnight. The suspension was filtered, washed with ethyl acetate, and dried under vacuum. The residue was purified by prep-TLC (DCM:MeOH=20:1) to get 5-(chloromethyl)-2,3-diphenyl-6-(quinolin-6-yl)pyrazolo[1,5-a]pyrimidin-7(4H)-one (300 mg). LC-MS: m/z 463.1 (M+H)+.

Step B: Compound 320: 5-((1H-pyrazol-1-yl)methyl)-2,3-diphenyl-6-(quinolin-6-yl)pyrazolo[1,5-a]pyrimidin-7(4H)-one

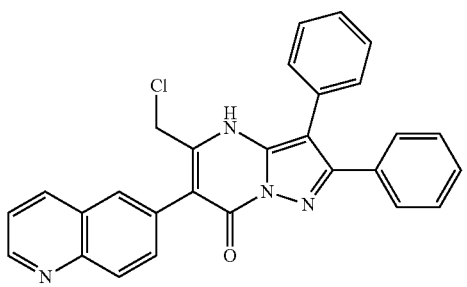

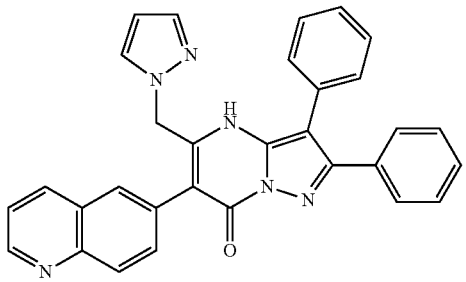 [SMILES: O=c1c(-c2ccc3ncccc3c2)c(Cn2cccn2)[nH]c2c(-c3ccccc3)c(-c3ccccc3)nn12]

To a solution of 5-(chloromethyl)-2,3-diphenyl-6-(quinolin-6-yl)pyrazolo[1,5-a]pyrimidin-7(4H)-one (100 mg, 0.22 mmol) in DMF (10 mL) were added 1H-pyrazole (30 mg, 0.433 mmol), K$_2$CO$_3$ (60 mg. 0.433 mmol) and KI (5 mg, 0.03 mmol). The mixture was stirred at 80° C. for 2 h to afford 5-((1H-pyrazol-1-yl)methyl)-2,3-diphenyl-6-(quinolin-6-yl)pyrazolo[1,5-a]pyrimidin-7(4H)-one.

$^1$H NMR (DMSO-d$_6$) δ: 12.45 (br. s., 1H), 8.93 (d, J=2.96 Hz, 1H), 8.27 (d, J=8.06 Hz, 1H), 8.00 (d, J=8.33 Hz, 1H), 7.75 (br. s., 1H), 7.64 (br. s., 1H), 7.56 (dd, J=4.03, 8.33 Hz, 1H), 7.26-7.52 (m, 10H), 6.15 (s, 1H), 5.22 (br. s., 2H). LC-MS: m/z 494.8 (M+H)$^+$.

Compound 321

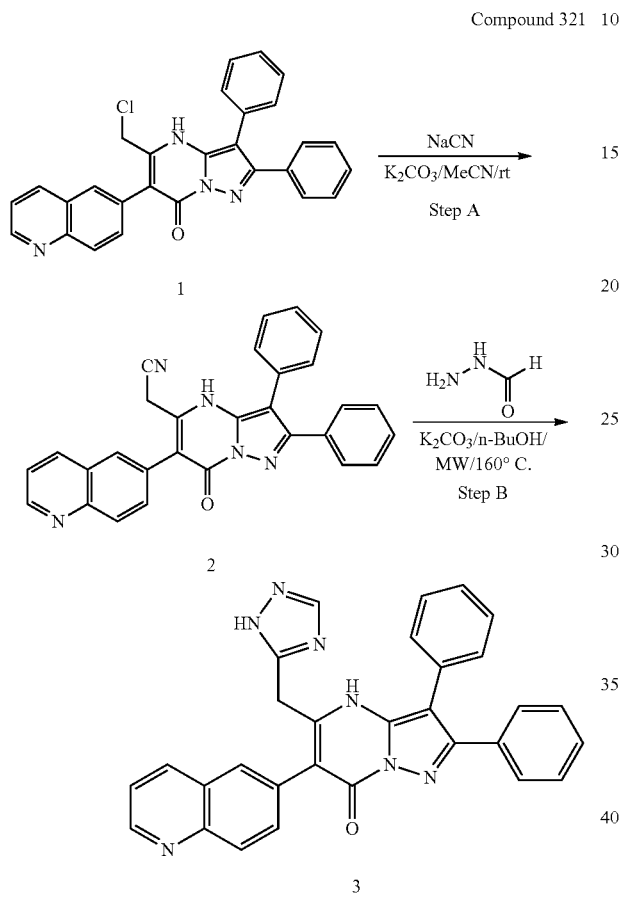

Step A: 2-(7-oxo-2,3-diphenyl-6-(quinolin-6-yl)-4,7-dihydropyrazolo[1,5-a]pyrimidin-5-yl)acetonitrile

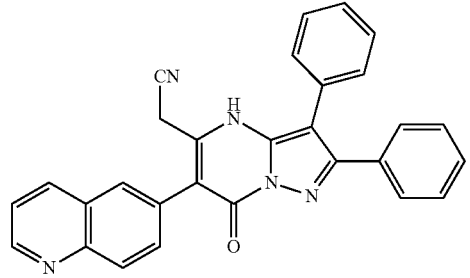

To a solution of 5-(chloromethyl)-2,3-diphenyl-6-(quinolin-6-yl)pyrazolo[1,5-a]pyrimidin-7(4H)-one (Synthesized in scheme of Compound 320, 1 g, 22 mmol) in CH$_3$CN (10 mL) were added K$_2$CO$_3$ (600 mg. 4.33 mmol) and NaCN (100 mg, 22 mmol). The mixture was stirred at r.t. for 2 h. The reaction mixture was poured into water and extracted with ethyl acetate. The organic layer was dried over anhydrous magnesium sulfate and concentrated in vacuo to dryness. The residue was purified by silica gel chromatography (methanol:dichloromethane=1:10) to afford 2-(7-oxo-2,3-diphenyl-6-(quinolin-6-yl)-4,7-dihydropyrazolo[1,5-a]pyrimidin-5-yl)acetonitrile (600 mg, 61% yield). LC-MS: m/z 454.2 (M+H)$^+$.

Step B: Compound 321: 5-((1H-1,2,4-triazol-5-yl)methyl)-2,3-diphenyl-6-(quinolin-6-yl)pyrazolo[1,5-a]pyrimidin-7(4H)-one

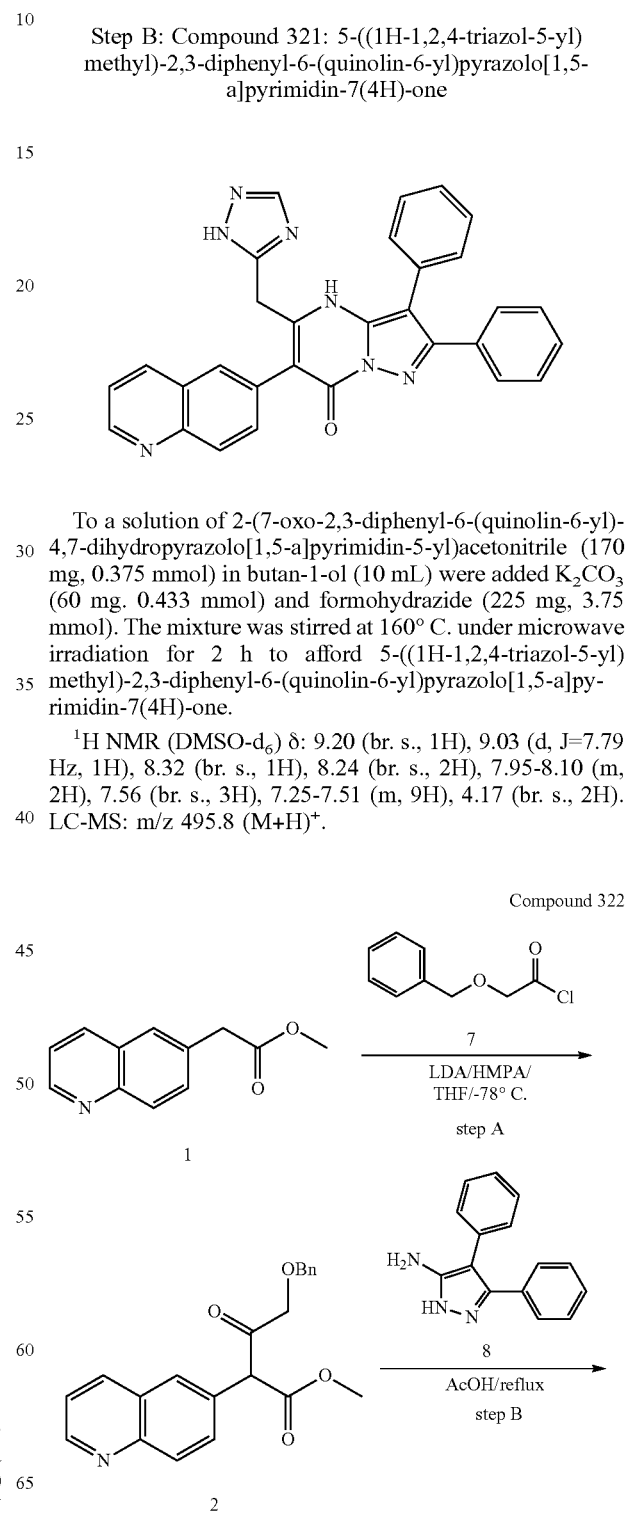

To a solution of 2-(7-oxo-2,3-diphenyl-6-(quinolin-6-yl)-4,7-dihydropyrazolo[1,5-a]pyrimidin-5-yl)acetonitrile (170 mg, 0.375 mmol) in butan-1-ol (10 mL) were added K$_2$CO$_3$ (60 mg. 0.433 mmol) and formohydrazide (225 mg, 3.75 mmol). The mixture was stirred at 160° C. under microwave irradiation for 2 h to afford 5-((1H-1,2,4-triazol-5-yl)methyl)-2,3-diphenyl-6-(quinolin-6-yl)pyrazolo[1,5-a]pyrimidin-7(4H)-one.

$^1$H NMR (DMSO-d$_6$) δ: 9.20 (br. s., 1H), 9.03 (d, J=7.79 Hz, 1H), 8.32 (br. s., 1H), 8.24 (br. s., 2H), 7.95-8.10 (m, 2H), 7.56 (br. s., 3H), 7.25-7.51 (m, 9H), 4.17 (br. s., 2H). LC-MS: m/z 495.8 (M+H)$^+$.

Compound 322

411

-continued

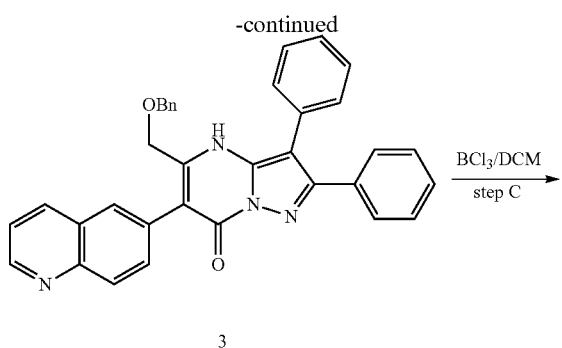
3

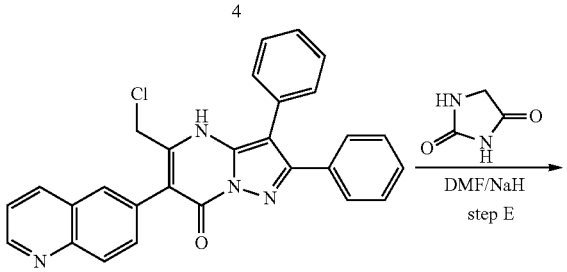
4

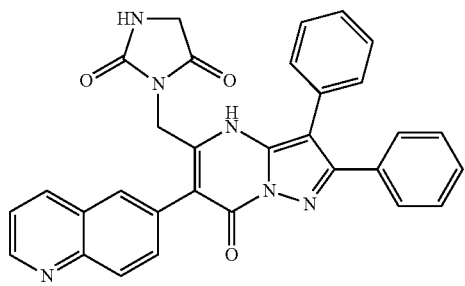 [SMILES: O=C1CNC(=O)N1Cc1[nH]c2c(-c3ccccc3)c(-c3ccccc3)nn2c(=O)c1-c1ccc2ncccc2c1]
5

Step E: Compound 322: 3-((7-oxo-2,3-diphenyl-6-(quinolin-6-yl)-4,7-dihydropyrazolo[1, 5-a]pyrimidin-5-yl)methyl)imidazolidine-2,4-dione To a mixture of hydantoin (324 mg, 3.24 mmol) in DMF (6 mL) was added NaH (60% dispersion in mineral oil, 143

412 mg, 3.56 mmol) in portionse at 0° C. After addition, the mixture was stirred at 0° C. for 30 min. Then the 5-(chloromethyl)-2,3-diphenyl-6-(quinolin-6-yl)pyrazolo[1,5-a]pyrimidin-7(4H)-one (150 mg, 0.324 mmol, synthesized in scheme of Compound 278) was added into the mixture. The reaction mixture was warmed to 80° C. and stirred overnight. The reaction was quenched with brine and mixed with EA to afford the title compound.

$^1$H NMR (400 MHz, TFA) δ: 9.37 (d, J=8.06 Hz, 1H), 9.29 (d, J=5.37 Hz, 1H), 8.61 (br. s., 2H), 8.20-8.42 (m, 2H), 7.47-7.66 (m, 7H), 7.13-7.35 (m, 3H), 5.00 (br. s., 1H), 4.35 (br. s., 1H), 3.22 (br. s., 2H). LC-MS: m/z 527.0 (M+H)$^+$.

Compound 323

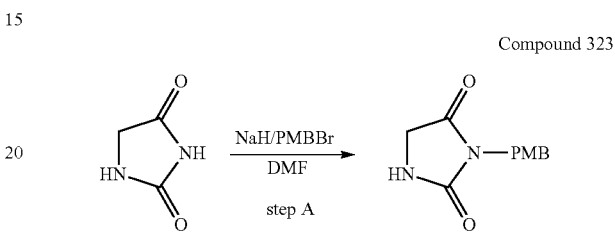

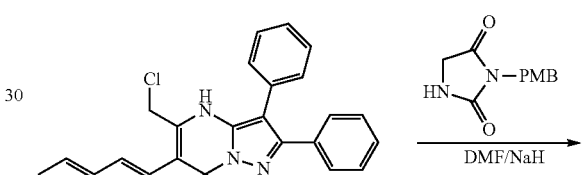
3

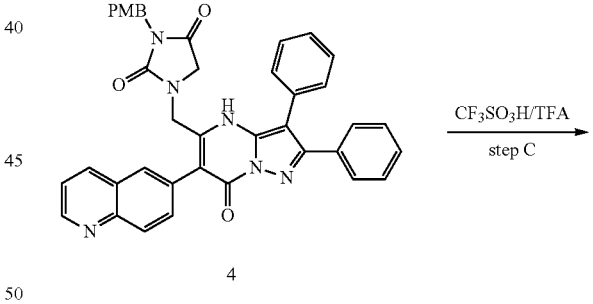
4

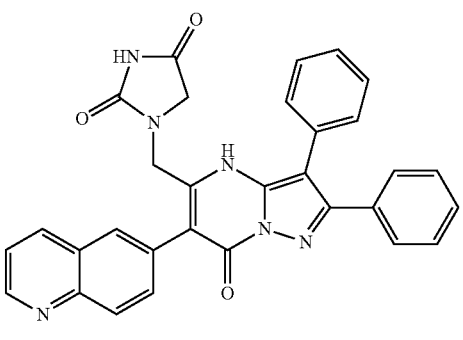
5

Step A: 3-(4-methoxybenzyl)imidazolidine-2,4-dione

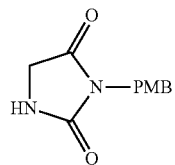

To a solution of imidazolidine-2,4-dione (500 mg, 5 mmol) in DMF (10 mL) was added NaH (600/% dispersion in mineral oil, 240 mg, 6 mmol) in portions at 0° C. After addition, the mixture was stirred at 0° C. for 40 min. Then PMBBr (1.0 g, 5 mmol) was added dropwise. The resultant mixture was warmed to 80° C. and stirred overnight. The reaction was quenched with brine (30 mL). The suspension was filtered off. The filter cake was washed with brine and EA, and then dried in vacuo to get the title compound (430 mg) as a white solid. LC-MS: m/z 221.1 (M+H)$^+$.

Step B: 3-(4-methoxybenzyl)-1-((7-oxo-2,3-diphenyl-6-(quinolin-6-yl)-4,7-dihydropyrazolo[1,5-a]pyrimidin-5-yl)methyl)imidazolidine-2,4-dione

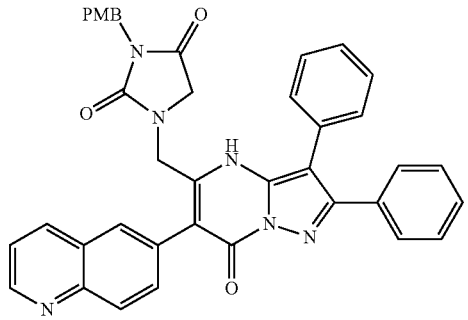

To a mixture of hydantoin (124 mg, 0.562 mmol) in DMF (6 mL) was added NaH (60%° dispersion in mineral oil, 27 mg, 0.674 mmol) in portions at 0° C. After addition, the mixture was stirred at 0° C. for 30 min. Then the 5-(chloromethyl)-2,3-diphenyl-6-(quinolin-6-yl)pyrazolo[1,5-a]pyrimidin-7(4H)-one (130 mg, 0.281 mmol, Synthesized in scheme of Compound 278) was added into the mixture. The reaction mixture was warmed to 80° C. and stirred overnight. The reaction was quenched with brine and then mixed with EA. The mixture was filtered off. The filter cake was purified by prep HPLC to get the title compound (100 mg) as a yellow solid. LC-MS: m/z 647.0 (M+H)$^+$.

Step C: Compound 323: 1-((7-oxo-2,3-diphenyl-6-(quinolin-6-yl)-4,7-dihydropyrazolo[1,5-a]pyrimidin-5-yl)methyl)imidazolidine-2,4-dione

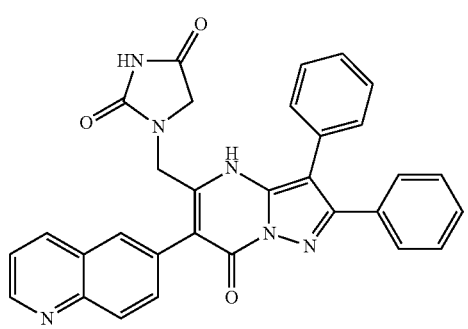 [SMILES: O=C1CN(Cc2[nH]c3c(-c4ccccc4)c(-c4ccccc4)nn3c(=O)c2-c2ccc3ncccc3c2)C(=O)N1]

A mixture of 3-(4-methoxybenzyl)-1-((7-oxo-2,3-diphenyl-6-(quinolin-6-yl)-4,7-dihydropyrazolo[1,5-a]pyrimidin-5-yl)methyl)imidazolidine-2,4-dione and CF$_3$SO$_3$H (0.5 mL) in TFA (2 mL) was heated to reflux overnight. The reaction mixture was cooled to room temperature, quenched with aq. NaHCO$_3$ to pH=7-8 to afford the title compound.

$^1$H NMR (400 MHz, TFA) δ: 9.34 (d, J=8.33 Hz, 1H), 9.25 (d, J=5.10 Hz, 1H), 8.49-8.64 (m, 2H), 8.34 (d, J=8.06 Hz, 1H), 8.24 (dd, J=8.06, 5.64 Hz, 1H), 7.55-7.71 (m, 6H), 7.46-7.53 (m, 2H), 7.43 (d, J=6.72 Hz, 2H), 4.88 (br. s., 2H), 4.27 (br. s., 2H). LC-MS: m/z 527.0 (M+H)$^+$.

Compound 324

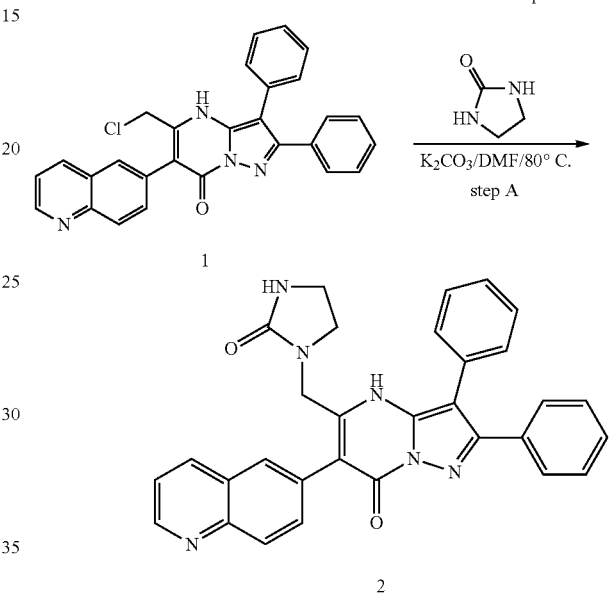

Step A: Compound 324: 5-((2-oxoimidazolidin-1-yl)methyl)-2,3-diphenyl-6-(quinolin-6-yl)pyrazolo[1,5-a]pyrimidin-7(4H)-one

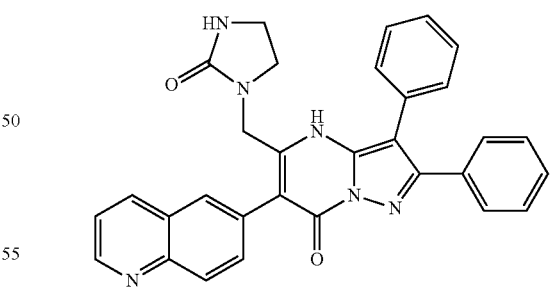

A mixture of 5-(chloromethyl)-2,3-diphenyl-6-(quinolin-6-yl)pyrazolo[1,5-a]pyrimidin-7(4H)-one (100 mg, 0.216 mmol, Synthesized in scheme of Compound 278), imidazolidin-2-one (93 mg, 1.08 mmol) and K$_2$CO$_3$ (136 mg, 0.259 mmol) in DMF (3 mL) was heated to 80° C. and stirred overnight. The reaction mixture was quenched with brine and then mixed with EA to get the title compound.

$^1$H NMR (400 MHz, DMSO-d$_6$) δ: 8.88 (br. s., 1H), 8.36 (d, J=7.52 Hz, 1H), 8.00 (d, J=8.06 Hz, 1H), 7.89 (br. s., 1H), 7.78 (d, J=8.33 Hz, 1H), 6.95-7.68 (m, 11H), 6.19 (br. s., 1H), 4.09-4.33 (m, 2H), 3.58 (br. s., 2H), 3.21 (br. s., 2H). LC-MS: m/z 513.0 (M+H)+.

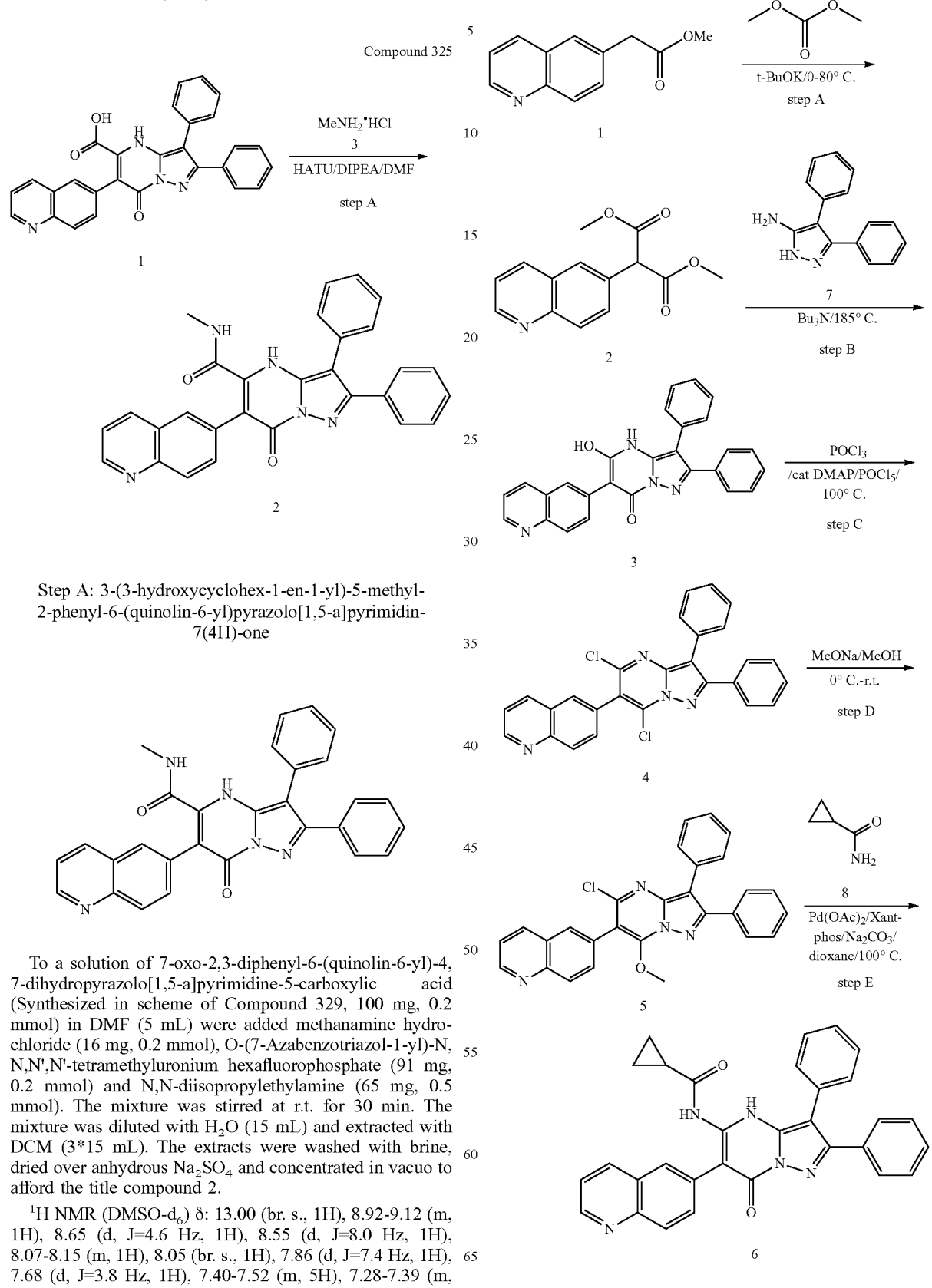

Compound 325

Compound 326

Step A: 3-(3-hydroxycyclohex-1-en-1-yl)-5-methyl-2-phenyl-6-(quinolin-6-yl)pyrazolo[1,5-a]pyrimidin-7(4H)-one To a solution of 7-oxo-2,3-diphenyl-6-(quinolin-6-yl)-4,7-dihydropyrazolo[1,5-a]pyrimidine-5-carboxylic acid (Synthesized in scheme of Compound 329, 100 mg, 0.2 mmol) in DMF (5 mL) were added methanamine hydrochloride (16 mg, 0.2 mmol), O-(7-Azabenzotriazol-1-yl)-N,N,N',N'-tetramethyluronium hexafluorophosphate (91 mg, 0.2 mmol) and N,N-diisopropylethylamine (65 mg, 0.5 mmol). The mixture was stirred at r.t. for 30 min. The mixture was diluted with H₂O (15 mL) and extracted with DCM (3*15 mL). The extracts were washed with brine, dried over anhydrous Na₂SO₄ and concentrated in vacuo to afford the title compound 2.

$^1$H NMR (DMSO-$d_6$) δ: 13.00 (br. s., 1H), 8.92-9.12 (m, 1H), 8.65 (d, J=4.6 Hz, 1H), 8.55 (d, J=8.0 Hz, 1H), 8.07-8.15 (m, 1H), 8.05 (br. s., 1H), 7.86 (d, J=7.4 Hz, 1H), 7.68 (d, J=3.8 Hz, 1H), 7.40-7.52 (m, 5H), 7.28-7.39 (m, 5H), 2.44 (d, J=4.6 Hz, 3H). LC-MS: m/z 472.2 (M+H)+.

Step C: 6-(5,7-dichloro-2,3-diphenylpyrazolo[1,5-a]pyrimidin-6-yl)quinoline

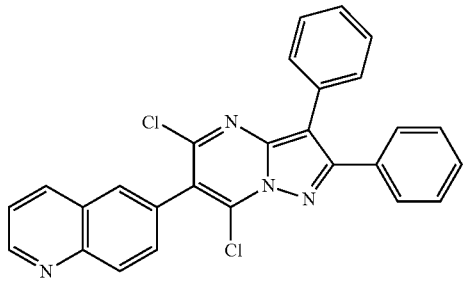 [SMILES: Clc1nc2c(-c3ccccc3)c(-c3ccccc3)nn2c(Cl)c1-c1ccc2ncccc2c1]

The solution of 2,3-diphenyl-6-(quinolin-6-yl)pyrazolo[1,5-a]pyrimidine-5,7(4H,6H)-dione (18 g, 42 mmol, Compound 275), DMAP (1 g) and PCl$_5$ (80 mg) in POCl$_3$ (180 mL) was stirred at 100° C. overnight. After cooling to room temperature, the solvent was removed by vacuum. The residue was cooled to 0° C. MeOH (60 mL) was added to quench the reaction. The resultant mixture was diluted with DCM (450 ml), washed with saturated NaHCO$_3$ (150 ml) and brine (100 ml), dried over anhydrous sodium sulfate, and concentrated to get crude product of 6-(5,7-dichloro-2,3-diphenylpyrazolo[1,5-a]pyrimidin-6-yl)quinoline (13 g) which was used in the next step without further purification. LC-MS: m/z 467.1 (M+H)$^+$.

Step D: 6-(5-chloro-7-methoxy-2,3-diphenylpyrazolo[1,5-a]pyrimidin-6-yl)quinoline

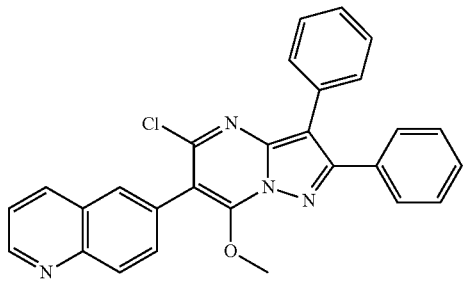 [SMILES: COc1c(-c2ccc3ncccc3c2)c(Cl)nc2c(-c3ccccc3)c(-c3ccccc3)nn12]

To a solution of 6-(5,7-dichloro-2,3-diphenylpyrazolo[1,5-a]pyrimidin-6-yl)quinoline (13.0 g, crude, 27.8 mmol) in DCM/MeOH (200 mL, 1:1) cooled at 0° C. was added sodium methoxide (14.9 mL, 5.0 M in methanol) dropwise. Then the mixture was stirred at 0° C. for 1 hour. Saturated NH$_4$Cl (150 mL) was added to quench the reaction. The resultant mixture was extracted with DCM (500 mL), washed with brine (150 mL), dried over anhydrous sodium sulfate, and concentrated in vacuo. The residue was purified by flash column (DCM/MeOH=40:1) to obtain 6-(5-chloro-7-methoxy-2,3-diphenylpyrazolo[1,5-a]pyrimidin-6-yl)quinoline (9.0 g) as a pale yellow solid.

$^1$H NMR (DMSO-d$_6$): δ 9.01 (dd, J=4.2, 1.7 Hz, 1H), 8.45-8.52 (m, 1H), 8.13-8.21 (m, 2H), 7.88 (dd, J=8.6, 1.9 Hz, 1H), 7.59-7.68 (m, 3H), 7.42-7.48 (m, 7H), 7.34-7.41 (m, 1H), 4.25 (s, 3H). LC-MS: m/z 463.1 (M+H)$^+$.

Step E: N-(7-oxo-2,3-diphenyl-6-(quinolin-6-yl)-4,7-dihydropyrazolo[1,5-a]pyrimidin-5-yl)cyclopropanecarboxamide

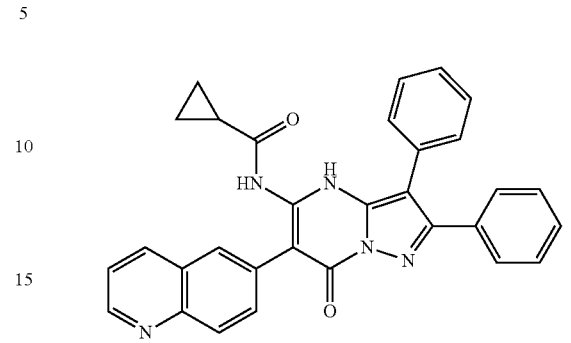

A mixture of 6-(5-chloro-7-methoxy-2,3-diphenylpyrazolo[1,5-a]pyrimidin-6-yl)quinoline (100 mg, 0.216 mmol), cyclopropanecarboxamide (55.2 mg, 0.65 mmol), palladium (II) acetate (9.7 mg, 0.04 mmol), xantphos (37.5 mg, 0.06 mmol) and sodium carbonate (140.8 mg, 0.43 mmol) in 1,4-dioxane (10 mL) was stirred at 100° C. under N$_2$ for 12 h to afford the desired product.

$^1$H NMR (DMSO-d$_6$) δ: 9.41-9.31 (m, 2H), 8.73-8.72 (m, 1H), 8.47-8.32 (m, 1H), 7.80-7.38 (m, 14H), 1.15-1.32 (m., 5H). LC-MS: m/z 498.2 (M+H)$^+$.

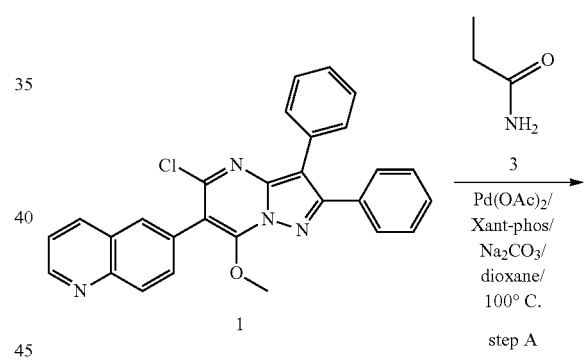

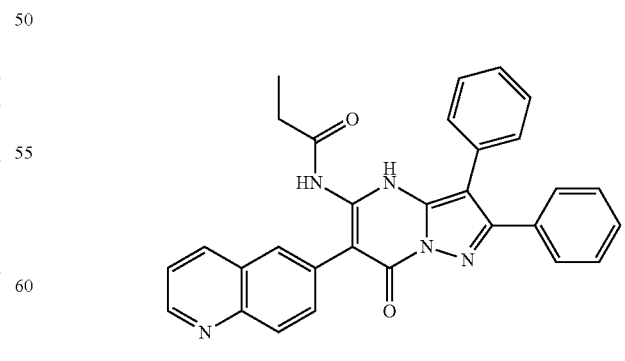

419

Step A: N-(7-oxo-2,3-diphenyl-6-(quinolin-6-yl)-4,7-dihydropyrazolo[1,5-a]pyrimidin-5-yl)propionamide

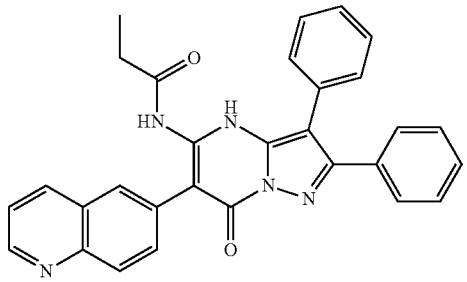 [SMILES: CCC(=O)Nc1[nH]c2c(-c3ccccc3)c(-c3ccccc3)nn2c(=O)c1-c1ccc2ncccc2c1]

A mixture of 6-(5-chloro-7-methoxy-2,3-diphenylpyrazolo[1,5-a]pyrimidin-6-yl)quinoline (Synthesized in scheme of Compound 326, 100 mg, 0.216 mmol), propionamide (47.4 mg, 0.65 mmol), palladium(II) acetate (9.7 mg, 0.04 mmol), xantphos (37.5 mg, 0.06 mmol) and sodium carbonate (140.8 mg, 0.43 mmol) in 1, 4-dioxane (10 mL) was stirred at 100° C. under $N_2$ for 12 h to afford the desired product.

$^1$H NMR (DMSO-$d_6$) δ: 12.92 (br. s., 1H), 10.08 (s, 1H), 8.94 (d, J=2.8 Hz, 1H), 8.40 (d, J=8.0 Hz, 1H), 8.08 (d, J=8.4 Hz, 1H), 8.00 (s, 1H), 7.75 (dd, J=1.6 Hz, 1.6 Hz, 1H), 7.55 (dd, J=4.4 Hz, 4.0 Hz, 4H), 7.51-7.41 (m, 4H), 7.39-7.35 (m, 6H), 2.28 (dd, J=7.6 Hz, 7.2 Hz, 2H), 0.94 (t, J=7.6 Hz, 3H). LC-MS: m/z 486.8 (M+H)$^+$.

420

Step A: N-((1H-pyrazol-3-yl)methyl)-7-oxo-2,3-diphenyl-6-(quinolin-6-yl)-4,7-dihydropyrazolo[1,5-a]pyrimidine-5-carboxamide

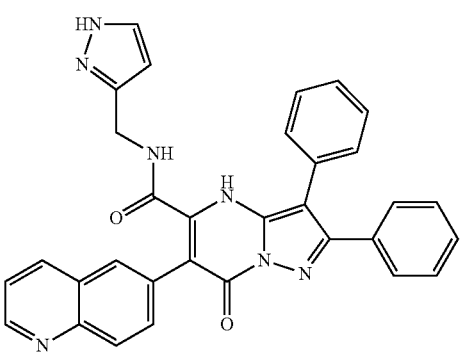

To a solution of 7-oxo-2,3-diphenyl-6-(quinolin-6-yl)-4,7-dihydropyrazolo[1,5-a]pyrimidine-5-carboxylic acid (Synthesized in scheme of Compound 329, 100 mg, 0.2 mmol) in DMF (5 mL) were added (1H-pyrazol-3-yl)methanamine (23 mg, 0.2 mmol), O-(7-Azabenzotriazol-1-yl)-N,N,N',N'-tetramethyluronium hexafluorophosphate (91 mg, 0.2 mmol) and N,N-diisopropylethylamine (65 mg, 0.5 mmol). The mixture was stirred at r.t. for 30 min. The mixture was diluted with $H_2O$ (15 mL) and extracted with DCM (3*15 mL). The extracts were washed with brine, dried over anhydrous $Na_2SO_4$ and concentrated in vacuo to afford the title compound 2.

$^1$H NMR (DMSO-$d_6$) δ: 12.51 (br. s., 1H), 8.85 (br. s., 1H), 8.54-8.94 (m, 1H), 8.18 (d, J=7.2 Hz, 1H), 7.82-7.94 (m, 2H), 7.78 (d, J=9.0 Hz, 1H), 7.40-7.66 (m, 6H), 7.11-7.40 (m, 7H), 5.85 (br. s., 1H), 4.22 (br. s., 2H). LC-MS: m/z 538.3 (M+H)$^+$.

Compound 328

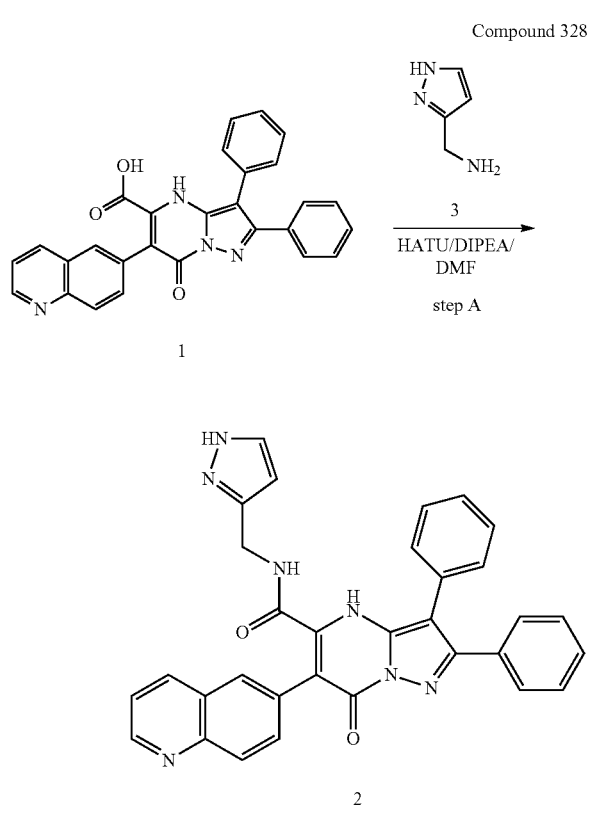 [SMILES: O=C(O)c1[nH]c2c(-c3ccccc3)c(-c3ccccc3)nn2c(=O)c1-c1ccc2ncccc2c1 ; NCc1cc[nH]n1 ; O=C(NCc1cc[nH]n1)c1[nH]c2c(-c3ccccc3)c(-c3ccccc3)nn2c(=O)c1-c1ccc2ncccc2c1]

Compound 329

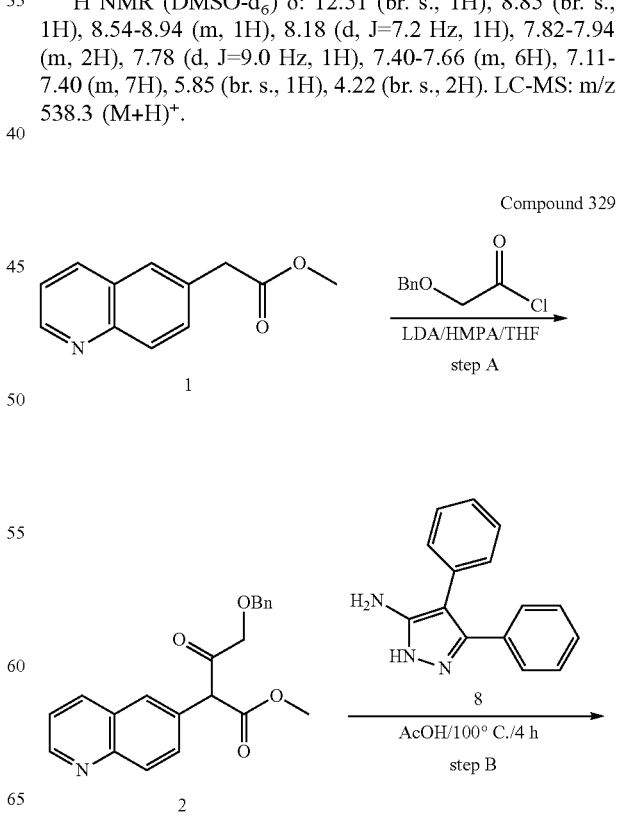

421
-continued

422

Step A: methyl 4-(benzyloxy)-3-oxo-2-(quinolin-6-yl)butanoate

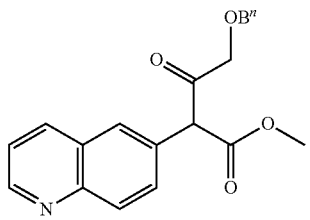 [SMILES: COC(=O)C(C(=O)COCc1ccccc1)c1ccc2ncccc2c1]

To a solution of methyl 2-(quinolin-6-yl)acetate (10.0 g, 49.7 mmol) in THF (60 mL) was added dropwise LDA (2.0 mol/L in THF, 29.8 mL) and HMPA (1.8 g, 9.9 mmol) at −78° C. After addition, the mixture was stirred at −78° C. for 0.5 h. The mixture was then cooled to −78° C. 2-(benzyloxy) acetyl chloride (11.0 g, 59.6 mmol) in dry THF (10 mL) was added slowly and stirred at r.t. overnight. The reaction mixture was diluted with EA (60 mL), quenched with NH$_4$Cl solution, extracted with EA (3*60 mL). The combined organic phase was washed with water and brine, dried over anhydrous Na$_2$SO$_4$, filtered, and concentrated under reduced pressure. The residue was purified by column chromatography on silica gel (EtOAc/PE=1/4) to afford the title compound 2 (8.6 g, 48% yield). LC-MS: m/z 350.1 (M+H)$^+$.

Step B: 5-((benzyloxy)methyl)-2,3-diphenyl-6-(quinolin-6-yl)pyrazolo[1,5-a]pyrimidin-7(4H)-one

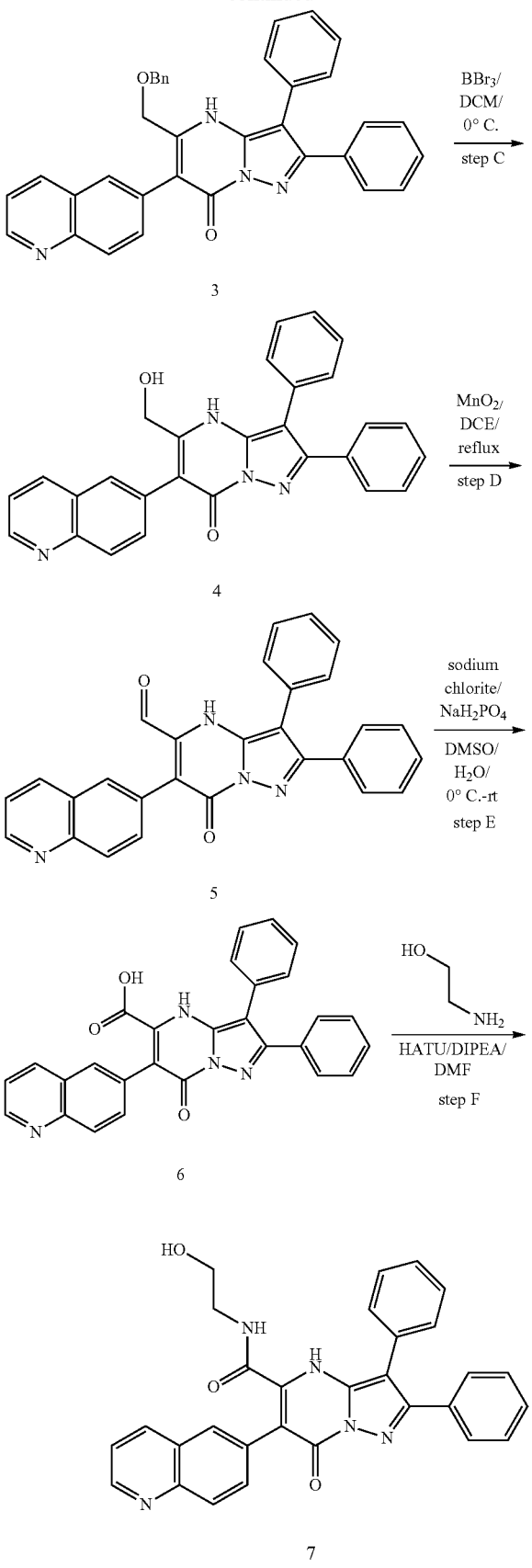

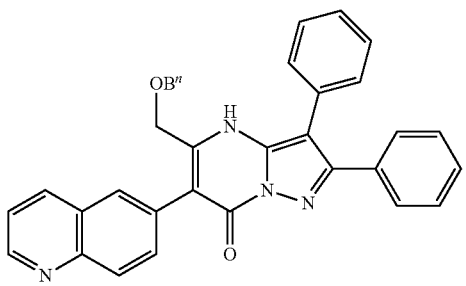

A mixture methyl 4-(benzyloxy)-3-oxo-2-(quinolin-6-yl)butanoate (8.6 g, 24.6 mmol) and 3,4-diphenyl-1H-pyrazol-5-amine (5.8 g, 24.6 mol) in AcOH (100 mL) was stirred at 100° C. for 4 h. After cooling to room temperature, the precipitate was filtered, wash with EA (3*10 mL), and dried under vacuum to afford the title compound 3 as a yellow solid (10.0 g, 78% yield). LC-MS: m/z 535.2 (M+H)$^+$.

Step C: 5-(hydroxymethyl)-2,3-diphenyl-6-(quinolin-6-yl)pyrazolo[1,5-a]pyrimidin-7(4H)-one

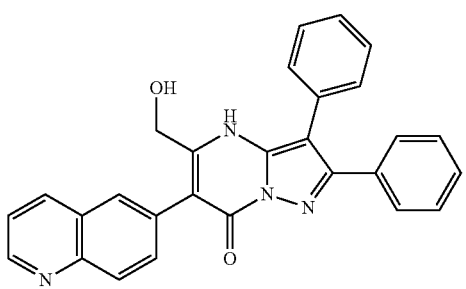 [SMILES: O=c1c(-c2ccc3ncccc3c2)c(CO)[nH]c2c(-c3ccccc3)c(-c3ccccc3)nn12]

To a solution of Intermediate 3 (10.0 g, 18.7 mmol) in DCM (100 mL) was added BCl₃ (1.0 mol/L in DCM, 25 mL) at 0° C. The resultant mixture was stirred at 0° C. for 4 h. The reaction was quenched with MeOH and evaporated. The residue was stirred with 10% NaHCO₃ (10 mL) aqueous solution and EA (10 mL) for 30 min. The precipitate was filtered off, washed with EA (3*2 mL) and dried under vacuum to afford the title compound 4 (8.0 g, 96% yield). LC-MS: m/z 445.1 (M+H)⁺.

Step D: 7-oxo-2,3-diphenyl-6-(quinolin-6-yl)-4,7-dihydropyrazolo[1,5-a]pyrimidine-5-carbaldehyde

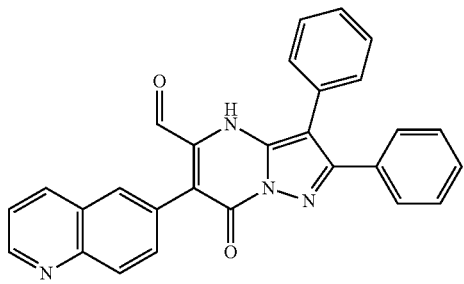 [SMILES: O=Cc1[nH]c2c(-c3ccccc3)c(-c3ccccc3)nn2c(=O)c1-c1ccc2ncccc2c1]

To a solution of Intermediate 4 (4.4 g, 10 mmol) in 1,2-dichloroethane (50 mL) was added MnO₂ (8.7 g, 100 mmol). The mixture was refluxed for 2 days. The reaction was cooled to r.t. and filtered through celite. The filtrate was concentrated in vacuo. The residue was purified by flash chromatography to afford the title compound 5 as a brown solid (1.5 g, 34% yield). LC-MS: m/z 443.1 (M+H)⁺.

Step E: 7-oxo-2,3-diphenyl-6-(quinolin-6-yl)-4,7-dihydropyrazolo[1,5-a]pyrimidine-5-carboxylic acid

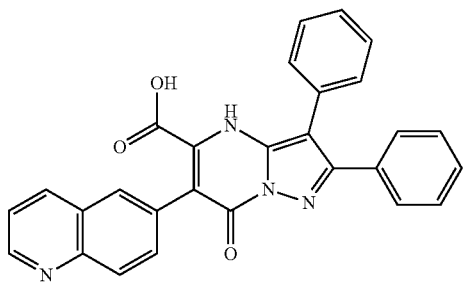 [SMILES: O=C(O)c1[nH]c2c(-c3ccccc3)c(-c3ccccc3)nn2c(=O)c1-c1ccc2ncccc2c1]

To a solution of Intermediate 5 (415 mg, 0.9 mmol) and NaH₂PO₄ (702 mg, 4.5 mmol) in DMSO/H₂O (5 mL/5 mL) was added sodium chlorite (203 mg in 1 mL H₂O, 2.3 mmol) at 0° C. After addition, the mixture was stirred at r.t. for 1 h and poured into H₂O (10 mL). The precipitate was filtered off, washed with MeOH (3*1 mL) and dried in vacuo to afford the title compound 6 as a brown solid (300 mg, 73%). LC-MS: m/z 459.1 (M+H)⁺

Step F: N-(2-hydroxyethyl)-7-oxo-2,3-diphenyl-6-(quinolin-6-yl)-4,7-dihydropyrazolo[1,5-a]pyrimidine-5-carboxamide

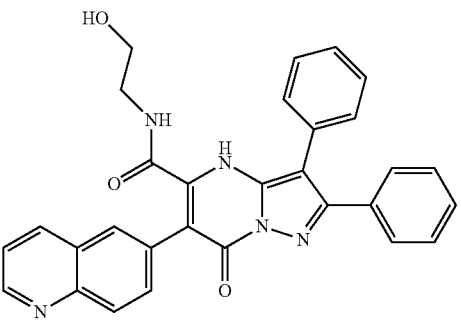 [SMILES: O=C(NCCO)c1[nH]c2c(-c3ccccc3)c(-c3ccccc3)nn2c(=O)c1-c1ccc2ncccc2c1]

To a solution of Intermediate 6 (140 mg, 0.3 mmol) in DMF (5 mL) were added 2-aminoethanol (22 mg, 0.4 mmol), O-(7-Azabenzotriazol-1-yl)-N,N,N',N'-tetramethyluronium hexafluorophosphate (137 mg, 0.4 mmol) and N,N-diisopropylethylamine (97 mg, 0.8 mmol). The mixture was stirred at r.t. for 30 min. The mixture was diluted with H₂O (15 mL) and extracted with DCM (3*15 mL). The extracts were washed with brine, dried over anhydrous Na₂SO₄ and concentrated in vacuo to afford the title compound 7.

¹H NMR (DMSO-d₆) δ: 8.81 (br. s., 1H), 8.24 (d, J=7.8 Hz, 1H), 8.18 (br. s., 1H), 7.75-7.94 (m, 3H), 7.44-7.57 (m, 5H), 7.35 (br. s., 3H), 7.29 (t, J=7.4 Hz, 2H), 7.12-7.17 (m, 1H), 3.25-3.30 (m, 2H), 3.10 (d, J=5.6 Hz, 2H). LC-MS: m/z 502.2 (M+H)⁺.

Compound 330

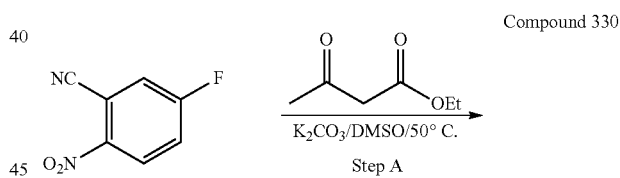

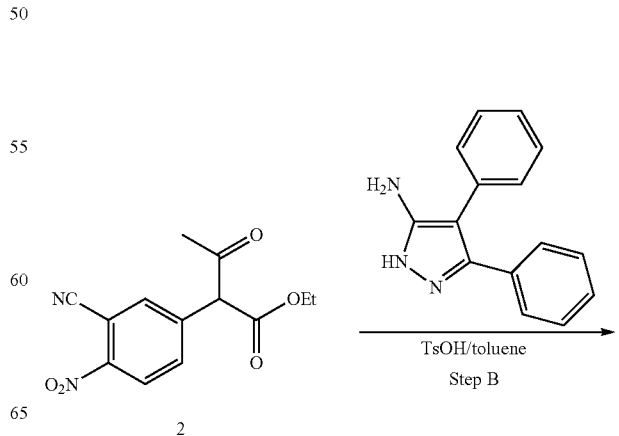

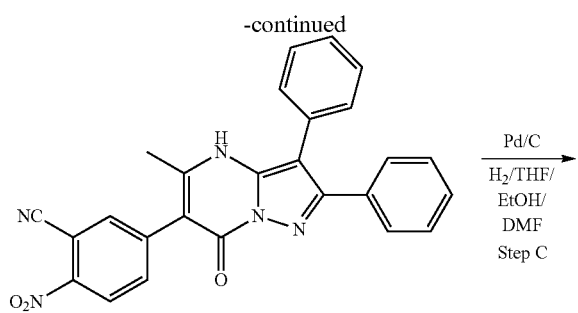

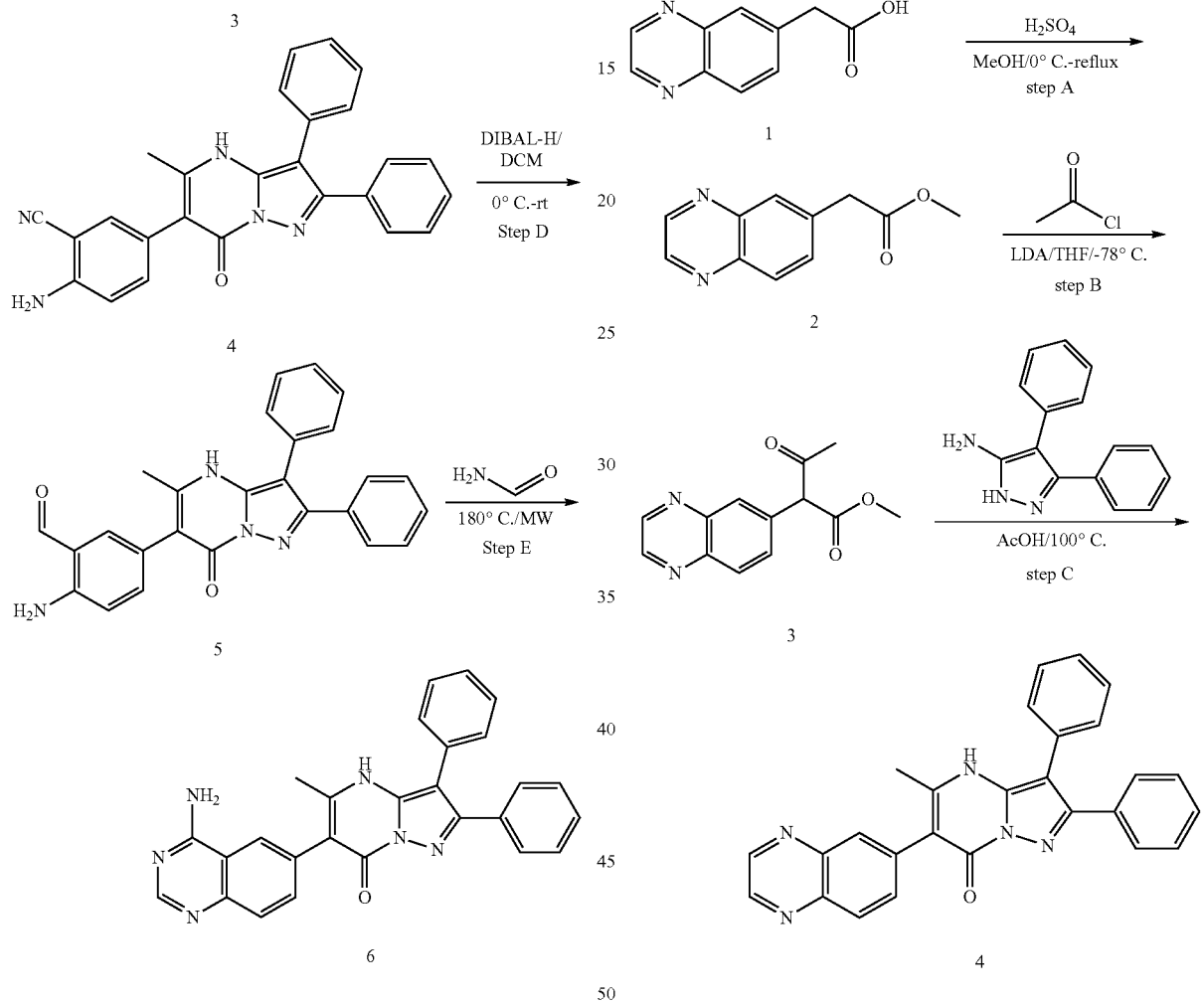

Step E: Compound 330: 6-(4-aminoquinazolin-6-yl)-5-methyl-2,3-diphenylpyrazolo[1,5-a]pyrimidin-7(4H)-one

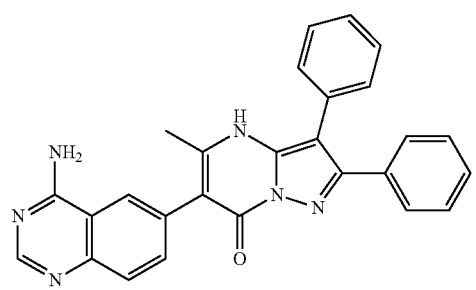 [SMILES: Cc1[nH]c2c(-c3ccccc3)c(-c3ccccc3)nn2c(=O)c1-c1ccc2ncnc(N)c2c1]

A mixture of Intermediate 5 (170 mg, 0.41 mmol, synthesized in scheme of Compound 245) and formamide (5 mL) was stirred at 180° C. for 2 h. under microwave irradiation. The mixture was concentrated under vacuum to afford the title compound 6.

$^1$H NMR (DMSO-$d_6$) δ: 8.40 (s, 1H), 8.18 (d, J=1.6 Hz, 1H), 7.90-7.63 (m, 4H), 7.53-7.24 (m, 11H), 2.23 (s, 3H). LC-MS: m/z 445.1 (M+H)$^+$.

Compound 331

Step A: methyl 2-(quinoxalin-6-yl)acetate

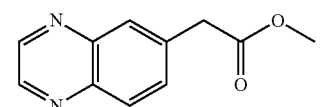

To 2-(quinoxalin-6-yl)acetic acid (1.0 g, 5.31 mmol) in methanol (20 mL) was added slowly conc. H$_2$SO$_4$ (1.0 mL) at 0° C., and the mixture was refluxed overnight. The reaction mixture was concentrated in vacuo, and the residue dissolved in EA. The organic solution was washed with saturated aqueous NaHCO$_3$ and brine, dried over Na$_2$SO$_4$, and concentrated in vacuo. The residue was purified by flash chromatography, eluting with PE/EA=4/1, to obtain the desired product as a yellow oil (0.47 g, 43% yield). LC-MS: m/z 203.2 (M+H)+.

Step B: methyl 3-oxo-2-(quinoxalin-6-yl)butanoate

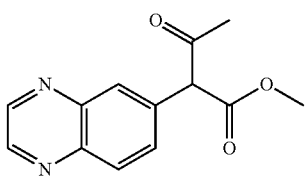 [SMILES: COC(=O)C(C(C)=O)c1ccc2nccnc2c1]

To a solution of methyl methyl 2-(quinoxalin-6-yl)acetate (0.45 g, 2.23 mmol) in THF (20 mL) was added LDA (2.0 M in THF, 1.4 mL, 2.90 mmol) dropwise at −40° C. The mixture was stirred at −78° C. for 30 min and acetyl chloride (0.17 mL, 2.33 mmol) was added dropwise. Then the mixture was slowly warmed to RT and stirred for 10 h. The mixture was poured slowly to saturated aq. NH$_4$Cl and extracted with EA (30 mL*3). The combined organic phase was washed with brine, dried over anhydrous MgSO$_4$ and concentrated in vacuo to get the desired product as a yellow oil (0.40 g, 88% yield). LC-MS: m/z 245.2 (M+H)+.

Step C: 5-methyl-2,3-diphenyl-6-(quinoxalin-6-yl)pyrazolo[1,5-a]pyrimidin-7(4H)-one

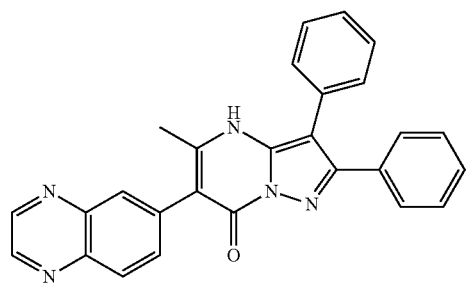 [SMILES: Cc1[nH]c2c(-c3ccccc3)c(-c3ccccc3)nn2c(=O)c1-c1ccc2nccnc2c1]

The mixture of 3,4-diphenyl-1H-pyrazol-5-amine (100 mg, 0.42 mmol) and methyl methyl 3-oxo-2-(quinoxalin-6-yl)butanoate (135 mg, 0.55 mmol) in AcOH (5 mL) was stirred at 100° C. for 1 h. After removal of AcOH, 10% of NaHCO$_3$ was added to afford the desired product.

$^1$H NMR (DMSO-d$_6$) δ: 12.05 (br. s., 1H), 8.95 (dd, J=1.6 Hz, 2.0 Hz, 2H), 8.12 (d, J=8.8 Hz, 1H), 8.06 (d, J=1.6 Hz, 1H), 7.90 (dd, J=1.6 Hz, 2.0 Hz, 1H), 7.51 (dd, J=3.6 Hz, 2.4 Hz, 2H), 7.44-7.28 (m, 8H), 2.26 (s, 3H). LC-MS: m/z 430.0 (M+H)+.

Compound 332

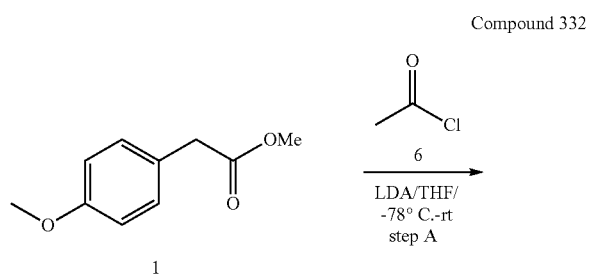

-continued

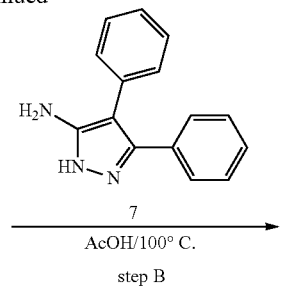

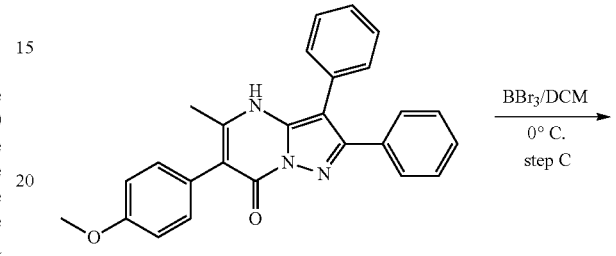

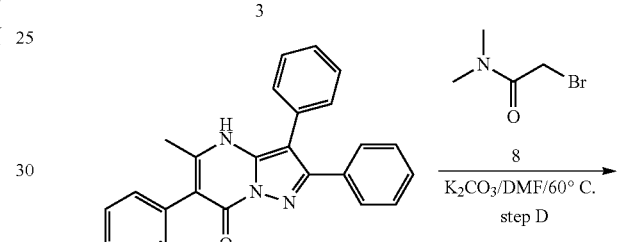

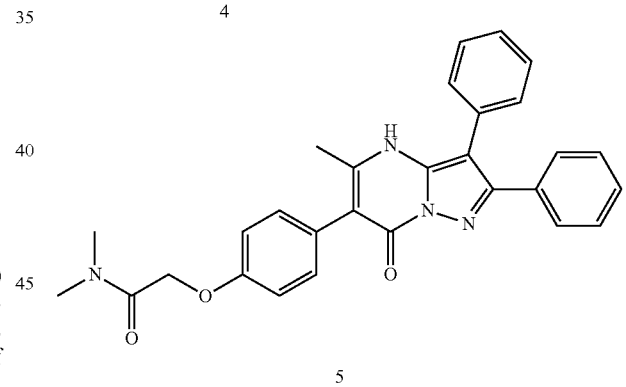

Step D: N,N-dimethyl-2-(4-(5-methyl-7-oxo-2,3-diphenyl-4,7-dihydropyrazolo[1,5-a]pyrimidin-6-yl)phenoxy)acetamide

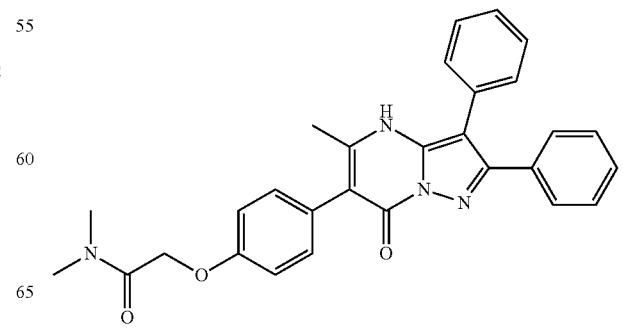

To a solution of Intermediate 4 (80 mg, 0.2 mmol, Compound 237) in DMF (5 mL) were added 2-bromo-N,N-dimethylacetamide (34 mg, 0.2 mmol) and $K_2CO_3$ (56 mg, 0.4 mmol). The mixture was stirred at 60° C. for 3 h. The mixture was poured into $H_2O$ (15 mL) and extracted with DCM (3*10 mL). The combined extracts were washed with brine and dried over anhydrous $Na_2SO_4$ and concentrated in vacuo to afford the title compound 5.

$^1$H NMR (DMSO-$d_6$) δ: 11.88 (br. s., 1H), 7.39-7.49 (m, 5H), 7.28-7.38 (m, 5H), 7.23 (d, J=8.8 Hz, 2H), 6.96 (d, J=8.8 Hz, 2H), 4.84 (s, 2H), 3.03 (s, 3H), 2.87 (s, 3H), 2.18 (s, 3H). LC-MS: m/z 480.0 (M+H)$^+$.

Compound 333

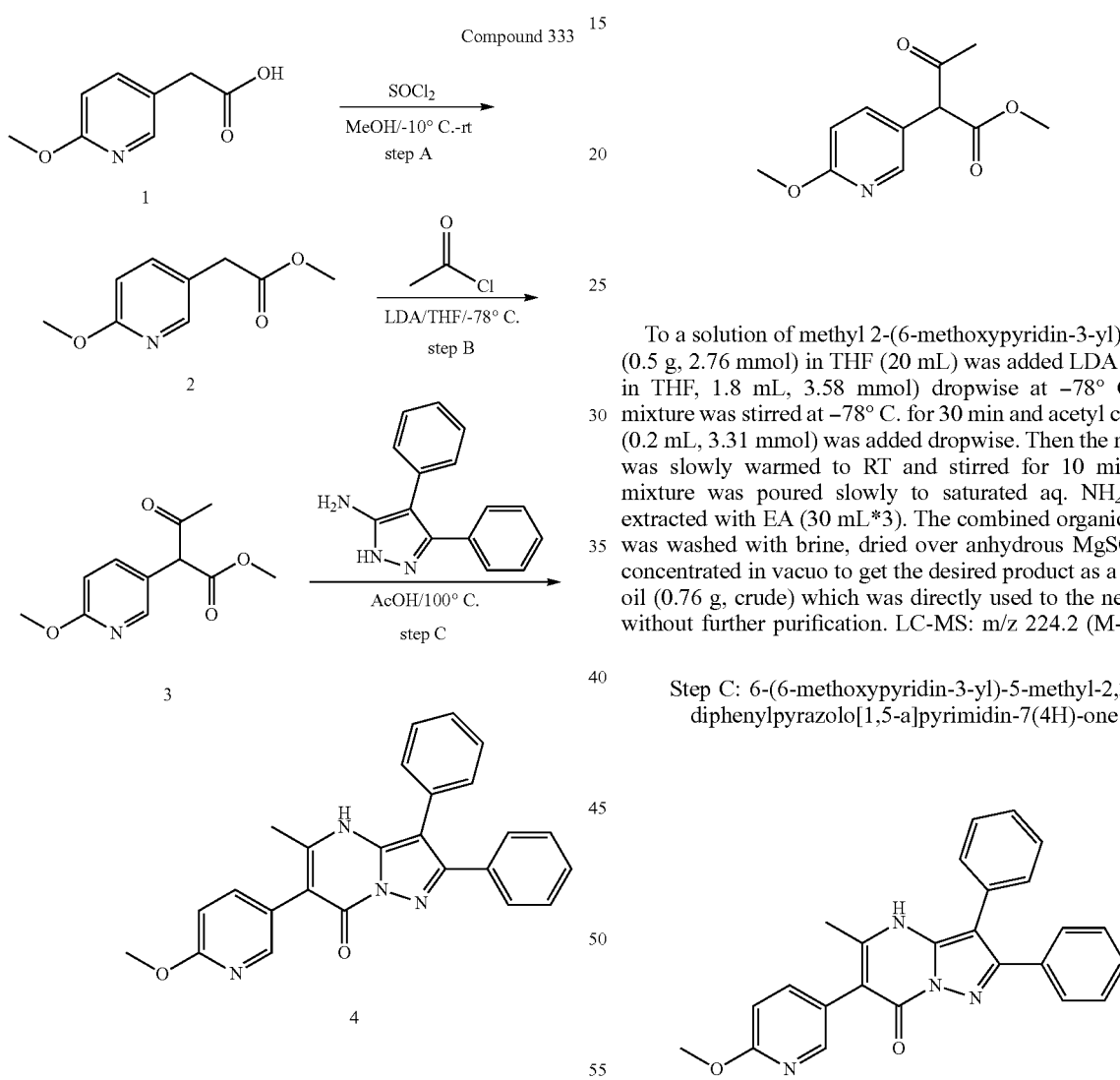

Step A: methyl 2-(6-methoxypyridin-3-yl)acetate

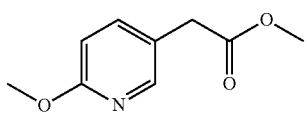

To 2-(6-methoxypyridin-3-yl)acetic acid (1.0 g, 5.98 mmol) in MeOH (20 mL) was slowly added thionyl chloride (4.0 mL, 55.1 mmol) at −10° C., and the mixture was stirred at RT overnight. The reaction mixture was concentrated in vacuo, and the residue was dissolved in DCM. The solution was washed with saturated aqueous $NaHCO_3$ and brine, dried over $Na_2SO_4$, and concentrated in vacuo. The residue was purified by flash chromatography, eluting with PE/EA=4/1, to obtain the desired product as yellow oil (1.0 g, 92% yield). LC-MS: m/z 182.2 (M+H)$^+$.

Step B: methyl 2-(6-methoxypyridin-3-yl)-3-oxobutanoate

To a solution of methyl 2-(6-methoxypyridin-3-yl)acetate (0.5 g, 2.76 mmol) in THF (20 mL) was added LDA (2.0 M in THF, 1.8 mL, 3.58 mmol) dropwise at −78° C. The mixture was stirred at −78° C. for 30 min and acetyl chloride (0.2 mL, 3.31 mmol) was added dropwise. Then the mixture was slowly warmed to RT and stirred for 10 min. The mixture was poured slowly to saturated aq. $NH_4C$ and extracted with EA (30 mL*3). The combined organic phase was washed with brine, dried over anhydrous $MgSO_4$ and concentrated in vacuo to get the desired product as a yellow oil (0.76 g, crude) which was directly used to the next step without further purification. LC-MS: m/z 224.2 (M+H)$^+$.

Step C: 6-(6-methoxypyridin-3-yl)-5-methyl-2,3-diphenylpyrazolo[1,5-a]pyrimidin-7(4H)-one The mixture of 3,4-diphenyl-1H-pyrazol-5-amine (150 mg, 1.06 mmol) and methyl 2-(6-methoxypyridin-3-yl)-3-oxobutanoate (309 mg, 1.38 mmol) in AcOH (5 mL) was stirred at 100° C. for 1 h. After removal of AcOH under reduced pressure, 10% of $NaHCO_3$ was added to afford the desired product.

$^1$H NMR (DMSO-$d_6$) δ: 12.01 (br. s., 1H), 8.13 (d, J=2.4 Hz, 1H), 7.70 (dd, J=2.4 Hz, 2.4 Hz, 1H), 7.47-7.42 (m, 5H), 7.33 (dd, J=1.6 Hz, 1.6 Hz, 5H), 6.91 (dd, J=0.4 Hz, 0.4 Hz, 1H), 3.91 (s, 3H), 2.22 (s, 3H). LC-MS: m/z 409.4 (M+H)$^+$.

Compound 334

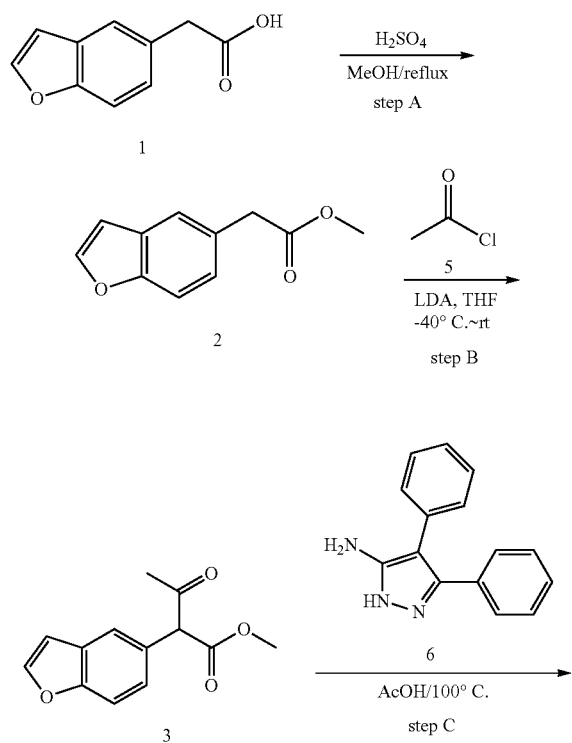

Step A: methyl 2-(benzofuran-5-yl)acetate

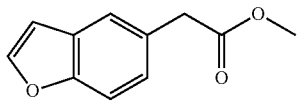

To a solution of 2-(benzofuran-5-yl)acetic acid (350 mg, 2 mmol) in MeOH (40 mL) was added one drop of concentrated $H_2SO_4$. The mixture was refluxed for 3 h. Then the mixture was cooled to r.t. and evaporated. The residue was dissolved in EA (30 mL), washed with 10/o $NaHCO_3$ aqueous solution and brine, dried over anhydrous $MgSO_4$, and concentrated in vacuo to afford the intermediate 2 as a colorless oil (340 mg, 90% yield) which was used to the next step without purification. LC-MS: m/z 191.0 (M+H)$^+$.

Step B: methyl 2-(benzofuran-5-yl)-3-oxobutanoate

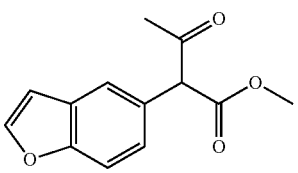 [SMILES: COC(=O)C(C(C)=O)c1ccc2occc2c1]

To a solution of Intermediate 2 (340 mg, 1.8 mmol) in THF (20 mL) was added LDA (2 mol/L in THF, 1.1 mL) at −40° C. dropwise. After the mixture was stirred at −40° C. for 30 min, acetyl chloride (173 mg, 2.2 mmol) was added dropwise. The mixture was then stirred at r.t. for 3 h. The mixture was diluted with EA (20 mL) and quenched with saturated $NH_4Cl$ aqueous solution. The organic phase was separated and washed with brine, dried over anhydrous $Na_2SO_4$, and concentrated in vacuo to afford the crude intermediate 3 as a yellow oil (250 mg, 60% yield) which was used to the next step without purification. LC-MS: m/z 233.0 (M+H)$^+$.

Step C: 6-(benzofuran-5-yl)-5-methyl-2,3-diphenylpyrazolo[1,5-a]pyrimidin-7(4H)-one

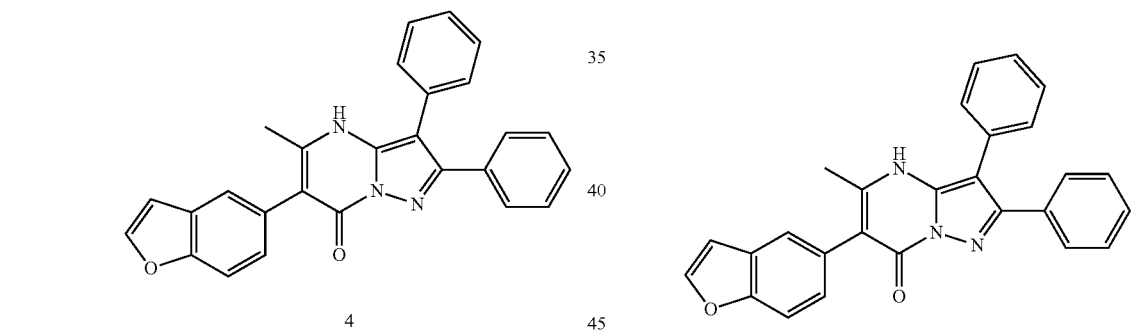

The mixture of Intermediate 3 (110 mg, 0.47 mmol) and 3,4-diphenyl-1H-pyrazol-5-amine (120 mg, 0.51 mmol) in AcOH (10 mL) was stirred at 100° C. for 1 h. Then the mixture was cooled to r.t. to afford the desired product 4.

$^1$H NMR (DMSO-d$_6$) δ: 11.94 (br. s., 1H), 8.04 (d, J=2.0 Hz, 1H), 7.65 (d, J=8.6 Hz, 1H), 7.60 (d, J=1.6 Hz, 1H), 7.38-7.48 (m, 5H), 7.31-7.37 (m, 5H), 7.25 (dd, J=8.4, 1.6 Hz, 1H), 7.00 (d, J=1.2 Hz, 1H), 2.17 (s, 3H). LC-MS: m/z 418.0 (M+H)$^+$.

Compound 335

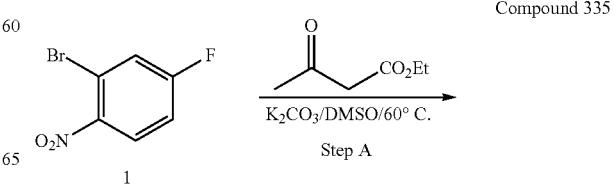

-continued

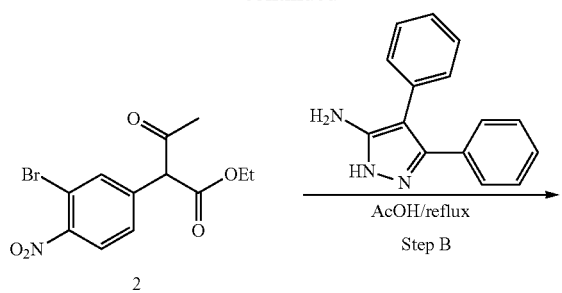

2

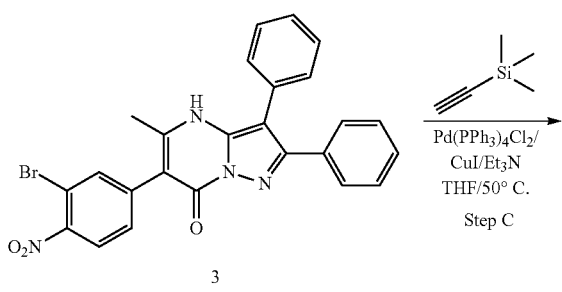

3

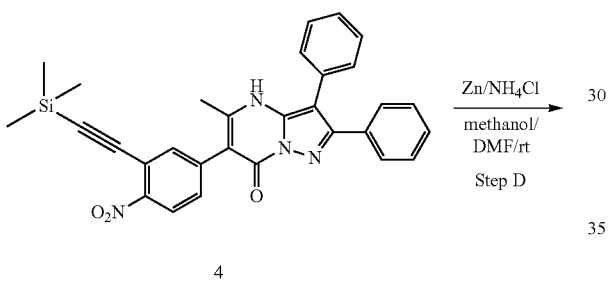

4

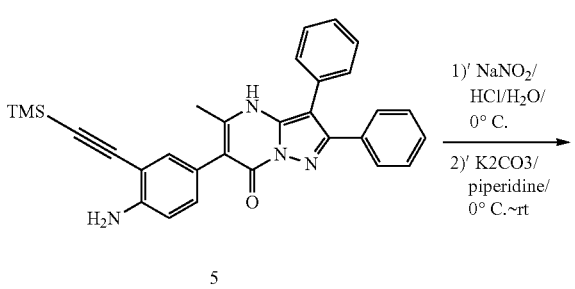

5

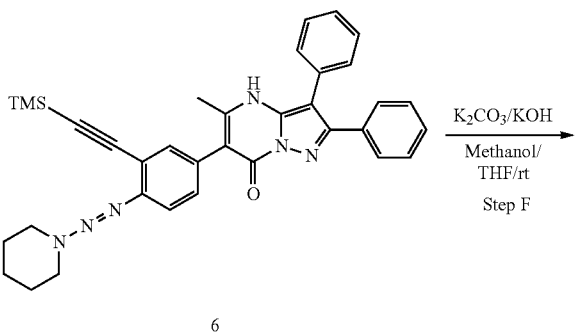

6

-continued

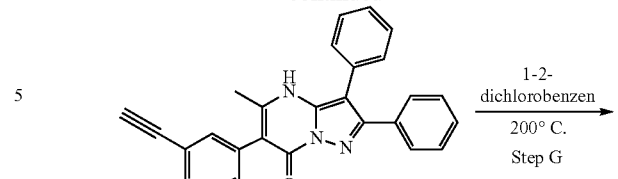

7

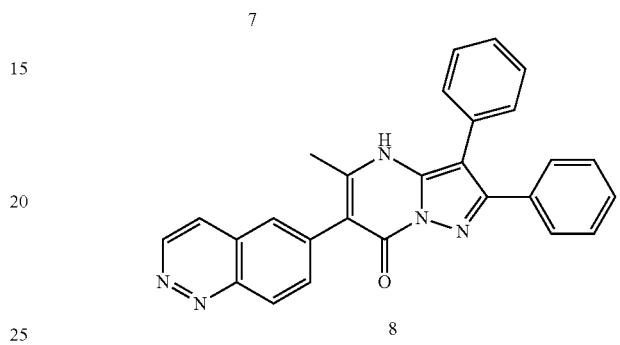

8

Step A: ethyl 2-(3-bromo-4-nitrophenyl)-3-oxobutanoate

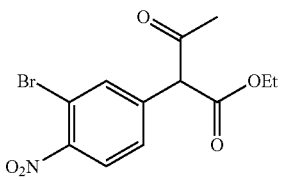 [SMILES: CCOC(=O)C(C(C)=O)c1ccc([N+](=O)[O-])c(Br)c1]

2-bromo-4-fluoro-1-nitrobenzene (6.6 g, 30 mmol), ethyl 3-oxobutanoate (7.8 g, 60 mmol) and K$_2$CO$_3$ (12.46 g, 90 mmol) in DMSO (50 mL) was stirred at 60° C. for 16 h. The mixture was acidified with 1M HCl to pH=7 and extracted with EA (50 mL*3). The organic layer was dried and concentrated to give the crude product, which was purified by silica gel chromatography (PE/EA=3/1) to obtain the desired product as yellow solid (7.6 g, 770% yield). LC-MS: m/z 331.2 (M+H)$^+$.

Step B: 6-(3-bromo-4-nitrophenyl)-5-methyl-2,3-diphenylpyrazolo[1,5-a]pyrimidin-7(4H)-one

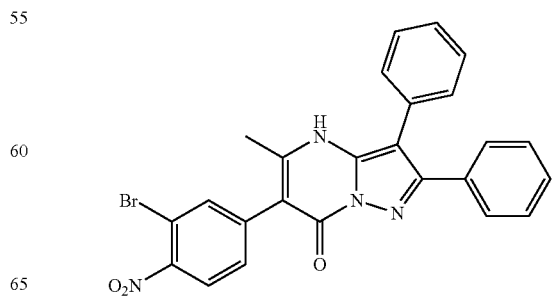

A suspension of 3,4-diphenyl-1H-pyrazol-5-amine (4.6 g, 19.6 mmol) and ethyl 2-(3-bromo-4-nitrophenyl)-3-oxobutanoate (7.2 g, 21.8 mmol) in AcOH (20 mL) was refluxed for 30 min under $N_2$ protection. The mixture was cooled to the RT, concentrated and neutralized with saturated sodium hydrogen carbonate solution to adjust to pH=7. The precipitates were collected by filtration, washed with petroleum ether and dried to obtain the desired product as a yellow solid (9.0 g, 92% yield). LC-MS: m/z 502.2 (M+H)+.

Step C: 5-methyl-6-(4-nitro-3-((trimethylsilyl)ethynyl)phenyl)-2,3-diphenylpyrazolo[1,5-a]pyrimidin-7(4H)-one

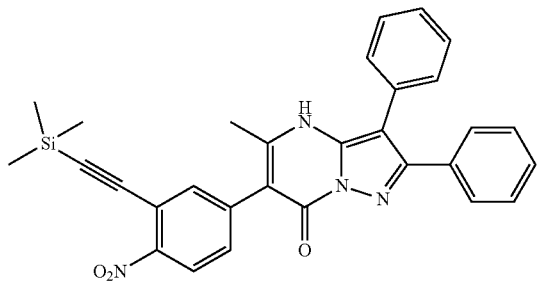 [SMILES: Cc1[nH]c2c(-c3ccccc3)c(-c3ccccc3)nn2c(=O)c1-c1ccc([N+](=O)[O-])c(C#C[Si](C)(C)C)c1]

A suspension of 6-(3-bromo-4-nitrophenyl)-5-methyl-2,3-diphenylpyrazolo[1,5-a]pyrimidin-7(4H)-one (3.0 g, 6.0 mmol), ethynyltrimethylsilane (1.18 g, 12.0 mmol), Pd(PPh$_3$)$_2$Cl$_2$ (42 mg, 0.6 mmol), CuI (228 mg, 1.2 mmol) and TEA (15 mL, 18.0 mmol) in THF (50 ml) was heated to 50° C. for 6 h under an atmosphere of $N_2$. The mixture was cooled to the RT, diluted with water, and extracted with EA (30 mL*3). The combined organic layers were washed with brine, dried over anhydrous sodium sulfate, and concentrated under vacuum. The residue was purified by silica gel column, eluting with DCM/MeOH (40/1), to obtain the desired product as a yellow solid (2.3 g, 74% yield). LC-MS: m/z 519.2 (M+H)+.

Step D: 6-(4-amino-3-((trimethylsilyl)ethynyl)phenyl)-5-methyl-2,3-diphenylpyrazolo[1,5-a]pyrimidin-7(4H)-one

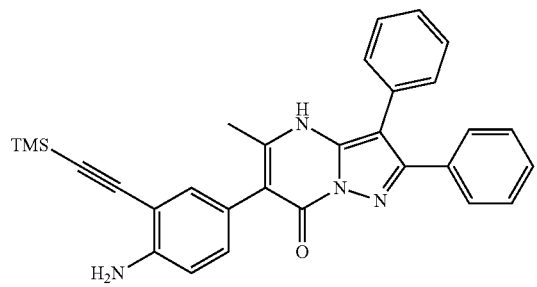 [SMILES: Cc1[nH]c2c(-c3ccccc3)c(-c3ccccc3)nn2c(=O)c1-c1ccc(N)c(C#C[Si](C)(C)C)c1]

To a suspension of 5-methyl-6-(4-nitro-3-((trimethylsilyl)ethynyl)phenyl)-2,3-diphenylpyrazolo[1,5-a]pyrimidin-7(4H)-one (2.3 g, 4.4 mmol) in DMF/MeOH (20 mL/30 mL) was added sat. ammonium chloride aqueous solution (20 mL) and zinc powder (2.88 g, 44.4 mmol). The resultant mixture was stirred at RT overnight. The reaction mixture was filtered and concentrated. The residue was purified by flash column chromatography, eluting with DCM/MeOH (20/1), to obtain the desired product as a yellow solid (600 mg, 28% yield). LC-MS: m/z 489.2 (M+H)+.

Step E: 5-methyl-6-(4-nitro-3-((trimethylsilyl)ethynyl)phenyl)-2,3-diphenylpyrazolo[1,5-a]pyrimidin-7(4H)-one

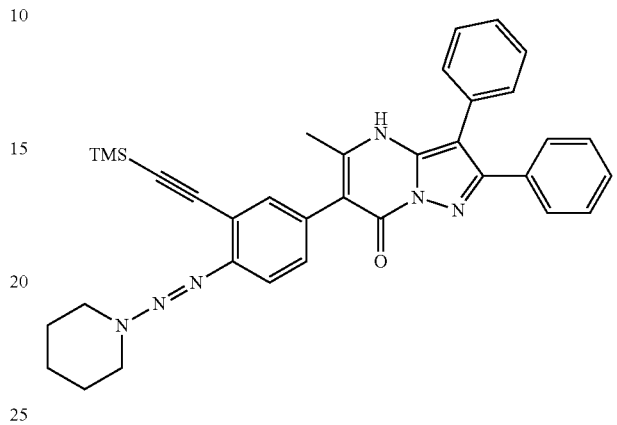

A suspension of 6-(4-amino-3-((trimethylsilyl)ethynyl)phenyl)-5-methyl-2,3-diphenylpyrazolo[1,5-a]pyrimidin-7(4H)-one (120 mg, 0.24 mmol) in acetonitrile/water (1.4 mL/0.7 mL) was added con. hydrochloric acid (0.2 mL, 2.4 mmol) at 0° C. Then a solution of sodium nitrite (25 mg, 0.37 mmol) in water (2 mL) was introduced slowly while keeping the temperature below 0° C. After the addition, the resultant mixture was stirred at 0° C. for 30 min. Then the mixture was added slowly to a stirred solution of piperidine (137 mg, 1.62 mmol) and potassium carbonate (260 mg, 1.88 mmol) in acetonitrile/water (2 mL/1 mL) at 0° C. The resultant mixture was allowed to warm to RT for 1 h. The reaction was quenched with water, extracted with EA (30 mL*3). The combined organic layers were washed with brine, dried over anhydrous sodium sulfate, and concentrated under vacuum. The residue was purified by silica gel column, eluting with DCM/MeOH (20/1), to obtain the desired product as a yellow solid (140 mg, 99% yield). LC-MS: m/z 585.3 (M+H)+.

Step F: 6-(3-ethynyl-4-(piperidin-1-yldiazenyl)phenyl)-5-methyl-2,3-diphenylpyrazolo[1,5-a]pyrimidin-7(4H)-one

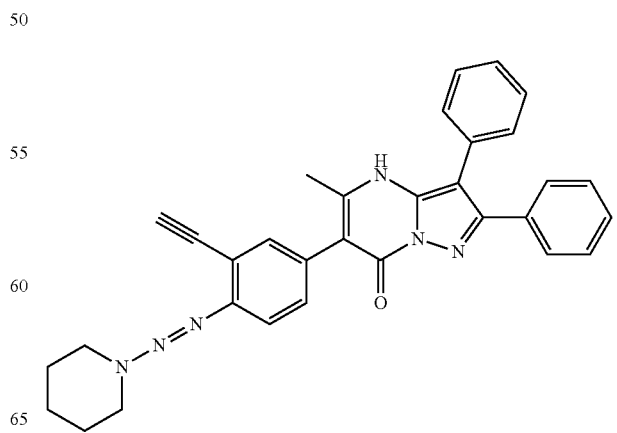

To a mixture of 5-methyl-6-(4-nitro-3-((trimethylsilyl) ethynyl)phenyl)-2,3-diphenylpyrazolo[1,5-a]pyrimidin-7 (4H)-one (50 mg, 0.08 mmol) in THF/MeOH (0.85 ml/0.17 mL) was added potassium carbonate (117 mg, 0.85 mmol) and potassium hydroxide (50 mg, 0.09 mmol). Then the mixture was stirred at RT for 2 h, The reaction mixture was diluted with water, extracted with EA (30 mL*3). The combined organic layers were washed with brine, dried over anhydrous sodium sulfate, and concentrated in vacuo. The residue was purified by silica gel column, eluting with DCM/MeOH (25/1), to obtain the desired product as a yellow solid (30 mg, 50% yield). LC-MS: m/z 513.2 (M+H)$^+$.

Step G: 6-(cinnolin-6-yl)-5-methyl-2,3-diphenylpyrazolo[1,5-a]pyrimidin-7(4H)-one

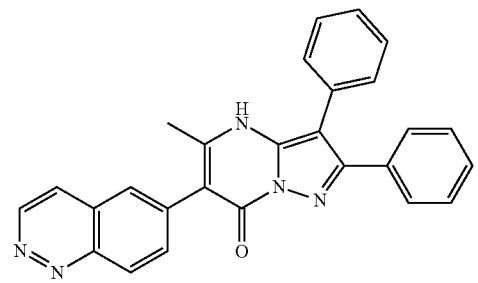 [SMILES: Cc1[nH]c2c(-c3ccccc3)c(-c3ccccc3)nn2c(=O)c1-c1ccc2nnccc2c1]

A mixture of 6-(3-ethynyl-4-(piperidin-1-yldiazenyl)phenyl)-5-methyl-2,3-diphenylpyrazolo[1,5-a]pyrimidin-7 (4H)-one (30 mg, 0.006 mmol) in 1,2-dichlorobenzen (2 mL) was heated at 200° C. for 16 h to obtain the desired product.

$^1$H NMR (DMSO-d$_6$) δ: 12.05 (br. s., 1H), 9.38 (d, J=5.6 Hz, 1H), 8.48 (d, J=8.4 Hz, 1H), 8.23 (d, J=6.0 Hz, 1H), 8.05 (s, 1H), 7.98 (dd, J=2.0 Hz, 1.6 Hz, 1H), 7.48-7.31 (m, 10H), 2.27 (s, 3H). LC-MS: m/z 430.2 (M+H)$^+$.

Compound 336

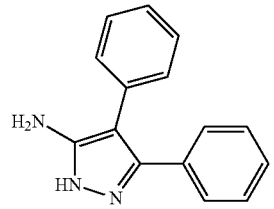

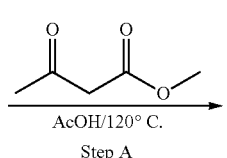

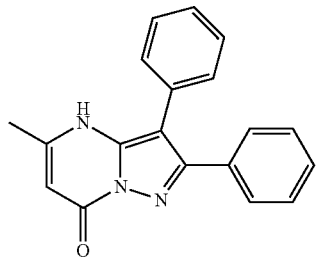

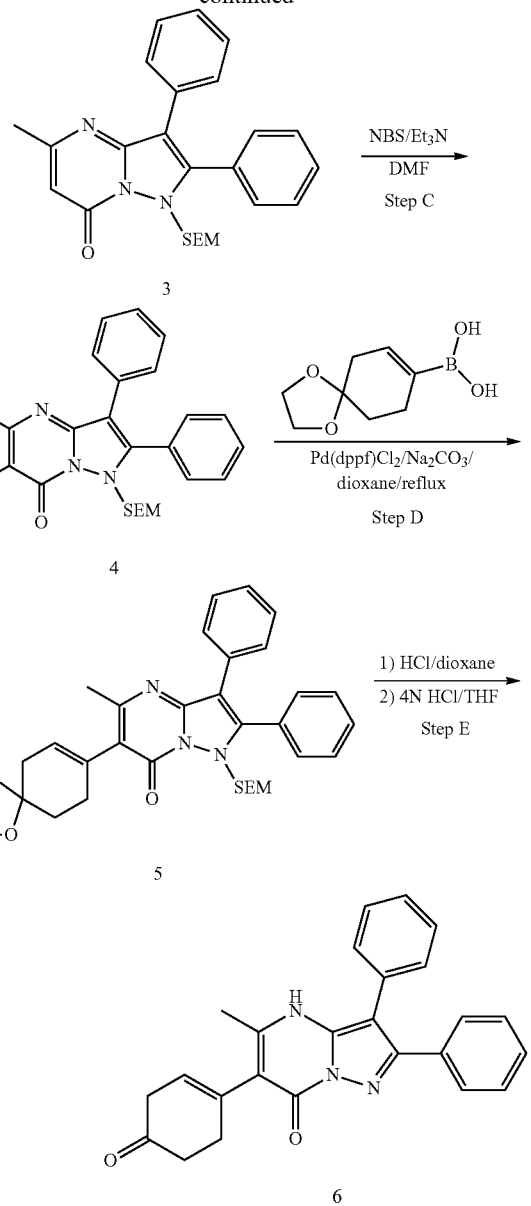

Step A: 5-methyl-2,3-diphenylpyrazolo[1,5-a]pyrimidin-7(4H)-one

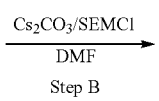

The mixture of 3,4-diphenyl-1H-pyrazol-5-amine (3 g, 12.8 mmol, 1 eq.) and methyl 3-oxobutanoate (2.96 g, 25.5 mmol) in AcOH (20 mL) was stirred at 120° C. for 4 h. Then the mixture was cooled to r.t. and filtered to give the crude solid which was washed with EA to afford the desired product 5-methyl-2,3-diphenylpyrazolo[1,5-a]pyrimidin-7 (4H)-one (3.5 g) LC-MS: m/z 302.1 (M+H)+.

Step B: 5-methyl-2,3-diphenyl-1-((2-(trimethylsilyl) ethoxy)methyl)pyrazolo[1,5-a]pyrimidin-7(1H)-one

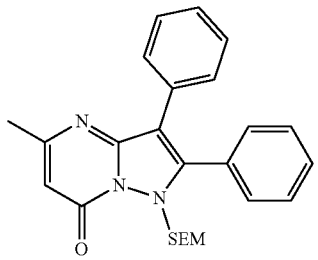 [SMILES: Cc1cc(=O)n2c(n1)c(-c1ccccc1)c(-c1ccccc1)n2COCC[Si](C)(C)C]

To the mixture of 5-methyl-2,3-diphenylpyrazolo[1,5-a] pyrimidin-7(4H)-one (3.5 g, 11.6 mmol), Cs$_2$CO$_3$ (7.58 g, 23.2 mmol) in DMF (50 mL) was added 1-(chloromethyl)-4-methoxybenzene (2.3 g, 13.9 mmol). The reaction was stirred at r.t. for 16 h. The mixture was diluted with H$_2$O (30 mL) and extracted with DCM (10 mL*3). The organic layer was dried over anhydrous sodium sulfate and concentrated in vacuo to dryness. The resulting solid was purified by silica gel chromatography (PE/EA=10:1) to give the desired product (3.19 g). LC-MS: m/z 432.3 (M+H)+.

Step C: 6-bromo-5-methyl-2,3-diphenyl-1-((2-(trimethylsilyl)ethoxy)methyl)pyrazolo[1,5-a]pyrimidin-7 (1H)-one

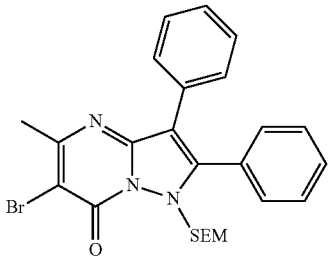 [SMILES: Cc1nc2c(-c3ccccc3)c(-c3ccccc3)n(COCC[Si](C)(C)C)n2c(=O)c1Br]

To a solution of 5-methyl-2,3-diphenyl-1-((2-(trimethylsilyl)ethoxy)methyl)pyrazolo[1,5-a]pyrimidin-7(1H)-one (3.1 g, 7.2 mmol) in DCM (50 mL) and TEA (1.45 g, 14.58 mmol) was added dropwise NBS (1.4 g, 7.9 mmol) in DCM (5 mL). The resultant mixture was stirred for 3 hours at ambient temperature and washed with water. The aqueous phase was extracted with DCM (20 mL). The combined organic layers were washed with brine (20 ml), dried over anhydrous sodium sulfate, and concentrated in vacuo. The residue was purified by silica gel chromatography (PE/EA=10/1) to obtain the 6-bromo-5-methyl-2,3-diphenyl-1-((2-(trimethylsilyl)ethoxy)methyl)pyrazolo[1,5-a]pyrimidin-7(1H)-one (3 g, 82% yield). LC-MS: m/z 510.1 (M+H)+.

Step D: 5-methyl-2,3-diphenyl-6-(1,4-dioxaspiro [4.5]dec-7-en-8-yl)-1-((2-(trimethylsilyl)ethoxy) methyl)pyrazolo[1,5-a]pyrimidin-7(1H)-one

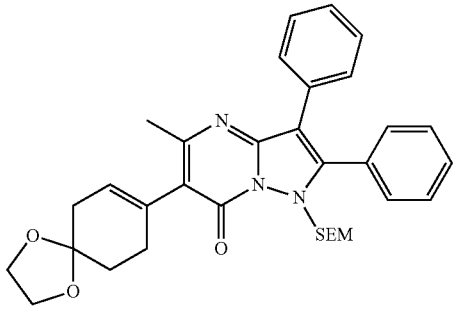 [SMILES: Cc1nc2c(-c3ccccc3)c(-c3ccccc3)n(COCC[Si](C)(C)C)n2c(=O)c1C1=CCC2(CC1)OCCO2]

To a solution of 6-bromo-5-methyl-2,3-diphenyl-1-((2-(trimethylsilyl)ethoxy)methyl)pyrazolo[1,5-a]pyrimidin-7 (1H)-one (400 mg, 0.786 mmol) and 1,4-dioxaspiro[4.5] dec-7-en-8-ylboronic acid (251 mg, 0.943 mmol) in dioxane/H$_2$O (26 mL/9 mL) was added 1,1'-bis(diphenylphosphino)ferrocene-palladium(II)dichloride dichloromethane complex (57 mg, 0.078 mmol) and sodium carbonate (166 mg, 1.57 mmol). The reaction mixture was then refluxed under nitrogen atmosphere overnight. The reaction mixture was filtered and concentrated in vacuo. The residue was purified by column chromatography (PE/EA=1/20) to afford 5-methyl-2,3-diphenyl-6-(1,4-dioxaspiro[4.5]dec-7-en-8-yl)-1-((2-(trimethylsilyl) ethoxy)methyl)pyrazolo[1,5-a]pyrimidin-7(1H)-one (100 mg, 22.3% yield) as a white solid. LC-MS: m/z 570.2 (M+H)+.

Step E: Compound 336: 5-methyl-6-(4-oxocyclohex-1-en-1-yl)-2,3-diphenylpyrazolo[1,5-a]pyrimidin-7(4H)-one

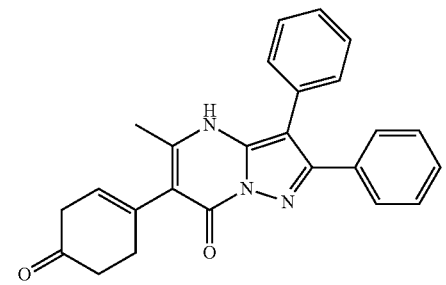 [SMILES: Cc1[nH]c2c(-c3ccccc3)c(-c3ccccc3)nn2c(=O)c1C1=CCC(=O)CC1]

A mixture of 5-methyl-2,3-diphenyl-6-(1,4-dioxaspiro [4.5]dec-7-en-8-yl)-1-((2-(trimethylsilyl) ethoxy)methyl) pyrazolo[1,5-a]pyrimidin-7(1H)-one 100 mg, 0.176 mmol) in HCl/dioxane (1.5 mL, 4M) was stirred at r.t. for 1 h. The mixture was concentrated in vacuo to dryness. The resulting residue was dissolved in 4N HCl and THF (10 mL) and stirred at r.t. for 1 h to afford 5-methyl-6-(4-oxocyclohex-1-en-1-yl)-2,3-diphenylpyrazolo[1,5-a]pyrimidin-7(4H)-one.

$^1$H NMR (DMSO-d$_6$) δ: 11.81 (br. s., 1H), 7.39-7.48 (m, 5H), 7.28-7.35 (m, 5H), 5.65-5.74 (m, 1H), 3.02 (br. s., 2H), 2.53-2.70 (m, 4H), 2.33 (s, 3H). LC-MS: m/z 396.1 (M+H)+.

Compound 337

Step A: 6-(4-hydroxycyclohex-1-en-1-yl)-5-methyl-2,3-diphenylpyrazolo[1,5-a]pyrimidin-7(4H)-one To a solution of 5-methyl-6-(4-oxocyclohex-1-en-1-yl)-2,3-diphenylpyrazolo[1,5-a]pyrimidin-7(4H)-one (Synthesized in scheme of Compound 336, 20 mg, 0.05 mmol) in MeOH (10 mL) was added NaBH$_4$ (2.3 mg, 0.06 mmol). The reaction mixture was stirred at r.t. for 1 h. The mixture was poured into water and extracted with EA (10 mL×3). The combined organic phase was washed with brine, dried over anhydrous sodium sulfate and concentrated in vacuo to afford 6-(4-hydroxycyclohex-1-en-1-yl)-5-methyl-2,3-diphenylpyrazolo[1,5-a]pyrimidin-7(4H)-one.

$^1$H NMR (DMSO-d$_6$) δ: 11.71 (br. s., 1H), 7.37-7.46 (m, 5H), 7.24-7.35 (m, 6H), 5.48 (br. s., 1H), 4.69 (d, J=4.03 Hz, 1H), 3.82 (br. s., 1H), 2.29-2.43 (m, 2H), 2.27 (s, 4H), 1.96-2.08 (m, 1H), 1.82-1.93 (m, 1H), 1.55-1.68 (m, 1H). LC-MS: m/z 398.2 (M+H)$^+$.

Compound 338 and Compound 339

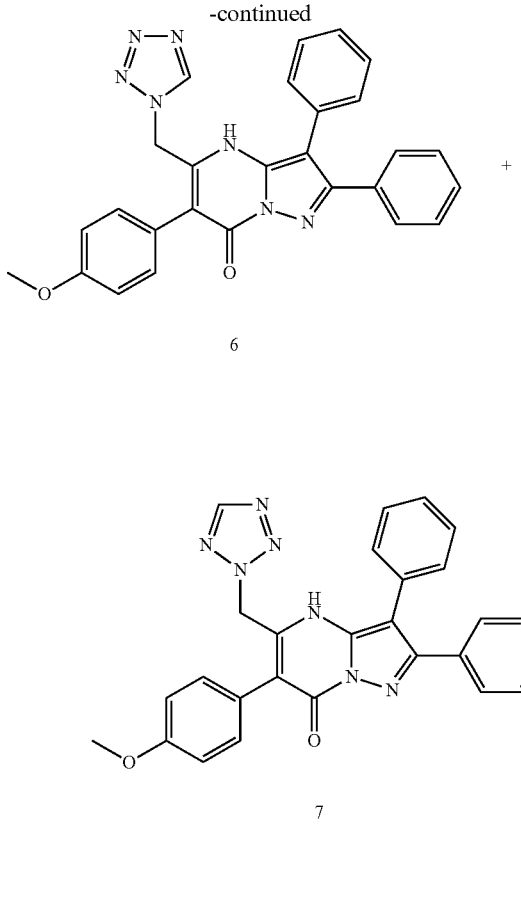

6

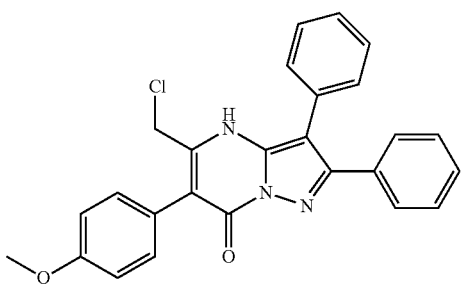 [SMILES: COc1ccc(-c2c(CCl)[nH]c3c(-c4ccccc4)c(-c4ccccc4)nn3c2=O)cc1]

7

Step E: Compound 338 and Compound 339: 5-((1H-tetrazol-1-yl)methyl)-6-(4-methoxyphenyl)-2,3-diphenylpyrazolo[1,5-a]pyrimidin-7(4H)-one and 5-((2H-tetrazol-2-yl)methyl)-6-(4-methoxyphenyl)-2,3-diphenylpyrazolo[1,5-a]pyrimidin-7(4H)-one

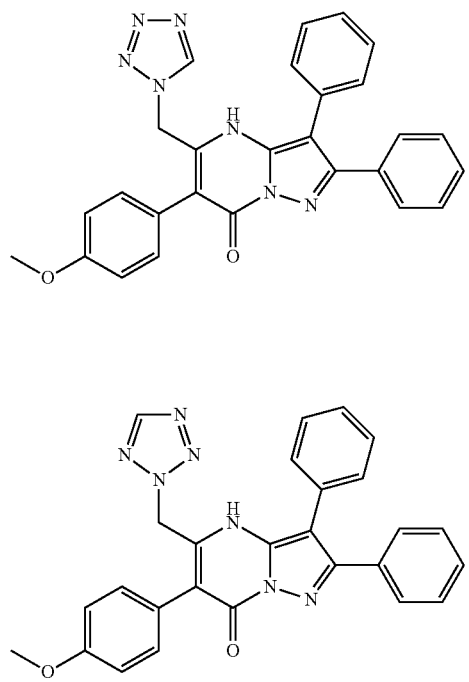 [SMILES: COc1ccc(-c2c(Cn3cnnn3)[nH]c3c(-c4ccccc4)c(-c4ccccc4)nn3c2=O)cc1 ; COc1ccc(-c2c(Cn3ncnn3)[nH]c3c(-c4ccccc4)c(-c4ccccc4)nn3c2=O)cc1]

Step D: 5-(chloromethyl)-6-(4-methoxyphenyl)-2,3-diphenylpyrazolo[1,5-a]pyrimidin-7(4H)-one To a suspension of 5-(hydroxymethyl)-6-(4-methoxyphenyl)-2,3-diphenylpyrazolo[1,5-a]pyrimidin-7(4H)-one (88 g, 0.208 mol, Compound 221) in DCM (500 mL) was added SOCl₂ (120 mL) with a funnel. The mixture was stirred at room temperature for 1 hour. The precipitates were filtered, washed with ethyl acetate, and dried under vacuum to give 5-(chloromethyl)-6-(4-methoxyphenyl)-2,3-diphenylpyrazolo[1,5-a]pyrimidin-7(4H)-one (110 g) as an off-white solid which was directly used to the next step without further purification.

A mixture of 5-(chloromethyl)-6-(4-methoxyphenyl)-2,3-diphenylpyrazolo[1,5-a]pyrimidin-7(4H)-one (200 mg, 0.453 mmol), 1H-tetrazole (63.4 mg, 0.905 mmol), and TEA (229 mg, 2.263 mmol) in DMF (5 mL) was stirred at 40° C. overnight. The mixture was concentrated under reduced pressure to afford 5-((1H-tetrazol-1-yl)methyl)-6-(4-methoxyphenyl)-2,3-diphenylpyrazolo[1, 5-a]pyrimidin-7(4H)-one and 5-((2H-tetrazol-2-yl)methyl)-6-(4-methoxyphenyl)-2,3-diphenylpyrazolo[1,5-a]pyrimidin-7(4H)-one.

Compound 338: 5-((1H-tetrazol-1-yl)methyl)-6-(4-methoxyphenyl)-2,3-diphenylpyrazolo[1,5-a]pyrimidin-7(4H)-one $^1$H NMR (400 MHz, DMSO-$d_6$) δ: 8.97 (br. s., 1H), 7.19-7.44 (m, 4H), 7.07-7.18 (m, 5H) 6.85-7.07 (m, 5H), 6.36-6.82 (m, 1H), 5.74-5.93 (m, 2H), 3.80 (s, 3H). LC-MS: m/z 476.1 (M+H)$^+$.

Compound 339: 5-((2H-tetrazol-2-yl)methyl)-6-(4-methoxyphenyl)-2,3-diphenylpyrazolo[1,5-a]pyrimidin-7(4H)-one $^1$H NMR (400 MHz, TFA) δ: 9.32 (br. s., 1H), 7.61 (br. s., 6H), 7.51 (br. s., 2H), 7.32-7.47 (m, 4H), 7.25 (br. s., 2H), 5.99 (br. s., 2H), 4.08 (br. s., 3H). LC-MS: m/z 476.0 (M+H)$^+$.

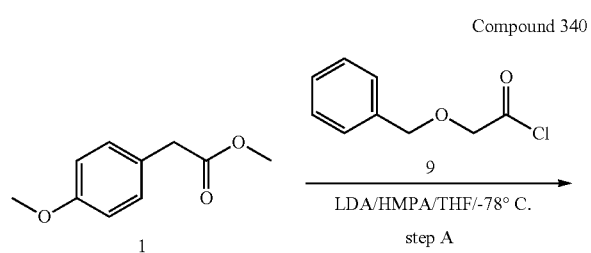
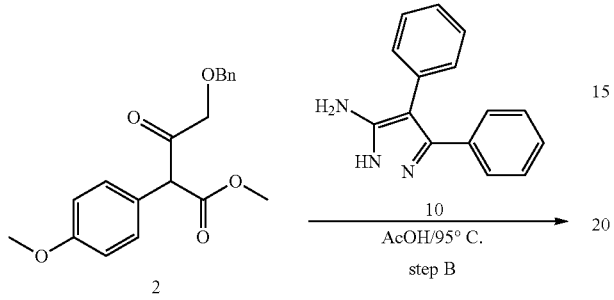
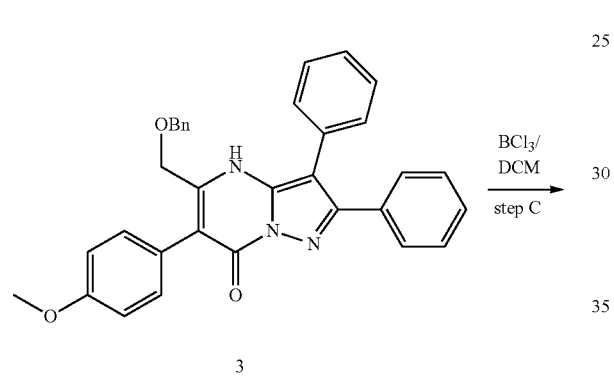
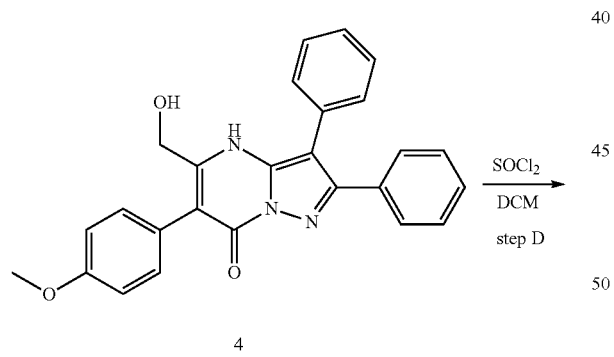
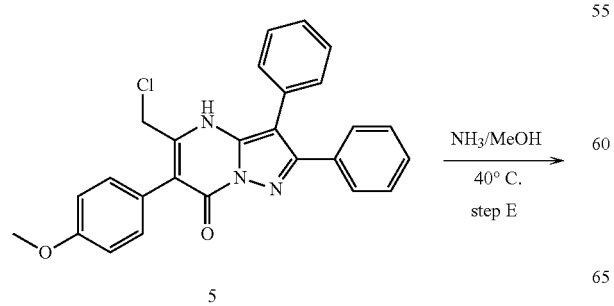
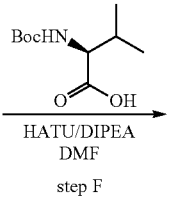
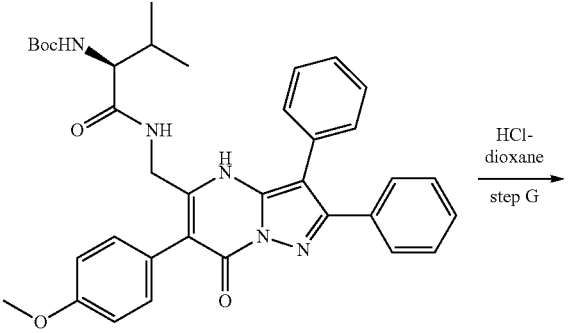
Step F: (S)-tert-butyl (1-(((6-(4-methoxyphenyl)-7-oxo-2,3-diphenyl-4,7-dihydropyrazolo[1,5-a]pyrimidin-5-yl)methyl)amino)-3-methyl-1-oxobutan-2-yl)carbamate
To a solution of Intermediate 6 (Compound 222, 200 mg, 0.45 mmol) in DMF (8 mL) were added (S)-2-((tert-butoxycarbonyl)amino)-3-methylbutanoic acid (117 mg, 0.54 mmol), O-(7-Azabenzotriazol-1-yl)-N,N,N',N'-tetramethyluronium hexafluorophosphate (258 mg, 0.68 mmol) and N,N-diisopropylethylamine (116 mg, 0.9 mmol). The mixture was stirred at r.t. overnight. The mixture was diluted with H₂O (30 ml) and extracted with DCM (3*30 mL). The extracts were washed with brine, dried over anhydrous Na₂SO₄, and concentrated in vacuo. The residue was purified by prep-TLC (DCM/MeOH=20:1) to afforded the title compound 7 as a white solid (230 mg, 82% yield). LC-MS: m/z 622.2 (M+H)⁺.

Step G: (S)-2-amino-N-((6-(4-methoxyphenyl)-7-oxo-2,3-diphenyl-4,7-dihydropyrazolo[1,5-a]pyrimidin-5-yl)methyl)-3-methylbutanamide

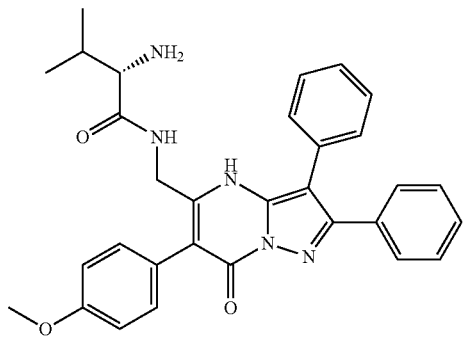 [SMILES: COc1ccc(-c2c(CNC(=O)[C@@H](N)C(C)C)[nH]c3c(-c4ccccc4)c(-c4ccccc4)nn3c2=O)cc1]

A solution of Intermediate 7 (180 mg, 0.29 mmol) in 4M HCl in 1,4-dioxane (8 mL) was stirred at 0° C. r.t. for 1 h and then at r.t. for 3 h. Solvent and other volatiles were removed in vacuo. The residue was dissolved in MeOH (10 mL) and treated with NaHCO₃ (2 mol/L, 10 mL) to afford the title compound 8.

¹H NMR (DMSO-d₆) δ: 8.45 (br. s., 1H), 7.50 (t, J=8.2 Hz, 4H), 7.31 (br. s., 3H), 7.18-7.27 (m, 4H), 7.07-7.12 (m, 1H), 6.94 (d, J=8.6 Hz, 2H), 4.18 (d, J=15.6 Hz, 1H), 3.91 (d, J=15.6 Hz, 1H), 3.79 (s, 3H), 3.52 (d, J=5.0 Hz, 1H), 2.06 (dd, J=12.4, 6.6 Hz, 1H), 0.91 (d, J=6.8 Hz, 3H), 0.85 (d, J=6.8 Hz, 3H). LC-MS: m/z 522.2 (M+H)⁺.

Compound 341

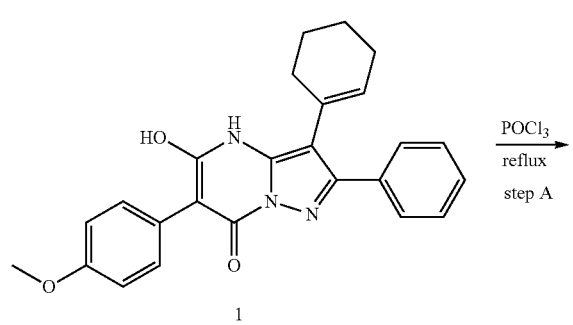

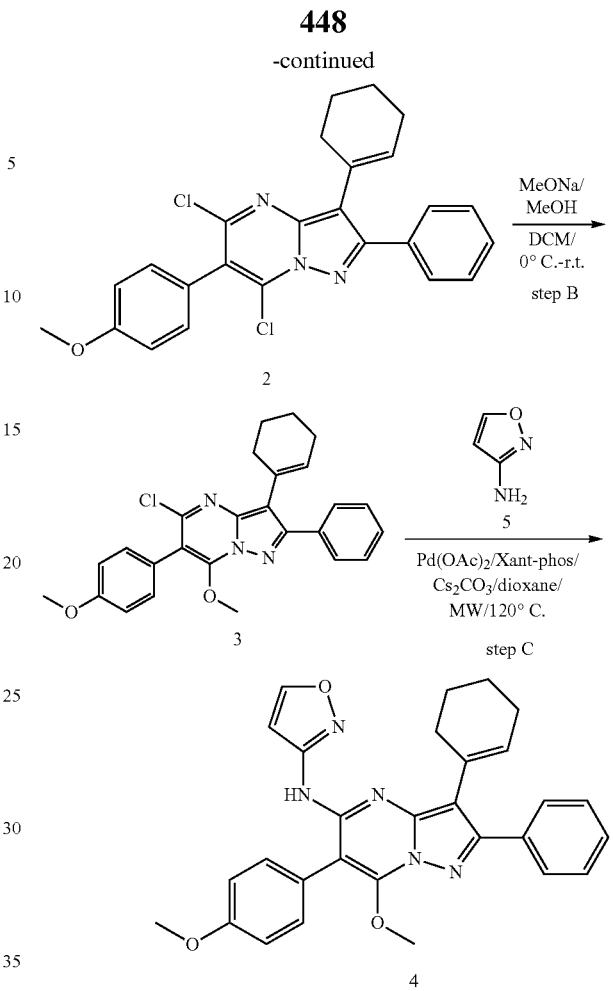

Step A: 5,7-dichloro-3-(cyclohex-1-en-1-yl)-6-(4-methoxyphenyl)-2-phenylpyrazolo[1,5-a]pyrimidine

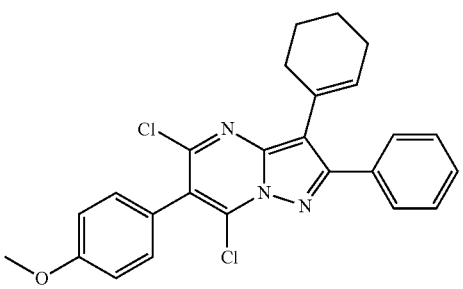 [SMILES: COc1ccc(-c2c(Cl)nc3c(C4=CCCCC4)c(-c4ccccc4)nn3c2Cl)cc1]

A solution of 3-(cyclohex-1-en-1-yl)-5-hydroxy-6-(4-methoxyphenyl)-2-phenylpyrazolo[1,5-a]pyrimidin-7(4H)-one (Synthesized in scheme of Compound 279, 47.0 g, 104 mmol) in phosphorus oxychloride (100 mL) was stirred at reflux for 16 hrs. The solvent was removed invacuo. The residue was added slowly to methanol (100 mL) cooled at 0° C. The precipitates were collected by filtration, washed with methanol, and dried under reduced pressure to give 5,7-dichloro-3-(cyclohex-1-en-1-yl)-6-(4-methoxyphenyl)-2-phenylpyrazolo[1,5-a]pyrimidine (50 g) as a yellow solid.

$^1$H NMR (DMSO-d$_6$): δ 1.70 (d, J=4.57 Hz, 4H) 2.20 (br. s., 4H) 3.84 (s, 4H) 5.87 (br. s., 1H) 7.10 (d, J=8.60 Hz, 2H) 7.36-7.56 (m, 5H) 7.82 (d, J=7.25 Hz, 2H). LC-MS: m/z 450.2 (M+H)$^+$.

Step B: 5-chloro-3-(cyclohex-1-en-1-yl)-7-methoxy-6-(4-methoxyphenyl)-2-phenylpyrazolo[1,5-a]pyrimidine

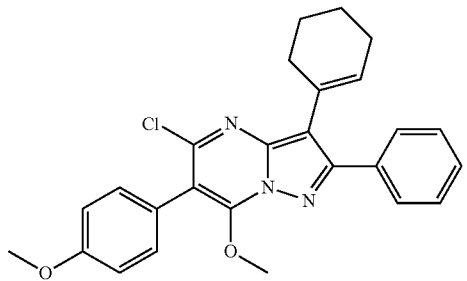 [SMILES: COc1ccc(-c2c(Cl)nc3c(C4=CCCCC4)c(-c4ccccc4)nn3c2OC)cc1]

To a solution of 5,7-dichloro-3-(cyclohex-1-en-1-yl)-6-(4-methoxyphenyl)-2-phenylpyrazolo[1,5-a]pyrimidine (40 g, 88 mmol) in dichloromethane (400 ml) at 0° C. was added sodium methoxide (30% in methanol, 80 g) dropwise. The resultant mixture was stirred for 10 min at 0° C. The reaction was quenched by adding ice water (100 mL) and extracted with dichloromethane (200 mL) three times. The combined organic layers were washed with brine (200 ml), dried over anhydrous sodium sulfate, and concentrated invacuo. The residue was suspended in MeOH (50 mL). The precipitates were collected by filtration, washed with MeOH, and dried under reduced pressure to give 5-chloro-3-(cyclohex-1-en-1-yl)-7-methoxy-6-(4-methoxyphenyl)-2-phenylpyrazolo[1,5-a]pyrimidine (36 g) as a yellow solid.

$^1$H NMR (DMSO-d$_6$): δ 7.78-7.91 (m, 2H), 7.42-7.58 (m, 3H), 7.33-7.42 (m, J=8.9 Hz, 2H), 7.00-7.14 (m, J=8.9 Hz, 2H), 5.83 (br. s., 1H), 4.14 (s, 3H), 3.84 (s, 3H), 2.20 (d, J=5.9 Hz, 4H), 1.61-1.77 (m, 4H). LC-MS: m/z 446.1 (M+H)$^+$.

Step C: N-(3-(cyclohex-1-en-1-yl)-7-methoxy-6-(4-methoxyphenyl)-2-phenylpyrazolo [1,5-a]pyrimidin-5-yl)isoxazol-3-amine

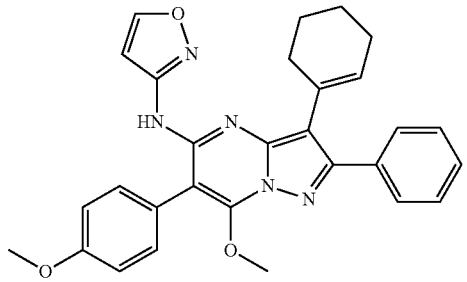 [SMILES: COc1ccc(-c2c(Nc3ccon3)nc3c(C4=CCCCC4)c(-c4ccccc4)nn3c2OC)cc1]

A mixture of 5-chloro-3-(cyclohex-1-en-1-yl)-7-methoxy-6-(4-methoxyphenyl)-2-phenylpyrazolo[1,5-a]pyrimidine (200 mg, 0.45 mmol), isoxazol-3-amine (113.4 mg, 1.35 mmol), and palladium diacetate (10.1 mg, 0.045 mmol), Xantphos (52 mg, 0.09 mmol) and sodium carbonate (143 mg, 1.35 mmol) in 1,4-dioxane (50 mL) was heated at 110° C. for 12 hours under nitrogen atmosphere. The mixture was filtered through celite and the filtrate was concentrated in vacuo. The residue was purified by flash chromatography to afford the desired product N-(3-(cyclohex-1-en-1-yl)-7-methoxy-6-(4-methoxyphenyl)-2-phenylpyrazolo[1,5-a]pyrimidin-5-yl)isoxazol-3-amine.

$^1$H NMR (DMSO-d$_6$): δ: 8.84 (d, J=1.61 Hz, 1H), 8.30 (s, 1H), 7.74-7.82 (m, 2H), 7.35-7.55 (m, 5H), 7.28 (d, J=1.61 Hz, 1H), 7.07-7.16 (m, 2H), 5.83 (s, 1H), 4.08 (s, 3H), 3.86 (s, 3H), 2.25 (br. s., 2H), 2.19 (br. s., 2H), 1.70 (d, J=4.84 Hz, 4H). LC-MS: m/z 493.9 (M+H)$^+$.

Compound 342

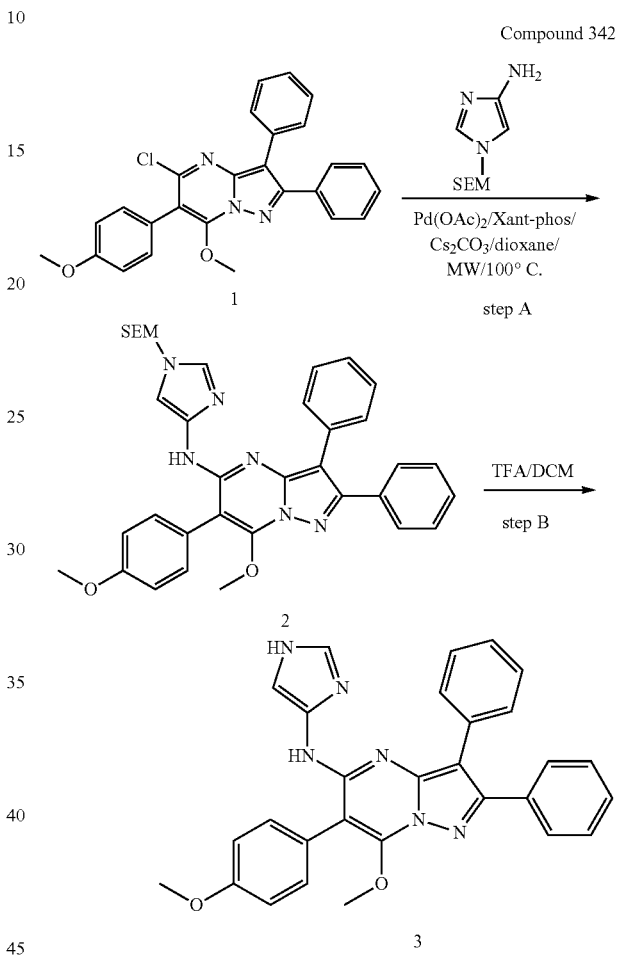

Step A: 7-methoxy-6-(4-methoxyphenyl)-2,3-diphenyl-N-(1-((2-(trimethylsilyl)ethoxy)methyl)-1H-imidazol-4-yl)pyrazolo[1,5-a]pyrimidin-5-amine

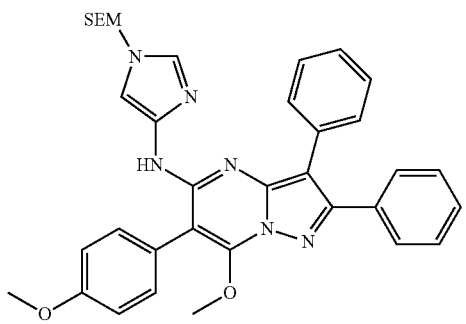 [SMILES: COc1ccc(-c2c(Nc3cn(COCC[Si](C)(C)C)cn3)nc3c(-c4ccccc4)c(-c4ccccc4)nn3c2OC)cc1]

A suspension of 5-chloro-7-methoxy-6-(4-methoxyphenyl)-2,3-diphenylpyrazolo[1,5-a]pyrimidine (Synthesized in Scheme of Compound 101, 300 mg, 0.68 mmol), 1-((2-(trimethylsilyl)ethoxy)methyl)-1H-imidazol-4-amine (230 mg, 1.36 mmol), Pd(OAc)$_2$ (30.5 mg, 0.14 mmol), Xantphos (118 mg, 0.20 mmol) and Cs$_2$CO$_3$ (487 mg, 1.49 mmol) in 1,4-dioxane (10 ml) was reacted at 100° C. for 45 min under N$_2$ atmosphere in a microwave reactor. The reaction was then cooled to RT and filtered. The dark filtrate was concentrated in vacuo and purified by flash column chromatography, eluting with DCM/MeOH=40:1, to get the desired product as a yellow solid (110 mg, 26% yield). LC-MS: m/z 619.5 (M+H)$^+$.

Step B: 7-methoxy-6-(4-methoxyphenyl)-2,3-diphenyl-N-(1-((2-(trimethylsilyl)ethoxy)methyl)-1H-imidazol-4-yl)pyrazolo[1,5-a]pyrimidin-5-amine

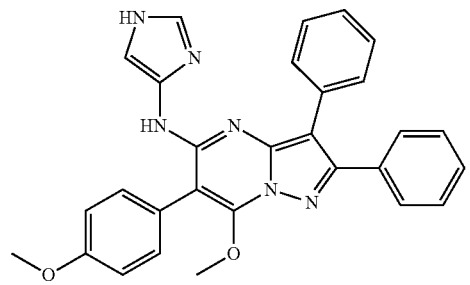 [SMILES: COc1ccc(-c2c(Nc3c[nH]cn3)nc3c(-c4ccccc4)c(-c4ccccc4)nn3c2OC)cc1]

The 7-methoxy-6-(4-methoxyphenyl)-2,3-diphenyl-N-(1-((2-(trimethylsilyl)ethoxy)methyl)-1H-imidazol-4-yl)pyrazolo[1,5-a]pyrimidin-5-amine (110 mg, 0.18 mmol) in DCM (5 mL) and TFA (5 mL) was stirred at 60° C. for 1 h. Then the mixture was concentrated to give the crude product, which was added into ammonia water (5 mL) and stirred on for 1 h to afford the desired product.

1H NMR (DMSO-d$_6$) δ: 8.20 (s, 1H), 7.44-7.30 (m, 14H), 7.15 (d, J=8.0 Hz, 2H), 3.88 (s, 3H), 3.74 (s, 3H). LC-MS: m/z 489.0 (M+H)$^+$.

Compound 343

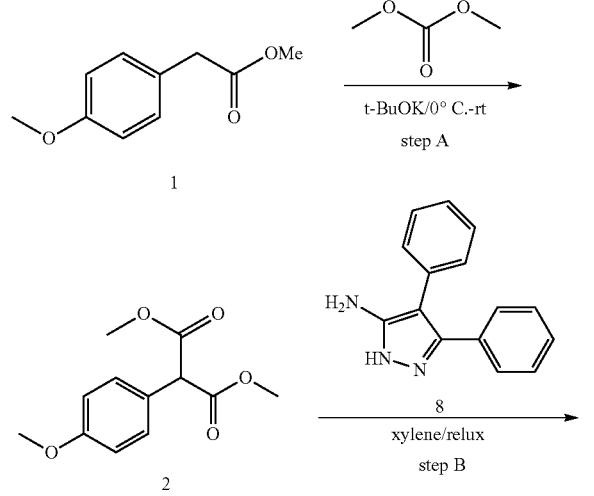

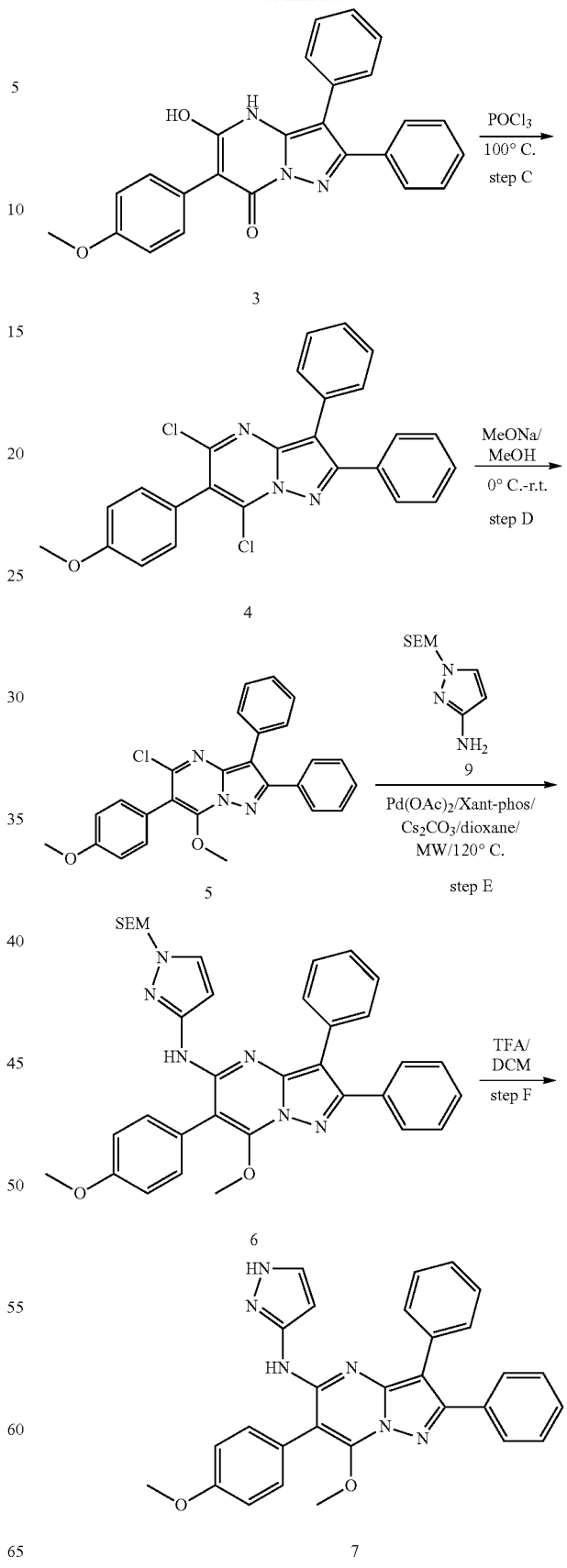

Step E: 7-methoxy-6-(4-methoxyphenyl)-2,3-diphenyl-N-(1-((2-(trimethylsilyl)ethoxy)methyl)-1H-pyrazol-3-yl)pyrazolo[1,5-a]pyrimidin-5-amine

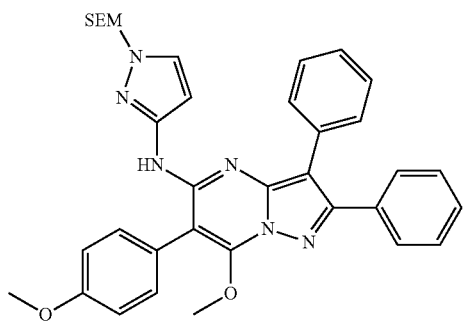 [SMILES: COc1ccc(-c2c(Nc3ccn(COCC[Si](C)(C)C)n3)nc3c(-c4ccccc4)c(-c4ccccc4)nn3c2OC)cc1]

A mixture of 5-chloro-7-methoxy-6-(4-methoxyphenyl)-2,3-diphenylpyrazolo[1,5-a]pyrimidine (600 mg, 1.36 mmol, Synthesized in Scheme of Compound 101), 1-((2-(trimethylsilyl)ethoxy)methyl)-1H-pyrazol-3-amine (580 mg, 2.72 mmol), Pd(OAc)$_2$ (61 mg, 0.27 mmol), xantphos (197 mg, 0.34 mmol) and Cs$_2$CO$_3$ (890 mg, 2.72 mmol) in 1,4-dioxane (5 mL) was stirred at 120° C. through microwave irradiation for 1 hour under N$_2$ atmosphere. The mixture was filtered through celite and the filtrate was concentrated in vacuo. The residue was purified by flash chromatography to afford the 7-methoxy-6-(4-methoxyphenyl)-2,3-diphenyl-N-(1-((2-(trimethylsilyl)ethoxy)methyl)-1H-pyrazol-3-yl)pyrazolo[1,5-a]pyrimidin-5-amine (150 mg) as a yellow solid. LC-MS: m/z 619.0 (M+H)$^+$.

Step F: Compound 343: 7-methoxy-6-(4-methoxyphenyl)-2,3-diphenyl-N-(1H-pyrazol-3-yl)pyrazolo[1,5-a]pyrimidin-5-amine

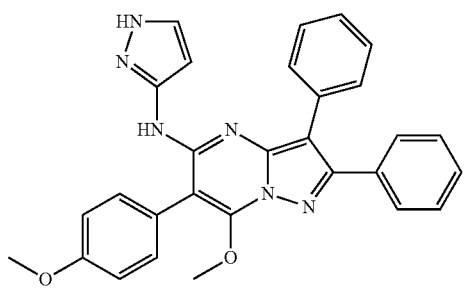 [SMILES: COc1ccc(-c2c(Nc3cc[nH]n3)nc3c(-c4ccccc4)c(-c4ccccc4)nn3c2OC)cc1]

To a solution of 7-methoxy-6-(4-methoxyphenyl)-2,3-diphenyl-N-(1-((2-(trimethylsilyl)ethoxy)methyl)-1H-pyrazol-3-yl)pyrazolo[1,5-a]pyrimidin-5-amine (150 mg, 0.243 mmol) in DCM (5 mL) was added TFA (2 mL), the mixture was stirred at room temperature for 3 h. The mixture was concentrated under reduced pressure. The residue was dissolved in ammonium hydroxide (3 mL) and stirred at room temperature overnight. The mixture was then concentrated to afford the title compound.

$^1$H NMR (400 MHz, DMSO-d$_6$) δ: 12.34 (br. s., 1H), 7.63 (br. s., 1H), 7.58 (d, J=3.49 Hz, 2H), 7.47 (d, J=8.33 Hz, 2H), 7.51 (d, J=7.52 Hz, 2H), 7.34-7.44 (m, 5H), 7.12-7.32 (m, 4H), 6.88 (br. s., 1H), 4.09 (s, 3H), 3.87 (s, 3H). LC-MS: m/z 488.9 (M+H)$^+$.

Compound 344

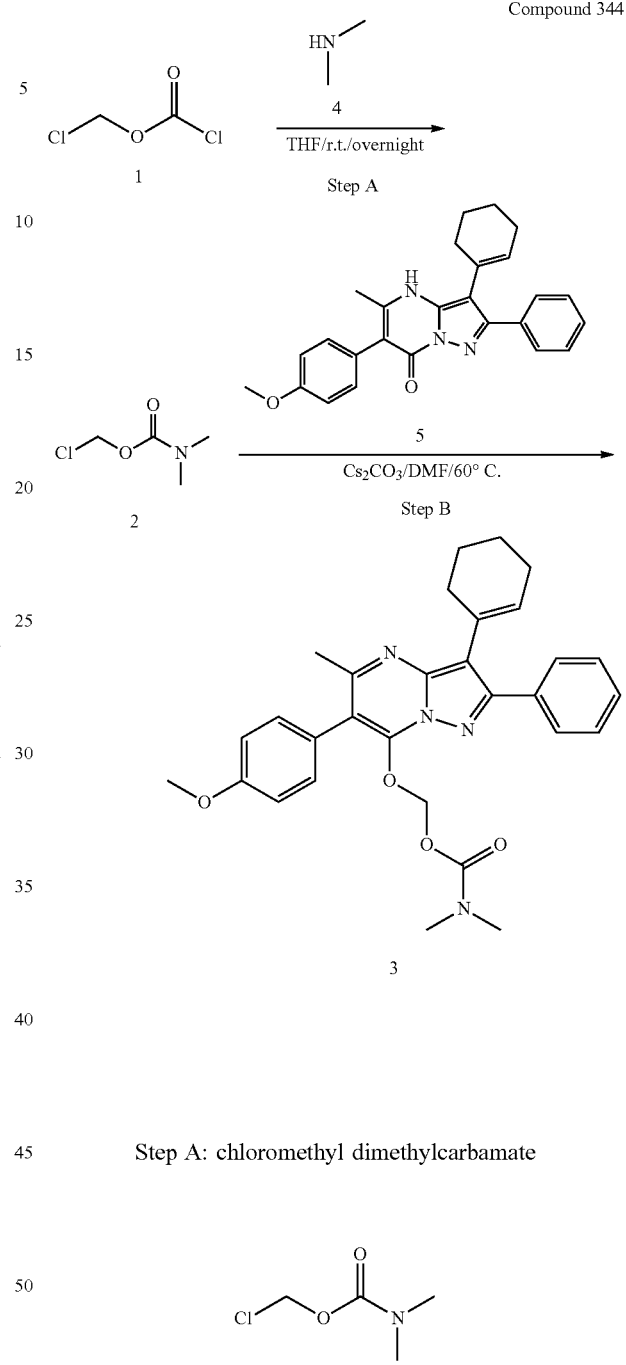

Step A: chloromethyl dimethylcarbamate

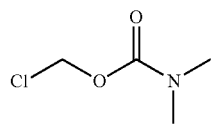

To a solution of chloromethyl carbonochloridate (500 mg, 3.9 mmol) in THF (30 mL) was added dimethylamine (2 mol/L in THF, 3.9 mL) dropwise at 0° C. under vigorous stirring. Then the mixture was stirred at r.t. overnight. The mixture was evaporated. The residue was stirred in toluene (5 mL) and filtered. The filtrate was washed with 10% NaHCO$_3$ aqueous solution, water and brine, dried over anhydrous Na$_2$SO$_4$ and concentrated in vacuo to afford the title compound 2 as a yellow oil (400 mg, 75 yield) which was used to the next step without further purification.

$^1$H NMR (DMSO-d$_6$) δ: 5.79 (s, 2H), 2.98 (s, 3H), 2.96 (s, 3H).

Step B: ((3-(cyclohex-1-en-1-yl)-6-(4-methoxyphenyl)-5-methyl-2-phenylpyrazolo[1,5-a]pyrimidin-7-yl)oxy)methyl dimethylcarbamate

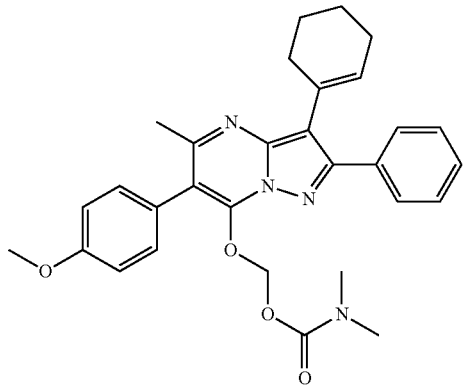 [SMILES: COc1ccc(-c2c(C)nc3c(C4=CCCCC4)c(-c4ccccc4)nn3c2OCOC(=O)N(C)C)cc1]

To a solution of 3-(cyclohex-1-en-1-yl)-6-(4-methoxyphenyl)-5-methyl-2-phenylpyrazolo[1,5-a]pyrimidin-7(4H)-one (Compound 212, 50 mg, 0.12 mmol) in DMF (3 mL) were added chloromethyl dimethylcarbamate (54 mg, 0.36 mmol) and $K_2CO_3$ (50 mg, 0.36 mmol). The mixture was stirred at 60° C. for 10 h. The mixture was poured into $H_2O$ (15 mL) and extracted with DCM (3*10 mL). The combined extracts were washed with brine, dried over anhydrous $Na_2SO_4$ and concentrated in vacuo to afford the title compound 3.

$^1$H NMR (DMSO-$d_6$) δ: 7.79-7.85 (m, 2H), 7.45-7.52 (m, 2H), 7.39-7.45 (m, 1H), 7.19-7.25 (m, 2H), 7.04 (d, J=8.8 Hz, 2H), 6.04 (s, 2H), 5.79 (dt, J=3.4, 2.0 Hz, 1H), 3.82 (s, 3H), 2.71 (s, 3H), 2.63 (s, 3H), 2.29 (s, 3H), 2.23-2.28 (m, 2H), 2.13-2.19 (m, 2H), 1.62-1.76 (m, 4H). LC-MS: m/z 513.1 (M+H)$^+$.

Step A: 7-methoxy-6-(4-methoxyphenyl)-2,3-diphenyl-N-(1,3,5-triazin-2-yl)pyrazolo[1,5-a]pyrimidin-5-amine

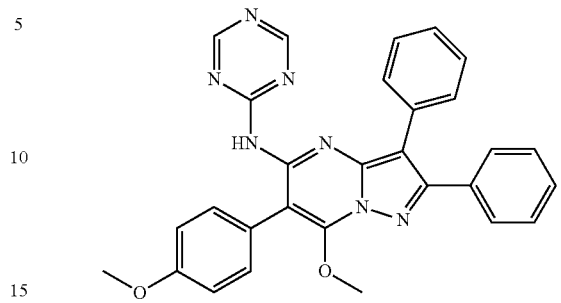

A mixture of 5-chloro-7-methoxy-6-(4-methoxyphenyl)-2,3-diphenylpyrazolo[1,5-a]pyrimidine (800 mg, 1.81 mmol), ethyl 1,3,5-triazin-2-amine (Synthesized in Scheme of Compound 101, 348 mg, 3.62 mmol), and Pd(OAc)$_2$ (81 mg, 0.36 mmol), Xantphos (260 mg, 0.45 mmol) and $Na_2CO_3$ (384 mg, 3.62 mmol) in 1.4-dioxane (15 mL) was heated at 110° C. for 4 hours under $N_2$ atmosphere. The mixture was filtered through celite, and the filtrate was concentrated in vacuo to afford the title product.

$^1$H NMR (DMSO-$d_6$) δ: 10.42 (s, 1H), 8.51 (s, 2H), 7.57-7.63 (m, 2H), 7.36-7.49 (m, 7H), 7.28-7.33 (m, 3H), 6.87-6.95 (m, 2H), 4.20 (s, 3H), 3.74 (s, 3H). LC-MS: m/z 502.0 (M+H)$^+$.

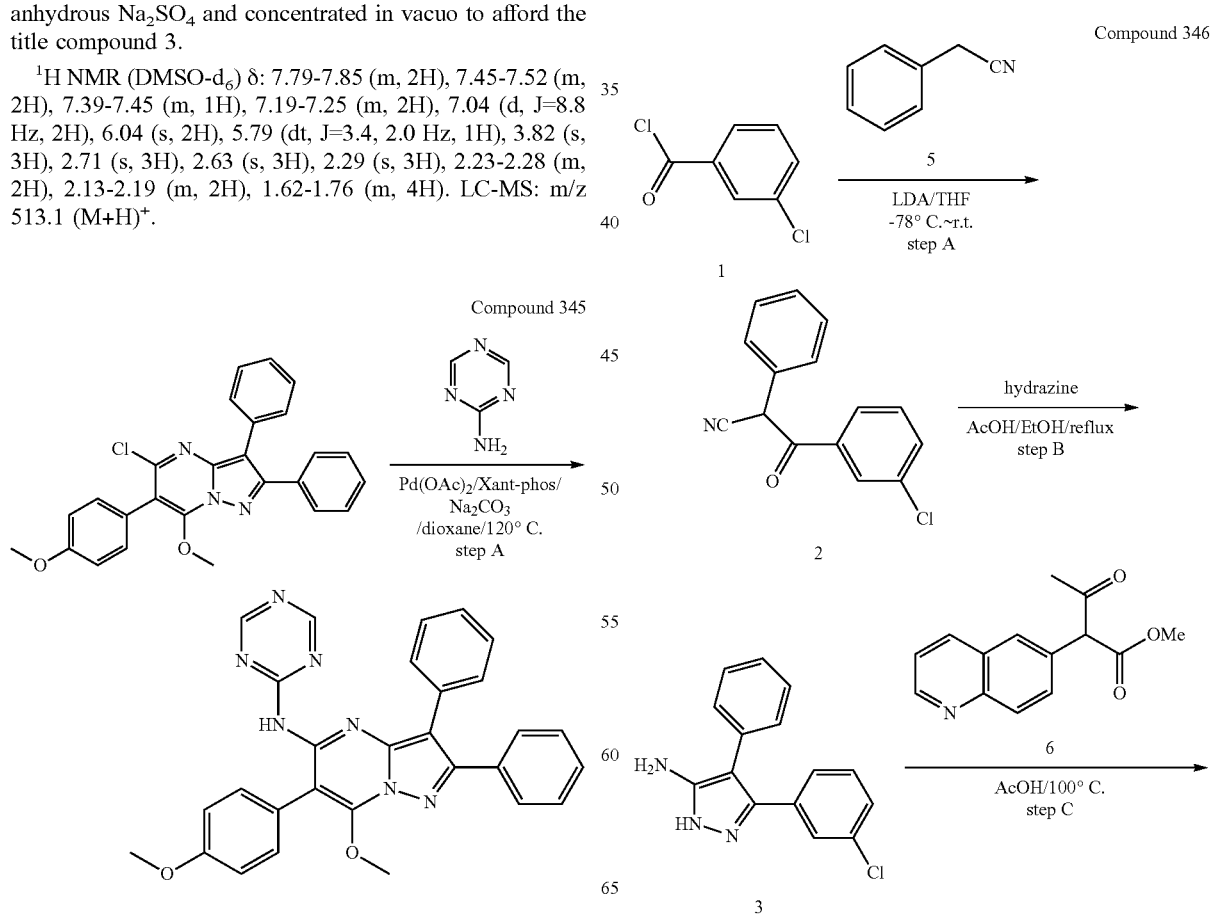

-continued

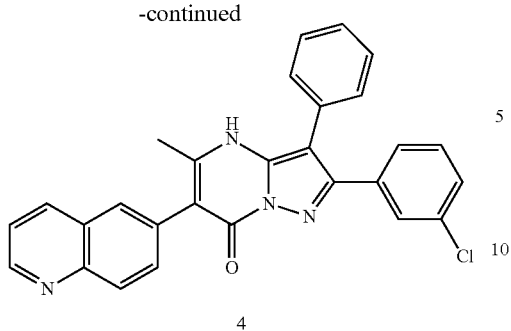

4

Step A:
3-(3-chlorophenyl)-3-oxo-2-phenylpropanenitrile

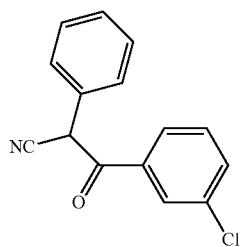 [SMILES: N#CC(C(=O)c1cccc(Cl)c1)c1ccccc1]

To a solution of 2-phenylacetonitrile (975 mg, 8.3 mmol) in THF (40 mL) was added lithium diisopropylamide (2.0 mol/L in THF, 5 mL, 10.0 mmol) at −78° C. After the mixture was stirred at −78° C. for 30 min, 3-chlorobenzoyl chloride (1.8 g, 10.0 mmol) was added dropwise. Then the mixture was stirred at r.t. for 2 h. The mixture was diluted with EA (30 mL) and quenched with saturated NH$_4$Cl. The organic phase was separated and washed with brine, dried over anhydrous Na$_2$SO$_4$ and concentrated in vacuo. The residue was washed with PE to afford the desired intermediate 2 as a white solid (1.2 g, 57% yield). LC-MS: m/z 256.0/258.0 (M+H)$^+$.

Step B:
3-(3-chlorophenyl)-4-phenyl-1H-pyrazol-5-amine

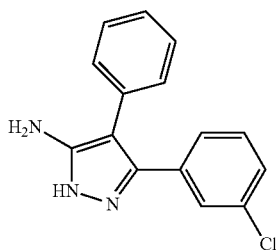 [SMILES: Nc1[nH]nc(-c2cccc(Cl)c2)c1-c1ccccc1]

The mixture of Intermediate 2 (500 mg, 2.0 mmol) and hydrazine hydrate (200 mg, 4.0 mmol) in EtOH/AcOH (5/1, 10 mL/2 mL) was refluxed for 2 h. Then the mixture was cooled to r.t. and evaporated. The residue was dissolved in EA (20 mL) and neutralized with 10% NaHCO$_3$. The organic phase was separated and the water phase was extracted with EA (10 mL*3). The combined organic phase was washed with brine, dried over anhydrous Na$_2$SO$_4$ and concentrated in vacuo to afford the crude desired intermediate 3 as a yellow oil (500 mg, 95% yield) which was used to the next step without purification. LC-MS: m/z 270.0/272.0 (M+H)$^+$.

Step C: 2-(3-chlorophenyl)-5-methyl-3-phenyl-6-(quinolin-6-yl)pyrazolo[1,5-a]pyrimidin-7(4H)-one

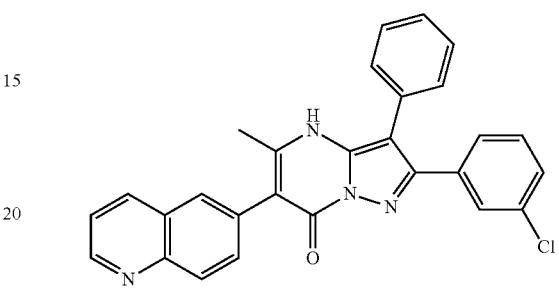

The mixture of Intermediate 3 (200 mg, 0.7 mmol) and methyl 3-oxo-2-(quinolin-6-yl)butanoate (270 mg, 1.1 mmol) in AcOH (10 mL) was stirred at 100° C. for 1 h. Then the mixture was cooled to r.t. and evaporated. The residue was dissolved in EA (15 mL) and neutralized with 10%, NaHCO$_3$. The organic phase was separated, and the water phase was extracted with EA (15 mL*3). The combined organic phase was washed with brine, dried over anhydrous Na$_2$SO$_4$ and concentrated in vacuo to afford the desired product 4.

$^1$H NMR (DMSO-d$_6$) δ: 12.15 (s, 1H), 8.94 (dd, J=4.2, 1.6 Hz, 1H), 8.40 (d, J=7.4 Hz, 1H), 8.08 (d, J=8.8 Hz, 1H), 7.97 (d, J=1.8 Hz, 1H), 7.75 (dd, J=8.6, 1.8 Hz, 1H), 7.57 (dd, J=8.2, 4.2 Hz, 1H), 7.40-7.53 (m, 5H), 7.33-7.40 (m, 4H), 2.25 (s, 3H). LC-MS: m/z 463.0/465.0 (M+H)$^+$.

Compound 347

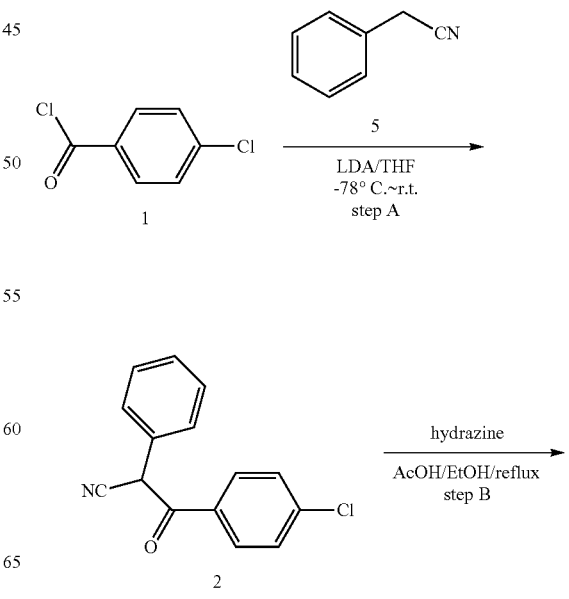

-continued

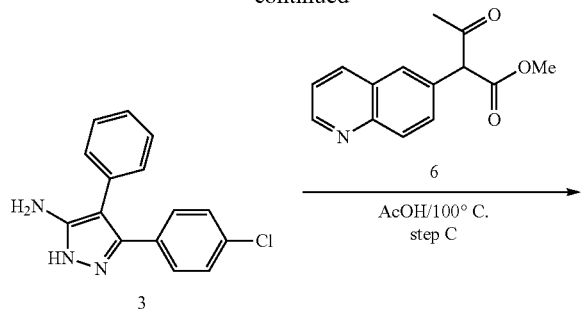

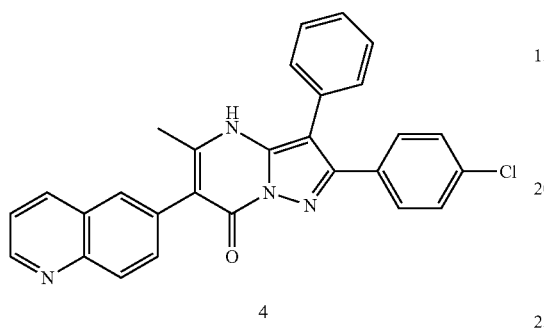

Step A:
3-(4-chlorophenyl)-3-oxo-2-phenylpropanenitrile

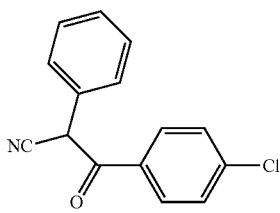 [SMILES: N#CC(C(=O)c1ccc(Cl)cc1)c1ccccc1]

To a solution of 2-phenylacetonitrile (975 mg, 8.3 mmol) in THF (40 mL) was added lithium diisopropylamide (2.0 mol/L in THF, 5 mL, 10.0 mmol) at −78° C. After the mixture was stirred at −78° C. for 30 min, 4-chlorobenzoyl chloride (1.8 g, 10.0 mmol) was added dropwise. Then the mixture was stirred at r.t. for 2 h. The mixture was diluted with EA (30 mL) and quenched with saturated NH$_4$Cl. The organic phase was separated and washed with brine, dried over anhydrous Na$_2$SO$_4$ and concentrated in vacuo. The residue was washed with PE to afford the desired intermediate 2 as a white solid (1.3 g, 61% yield). LC-MS: m/z 256.0/258.0 (M+H)$^+$.

Step B:
3-(4-chlorophenyl)-4-phenyl-1H-pyrazol-5-amine

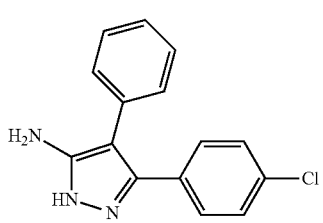 [SMILES: Nc1[nH]nc(-c2ccc(Cl)cc2)c1-c1ccccc1]

The mixture of Intermediate 2 (500 mg, 2.0 mmol) and hydrazine hydrate (200 mg, 4.0 mmol) in EtOH/AcOH (5/1, 10 mL/2 mL) was refluxed for 2 h. Then the mixture was cooled to r.t. and evaporated. The residue was dissolved in EA (20 mL) and neutralized with 10% NaHCO$_3$. The organic phase was separated and the water phase was extracted with EA (10 mL*3). The combined organic phase was washed with brine, dried over anhydrous Na$_2$SO$_4$ and concentrated in vacuo to afford the crude desired intermediate 3 as a yellow oil (500 mg, 95% yield) which was used to the next step without purification. LC-MS: m/z 270.0/272.0 (M+H)$^+$.

Step C: 2-(4-chlorophenyl)-5-methyl-3-phenyl-6-(quinolin-6-yl)pyrazolo[1,5-a]pyrimidin-7(4H)-one

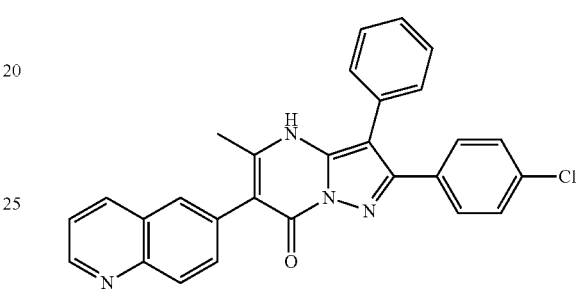

The mixture of Intermediate 3 (80 mg, 0.3 mmol) and methyl 3-oxo-2-(quinolin-6-yl)butanoate (108 mg, 0.5 mmol) in AcOH (5 mL) was stirred at 100° C. for 1 h. Then the mixture was cooled to r.t. and evaporated. The residue was dissolved in EA (10 mL) and neutralized with 10% NaHCO$_3$. The organic phase was separated and the water phase was extracted with EA (10 mL*3). The combined organic phase was washed with brine, dried over anhydrous Na$_2$SO$_4$ and concentrated in vacuo to afford the desired product 4.

$^1$H NMR (DMSO-d$_6$) δ: 12.10 (s, 1H), 8.94 (dd, J=4.2, 1.6 Hz, 1H), 8.39 (d, J=7.4 Hz, 1H), 8.07 (d, J=8.6 Hz, 1H), 7.96 (d, J=1.6 Hz, 1H), 7.74 (dd, J=8.6, 1.8 Hz, 1H), 7.57 (dd, J=8.2, 4.2 Hz, 1H), 7.44-7.52 (m, 3H), 7.40-7.44 (m, 4H), 7.34-7.38 (m, 2H), 2.24 (s, 3H). LC-MS: m/z 463.0/465.0 (M+H)$^+$.

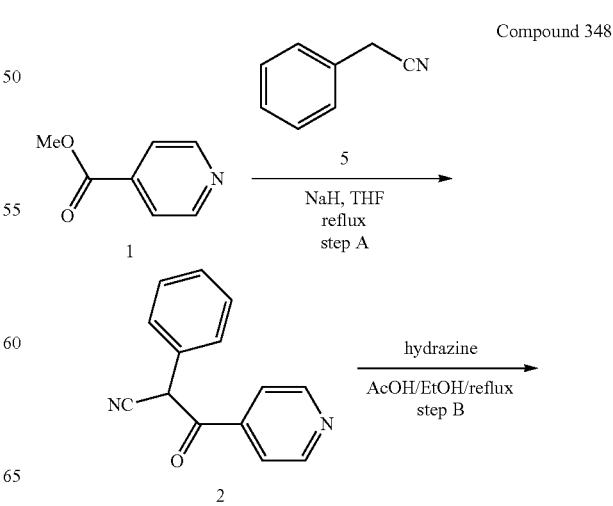

Compound 348

-continued

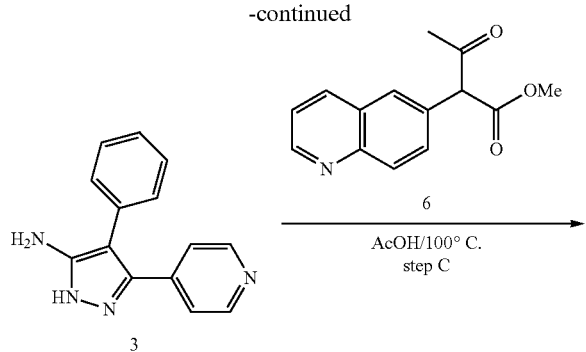

The mixture of Intermediate 2 (500 mg, 2.3 mmol) and hydrazine hydrate (230 mg, 4.6 mmol) in EtOH/AcOH (5/1, 10 mL/2 mL) was refluxed for 2 h. Then the mixture was cooled to r.t. and evaporated. The residue was dissolved in EA (15 mL) and neutralized with 10% NaHCO₃. The organic phase was separated and the water phase was extracted with EA (15 mL*3). The combined organic phase was washed with brine, dried over anhydrous Na₂SO₄ and concentrated in vacuo to afford the desired intermediate 3 as a yellow solid (250 mg, 46% yield) which was used to the next step without purification. LC-MS: m/z 237.1 (M+H)⁺.

Step C: 5-methyl-3-phenyl-2-(pyridin-4-yl)-6-(quinolin-6-yl)pyrazolo[1,5-a]pyrimidin-7(4H)-one

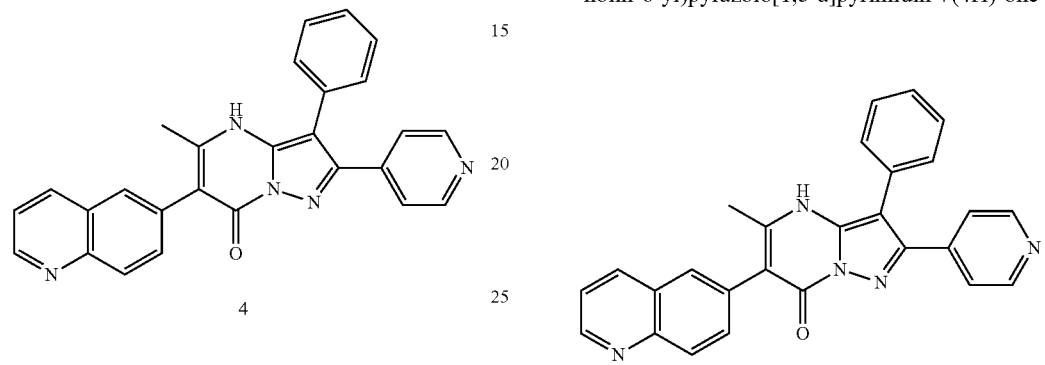

The mixture of Intermediate 3 (100 mg, 0.42 mmol) and methyl 3-oxo-2-(quinolin-6-yl)butanoate (150 mg, 0.64 mmol) in AcOH (10 mL) was stirred at 100° C. for 1 h. Then the mixture was cooled to r.t. and evaporated. The residue was dissolved in EA (10 mL) and neutralized with 10% NaHCO₃. The organic phase was separated and the water phase was extracted with EA (10 mL*3). The combined organic phase was washed with brine, dried over anhydrous Na₂SO₄ and concentrated in vacuo to afford the desired product 4.

$^1$H NMR (DMSO-d$_6$) δ: 12.22 (s, 1H), 8.94 (dd, J=4.2, 1.6 Hz, 1H), 8.54 (d, J=4.6 Hz, 2H), 8.36-8.43 (m, 1H), 8.08 (d, J=8.6 Hz, 1H), 7.97 (d, J=1.8 Hz, 1H), 7.75 (dd, J=8.6, 2.0 Hz, 1H), 7.58 (dd, J=8.2, 4.2 Hz, 1H), 7.44-7.54 (m, 3H), 7.36-7.42 (m, 4H), 2.25 (s, 3H). LC-MS: m/z 430.1 (M+H)⁺.

Step A:
3-oxo-2-phenyl-3-(pyridin-4-yl)propanenitrile

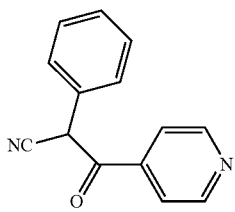 [SMILES: N#CC(C(=O)c1ccncc1)c1ccccc1]

To the mixture of methyl isonicotinate (1.4 g, 10 mmol) and 2-phenylacetonitrile (1.2 g, 10 mmol) in THF (50 mL) was added sodium hydride (480 mg, 60% content, 12 mmol) at r.t. The mixture was refluxed overnight. The mixture was diluted with EA (50 mL) and quenched with saturated NH₄Cl. The organic phase was separated and washed with brine, dried over anhydrous Na₂SO₄ and concentrated in vacuo. The residue was purified by flash chromatography to afford the desired intermediate 2 as a light yellow solid (800 mg, 36% yield). LC-MS: m/z 223.1 (M+H)⁺.

Step B: 4-phenyl-3-(pyridin-4-yl)-1H-pyrazol-5-amine

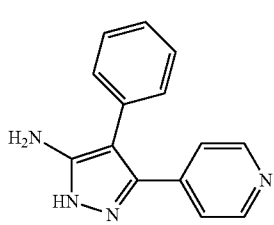 [SMILES: Nc1[nH]nc(-c2ccncc2)c1-c1ccccc1]

Compound 349

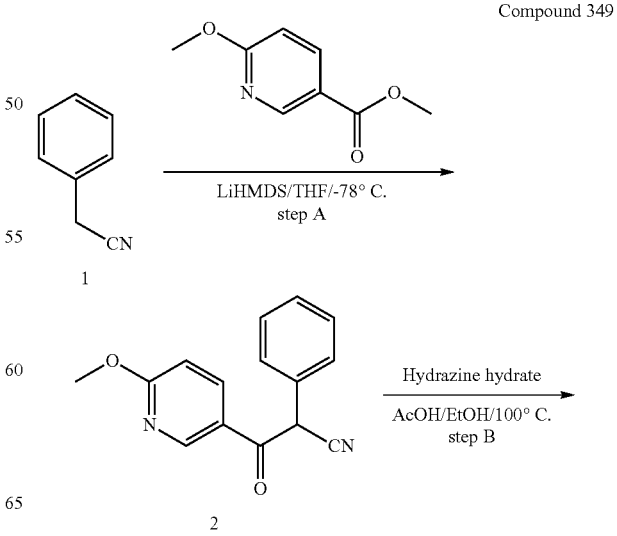

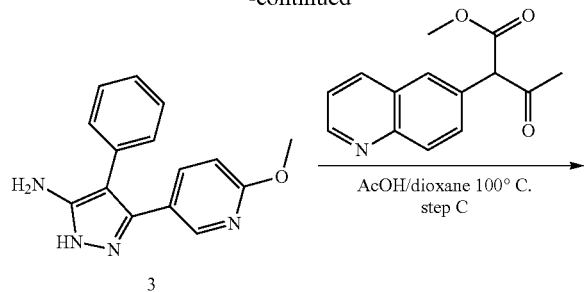

AcOH/dioxane 100° C.
step C

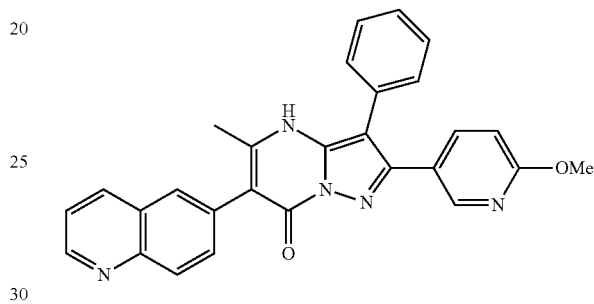

A mixture of 3-(6-methoxypyridin-3-yl)-3-oxo-2-phenyl-propanenitrile (2 g, crude) and NH₂NH₂ (2.37 g, 43.8 mmol) in EtOH/AcOH (20 mL/5 mL) was stirred at 100° C. for 8 hours. After cooling to room temperature, the mixture was concentrated by vacuum. The residue was diluted with EtOAc (20 mL), washed with saturated NaHCO₃ (20 mL) and brine (20 mL), dried over anhydrous sodium sulfate and concentrated. The residue was purified by flash column (petroleum ether/ethyl acetate=3:1) to obtain 3-(6-methoxypyridin-3-yl)-4-phenyl-1H-pyrazol-5-amine (150 mg) as a yellow solid. LC-MS: m/z 267.0 (M+H)⁺.

Step C: Compound 349: 2-(6-methoxypyridin-3-yl)-5-methyl-3-phenyl-6-(quinolin-6-yl)pyrazolo[1,5-a]pyrimidin-7(4H)-one A mixture of 3-(6-methoxypyridin-3-yl)-4-phenyl-1H-pyrazol-5-amine (150 mg, 0.564 mmol) and methyl 3-oxo-2-(quinolin-6-yl)butanoate (137 mg, 0.564 mmol) in AcOH (5 mL) and dioxane (1 mL) was stirred at 100° C. overnight to obtain the title compound.

¹H NMR (DMSO-d₆) δ: 12.11 (s, 1H), 8.95 (dd, J=4.16, 1.75 Hz, 1H), 8.37-8.44 (m, 1H), 8.11-8.15 (m, 1H), 8.08 (d, J=8.60 Hz, 1H), 7.97 (d, J=1.61 Hz, 1H),7.77-7.80 (m, 1H), 7.75 (dd, J=8.73, 2.01 Hz, 1H), 7.58 (dd, J=8.19, 4.16 Hz, 1H), 7.49-7.54 (m, 2H), 7.43-7.48 (m, 1H), 7.37-7.42 (m, 2H), 6.84 (d, J=8.60 Hz, 1H), 3.85 (s, 3H), 2.25 (s, 3H). LC-MS: m/z 460.1 (M+H)⁺.

Step A: 3-(6-methoxypyridin-3-yl)-3-oxo-2-phenyl-propanenitrile

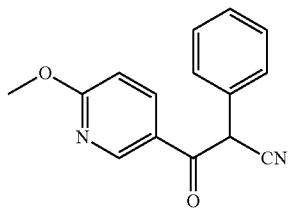 [SMILES: COc1ccc(C(=O)C(C#N)c2ccccc2)cn1]

To a solution of 2-phenylacetonitrile (1.0 g, 8.54 mmol) in THF (20 mL) was added LiHMDS (5.1 mL, 10.2 mmol, 2.0 M in THF) at −78° C. dropwise. After addition, the mixture was stirred at −78° C. for 1 hour. Then methyl 6-methoxynicotinate (1.43 g, 8.54 mmol) was added dropwise. The reaction was slowly warmed to room temperature and stirred for 12 hours. The reaction was quenched by adding saturated NH₄Cl (50 mL), extracted with ethyl acetate (50 mL), washed with water (50 mL) and brine (50 mL), dried over anhydrous sodium sulfate, filtered and concentrated to obtain the title compound (crude, 2 g) which was directly used in the next step without further purification.

Step B: 3-(6-methoxypyridin-3-yl)-4-phenyl-1H-pyrazol-5-amine

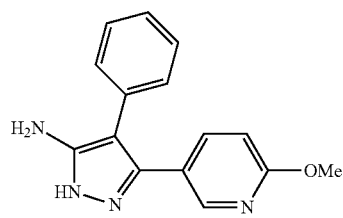 [SMILES: COc1ccc(-c2n[nH]c(N)c2-c2ccccc2)cn1]

Compound 350

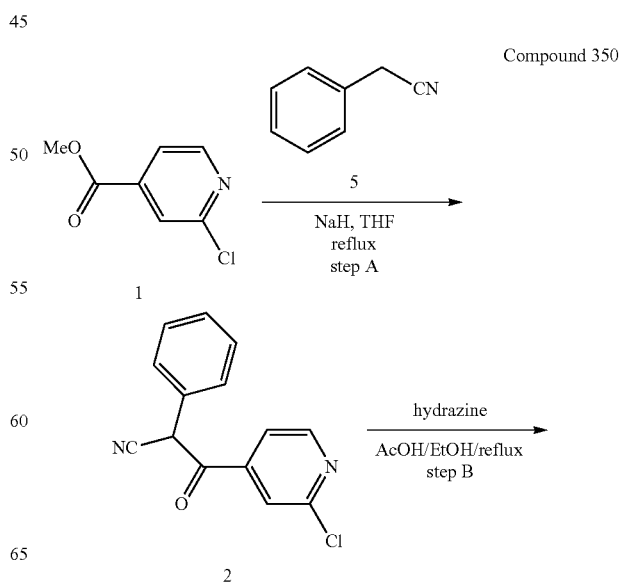

-continued

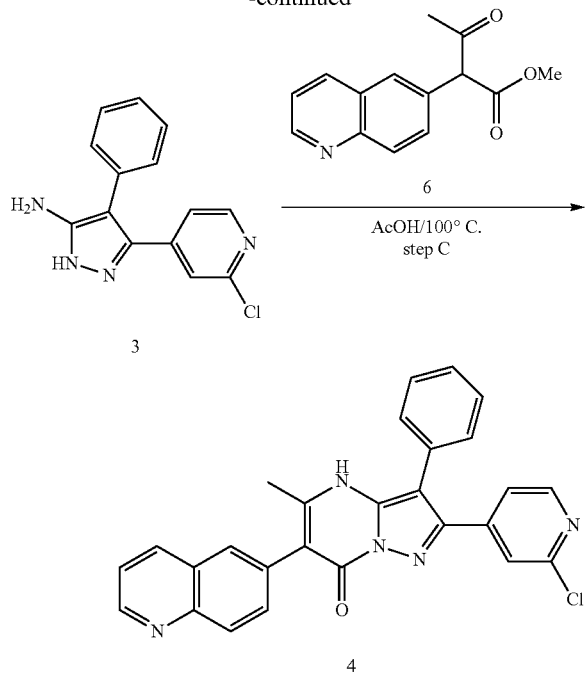

Step A: 3-(2-chloropyridin-4-yl)-3-oxo-2-phenylpropanenitrile

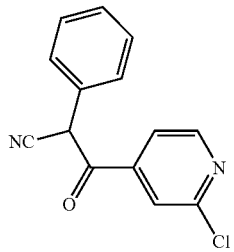 [SMILES: N#CC(C(=O)c1ccnc(Cl)c1)c1ccccc1]

To a solution of 2-phenylacetonitrile (1.2 g, 10 mmol) and methyl 2-chloroisonicotinate (1.7 g, 10.0 mmol) in THF (50 mL) was added sodium hydride (480 mg, 60% content, 12 mmol) at r.t. The mixture was refluxed for 5 h. The mixture was diluted with EA (50 mL) and quenched with saturated NH₄Cl. The organic phase was separated and washed with brine, dried over anhydrous Na₂SO₄, and concentrated in vacuo. The residue was purified by flash chromatography to afford the intermediate 2 as a yellow solid (800 mg, 31% yield). LC-MS: m/z 257.0/259.0 (M+H)⁺.

Step B: 3-(2-chloropyridin-4-yl)-4-phenyl-1H-pyrazol-5-amine

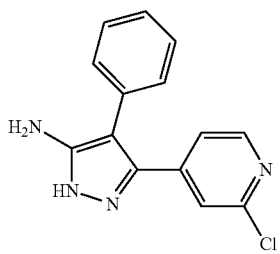 [SMILES: Nc1[nH]nc(-c2ccnc(Cl)c2)c1-c1ccccc1]

The mixture of Intermediate 2 (350 mg, 1.4 mmol) and hydrazine hydrate (140 mg, 2.8 mmol) in EtOH/AcOH (5/1, 10 mL/2 mL) was refluxed for 2 h. Then the mixture was cooled to r.t. and evaporated. The residue was dissolved in EA (10 mL) and neutralized with 10% NaHCO₃. The organic phase was separated and the water phase was extracted with EA (10 mL*3). The combined organic phase was washed with brine, dried over anhydrous Na₂SO₄, and concentrated in vacuo. The residue was purified by flash chromatography (PE/EA=3:1) to afford the crude intermediate 3 as a yellow solid (40 mg, 11% yield). LC-MS: m/z 271.0/273.0 (M+H)⁺.

Step C: 2-(2-chloropyridin-4-yl)-5-methyl-3-phenyl-6-(quinolin-6-yl)pyrazolo[1,5-a]pyrimidin-7(4H)-one

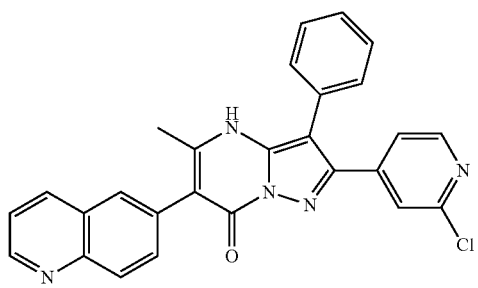 [SMILES: Cc1[nH]c2c(-c3ccccc3)c(-c3ccnc(Cl)c3)nn2c(=O)c1-c1ccc2ncccc2c1]

The mixture of Intermediate 3 (40 mg, 0.15 mmol) and methyl 3-oxo-2-(quinolin-6-yl)butanoate (54 mg, 0.22 mmol) in AcOH (5 mL) was stirred at 100° C. for 1 h. Then the mixture was cooled to r.t. and evaporated. The residue was dissolved in EA (10 mL) and neutralized with 10% NaHCO₃. The organic phase was separated and the water phase was extracted with EA (10 mL*3). The combined organic phase was washed with brine, dried over anhydrous Na₂SO₄, and concentrated in vacuo to afford the desired product 4.

¹H NMR (DMSO-d₆) δ: 12.26 (s, 1H), 8.95 (br. s., 1H), 8.35-8.43 (m, 2H), 8.09 (d, J=8.6 Hz, 1H), 7.93-8.00 (m, 1H), 7.75 (dd, J=8.6, 1.6 Hz, 1H), 7.47-7.62 (m, 4H), 7.36-7.46 (m, 4H), 2.25 (s, 3H). LC-MS: m/z 464.0/466.0 (M+H)⁺.

Compound 351

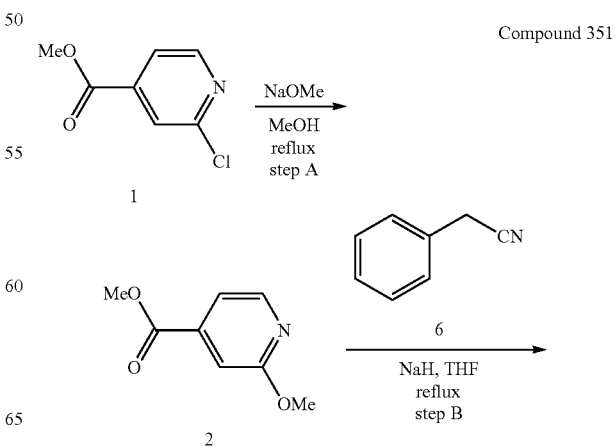

467
-continued

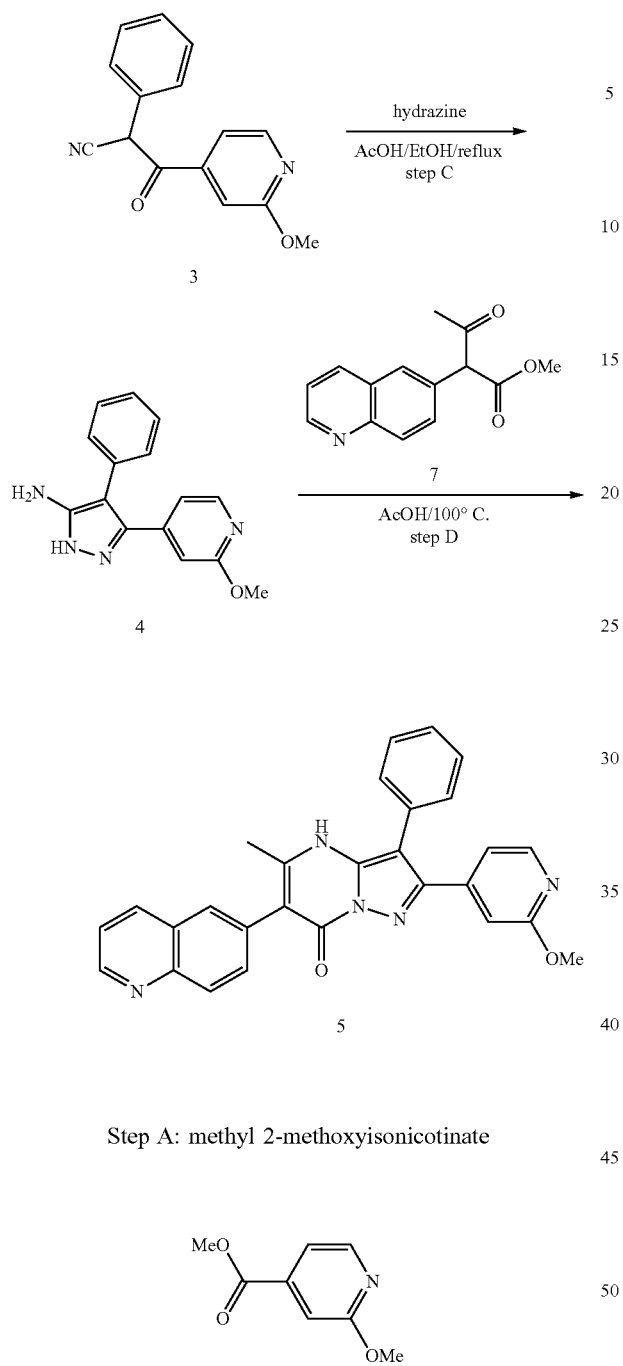

468

Step B: 3-(2-methoxypyridin-4-yl)-3-oxo-2-phenyl-propanenitrile

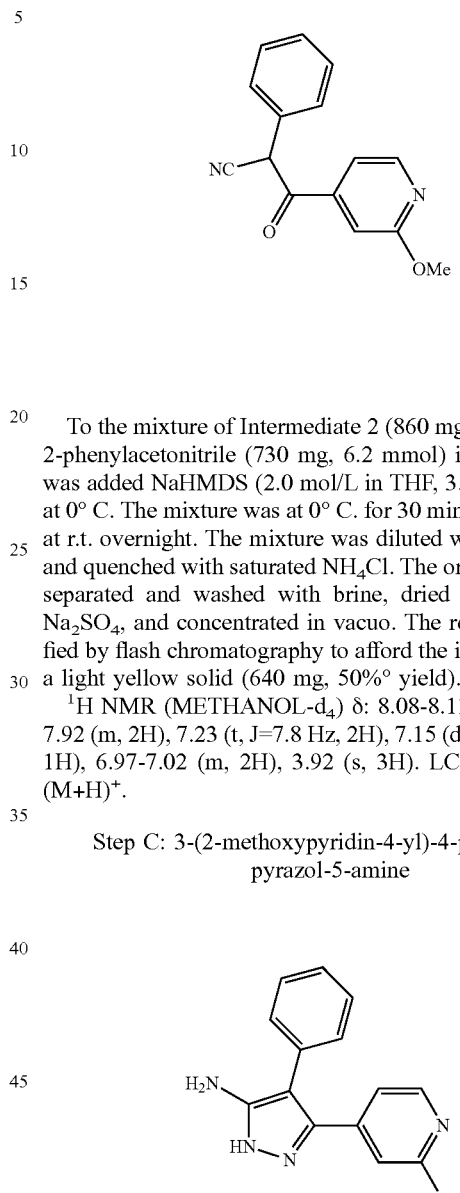

To the mixture of Intermediate 2 (860 mg, 5.1 mmol) and 2-phenylacetonitrile (730 mg, 6.2 mmol) in THF (20 mL) was added NaHMDS (2.0 mol/L in THF, 3.1 mL) dropwise at 0° C. The mixture was at 0° C. for 30 min and then stirred at r.t. overnight. The mixture was diluted with EA (30 mL) and quenched with saturated NH₄Cl. The organic phase was separated and washed with brine, dried over anhydrous Na₂SO₄, and concentrated in vacuo. The residue was purified by flash chromatography to afford the intermediate 3 as a light yellow solid (640 mg, 50%° yield).

$^1$H NMR (METHANOL-$d_4$) δ: 8.08-8.11 (m, 1H), 7.88-7.92 (m, 2H), 7.23 (t, J=7.8 Hz, 2H), 7.15 (dd, J=5.0, 1.2 Hz, 1H), 6.97-7.02 (m, 2H), 3.92 (s, 3H). LC-MS: m/z 253.1 (M+H)⁺.

Step C: 3-(2-methoxypyridin-4-yl)-4-phenyl-1H-pyrazol-5-amine

Step A: methyl 2-methoxyisonicotinate

To a solution of methyl 2-chloroisonicotinate (1.7 g, 10 mmol) in MeOH (30 mL) was added Sodium methoxide (1.1 g, 20 mmol). The resultant mixture was refluxed overnight. The mixture was then treated with HCl (2 mol/L) until pH=7 and evaporated. The residue was dissolved in EA (50 mL), washed with H₂O and brine, dried over anhydrous MgSO₄ and concentrated in vacuo. The residue was purified by flash chromatography to afford the intermediate 2 as a white solid (1.2 g, 72% yield).

$^1$H NMR (CHLOROFORM-d) δ: 8.26-8.30 (m, 1H), 7.40 (dd, J=5.1, 1.2 Hz, 1H), 7.30-7.33 (m, 1H), 3.97 (s, 3H), 3.94 (s, 3H). LC-MS: m/z 168.0 (M+H)⁺.

The mixture of Intermediate 3 (320 mg, 1.3 mmol) and hydrazine hydrate (130 mg, 2.6 mmol) in EtOH/AcOH (5/1, 10 mL/2 mL) was refluxed for 2 h. Then the mixture was cooled to r.t. and evaporated. The residue was dissolved in EA (10 mL) and neutralized with 10% NaHCO₃. The organic phase was separated and the water phase was extracted with EA (10 mL*3). The combined organic phase was washed with brine, dried over anhydrous Na₂SO₄, and concentrated in vacuo. The residue was purified by flash chromatography (PE/EA 3:1) to afford the crude intermediate 4 as a yellow solid (250 mg, 74% yield). LC-MS: m/z 267.1 (M+H)⁺.

Step D: 2-(2-methoxypyridin-4-yl)-5-methyl-3-phenyl-6-(quinolin-6-yl)pyrazolo[1,5-a]pyrimidin-7(4H)-one

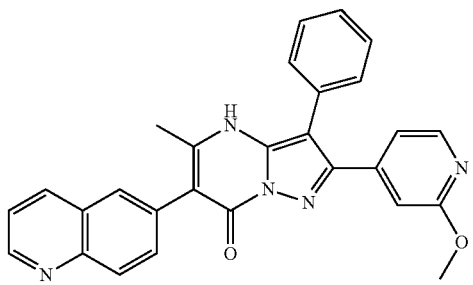 [SMILES: COc1cc(-c2nn3c(=O)c(-c4ccc5ncccc5c4)c(C)[nH]c3c2-c2ccccc2)ccn1]

The mixture of Intermediate 4 (250 mg, 0.94 mmol) and methyl 3-oxo-2-(quinolin-6-yl)butanoate (340 mg, 1.4 mmol) in AcOH (8 mL) was stirred at 100° C. for 1 h. Then the mixture was cooled to r.t. and evaporated. The residue was dissolved in EA (15 mL) and neutralized with 10% NaHCO₃. The organic phase was separated and the water phase was extracted with EA (15 mL*3). The combined organic phase was washed with brine, dried over anhydrous Na₂SO₄, and concentrated in vacuo to afford the desired product 5.

$^1$H NMR (DMSO-d$_6$) δ: 12.18 (s, 1H), 8.94 (dd, J=4.2, 1.6 Hz, 1H), 8.39 (d, J=7.4 Hz, 1H), 8.14 (d, J=5.6 Hz, 1H), 8.08 (d, J=8.6 Hz, 1H), 7.96 (d, J=1.8 Hz, 1H), 7.74 (dd, J=8.6, 2.0 Hz, 1H), 7.57 (dd, J=8.2, 4.2 Hz, 1H), 7.45-7.55 (m, 3H), 7.37-7.42 (m, 2H), 7.08 (dd, J=5.2, 1.4 Hz, 1H), 6.70 (s, 1H), 3.80 (s, 3H), 2.24 (s, 3H). LC-MS: m/z 460.0 (M+H)$^+$.

Compound 352

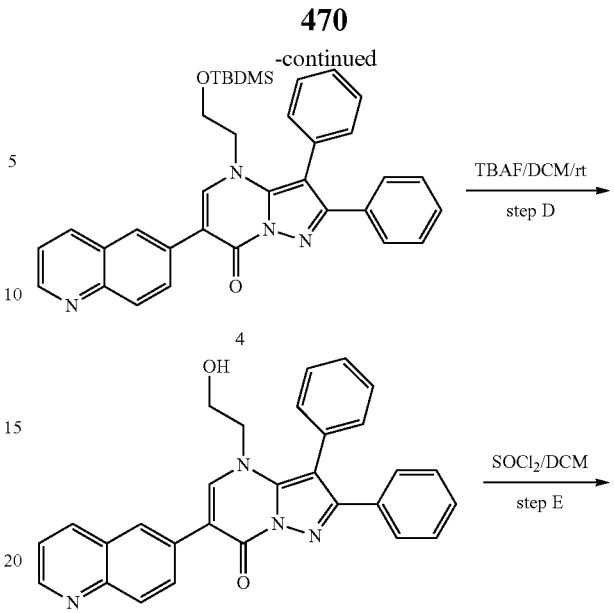

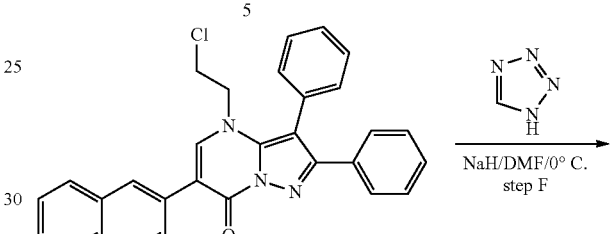

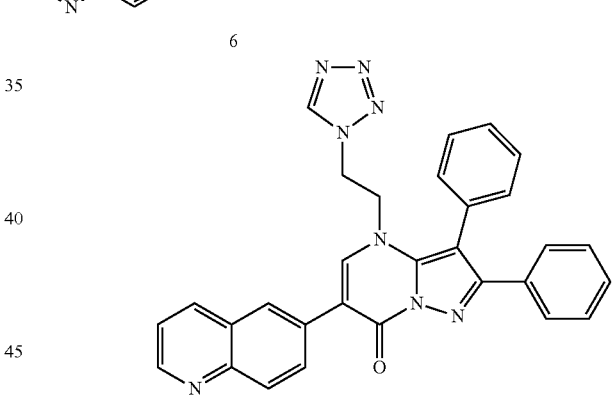

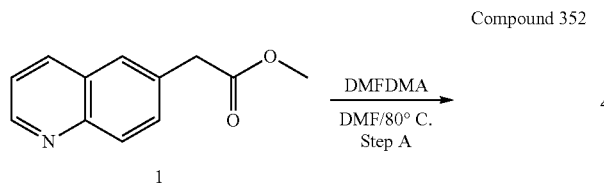

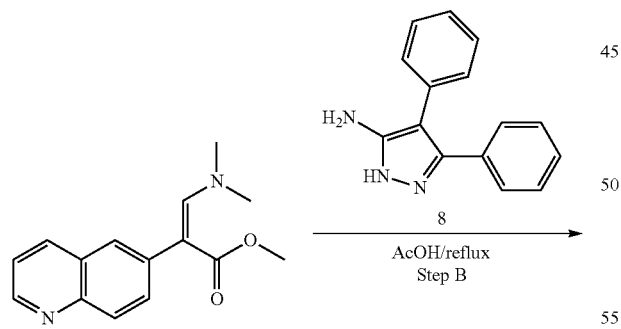

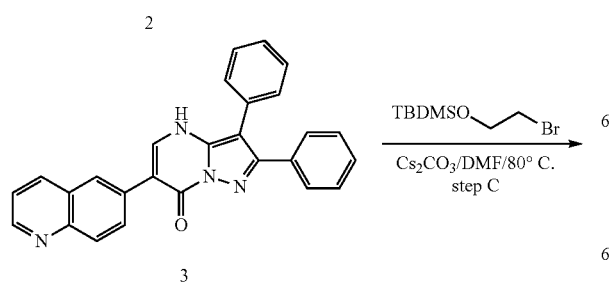

Step A: (E)-methyl 3-(dimethylamino)-2-(quinolin-6-yl)acrylate

A mixture of methyl 2-(quinolin-6-yl)acetate (3.0 g, 14.9 mmol) and DMF-DMA (4.0 mL) in DMF was stirred at 85° C. for 12 h. After cooling to room temperature, the mixture was poured into water, extracted with ethyl acetate, dried over Na$_2$SO$_4$, filtered and concentrated to get the crude product (3.8 g) which was directly used to the next step without further purification. LC-MS: m/z 257.3 (M+H)$^+$.

Step B: 2,3-diphenyl-6-(quinolin-6-yl)pyrazolo[1,5-a]pyrimidin-7(4H)-one

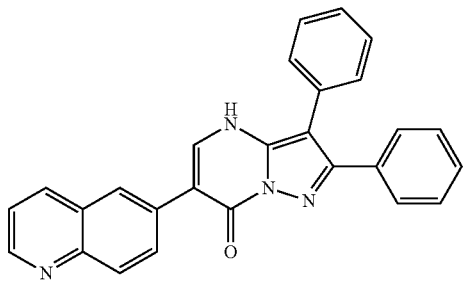 [SMILES: O=c1c(-c2ccc3ncccc3c2)c[nH]c2c(-c3ccccc3)c(-c3ccccc3)nn12]

A mixture of 3,4-diphenyl-1H-pyrazol-5-amine (200 mg, 0.9 mmol) and (E)-methyl 3-(dimethylamino)-2-(quinolin-6-yl)acrylate (283.2 mg, 1.1 mmol) in AcOH (3 mL) was stirred at 100° C. for 2 h. After cooling to room temperature, the solvent was removed by vacuum, saturated NaHCO$_3$ (6 mL) was added, and the precipitate was filtered. The filter cake was washed with water (2 mL) and MeOH (2 mL) to get 2,3-diphenyl-6-(quinolin-6-yl)pyrazolo[1,5-a]pyrimidin-7(4H)-one as yellow solid (300 mg, 85% yield).

$^1$H NMR (DMSO-d$_6$) δ: 12.69 (br. s., 1H), 8.91 (dd, J=4.0, 1.6 Hz, 1H), 8.37-8.47 (m, 1H), 8.32 (d, J=1.9 Hz, 1H), 8.10-8.16 (m, 2H), 8.03-8.10 (m, 1H), 7.56 (dd, J=8.3, 4.0 Hz, 1H), 7.45-7.54 (m, 4H), 7.32-7.45 (m, 6H). LC-MS: m/z 415.3 (M+H)$^+$.

Step C: 4-(2-(tert-butyldimethylsilyloxy)ethyl)-2,3-diphenyl-6-(quinolin-6-yl)pyrazolo[1,5-a]pyrimidin-7(4H)-one

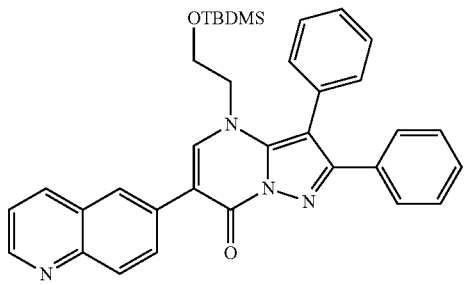 [SMILES: CC(C)(C)[Si](C)(C)OCCn1cc(-c2ccc3ncccc3c2)c(=O)n2nc(-c3ccccc3)c(-c3ccccc3)c12]

A mixture of 2,3-diphenyl-6-(quinolin-6-yl)pyrazolo[1,5-a]pyrimidin-7(4H)-one (200 mg, 0.483 mmol), (2-bromoethoxy)(tert-butyl)dimethylsilane (173 mg, 0.724 mmol) and Cs$_2$CO$_3$ (471 mg, 1.448 mmol) in DMF (10 mL) was stirred at 80° C. overnight. After cooling to room temperature, the mixture was poured into water (20 mL), and extract with EtOAc (3*30 mL). The combined organic layers were washed with water (2*30 mL) and brine (30 mL), and concentrated under reduce pressure. The residue was purified by column chromatography on silica gel (MeOH:DCM=5:100) to get the title compound (130 mg, 47% yield). LC-MS: m/z 573.2 (M+H)$^+$.

Step D: 4-(2-hydroxyethyl)-2,3-diphenyl-6-(quinolin-6-yl)pyrazolo[1,5-a]pyrimidin-7(4H)-one

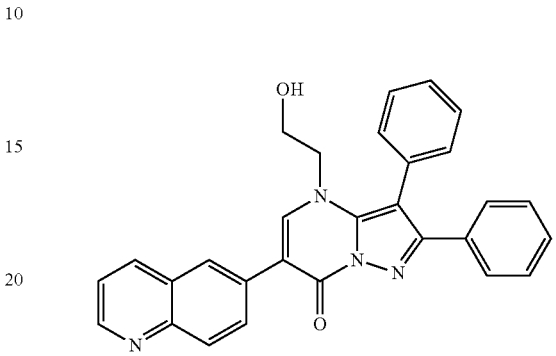

A mixture of 4-(2-(tert-butyldimethylsilyloxy)ethyl)-2,3-diphenyl-6-(quinolin-6-yl)pyrazolo[1,5-a]pyrimidin-7(4H)-one (130 mg, 0.227 mmol) and TBAF (59 mg, 0.227 mmol) in DCM (5 mL) was stirred at room temperature for 3 h. The mixture was poured into water (20 mL), and the precipitate was filtered. The filter cake was washed with water (2 mL) and dried to get the title compound (90 mg) as a white solid which was used directly in the next step without further purification. LC-MS: m/z 459.1 (M+H)$^+$.

Step E: 4-(2-chloroethyl)-2,3-diphenyl-6-(quinolin-6-yl)pyrazolo[1,5-a]pyrimidin-7(4H)-one

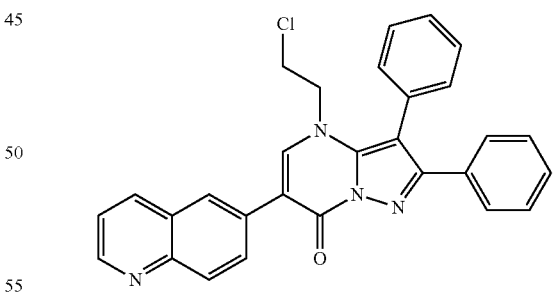

To a solution of 4-(2-hydroxyethyl)-2,3-diphenyl-6-(quinolin-6-yl)pyrazolo[1,5-a]pyrimidin-7(4H)-one (90 mg, 0.2 mol) in DCM (5 mL) was added SOCl$_2$ (0.5 mL) dropwise. The mixture was stirred at room temperature for 4 hours. The precipitates were filtered, washed with ethyl acetate, and dried under vacuum to give 4-(2-chloroethyl)-2,3-diphenyl-6-(quinolin-6-yl)pyrazolo[1,5-a]pyrimidin-7(4H)-one (80 mg) as a off-white solid which was used directly in the next step without further purification. LC-MS: m/z 477.0 (M+H)$^+$.

Step F: Compound 352: 4-(2-(1H-tetrazol-1-yl)ethyl)-2,3-diphenyl-6-(quinolin-6-yl)pyrazolo[1,5-a]pyrimidin-7(4H)-one

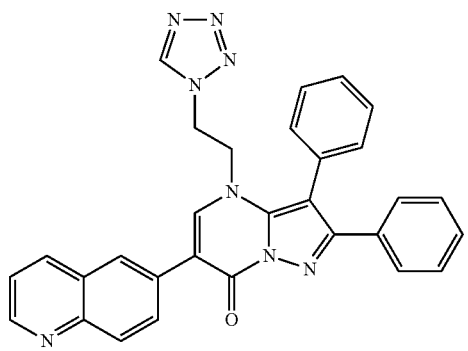 [SMILES: O=c1c(-c2ccc3ncccc3c2)cn(CCn2cnnn2)c2c(-c3ccccc3)c(-c3ccccc3)nn12]

To a solution of 1H-tetrazole (29.4 mg, 0.42 mmol) in DMF (10 mL) was added NaH (60% dispersion in mineral oil, 12.6 mg, 0.524 mmol) in portions at 0° C. The resulting mixture was stirred at 0° C. for 25 min. 4-(2-chloroethyl)-2,3-diphenyl-6-(quinolin-6-yl)pyrazolo[1,5-a]pyrimidin-7(4H)-one (50 mg, 0.105 mmol) was then added. The mixture was warmed to 80° C. and stirred for 10 h. After cooling to room temperature, water was added to get the title compound.

$^1$H NMR (DMSO-d$_6$) δ: 8.99 (s, 1H), 8.92 (dd, J=4.30, 1.61 Hz, 1H), 8.41 (d, J=8.33 Hz, 1H), 8.21 (d, J=1.88 Hz, 1H), 8.17 (s, 1H), 8.09 (d, J=8.87 Hz, 1H), 8.00 (dd, J=8.87, 2.15 Hz, 1H), 7.59 (dd, J=8.19, 4.16 Hz, 1H), 7.48 (s, 5H), 7.39-7.43 (m, 2H), 7.30-7.35 (m, 3H), 4.84 (t, J=6.04 Hz, 2H), 4.45 (t, J=5.78 Hz, 2H). LC-MS: m/z 511.1 (M+H)$^+$.

Compound 353

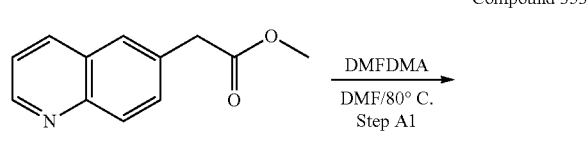

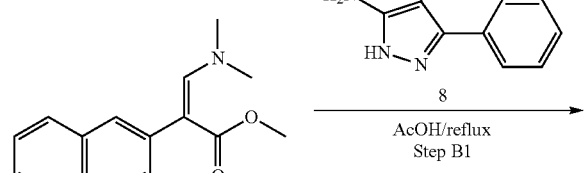

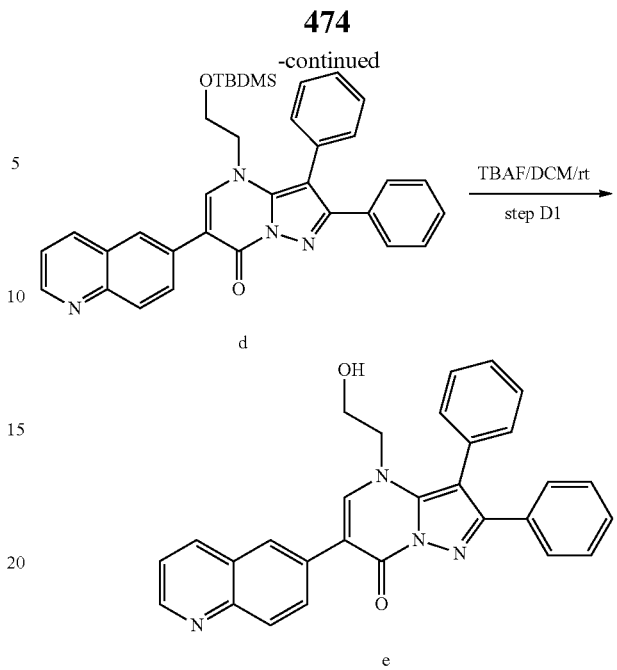

Step A1: (E)-methyl 3-(dimethylamino)-2-(quinolin-6-yl)acrylate

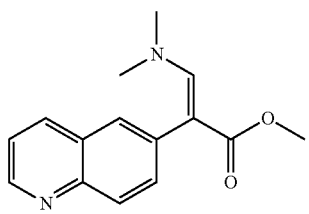 [SMILES: COC(=O)/C(=C/N(C)C)c1ccc2ncccc2c1]

A mixture of methyl 2-(quinolin-6-yl)acetate (3.0 g, 14.9 mmol) and DMF-DMA (4.0 mL) in DMF was stirred at 85° C. for 12 h. After cooling to room temperature, the mixture was poured into water, extracted with ethyl acetate, dried over Na$_2$SO$_4$, filtered and concentrated to get the crude product (3.8 g) which was directly used to the next step without further purification. LC-MS: m/z 257.3 (M+H)$^+$.

Step B1: 2,3-diphenyl-6-(quinolin-6-yl)pyrazolo[1,5-a]pyrimidin-7(4H)-one

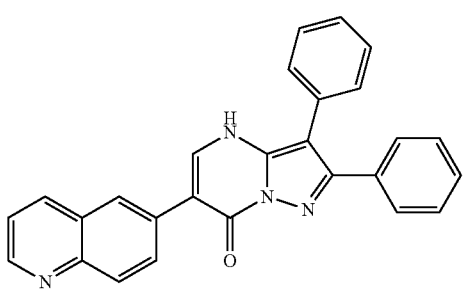 [SMILES: O=c1c(-c2ccc3ncccc3c2)c[nH]c2c(-c3ccccc3)c(-c3ccccc3)nn12]

A mixture of 3,4-diphenyl-1H-pyrazol-5-amine (200 mg, 0.9 mmol) and (E)-methyl 3-(dimethylamino)-2-(quinolin- 6-yl)acrylate (283.2 mg, 1.1 mmol) in AcOH (3 mL) was stirred at 100° C. for 2 h. After cooling to room temperature, the solvent was removed by vacuum, saturated NaHCO₃ (6 mL) was added, and the precipitate was filtered. The filter cake was washed with water (2 mL) and MeOH (2 mL) to get 2,3-diphenyl-6-(quinolin-6-yl)pyrazolo[1,5-a]pyrimidin-7(4H)-one as yellow solid (300 mg, 85% yield).

¹H NMR (DMSO-d₆) δ: 12.69 (br. s., 1H), 8.91 (dd, J=4.0, 1.6 Hz, 1H), 8.37-8.47 (m, 1H), 8.32 (d, J=1.9 Hz, 1H), 8.10-8.16 (m, 2H), 8.03-8.10 (m, 1H), 7.56 (dd, J=8.3, 4.0 Hz, 1H), 7.45-7.54 (m, 4H), 7.32-7.45 (m, 6H). LC-MS: m/z 415.3 (M+H)⁺.

Step C1: 4-(2-(tert-butyldimethylsilyloxy)ethyl)-2,3-diphenyl-6-(quinolin-6-yl)pyrazolo[1,5-a]pyrimidin-7(4H)-one

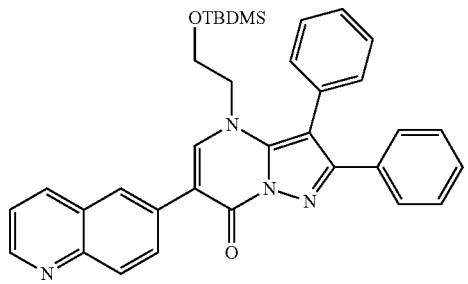 [SMILES: CC(C)(C)[Si](C)(C)OCCn1cc(-c2ccc3ncccc3c2)c(=O)n2nc(-c3ccccc3)c(-c3ccccc3)c12]

A mixture of 2,3-diphenyl-6-(quinolin-6-yl)pyrazolo[1,5-a]pyrimidin-7(4H)-one (200 mg, 0.483 mmol), (2-bromoethoxy)(tert-butyl)dimethylsilane (173 mg, 0.724 mmol) and Cs₂CO₃ (471 mg, 1.448 mmol) in DMF (10 mL) was stirred at 80° C. overnight. After cooling to room temperature, the mixture was poured into water (20 mL), and extract with EtOAc (3*30 mL). The combined organic layers were washed with water (2*30 mL) and brine (30 mL), and concentrated under reduce pressure. The residue was purified by column chromatography on silica gel (MeOH:DCM=5:100) to get the title compound (130 mg, 47% yield). LC-MS: m/z 573.2 (M+H)⁺.

Step D1: 4-(2-hydroxyethyl)-2,3-diphenyl-6-(quinolin-6-yl)pyrazolo[1,5-a]pyrimidin-7(4H)-one

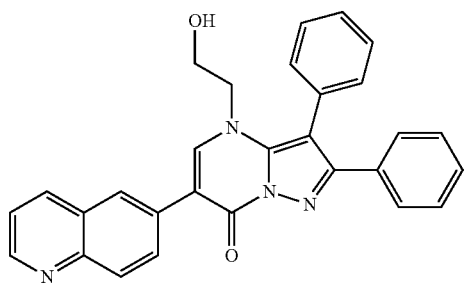 [SMILES: O=c1c(-c2ccc3ncccc3c2)cn(CCO)c2c(-c3ccccc3)c(-c3ccccc3)nn12]

A mixture of 4-(2-(tert-butyldimethylsilyloxy)ethyl)-2,3-diphenyl-6-(quinolin-6-yl)pyrazolo[1,5-a]pyrimidin-7(4H)-one (130 mg, 0.227 mmol) and TBAF (59 mg, 0.227 mmol) in DCM (5 mL) was stirred at room temperature for 3 h. The mixture was poured into water (20 mL), and the precipitate was filtered. The filter cake was washed with water (2 mL) and dried to get the title compound (90 mg) as a white solid which was used directly in the next step without further purification. LC-MS: m/z 459.1 (M+H)⁺.

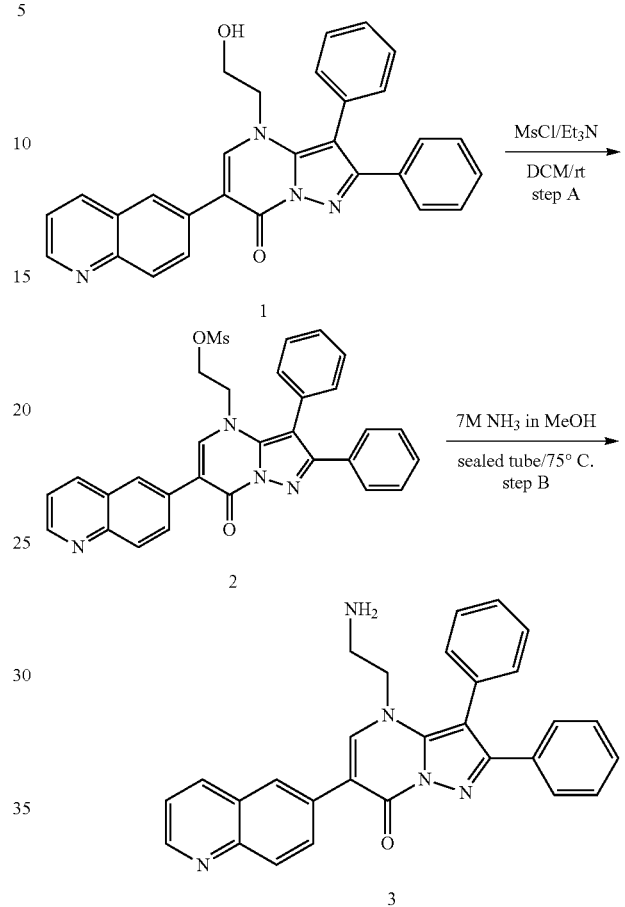

Step A: 2-(7-oxo-2,3-diphenyl-6-(quinolin-6-yl)pyrazolo[1,5-a]pyrimidin-4(7H)-yl)ethyl methanesulfonate

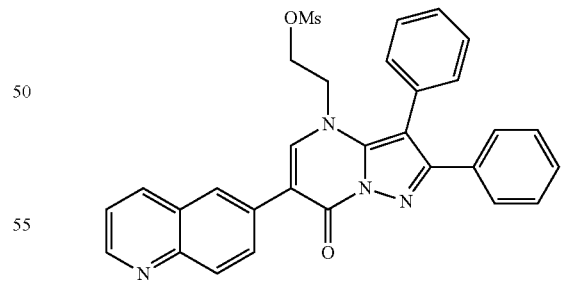

A mixture of 4-(2-hydroxyethyl)-2,3-diphenyl-6-(quinolin-6-yl)pyrazolo[1,5-a]pyrimidin-7(4H)-one (250 mg, 0.545 mmol), MsCl (187 mg, 1.636 mmol) and Et₃N (165 mg, 1.636 mmol) in DCM (10 mL) was stirred at room temperature for 3 h. The mixture was concentrated in vacuo, and the residue was purified by flash chromatography to afford 2-(7-oxo-2,3-diphenyl-6-(quinolin-6-yl)pyrazolo[1,5-a]pyrimidin-4(7H)-yl)ethyl methanesulfonate (200 mg) as a white solid. LC-MS: m/z 537.1 (M+H)⁺.

477

Step B: Compound 353: 4-(2-aminoethyl)-2,3-diphenyl-6-(quinolin-6-yl)pyrazolo[1,5-a]pyrimidin-7(4H)-one

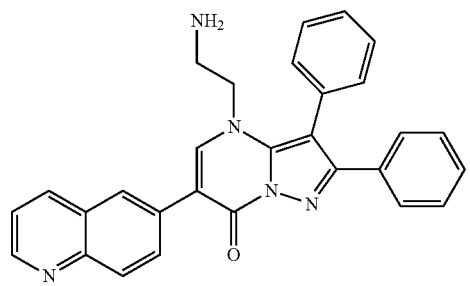 [SMILES: NCCn1cc(-c2ccc3ncccc3c2)c(=O)n2nc(-c3ccccc3)c(-c3ccccc3)c12]

A solution of 2-(7-oxo-2,3-diphenyl-6-(quinolin-6-yl)pyrazolo[1,5-a]pyrimidin-4(7H)-yl)ethyl methanesulfonate (75 mg, 0.14 mmol) in ammonia (7.0 M in MeOH, 10 mL) was stirred at 75° C. in a seal tube for 2 days to afford the title compound.

$^1$H NMR (400 MHz, DMSO-$d_6$) δ: 8.92 (dd, J=4.03, 1.34 Hz, 1H), 8.34-8.49 (m, 3H), 8.18 (dd, J=9.00, 1.75 Hz, 1H), 8.10 (d, J=8.87 Hz, 1H), 7.58 (dd, J=8.19, 4.16 Hz, 1H), 7.50 (s, 5H), 7.40 (d, J=2.15 Hz, 2H), 7.28-7.35 (m, 3H), 4.01 (br. s., 2H), 2.56 (br. s., 2H). LC-MS: m/z 458.0 (M+H)$^+$.

478

Step A: 5-chloro-1-(4-methoxybenzyl)-6-(4-methoxyphenyl)-2,3-diphenylpyrazolo[1,5-a]pyrimidin-7(1H)-one

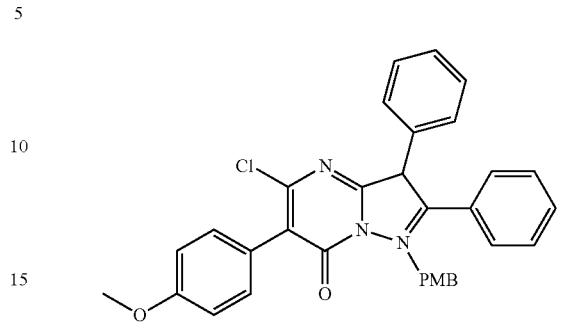

To a mixture of 5-chloro-6-(4-methoxyphenyl)-2,3-diphenylpyrazolo[1,5-a]pyrimidin-7(1H)-one (Synthesized in scheme of Compound 286, 2.29 g, 5.36 mmol), Cs$_2$CO$_3$ (3.49 g, 10.7 mmol) in DMF (30 mL) was added 1-(chloromethyl)-4-methoxybenzene (0.728 mL). The resultant mixture was stirred at 60° C. for 16 h. The mixture was added into H$_2$O (30 mL) and extracted with DCM (10

Compound 354

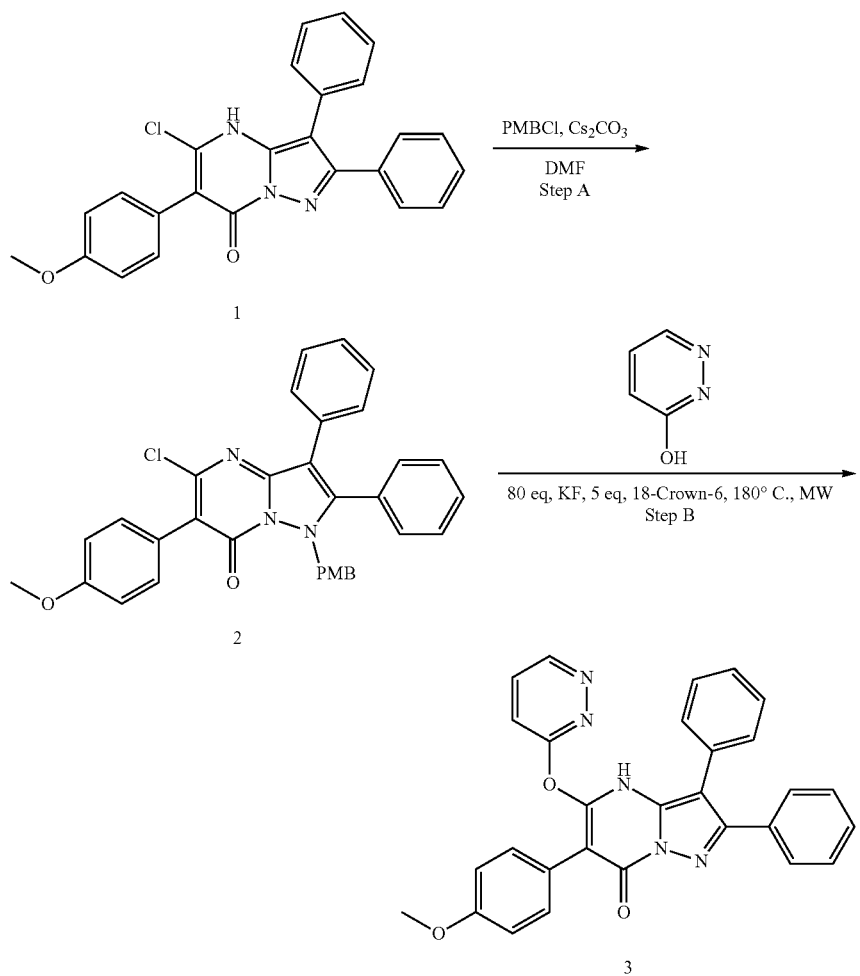

mL*3). The organic layer was dried over anhydrous sodium sulfate and concentrated in vacuo to dryness. The resulting solid was washed with MeOH (5 mL) to get 5-chloro-1-(4-methoxybenzyl)-6-(4-methoxyphenyl)-2,3-diphenylpyrazolo[1,5-a]pyrimidin-7(1H)-one (1.6 g) as a white solid. LC-MS: m/z 548.3 (M+H)$^+$.

Step B: Compound 354: 6-(4-methoxyphenyl)-2,3-diphenyl-5-(pyridazin-3-yloxy)pyrazolo[1,5-a]pyrimidin-7(4H)-one

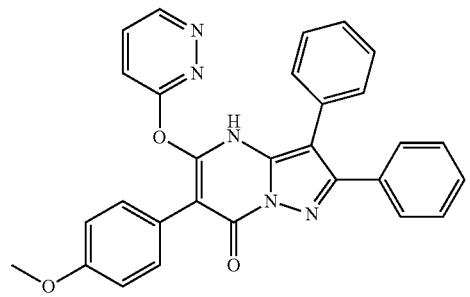 [SMILES: COc1ccc(-c2c(Oc3cccnn3)[nH]c3c(-c4ccccc4)c(-c4ccccc4)nn3c2=O)cc1]

The mixture of 5-chloro-1-(4-methoxybenzyl)-6-(4-methoxyphenyl)-2,3-diphenylpyrazolo[1,5-a]pyrimidin-7(1H)-one (200 mg, 0.365 mmol), KF (1.7 g, 29 mmol) and 18-Crown-6 (481 mg, 1.825 mmol) in NMP (3 mL) was stirred at 180° C. for 4 h under microwave irradiation in a sealed tube to afford 6-(4-methoxyphenyl)-2,3-diphenyl-5-(pyridazin-3-yloxy)pyrazolo[1,5-a]pyrimidin-7(4H)-one.

$^1$H NMR (DMSO-d$_6$) δ: 7.76 (br. s., 1H), 7.53 (d, J=6.98 Hz, 2H), 7.26-7.38 (m, 8H), 7.13-7.24 (m, 3H), 6.80 (d, J=8.60 Hz, 3H), 3.76 (s, 3H). LC-MS: m/z 488.1 (M+H)$^+$.

Compound 355

Step A: 6-(4-methoxyphenyl)-5-phenoxy-2,3-diphenylpyrazolo[1,5-a]pyrimidin-7(4H)-one

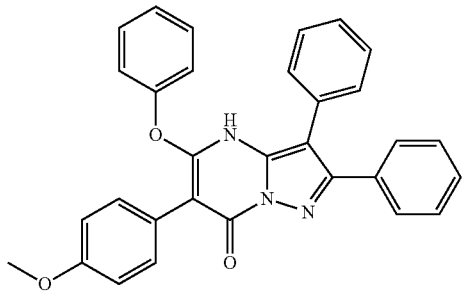

The mixture of 5-chloro-6-(4-methoxyphenyl)-2,3-diphenylpyrazolo [1,5-a]pyrimidin-7(4H)-one (Synthesized in scheme of Compound 286, 200 mg, 0.45 mmol) and sodium phenolate (105 mg, 0.9 mmol) in NMP (3 mL) was stirred at 170° C. for 2 h under microwave irradiation in a sealed tube to afford 6-(4-methoxyphenyl)-5-phenoxy-2,3-diphenylpyrazolo[1,5-a]pyrimidin-7(4H)-one.

$^1$H NMR (DMSO-d$_6$) δ: 7.48 (br. s., 2H), 7.42 (br. s., 4H), 7.26-7.37 (m, 5H), 7.23 (br. s., 2H), 7.10 (d, J=6.45 Hz, 3H), 6.92 (d, J=7.52 Hz, 2H), 3.76 (br. s., 3H). LC-MS: m/z 485.9 (M+H)$^+$.

Compound 356

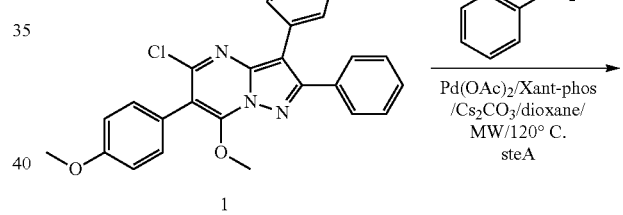

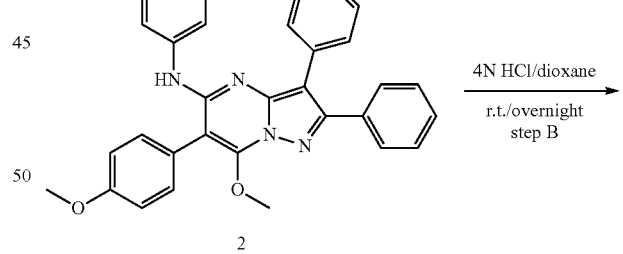

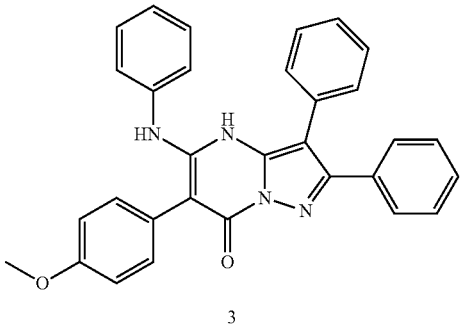

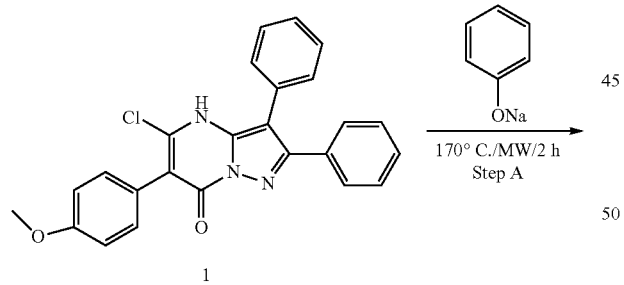

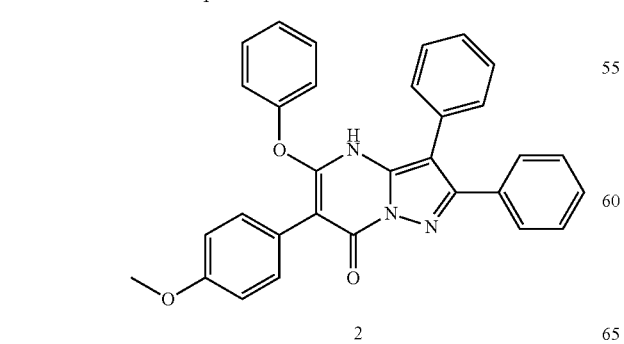

Step A: 7-methoxy-6-(4-methoxyphenyl)-N,2,3-triphenylpyrazolo[1,5-a]pyrimidin-5-amine

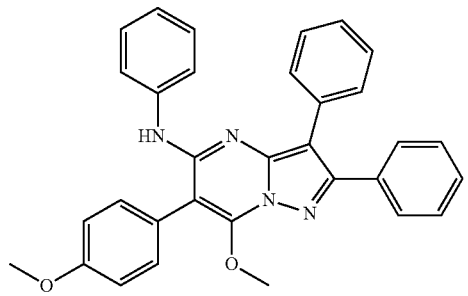

A suspension of 5-chloro-7-methoxy-6-(4-methoxyphenyl)-2,3-diphenylpyrazolo[1,5-a]pyrimidine (Synthesized in Scheme of Compound 101, 100 mg, 0.22 mmol), aniline (45 mg, 0.48 mmol, 2 eq.), Pd(OAc)$_2$ (20 mg, 0.09 mmol, 0.1 eq.), Xantphos (26 mg, 0.05 mmol, 0.2 eq.) and Cs$_2$CO$_3$ (150 mg, 0.46 mmol, 2 eq.) in 1,4-dioxane (5 mL) was stirred at 100° C. for 16 hours under N$_2$ atmosphere. The mixture was filtered through celite, and the filtrate was concentrated in vacuo. The residue was purified by flash chromatography to afford the title compound 2 (70 mg, 64.2% yield) as a yellow solid. LC-MS: m/z 520.7 (M+H)$^+$. LC-MS: m/z 499.1 (M+H)$^+$.

Step B: Compound 356: 6-(4-methoxyphenyl)-2,3-diphenyl-5-(phenylamino)pyrazolo[1,5-a]pyrimidin-7(4H)-one

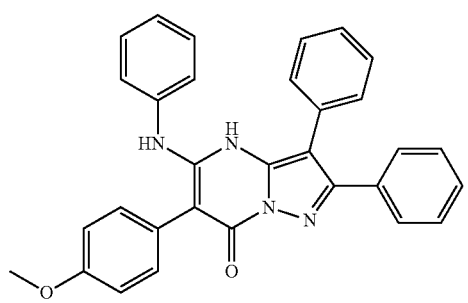

A solution of 7 7-methoxy-6-(4-methoxyphenyl)-N,2,3-triphenylpyrazolo[1,5-a]pyrimidin-5-amine (70 mg, 0.14 mmol) in 4M HCl in 1.4-dioxane (3 mL) was stirred at r.t. for 2 hours. Solvent and volatile were removed in vacuo. The mixture was basified with NaHCO$_3$ solution to pH=8 and concentrated in vacuo to give the title compound 6-(4-methoxyphenyl)-2,3-diphenyl-5-(phenylamino)pyrazolo[1,5-a]pyrimidin-7(4H)-one.

$^1$H NMR (DMSO-d$_6$) δ: 7.41-7.68 (m, 14H), 7.22-7.36 (m, 6H), 4.06 (s, 3H). LC-MS: m/z 484.9 (M+H)$^+$.

Compound 358

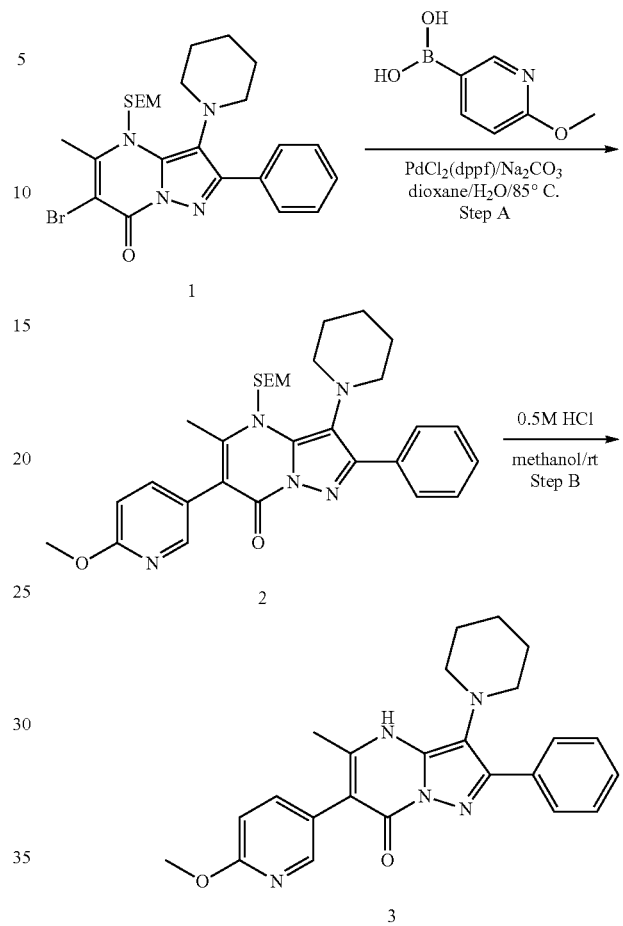

Step A: 6-(6-methoxypyridin-3-yl)-5-methyl-2-phenyl-3-(piperidin-1-yl)-4-((2-(trimethylsilyl)ethoxy)methyl)pyrazolo[1,5-a]pyrimidin-7(4H)-one

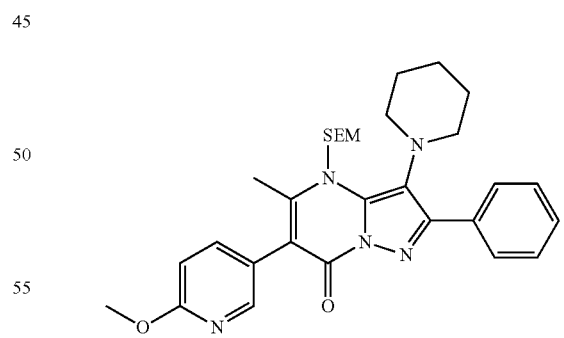

A suspension of 6-bromo-5-methyl-2-phenyl-3-(piperidin-1-yl)-4-((2-(trimethylsilyl)ethoxy)methyl)pyrazolo[1,5-a]pyrimidin-7(4H)-one (Synthesized in scheme of Compound 305, 150 mg, 0.29 mmol) and 6-methoxypyridin-3-ylboronic acid (133 mg, 0.87 mmol), PdCl$_2$(dppf) (21 mg, 0.03 mmol) and Na$_2$CO$_3$ (61 mg, 0.58 mmol) in 1.4-dioxane/water (10 mL/1 mL) was stirred and heated to 85° C. for 16 h under N$_2$ atmosphere. The reaction was then cooled to RT and filtered. The dark filtrate was concentrated in vacuo. The residue was purified by flash column chromatography, eluting with PE/EA (4/1), to get desired product (40 mg, 25% yield) as a white solid. LC-MS: m/z 546.3 (M+H)$^+$.

Step B: 6-(6-methoxypyridin-3-yl)-5-methyl-2-phenyl-3-(piperidin-1-yl)pyrazolo[1,5-a]pyrimidin-7(4H)-one

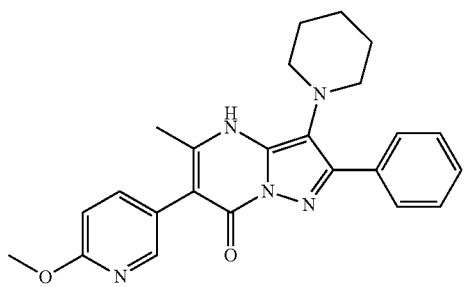 [SMILES: COc1ccc(-c2c(C)[nH]c3c(N4CCCCC4)c(-c4ccccc4)nn3c2=O)cn1]

The mixture of 6-(6-methoxypyridin-3-yl)-5-methyl-2-phenyl-3-(piperidin-1-yl)-4-((2-(trimethylsilyl)ethoxy)methyl)pyrazolo[1,5-a]pyrimidin-7(4H)-one (40 mg, 0.07 mmol) and HCl in MeOH (0.5 mol, 10 mL, 5 mmol) was stirred at RT for 1 h to get the desired product.

$^1$H NMR (DMSO-d$_6$) δ: 11.47 (br. s., 1H), 8.12 (dd, J=1.6 Hz, 2.8 Hz, 3H), 7.67 (dd, J=2.4 Hz, 2.4 Hz, 1H), 7.50-7.40 (m, 3H), 6.90 (d, J=8.0 Hz, 1H), 3.90 (s, 3H), 3.08 (t, J=4.8 Hz, 4H), 2.29 (s, 3H), 1.67-1.50 (m, 6H). LC-MS: m/z 416.2 (M+H)$^+$.

Example 2 Biochemical Assay

In the reaction catalyzed by MAT2A enzyme, L-Met and ATP were converted to SAM, inorganic phosphate, and inorganic diphosphate. Measurement of MAT2A enzymatic activity was made by direct chemical detection of the inorganic phosphate upon the addition of sulfuric acid and ammonium molybdate to the enzymatic reaction mixture, which stochiometrically formed highly chromogenic malachite green phosphomolybdate with an absorption maxima at 620 to 650 nM. The concentration of malachite green phosphomolybdate produced in the detection reaction is thus directly related to the quantity of product produced by the MAT2A enzyme. Multiple commercial kits exist for this method of phosphate detection and quantification, such as PiColorLock Gold (Innova Biosciences).

Typical reaction was performed in 50 μl final volume, containing buffer (Tris, pH 8.0, 50 mM KCl, 15 mM MgCl$_2$, 300 uM EDTA, bovine serum albumin at 0.005% w/v) and 1 μg/ml MAT2A. Compounds were added in 1 μl of DMSO at the desired concentration; a typical dose response curve contained ten points with three-fold dilution between compound concentrations. The mixture of MAT2a enzyme and inhibitor was preincubated for 60 minutes at 25° C.; the enzymatic reaction was started with the addition of L-Met and ATP to a final concentration of 80 μM and 100 μM respectively. The reaction was allowed to proceed for 60 minutes at room temperature then halted by the addition of 13 μl of PiColor Lock reagent. After a further 5 minutes of incubation at room temperature, 5 μl of PiColor Stabilizer was added and the reactions were further incubated at 25° C. for 25 minutes. Quantitative measurement of product produced was determined by spectrophotometric analysis at 623 nM and comparison to a phosphate standard curve.

Recombinant MAT2A protein was expressed in SF9 insect cells and purified by metal chelate affinity chromatography, using methods well known in the art. After expression of His6-tagged MAT2A cells were disrupted by 4 passes through an M-Y1 10 Micro fluidizer (Microfluidics) set to 500 psi, and then centrifuged at 22,000 rcf for 20 min at 4° C. The supernatant was harvested and loaded at 15 cm/h on a Histrap FF 5*1 ml column (GE) which was equilibrated with 50 mM Tris, 500 mM NaCl, pH7.4. Host cell contaminants were removed by washing the column with equilibration buffer followed by equilibration buffer containing 20 mM imidazole and 60 mM imidazole to baseline. MAT2A protein was eluted by the addition of buffer containing 250 mM imidazole, dialyzed into 50 mM NaCl, 50 mM Tris, pH 7.4, flash frozen in liquid nitrogen, and stored at –80° C. until use.

Compounds that are shown in Tables 1 and 2 were tested in the foregoing assay and they were determined to inhibit MAT2A with an IC$_{50}$ according to the following scores: (A) less than 100 nM, (B) between 100 nm and 1 μM, and (C) between 1 μM and 10 μM, as shown in Table 3 below.

TABLE 3

| Compound No. | MAT2A Inhibition Score |
| --- | --- |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | A |
| 132 | A |
| 133 | A |
| 134 | A |
| 135 | A |
| 136 | A |
| 137 | A |
| 138 | A |
| 139 | A |
| 140 | A |
| 141 | A |
| 142 | A |
| 143 | A |
| 144 | A |
| 145 | A |
| 146 | A |
| 147 | A |
| 148 | A |

TABLE 3-continued

| Compound No. | MAT2A Inhibition Score |
| --- | --- |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |
| 189 | A |
| 190 | A |
| 191 | A |
| 192 | A |
| 193 | A |
| 194 | A |
| 195 | A |
| 196 | A |
| 197 | A |
| 198 | A |
| 199 | A |
| 200 | A |
| 201 | A |
| 203 | A |
| 204 | A |
| 205 | A |
| 206 | A |
| 207 | A |
| 208 | A |
| 209 | A |
| 210 | A |
| 211 | A |
| 212 | A |
| 213 | A |
| 215 | A |
| 216 | A |
| 217 | A |
| 218 | A |
| 219 | A |
| 220 | A |
| 221 | A |
| 222 | A |
| 223 | A |
| 224 | A |
| 225 | A |
| 226 | A |
| 227 | A |
| 228 | A |

TABLE 3-continued

| Compound No. | MAT2A Inhibition Score |
| --- | --- |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | C |
| 244 | A |
| 245 | A |
| 246 | A |
| 247 | A |
| 248 | A |
| 249 | A |
| 250 | A |
| 251 | C |
| 252 | A |
| 253 | A |
| 254 | A |
| 255 | A |
| 256 | A |
| 257 | A |
| 258 | A |
| 259 | A |
| 260 | A |
| 261 | A |
| 262 | A |
| 263 | A |
| 264 | A |
| 265 | A |
| 266 | A |
| 267 | A |
| 268 | A |
| 269 | A |
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |
| 283 | A |
| 285 | A |
| 286 | A |
| 287 | A |
| 288 | A |
| 290 | A |
| 291 | A |
| 292 | A |
| 294 | A |
| 295 | A |
| 296 | A |
| 297 | A |
| 298 | B |
| 299 | B |
| 300 | B |
| 301 | B |
| 302 | B |
| 303 | C |
| 304 | B |
| 305 | B |
| 306 | C |
| 307 | B |
| 308 | C |
| 309 | B |
| 310 | C |

TABLE 3-continued

| Compound No. | MAT2A Inhibition Score |
| --- | --- |
| 311 | B |
| 312 | B |
| 313 | B |
| 314 | B |
| 315 | B |
| 316 | B |
| 317 | B |
| 318 | B |
| 319 | B |
| 320 | B |
| 321 | B |
| 322 | C |
| 323 | B |
| 324 | C |
| 325 | B |
| 326 | C |
| 327 | B |
| 328 | C |
| 329 | B |
| 330 | B |
| 331 | B |
| 332 | B |
| 333 | B |
| 334 | B |
| 335 | B |
| 336 | B |
| 337 | B |
| 338 | B |
| 339 | B |
| 340 | B |
| 346 | C |
| 347 | C |
| 348 | C |
| 349 | C |
| 350 | C |
| 351 | C |
| 352 | C |
| 353 | C |
| 354 | C |
| 355 | C |
| 356 | B |
| 358 | A |

Example 3 Cellular Assay of Target Engagement (SAM)

Measurement of MAT2A activity in cells was made by direct quantitation of the abundance of the product of its enzymatic activity, SAM. Cancer cells were treated with candidate MAT2A inhibitors for a suitable incubation period, and the cells were then lysed using a reagent which quenched any further enzyme activity. Soluble metabolites including SAM were collected and SAM itself was directly measured from the lysate using quantitative LC/MS.

A typical assay was performed using an HCT116 human colon carcinoma cell line which was genetically engineered to delete the MTAP gene (commercially available from Horizon Discovery). This cell line was utilized because it was determined that loss of the MTAP gene predicts sensitivity to MAT2A inhibitors. Cells were plated in 96-well dishes at appropriate cell density. Following 24 hours, cells were then treated with the candidate MAT2A inhibitor. Prior to addition to cells, the compound was first serially diluted in DMSO, typically as a 3-fold serial dilution with 10 dose points. Compound was then transferred to a working stock plate in cell culture media by adding 5 µl of compound in DMSO to 495 µl of cell culture media. This working stock was then added to cells via a further 5-fold dilution, by adding 25 µl of working stock to 100 µl of cells in culture media. Following compound addition, cells were incubated at 37° C./5% $CO_2$ for 4 hrs.

To quantitate SAM levels following compound treatment, cells were gently washed once in Ammonium Carbonate buffer (75 mM at pH 7.4), placed on dry ice, and lysed with metabolite extraction buffer (80% cold methanol and 20% acetic acid containing 50 ng/ml of deuterated d3SAM). Following centrifugation at 4° C. at 3200 rpm for 30 minutes, the supernatant was collected and stored at −80° C. until analysis by Liquid Chromatography-Mass Spectrometry (LC/MS). LC/MS analysis was performed using an Xevo TQS (Milford, Mass.) operating in positive electrospray mode, with chromatographic separation using a Waters Acquity BEH Amide column. Multiple Reaction Monitoring data was acquired for SAM and the d3SAM standard, using MRM transitions of 399.2/250.1 amu and 402.2/250.1 amu, respectively. In a typical LC/MS analysis, the initial flow rate was 0.5 ml/min of 25% $H_2O$:ACN(95/5,v/v)-1% FA-10 mM $NH_4OAc$ (Mobile Phase A), 75% $H_2O$:ACN(5/95,v/v)-1% FA-10 mM $NH_4OAc$ (Mobile Phase B), at 0.2 min 25% MA, at 0.5 min 65% MA, at 1.1 min 25% MA with a total run time of 2.5 minutes Example 4 Assay for Inhibition of Cellular Proliferation Test compound impact on cancer cell growth was assessed by treating cancer cells with compound for 4 days and then measuring proliferation using an ATP-based cell proliferation readout (Cell Titer Glo, Promega Corporation).

In a typical assay an isogenic pair of HCT116 human colon carcinoma cell lines which vary only in MTAP deletion status (HCT116 MTAP+/+ and HCT116 MTAP−/−) were plated in 96-well dishes at appropriate cell density. Following 24 hours, cells were then treated with the candidate MAT2A inhibitor. Prior to addition to cells, the compound was first serially diluted in DMSO, typically as a 3-fold serial dilution with 10 dose points. Compound was then transferred to a working stock plate in cell culture media by adding 5 µl of compound in DMSO to 495 µl of cell culture media. This working stock was then added to cells via a further 5-fold dilution, by adding 25 µl of working stock to 100 µl of cells in culture media. Following compound addition, cells were incubated at 37° C./5% $CO_2$ for 4 days.

To measure inhibition of cellular proliferation, cells were allowed to equilibrate to room temperature for 30 minutes, and were then treated with 125 µl of Cell Titer Glo reagent. The plate was then shaken for 15 minutes to ensure complete mixing and full cell lysis. Luminescent signal of the Cell Titer Glo reagent was then measured using a plate-based luminometer and normalized via an ATP standard curve. This luminescence measure was converted to a proliferation index by subtracting from each datapoint the ATP luminescence measured from a control cell plate that was measured at the time of compound treatment (i.e., day 0). Compound activity was then represented as a % change in proliferation relative to a within-plate DMSO control.

We claim:

1. A compound according to formula IA or a pharmaceutically acceptable salt thereof:

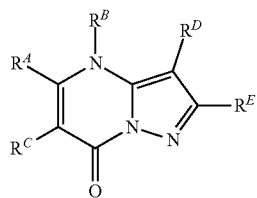

(IA)

wherein
R$^A$ is selected from the group consisting of H, C$_1$-C$_6$-alkyl, C$_2$-C$_6$-alkenyl, C$_1$-C$_6$-alkoxy, C$_3$-C$_{14}$-carbocycle, (C$_3$-C$_{14}$-carbocyclo)-C$_1$-C$_6$-alkyl-, 3- to 14-membered heterocycle or heterocyclo-C$_1$-C$_6$-alkyl- (wherein 1 to 4 heterocycle ring members are heteroatoms selected from N, O, and S), (3- to 14-membered heterocyclo)oxy-, C$_6$-C$_{14}$-aryl, (C$_6$-C$_{14}$-aryl)-C$_1$-C$_6$-alkyl-, C$_6$-C$_{14}$-aryloxy-, —(CH$_2$)$_{0-6}$NR$^1$(CH$_2$)$_{0-6}$C(O)R$^2$, NR$^1$R$^2$, C(O)NR$^1$R$^2$, NR$^1$C(NR$^2$)NR$^1$R$^2$, NR$^1$C(NR$^2$)(=NR$^1$), SR$^1$, —CN, and —OH;
   wherein each alkyl, alkenyl, alkoxy, aryl, and heterocycle is optionally substituted with one or more substituents selected from the group consisting of R, OR$^1$, halo, —N=N—R$^1$, NR$^1$R$^2$, —(C$_1$-C$_6$-alkyl)NR$^1$R$^2$, —C(O)OR$^1$, —C(O)NR$^1$R$^2$, —OC(O)R$^1$, —CN, —OP(O)(OR$^1$)$_{1-2}$, and oxo;

R$^B$ is selected from the group consisting of H, C$_2$-C$_6$-alkenyl, and C$_1$-C$_6$-alkyl, wherein R$^B$ is optionally substituted by one or more R$^1$;

R$^C$, R$^D$, and R$^E$ are independently selected from the group consisting of C$_3$-C$_{14}$-carbocycle, C$_6$-C$_{14}$-aryl, and 3- to 14-membered heterocycle (wherein 1 to 4 heterocycle ring members are heteroatoms selected from N, O, and S),
   wherein R$^C$, R$^D$, and R$^E$ are optionally substituted with one or more substituents selected from the group consisting of R$^1$, —OR$^1$, halo, —NR$^1$R$^2$, —(C$_1$-C$_6$-alkyl)-NR$^1$R$^2$, —C(O)OR$^1$, —C(O)NR$^1$R$^2$, —NO$_2$, —CN, and oxo; and R$^1$ and R$^2$ are independently selected from the group consisting of H, D ($^2$H), —CN, —OH, C$_1$-C$_6$-alkyl, C$_1$-C$_6$-alkoxy, C$_2$-C$_6$-alkenyl, C$_2$-C$_6$-alkynyl, NH$_2$, —S(O)$_{0-2}$—(C$_1$-C$_6$-alkyl), —S(O)$_{0-2}$-(C$_6$-C$_{14}$-aryl), —C(O)(C$_1$-C$_6$-alkyl), —C(O)(C$_3$-C$_{14}$-carbocyclo), —C$_3$-C$_{14}$-carbocycle, C$_6$-C$_{14}$-aryl, 3- to 14-membered heterocycle or heterocyclo(C$_1$-C$_6$-alkyl)- (wherein 1 to 4 heterocycle ring members are heteroatoms selected from N, O, and S),
   wherein each alkyl, alkoxy, alkenyl, alkynyl, aryl, carbocycle, and heterocycle moiety of R$^1$ and R$^2$ is optionally substituted with one or more substituents selected from the group consisting of hydroxy, halo, —NH$_2$, —NHC(O)(OC$_1$-C$_6$-alkyl), —NO$_2$, —CN, oxo, —C(O)OH, —C(O)O(C$_1$-C$_6$-alkyl), —C$_1$-C$_6$-alkyl(C$_1$-C$_6$-alkoxy), —C(O)NH$_2$, C$_1$-C$_6$-alkyl, —C(O)C$_1$-C$_6$-alkyl, —OC$_1$-C$_6$-alkyl, —Si(C$_1$-C$_6$-alkyl)$_3$, C$_6$-C$_{14}$-aryl, —(C$_1$-C$_6$-alkyl)(C$_6$-C$_{14}$-aryl), 3- to 14-membered heterocycle or heterocyclo(C$_1$-C$_6$-alkyl)- (wherein 1 to 4 heterocycle ring members are heteroatoms selected from N, O, and S), and —O(C$_6$-C$_{14}$-aryl),
wherein each alkyl, aryl, and heterocyclo in R$^1$ and R$^2$ is optionally substituted with one or more substituents selected from the group consisting of hydroxy, —OC$_1$-C$_6$-alkyl, halo, —NH$_2$, —(C$_1$-C$_6$-alkyl)NH$_2$, —C(O)OH, CN, and oxo.

2. The compound according to claim 1, or a pharmaceutically acceptable salt thereof, wherein R$^D$ and R$^E$ are independently selected from C$_3$-C$_{14}$-carbocycle, C$_6$-C$_{14}$-aryl, and 3- to 14-membered heterocycle (wherein 1 to 4 heterocycle ring members are heteroatoms selected from N, O, and S).

3. The compound according to claim 2, or a pharmaceutically acceptable salt thereof, wherein R$^D$ and R$^E$ are independently selected from C$_3$-C$_{14}$-carbocycle and C$_6$-C$_{14}$-aryl.

4. The compound according to claim 3, or a pharmaceutically acceptable salt thereof, wherein R$^D$ and R$^E$ are independently selected from C$_5$-C$_7$-carbocycle and C$_6$-C$_{10}$-aryl.

5. The compound according to claim 4, or a pharmaceutically acceptable salt thereof, wherein R$^D$ and R$^E$ are independently selected from cyclopentyl, cyclopentenyl, cyclohexyl, cyclohexenyl, and phenyl.

6. The compound according to claim 5, or a pharmaceutically acceptable salt thereof, wherein one of R$^D$ and R$^E$ is cyclohexyl or cyclohexenyl and the other is phenyl.

7. The compound according to claim 1, or a pharmaceutically acceptable salt thereof, wherein
R$^A$ is selected from the group consisting of C$_1$-C$_6$-alkyl, C$_2$-C$_6$-alkenyl, C$_1$-C$_6$-alkoxy, C$_3$-C$_{14}$-carbocycle, (C$_3$-C$_{14}$-carbocyclo)-C$_1$-C$_6$-alkyl-, 3- to 14-membered heterocycle or heterocyclo(C$_1$-C$_6$-alkyl)- (wherein 1 to 4 heterocycle ring members are heteroatoms selected from N, O, and S), C$_6$-C$_{14}$-aryl, (C$_6$-C$_{14}$-aryl)-C$_1$-C$_6$-alkyl-, C$_6$-C$_{14}$-aryloxy, —(CH$_2$)$_{0-6}$NR$^1$(CH$_2$)$_{0-6}$C(O)R$^2$, NR$^1$R$^2$, NR$^1$C(NR$^2$)NR$^1$R$^2$, —CN, and —OH.

8. The compound according to claim 7, or a pharmaceutically acceptable salt thereof, wherein R$^A$ is selected from the group consisting of C$_1$-C$_6$-alkyl, —(CH$_2$)$_{0-6}$)NR$^1$(CH$_2$)$_{0-6}$)C(O)R$^2$, NR$^1$R$^2$, and NR$^1$C(NR$^2$)NR$^1$R$^2$.

9. The compound according to claim 8, or a pharmaceutically acceptable salt thereof, wherein R$^A$ is C$_1$-C$_6$-alkyl or NR$^1$R$^2$.

10. The compound according to claim 9, or a pharmaceutically acceptable salt thereof, wherein R$^A$ is NR$^1$R$^2$.

11. The compound according to claim 10, or a pharmaceutically acceptable salt thereof, wherein R$^1$ is H.

12. The compound according to claim 1, or a pharmaceutically acceptable salt thereof, wherein the compound is one according to formula IB:

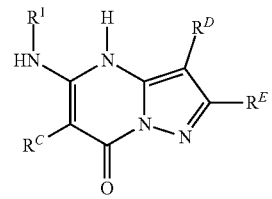

(IB)

wherein
R$^C$ is a C$_3$-C$_{14}$-carbocycle or a 3- to 14-membered heterocycle (wherein 1 to 4 heterocycle ring members are heteroatoms selected from N, O, and S),
   each optionally substituted with one or more substituents selected from the group consisting of hydroxy, halogen, —NH$_2$, C$_6$-C$_{14}$-aryl, (C$_6$-C$_{14}$-aryl)-C$_1$-C$_6$-alkyl-, carboxy, —CN, oxo, C$_1$-C$_6$-alkyl, C$_1$-C$_6$- alkoxy, and —NH(C$_1$-C$_6$-alkyl), wherein the C$_1$-C$_6$-alkyl, C$_1$-C$_6$-alkoxy, and NH(C$_1$-C$_6$-alkyl) are independently and optionally substituted with one or more of hydroxy, halogen, —NH$_2$, carboxy, —CN, and oxo;

R$^D$ and R$^E$ are independently a C$_3$-C$_{14}$-carbocycle or a 3- to 14-membered heterocycle (wherein 1 to 4 heterocycle ring members are heteroatoms selected from N, O, and S), each optionally substituted with one or more substituents selected from the group consisting of hydroxy, halogen, —NH$_2$, C$_6$-C$_{14}$-aryl, (C$_6$-C$_{14}$-aryl)-C$_1$-C$_6$-alkyl-, carboxy, —CN, oxo, C$_1$-C$_6$-alkyl, C$_1$-C$_6$-alkoxy, and —NH(C$_1$-C$_6$-alkyl), wherein the C$_1$-C$_6$-alkyl, C$_1$-C$_6$-alkoxy, and NH(C$_1$-C$_6$-alkyl) are independently and optionally substituted with one or more of hydroxy, halogen, —NH$_2$, carboxy, —CN, and oxo; and R$_1$ is selected from the group consisting of H, C$_1$-C$_6$-alkyl, C$_3$-C$_{14}$-carbocycle, and 3- to 14-membered heterocycle (wherein 1 to 4 heterocycle ring members are heteroatoms selected from N, O, and S), each optionally substituted with one or more substituents selected from the group consisting of hydroxy, halogen, —NH$_2$, —NO$_2$, —CN, oxo, carboxy, —C(O)OC$_1$-C$_6$-alkyl, (C$_1$-C$_6$-alkyl)OC$_1$-C$_6$-alkyl-, —C(O)NH$_2$, C$_1$-C$_6$-alkyl, —C(O)H, C$_1$-C$_6$-alkoxy, (C$_1$-C$_6$-alkyl)N(H)-aryl-, (C$_6$-C$_{14}$-aryl)C$_1$-C$_6$-alkyl-, 5- to 7-membered heteroaryl, (5- to 7-membered heteroaryl)-C$_1$-C$_6$-alkyl-, C$_6$-C$_{14}$-aryloxy, (C$_6$-C$_{14}$-aryl)(C$_1$-C$_6$-alkoxy)-, (5- to 7-membered heteroaryl)oxy-, and (5- to 7-membered heteroaryl)(C$_1$-C$_6$-alkoxy)-, wherein the C$_1$-C$_6$-alkyl, C$_1$-C$_6$-alkoxy, (C$_1$-C$_6$-alkyl)N(H)—, —C(O)OC$_1$-C$_6$-alkyl, (C$_1$-C$_6$-alkyl)OC$_1$-C$_6$-alkyl-, —C(O)NH$_2$, C$_6$-C$_{14}$-aryl, (C$_6$-C$_{14}$-aryl)C$_1$-C$_6$-alkyl-, 5- to 7-membered heteroaryl, (5- to 7-membered heteroaryl)-C$_1$-C$_6$-alkyl-, C$_6$-C$_{14}$-aryloxy, (C$_6$-C$_{14}$-aryl)(C$_1$-C$_6$-alkoxy)-, (5- to 7-membered heteroaryl)oxy-, and (5- to 7-membered heteroaryl)(C$_1$-C$_6$-alkoxy)-, are optionally substituted with one or more of hydroxy, halogen, —NH$_2$, (C$_1$-C$_6$-alkyl)N(H)—, —COOH, —CN, and oxo, wherein each heteroaryl in R$^1$ has 1 to 4 heteroaryl ring members that are heteroatoms selected from N, O, and S.

13. The compound according to claim 12, or a pharmaceutically acceptable salt thereof, wherein R$^D$ is C$_3$-C$_{14}$-carbocycle optionally substituted with one or more members of the group consisting of hydroxy, halogen, —NH$_2$, —C(O)OH, —CN, oxo, alkyl, C$_1$-C$_6$-alkyl, C$_1$-C$_6$-alkoxy, and (C$_1$-C$_6$-alkyl)N(H)—, wherein the C$_1$-C$_6$-alkyl, C$_1$-C$_6$-alkoxy, and (C$_1$-C$_6$-alkyl)N(H)- are optionally substituted with one or more of hydroxy, halogen, —NH$_2$, —C(O)OH, —CN, and oxo.

14. The compound according to claim 12, or a pharmaceutically acceptable salt thereof, wherein R$^D$ is phenyl.

15. The compound according claim 12, or a pharmaceutically acceptable salt thereof, wherein R$^D$ is cyclohex-1-en-1-yl.

16. The compound according to claim 12, or a pharmaceutically acceptable salt thereof, wherein R$^E$ is C$_3$-C$_{14}$-carbocycle optionally substituted with one or more members of the group consisting of hydroxy, halogen, —NH$_2$, —C(O)OH, —CN, oxo, alkyl, C$_1$-C$_6$-alkyl, C$_1$-C$_6$-alkoxy, and (C$_1$-C$_6$-alkyl)N(H)—, wherein the C$_1$-C$_6$-alkyl, C$_1$-C$_6$-alkoxy, and (C$_1$-C$_6$-alkyl)N(H)— are optionally substituted with one or more of hydroxy, halogen, —NH$_2$, —C(O)OH, —CN, and oxo.

17. The compound according to claim 12, or a pharmaceutically acceptable salt thereof, wherein R$^E$ is selected from the group consisting of cyclohex-1-en-1-yl, ($^2$H$_9$) cyclohex-1-en-1-yl, cyclohexan-1,3-dien-1-yl, 4,4-difluorocyclohex-1-en-1-yl, cyclopent-1-en-1yl, cyclopentyl, pyridin-3-yl, pyridin-2-yl, 4-methoxypyridin-3-yl, pyridin-2-yl, 1H-pyrazol-4-yl, 1H-pyrrol-3-yl, 4,4-difluoropiperidin-1-yl, 5,6-dihydro-2H-pyran-3-yl, 3,6-dihydro-2H-pyran-4-yl, 1H-pyrrol-3-yl, 1H-pyrrol-1-yl, tetrahydrofuran-3-yl, 3,3-difluoropyrrolidin-1-yl, and 3,6-dihydro-2H-pyran-4-yl.

18. The compound according to claim 12, or a pharmaceutically acceptable salt thereof, wherein R$^E$ is phenyl.

19. The compound according to claim 18, or a pharmaceutically acceptable salt thereof, wherein R$^D$ is cyclohex-1-en-1-yl.

20. The compound according to claim 12, or a pharmaceutically acceptable salt thereof, wherein R$^C$ is C$_3$-C$_{14}$-carbocycle or 3- to 14-membered heterocycle (wherein 1 to 4 heterocycle ring members are heteroatoms selected from N, O, and S) and that is optionally substituted with one or more substituents selected from the group consisting of hydroxy, halogen, —NH$_2$, —C(O)OH, —CN, oxo, C$_1$-C$_6$-alkyl, C$_1$-C$_6$-alkoxy, (C$_1$-C$_6$-alkyl)N(H)—, wherein the C$_1$-C$_6$-alkyl, C$_1$-C$_6$-alkoxy, and (C$_1$-C$_6$-alkyl)N(H)— are optionally substituted with hydroxy, halogen, —NH$_2$, —C(O)OH, —CN and oxo.

21. The compound according to claim 12, or a pharmaceutically acceptable salt thereof, wherein R$^C$ is selected from the group consisting of 4-hydroxyphenyl, 4-chlorophenyl, 4-fluorophenyl, 4-methoxyphenyl, 4-ethoxyphenyl, 4-trifluoromethoxyphenyl, 4-hydroxy-2-methylphenyl, 4-hydroxy-2-methoxyphenyl, 3,4-dihydroxyphenyl, 4-(2,2,2-trifluoroethoxy)phenyl, 4-(2-(dimethylamino)ethoxy)phenyl, 3-fluoro-4-hydroxyphenyl, 3-fluoro-4-methoxyphenyl, 2-chloro-4-hydroxyphenyl, 2-fluoro-4-methoxyphenyl, 3-amino-4-hydroxyphenyl, 3-amino-4-fluorophenyl, 3-(N,N-dimethylaminoethoxy)-4-hydroxyphenyl, 3-chloro-2-hydroxyphenyl, 3-hydroxyethoxy-4-hydroxyphenyl

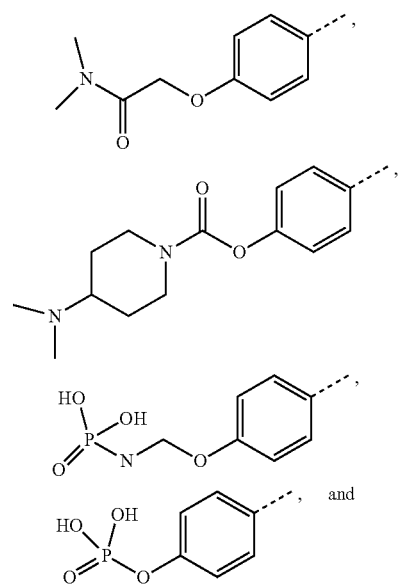

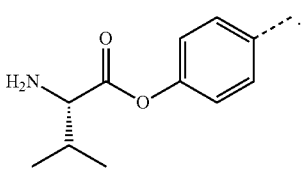

22. The compound according to claim 12, or a pharmaceutically acceptable salt thereof, wherein $R^C$ is selected from the group consisting of 6-methoxypyridin-3-yl, 2-methoxypyridin-4-yl, 1H-pyrazol-4-yl, quinolin-6-yl, 2-methylquinolin-6-yl, 2-methoxyquinolin-6-yl, 2-hydroxymethylquinolin-6-yl, 3-hydroxy-2-methylquinolin-6-yl, 2-aminoquniazolin-6-yl, 4-aminoquinazolin-6-yl, cinnolin-6-yl, quinoxalin-6-yl, 2-chloroquinoxalin-6-yl, 3-chloroquinoxalin-6-yl, 3-aminoquinoxalin-6-yl, 3-hydroxyquinoxalin-6-yl, 3-methoxyquinoxalin-6-yl, 1,8-naphthyridin-3-yl, imidazo[1,2-a]pyridin-6-yl,

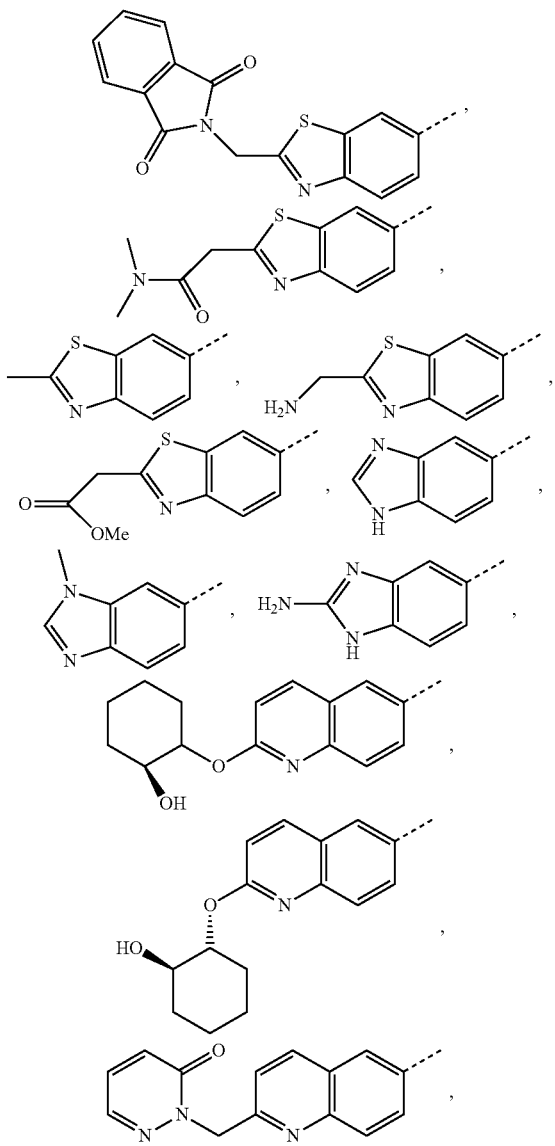

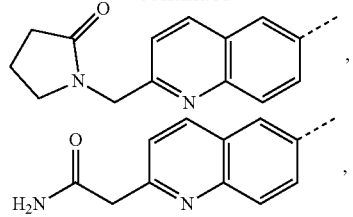

23. The compound according claim 12, or a pharmaceutically acceptable salt thereof, wherein $R^C$ is 4-methoxyphenyl.

24. The compound according claim 12, or a pharmaceutically acceptable salt thereof, wherein $R^1$ is a 3- to 14-membered heterocycle optionally substituted with one or more substituents selected from the group consisting of hydroxy, halogen, —$NH_2$, —$NO_2$, —C(O)OH, —C(O)O$C_1$-$C_6$-alkyl, ($C_1$-$C_6$-alkyl)N(H)C(O)—, —CN, oxo, $C_1$-$C_6$-alkyl, —C(O)H, $C_1$-$C_6$-alkoxy, and ($C_1$-$C_6$-alkyl)N(H)—,
wherein the $C_1$-$C_6$-alkyl, $C_1$-$C_6$-alkoxy, and ($C_1$-$C_6$-alkyl)N(H)—, C(O)O$C_1$-$C_6$-alkyl, and ($C_1$-$C_6$-alkyl)N(H)C(O)— are optionally substituted with one or more of hydroxy, halogen, —$NH_2$, ($C_1$-$C_6$-alkyl)N(H)—, —C(O)H, —CN, and oxo.

25. The compound according to claim 12, or a pharmaceutically acceptable salt thereof, wherein $R^1$ is selected from the group consisting of pyridin-2-yl, pyrazin-2-yl, pyrimidin-2-yl, pyrimidin-4-yl, pyrimidin-5-yl, pyridazin-3-yl, 1,3,5-triazin-2-yl, 1,2,4-triazin-3-yl, each of which is optionally substituted with one or more of F, Cl, CN, OH, —$NO_2$, —$NH_2$, —NHMe, —C(O)$NH_2$, and methoxy.

26. The compound according claim 12, or a pharmaceutically acceptable salt thereof, wherein $R^1$ is selected from the group consisting of:

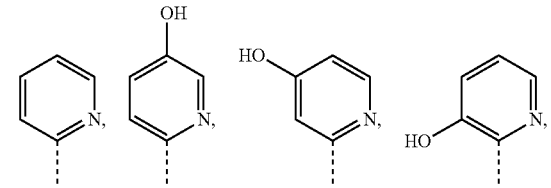

-continued
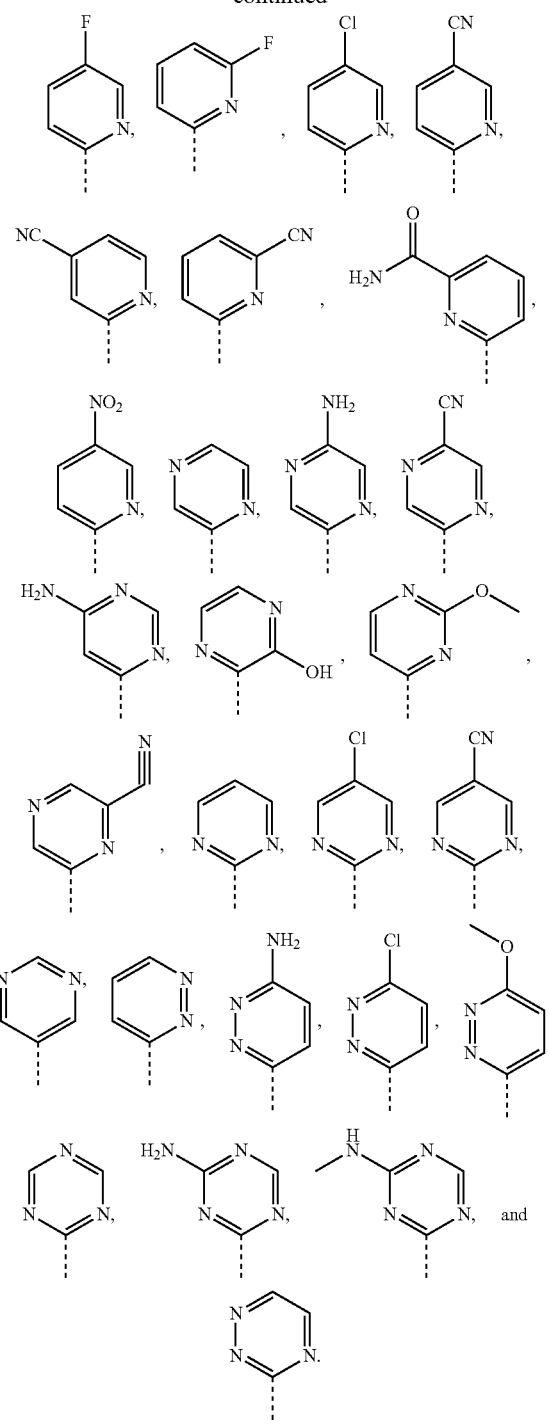
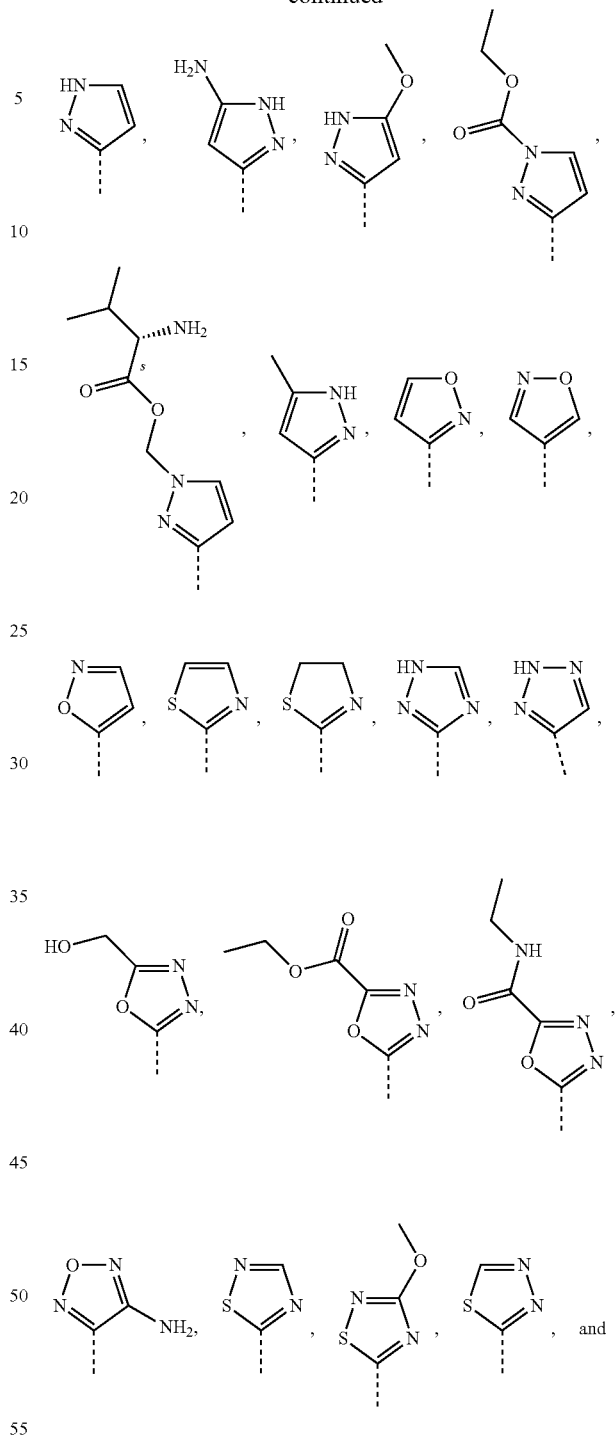
27. The compound according claim 12, or a pharmaceutically acceptable salt thereof, wherein R1 is selected from the group consisting of:
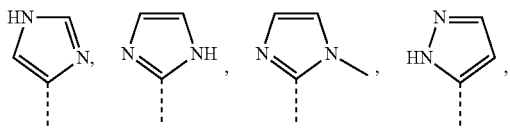
28. A compound of formula (I) or a pharmaceutically acceptable salt thereof:

(I)

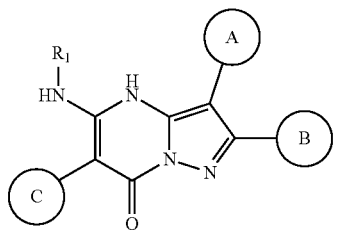

wherein:
ring A and ring B are independently a carbocycle or a heterocycle each optionally substituted with one or more substituents selected from the group consisting of hydroxy, halogen, amino, carboxy, CN, oxo, alkyl, alkoxy and alkylamino wherein said alkyl, alkoxy and alkylamino are optionally substituted with hydroxy, halogen, amino, carboxy, CN and oxo;
ring C is a carbocycle or a heterocycle each optionally substituted with one or more substituents selected from the group consisting of hydroxy, halogen, amino, carboxy, CN, oxo, alkyl, alkoxy and alkylamino wherein said alkyl, alkoxy and alkylamino are optionally substituted with hydroxy, halogen, amino, carboxy, CN and oxo; and
$R_1$ is H or alkyl, a carbocycle or a heterocycle each optionally substituted with one or more substituents selected from the group consisting of hydroxy, halogen, amino, $NO_2$, CN, oxo, carboxy, alkoxycarbonyl, alkoxyalkyl, aminocarbonyl, alkyl, acyl, alkoxy, alkylamino aryl, aralkyl, heteroaryl, heteroaralkyl, aryloxy, aralkoxy, heteroaryloxy and heteroaralkoxy wherein said alkyl, alkoxy, alkylamino, alkoxycarbonyl, alkoxyalkyl, aminocarbonyl, aryl, aralkyl, heteroaryl, heteroaralkyl, aryloxy, aralkoxy, heteroaryloxy and heteroaralkoxy are optionally substituted with hydroxy, halogen, amino, alkylamino, carboxy, CN or oxo.

29. A compound according to claim 1, or a pharmaceutically acceptable salt thereof, that is selected from the following table:

101

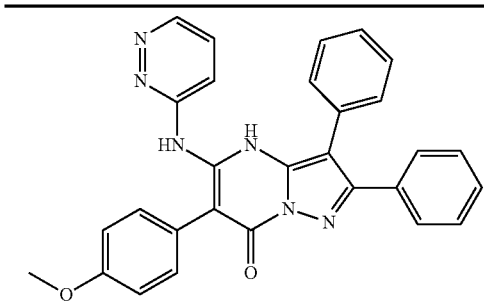

102

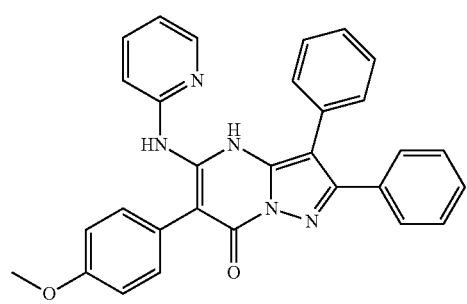

103

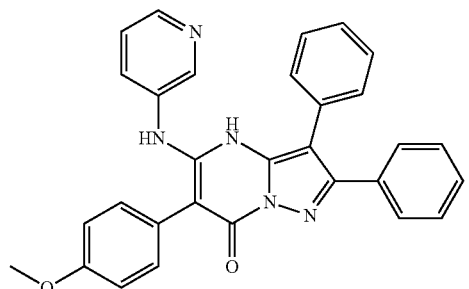

104

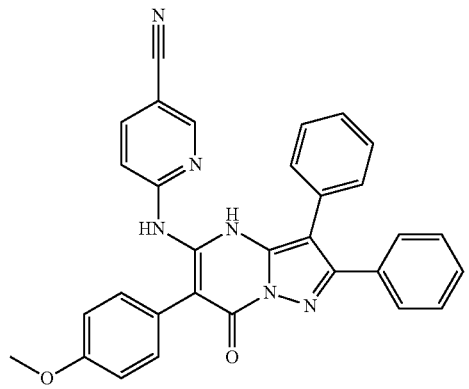 [SMILES: COc1ccc(-c2c(Nc3ccc(C#N)cn3)[nH]c3c(-c4ccccc4)c(-c4ccccc4)nn3c2=O)cc1]

105

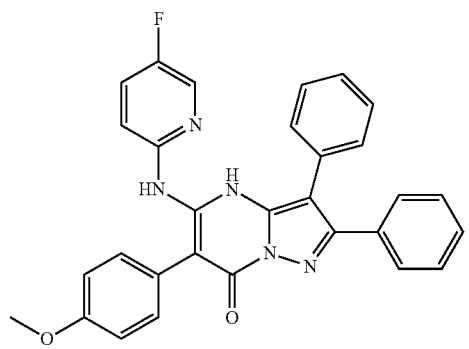 [SMILES: COc1ccc(-c2c(Nc3ccc(F)cn3)[nH]c3c(-c4ccccc4)c(-c4ccccc4)nn3c2=O)cc1]

106

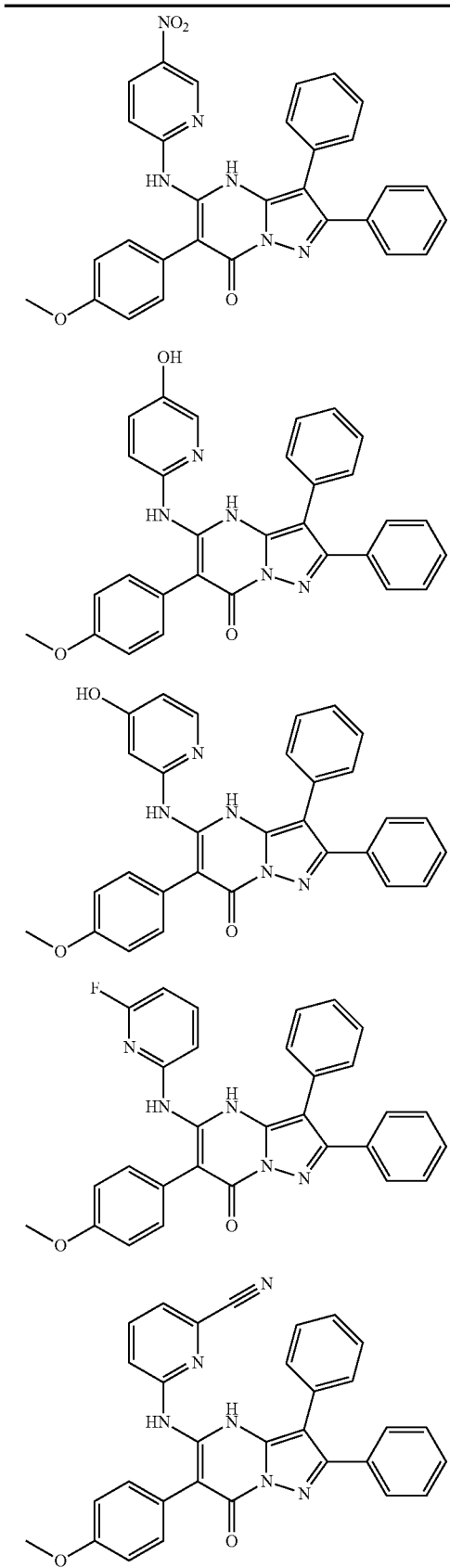

-continued
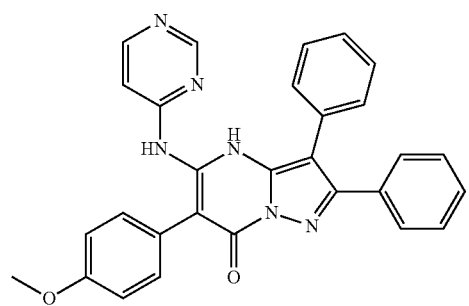
116
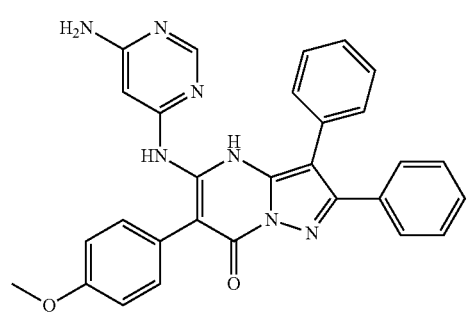
117
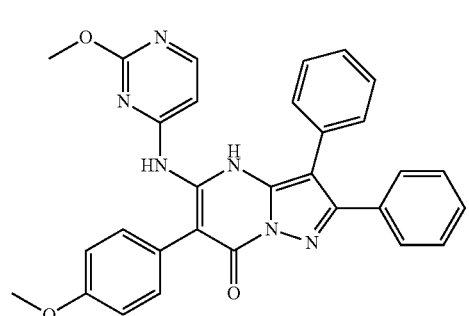
118
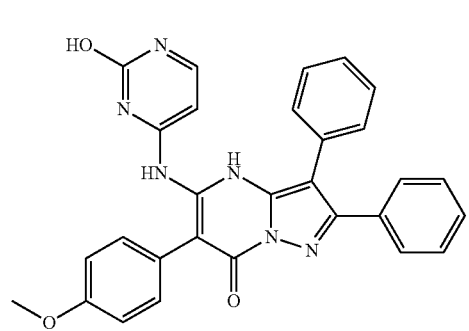
119
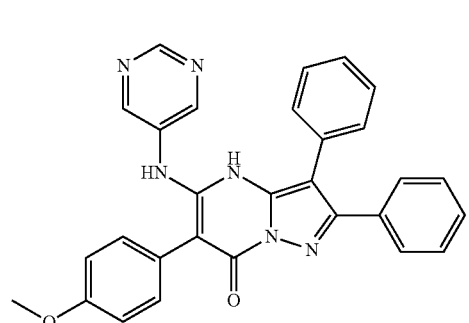
120
-continued
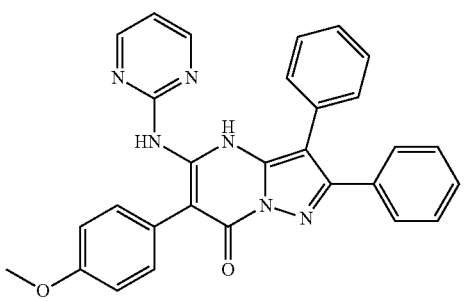
121
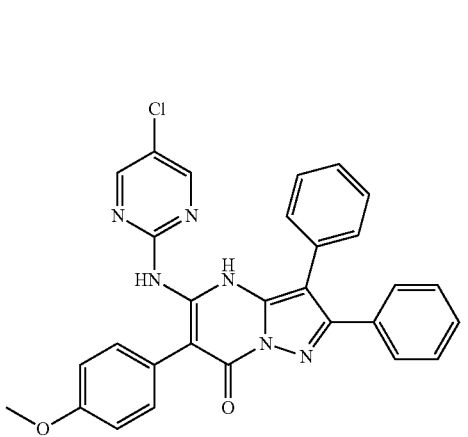 [SMILES: COc1ccc(-c2c(Nc3ncc(Cl)cn3)[nH]c3c(-c4ccccc4)c(-c4ccccc4)nn3c2=O)cc1]
122
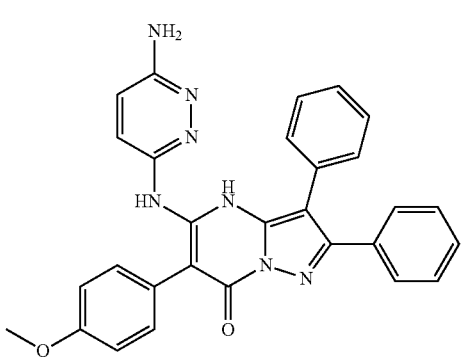
123
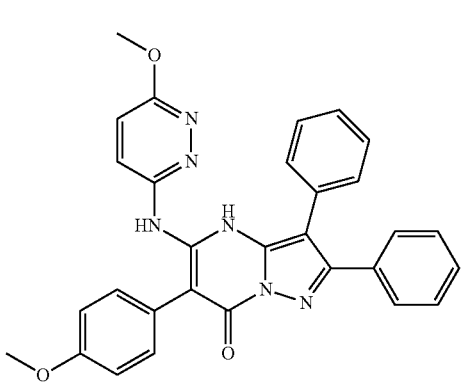 [SMILES: COc1ccc(-c2c(Nc3ccc(OC)nn3)[nH]c3c(-c4ccccc4)c(-c4ccccc4)nn3c2=O)cc1]
124

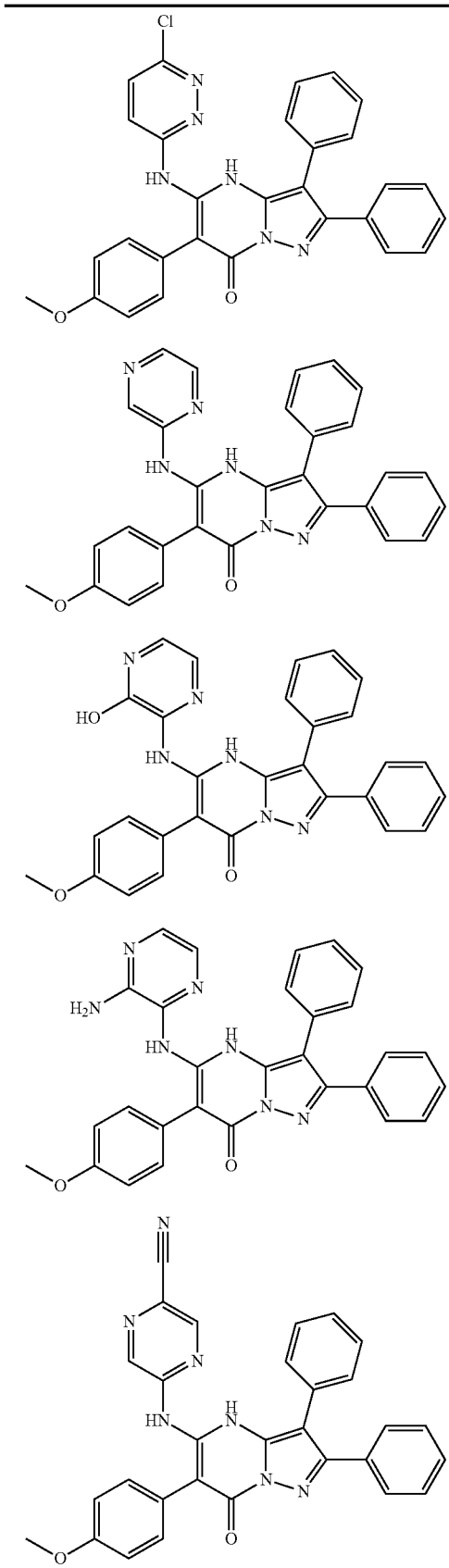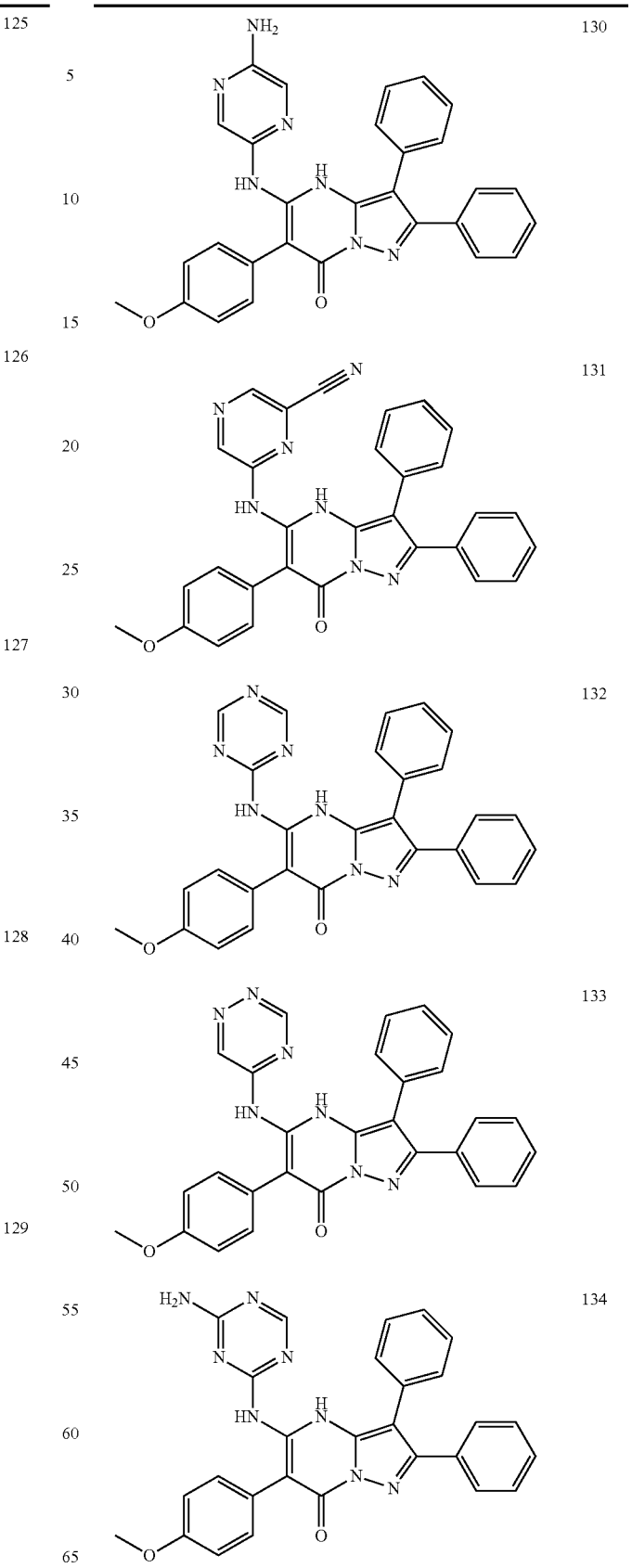

| 135 | 140 |
|---|---|
| 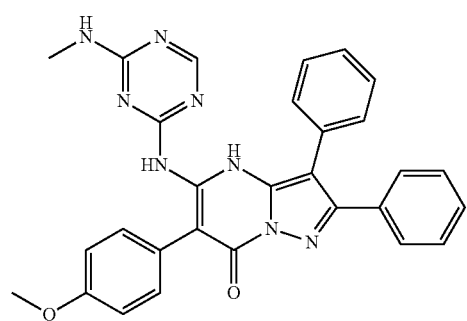 [SMILES: CNc1ncnc(Nc2[nH]c3c(-c4ccccc4)c(-c4ccccc4)nn3c(=O)c2-c2ccc(OC)cc2)n1] | 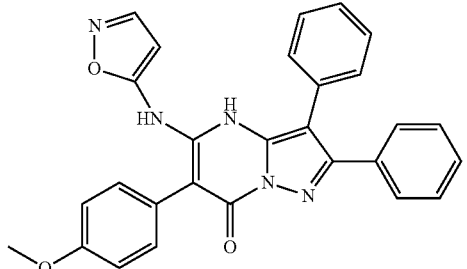 |
| 136 | 141 |
| 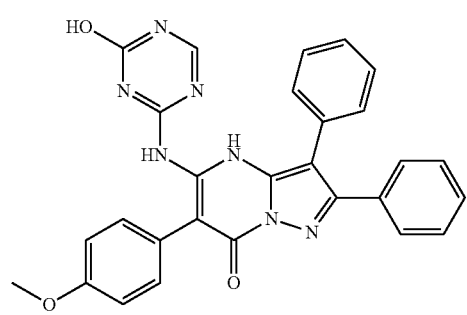 [SMILES: COc1ccc(-c2c(Nc3ncnc(O)n3)[nH]c3c(-c4ccccc4)c(-c4ccccc4)nn3c2=O)cc1] | 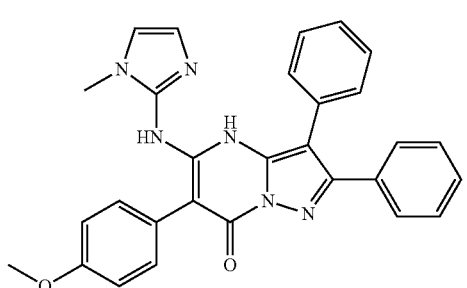 |
| 137 | 142 |
| 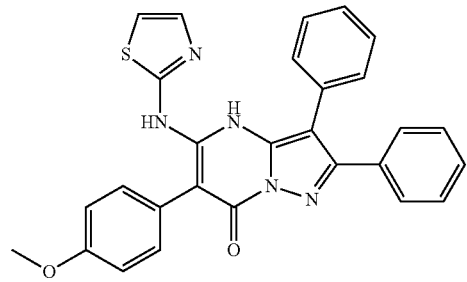 | 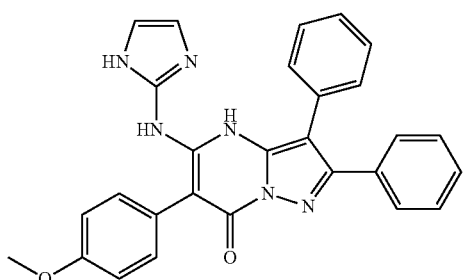 |
| 138 | 143 |
| 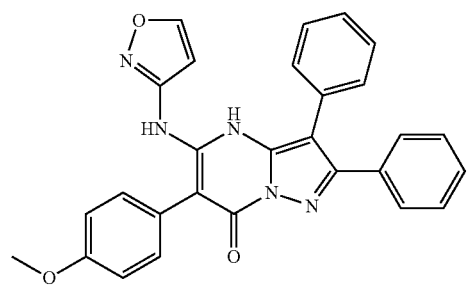 | 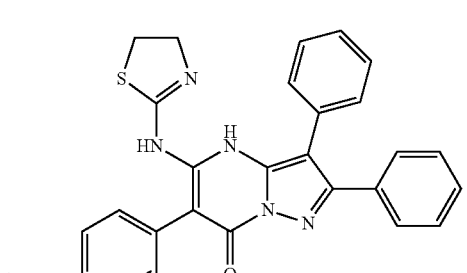 |
| 139 | 144 |
| 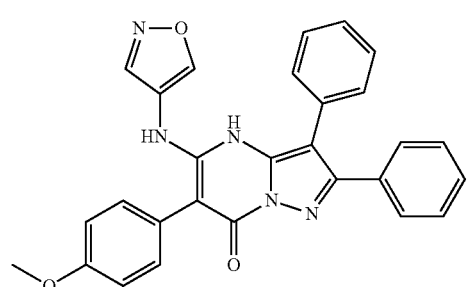 | 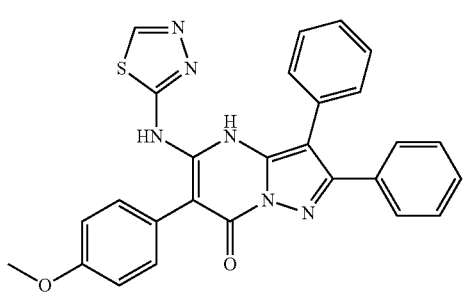 |

507
-continued
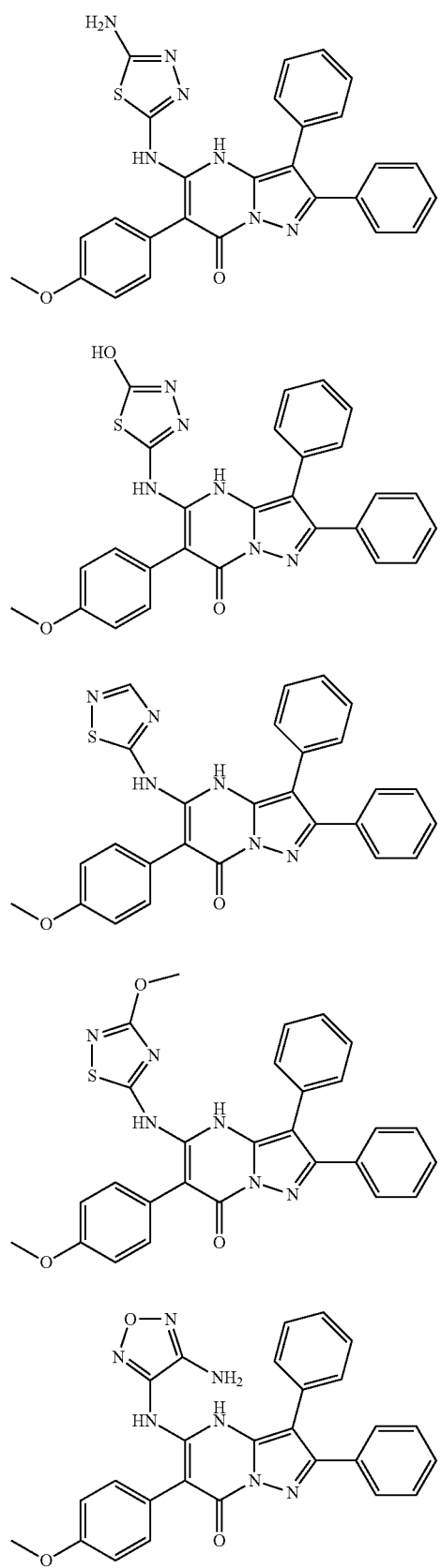
145
146
147
148
149
508
-continued
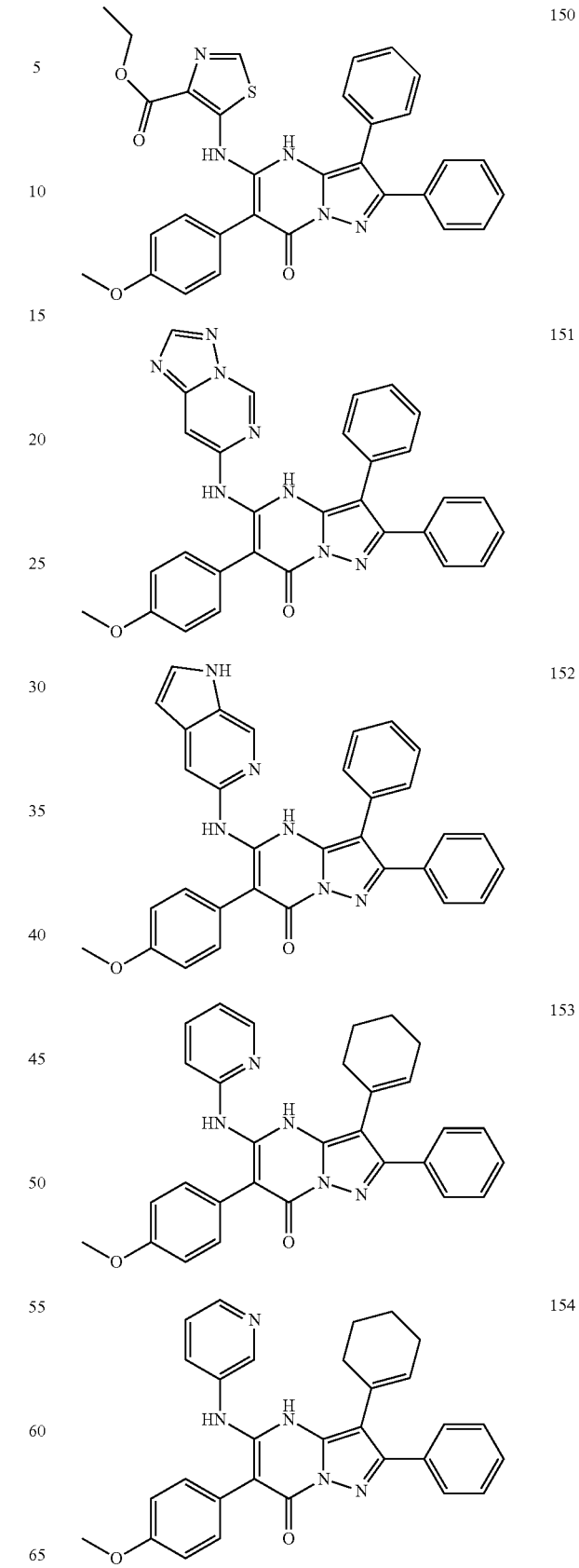
150
151
152
153
154

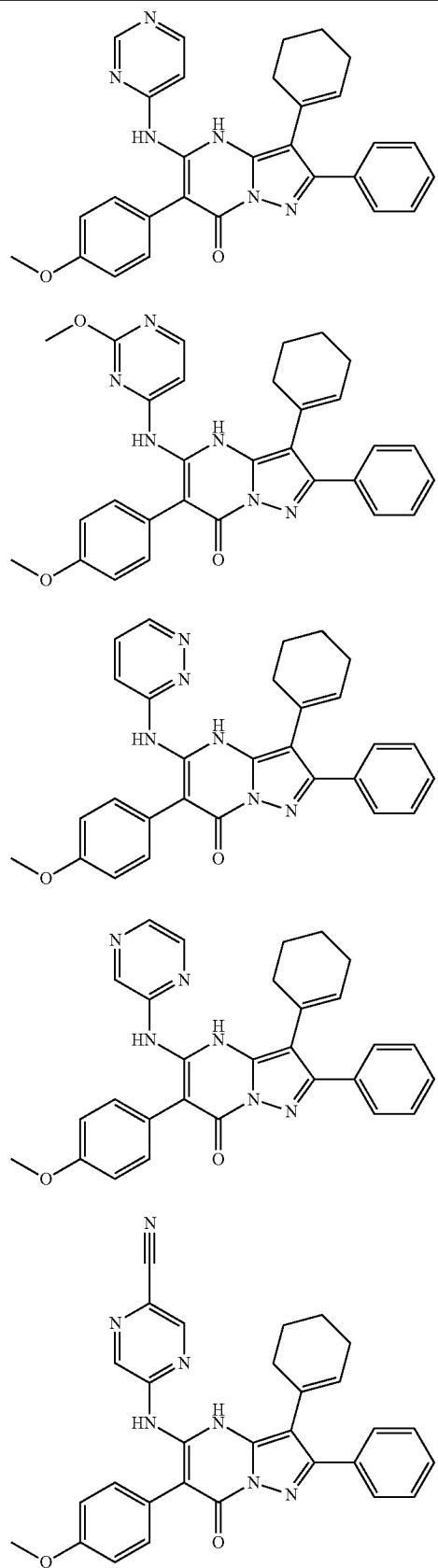
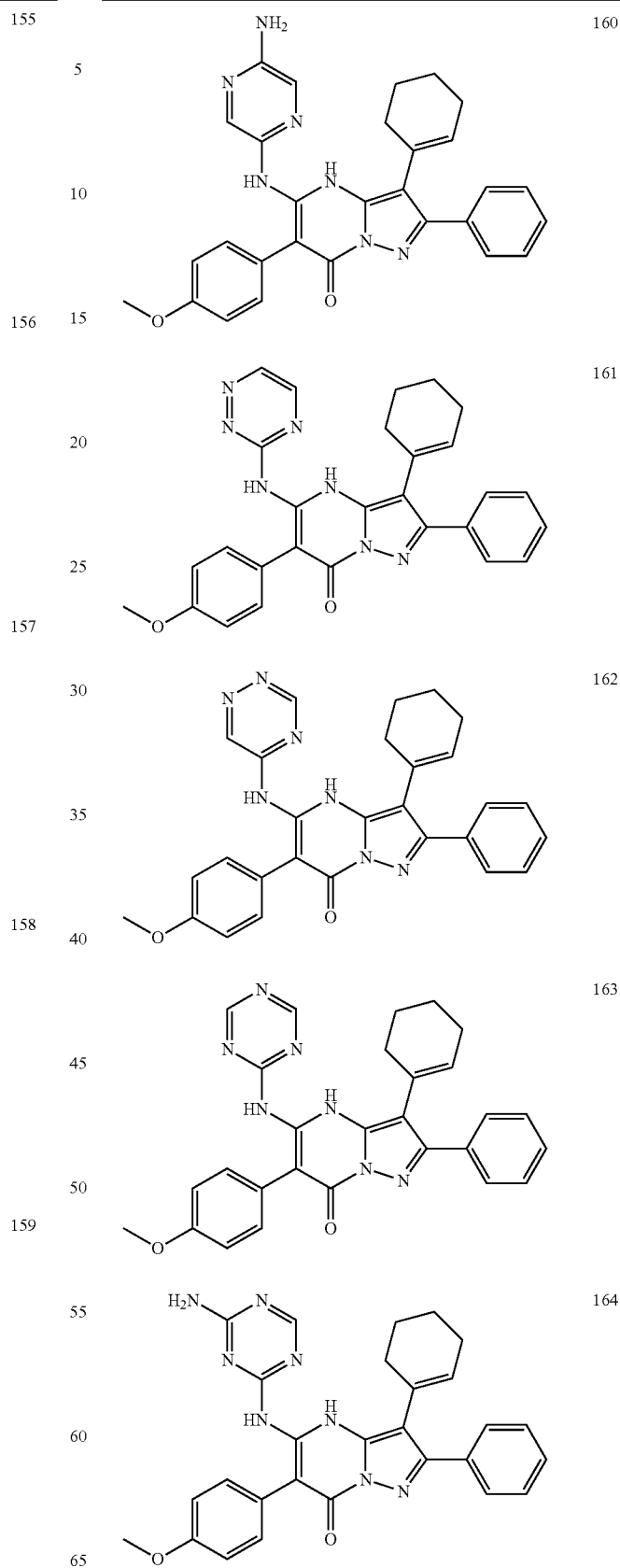

| 511 -continued | | 512 -continued | |
|---|---|---|---|
| 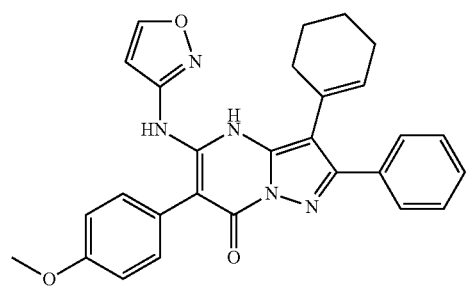 [SMILES: COc1ccc(-c2c(Nc3ccon3)[nH]c3c(C4=CCCCC4)c(-c4ccccc4)nn3c2=O)cc1] | 165 | 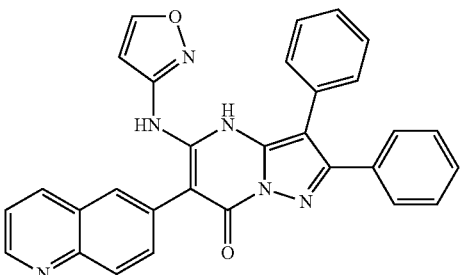 | 170 |
| 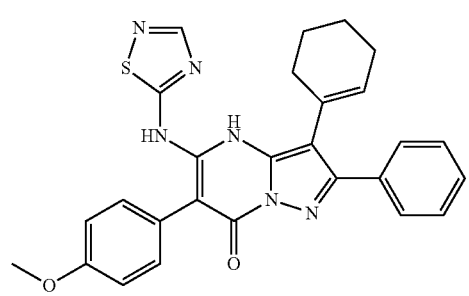 [SMILES: COc1ccc(-c2c(Nc3ncns3)[nH]c3c(C4=CCCCC4)c(-c4ccccc4)nn3c2=O)cc1] | 166 | 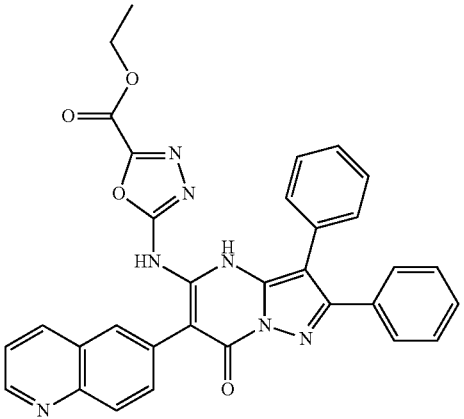 | 171 |
| 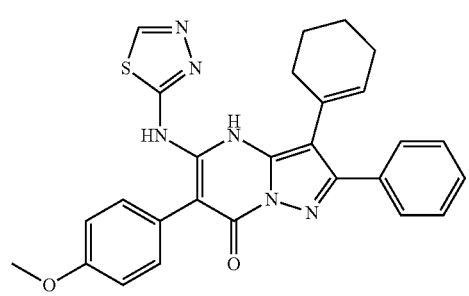 [SMILES: COc1ccc(-c2c(Nc3nncs3)[nH]c3c(C4=CCCCC4)c(-c4ccccc4)nn3c2=O)cc1] | 167 | 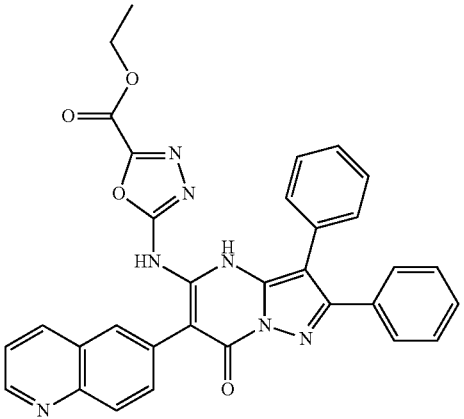 | 172 |
| 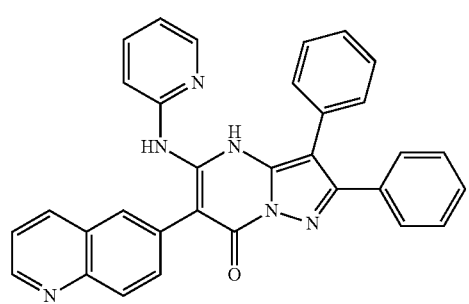 [SMILES: O=c1c(-c2ccc3ncccc3c2)c(Nc2ccccn2)[nH]c2c(-c3ccccc3)c(-c3ccccc3)nn12] | 168 | 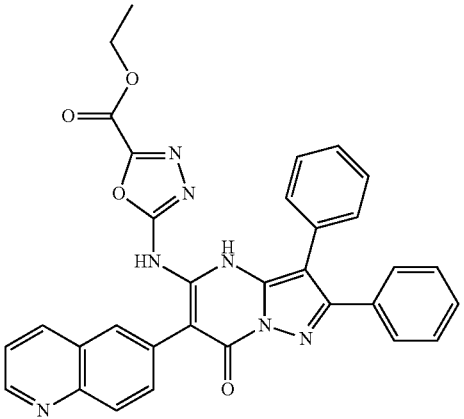 | 173 |
| 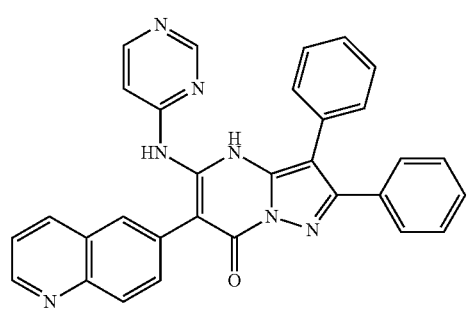 [SMILES: O=c1c(-c2ccc3ncccc3c2)c(Nc2ccncn2)[nH]c2c(-c3ccccc3)c(-c3ccccc3)nn12] | 169 | 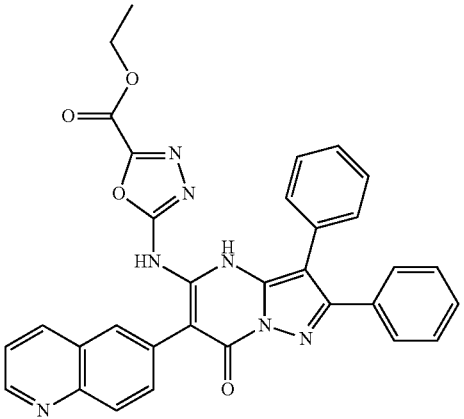 | 174 |

513
-continued
175
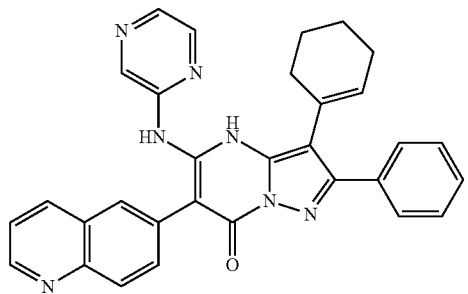
176
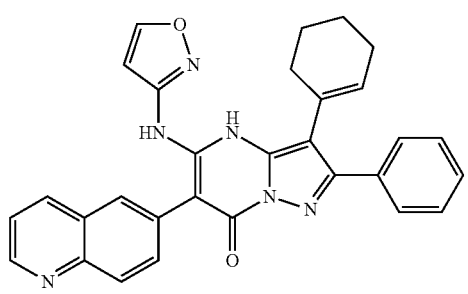
177
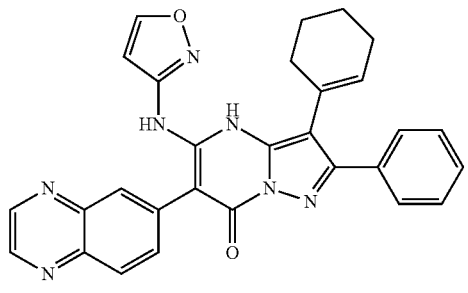 [SMILES: O=c1c(-c2ccc3nccnc3c2)c(Nc2ccon2)[nH]c2c(C3=CCCCC3)c(-c3ccccc3)nn12]
178
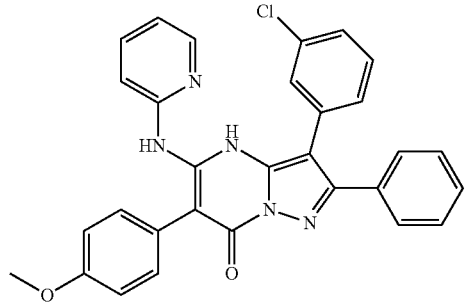 [SMILES: COc1ccc(-c2c(Nc3ccccn3)[nH]c3c(-c4cccc(Cl)c4)c(-c4ccccc4)nn3c2=O)cc1]
179
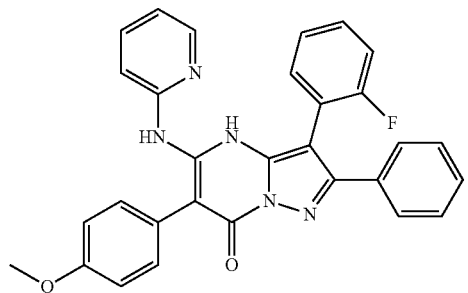 [SMILES: COc1ccc(-c2c(Nc3ccccn3)[nH]c3c(-c4ccccc4F)c(-c4ccccc4)nn3c2=O)cc1]
514
-continued
180
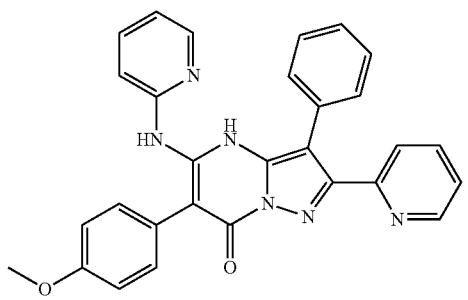 [SMILES: COc1ccc(-c2c(Nc3ccccn3)[nH]c3c(-c4ccccc4)c(-c4ccccn4)nn3c2=O)cc1]
181
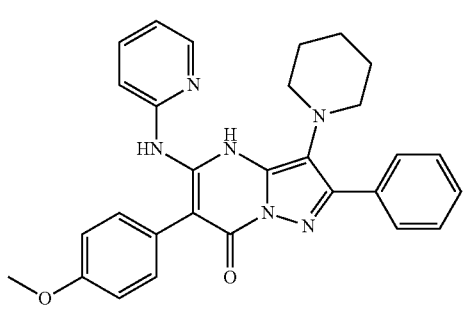 [SMILES: COc1ccc(-c2c(Nc3ccccn3)[nH]c3c(N4CCCCC4)c(-c4ccccc4)nn3c2=O)cc1]
182
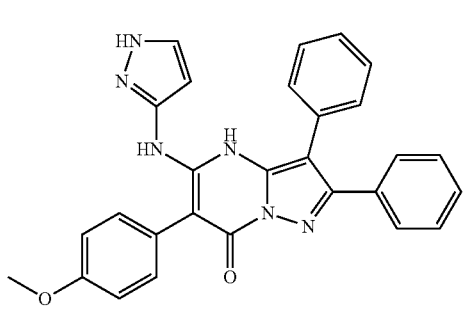
183
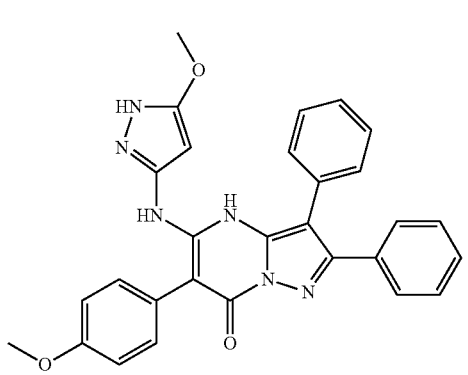 [SMILES: COc1ccc(-c2c(Nc3cc(OC)[nH]n3)[nH]c3c(-c4ccccc4)c(-c4ccccc4)nn3c2=O)cc1]
184
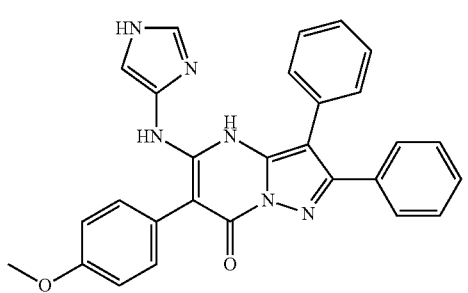 [SMILES: COc1ccc(-c2c(Nc3c[nH]cn3)[nH]c3c(-c4ccccc4)c(-c4ccccc4)nn3c2=O)cc1]

| 515 -continued | | 516 -continued | |
|---|---|---|---|
| 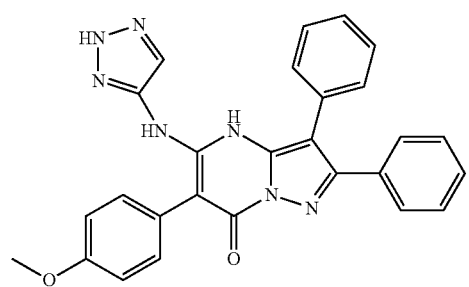 [SMILES: COc1ccc(-c2c(Nc3cn[nH]n3)[nH]c3c(-c4ccccc4)c(-c4ccccc4)nn3c2=O)cc1] | 185 | 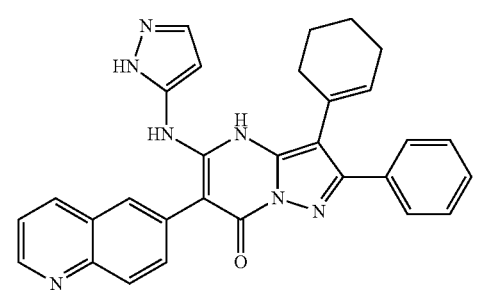 | 190 |
| 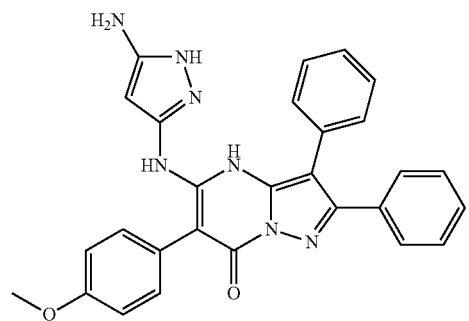 [SMILES: COc1ccc(-c2c(Nc3cc(N)[nH]n3)[nH]c3c(-c4ccccc4)c(-c4ccccc4)nn3c2=O)cc1] | 186 | 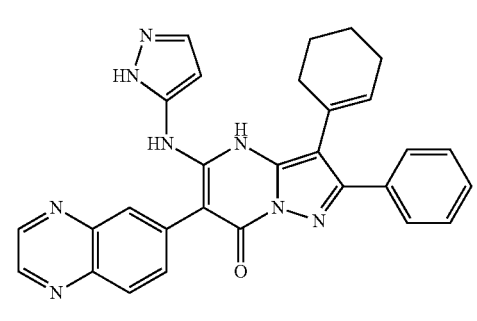 | 191 |
| 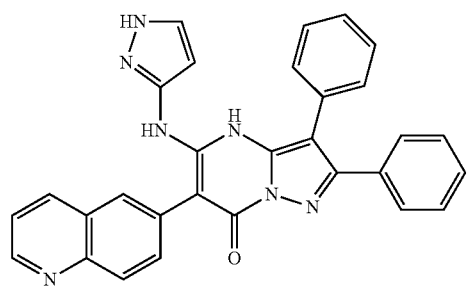 [SMILES: O=c1c(-c2ccc3ncccc3c2)c(Nc2cc[nH]n2)[nH]c2c(-c3ccccc3)c(-c3ccccc3)nn12] | 187 | 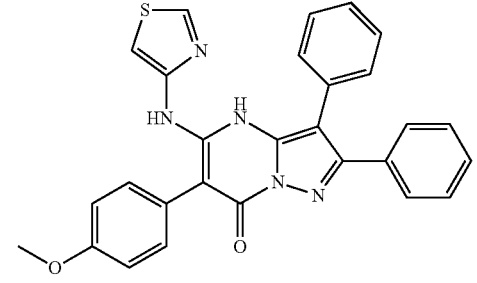 | 192 |
| 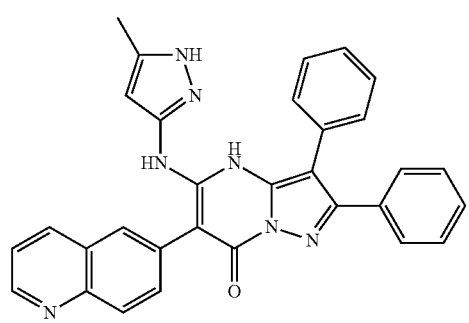 [SMILES: Cc1cc(Nc2[nH]c3c(-c4ccccc4)c(-c4ccccc4)nn3c(=O)c2-c2ccc3ncccc3c2)n[nH]1] | 188 | 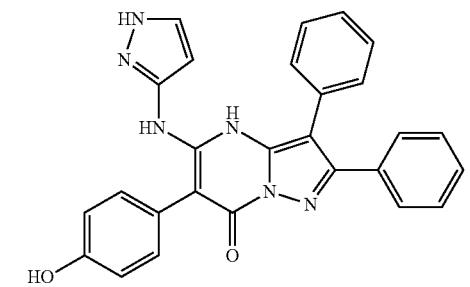 | 193 |
| 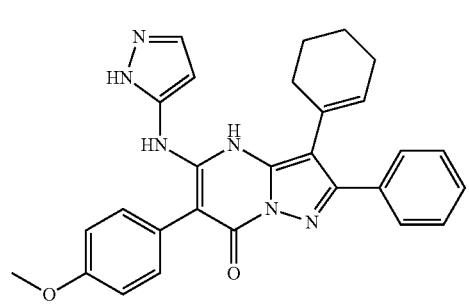 [SMILES: COc1ccc(-c2c(Nc3ccn[nH]3)[nH]c3c(C4=CCCCC4)c(-c4ccccc4)nn3c2=O)cc1] | 189 | 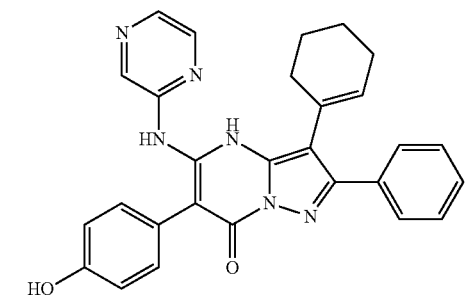 [SMILES: O=c1c(-c2ccc(O)cc2)c(Nc2cnccn2)[nH]c2c(C3=CCCCC3)c(-c3ccccc3)nn12] | 194 |

517
-continued
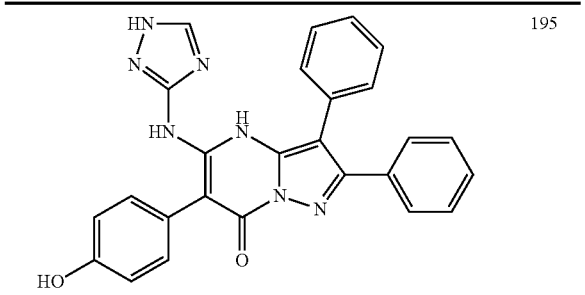
195
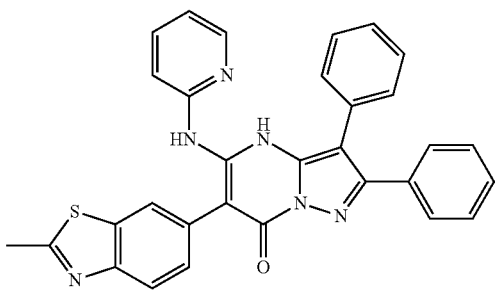 [SMILES: Cc1nc2ccc(-c3c(Nc4ccccn4)[nH]c4c(-c5ccccc5)c(-c5ccccc5)nn4c3=O)cc2s1]
196
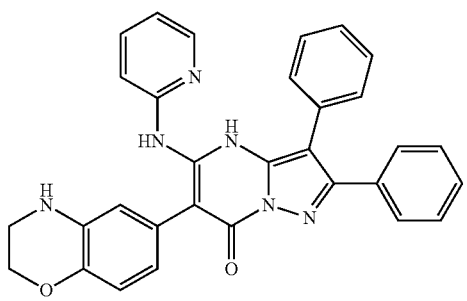 [SMILES: O=c1c(-c2ccc3c(c2)NCCO3)c(Nc2ccccn2)[nH]c2c(-c3ccccc3)c(-c3ccccc3)nn12]
197
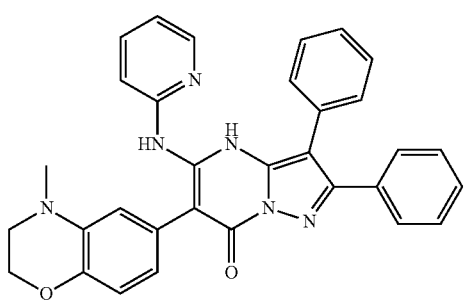 [SMILES: CN1CCOc2ccc(-c3c(Nc4ccccn4)[nH]c4c(-c5ccccc5)c(-c5ccccc5)nn4c3=O)cc21]
198
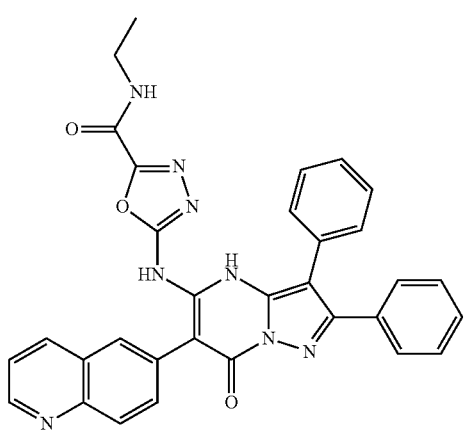 [SMILES: CCNC(=O)c1nnc(Nc2[nH]c3c(-c4ccccc4)c(-c4ccccc4)nn3c(=O)c2-c2ccc3ncccc3c2)o1]
199
518
-continued
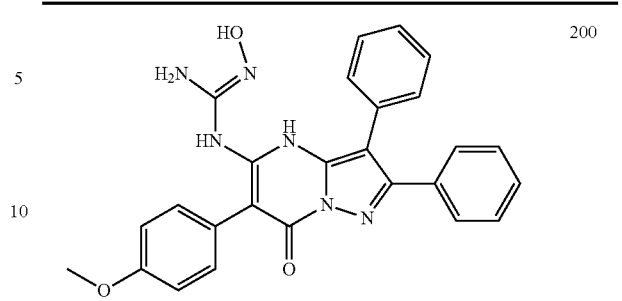
200
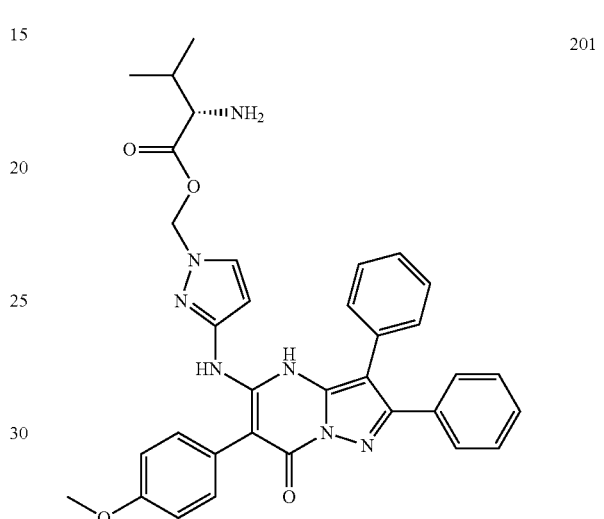
201
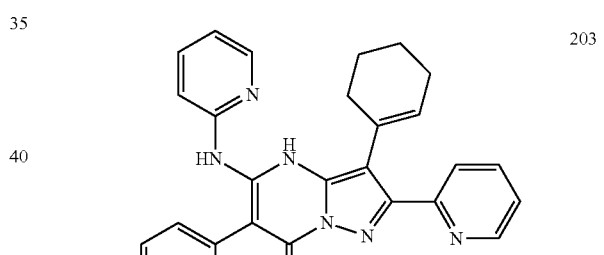
203
30. A compound according to claim 1, or a pharmaceutically acceptable salt thereof, that is selected from the following table:
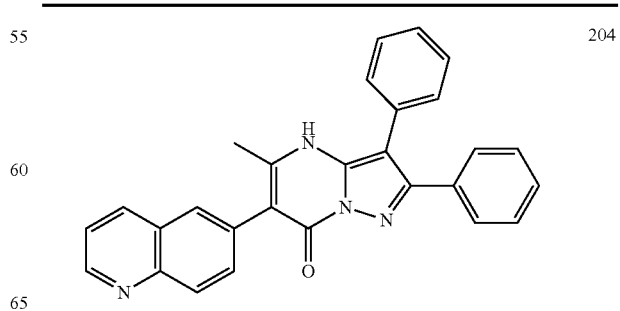
204

| 519 -continued | 520 -continued |
|---|---|
| 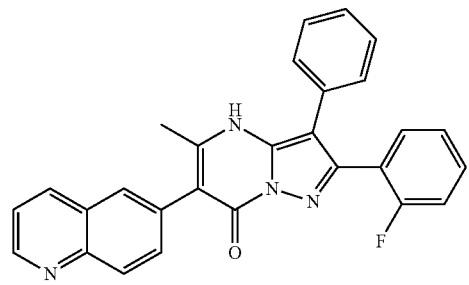 [SMILES: Cc1[nH]c2c(-c3ccccc3)c(-c3ccccc3F)nn2c(=O)c1-c1ccc2ncccc2c1] 205 | 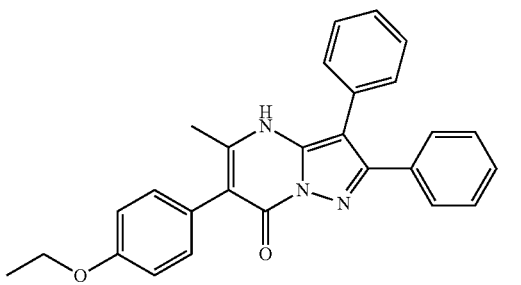 210 |
| 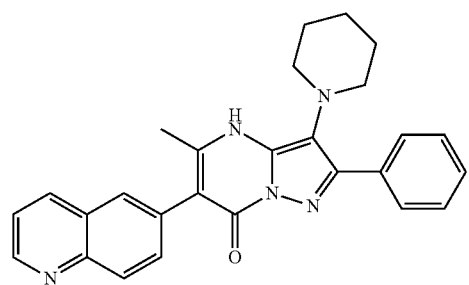 [SMILES: Cc1[nH]c2c(N3CCCCC3)c(-c3ccccc3)nn2c(=O)c1-c1ccc2ncccc2c1] 206 | 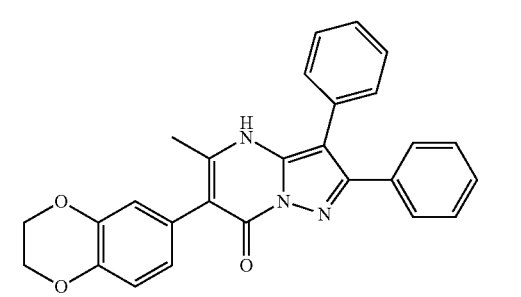 211 |
| 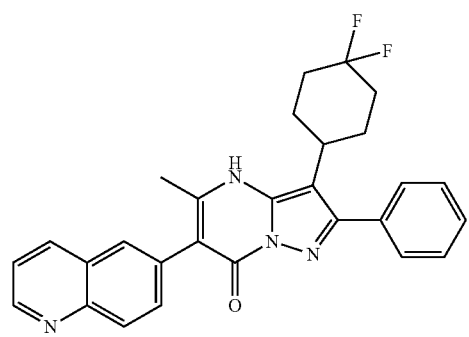 207 | 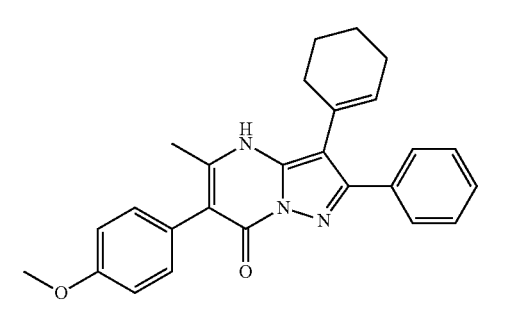 [SMILES: COc1ccc(-c2c(C)[nH]c3c(C4=CCCCC4)c(-c4ccccc4)nn3c2=O)cc1] 212 |
| 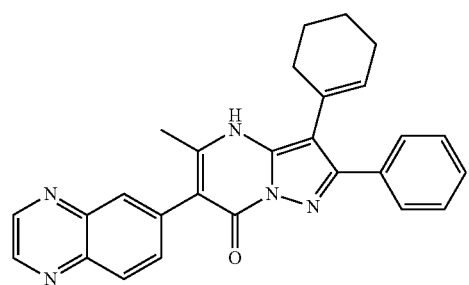 208 | 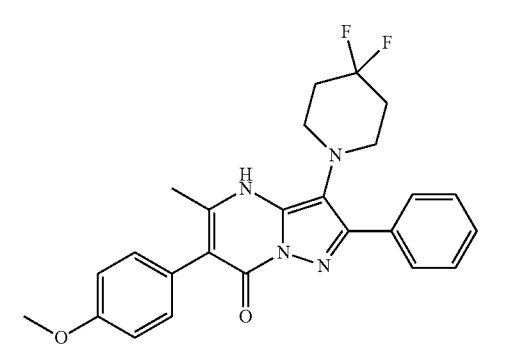 [SMILES: COc1ccc(-c2c(C)[nH]c3c(N4CCC(F)(F)CC4)c(-c4ccccc4)nn3c2=O)cc1] 213 |
| 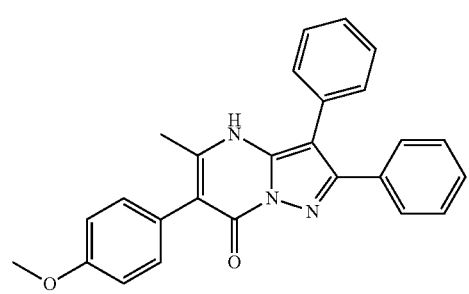 209 | 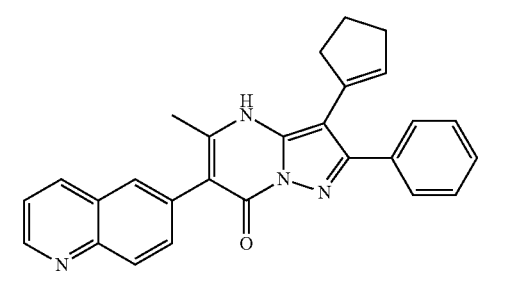 [SMILES: Cc1[nH]c2c(C3=CCCC3)c(-c3ccccc3)nn2c(=O)c1-c1ccc2ncccc2c1] 215 |

| 521 -continued | | 522 -continued | |
|---|---|---|---|
| 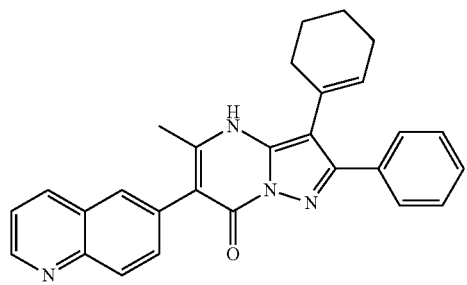 | 216 | 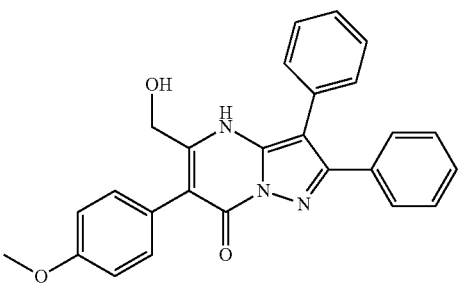 | 221 |
| 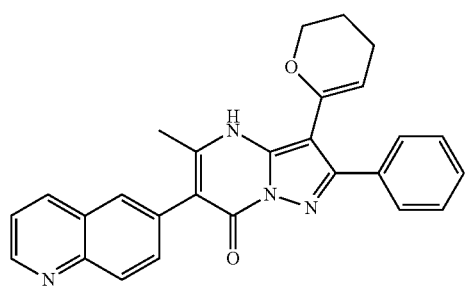 | 217 | 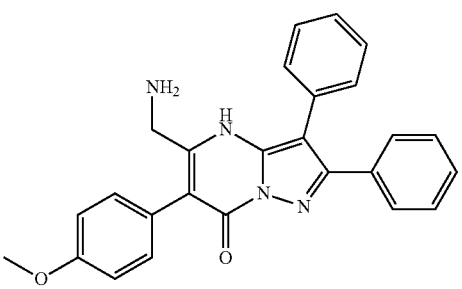 | 222 |
| 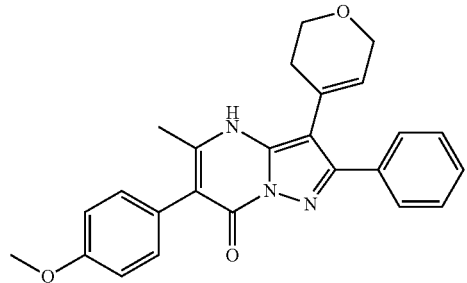 [SMILES: COc1ccc(-c2c(C)[nH]c3c(C4=CCOCC4)c(-c4ccccc4)nn3c2=O)cc1] | 218 | 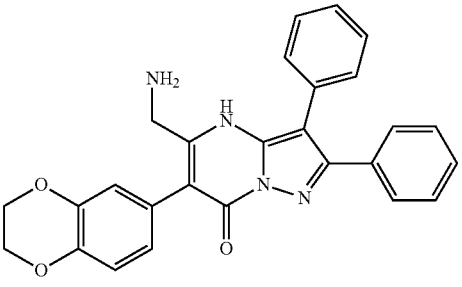 | 223 |
| 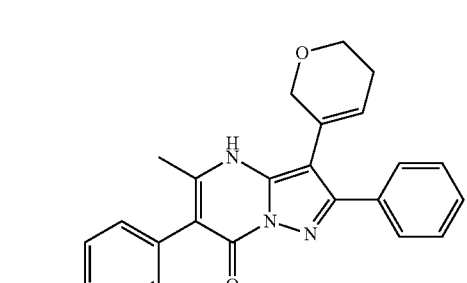 | 219 | 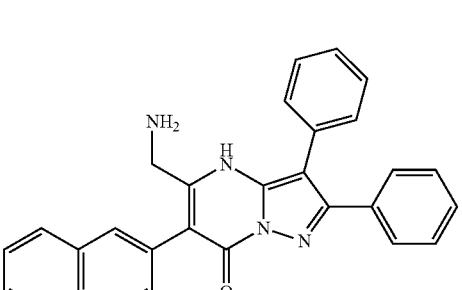 | 224 |
| 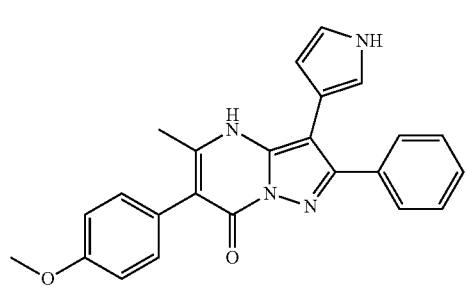 [SMILES: COc1ccc(-c2c(C)[nH]c3c(-c4cc[nH]c4)c(-c4ccccc4)nn3c2=O)cc1] | 220 | 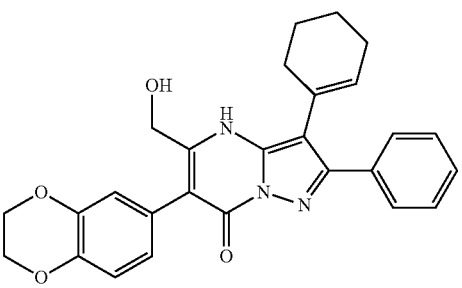 [SMILES: O=c1c(-c2ccc3c(c2)OCCO3)c(CO)[nH]c2c(C3=CCCCC3)c(-c3ccccc3)nn12] | 225 |

226
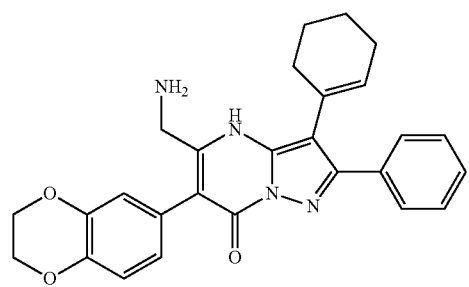 [SMILES: NCc1[nH]c2c(C3=CCCCC3)c(-c3ccccc3)nn2c(=O)c1-c1ccc2c(c1)OCCO2]
227
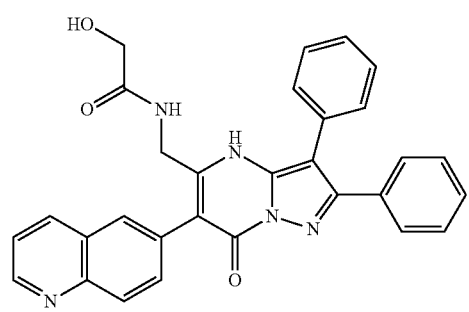 [SMILES: O=C(CO)NCc1[nH]c2c(-c3ccccc3)c(-c3ccccc3)nn2c(=O)c1-c1ccc2ncccc2c1]
228
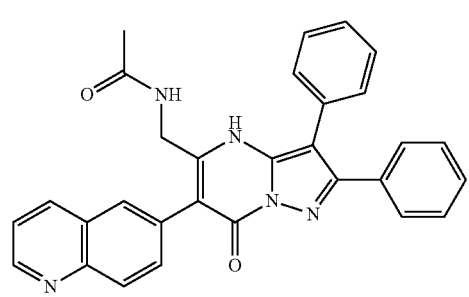 [SMILES: CC(=O)NCc1[nH]c2c(-c3ccccc3)c(-c3ccccc3)nn2c(=O)c1-c1ccc2ncccc2c1]
229
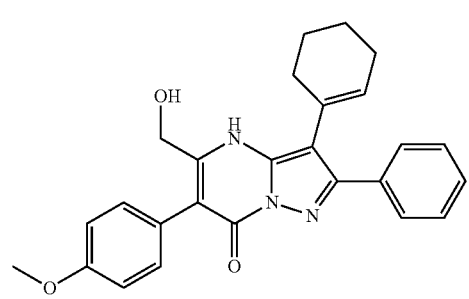 [SMILES: COc1ccc(-c2c(CO)[nH]c3c(C4=CCCCC4)c(-c4ccccc4)nn3c2=O)cc1]
230
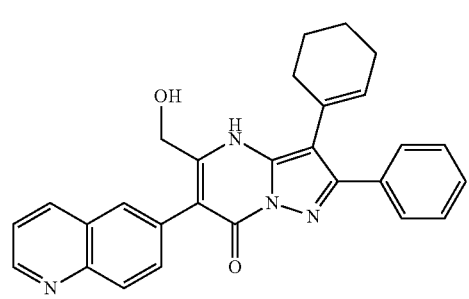
231
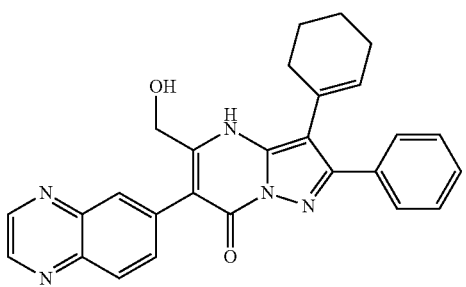
232
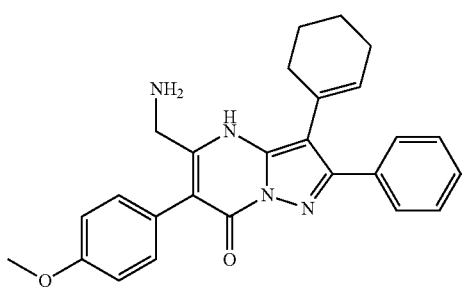
233
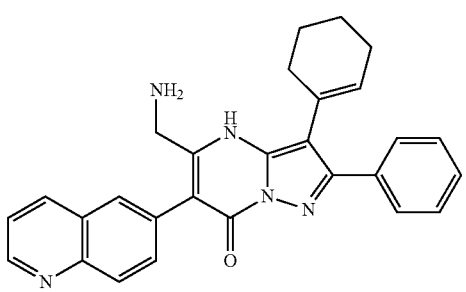 [SMILES: NCc1[nH]c2c(C3=CCCCC3)c(-c3ccccc3)nn2c(=O)c1-c1ccc2ncccc2c1]
234
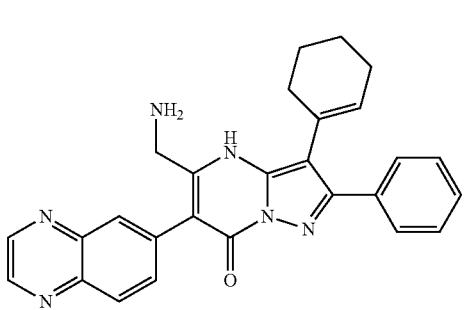 [SMILES: NCc1[nH]c2c(C3=CCCCC3)c(-c3ccccc3)nn2c(=O)c1-c1ccc2nccnc2c1]
235
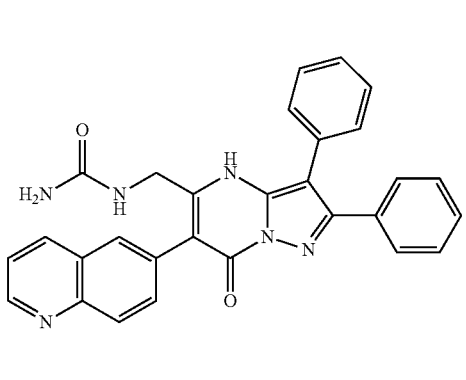 [SMILES: NC(=O)NCc1[nH]c2c(-c3ccccc3)c(-c3ccccc3)nn2c(=O)c1-c1ccc2ncccc2c1]

525
-continued
236 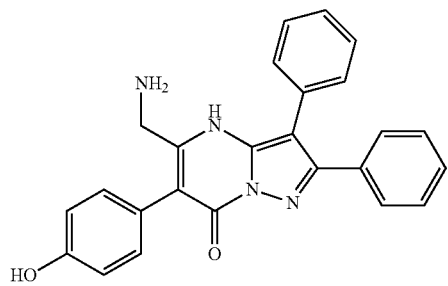 [SMILES: NCc1[nH]c2c(-c3ccccc3)c(-c3ccccc3)nn2c(=O)c1-c1ccc(O)cc1]
237 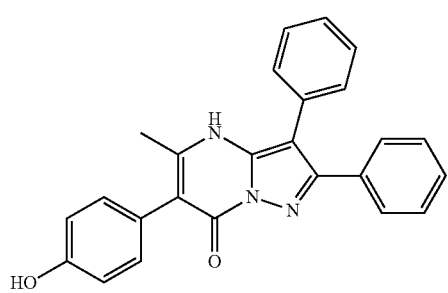 [SMILES: Cc1[nH]c2c(-c3ccccc3)c(-c3ccccc3)nn2c(=O)c1-c1ccc(O)cc1]
238 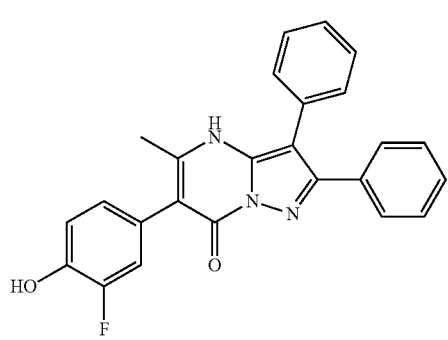 [SMILES: Cc1[nH]c2c(-c3ccccc3)c(-c3ccccc3)nn2c(=O)c1-c1ccc(O)c(F)c1]
239 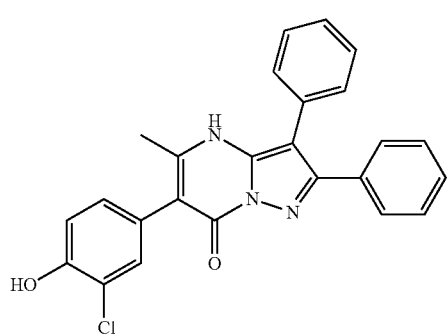
240 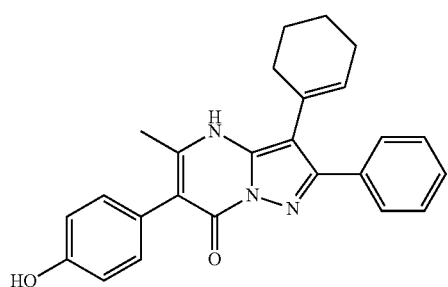 [SMILES: Cc1[nH]c2c(C3=CCCCC3)c(-c3ccccc3)nn2c(=O)c1-c1ccc(O)cc1]
526
-continued
241 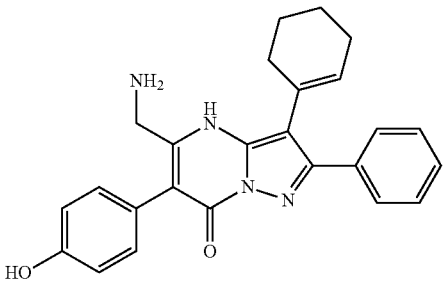 [SMILES: NCc1[nH]c2c(C3=CCCCC3)c(-c3ccccc3)nn2c(=O)c1-c1ccc(O)cc1]
242 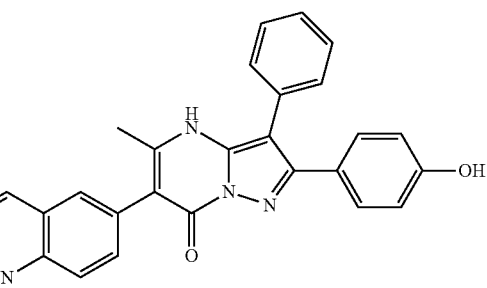
243 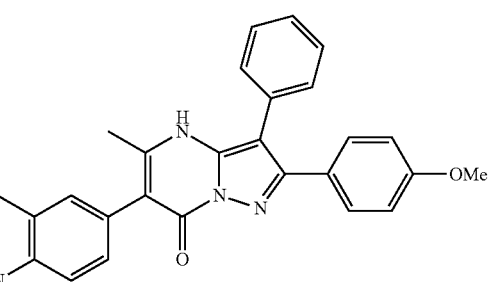
244 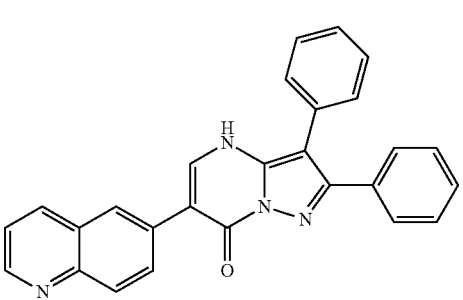 [SMILES: O=c1c(-c2ccc3ncccc3c2)c[nH]c2c(-c3ccccc3)c(-c3ccccc3)nn12]
245 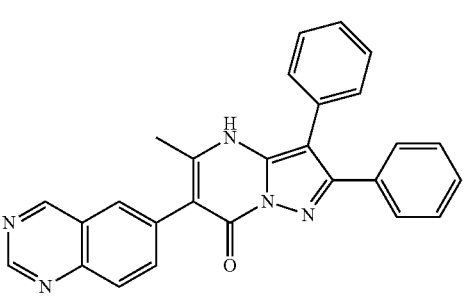 [SMILES: Cc1[nH]c2c(-c3ccccc3)c(-c3ccccc3)nn2c(=O)c1-c1ccc2ncncc2c1]

| 527 -continued | 528 -continued |
|---|---|
| 246 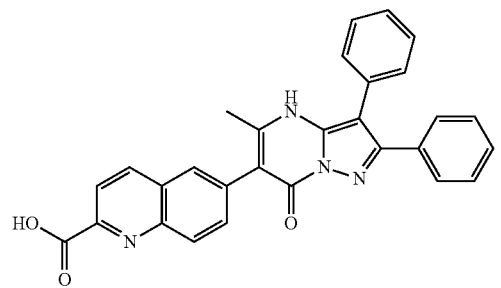 [SMILES: Cc1[nH]c2c(-c3ccccc3)c(-c3ccccc3)nn2c(=O)c1-c1ccc2nc(C(=O)O)ccc2c1] | 251 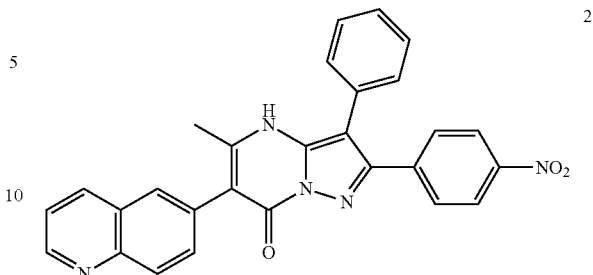 |
| 247 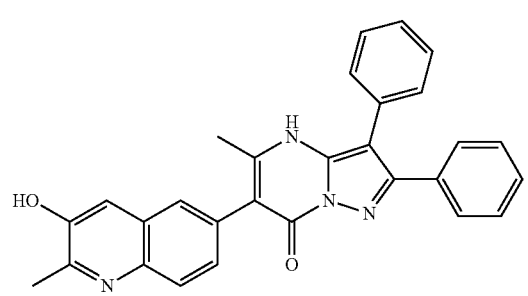 [SMILES: Cc1nc2ccc(-c3c(C)[nH]c4c(-c5ccccc5)c(-c5ccccc5)nn4c3=O)cc2cc1O] | 252 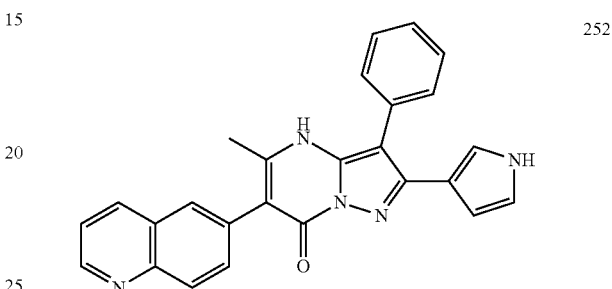 |
| 248 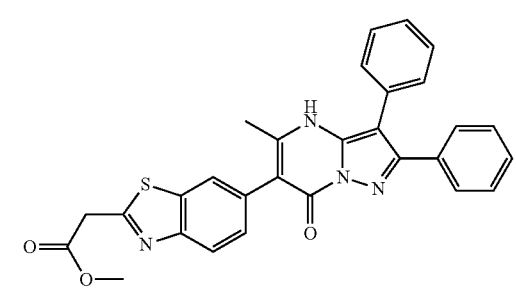 [SMILES: COC(=O)Cc1nc2ccc(-c3c(C)[nH]c4c(-c5ccccc5)c(-c5ccccc5)nn4c3=O)cc2s1] | 253 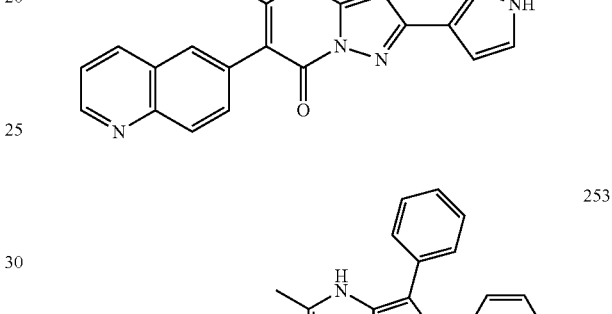 |
| 249 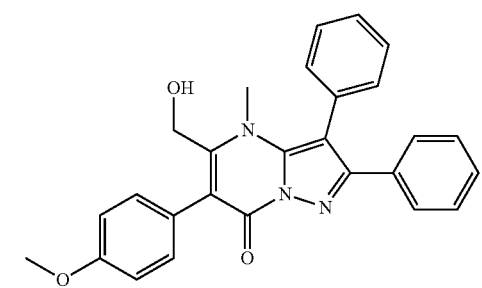 | 254 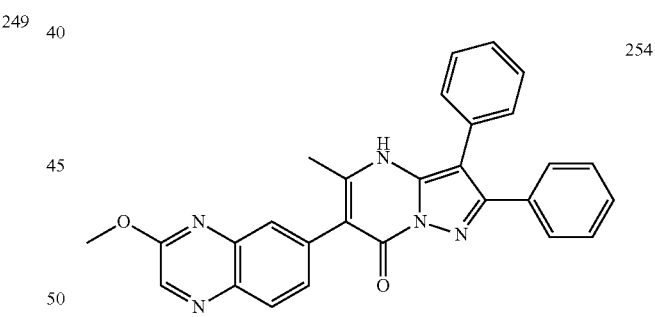 |
| 250 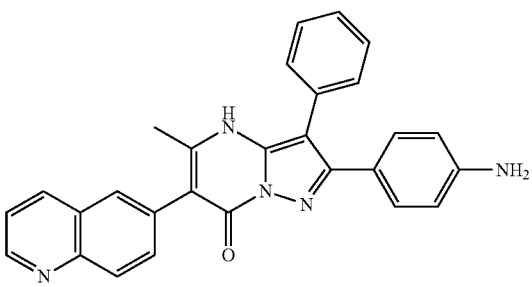 [SMILES: Cc1[nH]c2c(-c3ccccc3)c(-c3ccc(N)cc3)nn2c(=O)c1-c1ccc2ncccc2c1] | 255 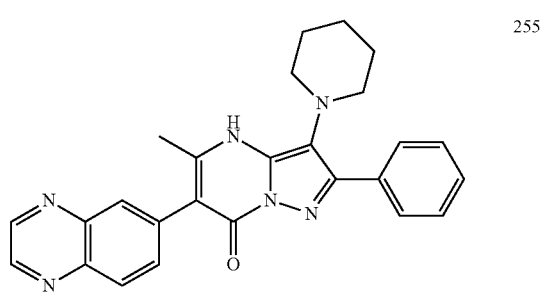 |

| 529 -continued | 530 -continued |
|---|---|
| 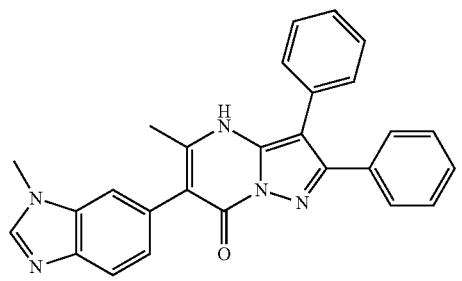 [SMILES: Cc1[nH]c2c(-c3ccccc3)c(-c3ccccc3)nn2c(=O)c1-c1ccc2ncn(C)c2c1] 256 | 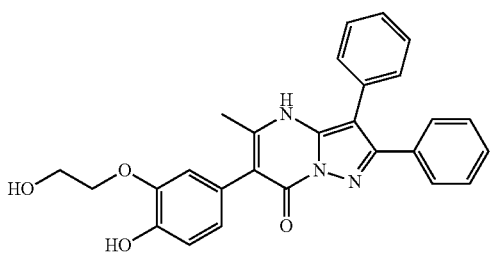 261 |
| 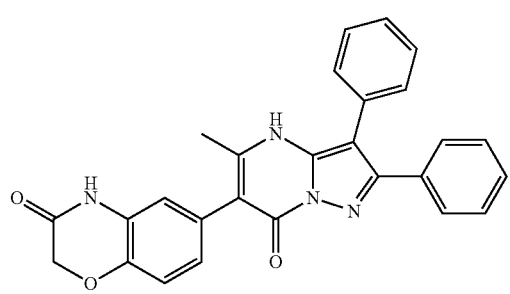 [SMILES: Cc1[nH]c2c(-c3ccccc3)c(-c3ccccc3)nn2c(=O)c1-c1ccc2c(c1)NC(=O)CO2] 257 | 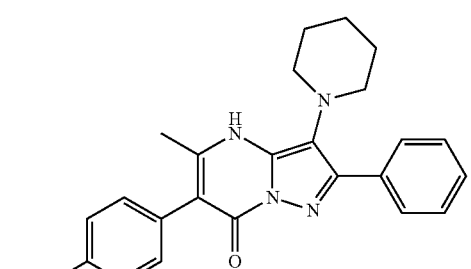 262 |
| 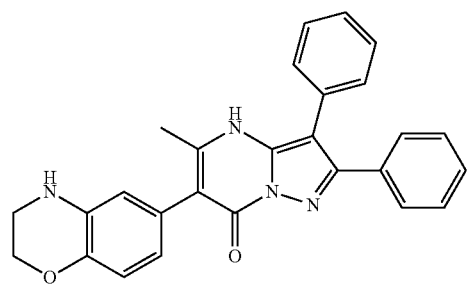 [SMILES: Cc1[nH]c2c(-c3ccccc3)c(-c3ccccc3)nn2c(=O)c1-c1ccc2c(c1)NCCO2] 258 | 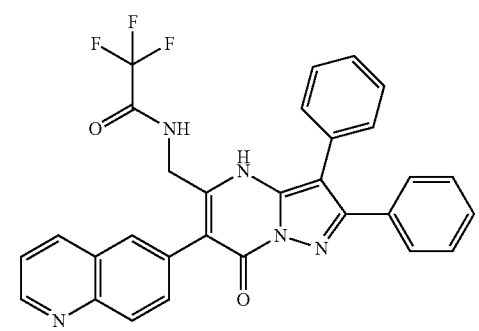 263 |
| 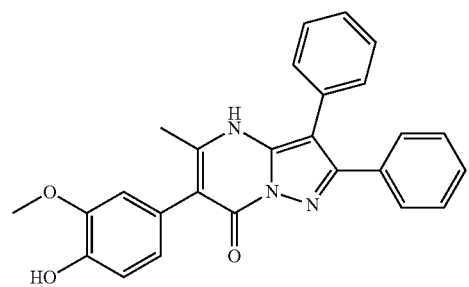 [SMILES: COc1cc(-c2c(C)[nH]c3c(-c4ccccc4)c(-c4ccccc4)nn3c2=O)ccc1O] 259 | 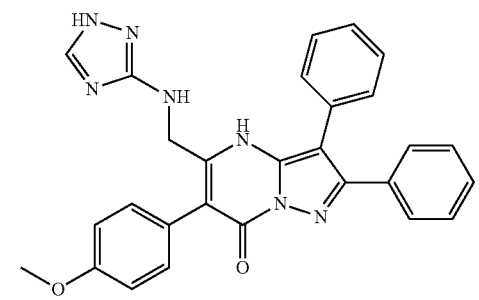 264 |
| 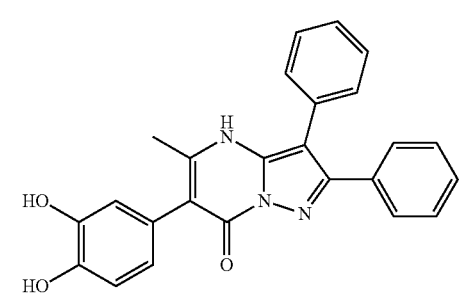 [SMILES: Cc1[nH]c2c(-c3ccccc3)c(-c3ccccc3)nn2c(=O)c1-c1ccc(O)c(O)c1] 260 | 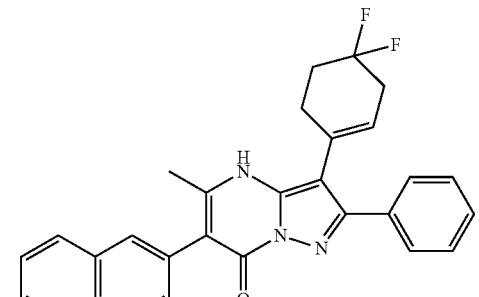 265 |

531
-continued
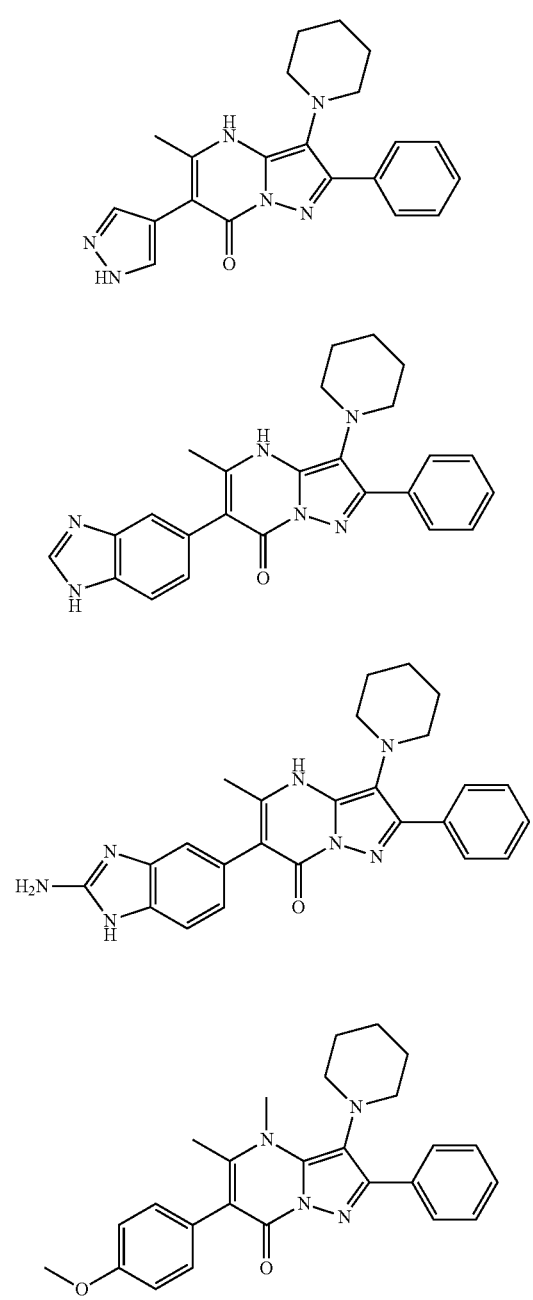
532
-continued
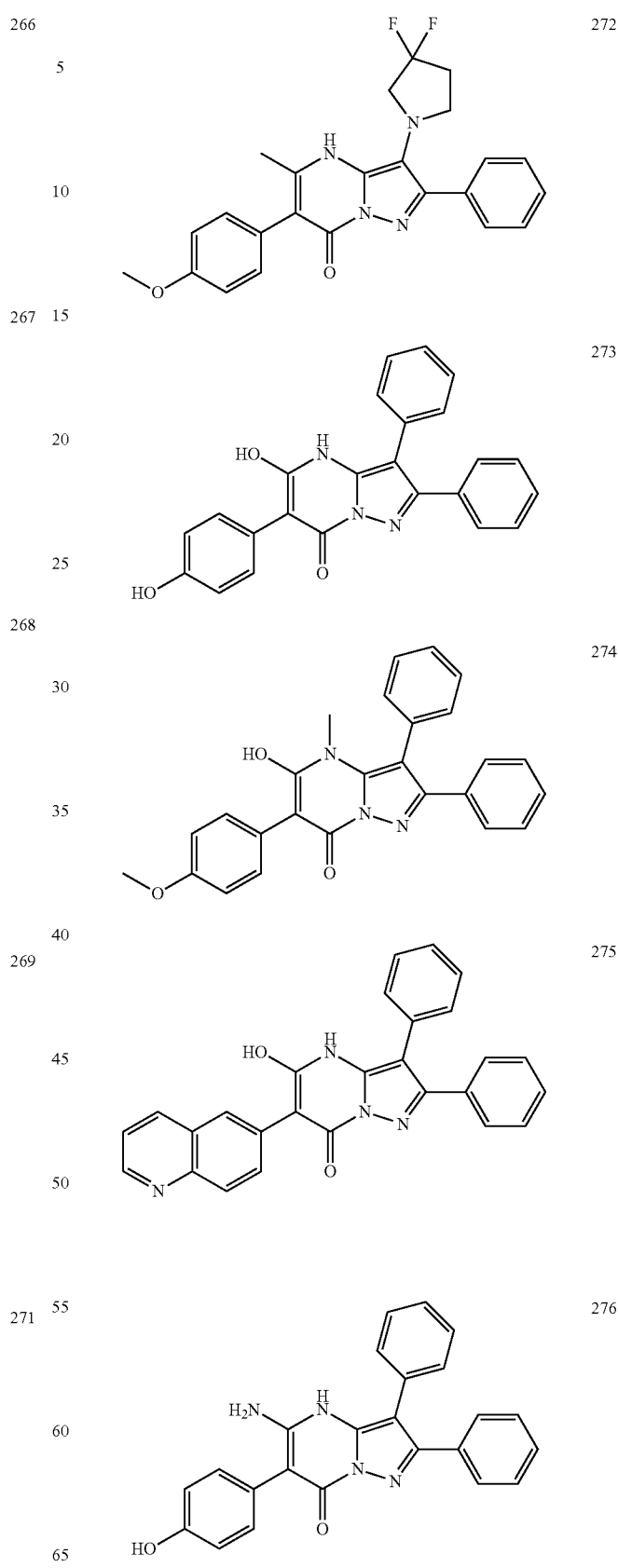

| 533 -continued | 534 -continued |
|---|---|
| 277 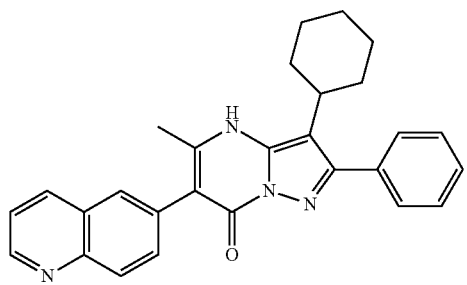 [SMILES: Cc1[nH]c2c(C3CCCCC3)c(-c3ccccc3)nn2c(=O)c1-c1ccc2ncccc2c1] | 282 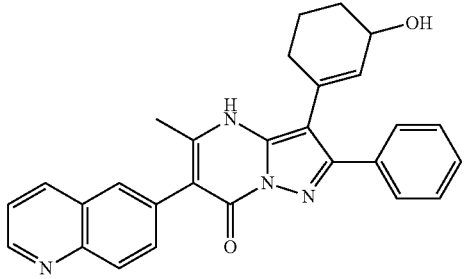 |
| 278 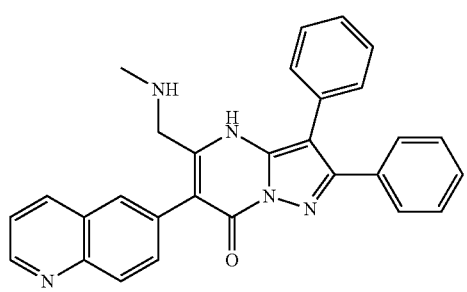 [SMILES: CNCc1[nH]c2c(-c3ccccc3)c(-c3ccccc3)nn2c(=O)c1-c1ccc2ncccc2c1] | 283 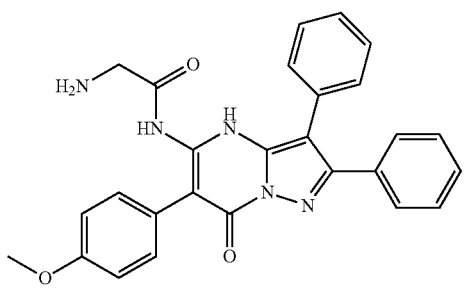 |
| 279 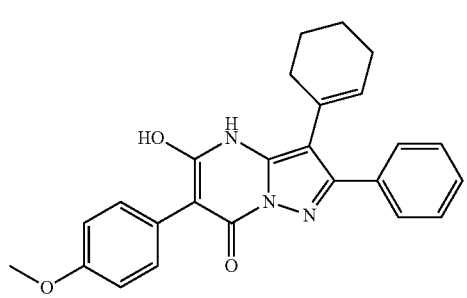 | 285 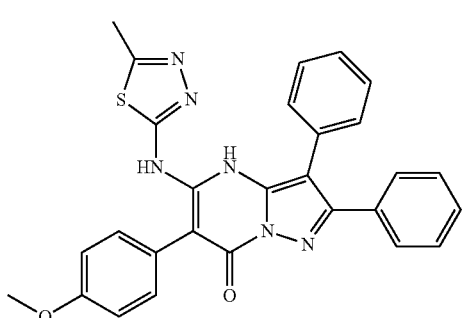 |
| 280 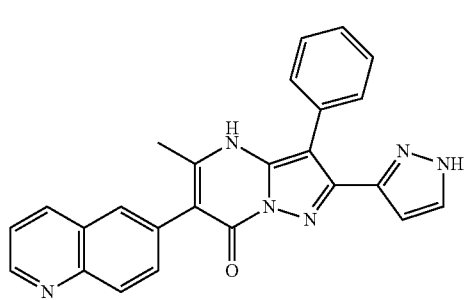 [SMILES: Cc1[nH]c2c(-c3ccccc3)c(-c3cc[nH]n3)nn2c(=O)c1-c1ccc2ncccc2c1] | 286 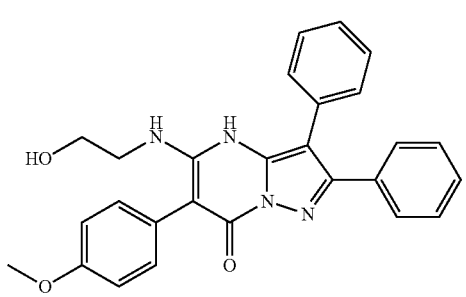 |
| 281 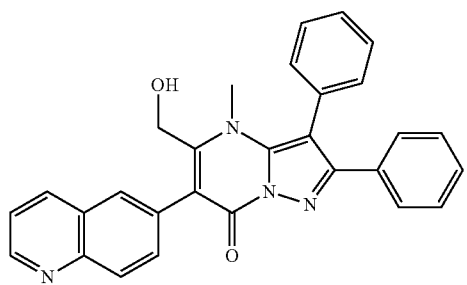 | 287 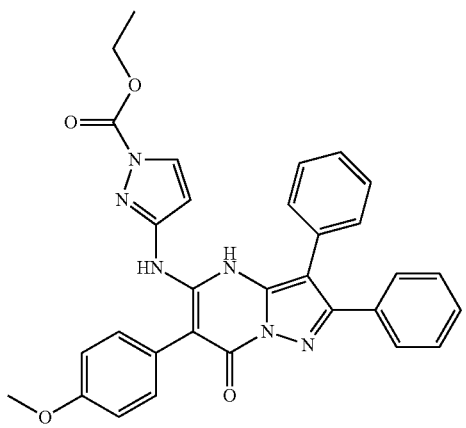 [SMILES: CCOC(=O)n1ccc(Nc2[nH]c3c(-c4ccccc4)c(-c4ccccc4)nn3c(=O)c2-c2ccc(OC)cc2)n1] |

535
-continued
288
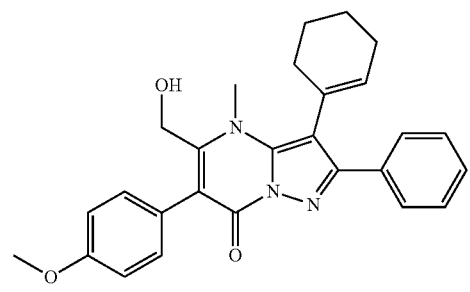 [SMILES: COc1ccc(-c2c(CO)n(C)c3c(C4=CCCCC4)c(-c4ccccc4)nn3c2=O)cc1]
290
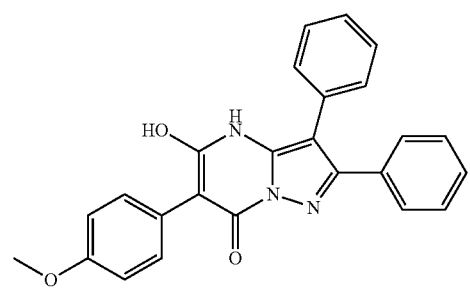
291
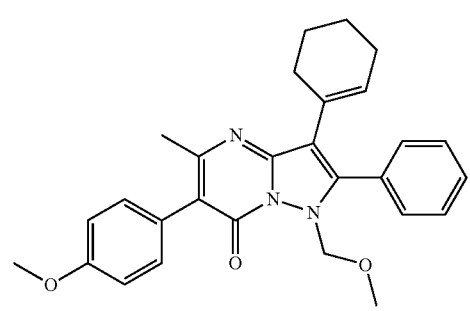 [SMILES: COCn1c(-c2ccccc2)c(C2=CCCCC2)c2nc(C)c(-c3ccc(OC)cc3)c(=O)n21]
292
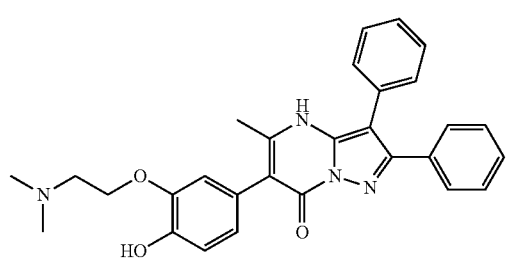 [SMILES: Cc1[nH]c2c(-c3ccccc3)c(-c3ccccc3)nn2c(=O)c1-c1ccc(O)c(OCCN(C)C)c1]
294
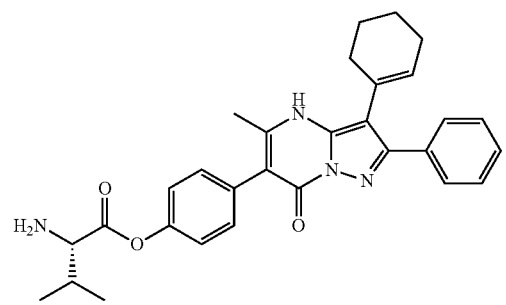 [SMILES: Cc1[nH]c2c(C3=CCCCC3)c(-c3ccccc3)nn2c(=O)c1-c1ccc(OC(=O)[C@@H](N)C(C)C)cc1]
536
-continued
295
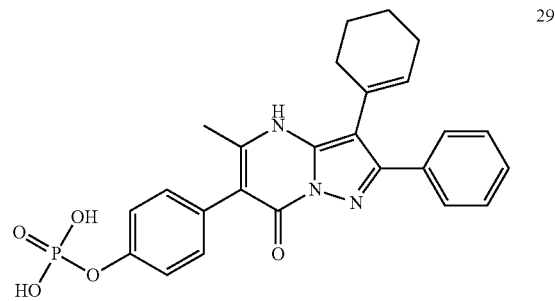
296
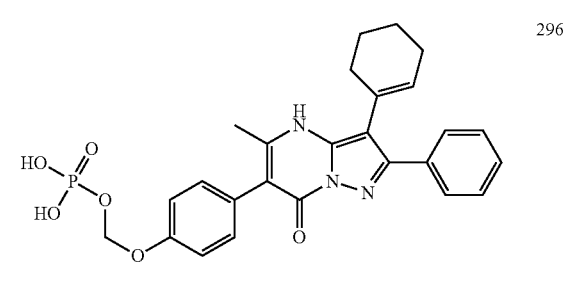
297
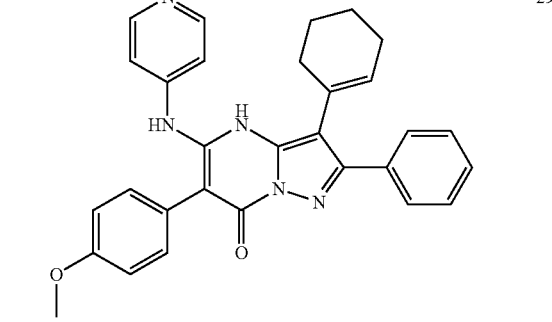
298
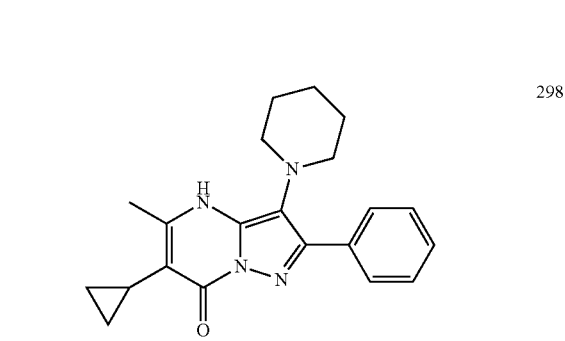
299
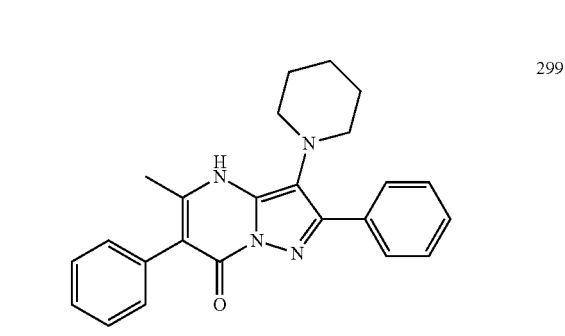

537
-continued
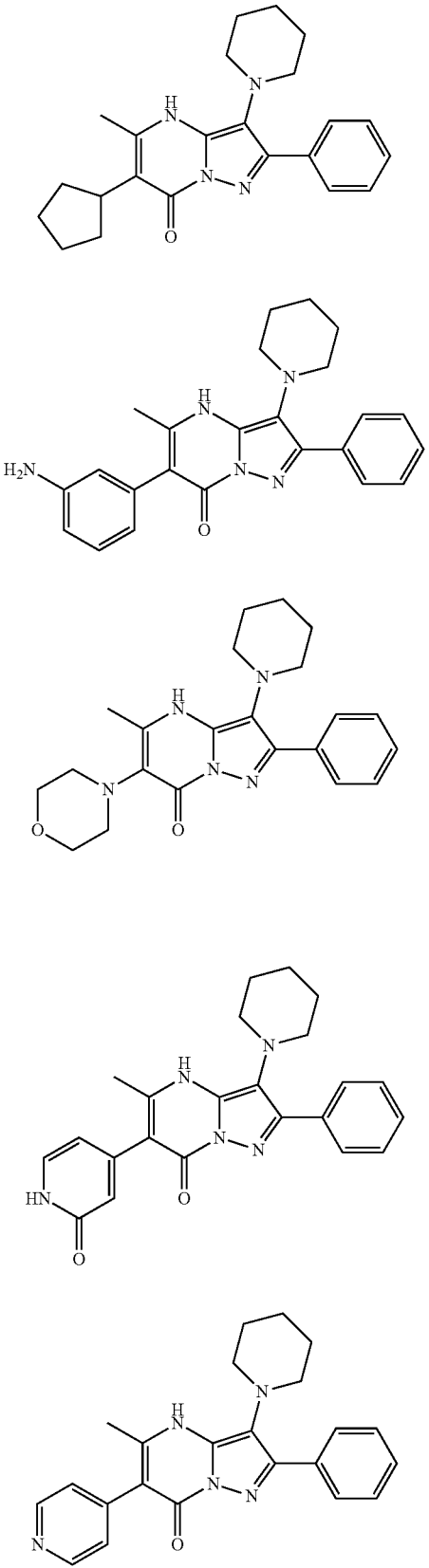
538
-continued
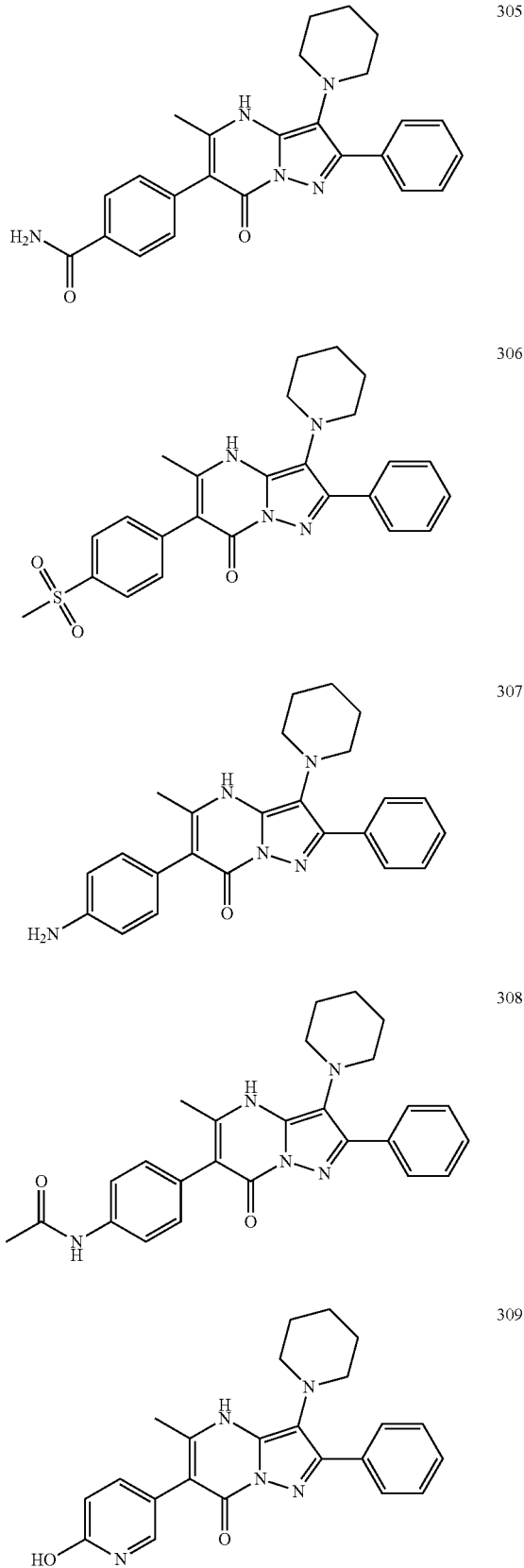

539
-continued
540
-continued
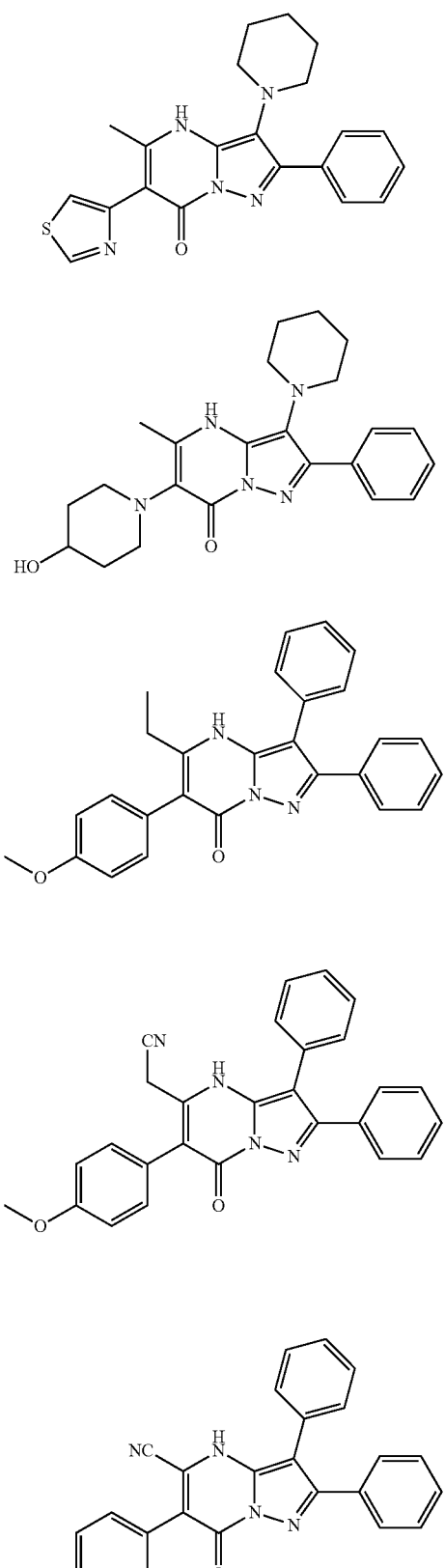
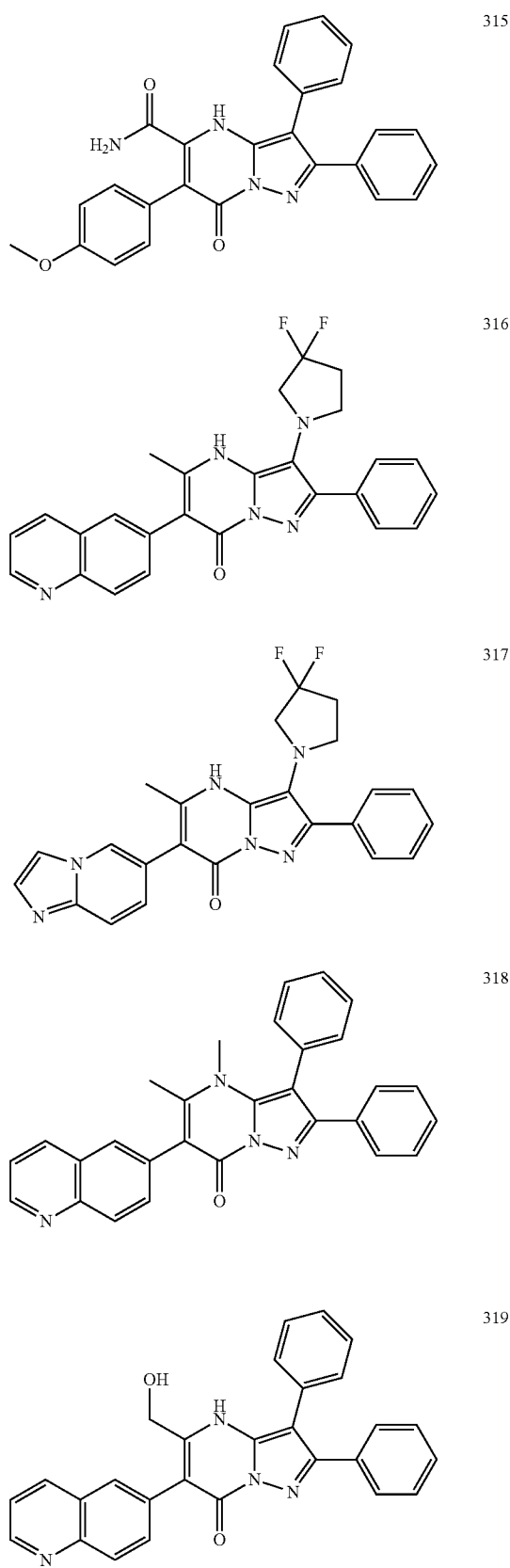

541
-continued
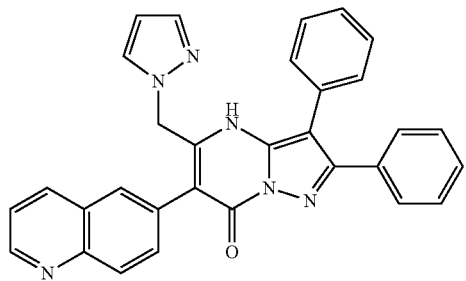 [SMILES: O=c1c(-c2ccc3ncccc3c2)c(Cn2cccn2)[nH]c2c(-c3ccccc3)c(-c3ccccc3)nn12]
320
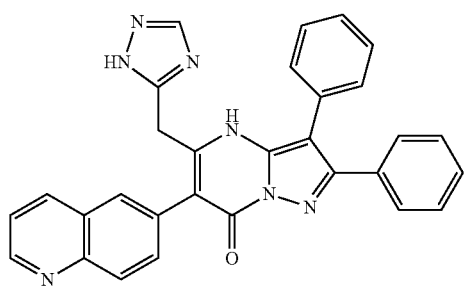 [SMILES: O=c1c(-c2ccc3ncccc3c2)c(Cc2ncn[nH]2)[nH]c2c(-c3ccccc3)c(-c3ccccc3)nn12]
321
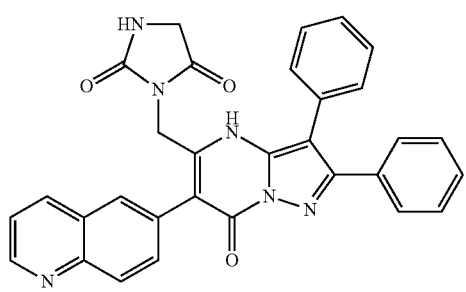 [SMILES: O=C1CNC(=O)N1Cc1[nH]c2c(-c3ccccc3)c(-c3ccccc3)nn2c(=O)c1-c1ccc2ncccc2c1]
322
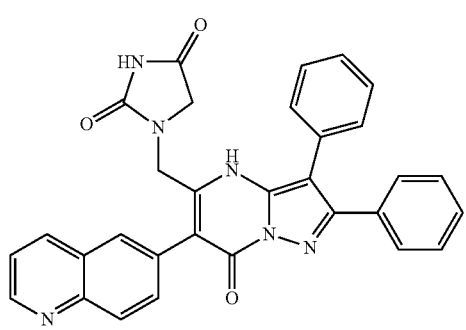 [SMILES: O=C1CN(Cc2[nH]c3c(-c4ccccc4)c(-c4ccccc4)nn3c(=O)c2-c2ccc3ncccc3c2)C(=O)N1]
323
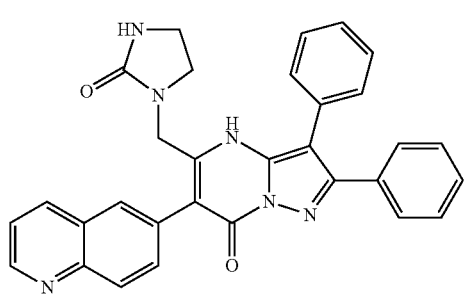 [SMILES: O=C1NCCN1Cc1[nH]c2c(-c3ccccc3)c(-c3ccccc3)nn2c(=O)c1-c1ccc2ncccc2c1]
324
542
-continued
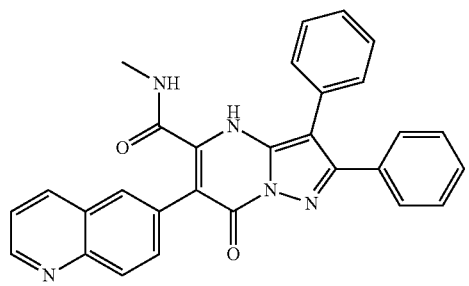 [SMILES: CNC(=O)c1[nH]c2c(-c3ccccc3)c(-c3ccccc3)nn2c(=O)c1-c1ccc2ncccc2c1]
325
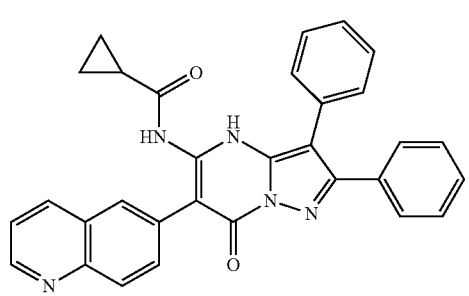 [SMILES: O=C(Nc1[nH]c2c(-c3ccccc3)c(-c3ccccc3)nn2c(=O)c1-c1ccc2ncccc2c1)C1CC1]
326
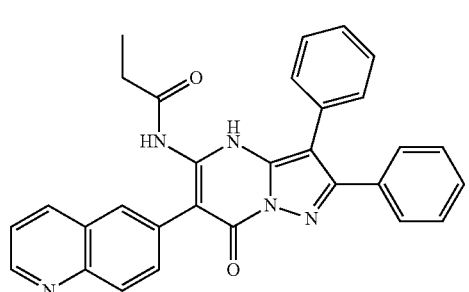
327
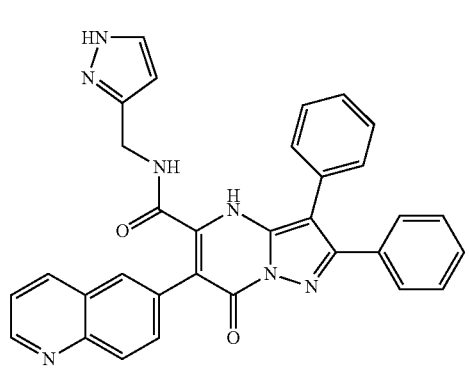 [SMILES: O=C(NCc1cc[nH]n1)c1[nH]c2c(-c3ccccc3)c(-c3ccccc3)nn2c(=O)c1-c1ccc2ncccc2c1]
328
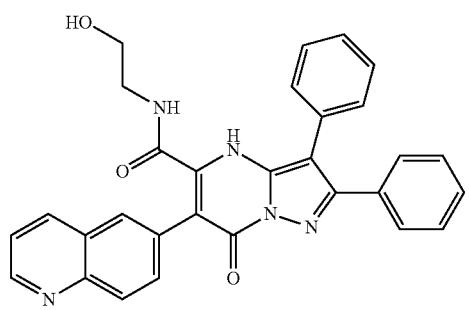 [SMILES: O=C(NCCO)c1[nH]c2c(-c3ccccc3)c(-c3ccccc3)nn2c(=O)c1-c1ccc2ncccc2c1]
329

US 10,329,298 B2
543
-continued
330
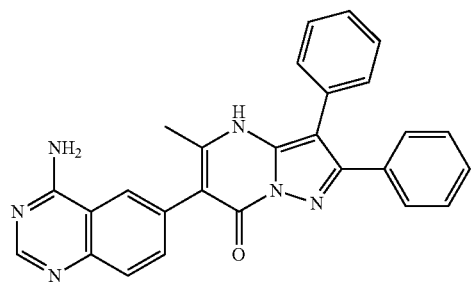 [SMILES: Cc1[nH]c2c(-c3ccccc3)c(-c3ccccc3)nn2c(=O)c1-c1ccc2ncnc(N)c2c1]
331
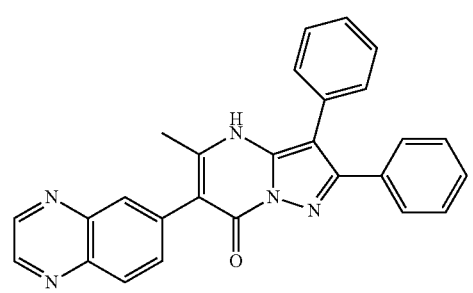 [SMILES: Cc1[nH]c2c(-c3ccccc3)c(-c3ccccc3)nn2c(=O)c1-c1ccc2nccnc2c1]
332
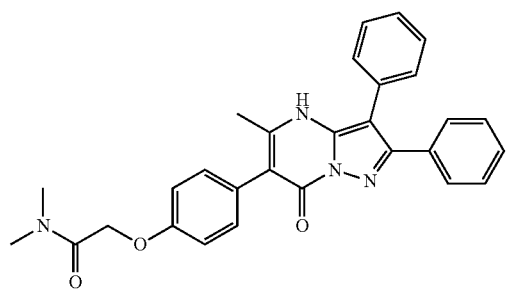 [SMILES: Cc1[nH]c2c(-c3ccccc3)c(-c3ccccc3)nn2c(=O)c1-c1ccc(OCC(=O)N(C)C)cc1]
333
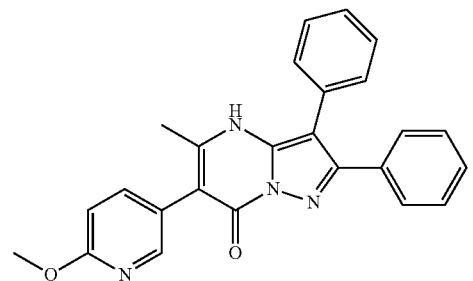
334
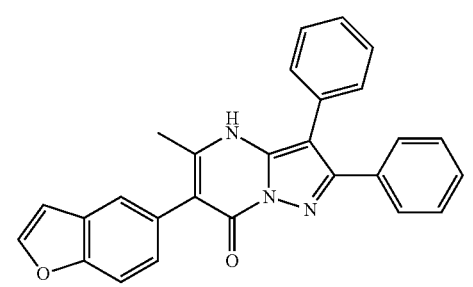 [SMILES: Cc1[nH]c2c(-c3ccccc3)c(-c3ccccc3)nn2c(=O)c1-c1ccc2occc2c1]
544
-continued
335
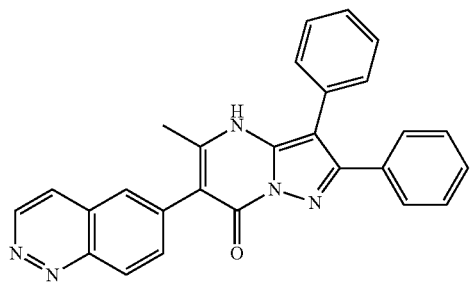
336
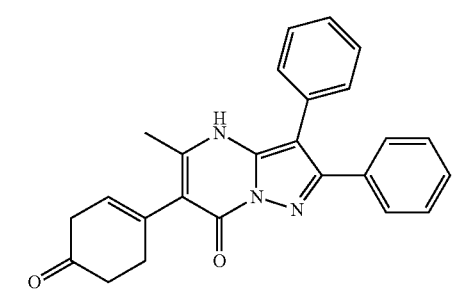 [SMILES: Cc1[nH]c2c(-c3ccccc3)c(-c3ccccc3)nn2c(=O)c1C1=CCC(=O)CC1]
337
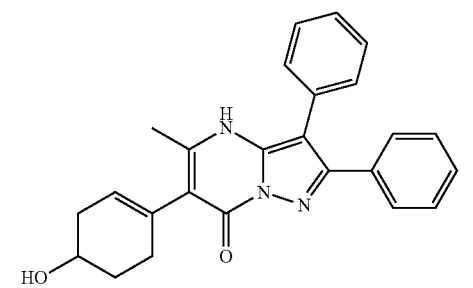 [SMILES: Cc1[nH]c2c(-c3ccccc3)c(-c3ccccc3)nn2c(=O)c1C1=CCC(O)CC1]
338
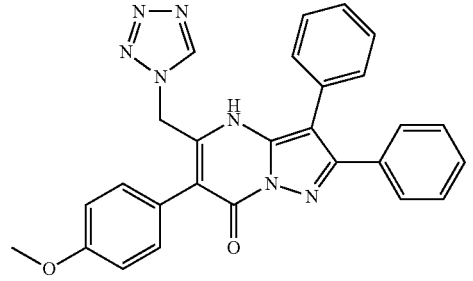 [SMILES: COc1ccc(-c2c(Cn3cnnn3)[nH]c3c(-c4ccccc4)c(-c4ccccc4)nn3c2=O)cc1]
339
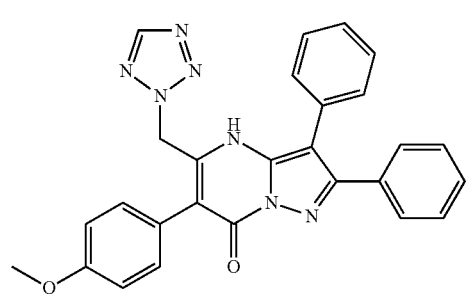

545
-continued
| | |
|---|---|
| 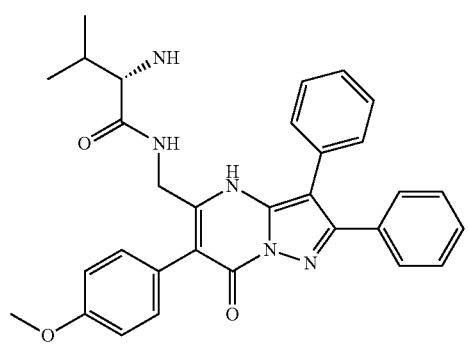 [SMILES: COc1ccc(-c2c(CNC(=O)[C@@H](N)C(C)C)[nH]c3c(-c4ccccc4)c(-c4ccccc4)nn3c2=O)cc1] 340 | 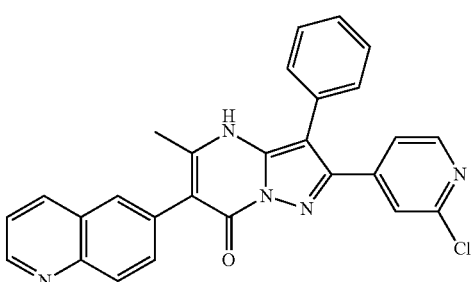 350 |
| 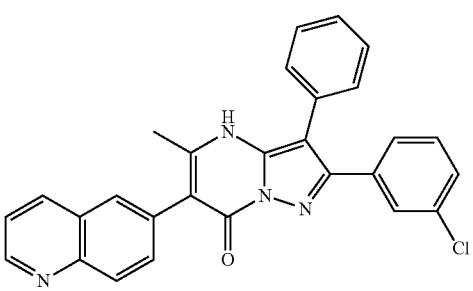 [SMILES: Cc1[nH]c2c(-c3ccccc3)c(-c3cccc(Cl)c3)nn2c(=O)c1-c1ccc2ncccc2c1] 346 | 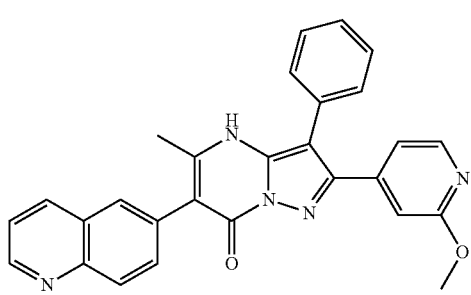 351 |
| 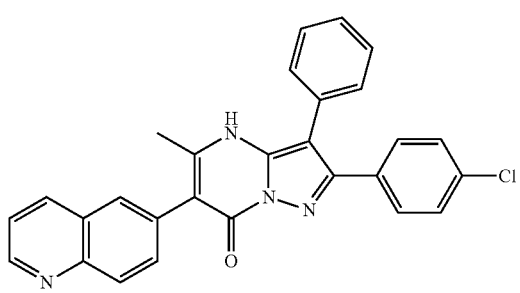 [SMILES: Cc1[nH]c2c(-c3ccccc3)c(-c3ccc(Cl)cc3)nn2c(=O)c1-c1ccc2ncccc2c1] 347 | 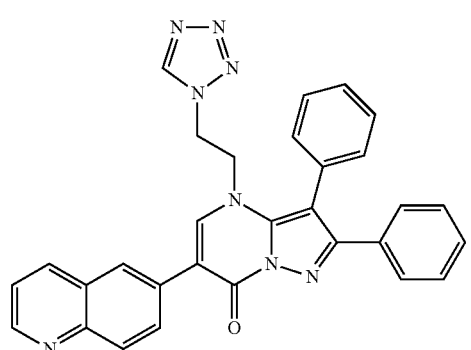 352 |
| 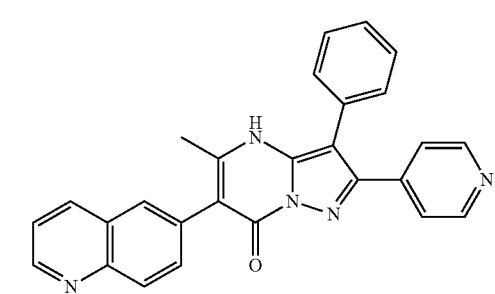 [SMILES: Cc1[nH]c2c(-c3ccccc3)c(-c3ccncc3)nn2c(=O)c1-c1ccc2ncccc2c1] 348 | 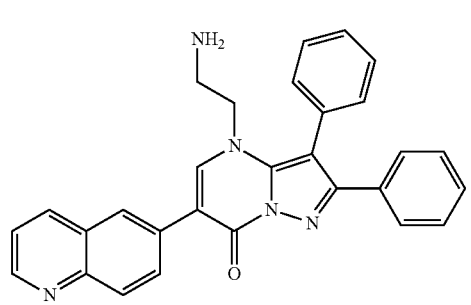 353 |
| 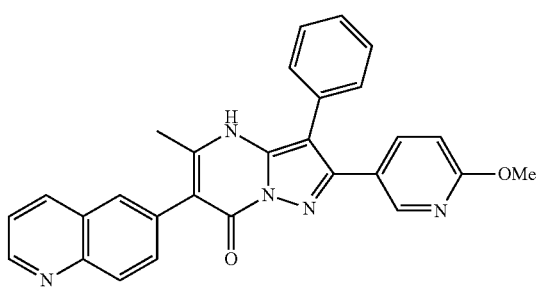 [SMILES: COc1ccc(-c2nn3c(=O)c(-c4ccc5ncccc5c4)c(C)[nH]c3c2-c2ccccc2)cn1] 349 | 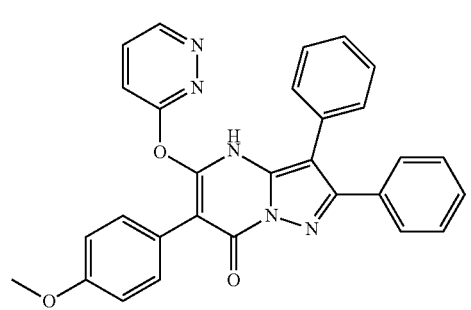 [SMILES: COc1ccc(-c2c(Oc3cccnn3)[nH]c3c(-c4ccccc4)c(-c4ccccc4)nn3c2=O)cc1] 354 |
546
-continued

355

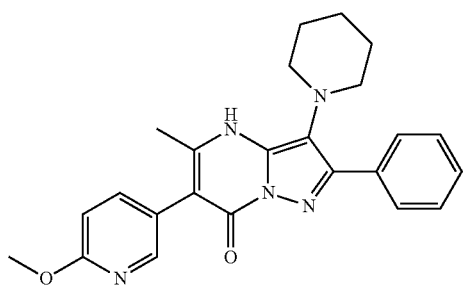 [SMILES: COc1ccc(-c2c(C)[nH]c3c(N4CCCCC4)c(-c4ccccc4)nn3c2=O)cn1]

356

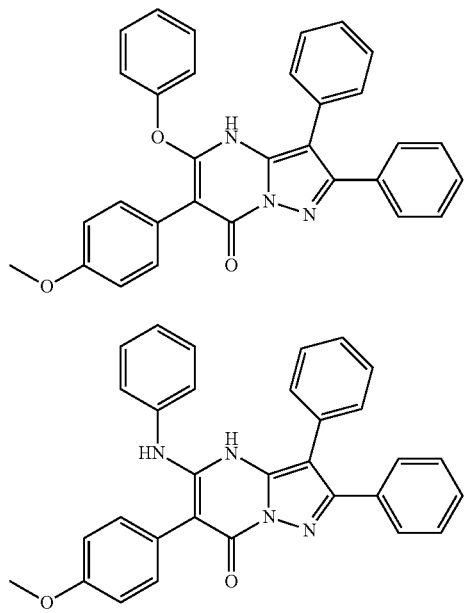

358

31. A method for inhibiting the synthesis of S-adenosyl methionine (SAM) from methionine and ATP by MAT2A in a cell, comprising introducing into the cell an effective amount of a compound, or a pharmaceutically acceptable salt thereof, according to any one of claims 1, 28, 29, and 30.

32. A pharmaceutical composition comprising a compound, or a pharmaceutically acceptable salt thereof, according to any one of claims 1, 28, 29, and 30, and a pharmaceutically acceptable carrier.

* * * * *